United States Patent
Mowat et al.

(10) Patent No.: US 11,427,578 B1
(45) Date of Patent: Aug. 30, 2022

(54) SUBSTITUTED PYRROLOPYRIDINE-DERIVATIVES

(71) Applicants: Bayer Pharma Aktiengesellschaft, Berlin (DE); Bayer Aktiengesellschaft, Leverkusen (DE); Deutsches Krebsforschungszentrum, Heidelberg (DE)

(72) Inventors: Jeffrey Stuart Mowat, Berlin (DE); Bernd Buchmann, Hohen Neuendorf (DE); Nuria Aiguabella Font, Berlin (DE); Gabriele Leder, Berlin (DE); Rafael Carretero, Heidelberg (DE); Olaf Panknin, Berlin (DE); Roland Neuhaus, Berlin (DE); Robin Michael Meier, Wain (DE); Sandra Berndt, Hohen Neuendorf (DE); Kirstin Petersen, Berlin (DE); Rienk Offringa, Heidelberg (DE)

(73) Assignees: Bayer Pharma Aktiengesellschaft, Berlin (DE); Bayer Aktiengesellschaft, Leverkusen (DE); Deutsches Krebsforschungszentrum, Heidelberg (DE)

( * ) Notice: Subject to any disclaimer, the term of this patent is extended or adjusted under 35 U.S.C. 154(b) by 3 days.

(21) Appl. No.: 16/632,273

(22) PCT Filed: Jul. 12, 2018

(86) PCT No.: PCT/EP2018/068974
§ 371 (c)(1),
(2) Date: Jan. 17, 2020

(87) PCT Pub. No.: WO2019/016071
PCT Pub. Date: Jan. 24, 2019

(30) Foreign Application Priority Data

Jul. 18, 2017 (EP) .................................... 17181945

(51) Int. Cl.
C07D 471/04 (2006.01)
A61K 45/06 (2006.01)

(52) U.S. Cl.
CPC ............ *C07D 471/04* (2013.01); *A61K 45/06* (2013.01)

(58) Field of Classification Search
CPC combination set(s) only.
See application file for complete search history.

(56) References Cited

U.S. PATENT DOCUMENTS 9,180,127 B2 * 11/2015 Gray .................... A61K 31/519

* cited by examiner

*Primary Examiner* — Heidi Reese

(74) *Attorney, Agent, or Firm* — Morrison & Foerster LLP

(57) ABSTRACT

The present invention relates to protein-inhibitory substituted pyrrolopyridine derivatives of formula (I), in which A, X, $R^1$, $R^{2a}$, $R^{2b}$, $R^{3a}$, $R^{3b}$, $R^{4a}$ and $R^{4b}$ are as defined herein, to pharmaceutical compositions and combinations comprising the compounds according to the invention, and to the prophylactic and therapeutic use of the inventive compounds, respectively to the use of said compounds for manufacturing pharmaceutical compositions for the treatment or prophylaxis of diseases, in particular for neoplastic disorders, respectively cancer or conditions with dysregulated immune responses or other disorders associated with aberrant MAP4K1 signaling, as a sole agent or in combination with other active ingredients. The present invention further relates to the use, respectively to the use of said compounds for manufacturing pharmaceutical compositions for the treatment or prophylaxis of protein inhibitors in benign hyperplasias, atherosclerotic disorders, sepsis, autoimmune disorders, vascular disorders, viral infections, in neurodegenerative disorders, in inflammatory disorders, in atherosclerotic disorders and in male fertility control.

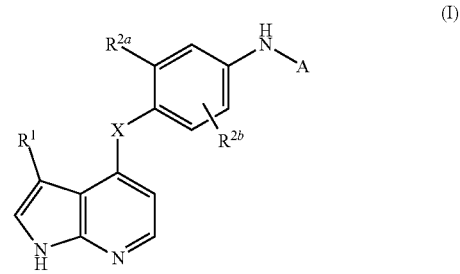

18 Claims, 1 Drawing Sheet
Specification includes a Sequence Listing.

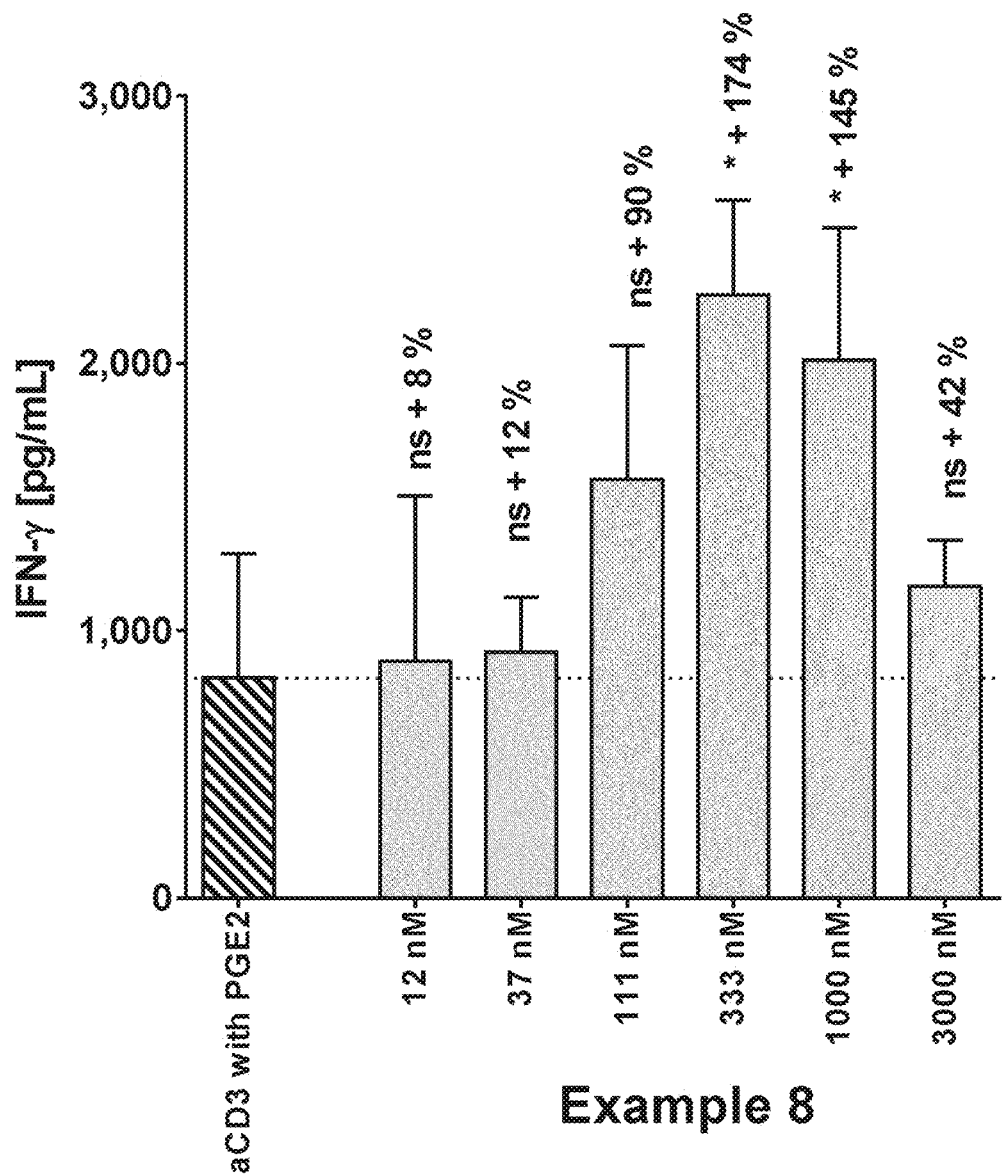

SUBSTITUTED PYRROLOPYRIDINE-DERIVATIVES

CROSS REFERENCE TO RELATED APPLICATIONS

This application is a national stage application under 35 U.S.C. § 371 of International Application No. PCT/EP2018/068974, filed internationally on Jul. 12, 2018, which claims the benefit of European Application No. 17181945.1, filed Jul. 18, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052040200SEQLIST.TXT, date recorded: Aug. 27, 2020, size: 1 KB).

The present invention relates to protein-inhibitory substituted pyrrolopyridine derivatives, to pharmaceutical compositions and combinations comprising the compounds according to the invention, and to the prophylactic and therapeutic use of the inventive compounds, respectively to the use of said compounds for manufacturing pharmaceutical compositions for the treatment or prophylaxis of diseases, in particular for neoplastic disorders, respectively cancer or conditions with dysregulated immune responses or other disorders associated with aberrant MAP4K1 signaling, as a sole agent or in combination with other active ingredients. The present invention further relates to the use, respectively to the use of said compounds for manufacturing pharmaceutical compositions for the treatment or prophylaxis of protein inhibitors in benign hyperplasias, atherosclerotic disorders, sepsis, autoimmune disorders, vascular disorders, viral infections, in neurodegenerative disorders, in inflammatory disorders, in atherosclerotic disorders and in male fertility control.

BACKGROUND

Although cancer cell commonly can be recognize by the adaptive immune system, the response generated is evidently not capable of eliminating the tumor. A major reason for this is the presence of immunosuppressive mechanisms in the tumor microenvironment. In this respect, inhibitors of T-cell immune checkpoint such as CTLA-4, PD-1 or PD-L1 were recently shown to result in a remarkable clinical efficacy in subsets of cancer patients. Besides cell surface receptors that act as negative immune regulators, several mediators of intracellular signaling have been identified that also represent potential immunoevasive mechanisms utilized by the tumor.

One of these is MAP4K1, also known as hematopoietic progenitor kinase 1 (HPK1). MAP4K1 (GeneID11184) is a serine/threonine kinase and member of the Germinal Center Kinase family. In the adult organism MAP4K1 expression is restricted to hematopoietic cell types. The MAP4K1 protein consist of a N-terminal kinase domain, followed by a proline-rich domain that can interact with adaptor molecules through SH2 and SH3 domains, and a C-terminal citron homology domain of which the exact function remains to be identified. Through its proline-rich domain, MAP4K1 is capable of binding to a diversity of adaptors in hematopoietic cells, including those involved in T-cell receptor (TCR), B-cell receptor (BCR) and cytokine signaling (Hu et al., Genes Dev. 1996 Sep. 15; 10(18):2251-64, 2; Ling et al., J Biol Chem. 2001 Jun. 1; 276(22), Sauer et al., J Biol Chem. 2001 Nov. 30; 276(48):45207-16, Tsuji et al., J Exp Med. 2001 Aug. 20; 194(4):529-39, Boomer et al., J Cell Biochem. 2005 May 1; 95(1):34-44). The function of MAP4K1 has been studied in greatest detail in the context of TCR signaling. Upon TCR stimulation, MAP4K1 is phosphorylated on tyrosine 381 (Y-381; Y-379 in mouse) (Di Bartolo et al., J Exp Med. 2007 Mar. 19; 204(3):681-91). Consequently, MAP4K1 is recruited to the TCR-signaling complex where it induces dissociation of this complex through its serine/threonine kinase function. In particular MAP4K1 phosphorylates the SLP-76 adaptor protein at Serine-376, resulting in downregulation of AP-1 and Erk2 pathways. As, such, MAPK1 acts as a negative feedback on TCR-signaling (Liou et al., Immunity. 2000 April; 12(4): 399-408; Lasserre et al., J Cell Biol. 2011 Nov. 28; 195(5): 839-53). Alternatively, MAP4K1 can be triggered to suppress T cell function by prostaglandin E2 (PGE2), and possibly also by transforming growth factor beta (TGF-beta), factors that are commonly found in the tumor microenvironment. Notably, MAP4K1 activation by these mediators involves protein kinase A (PKA)-dependent phosphorylation of Serine 171 (S-171; also in mouse) (Alzabin et al., Cancer Immunol Immunother. 2010 March; 59(3):419-29; Sawasdikosol et al., J Biol Chem. 2007 Nov. 30; 282(48):34693-9).

Further important insights into the function of MAP4K1 in the regulation of T cell immunity stem from in vivo and in vitro experiments respectively with MAP4K1 deficient mice produced by two laboratories and with immune cells isolated from these mice (Shui et al., Nat Immunol. 2007 January; 8(1):84-91; Alzabin et al., Cancer Immunol Immunother. 2010 March; 59(3):419-29). MAP4K1-deficient mice show an apparent normal phenotype, are fertile and exhibit normal lymphocyte development. These animals are prone to develop T-cell dependent autoimmune reactivity as indicated by development of a more severe disease score in the EAE (experimental autoimmune encephalomyelitis) model of multiple sclerosis (Shui et al., Nat Immunol. 2007 January; 8(1):84-91). In case of the second strain, a dysregulation of immune function was observed when, at the age of approximately 6 months, MAP4K1-deficient mice develop a spontaneous autoimmune phenotype (Alzabin et al., Cancer Immunol Immunother. 2010 March; 59(3):419-29). In vitro studies showed that MAP4K1−/− T-cells display hyper-responsiveness upon TCR-stimulation. These cells proliferate and secrete pro-inflammatory cytokines like IL-2 or IFNg to a significantly greater extent than their wild-type counterparts (Shui et al., Nat Immunol. 2007 January; 8(1):84-91). Furthermore, MAP4K1−/− T-cells are resistant to PGE2-mediated suppression of T cell proliferation, suppression of IL-2 production and induction of apoptosis (Alzabin et al., Cancer Immunol Immunother. 2010 March; 59(3):419-29). In the context of tumor immunology, in vivo experiments revealed that MAP4K1−/− mice are much more resistant to tumorigenesis by PGE2-producing Lewis lung carcinoma than wild type mice, which correlated with increased T-lymphocyte infiltration in the tumor areas. The crucial role of T-cells in tumor rejection was supported by experiments in which MAP4K1−/− T-cells adoptively transferred into T-cell-deficient mice were able to eradicate tumors more efficiently than wild-type T-cells (Alzabin et al., Cancer Immunol Immunother. 2010 March; 59(3):419-29). The important role of the kinase enzymatic activity was demonstrated by studies were only wild type MAP4K1, but not the MAP4K1 kinase-dead mutant, could mediate serine-phosphorylation of the TCR-signaling complex component SLP-76 and subsequent binding of SLP-76 to the negative regulator of TCR-signaling 14-3-3-t (Shui et al., Nat Immunol. 2007 January; 8(1):84-91). MAP4K1 also regulates the stimulation and activation of dendritic cells. MAP4K1 deficient Bone marrow derived cells (BMDC) express after maturation and stimulation higher level of costimulatory molecules and produce more proinflammatory cytokines. Also elimination of tumors was observed to be more efficient by MAP4K1-/- BMDC compared to their wildtype counterparts (Alzabin et al., J Immunol. 2009 May 15; 182(10): 6187-94).

PRIOR ART

In WO 2016/205942 HPK1, respectively inhibitors and methods of their use in cancer treatment are described. Especially, the application concerns thieno-pyridinones that can be used in anti-cancer therapy. These compounds differ from the instant compounds in their chemical structure.

In WO 2016/195776 inhibitors and methods for leukemia, cancer and diabetes treatment dependent on inhibition the interaction of menin with of MLL1, MLL2 and MLL-fusion oncoproteins are described. These compounds differ from the instant compounds in their chemical structure.

In WO 2006/014325 C-MET modulators and their use in cancer treatment are described. These compounds differ from the instant compounds in their chemical structure.

In WO 2005/058891 Rho kinase inhibitors and their use in cardiovascular and cancer treatment are described. These compounds differ from the instant compounds in their chemical structure.

In WO 2015/089479 several inhibitors are described that show inhibition of several kinases (e.g., BTK, HCK, TAK1 and HPK1). These compounds differ from the instant compounds in their chemical structure.

In WO2016/004272 BTK inhibitors and methods of their use in cancer treatment are described. No specific example is disclosed which falls in the group of compounds as defined according to the present invention.

In WO 2011/090738 Type II RAF kinase inhibitors and their use in various diseases are described. No specific example is disclosed which falls in the group of compounds as defined according to the present invention.

In CN102086211 and WO2006116713 protein kinase inhibitors and their use in prophylaxis and treatment of diseases including cancer are described. No specific example is disclosed which falls in the group of compounds as defined according to the present invention.

In WO 2010/045095 protein tyrosin kinase modulators and their use in the treatment of hyperproliferative disorders are described. No specific example is disclosed which falls in the group of compounds as defined according to the present invention.

In WO 2008/089307 compounds and methods of their use in the treatment of pain, inflammation and cancer are described. No specific example is disclosed which falls in the group of compounds as defined according to the present invention.

In WO 2006/114180 kinase inhibitors for treating diseases, particularly tumors are described. No specific example is disclosed which falls in the group of compounds as defined according to the present invention.

In WO 2006/014325 c-Met modulators and their methods of use to treat kinase-dependent diseases and conditions are described. No specific example is disclosed which falls in the group of compounds as defined according to the present invention.

In US 2003/0055049 compounds for treating disorders with abnormal cell growth in mammals are described. No specific example is disclosed which falls in the group of compounds as defined according to the present invention.

In WO 2001/23389 antagonists of NPY receptors compositions and methods of the treatment of physiological disorders associated with an excess of neuropeptide Y are described. No specific example is disclosed which falls in the group of compounds as defined according to the present invention.

It would therefore be desirable to provide novel compounds having prophylactic and therapeutic properties.

Accordingly, it is an object of the present invention to provide compounds and pharmaceutical compositions comprising these compounds used for prophylactic and therapeutic applications for hyperproliferative disorders, in particular for cancer, respectively tumour disorders, and conditions with dysregulated immune responses, as a sole agent or in combination with other active ingredients.

A further object of the present invention is to provide compounds and pharmaceutical compositions comprising these compounds for manufacturing pharmaceutical compositions for the treatment or prophylaxis of protein inhibitors in benign hyperplasias, atherosclerotic disorders, sepsis, autoimmune disorders, vascular disorders, viral infections, in neurodegenerative disorders, in inflammatory disorders, in atherosclerotic disorders and in male fertility control.

Surprisingly, the compounds according to the invention inhibit the MAP4K1 protein and inhibit the growth of cancer cells. Accordingly, they provide novel structures for the therapy of human and animal disorders, in particular of cancers.

The present invention relates to compounds of formula (I)

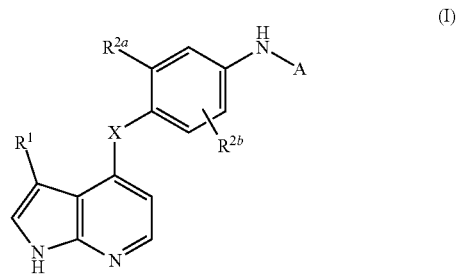

in which

A represents a monocyclic 5- to 7 membered ring selected from

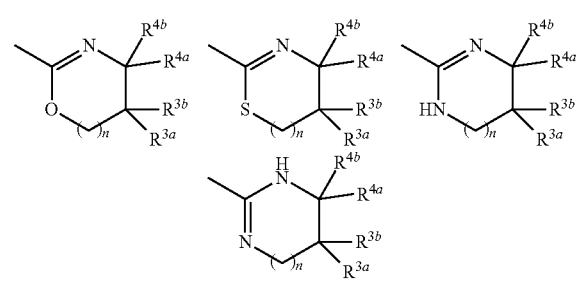

X represents a nitrogen, a sulphur or an oxygen atom,
n represents 0, 1, 2
$R^1$ represents a group selected from
hydrogen, halogen, cyano, $C_1$-$C_6$-haloalkyl,
a $C_1$-$C_6$-alkyl,
a phenyl,
a 5- or 6-membered heteroaryl,
a $C_3$-$C_8$-cycloalkyl-,
a monocyclic 4- to 7-membered heterocycloalkyl,
a bridged bicyclic 7- to 10-membered heterocycloalkyl
wherein said $C_1$-$C_6$-alkyl, phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, aminosulfonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_3$-$C_8$-cycloalkoxy, $C_3$-$C_8$-cycloalkyl-$C_1$-$C_6$-alkoxy, $C_1$-$C_6$-alkylcarbonyloxy, $C_1$-$C_3$-alkylcarbonyl, di-($C_1$-$C_4$)-alkylaminocarbonyl, mono-($C_1$-$C_4$)-alkylaminocarbonyl, di-($C_1$-$C_4$)-alkylaminosulfonyl, mono-($C_1$-$C_4$)-alkylaminosulfonyl, or
$R^1$ represents the group Z-L-,
wherein Z represents a 5- or 6-membered heteroaryl
which is optionally substituted with one or two substituents, identically or differently, selected from the group consisting of halogen, cyano, aminocarbonyl, $C_1$-$C_3$-alkyl, $C_1$-$C_3$-alkoxy, di-($C_1$-$C_4$)-alkylaminocarbonyl, mono-($C_1$-$C_4$)-alkylaminocarbonyl, and
L represents —$CH_2$—NHCO—, —$CH_2$—CONH—, $CH_2$—$NHSO_2$—, —$CH_2$—$SO_2NH$— and the $CH_2$-group of L can be bond to any atom of Z except to an oxygen or sulphur heteroatom, if present.
$R^{2a}$ represents hydrogen, halogen, $C_1$-$C_3$-alkyl, $C_1$-$C_3$-alkoxy, $C_1$-$C_3$-haloalkyl, $C_1$-$C_3$-haloalkoxy-
$R^{2b}$ represents hydrogen, halogen, cyano, methyl, methoxy, trifluoromethyl, trifluoromethoxy,
$R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, phenyl, $C_3$-$C_8$-cycloalkyl-, $C_1$-$C_6$-alkyl-$C_3$-$C_8$-cycloalkyl, $C_1$-$C_6$-alkyl-phenyl, $C_1$-$C_6$-alkyl-heteroaryl wherein a cycloalkyl, phenyl or heteroaryl ring is optionally substituted with one or two $C_1$-$C_3$-alkyl,
$R^{4a}$, $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, or
$R^{3a}$ and $R^{3b}$ together represent a monocyclic 3 to 6-membered cycloalkyl or heterocycloalkyl, wherein said 3 to 6-membered cycloalkyl or heterocycloalkyl is optionally substituted by fluorine, chlorine, methyl, methoxy, hydroxy, cyano, or
$R^{4a}$ and $R^{4b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano, and their polymorphs, enantiomers, diastereomers, racemates, tautomers, solvates, physiologically acceptable salts and solvates of these salts.

The compounds of formula (I) are particularly suitable for a large number of prophylactic and therapeutic applications, in particular for hyperproliferative disorders, for tumour disorders and as protein inhibitors and further for viral infections, for neurodegenerative disorders, for inflammatory disorders, for atherosclerotic disorders and for male fertility control.

Further, it covers their use in combination with other anti cancer medications such as immunotherapeutics, targeted anti cancer agents, radiation or chemotherapy.

The group of compounds according to the invention are compounds of formula (I), encompassing the subtypes

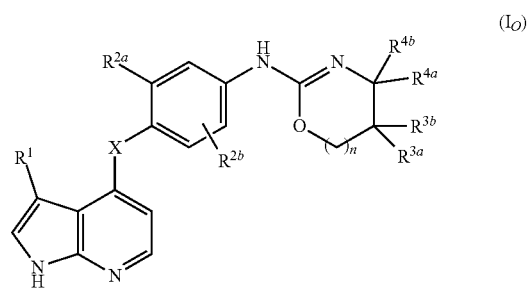

(I$_O$)

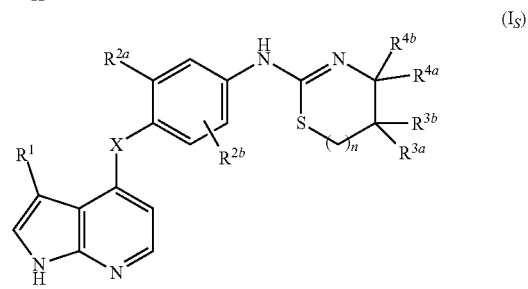

(I$_S$)

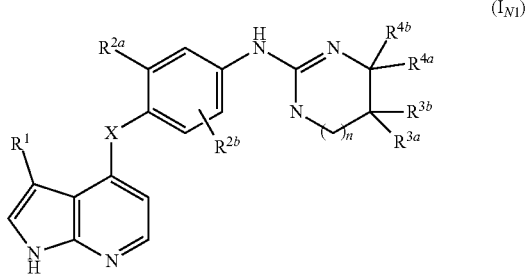

(I$_{N1}$)

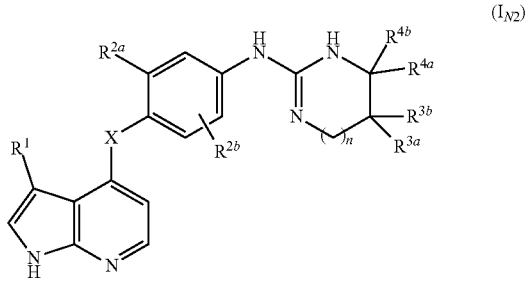

(I$_{N2}$)

including their polymorphs, enantiomers, diastereomers, racemates, tautomers, solvates, physiologically acceptable salts and solvates of these salts.

The compounds of the subtype (I$_{N2}$) are tautomeric forms of the subtype (I$_{N1}$).

The group of compounds according to the invention can also be described by: Compounds of formula (Ia)

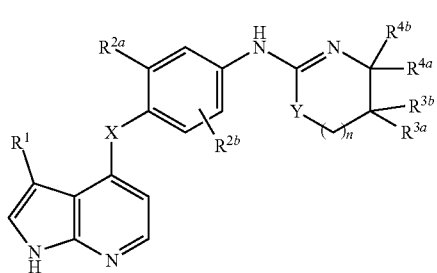

in which
Y represents a nitrogen, a sulphur or an oxygen atom
and their polymorphs, enantiomers, diastereomers, racemates, tautomers, solvates, physiologically acceptable salts and solvates of these salts.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen or . . . atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

The term "comprising" when used in the specification includes "consisting of".

If within the present text any item is referred to as "as mentioned herein", it means that it may be mentioned anywhere in the present text.

The terms as mentioned in the present text have the following meanings: The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-hydroxyalkyl" means a linear or branched, saturated, monovalent hydrocarbon group in which the term "$C_1$-$C_6$-alkyl" is defined supra, and in which 1, 2 or 3 hydrogen atoms are replaced with a hydroxy group, e.g. a hydroxymethyl, 1-hydroxyethyl, 2-hydroxyethyl, 1,2-dihydroxyethyl, 1-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

Preference is given to perfluorinated alkyl radicals which are named as "perfluoro-$C_1$-$C_x$-alkyl-" wherein x is the maximum number of carbon atoms such as trifluoromethyl or 2,2,2-trifluoroethyl.

The term "$C_1$-$C_6$-cyanoalkyl" means a linear or branched, saturated, monovalent hydrocarbon group in which the term "$C_1$-$C_6$-alkyl" is as defined supra, and in which one or more of the hydrogen atoms are replaced, identically or differently, with a cyano group.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

Preference is given to perfluorinated alkyl radicals which are named as "perfluoro-$C_1$-$C_x$-alkoxy-" wherein x is the maximum number of carbon atoms such as trifluoromethoxy and 2,2,2-trifluoroethoxy radicals.

The term "$C_1$-$C_6$-cyanoalkoxy" means a linear or branched, saturated, monovalent $C_1$-$C_6$-alkoxy group, as defined supra, in which one or more of the hydrogen atoms is replaced, identically or differently, with a cyano group.

Mono-$(C_1$-$C_4)$-alkylamino in the context of the invention means an amino group with one straight-chain or branched alkyl substituent which contains 1, 2, 3 or 4 carbon atoms, such as: methylamino, ethylamino, n-propylamino, isopropylamino, n-butylamino, and tert-butylamino, for example.

Di-$(C_1$-$C_4)$-alkylamino in the context of the invention means an amino group with two identical or different straight-chain or branched alkyl substituents which each contain 1, 2, 3 or 4 carbon atoms, such as: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino, for example.

$(C_1$-$C_4)$-Alkylcarbonyl in the context of the invention means a straight-chain or branched alkyl group having 1, 2, 3 or 4 carbon atoms which is bound to the rest of the molecule via a carbonyl group [—C(=O)—], such as: acetyl, propionyl, n-butyryl, isobutyryl, n-pentanoyl, and pivaloyl, for example.

$(C_1$-$C_4)$-Alkylcarbonyloxy in the context of the invention means a straight-chain or branched alkyl group having 1, 2, 3 or 4 carbon atoms which is bound to the rest of the molecule via a carboxy group [—C(=O)—O—], such as: acetoxy (=acyloxy), propionyloxy, n-butyryloxy, isobutyryloxy, n-pentanoyloxy, and pivaloyloxy, for example.

Mono-$(C_1$-$C_4)$-alkylaminocarbonyl in the context of the invention means an amino group which is bound to the rest of the molecule via a carbonyl group [—C(=O)-] and which has one straight-chain or branched alkyl substituent having 1, 2, 3 or 4 carbon atoms, such as: methylaminocarbonyl, ethylaminocarbonyl, n-propylaminocarbonyl, isopropylaminocarbonyl, n-butylaminocarbonyl, and tert-butylaminocarbonyl, for example.

Di-$(C_1$-$C_4)$-alkylaminocarbonyl in the context of the invention means an amino group which is bound to the rest of the molecule via a carbonyl group [—C(=O)-] and which has two identical or different straight-chain or branched alkyl substituents having in each case 1, 2, 3 or 4 carbon atoms, such as: N,N-dimethylaminocarbonyl, N,N-diethylaminocarbonyl, N-ethyl-N-methylaminocarbonyl, N-methyl-N-n-propylaminocarbonyl, N-isopropyl-N-methylaminocarbonyl, N,N-diisopropylaminocarbonyl, N-n-butyl-N-methylaminocarbonyl, and N-tert-butyl-N-methylaminocarbonyl, for example.

Mono-$(C_1$-$C_4)$-alkylaminosulfonyl in the context of the invention means an amino group which is bound to the rest of the molecule via a sulfonyl group [—S(=O)$_2$-] and which has one straight-chain or branched alkyl substituent having 1, 2, 3 or 4 carbon atoms, such as: methylaminosulfonyl, ethylaminosulfonyl, n-propylaminosulfonyl, isopropylaminosulfonyl, n-butylamino sulfonyl, and tert-butylaminosulfonyl, for example.

Di-$(C_1$-$C_4)$-alkylaminosulfonyl in the context of the invention means an amino group which is bound to the rest of the molecule via a sulfonyl group [—S(=O)$_2$-] and which has two identical or different straight-chain or branched alkyl substituents having in each case 1, 2, 3 or 4 carbon atoms, such as: N,N-dimethylaminosulfonyl, N,N-diethylaminosulfonyl, N-ethyl-N-methylaminosulfonyl, N-methyl-N-n-propylaminosulfonyl, N-isopropyl-N-methylaminosulfonyl, N,N-diisopropylaminosulfonyl, N-n-butyl-N-methylaminosulfonyl, and N-tert-butyl-N-methylaminosulfonyl, for example.

The term "$C_3$-$C_8$-cycloalkyl" means a saturated, monovalent, mono- or bicyclic hydrocarbon ring which contains 3, 4, 5, 6, 7 or 8 carbon atoms ("$C_3$-$C_8$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl.

The term "$C_3$-$C_8$-cycloalkoxy" means a saturated, monovalent, mono- or bicyclic group of formula ($C_3$-$C_8$-cycloalkyl)-O—, which contains 3, 4, 5, 6, 7 or 8 carbon atoms, in which the term "$C_3$-$C_8$-cycloalkyl" is defined supra, e.g. a cyclopropyloxy, cyclobutyloxy, cyclopentyloxy, cyclohexyloxy, cycloheptyloxy or cyclooctyloxy group.

The terms "4- to 7-membered heterocycloalkyl" and "4- to 6-membered heterocycloalkyl" mean a monocyclic, saturated or unsaturated heterocycle with 4, 5, 6 or 7 or, respectively, 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom. A carbon atom may be substituted with an oxo group or the sulphur atom with one or two oxo groups to form a —C=O, —S(=O)— or —S(=O)$_2$-group in the ring.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

Particularly, "4- to 6-membered heterocycloalkyl" means a 4- to 6-membered heterocycloalkyl as defined supra containing one ring nitrogen atom and optionally one further ring heteroatom from the series: N, O, S. More particularly, "5- or 6-membered heterocycloalkyl" means a monocyclic, saturated heterocycle with 5 or 6 ring atoms in total, containing one ring nitrogen atom and optionally one further ring heteroatom from the series: N, O.

The term "bridged heterocycloalkyl" means a bicyclic, saturated or unsaturated heterocycle with 7, 8, 9 or 10 ring atoms in total (="bridged bicyclic 7- to 10-membered heterocycloalkyl"), in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom. A carbon atom may be substituted with an oxo group or the sulphur atom with one or two oxo groups to form a —C=O, —S(=O)— or —S(=O)$_2$-group in the ring.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo-[2.2.2]octyl, diazabicyclo[2.2.2]octyl, oxazabicyclo [2.2.2]octyl, thiazabicyclo[2.2.2]octyl, azabicyclo[3.2.1] octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo [3.3.1]-nonyl, azabicyclo[4.2.1]nonyl, diazabicyclo[4.2.1] nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group such as, for example, pyridinyl (=pyridyl), pyridazinyl, pyrimidinyl, pyrazinyl or triazinyl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For Example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art. The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers or mixtures of tautomers, namely having instead of or in addition to the substructures defined for A of compounds according to formula (I) following moieties

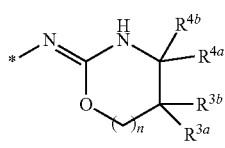

(1)

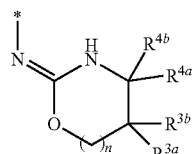

(2)

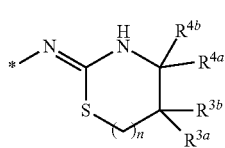

(3)

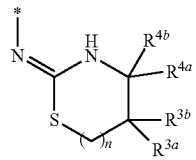

(4)

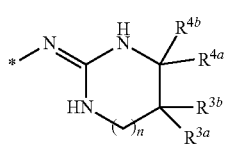

(5)

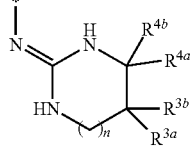

(6)

* connected to the benzene ring in some combinations of $R^{3a,b}$ and $R^{4a,b}$ and n=0,1,2

(5) and (6) are identical because of Cs symmetry

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown. Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition. Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible crystallized and polymorphic forms of the inventive compounds, whereby the polymorphs are existing either as a single polymorph form or are existing as a mixture of several polymorphs in all concentrations.

The invention further includes all possible cyclodextrin clathrates, i.e alpha-, beta-, or gamma-cyclodextrins, hydroxypropyl-beta-cyclodextrins, methylbetacyclodextrins.

Of selected interest are those compounds of formula (Ia,

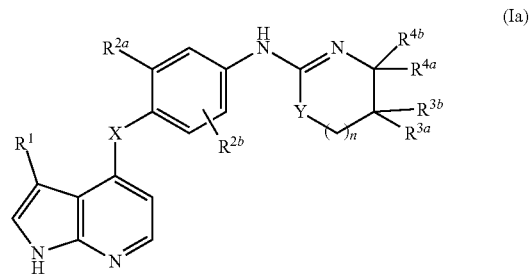

in which
X represents a nitrogen, a sulphur or an oxygen atom,
Y represents a nitrogen, a sulphur or an oxygen atom,
n represents 0, 1, 2
R$^1$ represents a group selected from
   halogen, cyano, C$_1$-C$_6$-haloalkyl,
   a phenyl,
   a 5- or 6-membered heteroaryl,
   a C$_3$-C$_8$-cycloalkyl-,
   a monocyclic 4- to 7-membered heterocycloalkyl,
   a bridged bicyclic 7- to 10-membered heterocycloalkyl
   wherein said phenyl, 5- or 6-membered heteroaryl, C$_3$-C$_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, aminosulfonyl, C$_1$-C$_6$-alkyl, C$_1$-C$_6$-haloalkyl, C$_1$-C$_6$-haloalkoxy, C$_1$-C$_6$-alkoxy, C$_1$-C$_6$-cyanoalkyl, C$_1$-C$_6$-cyanoalkoxy, C$_3$-C$_8$-cycloalkyl-, C$_3$-C$_8$-cycloalkoxy, C$_3$-C$_8$-cycloalkyl-C$_1$-C$_6$-alkoxy, C$_1$-C$_6$-alkylcarbonlyoxy, di-(C$_1$-C$_4$)-alkylaminocarbonyl, mono-(C$_1$-C$_4$)-alkylaminocarbonyl, di-(C$_1$-C$_4$)-alkylaminosulfonyl, mono-(C$_1$-C$_4$)-alkylaminosulfonyl, or
R$^1$ represents the group Z-L-,
   wherein Z represents a 5- or 6-membered heteroaryl
   which is optionally substituted with one or two substituents, identically or differently, selected from the group consisting of halogen, cyano, aminocarbonyl, C$_1$-C$_3$-alkyl, C$_1$-C$_3$-alkoxy, di-(C$_1$-C$_4$)-alkylaminocarbonyl, mono-(C$_1$-C$_4$)-alkylaminocarbonyl, and
   L represents —CH$_2$—NHCO—, —CH$_2$—CONH—, CH$_2$—NHSO$_2$—, —CH$_2$—SO$_2$NH— and the CH$_2$-group of L can be bond to any atom of Z except to an oxygen or sulphur heteroatom, if present.
R$^{2a}$ represents hydrogen, halogen, C$_1$-C$_3$-alkyl, C$_1$-C$_3$-alkoxy, C$_1$-C$_3$-haloalkyl, C$_1$-C$_3$-haloalkoxy-
R$^{2b}$ represents hydrogen, halogen, cyano, methyl, methoxy, trifluoromethyl, trifluoromethoxy,
R$^{3a}$, R$^{3b}$ represent independently from each other hydrogen or a substituent, identically or differently, selected from the group consisting of halogen, hydroxy, cyano, aminocarbonyl, C$_1$-C$_3$-alkyl, C$_1$-C$_3$-haloalkyl, C$_1$-C$_6$-hydroxyalkyl-, C$_1$-C$_3$-alkoxy-C$_1$-C$_3$-alkyl, C$_1$-C$_3$-alkylcarbonyl, di-(C$_1$-C$_4$)-alkylaminocarbonyl, mono-(C$_1$-C$_4$)-alkylaminocarbonyl, phenyl, $R^{4a}$, $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, or $R^{3a}$ and $R^{3b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano, or $R^{4a}$ and $R^{4b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano, and their polymorphs, enantiomers, diastereomers, racemates, tautomers, solvates, physiologically acceptable salts and solvates of these salts.

Of selected interest are those compounds of formula (Ia), in which

X represents a sulphur or an oxygen atom,

Y represents a sulphur or an oxygen atom, n represents 0, 1, $R^1$ represents a group selected from
halogen, cyano, $C_1$-$C_6$-haloalkyl,
a phenyl,
a 5- or 6-membered heteroaryl,
a $C_3$-$C_7$-cycloalkyl-,
a monocyclic 4- to 7-membered heterocycloalkyl,
a bridged bicyclic 7- to 10-membered heterocycloalkyl
wherein said phenyl, 5- or 6-membered heteroaryl, $C_3$-$C_7$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_6$-alkylcarbonyloxy, di-($C_1$-$C_4$)-alkylaminocarbonyl, mono-($C_1$-$C_4$)-alkylaminocarbonyl, or $R^1$ represents the group Z-L-,
wherein Z represents a 5- or 6-membered heteroaryl which is optionally substituted with one or two substituents, identically or differently, selected from the group consisting of halogen, $C_1$-$C_3$-alkyl, $C_1$-$C_3$-alkoxy, cyano, aminocarbonyl, di-($C_1$-$C_4$)-alkylaminocarbonyl, mono-($C_1$-$C_4$)-alkylaminocarbonyl, and
L represents —$CH_2$—NHCO—,
and the $CH_2$-group of L can be bond to any atom of Z except to an oxygen or sulphur heteroatom, if present.

$R^{2a}$ represents hydrogen, halogen, $C_1$-$C_3$-alkyl, $C_1$-$C_3$-alkoxy, $C_1$-$C_3$-haloalkyl, $C_1$-$C_3$-haloalkoxy- $R^{2b}$ represents hydrogen, halogen, cyano, methyl, methoxy, trifluoromethyl, trifluoromethoxy, $R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, phenyl, $R^{4a}$, $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, and their polymorphs, enantiomers, diastereomers, racemates, tautomers, solvates, physiologically acceptable salts and solvates of these salts.

Of selected interest are those compounds of formula (Ia), in which

X represents an oxygen atom,

Y represents an oxygen atom, n represents 0, 1, $R^1$ represents a group selected from
halogen, cyano, $C_1$-$C_3$-perfluoroalkyl,
a phenyl,
a 5- or 6-membered heteroaryl,
a $C_3$-$C_5$-cycloalkyl-,
a monocyclic 5 or 6-membered heterocycloalkyl,
a bridged bicyclic 8-membered heterocycloalkyl
wherein said phenyl, 5- or 6-membered heteroaryl, $C_3$-$C_5$-cycloalkyl-, monocyclic 5 or 6-membered heterocycloalkyl, bridged bicyclic 8-membered heterocycloalkyl is optionally substituted with one or two substituents, identically or differently, selected from the group consisting of halogen, cyano, aminocarbonyl, $C_1$-$C_3$-alkyl, $C_1$-$C_3$-haloalkyl, $C_1$-$C_3$-haloalkoxy, $C_1$-$C_3$-alkoxy, $R^1$ represents the group Z-L-,
wherein Z represents a 5-membered heteroaryl which is optionally substituted with one or two $C_1$-$C_3$-alkyl and
L represents —$CH_2$—NHCO—,
and the $CH_2$-group of L can be bond to any atom of Z except to an oxygen or
sulphur heteroatom, if present.

$R^{2a}$ represents halogen, $R^{2b}$ represents halogen, $R^{3a}$, $R^{3b}$ represent independently from each other hydrogen or a substituent, identically or differently, selected from the group consisting of halogen, hydroxy, cyano, $C_1$-$C_3$-alkyl, $C_1$-$C_3$-haloalkyl, $C_1$-$C_6$-hydroxyalkyl-, phenyl.

$R^{4a}$, $R^{4b}$ represent independently from each other hydrogen or a substituent, identically or differently, selected from the group consisting of methyl, aminocarbonyl, hydroxymethyland their polymorphs, enantiomers, diastereomers, racemates, tautomers, solvates, physiologically acceptable salts and solvates of these salts.

Of selected interest are those compounds of formula (Ia), in which

X represents an oxygen atom,

Y represents an oxygen atom, n represents 0, 1, $R^1$ represents a group selected from
bromine, chlorine, cyano, trifluoromethyl,
a cyclopropyl,
a phenyl,
a pyridinyl, a thienyl, a pyrazolyl,
wherein said cyclopropyl-, phenyl, pyridinyl, thienyl or pyrazolyl is optionally substituted with one or two substituents, identically or differently, selected from the group consisting of fluoro, chloro, methyl, ethyl, isopropyl, methoxy, isopropoxy, cyano, propanoyl, aminocarbonyl, cyanomethoxy or $R^1$ represents a group selected from

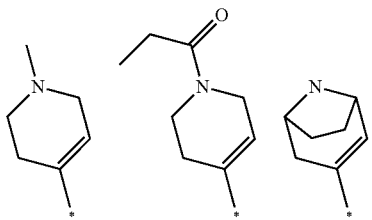

where "*" denotes the point of attachment to the remainder of the molecule, or $R^1$ represents

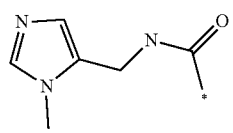 [SMILES: *C(=O)NCc1cncn1C]

where "*" denotes the point of attachment to the remainder of the molecule, $R^{2a}$ represents fluorine,
$R^{2b}$ represents fluorine,
$R^{3a}$, $R^{3b}$ represent independently from each other hydrogen or a substituent, identically or differently, selected from the group consisting of fluoro, hydroxy, cyano, methyl, isopropyl, difluoromethyl, hydroxymethyl-, 2-hydroxy-1,1-dimethylethyl, phenyl,
$R^{4a}$, $R^{4b}$ represent independently from each other hydrogen or a substituent, identically or differently, selected from the group consisting of methyl, aminocarbonyl, hydroxymethyland their polymorphs, enantiomers, diastereomers, racemates, tautomers, solvates, physiologically acceptable salts and solvates of these salts.

Of selected interest are those compounds of formula (I),

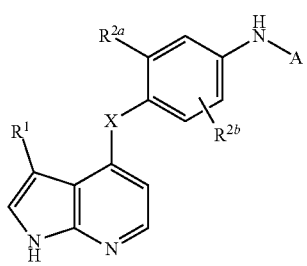 (I)

in which
A represents a monocyclic 5- to 7 membered ring selected from

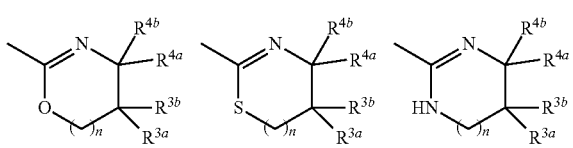

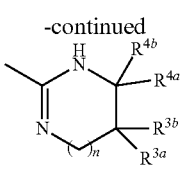

X represents a sulphur or an oxygen atom,
n represents 0 or 1,
$R^1$ represents a group selected from
hydrogen, halogen, cyano, $C_1$-$C_6$-haloalkyl,
a $C_1$-$C_6$-alkyl,
a phenyl,
a 5- or 6-membered heteroaryl,
a $C_3$-$C_8$-cycloalkyl-,
a monocyclic 4- to 7-membered heterocycloalkyl,
a bridged bicyclic 7- to 10-membered heterocycloalkyl
wherein said $C_1$-$C_6$-alkyl, phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_1$-$C_3$-alkylcarbonyl, di-($C_1$-$C_4$)-alkylaminocarbonyl, mono-($C_1$-$C_4$)-alkylaminocarbonyl, or
$R^1$ represents the group Z-L-,
wherein Z represents a 5- or 6-membered heteroaryl which is optionally substituted with one or two $C_1$-$C_3$-alkyl and
L represents —$CH_2$—NHCO
$R^{2a}$ represents hydrogen, halogen or $C_1$-$C_3$-haloalkyl,
$R^{2b}$ represents hydrogen or halogen,
$R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_8$-cycloalkyl-, $C_1$-$C_6$-alkyl-$C_3$-$C_8$-cycloalkyl, $C_1$-$C_6$-alkyl-phenyl, $C_1$-$C_6$-alkyl-heteroaryl wherein a cycloalkyl, phenyl or heteroaryl ring is optionally substituted with one or two $C_1$-$C_3$-alkyl,
$R^{4a}$, $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, or
$R^{3a}$ and $R^{3b}$ together represent a monocyclic 3 to 6-membered cycloalkyl or heterocycloalkyl, and their polymorphs, enantiomers, diastereomers, racemates, tautomers, solvates, physiologically acceptable salts and solvates of these salts.

Of selected interest are those compounds of formula (I),

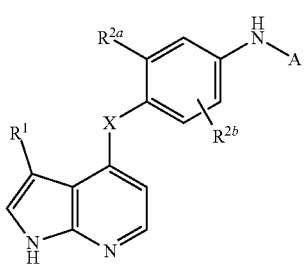 (I)

in which

A represents a monocyclic 5- or 6-membered ring selected from

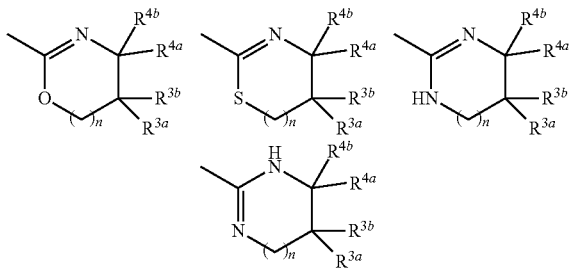

X represents a sulphur or an oxygen atom, n represents 0 or 1, $R^1$ represents a group selected from
hydrogen, halogen, cyano, $C_1$-$C_3$-haloalkyl,
a $C_1$-$C_6$-alkyl,
a phenyl,
a 5- or 6-membered heteroaryl,
a $C_3$-$C_6$-cycloalkyl-,
a monocyclic 4- to 6-membered heterocycloalkyl,
a bridged bicyclic 7- or 8-membered heterocycloalkyl
wherein said $C_1$-$C_6$-alkyl, phenyl, 5- or 6-membered heteroaryl, $C_3$-$C_6$-cycloalkyl-, monocyclic 4- to 6-membered heterocycloalkyl or bridged bicyclic 7- or 8-membered heterocycloalkyl is optionally substituted with one or two substituents, identically or differently, selected from the group consisting of halogen, hydroxy, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_3$-cyanoalkyl, $C_1$-$C_3$-cyanoalkoxy, $C_3$-$C_6$-cycloalkyl-, $C_1$-$C_3$-alkylcarbonyl, di-($C_1$-$C_4$)-alkylaminocarbonyl, mono-($C_1$-$C_4$)-alkylaminocarbonyl, or $R^1$ represents the group Z-L-,
wherein Z represents a 5-membered heteroaryl which is optionally substituted with one or two $C_1$-$C_3$-alkyl and
L represents —$CH_2$—NHCO $R^{2a}$ represents hydrogen, halogen or trifluoromethyl, $R^{2b}$ represents hydrogen or halogen, $R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_6$-cycloalkyl-, $C_1$-$C_3$-alkyl-$C_3$-$C_6$-cycloalkyl, $C_1$-$C_3$-alkylphenyl, $C_1$-$C_3$-alkyl-heteroaryl wherein a cycloalkyl, phenyl or heteroaryl ring is optionally substituted with one or two $C_1$-$C_3$-alkyl, $R^{4a}$, $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, or $R^{3a}$ and $R^{3b}$ together represent a monocyclic 3 to 6-membered cycloalkyl or heterocycloalkyl, and their polymorphs, enantiomers, diastereomers, racemates, tautomers, solvates, physiologically acceptable salts and solvates of these salts.

Compounds of most interest are those as follows:

(+/−)-{2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol (+/−)-{2-[(3,5-difluoro-4-{[3-(trifluoromethyl)-1H-pyrrolo[2,3-b]pyridin-4-yl]oxy}phenyl)amino]-5-methyl-5,6-dihydro-4H-1,3-oxazin-5-yl}methanol (+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazine-5-carbonitrile (+/−)-{5-(difluoromethyl)-2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol (+/−)-{2-[(3,5-difluoro-4-{[3-(trifluoromethyl)-1H-pyrrolo[2,3-b]pyridin-4-yl]oxy}phenyl)amino]-5-isopropyl-5,6-dihydro-4H-1,3-oxazin-5-yl}methanol (+/−)-2-{2-[(3,5-difluoro-4-{[3-(trifluoromethyl)-1H-pyrrolo[2,3-b]pyridin-4-yl]oxy}phenyl)amino]-4,5-dihydro-1,3-oxazol-5-yl}-2-methylpropan-1-ol (+/−)-{2-[(3,5-difluoro-4-{[3-(trifluoromethyl)-1H-pyrrolo[2,3-b]pyridin-4-yl]oxy}phenyl)amino]-4,5-dihydro-1,3-oxazol-4-yl}methanol (+/−)-{2-[(3,5-difluoro-4-{[3-(trifluoromethyl)-1H-pyrrolo[2,3-b]pyridin-4-yl]oxy}phenyl)amino]-5-fluoro-5,6-dihydro-4H-1,3-oxazin-5-yl}methanol (+/−)-2-[(3,5-difluoro-4-{[3-(trifluoromethyl)-1H-pyrrolo[2,3-b]pyridin-4-yl]oxy}phenyl)amino]-4-(hydroxymethyl)-4,5-dihydro-1,3-oxazole-4-carboxamide (+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazin-5-ol (+/−)-{2-[(3,5-difluoro-4-{[3-(trifluoromethyl)-1H-pyrrolo[2,3-b]pyridin-4-yl]oxy}phenyl)amino]-5-phenyl-5,6-dihydro-4H-1,3-oxazin-5-yl}methanol (+/−)-{2-[(3,5-difluoro-4-{[3-(trifluoromethyl)-1H-pyrrolo[2,3-b]pyridin-4-yl]oxy}phenyl)amino]-4-methyl-5,6-dihydro-4H-1,3-oxazin-5-yl}methanol (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile (+/−)-[2-({4-[(3-bromo-1H-pyrrolo[2,3-b]pyridin-4-yl)oxy]-3,5-difluorophenyl}amino)-5,6-dihydro-4H-1,3-oxazin-5-yl]methanol (+/−)-[2-({4-[(3-bromo-1H-pyrrolo[2,3-b]pyridin-4-yl)oxy]-3,5-difluorophenyl}amino)-5-methyl-5,6-dihydro-4H-1,3-oxazin-5-yl]methanol (+/−)-4-(2,6-difluoro-4-{[5-(hydroxymethyl)-4H-1,3-oxazin-2-yl]amino}phenoxy)-1H-pyrrolo[2,3-b]pyridine-3-carbonitrile (+/−)-4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridine-3-carbonitrile (+/−)-[2-({4-[(3-cyclopropyl-1H-pyrrolo[2,3-b]pyridin-4-yl)oxy]-3,5-difluorophenyl}amino)-5-methyl-5,6-dihydro-4H-1,3-oxazin-5-yl]methanol (+/−)-[2-({4-[(3-cyclopropyl-1H-pyrrolo[2,3-b]pyridin-4-yl)oxy]-3,5-difluorophenyl}amino)-5-fluoro-5,6-dihydro-4H-1,3-oxazin-5-yl]methanol (+/−)-{2-[(3,5-difluoro-4-{[3-(2-methyl-3-thienyl)-1H-pyrrolo[2,3-b]pyridin-4-yl]oxy}phenyl)amino]-5-methyl-5,6-dihydro-4H-1,3-oxazin-5-yl}methanol (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxynicotinonitrile (+/−)-{2-[(3,5-difluoro-4-{[3-(6-methoxypyridin-3-yl)-1H-pyrrolo[2,3-b]pyridin-4-yl]oxy}phenyl)amino]-5-methyl-5,6-dihydro-4H-1,3-oxazin-5-yl}methanol (+/−)-{2-[(3,5-difluoro-4-{[3-(1-methyl-1,2,3,6-tetrahydropyridin-4-yl)-1H-pyrrolo[2,3-b]pyridin-4-yl]oxy}phenyl)amino]-5-methyl-5,6-dihydro-4H-1,3-oxazin-5-yl}methanol (+/−)-1-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3,6-dihydropyridin-1(2H)-yl}propan-1-one (+/−)-{2-[(4-{[3-(8-azabicyclo[3.2.1]oct-2-en-3-yl)-1H-pyrrolo[2,3-b]pyridin-4-yl]oxy}-3,5-difluorophenyl)amino]-5-methyl-5,6-dihydro-4H-1,3-oxazin-5-yl}methanol (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carboxamide (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluorobenzonitrile (+/−)-[2-({4-[(3-chloro-1H-pyrrolo[2,3-b]pyridin-4-yl)oxy]-3,5-difluorophenyl}amino)-5-methyl-5,6-dihydro-4H-1,3-oxazin-5-yl]methanol (+/−)-[2-({4-[(3-chloro-1H-pyrrolo[2,3-b]pyridin-4-yl)oxy]-3,5-difluorophenyl}amino)-5,6-dihydro-4H-1,3-oxazin-5-yl]methanol (+/−)-[2-({4-[(3-chloro-1H-pyrrolo[2,3-b]pyridin-4-yl)oxy]-3,5-difluorophenyl}amino)-5-fluoro-5,6-dihydro-4H-1,3-oxazin-5-yl]methanol (+/−)-4-(2,6-difluoro-4-{[5-(hydroxymethyl)-5-methyl-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide (+/−)-4-(2,6-difluoro-4-{[5-(hydroxymethyl)-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide (+/−)-{2-[(4-{[3-(5-chloro-6-methoxypyridin-3-yl)-1H-pyrrolo[2,3-b]pyridin-4-yl]oxy}-3,5-difluorophenyl)amino]-5-methyl-5,6-dihydro-4H-1,3-oxazin-5-yl}methanol (+/−)-[2-{[3,5-difluoro-4-({3-[1-(propan-2-yl)-1H-pyrazol-3-yl]-1H-pyrrolo[2,3-b]pyridin-4-yl}oxy)phenyl]amino}-5-methyl-5,6-dihydro-4H-1,3-oxazin-5-yl]methanol (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(propan-2-yloxy)benzonitrile (+/−)-{2-[(3,5-difluoro-4-{[3-(2-fluoro-4-methoxyphenyl)-1H-pyrrolo[2,3-b]pyridin-4-yl]oxy}phenyl)amino]-5-methyl-5,6-dihydro-4H-1,3-oxazin-5-yl}methanol (+/−)-{2-[(3,5-difluoro-4-{[3-(1-methyl-1H-pyrazol-5-yl)-1H-pyrrolo[2,3-b]pyridin-4-yl]oxy}phenyl)amino]-5-methyl-5,6-dihydro-4H-1,3-oxazin-5-yl}methanol (+/−)-[2-{[3,5-difluoro-4-({3-[1-(propan-2-yl)-1H-pyrazol-5-yl]-1H-pyrrolo[2,3-b]pyridin-4-yl}oxy)phenyl]amino}-5-methyl-5,6-dihydro-4H-1,3-oxazin-5-yl]methanol (+/−)-{2-[(3,5-difluoro-4-{[3-(2-fluorophenyl)-1H-pyrrolo[2,3-b]pyridin-4-yl]oxy}phenyl)amino]-5-methyl-5,6-dihydro-4H-1,3-oxazin-5-yl}methanol (+/−)-{2-[(3,5-difluoro-4-{[3-(3-fluorophenyl)-1H-pyrrolo[2,3-b]pyridin-4-yl]oxy}phenyl)amino]-5-methyl-5,6-dihydro-4H-1,3-oxazin-5-yl}methanol (+/−)-{2-[(3,5-difluoro-4-{[3-(4-fluorophenyl)-1H-pyrrolo[2,3-b]pyridin-4-yl]oxy}phenyl)amino]-5-methyl-5,6-dihydro-4H-1,3-oxazin-5-yl}methanol (+/−)-2-{[4-({3-[3-cyano-4-(propan-2-yloxy)phenyl]-1H-pyrrolo[2,3-b]pyridin-4-yl}oxy)-3,5-difluorophenyl]amino}-5-(hydroxymethyl)-5,6-dihydro-4H-1,3-oxazine-5-carbonitrile (+/−)-5-[4-(4-{[5-(difluoromethyl)-5-(hydroxymethyl)-5,6-dihydro-4H-1,3-oxazin-2-yl]amino}-2,6-difluorophenoxy)-1H-pyrrolo[2,3-b]pyridin-3-yl]-2-(propan-2-yloxy)benzonitrile (+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(propan-2-yloxy)benzonitrile (+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-(propan-2-yloxy)benzonitrile (+/−)-{2-[(4-{[3-(1-ethyl-1H-pyrazol-5-yl)-1H-pyrrolo[2,3-b]pyridin-4-yl]oxy}-3,5-difluorophenyl)amino]-5-methyl-5,6-dihydro-4H-1,3-oxazin-5-yl}methanol (+/−)-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]phenoxy}acetonitrile (+/−)-{2-[(3,5-difluoro-4-{[3-(2-fluoro-3-methoxyphenyl)-1H-pyrrolo[2,3-b]pyridin-4-yl]oxy}phenyl)amino]-5-methyl-5,6-dihydro-4H-1,3-oxazin-5-yl}methanol (+/−)-[2-{[3,5-difluoro-4-({3-[2-fluoro-4-(propan-2-yloxy)phenyl]-1H-pyrrolo[2,3-b]pyridin-4-yl}oxy)phenyl]amino}-5-methyl-5,6-dihydro-4H-1,3-oxazin-5-yl]methanol

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol (+/−)-[2-{3,5-difluoro-4-[(1H-pyrrolo[2,3-b]pyridin-4-yl)oxy]anilino}-5-(propan-2-yl)-5,6-dihydro-4H-1,3-oxazin-5-yl]methanol (+/−)-[2-{3,5-difluoro-4-[(1H-pyrrolo[2,3-b]pyridin-4-yl)oxy]anilino}-5-methyl-5,6-dihydro-4H-1,3-oxazin-5-yl]methanol (+/−)-[2-{3,5-difluoro-4-[(1H-pyrrolo[2,3-b]pyridin-4-yl)oxy]anilino}-4-methyl-5,6-dihydro-4H-1,3-oxazin-5-yl]methanol (+/−)-[2-(3-fluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol (+/−)-[2-(2,5-difluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol (+/−)-[2-{4-[(3-bromo-1H-pyrrolo[2,3-b]pyridin-4-yl)sulfanyl]anilino}-5-methyl-5,6-dihydro-4H-1,3-oxazin-5-yl]methanol (+/−)-5-{4-[4-{[5-(hydroxymethyl)-5-phenyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile (+/−)-5-{4-[4-{[5-fluoro-5-(hydroxymethyl)-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile (+/−)-5-{4-[4-{5-(hydroxymethyl)-5-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile (+/−)-2-{4-[(3-{3-cyano-4-[(propan-2-yl)oxy]phenyl}-1H-pyrrolo[2,3-b]pyridin-4-yl)oxy]-3-(trifluoromethyl)anilino}-5-(hydroxymethyl)-5,6-dihydro-4H-1,3-oxazine-5-carbonitrile (+/−)-5-{4-[4-{[4-(hydroxymethyl)-4,5-dihydro-1,3-oxazol-2-yl]amino}-2-(trifluoromethyl)phenoxy]-1H-pyrrolo[2,3-b]pyridin-3-yl}-2-[(propan-2-yl)oxy]benzonitrile (+/−)-5-{4-[4-{[-5-(hydroxymethyl)-4-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile 5-(4-{4-[(5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile 5-(4-{4-[(5-oxa-7-azaspiro[2.5]oct-6-en-6-yl)amino]-2-(trifluoromethyl)phenoxy}-1H-pyrrolo[2,3-b]pyridin-3-yl)-2-[(propan-2-yl)oxy]benzonitrile 5-(4-{4-[(5,5-dimethyl-5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile (+/−)-5-[4-(2,6-difluoro-4-{[5-(1-hydroxy-2-methylpropan-2-yl)-4,5-dihydro-1,3-oxazol-2-yl]amino}phenoxy)-1H-pyrrolo[2,3-b]pyridin-3-yl]-2-[(propan-2-yl)oxy]benzonitrile (+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-5-[4-(2,6-difluoro-4-{[4-(hydroxymethyl)-4,5-dihydro-1,3-oxazol-2-yl]amino}phenoxy)-1H-pyrrolo[2,3-b]pyridin-3-yl]-2-[(propan-2-yl)oxy]benzonitrile (+/−)-5-[4-(2,6-difluoro-4-{[5-(hydroxymethyl)-5-phenyl-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-2-{4-[(3-{3-cyano-4-[(propan-2-yl)oxy]phenyl}-1H-pyrrolo[2,3-b]pyridin-4-yl)oxy]-3,5-difluoroanilino}-4-(hydroxymethyl)-4,5-dihydro-1,3-oxazole-4-carboxamide 5-(4-{4-[(5,5-diethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile 5-(4-{2,6-difluoro-4-[(4,4,5,5-tetramethyl-4,5-dihydro-1,3-oxazol-2-yl)amino]phenoxy}-1H-pyrrolo[2,3-b]pyridin-3-yl)-2-[(propan-2-yl)oxy]benzonitrile (+/−)-5-{4-[2,6-difluoro-4-({5-[(pyridin-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile (+/−)-5-[4-(4-{[(5-(cyclopropylmethyl)-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile (+/−)-5-[4-(4-{[5-cyclopropyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile (+/−)-5-[4-(4-{[5-benzyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile (+/−)-5-[4-(2,6-difluoro-4-{[5-(trifluoromethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-5-{4-[2,6-difluoro-4-({5-[(pyridin-3-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile (+/−)-5-{4-[2,6-difluoro-4-({5-[(1-methyl-1H-pyrazol-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethoxy)benzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methoxybenzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-methoxybenzonitrile (+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-fluorobenzonitrile (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2-methylpropoxy)benzonitrile (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2,2,2-trifluoroethoxy)benzonitrile (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile (+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-(propan-2-yl)benzonitrile (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methylbenzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methylbenzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethyl)benzonitrile (+/−)-{2-[3,5-difluoro-4-({3-[2-(propan-2-yl)phenyl]-1H-pyrrolo[2,3-b]pyridin-4-yl}oxy)anilino]-5-methyl-5,6-dihydro-4H-1,3-oxazin-5-yl}methanol (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-fluorobenzonitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile (+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-methoxybenzonitrile (+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(trifluoromethoxy)benzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-fluorobenzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-fluorobenzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methylbenzonitrile (+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]pyridine-2-carbonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methylbenzonitrile (+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-methoxybenzonitrile (+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-fluorobenzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methoxybenzonitrile (+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile (+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-3-[4-(2,6-difluoro-4-{[5-(hydroxymethyl)-5,6-dihydro-4H-1,3-oxazin-2-yl]amino}phenoxy)-1H-pyrrolo[2,3-b]pyridin-3-yl]benzonitrile (+/−)-[2-(3-fluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol (+/−)-[5-fluoro-2-(3-fluoro-4-{[3-(propan-2-yl)-1H-pyrrolo[2,3-b]pyridin-4-yl]oxy}anilino)-5,6-dihydro-4H-1,3-oxazin-5-yl]methanol (+/−)-[2-{3,5-difluoro-4-[(3-{2-fluoro-3-[(propan-2-yl)oxy]phenyl}-1H-pyrrolo[2,3-b]pyridin-4-yl)oxy]anilino}-5-methyl-5,6-dihydro-4H-1,3-oxazin-5-yl]methanol N-{4-[(3-chloro-1H-pyrrolo[2,3-b]pyridin-4-yl)oxy]-3,5-difluorophenyl}-5,6-dihydro-4H-1,3-oxazin-2-amine N-{4-[(3-chloro-1H-pyrrolo[2,3-b]pyridin-4-yl)oxy]-3,5-difluorophenyl}-4,5-dihydro-1,3-oxazol-2-amine N-{4-[(3-chloro-1H-pyrrolo[2,3-b]pyridin-4-yl)oxy]-3,5-difluorophenyl}-5,6-dihydro-4H-1,3-thiazin-2-amine N-{4-[(3-chloro-1H-pyrrolo[2,3-b]pyridin-4-yl)oxy]-3,5-difluorophenyl}-4,5-dihydro-1,3-thiazol-2-amine N-{4-[(3-chloro-1H-pyrrolo[2,3-b]pyridin-4-yl)oxy]-3,5-difluorophenyl}-5,5-dimethyl-5,6-dihydro-4H-1,3-oxazin-2-amine N-{4-[(3-chloro-1H-pyrrolo[2,3-b]pyridin-4-yl)oxy]-3,5-difluorophenyl}-5-oxa-7-azaspiro[2.5]oct-6-en-6-amine N-{4-[(3-chloro-1H-pyrrolo[2,3-b]pyridin-4-yl)oxy]-3,5-difluorophenyl}-6-oxa-8-azaspiro[3.5]non-7-en-7-amine (+/−)-[2-{4-[(3-chloro-1H-pyrrolo[2,3-b]pyridin-4-yl)oxy]-3,5-difluoroanilino}-4,5-dihydro-1,3-oxazol-5-yl]methanol (+/−)—N-{4-[(3-chloro-1H-pyrrolo[2,3-b]pyridin-4-yl)oxy]-3,5-difluorophenyl}-4-methyl-5,6-dihydro-4H-1,3-oxazin-2-amine N-{4-[(3-chloro-1H-pyrrolo[2,3-b]pyridin-4-yl)oxy]-3,5-difluorophenyl}-5,5-difluoro-5,6-dihydro-4H-1,3-oxazin-2-amine (+/−)-5-[4-(2,6-difluoro-4-{[5-hydroxy-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile (+/−)-[2-{4-[(3-chloro-1H-pyrrolo[2,3-b]pyridin-4-yl)oxy]-3,5-difluoroanilino}-5,6-dihydro-4H-1,3-oxazin-4-yl]methanol 5-[4-(2,6-difluoro-4-{[(5S)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile 5-[4-(2,6-difluoro-4-{[(5R)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile 5-(4-{4-[(5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile 5-(4-{2,6-difluoro-4-[(5-oxa-7-azaspiro[2.5]oct-6-en-6-yl)amino]phenoxy}-1H-pyrrolo[2,3-b]pyridin-3-yl)-2-[(propan-2-yl)oxy]benzonitrile 5-(4-{4-[(5,5-dimethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile 5-(4-{4-[(5,5-difluoro-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile N-[3,5-difluoro-4-({3-[1-(propan-2-yl)-1H-pyrazol-5-yl]-1H-pyrrolo[2,3-b]pyridin-4-yl}oxy)phenyl]-5,5-difluoro-5,6-dihydro-4H-1,3-oxazin-2-amine N-[3,5-difluoro-4-({3-[1-(propan-2-yl)-1H-pyrazol-5-yl]-1H-pyrrolo[2,3-b]pyridin-4-yl}oxy)phenyl]-5,5-dimethyl-5,6-dihydro-4H-1,3-oxazin-2-amine N-[3,5-difluoro-4-({3-[1-(propan-2-yl)-1H-pyrazol-5-yl]-1H-pyrrolo[2,3-b]pyridin-4-yl}oxy)phenyl]-5-oxa-7-azaspiro[2.5]oct-6-en-6-amine N-[3,5-difluoro-4-({3-[1-(propan-2-yl)-1H-pyrazol-5-yl]-1H-pyrrolo[2,3-b]pyridin-4-yl}oxy)phenyl]-5,6-dihydro-4H-1,3-oxazin-2-amine N-(3,5-difluoro-4-{[3-(trifluoromethyl)-1H-pyrrolo[2,3-b]pyridin-4-yl]oxy}phenyl)-5,6-dihydro-4H-1,3-oxazin-2-amine N-(3,5-difluoro-4-{[3-(trifluoromethyl)-1H-pyrrolo[2,3-b]pyridin-4-yl]oxy}phenyl)-5-oxa-7-azaspiro[2.5]oct-6-en-6-amine N-(3,5-difluoro-4-{[3-(trifluoromethyl)-1H-pyrrolo[2,3-b]pyridin-4-yl]oxy}phenyl)-5,5-dimethyl-5,6-dihydro-4H-1,3-oxazin-2-amine N-(3,5-difluoro-4-{[3-(trifluoromethyl)-1H-pyrrolo[2,3-b]pyridin-4-yl]oxy}phenyl)-5,5-difluoro-5,6-dihydro-4H-1,3-oxazin-2-amine N-(3,5-difluoro-4-{[3-(trifluoromethyl)-1H-pyrrolo[2,3-b]pyridin-4-yl]oxy}phenyl)-6-oxa-8-azaspiro[3.5]non-7-en-7-amine (+/−)-{2-[3,5-difluoro-4-({3-[2-(trifluoromethoxy)ethyl]-1H-pyrrolo[2,3-b]pyridin-4-yl}oxy)anilino]-5-fluoro-5,6-dihydro-4H-1,3-oxazin-5-yl}methanol N-{4-[(3-chloro-1H-pyrrolo[2,3-b]pyridin-4-yl)oxy]-3,5-difluorophenyl}-2,9-dioxa-4-azaspiro[5.5]undec-3-en-3-amine (+/−)—N-{4-[(3-chloro-1H-pyrrolo[2,3-b]pyridin-4-yl)oxy]-3,5-difluorophenyl}-5-methyl-5,6-dihydro-4H-1,3-oxazin-2-amine (+/−)—N-{4-[(3-chloro-1H-pyrrolo[2,3-b]pyridin-4-yl)oxy]-3,5-difluorophenyl}-4-(propan-2-yl)-5,6-dihydro-4H-1,3-oxazin-2-amine (+/−)-[2-(3,5-difluoro-4-{[3-(propan-2-yl)-1H-pyrrolo[2,3-b]pyridin-4-yl]oxy}anilino)-5-fluoro-5,6-dihydro-4H-1,3-oxazin-5-yl]methanol (+/−)-[2-(3,5-difluoro-4-{[3-(3,3,3-trifluoropropyl)-1H-pyrrolo[2,3-b]pyridin-4-yl]oxy}anilino)-5-fluoro-5,6-dihydro-4H-1,3-oxazin-5-yl]methanol (+/−)-[2-(3,5-difluoro-4-{[3-(tetrahydrofuran-3-yl)-1H-pyrrolo[2,3-b]pyridin-4-yl]oxy}anilino)-5-fluoro-5,6-dihydro-4H-1,3-oxazin-5-yl]methanol-mixture of isomers (+/−)-[2-{4-[(3-cyclobutyl-1H-pyrrolo[2,3-b]pyridin-4-yl)oxy]-3,5-difluoroanilino}-5-fluoro-5,6-dihydro-4H-1,3-oxazin-5-yl]methanol {2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol (mixture of stereoisomers)

{(5S)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5R)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5R)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5S)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol (+/−)-[2-(3,5-difluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol (+/−)-[2-(3,5-difluoro-4-{[3-(propan-2-yl)-1H-pyrrolo[2,3-b]pyridin-4-yl]oxy}anilino)-5-(propan-2-yl)-5,6-dihydro-4H-1,3-oxazin-5-yl]methanol N-(3,5-difluoro-4-{[3-(propan-2-yl)-1H-pyrrolo[2,3-b]pyridin-4-yl]oxy}phenyl)-5,5-dimethyl-5,6-dihydro-4H-1,3-oxazin-2-amine (+/−)—N-(3,5-difluoro-4-{[3-(propan-2-yl)-1H-pyrrolo[2,3-b]pyridin-4-yl]oxy}phenyl)-2,7-dioxa-9-azaspiro[4.5]dec-8-en-8-amine (+/−)—N-{4-[(3-chloro-1H-pyrrolo[2,3-b]pyridin-4-yl)oxy]-3,5-difluorophenyl}-4-methyl-5,6-dihydro-4H-1,3-thiazin-2-amine N-{4-[(3-chloro-1H-pyrrolo[2,3-b]pyridin-4-yl)oxy]-3,5-difluorophenyl}-5,5-dimethyl-5,6-dihydro-4H-1,3-thiazin-2-amine (+/−)-(2-{4-[(3-chloro-1H-pyrrolo[2,3-b]pyridin-4-yl)oxy]-3,5-difluoroanilino}-5,6-dihydro-4H-1,3-thiazin-5-yl)methanol (+/−)—N-{4-[(3-chloro-1H-pyrrolo[2,3-b]pyridin-4-yl)oxy]-3,5-difluorophenyl}-5-methyl-5,6-dihydro-4H-1,3-thiazin-2-amine N-{4-[(3-chloro-1H-pyrrolo[2,3-b]pyridin-4-yl)oxy]-3,5-difluorophenyl}-6-thia-8-azaspiro[3.5]non-7-en-7-amine (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]oxetan-3-ol (+/−)-[2-(3,5-difluoro-4-{[3-(3-methoxyoxetan-3-yl)-1H-pyrrolo[2,3-b]pyridin-4-yl]oxy}anilino)-5-methyl-5,6-dihydro-4H-1,3-oxazin-5-yl]methanol 3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]oxetan-3-ol (+/−)-[2-(3,5-difluoro-4-{[3-(3-methoxyoxetan-3-yl)-1H-pyrrolo[2,3-b]pyridin-4-yl]oxy}anilino)-5-fluoro-5,6-dihydro-4H-1,3-oxazin-5-yl]methanol (+/−)-[2-(4-{[3-(3-ethoxyoxetan-3-yl)-1H-pyrrolo[2,3-b]pyridin-4-yl]oxy}-3,5-difluoroanilino)-5-methyl-5,6-dihydro-4H-1,3-oxazin-5-yl]methanol (+/−)-{2-[3,5-difluoro-4-({3-[3-(2,2,2-trifluoroethoxy)oxetan-3-yl]-1H-pyrrolo[2,3-b]pyridin-4-yl}oxy)anilino]-5-methyl-5,6-dihydro-4H-1,3-oxazin-5-yl}methanol (+/−)-(2-{3,5-difluoro-4-[(3-{3-[(propan-2-yl)oxy]oxetan-3-yl}-1H-pyrrolo[2,3-b]pyridin-4-yl)oxy]anilino}-5-methyl-5,6-dihydro-4H-1,3-oxazin-5-yl)methanol (+/−)-4-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]butanenitrile (+/−)-4-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]butanenitrile (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]butanenitrile (+/−)-{(5S)-2-[3,5-difluoro-4-({3-(2-methyloxan-3-yl)-1H-pyrrolo[2,3-b]pyridin-4-yl}oxy)anilino]-5-fluoro-5,6-dihydro-4H-1,3-oxazin-5-yl}methanol-(mixture of isomers)

(+/−)-[2-{3,5-difluoro-4-[(1H-pyrrolo[2,3-b]pyridin-4-yl)oxy]anilino}-5-fluoro-5,6-dihydro-4H-1,3-oxazin-5-yl]methanol (+/−)-[(5R)-2-[3,5-difluoro-4-({3-(2-methyloxan-3-yl)-1H-pyrrolo[2,3-b]pyridin-4-yl}oxy)anilino]-5-(propan-2-yl)-5,6-dihydro-4H-1,3-oxazin-5-yl]methanol-(mixture of isomers)

(+/−)-[2-(3,5-difluoro-4-{[3-(2-methoxyphenyl)-1H-pyrrolo[2,3-b]pyridin-4-yl]oxy}anilino)-5-methyl-5,6-dihydro-4H-1,3-oxazin-5-yl]methanol (+/−)-[2-(3,5-difluoro-4-{[3-(3-methoxyphenyl)-1H-pyrrolo[2,3-b]pyridin-4-yl]oxy}anilino)-5-methyl-5,6-dihydro-4H-1,3-oxazin-5-yl]methanol (+/−)-[2-(3,5-difluoro-4-{[3-(4-methoxyphenyl)-1H-pyrrolo[2,3-b]pyridin-4-yl]oxy}anilino)-5-methyl-5,6-dihydro-4H-1,3-oxazin-5-yl]methanol (+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N,N-dimethylbenzamide (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N-methylbenzamide (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N,N-dimethylbenzamide (+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N,N-dimethylbenzamide (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-ethoxypyridine-3-carbonitrile (+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluorobenzamide (+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N-methylbenzamide (+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N,N-dimethylbenzamide (+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-ethoxypyridine-3-carboxamide N-{4-[(3-chloro-1H-pyrrolo[2,3-b]pyridin-4-yl)oxy]-3,5-difluorophenyl}-4,5-dihydro-1H-imidazol-2-amine (+/−)-[2-(4-{[3-(2,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol (+/−)-[2-(4-{[3-(3,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol (+/−)-[2-(4-{[3-(2,3-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol (+/−)-[2-(4-{[3-(2,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol (+/−)-{2-[4-({3-[4-(difluoromethyl)phenyl]-1H-pyrrolo[2,3-b]pyridin-4-yl}oxy)-3,5-difluoroanilino]-5-fluoro-5,6-dihydro-4H-1,3-oxazin-5-yl}methanol (+/−)-[2-(3,5-difluoro-4-{[3-(4-fluoro-3-methoxyphenyl)-1H-pyrrolo[2,3-b]pyridin-4-yl]oxy}anilino)-5-fluoro-5,6-dihydro-4H-1,3-oxazin-5-yl]methanol (+/−)-{2-[3,5-difluoro-4-({3-[3-methoxy-4-(trifluoromethyl)phenyl]-1H-pyrrolo[2,3-b]pyridin-4-yl}oxy)anilino]-5-fluoro-5,6-dihydro-4H-1,3-oxazin-5-yl}methanol N-{4-[(3-chloro-1H-pyrrolo[2,3-b]pyridin-4-yl)oxy]-3,5-difluorophenyl}-1,4,5,6-tetrahydropyrimidin-2-amine (+/−)-{2-[3,5-difluoro-4-({3-[4-(trifluoromethyl)phenyl]-1H-pyrrolo[2,3-b]pyridin-4-yl}oxy)anilino]-5-fluoro-5,6-dihydro-4H-1,3-oxazin-5-yl}methanol (+/−)-[2-(3,5-difluoro-4-{[3-(6-methylpyridazin-4-yl)-1H-pyrrolo[2,3-b]pyridin-4-yl]oxy}anilino)-5-fluoro-5,6-dihydro-4H-1,3-oxazin-5-yl]methanol (+/−)-[2-(4-{[3-(1-cyclopropyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol (+/−)-{2-[3,5-difluoro-4-({3-[1-(propan-2-yl)-3-(trifluoromethyl)-1H-pyrazol-5-yl]-1H-pyrrolo[2,3-b]pyridin-4-yl}oxy)anilino]-5-fluoro-5,6-dihydro-4H-1,3-oxazin-5-yl}methanol (+/−)-[2-(4-{[3-(1-ethyl-3-methyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol N-{4-[(3-chloro-1H-pyrrolo[2,3-b]pyridin-4-yl)oxy]-3,5-difluorophenyl}-5-methyl-1,4,5,6-tetrahydropyrimidin-2-amine N-{4-[(3-chloro-1H-pyrrolo[2,3-b]pyridin-4-yl)oxy]-3,5-difluorophenyl}-5,5-dimethyl-1,4,5,6-tetrahydropyrimidin-2-amine N-{4-[(3-chloro-1H-pyrrolo[2,3-b]pyridin-4-yl)oxy]-3,5-difluorophenyl}-6,6-dimethyl-1,4,5,6-tetrahydropyrimidin-2-amine (+/−)-[2-(4-{[3-(1,3-dimethyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol (+/−)-{2-[4-({3-[1-ethyl-3-(trifluoromethyl)-1H-pyrazol-5-yl]-1H-pyrrolo[2,3-b]pyridin-4-yl}oxy)-3,5-difluoroanilino]-5-fluoro-5,6-dihydro-4H-1,3-oxazin-5-yl}methanol (+/−)-[2-{3,5-difluoro-4-[(3-{2-fluoro-6-[(propan-2-yl)oxy]phenyl}-1H-pyrrolo[2,3-b]pyridin-4-yl)oxy]anilino}-5-fluoro-5,6-dihydro-4H-1,3-oxazin-5-yl]methanol (+/−)-[2-(3,5-difluoro-4-{[3-(2-fluoro-3-methoxyphenyl)-1H-pyrrolo[2,3-b]pyridin-4-yl]oxy}anilino)-5-fluoro-5,6-dihydro-4H-1,3-oxazin-5-yl]methanol N-{4-[(3-chloro-1H-pyrrolo[2,3-b]pyridin-4-yl)oxy]-3,5-difluorophenyl}-5,5-difluoro-1,4,5,6-tetrahydropyrimidin-2-amine (+/−)-[2-(4-{[3-(2-chloro-1-methyl-1H-imidazol-5-yl)-1H-pyrrolo[2,3-b]pyridin-4-yl]oxy}-3,5-difluoroanilino)-5-fluoro-5,6-dihydro-4H-1,3-oxazin-5-yl]methanol (+/−)-[2-(3,5-difluoro-4-{[3-(5-methyl-1,3,4-oxadiazol-2-yl)-1H-pyrrolo[2,3-b]pyridin-4-yl]oxy}anilino)-5-methyl-5,6-dihydro-4H-1,3-oxazin-5-yl]methanol N-{4-[(3-chloro-1H-pyrrolo[2,3-b]pyridin-4-yl)oxy]-3,5-difluorophenyl}-5,7-diazaspiro[2.5]oct-5-en-6-amine N-(3,5-difluoro-4-{[3-(trifluoromethyl)-1H-pyrrolo[2,3-b]pyridin-4-yl]oxy}phenyl)-5,5-dimethyl-1,4,5,6-tetrahydropyrimidin-2-amine N-(3,5-difluoro-4-{[3-(trifluoromethyl)-1H-pyrrolo[2,3-b]pyridin-4-yl]oxy}phenyl)-6,6-dimethyl-1,4,5,6-tetrahydropyrimidin-2-amine N-(3,5-difluoro-4-{[3-(trifluoromethyl)-1H-pyrrolo[2,3-b]pyridin-4-yl]oxy}phenyl)-5,7-diazaspiro[2.5]oct-5-en-6-amine N-{4-[(3-bromo-1H-pyrrolo[2,3-b]pyridin-4-yl)oxy]-3,5-difluorophenyl}-1,4,5,6-tetrahydropyrimidin-2-amine (+/−)-[2-(4-{[3-(5-cyclopropyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol (+/−)-[2-(4-{[3-(5-cyclobutyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol (+/−)-{2-[3,5-difluoro-4-({3-[5-(propan-2-yl)-1,3,4-oxadiazol-2-yl]-1H-pyrrolo[2,3-b]pyridin-4-yl}oxy)anilino]-5-methyl-5,6-dihydro-4H-1,3-oxazin-5-yl}methanol (+/−)-[2-(4-{[3-(3,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol (+/−)-[2-(4-{[3-(3,4-difluorophenyl)-1H-pyrrolo[2,3-b]pyridin-4-yl]oxy}-3,5-difluoroanilino)-5-methyl-5,6-dihydro-4H-1,3-oxazin-5-yl]methanol (+/−)-3-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]propanenitrile N-{4-[(3-chloro-1H-pyrrolo[2,3-b]pyridin-4-yl)oxy]-3,5-difluorophenyl}-7-oxa-9-azaspiro[4.5]dec-8-en-8-amine (+/−)—N-{4-[(3-chloro-1H-pyrrolo[2,3-b]pyridin-4-yl)oxy]-3,5-difluorophenyl}-5-(methoxymethyl)-5-methyl-5,6-dihydro-4H-1,3-oxazin-2-amine (+/−)—N-{4-[(3-chloro-1H-pyrrolo[2,3-b]pyridin-4-yl)oxy]-3,5-difluorophenyl}-5-methyl-5-{[(propan-2-yl)oxy]methyl}-5,6-dihydro-4H-1,3-oxazin-2-amine N-(3,5-difluoro-4-{[3-(propan-2-yl)-1H-pyrrolo[2,3-b]pyridin-4-yl]oxy}phenyl)-5-methyl-5-{[(propan-2-yl)oxy]methyl}-5,6-dihydro-4H-1,3-oxazin-2-amine (+/−)-{2-[3,5-difluoro-4-({3-[1-(trifluoromethyl)cyclopropyl]-1H-pyrrolo[2,3-b]pyridin-4-yl}oxy)anilino]-5-methyl-5,6-dihydro-4H-1,3-oxazin-5-yl}methanol and their polymorphs, enantiomers, diastereomers, racemates, tautomers, solvates, physiologically acceptable salts and solvates of these salts.

In accordance with a further embodiment, the present invention covers compounds of general formula (I) and general formula (Ia), in which X represents a sulphur or an oxygen atom.

In accordance with a further embodiment, the present invention covers compounds of general formula (I) and general formula (Ia), in which X represents an oxygen atom.

In accordance with a further embodiment, the present invention covers compounds of general formula (Ia), in which Y represents a sulphur or an oxygen atom.

In accordance with a further embodiment, the present invention covers compounds of general formula (Ia), in which Y represents an oxygen atom.

In accordance with a further embodiment, the present invention covers compounds of general formula (Ia), in which X and Y represent an oxygen atom.

In accordance with a further embodiment, the present invention covers compounds of general formula (I) and general formula (Ia), in which n represents 0 or 1.

In accordance with a further embodiment, the present invention covers compounds of general formula (I) or general formula (Ia), in which $R^1$ represents a group selected from hydrogen, halogen, cyano, $C_1$-$C_6$-haloalkyl, a $C_1$-$C_6$-alkyl,
a phenyl,
a 5- or 6-membered heteroaryl,
a $C_3$-$C_8$-cycloalkyl-,
a monocyclic 4- to 7-membered heterocycloalkyl,
a bridged bicyclic 7- to 10-membered heterocycloalkyl
  wherein said $C_1$-$C_6$-alkyl, phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_1$-$C_3$-alkylcarbonyl, di-($C_1$-$C_4$)-alkylaminocarbonyl, mono-($C_1$-$C_4$)-alkylaminocarbonyl, or $R^1$ represents the group Z-L-,
  wherein Z represents a 5- or 6-membered heteroaryl
  which is optionally substituted with one or two $C_1$-$C_3$-alkyl and
  L represents —$CH_2$—NHCO In accordance with a further embodiment, the present invention covers compounds of general formula (I) or general formula (Ia), in which $R^1$ represents a group selected from hydrogen, halogen, cyano, $C_1$-$C_3$-haloalkyl,
a $C_1$-$C_6$-alkyl,
a phenyl,
a 5- or 6-membered heteroaryl,
a $C_3$-$C_6$-cycloalkyl-,
a monocyclic 4- to 6-membered heterocycloalkyl,
a bridged bicyclic 7- or 8-membered heterocycloalkyl
  wherein said $C_1$-$C_6$-alkyl, phenyl, 5- or 6-membered heteroaryl,
  $C_3$-$C_6$-cycloalkyl-, monocyclic 4- to 6-membered heterocycloalkyl or bridged bicyclic 7- or 8-membered heterocycloalkyl is optionally substituted with one or two substituents, identically or differently, selected from the group consisting of halogen, hydroxy, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_3$-cyanoalkyl, $C_1$-$C_3$-cyanoalkoxy, $C_3$-$C_6$-cycloalkyl-, $C_1$-$C_3$-alkylcarbonyl, di-($C_1$-$C_4$)-alkylaminocarbonyl, mono-($C_1$-$C_4$)-alkylaminocarbonyl, or $R^1$ represents the group Z-L-,
  wherein Z represents a 5-membered heteroaryl
  which is optionally substituted with one or two $C_1$-$C_3$-alkyl and
  L represents —$CH_2$—NHCO.

In accordance with a further embodiment, the present invention covers compounds of general formula (I) or general formula (Ia), in which $R^1$ represents a group selected from halogen, cyano, $C_1$-$C_6$-haloalkyl,
a phenyl,
a 5- or 6-membered heteroaryl,
a $C_3$-$C_7$-cycloalkyl-,
a monocyclic 4- to 7-membered heterocycloalkyl,
a bridged bicyclic 7- to 10-membered heterocycloalkyl
  wherein said phenyl, 5- or 6-membered heteroaryl, $C_3$-$C_7$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, aminosulfonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_7$-cycloalkyl-, $C_3$-$C_7$-cycloalkoxy, $C_3$-$C_7$-cycloalkyl-$C_1$-$C_6$-alkoxy, $C_1$-$C_6$-alkylcarbonlyoxy, di-($C_1$-$C_4$)-alkylaminocarbonyl, mono-($C_1$-$C_4$)-alkylaminocarbonyl, di-($C_1$-$C_4$)-alkylaminosulfonyl, mono-($C_1$-$C_4$)-alkylaminosulfonyl, or $R^1$ represents the group Z-L-,
  wherein Z represents a 5- or 6-membered heteroaryl
  which is optionally substituted with one or two substituents, identically or differently, selected from the group consisting of halogen, cyano, aminocarbonyl, $C_1$-$C_3$-alkyl, $C_1$-$C_3$-alkoxy, di-($C_1$-$C_4$)-alkylaminocarbonyl, mono-($C_1$-$C_4$)-alkylaminocarbonyl, and L represents —$CH_2$—NHCO—, —$CH_2$—CONH—, $CH_2$—NHSO_2$—, —$CH_2$—$SO_2$NH—
  and the $CH_2$-group of L can be bond to any atom of Z except to an oxygen or sulphur heteroatom, if present.

In accordance with a further embodiment, the present invention covers compounds of general formula (I) or general formula (Ia), in which $R^1$ represents a group selected from
halogen, cyano, $C_1$-$C_6$-haloalkyl,
a phenyl,
a 5- or 6-membered heteroaryl,
a $C_3$-$C_7$-cycloalkyl-,
a monocyclic 4- to 7-membered heterocycloalkyl,
a bridged bicyclic 7- to 10-membered heterocycloalkyl
  wherein said phenyl, 5- or 6-membered heteroaryl, $C_3$-$C_7$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_6$-alkylcarbonlyoxy, di-($C_1$-$C_4$)-alkylaminocarbonyl, mono-($C_1$-$C_4$)-alkylaminocarbonyl, or $R^1$ represents the group Z-L-,
wherein Z represents a 5- or 6-membered heteroaryl
which is optionally substituted with one or two substituents, identically or differently, selected from the group consisting of halogen, cyano, aminocarbonyl, $C_1$-$C_3$-alkyl, $C_1$-$C_3$-alkoxy, di-($C_1$-$C_4$)-alkylaminocarbonyl, mono-($C_1$-$C_4$)-alkylaminocarbonyl, and L represents —$CH_2$—NHCO—, —$CH_2$—CONH—, $CH_2$—$NHSO_2$—, —$CH_2$—$SO_2$NH—
and the $CH_2$-group of L can be bond to any atom of Z except to an oxygen or sulphur heteroatom, if present.

In accordance with a further embodiment, the present invention covers compounds of general formula (I) or general formula (Ia), in which $R^1$ represents the group Z-L-,
wherein Z represents a 5- or 6-membered heteroaryl
which is optionally substituted with one or two substituents, identically or differently, selected from the group consisting of halogen, $C_1$-$C_3$-alkyl, $C_1$-$C_3$-alkoxy, cyano, aminocarbonyl, di-($C_1$-$C_4$)-alkylaminocarbonyl, mono-($C_1$-$C_4$)-alkylaminocarbonyl, and
L represents —$CH_2$—NHCO—,
and the $CH_2$-group of L can be bond to any atom of Z except to an oxygen or sulphur heteroatom, if present.

In accordance with a further embodiment, the present invention covers compounds of general formula (I) or general formula (Ia), in which $R^1$ represents a group selected from
halogen, cyano, $C_1$-$C_3$-perfluoroalkyl,
a phenyl,
a 5- or 6-membered heteroaryl,
a $C_3$-$C_8$-cycloalkyl-,
a monocyclic 5 or 6-membered heterocycloalkyl,
a bridged bicyclic 8-membered heterocycloalkyl
wherein said phenyl, 5- or 6-membered heteroaryl, $C_3$-$C_5$-cycloalkyl-, monocyclic 5 or 6-membered heterocycloalkyl, bridged bicyclic 8-membered heterocycloalkyl is optionally substituted with one or two substituents, identically or differently, selected from the group consisting of halogen, cyano, aminocarbonyl, $C_1$-$C_3$-alkyl, $C_1$-$C_3$-haloalkyl, $C_1$-$C_3$-haloalkoxy, $C_1$-$C_3$-alkoxy, or
$R^1$ represents the group Z-L-,
wherein Z represents a 5-membered heteroaryl
which is optionally substituted with one or two $C_1$-$C_3$-alkyl and
L represents —$CH_2$—NHCO—,
and the $CH_2$-group of L can be bond to any atom of Z except to an oxygen or sulphur heteroatom, if present.

In accordance with a further embodiment, the present invention covers compounds of general formula (I) or general formula (Ia), in which $R^1$ represents a group selected from bromine, chlorine, cyano, trifluoromethyl,
a cyclopropyl,
a phenyl,
a pyridinyl, a thienyl, a pyrazolyl,
wherein said cyclopropyl-, phenyl, pyridinyl, thienyl or pyrazolyl is optionally substituted with one or two substituents, identically or differently, selected from the group consisting of fluoro, chloro, methyl, ethyl, isopropyl, methoxy, isopropoxy, cyano, propanoyl, aminocarbonyl, cyanomethoxy, or $R^1$ represents a group selected from

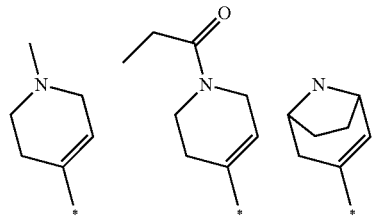

where "*" denotes the point of attachment to the remainder of the molecule,
or
$R^1$ represents

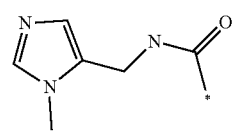 [SMILES: *C(=O)NCc1cncn1C]

where "*" denotes the point of attachment to the remainder of the molecule,

In accordance with a further embodiment, the present invention covers compounds of general formula (I) or general formula (Ia), in which $R^1$ represents the group Z-L-,
wherein Z represents a 5- or 6-membered heteroaryl
which is optionally substituted with one or two substituents, identically or differently, selected from the group consisting of halogen, $C_1$-$C_3$-alkyl,
$C_1$-$C_3$-alkoxy, cyano, aminocarbonyl, di-($C_1$-$C_4$)-alkylaminocarbonyl,
mono-($C_1$-$C_4$)-alkylaminocarbonyl, and
L represents —$CH_2$—NHCO—,
and the $CH_2$-group of L can be bond to any atom of Z except to an oxygen or sulphur heteroatom, if present.

In accordance with a further embodiment, the present invention covers compounds of general formula (I), in which $R^{2a}$ represents hydrogen, halogen, $C_1$-$C_3$-alkyl, $C_1$-$C_3$-alkoxy, $C_1$-$C_3$-haloalkyl- or $C_1$-$C_3$-haloalkoxy-.

In accordance with a further embodiment, the present invention covers compounds of general formula (I), in which $R^{2b}$ represents hydrogen, halogen, cyano, methyl, methoxy, trifluoromethyl or trifluoromethoxy.

In accordance with a further embodiment, the present invention covers compounds of general formula (I), in which $R^{2a}$ represents halogen.

In accordance with a further embodiment, the present invention covers compounds of general formula (I), in which $R^{2a}$ represents fluorine.

In accordance with a further embodiment, the present invention covers compounds of general formula (I), in which $R^{2b}$ represents halogen.

In accordance with a further embodiment, the present invention covers compounds of general formula (I), in which $R^{2b}$ represents fluorine.

In accordance with a further embodiment, the present invention covers compounds of general formula (I) or general formula (Ia), in which $R^{2a}$ represents hydrogen, halogen or $C_1$-$C_3$-haloalkyl, and $R^{2b}$ represents hydrogen or halogen.

In accordance with a further embodiment, the present invention covers compounds of general formula (I) or general formula (Ia), in which $R^{2a}$ represents hydrogen, halogen or trifluoromethyl, and $R^{2b}$ represents hydrogen or halogen.

In accordance with a further embodiment, the present invention covers compounds of general formula (Ia), in which $R^{2a}$ represents hydrogen, halogen, $C_1$-$C_3$-alkyl, $C_1$-$C_3$-alkoxy, $C_1$-$C_3$-haloalkyl- or $C_1$-$C_3$-haloalkoxy-.

In accordance with a further embodiment, the present invention covers compounds of general formula (Ia), in which $R^{2b}$ represents hydrogen, halogen, cyano, methyl, methoxy, trifluoromethyl or trifluoromethoxy.

In accordance with a further embodiment, the present invention covers compounds of general formula (Ia), in which $R^{2a}$ represents halogen.

In accordance with a further embodiment, the present invention covers compounds of general formula (Ia), in which $R^{2a}$ represents fluorine.

In accordance with a further embodiment, the present invention covers compounds of general formula (Ia), in which $R^{2b}$ represents halogen.

In accordance with a further embodiment, the present invention covers compounds of general formula (Ia), in which $R^{2b}$ represents fluorine.

In accordance with a further embodiment, the present invention covers compounds of general formula (I), in which $R^{3a}$ and $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, phenyl.

In accordance with a further embodiment, the present invention covers compounds of general formula (I), in which $R^{3a}$ and $R^{3b}$ represent independently from each other hydrogen or a substituent, identically or differently, selected from the group consisting of halogen, hydroxy, cyano, $C_1$-$C_3$-alkyl, $C_1$-$C_3$-haloalkyl, $C_1$-$C_6$-hydroxyalkyl-, phenyl.

In accordance with a further embodiment, the present invention covers compounds of general formula (I), in which $R^{3a}$ and $R^{3b}$ represent independently from each other hydrogen or a substituent, identically or differently, selected from the group consisting of fluoro, hydroxy, cyano, methyl, isopropyl, difluoromethyl, hydroxymethyl-, 2-hydroxy-1,1-dimethylethyl, phenyl.

In accordance with a further embodiment, the present invention covers compounds of general formula (I) or general formula (Ia), in which $R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_8$-cycloalkyl-, $C_1$-$C_6$-alkyl-$C_3$-$C_8$-cycloalkyl, $C_1$-$C_6$-alkyl-phenyl, $C_1$-$C_6$-alkyl-heteroaryl wherein a cycloalkyl, phenyl or heteroaryl ring is optionally substituted with one or two $C_1$-$C_3$-alkyl, or $R^{3a}$ and $R^{3b}$ together represent a monocyclic 3 to 6-membered cycloalkyl or heterocycloalkyl.

In accordance with a further embodiment, the present invention covers compounds of general formula (I) or general formula (Ia), in which $R^{3a}$, $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_6$-cycloalkyl-, $C_1$-$C_3$-alkyl-$C_3$-$C_6$-cycloalkyl, $C_1$-$C_3$-alkyl-phenyl, $C_1$-$C_3$-alkyl-heteroaryl wherein a cycloalkyl, phenyl or heteroaryl ring is optionally substituted with one or two $C_1$-$C_3$-alkyl, or $R^{3a}$ and $R^{3b}$ together represent a monocyclic 3 to 6-membered cycloalkyl or heterocycloalkyl, In accordance with a further embodiment, the present invention covers compounds of general formula (I), in which $R^{4a}$ and $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl.

In accordance with a further embodiment, the present invention covers compounds of general formula (I), in which $R^{4a}$ and $R^{4b}$ represent independently from each other hydrogen or a substituent, identically or differently, selected from the group consisting of methyl, aminocarbonyl, hydroxymethyl-.

In accordance with a further embodiment, the present invention covers compounds of general formula (I), in which $R^{3a}$ and $R^{3b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano.

In accordance with a further embodiment, the present invention covers compounds of general formula (I) or general formula (Ia), in which $R^{4a}$, $R^{4b}$ represent independently from each other represent independently from each other hydrogen or a substituent, identically or differently, selected from the group consisting of aminocarbonyl, $C_1$-$C_3$-alkyl, $C_1$-$C_3$-hydroxyalkyl-.

In accordance with a further embodiment, the present invention covers compounds of general formula (Ia), in which $R^{3a}$ and $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, phenyl.

In accordance with a further embodiment, the present invention covers compounds of general formula (Ia), in which $R^{3a}$ and $R^{3b}$ represent independently from each other hydrogen or a substituent, identically or differently, selected from the group consisting of halogen, hydroxy, cyano, $C_1$-$C_3$-alkyl, $C_1$-$C_3$-haloalkyl, $C_1$-$C_6$-hydroxyalkyl-, phenyl.

In accordance with a further embodiment, the present invention covers compounds of general formula (Ia), in which $R^{3a}$ and $R^{3b}$ represent independently from each other hydrogen or a substituent, identically or differently, selected from the group consisting of fluoro, hydroxy, cyano, methyl, isopropyl, difluoromethyl, hydroxymethyl-, 2-hydroxy-1,1-dimethyl-ethyl, phenyl.

In accordance with a further embodiment, the present invention covers compounds of general formula (Ia), in which $R^{4a}$ and $R^{4b}$ represent independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl.

In accordance with a further embodiment, the present invention covers compounds of general formula (Ia), in which $R^{4a}$ and $R^{4b}$ represent independently from each other hydrogen or a substituent, identically or differently, selected from the group consisting of methyl, aminocarbonyl, hydroxymethyl-.

In accordance with a further embodiment, the present invention covers compounds of general formula (Ia), in which $R^{3a}$ and $R^{3b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano.

In accordance with a further embodiment, the present invention covers compounds of general formula (Ia), in which $R^{4a}$ and $R^{4b}$ together represent a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, cyano.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit MAP4K1 and it is possible therefore that said compounds be used for the treatment or prophylaxis of diseases, preferably cancer or conditions with dysregulated immune responses or other disorders associated with aberrant MAP4K1 signaling, in humans and animals.

Disorders and conditions particularly suitable for treatment with an MAP4K1 inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers.

Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms' tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma. The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone, 2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with: $^{131}$I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, 1-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane ($^{123}$I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium ($^{153}$Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium ($^{99m}$Tc) nofetumomab merpentan, $^{99m}$Tc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors, e.g. aPD-1/-L1 axis antagonists. PD-1, along with its ligands PD-L1 and PD-L2, function as negative regulators of T cell activation. MAP4K1 suppresses immune cell function. PD-L1 is overexpressed in many cancers and overexpression of PD-1 often occurs concomitantly in tumor infiltrating T cells. Thus results in attenuation of T cell activation and evasion of immune surveillance, which contributes to impaired antitumor immune responses. (Keir M E et al. (2008) Annu. Rev. Immunol. 26:677).

In addition, the inventive compounds can also be used as a therapeutic in a variety of other disorders wherein MAP4K1 is involved such as, cardiovascular and lung diseases. Accordingly, the compounds according to the invention are suitable for the treatment and/or prophylaxis in particular of cardiovascular, inflammatory and fibrotic disorders and of renal disorders, in particular of acute and chronic renal insufficiency, and also of acute and chronic renal failure.

Accordingly, the compounds according to the invention can be used in medicaments for the treatment and/or prophylaxis of cardiovascular, inflammatory and fibrotic disorders, renal disorders, in particular of acute and chronic renal insufficiency, and also of acute and chronic renal failure.

For the purpose of the present invention the term renal insufficiency comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoid-nephrosis); membranous glomerulonephritis; focal segmental glomerulosclerosis (FSGS); membrane-proliferative glomerulonephritis; crescentic glomerulonephritis; mesangioproliferative glomerulonephritis (IgA nephritis, Berger's disease); post-infectious glomerulonephritis; secondary glomerulonephritides: diabetes mellitus, lupus erythematosus, amyloidosis, Goodpasture syndrome, Wegener granulomatosis, Henoch-Schönlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or aquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis. The present invention also comprises the use of the compounds according to the invention for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

The present invention also comprises the use of the compounds according to the invention for the treatment and/or prevention of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

The compounds according to the invention are further suitable for the treatment and/or prevention of polycystic kidney disease (PCKD) and of the syndrome of inappropriate ADH secretion (SIADH).

Furthermore, the compounds according to the invention are also suitable for the treatment and/or prophylaxis of metabolic syndrome, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In addition, the compounds according to the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In addition, the compounds according to the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds according to the invention can also be used for treatment and/or prophylaxis of autoimmune diseases.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are also suitable for controlling postoperative scarring, for example as a result of glaucoma operations.

The compounds according to the invention can also be used cosmetically for ageing and keratinized skin.

Moreover, the compounds according to the invention are suitable for treatment and/or prophylaxis of hepatitis, neoplasms, osteoporosis, glaucoma and gastroparesis.

The present invention further provides the use of the compounds according to the invention for treatment and/or prophylaxis of disorders, especially the disorders mentioned above.

The present invention further provides the use of the compounds according to the invention for the treatment and/or prophylaxis of chronic renal disorders, acute and chronic renal insufficiency, diabetic, inflammatory or hypertensive nephropaties, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention further provides a method for treatment and/or prophylaxis of disorders, in particular the disorders mentioned above, using an effective amount of at least one of the compounds according to the invention.

The present invention further provides a method for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

In another embodiment, the inventive compounds can also be used to treat or to prevent uterine fibroids (uterine leiomyoma or uterine myoma) in women.

Uterine fibroids are benign tumors of the myometrium, the smooth muscle layer of the uterus. Uterine fibroids grow slowly during a women's life, and their growth is dependent on the female sexual hormones estradiol and progesterone [Kawaguchi K et al. Immunohistochemical analysis of oestrogen receptors, progesterone receptors and Ki-67 in leiomyoma and myometrium during the menstrual cycle and pregnancy Virchows Arch A Pathol Anat Histopathol. 1991; 419(4):309-15.], therefore the highest prevalence of uterine fibroids with approx. 70% and >80% in white and afro-american women, respectively, is found from 35 years of age onwards to menopause, when they shrink due to reduced hormone levels [Baird D D et al. High cumulative incidence of uterine leiomyoma in black and white women: Ultrasound evidence Am J Obstet Gynecol. 2003 January; 188(1):100-7.]. Approx 30% and 45% of white and afro-american women, respectively, do show clinically relevant symptoms due to their fibroids, which are heavy menstrual bleeding and pain, which is related to the menstrual cycle [David M et al. Myoma-associated pain frequency and intensity: a retrospective evaluation of 1548 myoma patients. Eur J Obstet Gynecol Reprod Biol. 2016 April; 199:137-40]. Heavy menstrual bleeding in this respect is defined by a blood loss of more than 80 mL in a menstrual bleeding period [Fraser I S et al. The FIGO Recommendations on Terminologies and Definitions for Normal and Abnormal Uterine Bleeding, Semin Reprod Med 2011; 29(5): 383-390]. Submucosal position of the uterine fibroids, e.g. those located directly below the endometrium, seems to have an even more severe effect on uterine bleeding, which may result in anemia in affected women [Yang J H et al. Impact of submucous myoma on the severity of anemia. Fertil Steril. 2011 April; 95(5):1769-72]. Furthermore, uterine fibroids, due to their symptoms, do severely affect the quality of life of affected women [Downes E et al. The burden of uterine fibroids in five European countries. Eur J Obstet Gynecol Reprod Biol. 2010 September; 152(1):96-102].

Compounds of the present invention can be utilized to inhibit, block, reduce or decrease MAP4K1 activation by exogenous and/or endogenous ligands for the reduction of tumour growth and the modulation of dysregulated immune responses e.g. to block immunosuppression and increase immune cell activation and infiltration in the context of cancer and cancer immunotherapy; This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating a variety of other disorders wherein MAP4K1 is involved such as, but not limited to, disorders with dysregulated immune responses, inflammation, vaccination for infection & cancer, viral infections, obesity and diet-induced obesity, adiposity, metabolic disorders, hepatic steatosis and uterine fibroids. These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as liquid and solid tumours.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant MAP4K1 signaling.

The pharmaceutical activity of the compounds according to the invention can be explained by their activity as MAP4K1 inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant MAP4K1 signaling, particularly liquid and solid tumours.

In accordance with a further aspect, the present invention covers the compounds of general formula (I), as described supra, or stereoisomers, tautomers, N-oxides, hydrates, solvates, and salts thereof, particularly pharmaceutically acceptable salts thereof, or mixtures of same, for the use of treatment or prophylaxis of diseases, in particular cancer or conditions with dysregulated immune responses or other disorders associated with aberrant MAP4K1 signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant MAP4K1 signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant MAP4K1 signaling, particularly liquid and solid tumours.

In accordance with a further aspect, the present invention covers a method of treatment or prophylaxis of diseases, in particular cancer or conditions with dysregulated immune responses or other disorders associated with aberrant MAP4K1 signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention. In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant MAP4K1 signalinggeneric name disorders, particularly liquid and solid tumours.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant MAP4K1 signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, quin=quintet, br=broad signal, m=multiplet. NMR signals: shift in [ppm]. Combinations of multiplicity could be e.g. dd=doublet from doublet.

In some cases not all H atoms are found as a signal in the NMR because the signal could overlays with a solvent signal or it is a very broad signal dependent on the NMR solvent used. The $^1$H-NMR data of selected examples/intermediates are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity2), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

TABLE 1

| Abbreviations | |
|---|---|
| PBMCs | Peripheral blood mononuclear cells |
| AUC | Area Under Curve |
| DCM | dichloromethane |
| DMF | N,N-dimethylformamide |
| DMSO | dimethylsulphoxide |
| EAE | experimental autoimmune encephalomyelitis |
| EDTA | Ethylenediaminetetraacetic acid |
| Expl. | Example |
| h | hour |
| FCS | fetal calf serum |
| HMDS | Hexamethyldisilazane |
| LPS | lipopolysaccharide |
| MCPBA | 3-chloroperbenzoic acid |
| mL | milliliter |
| μL | microliter |
| min. | minute(s) |
| MW | microwave |
| PBMC | peripheral blood mononuclear cells |
| RT or rt | room temperature |
| sat. | saturated |

TABLE 1-continued

| Abbreviations | |
|---|---|
| SDS | Sodium dodecyl sulfate |
| THF | tetrahydrofuran |
| TNFa | tumour necrosis factor alpha |
| uM | micromolar |
| IFNg | Interferon gamma |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate, DCM/methanol, or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Experimental Section—General Synthesis

The following paragraphs outline a variety of synthetic approaches suitable to prepare compounds of the general formula (Ia), and intermediates useful for their synthesis.

In addition to the routes described below, also other routes may be used to synthesize the target compounds, in accordance with common general knowledge of a person skilled in the art of organic synthesis. The order of transformations exemplified in the following schemes is therefore not intended to be limiting, and suitable synthesis steps from various schemes can be combined to form additional synthesis sequences. In addition, interconversion of any of the substituents, in particular $R^1$, $R^{2a}$, $R^{2b}$, $R^{3a}$, $R^{3b}$, $R^{4a}$ and $R^{4b}$, which are as defined in formula (Ia) supra, can be achieved before and/or after the exemplified transformations. These modifications can be, for example, the introduction of protective groups, cleavage of protective groups, reduction or oxidation of functional groups, halogenation, metallation, metal catalysed coupling reactions, exemplified by but not limited to e.g. Buchwald, Suzuki, Sonogashira and Ullmann coupling, ester saponifications, amide coupling reactions, and/or substitution or other reactions known to a person skilled in the art. These transformations include those which introduce a functionality allowing for further interconversion of substituents. Appropriate protective groups and their introduction and cleavage are well-known to a person skilled in the art (see for example T.W. Greene and P.G.M. Wuts in Protective Groups in Organic Synthesis, 4$^{th}$ edition, Wiley 2006).

Further, it is possible that two or more successive steps may be performed without work-up being performed between said steps, e.g. a "one-pot" reaction, as it is well-known to a person skilled in the art.

Compounds of general formula (Ia), with n=1 and $R^{3b}$=CH$_2$OH, can be assembled according to Scheme 1, by reaction of a urea or thiourea derivative of formula (IIa), in which $R^1$, $R^{2a}$, $R^{2b}$, $R^{3a}$, $R^{4a}$, $R^{4b}$ X, and Y are as defined for the compounds of general formula (Ia), by means of protecting group cleavage with concomitant acid-mediated oxetane opening and subsequent oxazine formation. Via this protecting group cleavage, oxetane rearrangement sequence, compounds of general formula (Ia), with n=0 and $R^{3b}$=C(CH$_3$)$_2$CH$_2$OH are assembled from compounds of general formula (IIb), where $R^1$, $R^{2a}$, $R^{2b}$, $R^{3a}$, $R^{4a}$, $R^{4b}$ X, and Y are as defined for the compounds of general formula (Ia). Similarly, compounds of formula (Ia), with n=0 and $R^{4b}$=CH$_2$OH are prepared from compounds of general formula (IIc), as shown in Scheme 1, where $R^1$, $R^{2a}$, $R^{2b}$, $R^{3a}$, $R^{3b}$, $R^{4a}$, X, and Y are as defined for compounds of general formula (Ia).

The transformation of compounds of formula (IIa, IIb, or IIc) to compounds of formula (Ia) can be performed in either a step wise or one-pot fashion. The step-wise transformation begins with the intermediacy of a formed and potentially isolated, deprotected intermediate (IIIa), (IIIb), and (IIIc) from (IIa), (IIb), and (IIc), respectively, using suitable reagents known to one skilled in the art.

Scheme 1: Preparation of compounds of general formula (Ia) from intermediates of formula (IIa), (IIb) and (IIc).

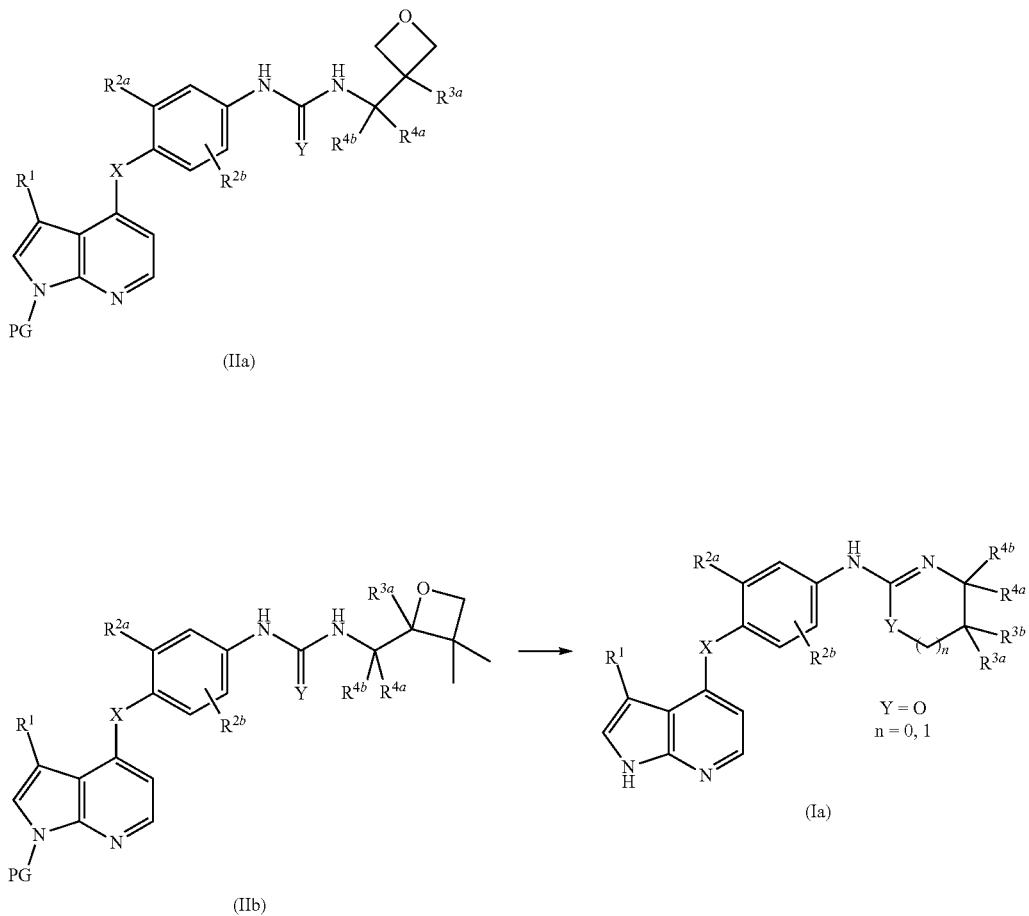

(IIa)

(IIb)

(Ia)

Y = O
n = 0, 1

-continued

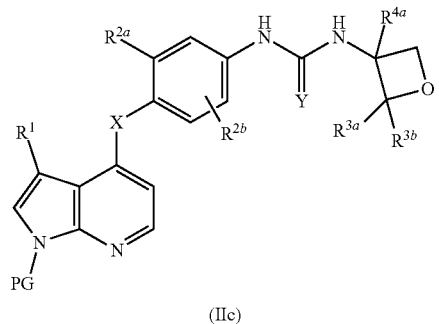

(IIc)

The subsequent rearrangement of the oxetane moiety contained in compounds of the formula (IIIa, IIIb, or IIIc) can then be performed by reaction of such compounds in an appropriate solvent, such as dichloromethane, tetrahydrofuran, methanol, or toluene in the presence of an appropriate bronsted or lewis acid such as trifluoroacetic acid, p-toluenesulfonic acid, hydrochloric acid, or boron trifluoride (Scheme 2).

Scheme 2: Preparation of compounds of general formula (Ia) from intermediates of formula (IIIa), (IIIb), and (IIIc).

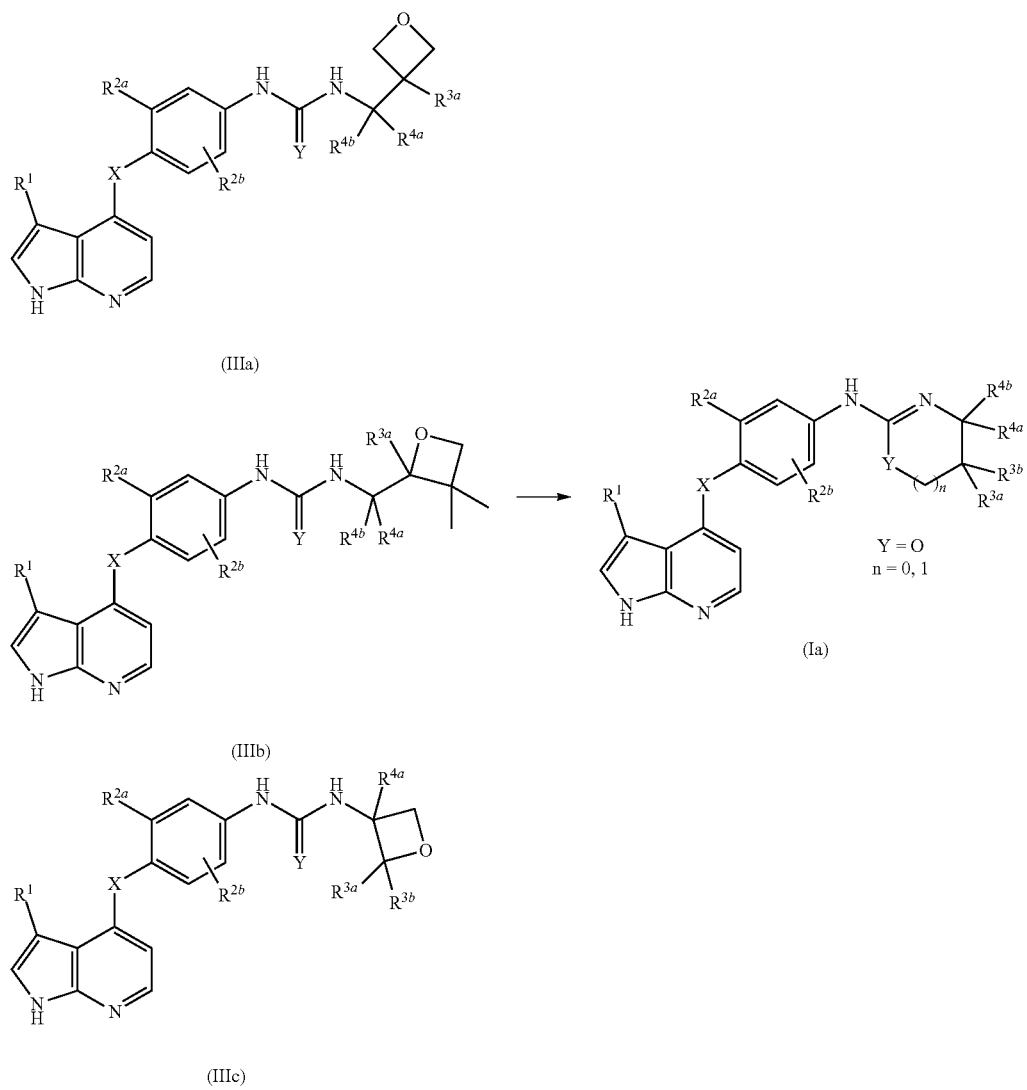

Depending on the choice of protecting group PG in formula (IIa, IIb, or IIc), which is preferentially trimethylsilylethyloxymethyl (SEM), but can be any other protecting group well known to the person skilled in the art, the deprotection and oxazine formation can be performed in a one-pot reaction manner using trifluoroacetic acid in an inert solvent such as dichloromethane, within a temperature range from 0° C. to the boiling point of the used solvent. Preferably the reaction is carried out at room temperature to afford compounds of general formula (Ia).

When the protecting group appending to compounds of formula (IIa, IIb, or IIc) is toluenesulfonyl (Ts) or benzenesulfonyl, the protecting group is first cleaved to give compounds of formula (IIIa, IIIb, or IIIc). The deprotection is preferentially carried out using bases such as sodium hydroxide or potassium carbonate in solvents such as methanol or ethanol within a temperature range from 0° C. to the boiling point of the respective solvent. Preferably the reaction is carried out at room temperature to give deprotected compounds of formula (IIIa, IIIb, or IIIc).

Compounds of general formula (IIa, IIb, or IIc) can be assembled according to Scheme 3, by reaction of amine derivatives of formula (IV), in which $R^1$, $R^{2a}$, $R^{2b}$, and X are as defined for the compounds of general formula (Ia), and a second amine derivative (Va, Vb or Vc), in which $R^3$ and $R^4$ are as defined for the compounds of general formula (Ia), by means of urea formation well known to the person skilled in the art.

Scheme 3: Preparation of compounds of general formula (IIa, IIb, IIc) from two amines (IV) and (Va, Vb, Vc)

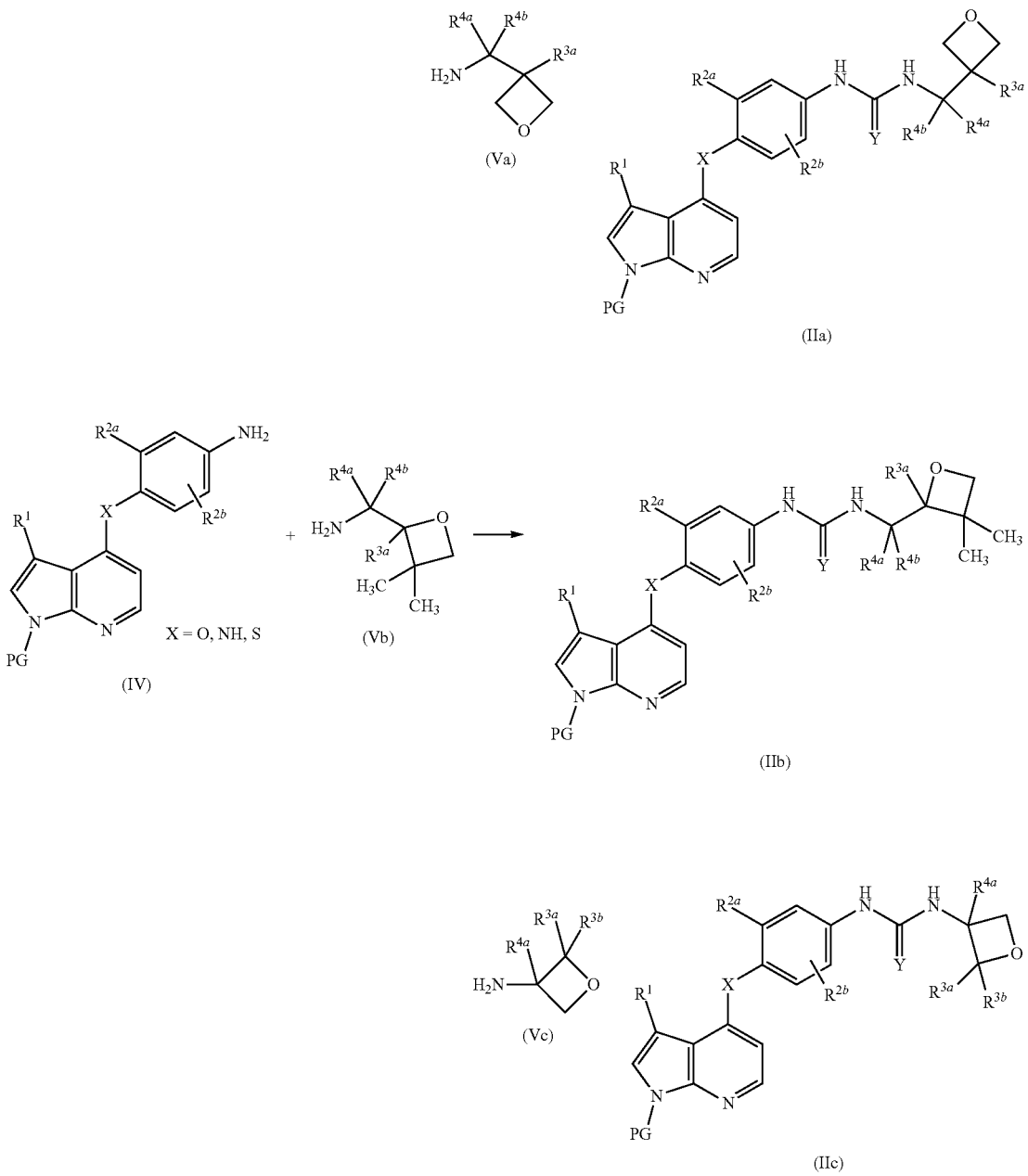

Said urea formation can be performed by reaction of compounds of general formula (IV) with the intermediacy of a formed and possibly isolated isocyanate or isothiocyanate (VIa) (Scheme 4) using a suitable reagent such as 1,1'-carbonylbis-1H-imidazole, di- or triphosgene for Y=O, or as thiophosgene or 1,1'-thiocarbonylbis-1H-imidazole for Y=S.

Scheme 4: Intermediately formed isocyanate or isothiocyanate (VIa) or (VIIa, VIIb, VIIc) and intermediately formed activated carbamate or thiocarbamate (VIb) or (VIIIa, VIIIb, VIIIc) during preparation of compounds of general formula (IIa, IIb, IIc) from two amines (IV) and (Va, Vb, Vc,) (Scheme 3)

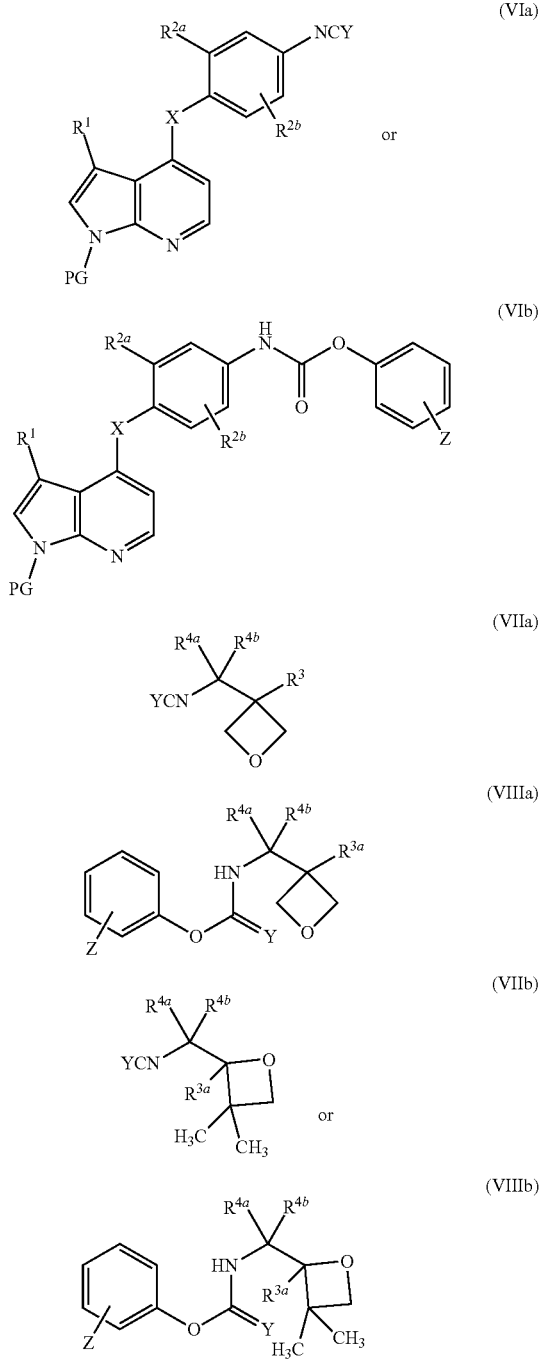
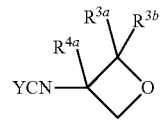
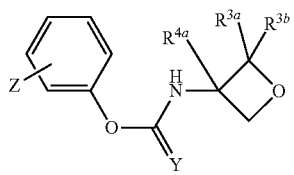

Compounds of general formula (IIa, IIb or IIc) can also be assembled by conversion of amine derivatives of formula (IV) to an intermediately formed and possibly isolated carbamate or thiocarbamate (VIb) (Scheme 4) using a suitable reagent such as phenyl chloroformate or 0-phenyl chlorothionoformate in which Z is H, $NO_2$, or perfluoro in an appropriate solvent such as tetrahydrofuran, dichloromethane, or ethylacetate in the presence of an appropriate base such as pyridine, sodium hydrogencarbonate, or triethylamine. This intermediate (VIb) is then reacted with the second amine derivative (Va, Vb or Vc) in an appropriate solvent such as pyridine, or N,N-dimethylformamide. In a similar way the compounds of general formula (IIa, IIb or IIc) can be assembled using the amine (Va, Vb or Vc) as starting material. Using the previously described reaction sequence, amine (Va, Vb or Vc) can be reacted to the intermediately formed isocyanate or isothiocyanate (VIIa, VIIb or VIIc), if it is not commercially available, in which $R^3$, $R^4$ and Y are as defined for the compounds of general formula (Ia), or the carbamate or thiocarbamate (VIIIa, VIIIb or VIIIc) using a suitable reagent such as phenyl chloroformate or O-phenyl chlorothionoformate in which Z is H, $NO_2$, or perfluoro and $R^3$, $R^4$, and Y are as defined for the compounds of general formula (Ia). This activated intermediate is then reacted with the second amine of general formula (IV).

Preferably the urea formation is carried out using the carbamate (VIb), where Z=H and the respective second amine of formula (Va, Vb, Vc) in N,N-dimethylformamide at 60° C. Alternatively, amine (IV) is reacted with the isocyanate (VIIIa, VIIIb, VIIIc), where Y=O in a mixture of pyridine and tetrahydrofuran at 60° C. to obtain compounds of formula (IIa, IIb, IIc).

Alternatively, compounds of general formula (Ia) can also be assembled according to Scheme 5, by reaction of thiocarbamates of formula (VIb) in which $R^1$, $R^{2a}$, $R^{2b}$, and X are as defined for the compounds of general formula (Ia) and Z is H, $NO_2$ or perfluoro with aminoalcohols of general formula (IX) in which $R^{3a}$, $R^{3b}$, $R^{4a}$ and $R^{4b}$ are as defined for the compounds of general formula (Ia) and n=0 or 1 in an appropriate solvent such as tetrahydrofuran, dichloromethane, or ethylacetate, optionally in the presence of an appropriate base such as pyridine, sodium hydrogencarbonate, or triethylamine.

Amino alcohols of formula (IX) are either commercially available, synthesized according to Scheme 11 and 12, or synthesized according to other methods known to one skilled in the art. Intermediates of formula (X) are then cyclized to a compound of general formula (XI) by reaction with an appropriate reagent, such as N-(3-dimethylaminopropyl)-N'-ethylcarbodiimide hydrochloride, p-toluenesulfonyl chloride, 1,1'-carbonylbis-1H-imidazole or methyl iodide in an appropriate solvent such as acetonitrile, methanol or tetrahydrofuran optionally in the presence of a base such as for example triethylamine, sodium hydroxide, or potassium hydroxide at a temperature ranging from room temperature to the boiling point of the used solvent.

Preferably, for compounds of formula (XI) were Y=O, the reaction will be performed in the presence of N-(3-dimethylaminopropyl)-N'-ethylcarbodiimide hydrochloride and trimethylamine in acetonitrile as a solvent and a temperature of 40° C. For the compounds of formula (XI) where Y=S, the reaction will be carried out in the presence of 1,1'-carbonylbis-1H-imidazole with tetrahydrofuran as a solvent at a temperature of 70° C. Depending on the choice of protecting group PG in formula (XI), which is preferentially trimethylsilylethyloxymethyl (SEM) or toluenesulfonyl (Ts), but can be any other protecting group well known to the person skilled in the art, the deprotection of compounds of general formula (XI) with PG=SEM can be performed using trifluoroacetic acid in an inert solvent such as dichloromethane, within a temperature range from 0° C. to the boiling point of the used solvent. Alternatively, the deprotection of compounds of general formula (XI) with PG=Ts can be performed using sodium hydroxide or potassium carbonate, in a solvent such as methanol or ethanol, within a temperature range from 0° C. to the boiling point of the used solvent Preferably the reaction is carried out at room temperature to afford compounds of general formula (Ia). The deprotection in the case of trimethylsilylethyloxymethyl can be also performed using tetra-butylammonium fluoride in the presence of ethylenediamine in an inert solvent such as tetrahydrofuran within a temperature range from 0° C. to the boiling point of the used solvent to afford compounds of general formula (Ia). Alternatively a one pot transformation of compounds of general formula (X) where PG=SEM to compounds of general formula (Ia) where Y=S can be performed in solvent mixtures such as methanol and water and ethanol and water with strong acids such as hydrochloric acid in a temperature range between room temperature and the boiling point of the respective solvent mixture. Preferably the reaction is carried out at room temperature to afford compounds of general formula (Ia) where Y=S.

Scheme 5: Preparation of compounds of general formula (Ia) by deprotection of compounds of formula (XI) prepared by reaction of compounds of formula (VIb) with aminoalcohols of formula (IX).

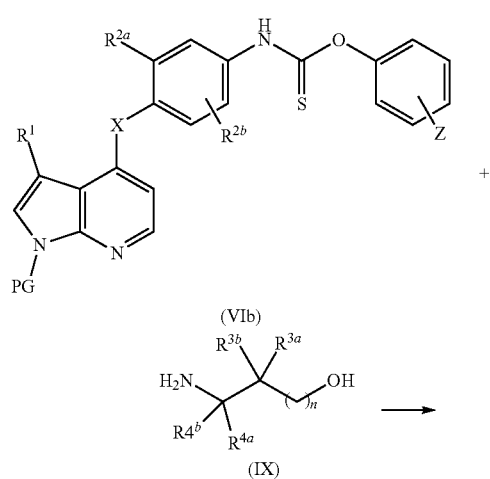

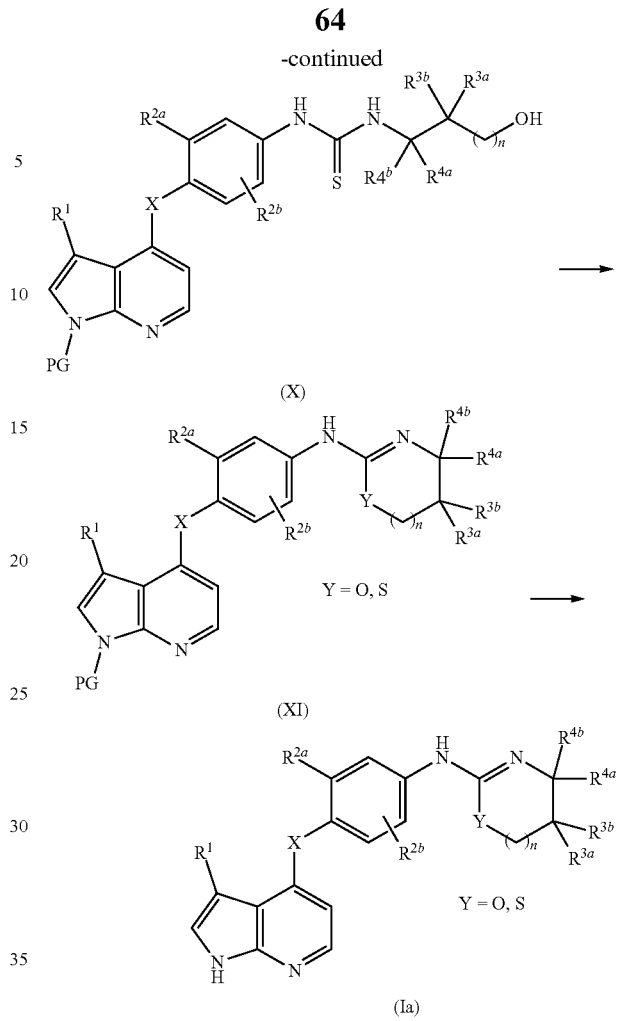

The amine intermediates of formula (IV) are known to one skilled in the art and can be prepared according to Schemes 6 and 7 if they are not commercially available. The second amine derivatives of formula (Va, Vb, Vc) are either commercially available in some structural variety, or they can be prepared using synthetic methods described in many textbooks such as March's Advanced Organic Chemistry: Reactions, Mechanisms, and Structure, 7th Edition. As illustrated in Scheme 6, the amine derivatives of formula (IVa) are known, commercially available, or can be prepared from the commercially available heterocyle of the formula (XII), in which $R^{1a}$ represents a hydrogen, a trifluoromethyl group, or a cyclopropyl-trifluoromethyl group. Alternatively heterocycles of formula (XII) are prepared according to Scheme 13.

Said heterocycle of the formula (XII) can be reacted with nitric acid, in the case of leaving group (LG)=NO$_2$, or in a two-step sequence for LG=Cl using MCPBA to form a 7-N-oxide, which then reacts in a subsequent step with methanesulfonyl chloride to give intermediate heterocycles of formula (XIII).

Compounds of the formula (XIII) are converted to chlorides of formula (XIV) using a two-step sequence, which begins with production of a 7-N-oxide using MCPBA which then reacts in a subsequent step with acetyl chloride or trichloroacetyl chloride in the presence of hexamethyldisilazane. Said heterocycles of formula (XIV) can be transformed to the protected intermediates of the formula (XV)

using an appropriate reagent such as trimetylsilylethoxymethyl chloride, triisopropylsilyl chloride or trityl chloride or other reagents known to a person skilled in the art. Preferably, trimetylsilylethoxymethyl chloride is used, in the presence of a base such as sodium hydride, triethyl amine, or ethyl diisopropyl amine in an inert solvent such as tetrahydrofuran, dimethylsulfoxide or N,N-dimethylformamide.

Protected heterocycles of the formula (XV) are then reacted with a compound of the formula (XVI) in the presence of sodium hydride or an alkali carbonate, such as sodium carbonate, potassium carbonate, or cesium carbonate, in a suitable solvent such as dimethylsulfoxide or N,N-dimethylformamide, as well known to the person skilled in the art, to give compounds of formula (XVII). For compounds of formula (XVI) with X=NH it may be necessary to protect the other amino function in an intermediate fashion.

Dechlorination is preferentially performed using a hydrogen atmosphere and palladium on carbon as catalyst in an inert solvent such as ethanol, ethyl acetate or dichloromethane at 20-50° C. as described in Org. Process Res. Dev. 2010, page 168-173, to give a subset of the amines of the formula (IV) named (IVa) in which $R^{1a}$ is a hydrogen, trifluoromethyl group, or a cyclopropyl-trifluoromethyl group.

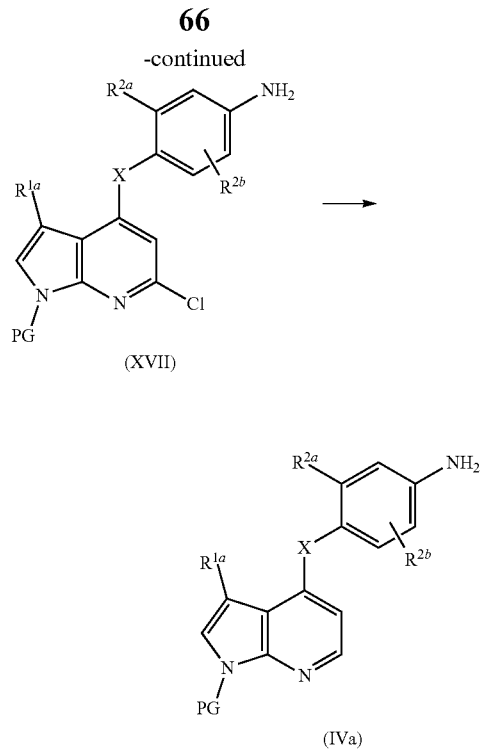

All other amines of the subset (IVb) from the general formula (IV) can be assembled from the amine (IVa) with $R^{1a}$=H according to Scheme 7.

Scheme 7: Preparation of compounds of formula (IVb) from compounds of formula (IVa). (IVb with $R^{1b}$ = Cl, Br, I, CN, aryl, aminocarbonyl, $C_1$-$C_6$-alykl, 5- or 6-membered heteroaryl, $C_3$-$C_8$-cycloalkyl, monocyclic 4- to 7-membered heteroalkyl)

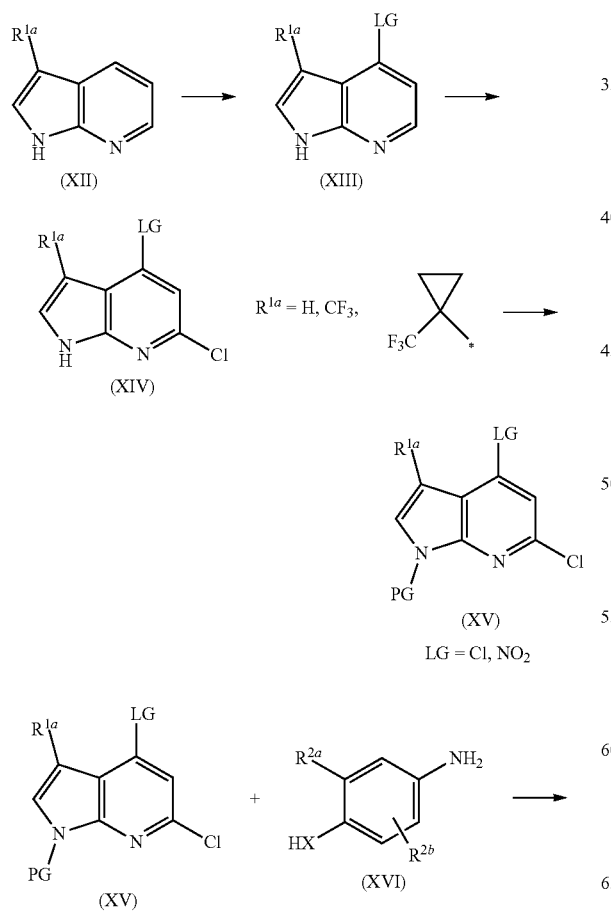

Scheme 6: Preparation of compounds of formula (IVa) from compounds of formula (XII).

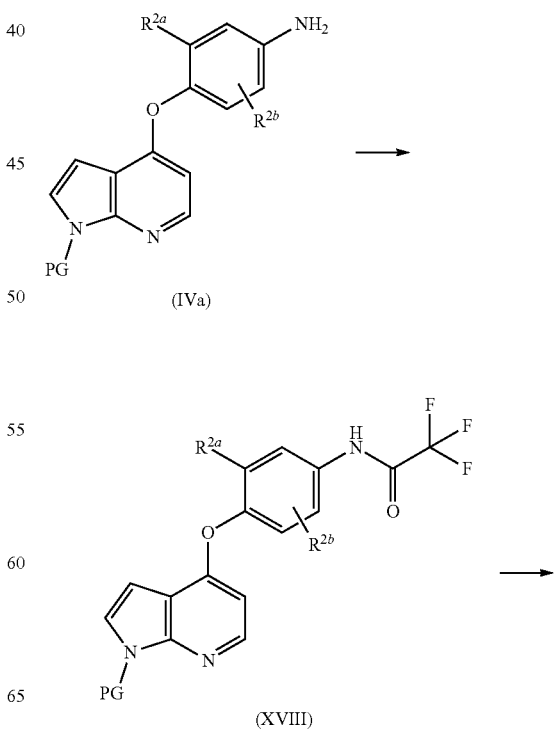

-continued

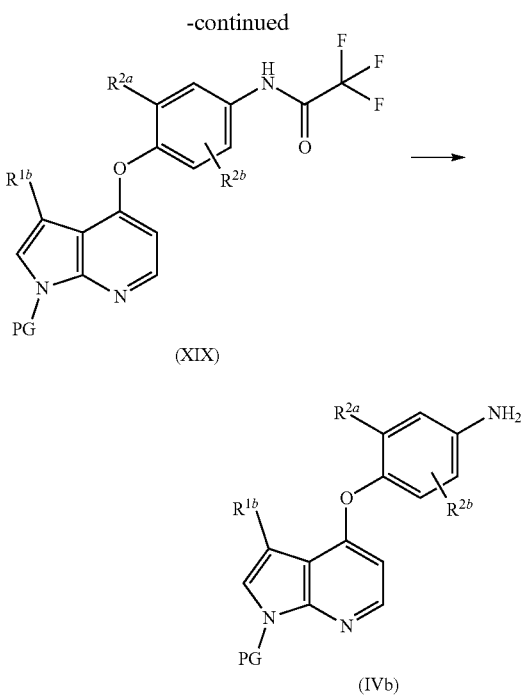

Protection of the free amine in (IVa) with $R^{1a}$=H using trifluoroacetic anhydride in an inert solvent such as dichloromethane in the presence of an amine such as triethyl amine or ethyl diisopropyl amine, yields the amides of the general formula (XVIII) in which $R^{2a}$ and $R^{2b}$ are as defined for the compounds of general formula (Ia). Said amides of formula (XVIII) can be converted into halogen substituted compounds of the general formula (XIX) with $R^{1b}$=Cl, Br, or I using the corresponding N-halo-succinimide in an inert solvent such as dichloromethane or tetrachloromethane. In the case of compounds of the general formula (XIX) with $R^{1b}$=CN, $C_1$-$C_6$-alkyl, aryl, 5- or 6-membered heteroaryl, $C_3$-$C_8$-cycloalkyl, or monocyclic 4- to 7-membered heterocycloalkyl, a subsequent reaction of a said halogen compound of the general formula (XIX) with $R^{1b}$=Br or I is used as starting material. For formation of the corresponding nitrile ($R^{1b}$=CN), a reaction using cuprous cyanide in an inert solvent such as N,N-dimethylformamide or N,N-dimethylacetamide at elevated temperatures, for example between 90-120° C. is required. Furthermore, a palladium-catalyzed method known to the person skilled in the art, for example, with zinc cyanide or potassium ferrocyanide as described in Chem. Soc. Rev., 2011, 40, 5049-5067 can be utilized. For the preparation of compounds of the general formula (XIX) with $R^{1b}$=aryl, $C_1$-$C_6$-alkyl, 5- or 6-membered heteroaryl, $C_3$-$C_8$-cycloalkyl, or monocyclic 4- to 7-membered heterocycloalkyl, a Suzuki reaction known to the person skilled in the art is used as described. Heterocycles of the formula (XIX), where $R^{1b}$=Br or I are used as starting material and reacted with the corresponding boronic acids, boronic ester or boron trifluoride potassium salts of the aryl, $C_1$-$C_6$-alkyl, 5- or 6-membered heteroaryl, $C_3$-$C_8$-cycloalkyl, or monocyclic 4- to 7-membered heterocycloalkyl of choice. This reaction is catalysed by a palladium complex, typically but not exclusively palladium(II) acetate, palladium(0) tetrakis triphenylphosphine, or [1,1'-bis(diphenylphosphino)ferrocene]dichloropalladium(II), and is run in the presence of a base, for example potassium or sodium carbonate, which can, but not required, to be used as aqueous solutions, and an inert solvent of choice such as dioxane, toluene, N,N-dimethylformamide or N,N-dimethylacetamide at elevated temperatures, typically 80-120° C.

In the case of compounds of the general formula (XIX) with $R^{1b}$ having an aminocarbonyl function, a subsequent reaction of a said halogen compound of the general formula (XIX) with $R^{1b}$=Br or I is used as starting material. For formation of the corresponding ester, a reaction in the presence of carbon monoxide (C≡O) or a metal carbonyl complex from which carbon monoxide can be released under the reaction conditions in situ, by means of a palladium catalysed carbonylation reaction in the presence of an alcohol is used. Such palladium catalysed carbonylation reactions are well known to the person skilled in the art, see e.g. J. Georgsson et al., J. Comb. Chem. 5, 350 (2003). Preferably, said carbonylation reactions can be performed in the presence of molybdenum hexacarbonyl (Mo(CO)6) as source of carbon monoxide, trans-bis(acetato)bis[o-(di-o-tolylphosphino)benzyl]dipalladium(II) as a catalyst, tri-tert.-butylphosphonium tetrafluoroborate as an air stable replacement for tri-tert.-butylphosphine, a ligand for palladium catalysed reactions, 1,8-diazabicyclo[5.4.0]undec-7-ene as a base, in a solvent selected from tetrahydrofuran, 1,2-dimethoxyethane, and 1,4-dioxane, preferably tetrahydrofuran. Subsequent transformations e.g. saponification of the ester and amide bond formation, well known to one skilled in the art, can then be used to obtain compounds of the general formula (XIX) with $R^{1b}$ having an aminocarbonyl function. After trifluoromethylacetamide cleavage of compounds of the general formula (XIX) using aqueous lithium, sodium or potassium hydroxide solutions, at a temperature for example between room temperature the boiling point of the solvent, the compounds of the general formula (IVb) are obtained. Ideally, the reaction is carried out at 50° C. to furnish compounds of formula (IVb). Taken together, formulae (IVa) and (IVb) constitute formula (IV).

Scheme 8: Preparation of compounds of formula (IV) from compounds of formula (XX).

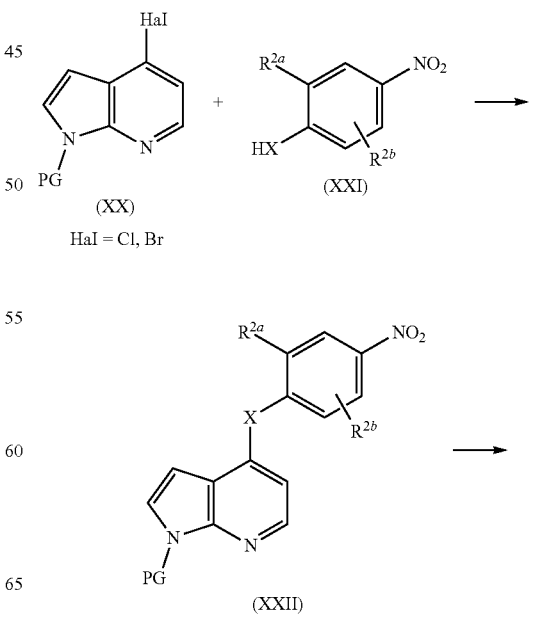

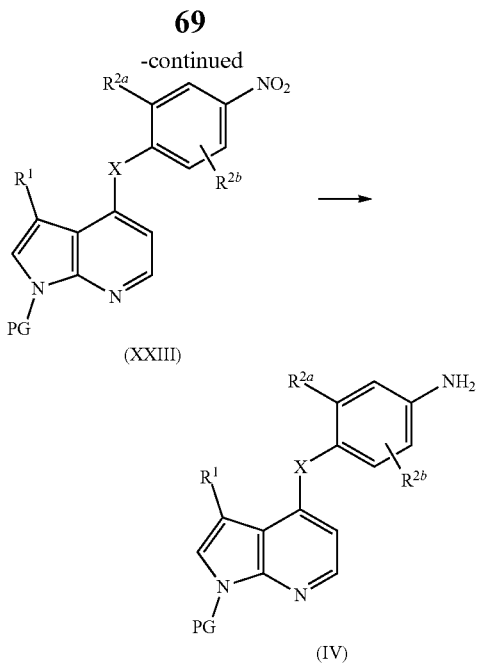

(XXIII)

(IV)

An alternative approach to compounds of formula (IV) is described in Scheme 8. The respective fluoro-nitrobenzene derivatives of formula (XXI) are reacted with the appropriate protected 4-chloro or 4-bromo-7-azaindole (XX) (e.g. US20050288290, US2006/241104, WO2013/167730) in a suitable solvent system, for example dimethylsulfoxide, dimethylformamide, N-methylpyrrolidone or diphenylether, in the presence of a base, for example sodium hydride, trimethylamine, diisopropylethaylamine, potassium carbonate or cesium carbonate, in a temperature range from room temperature to the boiling point of the respective solvent. Preferable the reaction is carried out at higher temperature to furnish intermediates of general formula (XXII). An appropriate protecting group for example is trimetylsilylethoxymethyl chloride, triisopropylsilyl chloride, toluenesulfonyl chloride, benzenesulfonyl chloride, or trityl chloride or other known to a person skilled in the art. Preferably, trimetylsilylethoxymethyl chloride, or toluene sulfonyl chloride is used. Compounds of formula (XXII) can be subsequently converted into halogen substituted compounds of the general formula (XXIII) with $R^1$=Cl, Br, or I using the corresponding N-halo-succinimide in an inert solvent such as dichloromethane, N,N-dimethylformamide, or tetrachloromethane, in a temperature range from room temperature to the boiling point of the respective solvent. Preferably the reaction is carried out at room temperature to furnish intermediates of general formula (XXIII).

Compounds of general formula (XXIII), where $R^1$=I, can be reacted with trifluoromethylating reagents, for example diphenyl(trifluoromethyl)sulfonium trifluoromethanesulfonate as described in Angew. Chem. Int. Ed. 2011, 50, pg. 1896-1900, or any other reagent known to one skilled in the art, to afford compounds of general formula (XXIII) where $R^1$=$CF_3$. Preferably, diphenyl(trifluoromethyl)sulfonium trifluoromethanesulfonate is used, in the presence of additives, such as copper(0), in a solvent such as N,N-dimethylformamide, in a temperature range from room temperature to the boiling point of the respective solvent. Ideally, the reaction is carried out at 60° C. to furnish intermediates of general formula (XXIII) where $R^1$=$CF_3$. In the case of compounds of the general formula (XXIII) with $R^1$=CN, $C_1$-$C_3$-alkyl, aryl, 5- or 6-membered heteroaryl, $C_3$-$C_8$-cycloalkyl, or monocyclic 4- to 7-membered heterocycloalkyl, a subsequent reaction of a said halogen compounds of the general formula (XXIII) with $R^1$=Br or I is required. For the formation of the corresponding nitrile, a reaction using cuprous cyanide in an inert solvent such as N,N-dimethylformamide or N,N-dimethylacetamide at elevated temperatures, for example between 90-120° C. is required. For the preparation of compounds of the general formula (XXIII) with $R^1$=aryl, $C_1$-$C_6$-alkyl, 5- or 6-membered heteroaryl, $C_3$-$C_8$-cycloalkyl, or monocyclic 4- to 7-membered heterocycloalkyl, a Suzuki reaction known to the person skilled in the art is used as described. Compounds of the formula (XXIII), where $R^1$=Br or I are used as starting material and reacted with the corresponding boronic acids, boronic ester or boron trifluoride potassium salts of the aryl, $C_1$-$C_6$-alkyl, 5- or 6-membered heteroaryl, $C_3$-$C_8$-cycloalkyl, or monocyclic 4- to 7-membered heterocycloalkyl of choice. This reaction is catalysed by a palladium complex, typically but not exclusively palladium(II) acetate, palladium(0) tetrakis triphenylphosphine, or [1,1'-bis(diphenylphosphino)ferrocene] dichloropalladium(II), and is run in the presence of a base, for example potassium or sodium carbonate, which can, but not required, to be used as aqueous solutions, and an inert solvent of choice such as dioxane, toluene, N,N-dimethylformamide or N,N-dimethylacetamide at elevated temperatures, typically 80-120° C. In the case of compounds of the general formula (XXIII) with $R^1$ having an aminocarbonyl function, a subsequent reaction of a said halogen compound of the general formula (XXIII) with $R^1$=Br or I is used as starting material. For formation of the corresponding ester, a reaction in the presence of carbon monoxide (C≡O) or a metal carbonyl complex from which carbon monoxide can be released under the reaction conditions in situ, by means of a palladium catalysed carbonylation reaction in the presence of an alcohol is used. Such palladium catalysed carbonylation reactions are well known to the person skilled in the art, see e.g. J. Georgsson et al., J. Comb. Chem. 5, 350 (2003).

Preferably, said carbonylation reactions can be performed in the presence of molybdenum hexacarbonyl (Mo(CO)6) as source of carbon monoxide, trans-bis(acetato)bis[o-(di-o-tolylphosphino)benzyl]dipalladium(II) as a catalyst, tri-tert.-butylphosphonium tetrafluoroborate as an air stable replacement for tri-tert.-butylphosphine, a ligand for palladium catalysed reactions, 1,8-diazabicyclo[5.4.0]undec-7-ene as a base, in a solvent selected from tetrahydrofuran, 1,2-dimethoxyethane, and 1,4-dioxane, preferably tetrahydrofuran. Subsequent transformations e.g. saponification of the ester and amide bond formation, well known to one skilled in the art, can then be used to obtain compounds of the general formula (XXIII) with $R^1$ having an aminocarbonyl function. Reduction of the nitro functionality contained within compounds of formula (XXIII) affords amines of formula (IV). Preferentially, the reaction is performed with the addition of a reducing agent, for example iron(0), with additives such as ammonium chloride, in an appropriate mixture of solvents, for example a mixture of water, tetrahydrofuran, and methanol, in a temperature range from room temperature to the boiling point of the respective solvent. Ideally the reaction is performed at 80° C. to furnish amine intermediates of general formula (IV). The reaction can be carried out using alternative reducing agents known to those skilled in the art, for example tin(II)chloride, in an appropriate solvent, such as methanol, in a temperature range from room temperature to the boiling point of the respective solvent. Ideally the reaction is performed at room temperature to furnish amine intermediates of general formula (IV).

A complementary approach to compounds of formula (IV) is described in Scheme 9.

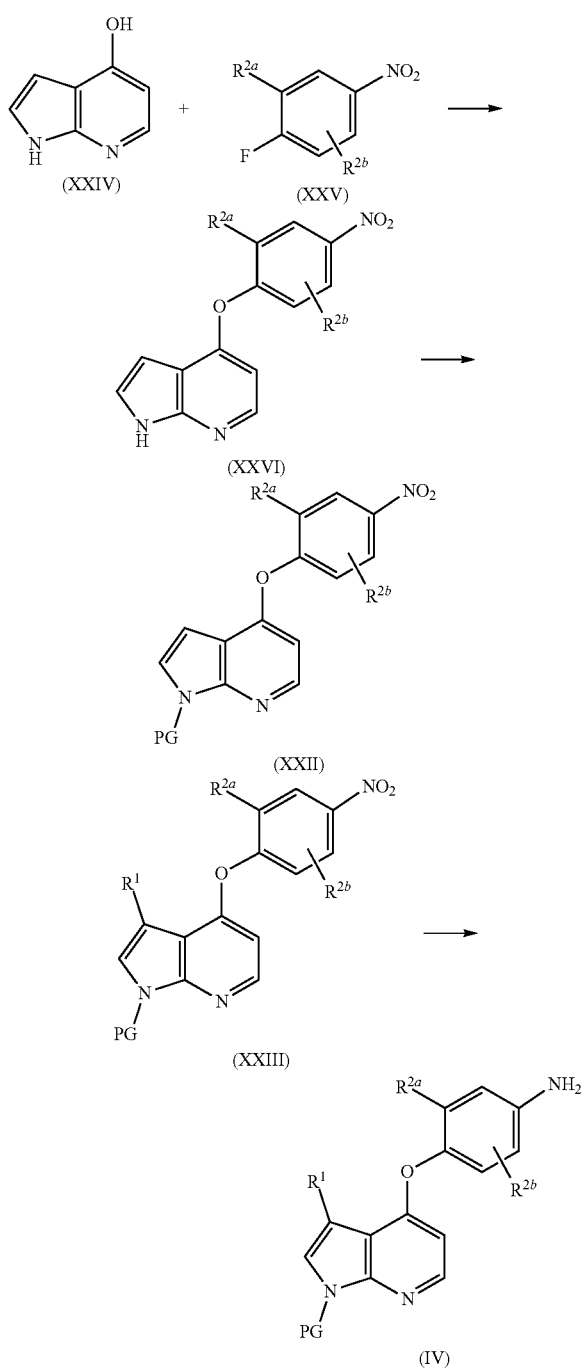

Scheme 9: Preparation of compounds of formula (IV for X = O) from compounds of formula (XXIV).

The respective fluoro-nitrobenzene derivatives of formula (XXV) are reacted with 4-hydroxy-7-azaindole (XXIV) (e.g. US2007/238726) in a suitable solvent system, for example dimethylsulfoxide, in the presence of a base, for example potassium carbonate or cesium carbonate, in a temperature range from room temperature to the boiling point of the respective solvent. Preferable the reaction is carried out at room temperature to furnish intermediates of general formula (XXVI). Intermediates of general formula (XXVI) are then protected with an appropriate protecting group, for example using an appropriate reagent such as trimethylsilylethoxymethyl chloride, triisopropylsilyl chloride, toluenesulfonyl chloride, benzenesulfonyl chloride, or trityl chloride or other reagents known to a person skilled in the art. Preferably, trimethylsilylethoxymethyl chloride, or toluene sulfonyl chloride is used, in the presence of a base such as sodium hydride, triethylamine, or ethyldiisopropylamine in an inert solvent such as tetrahydrofuran, dimethylsulfoxide or N,N-dimethylformamide to afford compounds of formula (XXII). Compounds of formula (XXII) can be subsequently converted into halogen substituted compounds of the general formula (XXIII) with $R^1$=Cl, Br, or I using the corresponding N-halo-succinimide in an inert solvent such as dichloromethane, N,N-dimethylformamide, or tetrachloromethane, in a temperature range from room temperature to the boiling point of the respective solvent. Preferably the reaction is carried out at room temperature to furnish intermediates of general formula (XXIII). Compounds of general formula (XXIII), where $R^1$=I, can be reacted with trifluoromethylating reagents, for example diphenyl(trifluoromethyl)sulfonium trifluoromethanesulfonate as described in Angew. Chem. Int. Ed. 2011, 50, pg. 1896-1900, or any other reagent known to one skilled in the art, to afford compounds of general formula (XXIII) where $R^1$=$CF_3$. Preferably, diphenyl(trifluoromethyl)sulfonium trifluoromethanesulfonate is used, in the presence of additives, such as copper(0), in a solvent such as N,N-dimethylformamide, in a temperature range from room temperature to the boiling point of the respective solvent. Ideally, the reaction is carried out at 60° C. to furnish intermediates of general formula (XXIII) where $R^1$=$CF_3$. In the case of compounds of the general formula (XXIII) with $R^1$=CN, $C_1$-$C_6$-alkyl, aryl, 5- or 6-membered heteroaryl, $C_3$-$C_8$-cycloalkyl, or monocyclic 4- to 7-membered heterocycloalkyl, a subsequent reaction of a said halogen compounds of the general formula (XXIII) with $R^1$=Br or I is required. For the formation of the corresponding nitrile, a reaction using cuprous cyanide in an inert solvent such as N,N-dimethylformamide or N,N-dimethylacetamide at elevated temperatures, for example between 90-120° C. is required. For the preparation of compounds of the general formula (XXIII) with $R^1$=aryl, $C_1$-$C_6$-alkyl, 5- or 6-membered heteroaryl, $C_3$-$C_8$-cycloalkyl, or monocyclic 4- to 7-membered heterocycloalkyl, a Suzuki reaction known to the person skilled in the art is used as described. Compounds of the formula (XXIII), where $R^1$=Br or I are used as starting material and reacted with the corresponding boronic acids, boronic ester or boron trifluoride potassium salts of the aryl, $C_1$-$C_n$-alkyl, 5- or 6-membered heteroaryl, $C_3$-$C_8$-cycloalkyl, or monocyclic 4- to 7-membered heterocycloalkyl of choice. This reaction is catalysed by a palladium complex, typically but not exclusively palladium(II) acetate, palladium(0) tetrakis triphenylphosphine, or [1,1'-bis(diphenylphosphino)ferrocene]dichloropalladium(II), and is run in the presence of a base, for example potassium or sodium carbonate, which can, but not required, to be used as aqueous solutions, and an inert solvent of choice such as dioxane, toluene, N,N-dimethylformamide or N,N-dimethylacetamide at elevated temperatures, typically 80-120° C. In the case of compounds of the general formula (XXIII) with $R^1$ having an aminocarbonyl function, a subsequent reaction of a said halogen compound of the general formula (XXIII) with $R^1$=Br or I is used as starting material. For formation of the corresponding ester, a reaction in the presence of carbon monoxide (C≡O) or a metal carbonyl complex from which carbon monoxide can be released under the reaction conditions in situ, by means of a palladium catalysed carbonylation reaction in the presence of an alcohol is used. Such palladium catalysed carbonylation reactions are well known to the person skilled in the art, see e.g. J. Georgsson et al., J. Comb. Chem. 5, 350 (2003). Preferably, said carbonylation reactions can be performed in the presence of molybdenum hexacarbonyl (Mo(CO)6) as source of carbon monoxide, trans-bis(acetato)bis[o-(di-o-tolylphosphino) benzyl]dipalladium(II) as a catalyst, tri-tert.-butylphosphonium tetrafluoroborate as an air stable replacement for tri-tert.-butylphosphine, a ligand for palladium catalysed reactions, 1,8-diazabicyclo[5.4.0]undec-7-ene as a base, in a solvent selected from tetrahydrofuran, 1,2-dimethoxyethane, and 1,4-dioxane, preferably terahydrofuran. Subsequent transformations e.g. saponification of the ester and amide bond formation, well known to one skilled in the art, can then be used to obtain compounds of the general formula (XXIII) with $R^1$ having an aminocarbonyl function. Reduction of the nitro functionality contained within compounds of formula (XXIII) affords amines of formula (IV). Preferentially, the reaction is performed with the addition of a reducing agent, for example iron(0), with additives such as ammonium chloride, in an appropriate mixture of solvents, for example a mixture of water, tetrahydrofuran, and methanol, in a temperature range from room temperature to the boiling point of the respective solvent. Ideally the reaction is performed at 80° C. to furnish amine intermediates of general formula (IV). The reaction can be carried out using alternative reducing agents known to those skilled in the art, for example tin(II)chloride, in an appropriate solvent, such as methanol, in a temperature range from room temperature to the boiling point of the respective solvent. Ideally the reaction is performed at room temperature to furnish amine intermediates of general formula (IV).

Additionally, compounds of the general formula (IV) with $R^1=C_4-C_8$ cycloalkoxy, where the $C_4-C_8$ cycloalkoxy is optionally substituted with hydroxy, methoxy, ethoxy, trifluoroethoxy, or isopropoxy, can be formed from subsequent reactions of compounds of the general formula (IV) with $R^1=$Br or I, where the free aniline is protected by either tert-butyloxycarbonyl (BOC), carboxybenzyl (Cbz), or any other protecting group known to one skilled in the art. In a first step, compounds of general formula (IV) with $R^1=$Br or I where the aniline is protected with BOC or Cbz, are treated with transmetallating reagents such as n-butyllithium, lithium diisopropylamide, or isopropylmagnesium chloride at –78° C. in solvents such as tetrahydrofuran and diethylether, and subsequently reacted with appropriate ketones of the respective $C_4-C_8$ cycloalkoxy, at temperatures between –78° C. and the boiling point of the respective solvent. The reaction is preferably carried out by slowly warming the reaction from –78° C. to room temperature to afford compounds having a $C_4-C_8$ cycloalkoxy appended with a hydroxyl function. Compounds with $C_4-C_8$ cycloalkoxy appended with a hydroxyl function can be further reacted with fluorinating reagents such as N-(difluoro-λ$^4$-sulfanylidene)-N-ethylethanaminium tetrafluoroborate (XtalFluor-E®) or other fluorinating reagents known to one skilled in the art, in solvents such as dichloromethane, at a temperature between 0° C. and the boiling point of the respective solvent. Preferably the reaction is carried out at 0° C. to give compounds having a $C_4-C_8$ cycloalkoxy group appended with a fluoro function. Compounds with a $C_4-C_8$ cycloalkoxy group appended with a fluoro function can be further reacted with alcohol based solvents such as methanol, ethanol, trifluoroethanol, or isopropanol, in the presence of a base such as potassium carbonate, a temperatures between room temperature and the boiling point of the respective solvent to give compounds containing an $C_4-C_8$ cycloalkoxy group appended with an alkoxy function where the alkoxy group is methoxy, ethyoxy, trifluoroethoxy, or isopropoxy. Alternatively, compounds containing a $C_4-C_8$ cycloalkoxy group appended with a fluoro function can be reacted with alcohol based solvents such as methanol, ethanol, trifluoroethanol, or isopropanol in the presence of silica gel at temperatures between room temperature and the boiling point of the respective solvent. Preferably the reaction is carried out at either room temperature or 50° C. to afford compounds containing a $C_4-C_8$ cycloalkoxy group appended with an alkoxy function where the alkoxy group is methoxy, ethoxy, trifluoroethoxy, or isopropoxy. Subsequent transformations e.g. deprotection of the Cbz or BOC group on the aniline, well known to one skilled in the art, can then be used to obtain compounds of the general formula (IV) with $R^1=C_4-C_8$ cycloalkoxy, where the $C_4-C_8$ cycloalkoxy is substituted with hydroxy, methoxy, ethoxy, trifluoroethoxy, or isopropoxy.

Additionally, compounds of the general formula (IV) with $R^1=C_1-C_6$-alkyl, $C_1-C_6$-haloalkyl, $C_1-C_6$-alkyl substituted with $C_1-C_6$-haloalkoxy, $C_1-C_6$-cyanoalkyl, $C_4-C_8$-cycloalkyl, and $C_3-C_8$-cycloalkoxy, can be formed from subsequent reaction of compounds of the general formula (IV) with $R^1=$Br, where the free aniline is bis-protected by tert-butyloxycarbonyl (BOC), or any other protecting group known to one skilled in the art, by a light promoted, nickel catalysed reaction as described in J. Am. Chem. Soc. 2016, 138, 8084-8087 and Org. Lett. 2016, 18, 4012. Preferentially, compounds of general formula (IV) with $R^1=$Br and the aniline function is bis protected by BOC, are reacted with an appropriate alkylbromide of the corresponding $C_1-C_6$-alkyl, $C_1-C_6$-haloalkyl, $C_1-C_6$-alkyl substituted with $C_1-C_6$-haloalkoxy, $C_1-C_6$-cyanoalkyl, $C_4-C_8$-cycloalkyl, and $C_3-C_8$-cycloalkoxy, in the presence of a photoredox catalyst such as Ir(4',6'-dF-5-CF$_3$-ppy)$_2$(4,4'-dtbbpy)PF$_6$, a nickel precatalyst such as nickel II chloride dimethoxyethane adduct, and a ligand such as 4,4'-Di-tert-butyl-2,2'-bipyridine, with a base such as sodium carbonate, 2,6-dimethoxypyridine, or lithium carbonate, with additives such as tris(trimethylsilyl)silane, in a solvent or solvent mixture such as dimethoxyethane, N,N-dimethylacetamide/ trifluorotoluene or 1,3-Dimethyl-2-imidazolidinone/trifluorotoluene, irradiated with light generated by two 40 W Kessil LED aquarium lights, at a temperature between 0° C. and the boiling point of the respective solvent. The reaction can alternatively be carried out in a flow reactor in accordance to procedures known to one skilled in the art. Ideally the reaction is performed between room temperature and 35° C. A subsequent deprotection of the bis-BOC protecting group, for example in the presence of trifluoroacetic acid and known to one skilled in the art, affords compounds of general formula (IV) where $R^1=C_1-C_6$-alkyl, $C_1-C_6$-haloalkyl, $C_1-C_6$-alkyl substituted with $C_1-C_6$-haloalkoxy, $C_1-C_6$-cyanoalkyl, $C_4-C_8$-cycloalkyl, $C_3-C_8$-cycloalkoxy.

In the case of compounds of general formula (Ia), with n=0 or 1, in which $R^1$, $R^{2a}$, $R^{2b}$, $R^{3a}$, $R^{3b}$, $R^{4a}$, $R^{4b}$ and X are as defined for the compounds of general formula (Ia) and Y=N, a reaction between thiocarbamates of formula (VIb) in which $R^1$, $R^{2a}$, $R^{2b}$, and X are as defined for the compounds of general formula (Ia) and Z is H, NO$_2$ or perfluoro with diamines of general formula (XXIV) in which $R^{3a}$, $R^{3b}$, $R^{4a}$ and $R^{4b}$ are as defined for the compounds of general formula (Ia) and n=0 or 1 and where PG2 is an appropriate protecting group, preferably tert-butyloxycarbonyl (BOC) but can be any other protecting group well known to the person skilled in the art is used (Scheme 10). Diamines of general formula (XXIV) are either commercially available or their synthesis is known to one skilled in the art. An appropriate solvent is used such as tetrahydrofuran, dichloromethane, or ethylacetate, optionally in the presence of an appropriate base such as pyridine, sodium hydrogencarbonate, or trimethylamine. Intermediates of formula (XXV) are then converted to intermediates of formula (XXVI) by reaction with methyl iodide in an appropriate solvent, such as acetone, optionally in the presence of a base, such as sodium hydrogencarbonate, or trimethylamine at a temperature ranging from room temperature to the boiling point of the solvent used. Depending on the choice of protecting group PG in formula (XXVI), which is preferentially trimethylsilylethyloxymethyl (SEM), but can be any other protecting group well known to the person skilled in the art, and the choice of protecting group PG2 in formula (XXIV), which is preferably tert-butyloxycarbonyl (BOC) but can be any other protecting group well known to the person skilled in the art, the deprotection and subsequent cyclisation of compounds of general formula (XXVI) can be performed using trifluoroacetic acid in an inert solvent such as dichloromethane, within a temperature range from 0° C. to the boiling point of the used solvent. Preferably the reaction is carried out at room temperature to afford compounds of general formula (Ia).

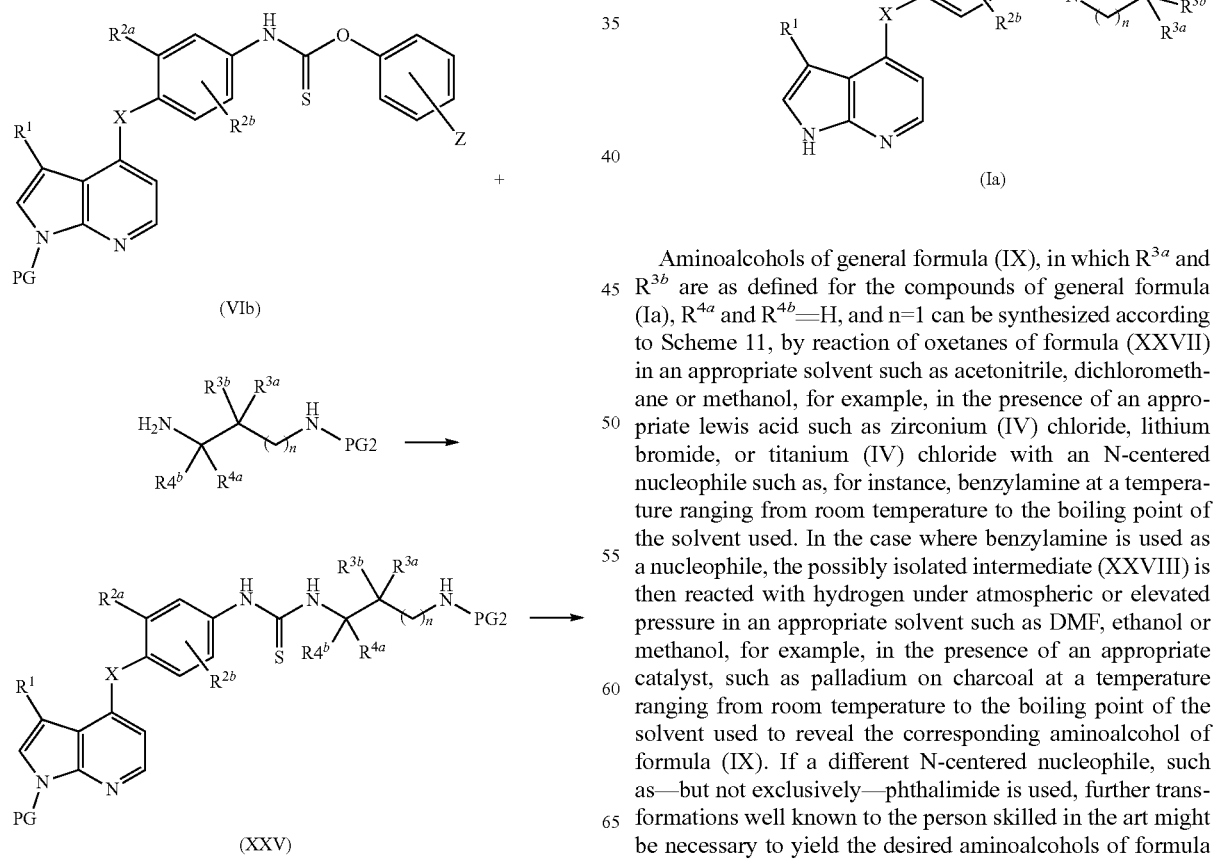

Aminoalcohols of general formula (IX), in which $R^{3a}$ and $R^{3b}$ are as defined for the compounds of general formula (Ia), $R^{4a}$ and $R^{4b}$=H, and n=1 can be synthesized according to Scheme 11, by reaction of oxetanes of formula (XXVII) in an appropriate solvent such as acetonitrile, dichloromethane or methanol, for example, in the presence of an appropriate lewis acid such as zirconium (IV) chloride, lithium bromide, or titanium (IV) chloride with an N-centered nucleophile such as, for instance, benzylamine at a temperature ranging from room temperature to the boiling point of the solvent used. In the case where benzylamine is used as a nucleophile, the possibly isolated intermediate (XXVIII) is then reacted with hydrogen under atmospheric or elevated pressure in an appropriate solvent such as DMF, ethanol or methanol, for example, in the presence of an appropriate catalyst, such as palladium on charcoal at a temperature ranging from room temperature to the boiling point of the solvent used to reveal the corresponding aminoalcohol of formula (IX). If a different N-centered nucleophile, such as—but not exclusively—phthalimide is used, further transformations well known to the person skilled in the art might be necessary to yield the desired aminoalcohols of formula (IX).

Scheme 11: Preparation of compounds of formula (IX) from compounds of formula (XXVII).

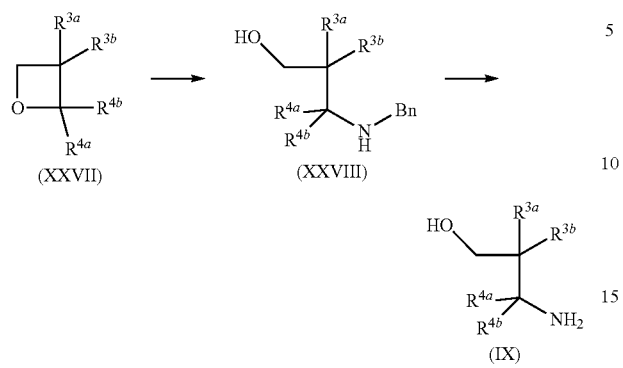

Additionally, aminoalcohols of general formula (IX), in which $R^{3a}$ and $R^{3b}$ are as defined for the compounds of general formula (Ia), n=1, and $R^{4a}$ and $R^{4b}$=H can be also assembled according to Scheme 12, by the reaction of a malonic ester derivative of formula (XXIX), which are known or can be prepared using suitable alkylation reaction of malonic ester or corresponding known derivatives known to one skilled in the art (see March's Advanced Organic Chemistry: Reactions, Mechanisms, and Structure, 7th Edition), in which $R^{3a}$ and $R^{3b}$ are as defined for the compounds of general formula (Ia), by reduction using for example lithium tri(tert-butoxy)aluminium hydride in an inert solvent such as THF (e.g. see US2012/110702) at a temperature ranging from 0° C. to the boiling point of the solvent used to get the alcohol of formula (XXX). Introduction of a leaving group using for example tosylchloride in an inert solvent such as pyridine or methylene chloride in the presence of trimethylamine or a different tert.-amine followed by the reaction with bis(1,1-dimethylethyl)imidodicarbonate in the presence of a base such as cesium carbonate or potassium carbonate in an inert solvent such as DMF or DMSO at a temperature ranging from 0° C. to the boiling point of the solvent used gives the protected amine of formula (XXXI) (e.g. see WO2007/58852). PG3 in this case is dependent on the used reagent for example using bis(1,1-dimethylethyl)imidodicarbonate PG3 is a BOC-group but is not limited to this reagent and this PG3.

Scheme 12: Preparation of compounds of formula (IX) from compounds of formula (XXIX).

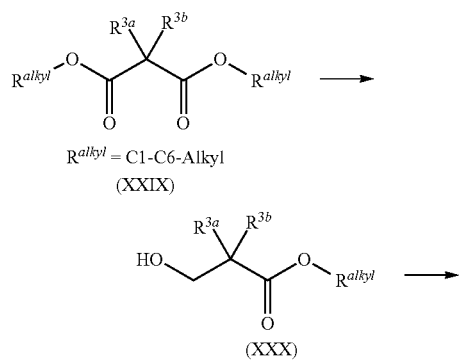

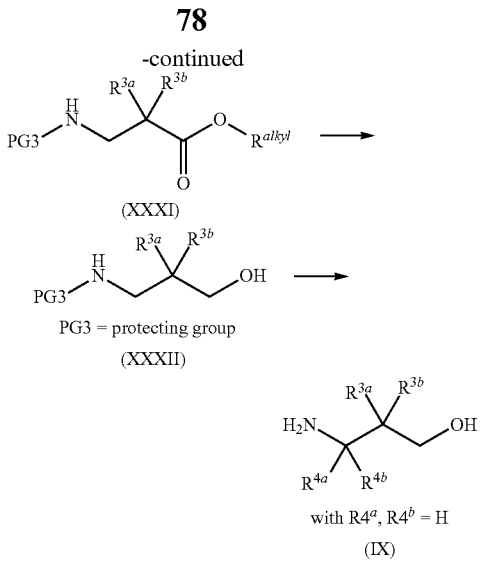

The ester group in the protected amine (XXXI) is then reduced using for example lithium aluminumhydride in an inert solvent such as THF (e.g. see CN107235896) at a temperature ranging from 0° C. to the boiling point of the solvent used to afford the alcohol of formula (XXXII). Deprotection known to the person skilled in the art gives the aminoalcohols of general formula (IX), in which $R^{3a}$ and $R^{3b}$ are as defined for the compounds of general formula (Ia) and $R^{4a}$ and $R^{4b}$=H. In the case of a BOC-group the deprotection using trifluoroacetic acid in an inert solvent such as methylene chloride at a temperature ranging from 0° C. to the boiling point of the solvent used is the preferred method.

Compounds of the general formula (XII) where $R^{1a}$=cyclopropyl-trifluoromethyl can be assembled according to Scheme 13. Halo-pyridines of general formula (XXXIII) where X=F, or C, are treated with bases such as n-butyllithium, or lithium diisopropylamide, in solvents such as tetrahydrofuran, at −78° C. and subsequently reacted with amides of general formula (XXXIV), which are commercially available or synthesized by methods known to one skilled in the art as described in Org. Process Res. Dev., 2009, 13 (3), pp 576-580. Preferably the reaction is carried out by warming the reaction slowly from −78° C. to room temperature to give compounds of general formula (XXXV). Compounds of general formula (XXXV) are then converted into the corresponding epoxide of general formula (XXXVI) by methods known to one skilled in the art as reported in Journal of Organic Chemistry, 2006, vol. 71, #15, p. 5538-5545. Compounds of general formula (XXXV) are reacted with reagents such as trimethylsulfonium iodide, in the presence of a base such as sodium hydride or potassium tert-butoxide, in a solvent such as dimethylsulfoxide or tetrahydrofuran, at a temperature between 0° C. and the boiling point of the respective solvent. Preferably the reaction is carried out at 15° C. to give compounds of formula (XXXVI). The epoxide function of compounds of general formula (XXXVI) is then opened with ammonia with subsequent cyclization as reported in Journal of Organic Chemistry, 2006, vol. 71, #15, p. 5538-5545. Compounds of general formula (XXXVI) are treated with a solution of ammonia in water, in solvents such as tetrahydrofuran, at temperatures between room temperature and the boiling point of the respective solvent. Preferably the reaction is carried out at 60° C. to give compounds of general formula (XXXVII). Compounds of general formula (XXXVII) are then dehydrated with appropriate dehydrating agents such as thionyl chloride, in the presences of a base such as pyridine, in an appropriate solvent such as dichloromethane, at a temperature between room temperature and the boiling point of the respective solvent. Preferably the reaction is carried out at room temperature to afford compounds of general formula (XII) where $R^{1a}$=cyclopropyl-trifluoromethyl.

Scheme 13: Preparation of compounds of formula (XII), where $R^{1a}$ = cyclopropyl-trifluoromethyl from compounds of formula (XXXIII).

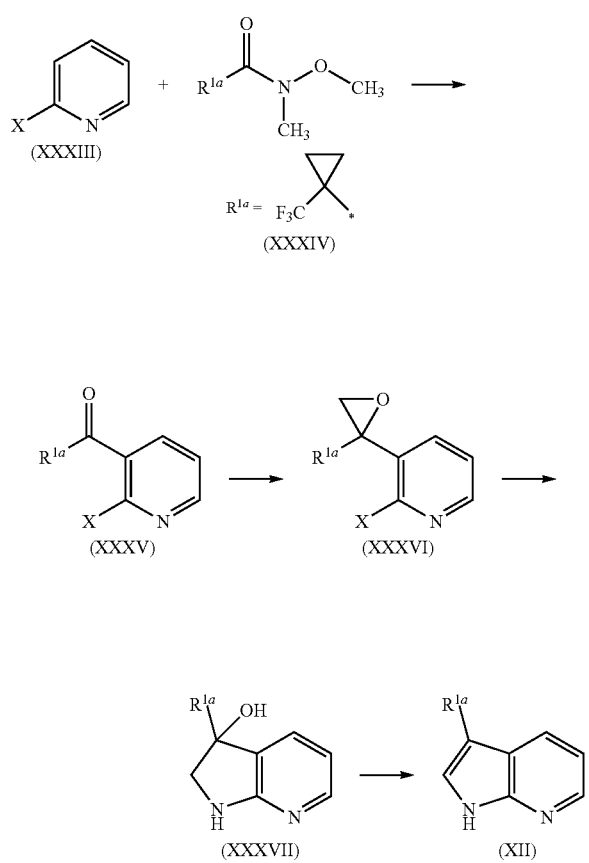

Experimental Section—Methods

Method 1:
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:
Instrument: Waters Acquity UPLCMS SingleQuad; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 4:
Instrument: Waters Acquity UPLCMS Single Quad; column: Kinetex 2.6 µm, 50×2.1 mm; Eluent A: water+0.05% formic acid (99%); Eluent B: acetonitrile+0.05% formic acid (99%); gradient: 0-1.91-99% B, 1.9-2.1 99% B; flow 1.3 mL/min; temperature: 60° C.; DAD scan: 200-400 nm.

Method 5:
(prep. HPLC) System: Labomatic, Pump: HD-5000, Fraction Collector: LABOCOL Vario-4000, UV-Detector: Knauer UVD 2.1S; Column: Chromatorex RP C18 10 µm 125×30 mm; Solvent: A=water+0.1% Vol. ammonia (99%), B=Acetonitril; Flow: 150 mL/min; temperature: room temperature Method 6:
Instrument: Waters Acquity UPLCMS SingleQuad; Colum: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm Method 7:
Instrument: Agilent 1290 UPLCMS 6230 TOF; column: BEH C 18 1.7 µm, 50×2.1 mm; Eluent A: water+0.05% formic acid (99%); Eluent B: acetonitrile+0.05% formic acid (99%); gradient: 0-1.72-90% B, 1.7-2.0 90% B; flow 1.2 mL/min; temperature: 60° C.; DAD scan: 190-400 nm.

Method 8:
Waters Acquity Binary pump (Flow 0.8 mL/min), column: CSH C18 1.7 µm 2.1×50 mm, Waters Acquity Autosampler, Waters Acquity QDA, Waters Acquity PDA, Run Time: 4.60 min, solvents: C) 10 mM ammonium bicarbonate pH 10, B) MeCN, gradient: 2-98% B in 4.00 min, hold at 98% B to 4.60 min.

Method 9:
MS instrument type: Agilent 1200 LC/G1956A MSD; HPLC instrument type: Agilent ChemStation Rev.B.04.03; column: Kinetex EVO C18 2.1×30 mm, 5 µm; mobile phase A: 0.0375% TFA in Water (v/v), mobile phase B: 0.01875% TFA in Acetonitrile (v/v); gradient: 0.01 min 5% B® 0.80 min 95% B® 1.2 min 95% B® 1.21 min 5% B® 1.5 min 5% B; flow rate: 1.5 mL/min; oven temperature: 50° C.; UV detection: 220 nm & 254 nm.

Method 10:
MS instrument type: SHIMADZU LCMS-2020; HPLC instrument type: LabSolutions Version 5.72; column: Chromolith@Flash RP-18E 25-2 MM; mobile phase A: 0.0375% TFA in water (v/v), mobile phase B: 0.01875% TFA in Acetonitrile (v/v); gradient: 0.00 min 0% B® 0.80 min 60% B® 1.20 min 60% B® 1.21 min 0% B® 1.5 min 0% B; flow rate: 1.5 mL/min; oven temperature: 50° C.; UV detection: 220 nm & 254 nm.

Experimental Section—Intermediates

Intermediate 1 phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate

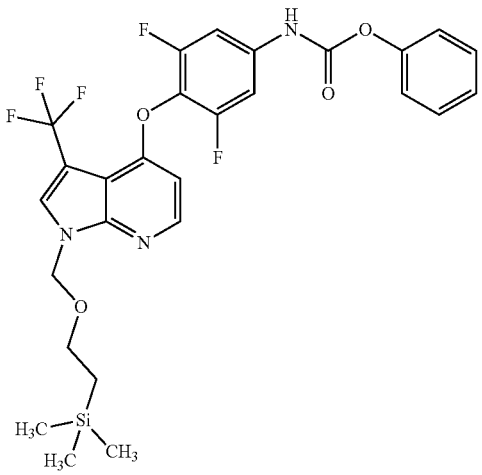 [SMILES: C[Si](C)(C)CCOCn1cc(C(F)(F)F)c2c(Oc3c(F)cc(NC(=O)Oc4ccccc4)cc3F)ccnc21]

To solution of 3,5-difluoro-4-{[3-(trifluoromethyl)-1-{[2-(trimethylsilyl)ethoxy]methyl}-1H-pyrrolo[2,3-b]pyridin-4-yl]oxy}aniline (4.00 g, 8.71 mmol, see *Synthesis* 2007, page 251-258, *Org. Process Res. Dev.* 2010, page 168-173) in pyridine (4.0 mL) and THF (60 mL) was slowly added at 0° C. phenyl carbonochloridate (1.2 mL, 9.6 mmol). After stirring this mixture 5 minutes at 0° C. and then 30 minutes at room temperature ethyl acetate was added. This organic phase was washed with 1N hydrochloric acid (75 mL), water, concentrated aqueous sodium hydrogencarbonate, brine, dried over sodium sulfate, filtered and concentrated to dryness. The resulting residue was purified via a Biotage chromatography system (100 g snap KP-Sil column, hexane/0-100% ethyl acetate, then ethyl acetate/0-75% methanol) to obtain 4.53 g (92% purity, 83% yield) of the desired title compound.

$^1$H-NMR (400 MHz, DMSO-d6) δ [ppm]: −0.10 (s, 9H), 0.79-0.86 (m, 2H), 3.54-3.61 (m, 2H), 5.69 (s, 2H), 6.61 (d, 1H), 7.24-7.32 (m, 3H), 7.42-7.50 (m, 4H), 8.27-8.33 (m, 1H), 8.35-8.40 (m, 1H), 10.81 (s, 1H).

Intermediate 2

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-(oxetan-3-ylmethyl)urea

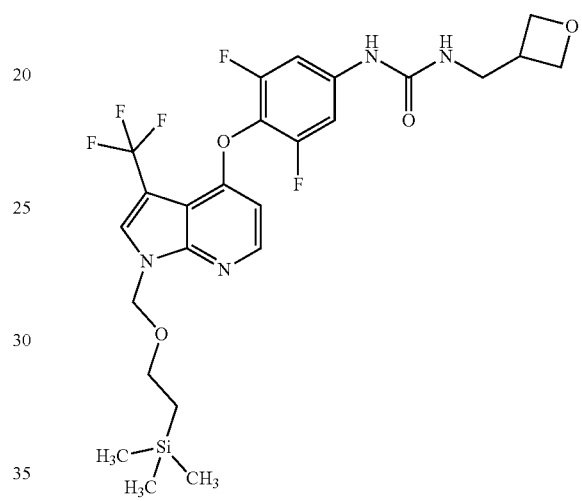

To solution of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1) in DMF (1.5 mL) was added 1-(oxetan-3-yl)methanamine (22.5 mg, 259 μmol, CAS No. [6246-05-5]) and this mixture was stirred at 60° C. for 2 hours. After cooling to room temperature ethyl acetate and water was added. After separation of the organic phase the aqueous phase was extracted two times with ethyl acetate. The combined organic phases were washed with brine, dried over sodium sulfate, filtered and concentrated to dryness. The resulting residue was purified via a Biotage chromatography system (11 g snap KP-NH column, hexane/0-100% ethyl acetate, then ethyl acetate/0-100% methanol) to obtain 151 mg (94% purity, 96% yield) of the desired title compound.

$^1$H-NMR (400 MHz, DMSO-d6) δ [ppm]: −0.11--0.08 (m, 9H), 0.80-0.86 (m, 2H), 3.09 (spt, 1H), 3.34-3.40 (m, 2H), 3.54-3.60 (m, 2H), 4.31 (t, 2H), 4.62 (dd, 2H), 5.68 (s, 2H), 6.57 (d, 1H), 6.67 (t, 1H), 7.36-7.42 (m, 2H), 8.28 (d, 1H), 8.36 (s, 1H), 9.08 (s, 1H).

Intermediate 3

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

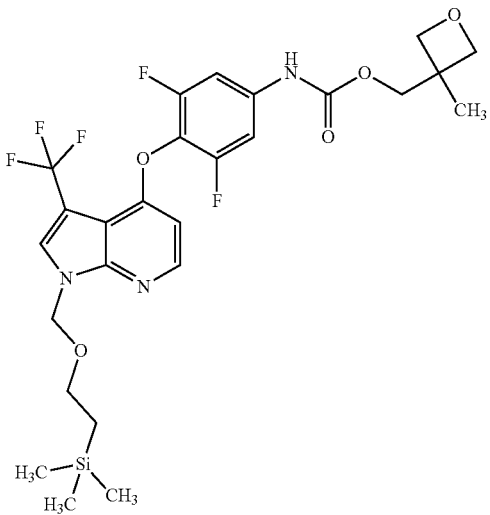 [SMILES: CC1(COC(=O)Nc2cc(F)c(Oc3ccnc4c3c(C(F)(F)F)cn4COCC[Si](C)(C)C)c(F)c2)COC1]

To a solution of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (250 mg, 431 µmol intermediate 1) in DMF (2.1 mL) was added 1-(3-methyloxetan-3-yl)methanamine (43.6 mg, 431 µmol, CAS No. [153209-97-3]) and this mixture was stirred at 50° C. for 12 hours. After cooling to room temperature ethyl acetate and water was added. After separation of the organic phase the aqueous phase was extracted two times with ethyl acetate. The combined organic phases were washed with brine, dried over sodium sulfate, filtered and concentrated to dryness. The resulting residue was purified via a Biotage chromatography system (10 g snap KP-Sil hexane/0-100% ethyl acetate, then ethyl acetate/0-100% methanol) to obtain 178 mg (80% purity, 56% yield) of the desired title compound.

$^1$H-NMR (400 MHz, DMSO-d6) δ [ppm]: −0.15--−0.06 (m, 9H), 0.79-0.87 (m, 2H), 1.23 (s, 3H), 3.25-3.31 (m, 2H), 3.54-3.62 (m, 2H), 4.20 (d, 2H), 4.39 (d, 2H), 5.68 (s, 2H), 6.58 (d, 1H), 6.93 (t, 1H), 7.36-7.44 (m, 2H), 8.28 (d, 1H), 8.36 (s, 1H), 9.26 (br s, 1H).

Intermediate 4

1-[(3-cyanooxetan-3-yl)methyl]-3-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)urea

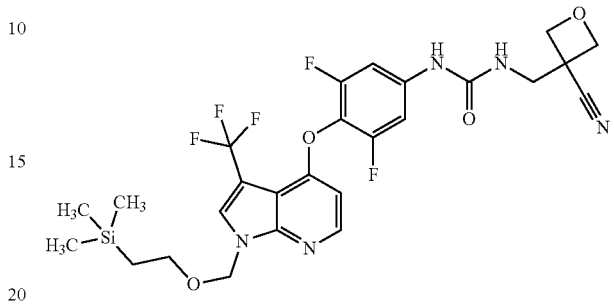

To a solution of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 µmol, intermediate 1) in DMF (0.7 mL) was added 3-(aminomethyl)oxetane-3-carbonitrile hydrochloride (1:1) (38.5 mg, 259 µmol, ordered from SpiroChem AG, CAS No. for free base [1374653-22-1]) and N,N-diisopropylethylamine (45 µL, 260 µmol) and this mixture was stirred at 60° C. for 2 hours. After cooling to room temperature ethylacetate and water was added. After separation of the organic phase the aqueous phase was extracted two times with ethaylacetate. The combined organic phases were washed with brine, dried over sodium sulfate, filtered and concentrated to dryness. The resulting residue was purified via a Biotage chromatography system (11 g snap KP-NH column, hexane/ethylacetate/50-100% ethylacetate and ethylacetate/ethanol/0-40% ethanol) to obtain 136 mg (100% purity, 88% yield) of the desired title compound.

LC-MS (Method 2): $R_t$=1.48 min; MS (ESIneg): m/z=597 [M−H]$^−$ $^1$H-NMR (400 MHz, DMSO-d6) δ [ppm]: −0.13--−0.06 (m, 9H), 0.79-0.86 (m, 2H), 3.54-3.60 (m, 2H), 3.76 (d, 2H), 4.61 (d, 2H), 4.78 (d, 2H), 5.68 (s, 2H), 6.59 (d, 1H), 7.03 (t, 1H), 7.37-7.44 (m, 2H), 8.28 (d, 1H), 8.36 (s, 1H), 9.23 (s, 1H).

Intermediate 5

1-{[3-(difluoromethyl)oxetan-3-yl]methyl}-3-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)urea

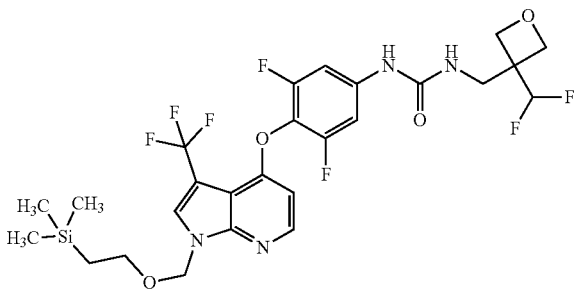 [SMILES: C[Si](C)(C)CCOCn1cc(C(F)(F)F)c2c(Oc3c(F)cc(NC(=O)NCC4(C(F)F)COC4)cc3F)ccnc21]

In analogy to intermediate 2), phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1), 1-[3-(difluoromethyl)oxetan-3-yl]methanamine (40.8 mg, 298 μmol, CAS No. [1781121-31-0]) together in DMF (0.7 mL) we obtained the crude product, which was purified via a Biotage chromatography system (11 g snap KP-NH column, hexane/ethylacetate/50-100% ethylacetate and ethylacetate/ethanol/0-50% ethanol) to obtain 126 mg (100% purity, 78% yield) of the desired title compound.

LC-MS (Method 2): $R_t$=1.54 min; MS (ESIpos): m/z=623 [M+H]$^+$ $^1$H-NMR (400 MHz, DMSO-d6) δ [ppm]: −0.11−−0.08 (m, 9H), 0.79-0.87 (m, 2H), 3.50-3.54 (m, 2H), 3.54-3.60 (m, 2H), 4.42-4.47 (m, 2H), 4.48-4.53 (m, 2H), 5.68 (s, 2H), 6.31 (t, 1H), 6.58 (d, 1H), 6.88 (t, 1H), 7.38-7.44 (m, 2H), 8.29 (d, 1H), 8.36 (s, 1H), 9.26 (s, 1H).

Intermediate 6

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-{[3-(propan-2-yl)oxetan-3-yl]methyl}urea

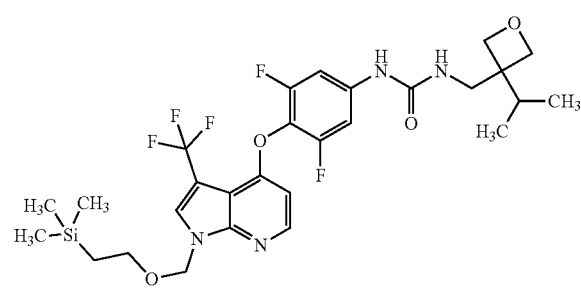 [SMILES: CC(C)C1(CNC(=O)Nc2cc(F)c(Oc3ccnc4c3c(C(F)(F)F)cn4COCC[Si](C)(C)C)c(F)c2)COC1]

In analogy to intermediate 2), phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1), 1-[3-(propan-2-yl)oxetan-3-yl]methanamine (38.5 mg, 298 μmol, CAS No. [1539197-30-2]) together in DMF (0.7 mL) we obtained the crude product, which was purified via a Biotage chromatography system (11 g snap KP-NH column, hexane/ethylacetate/50-100% ethylacetate and ethylacetate/ethanol/0-50% ethanol) to obtain 131 mg (100% purity, 82% yield) of the desired title compound.

LC-MS (Method 2): $R_t$=1.57 min; MS (ESIpos): m/z=615 [M+H]$^+$ $^1$H-NMR (400 MHz, DMSO-d6) δ [ppm]: −0.11−−0.08 (m, 9H), 0.80-0.86 (m, 2H), 0.91 (d, 6H), 1.96-2.05 (m, 1H), 3.32 (d, 2H), 3.54-3.61 (m, 2H), 4.28-4.34 (m, 4H), 5.68 (s, 2H), 6.59 (d, 1H), 6.75 (t, 1H), 7.38-7.44 (m, 2H), 8.28 (d, 1H), 8.36 (s, 1H), 9.12 (s, 1H).

Intermediate 7

(+/−)-1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3,3-dimethyloxetane-2-yl)methyl]urea

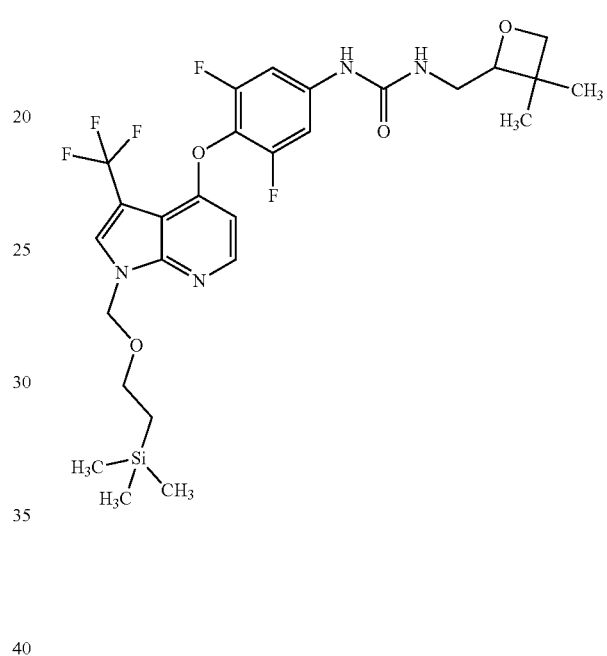

To a solution of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1) in DMF (1.3 mL) was added 1-(3,3-dimethyloxetane-2-yl)methanamine (29.8 mg, 259 μmol, CAS No. [34795-24-9]) and this mixture was stirred at 60° C. overnight. After cooling to room temperature ethylacetate and water was added. After separation of the organic phase the aqueous phase was extracted two times with ethaylacetate. The combined organic phases were washed with brine, dried with a hydrophobic filter and concentrated to dryness. The resulting residue was purified via a Biotage chromatography system (10 g snap KP-Sil column, hexane/ethylacetate/0-100% ethylacetate and ethylacetate/ethanol/0-100% ethanol) to obtain 169 mg (100% purity, 109% yield) of the desired title compound.

LC-MS (Method 1): $R_t$=1.55 min; MS (ESIpos): m/z=601 [M+H]$^+$ $^1$H-NMR (400 MHz, DMSO-d6) δ [ppm]: −0.13−−0.06 (m, 9H), 0.79-0.87 (m, 2H), 1.17 (s, 3H), 1.24 (s, 3H), 3.28-3.43 (m, 2H), 3.54-3.60 (m, 2H), 4.10 (d, 1H), 4.19 (d, 1H), 4.31 (dd, 1H), 5.68 (s, 2H), 6.48 (t, 1H), 6.58 (d, 1H), 7.34-7.41 (m, 2H), 8.28 (d, 1H), 8.36 (s, 1H), 9.08 (s, 1H).

Intermediate 8

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-oxetan-3-ylurea

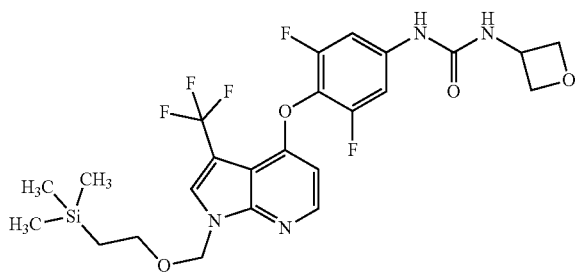 [SMILES: C[Si](C)(C)CCOCn1cc(C(F)(F)F)c2c(Oc3c(F)cc(NC(=O)NC4COC4)cc3F)ccnc21]

In analogy to intermediate 7), of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 µmol, intermediate 1), oxetan-3-amine (18.9 mg, 259 µmol, CAS No. [21635-88-1]) together in DMF (1.3 mL) we obtained the crude product, which was purified via a Biotage chromatography system (10 g snap KP-Sil column, hexane/ethylacetate/0-100% ethylacetate and ethylacetate/ethanol/0-100% ethanol) to obtain 96.0 mg (100% purity, 66% yield) of the desired title compound.

LC-MS (Method 1): $R_t$=1.46 min; MS (ESIpos): m/z=559 [M+H]$^+$ $^1$H-NMR (400 MHz, DMSO-d6) δ [ppm]: −0.12-−0.06 (m, 9H), 0.79-0.87 (m, 2H), 3.54-3.60 (m, 2H), 4.46 (t, 2H), 4.70-4.81 (m, 3H), 5.68 (s, 2H), 6.57 (d, 1H), 7.34 (d, 1H), 7.36-7.43 (m, 2H), 8.28 (d, 1H), 8.36 (s, 1H), 9.22 (s, 1H).

Intermediate 9

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-fluorooxetan-3-yl)methyl]urea

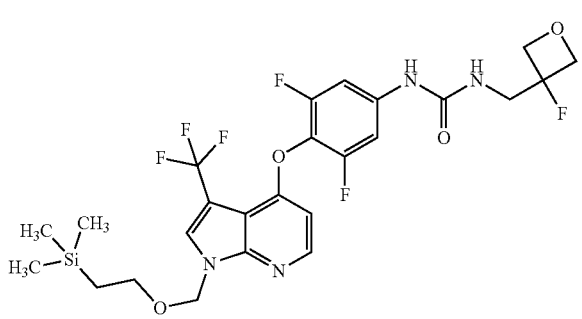 [SMILES: C[Si](C)(C)CCOCn1cc(C(F)(F)F)c2c(Oc3c(F)cc(NC(=O)NCC4(F)COC4)cc3F)ccnc21]

In analogy to intermediate 4), phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 µmol, intermediate 1), 1-(3-fluorooxetan-3-yl)methanamine (27.2 mg, 259 µmol, CAS No. [883311-82-8]) together in DMF (1.5 mL) and N,N-diisopropylethylamine (45 µL, 260 µmol) we obtained the crude product, which was purified via a Biotage chromatography system (11 g snap KP-NH column, hexane/ethylacetate/50-100% ethylacetate and ethylacetate/ethanol/0-40% ethanol) to obtain 133 mg (100% purity, 87% yield) of the desired title compound.

LC-MS (Method 2): $R_t$=1.49 min; MS (ESIpos): m/z=591 [M+H]$^+$ $^1$H-NMR (400 MHz, DMSO-d6) δ [ppm]: −0.12-−0.06 (m, 9H), 0.79-0.86 (m, 2H), 3.54-3.60 (m, 2H), 3.61-3.70 (m, 2H), 4.55-4.67 (m, 4H), 5.68 (s, 2H), 6.58 (d, 1H), 6.81 (t, 1H), 7.37-7.43 (m, 2H), 8.28 (d, 1H), 8.36 (s, 1H), 9.13 (s, 1H).

Intermediate 10

3-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamoyl]amino}oxetane-3-carboxamide

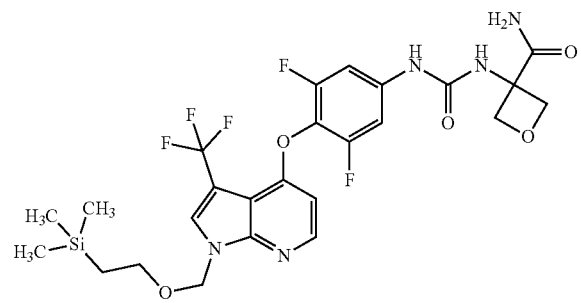 [SMILES: C[Si](C)(C)CCOCn1cc(C(F)(F)F)c2c(Oc3c(F)cc(NC(=O)NC4(C(N)=O)COC4)cc3F)ccnc21]

In analogy to intermediate 4 phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 µmol, intermediate 1), 3-aminooxetane-3-carboxamide (34.6 mg, 298 µmol, CAS No. [138650-60-9]) together in DMF (0.7 mL) and N,N-diisopropylethylamine (52 µL, 300 µmol) we obtained the crude product, which was purified via a Biotage chromatography system (11 g snap KP-NH column, hexane/ethylacetate/50-100% ethylacetate and ethylacetate/ethanol/0-50% ethanol) to obtain 66.6 mg (99% purity, 42% yield) of the desired title compound.

LC-MS (Method 2): $R_t$=1.37 min; MS (ESIpos): m/z=602 [M+H]$^+$ $^1$H-NMR (400 MHz, DMSO-d6) δ [ppm]: −0.12-−0.08 (m, 9H), 0.80-0.86 (m, 2H), 3.54-3.60 (m, 2H), 4.52 (d, 2H), 4.81 (d, 2H), 5.68 (s, 2H), 6.57 (d, 1H), 7.25 (s, 1H), 7.34 (s, 1H), 7.37-7.45 (m, 3H), 8.28 (d, 1H), 8.36 (s, 1H), 9.34 (s, 1H).

Intermediate 11

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-hydroxyoxetan-3-yl)methyl]urea

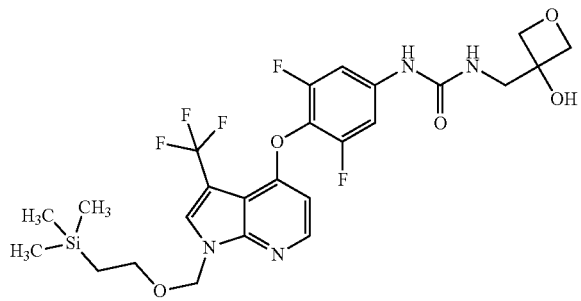 [SMILES: C[Si](C)(C)CCOCn1cc(C(F)(F)F)c2c(Oc3c(F)cc(NC(=O)NCC4(O)COC4)cc3F)ccnc21]

To solution of phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1) in DMF (1.2 mL) was added 3-(aminomethyl)oxetan-3-ol (26.7 mg, 259 μmol, CAS No. [1305208-47-2]) and this mixture was stirred at 60° C. for 16 hours. After cooling to room temperature ethyl acetate and water was added. After separation of the organic phase the aqueous phase was extracted two times with ethyl acetate. The combined organic phases were washed with brine, dried over sodium sulfate, filtered and concentrated to dryness. The resulting residue was purified via a Biotage chromatography system (10 g snap KP-Sil column, hexane/0-100% ethyl acetate, then ethyl acetate/0-100% ethanol) to obtain 200 mg (65% purity, 85% yield) of the desired title compound.

LC-MS (Method 1): $R_t$=1.41 min; MS (ESIpos): m/z=589 [M+H]$^+$ $^1$H-NMR (400 MHz, DMSO-d6) δ [ppm]: $^1$H-NMR (400 MHz, DMSO-d6): δ [ppm]=−0.15-−0.06 (m, 9H), 0.78-0.87 (m, 2H), 3.43 (d, 2H), 3.53-3.61 (m, 2H), 4.34-4.43 (m, 4H), 5.68 (s, 2H), 6.58 (br d, 2H), 7.37 (br d, 2H), 8.24-8.39 (m, 3H), 9.27 (s, 1H).

Intermediate 12

1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-phenyloxetan-3-yl)methyl]urea

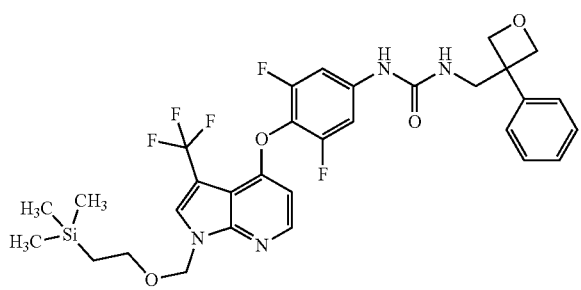 [SMILES: C[Si](C)(C)CCOCn1cc(C(F)(F)F)c2c(Oc3c(F)cc(NC(=O)NCC4(c5ccccc5)COC4)cc3F)ccnc21]

In analogy to intermediate 2), phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1), 1-(3-phenyloxetan-3-yl)methanamine (48.6 mg, 298 μmol, CAS No. [497239-45-9]) together in DMF (0.7 mL) we obtained the crude product, which was purified via a Biotage chromatography system (11 g snap KP-NH column, hexane/ethylacetate/50-100% ethylacetate and ethylacetate/ethanol/0-50% ethanol) to obtain 124 mg (100% purity, 74% yield) of the desired title compound.

LC-MS (Method 2): $R_t$=1.56 min; MS (ESIpos): m/z=649 [M+H]$^+$ $^1$H-NMR (400 MHz, DMSO-d6) δ [ppm]: −0.11-−0.08 (m, 9H), 0.79-0.87 (m, 2H), 3.53-3.61 (m, 2H), 3.65 (d, 2H), 4.70-4.79 (m, 4H), 5.68 (s, 2H), 6.53-6.62 (m, 2H), 7.16-7.20 (m, 2H), 7.26-7.43 (m, 5H), 8.28 (d, 1H), 8.36 (s, 1H), 9.13 (s, 1H).

Intermediate 13

(+/−)-1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(1R)-1-(oxetan-3-yl)ethyl]urea

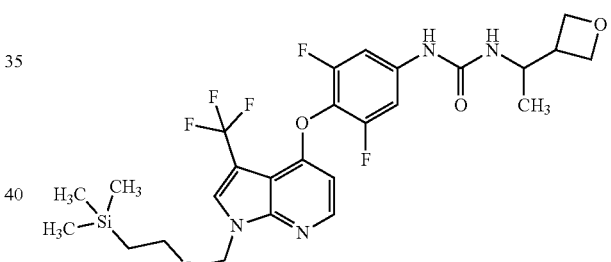

In analogy to intermediate 4), phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (150 mg, 259 μmol, intermediate 1), (+/−)-1-(oxetan-3-yl)ethanamine hydrochloride (41.0 mg, 298 μmol, CAS No. [2055842-00-5]) together in DMF (0.7 mL) and N,N-diisopropylethylamine (52 μL, 300 μmol) we obtained the crude product, which was purified via a Biotage chromatography system (11 g snap KP-NH column, hexane/ethylacetate/50-100% ethylacetate and ethylacetate/ethanol/0-50% ethanol) to obtain 79.5 mg (95% purity, 49% yield) of the desired title compound.

LC-MS (Method 2): $R_t$=1.47 min; MS (ESIpos): m/z=587 [M+H]$^+$ $^1$H-NMR (400 MHz, DMSO-d6) δ [ppm]: −0.12-−0.06 (m, 9H), 0.80-0.86 (m, 2H), 1.02 (d, 3H), 2.95-3.04 (m, 1H), 3.55-3.60 (m, 2H), 3.97-4.08 (m, 1H), 4.31 (t, 1H), 4.39 (t, 1H), 4.59 (ddd, 2H), 5.68 (s, 2H), 6.51 (d, 1H), 6.57 (d, 1H), 7.35-7.43 (m, 2H), 8.28 (d, 1H), 8.36 (s, 1H), 8.94 (s, 1H).

Intermediate 14

4-(2,6-difluoro-4-nitrophenoxy)-1H-pyrrolo[2,3-b]pyridine

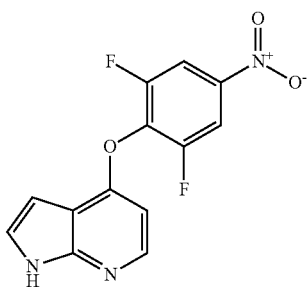 [SMILES: O=[N+]([O-])c1cc(F)c(Oc2ccnc3[nH]ccc23)c(F)c1]

A solution of 1,2,3-trifluoro-5-nitrobenzene (CAS No. [66684-58-0]; 3.59 g, 20.3 mmol) and 1H-pyrrolo[2,3-b]pyridin-4-ol (CAS No. [74420-02-3]; 1.10 eq., 2.99 g, 22.3 mmol) in DMSO (65 mL) was treated with potassium carbonate (4.00 eq, 11.2 g, 81.1 mmol) and stirred at room temperature for 1 hour. The reaction mixture was diluted with ethyl acetate (500 mL) and washed with water (3×200 mL) and brine (150 mL), dried with sodium sulfate and concentrated in vacuo. The obtained material was purified by flash chromatography (SiO$_2$-hexane/ethyl acetate) to give the title compound (3.1 g, 52%).

LC-MS (Method 2): R$_t$=1.13 min; MS (ESIpos): m/z=292 [M+H]$^+$.

$^1$H-NMR (400 MHz, DMSO-d$_6$) δ [ppm]=6.35 (d, 1H), 6.59 (d, 1H), 7.47 (d, 1H), 8.13 (d, 1H), 8.37-8.43 (m, 2H), 11.97 (br s, 1H).

Intermediate 15

4-(2,6-difluoro-4-nitrophenoxy)-1-{[2-(trimethylsilyl)ethoxy]methyl}-1H-pyrrolo[2,3-b]pyridine

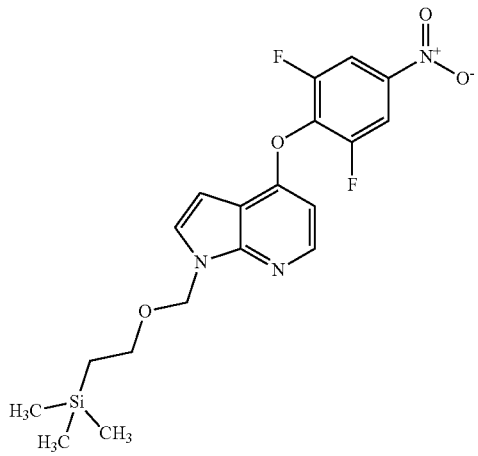 [SMILES: C[Si](C)(C)CCOCn1ccc2c(Oc3c(F)cc([N+](=O)[O-])cc3F)ccnc21]

An ice-cooled solution of 4-(2,6-difluoro-4-nitrophenoxy)-1H-pyrrolo[2,3-b]pyridine (intermediate 14; 3.11 g, 10.7 mmol) in acetonitrile (100 mL) was treated with N,N-diisopropyl ethylamine (1.80 eq, 3.35 mL, 19.2 mmol) and [2-(chloromethoxy)ethyl](trimethyl)silane (CAS No. [76513-69-4]; 1.40 eq, 2.65 mL, 15.0 mmol), warmed to rt and stirring continued overnight. The reaction mixture was poured on ice water (150 mL) and the aqueous phase extracted with ethyl acetate (2×400 mL). The combined organic layers were washed with brine (150 mL), dried with sodium sulfate and concentrated in vacuo. The obtained material was purified by flash chromatography (KP-NH®-SiO$_2$-hexane/ethyl acetate) to give the title compound (3.9 g, 85%).

LC-MS (Method 2): R$_t$=1.58 min; MS (ESIpos): m/z=422 [M+H]$^+$.

$^1$H-NMR (400 MHz, DMSO-d$_6$) δ [ppm]=−0.11 (s, 9H), 0.79-0.83 (m, 2H), 3.50-3.54 (m, 2H), 5.64 (s, 2H), 6.48 (d, 1H), 6.69 (d, 1H), 7.66 (d, 1H), 8.20 (d, 1H), 8.38-8.44 (m, 2H).

Intermediate 16

3-bromo-4-(2,6-difluoro-4-nitrophenoxy)-1-{[2-(trimethylsilyl)ethoxy]methyl}-1H-pyrrolo[2,3-b]pyridine

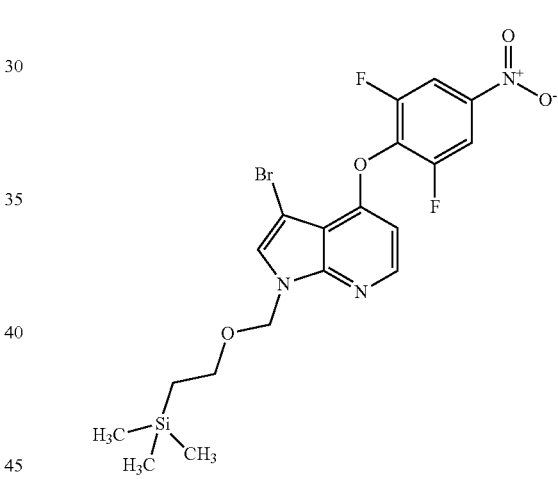

A solution of 4-(2,6-difluoro-4-nitrophenoxy)-1-{[2-(trimethylsilyl)ethoxy]methyl}-1H-pyrrolo[2,3-b]pyridine (intermediate 15; 1.55 g, 3.68 mmol) in DMF (31 mL) was treated with 1-bromopyrrolidine-2,5-dione (CAS No. [128-08-5]; 1.10 eq, 720 mg, 4.05 mmol) and stirred at rt overnight. The reaction mixture was diluted with water and extracted with ethyl acetate. The organic layer was washed with aqueous sat. sodium hydrocarbonate solution and brine, filtrated over a hydrophobic phase separation filter paper and concentrated in vacuo. The obtained material was purified by flash chromatography (SiO$_2$-hexane/ethyl acetate) to give the title compound (1.57 g, 85%).

LC-MS (Method 2): R$_t$=1.61 min; MS (ESIpos): m/z=500/502 [M+H]$^+$ (Br isotope pattern).

$^1$H-NMR (400 MHz, DMSO-d$_6$) δ [ppm]=−0.09 (s, 9H), 0.79-0.86 (m, 2H), 3.52-3.56 (m, 2H), 5.62 (s, 2H), 6.67 (d, 1H), 7.94 (s, 1H), 8.22 (d, 1H), 8.40-8.45 (m, 2H).

Intermediate 17

4-[4-(2,6-difluoro-4-nitrophenoxy)-1-{[2-(trimethylsilyl)ethoxy]methyl}-1H-pyrrolo[2,3-b]pyridin-3-yl]benzonitrile

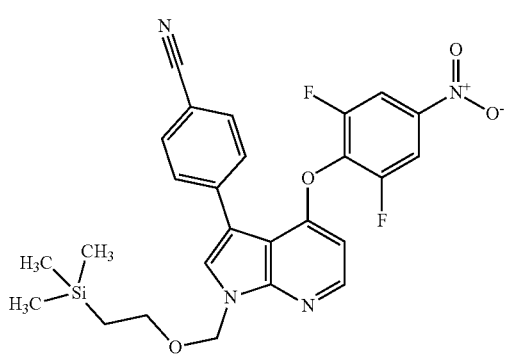 [SMILES: C[Si](C)(C)CCOCn1cc(-c2ccc(C#N)cc2)c2c(Oc3c(F)cc([N+](=O)[O-])cc3F)ccnc21]

A mixture of 3-bromo-4-(2,6-difluoro-4-nitrophenoxy)-1-{[2-(trimethylsilyl)ethoxy]methyl}-1H-pyrrolo[2,3-b]pyridine (100 mg, 200 µmol, intermediate 16), (4-cyanophenyl)boronic acid (58.7 mg, 400 µmol, CAS No. [126747-14-6]), [1,1'-bis (diphenylphosphino)ferrocene]dichloropalladium (II) (14.6 mg, 20.0 µmol), potassium carbonate (138 mg, 999 µmol) in water (1.0 mL) and dioxan (2.0 mL) in an argon atmosphere was heated for 3 hours at 100° C. In a second experiment we used in analogy to the first experiment 3-bromo-4-(2,6-difluoro-4-nitrophenoxy)-1-{[2-(trimethylsilyl)ethoxy]methyl}-1H-pyrrolo[2,3-b]pyridine (400 mg, 800 µmol, intermediate 16), (4-cyanophenyl)boronic acid (235 mg, 1.6 mmol), [1,1'-bis (diphenylphosphino)ferrocene]dichloropalladium(II) (58.5 mg, 80.0 µmol), potassium carbonate (552 mg, 4.0 mmol) in water (4.0 mL) and dioxan (8.0 mL) heated in an argon atmosphere for 3 hours at 100° C. After cooling of each experiment the combined reaction mixture were diluted with ethyl acetate and this organic phase was washed with water and brine, filtrated over a hydrophobic phase separation filter paper and evaporated to dryness in vacuum. The residue was purified via a Biotage chromatography system (28 g snap KP-NH column, hexane/0-80% ethyl acetate) to obtain 396 mg (purity 65%, yield 62%) of the desired title compound.

$^1$H-NMR (400 MHz, DMSO-d6) δ [ppm]: −0.12--0.07 (m, 9H), 0.82-0.88 (m, 2H), 3.58-3.64 (m, 2H), 5.71 (s, 2H), 6.69 (d, 1H), 7.85 (d, 2H), 7.98 (d, 2H), 8.12 (s, 1H), 8.26 (d, 1H), 8.38-8.44 (m, 2H).

Intermediate 18

4-[4-(4-amino-2,6-difluorophenoxy)-1-{[2-(trimethylsilyl)ethoxy]methyl}-1H-pyrrolo[2,3-b]pyridin-3-yl]benzonitrile

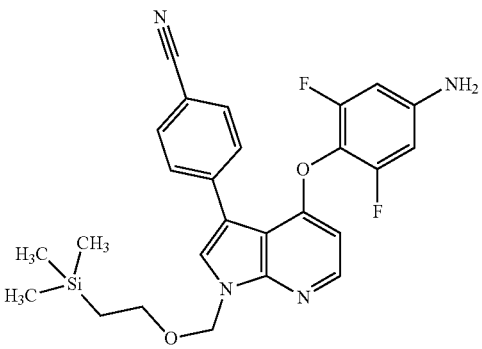 [SMILES: C[Si](C)(C)CCOCn1cc(-c2ccc(C#N)cc2)c2c(Oc3c(F)cc(N)cc3F)ccnc21]

Ammonium chloride (201 mg, 3.76 mmol) and iron (210 mg, 3.76 mmol) were suspended in water (10 mL). 4-[4-(2,6-difluoro-4-nitrophenoxy)-1-{[2-(trimethylsilyl)ethoxy]methyl}-1H-pyrrolo[2,3-b]pyridin-3-yl]benzonitrile (393 mg, 752 µmol, intermediate 17) was dissolved in THF (5.2 mL) and methanol (5.2 mL) and added to the suspension, that was heated at 80° C. for 3 h with stirring. The mixture was diluted with ethyl acetate and filtered. The phases were separated and the organic phase was washed with brine, filtrated over a hydrophobic phase separation filter paper and evaporated to dryness. The crude product was purified via a Biotage chromatography system (11 g snap KP-NH column, hexane/10-80% ethyl acetate) to obtain 253 mg (97% purity, 66% yield) of the desired title compound.

LC-MS (Method 2): $R_t$=1.51 min; MS (ESIpos): m/z=493 [M+H]$^+$ $^1$H-NMR (400 MHz, DMSO-d6) δ [ppm]: −0.12--0.08 (m, 9H), 0.80-0.89 (m, 2H), 3.56-3.63 (m, 2H), 5.68 (s, 2H), 5.83 (s, 2H), 6.35-6.43 (m, 2H), 6.45 (d, 1H), 7.86 (s, 4H), 8.04 (s, 1H), 8.21 (d, 1H).

Intermediate 19 phenyl (4-{[3-(4-cyanophenyl)-1-{[2-(trimethylsilyl)ethoxy]methyl}-1H-pyrrolo[2,3-b]pyridin-4-yl]oxy}-3,5-difluorophenyl)carbamate

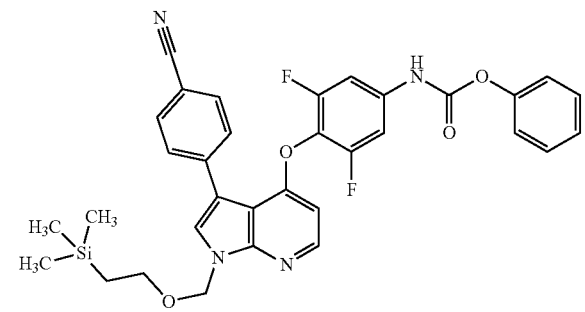 [SMILES: C[Si](C)(C)CCOCn1cc(-c2ccc(C#N)cc2)c2c(Oc3c(F)cc(NC(=O)Oc4ccccc4)cc3F)ccnc21]

In analogy to intermediate 1), 4-[4-(4-amino-2,6-difluorophenoxy)-1-{[2-(trimethylsilyl)ethoxy]methyl}-1H-pyrrolo[2,3-b]pyridin-3-yl]benzonitrile (248 mg, 503 µmol,

95 intermediate 18), phenyl carbonochloridate (69 μL, 550 μmol) together in pyridine (240 μL, 2.9 mmol) and THF (3.6 mL) we obtained the crude product, which was purified via a Biotage chromatography system (10 g snap KP-Sil column, hexane/ethylacetate/0-70% ethylacetate) to obtain 263 mg (99% purity, 84% yield) of the desired title compound.

LC-MS (Method 2): $R_t$=1.63 min; MS (ESIpos): m/z=614 [M+H]$^+$ $^1$H-NMR (400 MHz, DMSO-d6) δ [ppm]: −0.09 (s, 9H), 0.80-0.89 (m, 2H), 3.55-3.65 (m, 2H), 5.70 (s, 2H), 6.52 (br d, 1H), 7.23-7.33 (m, 3H), 7.40-7.51 (m, 4H), 7.87 (s, 4H), 8.08 (s, 1H), 8.23 (d, 1H), 10.80 (br s, 1H).

Intermediate 20

1-(4-{[3-(4-cyanophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

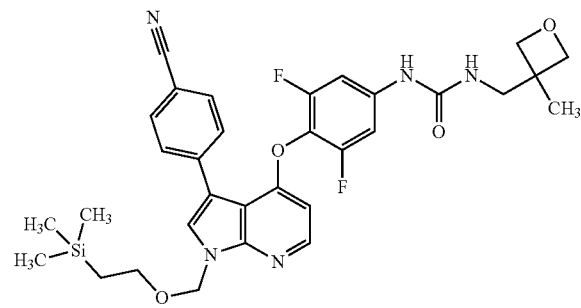 [SMILES: CC1(CNC(=O)Nc2cc(F)c(Oc3ccnc4c3c(-c3ccc(C#N)cc3)cn4COCC[Si](C)(C)C)c(F)c2)COC1]

In analogy to intermediate 2), phenyl (4-{[3-(4-cyanophenyl)-1-{[2-(trimethylsilyl)ethoxy]methyl}-1H-pyrrolo[2,3-b]pyridin-4-yl]oxy}-3,5-difluorophenyl)carbamate (85.0 mg, 139 μmol, intermediate 19), 1-(3-methyloxetan-3-yl)methanamine (14.0 mg, 139 μmol, CAS No. [153209-97-3]) together in DMF (0.7 mL) we obtained the crude product, which was purified via a Biotage chromatography system (11 g snap KP-NH column, hexane/ethylacetate/50-100% ethylacetate and ethylacetate/ethanol/0-40% ethanol) to obtain 67.6 mg (100% purity, 79% yield) of the desired title compound.

LC-MS (Method 2): $R_t$=1.47 min; MS (ESIpos): m/z=621 [M+H]$^+$ $^1$H-NMR (400 MHz, DMSO-d6) δ [ppm]: −0.09 (s, 9H), 0.81-0.88 (m, 2H), 1.23 (s, 3H), 3.30 (br d, 2H), 3.56-3.63 (m, 2H), 4.21 (d, 2H), 4.38 (d, 2H), 5.69 (s, 2H), 6.49 (d, 1H), 6.71 (t, 1H), 7.35-7.43 (m, 2H), 7.86 (s, 4H), 8.07 (s, 1H), 8.21 (d, 1H), 9.02 (s, 1H).

96

Intermediate 21

4-[(3-bromo-1-{[2-(trimethylsilyl)ethoxy]methyl}-1H-pyrrolo[2,3-b]pyridin-4-yl)oxy]-3,5-difluoroaniline

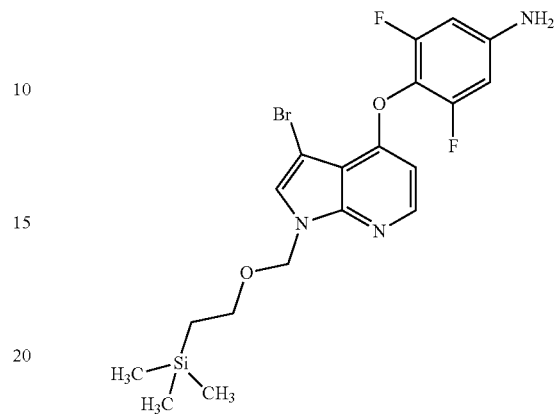

A solution of 3-bromo-4-(2,6-difluoro-4-nitrophenoxy)-1-{[2-(trimethylsilyl)ethoxy]methyl}-1H-pyrrolo[2,3-b]pyridine (intermediate 16; 3.25 g, 6.50 mmol) in methanol (130 mL) was treated with tin(II) chloride dihydrate (CAS No. [10025-69-1]; 3.00 eq, 4.40 g, 19.5 mmol) and stirred at 65 C overnight. The reaction mixture was cooled to rt and concentrated in vacuo. The residue was taken up with ethyl acetate and aqueous sat. sodium carbonate solution, filtrated over diatomite and the phases separated. The organic phase was washed with aqueous sat. sodium carbonate solution, dried with sodium sulfate and concentrated in vacuo. The obtained material was purified by flash chromatography (SiO$_2$-hexane/ethyl acetate) to give the title compound (2.28 g, 67%).

LC-MS (Method 2): $R_t$=1.53 min; MS (ESIpos): m/z=470/472 [M+H]$^+$ (Br isotope pattern).

$^1$H-NMR (400 MHz, DMSO-d$_6$) δ [ppm]=−0.09 (s, 9H), 0.80-0.84 (m, 2H), 3.50-3.54 (m, 2H), 5.59 (s, 2H), 5.82 (br s, 2H), 6.36-6.42 (m, 3H), 7.83 (s, 1H), 8.16 (d, 1H).

Intermediate 22 phenyl {4-[(3-bromo-1-{[2-(trimethylsilyl)ethoxy]methyl}-1H-pyrrolo[2,3-b]pyridin-4-yl)oxy]-3,5-difluorophenyl}carbamate

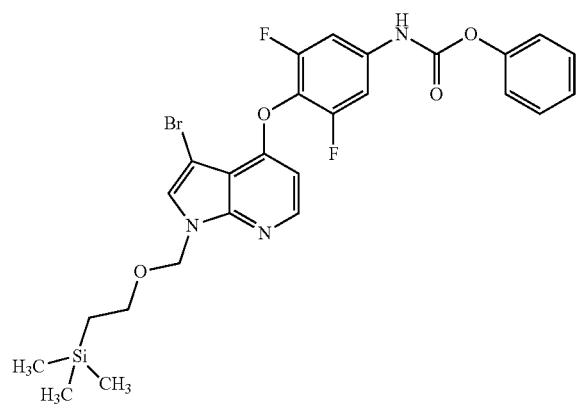 [SMILES: C[Si](C)(C)CCOCn1cc(Br)c2c(Oc3c(F)cc(NC(=O)Oc4ccccc4)cc3F)ccnc21]

An ice-cooled solution of 4-[(3-bromo-1-{[2-(trimethyl-silyl)ethoxy]methyl}-1H-pyrrolo[2,3-b]pyridin-4-yl)oxy]-3,5-difluoroaniline (intermediate 21; 2.20 g, 4.68 mmol) and pyridine (5.0 eq., 1.9 mL, 23 mmol) in THF (25 mL) was treated with phenyl chloroformate (CAS No. [1885-14-9]; 1.3 eq, 0.76 mL, 6.1 mmol), the mixture warmed to rt and stirring continued for 4 hours. The reaction mixture was diluted with ethyl acetate and washed with 1 M aqueous hydrochloric acid, aqueous sat. sodium hydrocarbonate solution and brine. The resulting organic layer was dried with sodium sulfate and concentrated in vacuo to give the crude title compound (3.5 g) containing 1-{4-[(3-bromo-1-{[2-(trimethylsilyl)ethoxy]methyl}-1H-pyrrolo[2,3-b]pyridin-4-yl)oxy]-3,5-difluorophenyl}urea which was used as is in the next steps.

LC-MS (Method 2): $R_t$=1.66 min; MS (ESIpos): m/z=590/592 [M+H]$^+$ (Br isotope pattern).

Intermediate 23

1-{4-[(3-bromo-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea

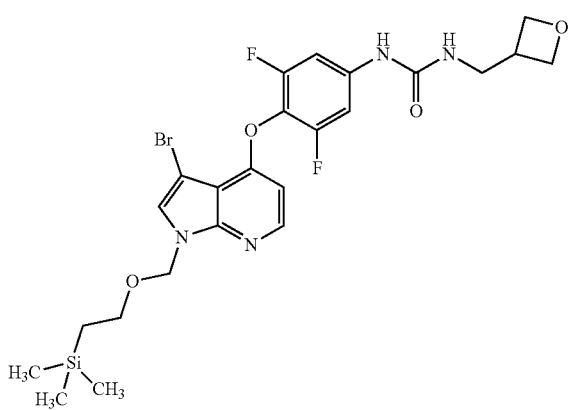 [SMILES: C[Si](C)(C)CCOCn1cc(Br)c2c(Oc3c(F)cc(NC(=O)NCC4COC4)cc3F)ccnc21]

A solution of phenyl {4-[(3-bromo-1-{[2-(trimethylsilyl)ethoxy]methyl}-1H-pyrrolo[2,3-b]pyridin-4-yl)oxy]-3,5-difluorophenyl}carbamate (150 mg, 81% purity, 206 µmol, intermediate 22) in DMF (1.5 mL) was treated with 1-(oxetan-3-yl)methanamine (1.0 eq., 18 mg, 206 µmol, CAS No. [6246-05-5]) and stirred at 60° C. for 2 hours. The reaction mixture was concentrated in vacuo to give the crude title compound which was used in the next step without any further purification.

LC-MS (Method 2): $R_t$=1.44 min; MS (ESIpos): m/z=583/585 [M+H]$^+$ (Br isotope pattern).

Intermediate 24

1-{4-[(3-bromo-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea

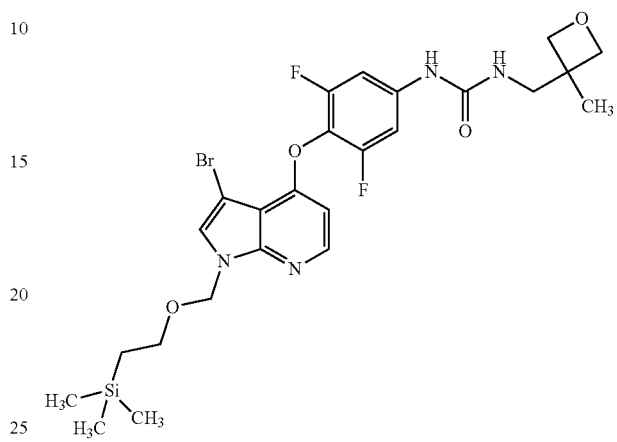

A solution of phenyl {4-[(3-bromo-1-{[2-(trimethylsilyl)ethoxy]methyl}-1H-pyrrolo[2,3-b]pyridin-4-yl)oxy]-3,5-difluorophenyl}carbamate (225 mg, 381 µmol, intermediate 22) in DMF (4 mL) was treated with 1-(3-methyloxetan-3-yl)methanamine (1.2 eq., 46 mg, 457 µmol, CAS No. [153209-97-3]) and stirred at 70° C. for 18 hours. The reaction mixture was diluted with ethyl acetate and water and the layers separated. The organic layer was concentrated in vacuo to give the crude title compound which was used in the next step without any further purification.

LC-MS (Method 2): $R_t$=1.44 min; MS (ESIpos): m/z=597/599 [M+H]$^+$ (Br isotope pattern).

Intermediate 25

4-(2,6-difluoro-4-nitrophenoxy)-3-iodo-1-{[2-(trimethylsilyl)ethoxy]methyl}-1H-pyrrolo[2,3-b]pyridine

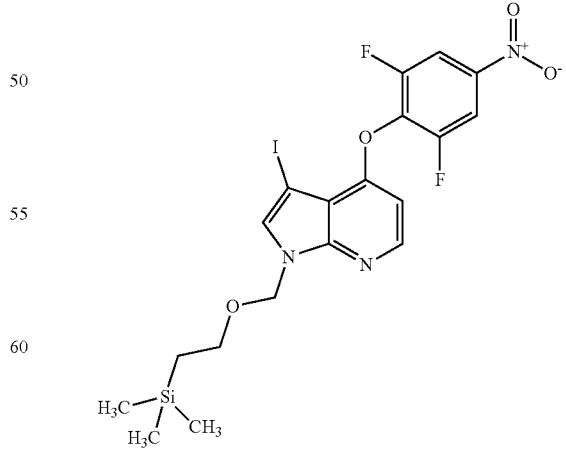

A solution of 4-(2,6-difluoro-4-nitrophenoxy)-1-{[2-(trimethylsilyl)ethoxy]methyl}-1H-pyrrolo[2,3-b]pyridine (5.00 g, 11.9 mmol, intermediate 15) in DMF (100 mL) was treated with 1-iodopyrrolidine-2,5-dione (1.50 eq, 4.00 g, 17.8 mmol) and stirred at room temperature for 2 hours. The reaction mixture was diluted with water and ethyl acetate, the layers were separated and the aqueous layer extracted with ethyl acetate. The combined organic layers were washed with aqueous sat. sodium hydrocarbonate solution and brine, filtrated over a hydrophobic phase separation filter paper and concentrated in vacuo. The obtained material was purified by flash chromatography (100 g SI Snap-column, hexane/0-34% ethyl acetate) to give the title compound (6.27 g, 92% yield).

LC-MS (Method 2): $R_t$=1.64 min; MS (ESIpos): m/z=548 [M+H]$^+$.

$^1$H-NMR (400 MHz, DMSO-d$_6$) δ [ppm]=−0.09 (s, 9H), 0.80-0.84 (m, 2H), 3.51-3.55 (m, 2H), 5.61 (s, 2H), 6.64 (d, 1H), 7.93 (s, 1H), 8.21 (d, 1H), 8.40-8.45 (m, 2H).

Intermediate 26

4-(2,6-difluoro-4-nitrophenoxy)-1-{[2-(trimethylsilyl)ethoxy]methyl}-1H-pyrrolo[2,3-b]pyridine-3-carbonitrile

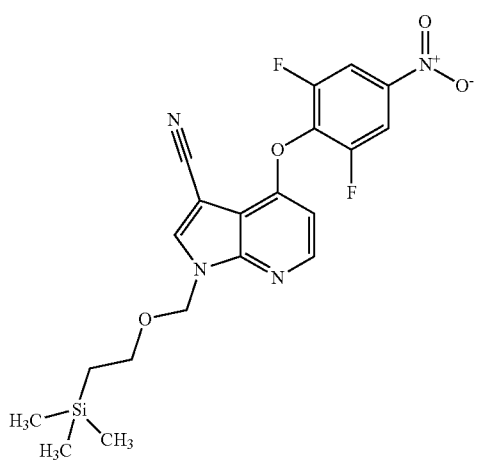 [SMILES: C[Si](C)(C)CCOCn1cc(C#N)c2c(Oc3c(F)cc([N+](=O)[O-])cc3F)ccnc21]

A solution of 4-(2,6-difluoro-4-nitrophenoxy)-3-iodo-1-{[2-(trimethylsilyl)ethoxy]methyl}-1H-pyrrolo[2,3-b]pyridine (intermediate 25; 3.04 g, 5.55 mmol) in DMF (15 mL) was treated with copper(I) cyanide (CAS No. [544-92-3]; 1.30 eq., 647 mg, 7.22 mmol) and stirred at 120 C for 20 hours. The reaction mixture was taken up with ethyl acetate and water, the phases separated and the aqueous phase extracted with ethyl acetate (2×). The combined organic phases were washed with water and brine, dried with sodium sulfate and concentrated in vacuo. The obtained material was purified by flash chromatography (SiO$_2$-hexane/ethyl acetate) to give the title compound (2.17 g, 87%).

LC-MS (Method 2): $R_t$=1.50 min; MS (ESIpos): m/z=447 [M+H]$^+$.

$^1$H-NMR (400 MHz, DMSO-d$_6$) δ [ppm]=−0.10 (s, 9H), 0.82-0.86 (m, 2H), 3.56-3.60 (m, 2H), 5.70 (s, 2H), 6.87 (d, 1H), 8.36 (d, 1H), 8.43-8.48 (m, 2H), 8.73 (s, 1H).

Intermediate 27

4-(4-amino-2,6-difluorophenoxy)-1-{[2-(trimethylsilyl)ethoxy]methyl}-1H-pyrrolo[2,3-b]pyridine-3-carbonitrile

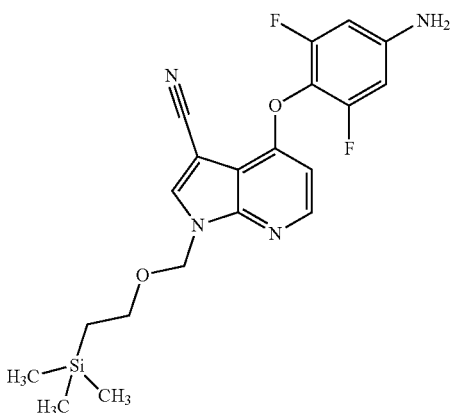 [SMILES: C[Si](C)(C)CCOCn1cc(C#N)c2c(Oc3c(F)cc(N)cc3F)ccnc21]

A solution of 4-(2,6-difluoro-4-nitrophenoxy)-1-{[2-(trimethylsilyl)ethoxy]methyl}-1H-pyrrolo[2,3-b]pyridine-3-carbonitrile (intermediate 26; 1.05 g, 2.35 mmol) in methanol (15 mL) was treated with tin(II) chloride dihydrate (CAS No. [10025-69-1]; 3.00 eq, 1.59 g, 7.06 mmol) and stirred at 65° C. overnight. The reaction mixture was cooled to rt and concentrated in vacuo. The residue was taken up with ethyl acetate and aqueous sat. sodium carbonate solution, filtrated over diatomite and the phases separated. The organic phase was washed with aqueous sat. sodium carbonate solution, dried with sodium sulfate and concentrated in vacuo to give the title compound (630 mg, 61%) which was not further purified.

LC-MS (Method 2): $R_t$=1.37 min; MS (ESIpos): m/z=417 [M+H]$^+$.

$^1$H-NMR (400 MHz, DMSO-d$_6$) δ [ppm]=−0.09 (s, 9H), 0.81-0.85 (m, 2H), 3.55-3.59 (m, 2H), 5.66 (s, 2H), 5.86 (br s, 2H), 6.38-6.44 (m, 2H), 6.57 (d, 1H), 8.29 (d, 1H), 8.63 (s, 1H).

Intermediate 28 phenyl {4-[(3-cyano-1-{[2-(trimethylsilyl)ethoxy]methyl}-1H-pyrrolo[2,3-b]pyridin-4-yl)oxy]-3,5-difluorophenyl}carbamate

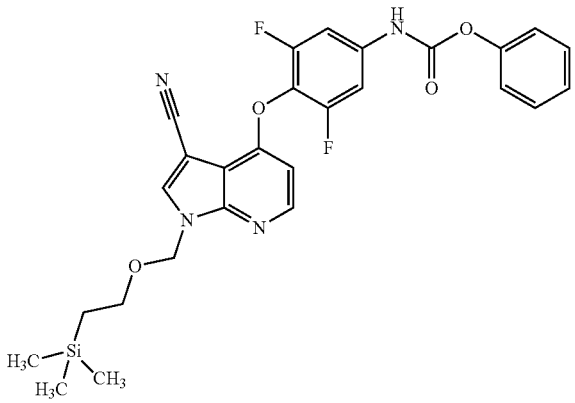 [SMILES: C[Si](C)(C)CCOCn1cc(C#N)c2c(Oc3c(F)cc(NC(=O)Oc4ccccc4)cc3F)ccnc21]

A solution of 4-(4-amino-2,6-difluorophenoxy)-1-{[2-(trimethylsilyl)ethoxy]methyl}-1H-pyrrolo[2,3-b]pyridine-3-carbonitrile (intermediate 27; 390 mg, 0.936 mmol) in ethyl acetate (5 mL) was treated with an aqueous sat. sodium hydrocarbonate solution (5 mL) and with phenyl chloroformate (CAS No. [1885-14-9]; 5.0 eq, 0.59 mL, 4.7 mmol) and the mixture stirred at rt for 18 hours. The reaction mixture was diluted with ethyl acetate and water, the phases separated and the aqueous phase extracted with ethyl acetate (twice). The combined organic phases were washed with brine, dried with sodium sulfate and concentrated in vacuo. The obtained material was purified by flash chromatography (SiO$_2$-hexane/ethyl acetate) to give the title compound (310 mg) containing 1-{4-[(3-cyano-1-{[2-(trimethylsilyl)ethoxy]methyl}-1H-pyrrolo[2,3-b]pyridin-4-yl)oxy]-3,5-difluorophenyl}urea.

LC-MS (Method 2): R$_t$=1.53 min; MS (ESIpos): m/z=537 [M+H]$^+$.

Intermediate 29

1-{4-[(3-cyano-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea

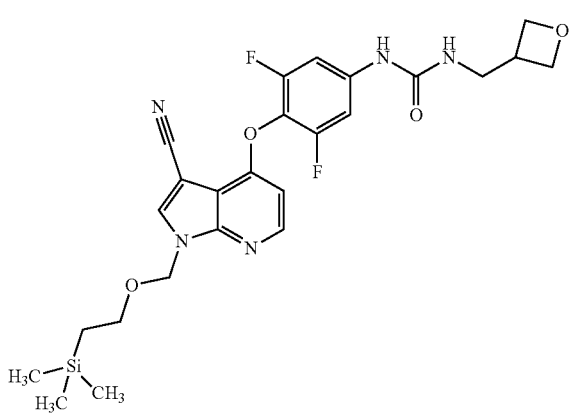 [SMILES: C[Si](C)(C)CCOCn1cc(C#N)c2c(Oc3c(F)cc(NC(=O)NCC4COC4)cc3F)ccnc21]

A solution of phenyl {4-[(3-cyano-1-{[2-(trimethylsilyl)ethoxy]methyl}-1H-pyrrolo[2,3-b]pyridin-4-yl)oxy]-3,5-difluorophenyl}carbamate (322 mg, 600 μmol, intermediate 28) in DMF (3 mL) was treated with 1-(oxetan-3-yl)methanamine (1.2 eq., 63 mg, 720 μmol, CAS No. [6246-05-5]) and stirred at 70° C. for 20 hours. The reaction mixture was diluted with ethyl acetate and water and the layers separated. The organic layer was concentrated in vacuo to give the crude title compound which was used in the next step without any further purification.

LC-MS (Method 2): R$_t$=1.30 min; MS (ESIpos): m/z=530 [M+H]$^+$.

Intermediate 30

1-{4-[(3-cyano-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea

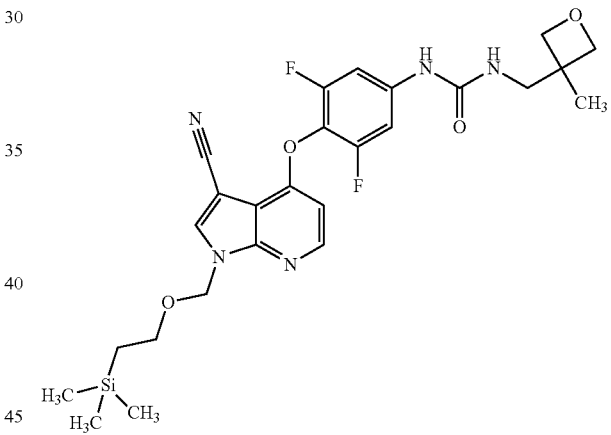

A solution of phenyl {4-[(3-cyano-1-{[2-(trimethylsilyl)ethoxy]methyl}-1H-pyrrolo[2,3-b]pyridin-4-yl)oxy]-3,5-difluorophenyl}carbamate (330 mg, 615 μmol, intermediate 28) in DMF (3 mL) was treated with 1-(3-methyloxetan-3-yl)methanamine (1.2 eq., 75 mg, 738 μmol) and stirred at 70° C. for 20 hours. The reaction mixture was diluted with ethyl acetate and water and the layers separated. The organic layer was concentrated in vacuo to give the crude title compound which was used in the next step without any further purification.

LC-MS (Method 2): R$_t$=1.34 min; MS (ESIpos): m/z=544 [M+H]$^+$.

Intermediate 31

3-cyclopropyl-4-(2,6-difluoro-4-nitrophenoxy)-1-{[2-(trimethylsilyl)ethoxy]methyl}-1H-pyrrolo[2,3-b]pyridine

Intermediate 32

4-[(3-cyclopropyl-1-{[2-(trimethylsilyl)ethoxy]methyl}-1H-pyrrolo[2,3-b]pyridin-4-yl)oxy]-3,5-difluoroaniline

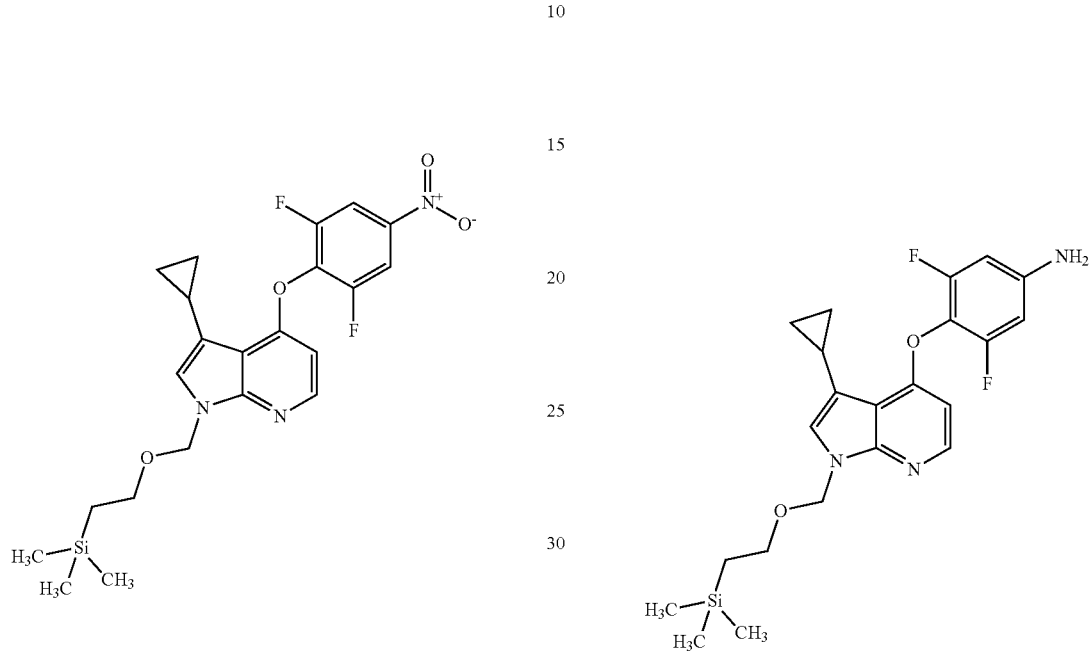

In a microwave glass vial a mixture of 3-bromo-4-(2,6-difluoro-4-nitrophenoxy)-1-{[2-(trimethylsilyl)ethoxy]methyl}-1H-pyrrolo[2,3-b]pyridine (6.00 g, 12.0 mmol, intermediate 16), potassium cyclopropyl(trifluoro)borate (1.10 eq, 1.95 g, 13.2 mmol), palladium acetate (CAS No. [3375-31-3]; 0.02 eq., 54 mg, 240 µmol), potassium carbonate (2.0 eq., 3.3 g, 24 mmol) and tricyclohexylphosphine (0.04 eq., 135 mg, 480 µmol) in a mixture of toluene (60 mL) and water (2.4 mL) was evacuated and back-filled with nitrogen several times under stirring. The vial was closed and stirred at 90° C. overnight. The reaction mixture was cooled to rt, filtrated over a pad of Celite® and the filter cake washed with ethyl acetate. The filtrate was concentrated in vacuo and the obtained material purified by flash chromatography (SiO$_2$-hexane/dichloromethane to dichloromethane/methanol) to give the title compound (2.37 g, 36%, contaminated with small amounts of dehalogenated starting material) along with reisolated starting material (2.1 g, 35%).

LC-MS (Method 2): R$_t$=1.64 min; MS (ESIpos): m/z=462 [M+H]$^+$.

$^1$H-NMR (400 MHz, DMSO-d$_6$) δ [ppm]=−0.11 (s, 9H), 0.61-0.65 (m, 2H), 0.78-0.88 (m, 4H), 2.12-2.18 (m, 1H), 3.47-3.51 (m, 2H), 5.54 (s, 2H), 6.52 (d, 1H), 7.33 (d, 1H), 8.11 (d, 1H), 8.38-8.44 (m, 2H).

A solution of 3-cyclopropyl-4-(2,6-difluoro-4-nitrophenoxy)-1-{[2-(trimethylsilyl)ethoxy]methyl}-1H-pyrrolo[2,3-b]pyridine (intermediate 31; 2.3 g, 5.0 mmol) in methanol (41 mL) was treated with tin(II) chloride dihydrate (CAS No. [10025-69-1]; 1.6 eq, 1.8 g, 7.8 mmol) and stirred at 64° C. for 5 hours followed by stirring at rt overnight. The reaction mixture was concentrated in vacuo, the residue taken up with ethyl acetate and aqueous sat. sodium carbonate solution, filtrated over diatomite and the phases separated. The organic phase was washed with aqueous sat. sodium carbonate solution, dried with sodium sulfate and concentrated in vacuo. The obtained material was used in the next step without further purification (1.49 g).

LC-MS (Method 2): R$_t$=1.52 min; MS (ESIpos): m/z=432 [M+H]$^+$.

$^1$H-NMR (400 MHz, DMSO-d$_6$) δ [ppm]=−0.10 (s, 9H), 0.60-0.65 (m, 2H), 0.78-0.82 (m, 2H), 0.84-0.88 (m, 2H), 2.15-2.22 (m, 1H), 3.45-3.49 (m, 2H), 5.51 (s, 2H), 5.78 (br s, 2H), 6.28 (d, 1H), 6.36-6.42 (m, 2H), 7.22 (s, 1H), 8.05 (d, 1H).

Intermediate 33 phenyl {4-[(3-cyclopropyl-1-{[2-(trimethylsilyl)ethoxy]methyl}-1H-pyrrolo[2,3-b]pyridin-4-yl)oxy]-3,5-difluorophenyl}carbamate

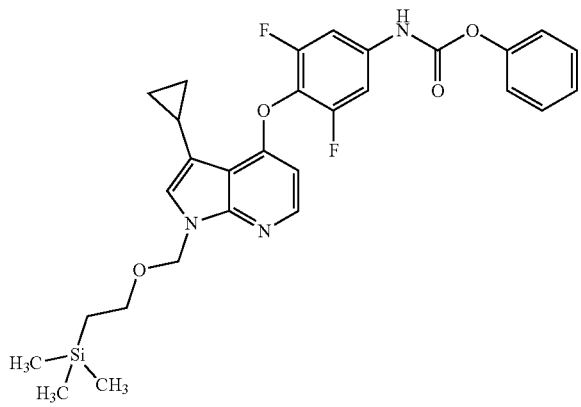 [SMILES: C[Si](C)(C)CCOCn1cc(C2CC2)c2c(Oc3c(F)cc(NC(=O)Oc4ccccc4)cc3F)ccnc21]

An ice-cooled solution of 4-[(3-cyclopropyl-1-{[2-(trimethylsilyl)ethoxy]methyl}-1H-pyrrolo[2,3-b]pyridin-4-yl)oxy]-3,5-difluoroaniline (intermediate 32, 186 mg, 345 µmol) and pyridine (5.0 eq., 140 µL, 1.7 mmol) in THF (2 mL) was treated with phenyl chloroformate (CAS No. [1885-14-9]; 1.1 eq, 48 µL, 380 µmol), the mixture warmed to rt and stirring continued for 25 minutes.

The reaction mixture was diluted with ethyl acetate and washed with 1 M aqueous hydrochloric acid, aqueous sat. sodium hydrocarbonate solution and brine. The resulting organic layer was dried with sodium sulfate and concentrated in vacuo to give the crude title compound (295 mg) which was used as is in the next steps.

LC-MS (Method 2): $R_t$=1.66 min; MS (ESIpos): m/z=552 [M+H]$^+$.

Intermediate 34

1-{4-[(3-cyclopropyl-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea

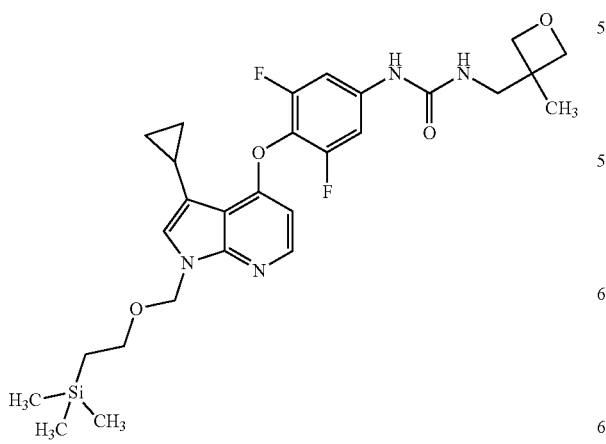

A solution of crude phenyl {4-[(3-cyclopropyl-1-{[2-(trimethylsilyl)ethoxy]methyl}-1H-pyrrolo[2,3-b]pyridin-4-yl)oxy]-3,5-difluorophenyl}carbamate (intermediate 33, 300 mg, 0.5 mmol) in N,N-dimethylformamide (6 mL) was treated with 1-(3-methyloxetan-3-yl)methanamine (CAS No. [153209-97-3]; 1.2 eq, 66 mg, 650 µmol) and the mixture stirred at 70° C. for 18 hours. The reaction mixture was diluted with ethyl acetate and water and the phases separated. The organic layer was concentrated in vacuo to give the crude title compound (303 mg) which was used as is in the next step.

LC-MS (Method 2): $R_t$=1.49 min; MS (ESIpos): m/z=559 [M+H]$^+$.

Intermediate 35

1-{4-[(3-cyclopropyl-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea

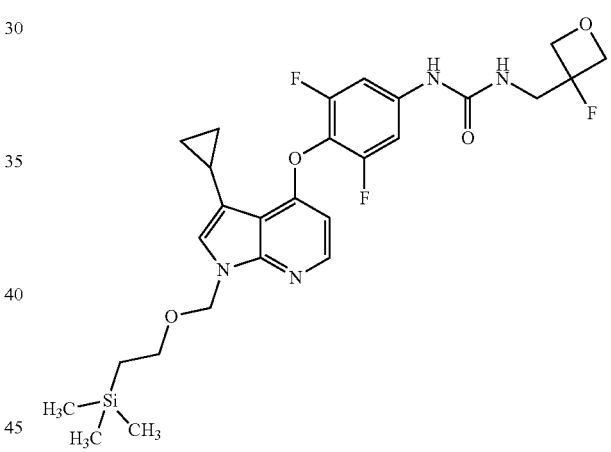

A solution of crude phenyl {4-[(3-cyclopropyl-1-{[2-(trimethylsilyl)ethoxy]methyl}-1H-pyrrolo[2,3-b]pyridin-4-yl)oxy]-3,5-difluorophenyl}carbamate (intermediate 33, 300 mg, 0.5 mmol) in N,N-dimethylformamide (6 mL) was treated with 1-(3-fluorooxetan-3-yl)methanamine (CAS No. [883311-82-8]; 1.2 eq, 69 mg, 650 µmol) and the mixture stirred at 70° C. for 18 hours. The reaction mixture was diluted with ethyl acetate and water and the phases separated. The organic layer was concentrated in vacuo to give the crude title compound (305 mg) which was used as is in the next step.

LC-MS (Method 2): $R_t$=1.48 min; MS (ESIpos): m/z=563 [M+H]$^+$.

107

Intermediate 36

4-(2,6-difluoro-4-nitrophenoxy)-3-(2-methyl-3-thie-nyl)-1-{[2-(trimethylsilyl)ethoxy]methyl}-1H-pyr-rolo[2,3-b]pyridine

108

Intermediate 37

3,5-difluoro-4-{[3-(2-methyl-3-thienyl)-1-{[2-(trim-ethylsilyl)ethoxy]methyl}-1H-pyrrolo[2,3-b]pyridin-4-yl]oxy}aniline

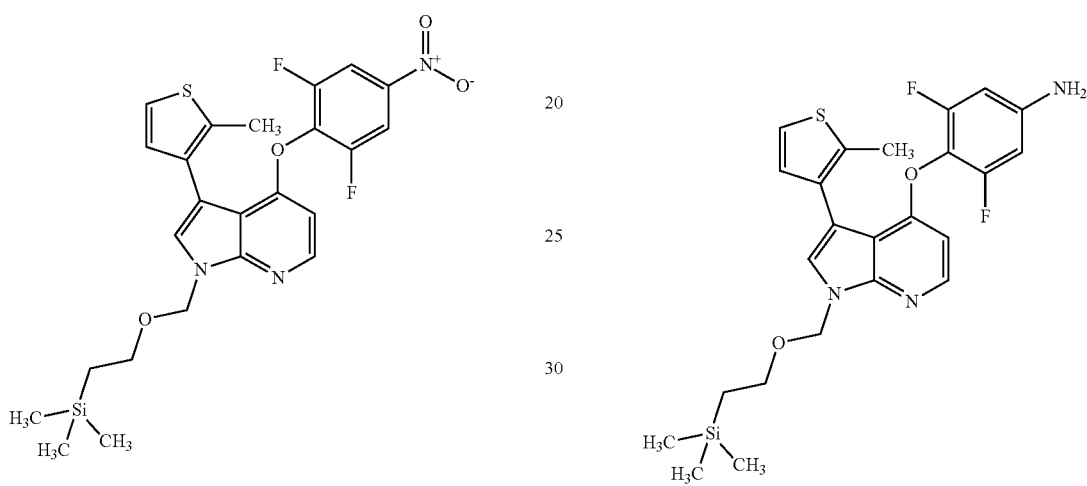

3-bromo-4-(2,6-difluoro-4-nitrophenoxy)-1-{[2-(trimeth-ylsilyl)ethoxy]methyl}-1H-pyrrolo[2,3-b]pyridine (1.20 g, 2.40 mmol, intermediate 16), (2-methylthiophen-3-yl)bo-ronic acid (CAS No. [177735-10-3]) (409 mg, 2.88 mmol), tetrakis(triphenylphosphin)palladium(0) (139 mg, 120 µmol), and aq. sodium carbonate (2.6 mL, 2.0 M, 5.3 mmol) were combined in 1,4-dioxane (42 mL), degassed and flushed with argon. The mixture was heated up to 100° C. for 9 h, diluted with ethyl acetated and filtered. To the filtrate was added water and the phases were separated. The aque-ous phase was washed with ethyl acetate, and the combined organic phases were washed with brine, dried with sodium sulfate, filtered and evaporated. The crude product was purified by flash chromatography (25 g SiO$_2$ SNAP Ultra-column, hexane/2-20% ethyl acetate) to give the title com-pound (1.02 g, 51% yield).

LC-MS (Method 2): R$_t$=1.69 min; MS (ESIpos): m/z=518 [M+H]$^+$.

$^1$H-NMR (400 MHz, DMSO-d6) δ [ppm]: −0.10 (s, 9H) 0.77-0.89 (m, 2H) 2.44 (s, 3H) 3.53-3.65 (m, 2H) 5.69 (s, 2H) 5.76 (s, 1H) 6.59-6.65 (m, 1H) 7.04-7.11 (m, 1H) 7.26 (d, 1H) 7.73 (s, 1H) 8.16-8.25 (m, 1H) 8.30-8.39 (m, 2H).

Ammonium chloride (512 mg, 9.56 mmol) and iron (534 mg, 9.56 mmol) were suspended in water (22 mL). 4-(2,6-difluoro-4-nitrophenoxy)-3-(2-methylthiophen-3-yl)-1-{[2-(trimethylsilyl)ethoxy]methyl}-1H-pyrrolo[2,3-b]pyridine (990 mg, 1.91 mmol, intermediate 36) was dissolved in THF (11 mL) and methanol (11 mL) and added to the suspension, that was heated at 80° C. for 16 h without stirrer. The mixture was diluted with ethyl acetate and filtered. The phases were separated and the organic phase was washed with brine, dried with sodium sulfate, filtered and evapo-rated. The crude product was purified by flash chromatog-raphy (50 g SiO$_2$ SNAP Ultra-column, dichloromethane/0-11% methanol) to give the title compound (713 mg, 73% yield).

LC-MS (Method 2): R$_t$=1.57 min; MS (ESIneg): m/z=487 [M−H]$^-$.

$^1$H-NMR (400 MHz, DMSO-d6) δ [ppm]: −0.10 (s, 9H) 0.74-0.89 (m, 2H) 2.47 (s, 3H) 3.52-3.65 (m, 2H) 5.62-5.68 (m, 2H) 5.76-5.82 (m, 2H) 6.31-6.40 (m, 3H) 7.10-7.16 (m, 1H) 7.22-7.29 (m, 1H) 7.61-7.67 (m, 1H) 8.10-8.18 (m, 1H).

Intermediate 38

1-(3,5-difluoro-4-{[3-(2-methyl-3-thienyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

Intermediate 39

5-[4-(2,6-difluoro-4-nitrophenoxy)-1-{[2-(trimethylsilyl)ethoxy]methyl}-1H-pyrrolo[2,3-b]pyridin-3-yl]-2-methoxynicotinonitrile

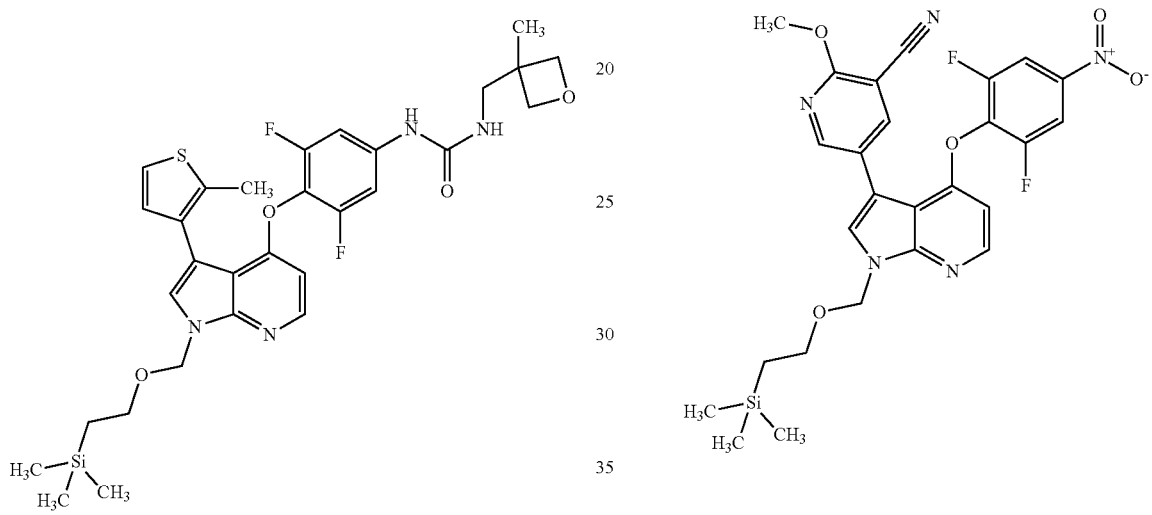

3,5-difluoro-4-{[3-(2-methylthiophen-3-yl)-1-{[2-(trimethylsilyl)ethoxy]methyl}-1H-pyrrolo[2,3-b]pyridin-4-yl]oxy}aniline (150 mg, 308 μmol), 3-(isocyanatomethyl)-3-methyloxetane (CAS No. [1260665-88-0]) (78.2 mg, 615 μmol, intermediate 37), and pyridine (2.7 mL) were dissolved in dichloromethane (2.7 mL) and the mixture was stirred overnight at 60° C. in a closed microwave vial. Toluene was added and the mixture was concentrated in vacuo. The residue was purified by flash chromatography (25 g SiO$_2$ SNAP Ultra-column, dichloromethane/0-7% methanol) to give the title compound (181 mg, 86% yield).

LC-MS (Method 2): R$_t$=1.54 min; MS (ESIpos): m/z=615 [M+H]$^+$ $^1$H-NMR (400 MHz, DMSO-d6) δ [ppm]: −0.10 (s, 9H) 0.76-0.90 (m, 2H) 1.23 (s, 3H) 2.48 (s, 3H) 3.24-3.32 (m, 2H) 3.52-3.64 (m, 2H) 4.12-4.25 (m, 2H) 4.33-4.44 (m, 2H) 5.59-5.72 (m, 2H) 6.32-6.43 (m, 1H) 6.65-6.76 (m, 1H) 7.09-7.17 (m, 1H) 7.24-7.29 (m, 1H) 7.32-7.43 (m, 2H) 7.66-7.70 (m, 1H) 8.12-8.17 (m, 1H) 8.97-9.03 (m, 1H).

3-bromo-4-(2,6-difluoro-4-nitrophenoxy)-1-{[2-(trimethylsilyl)ethoxy]methyl}-1H-pyrrolo[2,3-b]pyridine (1.81 g, 3.62 mmol, intermediate 16), 2-methoxy-5-(4,4,5,5-tetramethyl-1,3,2-dioxaborolan-2-yl)pyridine-3-carbonitrile (CAS No. [1073354-05-8]) (1.13 g, 4.34 mmol), tetrakis(triphenylphosphin)palladium(0) (335 mg, 290 μmol), and aq. sodium carbonate (4.0 mL, 2.0 M, 8.0 mmol) were combined in 1,4-dioxane (63 mL), degassed and flushed with argon. The mixture was heated up to 100° C. for 16 h, diluted with ethyl acetated and filtered. To the filtrate was added water and the phases were separated. The aqueous phase was washed with ethyl acetate, and the combined organic phases were washed with brine, dried with sodium sulfate, filtered and evaporated. The crude product was purified by flash chromatography (to give the title compound (1.42 g, 67% yield).

LC-MS (Method 2): R$_t$=1.60 min; MS (ESIpos): m/z=554 [M+H]$^+$ $^1$H-NMR (400 MHz, DMSO-d6) δ [ppm]: −0.08 (s, 9H) 0.79-0.91 (m, 2H) 3.57-3.65 (m, 2H) 4.00 (s, 3H) 5.69 (s, 2H) 6.66-6.72 (m, 1H) 8.06 (s, 1H) 8.26 (d, 1H) 8.38-8.47 (m, 3H) 8.70 (d, 1H).

111

Intermediate 40

5-[4-(4-amino-2,6-difluorophenoxy)-1-{[2-(trimethylsilyl)ethoxy]methyl}-1H-pyrrolo[2,3-b]pyridin-3-yl]-2-methoxynicotinonitrile

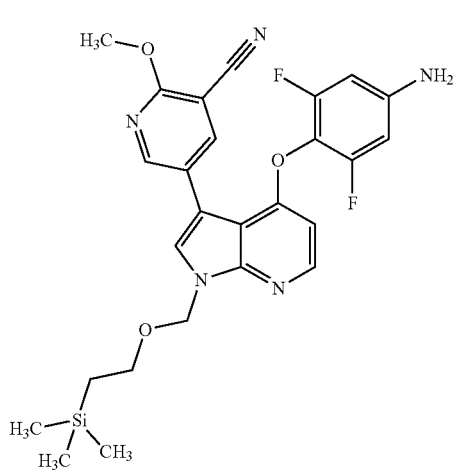 [SMILES: COc1ncc(-c2cn(COCC[Si](C)(C)C)c3nccc(Oc4c(F)cc(N)cc4F)c23)cc1C#N]

Ammonium chloride (586 mg, 10.9 mmol) and iron (611 mg, 10.9 mmol) were suspended in water (26 mL). 5-[4-(2,6-difluoro-4-nitrophenoxy)-1-{[2-(trimethylsilyl)ethoxy]methyl}-1H-pyrrolo[2,3-b]pyridin-3-yl]-2-methoxynicotinonitrile (1.21 g, 2.19 mmol, intermediate 39) was dissolved in THF (13 mL) and methanol (13 mL) and added to the suspension, that was heated at 80° C. for 10 h. The mixture was diluted with ethyl acetate and filtered. The phases were separated and the organic phase was washed with brine, dried with sodium sulfate, filtered and evaporated. The crude product was purified by flash chromatography to give the title compound (923 mg, 76% yield).

LC-MS (Method 2): $R_t$=1.51 min; MS (ESIpos): m/z=524 [M+H]$^+$ $^1$H-NMR (400 MHz, DMSO-d6) δ [ppm]: −0.08 (s, 9H) 0.76-0.92 (m, 2H) 3.53-3.65 (m, 2H) 4.01 (s, 3H) 5.66 (s, 2H) 5.83 (s, 2H) 6.39 (d, 2H) 6.46 (d, 1H) 7.97 (s, 1H) 8.21 (d, 1H) 8.42 (d, 1H) 8.72 (d, 1H).

112

Intermediate 41

1-(4-{[3-(5-cyano-6-methoxypyridin-3-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

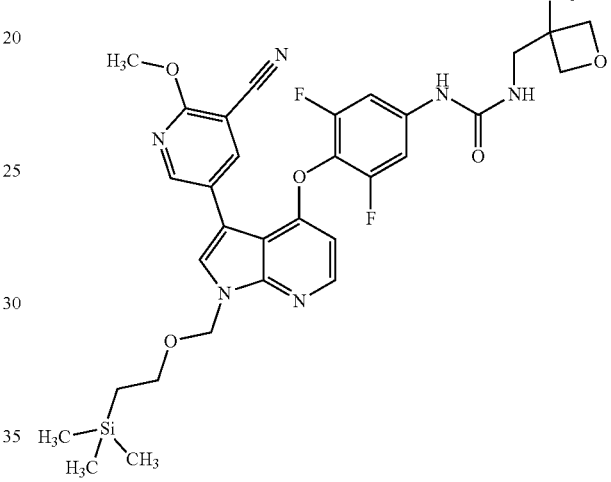

5-[4-(4-amino-2,6-difluorophenoxy)-1-{[2-(trimethylsilyl)ethoxy]methyl}-1H-pyrrolo[2,3-b]pyridin-3-yl]-2-methoxynicotinonitrile (72.8 mg, 573 μmol, intermediate 40), 3-(isocyanatomethyl)-3-methyloxetane (CAS No. [1260665-88-0]) (72.8 mg, 573 μmol), and pyridine (2.5 mL, 32 mmol) were dissolved in dichloromethane (2.5 mL) and the mixture was stirred overnight at 60° C. in a closed microwave vial. Toluene was added and the mixture was concentrated in vacuo. The residue was purified by flash chromatography (28 g SNAP-NH column, ethyl acetate/0-80% dichloromethane) to give the title compound (191 mg, 92% yield).

LC-MS (Method 2): $R_t$=1.47 min; MS (ESIpos): m/z=651 [M+H]$^+$ $^1$H-NMR (400 MHz, DMSO-d6) δ [ppm]: −0.07 (s, 9H) 0.79-0.92 (m, 2H) 1.23 (s, 3H) 3.29 (d, 2H) 3.55-3.65 (m, 2H) 4.01 (s, 3H) 4.20 (d, 2H) 4.38 (d, 2H) 5.67 (s, 2H) 6.49 (d, 1H) 6.67-6.79 (m, 1H) 7.39 (d, 2H) 8.01 (s, 1H) 8.23 (d, 1H) 8.43 (d, 1H) 8.73 (d, 1H) 9.02 (s, 1H).

Intermediate 42

4-(2,6-difluoro-4-nitrophenoxy)-3-(6-methoxypyridin-3-yl)-1-{[2-(trimethylsilyl)ethoxy]methyl}-1H-pyrrolo[2,3-b]pyridine

Intermediate 43

3,5-difluoro-4-{[3-(6-methoxypyridin-3-yl)-1-{[2-(trimethylsilyl)ethoxy]methyl}-1H-pyrrolo[2,3-b]pyridin-4-yl]oxy}aniline

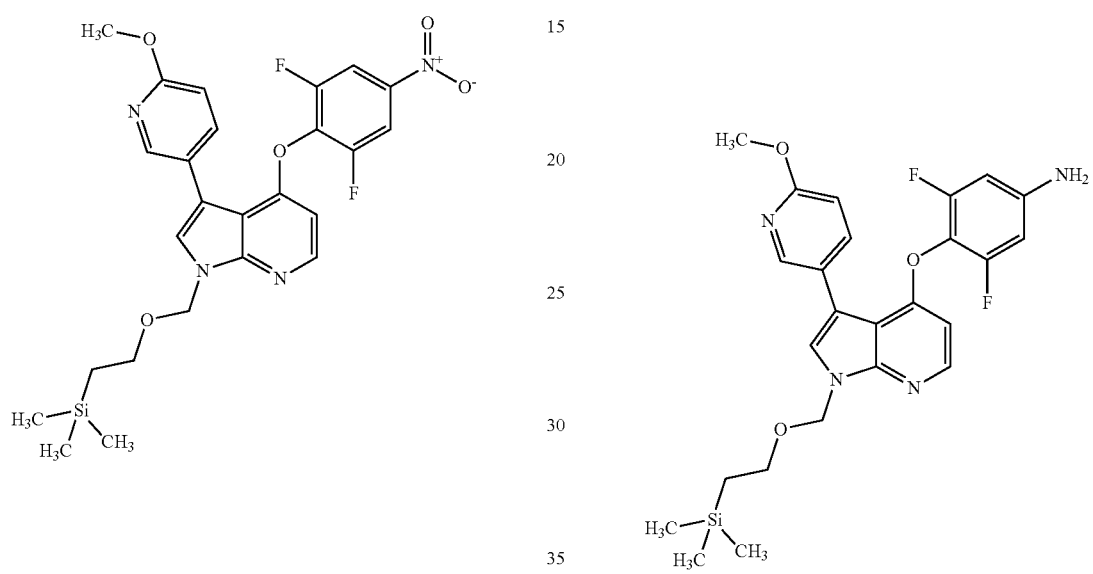

3-bromo-4-(2,6-difluoro-4-nitrophenoxy)-1-{[2-(trimethylsilyl)ethoxy]methyl}-1H-pyrrolo[2,3-b]pyridine (1.20 g, 2.40 mmol, intermediate 16), (6-methoxypyridin-3-yl)boronic acid (CAS No. [163105-89-3]) (440 mg, 2.88 mmol), tetrakis(triphenylphosphin)palladium(0) (222 mg, 192 µmol), and aq. sodium carbonate (2.6 mL, 2.0 M, 5.3 mmol) were combined in 1,4-dioxane (42 mL, 490 mmol), degassed and flushed with argon. The mixture was heated up to 100° C. for 16 h, and further (6-methoxypyridin-3-yl)boronic acid (220 mg, 1.44 mmol) and tetrakis(triphenylphosphin)palladium(0) (110 mg, 95 µmol) were added. The reaction was stirred at 100° C. for an additional 16 h, diluted with ethyl acetated and filtered. To the filtrate was added water and the phases were separated.

The aqueous phase was washed with ethyl acetate, and the combined organic phases were washed with brine, dried with sodium sulfate, filtered and evaporated. The crude product was purified by flash chromatography (50 g SNAP-KP Sil, hexane/0-25% ethyl acetate) to give the title compound (574 mg, 44% yield).

LC-MS (Method 2): $R_t$=1.63 min; MS (ESIpos): m/z=529 [M+H]$^+$ $^1$H NMR (400 MHz, DMSO-d$_6$) δ ppm −0.08 (s, 9H) 0.79-0.91 (m, 2H) 3.53-3.65 (m, 2H) 3.85 (s, 3H) 5.68 (s, 2H) 6.59-6.70 (m, 1H) 6.87 (d, 1H) 7.91 (s, 1H) 7.93 (dd, 1H) 8.22 (d, 1H) 8.36-8.43 (m, 3H).

Ammonium chloride (289 mg, 5.40 mmol) and iron (302 mg, 5.40 mmol) were suspended in water (13 mL). 4-(2,6-difluoro-4-nitrophenoxy)-3-(6-methoxypyridin-3-yl)-1-{[2-(trimethylsilyl)ethoxy]methyl}-1H-pyrrolo[2,3-b]pyridine (571 mg, 1.08 mmol, intermediate 42) was dissolved in THF (6.3 mL) and methanol (6.3 mL) and added to the suspension, that was heated at 80° C. for 16 h. The mixture was diluted with ethyl acetate and filtered. The phases were separated and the organic phase was washed with brine, dried with sodium sulfate, filtered and evaporated. The crude product was digested with hexanes and filtered to yield the title compound (349 mg, 63% yield).

LC-MS (Method 2): $R_t$=1.49 min; MS (ESIpos): m/z=499 [M+H]$^+$ $^1$H NMR (400 MHz, DMSO-d$_6$) δ ppm −0.08 (s, 9H) 0.79-0.90 (m, 2H) 3.54-3.62 (m, 2H) 3.86 (s, 3H) 5.66 (s, 2H) 5.82 (s, 2H) 6.34-6.46 (m, 3H) 6.87 (d, 1H) 7.81 (s, 1H) 7.94 (dd, 1H) 8.18 (d, 1H) 8.39-8.47 (m, 1H).

115

Intermediate 44

1-(3,5-difluoro-4-{[3-(6-methoxypyridin-3-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

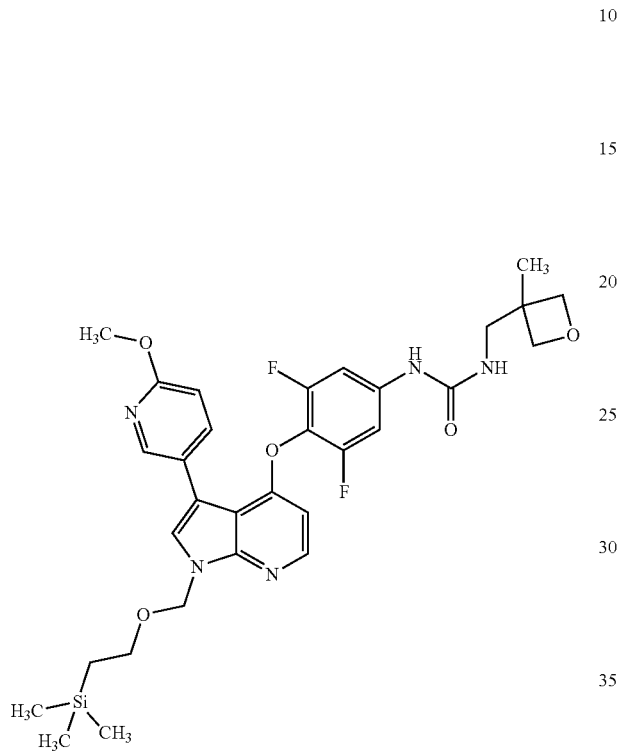

3,5-difluoro-4-{[3-(6-methoxypyridin-3-yl)-1-{[2-(trimethylsilyl)ethoxy]methyl}-1H-pyrrolo[2,3-b]pyridin-4-yl]oxy}aniline (80.0 mg, 160 µmol, intermediate 43), 3-(isocyanatomethyl)-3-methyloxetane (CAS No. [1260665-88-0]) (40.8 mg, 321 µmol) and pyridine (1.4 mL, 18 mmol) were dissolved in dichloromethane (1.4 mL) and the mixture was stirred overnight at 60° C. in a closed microwave vial. Toluene was added and the mixture was concentrated in vacuo. The residue was purified by flash chromatography to give the title compound (105 mg, 83% yield).

LC-MS (Method 2): $R_t$=1.45 min; MS (ESIpos): m/z=626 [M+H]$^+$ $^1$H NMR (400 MHz, DMSO-d$_6$) δ ppm −0.08 (s, 9H) 0.79-0.92 (m, 2H) 1.23 (s, 3H) 3.29 (d, 2H) 3.53-3.62 (m, 2H) 3.86 (s, 3H) 4.21 (d, 2H) 4.38 (d, 2H) 5.68 (s, 2H) 6.09-6.18 (m, 1H) 6.43 (d, 1H) 6.67-6.77 (m, 1H) 6.88 (d, 1H) 7.34-7.43 (m, 2H) 7.85 (s, 1H) 7.96 (dd, 1H) 8.17 (d, 1H) 8.39-8.46 (m, 1H) 9.02 (s, 1H).

116

Intermediate 45

4-(2,6-difluoro-4-nitrophenoxy)-3-(1-methyl-1,2,3,6-tetrahydropyridin-4-yl)-1-{[2-(trimethylsilyl)ethoxy]methyl}-1H-pyrrolo[2,3-b]pyridine

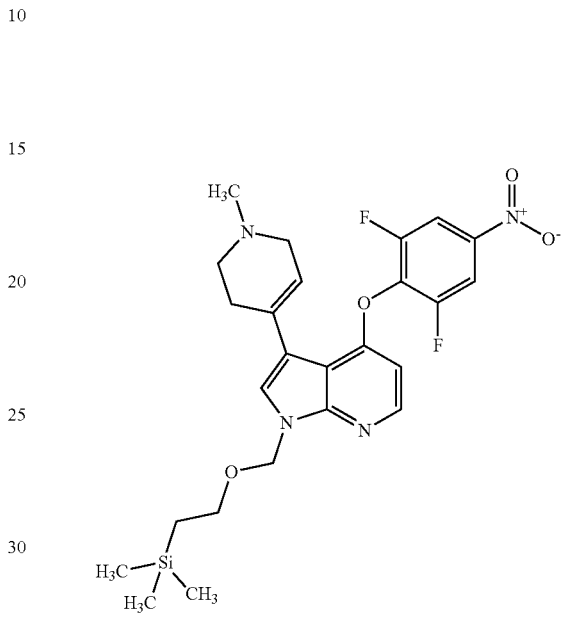

3-bromo-4-(2,6-difluoro-4-nitrophenoxy)-1-{[2-(trimethylsilyl)ethoxy]methyl}-1H-pyrrolo[2,3-b]pyridine (1.10 g, 2.20 mmol, intermediate 16), 1-methyl-4-(4,4,5,5-tetramethyl-1,3,2-dioxaborolan-2-yl)-1,2,3,6-tetrahydropyridine (CAS No. [454482-11-2]) (589 mg, 2.64 mmol), tetrakis(triphenylphosphin)palladium(0) (127 mg, 110 µmol), and aq. sodium carbonate (2.4 mL, 2.0 M, 4.8 mmol) were combined in 1,4-dioxane (39 mL), degassed and flushed with argon. The mixture was heated up to 100° C. for 12 h, diluted with ethyl acetated and filtered. To the filtrate was added water and the phases were separated. The aqueous phase was washed with ethyl acetate, and the combined organic phases were washed with brine, dried with sodium sulfate, filtered and evaporated. The crude product was purified by flash chromatography (50 g SiO$_2$ SNAP, dichloromethane/0-20% methanol) to give the title compound (288 mg, 24% yield).

LC-MS (Method 2): $R_t$=1.63 min; MS (ESIpos): m/z=517 [M+H]$^+$ $^1$H-NMR (400 MHz, DMSO-d6) δ [ppm]: −0.10 (s, 9H) 0.75-0.88 (m, 2H) 2.24 (s, 3H) 2.51-2.58 (m, 4H) 2.93-3.01 (m, 2H) 3.48-3.59 (m, 2H) 5.54-5.67 (m, 2H) 5.97-6.06 (m, 1H) 6.54-6.62 (m, 1H) 7.65 (s, 1H) 8.15 (d, 1H) 8.34-8.46 (m, 2H).

Intermediate 46

3,5-difluoro-4-{[3-(1-methyl-1,2,3,6-tetrahydropyridin-4-yl)-1-{[2-(trimethylsilyl)ethoxy]methyl}-1H-pyrrolo[2,3-b]pyridin-4-yl]oxy}aniline

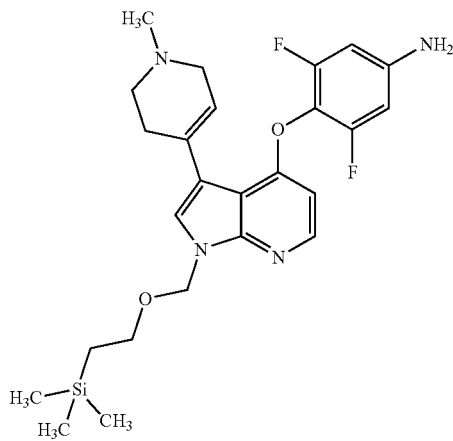 [SMILES: CN1CC=C(c2cn(COCC[Si](C)(C)C)c3nccc(Oc4c(F)cc(N)cc4F)c23)CC1]

Ammonium chloride (252 mg, 4.70 mmol) and iron (263 mg, 4.70 mmol) were suspended in water (11 mL). 4-(2,6-difluoro-4-nitrophenoxy)-3-(1-methyl-1,2,3,6-tetrahydropyridin-4-yl)-1-{[2-(trimethylsilyl)ethoxy]methyl}-1H-pyrrolo[2,3-b]pyridine (486 mg, 941 µmol, intermediate 45) was dissolved in THF (5.5 mL) and methanol (5.5 mL) and added to the suspension, that was heated at 100° C. for 16 h. The mixture was diluted with ethyl acetate and filtered. The phases were separated and the organic phase was washed with brine, dried with sodium sulfate, filtered and evaporated. The crude product was filtered through a NH-silica column and used directly in the following reaction.

Intermediate 47

1-(3,5-difluoro-4-{[3-(1-methyl-1,2,3,6-tetrahydropyridin-4-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

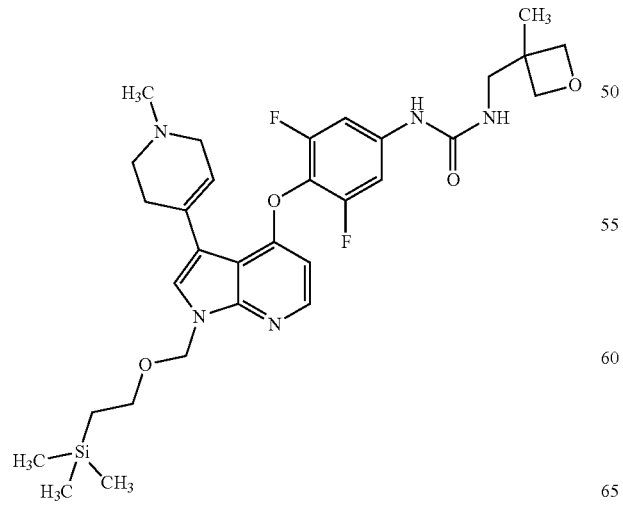

3,5-difluoro-4-{[3-(1-methyl-1,2,3,6-tetrahydropyridin-4-yl)-1-{[2-(trimethylsilyl)ethoxy]methyl}-1H-pyrrolo[2,3-b]pyridin-4-yl]oxy}aniline (122 mg, 251 µmol, intermediate 46), 3-(isocyanatomethyl)-3-methyloxetane (CAS No. [1260665-88-0]) (63.7 mg, 501 µmol), and pyridine (2.2 mL, 28 mmol) were dissolved in dichloromethane (2.2 mL) and the mixture was stirred overnight at 60° C. in a closed microwave vial. Toluene was added and the mixture was concentrated in vacuo. The residue was purified by preparative HPLC to give the title compound (21.0 mg, 13% yield).

LC-MS (Method 2): $R_t$=1.41 min; MS (ESIpos): m/z=615 $[M+H]^+$ $^1$H-NMR (400 MHz, DMSO-d6) δ [ppm]: −0.09 (s, 9H) 0.77-0.86 (m, 2H) 1.23 (s, 3H) 2.24 (s, 3H) 2.52-2.58 (m, 4H) 2.93-3.00 (m, 2H) 3.30 (d, 2H) 3.45-3.57 (m, 2H) 4.20 (d, 2H) 4.39 (d, 2H) 5.59 (s, 2H) 6.01-6.12 (m, 1H) 6.38 (d, 1H) 6.73-6.83 (m, 1H) 7.32-7.46 (m, 2H) 7.58 (s, 1H) 8.11 (d, 1H) 9.09 (s, 1H).

Intermediate 48 tert-butyl 4-[4-(2,6-difluoro-4-nitrophenoxy)-1-{[2-(trimethylsilyl)ethoxy]methyl}-1H-pyrrolo[2,3-b]pyridin-3-yl]-3,6-dihydropyridine-1(2H)-carboxylate

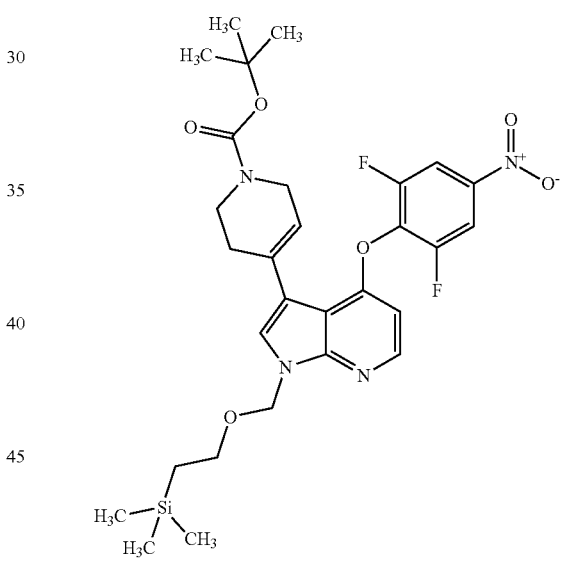

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), tert-butyl 4-(4,4,5,5-tetramethyl-1,3,2-dioxaborolan-2-yl)-3,6-dihydropyridine-1(2H)-carboxylate (CAS No. [286961-14-6]) (742 mg, 2.40 mmol), tetrakis(triphenylphosphin)palladium(0) (115 mg, 99.9 µmol), and aq. sodium carbonate (2.2 mL, 2.0 M, 4.4 mmol) were combined in 1,4-dioxane (35 mL), degassed and flushed with argon. The mixture was heated up to 100° C. for 10 h, diluted with ethyl acetated and filtered. To the filtrate was added water and the phases were separated. The aqueous phase was washed with ethyl acetate, and the combined organic phases were washed with brine, dried with sodium sulfate, filtered and evaporated. The crude product was purified by flash chromatography (50 g SiO₂ SNAP Ultra, hexane/2-25% ethyl acetate) to give the title compound (774 mg, 61% yield).

LC-MS (Method 2): R$_t$=1.72 min; MS (ESIpos): m/z=603 [M+H]$^+$ $^1$H-NMR (400 MHz, DMSO-d6) δ [ppm]: −0.10 (s, 9H) 0.78-0.86 (m, 2H) 1.39 (s, 9H) 3.46-3.58 (m, 4H) 3.90-3.98 (m, 2H) 5.62 (s, 2H) 5.97-6.10 (m, 1H) 6.50-6.67 (m, 1H) 7.70 (s, 1H) 8.16 (d, 1H) 8.35-8.50 (m, 2H).

Intermediate 49

4-(2,6-difluoro-4-nitrophenoxy)-3-(1,2,3,6-tetrahydropyridin-4-yl)-1-{[2-(trimethylsilyl)ethoxy]methyl}-1H-pyrrolo[2,3-b]pyridine

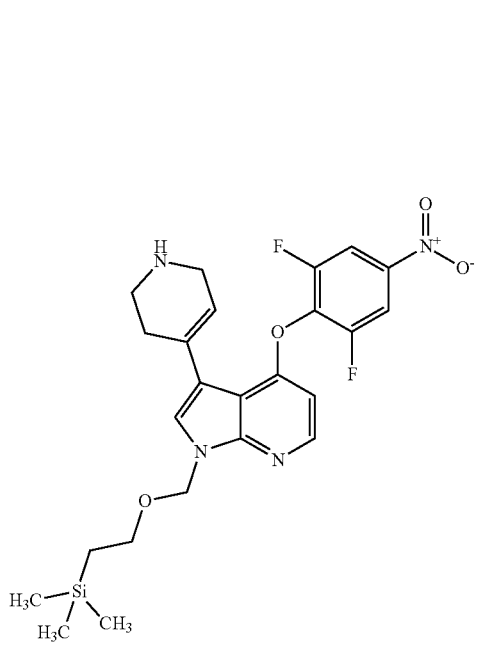 [SMILES: C[Si](C)(C)CCOCn1cc(C2=CCNCC2)c2c(Oc3c(F)cc([N+](=O)[O-])cc3F)ccnc21]

tert-butyl 4-[4-(2,6-difluoro-4-nitrophenoxy)-1-{[2-(trimethylsilyl)ethoxy]methyl}-1H-pyrrolo[2,3-b]pyridin-3-yl]-3,6-dihydropyridine-1(2H)-carboxylate (500 mg, 830 μmol, intermediate 48) was dissolved in dichloromethane (5.1 mL) and trimethylsilyl iodide (150 μL, 1.1 mmol) was added at 0° C. The mixture was stirred at low temperature for 1 h, dried and purified by silica gel chromatography (10 g SNAP KP-Sil, dichloromethane/0-15% methanol) to give the title compound (440 mg, 100% yield).

LC-MS (Method 2): R$_t$=1.51 min; MS (ESIpos): m/z=503 [M+H]$^+$ $^1$H NMR (400 MHz, DMSO-d$_6$) δ ppm −0.10 (s, 9H) 0.77-0.88 (m, 2H) 2.70-2.83 (m, 2H) 3.23-3.32 (m, 2H) 3.50-3.62 (m, 2H) 3.67-3.78 (m, 2H) 5.65 (s, 2H) 6.04-6.26 (m, 1H) 6.52-6.71 (m, 1H) 7.81 (s, 1H) 8.18 (d, 1H) 8.37-8.54 (m, 2H) 8.93 (br s, 1H).

Intermediate 50

1-{4-[4-(2,6-difluoro-4-nitrophenoxy)-1-{[2-(trimethylsilyl)ethoxy]methyl}-1H-pyrrolo[2,3-b]pyridin-3-yl]-3,6-dihydropyridin-1(2H)-yl}propan-1-one

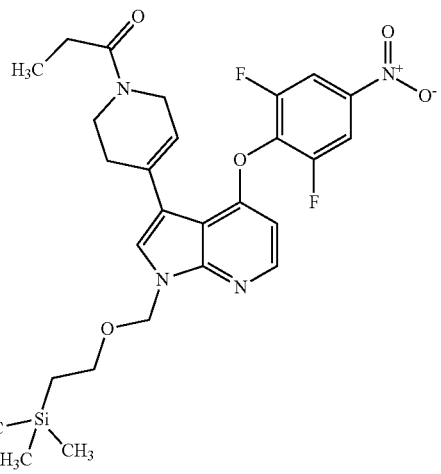

4-(2,6-difluoro-4-nitrophenoxy)-3-(1,2,3,6-tetrahydropyridin-4-yl)-1-{[2-(trimethylsilyl)ethoxy]methyl}-1H-pyrrolo[2,3-b]pyridine (35.0 mg, 69.6 μmol, intermediate 49) was dissolved in DMF (800 μL), and N,N-diisopropylethylamine (36 μL, 210 μmol) and propanoic acid (6.2 μL, 84 μmol) were added. Propylphosphonic anhydride solution (45 μL, 50% in DMF, 77 μmol) was added dropwise at room temperature, and the mixture was stirred overnight, then diluted with water and extracted with ethyl acetate (×3). The organic phases were combined, dried with sodium sulphate, filtered and evaporated. The residue was purified by silica gel chromatography (25 g SNAP KP-Sil, hexane/0-65% ethyl acetate) to give the title compound (24.4 mg, 60% yield).

LC-MS (Method 2): R$_t$=1.51 min; MS (ESIpos): m/z=559 [M+H]$^+$ $^1$H NMR (400 MHz, DMSO-d$_6$) δ ppm −0.10 (s, 9H) 0.79-0.85 (m, 2H) 0.98 (q, 3H) 2.29-2.43 (m, 2H) 2.54-2.63 (m, 1H) 3.50-3.57 (m, 2H) 3.58-3.69 (m, 2H) 4.00-4.14 (m, 2H) 5.63 (s, 2H) 6.00-6.16 (m, 1H) 6.51-6.66 (m, 1H) 7.62-7.77 (m, 1H) 8.17 (d, 1H) 8.34-8.52 (m, 2H).

121

Intermediate 51

1-{4-[4-(4-amino-2,6-difluorophenoxy)-1-{[2-(trimethylsilyl)ethoxy]methyl}-1H-pyrrolo[2,3-b]pyridin-3-yl]-3,6-dihydropyridin-1(2H)-yl}propan-1-one

122

Intermediate 52

1-(3,5-difluoro-4-{[3-(1-propanoyl-1,2,3,6-tetrahydropyridin-4-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

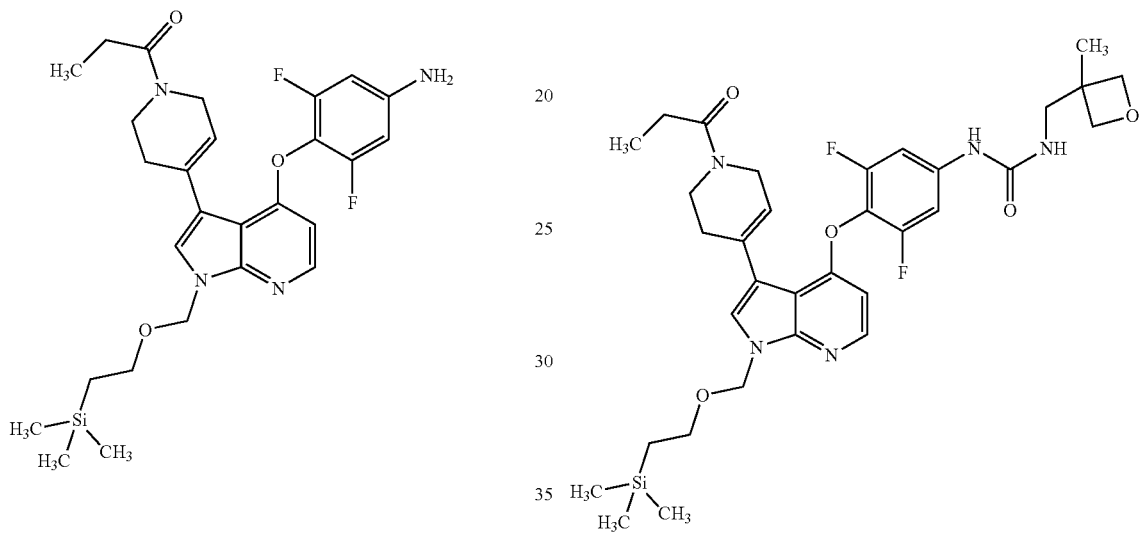

Ammonium chloride (164 mg, 3.06 mmol) and iron (171 mg, 3.06 mmol) were suspended in water (7.2 mL). 1-{4-[4-(2,6-difluoro-4-nitrophenoxy)-1-{[2-(trimethylsilyl)ethoxy]methyl}-1H-pyrrolo[2,3-b]pyridin-3-yl]-3,6-dihydropyridin-1(2H)-yl}propan-1-one (342 mg, 612 µmol, intermediate 50) was dissolved in THF (3.6 mL) and methanol (3.6 mL) and added to the suspension, that was heated at 80° C. for 16 h. The mixture was diluted with ethyl acetate and filtered. The phases were separated and the organic phase was washed with brine, dried with sodium sulfate, filtered and evaporated. The crude product was purified by flash chromatography (25 g $SiO_2$ SNAP Ultra-column, dichloromethane/0-8% methanol) to give the title compound (303 mg, 89% yield).

LC-MS (Method 2): $R_t$=1.39 min; MS (ESIneg): m/z=527 [M−H]⁻

¹H NMR (400 MHz, DMSO-d₆) δ ppm −0.09 (s, 9H) 0.77-0.88 (m, 2H) 0.94-1.04 (m, 3H) 2.28-2.43 (m, 2H) 2.56-2.65 (m, 1H) 3.48-3.58 (m, 2H) 3.59-3.72 (m, 2H) 4.00-4.15 (m, 2H) 5.60 (s, 2H) 5.84 (br s, 2H) 6.04-6.17 (m, 1H) 6.31-6.37 (m, 1H) 6.39 (m, 2H) 7.53-7.67 (m, 1H) 8.11 (d, 1H).

1-{4-[4-(4-amino-2,6-difluorophenoxy)-1-{[2-(trimethylsilyl)ethoxy]methyl}-1H-pyrrolo[2,3-b]pyridin-3-yl]-3,6-dihydropyridin-1(2H)-yl}propan-1-one (100 mg, 189 µmol, intermediate 51), 3-(isocyanatomethyl)-3-methyloxetane (CAS No. [1260665-88-0]) (48.1 mg, 378 µmol) and pyridine (1.7 mL, 21 mmol) were dissolved in dichloromethane (1.6 mL) and the mixture was stirred overnight at 60° C. in a closed microwave vial. Toluene was added and the mixture was concentrated in vacuo. The residue was purified by flash chromatography (11 g SNAP NH, ethyl acetate/0-100% dichloromethane) to give the title compound (125 mg, 80% yield).

LC-MS (Method 2): $R_t$=1.36 min; MS (ESIpos): m/z=656 [M+H]⁺

¹H NMR (400 MHz, DMSO-d6) δ ppm −0.09 (s, 9H) 0.79-0.88 (m, 2H) 0.98 (q, 3H) 1.23 (s, 3H) 2.30-2.43 (m, 2H) 2.58-2.65 (m, 1H) 3.29 (d, 2H) 3.50-3.59 (m, 2H) 3.60-3.69 (m, 2H) 4.05-4.13 (m, 2H) 4.21 (d, 2H) 4.39 (d, 2H) 5.60 (s, 2H) 6.13-6.16 (m, 1H) 6.35-6.43 (m, 1H) 6.68-6.79 (m, 1H) 7.33-7.47 (m, 2H) 7.57-7.69 (m, 1H) 8.13 (d, 1H) 9.03 (s, 1H).

123

Intermediate 53 tert-butyl 3-[4-(2,6-difluoro-4-nitrophenoxy)-1-{[2-(trimethylsilyl)ethoxy]methyl}-1H-pyrrolo[2,3-b]pyridin-3-yl]-8-azabicyclo[3.2.1]oct-2-ene-8-carboxylate

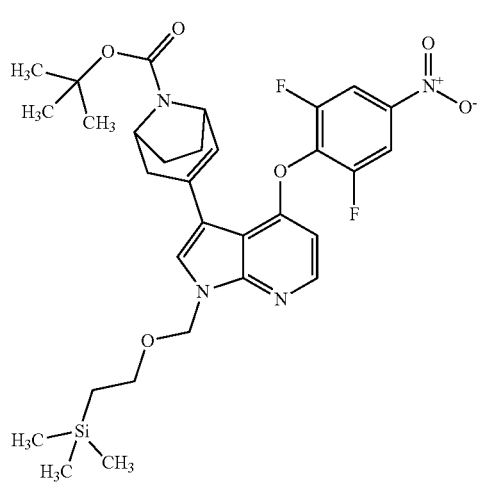 [SMILES: CC(C)(C)OC(=O)N1C2C=C(c3cn(COCC[Si](C)(C)C)c4nccc(Oc5c(F)cc([N+](=O)[O-])cc5F)c34)CC1CC2]

3-bromo-4-(2,6-difluoro-4-nitrophenoxy)-1-{[2-(trimethylsilyl)ethoxy]methyl}-1H-pyrrolo[2,3-b]pyridine (100 mg, 200 µmol, intermediate 16), tert-butyl 3-(4,4,5,5-tetramethyl-1,3,2-dioxaborolan-2-yl)-8-azabicyclo[3.2.1]oct-2-ene-8-carboxylate (CAS No. [900503-08-4]) (80.4 mg, 240 µmol), tetrakis(triphenylphosphin)palladium(0) (11.5 mg, 9.99 µmol), and aq. sodium carbonate (220 µL, 2.0 M, 440 µmol) were combined in 1,4-dioxane (3.5 mL), degassed and flushed with argon. The mixture was heated up to 100° C. for 12 h, diluted with ethyl acetated and filtered. To the filtrate was added water and the phases were separated. The aqueous phase was washed with ethyl acetate, and the combined organic phases were washed with brine, dried with sodium sulfate, filtered and evaporated. The crude product was purified by flash chromatography (50 g SiO$_2$ SNAP Ultra-column, hexane/0-35% ethyl acetate) to give the title compound (41.4 mg, 30% yield).

LC-MS (Method 2): R$_t$=1.74 min; MS (ESIpos): m/z=629 [M+H]$^+$ $^1$H-NMR (400 MHz, DMSO-d6) δ [ppm]: −0.10 (s, 9H) 0.78-0.86 (m, 2H) 1.30 (br d, 9H) 1.61-1.73 (m, 1H) 1.79-1.94 (m, 2H) 2.04-2.19 (m, 1H) 2.28 (d, 1H) 2.98-3.08 (m, 1H) 3.50-3.56 (m, 2H) 4.20-4.35 (m, 2H) 5.60 (s, 2H) 6.35 (br s, 1H) 6.58 (d, 1H) 7.63 (s, 1H) 8.16 (d, 1H) 8.44 (d, 2H).

124

Intermediate 54 tert-butyl 3-[4-(4-amino-2,6-difluorophenoxy)-1-{[2-(trimethylsilyl)ethoxy]methyl}-1H-pyrrolo[2,3-b]pyridin-3-yl]-8-azabicyclo[3.2.1]oct-2-ene-8-carboxylate

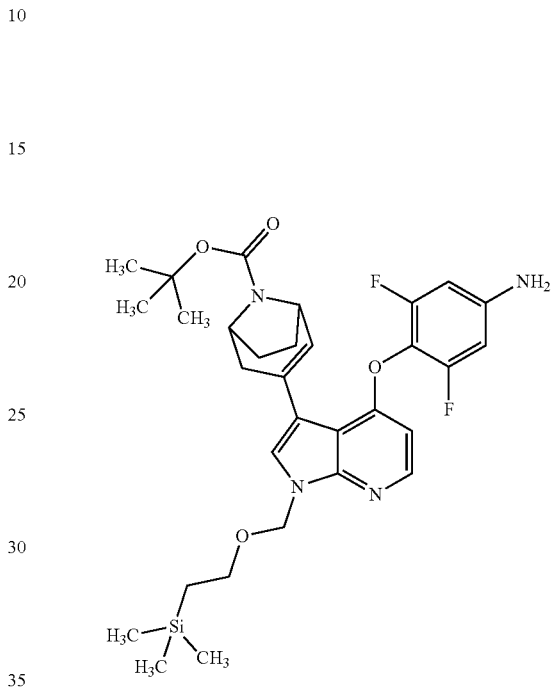

Ammonium chloride (205 mg, 3.83 mmol) and iron (214 mg, 3.83 mmol) were suspended in water (9.0 mL). tert-butyl 3-[4-(2,6-difluoro-4-nitrophenoxy)-1-{[2-(trimethylsilyl)ethoxy]methyl}-1H-pyrrolo[2,3-b]pyridin-3-yl]-8-azabicyclo[3.2.1]oct-2-ene-8-carboxylate (482 mg, 767 µmol, intermediate 53) was dissolved in THF (4.5 mL) and methanol (4.5 mL) and added to the suspension, that was heated overnight at 80° C. The mixture was diluted with ethyl acetate and filtered. The phases were separated and the organic phase was washed with brine, dried with sodium sulfate, filtered and evaporated. The crude product was purified by flash chromatography (28 g SNAP-NH, hexane/2-35% ethyl acetate) to give the title compound (298 mg, 62% yield).

LC-MS (Method 2): R$_t$=1.63 min; MS (ESIpos): m/z=599 [M+H]$^+$ $^1$H-NMR (400 MHz, DMSO-d6) δ [ppm]: $^1$H NMR (400 MHz, DMSO-d$_6$) δ ppm −0.09 (s, 9H) 0.77-0.84 (m, 2H) 1.32 (br s, 9H) 1.63-1.77 (m, 1H) 1.81-1.96 (m, 2H) 2.04-2.20 (m, 1H) 2.21-2.31 (m, 1H) 2.93-3.18 (m, 1H) 3.45-3.58 (m, 2H) 4.18-4.34 (m, 2H) 5.58 (s, 2H) 5.80 (s, 2H) 6.23-6.48 (m, 4H) 7.51 (s, 1H) 8.10 (d, 1H).

Intermediate 55 tert-butyl 3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-8-azabicyclo[3.2.1]oct-2-ene-8-carboxylate

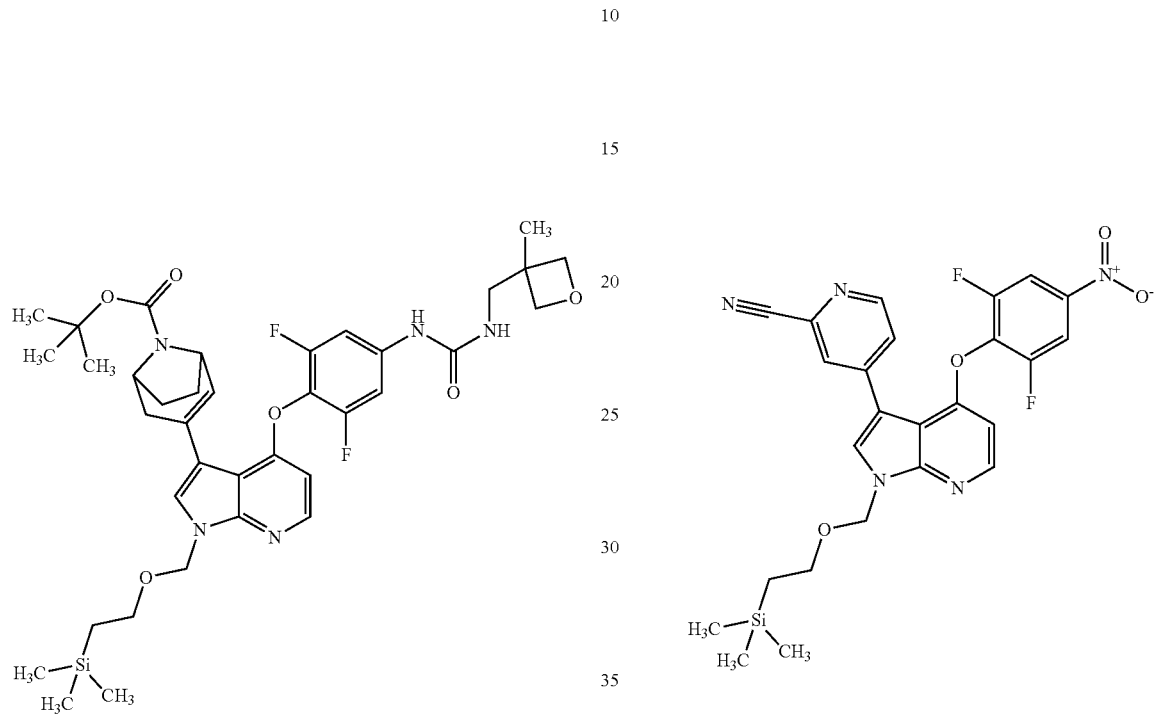

Intermediate 56

4-[4-(2,6-difluoro-4-nitrophenoxy)-1-{[2-(trimethylsilyl)ethoxy]methyl}-1H-pyrrolo[2,3-b]pyridin-3-yl]pyridine-2-carbonitrile

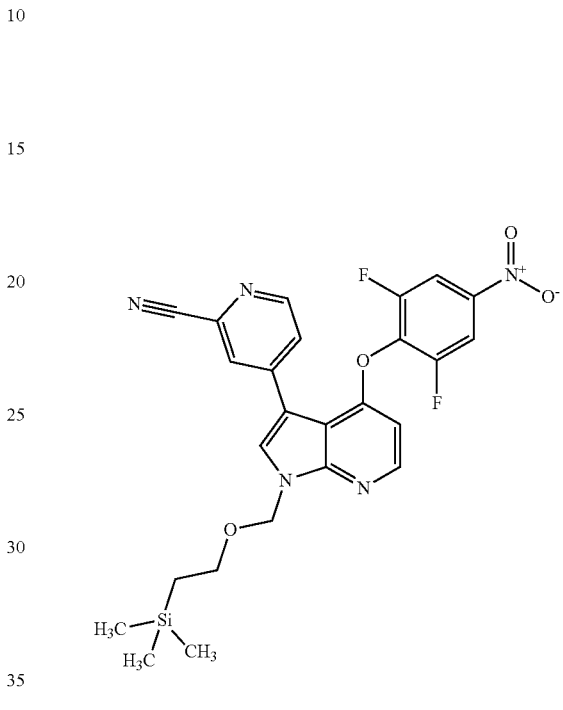

tert-butyl 3-[4-(4-amino-2,6-difluorophenoxy)-1-{[2-(trimethylsilyl)ethoxy]methyl}-1H-pyrrolo[2,3-b]pyridin-3-yl]-8-azabicyclo[3.2.1]oct-2-ene-8-carboxylate (140 mg, 234 μmol, intermediate 54), 3-(isocyanatomethyl)-3-methyloxetane (CAS No. [1260665-88-0]) (59.5 mg, 468 μmol), and pyridine (2.1 mL, 26 mmol) were dissolved in dichloromethane (2.0 mL) and the mixture was stirred overnight at 60° C. in a closed microwave vial. Toluene was added and the mixture was concentrated in vacuo. The residue was purified by flash chromatography (25 g SNAP-KP Sil column, dichloromethane/0-14% methanol) to give the title compound (169 mg, 90% yield).

LC-MS (Method 2): $R_t$=1.59 min; MS (ESIpos): m/z=727 [M+H]$^+$ $^1$H-NMR (400 MHz, DMSO-d6) δ [ppm]: −0.09 (s, 9H) 0.78-0.86 (m, 2H) 1.23 (s, 3H) 1.30 (br s, 9H) 1.61-1.75 (m, 1H) 1.80-1.94 (m, 2H) 2.09-2.19 (m, 1H) 2.23-2.32 (m, 1H) 2.96-3.11 (m, 1H) 3.30 (d, 2H) 3.48-3.55 (m, 2H) 4.21 (d, 2H) 4.38 (s, 2H) 5.59 (s, 2H) 6.40 (d, 1H) 6.68-6.84 (m, 1H) 7.31-7.48 (m, 3H) 7.56 (br s, 1H) 8.11 (d, 1H) 9.05 (s, 1H).

3-bromo-4-(2,6-difluoro-4-nitrophenoxy)-1-{[2-(trimethylsilyl)ethoxy]methyl}-1H-pyrrolo[2,3-b]pyridine (1.20 g, 2.40 mmol, intermediate 16), 4-(4,4,5,5-tetramethyl-1,3,2-dioxaborolan-2-yl)pyridine-2-carbonitrile (CAS No. [741709-62-6]) (662 mg, 2.88 mmol), tetrakis(triphenylphosphin)palladium(0) (222 mg, 192 μmol), and aq. sodium carbonate (2.6 mL, 2.0 M, 5.3 mmol) were combined in 1,4-dioxane (42 mL), degassed and flushed with argon. The mixture was heated up to 100° C. for 16 h, diluted with ethyl acetated and filtered. To the filtrate was added water and the phases were separated. The aqueous phase was washed with ethyl acetate, and the combined organic phases were washed with brine, dried with sodium sulfate, filtered and evaporated. The crude product was purified by flash chromatography (50 g SNAP KP-Sil, hexane/0-35% ethyl acetate) to give the title compound (320 mg, 23% yield).

LC-MS (Method 2): $R_t$=1.57 min; MS (ESIpos): m/z=524 [M+H]$^+$ $^1$H-NMR (400 MHz, DMSO-d6) δ [ppm]: −0.08 (s, 9H) 0.80-0.89 (m, 2H) 3.57-3.70 (m, 2H) 5.73 (s, 2H) 6.73-6.79 (m, 1H) 7.98-8.03 (m, 1H) 8.27-8.32 (m, 2H) 8.40-8.49 (m, 3H) 8.69-8.75 (m, 1H).

Intermediate 57

4-[4-(4-amino-2,6-difluorophenoxy)-1-{[2-(trimethylsilyl)ethoxy]methyl}-1H-pyrrolo[2,3-b]pyridin-3-yl]pyridine-2-carbonitrile

Intermediate 58

1-(4-{[3-(2-cyanopyridin-4-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

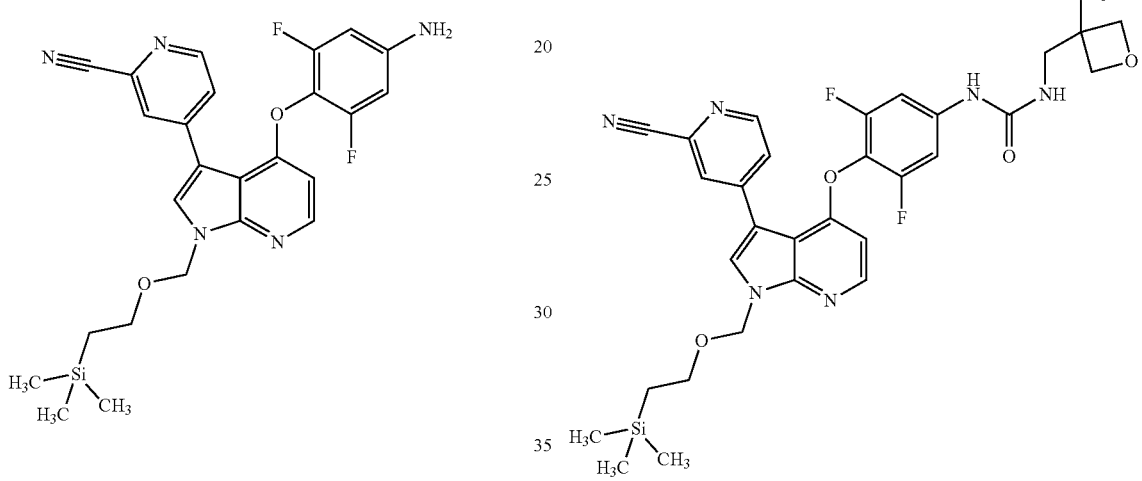

Ammonium chloride (175 mg, 3.27 mmol) and iron (182 mg, 3.27 mmol) were suspended in water (7.7 mL). 4-[4-(2,6-difluoro-4-nitrophenoxy)-1-{[2-(trimethylsilyl)ethoxy]methyl}-1H-pyrrolo[2,3-b]pyridin-3-yl]pyridine-2-carbonitrile (342 mg, 653 µmol, intermediate 56) was dissolved in THF (3.8 mL) and methanol (3.8 mL) and added to the suspension, that was heated at 80° C. for 16 h. The mixture was diluted with ethyl acetate and filtered. The phases were separated and the organic phase was washed with brine, dried with sodium sulfate, filtered and evaporated. The crude product was purified by flash chromatography (28 g SNAP-NH, hexane/2-35% ethyl acetate) to give the title compound (67.5 mg, 17% yield).

LC-MS (Method 2): $R_t$=1.31 min; MS (ESIpos): m/z=494 [M+H]$^+$ $^1$H-NMR (400 MHz, DMSO-d6) δ [ppm]: −0.08 (s, 9H) 0.79-0.89 (m, 2H) 3.57-3.68 (m, 2H) 5.69 (s, 2H) 5.86 (br s, 2H) 6.35-6.46 (m, 2H) 8.01-8.06 (m, 2H) 8.25 (d, 1H) 8.28-8.31 (m, 1H) 8.35 (s, 1H) 8.70-8.75 (m, 1H).

4-[4-(4-amino-2,6-difluorophenoxy)-1-{[2-(trimethylsilyl)ethoxy]methyl}-1H-pyrrolo[2,3-b]pyridin-3-yl]pyridine-2-carbonitrile (65.0 mg, 80% purity, 105 µmol, intermediate 57), 3-(isocyanatomethyl)-3-methyloxetane (CAS No. [1260665-88-0]) (26.8 mg, 211 µmol), and pyridine (940 µL, 12 mmol) were dissolved in dichloromethane (920 µL) and the mixture was stirred overnight at 60° C. in a closed microwave vial. Toluene was added and the mixture was concentrated in vacuo. The residue was purified by flash chromatography (11 g SNAP-NH column, hexane/30-100% ethyl acetate; then dichloromethane/5% methanol) to give the title compound (70.1 mg, 86% yield).

LC-MS (Method 2): $R_t$=1.39 min; MS (ESIpos): m/z=621 [M+H]$^+$ $^1$H-NMR (400 MHz, DMSO-d6) δ [ppm]: −0.08 (s, 9H) 0.81-0.92 (m, 2H) 1.23 (s, 3H) 3.30 (d, 2H) 3.54-3.72 (m, 2H) 4.22 (d, 2H) 4.39 (d, 2H) 5.76 (s, 2H) 6.58 (d, 1H) 6.70-6.83 (m, 1H) 7.36-7.48 (m, 2H) 8.02 (dd, 1H) 8.26 (d, 1H) 8.28-8.34 (m, 1H) 8.39 (s, 1H) 8.71 (dd, 1H) 9.09 (s, 1H).

129

Intermediate 59

5-[4-(2,6-difluoro-4-nitrophenoxy)-1-{[2-(trimethylsilyl)ethoxy]methyl}-1H-pyrrolo[2,3-b]pyridin-3-yl]-2-fluorobenzonitrile

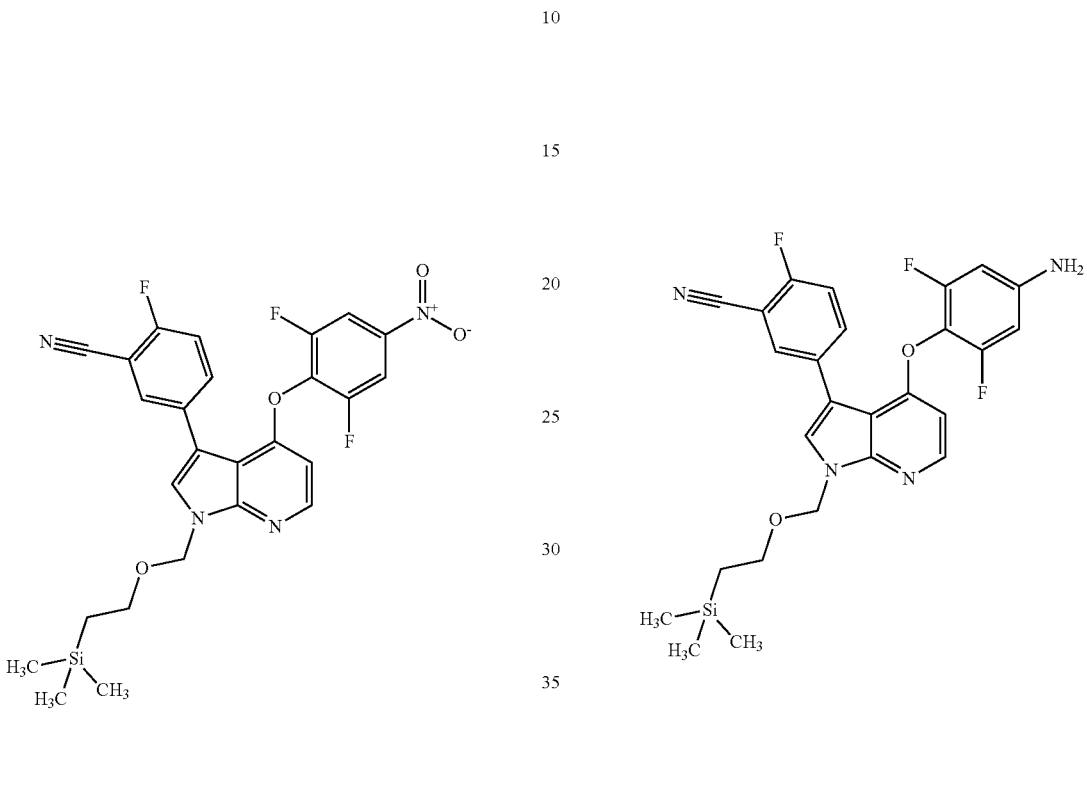

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), (3-cyano-4-fluorophenyl)boronic acid (CAS No. [214210-21-6]) (659 mg, 4.00 mmol), and Pd(dppf)Cl$_2$ (146 mg, 200 µmol) were dissolved in degassed 1,4-dioxane (15 mL) and water (7.5 mL) and stirred under argon 3 h at 95° C. The mixture was diluted with water and extracted with ethyl acetate. The combined organic phases were dried with sodium sulfate, filtered and evaporated. The crude product was purified by flash chromatography to give the title compound (745 mg, 48% yield).

LC-MS (Method 2): R$_t$=1.66 min; MS (ESIpos): m/z=541 [M+H]$^+$ $^1$H-NMR (400 MHz, DMSO-d6) δ [ppm]: −0.09 (s, 9H) 0.82-0.90 (m, 2H) 3.57-3.65 (m, 2H) 5.70 (s, 2H) 6.66-6.71 (m, 1H) 7.58 (t, 1H) 7.96-8.04 (m, 1H) 8.06 (s, 1H) 8.11 (dd, 1H) 8.24 (d, 1H) 8.38-8.43 (m, 2H).

130

Intermediate 60

5-[4-(4-amino-2,6-difluorophenoxy)-1-{[2-(trimethylsilyl)ethoxy]methyl}-1H-pyrrolo[2,3-b]pyridin-3-yl]-2-fluorobenzonitrile

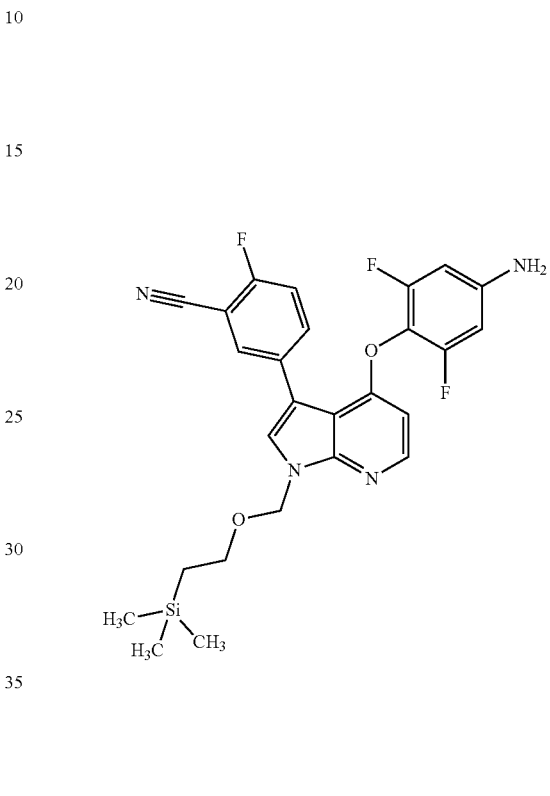

Ammonium chloride (258 mg, 4.82 mmol) and iron (269 mg, 4.82 mmol) were suspended in water (10 mL). 5-[4-(2,6-difluoro-4-nitrophenoxy)-1-{[2-(trimethylsilyl)ethoxy]methyl}-1H-pyrrolo[2,3-b]pyridin-3-yl]-2-fluorobenzonitrile (745 mg, 70% purity, 965 µmol, intermediate 59) was dissolved in THF (15 mL) and methanol (15 mL) and added to the suspension, that was heated at reflux for 4 h. Additional ammonium chloride (258 mg, 4.82 mmol) and iron (269 mg, 4.82 mmol) were added and the suspension was further heated overnight. The mixture was filtered, and diluted with water and ethyl acetate. The phases were separated and the organic phase was washed with brine, dried with sodium sulfate, filtered and evaporated. The crude product was purified by preparative HPLC to yield the title compound (240 mg, 46% yield).

LC-MS (Method 2): R$_t$=1.54 min; MS (ESIpos): m/z=511 [M+H]$^+$ $^1$H-NMR (400 MHz, DMSO-d6) δ [ppm]: −0.08 (s, 9H) 0.79-0.92 (m, 2H) 3.55-3.63 (m, 2H) 5.66 (s, 2H) 5.83 (br s, 2H) 6.36-6.42 (m, 2H) 6.46 (d, 1H) 7.60 (t, 1H) 7.99 (s, 1H) 8.01-8.07 (m, 1H) 8.11 (dd, 1H) 8.21 (d, 1H).

Intermediate 61

1-(4-{[3-(3-cyano-4-fluorophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

Intermediate 62

3-[4-(2,6-difluoro-4-nitrophenoxy)-1-{[2-(trimethylsilyl)ethoxy]methyl}-1H-pyrrolo[2,3-b]pyridin-3-yl]-5-fluorobenzonitrile

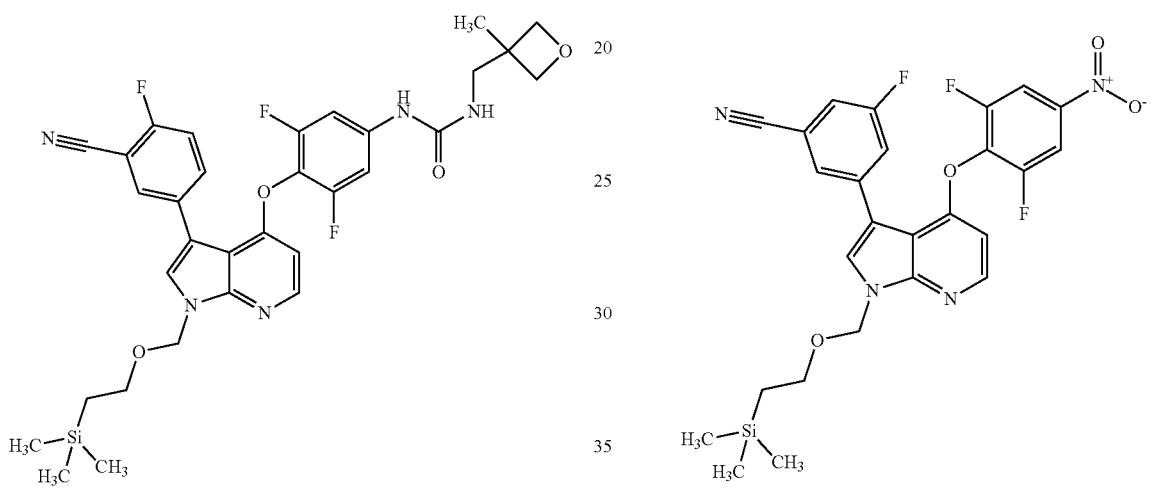

5-[4-(4-amino-2,6-difluorophenoxy)-1-{[2-(trimethylsilyl)ethoxy]methyl}-1H-pyrrolo[2,3-b]pyridin-3-yl]-2-fluorobenzonitrile (120 mg, 235 µmol, intermediate 60), 3-(isocyanatomethyl)-3-methyloxetane (CAS No. [1260665-88-0]) (59.8 mg, 470 µmol), and pyridine (2.1 mL, 26 mmol) were dissolved in dichloromethane (2.0 mL) and the mixture was stirred overnight at 60° C. in a closed microwave vial. Toluene was added and the mixture was concentrated in vacuo. The residue was purified by flash chromatography to give the title compound (75.0 mg, 50% yield).

LC-MS (Method 2): $R_t$=1.51 min; MS (ESIpos): m/z=638 [M+H]$^+$ $^1$H-NMR (400 MHz, DMSO-d6) δ [ppm]: −0.08 (s, 9H) 0.80-0.89 (m, 2H) 1.23 (s, 3H) 3.29-3.32 (m, 2H) 3.55-3.64 (m, 2H) 4.21 (d, 2H) 4.38 (d, 2H) 5.68 (s, 2H) 6.45-6.53 (m, 1H) 6.66-6.75 (m, 1H) 7.35-7.45 (m, 2H) 7.59 (t, 1H) 8.01 (s, 1H) 8.02-8.07 (m, 1H) 8.11 (dd, 1H) 8.21 (d, 1H) 9.01 (s, 1H).

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), (3-cyano-5-fluorophenyl)boronic acid (CAS No. [304858-67-1]) (659 mg, 4.00 mmol), and Pd(dppf)Cl$_2$ (146 mg, 200 µmol) were dissolved in degassed 1,4-dioxane (15 mL) and water (7.5 mL) and stirred under argon 3 h at 95° C. The mixture was diluted with water and extracted with ethyl acetate. The combined organic phases were dried with sodium sulfate, filtered and evaporated. The crude product was purified by flash chromatography to give the title compound (610 mg, 40% yield).

LC-MS (Method 2): $R_t$=1.64 min; MS (ESIpos): m/z=541 [M+H]$^+$ $^1$H-NMR (400 MHz, DMSO-d6) δ [ppm]: −0.08 (s, 9H) 0.82-0.92 (m, 2H) 3.58-3.64 (m, 2H) 5.70 (s, 2H) 6.69-6.77 (m, 1H) 7.71-7.78 (m, 1H) 7.79-7.88 (m, 1H) 7.92-7.97 (m, 1H) 8.19 (s, 1H) 8.26 (d, 1H) 8.40-8.48 (m, 2H).

Intermediate 63

3-[4-(4-amino-2,6-difluorophenoxy)-1-{[2-(trimethylsilyl)ethoxy]methyl}-1H-pyrrolo[2,3-b]pyridin-3-yl]-5-fluorobenzonitrile

Intermediate 64

1-(4-{[3-(3-cyano-5-fluorophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

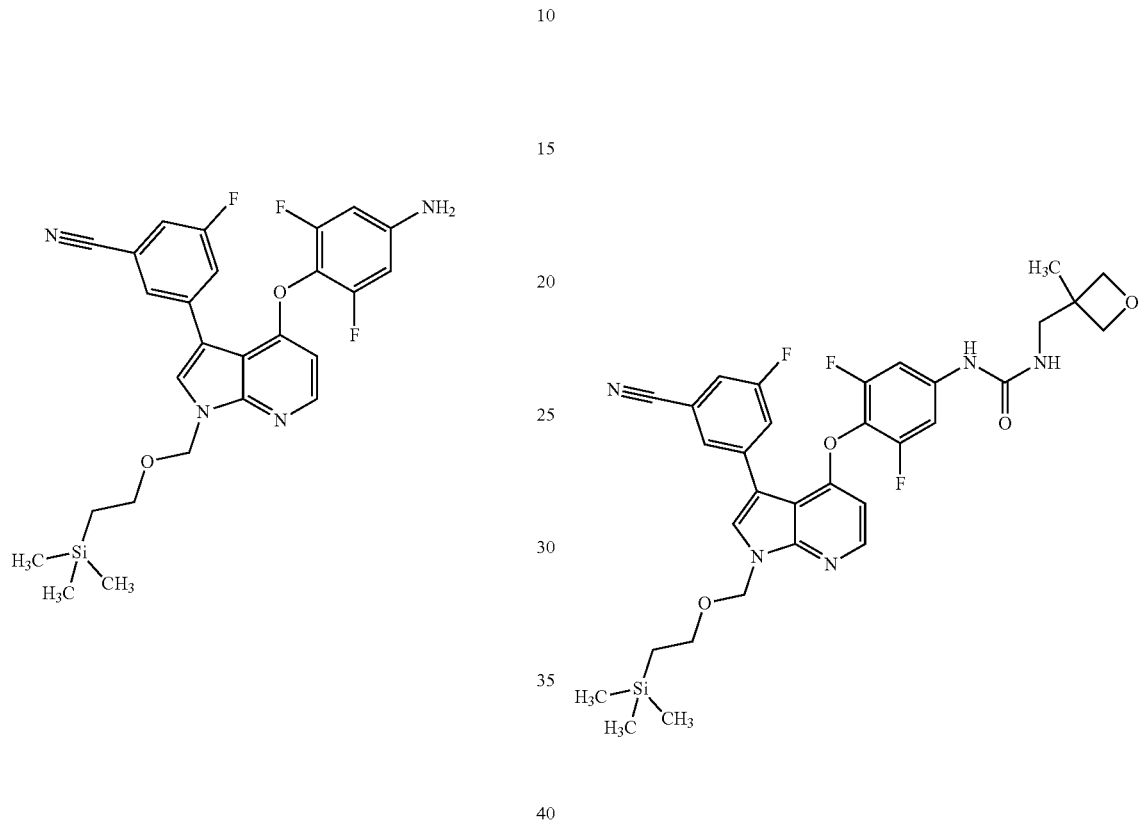

Ammonium chloride (211 mg, 3.95 mmol) and iron (221 mg, 3.95 mmol) were suspended in water (10 mL). 3-[4-(2,6-difluoro-4-nitrophenoxy)-1-{[2-(trimethylsilyl)ethoxy]methyl}-1H-pyrrolo[2,3-b]pyridin-3-yl]-5-fluorobenzonitrile (610 mg, 70% purity, 790 μmol, intermediate 62) was dissolved in THF (15 mL) and methanol (15 mL) and added to the suspension, that was heated at reflux for 4 h. Additional ammonium chloride (211 mg, 3.95 mmol) and iron (221 mg, 3.95 mmol) were added and the suspension was further heated overnight. The mixture was filtered, and diluted with water and ethyl acetate. The phases were separated and the organic phase was washed with brine, dried with sodium sulfate, filtered and evaporated. The crude was filtered over silica gel and the residue was purified by preparative HPLC to give the title compound (210 mg, 49% yield).

LC-MS (Method 2): $R_t$=1.55 min; MS (ESIpos): m/z=511 [M+H]$^+$ $^1$H-NMR (400 MHz, DMSO-d6) δ [ppm]: −0.08 (s, 9H) 0.81-0.92 (m, 2H) 3.53-3.69 (m, 2H) 5.67 (s, 2H) 5.85 (br s, 2H) 6.37-6.45 (m, 2H) 6.46-6.54 (m, 1H) 7.67-7.76 (m, 1H) 7.81-7.88 (m, 1H) 7.94-8.01 (m, 1H) 8.12 (s, 1H) 8.23 (d, 1H).

3-[4-(4-amino-2,6-difluorophenoxy)-1-{[2-(trimethylsilyl)ethoxy]methyl}-1H-pyrrolo[2,3-b]pyridin-3-yl]-5-fluorobenzonitrile (105 mg, 206 μmol, intermediate 63), 3-(isocyanatomethyl)-3-methyloxetane (CAS No. [1260665-88-0]) (52.3 mg, 411 μmol), and pyridine (1.8 mL, 23 mmol) were dissolved in dichloromethane (1.8 mL) and the mixture was stirred overnight at 60° C. in a closed microwave vial. Toluene was added and the mixture was concentrated in vacuo. The residue was purified by flash chromatography to give the title compound (92.0 mg, 70% yield).

LC-MS (Method 2): $R_t$=1.52 min; MS (ESIpos): m/z=638 [M+H]$^+$ $^1$H NMR (400 MHz, DMSO-d$_6$) δ ppm −0.08 (s, 9H) 0.84-0.89 (m, 2H) 1.24 (s, 3H) 3.30 (d, 2H) 3.57-3.63 (m, 2H) 4.21 (d, 2H) 4.38 (d, 2H) 5.70 (s, 2H) 6.50-6.60 (m, 1H) 6.68-6.75 (m, 1H) 7.36-7.48 (m, 2H) 7.70-7.77 (m, 1H) 7.81-7.88 (m, 1H) 7.95-8.02 (m, 1H) 8.16 (s, 1H) 8.24 (d, 1H) 9.02 (s, 1H).

Intermediate 65 phenyl {4-[(3-chloro-1-{[2-(trimethylsilyl)ethoxy]methyl}-1H-pyrrolo[2,3-b]pyridin-4-yl)oxy]-3,5-difluorophenyl}carbamate

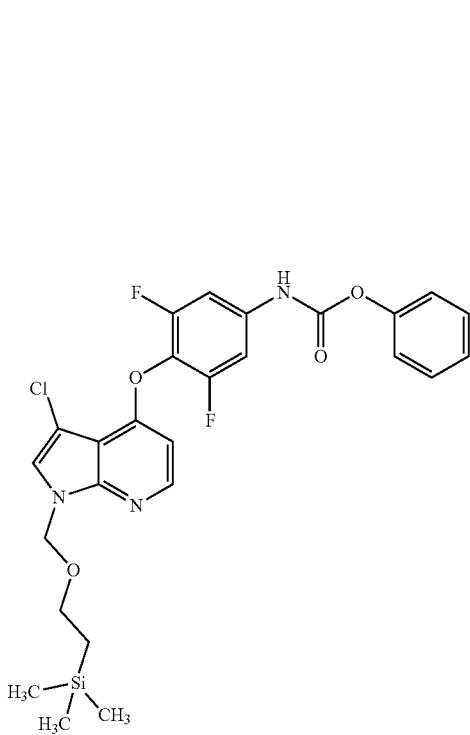 [SMILES: C[Si](C)(C)CCOCn1cc(Cl)c2c(Oc3c(F)cc(NC(=O)Oc4ccccc4)cc3F)ccnc21]

To solution of 4-[(3-chloro-1-{[2-(trimethylsilyl)ethoxy]methyl}-1H-pyrrolo[2,3-b]pyridin-4-yl)oxy]-3,5-difluoroaniline (1.20 g, 2.82 mmol, synthesis see ChemMedChem 3, (2008), p. 1893 ff., cpd 63) in ethyl acetate (20 mL) and saturated sodium bicarbonate solution (10 mL) was slowly added at RT phenyl carbonochloridate (441 mg, 2.82 mmol). After stirring this mixture 5 hours, the mixture was diluted with water. The organic phase was washed with brine, dried over sodium sulfate, filtered and concentrated to dryness. The resulting residue was purified via a Biotage chromatography system (KP-Sil snap column; hexane/ethyl acetate gradient with up to 35% ethyl acetate) to obtain 1.37 g (89% yield) of the desired title compound.

$^1$H-NMR (400 MHz, CDCl$_3$) δ [ppm]: −0.05 (s, 9H), 0.89-0.95 (m, 2H), 3.52-3.58 (m, 2H), 5.63 (s, 2H), 6.31 (d, 1H), 7.12 (bs, 1H); 7.17-7.22 (m, 2H); 7.23-7.31 (m, 4H+CHCl$_3$); 7.40-7.45 (m, 2H); 8.14 (d, 1H).

Intermediate 66

1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea

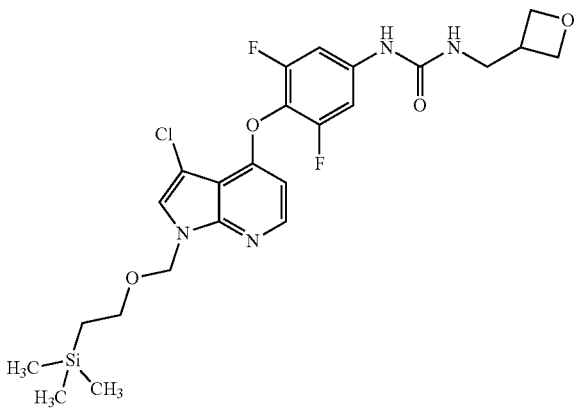 [SMILES: C[Si](C)(C)CCOCn1cc(Cl)c2c(Oc3c(F)cc(NC(=O)NCC4COC4)cc3F)ccnc21]

To solution of phenyl {4-[(3-chloro-1-{[2-(trimethylsilyl)ethoxy]methyl}-1H-pyrrolo[2,3-b]pyridin-4-yl)oxy]-3,5-difluorophenyl}carbamate (150 mg, 275 μmol, intermediate 65) in DMF (4.0 mL) was added 1-(3-methyloxetan-3-yl)methanamine (55.6 mg, 549 μmol, CAS No. [153209-97-3]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea, which was used in the subsequent reaction without further purification.

Intermediate 67

1-{4-[(3-chloro-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea To solution of phenyl {4-[(3-chloro-1-{[2-(trimethylsilyl)ethoxy]methyl}-1H-pyrrolo[2,3-b]pyridin-4-yl)oxy]-3,5-difluorophenyl}carbamate (150 mg, 275 µmol, intermediate 65) in DMF (4.0 mL) was added 1-(oxetan-3-yl)methanamine (47.9 mg, 549 µmol, CAS No. [6246-05-5]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-{4-[(3-chloro-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea, which was used in the subsequent reaction without further purification.

Intermediate 68

1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea

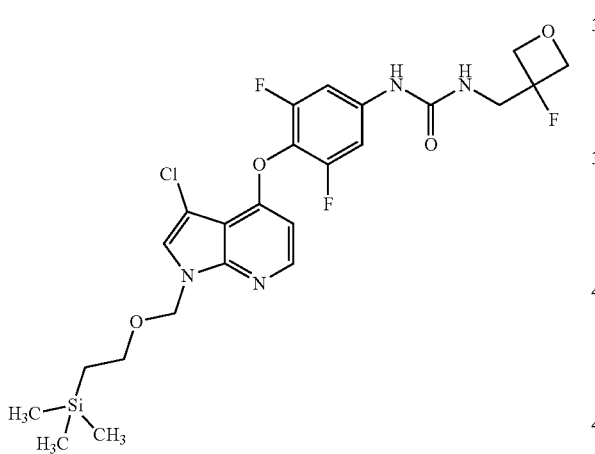

To solution of phenyl {4-[(3-chloro-1-{[2-(trimethylsilyl)ethoxy]methyl}-1H-pyrrolo[2,3-b]pyridin-4-yl)oxy]-3,5-difluorophenyl}carbamate (150 mg, 275 µmol, intermediate 65) in DMF (4.0 mL) was added 1-(3-fluorooxetan-3-yl)methanamine (57.7 mg, 549 µmol, CAS No. [883311-82-8]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea, which was used in the subsequent reaction without further purification.

Intermediate 69

4-(2,6-difluoro-4-nitrophenoxy)-1-{[2-(trimethylsilyl)ethoxy]methyl}-1H-pyrrolo[2,3-b]pyridine-3-carbaldehyde

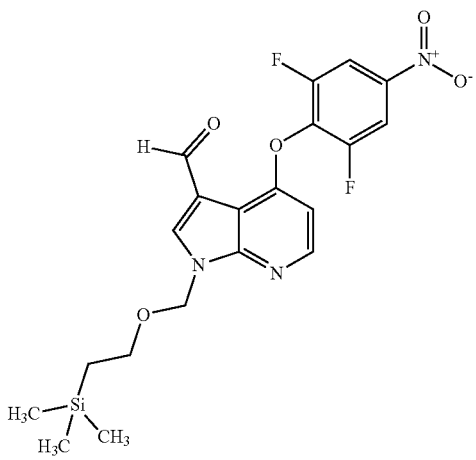 [SMILES: C[Si](C)(C)CCOCn1cc(C=O)c2c(Oc3c(F)cc([N+](=O)[O-])cc3F)ccnc21]

To a cold (0° C.) solution of DMF (14 mL) was slowly added phosphorus trichloride (1.0 mL, 11 mmol). After 15 min, a solution of 4-(2,6-difluoro-4-nitrophenoxy)-1-{[2-(trimethylsilyl)ethoxy]methyl}-1H-pyrrolo[2,3-b]pyridine (3.00 g, 7.12 mmol, intermediate 15) in DMF (5.5 mL) was added dropwise, and the resulting mixture was heated to 60° C. for 3 h. After this time, the reaction mixture was quenched with icewater, and the solution basified to pH >10 by the addition of NaHCO$_3$. The resulting mixture was extracted with ethyl acetate three times. The combined organic phases were washed with brine, dried over sodium sulfate, filtered and concentrated to dryness to give 4-(2,6-difluoro-4-nitrophenoxy)-1-{[2-(trimethylsilyl)ethoxy]methyl}-1H-pyrrolo[2,3-b]pyridine-3-carbaldehyde (3.53 g, 99% yield), which required no further purification.

LC-MS (Method 1): R$_t$=1.47 min; MS (ESIpos): m/z=450 [M+H]$^+$ $^1$H NMR (400 MHz, DMSO-d$_6$) δ ppm −0.10 (s, 9H), 0.78-0.89 (m, 2H), 3.55-3.65 (m, 2H), 5.75 (s, 2H), 6.86 (d, 1H), 8.31 (d, 1H), 8.37-8.46 (m, 2H), 8.66 (s, 1H), 10.17 (s, 1H)

Intermediate 70

4-(2,6-difluoro-4-nitrophenoxy)-1-{[2-(trimethylsilyl)ethoxy]methyl}-1H-pyrrolo[2,3-b]pyridine-3-carboxylic Acid

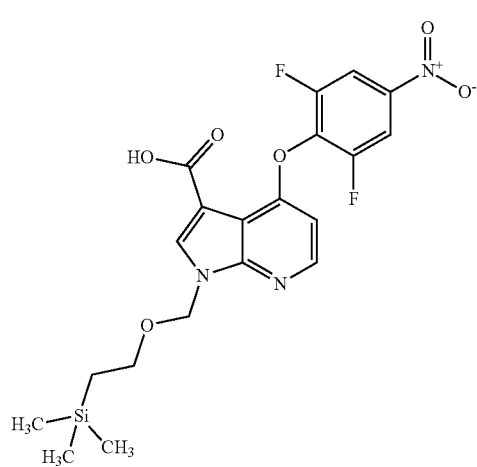 [SMILES: C[Si](C)(C)CCOCn1cc(C(=O)O)c2c(Oc3c(F)cc([N+](=O)[O-])cc3F)ccnc21]

Intermediate 71

4-(2,6-difluoro-4-nitrophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide

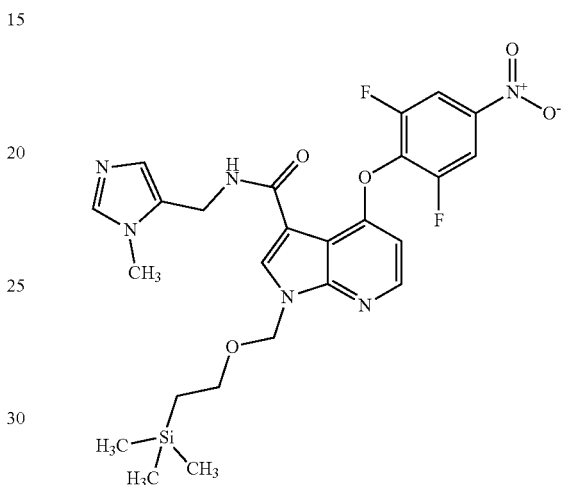

To a stirred solution of 4-(2,6-difluoro-4-nitrophenoxy)-1-{[2-(trimethylsilyl)ethoxy]methyl}1H-pyrrolo[2,3-b]pyridine-3-carbaldehyde (3.53 g, 7.85 mmol, intermediate 69), and 2-methylbut-2-ene (7.9 mL, 0.10 M in THF, 790 μmol) in tert-butanol (45 mL), was added a solution of sodium phosphate monobasic dihydrate (4.90 g, 31.4 mmol), and sodium chlorite (1.42 g, 15.7 mmol) in water (7.0 mL). The resulting reaction mixture was stirred at room temperature for 4 hours, at which time it was partially concentrated, diluted with ethyl acetate, and 1N HCl was added until pH<2. The phases were separated and the aqueous phase extracted two times with ethyl acetate. The combined organic phases were washed with brine, dried over sodium sulfate, filtered and concentrated to dryness to give the crude acid. Purification of the crude material by crystallization from hexane gave 4-(2,6-difluoro-4-nitrophenoxy)-1-{[2-(trimethylsilyl)ethoxy]methyl}-1H-pyrrolo[2,3-b]pyridine-3-carboxylic acid (2.46 g, 59% yield) as a white solid.

LC-MS (Method 1): $R_t$=1.40 min; MS (ESIpos): m/z=466 [M+H]$^+$ $^1$H NMR (400 MHz, DMSO-d$_6$) δ ppm −0.10 (s, 9H), 0.79-0.87 (m, 2H), 3.37 (br s, 1H), 3.53-3.62 (m, 2H), 5.70 (s, 2H), 6.80 (d, 1H), 8.26 (d, 1H), 8.34-8.39 (m, 2H), 8.41 (s, 1H)

To a stirred solution of 4-(2,6-difluoro-4-nitrophenoxy)-1-{[2-(trimethylsilyl)ethoxy]methyl}-1H-pyrrolo[2,3-b]pyridine-3-carboxylic acid (1.50 g, 3.22 mmol, intermediate 70) in DMF (22 mL), was added N,N-diisopropylethylamine (1.7 mL, 9.7 mmol) followed by HATU (2.45 g, 6.45 mmol). The reaction mixture was stirred for 30 min, at which time 1-(1-methyl-1H-imidazol-5-yl)methanamine (394 mg, 3.54 mmol, CAS No. [486414-86-2]) was added The reaction mixture was stirred at room temperature for 2 hours, at which time the reaction was diluted with ethyl acetate and water. The phases were separated and the aqueous phase extracted two times with ethyl acetate. The combined organic phases were washed with brine, dried over sodium sulfate, filtered, and concentrated to dryness to give the crude amide. The crude material was purified by flash column chromatography to afford 4-(2,6-difluoro-4-nitrophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide (1.14 g, 63% Yield).

LC-MS (Method 1): $R_t$=1.05 min; MS (ESIpos): m/z=559 [M+H]$^+$ $^1$H NMR (400 MHz, DMSO-d$_6$) δ ppm −0.09 (s, 9H), 0.77-0.91 (m, 2H), 3.52-3.59 (m, 2H), 3.60 (s, 3H), 4.47 (d, 2H), 5.68 (s, 2H), 6.74 (d, 1H), 6.92 (s, 1H), 7.75 (s, 1H), 8.22-8.25 (m, 2H), 8.28 (t, 1H), 8.34-8.40 (m, 2H)

141

Intermediate 72

4-(4-amino-2,6-difluorophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide To a solution of 4-(2,6-difluoro-4-nitrophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide (4.00 g, 85% purity, 6.09 mmol) in a mixture of THF (17 mL), water (11 mL), and methanol (9 mL) was added ammonium chloride (1.63 g, 30.4 mmol) and iron powder (1.70 g, 30.4 mmol). The resulting mixture was stirred at 80 degrees for 3 hours at which time the mixture was cooled and filtered. The filtrate was extracted three times with ethyl acetate and the combined organic layers washed with brine, dried (Na$_2$SO$_4$), and evaporated to give the crude aniline. The crude product was purified by flash column chromatography to afford 4-(4-amino-2,6-difluorophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide (1.50 g, 42% Yield).

LC-MS (Method 2): R$_t$=1.20 min; MS (ESIpos): m/z=529 [M+H]$^+$ $^1$H NMR (400 MHz, DMSO-d$_6$) δ ppm −0.09 (s, 9H), 0.79-0.86 (m, 2H), 3.52-3.58 (m, 5H), 4.51 (d, 2H), 5.67 (s, 2H), 5.86 (s, 2H), 6.33-6.40 (m, 2H), 6.50 (d, 1H), 6.75 (d, 1H), 7.44 (s, 1H), 8.16 (br s, 1H), 8.20 (d, 1H), 8.25 (s, 1H)

142

Intermediate 73 phenyl {3,5-difluoro-4-[(3-{[(1-methyl-1H-imidazol-5-yl)methyl]carbamoyl}-1-{[2-(trimethylsilyl)ethoxy]methyl}-1H-pyrrolo[2,3-b]pyridin-4-yl)oxy]phenyl}carbamate

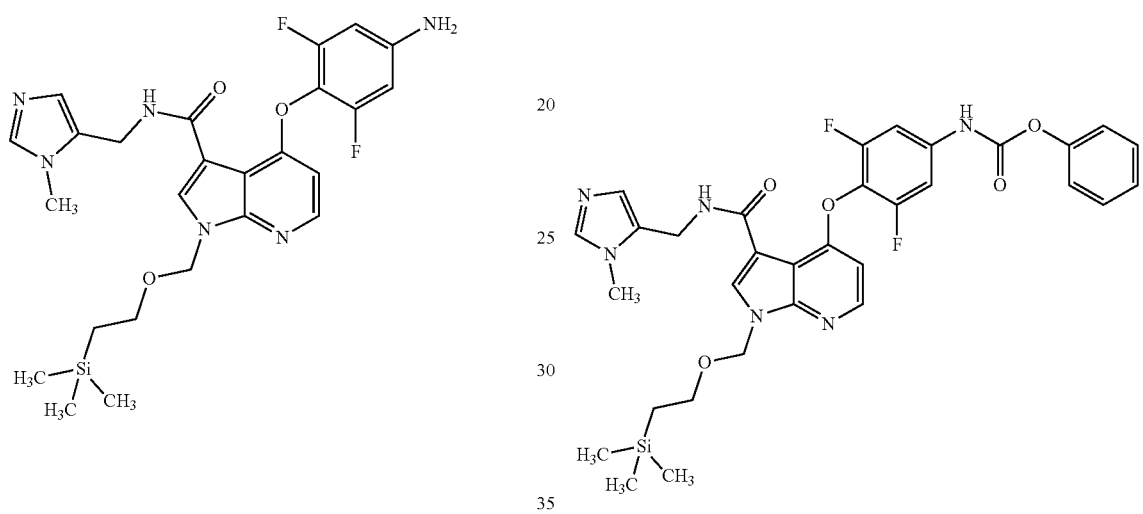

A stirred solution of 4-(4-amino-2,6-difluorophenoxy)-N-[(1-methyl-1H-imidazol-5-yl)methyl]-1-{[2-(trimethylsilyl)ethoxy]methyl}-1H-pyrrolo[2,3-b]pyridine-3-carboxamide (860 mg, 1.63 mmol, intermediate 72), in THF (5.0 mL) and pyridine (5.0 mL) was added phenylchloroformate (0.31 mL, 2.4 mmol). The resulting reaction mixture was stirred at room temperature overnight, at which time ethyl acetate and NaHCO$_3$ were added. The phases were separated and the aqueous phase extracted two times with ethyl acetate. The combined organic phases were washed with brine, dried over sodium sulfate, filtered, and concentrated to dryness to give crude phenyl {3,5-difluoro-4-[(3-{[(1-methyl-1H-imidazol-5-yl)methyl]carbamoyl}-1-{[2-(trimethylsilyl)ethoxy]methyl}-1H-pyrrolo[2,3-b]pyridin-4-yl)oxy]phenyl}carbamate, which was used without further purification.

LC-MS (Method 1): R$_t$=1.20 min; MS (ESIpos): m/z=649 [M+H]$^+$

143

Intermediate 74

4-[2,6-difluoro-4-({[(3-methyloxetan-3-yl)methyl]carbamoyl}amino)phenoxy]-N-[(1-methyl-1H-imidazol-5-yl)methyl]-1-{[2-(trimethylsilyl)ethoxy]methyl}-1H-pyrrolo[2,3-b]pyridine-3-carboxamide

144

Intermediate 75

4-(2,6-difluoro-4-{[(oxetan-3-ylmethyl)carbamoyl]amino}phenoxy)-N-[(1-methyl-1H-imidazol-5-yl)methyl]-1-{[2-(trimethylsilyl)ethoxy]methyl}-1H-pyrrolo[2,3-b]pyridine-3-carboxamide

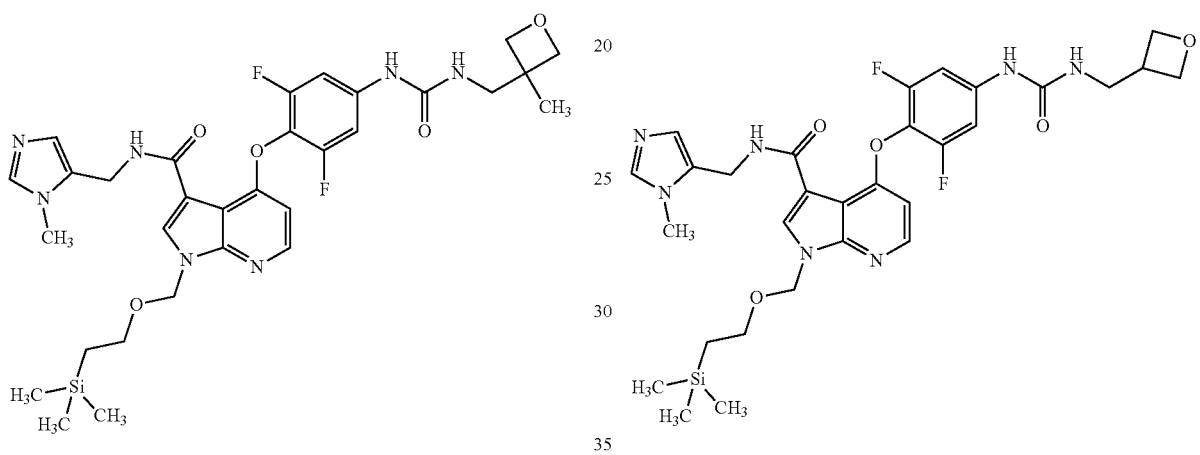

To solution of phenyl {3,5-difluoro-4-[(3-{[(1-methyl-1H-imidazol-5-yl)methyl]carbamoyl}-1-{[2-(trimethylsilyl)ethoxy]methyl}-1H-pyrrolo[2,3-b]pyridin-4-yl)oxy]phenyl}carbamate (100 mg, 154 μmol, intermediate 73) in DMF (0.4 mL) was added 1-(3-methyloxetan-3-yl)methanamine (17.2 mg, 170 μmol, CAS No. [153209-97-3]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 4-[2,6-difluoro-4-({[(3-methyloxetan-3-yl)methyl]carbamoyl}amino)phenoxy]-N-[(1-methyl-1H-imidazol-5-yl)methyl]-1-{[2-(trimethylsilyl)ethoxy]methyl}-1H-pyrrolo[2,3-b]pyridine-3-carboxamide, which was used in the subsequent reaction without further purification.

LC-MS (Method 1): $R_t$=1.01 min; MS (ESIpos): m/z=656 [M+H]$^+$

To solution of phenyl {3,5-difluoro-4-[(3-{[(1-methyl-1H-imidazol-5-yl)methyl]carbamoyl}-1-{[2-(trimethylsilyl)ethoxy]methyl}-1H-pyrrolo[2,3-b]pyridin-4-yl)oxy]phenyl}carbamate (100 mg, 154 μmol, intermediate 73) in DMF (0.4 mL) was added 1-(oxetan-3-yl)methanamine (14.8 mg, 170 μmol, CAS No. [6246-05-5]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 4-(2,6-difluoro-4-{[(oxetan-3-ylmethyl)carbamoyl]amino}phenoxy)-N-[(1-methyl-1H-imidazol-5-yl)methyl]-1-{[2-(trimethylsilyl)ethoxy]methyl}-1H-pyrrolo[2,3-b]pyridine-3-carboxamide, which was used in the subsequent reaction without further purification.

LC-MS (Method 1): $R_t$=0.95 min; MS (ESIpos): m/z=642 [M+H]$^+$.

145

Intermediate 76

3-(5-chloro-6-methoxypyridin-3-yl)-4-(2,6-difluoro-4-nitrophenoxy)-1-{[2-(trimethylsilyl)ethoxy]methyl}-1H-pyrrolo[2,3-b]pyridine

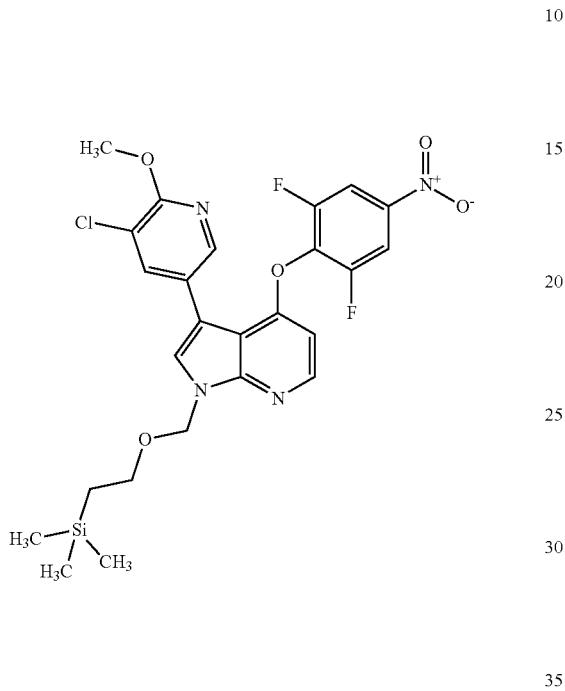

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), (5-chloro-6-methoxypyridin-3-yl)boronic acid (749 mg, 4.00 mmol, CAS No. [942438-89-3]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h.

The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 3-(5-chloro-6-methoxypyridin-3-yl)-4-(2,6-difluoro-4-nitrophenoxy)-1-{[2-(trimethylsilyl)ethoxy]methyl}-1H-pyrrolo[2,3-b]pyridine (517 mg, 46% Yield).

LC-MS (Method 2): $R_t$=1.70 min; MS (ESIpos): m/z=563 [M+H]$^+$ $^1$H NMR (400 MHz, DMSO-d$_6$) δ ppm −0.07 (s, 9H), 0.82-0.88 (m, 2H), 3.58-3.64 (m, 2H), 3.82 (s, 3H), 5.69 (s, 1H), 6.66 (d, 1H), 7.82 (d, 1H), 7.91 (s, 1H), 8.14 (d, 1H), 8.23 (d, 1H), 8.31-8.37 (m, 2H)

146

Intermediate 77

4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluoroaniline

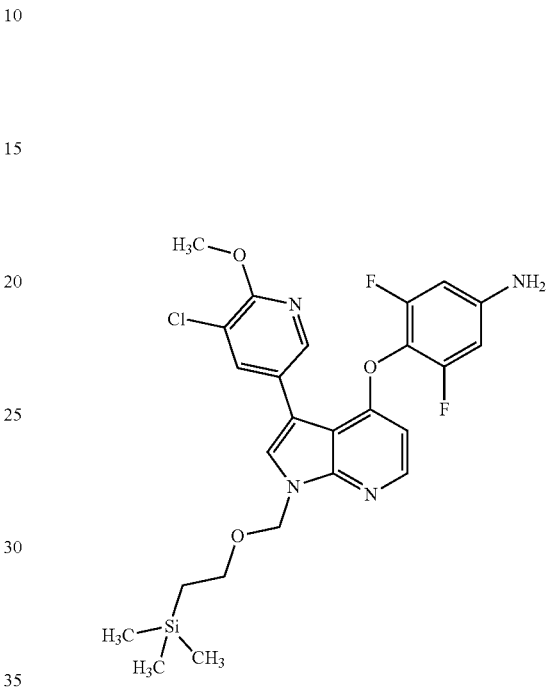

To a solution of 3-(5-chloro-6-methoxypyridin-3-yl)-4-(2,6-difluoro-4-nitrophenoxy)-1-{[2-(trimethylsilyl)ethoxy]methyl}-1H-pyrrolo[2,3-b]pyridine (517 mg, 0.92 mmol, intermediate 76) in a mixture of THF (8 mL), water (15 mL), and methanol (8 mL) was added ammonium chloride (246 mg, 4.59 mmol) and iron powder (256 mg, 4.59 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluoroaniline (486 mg, 99% Yield), which required no further purification.

LC-MS (Method 2): $R_t$=1.61 min; MS (ESIpos): m/z=533 [M+H]$^+$ $^1$H NMR (400 MHz, DMSO-d$_6$) δ ppm −0.07 (s, 9H), 0.81-0.89 (m, 3H), 3.60 (t, 3H), 3.86 (s, 3H), 5.67 (s, 2H), 5.79 (s, 2H), 6.33-6.41 (m, 3H), 7.86 (s, 1H), 7.88 (d, 1H), 8.13 (d, 1H), 8.17 (d, 1H)

147

Intermediate 78

1-(4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea

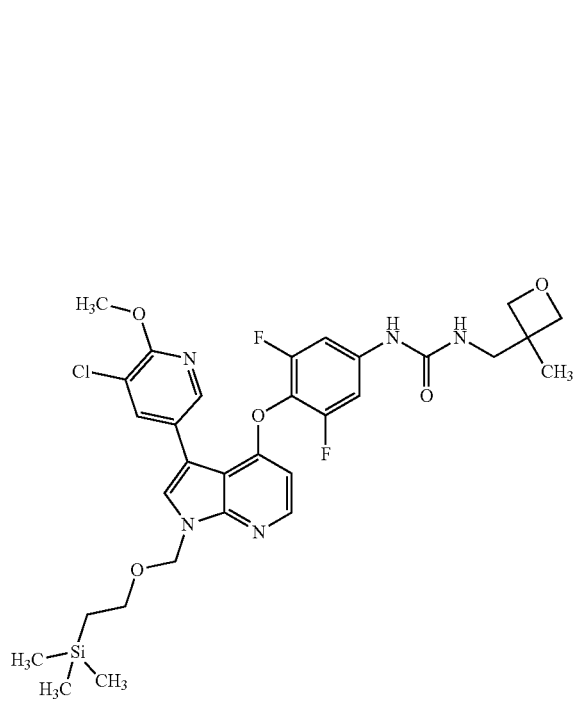 [SMILES: COc1ncc(-c2cn(COCC[Si](C)(C)C)c3nccc(Oc4c(F)cc(NC(=O)NCC5(C)COC5)cc4F)c23)cc1Cl]

To a stirred solution of 4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluoroaniline (97 mg, 0.18 mmol, intermediate 78) in a mixture of dichloromethane (1.0 mL) and pyridine (1.0 mL) was added 3-(isocyanatomethyl)-3-methyloxetane (CAS No. [1260665-88-0]) (116 mg, 0.91 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea, which was used in the subsequent reaction without further purification.

LC-MS (Method 2): $R_t$=1.58 min; MS (ESIpos): m/z=660 [M+H]$^+$

148

Intermediate 79

4-(2,6-difluoro-4-nitrophenoxy)-3-[1-(propan-2-yl)-1H-pyrazol-3-yl]-1-{[2-(trimethylsilyl)ethoxy]methyl}-1H-pyrrolo[2,3-b]pyridine

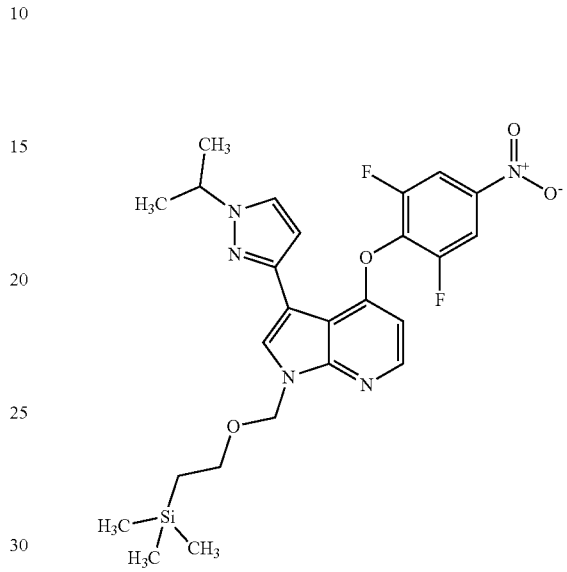

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), 1-(propan-2-yl)-3-(4,4,5,5-tetramethyl-1,3,2-dioxaborolan-2-yl)-1H-pyrazole (944 mg, 4.00 mmol, CAS No. [1071496-88-2]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-[1-(propan-2-yl)-1H-pyrazol-3-yl]-1-{[2-(trimethylsilyl)ethoxy]methyl}-1H-pyrrolo[2,3-b]pyridine (572 mg, 54% Yield).

LC-MS (Method 2): $R_t$=1.66 min; MS (ESIpos): m/z=530 [M+H]$^+$ $^1$H NMR (400 MHz, DMSO-d$_6$) δ ppm −0.09 (s, 9H), 0.81-0.88 (m, 2H), 1.40 (d, 6H), 3.52-3.59 (m, 1H), 4.49 (spt, 1H), 5.65 (s, 2H), 6.60 (d, 1H), 7.73 (s, 1H), 7.84 (s, 1H), 7.98 (s, 1H), 8.17 (d, 1H), 8.39-8.46 (m, 2H)

Intermediate 80

3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]aniline

Intermediate 81

1-{3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea

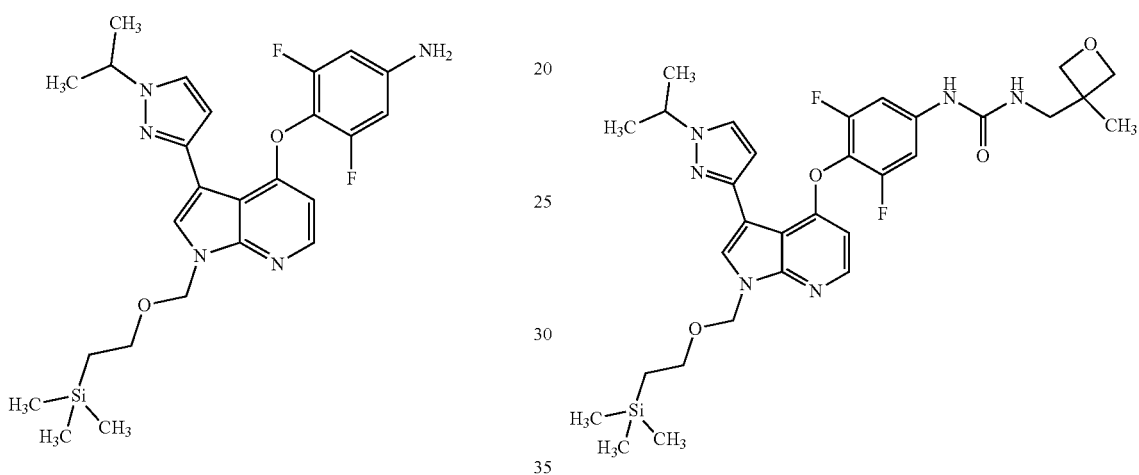

To a solution of 4-(2,6-difluoro-4-nitrophenoxy)-3-[1-(propan-2-yl)-1H-pyrazol-3-yl]-1-{[2-(trimethylsilyl)ethoxy]methyl}-1H-pyrrolo[2,3-b]pyridine (572 mg, 1.08 mmol, intermediate 79) in a mixture of THF (8 mL), water (15 mL), and methanol (8 mL) was added ammonium chloride (289 mg, 5.40 mmol) and iron powder (302 mg, 5.40 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]aniline (528 mg, 98% Yield), which required no further purification.

LC-MS (Method 2): $R_t$=1.44 min; MS (ESIpos): m/z=500 [M+H]$^+$ $^1$H NMR (400 MHz, DMSO-d$_6$) δ ppm −0.08 (s, 9H), 0.80-0.88 (m, 2H), 1.41 (d, 6H), 3.54 (t, 2H), 4.48 (spt, 1H), 5.62 (s, 2H), 5.82 (s, 3H), 6.36 (d, 1H), 6.39-6.45 (m, 2H), 7.75 (s, 1H), 7.75 (s, 1H), 7.98 (s, 1H), 8.12 (d, 1H)

To a stirred solution of 3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]aniline (105 mg, 0.21 mmol, intermediate 80) in a mixture of dichloromethane (1.0 mL) and pyridine (1.0 mL) was added 3-(isocyanatomethyl)-3-methyloxetane (CAS No. [1260665-88-0]) (134 mg, 1.05 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-{3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea, which was used in the subsequent reaction without further purification.

LC-MS (Method 2): $R_t$=1.41 min; MS (ESIpos): m/z=627 [M+H]$^+$

Intermediate 82

5-[4-(2,6-difluoro-4-nitrophenoxy)-1-{[2-(trimethylsilyl)ethoxy]methyl}-1H-pyrrolo[2,3-b]pyridin-3-yl]-2-(propan-2-yloxy)benzonitrile

Intermediate 83

5-[4-(4-amino-2,6-difluorophenoxy)-1-{[2-(trimethylsilyl)ethoxy]methyl}-1H-pyrrolo[2,3-b]pyridin-3-yl]-2-(propan-2-yloxy)benzonitrile

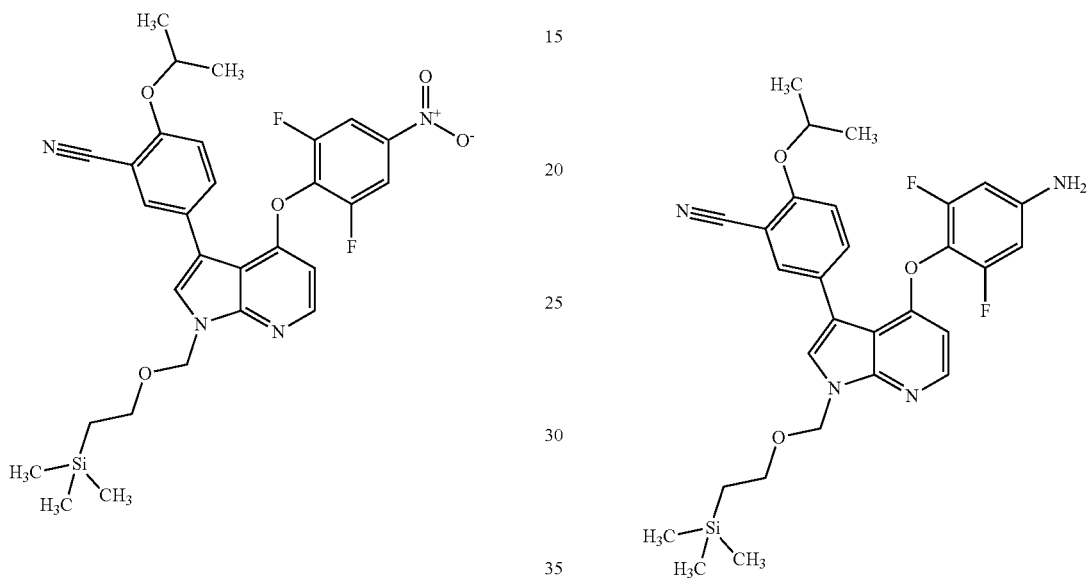

3-bromo-4-(2,6-difluoro-4-nitrophenoxy)-1-{[2-(trimethylsilyl)ethoxy]methyl}-1H-pyrrolo[2,3-b]pyridine (3.66 g, 7.32 mmol, intermediate 16), [1,1'-Bis(diphenylphosphino)-ferrocene]dichloropalladium(II) (535 mg, 0.73 mmol), [3-cyano-4-(propan-2-yloxy)phenyl]boronic acid (3.0 mg, 14.6 mmol, CAS No. [1009303-59-6]), and potassium carbonate (5.06 g, 36.6 mmol), were dissolved in a mixture of 1,4-dioxane (70 mL), and water (35 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 5-[4-(2,6-difluoro-4-nitrophenoxy)-1-{[2-(trimethylsilyl)ethoxy]methyl}-1H-pyrrolo[2,3-b]pyridin-3-yl]-2-(propan-2-yloxy)benzonitrile (2.92 g, 69% Yield).

LC-MS (Method 2): $R_t$=1.66 min; MS (ESIpos): m/z=581 [M+H]$^+$ $^1$H NMR (400 MHz, DMSO-d$_6$) δ ppm −0.09 (s, 9H), 0.78-0.93 (m, 1H), 1.31 (d, 6H), 3.52-3.65 (m, 4H), 4.80 (spt, 1H), 5.68 (s, 1H), 6.66 (d, 1H), 7.32 (d, 1H), 7.85-7.90 (m, 2H), 7.96 (s, 1H), 8.23 (d, 1H), 8.38-8.46 (m, 2H)

To a solution of 5-[4-(2,6-difluoro-4-nitrophenoxy)-1-{[2-(trimethylsilyl)ethoxy]methyl}-1H-pyrrolo[2,3-b]pyridin-3-yl]-2-(propan-2-yloxy)benzonitrile (2.92 g, 5.03 mmol, intermediate 82) in a mixture of THF (35 mL), water (70 mL), and methanol (35 mL) was added ammonium chloride (1.35 g, 25.1 mmol) and iron powder (1.40 g, 25.4 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 5-[4-(4-amino-2,6-difluorophenoxy)-1-{[2-(trimethylsilyl)ethoxy]methyl}-1H-pyrrolo[2,3-b]pyridin-3-yl]-2-(propan-2-yloxy)benzonitrile (2.21 g, 80% Yield), which required no further purification.

LC-MS (Method 2): $R_t$=1.57 min; MS (ESIpos): m/z=551 [M+H]$^+$ $^1$H NMR (400 MHz, DMSO-d$_6$) δ ppm −0.08 (s, 9H), 0.79-0.94 (m, 2H), 1.32 (d, 6H), 3.53-3.66 (m, 2H), 4.81 (spt, 1H), 5.65 (s, 2H), 5.82 (s, 2H), 6.37-6.44 (m, 3H), 7.32 (d, 1H), 7.87-7.94 (m, 3H), 8.18 (d, 1H)

153

Intermediate 84

1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-methyl-oxetan-3-yl)methyl]urea

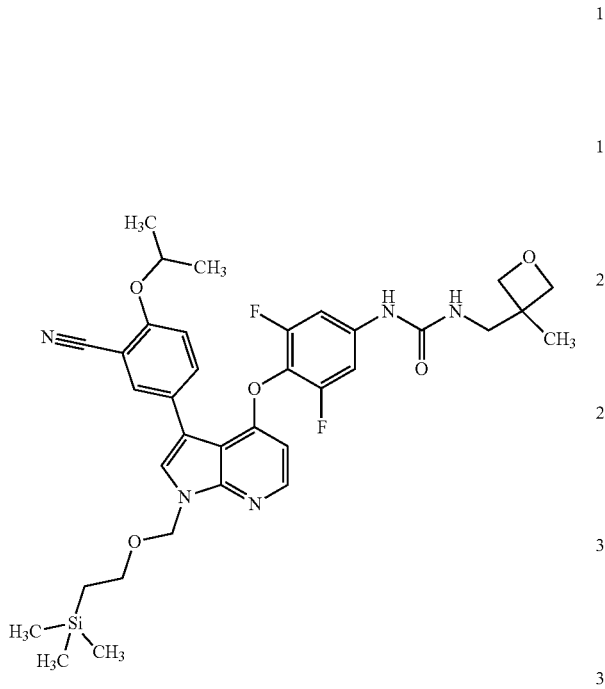

To a stirred solution of 5-[4-(4-amino-2,6-difluorophenoxy)-1-{[2-(trimethylsilyl)ethoxy]methyl}-1H-pyrrolo[2,3-b]pyridin-3-yl]-2-(propan-2-yloxy)benzonitrile (118 mg, 0.21 mmol, intermediate 83) in a mixture of dichloromethane (1.0 mL) and pyridine (1.0 mL) was added 3-(isocyanatomethyl)-3-methyloxetane (CAS No. [1260665-88-0]) (136 mg, 1.07 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea, which was used in the subsequent reaction without further purification.

LC-MS (Method 2): $R_t$=1.55 min; MS (ESIneg): m/z=677 [M−H]⁻

154

Intermediate 85

4-(2,6-difluoro-4-nitrophenoxy)-3-(2-fluoro-4-methoxyphenyl)-1-{[2-(trimethylsilyl)ethoxy]methyl}-1H-pyrrolo[2,3-b]pyridine

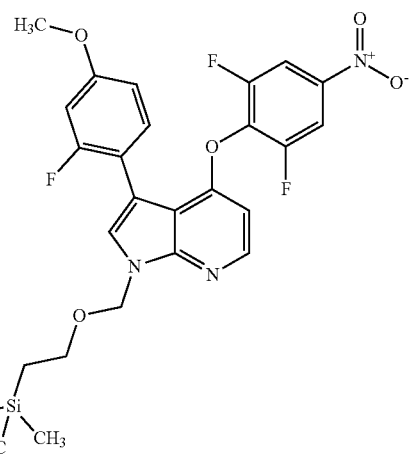

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)-ferrocene]dichloropalladium(II) (146 mg, 0.20 mmol), (2-fluoro-4-methoxyphenyl)boronic acid (679 mg, 4.00 mmol, CAS No. [162101-31-7]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(2-fluoro-4-methoxyphenyl)-1-{[2-(trimethylsilyl)ethoxy]methyl}-1H-pyrrolo[2,3-b]pyridine (735 mg, 67% Yield).

LC-MS (Method 2): $R_t$=1.65 min; MS (ESIpos): m/z=546 [M+H]⁺

¹H NMR (400 MHz, DMSO-$d_6$) δ ppm −0.08 (s, 9H), 0.81-0.88 (m, 2H), 3.56-3.63 (m, 2H), 3.77 (s, 3H), 5.69 (s, 2H), 6.62 (d, 1H), 6.81 (dd, 1H), 6.88 (dd, 1H), 7.42 (t, 1H), 7.75 (s, 1H), 8.21 (d, 1H), 8.31-8.37 (m, 2H)

155

Intermediate 86

3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}aniline

156

Intermediate 87

1-(3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

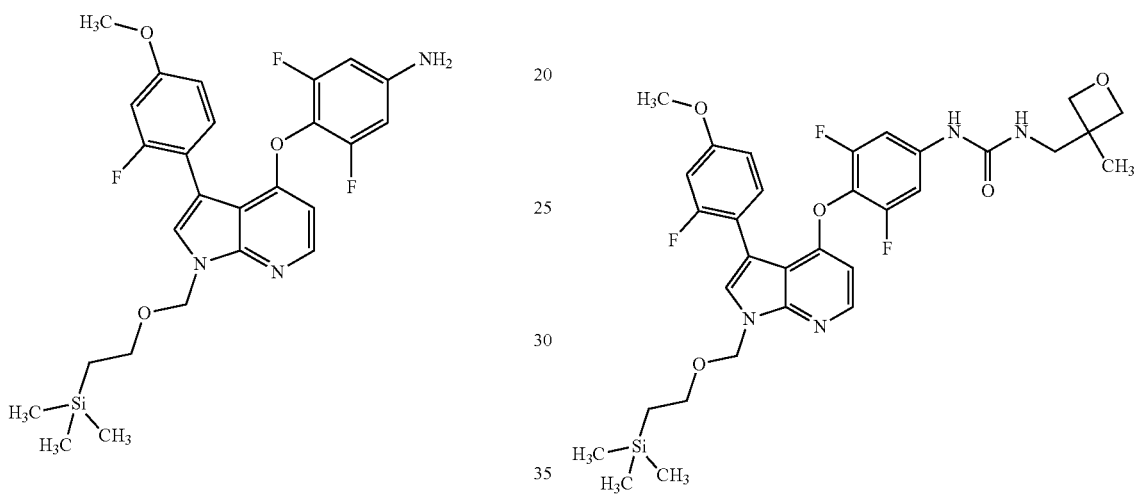

To a solution of 4-(2,6-difluoro-4-nitrophenoxy)-3-(2-fluoro-4-methoxyphenyl)-1-{[2-(trimethylsilyl)ethoxy]methyl}-1H-pyrrolo[2,3-b]pyridine (753 mg, 1.38 mmol, intermediate 85) in a mixture of THF (8 mL), water (16 mL), and methanol (8 mL) was added ammonium chloride (369 mg, 6.90 mmol) and iron powder (385 mg, 6.90 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}aniline (560 mg, 79% Yield), which required no further purification.

LC-MS (Method 2): $R_t$=1.54 min; MS (ESIpos): m/z=517 [M+H]$^+$ $^1$H NMR (400 MHz, DMSO-d$_6$) δ ppm −0.08 (s, 9H), 0.80-0.90 (m, 2H), 3.54-3.62 (m, 2H), 3.78 (s, 3H), 5.66 (s, 2H), 5.77 (s, 2H), 6.30-6.41 (m, 3H), 6.81 (dd, 1H), 6.89 (dd, 1H), 7.46 (t, 1H), 7.66 (d, 1H), 8.15 (d, 1H)

To a stirred solution of 3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}aniline (112 mg, 0.22 mmol, intermediate 86) in a mixture of dichloromethane (1.0 mL) and pyridine (1.0 mL) was added 3-(isocyanatomethyl)-3-methyloxetane (CAS No. [1260665-88-0]) (138 mg, 1.09 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 2): $R_t$=1.52 min; MS (ESIpos): m/z=643 [M+H]$^+$

157
Intermediate 88

4-(2,6-difluoro-4-nitrophenoxy)-3-(1-methyl-1H-pyrazol-5-yl)-1-{[2-(trimethylsilyl)ethoxy]methyl}-1H-pyrrolo[2,3-b]pyridine

158
Intermediate 89

3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}aniline

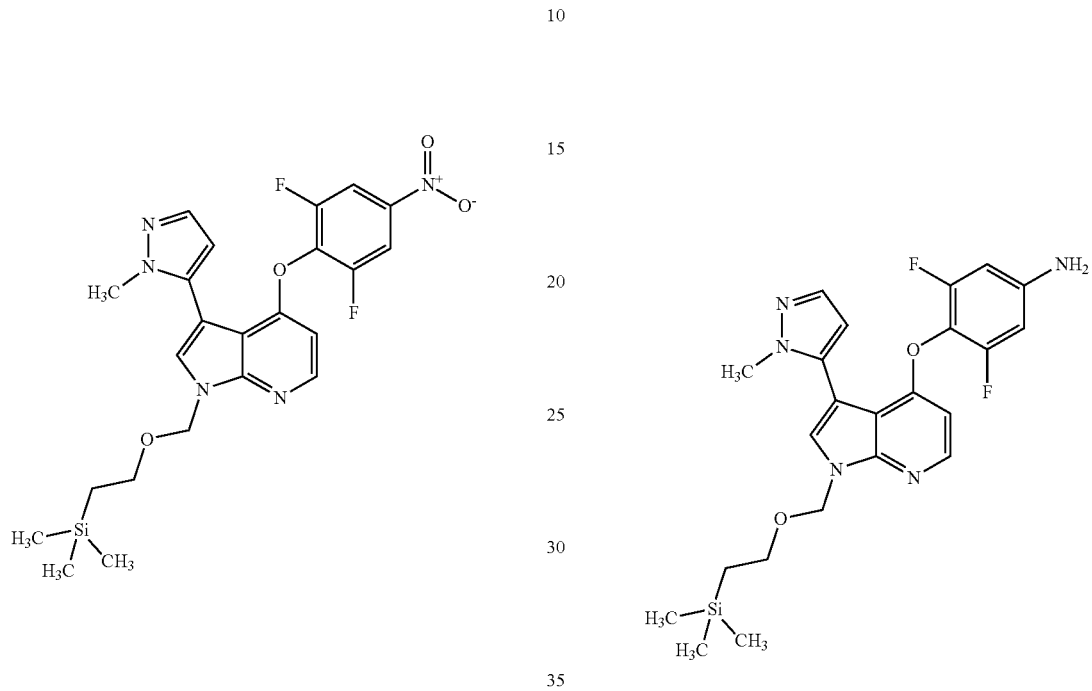

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), (1-methyl-1H-pyrazol-5-yl)boronic acid (503 mg, 4.00 mmol, CAS No. [720702-41-0]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product.

The crude product was purified by flash column chromatography to afford 4-(2,6-difluoro-4-nitrophenoxy)-3-(1-methyl-1H-pyrazol-5-yl)-1-{[2-(trimethylsilyl)ethoxy]methyl}-1H-pyrrolo[2,3-b]pyridine (162 mg, 16% Yield).

LC-MS (Method 2): $R_t$=1.48 min; MS (ESIpos): m/z=502 $[M+H]^+$ $^1$H NMR (400 MHz, DMSO-$d_6$) δ ppm −0.10 (s, 9H), 0.80-0.90 (m, 2H), 3.56-3.66 (m, 2H), 3.79 (s, 3H), 5.71 (s, 2H), 6.33 (d, 1H), 6.67 (d, 1H), 7.42 (d, 1H), 7.95 (s, 1H), 8.25 (d, 1H), 8.32-8.43 (m, 2H)

To a solution of 4-(2,6-difluoro-4-nitrophenoxy)-3-(1-methyl-1H-pyrazol-5-yl)-1-{[2-(trimethylsilyl)ethoxy]methyl}-1H-pyrrolo[2,3-b]pyridine (162 mg, 0.32 µmol, intermediate 88) in a mixture of THF (2 mL), water (4 mL), and methanol (2 mL) was added ammonium chloride (86.4 mg, 1.61 mmol) and iron powder (90.2 mg, 1.61 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}aniline (156 mg, 100% Yield), which required no further purification.

LC-MS (Method 2): $R_t$=1.38 min; MS (ESIpos): m/z=472 $[M+H]^+$ $^1$H NMR (400 MHz, DMSO-$d_6$) δ ppm −0.09 (s, 9H), 0.84 (t, 2H), 3.59 (t, 2H), 3.78 (s, 3H), 5.67 (s, 2H), 5.80 (s, 2H), 6.33-6.41 (m, 4H), 7.43 (d, 1H), 7.83 (s, 1H), 8.19 (d, 1H)

Intermediate 90

1-(3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

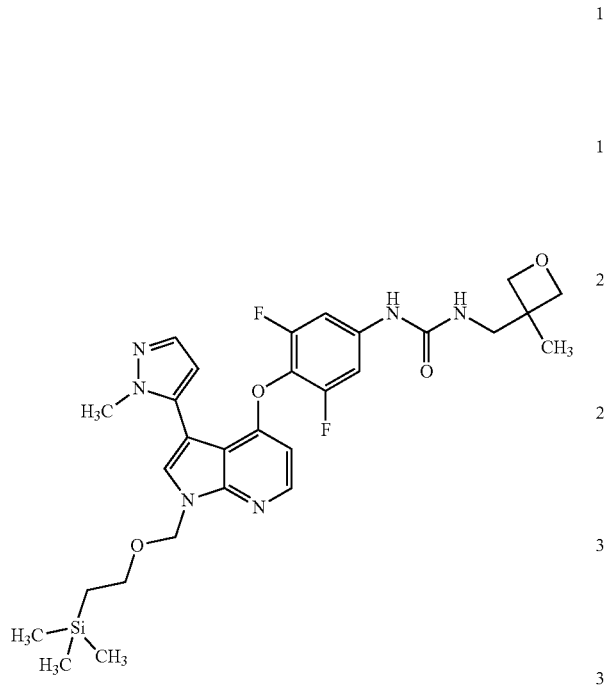

To a stirred solution of 3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}aniline (75.0 mg, 159 μmol, intermediate 89) in a mixture of dichloromethane (1.0 mL) and pyridine (1.0 mL) was added 3-(isocyanatomethyl)-3-methyloxetane (CAS No. [1260665-88-0]) (101 mg, 0.80 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 2): $R_t$=1.37 min; MS (ESIpos): m/z=600 [M+H]$^+$

Intermediate 91

4-(2,6-difluoro-4-nitrophenoxy)-3-[1-(propan-2-yl)-1H-pyrazol-5-yl]-1-{[2-(trimethylsilyl)ethoxy]methyl}-1H-pyrrolo[2,3-b]pyridine

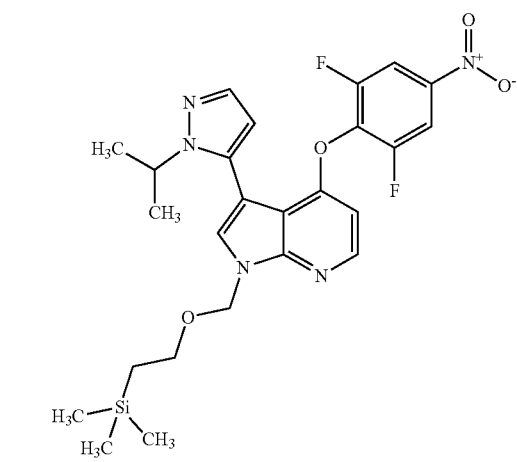 [SMILES: CC(C)n1nccc1-c1cn(COCC[Si](C)(C)C)c2nccc(Oc3c(F)cc([N+](=O)[O-])cc3F)c12]

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)-ferrocene]dichloropalladium(II) (146 mg, 0.20 mmol), [1-(propan-2-yl)-1H-pyrazol-5-yl]boronic acid (615 mg, 4.00 mmol, CAS No. [839714-33-9]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-[1-(propan-2-yl)-1H-pyrazol-5-yl]-1-{[2-(trimethylsilyl)ethoxy]methyl}-1H-pyrrolo[2,3-b]pyridine (278 mg, 26% Yield).

LC-MS (Method 2): $R_t$=1.58 min; MS (ESIpos): m/z=530 [M+H]$^+$ $^1$H NMR (400 MHz, DMSO-d$_6$) δ ppm −0.11 (s, 9H), 0.78-0.87 (m, 2H), 1.30 (d, 6H), 3.55-3.67 (m, 2H), 4.51 (spt, 1H), 5.71 (s, 2H), 6.28 (d, 1H), 6.63 (d, 1H), 7.47 (d, 1H), 7.87 (s, 1H), 8.24 (d, 1H), 8.33-8.40 (m, 2H)

161
Intermediate 92

3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]aniline

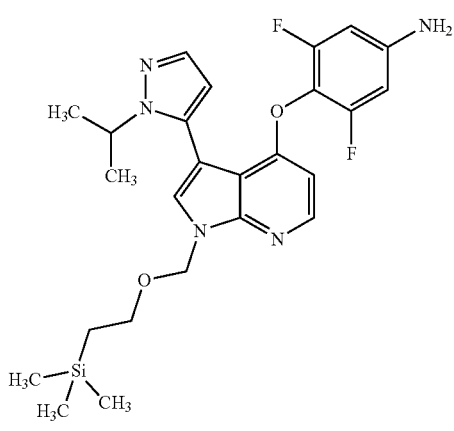 [SMILES: CC(C)n1nccc1-c1cn(COCC[Si](C)(C)C)c2nccc(Oc3c(F)cc(N)cc3F)c12]

To a solution of 4-(2,6-difluoro-4-nitrophenoxy)-3-[1-(propan-2-yl)-1H-pyrazol-5-yl]-1-{[2-(trimethylsilyl)ethoxy]methyl}-1H-pyrrolo[2,3-b]pyridine (278 mg, 0.53 mmol, intermediate 91) in a mixture of THF (2 mL), water (4 mL), and methanol (2 mL) was added ammonium chloride (140 mg, 2.62 mmol) and iron powder (147 mg, 2.62 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]aniline (259 mg, 99% Yield), which required no further purification.

LC-MS (Method 2): $R_t$=1.46 min; MS (ESIpos): m/z=500 [M+H]$^+$ $^1$H NMR (400 MHz, DMSO-d$_6$) δ ppm −0.10 (s, 9H), 0.78-0.87 (m, 2H), 1.29 (d, 6H), 3.58 (t, 2H), 4.53 (spt, 1H), 5.67 (s, 2H), 5.78 (s, 2H), 6.26 (d, 1H), 6.31-6.41 (m, 3H), 7.47 (d, 1H), 7.75 (s, 1H), 8.18 (d, 1H)

162
Intermediate 93

1-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea

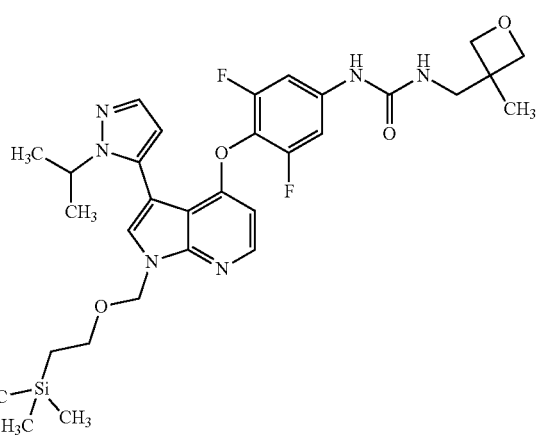

To a stirred solution of 3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]aniline (85.0 mg, 0.17 mmol, intermediate 92) in a mixture of dichloromethane (1.0 mL) and pyridine (1.0 mL) was added 3-(isocyanatomethyl)-3-methyloxetane (CAS No. [1260665-88-0]) (108 mg, 0.85 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea, which was used in the subsequent reaction without further purification.

LC-MS (Method 2): $R_t$=1.45 min; MS (ESIpos): m/z=628 [M+H]$^+$

163

Intermediate 94

4-(2,6-difluoro-4-nitrophenoxy)-3-(2-fluorophenyl)-1-{[2-(trimethylsilyl)ethoxy]methyl}-1H-pyrrolo[2,3-b]pyridine

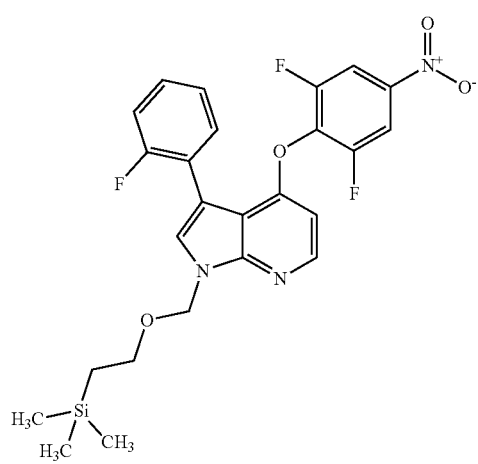 [SMILES: C[Si](C)(C)CCOCn1cc(-c2ccccc2F)c2c(Oc3c(F)cc([N+](=O)[O-])cc3F)ccnc21]

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)-ferrocene]dichloropalladium(II) (146 mg, 0.20 mmol), (2-fluorophenyl)boronic acid (559 mg, 4.00 mmol, CAS No. [1765-93-1]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(2-fluorophenyl)-1-{[2-(trimethylsilyl)ethoxy]methyl}-1H-pyrrolo[2,3-b]pyridine (788 mg, 76% Yield).

LC-MS (Method 2): $R_t$=1.66 min; MS (ESIpos): m/z=516 [M+H]$^+$ $^1$H NMR (400 MHz, DMSO-d$_6$) δ ppm −0.09 (s, 9H), 0.82-0.88 (m, 2H), 3.56-3.66 (m, 2H), 5.71 (s, 2H), 6.64 (d, 1H), 7.18-7.27 (m, 2H), 7.30-7.38 (m, 1H), 7.54 (td, 1H), 7.85 (s, 1H), 8.23 (d, 1H), 8.30-8.37 (m, 2H)

164

Intermediate 95

3,5-difluoro-4-{[3-(2-fluorophenyl)-1-{[2-(trimethylsilyl)ethoxy]methyl}-1H-pyrrolo[2,3-b]pyridin-4-yl]oxy}aniline

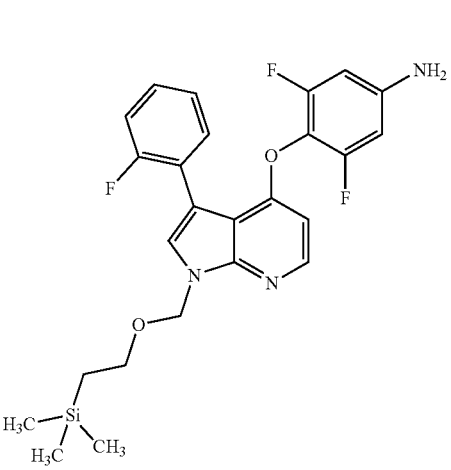 [SMILES: C[Si](C)(C)CCOCn1cc(-c2ccccc2F)c2c(Oc3c(F)cc(N)cc3F)ccnc21]

To a solution of 4-(2,6-difluoro-4-nitrophenoxy)-3-(2-fluorophenyl)-1-{[2-(trimethylsilyl)ethoxy]methyl}-1H-pyrrolo[2,3-b]pyridine (788 mg, 1.53 mmol, intermediate 94) in a mixture of THF (10 mL), water (20 mL), and methanol (10 mL) was added ammonium chloride (409 mg, 7.64 mmol) and iron powder (427 mg, 7.64 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to give the crude aniline. The crude material was purified by preparative HPLC to afford 3,5-difluoro-4-{[3-(2-fluorophenyl)-1-{[2-(trimethylsilyl)ethoxy]methyl}-1H-pyrrolo[2,3-b]pyridin-4-yl]oxy}aniline (249 mg, 34% Yield).

LC-MS (Method 2): $R_t$=1.56 min; MS (ESIpos): m/z=486 [M+H]$^+$ $^1$H NMR (400 MHz, DMSO-d$_6$) δ ppm −0.08 (s, 9H), 0.81-0.88 (m, 2H), 3.54-3.65 (m, 2H), 5.68 (s, 2H), 5.77 (s, 2H), 6.31-6.40 (m, 3H), 7.19-7.28 (m, 2H), 7.30-7.37 (m, 1H), 7.58 (td, 1H), 7.76 (d, 1H), 8.17 (d, 1H)

165
Intermediate 96

1-(3,5-difluoro-4-{[3-(2-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

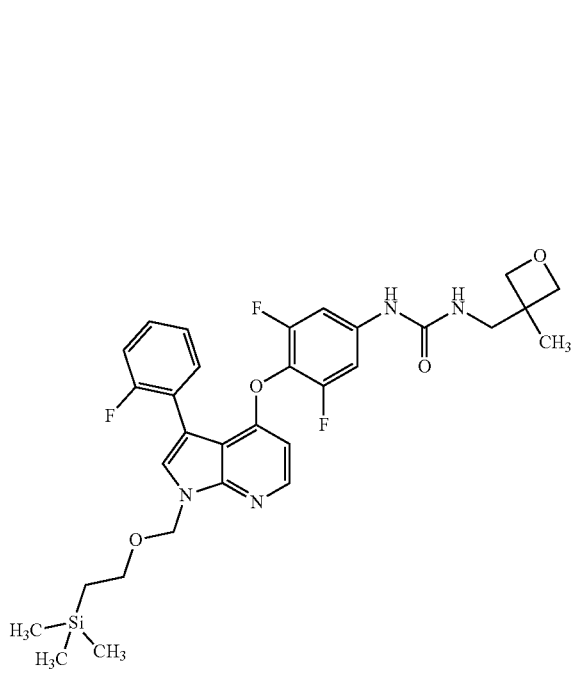 [SMILES: CC1(CNC(=O)Nc2cc(F)c(Oc3ccnc4c3c(-c3ccccc3F)cn4COCC[Si](C)(C)C)c(F)c2)COC1]

To a stirred solution of 3,5-difluoro-4-{[3-(2-fluorophenyl)-1-{[2-(trimethylsilyl)ethoxy]methyl}-1H-pyrrolo[2,3-b]pyridin-4-yl]oxy}aniline (80.0 mg, 0.17 mmol, intermediate 95) in a mixture of dichloromethane (1.0 mL) and pyridine (1.0 mL) was added 3-(isocyanatomethyl)-3-methyloxetane (CAS No. [1260665-88-0]) (105 mg, 0.82 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(2-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 2): $R_t$=1.52 min; MS (ESIpos): m/z=613 [M+H]$^+$

166
Intermediate 97

4-(2,6-difluoro-4-nitrophenoxy)-3-(3-fluorophenyl)-1-{[2-(trimethylsilyl)ethoxy]methyl}-1H-pyrrolo[2,3-b]pyridine

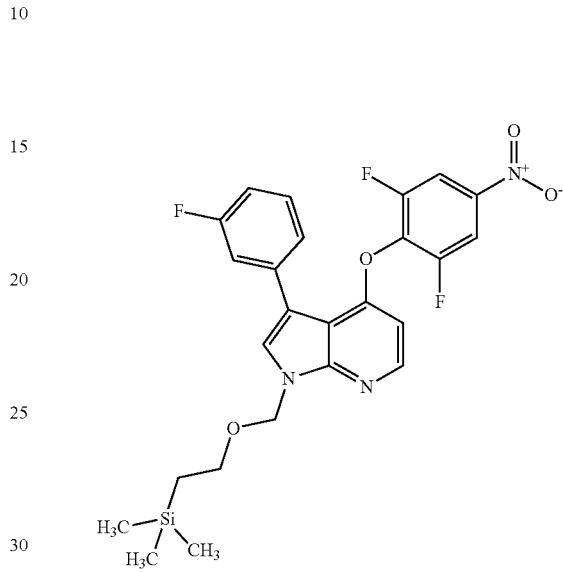

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), (3-fluorophenyl)boronic acid (559 mg, 4.00 mmol, CAS No. [768-35-4]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate.

The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(3-fluorophenyl)-1-{[2-(trimethylsilyl)ethoxy]methyl}-1H-pyrrolo[2,3-b]pyridine (1.01 g, 98% Yield).

LC-MS (Method 2): $R_t$=1.68 min; MS (ESIpos): m/z=516 [M+H]$^+$ $^1$H NMR (400 MHz, DMSO-d$_6$) δ ppm −0.09 (s, 9H), 0.82-0.89 (m, 2H), 3.56-3.64 (m, 2H), 5.70 (s, 2H), 6.67 (d, 1H), 7.06-7.14 (m, 1H), 7.40-7.55 (m, 2H), 8.00 (s, 1H), 8.21-8.26 (m, 2H), 8.36-8.45 (m, 2H)

167

Intermediate 98

3,5-difluoro-4-{[3-(3-fluorophenyl)-1-{[2-(trimethylsilyl)ethoxy]methyl}-1H-pyrrolo[2,3-b]pyridin-4-yl]oxy}aniline

168

Intermediate 99

1-(3,5-difluoro-4-{[3-(3-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

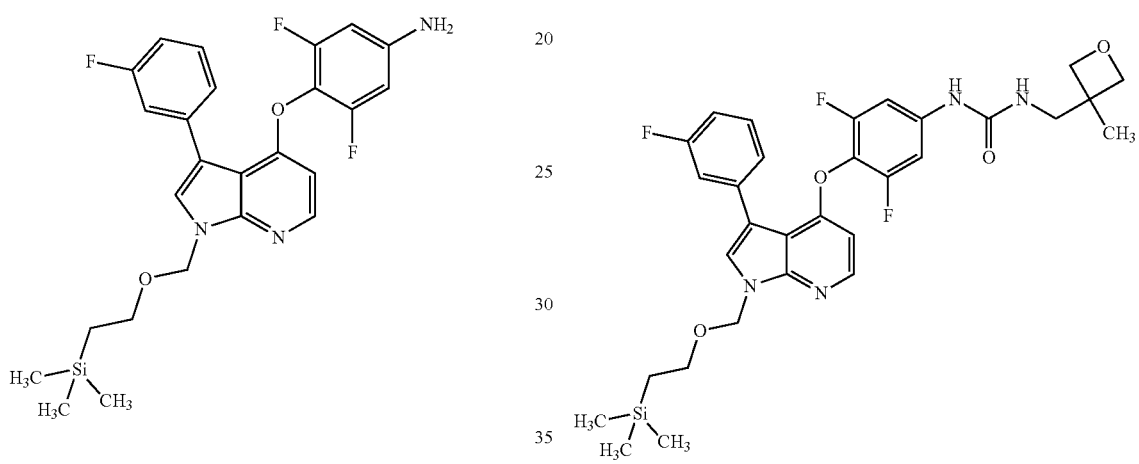

To a solution of 4-(2,6-difluoro-4-nitrophenoxy)-3-(3-fluorophenyl)-1-{[2-(trimethylsilyl)ethoxy]methyl}-1H-pyrrolo[2,3-b]pyridine (1.00 g, 1.94 mmol, intermediate 97) in a mixture of THF (13 mL), water (25 mL), and methanol (13 mL) was added ammonium chloride (519 mg, 9.70 mmol) and iron powder (542 mg, 9.70 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-{[3-(3-fluorophenyl)-1-{[2-(trimethylsilyl)ethoxy]methyl}-1H-pyrrolo[2,3-b]pyridin-4-yl]oxy}aniline (960 mg, 99% Yield), which required no further purification.

LC-MS (Method 2): $R_t$=1.58 min; MS (ESIpos): m/z=486 [M+H]$^+$ $^1$H NMR (400 MHz, DMSO-d$_6$) δ ppm −0.08 (s, 9H), 0.81-0.88 (m, 2H), 3.55-3.62 (m, 2H), 5.67 (s, 2H), 5.82 (s, 2H), 6.37-6.45 (m, 3H), 7.05-7.14 (m, 1H), 7.43-7.54 (m, 2H), 7.92 (s, 1H), 8.18 (d, 1H), 8.23 (s, 1H)

To a stirred solution of 3,5-difluoro-4-{[3-(3-fluorophenyl)-1-{[2-(trimethylsilyl)ethoxy]methyl}-1H-pyrrolo[2,3-b]pyridin-4-yl]oxy}aniline (100 mg, 0.21 mmol, intermediate 98) in a mixture of dichloromethane (1.0 mL) and pyridine (1.0 mL) was added 3-(isocyanatomethyl)-3-methyloxetane (CAS No. [1260665-88-0]) (131 mg, 1.03 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(3-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 2): $R_t$=1.54 min; MS (ESIpos): m/z=614 [M+H]$^+$

Intermediate 100

4-(2,6-difluoro-4-nitrophenoxy)-3-(4-fluorophenyl)-1-{[2-(trimethylsilyl)ethoxy]methyl}-1H-pyrrolo[2,3-b]pyridine

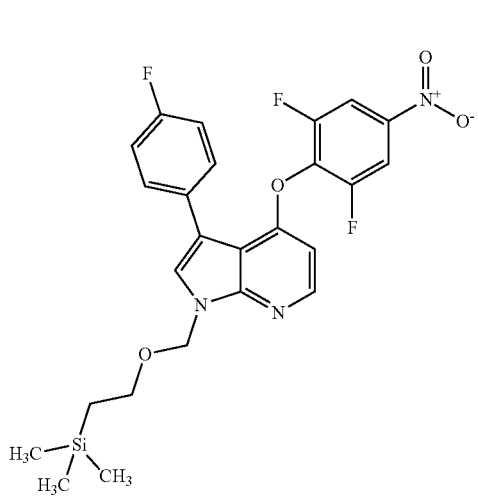 [SMILES: C[Si](C)(C)CCOCn1cc(-c2ccc(F)cc2)c2c(Oc3c(F)cc([N+](=O)[O-])cc3F)ccnc21]

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)-ferrocene]dichloropalladium(II) (146 mg, 0.20 mmol), (4-fluorophenyl)boronic acid (559 mg, 4.00 mmol, CAS No. [1993-03-9]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(4-fluorophenyl)-1-{[2-(trimethylsilyl)ethoxy]methyl}-1H-pyrrolo[2,3-b]pyridine (1.02 g, 98% Yield).

LC-MS (Method 2): $R_t$=1.68 min; MS (ESIpos): m/z=516 [M+H]$^+$ $^1$H NMR (400 MHz, DMSO-d$_6$) δ ppm −0.09 (s, 9H), 0.81-0.88 (m, 2H), 3.55-3.65 (m, 2H), 5.69 (s, 2H), 6.64 (d, 1H), 7.20-7.26 (m, 2H), 7.61-7.68 (m, 2H), 7.88 (s, 1H), 8.22 (d, 1H), 8.37-8.41 (m, 2H)

Intermediate 101

3,5-difluoro-4-{[3-(4-fluorophenyl)-1-{[2-(trimethylsilyl)ethoxy]methyl}-1H-pyrrolo[2,3-b]pyridin-4-yl]oxy}aniline

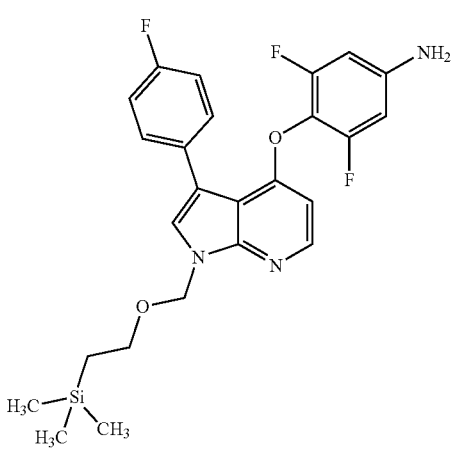 [SMILES: C[Si](C)(C)CCOCn1cc(-c2ccc(F)cc2)c2c(Oc3c(F)cc(N)cc3F)ccnc21]

To a solution of 4-(2,6-difluoro-4-nitrophenoxy)-3-(4-fluorophenyl)-1-{[2-(trimethylsilyl)ethoxy]methyl}-1H-pyrrolo[2,3-b]pyridine (1.00 g, 1.94 mmol, intermediate 100) in a mixture of THF (13 mL), water (25 mL), and methanol (13 mL) was added ammonium chloride (519 mg, 9.70 mmol) and iron powder (542 mg, 9.70 mmol). The resulting mixture was stirred at 80 degrees for 2 hours at which time the mixture was cooled and filtered.

The filtrate was extracted three times with ethyl acetate and the combined organic layers washed with brine, dried over sodium sulfate, and evaporated to afford 3,5-difluoro-4-{[3-(4-fluorophenyl)-1-{[2-(trimethylsilyl)ethoxy]methyl}-1H-pyrrolo[2,3-b]pyridin-4-yl]oxy}aniline (780 mg, 83% Yield), which required no further purification.

LC-MS (Method 2): $R_t$=1.58 min; MS (ESIpos): m/z=486 [M+H]$^+$ $^1$H NMR (400 MHz, DMSO-d$_6$) δ ppm −0.08 (s, 9H), 0.81-0.88 (m, 2H), 3.56-3.61 (m, 2H), 5.66 (s, 2H), 5.80 (s, 2H), 6.35-6.42 (m, 3H), 7.20-7.27 (m, 2H), 7.64-7.70 (m, 2H), 7.79 (s, 1H), 8.17 (d, 1H)

Intermediate 102

1-(3,5-difluoro-4-{[3-(4-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

Intermediate 103 phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate

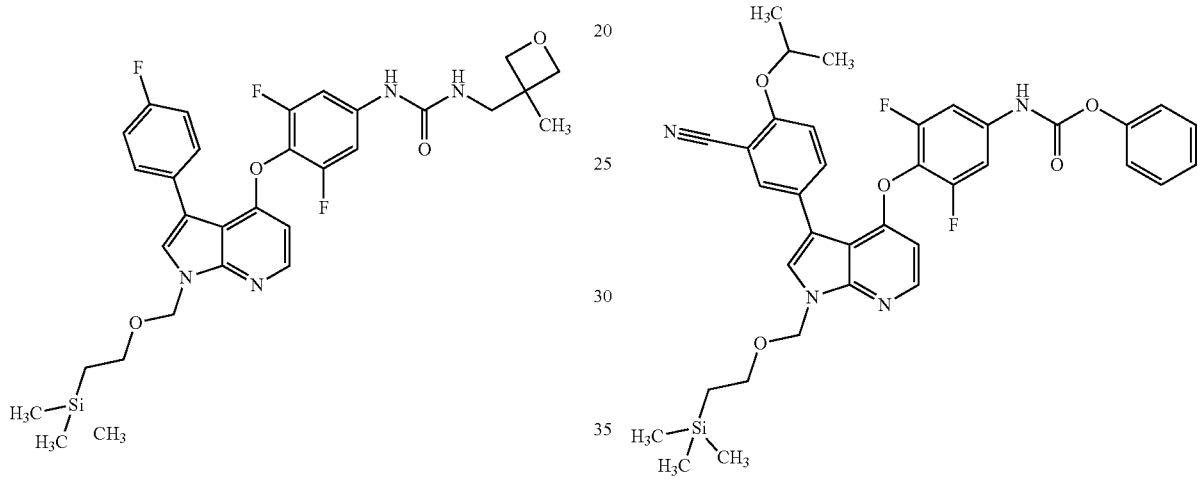

To a stirred solution of 3,5-difluoro-4-{[3-(4-fluorophenyl)-1-{[2-(trimethylsilyl)ethoxy]methyl}-1H-pyrrolo[2,3-b]pyridin-4-yl]oxy}aniline (80.0 mg, 0.17 mmol, intermediate 101) in a mixture of dichloromethane (1.0 mL) and pyridine (1.0 mL) was added 3-(isocyanatomethyl)-3-methyloxetane (CAS No. [1260665-88-0]) (105 mg, 0.82 mmol). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(4-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 2): $R_t$=1.54 min; MS (ESIpos): m/z=613 [M+H]$^+$

To solution of 5-[4-(4-amino-2,6-difluorophenoxy)-1-{[2-(trimethylsilyl)ethoxy]methyl}-1H-pyrrolo[2,3-b]pyridin-3-yl]-2-(propan-2-yloxy)benzonitrile (1.00 g, 1.82 mmol, intermediate 83) in ethyl acetate (14 mL) and saturated sodium bicarbonate solution (7 mL) was slowly added at RT phenyl chloroformate (0.23 mL, 1.82 mmol). The reaction mixture was stirred for 20 min at room temperature, at which time the reaction was diluted with ethyl acetate and water. The layers were separated, and the aqueous phase was extracted two times with ethyl acetate. The combined organic phases were washed with brine, dried over sodium sulfate, filtered and concentrated to dryness to give phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate, which was used in the subsequent step without further purification.

LC-MS (Method 1): $R_t$=1.67 min; MS (ESIpos): m/z=671 [M+H]$^+$

Intermediate 104

1-[(3-cyanooxetan-3-yl)methyl]-3-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}urea

Intermediate 105

1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(difluoromethyl)oxetan-3-yl]methyl}urea

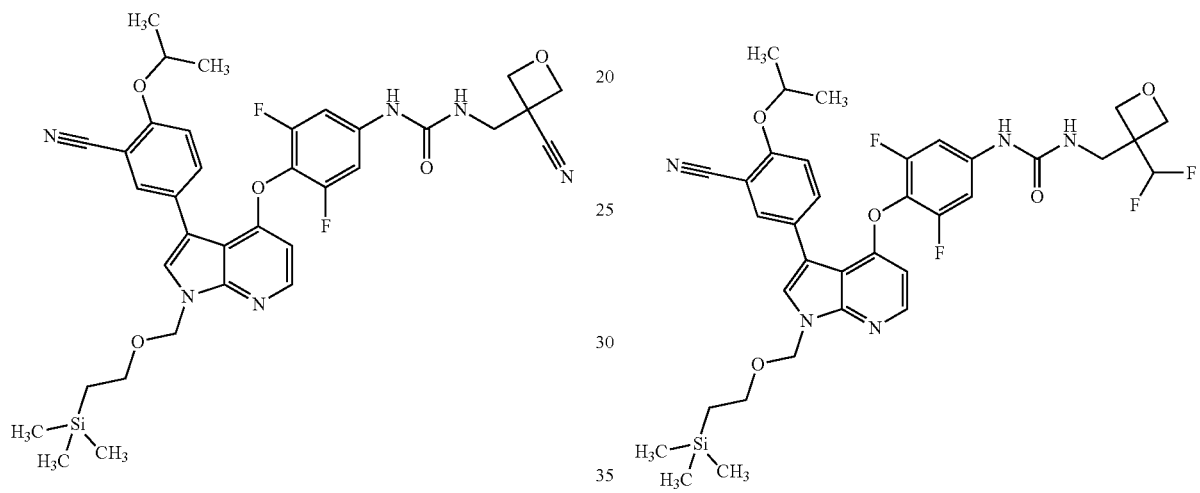

To solution of phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate (100 mg, 0.13 mmol, intermediate 103) in DMF (2.0 mL) was added 3-(aminomethyl)oxetane-3-carbonitrile hydrochloride (39.9 mg, 0.27 mmol, ordered from SpiroChem AG, CAS No. for free base [1374653-22-1]) and triethylamine (37 µL, 0.27 mmol). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-[(3-cyanooxetan-3-yl)methyl]-3-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}urea, which was used in the subsequent reaction without further purification.

LC-MS (Method 2): $R_t$=1.52 min; MS (ESIpos): m/z=689 [M+H]$^+$

To solution of phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate (100 mg, 0.13 mmol, intermediate 103) in DMF (2.0 mL) was added 1-[3-(difluoromethyl)oxetan-3-yl]methanamine (37 mg, 0.27 mmol, CAS No. [1781121-31-0]. The resulting mixture was stirred at 60° C. for 16 hours, at which time the reaction mixture was cooled to room temperature, diluted with ethyl acetate and water was added. The layers were separated, and the aqueous phase was extracted two times with ethyl acetate.

The combined organic phases were washed with brine, dried over sodium sulfate, filtered and concentrated to dryness to give crude 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(difluoromethyl)oxetan-3-yl]methyl}urea, which was used in the subsequent reaction without further purification.

LC-MS (Method 2): $R_t$=1.55 min; MS (ESIpos): m/z=714 [M+H]$^+$

Intermediate 106

1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(propan-2-yl)oxetan-3-yl]methyl}urea

Intermediate 107

1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea

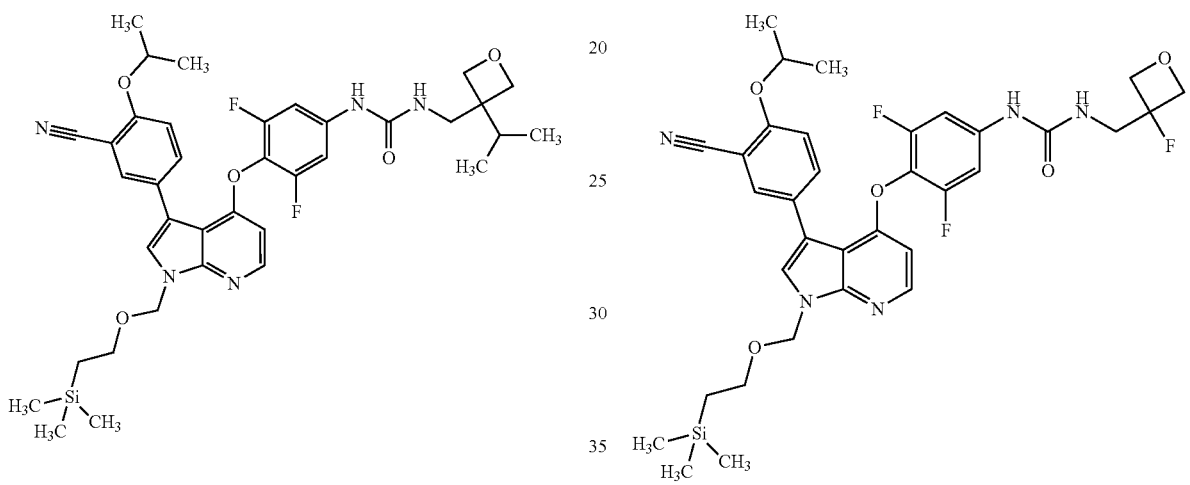

To solution of phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate (100 mg, 0.13 mmol, intermediate 103) in DMF (2.0 mL) was added 1-[3-(propan-2-yl)oxetan-3-yl]methanamine (35 mg, 0.27 μmol, CAS No. [1539197-30-2]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(propan-2-yl)oxetan-3-yl]methyl}urea, which was used in the subsequent reaction without further purification.

LC-MS (Method 2): $R_t$=1.61 min; MS (ESIpos): m/z=706 [M+H]$^+$

To solution of phenyl {4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}carbamate (100 mg, 0.13 mmol, intermediate 103) in DMF (2.0 mL) was added 1-(3-fluorooxetan-3-yl)methanamine (28 mg, 0.27 μmol, CAS No. [883311-82-8]). The resulting mixture was stirred at 60° C. for 16 hours, at which time the reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give crude 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea, which was used in the subsequent reaction without further purification.

LC-MS (Method 2): $R_t$=1.53 min; MS (ESIpos): m/z=683 [M+H]$^+$

177

Intermediate 108

4-(2,6-difluoro-4-nitrophenoxy)-3-(1-ethyl-1H-pyrazol-5-yl)-1-{[2-(trimethylsilyl)ethoxy]methyl}-1H-pyrrolo[2,3-b]pyridine

178

Intermediate 109

4-{[3-(1-ethyl-1H-pyrazol-5-yl)-1-{[2-(trimethylsilyl)ethoxy]methyl}-1H-pyrrolo[2,3-b]pyridin-4-yl]oxy}-3,5-difluoroaniline

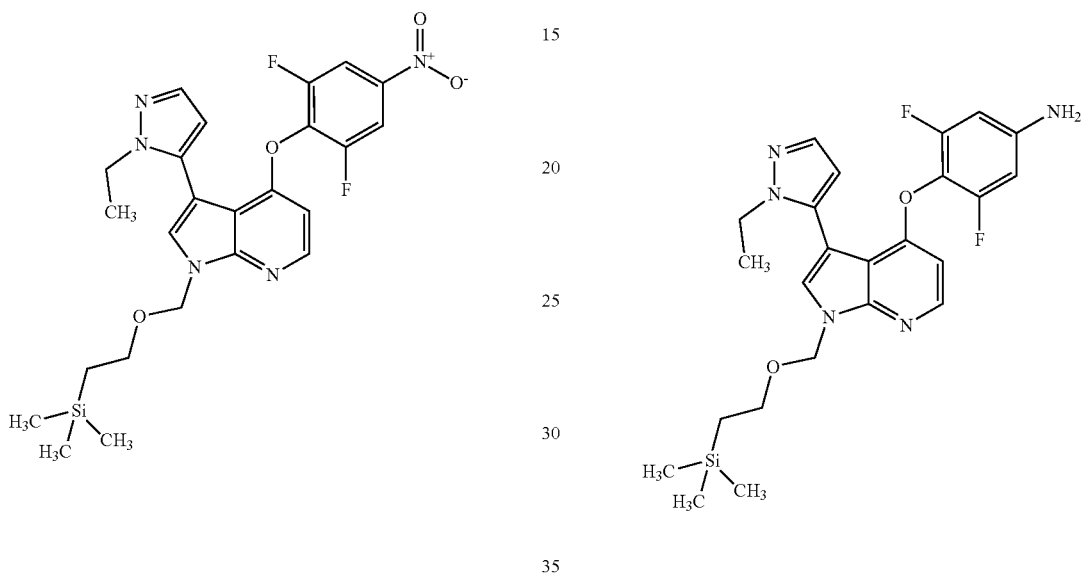

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), (1-ethyl-1H-pyrazol-5-yl)boronic acid (559 mg, 4.00 mmol, CAS No. [1095080-54-8]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(1-ethyl-1H-pyrazol-5-yl)-1-{[2-(trimethylsilyl)ethoxy]methyl}-1H-pyrrolo[2,3-b]pyridine (260 mg, 20% Yield).

LC-MS (Method 2): $R_t$=1.52 min; MS (ESIpos): m/z=516 [M+H]$^+$ $^1$H NMR (400 MHz, DMSO-d$_6$) δ ppm −0.10 (s, 9H), 0.80-0.88 (m, 2H), 1.25 (t, 3H), 3.56-3.65 (m, 2H), 4.10 (q, 2H), 5.71 (s, 2H), 6.30 (d, 1H), 6.66 (d, 1H), 7.45 (d, 1H), 7.90 (s, 1H), 8.25 (d, 1H), 8.32-8.38 (m, 2H)

To a solution of 4-(2,6-difluoro-4-nitrophenoxy)-3-(1-ethyl-1H-pyrazol-5-yl)-1-{[2-(trimethylsilyl)ethoxy]methyl}-1H-pyrrolo[2,3-b]pyridine (260 mg, 0.51 mmol, intermediate 108) in a mixture of THF (1.6 mL), water (0.7 mL), and methanol (0.8 mL) was added ammonium chloride (135 mg, 2.52 mmol) and iron powder (141 mg, 2.52 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford the crude aniline.

The crude product was purified by flash column chromatography to afford 4-{[3-(1-ethyl-1H-pyrazol-5-yl)-1-{[2-(trimethylsilyl)ethoxy]methyl}-1H-pyrrolo[2,3-b]pyridin-4-yl]oxy}-3,5-difluoroaniline (150 mg, 43% Yield).

LC-MS (Method 2): $R_t$=1.40 min; MS (ESIpos): m/z=486 [M+H]$^+$ $^1$H NMR (400 MHz, DMSO-d$_6$) δ ppm −0.10 (s, 9H), 0.79-0.86 (m, 2H), 1.23 (t, 3H), 3.56-3.60 (m, 2H), 4.10 (q, 2H), 5.68 (s, 2H), 5.79 (br s, 2H), 6.30 (d, 1H), 6.32-6.40 (m, 3H), 7.46 (d, 1H), 7.78 (s, 1H), 8.19 (d, 1H)

Intermediate 110

1-(4-{[3-(1-ethyl-1H-pyrazol-5-yl)-1-{[2-(trimethyl-silyl)ethoxy]methyl}-1H-pyrrolo[2,3-b]pyridin-4-yl]oxy}-3,5-difluorophenyl)-3-[(3-methyloxetan-3-yl)methyl]urea

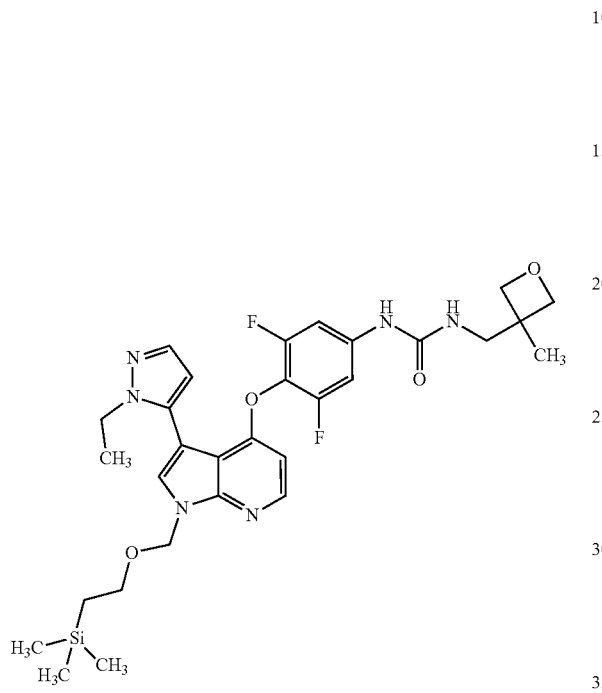

To a stirred solution of 4-{[3-(1-ethyl-1H-pyrazol-5-yl)-1-{[2-(trimethylsilyl)ethoxy]methyl}-1H-pyrrolo[2,3-b]pyridin-4-yl]oxy}-3,5-difluoroaniline (150 mg, 0.31 mmol, intermediate 109) in a mixture of dichloromethane (0.8 mL) and pyridine (1.0 mL) was added 3-(isocyanatomethyl)-3-methyloxetane (79 mg, 0.62 mmol, CAS No. [1260665-88-0]). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(4-{[3-(1-ethyl-1H-pyrazol-5-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea, which was used in the subsequent reaction without further purification.

LC-MS (Method 2): $R_t$=1.36 min; MS (ESIpos): m/z=613 [M+H]$^+$

Intermediate 111

{4-[4-(2,6-difluoro-4-nitrophenoxy)-1-{[2-(trimethylsilyl)ethoxy]methyl}-1H-pyrrolo[2,3-b]pyridin-3-yl]phenoxy}acetonitrile

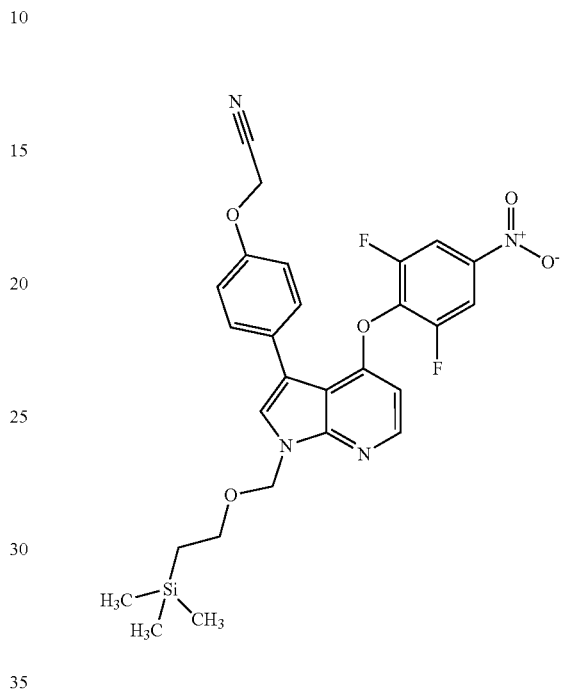

3-bromo-4-(2,6-difluoro-4-nitrophenoxy)-1-{[2-(trimethylsilyl)ethoxy]methyl}-1H-pyrrolo[2,3-b]pyridine (0.68 g, 1.36 mmol, intermediate 16), [1,1'-Bis(diphenylphosphino)ferrocene]dichloropalladium(II) (99 mg, 0.14 mmol), [4-(cyanomethoxy)phenyl]-boronic acid (481 mg, 2.72 mmol, CAS No. [947533-23-5]), and potassium carbonate (939 mg, 6.79 mmol) were dissolved in a mixture of 1,4-dioxane (13 mL), and water (6.5 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to {4-[4-(2,6-difluoro-4-nitrophenoxy)-1-{[2-(trimethylsilyl)ethoxy]methyl}-1H-pyrrolo[2,3-b]pyridin-3-yl]phenoxy}acetonitrile (680 mg, 91% Yield).

LC-MS (Method 1): $R_t$=1.54 min; MS (ESIpos): m/z=555 [M+H]$^+$ $^1$H NMR (400 MHz, DMSO-d$_6$) δ ppm −0.09 (s, 9H), 0.82-0.88 (m, 2H), 3.56-3.64 (m, 2H), 5.18 (s, 2H), 5.69 (s, 2H), 6.63 (d, 1H), 7.08-7.13 (m, 2H), 7.60-7.65 (m, 2H), 7.85 (s, 1H), 8.21 (d, 1H), 8.36-8.43 (m, 2H)

Intermediate 112

{4-[4-(4-amino-2,6-difluorophenoxy)-1-{[2-(trimethylsilyl)ethoxy]methyl}-1H-pyrrolo[2,3-b]pyridin-3-yl]phenoxy}acetonitrile

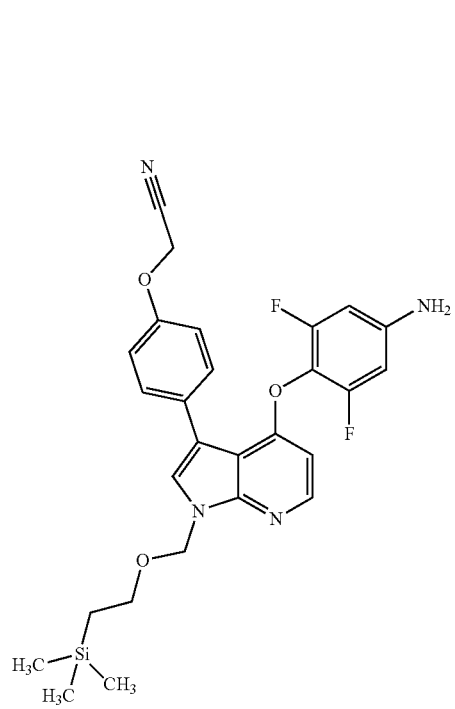 [SMILES: C[Si](C)(C)CCOCn1cc(-c2ccc(OCC#N)cc2)c2c(Oc3c(F)cc(N)cc3F)ccnc21]

To a solution of {4-[4-(2,6-difluoro-4-nitrophenoxy)-1-{[2-(trimethylsilyl)ethoxy]methyl}-1H-pyrrolo[2,3-b]pyridin-3-yl]phenoxy}acetonitrile (680 mg, 1.23 mmol, intermediate 111) in a mixture of THF (4.0 mL), water (1.7 mL), and methanol (2.0 mL) was added ammonium chloride (329 mg, 6.15 mmol) and iron powder (344 mg, 6.15 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford the crude aniline. The crude product was purified by flash column chromatography to afford {4-[4-(4-amino-2,6-difluorophenoxy)-1-{[2-(trimethylsilyl)ethoxy]methyl}-1H-pyrrolo[2,3-b]pyridin-3-yl]phenoxy}acetonitrile (400 mg, 44% Yield)

LC-MS (Method 2): $R_t$=1.48 min; MS (ESIpos): m/z=523 [M+H]$^+$ $^1$H NMR (400 MHz, DMSO-d$_6$) δ ppm −0.08 (s, 9H), 0.81-0.88 (m, 2H), 3.55-3.62 (m, 2H), 5.19 (s, 2H), 5.66 (s, 2H), 5.80 (s, 2H), 6.35-6.43 (m, 3H), 7.08-7.12 (m, 2H), 7.62-7.68 (m, 2H), 7.76 (s, 1H), 8.16 (d, 1H)

Intermediate 113

1-{4-[(3-[4-(cyanomethoxy)phenyl]-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea

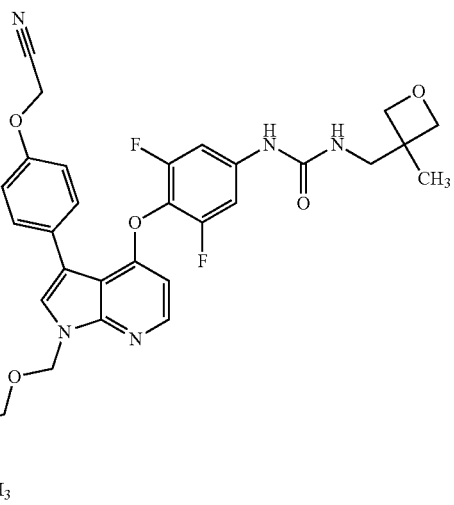

To a stirred solution of {4-[4-(4-amino-2,6-difluorophenoxy)-1-{[2-(trimethylsilyl)ethoxy]methyl}-1H-pyrrolo[2,3-b]pyridin-3-yl]phenoxy}acetonitrile (100 mg, 191 μmol, intermediate 112) in a mixture of dichloromethane (0.5 mL) and pyridine (0.6 mL) was added 3-(isocyanatomethyl)-3-methyloxetane (49 mg, 0.38 mmol, CAS No. [1260665-88-0]). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-{4-[(3-[4-(cyanomethoxy)phenyl]-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea, which was used in the subsequent reaction without further purification.

LC-MS (Method 1): $R_t$=1.43 min; MS (ESIpos): m/z=650 [M+H]$^+$

Intermediate 114

4-(2,6-difluoro-4-nitrophenoxy)-3-(2-fluoro-3-methoxyphenyl)-1-{[2-(trimethylsilyl)ethoxy]methyl}-1H-pyrrolo[2,3-b]pyridine

Intermediate 115

3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}aniline

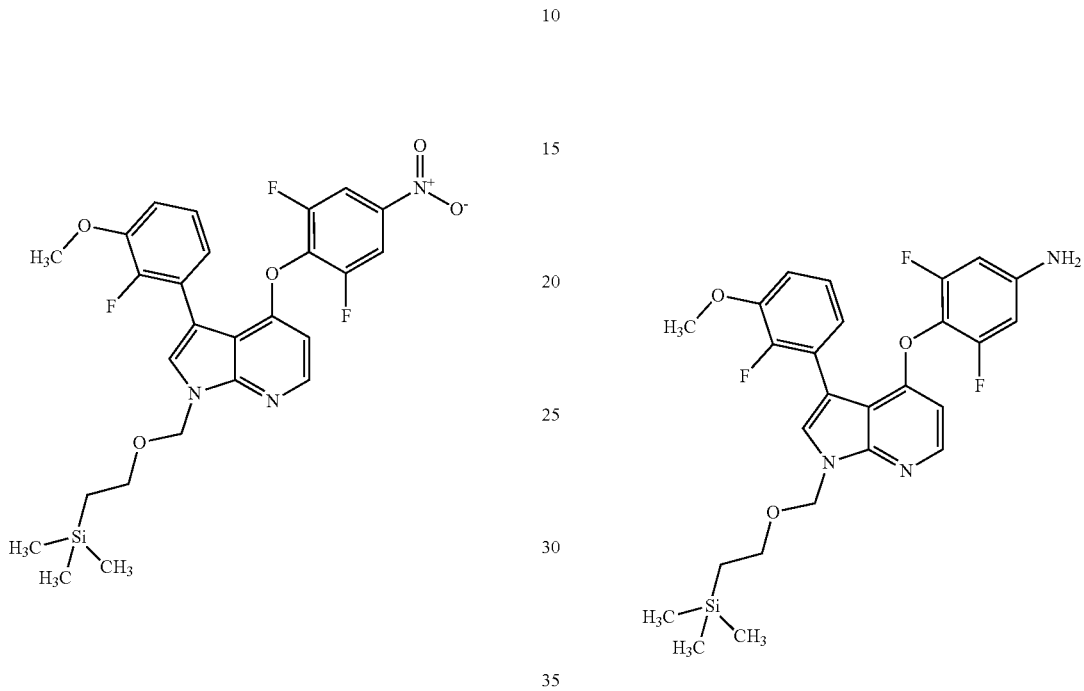

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, intermediate 16), [1,1'-Bis(diphenylphosphino)ferrocene]dichloropalladium(II) (146 mg, 0.20 mmol), (2-fluoro-3-methoxyphenyl)boronic acid (679 mg, 4.00 mmol, CAS No. [352303-67-4]), and potassium carbonate (1.38 g, 9.99 mmol), were dissolved in a mixture of 1,4-dioxane (20 mL), and water (10 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by flash column chromatography to afford 4-(2,6-difluoro-4-nitrophenoxy)-3-(2-fluoro-3-methoxyphenyl)-1-{[2-(trimethylsilyl)ethoxy]methyl}-1H-pyrrolo[2,3-b]pyridine (981 mg, 90% Yield).

LC-MS (Method 1): $R_f$=1.62 min; MS (ESIpos): m/z=546 [M+H]$^+$ $^1$H NMR (400 MHz, DMSO-d$_6$) δ ppm −0.09 (s, 9H), 0.82-0.88 (m, 2H), 3.56-3.63 (m, 2H), 3.82 (s, 3H), 5.70 (s, 2H), 6.65 (d, 1H), 7.03-7.15 (m, 3H), 7.83 (s, 1H), 8.23 (d, 1H), 8.33 (d, 2H)

To a solution of 4-(2,6-difluoro-4-nitrophenoxy)-3-(2-fluoro-3-methoxyphenyl)-1-{[2-(trimethylsilyl)ethoxy]methyl}-1H-pyrrolo[2,3-b]pyridine (1.44 g, 2.64 mmol, intermediate 114) in a mixture of THF (8.6 mL), water (3.6 mL), and methanol (4.3 mL) was added ammonium chloride (706 mg, 13.2 mmol) and iron powder (737 mg, 13.2 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford the crude aniline. The crude product was purified by flash column chromatography to 3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}aniline (150 mg, 8% Yield) LC-MS (Method 1): $R_f$=1.94 min; MS (ESIpos): m/z=516 [M+H]$^+$ $^1$H NMR (400 MHz, DMSO-d$_6$) δ ppm −0.08 (s, 9H), 0.79-0.90 (m, 2H), 3.54-3.66 (m, 2H), 3.84 (s, 3H), 5.67 (s, 2H), 5.77 (s, 2H), 6.30-6.42 (m, 3H), 7.04-7.17 (m, 3H), 7.73 (d, 1H), 8.16 (d, 1H)

Intermediate 116

1-(3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea

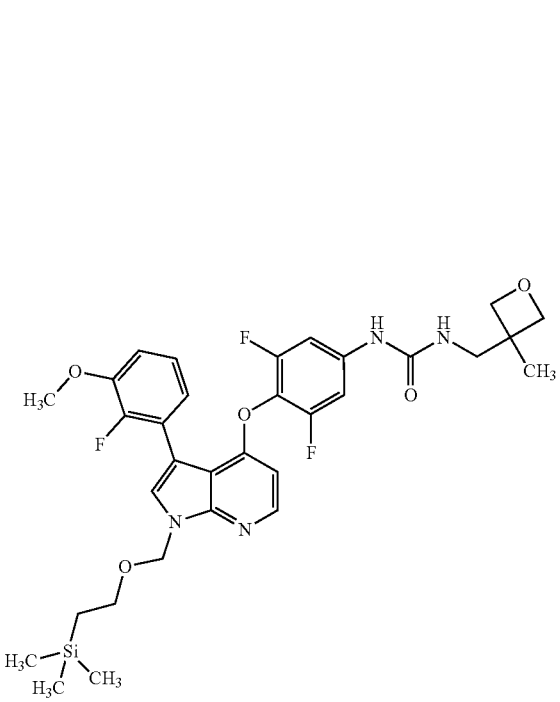 [SMILES: COc1cccc(-c2cn(COCC[Si](C)(C)C)c3nccc(Oc4c(F)cc(NC(=O)NCC5(C)COC5)cc4F)c23)c1F]

To a stirred solution of 3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}aniline (100 mg, 194 μmol, intermediate 115) in a mixture of dichloromethane (0.5 mL) and pyridine (0.6 mL) was added 3-(isocyanatomethyl)-3-methyloxetane (49 mg, 0.38 mmol, CAS No. [1260665-88-0]). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-(3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea, which was used in the subsequent reaction without further purification.

LC-MS (Method 1): $R_t$=1.48 min; MS (ESIpos): m/z=643 [M+H]$^+$

Intermediate 117

4-(2,6-difluoro-4-nitrophenoxy)-3-[2-fluoro-4-(propan-2-yloxy)phenyl]-1-{[2-(trimethylsilyl)ethoxy]methyl}-1H-pyrrolo[2,3-b]pyridine

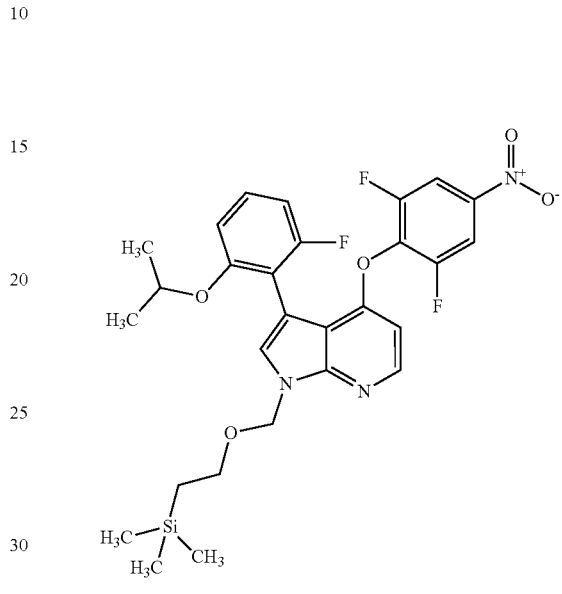

3-bromo-4-(2,6-difluoro-4-nitrophenoxy)-1-{[2-(trimethylsilyl)ethoxy]methyl}-1H-pyrrolo[2,3-b]pyridine (1.50 g, 3.00 mmol, intermediate 16), [1,1'-Bis(diphenylphosphino)ferrocene]dichloropalladium(II) (219 mg, 0.30 mmol), [2-fluoro-4-(propan-2-yloxy)phenyl]boronic acid (1.19 g, 6.00 mmol, CAS No. [586389-90-4]), and potassium carbonate (2.07 g, 15.0 mmol), were dissolved in a mixture of 1,4-dioxane (30 mL), and water (15 mL). The resulting mixture was degassed with argon for 10 min, after which time it was heated to 100° C. for 3 h. The reaction mixture was cooled to room temperature, diluted with ethyl acetate and water was added. The layers were separated, and the aqueous phase was extracted two times with ethyl acetate. The combined organic phases were washed with brine, dried over sodium sulfate, filtered and concentrated to dryness to give the crude product. The crude product was purified by preparative HPLC to afford 4-(2,6-difluoro-4-nitrophenoxy)-3-[2-fluoro-4-(propan-2-yloxy)phenyl]-1-{[2-(trimethylsilyl)ethoxy]methyl}-1H-pyrrolo[2,3-b]pyridine (219 mg, 13% Yield).

LC-MS (Method 2): $R_t$=1.70 min; MS (ESIpos): m/z=574 [M+H]$^+$ $^1$H NMR (400 MHz, DMSO-$d_6$) δ ppm −0.10 (s, 9H), 0.76-0.91 (m, 2H), 1.09 (d, 3H), 1.17 (d, 3H), 3.58 (t, 2H), 4.52 (spt, 1H), 5.65 (d, 1H), 5.75 (d, 1H), 6.62 (d, 1H), 6.76 (t, 1H), 6.87 (d, 1H), 7.25 (td, 1H), 7.64 (s, 1H), 8.19 (d, 1H), 8.21-8.27 (m, 2H)

Intermediate 118

3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]aniline

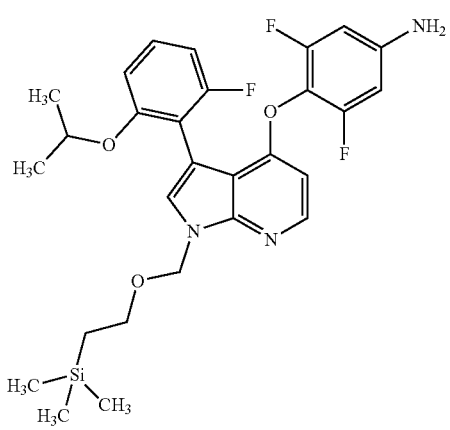 [SMILES: CC(C)Oc1cccc(F)c1-c1cn(COCC[Si](C)(C)C)c2nccc(Oc3c(F)cc(N)cc3F)c12]

To a solution of 4-(2,6-difluoro-4-nitrophenoxy)-3-[2-fluoro-4-(propan-2-yloxy)phenyl]-1-{[2-(trimethylsilyl)ethoxy]methyl}-1H-pyrrolo[2,3-b]pyridine (219 mg, 0.38 mmol, intermediate 117) in a mixture of THF (3 mL), water (6 mL), and methanol (3 mL) was added ammonium chloride (102 mg, 1.91 mmol) and iron powder (107 mg, 1.91 mmol). The resulting mixture was stirred at 80 degrees for 2 hours at which time the mixture was cooled and filtered. The filtrate was extracted three times with ethyl acetate and the combined organic layers washed with brine, dried over sodium sulfate, and evaporated to afford 3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]aniline (186 mg, 90% Yield), which required no further purification.

LC-MS (Method 2): $R_t$=1.58 min; MS (ESIpos): m/z=544 [M+H]$^+$ $^1$H NMR (400 MHz, DMSO-d$_6$) δ ppm −0.09 (s, 9H), 0.76-0.91 (m, 1H) 1.08 (d, 3H), 1.18 (d, 3H), 3.57 (t, 2H), 4.48-4.55 (m, 1H), 5.59-5.75 (m, 4H), 6.26-6.32 (m, 3H), 6.79 (t, 1H), 6.90 (d, 1H), 7.21-7.29 (m, 1H), 7.53 (s, 1H), 8.11 (d, 1H)

Intermediate 119

1-{3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea To a stirred solution of 3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]aniline (100 mg, 184 μmol, intermediate 118) in a mixture of dichloromethane (0.5 mL) and pyridine (0.6 mL) was added 3-(isocyanatomethyl)-3-methyloxetane (47 mg, 0.37 mmol, CAS No. [1260665-88-0]). The resulting mixture was stirred at 60° C. for 16 hours, at which time the reaction was cooled to room temperature and ethyl acetate and water were added. The layers were separated, and the aqueous phase was extracted two times with ethyl acetate. The combined organic phases were washed with brine, dried over sodium sulfate, filtered and concentrated to dryness to give 1-{3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea, which was used in the subsequent reaction without further purification.

LC-MS (Method 1): $R_t$=1.56 min; MS (ESIpos): m/z=671 [M+H]$^+$

Intermediate 120 phenyl {3,5-difluoro-4-[(1-{[2-(trimethylsilyl)ethoxy]methyl}-1H-pyrrolo[2,3-b]pyridin-4-yl)oxy]phenyl}carbamate In analogy to intermediate 1,3,5-difluoro-4-[(1-{[2-(trimethylsilyl)ethoxy]methyl}-1H-pyrrolo[2,3-b]pyridin-4-yl)oxy]aniline (309 mg, 789 µmol, see *Org. Process Res. Dev.* 2010, page 168-173) was reacted with phenyl carbonochloridate (110 µL, 870 µmol) in pyridine (370 µL) and THF (5.6 mL). After purification using a Biotage chromatography system we obtained 410 mg (91% purity, 93% yield) of the desired title compound.

LC-MS (Method 2): $R_t$=1.59 min; MS (ESIpos): m/z=512 [M+H]$^+$ $^1$H-NMR (400 MHz, DMSO-d6) δ [ppm]: −0.12−−0.09 (m, 9H), 0.77-0.85 (m, 2H), 3.49-3.55 (m, 2H), 5.63 (s, 2H), 6.42 (d, 1H), 6.52 (d, 1H), 7.25-7.32 (m, 3H), 7.40-7.49 (m, 4H), 7.61 (d, 1H), 8.16 (d, 1H), 10.80 (s, 1H).

Intermediate 121

N-{3,5-difluoro-4-[(1-{[2-(trimethylsilyl)ethoxy]methyl}-1H-pyrrolo[2,3-b]pyridin-4-yl)oxy]phenyl}-N'-{[3-(propan-2-yl)oxetan-3-yl]methyl}urea

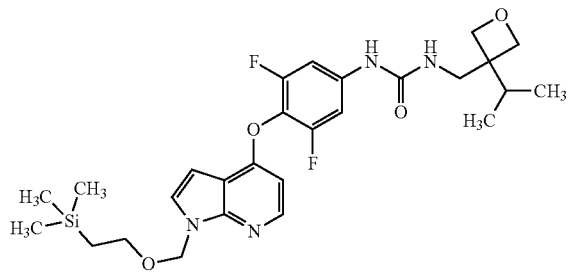 [SMILES: CC(C)C1(CNC(=O)Nc2cc(F)c(Oc3ccnc4c3ccn4COCC[Si](C)(C)C)c(F)c2)COC1]

In analogy to intermediate 2, {3,5-difluoro-4-[(1-{[2-(trimethylsilyl)ethoxy]methyl}-1H-pyrrolo[2,3-b]pyridin-4-yl)oxy]phenyl}carbamate (100 mg, 195 µmol, intermediate 120) was reacted with 1-[3-(propan-2-yl)oxetan-3-yl]methanamine (27.8 mg, 215 µmol) in DMF (1.1 mL). After purification using a Biotage chromatography system we obtained 96.0 mg (100% purity, 90% yield) of the desired title compound.

LC-MS (Method 2): $R_t$=1.49 min; MS (ESIpos): m/z=547 [M+H]$^+$ $^1$H-NMR (400 MHz, DMSO-d6) δ [ppm]: −0.12−−0.08 (m, 9H), 0.77-0.84 (m, 2H), 0.91 (d, 4H), 2.01 (spt, 1H), 3.49-3.54 (m, 2H), 4.28-4.34 (m, 4H), 5.62 (s, 2H), 6.42 (d, 1H), 6.50 (d, 1H), 6.73 (t, 1H), 7.36-7.44 (m, 2H), 7.59 (d, 1H), 8.14 (d, 1H), 9.09 (s, 1H).

Intermediate 122

N-{3,5-difluoro-4-[(1-{[2-(trimethylsilyl)ethoxy]methyl}-1H-pyrrolo[2,3-b]pyridin-4-yl)oxy]phenyl}-N'-[(3-methyloxetan-3-yl)methyl]urea

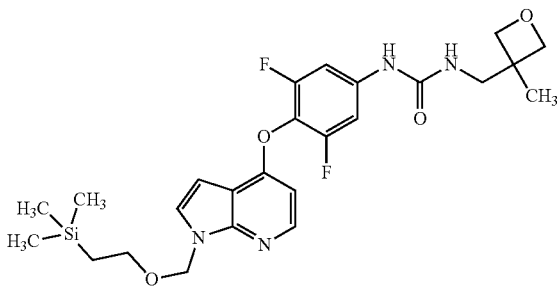 [SMILES: CC1(CNC(=O)Nc2cc(F)c(Oc3ccnc4c3ccn4COCC[Si](C)(C)C)c(F)c2)COC1]

In analogy to intermediate 2, {3,5-difluoro-4-[(1-{[2-(trimethylsilyl)ethoxy]methyl}-1H-pyrrolo[2,3-b]pyridin-4-yl)oxy]phenyl}carbamate (100 mg, 195 µmol, intermediate 120) was reacted with 1-(3-methyloxetan-3-yl)methanamine (21.7 mg, 215 µmol) in DMF (1.1 mL). After purification using a Biotage chromatography system we obtained 84.6 mg (100% purity, 83% yield) of the desired title compound.

LC-MS (Method 2): $R_t$=1.40 min; MS (ESIpos): m/z=519 [M+H]$^+$ $^1$H-NMR (400 MHz, DMSO-d6) δ [ppm]: −0.12−−0.08 (m, 9H), 0.77-0.85 (m, 2H), 1.23 (s, 3H), 3.28-3.32 (m, 2H), 3.48-3.54 (m, 2H), 4.21 (d, 2H), 4.38 (d, 2H), 5.62 (s, 2H), 6.42 (d, 1H), 6.49 (d, 1H), 6.71 (t, 1H), 7.35-7.42 (m, 2H), 7.59 (d, 1H), 8.14 (d, 1H), 9.01 (s, 1H).

Intermediate 123

(+/−)—N-{3,5-difluoro-4-[(1-{[2-(trimethylsilyl)ethoxy]methyl}-1H-pyrrolo[2,3-b]pyridin-4-yl)oxy]phenyl}-N'-[1-(oxetan-3-yl)ethyl]urea

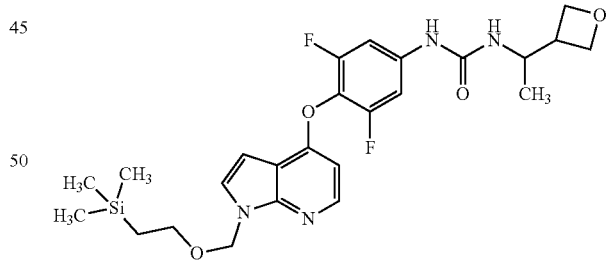

In analogy to intermediate 2, {3,5-difluoro-4-[(1-{[2-(trimethylsilyl)ethoxy]methyl}-1H-pyrrolo[2,3-b]pyridin-4-yl)oxy]phenyl}carbamate (205 mg, 401 µmol, intermediate 120) was reacted with (+/−)-1-(oxetan-3-yl)ethan-1-amine (44.6 mg, 441 µmol, CAS No. [1544892-89-8]) in DMF (2.3 mL). After purification using a Biotage chromatography system we obtained 174 mg (98% purity, 82% yield) of the desired title compound.

LC-MS (Method 2): $R_t$=1.39 min; MS (ESIpos): m/z=519 [M+H]$^+$ $^1$H-NMR (400 MHz, DMSO-d6) δ [ppm]: −0.11−−0.09 (m, 9H), 0.78-0.84 (m, 2H), 1.02 (d, 3H), 2.95-3.05 (m, 1H), 3.48-3.55 (m, 2H), 3.98-4.08 (m, 1H), 4.29-4.41 (m, 2H), 4.56-4.63 (m, 2H), 5.62 (s, 2H), 6.41 (d, 1H), 6.46 (d, 1H), 6.49 (d, 1H), 7.34-7.41 (m, 2H), 7.59 (d, 1H), 8.14 (d, 1H), 8.88 (s, 1H).

Intermediate 124

4-{[6-chloro-3-(trifluoromethyl)-1-{[2-(trimethylsilyl)ethoxy]methyl}-1H-pyrrolo[2,3-b]pyridin-4-yl]oxy}-3-fluoroaniline

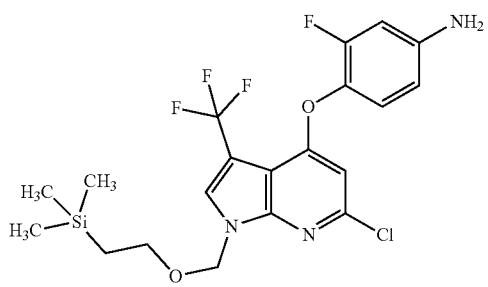 [SMILES: C[Si](C)(C)CCOCn1cc(C(F)(F)F)c2c(Oc3ccc(N)cc3F)cc(Cl)nc21]

A solution of 6-chloro-4-nitro-3-(trifluoromethyl)-1-{[2-(trimethylsilyl)ethoxy]methyl}-1H-pyrrolo[2,3-b]pyridine (500 mg, 1.26 mmol, see Synthesis 2007, page 251-258, Org. Process Res. Dev. 2010, page 168-173), 4-amino-2-fluorophenol (241 mg, 1.89 mmol) and potassium carbonate (524 mg, 3.79 mmol) in DMSO (5.0 mL) was stirred at 120° C. for 3 hours. After cooling to room temperature the reaction mixture was diluted with ethyl acetate (200 mL). This organic phase was washed two times with water (30 mL) and once with brine (20 mL), then dried over sodium sulfate and after filtration dried to dryness. The resulting residue was purified via a Biotage chromatography system (28 g snap KP-NH column, hexane/0-70% ethyl acetate) to obtain 370 mg (92% purity, 57% yield) of the desired title compound.

$^1$H-NMR (400 MHz, DMSO-d6) δ [ppm]: −0.10−−0.06 (m, 9H), 0.81-0.88 (m, 2H), 3.54-3.60 (m, 2H), 5.57 (s, 2H), 5.61 (s, 2H), 6.36 (d, 1H), 6.45 (ddd, 1H), 6.54 (dd, 1H), 7.07 (t, 1H), 8.35 (d, 1H).

Intermediate 125

3-fluoro-4-{[3-(trifluoromethyl)-1-{[2-(trimethylsilyl)ethoxy]methyl}-1H-pyrrolo[2,3-b]pyridin-4-yl]oxy}aniline

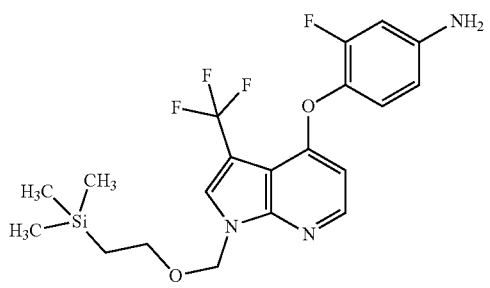 [SMILES: C[Si](C)(C)CCOCn1cc(C(F)(F)F)c2c(Oc3ccc(N)cc3F)ccnc21]

To a solution of 4-{[6-chloro-3-(trifluoromethyl)-1-{[2-(trimethylsilyl)ethoxy]methyl}-1H-pyrrolo[2,3-b]pyridin-4-yl]oxy}-3-fluoroaniline (350 mg, 0.74 mmol, intermediate 124) and triethylamine (123 μL, 882 μmol) in ethanol (25 mL) was given 10% Pd on carbon (36.2 mg). This mixture was stirred in an hydrogen atmosphere for 7 hours at room temperature. Then the mixture was filtered through Celite and the Celite was washed with ethyl acetate. The organic phase was evaporated to dryness and the resulting residue was purified via a Biotage chromatography system (28 g snap KP-NH column, hexane/0-70% ethyl acetate) to obtain 320 mg (92% purity, 91% yield) of the desired title compound.

$^1$H-NMR (400 MHz, DMSO-d6) δ [ppm]: −0.11−−0.07 (m, 9H), 0.77-0.89 (m, 2H), 3.53-3.60 (m, 2H), 5.49 (s, 2H), 5.66 (s, 2H), 6.40-6.47 (m, 2H), 6.52 (dd, 1H), 7.03 (t, 1H), 8.24 (d, 1H), 8.29 (s, 1H).

Intermediate 126

N-(3-fluoro-4-{[3-(trifluoromethyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

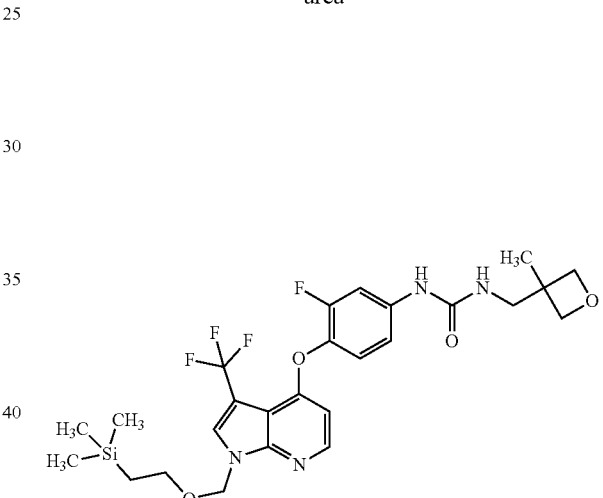

In analogy to intermediate 41, 3-fluoro-4-{[3-(trifluoromethyl)-1-{[2-(trimethylsilyl)ethoxy]methyl}-1H-pyrrolo[2,3-b]pyridin-4-yl]oxy}aniline (250 mg, 566 μmol, intermediate 125) was reacted with 3-(isocyanatomethyl)-3-methyloxetane (140 μL, 1.1 mmol) in pyridine (5.0 mL) and dichloromethane (5.0 mL). After purification using a Biotage chromatography system we obtained 308 mg (92% purity, 88% yield) of the desired title compound.

LC-MS (Method 2): $R_t$=1.43 min; MS (ESIpos): m/z=569 [M+H]$^+$ $^1$H-NMR (400 MHz, DMSO-d6) δ [ppm]: −0.11−−0.05 (m, 9H), 0.79-0.87 (m, 2H), 1.24 (s, 3H), 3.30 (d, 2H), 3.52-3.62 (m, 2H), 4.21 (d, 2H), 4.39 (d, 2H), 5.68 (s, 2H), 6.46 (d, 1H), 6.59 (t, 1H), 7.16 (br d, 1H), 7.28 (t, 1H), 7.69 (dd, 1H), 8.26 (d, 1H), 8.33 (s, 1H), 8.87 (s, 1H).

Intermediate 127

4-{[6-chloro-3-(trifluoromethyl)-1-{[2-(trimethylsilyl)ethoxy]methyl}-1H-pyrrolo[2,3-b]pyridin-4-yl]oxy}-2,5-difluoroaniline

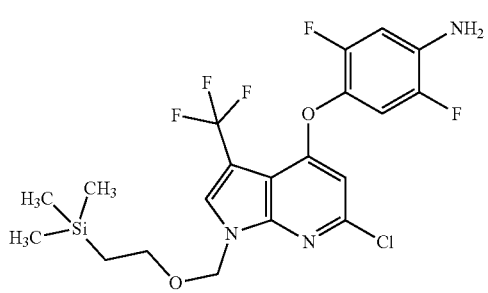 [SMILES: C[Si](C)(C)CCOCn1cc(C(F)(F)F)c2c(Oc3cc(F)c(N)cc3F)cc(Cl)nc21]

In analogy to intermediate 124, 6-chloro-4-nitro-3-(trifluoromethyl)-1-{[2-(trimethylsilyl)ethoxy]methyl}-1H-pyrrolo[2,3-b]pyridine (500 mg, 1.26 mmol, see *Synthesis* 2007, page 251-258, *Org. Process Res. Dev.* 2010, page 168-173) was reacted with 4-amino-2,5-difluorophenol (202 mg, 1.39 mmol) and potassium carbonate (524 mg, 3.79 mmol) in DMSO (5.0 mL). After purification using a Biotage chromatography system we obtained 364 mg (90% purity, 53% yield) of the desired title compound.

LC-MS (Method 2): $R_t$=1.61 min; MS (ESIpos): m/z=494 $[M+H]^+$ $^1$H-NMR (400 MHz, DMSO-d6) δ [ppm]: −0.10--0.07 (m, 9H), 0.82-0.88 (m, 2H), 3.54-3.60 (m, 2H), 5.61 (br s, 2H), 5.62 (s, 2H), 6.47-6.49 (m, 1H), 6.76 (dd, 1H), 7.30 (dd, 1H), 8.36-8.38 (m, 1H).

Intermediate 128

2,5-difluoro-4-{[3-(trifluoromethyl)-1-{[2-(trimethylsilyl)ethoxy]methyl}-1H-pyrrolo[2,3-b]pyridin-4-yl]oxy}aniline

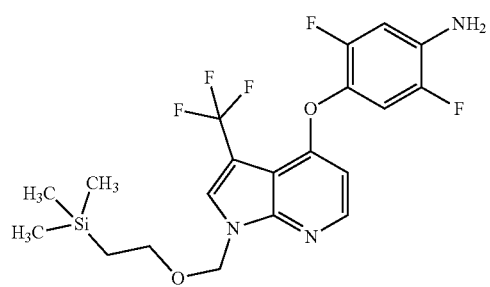 [SMILES: C[Si](C)(C)CCOCn1cc(C(F)(F)F)c2c(Oc3cc(F)c(N)cc3F)ccnc21]

In analogy to intermediate 124, 4-{[6-chloro-3-(trifluoromethyl)-1-{[2-(trimethylsilyl)ethoxy]methyl}-1H-pyrrolo[2,3-b]pyridin-4-yl]oxy}-2,5-difluoroaniline (350 mg, 709 µmol, intermediate 127) was reacted with hydrogen/10% Pd on carbon (35.0 mg) in triethylamine (120 µL, 880 µmol) in ethanol (25 mL). After purification using a Biotage chromatography system we obtained 320 mg (90% purity, 88% yield) of the desired title compound.

LC-MS (Method 1): $R_t$=1.54 min; MS (ESIpos): m/z=460 $[M+H]^+$ $^1$H-NMR (400 MHz, DMSO-d6) δ [ppm]: −0.10--0.05 (m, 9H), 0.78-0.88 (m, 2H), 3.53-3.60 (m, 2H), 5.54 (s, 2H), 5.67 (s, 2H), 6.50 (dd, 1H), 6.75 (dd, 1H), 7.23 (dd, 1H), 8.25 (d, 1H), 8.31 (s, 1H).

Intermediate 129

N-(2,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

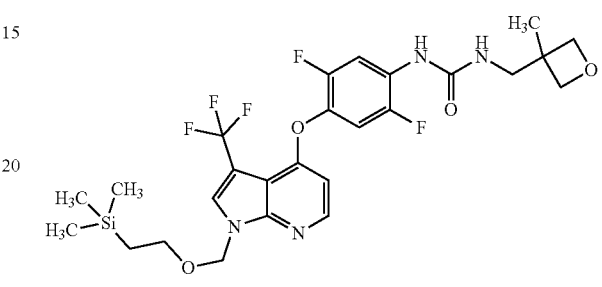

In analogy to intermediate 41, 2,5-difluoro-4-{[3-(trifluoromethyl)-1-{[2-(trimethylsilyl)ethoxy]methyl}-1H-pyrrolo[2,3-b]pyridin-4-yl]oxy}aniline (250 mg, 544 µmol, intermediate 128) was reacted with 3-(isocyanatomethyl)-3-methyloxetane (140 µL, 1.1 mmol) in pyridine (4.8 mL) and dichloromethane (4.6 mL). After purification using a Biotage chromatography system we obtained 244 mg (95% purity, 73% yield) of the desired title compound.

LC-MS (Method 1): $R_t$=1.48 min; MS (ESIpos): m/z=587 $[M+H]^+$ $^1$H-NMR (400 MHz, DMSO-d6) δ [ppm]: −0.12--0.04 (m, 9H), 0.79-0.87 (m, 2H), 1.24 (s, 3H), 3.33 (d, 1H), 3.53-3.61 (m, 2H), 4.23 (d, 2H), 4.36 (d, 2H), 5.68 (s, 2H), 6.57 (d, 1H), 6.99 (t, 1H), 7.53 (dd, 1H), 8.24-8.30 (m, 2H), 8.35 (s, 1H), 8.67 (s, 1H).

Intermediate 130

4-[(4-nitrophenyl)sulfanyl]-1-{[2-(trimethylsilyl)ethoxy]methyl}-1H-pyrrolo[2,3-b]pyridine

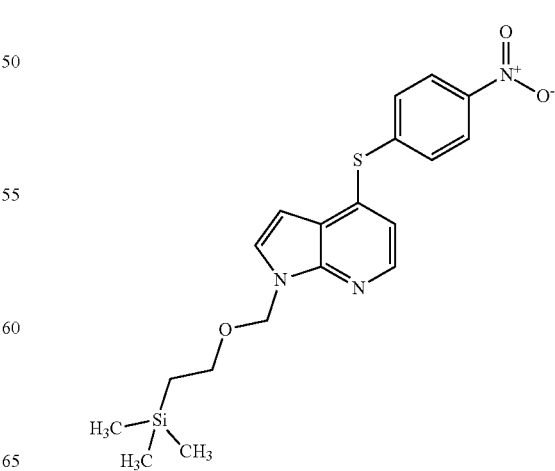

To a solution of 4-chloro-1-{[2-(trimethylsilyl)ethoxy]methyl}-1H-pyrrolo[2,3-b]pyridine (35.5 g, 125 mmol, CAS [869335-19] and 4-nitrobenzenethiol (21.4 g, 138 mmol) in NMP (350 mL) was added diisopropyl-ethylamine (65.5 mL, 376 mmol) This mixture was stirred at 100° C. for 12 hrs. After cooling the reaction mixture was poured into water (1.0 L) and extracted three times with ethyl acetate. The combined organic layer was washed with brine (2.0 L), dried over Na2SO4, filtered and concentrated. The crude product was purified by column chromatography (SiO2, petrolether:ethyl acetate=50:1 to 15:1) to give the desired title compound (24 g, crude) as a black brown oil.

$^1$H-NMR (400 MHz, DMSO-d6) δ [ppm]: −0.14--0.10 (m, 9H), 0.78-0.84 (m, 2H), 3.52 (t, 2H), 5.65 (s, 2H), 6.32 (d, 1H), 7.18 (d, 1H), 7.45-7.51 (m, 2H), 7.73 (d, 1H), 8.12-8.19 (m, 2H), 8.30 (d, 1H).

Intermediate 131

3-bromo-4-[(4-nitrophenyl)sulfanyl]-1-{[2-(trimethylsilyl)ethoxy]methyl}-1H-pyrrolo[2,3-b]pyridine

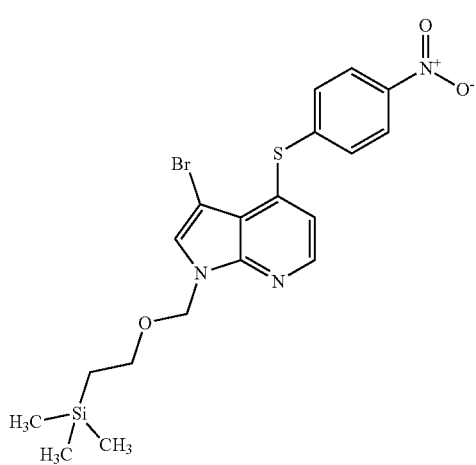 [SMILES: C[Si](C)(C)CCOCn1cc(Br)c2c(Sc3ccc([N+](=O)[O-])cc3)ccnc21]

To a solution of 4-[(4-nitrophenyl)sulfanyl]-1-{[2-(trimethylsilyl)ethoxy]methyl}-1H-pyrrolo[2,3-b]pyridine (21 g, 52.3 mmol, intermediate 130) in dichloromethane (210 mL) was added 1-bromopyrrolidine-2,5-dione (9.79 g, 55 mmol) in one portion and stirred at 25° C. for 12 hours.

Then the reaction mixture was poured into water (500 mL) and concentrated under vacuum to remove most of dichloromethane, extracted with ethyl acetate (250 mL*3). The combined organic layer was washed with brine (800 mL), dried over Na$_2$SO$_4$, filtered and concentrated. The crude product was purified by column chromatography (SiO$_2$, petrolether:ethyl acetate=10:1 to 5:1) to give the desired title compound (22.6 g, 89.9% yield) as a yellow oil.

$^1$H-NMR (400 MHz, DMSO-d6) δ [ppm]-0.10 (s, 9H) 0.77-0.87 (m, 2H) 3.53 (t, J=8.0 Hz, 2H) 5.63 (s, 2H) 6.97 (d, J=5.2 Hz, 1H) 7.52-7.63 (m, 2H) 8.01 (s, 1H) 8.19-8.24 (m, 2H) 8.26 (d, J=4.8 Hz, 1H).

Intermediate 132

4-[(3-bromo-1-{[2-(trimethylsilyl)ethoxy]methyl}-1H-pyrrolo[2,3-b]pyridin-4-yl)sulfanyl]aniline

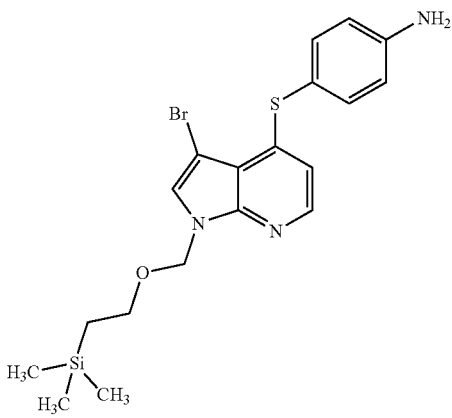 [SMILES: C[Si](C)(C)CCOCn1cc(Br)c2c(Sc3ccc(N)cc3)ccnc21]

To a mixture of 3-bromo-4-[(4-nitrophenyl)sulfanyl]-1-{[2-(trimethylsilyl)ethoxy]methyl}-1H-pyrrolo[2,3-b]pyridine (15.2 g, 31.6 mmol, intermediate 131) in ethanol (100 mL) and water (50 mL) was added iron powder (8.83 g, 158 mmol) and ammoniumchloride (8.46 g, 158 mmol) slowly. The mixture was stirred at 50° C. for 4 hours. The reaction mixture was filtered to remove solid, then poured into water (300 mL) and extracted three times with ethyl acetate (100 mL). The combined organic layer was washed with brine (500 mL), dried over Na2SO4, filtered and concentrated. The crude product was purified by column chromatography (SiO2, petrolether:ethyl acetate=10:1 to 3:1) to give the desired title compound (10 g).

$^1$H-NMR (400 MHz, DMSO-d6) δ [ppm]-0.11--0.07 (m, 9H), 0.77-0.86 (m, 2H), 3.44-3.54 (m, 2H), 5.56 (s, 2H), 5.69 (s, 2H), 6.27 (d, 1H), 6.70 (d, 2H), 7.23 (d, 2H), 7.83 (s, 1H), 8.00 (d, 1H).

Intermediate 133

N-{4-[(3-bromo-1-{[2-(trimethylsilyl)ethoxy]methyl}-1H-pyrrolo[2,3-b]pyridin-4-yl)sulfanyl]phenyl}-N'-[(3-methyloxetan-3-yl)methyl]urea

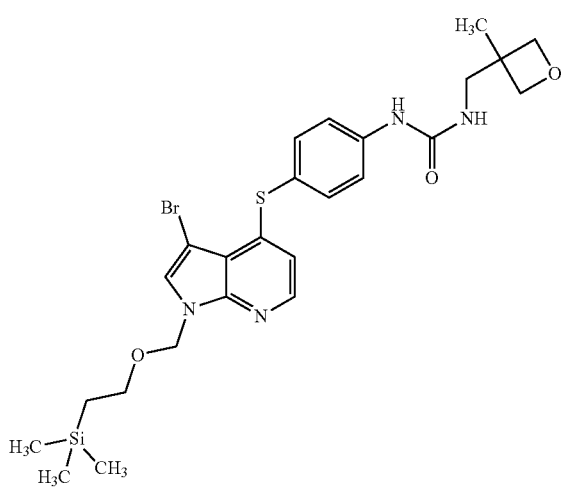 [SMILES: CC1(CNC(=O)Nc2ccc(Sc3ccnc4c3c(Br)cn4COCC[Si](C)(C)C)cc2)COC1]

In analogy to intermediate 41, 4-[(3-bromo-1-{[2-(trimethylsilyl)ethoxy]methyl}-1H-pyrrolo[2,3-b]pyridin-4-yl)sulfanyl]aniline (100 mg, 222 μmol, intermediate 132) was reacted with 3-(isocyanatomethyl)-3-methyloxetane (55 μL, 440 μmol) in pyridine (2.0 mL) and dichloromethane (2.2 mL). After purification using a Biotage chromatography system we obtained 179 mg (70% purity, 98% yield) of the desired title compound.

LC-MS (Method 2): $R_t$=1.49 min; MS (ESIpos): m/z=575/577 [M+H]$^+$ (Br isotope pattern)

$^1$H-NMR (400 MHz, DMSO-d6) δ [ppm]: −0.11--0.07 (m, 9H), 0.78-0.85 (m, 2H), 1.24 (s, 3H), 3.31 (d, 2H), 3.45-3.54 (m, 2H), 4.21 (d, 2H), 4.39 (d, 2H), 5.57 (s, 2H), 6.26 (d, 1H), 6.61 (t, 1H), 7.47-7.51 (m, 2H), 7.58-7.62 (m, 2H), 7.88 (s, 1H), 8.02 (d, 1H), 8.88 (s, 1H).

Intermediate 134

4-[4-nitro-2-(trifluoromethyl)phenoxy]-1H-pyrrolo[2,3-b]pyridine

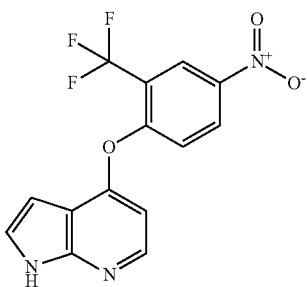 [SMILES: O=[N+]([O-])c1ccc(Oc2ccnc3[nH]ccc23)c(C(F)(F)F)c1]

A solution of 1-fluoro-4-nitro-2-(trifluoromethyl)benzene (5.3 mL, 38 mmol) and 1H-pyrrolo[2,3-b]pyridin-4-ol (CAS No. [74420-02-3]; 4.67 g, 34.8 mmol) in DMSO (110 mL) was treated with potassium carbonate (19.2 g, 139 mmol) and stirred at room temperature for 1 hour. The reaction mixture was diluted with ethyl acetate (200 mL) and washed with two times with 20 mL water and brine (20 mL), dried with sodium sulfate and concentrated in vacuo. The resulting residue was purified via a Biotage chromatography system (100 g snap KP-Sil column, hexane/20-100% ethyl acetate) to obtain 4.62 g (96% purity, 39% yield) of the desired title compound.

$^1$H-NMR (400 MHz, DMSO-d6) δ [ppm]: 6.11 (d, 1H), 6.92 (d, 1H), 7.25 (d, 1H), 7.48 (d, 1H), 8.28 (d, 1H), 8.46 (dd, 1H), 8.58 (d, 1H), 12.05 (br s, 1H).

Intermediate 135

4-[4-nitro-2-(trifluoromethyl)phenoxy]-1-{[2-(trimethylsilyl)ethoxy]methyl}-1H-pyrrolo[2,3-b]pyridine

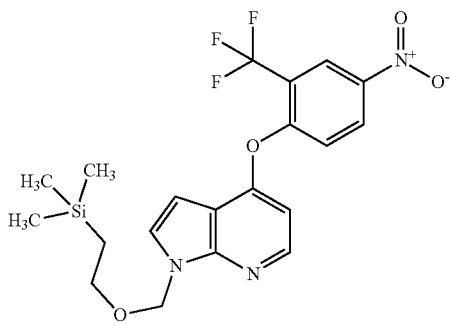 [SMILES: C[Si](C)(C)CCOCn1ccc2c(Oc3ccc([N+](=O)[O-])cc3C(F)(F)F)ccnc21]

An ice-cooled solution of 4-[4-nitro-2-(trifluoromethyl)phenoxy]-1H-pyrrolo[2,3-b]pyridine (4.62 g, 14.3 mmol, intermediate 134) in acetonitrile (90 mL) was treated with N,N-diisopropyl ethylamine (6.2 mL, 36 mmol) and [2-(chloromethoxy)ethyl](trimethyl)silane (CAS No. [76513-69-4]; 3.5 mL, 20.0 mmol), warmed to rt and stirred overnight. The reaction mixture was diluted with ethyl acetate (200 mL)) and washed with water (30 mL) and brine (20 mL), dried with sodium sulfate and concentrated in vacuo.

The resulting residue was purified via a Biotage chromatography system (50 g snap KP-Sil column, hexane/0-80% ethyl acetate) to obtain 6.5 g (100% purity, 99% yield) of the desired title compound.

$^1$H-NMR (400 MHz, DMSO-d6) δ [ppm]: −0.12--0.06 (m, 9H), 0.78-0.87 (m, 2H), 3.51-3.57 (m, 2H), 5.65 (s, 2H), 6.23 (d, 1H), 6.99 (d, 1H), 7.30 (d, 1H), 7.67 (d, 1H), 8.35 (d, 1H), 8.48 (dd, 1H), 8.59 (d, 1H).

Intermediate 136

3-bromo-4-[4-nitro-2-(trifluoromethyl)phenoxy]-1-{[2-(trimethylsilyl)ethoxy]methyl}-1H-pyrrolo[2,3-b]pyridine

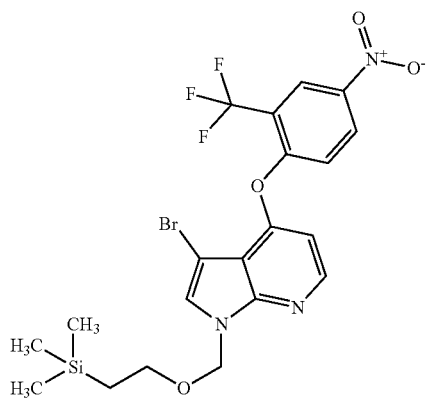 [SMILES: C[Si](C)(C)CCOCn1cc(Br)c2c(Oc3ccc([N+](=O)[O-])cc3C(F)(F)F)ccnc21]

In analogy to intermediate 16, 4-[4-nitro-2-(trifluoromethyl)phenoxy]-1-{[2-(trimethylsilyl)ethoxy]methyl}-1H-pyrrolo[2,3-b]pyridine (8.59 g, 18.9 mmol, intermediate 135) was reacted with 1-bromopyrrolidine-2,5-dione (3.71 g, 20.8 mmol) in DMF (170 mL). After purification using a Biotage chromatography system we obtained 8.72 g (95% purity, 82% yield) of the desired title compound.

LC-MS (Method 2): $R_t$=1.68 min; MS (ESIpos): m/z=532/534 [M+H]$^+$ (Br isotope pattern)

$^1$H-NMR (400 MHz, DMSO-d6) δ [ppm]: −0.09−−0.05 (m, 9H), 0.82-0.87 (m, 2H), 3.54-3.59 (m, 2H), 5.65 (s, 2H), 6.98 (d, 1H), 7.22 (d, 1H), 7.98 (s, 1H), 8.40 (d, 1H), 8.48 (dd, 1H), 8.59 (d, 1H).

Intermediate 137

5-(4-[4-nitro-2-(trifluoromethyl)phenoxy]-1-{[2-(trimethylsilyl)ethoxy]methyl}-1H-pyrrolo[2,3-b]pyridin-3-yl)-2-[(propan-2-yl)oxy]benzonitrile

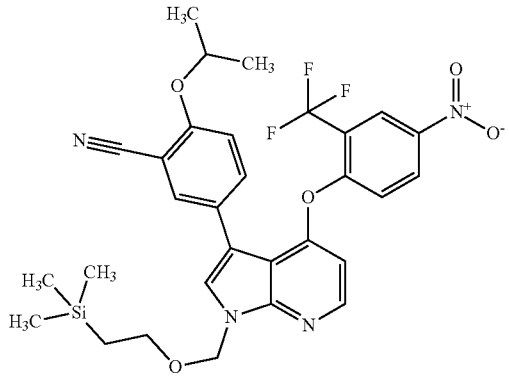 [SMILES: CC(C)Oc1ccc(-c2cn(COCC[Si](C)(C)C)c3nccc(Oc4ccc([N+](=O)[O-])cc4C(F)(F)F)c23)cc1C#N]

In analogy to intermediate 17, 3-bromo-4-[4-nitro-2-(trifluoromethyl)phenoxy]-1-{[2-(trimethylsilyl)ethoxy]methyl}-1H-pyrrolo[2,3-b]pyridine (1.00 g, 1.88 mmol, intermediate 136) was reacted with {3-cyano-4-[(propan-2-yl)oxy]phenyl}boronic acid (770 mg, 3.76 mmol) in the presence of [1,1'-bis(diphenylphosphino)ferrocene]dichloropalladium(II) (137 mg, 188 μmol) and potassium carbonate (1.30 g, 9.39 mmol) in water (9.4 mL) and dioxane (19 mL). After purification using a Biotage chromatography system we obtained 1.37 g (75% purity, 89% yield) of the desired title compound.

LC-MS (Method 2): $R_t$=1.71 min; MS (ESIpos): m/z=613 [M+H]$^+$ $^1$H-NMR (400 MHz, DMSO-d6) δ [ppm]: −0.08−−0.04 (m, 9H), 0.85-0.91 (m, 2H), 1.26 (d, 6H), 3.60-3.66 (m, 2H), 4.73 (spt, 1H), 5.71 (s, 2H), 6.89 (d, 1H), 7.15 (d, 1H), 7.26 (d, 1H), 7.61-7.72 (m, 2H), 7.95 (s, 1H), 8.09 (d, 1H), 8.37 (d, 1H), 8.42 (dd, 1H), 8.46-8.50 (m, 1H).

Intermediate 138

5-(4-[4-amino-2-(trifluoromethyl)phenoxy]-1-{[2-(trimethylsilyl)ethoxy]methyl}-1H-pyrrolo[2,3-b]pyridin-3-yl)-2-[(propan-2-yl)oxy]benzonitrile

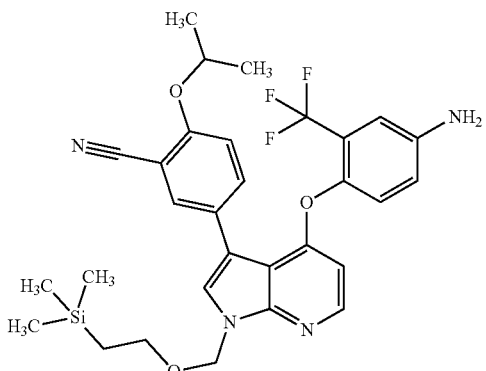

In analogy to intermediate 18, 5-(4-[4-nitro-2-(trifluoromethyl)phenoxy]-1-{[2-(trimethylsilyl)ethoxy]methyl}-1H-pyrrolo[2,3-b]pyridin-3-yl)-2-[(propan-2-yl)oxy]benzonitrile (1.37 g, 1.68 mmol, intermediate 137) was reacted with iron powder (468 mg, 8.39 mmol) and ammonium chloride (449 mg, 8.39 mmol) in a mixture of water (15 mL), tetrahydrofuran (9.0 mL) and methanol (9.0 mL). After purification using a Biotage chromatography system we obtained 902 mg (95% purity, 88% yield) of the desired title compound.

LC-MS (Method 2): $R_t$=1.62 min; MS (ESIneg): m/z=581 [M−H]$^−$ $^1$H-NMR (400 MHz, DMSO-d6) δ [ppm]: −0.12−−0.04 (m, 9H), 0.82-0.88 (m, 2H), 1.31 (d, 6H), 3.56-3.62 (m, 2H), 4.80 (spt, 1H), 5.62 (s, 2H), 5.65 (s, 2H), 6.25 (d, 1H), 6.84 (dd, 1H), 6.96 (d, 1H), 7.03 (d, 1H), 7.25 (d, 1H), 7.84-7.92 (m, 3H), 8.13 (d, 1H).

Intermediate 139 phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate

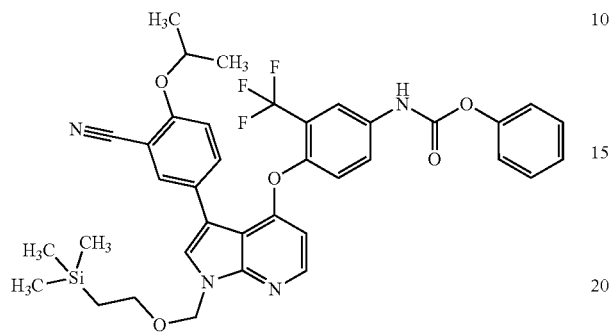

In analogy to intermediate 1, 5-(4-[4-amino-2-(trifluoromethyl)phenoxy]-1-{[2-(trimethylsilyl)ethoxy]methyl}-1H-pyrrolo[2,3-b]pyridin-3-yl)-2-[(propan-2-yl)oxy]benzonitrile (900 mg, 1.47 mmol, intermediate 138) was reacted with phenyl carbonochloridate (200 µL, 1.6 mmol) in a mixture pyridine (550 µL) and THF (9.0 mL). After purification using a Biotage chromatography system we obtained 802 mg (92% purity, 72% yield) of the desired title compound.

LC-MS (Method 1): $R_t$=1.70 min; MS (ESIpos): m/z=703 [M+H]$^+$ $^1$H-NMR (400 MHz, DMSO-d6) δ [ppm]: −0.10-−0.05 (m, 9H), 0.82-0.89 (m, 2H), 1.30 (d, 6H), 3.56-3.64 (m, 2H), 4.79 (spt, 1H), 5.67 (s, 2H), 6.39 (d, 1H), 6.73-6.78 (m, 1H), 7.15 (t, 1H), 7.22-7.31 (m, 3H), 7.37 (d, 1H), 7.42-7.46 (m, 1H), 7.74-7.79 (m, 1H), 7.80-7.94 (m, 3H), 8.03 (s, 1H), 8.20 (d, 1H), 10.66 (br s, 1H).

Intermediate 140

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(3-phenyloxetan-3-yl)methyl]urea

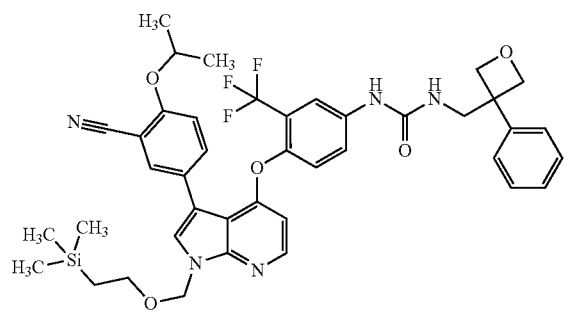 [SMILES: CC(C)Oc1ccc(-c2cn(COCC[Si](C)(C)C)c3nccc(Oc4ccc(NC(=O)NCC5(c6ccccc6)COC5)cc4C(F)(F)F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 µmol, intermediate 139) was reacted with 1-(3-phenyloxetan-3-yl)methanamine (26.7 mg, 164 µmol) in DMF (1.0 mL). After purification using a Biotage chromatography system we obtained 103 mg (97% purity, 91% yield) of the desired title compound.

LC-MS (Method 1): $R_t$=1.62 min; MS (ESIpos): m/z=772 [M+H]$^+$ $^1$H-NMR (400 MHz, DMSO-d6) δ [ppm]: −0.12-−0.03 (m, 9H), 0.81-0.89 (m, 2H), 1.30 (d, 6H), 3.57-3.66 (m, 4H), 4.70-4.84 (m, 5H), 5.66 (s, 2H), 6.33 (d, 1H), 6.51 (br s, 1H), 7.15-7.30 (m, 5H), 7.36-7.42 (m, 2H), 7.55 (dd, 1H), 7.84-7.90 (m, 3H), 8.03 (d, 1H), 8.16 (d, 1H), 9.11 (s, 1H).

Intermediate 141

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(3-fluorooxetan-3-yl)methyl]urea

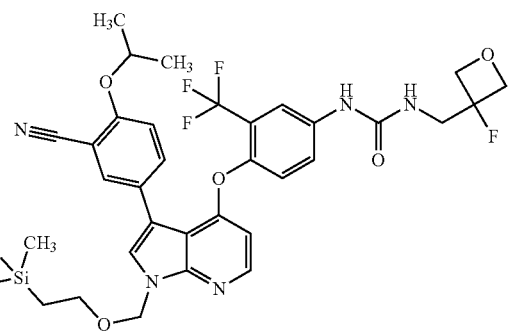

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 µmol, intermediate 139) was reacted with 1-(3-fluorooxetan-3-yl)methanamine (17.2 mg, 164 µmol) in DMF (1.0 mL). After purification using a Biotage chromatography system we obtained 83.6 mg (97% purity, 80% yield) of the desired title compound.

LC-MS (Method 1): $R_t$=1.55 min; MS (ESIpos): m/z=714 [M+H]$^+$ $^1$H-NMR (400 MHz, DMSO-d6) δ [ppm]: −0.10-−0.05 (m, 9H), 0.81-0.89 (m, 2H), 1.30 (d, 6H), 3.57-3.69 (m, 4H), 4.56-4.65 (m, 4H), 4.79 (spt, 1H), 5.66 (s, 2H), 6.34 (d, 1H), 6.81 (br t, 1H), 7.22-7.28 (m, 2H), 7.60 (dd, 1H), 7.84-7.90 (m, 3H), 8.04 (d, 1H), 8.17 (d, 1H), 9.16 (s, 1H).

Intermediate 142

N-{4-[(3-{3-cyano-4-[(propan-2-yl)oxy]phenyl}-1-{[2-(trimethyl silyl)eth oxy]methyl}-1H-pyrrolo[2,3-b]pyridin-4-yl)oxy]-3-(trifluoromethyl) phenyl}-N'-[(3-methyl oxetan-3-yl)methyl]urea

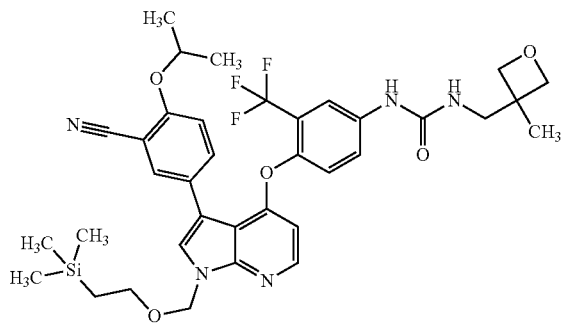 [SMILES: CC(C)Oc1ccc(-c2cn(COCC[Si](C)(C)C)c3nccc(Oc4ccc(NC(=O)NCC5(C)COC5)cc4C(F)(F)F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 µmol, intermediate 139) was reacted with 1-(3-methyloxetan-3-yl)methanamine (16.6 mg, 164 µmol) in DMF (1.0 mL). After purification using a Biotage chromatography system we obtained 90.0 mg (98% purity, 87% yield) of the desired title compound.

LC-MS (Method 1): $R_t$=1.56 min; MS (ESIpos): m/z=710 [M+H]$^+$ $^1$H-NMR (400 MHz, DMSO-d6) δ [ppm]: −0.11--0.05 (m, 9H), 0.82-0.89 (m, 2H), 1.23 (s, 3H), 1.30 (d, 6H), 3.30 (d, 2H), 3.57-3.62 (m, 2H), 4.20 (d, 2H), 4.39 (d, 2H), 4.79 (spt, 1H), 5.66 (s, 2H), 6.34 (d, 1H), 6.70 (br t, 1H), 7.25 (dd, 2H), 7.59 (dd, 1H), 7.85-7.90 (m, 3H), 8.06 (d, 1H), 8.17 (d, 1H), 9.04 (s, 1H).

Intermediate 143

N-[(3-cyanooxetan-3-yl)methyl]-N'-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}urea

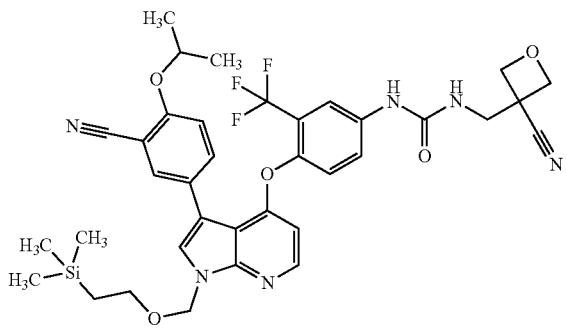 [SMILES: CC(C)Oc1ccc(-c2cn(COCC[Si](C)(C)C)c3nccc(Oc4ccc(NC(=O)NCC5(C#N)COC5)cc4C(F)(F)F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 µmol, intermediate 139) was reacted with 3-(aminomethyl)oxetane-3-carbonitrile hydrogen chloride (1/1) (24.3 mg, 164 µmol, purchased from Spirochem AG) together with N,N-diisopropylethylamine (94 µL, 541 µmol) in DMF (1.0 mL). After purification using a Biotage chromatography system we obtained 75.0 mg (97% purity, 71% yield) of the desired title compound.

LC-MS (Method 1): $R_t$=1.54 min; MS (ESIpos): m/z=721 [M+H]$^+$ $^1$H-NMR (400 MHz, DMSO-d6) δ [ppm]: −0.11--0.04 (m, 9H), 0.82-0.89 (m, 2H), 1.30 (d, 6H), 3.55-3.64 (m, 2H), 3.75 (d, 2H), 4.62 (d, 2H), 4.74-4.84 (m, 3H), 5.66 (s, 2H), 6.35 (d, 1H), 7.06 (t, 1H), 7.25 (t, 2H), 7.63 (dd, 1H), 7.83-7.92 (m, 3H), 8.04 (d, 1H), 8.17 (d, 1H), 9.27 (s, 1H).

Intermediate 144

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-oxetan-3-ylurea

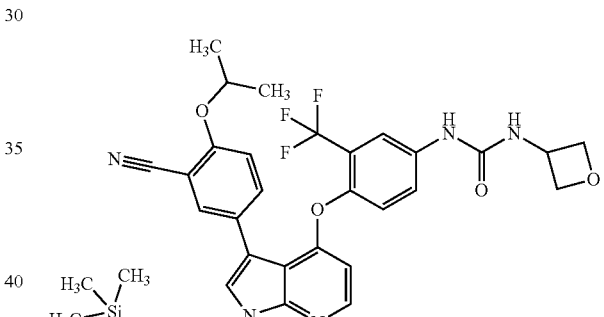

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 µmol, intermediate 139) was reacted with oxetan-3-amine (12.0 mg, 164 µmol) in DMF (1.0 mL). After purification using a Biotage chromatography system we obtained 93.5 mg (92% purity, 89% yield) of the desired title compound.

LC-MS (Method 1): $R_t$=1.51 min; MS (ESIpos): m/z=683 [M+H]$^+$ $^1$H-NMR (400 MHz, DMSO-d6) δ [ppm]: −0.10--0.05 (m, 9H), 0.82-0.88 (m, 2H), 1.30 (d, 6H), 3.57-3.62 (m, 2H), 4.46 (t, 2H), 4.69-4.83 (m, 4H), 5.66 (s, 2H), 6.33 (d, 1H), 7.15-7.20 (m, 1H), 7.25 (dd, 2H), 7.60 (dd, 1H), 7.84-7.90 (m, 3H), 8.03 (d, 1H), 8.17 (d, 1H), 9.07 (s, 1H).

Intermediate 145

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[1-(oxetan-3-yl)ethyl]urea

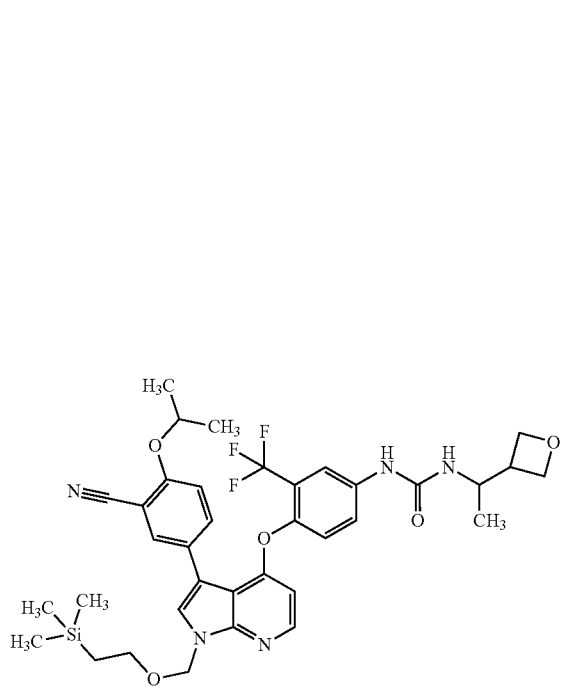 [SMILES: CC(C)Oc1ccc(-c2cn(COCC[Si](C)(C)C)c3nccc(Oc4ccc(NC(=O)NC(C)C5COC5)cc4C(F)(F)F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamate (100 mg, 142 μmol, intermediate 139) was reacted with 1-(oxetan-3-yl)ethan-1-amine hydrogen chloride (1/1) (56.3 mg, 409 μmol) in DMF (1.0 mL). After purification using a Biotage chromatography system we obtained 277 mg (80% purity, 88% yield) of the desired title compound.

LC-MS (Method 1): R$_t$=1.53 min; MS (ESIpos): m/z=710 [M+H]$^+$ $^1$H-NMR (400 MHz, DMSO-d6) δ [ppm]: −0.12--0.05 (m, 9H), 0.82-0.89 (m, 2H), 1.02 (d, 3H), 1.30 (d, 6H), 2.94-3.05 (m, 1H), 3.57-3.63 (m, 2H), 3.97-4.08 (m, 1H), 4.31 (t, 1H), 4.39 (t, 1H), 4.56-4.62 (m, 2H), 4.79 (spt, 1H), 5.66 (s, 2H), 6.33 (d, 1H), 6.47 (br d, 1H), 7.24 (d, 2H), 7.57 (dd, 1H), 7.84-7.90 (m, 3H), 8.05 (d, 1H), 8.17 (d, 1H), 8.95 (s, 1H).

Intermediate 146

O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamothioate

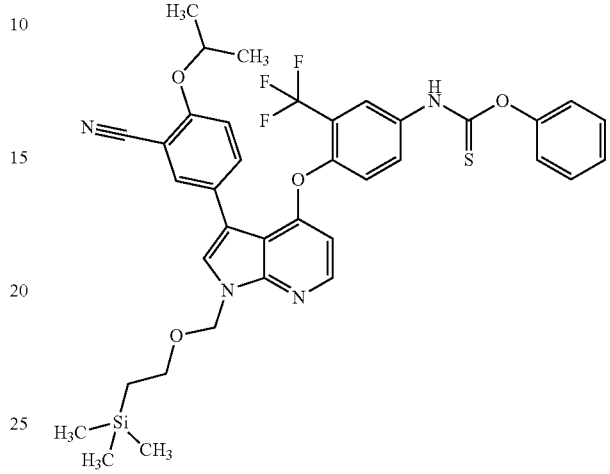

To a solution 5-(4-[4-amino-2-(trifluoromethyl)phenoxy]-1-{[2-(trimethylsilyl)ethoxy]methyl}-1H-pyrrolo[2,3-b]pyridin-3-yl)-2-[(propan-2-yl)oxy]benzonitrile (720 mg, 1.24 mmol), intermediate 139) in pyridine (1.2 mL) and THF (12 mL) was slowly added at 0° C. O-phenyl carbonochloridothioate (235 mg, 1.36 mmol). The reaction mixture was evaporated to dryness and the resulting raw desired compound (1.0 g) was used in the next step without any further purification.

LC-MS (Method 1): R$_t$=1.73 min; MS (ESIpos): m/z=719 [M+H]$^+$

Intermediate 147

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-(3-hydroxypropyl)thiourea

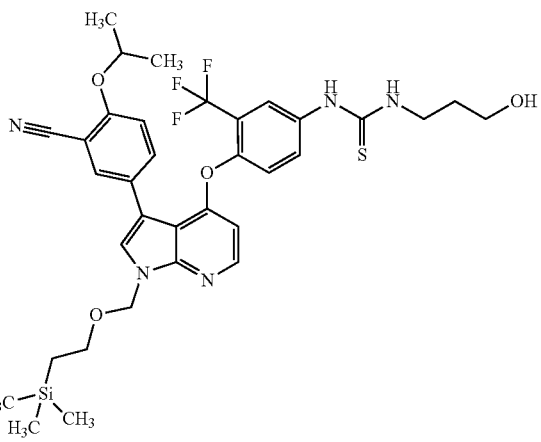

To a solution of O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamothioate (250 mg, 348 µmol, intermediate 146) in DMF (6.0 mL) was added 3-aminopropan-1-ol (52.2 mg, 696 µmol). This mixture was stirred for 2 hours at 60° C. After cooling to room temperature brine was added and the mixture was extracted two times with ethyl acetate. The combined organic phase was washed with water, brine, filtrated over a hydrophobic phase separation filter paper and evaporated to dryness. The resulting residue was purified via a Biotage chromatography system (10 g snap Ultra column, hexane/20-100% ethyl acetate, then ethyl acetate/0-20% ethanol) to obtain 120 mg (90% purity, 44% yield) of the desired title compound.

LC-MS (Method 1): $R_t$=1.52 min; MS (ESIpos): m/z=700 [M+H]$^+$ $^1$H-NMR (400 MHz, DMSO-d6) δ [ppm]: −0.10−−0.03 (m, 9H), 0.82-0.90 (m, 2H), 1.30 (d, 6H), 1.70 (quin, 2H), 3.44-3.63 (m, 6H), 4.57 (br s, 1H), 4.79 (spt, 1H), 5.67 (s, 2H), 6.39 (d, 1H), 7.24 (d, 1H), 7.30 (d, 1H), 7.71 (br d, 1H), 7.84-7.92 (m, 3H), 8.04 (br s, 2H), 8.20 (d, 1H), 9.82 (br s, 1H).

Intermediate 148

5-(4-{4-[(5,6-dihydro-4H-1,3-oxazin-2-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile

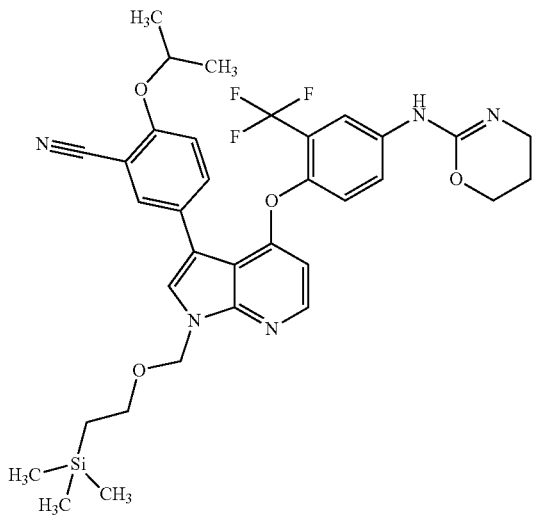 [SMILES: CC(C)Oc1ccc(-c2cn(COCC[Si](C)(C)C)c3nccc(Oc4ccc(NC5=NCCCO5)cc4C(F)(F)F)c23)cc1C#N]

To a solution of N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-(3-hydroxypropyl)thiourea (120 mg, 171 µmol, intermediate 147) in acetonitrile (3.0 mL) was added 1-(3-Dimethylaminopropyl)-3-ethylcarbodiimide hydrochloride (78.8 mg, 412 µmol) and triethylamine (86 µL, 609 µmol). This mixture was stirred for 1 day at 40° C. After cooling to room temperature brine was added and the mixture was extracted two times with ethyl acetate.

The combined organic phase was washed with brine, filtrated over a hydrophobic phase separation filter paper and evaporated to dryness. The resulting residue was purified via a Biotage chromatography system (10 g snap Ultra column, hexane/50-100% ethyl acetate, then ethyl acetate/0-90% ethanol) to obtain 23.0 mg (90% purity, 18% yield) of the desired title compound.

LC-MS (Method 2): $R_t$=1.59 min; MS (ESIpos): m/z=666 [M+H]$^+$ $^1$H-NMR (400 MHz, METHANOL-d4) δ [ppm]: −0.12−−0.04 (m, 9H), 0.85-0.93 (m, 2H), 1.37 (d, 6H), 1.96-2.04 (m, 2H), 3.36 (t, 2H), 3.59-3.66 (m, 2H), 4.28-4.34 (m, 2H), 4.74 (spt, 1H), 5.71 (s, 2H), 6.41 (d, 1H), 7.06 (d, 1H), 7.09-7.14 (m, 1H), 7.35 (br d, 1H), 7.51 (br s, 1H), 7.60 (s, 1H), 7.83-7.88 (m, 2H), 8.14 (d, 1H).

Intermediate 149

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-{[1-(hydroxymethyl)cyclopropyl]methyl}thiourea

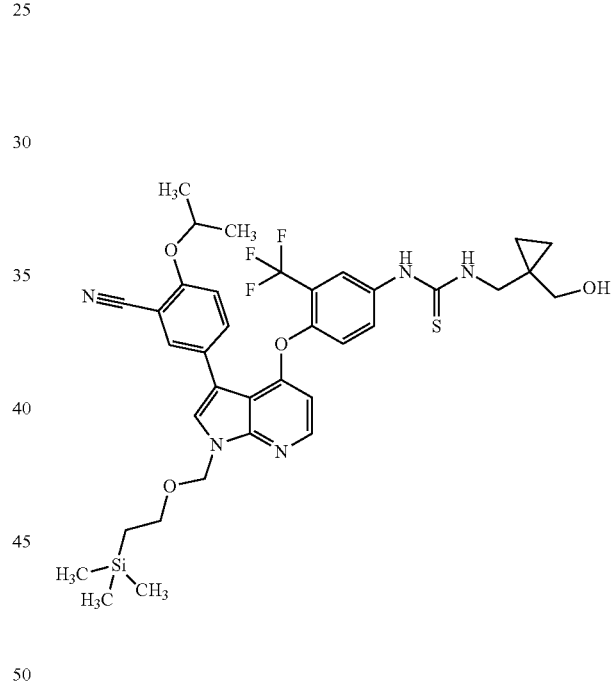

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamothioate (250 mg, 348 µmol, intermediate 146) was reacted with [1-(aminomethyl)cyclopropyl]methanol (70.4 mg, 696 µmol) in DMF (6.0 mL). After two subsequent purification using a Biotage chromatography system we obtained 169 mg (40% purity, 27% yield) of the desired title compound.

LC-MS (Method 2): $R_t$=1.79 min; MS (ESIpos): m/z=726 [M+H]$^+$

Intermediate 150

5-(4-{4-[(5-oxa-7-azaspiro[2.5]oct-6-en-6-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile

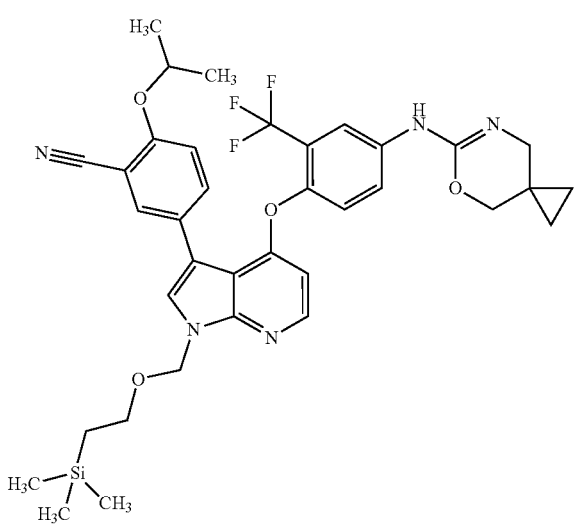 [SMILES: CC(C)Oc1ccc(-c2cn(COCC[Si](C)(C)C)c3nccc(Oc4ccc(NC5=NCC6(CC6)CO5)cc4C(F)(F)F)c23)cc1C#N]

In analogy to intermediate 148, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-{[1-(hydroxymethyl)cyclopropyl]methyl}thiourea (160 mg, 110 μmol, intermediate 149) was reacted 1-(3-Dimethylaminopropyl)-3-ethylcarbodiimide hydrochloride (42.3 mg, 220 μmol) and triethylamine (46 μL, 330 μmol) in acetonitrile (2.0 mL). After workup and evaporation to dryness we obtained 167 mg (40% purity, 88% yield) of the desired title compound which was used in the next step without any further purification.

LC-MS (Method 2): $R_t$=1.65 min; MS (ESIpos): m/z=692 [M+H]$^+$

Intermediate 151

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-(3-hydroxy-2,2-dimethylpropyl)thiourea

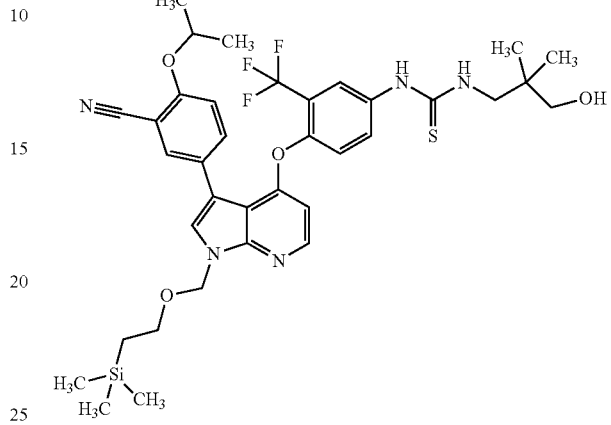

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}carbamothioate (250 mg, 348 μmol, intermediate 146) was reacted with 3-amino-2,2-dimethyl-propan-1-ol (71.8 mg, 696 μmol) in DMF (6.0 mL). After two subsequent purification using a Biotage chromatography system we obtained 215 mg (40% purity, 34% yield) of the desired title compound.

LC-MS (Method 2): $R_t$=1.56 min; MS (ESIpos): m/z=728 [M+H]$^+$

Intermediate 152

5-(4-{4-[(5,5-dimethyl-5,6-dihydro-4H-1,3-oxazin-2-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile

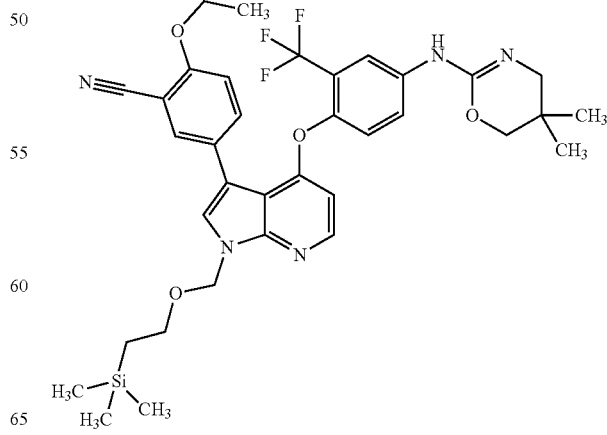

In analogy to intermediate 148, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-(3-hydroxy-2,2-dimethylpropyl)thiourea (215 mg, 148 µmol), intermediate 151) was reacted 1-(3-dimethylaminopropyl)-3-ethylcarbodiimide hydrochloride (56.6 mg, 295 µmol) and triethylamine (62 µL, 440 µmol) in acetonitrile (3.0 mL). After purification using a Biotage chromatography system we obtained 31.5 mg (30% purity, 9% yield) of the desired title compound LC-MS (Method 2): R$_t$=1.66 min; MS (ESIpos): m/z=694 [M+H]$^+$ Intermediate 153

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-{[3,3-dimethyloxetane-2-yl]methyl}urea

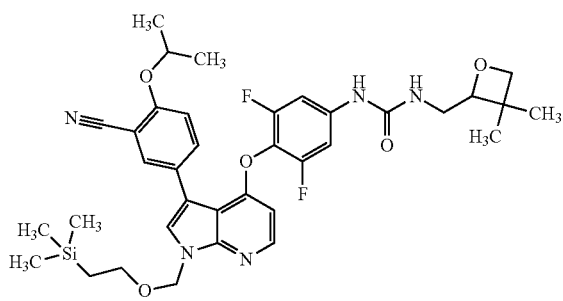

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamate (100 mg, 149 µmol, intermediate 103) was reacted with (+/−)-1-(3,3-dimethyloxetane-2-yl)methanamine (17.2 mg, 149 µmol, CAS No. [34795-24-9]) in DMF (750 µL). After purification using a Biotage chromatography system we obtained 90.5 mg (100% purity, 88% yield) of the desired title compound.

LC-MS (Method 2): R$_t$=1.59 min; MS (ESIpos): m/z=692 [M+H]$^+$ $^1$H-NMR (400 MHz, DMSO-d6) δ [ppm]: −0.10−−0.07 (m, 9H), 0.81-0.89 (m, 2H), 1.17 (s, 3H), 1.24 (s, 3H), 1.32 (d, 6H), 3.28-3.35 (m, 1H), 3.36-3.43 (m, 1H), 3.55-3.63 (m, 2H), 4.10 (d, 1H), 4.19 (d, 1H), 4.31 (dd, 1H), 4.81 (spt, 1H), 5.66 (s, 2H), 6.41-6.47 (m, 2H), 7.31-7.40 (m, 3H), 7.88-7.93 (m, 3H), 8.18 (d, 1H), 9.02 (s, 1H).

Intermediate 154

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[1-(oxetan-3-yl)ethyl]urea

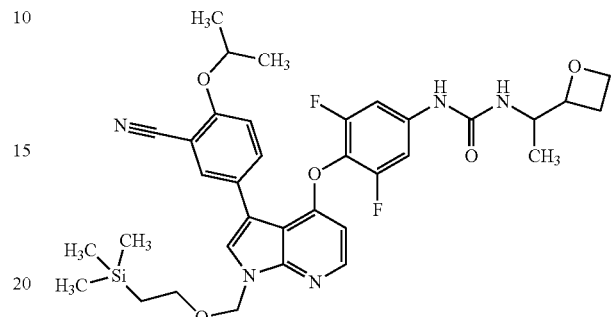

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamate (100 mg, 149 µmol, intermediate 103) was reacted with (+/−)-1-(oxetan-3-yl)ethan-1-amine hydrogen chloride (1/1) (20.5 mg, 149 µmol) and triethylamine (31 µL, 220 µmol) in DMF (750 µL). After purification using a Biotage chromatography system we obtained 93.6 mg (100% purity, 93% yield) of the desired title compound.

LC-MS (Method 2): R$_t$=1.53 min; MS (ESIpos): m/z=678 [M+H]$^+$ $^1$H-NMR (400 MHz, DMSO-d6) δ [ppm]: −0.10−−0.07 (m, 9H), 0.81-0.88 (m, 2H), 1.02 (d, 3H), 1.32 (d, 6H), 2.95-3.05 (m, 1H), 3.55-3.62 (m, 2H), 3.98-4.08 (m, 1H), 4.31 (t, 1H), 4.38 (t, 1H), 4.59 (ddd, 2H), 4.81 (spt, 1H), 5.66 (s, 2H), 6.43-6.49 (m, 2H), 7.31-7.42 (m, 3H), 7.89-7.93 (m, 3H), 8.19 (d, 1H), 8.88 (s, 1H).

Intermediate 155

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-oxetan-3-ylurea

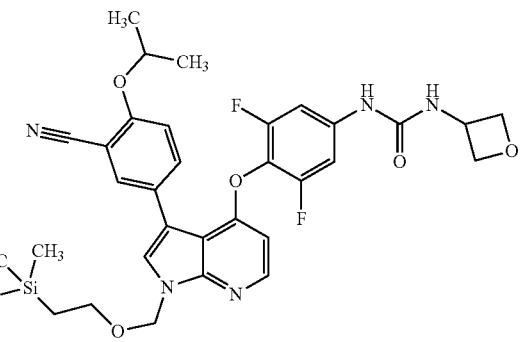

In analogy to intermediate 2, phenyl {4-[(3-{3-cyano-4-[(propan-2-yl)oxy]phenyl}-1-{[2-(trimethylsilyl)ethoxy]

methyl}-1H-pyrrolo[2,3-b]pyridin-4-yl)oxy]-3,5-difluorophenyl}carbamate (100 mg, 149 μmol, intermediate 103) was reacted with oxetan-3-amine (10 μL, 150 μmol) in DMF (750 μL). After purification using a Biotage chromatography system we obtained 90.7 mg (100% purity, 94% yield) of the desired title compound.

LC-MS (Method 2): $R_t$=1.48 min; MS (ESIpos): m/z=650 [M+H]$^+$ $^1$H-NMR (400 MHz, DMSO-d6) δ [ppm]: −0.10−−0.06 (m, 9H), 0.81-0.88 (m, 2H), 1.32 (d, 6H), 3.55-3.62 (m, 2H), 4.46 (t, 2H), 4.70-4.86 (m, 4H), 5.66 (s, 2H), 6.44 (d, 1H), 7.23 (d, 1H), 7.31-7.43 (m, 3H), 7.88-7.94 (m, 3H), 8.18 (d, 1H), 9.09 (s, 1H).

Intermediate 156

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-phenyloxetan-3-yl)methyl]urea

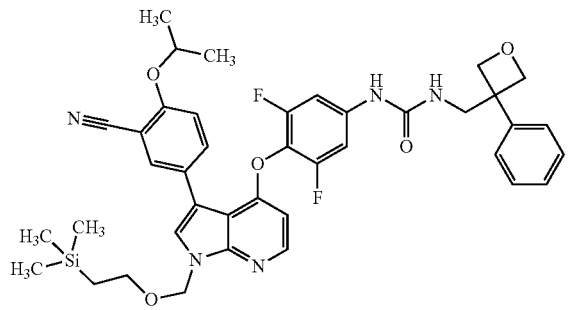 [SMILES: CC(C)Oc1ccc(-c2cn(COCC[Si](C)(C)C)c3nccc(Oc4c(F)cc(NC(=O)NCC5(c6ccccc6)COC5)cc4F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamate (100 mg, 149 μmol, intermediate 103) was reacted with 1-(3-phenyloxetan-3-yl)methanamine (24.3 mg, 149 μmol) in DMF (750 μL). After purification using a Biotage chromatography system we obtained 129 mg (93% purity, 109% yield) of the desired title compound.

LC-MS (Method 2): $R_t$=1.59 min; MS (ESIpos): m/z=740 [M+H]$^+$.

Intermediate 157

3-[({4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamoyl)amino]oxetane-3-carboxamide

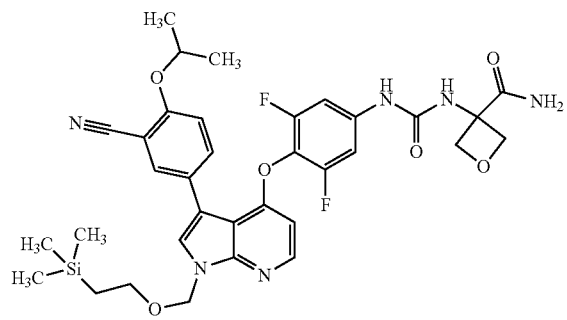 [SMILES: CC(C)Oc1ccc(-c2cn(COCC[Si](C)(C)C)c3nccc(Oc4c(F)cc(NC(=O)NC5(C(N)=O)COC5)cc4F)c23)cc1C#N]

In analogy to intermediate 2, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamate (100 mg, 149 μmol, intermediate 103) was reacted with 3-aminooxetane-3-carboxamide acetic acid salt (1/1) (26.3 mg, 149 μmol) and triethylamine (31 μL, 220 μmol) in DMF (750 μL). After purification using a Biotage chromatography system we obtained 27.6 mg (91% purity, 24% yield) of the desired title compound.

LC-MS (Method 2): $R_t$=1.41 min; MS (ESIneg): m/z=693 [M−H]$^-$ $^1$H-NMR (400 MHz, DMSO-d6) δ [ppm]: −0.10−−0.07 (m, 9H), 0.82-0.88 (m, 2H), 1.32 (d, 6H), 3.56-3.62 (m, 2H), 4.52 (d, 2H), 4.76-4.86 (m, 3H), 5.66 (s, 2H), 6.44 (d, 1H), 7.25 (s, 1H), 7.30-7.46 (m, 5H), 7.87-7.96 (m, 3H), 8.18 (d, 1H), 9.32 (s, 1H).

Intermediate 158

O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate

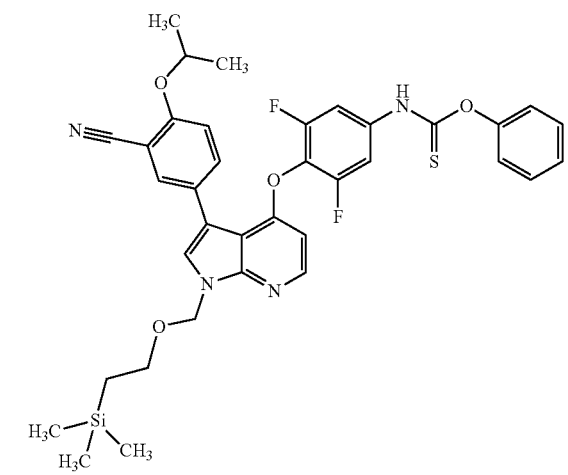 [SMILES: CC(C)Oc1ccc(-c2cn(COCC[Si](C)(C)C)c3nccc(Oc4c(F)cc(NC(=S)Oc5ccccc5)cc4F)c23)cc1C#N]

In analogy to intermediate 146, 5-[4-(4-amino-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile (200 mg, 363 μmol, intermediate 83) was reacted with O-phenyl carbonochloridothioate (55 μL, 400 μmol) in pyridine (410 μL) and THF (4.0 mL). The resulting raw desired compound (300 mg) was used in the next step without any further purification.

LC-MS (Method 1): $R_t$=1.72 min; MS (ESIpos): m/z=687 [M+H]$^+$

Intermediate 159

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-ethyl-2-(hydroxymethyl)butyl]thiourea

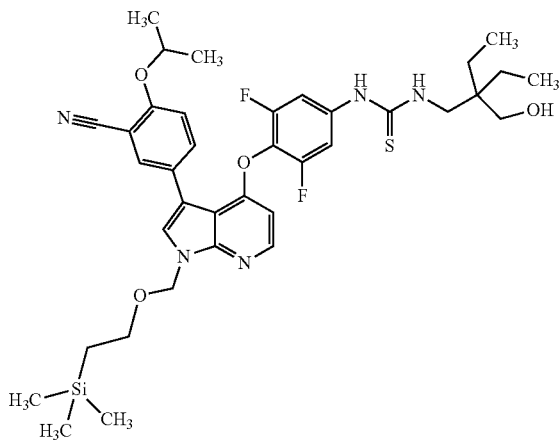 [SMILES: CCC(CC)(CO)CNC(=S)Nc1cc(F)c(Oc2ccnc3c2c(-c2ccc(OC(C)C)c(C#N)c2)cn3COCC[Si](C)(C)C)c(F)c1]

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (290 mg, 317 μmol, intermediate 158) was reacted with 2-(aminomethyl)-2-ethylbutan-1-ol (83.1 mg, 633 μmol) in DMF (5.5 mL). After two subsequent purification using a Biotage chromatography system we obtained 123 mg (75% purity, 40% yield) of the desired title compound.

LC-MS (Method 1): $R_t$=1.67 min; MS (ESIpos): m/z=724 [M+H]$^+$

Intermediate 160

5-(4-{4-[(5,5-diethyl-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile

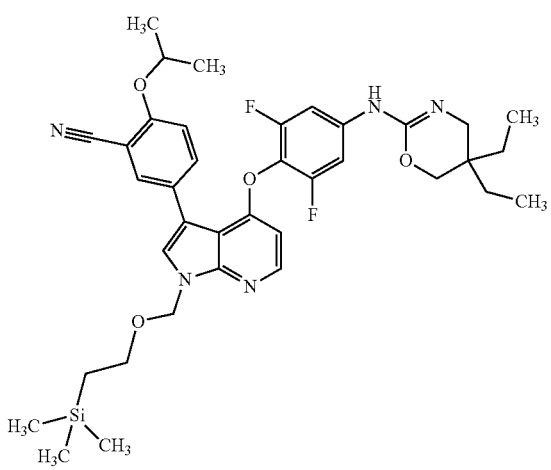 [SMILES: CCC1(CC)CN=C(Nc2cc(F)c(Oc3ccnc4c3c(-c3ccc(OC(C)C)c(C#N)c3)cn4COCC[Si](C)(C)C)c(F)c2)OC1]

In analogy to intermediate 148, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-ethyl-2-(hydroxymethyl)butyl]thiourea (100 mg, 138 μmol, intermediate 159) was reacted 1-(3-dimethylaminopropyl)-3-ethylcarbodiimide hydrochloride (53.0 mg, 276 μmol) and triethylamine (58 μL, 410 μmol) in acetonitrile (2.5 mL). After purification using a Biotage chromatography system we obtained 13.2 mg (100% purity, 14% yield) of the desired title compound.

LC-MS (Method 1): $R_t$=1.52 min; MS (ESIpos): m/z=690 [M+H]$^+$ $^1$H-NMR (400 MHz, DMSO-d6) δ [ppm]: −0.11−−0.06 (m, 9H), 0.78-0.88 (m, 8H), 1.32 (d, 10H), 3.10 (br s, 2H), 3.54-3.62 (m, 2H), 3.95 (br s, 2H), 4.81 (spt, 1H), 5.66 (s, 2H), 6.44 (d, 1H), 7.33 (d, 1H), 7.56 (br s, 1H), 7.87-7.94 (m, 3H), 8.18 (d, 1H), 9.07 (br s, 1H).

Intermediate 161

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxy-2,3-dimethylbutan-2-yl)thiourea

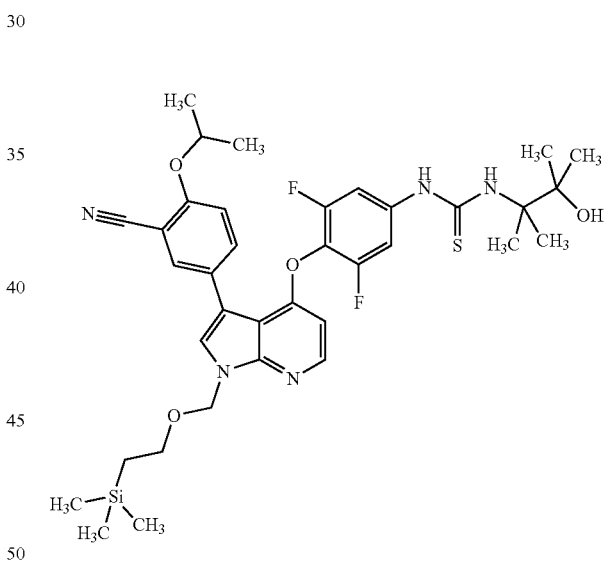

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (300 mg, 349 μmol, intermediate 158) was reacted with 3-amino-2,3-dimethylbutan-2-ol (81.9 mg, 699 μmol, CAS No. [89585-13-7]) in DMF (6.0 mL).

After purification using a Biotage chromatography system we obtained 164 mg (70% purity, 46% yield) of the desired title compound.

LC-MS (Method 1): $R_t$=1.63 min; MS (ESIneg): m/z=708 [M−H]$^-$

Intermediate 162

5-(4-{2,6-difluoro-4-[(4,4,5,5-tetramethyl-4,5-dihydro-1,3-oxazol-2-yl)amino]phenoxy}-1-{[2-(trimethylsilyl)ethoxy]methyl}-1H-pyrrolo[2,3-b]pyridin-3-yl)-2-[(propan-2-yl)oxy]benzonitrile

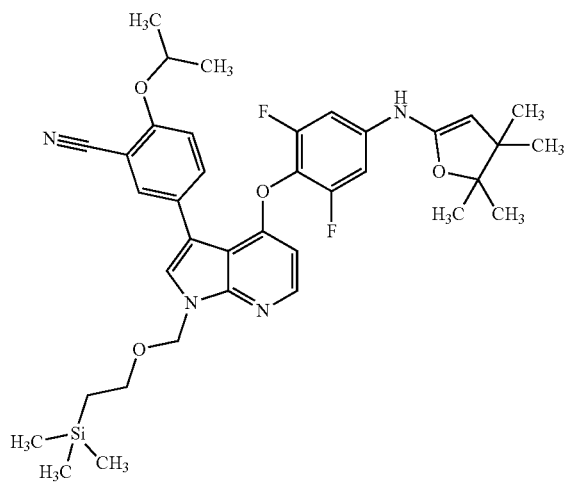

In analogy to intermediate 148, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxy-2,3-dimethylbutan-2-yl)thiourea (160 mg, 80% purity, 180 μmol, intermediate 161) was reacted 1-(3-dimethylaminopropyl)-3-ethylcarbodiimide hydrochloride (69.1 mg, 361 μmol) and triethylamine (75 μL, 540 μmol) in acetonitrile (3.5 mL). After purification using a Biotage chromatography system we obtained 100 mg (100% purity, 82% yield) of the desired title compound.

LC-MS (Method 1): $R_t$=1.44 min; MS (ESIneg): m/z=674 [M−H]⁻

¹H-NMR (400 MHz, DMSO-d6) δ [ppm]: −0.10--−0.05 (m, 9H), 0.79-0.89 (m, 2H), 1.15 (s, 6H), 1.32 (d, 6H), 1.33 (s, 6H), 3.56-3.62 (m, 2H), 4.81 (spt, 1H), 5.66 (s, 2H), 6.45 (br d, 1H), 6.80 (br d, 1H), 7.33 (d, 1H), 7.46-7.70 (m, 2H), 7.87-7.94 (m, 3H), 8.19 (d, 1H).

Intermediate 163

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(pyridin-4-yl)propyl]thiourea

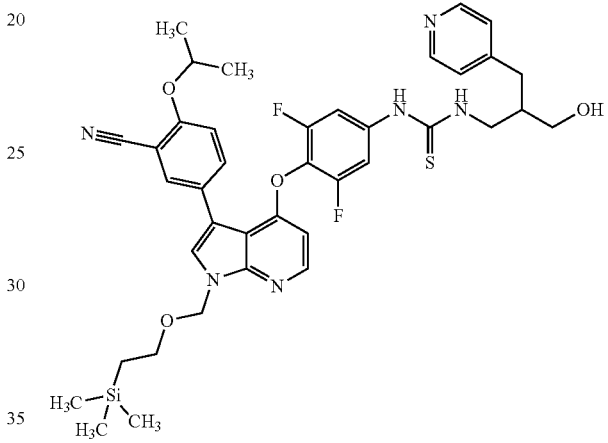

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (3000 mg, 349 μmol, intermediate 158) was reacted with (+/−)-2-(aminomethyl)-3-(pyridin-4-yl)propan-1-ol hydrogen chloride (1/2) (167 mg, 699 μmol, CAS No. [1803591-33-4]) and N,N-diisopropylethylamine (130 μL, 730 μmol) in DMF (6.1 mL). After purification using a Biotage chromatography system we obtained 119 mg (87% purity, 39% yield) of the desired title compound.

LC-MS (Method 1): $R_t$=1.33 min; MS (ESIneg): m/z=757 [M−H]⁻

¹H-NMR (400 MHz, DMSO-d6) δ [ppm]: −0.11--−0.06 (m, 9H), 0.80-0.89 (m, 2H), 1.32 (d, 6H), 2.11-2.21 (m, 1H), 2.57-2.68 (m, 2H), 3.35-3.62 (m, 6H), 4.73-4.87 (m, 2H), 5.67 (s, 2H), 6.46 (d, 1H), 7.26 (d, 2H), 7.34 (d, 1H), 7.52-7.62 (m, 2H), 7.89-7.96 (m, 3H), 8.13-8.24 (m, 2H), 8.46 (d, 2H), 9.96 (br s, 1H).

Intermediate 164

(+/−)-5-(4-[2,6-difluoro-4-({5-[(pyridin-4-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]benzonitrile

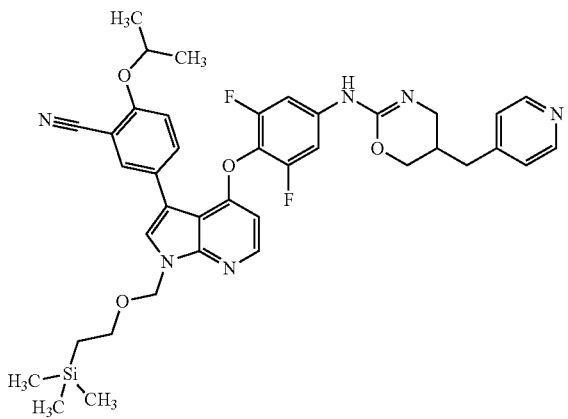 [SMILES: CC(C)Oc1ccc(-c2cn(COCC[Si](C)(C)C)c3nccc(Oc4c(F)cc(NC5=NCC(Cc6ccncc6)CO5)cc4F)c23)cc1C#N]

In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(pyridin-4-yl)propyl]thiourea (110 mg, 130 µmol, intermediate 163) was reacted 1-(3-dimethylaminopropyl)-3-ethylcarbodiimide hydrochloride (50.0 mg, 261 µmol) and triethylamine (55 µL, 390 µmol) in acetonitrile (2.5 mL). After workup and evaporation to dryness we obtained 133 mg (130% yield) of the desired title compound as crude product which was used in the next step without any further purification.

LC-MS (Method 1): $R_t$=1.27 min; MS (ESIpos): m/z=725 [M+H]$^+$

Intermediate 165

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(cyclopropylmethyl)-3-hydroxypropyl]thiourea

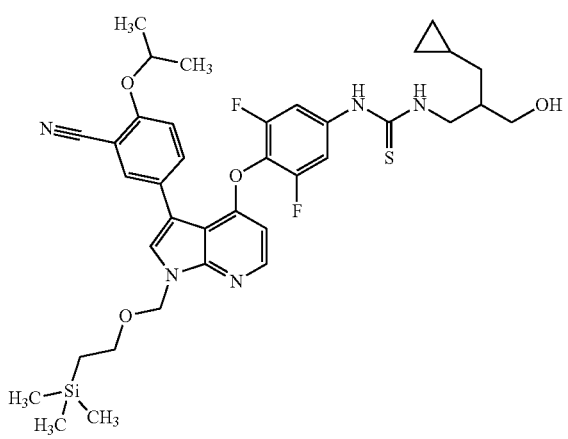 [SMILES: CC(C)Oc1ccc(-c2cn(COCC[Si](C)(C)C)c3nccc(Oc4c(F)cc(NC(=S)NCC(CO)CC5CC5)cc4F)c23)cc1C#N]

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 349 µmol, intermediate 158) was reacted with (+/−)-2-(aminomethyl)-3-cyclopropylpropan-1-ol (90.3 mg, 699 µmol, CAS No. [1247915-82-7]) in DMF (6.0 mL). After purification using a Biotage chromatography system we obtained 142 mg (82% purity, 46% yield) of the desired title compound.

LC-MS (Method 1): $R_t$=1.61 min; MS (ESIneg): m/z=720 [M−H]$^-$ $^1$H-NMR (400 MHz, DMSO-d6) δ [ppm]: −0.13--0.04 (m, 9H), 0.00-0.07 (m, 2H), 0.37-0.46 (m, 2H), 0.67-0.79 (m, 1H), 0.81-0.89 (m, 2H), 1.12-1.29 (m, 2H), 1.32 (d, 6H), 1.82-1.93 (m, 1H), 3.37-3.65 (m, 6H), 4.64 (br s, 1H), 4.81 (spt, 1H), 5.67 (s, 2H), 6.46 (d, 1H), 7.34 (d, 1H), 7.56-7.65 (m, 2H), 7.88-7.96 (m, 3H), 8.12 (br s, 1H), 8.21 (d, 1H), 9.98 (br s, 1H).

Intermediate 166

(+/−)-5-[4-(4-{[5-(cyclopropylmethyl)-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile

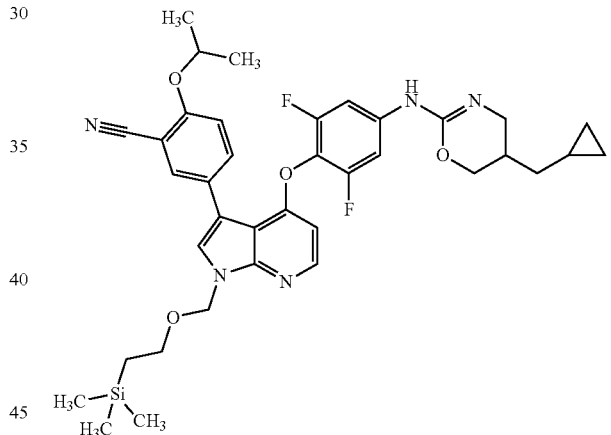

In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(cyclopropylmethyl)-3-hydroxypropyl]thiourea (180 mg, 224 µmol) intermediate 165) was reacted 1-(3-dimethylaminopropyl)-3-ethylcarbodiimide hydrochloride (86.0 mg, 449 µmol) and triethylamine (94 µL, 670 µmol) in acetonitrile (5.0 mL). After purification using a Biotage chromatography system we obtained 116 mg (95% purity, 71% yield) of the desired title compound.

LC-MS (Method 1): $R_t$=1.40 min; MS (ESIpos): m/z=688 [M+H]$^+$ $^1$H-NMR (400 MHz, DMSO-d6) δ [ppm]: −0.12--0.05 (m, 9H), 0.04-0.10 (m, 2H), 0.42-0.49 (m, 2H), 0.71-0.88 (m, 3H), 1.21-1.34 (m, 9H), 3.13 (dd, 1H), 3.49-3.63 (m, 3H), 4.20-4.37 (m, 1H), 4.60-4.72 (m, 1H), 4.81 (spt, 1H), 5.67 (s, 2H), 6.47 (d, 1H), 7.33 (d, 1H), 7.37-7.45 (m, 2H), 7.88-7.95 (m, 3H), 8.22 (d, 1H).

Intermediate 167

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-cyclopropyl-3-hydroxypropyl]thiourea

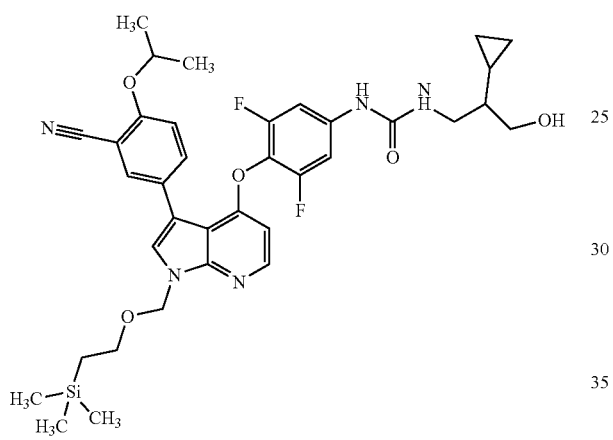

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 349 μmol, intermediate 158) was reacted with (+/−)-3-amino-2-cyclopropylpropan-1-ol (80.5 mg, 699 μmol, CAS No. [1314910-96-7]) in DMF (6.0 mL). After purification using a Biotage chromatography system we obtained 195 mg (96% purity, 76% yield) of the desired title compound.

LC-MS (Method 1): $R_t$=1.59 min; MS (ESIneg): m/z=706 [M−H]⁻

¹H-NMR (400 MHz, DMSO-d6) δ [ppm]: −0.11−−0.05 (m, 9H), 0.09-0.24 (m, 2H), 0.37-0.49 (m, 2H), 0.59-0.70 (m, 1H), 0.81-0.89 (m, 2H), 1.01 (br s, 1H), 1.32 (d, 6H), 3.39-3.76 (m, 6H), 4.69 (t, 1H), 4.82 (spt, 1H), 5.67 (s, 2H), 6.46 (d, 1H), 7.32-7.37 (m, 1H), 7.56-7.64 (m, 2H), 7.89-7.95 (m, 3H), 8.10 (br s, 1H), 8.21 (d, 1H), 10.03 (br s, 1H).

Intermediate 168

(+/−)-5-[4-(4-{[5-cyclopropyl-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile

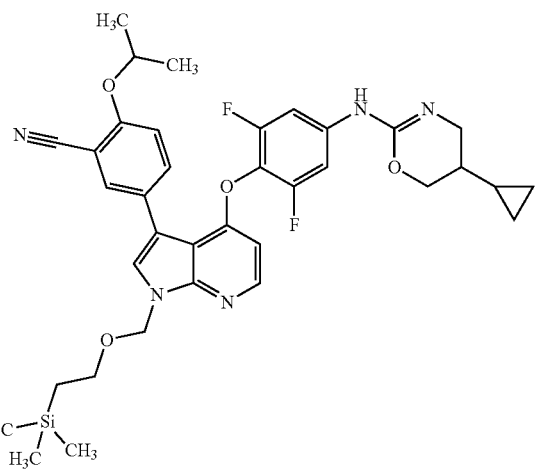

In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-cyclopropyl-3-hydroxypropyl]thiourea (190 mg, 268 μmol, intermediate 167) was reacted 1-(3-dimethylaminopropyl)-3-ethylcarbodiimide hydrochloride (103 mg, 537 μmol) and triethylamine (110 μL, 810 μmol) in acetonitrile (5.0 mL). After purification using a Biotage chromatography system we obtained 123 mg (93% purity, 63% yield) of the desired title compound.

LC-MS (Method 1): $R_t$=1.40 min; MS (ESIneg): m/z=672 [M−H]⁻

¹H-NMR (400 MHz, DMSO-d6) δ [ppm]: −0.12−−0.06 (m, 9H), 0.18-0.26 (m, 2H), 0.38-0.48 (m, 2H), 0.58 (br s, 1H), 0.79-0.90 (m, 2H), 1.32 (d, 7H), 3.16 (br s, 1H), 3.43 (br s, 1H), 3.54-3.61 (m, 2H), 3.99-4.07 (m, 1H), 4.29 (br dd, 1H), 4.81 (spt, 1H), 5.66 (s, 2H), 6.42 (d, 1H), 7.33 (d, 1H), 7.57 (br s, 2H), 7.88-7.94 (m, 3H), 8.18 (d, 1H), 9.03 (br s, 1H).

223

Intermediate 169

(+/−)—N-[2-benzyl-3-hydroxypropyl]-N'-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}thiourea

224

Intermediate 170

(+/−)-5-[4-(4-{[5-benzyl-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile

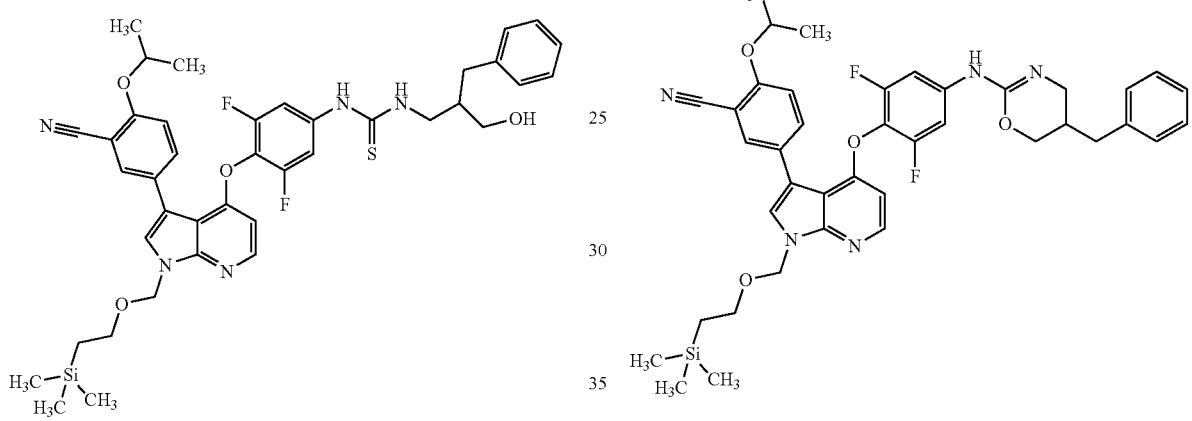

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 349 µmol, intermediate 158) was reacted with (+/−)-2-(aminomethyl)-3-phenylpropan-1-ol (115 mg, 699 µmol, CAS No. [66102-69-0]) in DMF (6.0 mL). After purification using a Biotage chromatography system we obtained 199 mg (90% purity, 68% yield) of the desired title compound.

LC-MS (Method 1): $R_t$=1.63 min; MS (ESIneg): m/z=756 [M−H]$^-$ $^1$H-NMR (400 MHz, DMSO-d6) δ [ppm]: −0.11--0.06 (m, 9H), 0.82-0.88 (m, 2H), 1.32 (d, 6H), 2.02-2.13 (m, 1H), 2.61 (br t, 2H), 3.34-3.62 (m, 6H), 4.72 (br s, 1H), 4.81 (spt, 1H), 5.67 (s, 2H), 6.46 (d, 1H), 7.16-7.36 (m, 6H), 7.54-7.62 (m, 2H), 7.89-7.95 (m, 3H), 8.12-8.22 (m, 2H), 9.96 (br s, 1H).

In analogy to intermediate 148, (+/−)—N-(2-benzyl-3-hydroxypropyl)-N'-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}thiourea (190 mg, 251 µmol, intermediate 169) was reacted 1-(3-dimethylaminopropyl)-3-ethylcarbodiimide hydrochloride (96.1 mg, 501 µmol) and triethylamine (100 µL, 750 µmol) in acetonitrile (5.0 mL). After purification using a Biotage chromatography system we obtained 130 mg (95% purity, 68% yield) of the desired title compound.

LC-MS (Method 1): $R_t$=1.45 min; MS (ESIneg): m/z=722 [M−H]$^-$ $^1$H-NMR (400 MHz, DMSO-d6) δ [ppm]: −0.15--0.04 (m, 9H), 0.81-0.88 (m, 2H), 1.20-1.27 (m, 1H), 1.32 (d, 6H), 2.11-2.26 (m, 1H), 2.58-2.65 (m, 1H), 3.12 (br s, 1H), 3.36-3.44 (m, 1H), 3.55-3.62 (m, 2H), 3.95 (br s, 1H), 4.18 (br s, 1H), 4.81 (spt, 1H), 5.66 (s, 2H), 6.38-6.47 (m, 1H), 7.18-7.27 (m, 3H), 7.27-7.37 (m, 3H), 7.46-7.69 (m, 1H), 7.87-7.94 (m, 3H), 8.17 (d, 1H), 9.06 (br s, 1H).

Intermediate 171

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[3,3,3-trifluoro-2-(hydroxymethyl)propyl]thiourea In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 466 μmol, intermediate 158) was reacted with (+/−)-2-(aminomethyl)-3,3,3-trifluoropropan-1-ol (133 mg, 932 μmol, CAS No. [1529181-01-8]) in DMF (8.0 mL). After purification using a Biotage chromatography system we obtained 313 mg (100% purity, 91% yield) of the desired title compound.

LC-MS (Method 1): $R_t$=1.59 min; MS (ESIpos): m/z=736 [M+H]$^+$ $^1$H-NMR (400 MHz, DMSO-d6) δ [ppm]: −0.11--0.06 (m, 9H), 0.82-0.88 (m, 2H), 1.32 (d, 6H), 3.56-3.78 (m, 6H), 4.82 (spt, 1H), 5.00 (br s, 1H), 5.09 (br s, 1H), 5.67 (s, 2H), 6.46 (d, 1H), 7.34 (d, 1H), 7.52-7.59 (m, 2H), 7.74 (t, 1H), 7.89-7.94 (m, 3H), 8.21 (d, 1H), 10.13 (br s, 1H).

Intermediate 172

(+/−)-5-[4-(2,6-difluoro-4-{[5-(trifluoromethyl)-5,6-dihydro-4H-1,3-oxazin-2-yl]amino}phenoxy)-1-{[2-(trimethylsilyl)ethoxy]methyl}-1H-pyrrolo[2,3-b]pyridin-3-yl]-2-[(propan-2-yl)oxy]benzonitrile In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[3,3,3-trifluoro-2-(hydroxymethyl)propyl]thiourea (300 mg, 408 μmol), intermediate 171) was reacted 1-(3-dimethylaminopropyl)-3-ethylcarbodiimide hydrochloride (156 mg, 815 μmol) and triethylamine (170 μL, 1.2 mmol) in acetonitrile (7.0 mL). After purification using a Biotage chromatography system we obtained 171 mg (93% purity, 56% yield) of the desired title compound.

LC-MS (Method 1): $R_t$=1.45 min; MS (ESIneg): m/z=700 [M−H]$^-$ $^1$H-NMR (400 MHz, DMSO-d6) δ [ppm]: −0.11--0.06 (m, 9H), 0.81-0.88 (m, 2H), 1.32 (d, 6H), 3.09 (br s, 1H), 3.47-3.62 (m, 3H), 3.64-3.75 (m, 1H), 4.37 (br dd, 1H), 4.48 (dd, 1H), 4.81 (spt, 1H), 5.66 (s, 2H), 6.44 (d, 1H), 7.33 (d, 1H), 7.47-7.65 (m, 2H), 7.87-7.93 (m, 3H), 8.17 (d, 1H), 9.23 (br s, 1H).

Intermediate 173

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(pyridin-3-yl)propyl]thiourea

Intermediate 174

(+/−)-5-(4-[2,6-difluoro-4-({5-[(pyridin-3-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]benzonitrile

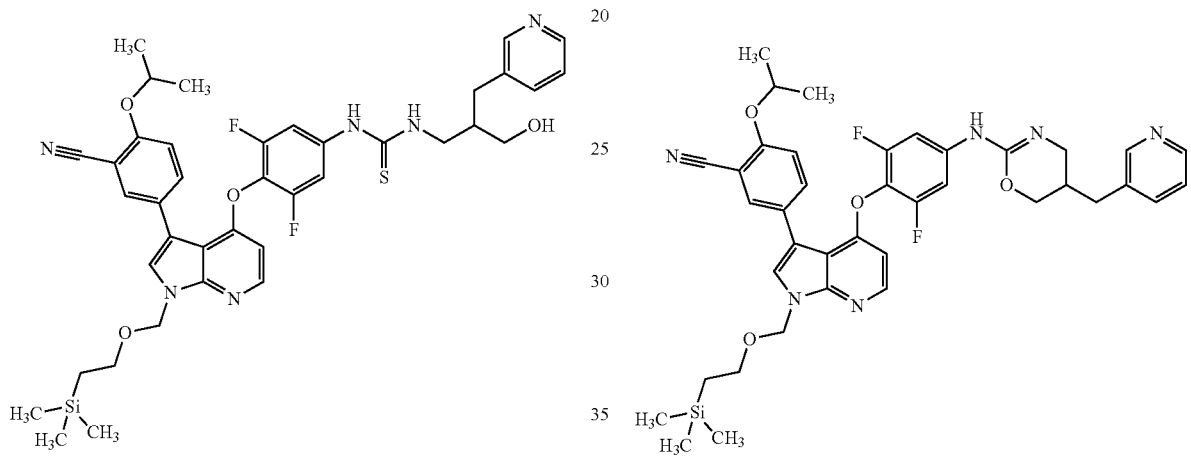

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 349 μmol, intermediate 158) was reacted with (+/−)-2-(aminomethyl)-3-(pyridin-3-yl)propan-1-ol (129 mg, 699 μmol, CAS No. [1017125-32-4]) in DMF (6.0 mL). After purification using a Biotage chromatography system we obtained 220 mg (84% purity, 70% yield) of the desired title compound.

LC-MS (Method 1): $R_t$=1.40 min; MS (ESIneg): m/z=757 [M−H]−

$^1$H-NMR (400 MHz, DMSO-d6) δ [ppm]: −0.11--0.06 (m, 9H), 0.82-0.88 (m, 2H), 1.32 (d, 5H), 2.06-2.17 (m, 1H), 2.56-2.68 (m, 2H), 3.34-3.62 (m, 6H), 4.73-4.88 (m, 2H), 5.67 (s, 2H), 6.46 (d, 1H), 7.29-7.37 (m, 2H), 7.52-7.69 (m, 3H), 7.89-7.94 (m, 3H), 8.14-8.24 (m, 2H), 8.41 (dd, 1H), 8.45 (d, 1H), 9.97 (br s, 1H).

In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(pyridin-3-yl)propyl]thiourea (210 mg, 249 μmol), intermediate 173) was reacted 1-(3-dimethylaminopropyl)-3-ethylcarbodiimide hydrochloride (95.5 mg, 498 μmol) and triethylamine (100 μL, 750 μmol) in acetonitrile (5.0 mL). After purification using a Biotage chromatography system we obtained 128 mg (88% purity, 63% yield) of the desired title compound.

LC-MS (Method 1): $R_t$=1.35 min; MS (ESIpos): m/z=725 [M+H]+

$^1$H-NMR (400 MHz, DMSO-d6) δ [ppm]: −0.12--0.06 (m, 9H), 0.82-0.87 (m, 2H), 1.32 (d, 6H), 2.15-2.27 (m, 1H), 2.60-2.69 (m, 2H), 3.12 (br s, 1H), 3.35-3.44 (m, 1H), 3.55-3.61 (m, 2H), 3.96 (br s, 1H), 4.21 (br d, 1H), 4.81 (spt, 1H), 5.66 (s, 2H), 6.42 (d, 1H), 7.30-7.37 (m, 2H), 7.48-7.63 (m, 1H), 7.69 (br d, 1H), 7.87-7.93 (m, 3H), 8.18 (d, 1H), 8.44 (dd, 1H), 8.47 (d, 1H), 9.08 (br s, 1H).

Intermediate 175

(+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(1-methyl-1H-pyrazol-4-yl)propyl]thiourea

Intermediate 176

(+/−)-5-(4-[2,6-difluoro-4-({5-[(1-methyl-1H-pyrazol-4-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]benzonitrile

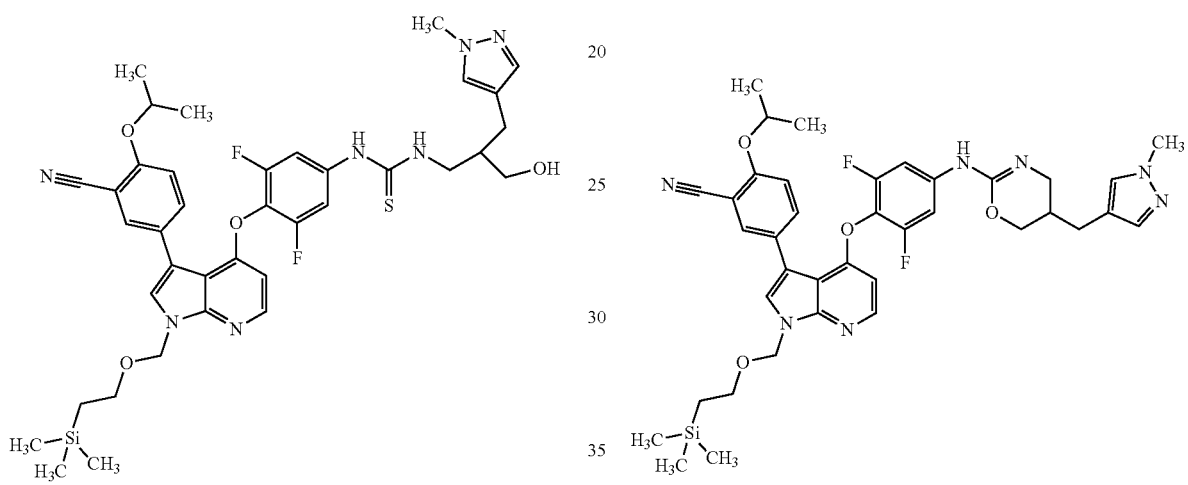

In analogy to intermediate 147, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (400 mg, 349 µmol, intermediate 158) was reacted with (+/−)-2-(aminomethyl)-3-(1-methyl-1H-pyrazol-4-yl)propan-1-ol hydrogen chloride (1/2) (169 mg, 699 µmol, CAS No. [1803581-22-7]) and N,N-diisopropylethylamine (130 µL, 730 µmol) in DMF (6.0 mL). After purification using a Biotage chromatography system we obtained 132 mg (84% purity, 42% yield) of the desired title compound.

LC-MS (Method 1): $R_t$=1.50 min; MS (ESIneg): m/z=760 [M−H]⁻

¹H-NMR (400 MHz, DMSO-d6) δ [ppm]: −0.11−−0.07 (m, 9H), 0.81-0.90 (m, 2H), 1.32 (d, 6H), 1.89-1.98 (m, 1H), 2.40-2.45 (m, 1H), 2.53-2.58 (m, 1H), 3.34-3.63 (m, 6H), 3.77 (s, 3H), 4.68 (br s, 1H), 4.82 (spt, 1H), 5.67 (s, 2H), 6.46 (d, 1H), 7.25 (s, 1H), 7.34 (d, 1H), 7.47 (s, 1H), 7.55-7.62 (m, 2H), 7.88-7.94 (m, 3H), 8.13 (br s, 1H), 8.21 (d, 1H), 9.96 (br s, 1H).

In analogy to intermediate 148, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-(1-methyl-1H-pyrazol-4-yl)propyl]thiourea (130 mg, 154 µmol, intermediate 175) was reacted 1-(3-dimethylaminopropyl)-3-ethylcarbodiimide hydrochloride (58.9 mg, 307 µmol) and triethylamine (64 µL, 460 µmol) in acetonitrile (4.0 mL). After purification using a Biotage chromatography system we obtained 65.4 mg (91% purity, 53% yield) of the desired title compound.

LC-MS (Method 1): $R_t$=1.55 min; MS (ESIpos): m/z=728 [M+H]⁺

¹H-NMR (400 MHz, DMSO-d6) δ [ppm]: −0.14−−0.06 (m, 9H), 0.80-0.87 (m, 2H), 1.32 (d, 6H), 2.00-2.11 (m, 1H), 2.34-2.44 (m, 1H), 3.08 (br s, 1H), 3.36-3.54 (m, 2H), 3.55-3.61 (m, 2H), 3.78 (s, 3H), 3.93 (br d, 1H), 4.17-4.32 (m, 1H), 4.81 (spt, 1H), 5.66 (s, 2H), 6.42 (d, 1H), 7.28 (s, 1H), 7.33 (d, 1H), 7.51-7.63 (m, 3H), 7.87-7.94 (m, 3H), 8.18 (d, 1H), 9.05 (br s, 1H).

Intermediate 177

5-[4-(2,6-difluoro-4-nitrophenoxy)-1-{[2-(trimethylsilyl)ethoxy]methyl}-1H-pyrrolo[2,3-b]pyridin-3-yl]-2-(trifluoromethoxy)benzonitrile

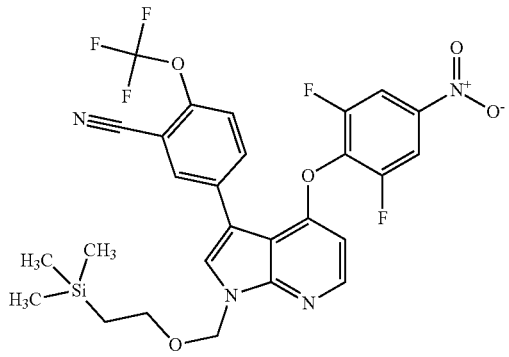 [SMILES: C[Si](C)(C)CCOCn1cc(-c2ccc(OC(F)(F)F)c(C#N)c2)c2c(Oc3c(F)cc([N+](=O)[O-])cc3F)ccnc21]

In analogy to intermediate 17, 3-bromo-4-(2,6-difluoro-4-nitrophenoxy)-1-{[2-(trimethylsilyl)ethoxy]methyl}-1H-pyrrolo[2,3-b]pyridine (500 mg, 999 µmol, intermediate 16) was reacted with [3-cyano-4-(trifluoromethoxy)phenyl]boronic acid (462 mg, 2.00 mmol, purchased from Atlantic Research Chemicals Ltd.) in the presence of [1,1'-bis (diphenylphosphino)ferrocene]dichloropalladium(II) (73.1 mg, 99.9 µmol) and potassium carbonate (691 mg, 5.00 mmol) in water (4.8 mL) and dioxane (9.6 mL). After purification using a Biotage chromatography system we obtained 631 mg (67% purity, 70% yield) of the desired title compound.

LC-MS (Method 2): $R_t$=1.67 min; MS (ESIpos): m/z=607 [M+H]$^+$

Intermediate 178

5-[4-(4-amino-2,6-difluorophenoxy)-1-{[2-(trimethylsilyl)ethoxy]methyl}-1H-pyrrolo[2,3-b]pyridin-3-yl]-2-(trifluoromethoxy)benzonitrile

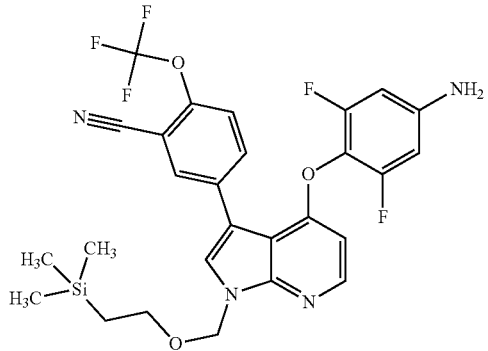 [SMILES: C[Si](C)(C)CCOCn1cc(-c2ccc(OC(F)(F)F)c(C#N)c2)c2c(Oc3c(F)cc(N)cc3F)ccnc21]

In analogy to intermediate 18, 5-[4-(2,6-difluoro-4-nitrophenoxy)-1-{[2-(trimethylsilyl)ethoxy]methyl}-1H-pyrrolo[2,3-b]pyridin-3-yl]-2-(trifluoromethoxy)benzonitrile (627 mg, 1.03 mmol, intermediate 177) was reacted with iron powder (289 mg, 5.17 mmol) and ammonium chloride (276 mg, 5.17 mmol) in a mixture of water (10 mL), tetrahydrofuran (5.1 mL) and methanol (5.1 mL). After purification using a Biotage chromatography system we obtained 190 mg (94% purity, 30% yield) of the desired title compound.

LC-MS (Method 1): $R_t$=1.59 min; MS (ESIpos): m/z=577 [M+H]$^+$ $^1$H-NMR (400 MHz, DMSO-d6) δ [ppm]: −0.12−−0.06 (m, 9H), 0.81-0.89 (m, 2H), 3.56-3.63 (m, 2H), 5.68 (s, 2H), 5.84 (s, 2H), 6.36-6.44 (m, 2H), 6.47 (d, 1H), 7.76 (dq, 1H), 8.08 (s, 1H), 8.12 (dd, 1H), 8.22 (d, 1H), 8.24 (d, 1H).

Intermediate 179 phenyl {4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}carbamate

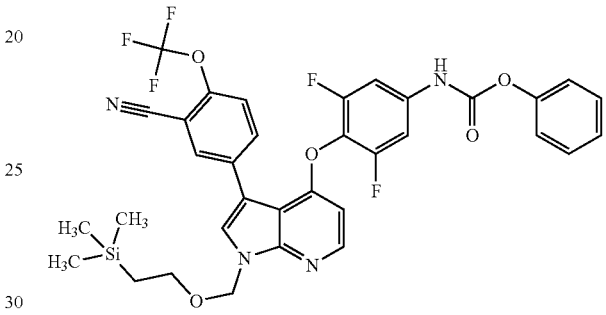

In analogy to intermediate 1, 5-[4-(4-amino-2,6-difluorophenoxy)-1-{[2-(trimethylsilyl)ethoxy]methyl}-1H-pyrrolo[2,3-b]pyridin-3-yl]-2-(trifluoromethoxy)benzonitrile (185 mg, 321 µmol), intermediate 178) was reacted with phenyl carbonochloridate (44 µL, 350 µmol) in pyridine (150 µL) and THF (2.3 mL). After purification using a Biotage chromatography system we obtained 216 mg (87% purity, 84% yield) of the desired title compound.

LC-MS (Method 2): $R_t$=1.70 min; MS (ESIpos): m/z=697 [M+H]$^+$

Intermediate 180

N-{4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

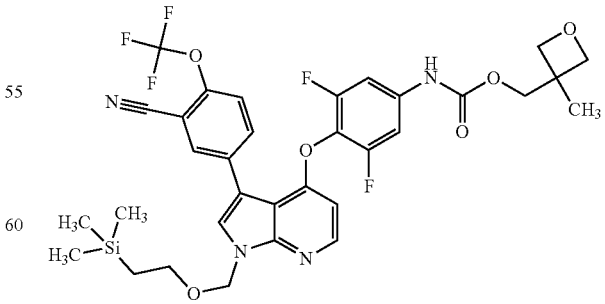

In analogy to intermediate 2, phenyl {4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5- difluorophenyl}carbamate (100 mg, 144 µmol, intermediate 179) was reacted with 1-(3-methyloxetan-3-yl)methanamine (16.0 mg, 158 µmol) in DMF (850 µL). After purification using a Biotage chromatography system we obtained 93.7 mg (100% purity, 93% yield) of the desired title compound.

LC-MS (Method 2): R$_t$=1.56 min; MS (ESIpos): m/z=704 [M+H]$^+$ $^1$H-NMR (400 MHz, DMSO-d6) δ [ppm]: −0.11−−0.07 (m, 9H), 0.82-0.89 (m, 2H), 1.23 (s, 3H), 3.30 (d, 2H), 3.57-3.64 (m, 2H), 4.21 (d, 2H), 4.38 (d, 2H), 5.69 (s, 2H), 6.52 (d, 1H), 6.72 (t, 1H), 7.37-7.44 (m, 2H), 7.76 (dq, 1H), 8.09-8.15 (m, 2H), 8.23 (d, 1H), 8.25 (s, 1H), 9.02 (s, 1H).

Intermediate 181

N-(4-{[3-(4-cyano-2-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

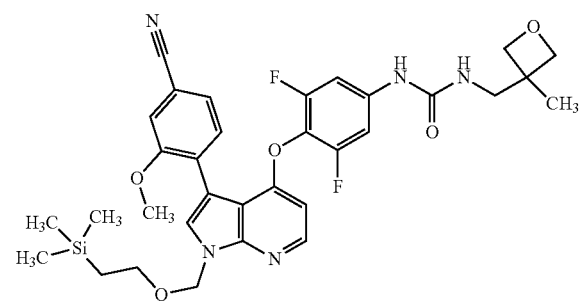 [SMILES: COc1cc(C#N)ccc1-c1cn(COCC[Si](C)(C)C)c2nccc(Oc3c(F)cc(NC(=O)NCC4(C)COC4)cc3F)c12]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl) methyl]urea (150 mg, 251 µmol, intermediate 24) was reacted with (4-cyano-2-methoxyphenyl)boronic acid (53.3 mg, 301 µmol) in the presence of tetrakis(triphenylphosphin)palladium(0) (23.2 mg, 20.1 µmol), and aq. sodium carbonate (251 µL, 2.0 M, 502 µmol) in 1,4-dioxane (2.3 mL). After purification using a Biotage chromatography system we obtained 82.2 mg (82% purity, 41% yield) of the desired title compound.

LC-MS (Method 1): R$_t$=1.45 min; MS (ESIpos): m/z=650 [M+H]$^+$ $^1$H-NMR (400 MHz, DMSO-d6) δ [ppm]: −0.12−−0.06 (m, 9H), 0.82-0.89 (m, 2H), 1.22 (s, 3H), 3.29 (d, 2H), 3.57-3.63 (m, 2H), 3.80 (s, 3H), 4.20 (d, 2H), 4.37 (d, 2H), 5.67 (s, 2H), 6.38 (d, 1H), 6.68-6.76 (m, 1H), 7.30-7.37 (m, 2H), 7.44 (dd, 1H), 7.49-7.52 (m, 1H), 7.57 (d, 1H), 7.79 (s, 1H), 8.16 (d, 1H), 9.01 (s, 1H).

Intermediate 182

N-{4-[(3-{4-cyano-3-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

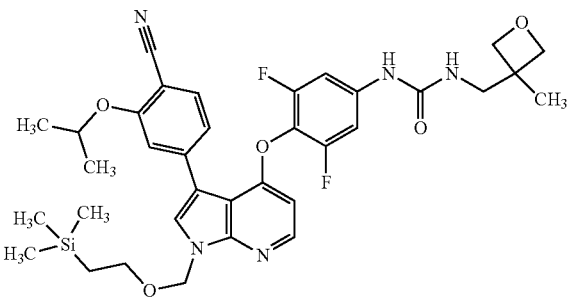 [SMILES: CC(C)Oc1cc(-c2cn(COCC[Si](C)(C)C)c3nccc(Oc4c(F)cc(NC(=O)NCC5(C)COC5)cc4F)c23)ccc1C#N]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl) methyl]urea (150 mg, 251 µmol, intermediate 24) was reacted with {4-cyano-3-[(propan-2-yl)oxy]phenyl}boronic acid (61.8 mg, 301 µmol, CAS No. [2096339-85-2]) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 95.1 mg (84% purity, 47% yield) of the desired title compound.

LC-MS (Method 1): R$_t$=1.52 min; MS (ESIpos): m/z=678 [M+H]$^+$ $^1$H-NMR (400 MHz, DMSO-d6) δ [ppm]: −0.11−−0.07 (m, 9H), 0.82-0.89 (m, 2H), 1.24 (d, 6H), 1.26 (s, 3H), 3.30 (d, 2H), 3.57-3.63 (m, 2H), 4.21 (d, 2H), 4.38 (d, 2H), 4.76 (spt, 1H), 5.69 (s, 2H), 6.50 (d, 1H), 6.73 (t, 1H), 7.35-7.44 (m, 3H), 7.53 (d, 1H), 7.72 (d, 1H), 8.13 (s, 1H), 8.21 (d, 1H), 9.04 (s, 1H).

Intermediate 183

N-(4-{[3-(2-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

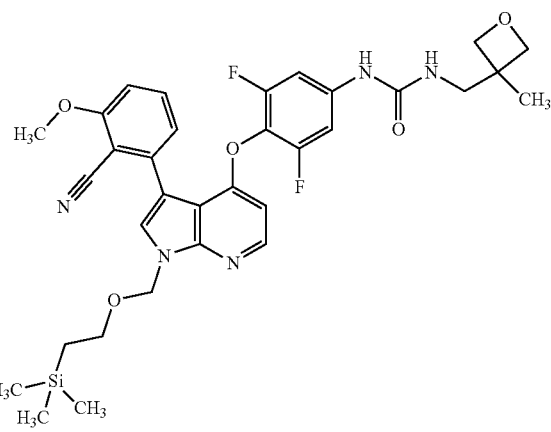

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 μmol, intermediate 24) was reacted with 2-(5,5-dimethyl-1,3,2-dioxaborinan-2-yl)-6-methoxybenzonitrile (73.8 mg, 301 μmol, CAS No. [883899-02-3]) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 134 mg (97% purity, 79% yield) of the desired title compound.

LC-MS (Method 1): R$_t$=1.41 min; MS (ESIpos): m/z=650 [M+H]$^+$ $^1$H-NMR (400 MHz, DMSO-d6) δ [ppm]: −0.11−−0.07 (m, 9H), 0.82-0.88 (m, 2H), 1.22 (s, 3H), 3.29 (d, 2H), 3.57-3.63 (m, 2H), 3.93 (s, 3H), 4.20 (d, 2H), 4.37 (d, 2H), 5.70 (s, 2H), 6.45 (d, 1H), 6.70 (t, 1H), 7.17 (d, 1H), 7.22 (d, 1H), 7.30-7.37 (m, 2H), 7.63 (t, 1H), 7.92 (s, 1H), 8.21 (d, 1H), 9.00 (s, 1H).

Intermediate 184

N-(4-{[3-(2-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

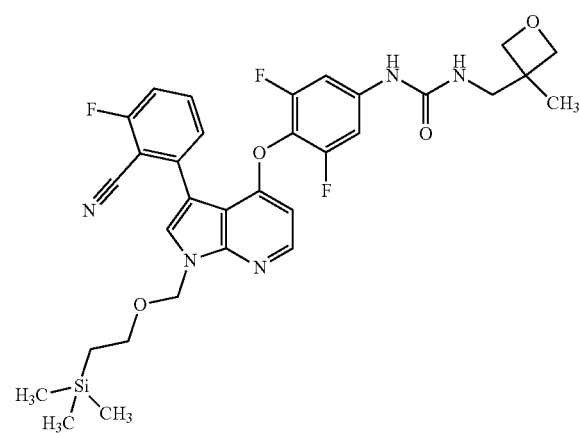 [SMILES: CC1(CNC(=O)Nc2cc(F)c(Oc3ccnc4c3c(-c3cccc(F)c3C#N)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 μmol, intermediate 24) was reacted with 2-fluoro-6-(4,4,5,5-tetramethyl-1,3,2-dioxaborolan-2-yl)benzonitrile (74.4 mg, 301 μmol, CAS No. [765916-91-4]) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 98.9 mg (89% purity, 55% yield) of the desired title compound.

LC-MS (Method 1): R$_t$=1.44 min; MS (ESIpos): m/z=638 [M+H]$^+$ $^1$H-NMR (400 MHz, DMSO-d6) δ [ppm]: −0.12−−0.08 (m, 9H), 0.82-0.88 (m, 2H), 1.22 (s, 3H), 3.29 (d, 2H), 3.58-3.65 (m, 2H), 4.20 (d, 2H), 4.37 (d, 2H), 5.72 (s, 2H), 6.49 (br d, 1H), 6.67-6.75 (m, 1H), 7.31-7.38 (m, 2H), 7.43-7.49 (m, 1H), 7.52-7.56 (m, 1H), 7.78 (td, 1H), 8.04 (s, 1H), 8.24 (d, 1H), 9.01 (s, 1H).

Intermediate 185

N-{4-[(3-[3-cyano-4-(2-methylpropoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

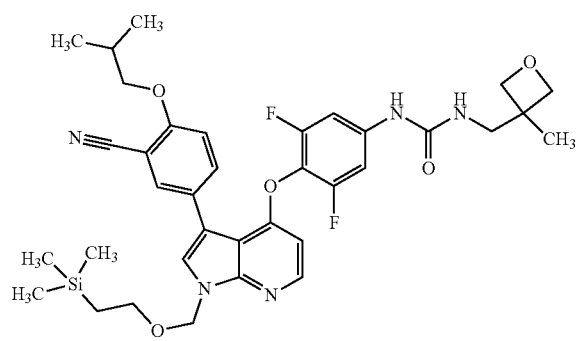 [SMILES: CC(C)COc1ccc(-c2cn(COCC[Si](C)(C)C)c3nccc(Oc4c(F)cc(NC(=O)NCC5(C)COC5)cc4F)c23)cc1C#N]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 μmol, intermediate 24) was reacted with [3-cyano-4-(2-methylpropoxy)phenyl]boronic acid (66.0 mg, 301 μmol, CAS No. [876918-32-0]) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 93.6 mg (72% purity, 39% yield) of the desired title compound.

LC-MS (Method 2): R$_t$=1.60 min; MS (ESIpos): m/z=692 [M+H]$^+$ $^1$H-NMR (400 MHz, DMSO-d6) δ [ppm]: −0.11−−0.07 (m, 9H), 0.82-0.88 (m, 2H), 1.00 (d, 6H), 1.23 (s, 3H), 2.01-2.11 (m, 1H), 3.30 (d, 2H), 3.56-3.62 (m, 2H), 3.93 (d, 2H), 4.21 (d, 2H), 4.38 (d, 2H), 5.67 (s, 2H), 6.45 (d, 1H), 6.74 (br t, 1H), 7.30 (d, 1H), 7.36-7.44 (m, 2H), 7.89-7.94 (m, 3H), 8.18 (d, 1H), 9.04 (s, 1H).

Intermediate 186

N-{4-[(3-[3-cyano-4-(2,2,2-trifluoroethoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

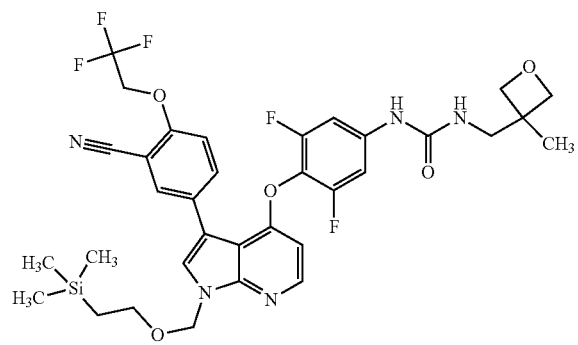 [SMILES: CC1(CNC(=O)Nc2cc(F)c(Oc3ccnc4c3c(-c3ccc(OCC(F)(F)F)c(C#N)c3)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with 3-cyano-4-(2,2,2-trifluoroethoxy)phenyl]boronic acid (73.8 mg, 301 µmol, CAS No. [876918-84-2]) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 69.2 mg (69% purity, 26% yield) of the desired title compound.

LC-MS (Method 2): $R_t$=1.48 min; MS (ESIneg): m/z=716 [M−H]⁻

¹H-NMR (400 MHz, DMSO-d6) δ [ppm]: −0.12−−0.07 (m, 9H), 0.82-0.88 (m, 2H), 0.90 (s, 3H), 3.16-3.30 (m, 2H), 3.47-3.55 (m, 2H), 3.56-3.62 (m, 2H), 3.87 (br d, 2H), 4.04-4.09 (m, 2H), 5.67 (s, 2H), 6.46 (d, 1H), 7.45 (d, 1H), 7.49-7.69 (m, 3H), 7.95-8.02 (m, 3H), 8.19 (d, 1H), 9.05 (br s, 1H).

Intermediate 187

N-(4-{[3-(3-cyanophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

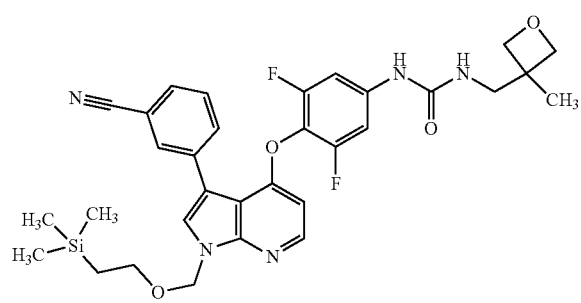 [SMILES: CC1(CNC(=O)Nc2cc(F)c(Oc3ccnc4c3c(-c3cccc(C#N)c3)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with (3-cyanophenyl)boronic acid (44.3 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 97.5 mg (94% purity, 59% yield) of the desired title compound.

LC-MS (Method 2): $R_t$=1.47 min; MS (ESIpos): m/z=620 [M+H]⁺

¹H-NMR (400 MHz, DMSO-d6) δ [ppm]: −0.11−−0.07 (m, 9H), 0.82-0.89 (m, 2H), 1.23 (s, 3H), 3.30 (d, 2H), 3.57-3.63 (m, 2H), 4.21 (d, 2H), 4.38 (d, 2H), 5.69 (s, 2H), 6.49 (d, 1H), 6.73 (t, 1H), 7.36-7.44 (m, 2H), 7.62 (t, 1H), 7.73 (dt, 1H), 8.00 (ddd, 1H), 8.04 (s, 1H), 8.07 (t, 1H), 8.21 (d, 1H), 9.04 (s, 1H).

Intermediate 188

5-[4-(2,6-difluoro-4-nitrophenoxy)-1-{[2-(trimethylsilyl)ethoxy]methyl}-1H-pyrrolo[2,3-b]pyridin-3-yl]-2-methoxybenzonitrile

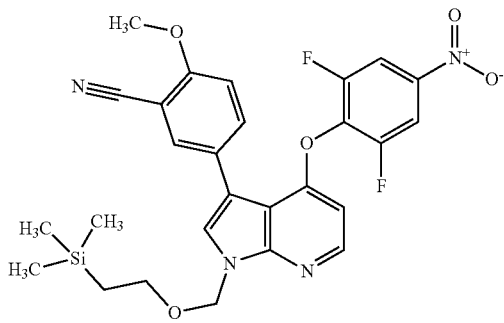 [SMILES: COc1ccc(-c2cn(COCC[Si](C)(C)C)c3nccc(Oc4c(F)cc([N+](=O)[O-])cc4F)c23)cc1C#N]

In analogy to intermediate 17, 3-bromo-4-(2,6-difluoro-4-nitrophenoxy)-1-{[2-(trimethylsilyl)ethoxy]methyl}-1H-pyrrolo[2,3-b]pyridine (400 mg, 799 µmol intermediate 16) was reacted with (3-cyano-4-methoxyphenyl)boronic acid (283 mg, 1.60 mmol, CAS No. [911210-48-5]) in the presence of [1,1'-bis (diphenylphosphino)ferrocene]dichloropalladium(II) (58.5 mg, 79.9 µmol) and potassium carbonate (552 mg, 4.00 mmol) in water (4.0 mL) and dioxane (8.0 mL). After purification using a Biotage chromatography system we obtained 404 mg (95% purity, 87% yield) of the desired title compound.

LC-MS (Method 2): $R_t$=1.58 min; MS (ESIpos): m/z=553 [M+H]⁺

¹H-NMR (400 MHz, DMSO-d6) δ [ppm]: −0.14−−0.07 (m, 9H), 0.81-0.88 (m, 2H), 3.56-3.63 (m, 2H), 3.92 (s, 3H), 5.69 (s, 2H), 6.66 (d, 1H), 7.31 (d, 1H), 7.89-7.94 (m, 2H), 7.97 (s, 1H), 8.23 (d, 1H), 8.42 (d, 2H).

Intermediate 189

5-[4-(4-amino-2,6-difluorophenoxy)-1-{[2-(trimethylsilyl)ethoxy]methyl}-1H-pyrrolo[2,3-b]pyridin-3-yl]-2-methoxybenzonitrile

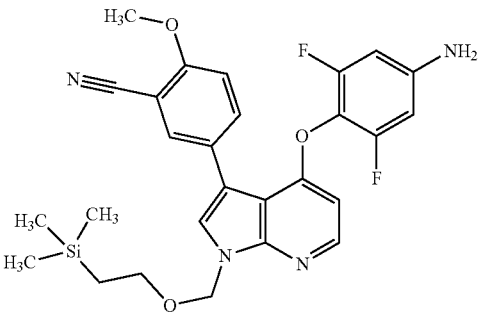 [SMILES: COc1ccc(-c2cn(COCC[Si](C)(C)C)c3nccc(Oc4c(F)cc(N)cc4F)c23)cc1C#N]

In analogy to intermediate 18, 5-[4-(2,6-difluoro-4-nitrophenoxy)-1-{[2-(trimethylsilyl)ethoxy]methyl}-1H-pyrrolo[2,3-b]pyridin-3-yl]-2-methoxybenzonitrile (401 mg, 726 µmol, intermediate 188) was reacted with iron powder (203 mg, 3.63 mmol) and ammonium chloride (194 mg, 3.63 mmol) in a mixture of water (7.2 mL), tetrahydrofuran (3.6 mL) and methanol (3.6 mL). After purification using a Biotage chromatography system we obtained 316 mg (100% purity, 83% yield) of the desired title compound.

LC-MS (Method 2): $R_t$=1.48 min; MS (ESIneg): m/z=521 [M−H]⁻

¹H-NMR (400 MHz, DMSO-d6) δ [ppm]: −0.11--0.07 (m, 9H), 0.81-0.88 (m, 2H), 3.55-3.62 (m, 2H), 3.93 (s, 3H), 5.66 (s, 2H), 5.82 (s, 2H), 6.37-6.43 (m, 3H), 7.31 (d, 1H), 7.88-7.97 (m, 3H), 8.18 (d, 1H).

Intermediate 190 phenyl (4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)carbamate

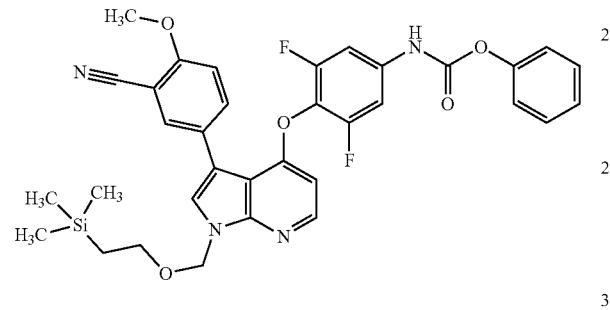

In analogy to intermediate 1, 5-[4-(4-amino-2,6-difluorophenoxy)-1-{[2-(trimethylsilyl)ethoxy]methyl}-1H-pyrrolo[2,3-b]pyridin-3-yl]-2-methoxybenzonitrile (312 mg, 597 μmol, intermediate 189) was reacted with phenyl carbonochloridate (82 μL, 660 μmol) in a mixture pyridine (280 μL) and THF (4.2 mL). After purification using a Biotage chromatography system we obtained 361 mg (100% purity, 94% yield) of the desired title compound.

LC-MS (Method 2): $R_t$=1.61 min; MS (ESIpos): m/z=643 [M+H]⁺

¹H-NMR (400 MHz, DMSO-d6) δ [ppm]: −0.09--0.07 (m, 9H), 0.81-0.89 (m, 2H), 3.56-3.63 (m, 2H), 3.93 (s, 3H), 5.67 (s, 2H), 6.48 (d, 1H), 7.24-7.34 (m, 4H), 7.42-7.50 (m, 4H), 7.92-7.97 (m, 3H), 8.20 (d, 1H), 10.80 (s, 1H).

Intermediate 191

N-(4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

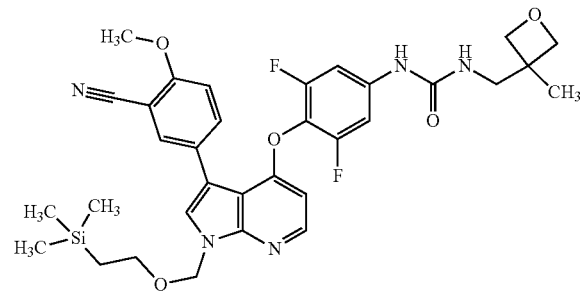 [SMILES: COc1ccc(-c2cn(COCC[Si](C)(C)C)c3nccc(Oc4c(F)cc(NC(=O)NCC5(C)COC5)cc4F)c23)cc1C#N]

In analogy to intermediate 2, phenyl (4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)carbamate (270 mg, 420 μmol, intermediate 190) was reacted with 1-(3-methyloxetan-3-yl)methanamine (42.5 mg, 420 μmol) in DMF (2.1 mL). After purification using a Biotage chromatography system we obtained 264 mg (100% purity, 97% yield) of the desired title compound.

LC-MS (Method 2): $R_t$=1.45 min; MS (ESIpos): m/z=650 [M+H]⁺

¹H-NMR (400 MHz, DMSO-d6) δ [ppm]: −0.10--0.06 (m, 9H), 0.81-0.89 (m, 2H), 1.23 (s, 3H), 3.30 (d, 2H), 3.55-3.62 (m, 2H), 3.93 (s, 3H), 4.21 (d, 2H), 4.38 (d, 2H), 5.67 (s, 2H), 6.46 (d, 1H), 6.72 (t, 1H), 7.29-7.34 (m, 1H), 7.37-7.43 (m, 2H), 7.91-7.97 (m, 3H), 8.19 (d, 1H), 9.02 (s, 1H).

Intermediate 192

2-[4-(2,6-difluoro-4-nitrophenoxy)-1-{[2-(trimethylsilyl)ethoxy]methyl}-1H-pyrrolo[2,3-b]pyridin-3-yl]benzonitrile

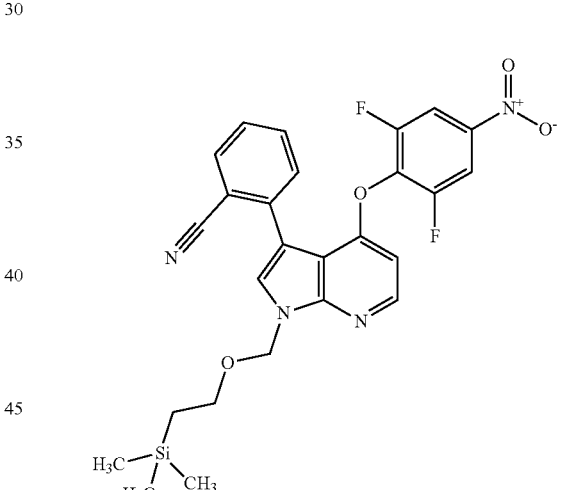

In analogy to intermediate 17, 3-bromo-4-(2,6-difluoro-4-nitrophenoxy)-1-{[2-(trimethylsilyl)ethoxy]methyl}-1H-pyrrolo[2,3-b]pyridine (500 mg, 999 μmol, intermediate 16) was reacted with (2-cyanophenyl)boronic acid (294 mg, 2.00 mmol) in the presence of [1,1'-bis(diphenylphosphino)ferrocene]dichloropalladium(II) (73.1 mg, 99.9 μmol) and potassium carbonate (691 mg, 5.00 mmol) in water (5.0 mL) and dioxane (10 mL). After purification using a Biotage chromatography system we obtained 192 mg (32% purity, 12% yield) of the desired title compound.

LC-MS (Method 2): $R_t$=1.57 min; MS (ESIpos): m/z=523 [M+H]⁺

Intermediate 193

2-[4-(4-amino-2,6-difluorophenoxy)-1-{[2-(trimethylsilyl)ethoxy]methyl}-1H-pyrrolo[2,3-b]pyridin-3-yl]benzonitrile

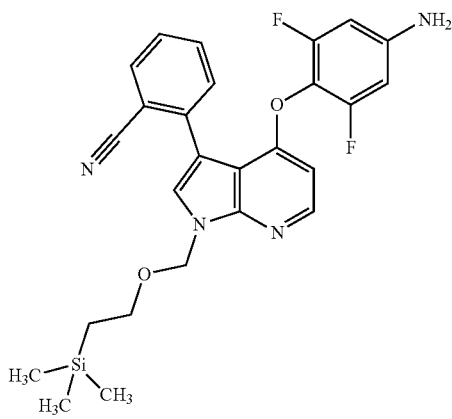 [SMILES: C[Si](C)(C)CCOCn1cc(-c2ccccc2C#N)c2c(Oc3c(F)cc(N)cc3F)ccnc21]

In analogy to intermediate 18, 2-[4-(2,6-difluoro-4-nitrophenoxy)-1-{[2-(trimethylsilyl)ethoxy]methyl}-1H-pyrrolo[2,3-b]pyridin-3-yl]benzonitrile (188 mg, 360 µmol, intermediate 192) was reacted with iron powder (100 mg, 1.80 mmol) and ammonium chloride (96.2 mg, 1.80 mmol) in a mixture of water (3.6 mL), tetrahydrofuran (1.8 mL) and methanol (1.8 mL). After purification using a Biotage chromatography system we obtained 45.1 mg (86% purity, 22% yield) of the desired title compound.

LC-MS (Method 2): $R_t$=1.50 min; MS (ESIpos): m/z=493 [M+H]$^+$ $^1$H-NMR (400 MHz, DMSO-d6) δ [ppm]: −0.11−−0.07 (m, 9H), 0.81-0.88 (m, 2H), 3.58-3.64 (m, 2H), 5.71 (s, 2H), 5.78 (s, 2H), 6.29-6.37 (m, 2H), 6.42 (d, 1H), 7.46-7.52 (m, 1H), 7.66-7.73 (m, 2H), 7.87-7.90 (m, 1H), 7.92 (s, 1H), 8.21 (d, 1H).

Intermediate 194 phenyl (4-{[3-(2-cyanophenyl)-1-{[2-(trimethylsilyl)ethoxy]methyl}-1H-pyrrolo[2,3-b]pyridin-4-yl]oxy}-3,5-difluorophenyl)carbamate

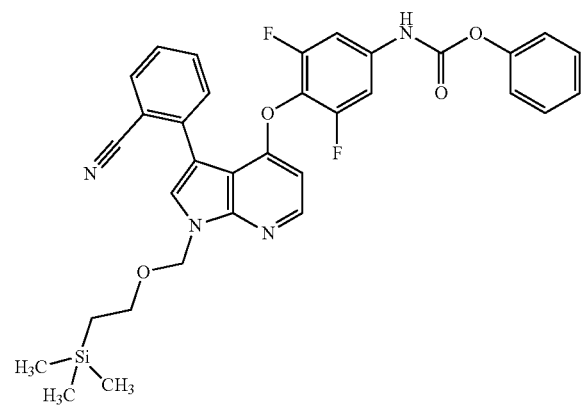 [SMILES: C[Si](C)(C)CCOCn1cc(-c2ccccc2C#N)c2c(Oc3c(F)cc(NC(=O)Oc4ccccc4)cc3F)ccnc21]

In analogy to intermediate 1, 2-[4-(4-amino-2,6-difluorophenoxy)-1-{[2-(trimethylsilyl)ethoxy]methyl}-1H-pyrrolo[2,3-b]pyridin-3-yl]benzonitrile (43.0 mg, 87.3 µmol, intermediate 193) was reacted with phenyl carbonochloridate (12 µL, 96 µmol) in a mixture pyridine (510 µL) and THF (600 µL). After purification using a Biotage chromatography system we obtained 54.2 mg (91% purity, 92% yield) of the desired title compound.

LC-MS (Method 2): $R_t$=1.60 min; MS (ESIpos): m/z=613 [M+H]$^+$

Intermediate 195

N-(4-{[3-(2-cyanophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

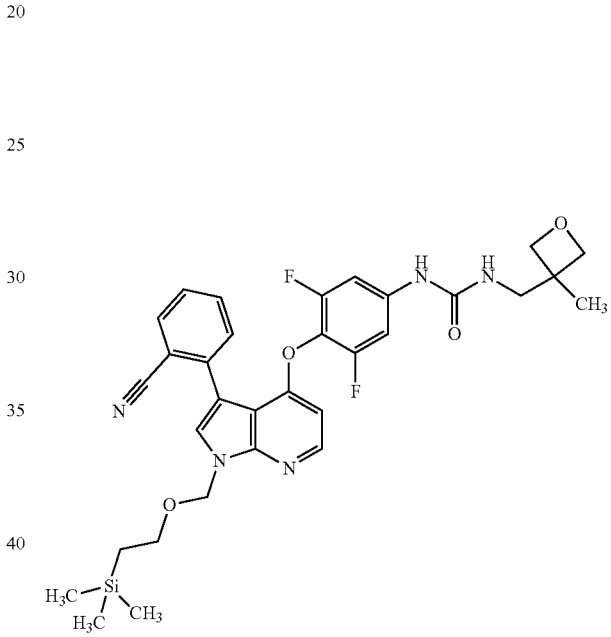

In analogy to intermediate 2, phenyl (4-{[3-(2-cyanophenyl)-1-{[2-(trimethylsilyl)ethoxy]methyl}-1H-pyrrolo[2,3-b]pyridin-4-yl]oxy}-3,5-difluorophenyl)carbamate (51.0 mg, 83.2 µmol, intermediate 194) was reacted with 1-(3-methyloxetan-3-yl)methanamine (8.42 mg, 83.2 µmol) in DMF (400 µL). After purification using a Biotage chromatography system we obtained 37.9 mg (90% purity, 66% yield) of the desired title compound.

LC-MS (Method 2): $R_t$=1.44 min; MS (ESIpos): m/z=620 [M+H]$^+$ $^1$H-NMR (400 MHz, DMSO-d6) δ [ppm]: −0.11−−0.06 (m, 9H), 0.82-0.88 (m, 2H), 1.22 (s, 3H), 3.28 (d, 2H), 3.58-3.65 (m, 2H), 4.20 (d, 2H), 4.37 (d, 2H), 5.72 (s, 2H), 6.46 (d, 1H), 6.80 (br s, 1H), 7.30-7.38 (m, 2H), 7.49 (ddd, 1H), 7.67-7.74 (m, 2H), 7.86-7.92 (m, 1H), 7.95 (s, 1H), 8.22 (d, 1H), 9.10 (br s, 1H).

Intermediate 196

N-{4-[(3-[4-cyano-2-(propan-2-yl)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

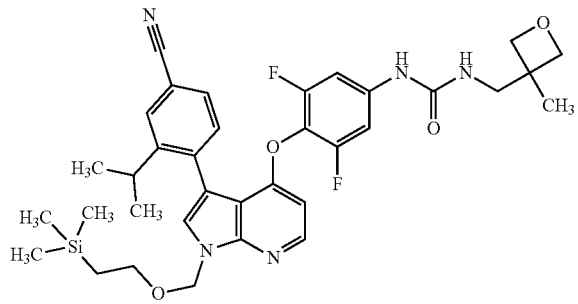 [SMILES: CC(C)c1cc(C#N)ccc1-c1cn(COCC[Si](C)(C)C)c2nccc(Oc3c(F)cc(NC(=O)NCC4(C)COC4)cc3F)c12]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with 3-(propan-2-yl)-4-(4,4,5,5-tetramethyl-1,3,2-dioxaborolan-2-yl)benzonitrile (74.9 mg, 276 µmol, purchased from Enamine Ltd.) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 77.5 mg (66% purity, 31% yield) of the desired title compound.

LC-MS (Method 2): $R_t$=1.55 min; MS (ESIpos): m/z=662 [M+H]$^+$

Intermediate 197

N-(4-{[3-(6-cyanopyridin-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

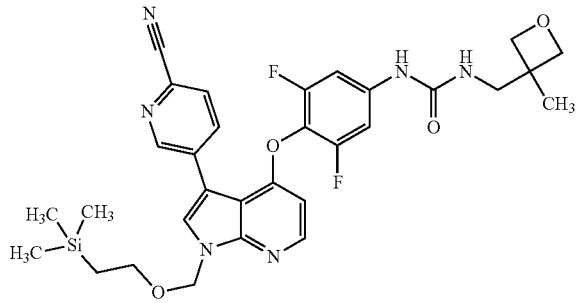 [SMILES: CC1(CNC(=O)Nc2cc(F)c(Oc3ccnc4c3c(-c3ccc(C#N)nc3)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with (6-cyanopyridin-3-yl)boronic acid (44.6 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 88.4 mg (74% purity, 42% yield) of the desired title compound.

LC-MS (Method 2): $R_t$=1.42 min; MS (ESIpos): m/z=621 [M+H]$^+$ $^1$H-NMR (400 MHz, DMSO-d6) δ [ppm]: −0.11–−0.07 (m, 9H), 0.83-0.89 (m, 2H), 1.23 (s, 3H), 3.30 (d, 2H), 3.58-3.64 (m, 2H), 4.21 (d, 2H), 4.38 (d, 2H), 5.71 (s, 2H), 6.54 (d, 1H), 6.69-6.76 (m, 1H), 7.36-7.44 (m, 2H), 8.09 (dd, 1H), 8.23-8.26 (m, 2H), 8.27 (dd, 1H), 9.01-9.05 (m, 1H), 9.06 (dd, 1H).

Intermediate 198

N-(4-{[3-(4-cyano-2-methylphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

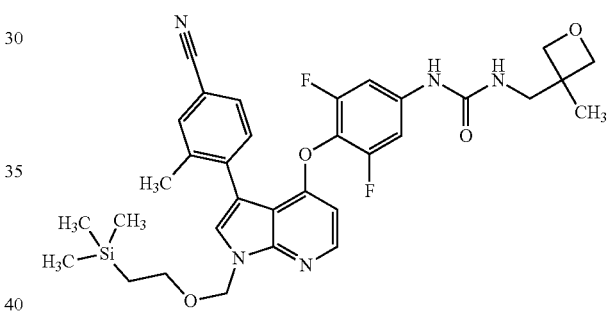

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with (4-cyano-2-methylphenyl)boronic acid (48.5 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 75.1 mg (90% purity, 42% yield) of the desired title compound.

LC-MS (Method 2): $R_t$=1.50 min; MS (ESIpos): m/z=634 [M+H]$^+$ $^1$H-NMR (400 MHz, DMSO-d6) δ [ppm]: −0.13–−0.09 (m, 9H), 0.79-0.85 (m, 2H), 1.22 (s, 3H), 2.34 (s, 3H), 3.28 (d, 2H), 3.56-3.62 (m, 2H), 4.20 (d, 2H), 4.37 (d, 2H), 5.69 (s, 2H), 6.40 (d, 1H), 6.69 (t, 1H), 7.29-7.36 (m, 2H), 7.52 (d, 1H), 7.67 (dd, 1H), 7.75-7.78 (m, 2H), 8.19 (d, 1H), 8.99 (s, 1H).

Intermediate 199

N-(4-{[3-(4-cyano-3-methylphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

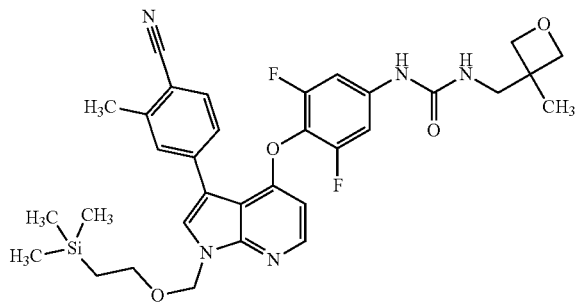 [SMILES: Cc1cc(-c2cn(COCC[Si](C)(C)C)c3nccc(Oc4c(F)cc(NC(=O)NCC5(C)COC5)cc4F)c23)ccc1C#N]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with (4-cyano-3-methylphenyl)boronic acid (48.5 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 75.0 mg (88% purity, 41% yield) of the desired title compound.

LC-MS (Method 2): $R_t$=1.51 min; MS (ESIpos): m/z=634 [M+H]$^+$ $^1$H-NMR (400 MHz, DMSO-d6) δ [ppm]: −0.12--0.08 (m, 9H), 0.81-0.88 (m, 2H), 1.23 (s, 3H), 2.48 (s, 3H), 3.30 (d, 2H), 3.56-3.62 (m, 2H), 4.21 (d, 2H), 4.38 (d, 2H), 5.69 (s, 2H), 6.49 (d, 1H), 6.72 (t, 1H), 7.35-7.45 (m, 2H), 7.67 (dd, 1H), 7.77-7.80 (m, 2H), 8.04 (s, 1H), 8.21 (d, 1H), 9.03 (s, 1H).

Intermediate 200

N-{4-[(3-[4-cyano-3-(trifluoromethyl)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

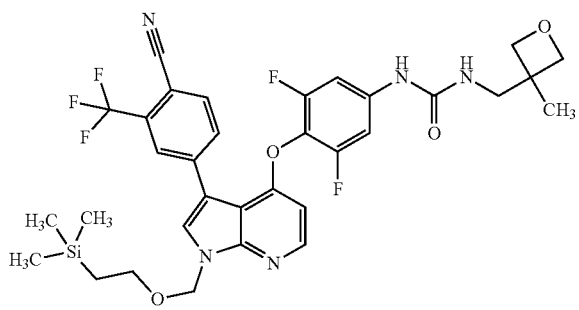 [SMILES: CC1(CNC(=O)Nc2cc(F)c(Oc3ccnc4c3c(-c3ccc(C#N)c(C(F)(F)F)c3)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with [4-cyano-3-(trifluoromethyl)phenyl]boronic acid (64.7 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 99.3 mg (77% purity, 44% yield) of the desired title compound.

LC-MS (Method 2): $R_t$=1.54 min; MS (ESIpos): m/z=688 [M+H]$^+$ $^1$H-NMR (400 MHz, DMSO-d6) δ [ppm]: −0.11--0.07 (m, 9H), 0.82-0.89 (m, 2H), 1.23 (s, 3H), 3.30 (d, 2H), 3.57-3.64 (m, 2H), 4.21 (d, 2H), 4.38 (d, 2H), 5.71 (s, 2H), 6.55 (d, 1H), 6.73 (t, 1H), 7.36-7.45 (m, 3H), 8.13-8.27 (m, 3H), 8.32 (s, 1H), 9.04 (s, 1H).

Intermediate 201

N-{3,5-difluoro-4-[(3-[2-(propan-2-yl)phenyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

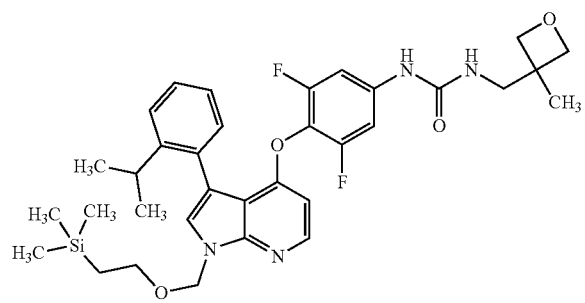 [SMILES: CC(C)c1ccccc1-c1cn(COCC[Si](C)(C)C)c2nccc(Oc3c(F)cc(NC(=O)NCC4(C)COC4)cc3F)c12]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with [2-(propan-2-yl)phenyl]boronic acid (49.4 mg, 301 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 66.1 mg (82% purity, 34% yield) of the desired title compound.

LC-MS (Method 2): $R_t$=1.60 min; MS (ESIpos): m/z=637 [M+H]$^+$

Intermediate 202

N-(4-{[3-(4-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

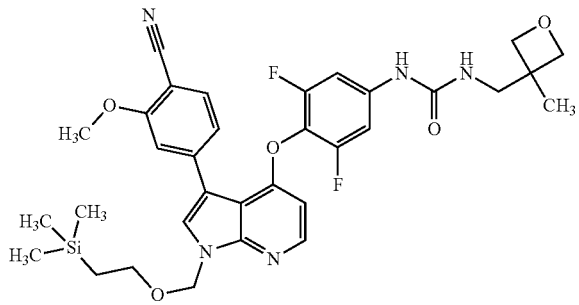 [SMILES: COc1cc(-c2cn(COCC[Si](C)(C)C)c3nccc(Oc4c(F)cc(NC(=O)NCC5(C)COC5)cc4F)c23)ccc1C#N]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 μmol, intermediate 24) was reacted with (4-cyano-3-methoxyphenyl)boronic acid (53.3 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 97.9 mg (89% purity, 54% yield) of the desired title compound.

LC-MS (Method 2): $R_t$=1.47 min; MS (ESIpos): m/z=650 [M+H]$^+$ $^1$H-NMR (400 MHz, DMSO-d6) δ [ppm]: −0.12-−0.06 (m, 9H), 0.82-0.89 (m, 2H), 1.23 (s, 3H), 3.30 (d, 2H), 3.56-3.63 (m, 2H), 3.90 (s, 3H), 4.21 (d, 2H), 4.38 (d, 2H), 5.70 (s, 2H), 6.50 (d, 1H), 6.73 (t, 1H), 7.36-7.45 (m, 3H), 7.53 (s, 1H), 7.74 (d, 1H), 8.13 (s, 1H), 8.22 (d, 1H), 9.04 (s, 1H).

Intermediate 203

N-(4-{[3-(4-cyano-2-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

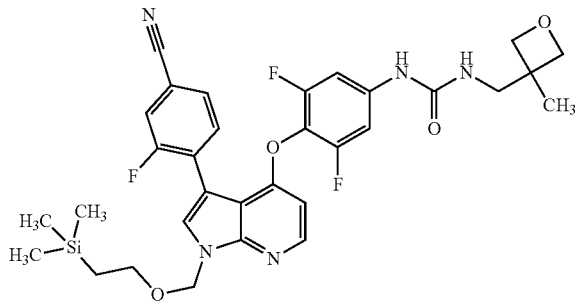 [SMILES: CC1(CNC(=O)Nc2cc(F)c(Oc3ccnc4c3c(-c3ccc(C#N)cc3F)cn4COCC[Si](C)(C)C)c(F)c2)COC1]

In analogy to intermediate 36, N-{4-[(3-bromo-1-{[2-(trimethyl silyl)ethoxy]methyl}-1H-pyrrolo[2,3-b]pyridin-4-yl)oxy]-3,5-difluorophenyl}-N'-[(3-methyl oxetan-3-yl)methyl]urea (150 mg, 251 μmol, intermediate 24) was reacted with (4-cyano-2-fluorophenyl)boronic acid (49.7 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 86.6 mg (89% purity, 48% yield) of the desired title compound.

LC-MS (Method 2): $R_t$=1.48 min; MS (ESIpos): m/z=638 [M+H]$^+$ $^1$H-NMR (400 MHz, DMSO-d6) δ [ppm]: −0.12-−0.07 (m, 9H), 0.82-0.87 (m, 2H), 1.23 (s, 3H), 3.29 (d, 2H), 3.57-3.64 (m, 2H), 4.20 (d, 2H), 4.38 (d, 2H), 5.71 (s, 2H), 6.47 (d, 1H), 6.71 (t, 1H), 7.36 (d, 2H), 7.72-7.80 (m, 2H), 7.92 (dd, 1H), 7.98 (d, 1H), 8.21 (d, 1H), 9.01 (s, 1H).

Intermediate 204

N-(4-{[3-(4-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

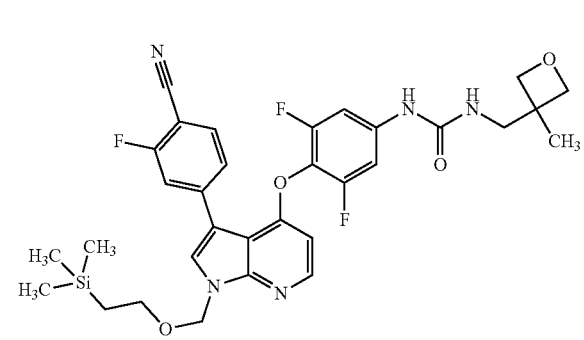 [SMILES: CC1(CNC(=O)Nc2cc(F)c(Oc3ccnc4c3c(-c3ccc(C#N)c(F)c3)cn4COCC[Si](C)(C)C)c(F)c2)COC1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 μmol, intermediate 24) was reacted with (4-cyano-3-fluorophenyl)boronic acid (49.7 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 72.8 mg (84% purity, 38% yield) of the desired title compound.

LC-MS (Method 2): $R_t$=1.50 min; MS (ESIpos): m/z=638 [M+H]$^+$ $^1$H-NMR (400 MHz, DMSO-d6) δ [ppm]: −0.11-−0.07 (m, 9H), 0.82-0.88 (m, 2H), 1.23 (s, 3H), 3.30 (d, 2H), 3.57-3.63 (m, 2H), 4.21 (d, 2H), 4.38 (d, 2H), 5.69 (s, 2H), 6.53 (d, 1H), 6.71-6.77 (m, 1H), 7.38-7.45 (m, 2H), 7.74 (dd, 1H), 7.78 (dd, 1H), 7.95 (t, 1H), 8.21 (s, 1H), 8.23 (d, 1H), 9.05 (s, 1H).

Intermediate 205

N-(4-{[3-(2-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

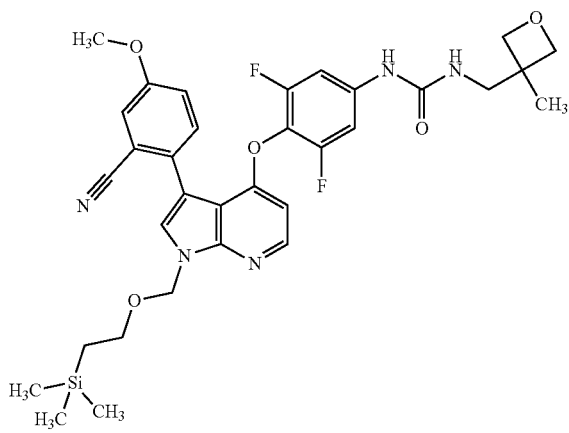 [SMILES: COc1ccc(-c2cn(COCC[Si](C)(C)C)c3nccc(Oc4c(F)cc(NC(=O)NCC5(C)COC5)cc4F)c23)c(C#N)c1]

In analogy to intermediate 36, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (150 mg, 251 µmol, intermediate 24) was reacted with 5-methoxy-2-(4,4,5,5-tetramethyl-1,3,2-dioxaborolan-2-yl)benzonitrile (78.1 mg, 301 µmol, CAS No. [1116097-04-1]) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 63.7 mg (70% purity, 27% yield) of the desired title compound.

LC-MS (Method 1): $R_t$=1.44 min; MS (ESIpos): m/z=650 [M+H]$^+$

Intermediate 206

N-{4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}-N'-{[3-(propan-2-yl)oxetan-3-yl]methyl}urea

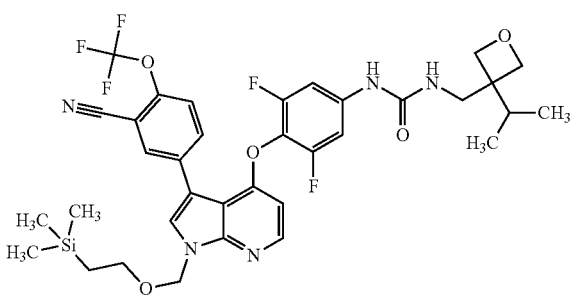 [SMILES: CC(C)C1(CNC(=O)Nc2cc(F)c(Oc3ccnc4c3c(-c3ccc(OC(F)(F)F)c(C#N)c3)cn4COCC[Si](C)(C)C)c(F)c2)COC1]

In analogy to intermediate 2, phenyl {4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}carbamate (100 mg, 144 µmol, intermediate 179) was reacted with 1-[3-(propan-2-yl)oxetan-3-yl]methanamine (22.6 mg, 175 µmol) in DMF (950 µL). After purification using a Biotage chromatography system we obtained 113 mg (100% purity, 97% yield) of the desired title compound.

LC-MS (Method 2): $R_t$=1.63 min; MS (ESIpos): m/z=732 [M+H]$^+$ $^1$H-NMR (400 MHz, DMSO-d6) δ [ppm]: −0.11−−0.07 (m, 9H), 0.82-0.88 (m, 2H), 0.91 (d, 6H), 2.01 (spt, 1H), 3.32 (d, 2H), 3.57-3.63 (m, 2H), 4.28-4.34 (m, 4H), 5.69 (s, 2H), 6.52 (d, 1H), 6.73 (t, 1H), 7.38-7.45 (m, 2H), 7.76 (dq, 1H), 8.10-8.15 (m, 2H), 8.23 (d, 1H), 8.25 (d, 1H), 9.10 (s, 1H).

Intermediate 207

(+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1-(oxetan-3-yl)ethyl]urea

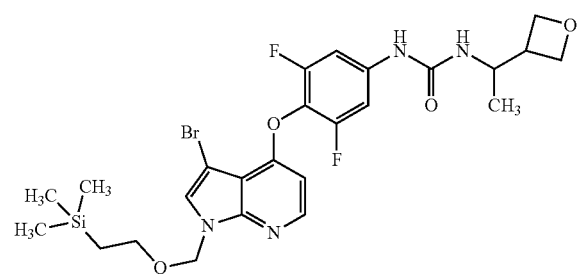 [SMILES: CC(NC(=O)Nc1cc(F)c(Oc2ccnc3c2c(Br)cn3COCC[Si](C)(C)C)c(F)c1)C1COC1]

In analogy to intermediate 2, {4-[(3-bromo-1-{[2-(trimethylsilyl)ethoxy]methyl}-1H-pyrrolo[2,3-b]pyridin-4-yl)oxy]-3,5-difluorophenyl}carbamate (2.60 g, 4.40 mmol, intermediate 22) was reacted with (+/−)-1-(oxetan-3-yl)ethan-1-amine (490 mg, 4.84 mmol) in DMF (22 mL). After purification using a Biotage chromatography system we obtained 2.96 g (97% purity, 109% yield) of the desired title compound.

LC-MS (Method 1): $R_t$=1.47 min; MS (ESIpos): m/z=599 [M+H]$^+$ $^1$H-NMR (400 MHz, DMSO-d6) δ [ppm]: −0.11−−0.07 (m, 9H), 0.79-0.86 (m, 2H), 1.02 (d, 3H), 2.95-3.05 (m, 1H), 3.50-3.56 (m, 2H), 3.98-4.08 (m, 1H), 4.31 (t, 1H), 4.39 (t, 1H), 4.56-4.62 (m, 2H), 5.60 (s, 2H), 6.39-6.44 (m, 1H), 6.71-6.77 (m, 1H), 7.36-7.42 (m, 2H), 7.87 (s, 1H), 8.17 (d, 1H), 8.90 (s, 1H).

Intermediate 208

(+/−)—N-(4-{[3-(4-cyano-2-fluorophenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

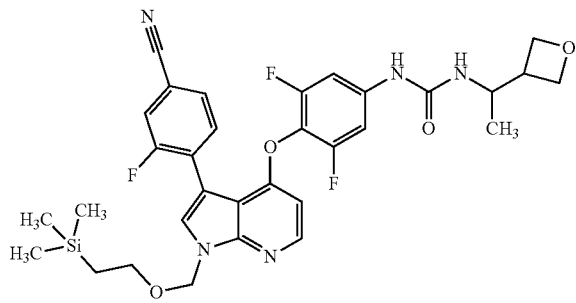 [SMILES: CC(NC(=O)Nc1cc(F)c(Oc2ccnc3c2c(-c2ccc(C#N)cc2F)cn3COCC[Si](C)(C)C)c(F)c1)C1COC1]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-2-fluorophenyl)boronic acid (49.7 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 53.1 mg (86% purity, 29% yield) of the desired title compound.

LC-MS (Method 1): $R_t$=1.48 min; MS (ESIpos): m/z=638 [M+H]$^+$ $^1$H-NMR (400 MHz, DMSO-d6) δ [ppm]: −0.12--−0.06 (m, 9H), 0.81-0.88 (m, 2H), 1.01 (d, 3H), 2.95-3.05 (m, 1H), 3.57-3.63 (m, 2H), 3.97-4.07 (m, 1H), 4.28-4.41 (m, 2H), 4.56-4.62 (m, 2H), 5.71 (s, 2H), 6.42-6.50 (m, 2H), 7.31-7.38 (m, 2H), 7.72-7.80 (m, 2H), 7.92 (dd, 1H), 7.98 (d, 1H), 8.22 (d, 1H), 8.87 (s, 1H).

Intermediate 209

(+/−)—N-(4-{[3-(4-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

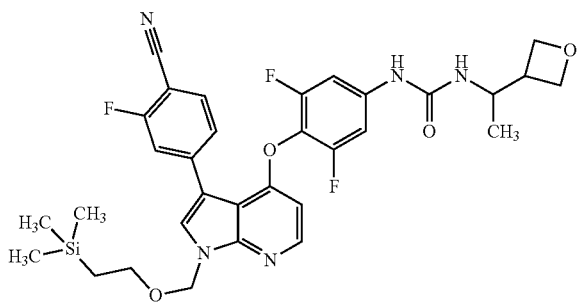 [SMILES: CC(NC(=O)Nc1cc(F)c(Oc2ccnc3c2c(-c2ccc(C#N)c(F)c2)cn3COCC[Si](C)(C)C)c(F)c1)C1COC1]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-3-fluorophenyl)boronic acid (49.7 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 59.7 mg (86% purity, 32% yield) of the desired title compound.

LC-MS (Method 1): $R_t$=1.50 min; MS (ESIpos): m/z=638 [M+H]$^+$ $^1$H-NMR (400 MHz, DMSO-d6) δ [ppm]: −0.11--−0.07 (m, 9H), 0.82-0.88 (m, 2H), 1.02 (d, 3H), 2.95-3.05 (m, 1H), 3.57-3.63 (m, 2H), 3.98-4.08 (m, 1H), 4.31 (t, 1H), 4.39 (t, 1H), 4.59 (ddd, 2H), 5.69 (s, 2H), 6.47-6.51 (m, 1H), 6.53 (d, 1H), 7.37-7.43 (m, 2H), 7.74 (dd, 1H), 7.77 (dd, 1H), 7.95 (t, 1H), 8.21 (s, 1H), 8.24 (d, 1H), 8.92 (s, 1H).

Intermediate 210

(+/−)—N-(4-{[3-(4-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

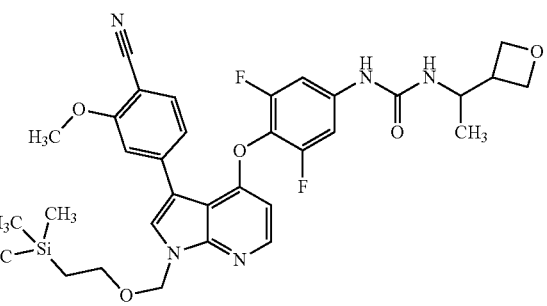

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-3-methoxyphenyl)boronic acid (61.4 mg, 347 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 61.7 mg (90% purity, 29% yield) of the desired title compound.

LC-MS (Method 1): $R_t$=1.47 min; MS (ESIpos): m/z=650 [M+H]$^+$ $^1$H-NMR (400 MHz, DMSO-d6) δ [ppm]: −0.11--−0.07 (m, 9H), 0.82-0.89 (m, 2H), 1.02 (d, 3H), 2.95-3.05 (m, 1H), 3.57-3.63 (m, 2H), 3.90 (s, 3H), 3.98-4.08 (m, 1H), 4.31 (t, 1H), 4.38 (t, 1H), 4.59 (ddd, 2H), 5.70 (s, 2H), 6.46-6.51 (m, 2H), 7.35-7.44 (m, 3H), 7.53 (d, 1H), 7.74 (d, 1H), 8.13 (s, 1H), 8.22 (d, 1H), 8.91 (s, 1H).

Intermediate 211

(+/−)—N-(4-{[3-(4-cyano-3-methylphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

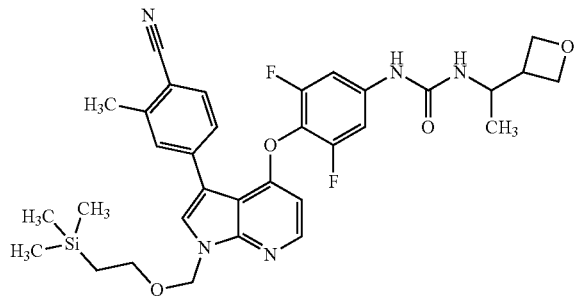 [SMILES: Cc1cc(-c2cn(COCC[Si](C)(C)C)c3nccc(Oc4c(F)cc(NC(=O)NC(C)C5COC5)cc4F)c23)ccc1C#N]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-3-methylphenyl)boronic acid (48.5 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 25.0 mg (71% purity, 11% yield) of the desired title compound.

LC-MS (Method 1): R$_t$=1.51 min; MS (ESIpos): m/z=634 [M+H]$^+$ $^1$H-NMR (400 MHz, DMSO-d6) δ [ppm]: −0.12−−0.07 (m, 9H), 0.82-0.88 (m, 2H), 1.02 (d, 3H), 2.94-3.05 (m, 1H), 3.59 (t, 2H), 3.98-4.07 (m, 1H), 4.31 (t, 1H), 4.39 (t, 1H), 4.57-4.62 (m, 2H), 5.69 (s, 2H), 6.49 (br d, 1H), 7.35-7.43 (m, 2H), 7.67 (dd, 1H), 7.75-7.82 (m, 2H), 7.78 (s, 1H), 8.04 (s, 1H), 8.21 (d, 1H), 8.91 (s, 1H).

Intermediate 212

(+/−)—N-(4-{[3-(6-cyanopyridin-3-yl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

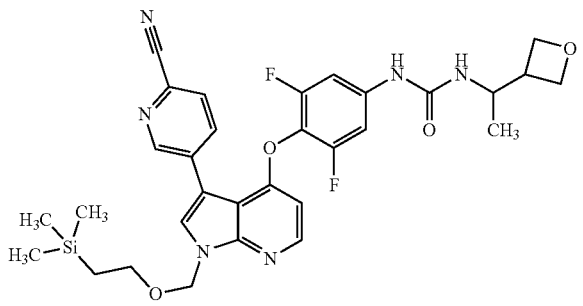 [SMILES: CC(NC(=O)Nc1cc(F)c(Oc2ccnc3c2c(-c2ccc(C#N)nc2)cn3COCC[Si](C)(C)C)c(F)c1)C1COC1]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (6-cyanopyridin-3-yl)boronic acid (44.6 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 80.3 mg (82% purity, 42% yield) of the desired title compound.

LC-MS (Method 1): R$_t$=1.41 min; MS (ESIpos): m/z=621 [M+H]$^+$ $^1$H-NMR (400 MHz, DMSO-d6) δ [ppm]: −0.12−−0.06 (m, 9H), 0.83-0.89 (m, 2H), 1.02 (d, 3H), 2.95-3.05 (m, 1H), 3.58-3.64 (m, 2H), 3.98-4.08 (m, 1H), 4.31 (t, 1H), 4.39 (t, 1H), 4.59 (ddd, 2H), 5.71 (s, 2H), 6.47-6.54 (m, 2H), 7.35-7.43 (m, 2H), 8.09 (dd, 1H), 8.22-8.29 (m, 2H), 8.92 (s, 1H), 9.06 (dd, 1H).

Intermediate 213

(+/−)—N-(4-{[3-(4-cyano-2-methylphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

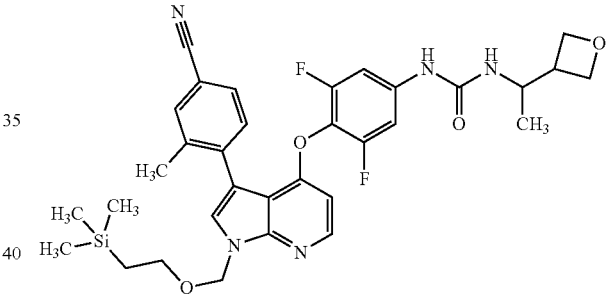

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-2-methylphenyl)boronic acid (48.5 mg, 301 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 79.3 mg (82% purity, 41% yield) of the desired title compound.

LC-MS (Method 1): R$_t$=1.49 min; MS (ESIpos): m/z=634 [M+H]$^+$ $^1$H-NMR (400 MHz, DMSO-d6) δ [ppm]: −0.12−−0.09 (m, 9H), 0.80-0.85 (m, 2H), 1.01 (d, 3H), 2.34 (s, 3H), 2.94-3.03 (m, 1H), 3.56-3.62 (m, 2H), 3.96-4.06 (m, 1H), 4.30 (t, 1H), 4.37 (t, 1H), 4.55-4.62 (m, 2H), 5.69 (s, 2H), 6.38-6.47 (m, 2H), 7.29-7.35 (m, 2H), 7.52 (d, 1H), 7.67 (dd, 1H), 7.74-7.78 (m, 2H), 8.19 (d, 1H), 8.86 (s, 1H).

Intermediate 214

(+/−)—N-(4-{[3-(2-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

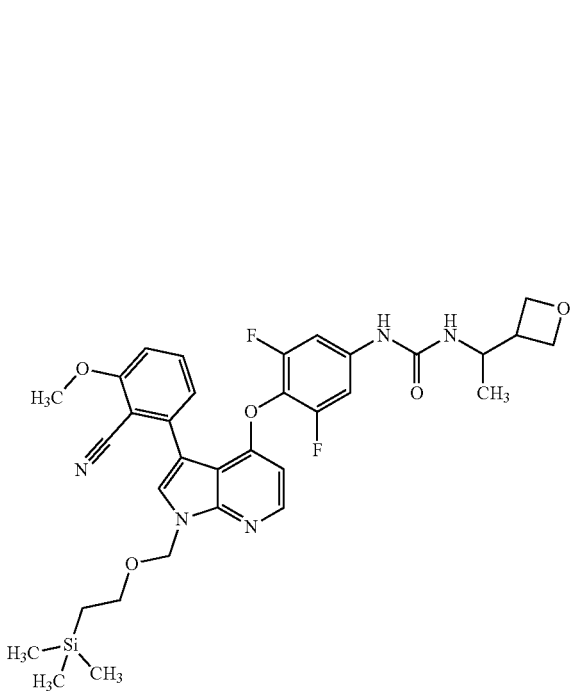 [SMILES: COc1cccc(-c2cn(COCC[Si](C)(C)C)c3nccc(Oc4c(F)cc(NC(=O)NC(C)C5COC5)cc4F)c23)c1C#N]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 µmol, intermediate 207) was reacted with 2-(5,5-dimethyl-1,3,2-dioxaborinan-2-yl)-6-methoxybenzonitrile (67.7 mg, 276 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 87.5 mg (79% purity, 42% yield) of the desired title compound.

LC-MS (Method 2): $R_t$=1.39 min; MS (ESIpos): m/z=650 [M+H]$^+$ $^1$H-NMR (400 MHz, DMSO-d6) δ [ppm]: −0.13–−0.07 (m, 9H), 0.81-0.88 (m, 2H), 1.01 (d, 3H), 2.93-3.04 (m, 1H), 3.57-3.63 (m, 2H), 3.93 (s, 3H), 3.98-4.06 (m, 1H), 4.30 (t, 1H), 4.35-4.40 (m, 1H), 4.58 (ddd, 2H), 5.70 (s, 2H), 6.42-6.47 (m, 2H), 7.17 (d, 1H), 7.22 (d, 1H), 7.29-7.36 (m, 2H), 7.64 (t, 1H), 7.89-7.94 (m, 1H), 8.18-8.23 (m, 1H), 8.86 (s, 1H).

Intermediate 215

(+/−)—N-(4-{[3-(2-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

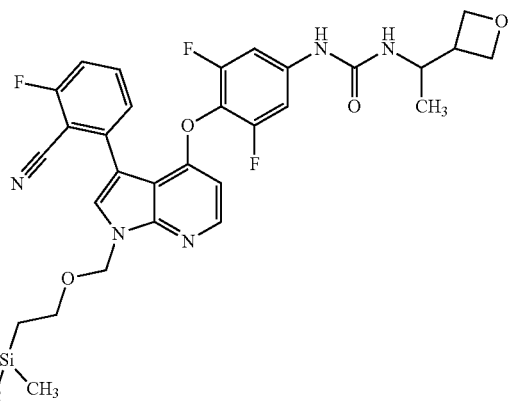

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 µmol, intermediate 207) was reacted with 2-fluoro-6-(4,4,5,5-tetramethyl-1,3,2-dioxaborolan-2-yl)benzonitrile (68.2 mg, 276 µmol) in the presence of tetrakis(triphenylphosphin)palladium(0) (23.2 mg, 20.1 µmol), and aq. sodium carbonate (250 µL, 2.0 M, 500 µmol) in 1,4-dioxane (2.3 mL). After purification using a Biotage chromatography system we obtained 75.5 mg (77% purity, 36% yield) of the desired title compound.

LC-MS (Method 2): $R_t$=1.42 min; MS (ESIpos): m/z=638 [M+H]$^+$ $^1$H-NMR (400 MHz, DMSO-d6) δ [ppm]: −0.12–−0.08 (m, 9H), 0.82-0.88 (m, 2H), 1.01 (d, 3H), 2.94-3.04 (m, 1H), 3.58-3.64 (m, 2H), 3.96-4.06 (m, 1H), 4.30 (t, 1H), 4.37 (t, 1H), 4.55-4.62 (m, 2H), 5.72 (s, 2H), 6.45 (d, 1H), 6.48 (d, 1H), 7.31-7.36 (m, 2H), 7.43-7.49 (m, 1H), 7.52-7.56 (m, 1H), 7.78 (td, 1H), 8.04 (s, 1H), 8.24 (d, 1H), 8.87 (s, 1H).

Intermediate 216

(+/−)—N-(4-{[3-(4-cyano-2-methoxyphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

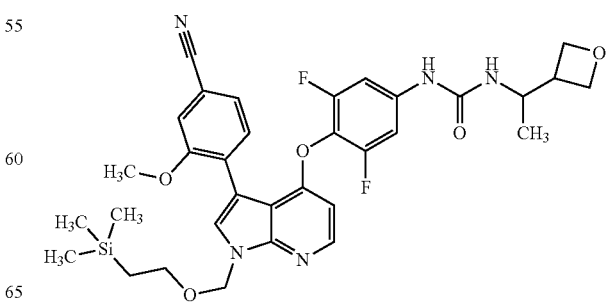

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (4-cyano-2-methoxyphenyl)boronic acid (48.9 mg, 276 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 59.9 mg (80% purity, 29% yield) of the desired title compound.

LC-MS (Method 2): $R_t$=1.43 min; MS (ESIpos): m/z=650 [M+H]$^+$

Intermediate 217

(+/−)—N-(4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

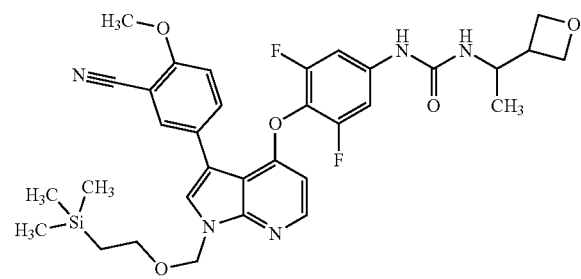 [SMILES: COc1ccc(-c2cn(COCC[Si](C)(C)C)c3nccc(Oc4c(F)cc(NC(=O)NC(C)C5COC5)cc4F)c23)cc1C#N]

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (3-cyano-4-methoxyphenyl)boronic acid (48.9 mg, 276 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 65.1 mg (90% purity, 36% yield) of the desired title compound.

LC-MS (Method 2): $R_t$=1.43 min; MS (ESIpos): m/z=650 [M+H]$^+$

Intermediate 218

(+/−)—N-{4-[(3-{4-cyano-3-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[1-(oxetan-3-yl)ethyl]urea

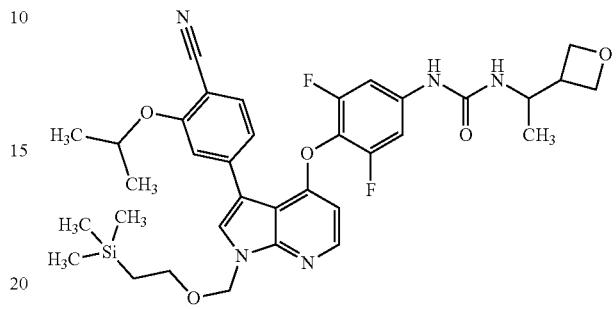

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with {4-cyano-3-[(propan-2-yl)oxy]phenyl}boronic acid (56.6 mg, 276 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 64.1 mg (74% purity, 28% yield) of the desired title compound.

LC-MS (Method 2): $R_t$=1.50 min; MS (ESIpos): m/z=678 [M+H]$^+$ $^1$H-NMR (400 MHz, DMSO-d6) δ [ppm]: −0.12−−0.07 (m, 9H), 0.81-0.88 (m, 2H), 1.02 (d, 3H), 1.25 (d, 6H), 2.94-3.05 (m, 1H), 3.57-3.63 (m, 2H), 3.98-4.08 (m, 1H), 4.31 (t, 1H), 4.38 (t, 1H), 4.59 (ddd, 2H), 4.76 (spt, 1H), 5.69 (s, 2H), 6.45-6.51 (m, 2H), 7.34-7.43 (m, 3H), 7.53 (s, 1H), 7.72 (d, 1H), 8.13 (s, 1H), 8.21 (d, 1H), 8.90 (s, 1H).

Intermediate 219

(+/−)—N-(4-{[3-(3-cyanophenyl)-1-{[2-(trimethylsilyl)ethoxy]methyl}-1H-pyrrolo[2,3-b]pyridin-4-yl]oxy}-3,5-difluorophenyl)-N'-[1-(oxetan-3-yl)ethyl]urea

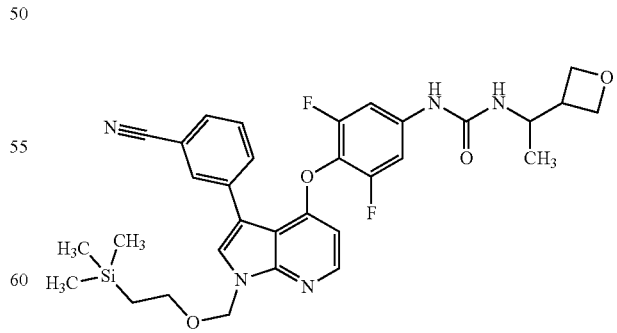

In analogy to intermediate 36, (+/−)—N-{4-[(3-bromo-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (150 mg, 251 μmol, intermediate 207) was reacted with (3-cyanophenyl)boronic acid (40.6 mg, 276 μmol) in the presence of tetrakis(triphenylphosphin)palladium(0) (23.2 mg, 20.1 μmol), and aq. sodium carbonate (250 μL, 2.0 M, 500 μmol) in 1,4-dioxane (2.3 mL). After purification using a Biotage chromatography system we obtained 53.6 mg (86% purity, 30% yield) of the desired title compound.

LC-MS (Method 2): $R_t$=1.45 min; MS (ESIpos): m/z=620 $[M+H]^+$ $^1$H-NMR (400 MHz, DMSO-d6) δ [ppm]: −0.11−−0.07 (m, 9H), 0.83-0.88 (m, 2H), 1.02 (d, 3H), 2.95-3.04 (m, 1H), 3.57-3.63 (m, 2H), 3.98-4.08 (m, 1H), 4.31 (t, 1H), 4.38 (t, 1H), 4.59 (ddd, 2H), 5.69 (s, 2H), 6.45-6.50 (m, 2H), 7.35-7.43 (m, 2H), 7.59-7.64 (m, 1H), 7.73 (dt, 1H), 7.98-8.02 (m, 1H), 8.03 (s, 1H), 8.07 (t, 1H), 8.21 (d, 1H), 8.90 (s, 1H).

Intermediate 220

4-(2-fluoro-4-nitrophenoxy)-1H-pyrrolo[2,3-b]pyridine

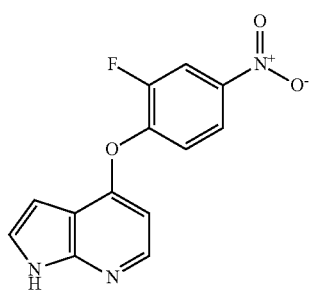 [SMILES: O=[N+]([O-])c1ccc(Oc2ccnc3[nH]ccc23)c(F)c1]

In analogy to intermediate 134, 1H-pyrrolo[2,3-b]pyridin-4-ol hydrate (2.10 g, 13.8 mmol) was reacted with 1,2-difluoro-4-nitrobenzene (1.4 mL, 13 mmol) and potassium carbonate (6.95 g, 50.3 mmol) in DMSO (40 mL). After dilution with ethyl acetate a solid was formed. The desired title compound was obtained after filtration as the solid 2.13 g (98% purity, 60% yield).

LC-MS (Method 2): $R_t$=1.08 min; MS (ESIpos): m/z=274 $[M+H]^+$ $^1$H-NMR (500 MHz, DMSO-d6) δ [ppm]: 6.25 (d, 1H), 6.72 (d, 1H), 7.43 (dd, 1H), 7.46 (d, 1H), 8.14 (ddd, 1H), 8.20 (d, 1H), 8.42 (dd, 1H), 11.97 (br s, 1H).

Intermediate 221

4-(2-fluoro-4-nitrophenoxy)-1-{[2-(trimethylsilyl)ethoxy]methyl}-1H-pyrrolo[2,3-b]pyridine

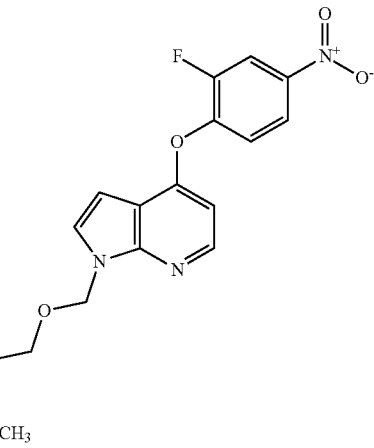

In analogy to intermediate 135, 4-(2-fluoro-4-nitrophenoxy)-1H-pyrrolo[2,3-b]pyridine (2.13 g, 7.78 mmol, intermediate 220) was reacted with [3-(chloromethoxy)propyl](trimethyl)silane (1.93 mL, 10.9 mmol) and N,N-diisopropylethylamine (3.39 mL, 19.4 mmol) in acetonitrile (72 mL). After purification using a Biotage chromatography system we obtained 2.86 g (98% purity, 89% yield) of the desired title compound.

LC-MS (Method 2): $R_t$=1.56 min; MS (ESIpos): m/z=404 $[M+H]^+$ $^1$H-NMR (400 MHz, DMSO-d6) δ [ppm]: −0.12−−0.07 (m, 9H), 0.77-0.87 (m, 2H), 3.50-3.56 (m, 2H), 5.64 (s, 2H), 6.38 (d, 1H), 6.79 (d, 1H), 7.49 (t, 1H), 7.65 (d, 1H), 8.16 (ddd, 1H), 8.26 (d, 1H), 8.43 (dd, 1H).

Intermediate 222

3-bromo-4-(2-fluoro-4-nitrophenoxy)-1-{[2-(trimethylsilyl)ethoxy]methyl}-1H-pyrrolo[2,3-b]pyridine

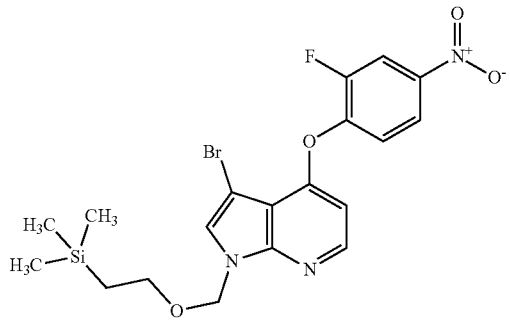 [SMILES: C[Si](C)(C)CCOCn1cc(Br)c2c(Oc3ccc([N+](=O)[O-])cc3F)ccnc21]

In analogy to intermediate 16, 4-(2-fluoro-4-nitrophenoxy)-1-{[2-(trimethylsilyl)ethoxy]methyl}-1H-pyrrolo[2,3-b]pyridine (2.55 g, 6.32 mmol, intermediate 221) was reacted with 1-bromopyrrolidine-2,5-dione (1.24 g, 6.95 mmol) in dichloromethane (130 mL). After purification using a Biotage chromatography system we obtained 0.03 g (96% purity, 95% yield) of the desired title compound.

LC-MS (Method 2): $R_t$=1.62 min; MS (ESIpos): m/z=482/484 [M+H]$^+$ (Br isotope pattern).

$^1$H-NMR (400 MHz, DMSO-d6) δ [ppm]: −0.11--−0.07 (m, 9H), 0.80-0.87 (m, 2H), 3.52-3.58 (m, 2H), 5.64 (s, 2H), 6.86 (d, 1H), 7.35 (dd, 1H), 7.95 (s, 1H), 8.13 (ddd, 1H), 8.33 (d, 1H), 8.43 (dd, 1H).

Intermediate 223

4-(2-fluoro-4-nitrophenoxy)-3-(prop-1-en-2-yl)-1-{[2-(trimethylsilyl)ethoxy]methyl}-1H-pyrrolo[2,3-b]pyridine Intermediate 224

3-fluoro-4-{[3-(propan-2-yl)-1-{[2-(trimethylsilyl)ethoxy]methyl}-1H-pyrrolo[2,3-b]pyridin-4-yl]oxy}aniline

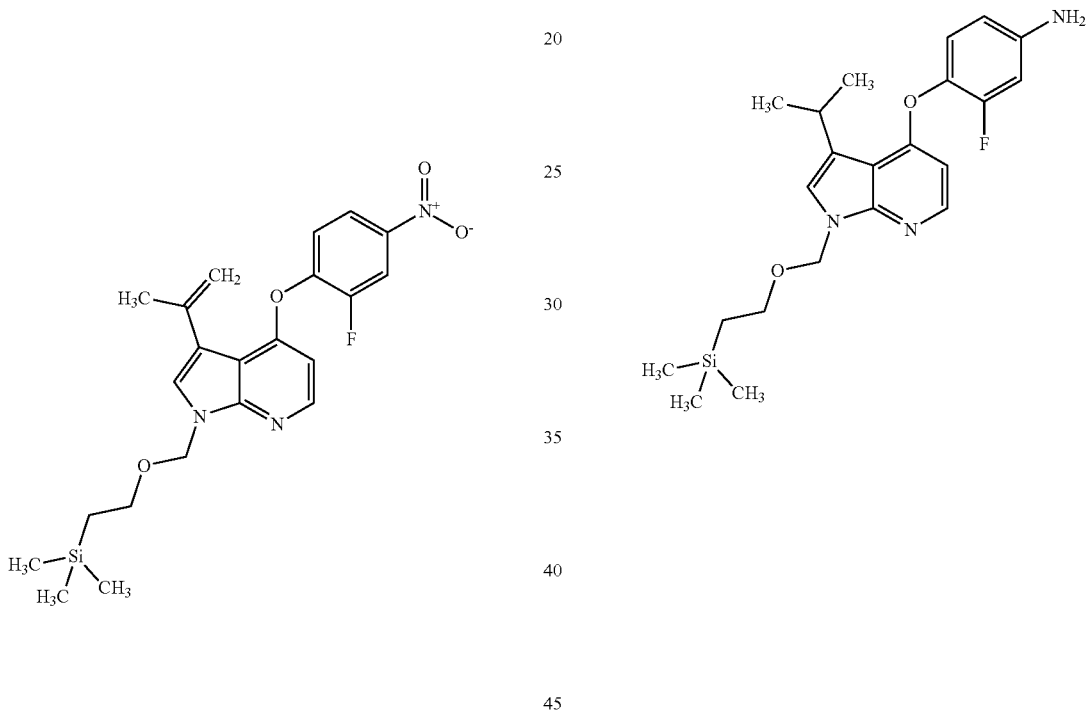

In analogy to intermediate 17, 3-bromo-4-(2-fluoro-4-nitrophenoxy)-1-{[2-(trimethylsilyl)ethoxy]methyl}-1H-pyrrolo[2,3-b]pyridine (2.93 g, 6.07 mmol, intermediate 222) was reacted with 4,4,5,5-tetramethyl-2-(prop-1-en-2-yl)-1,3,2-dioxaborolane (1.28 g, 7.59 mmol) in the presence of [1,1'-bis (diphenylphosphino)ferrocene]dichloropalladium(II) (444 mg, 607 μmol) and potassium carbonate (2.52 g, 18.2 mmol) in water (45 mL) and THF (90 mL). After purification using a Biotage chromatography system we obtained 1.96 g (100% purity, 73% yield) of the desired title compound.

LC-MS (Method 2): $R_t$=1.65 min; MS (ESIpos): m/z=444 [M+H]$^+$ $^1$H-NMR (400 MHz, DMSO-d6) δ [ppm]: −0.12--−0.06 (m, 9H), 0.80-0.87 (m, 2H), 2.06 (s, 3H), 3.51-3.59 (m, 2H), 4.96-5.00 (m, 1H), 5.29 (d, 1H), 5.60-5.69 (m, 2H), 6.78 (d, 1H), 7.27 (t, 1H), 7.76 (s, 1H), 8.10 (ddd, 1H), 8.28 (d, 1H), 8.41 (dd, 1H).

To a solution of 4-(2-fluoro-4-nitrophenoxy)-3-(prop-1-en-2-yl)-1-{[2-(trimethylsilyl)ethoxy]methyl}-1H-pyrrolo[2,3-b]pyridine (1.86 g, 4.19 mmol, intermediate 223) in a mixture of ethanol (90 mL) and THF (18 mL) was given 10% Pd on carbon (446 mg). This mixture was stirred in an hydrogen atmosphere for 3 hours at room temperature. Then the mixture was filtered through Celite and the Celite was washed with ethyl acetate. The organic phase was evaporated to dryness and the resulting residue was purified via a Biotage chromatography system to obtain 1.43 g (92% purity, 90% yield) of the desired title compound.

LC-MS (Method 2): $R_t$=1.57 min; MS (ESIpos): m/z=416 [M+H]$^+$ $^1$H-NMR (400 MHz, DMSO-d6) δ [ppm]: −0.11--−0.07 (m, 9H), 0.77-0.85 (m, 2H), 1.31 (d, 6H), 3.27-3.38 (m, 1H), 3.45-3.53 (m, 2H), 5.45 (s, 2H), 5.55 (s, 2H), 6.18 (dd, 1H), 6.44 (dd, 1H), 6.53 (dd, 1H), 7.02 (t, 1H), 7.27 (s, 1H), 8.02 (d, 1H).

Intermediate 225 phenyl (3-fluoro-4-{[3-(propan-2-yl)-1-{[2-(trimethylsilyl)ethoxy]methyl}-1H-pyrrolo[2,3-b]pyridin-4-yl]oxy}phenyl)carbamate

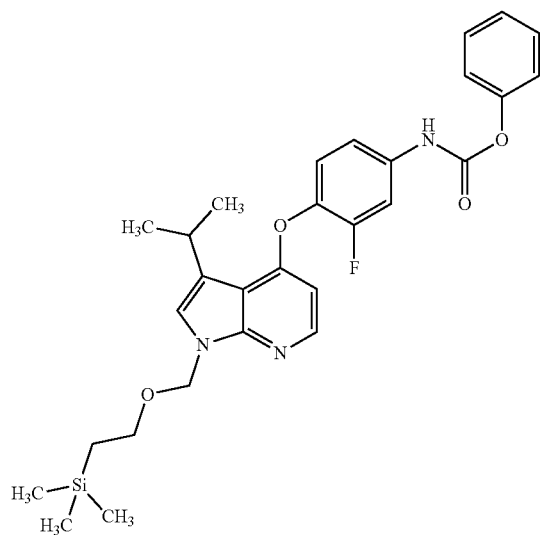 [SMILES: CC(C)c1cn(COCC[Si](C)(C)C)c2nccc(Oc3ccc(NC(=O)Oc4ccccc4)cc3F)c12]

In analogy to intermediate 1, 3-fluoro-4-{[3-(propan-2-yl)-1-{[2-(trimethylsilyl)ethoxy]methyl}-1H-pyrrolo[2,3-b]pyridin-4-yl]oxy}aniline (300 mg, 722 μmol, intermediate 224) was reacted with phenyl carbonochloridate (100 μL, 790 μmol) in pyridine (270 μL) and THF (8.9 mL). The raw material was used in the next step without any further purification LC-MS (Method 2): $R_t$=1.69 min; MS (ESIpos): m/z=536 [M+H]$^+$

Intermediate 226

N-(3-fluoro-4-{[3-(propan-2-yl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

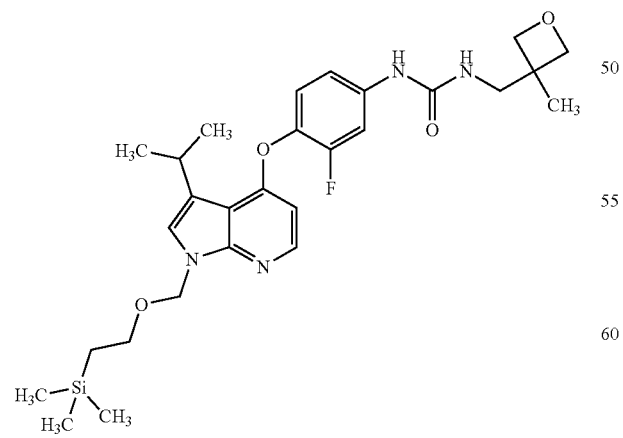

In analogy to intermediate 2, phenyl (3-fluoro-4-{[3-(propan-2-yl)-1-{[2-(trimethylsilyl)ethoxy]methyl}-1H-pyrrolo[2,3-b]pyridin-4-yl]oxy}phenyl)carbamate (180 mg, 336 μmol, intermediate 225) was reacted with 1-(3-methyloxetan-3-yl)methanamine (51.0 mg, 504 μmol) in DMF (2.1 mL) and trimethylamine (70 μL). After purification using a Biotage chromatography system we obtained 164 mg (90% purity, 90% yield) of the desired title compound.

LC-MS (Method 2): $R_t$=1.51 min; MS (ESIpos): m/z=543 [M+H]$^+$ $^1$H-NMR (400 MHz, DMSO-d6) δ [ppm]: −0.11--0.06 (m, 9H), 0.77-0.84 (m, 2H), 1.24 (s, 3H), 1.32 (d, 6H), 3.28-3.37 (m, 3H), 3.46-3.54 (m, 2H), 4.21 (d, 2H), 4.39 (d, 2H), 5.56 (s, 2H), 6.21 (dd, 1H), 6.59 (t, 1H), 7.15 (dd, 1H), 7.25-7.32 (m, 2H), 7.69 (dd, 1H), 8.04 (d, 1H), 8.86 (s, 1H).

Intermediate 227

N-[(3-fluorooxetan-3-yl)methyl]-N'-(3-fluoro-4-{[3-(propan-2-yl)-1-{[2-(trimethylsilyl)ethoxy]methyl}-1H-pyrrolo[2,3-b]pyridin-4-yl]oxy}phenyl)urea

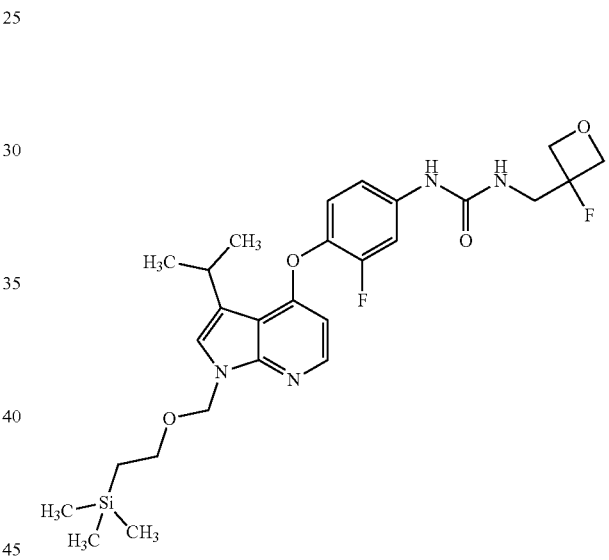

In analogy to intermediate 2, phenyl (3-fluoro-4-{[3-(propan-2-yl)-1-{[2-(trimethylsilyl)ethoxy]methyl}-1H-pyrrolo[2,3-b]pyridin-4-yl]oxy}phenyl)carbamate (180 mg, 336 μmol, intermediate 225) was reacted with 1-(3-fluorooxetan-3-yl)methanamine (53.0 mg, 504 μmol) in DMF (2.1 mL) and trimethylamine (70 μL). After purification using a Biotage chromatography system we obtained 173 mg (90% purity, 94% yield) of the desired title compound.

LC-MS (Method 2): $R_t$=1.51 min; MS (ESIpos): m/z=547 [M+H]$^+$ $^1$H-NMR (400 MHz, DMSO-d6) δ [ppm]: −0.11--0.06 (m, 9H), 0.77-0.84 (m, 2H), 1.32 (d, 6H), 3.29-3.37 (m, 1H), 3.46-3.54 (m, 2H), 3.66 (dd, 2H), 4.55-4.67 (m, 4H), 5.56 (s, 2H), 6.22 (d, 1H), 6.67 (t, 1H), 7.16 (d, 1H), 7.24-7.33 (m, 2H), 7.68 (dd, 1H), 8.04 (d, 1H), 8.95 (s, 1H).

Intermediate 228

4-(2,6-difluoro-4-nitrophenoxy)-3-{2-fluoro-3-[(propan-2-yl)oxy]phenyl}-1-{[2-(trimethylsilyl)ethoxy]methyl}-1H-pyrrolo[2,3-b]pyridine

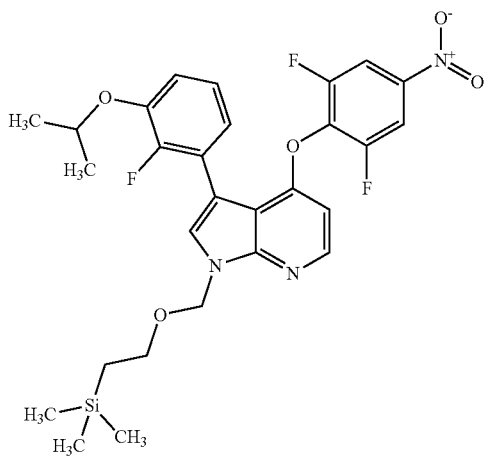 [SMILES: CC(C)Oc1cccc(-c2cn(COCC[Si](C)(C)C)c3nccc(Oc4c(F)cc([N+](=O)[O-])cc4F)c23)c1F]

In analogy to intermediate 76, 3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol) was reacted with {2-fluoro-3-[(propan-2-yl)oxy]phenyl}boronic acid (791 mg, 4.00 mmol, CAS No. [855230-63-6]) in the presence of [1,1'-Bis(diphenylphosphino)-ferrocene]dichloropalladium (II) (146 mg, 200 μmol), potassium carbonate (1.38 g, 9.99 mmol) in a mixture of 1,4-dioxane (19 mL) and water (9.6 mL) to afford after purification by flash column chromatography on a Biotage the title compound (1.44 g, 94% yield) LC-MS (Method 1): $R_t$=1.71 min; MS (ESIpos): m/z=575 [M+H]$^+$ $^1$H NMR (400 MHz, DMSO-d$_6$) δ ppm −0.09 (s, 9H), 0.81-0.87 (m, 2H), 3.58-3.64 (m, 2H), 4.53 (spt, 1H), 5.70 (s, 2H), 6.66 (d, 1H), 7.05-7.11 (m, 3H), 7.84 (s, 1H), 8.23 (d, 1H), 8.33 (d, 2H)

Intermediate 229

3,5-difluoro-4-[(3-{2-fluoro-3-[(propan-2-yl)oxy]phenyl}-1-{[2-(trimethylsilyl)ethoxy]methyl}-1H-pyrrolo[2,3-b]pyridin-4-yl)oxy]aniline

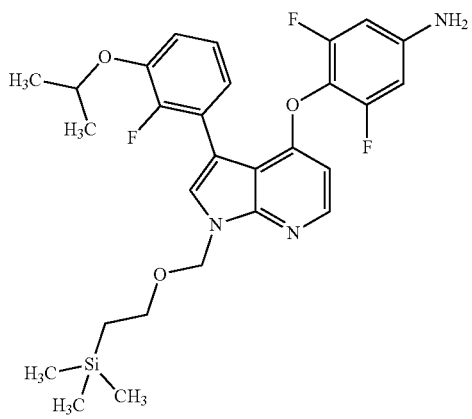 [SMILES: CC(C)Oc1cccc(-c2cn(COCC[Si](C)(C)C)c3nccc(Oc4c(F)cc(N)cc4F)c23)c1F]

In analogy to intermediate 77, 4-(2,6-difluoro-4-nitrophenoxy)-3-{2-fluoro-3-[(propan-2-yl)oxy]phenyl}-1-{[2-(trimethylsilyl)ethoxy]methyl}-1H-pyrrolo[2,3-b]pyridine (1.51 g, 2.63 mmol, intermediate 228) was reacted with iron (735 mg, 13.2 mmol) and ammonium chloride (704 mg, 13.2 mmol) in a mixture of water (3.6 mL), THF (8.5 mL), and methanol (4.3 mL) to afford after purification by flash column chromatography on a Biotage the title compound (150 mg, 9% yield) LC-MS (Method 1): $R_t$=1.59 min; MS (ESIpos): m/z=544 [M+H]$^+$ $^1$H NMR (400 MHz, DMSO-d$_6$) δ ppm −0.08 (s, 9H), 0.82-0.88 (m, 2H), 1.25 (d, 6H), 3.55-3.63 (m, 2H), 4.57 (spt, 1H), 5.67 (s, 2H), 5.75-5.78 (m, 2H), 6.32-6.40 (m, 3H), 7.06-7.14 (m, 3H), 7.74 (s, 1H), 8.16 (d, 1H)

Intermediate 230

N-{3,5-difluoro-4-[(3-{2-fluoro-3-[(propan-2-yl)oxy]phenyl}-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

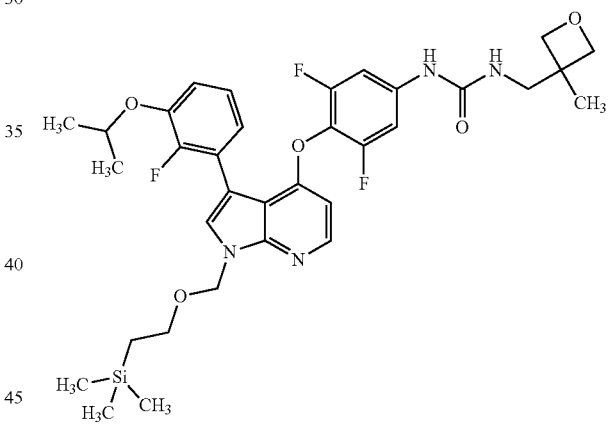

To a stirred solution of 3,5-difluoro-4-[(3-{2-fluoro-3-[(propan-2-yl)oxy]phenyl}-1-{[2-(trimethylsilyl)ethoxy]methyl}-1H-pyrrolo[2,3-b]pyridin-4-yl)oxy]aniline (100 mg, 184 μmol, Intermediate 229) in dichloromethane (470 μL) was added 3-(isocyanatomethyl)-3-methyloxetane (46.8 mg, 368 μmol, CAS No. [1260665-88-0]) and pyridine (600 μL, 7.4 mmol). The resulting mixture was heated to 60° C. overnight at which time water and ethyl acetate were added and the layers were separated. The aqueous phase was extracted twice with ethyl acetate and the combined organic layers were washed with brine, dried over sodium sulfate, filtered and evaporated to give the crude product which was used without further purification.

LC-MS (Method 2): $R_t$=1.57 min; MS (ESIpos): m/z=672 [M+H]$^+$

Intermediate 231

N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxypropyl)thiourea

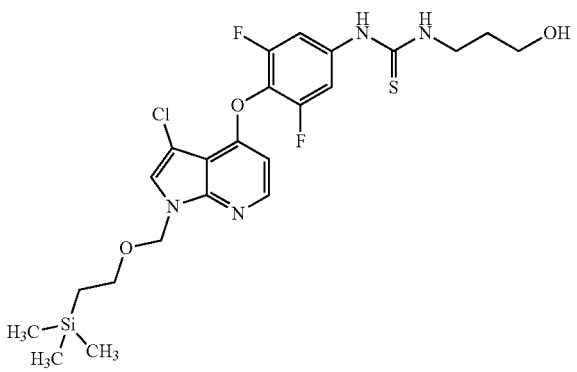 [SMILES: C[Si](C)(C)CCOCn1cc(Cl)c2c(Oc3c(F)cc(NC(=S)NCCCO)cc3F)ccnc21]

To a stirred solution of O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (600 mg, 1.07 mmol, intermediate 424) in DMF (7.0 mL) was added 3-aminopropan-1-ol (160 mg, 2.13 mmol, CAS No. [156-87-6]). The resulting mixture was heated to 60° C. for 2 h at which time water and ethyl acetate were added and the layers were separated. The aqueous phase was extracted twice with ethyl acetate and the combined organic layers were washed with brine, dried over sodium sulfate, filtered and evaporated to give the crude product which was used without further purification.

LC-MS (Method 2): $R_t$=1.43 min; MS (ESIpos): m/z=543 [M+H]$^+$

Intermediate 232

N-{4-[(3-chloro-1-{[2-(trimethylsilyl)ethoxy]methyl}-1H-pyrrolo[2,3-b]pyridin-4-yl)oxy]-3,5-difluorophenyl}-5,6-dihydro-4H-1,3-oxazin-2-amine

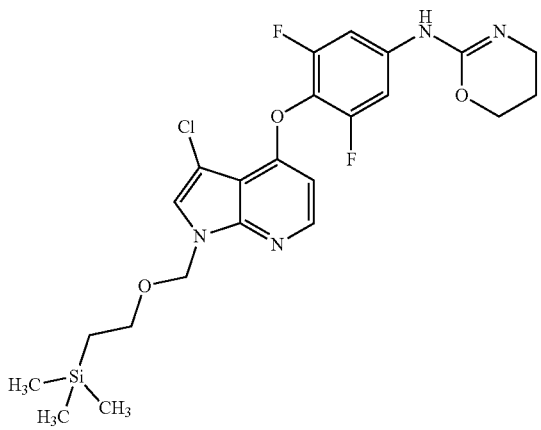 [SMILES: C[Si](C)(C)CCOCn1cc(Cl)c2c(Oc3c(F)cc(NC4=NCCCS4)cc3F)ccnc21]

To a solution of N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxypropyl)thiourea (290 mg, 534 µmol, Intermediate 231) in acetonitrile (25 mL, 470 mmol) was added 1-(3-Dimethylaminopropyl)-3-ethylcarbodiimide hydrochloride (205 mg, 1.07 mmol) and triethylamine (220 µL, 1.6 mmol). The resulting mixture was stirred at 40° C. overnight at which time water and ethyl acetate were added and the layers separated. The aqueous phase was extracted twice with ethyl acetate and the combined organic layers were washed with brine, dried over sodium sulfate, filtered and evaporated to afford the crude product which was used without further purification.

LC-MS (Method 2): $R_t$=1.52 min; MS (ESIpos): m/z=510 [M+H]$^+$

Intermediate 233

N-{4-[(3-chloro-1-{[2-(trimethylsilyl)ethoxy]methyl}-1H-pyrrolo[2,3-b]pyridin-4-yl)oxy]-3,5-difluorophenyl}-N'-(2-hydroxyethyl)thiourea In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (600 mg, 1.07 mmol, intermediate 424) and 2-aminoethane-1-ol (130 µL, 2.1 mmol, CAS No. [141-43-5], in DMF (7.0 mL) were reacted to obtain a crude product which was used in the next step without further purification.

LC-MS (Method 2): $R_t$=1.42 min; MS (ESIpos): m/z=529 [M+H]$^+$

Intermediate 234

N-{4-[(3-chloro-1-{[2-(trimethylsilyl)ethoxy]methyl}-1H-pyrrolo[2,3-b]pyridin-4-yl)oxy]-3,5-difluorophenyl}-4,5-dihydro-1,3-oxazol-2-amine

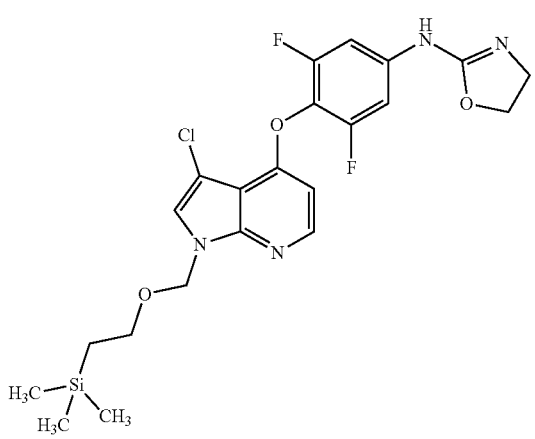 [SMILES: C[Si](C)(C)CCOCn1cc(Cl)c2c(Oc3c(F)cc(NC4=NCCS4)cc3F)ccnc21]

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-(2-hydroxyethyl)thiourea (280 mg, 529 µmol, Intermediate 233) was reacted with 1-(3-Dimethylaminopropyl)-3-ethylcarbodiimide hydrochloride (203 mg, 1.06 mmol) and triethylamine (220 µL, 1.6 mmol) in acetonitrile (25 mLI) to obtain a crude product which was used in the next step without further purification.

LC-MS (Method 2): $R_t$=1.48 min; MS (ESIpos): m/z=496 [M+H]$^+$

Intermediate 235

N-{4-[(3-chloro-1-{[2-(trimethylsilyl)ethoxy]methyl}-1H-pyrrolo[2,3-b]pyridin-4-yl)oxy]-3,5-difluorophenyl}-5,6-dihydro-4H-1,3-thiazin-2-amine

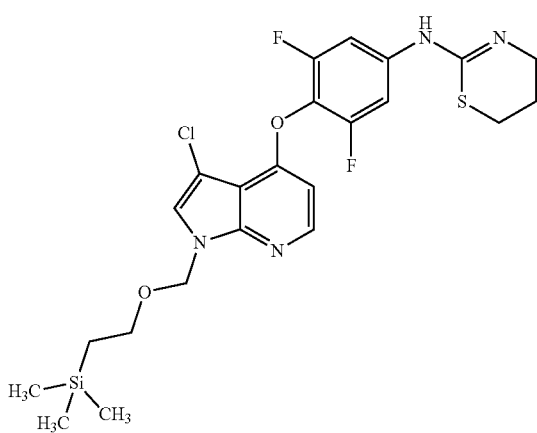

To a stirred solution of N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxypropyl)thiourea (290 mg, 534 µmol, Intermediate 231) in THF (25 mL) was added 1,1'-Carbonyldiimidazole (173 mg, 1.07 mmol). The resulting mixture was stirred at 70° C. overnight at which time the solvent was evaporated to give a crude product which was used without further purification.

LC-MS (Method 2): $R_t$=1.59 min; MS (ESIpos): m/z=526 [M+H]$^+$.

Intermediate 236

N-{4-[(3-chloro-1-{[2-(trimethylsilyl)ethoxy]methyl}-1H-pyrrolo[2,3-b]pyridin-4-yl)oxy]-3,5-difluorophenyl}-4,5-dihydro-1,3-thiazol-2-amine

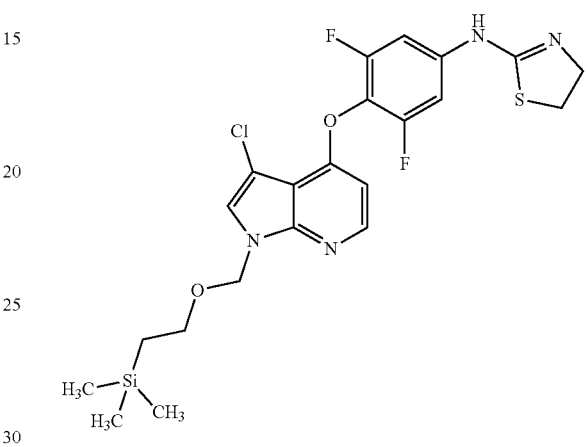

To a stirred solution of N-{4-[(3-chloro-1-{[2-(trimethylsilyl)ethoxy]methyl}-1H-pyrrolo[2,3-b]pyridin-4-yl)oxy]-3,5-difluorophenyl}-N'-(2-hydroxyethyl)thiourea (280 mg, 0.58 mmol, Intermediate 233) in THF (25 mL) was added 1,1'-Carbonyldiimidazole (94 mg, 0.58 mmol). The resulting mixture was stirred at 70° C. for 3 hours at which time the solvent was evaporated to give a crude product which was used without further purification.

LC-MS (Method 2): $R_t$=1.57 min; MS (ESIpos): m/z=512 [M+H]$^+$

Intermediate 237

N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea

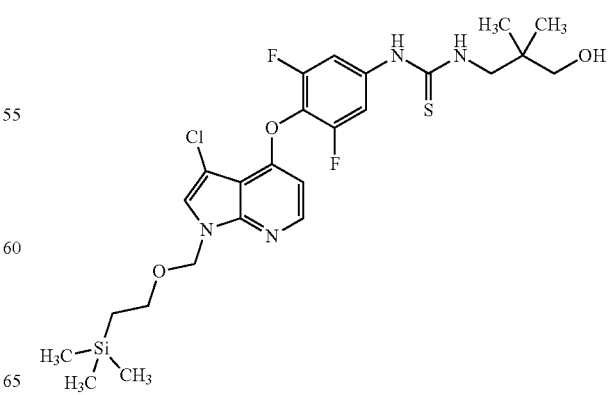

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (300 mg, 534 µmol, intermediate 424), and 3-amino-2,2-dimethylpropan-1-ol (116 mg, 1.07 mmol, CAS No. [141-43-5]), in DMF (5.0 mL) were reacted to obtain a crude product which was used in the next step without further purification.

LC-MS (Method 2): $R_t$=1.53 min; MS (ESIpos): m/z=572 [M+H]$^+$

Intermediate 238

N-{4-[(3-chloro-1-{[2-(trimethylsilyl)ethoxy]methyl}-1H-pyrrolo[2,3-b]pyridin-4-yl)oxy]-3,5-difluorophenyl}-5,5-dimethyl-5,6-dihydro-4H-1,3-oxazin-2-amine

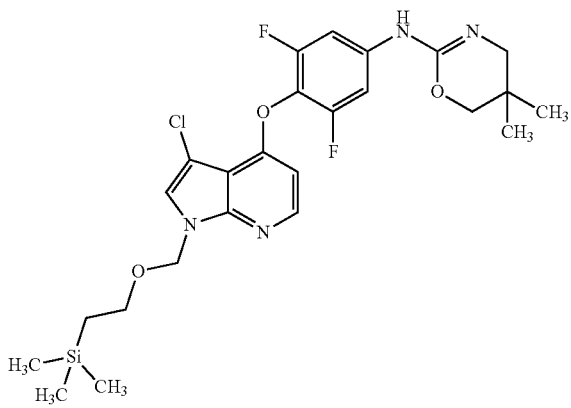

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea (300 mg, 525 µmol, Intermediate 237) was reacted with 1-(3-Dimethylaminopropyl)-3-ethylcarbodiimide hydrochloride (201 mg, 1.05 mmol) and triethylamine (220 µL, 1.6 mmol) in acetonitrile (10 mL) to obtain a crude product which was used in the next step without further purification.

LC-MS (Method 2): $R_t$=1.61 min; MS (ESIpos): m/z=538 [M+H]$^+$

Intermediate 239

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopropyl]methyl}thiourea

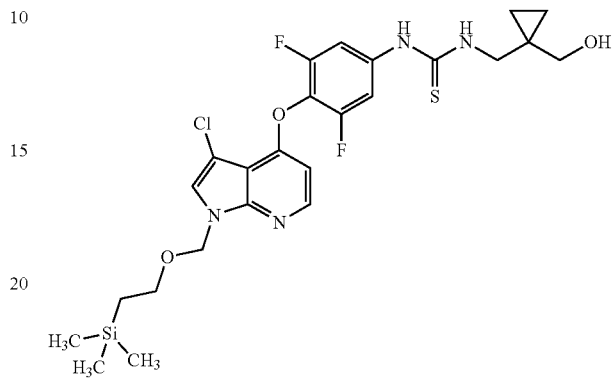

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (300 mg, 534 µmol, intermediate 424), and [1-(aminomethyl)cyclopropyl]methanol (114 mg, 1.07 mmol, CAS No. [45434-02-4]), in DMF (5.0 mL) were reacted to obtain a crude product which was used in the next step without further purification.

LC-MS (Method 2): $R_t$=1.49 min; MS (ESIpos): m/z=570 [M+H]$^+$

Intermediate 240

N-{4-[(3-chloro-1-{[2-(trimethylsilyl)ethoxy]methyl}-1H-pyrrolo[2,3-b]pyridin-4-yl)oxy]-3,5-difluorophenyl}-5-oxa-7-azaspiro[2.5]oct-6-en-6-amine

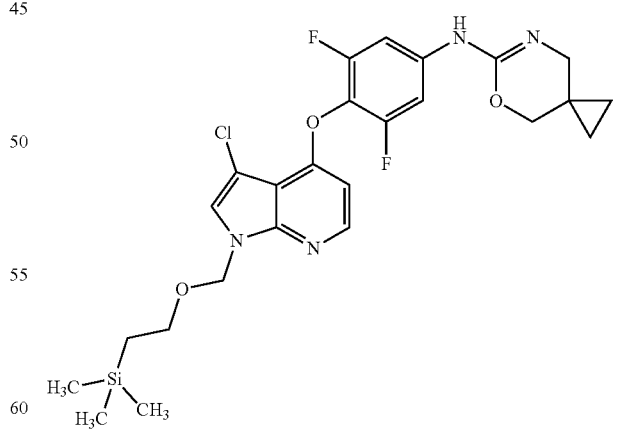

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopropyl]methyl}thiourea (300 mg, 527 µmol, Intermediate 239) was reacted with 1-(3-Dimethylaminopropyl)-3-ethylcarbodiimide hydrochloride (202 mg, 1.05 mmol) and triethylamine (220 µL, 1.6 mmol) in acetonitrile (10 mL) to obtain a crude product which was used in the next step without further purification.

LC-MS (Method 2): R$_t$=1.59 min; MS (ESIpos): m/z=536 [M+H]$^+$

Intermediate 241

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclobutyl]methyl}thiourea

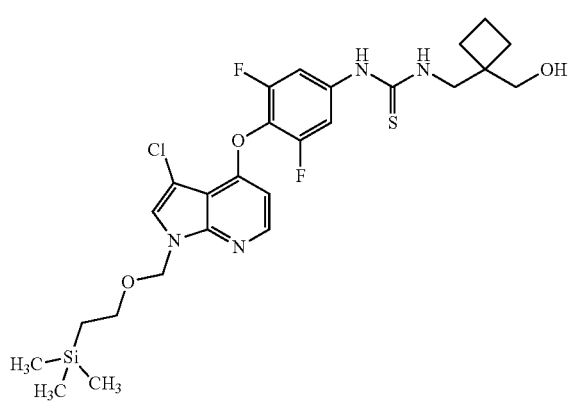 [SMILES: C[Si](C)(C)CCOCn1cc(Cl)c2c(Oc3c(F)cc(NC(=S)NCC4(CO)CCC4)cc3F)ccnc21]

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (370 mg, 658 µmol, intermediate 424), and [1-(aminomethyl)cyclobutyl]methanol (152 mg, 1.32 mmol, CAS No. [2041-56-7]), in DMF (3.0 mL) were reacted to obtain a crude product which was used in the next step without further purification.

LC-MS (Method 2): R$_t$=1.53 min; MS (ESIpos): m/z=583 [M+H]$^+$

Intermediate 242

N-{4-[(3-chloro-1-{[2-(trimethylsilyl)ethoxy]methyl}-1H-pyrrolo[2,3-b]pyridin-4-yl)oxy]-3,5-difluorophenyl}-6-oxa-8-azaspiro[3.5]non-7-en-7-amine

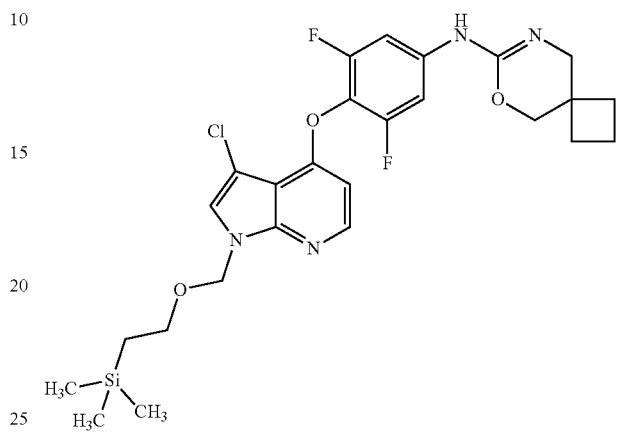

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclobutyl]methyl}thiourea (380 mg, 652 µmol, Intermediate 241) was reacted with 1-(3-Dimethylaminopropyl)-3-ethylcarbodiimide hydrochloride (250 mg, 1.30 mmol) and triethylamine (270 µL, 2.0 mmol) in acetonitrile (10 mL) to obtain a crude product which was used in the next step without further purification.

LC-MS (Method 2): R$_t$=1.61 min; MS (ESIpos): m/z=551 [M+H]$^+$

Intermediate 243

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-3-(2,3-dihydroxypropyl)thiourea

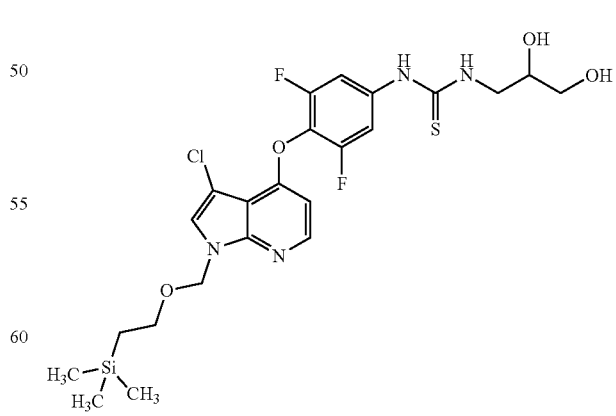

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (370 mg, 658 µmol, intermediate 424), and (+/−)-3-aminopropane-1,2-diol (120 mg, 1.32 mmol, CAS No. [616-30-8]), in DMF (3.0 mL) were reacted to obtain a crude product which was used in the next step without further purification.

LC-MS (Method 2): $R_t$=1.34 min; MS (ESIpos): m/z=559 [M+H]$^+$

Intermediate 244

(+/−)-[2-{4-[(3-chloro-1-{[2-(trimethylsilyl)ethoxy]methyl}-1H-pyrrolo[2,3-b]pyridin-4-yl)oxy]-3,5-difluoroanilino}-4,5-dihydro-1,3-oxazol-5-yl]methanol

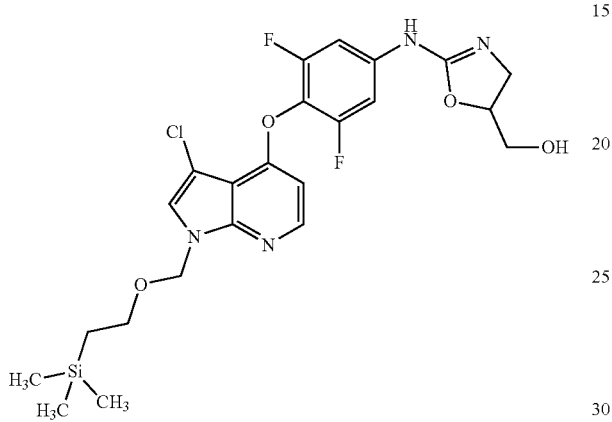

In analogy to Intermediate 232, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(2,3-dihydroxypropyl)thiourea (360 mg, 644 µmol, Intermediate 243) was reacted with 1-(3-Dimethylaminopropyl)-3-ethylcarbodiimide hydrochloride (247 mg, 1.29 mmol) and triethylamine (270 µL, 1.9 mmol) in acetonitrile (10 mL) to obtain a crude product which was used in the next step without further purification.

LC-MS (Method 2): $R_t$=1.37 min; MS (ESIpos): m/z=526 [M+H]$^+$

Intermediate 245

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(-4-hydroxybutan-2-yl)thiourea

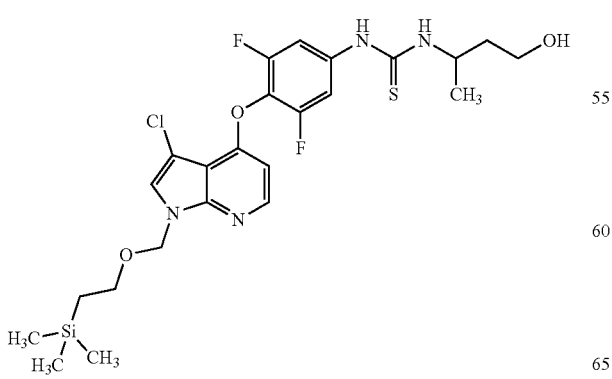

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (370 mg, 658 µmol, intermediate 424), and (+/−)-3-aminobutan-1-ol (117 mg, 1.32 mmol, CAS No. [2867-59-6], in DMF (3.0 mL) were reacted to obtain a crude product which was used in the next step without further purification.

LC-MS (Method 2): $R_t$=1.45 min; MS (ESIpos): m/z=558 [M+H]$^+$

Intermediate 246

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-methyl-5,6-dihydro-4H-1,3-oxazin-2-amine

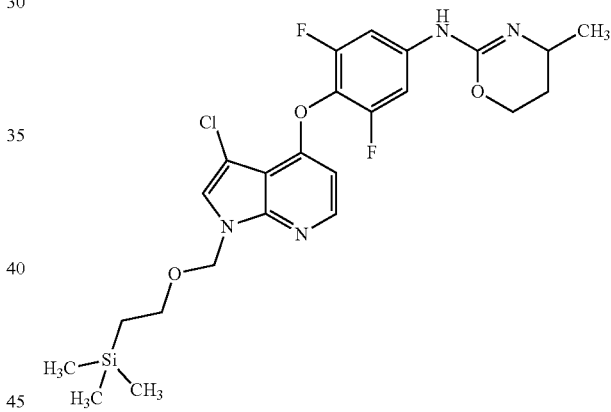

In analogy to Intermediate 232, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(4-hydroxybutan-2-yl)thiourea (360 mg, 646 µmol, Intermediate 245) was reacted with 1-(3-Dimethylaminopropyl)-3-ethylcarbodiimide hydrochloride (248 mg, 1.29 mmol) and triethylamine (270 µL, 1.9 mmol) in acetonitrile (10 mL) to obtain a crude product which was used in the next step without further purification.

LC-MS (Method 2): $R_t$=1.54 min; MS (ESIpos): m/z=525 [M+H]$^+$

Intermediate 247

N-{4-[(3-chloro-1-{[2-(trimethylsilyl)ethoxy]methyl}-1H-pyrrolo[2,3-b]pyridin-4-yl)oxy]-3,5-difluorophenyl}-N'-(2,2-difluoro-3-hydroxypropyl)thiourea

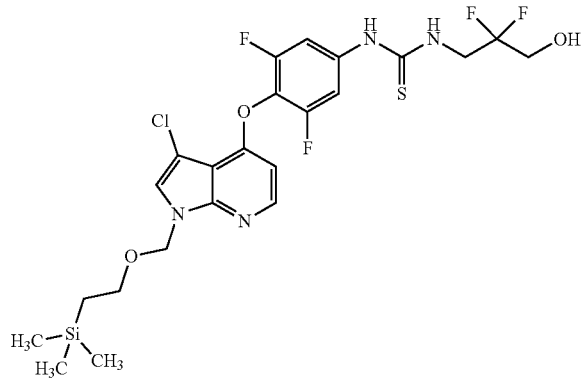 [SMILES: C[Si](C)(C)CCOCn1cc(Cl)c2c(Oc3c(F)cc(NC(=S)NCC(F)(F)CO)cc3F)ccnc21]

In analogy to Intermediate 231, O-phenyl {4-[(3-chloro-1-{[2-(trimethylsilyl)methyl}-1H-pyrrolo[2,3-b]pyridin-4-yl)oxy]-3,5-difluorophenyl}carbamothioate (370 mg, 658 μmol, intermediate 424), and 3-amino-2,2-difluoropropan-1-ol (146 mg, 1.32 mmol, CAS No. [2867-59-6]), in DMF (3.0 mL) were reacted to obtain a crude product which was used in the next step without further purification.

LC-MS (Method 2): R$_t$=1.43 min; MS (ESIpos): m/z=579 [M+H]$^+$

Intermediate 248

N-{4-[(3-chloro-1-{[2-(trimethylsilyl)ethoxy]methyl}-1H-pyrrolo[2,3-b]pyridin-4-yl)oxy]-3,5-difluorophenyl}-5,5-difluoro-5,6-dihydro-4H-1,3-oxazin-2-amine

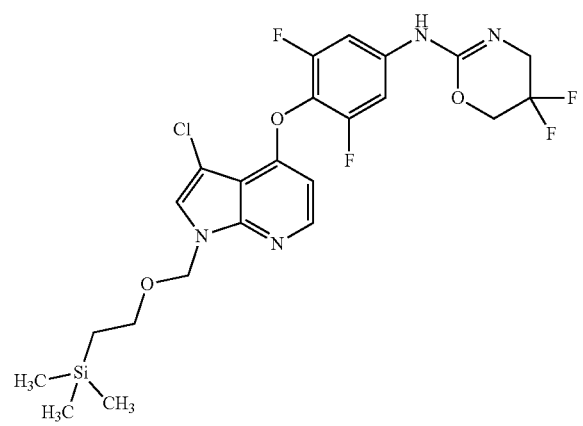 [SMILES: C[Si](C)(C)CCOCn1cc(Cl)c2c(Oc3c(F)cc(NC4=NCC(F)(F)CO4)cc3F)ccnc21]

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-(2,2-difluoro-3-hydroxypropyl)thiourea (380 mg, 656 μmol, Intermediate 247) was reacted with 1-(3-Dimethylaminopropyl)-3-ethylcarbodiimide hydrochloride (252 mg, 1.31 mmol) and triethylamine (270 μL, 2.0 mmol) in acetonitrile (10 mL) to obtain a crude product which was used in the next step without further purification.

LC-MS (Method 2): R$_t$=1.58 min; MS (ESIpos): m/z=545 [M+H]$^+$

Intermediate 249

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-hydroxyoxetan-3-yl)methyl]urea

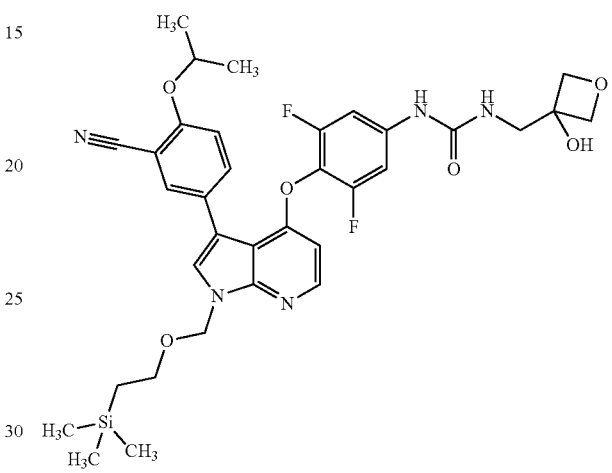

In analogy to intermediate 104, phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamate (85.0 mg, 127 μmol, intermediate 103), and 3-(aminomethyl)oxetan-3-ol (26.1 mg, 253 μmol, CAS No. [1305208-47-2], in DMF (3.0 mL) were reacted to obtain a crude product which was used in the next step without further purification.

LC-MS (Method 2): R$_t$=1.45 min; MS (ESIpos): m/z=681 [M+H]$^+$

Intermediate 250

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(1,4-dihydroxybutane-2-yl)thiourea

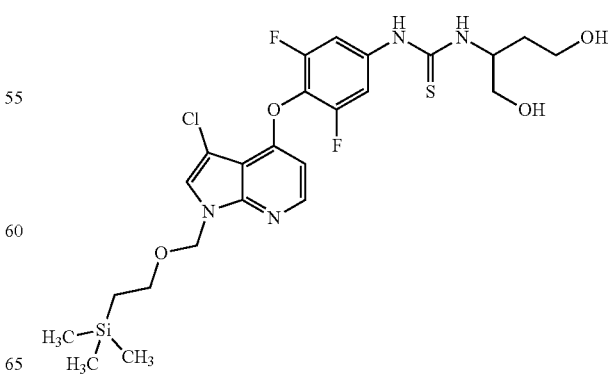

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (430 mg, 765 µmol, intermediate 424), and (+/−)-2-aminobutane-1,4-diol (161 mg, 1.53 mmol, CAS No. [4426-52-2], in DMF (4.0 mL) were reacted to obtain a crude product which was used in the next step without further purification.

LC-MS (Method 2): $R_t$=1.34 min; MS (ESIpos): m/z=573 [M+H]$^+$.

Intermediate 251

(+/−)-[2-{4-[(3-chloro-1-{[2-(trimethylsilyl)ethoxy]methyl}-1H-pyrrolo[2,3-b]pyridin-4-yl)oxy]-3,5-difluoroanilino}-5,6-dihydro-4H-1,3-oxazin-4-yl]methanol

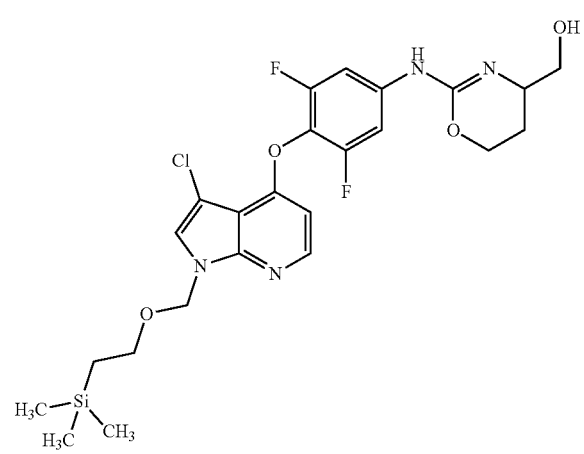 [SMILES: C[Si](C)(C)CCOCn1cc(Cl)c2c(Oc3c(F)cc(NC4=NC(CO)CCO4)cc3F)ccnc21]

In analogy to Intermediate 232, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(1,4-dihydroxybutane-2-yl)thiourea (430 mg, 750 µmol, Intermediate 250) was reacted with 1-(3-Dimethylaminopropyl)-3-ethylcarbodiimide hydrochloride (288 mg, 1.50 mmol) and triethylamine (310 µL, 2.3 mmol) in acetonitrile (8.0 mL) to obtain a crude product which was used in the next step without further purification.

LC-MS (Method 2): $R_t$=1.40 min; MS (ESIpos): m/z=540 [M+H]$^+$.

Intermediate 252

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxypropyl)thiourea

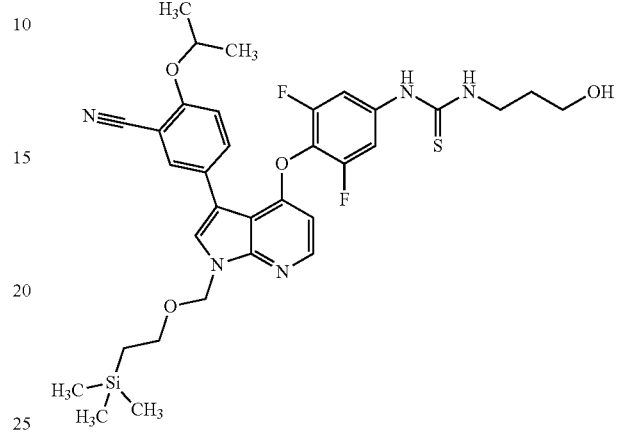

In analogy to Intermediate 231, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (150 mg, 218 µmol, intermediate 158), and 3-aminopropan-1-ol (32.8 mg, 437 µmol, CAS No. [156-87-6]), in DMF (3.0 mL) were reacted to obtain a crude product which was used in the next step without further purification.

LC-MS (Method 2): $R_t$=1.49 min; MS (ESIpos): m/z=669 [M+H]$^+$.

Intermediate 253

5-(4-{4-[(5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile

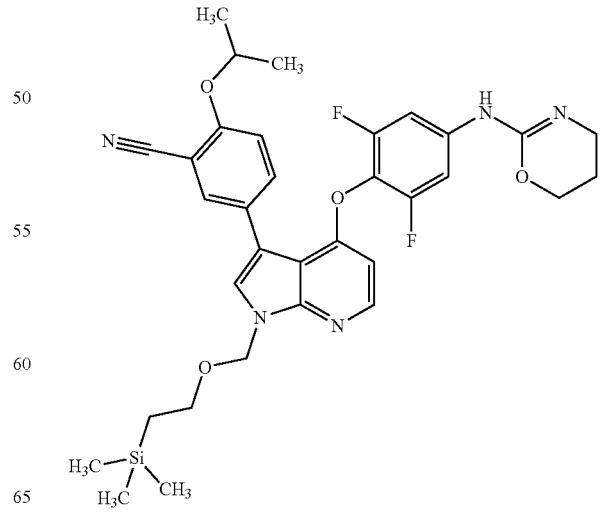

In analogy to Intermediate 232, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxypropyl)thiourea (145 mg, 217 µmol, intermediate 252) was reacted with 1-(3-Dimethylaminopropyl)-3-ethylcarbodiimide hydrochloride (83.2 mg, 434 µmol) and triethylamine (91 µL, 650 µmol) in acetonitrile (3.0 mL) to obtain a crude product which was used in the next step without further purification.

LC-MS (Method 2): $R_t$=1.57 min; MS (ESIneg): m/z=635 [M–H]⁻

Intermediate 254

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopropyl]methyl}thiourea

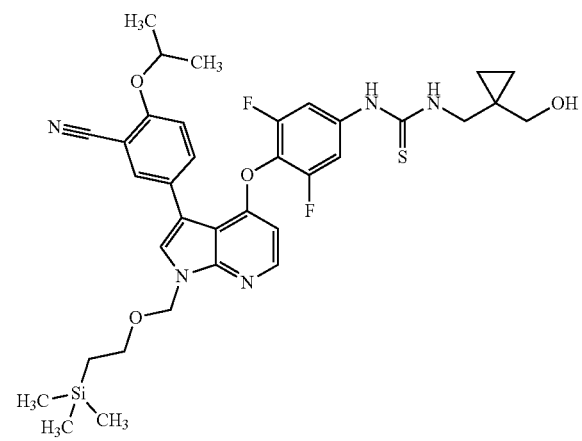 [SMILES: CC(C)Oc1ccc(-c2cn(COCC[Si](C)(C)C)c3nccc(Oc4c(F)cc(NC(=S)NCC5(CO)CC5)cc4F)c23)cc1C#N]

In analogy to Intermediate 231, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (150 mg, 218 µmol, intermediate 158), and [1-(aminomethyl)cyclopropyl]methanol (44.2 mg, 437 µmol, CAS No. [45434-02-4]), in DMF (3.0 mL) were reacted to obtain a crude product which was used in the next step without further purification.

LC-MS (Method 2): $R_t$=1.54 min; MS (ESIpos): m/z=695 [M+H]⁺.

Intermediate 255

5-(4-{2,6-difluoro-4-[(5-oxa-7-azaspiro[2.5]oct-6-en-6-yl)amino]phenoxy}-1-{[2-(trimethylsilyl)ethoxy]methyl}-1H-pyrrolo[2,3-b]pyridin-3-yl)-2-[(propan-2-yl)oxy]benzonitrile

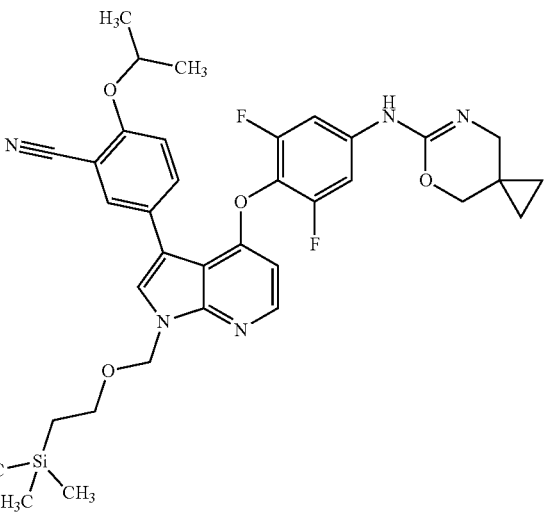

In analogy to Intermediate 232, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopropyl]methyl}thiourea (150 mg, 216 µmol, Intermediate 254) was reacted with 1-(3-Dimethylaminopropyl)-3-ethylcarbodiimide hydrochloride (82.9 mg, 432 µmol) and triethylamine (90 µL, 650 µmol) in acetonitrile (3.0 mL) to obtain a crude product which was used in the next step without further purification.

LC-MS (Method 2): $R_t$=1.62 min; MS (ESIpos): m/z=661 [M+H]⁺

Intermediate 256

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea

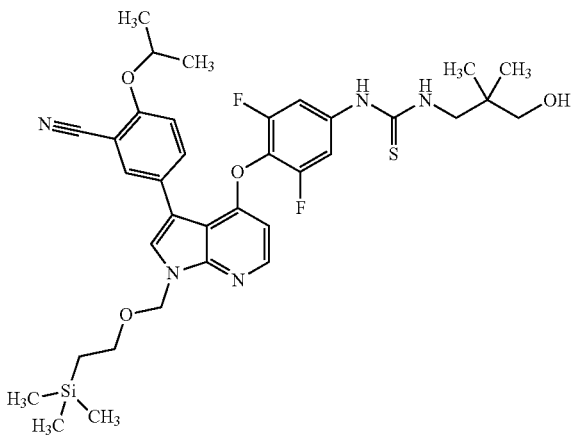 [SMILES: CC(C)Oc1ccc(-c2cn(COCC[Si](C)(C)C)c3nccc(Oc4c(F)cc(NC(=S)NCC(C)(C)CO)cc4F)c23)cc1C#N]

In analogy to Intermediate 231, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (150 mg, 218 µmol, intermediate 158), and 3-amino-2,2-dimethylpropan-1-ol (45.1 mg, 437 µmol, CAS No. [141-43-5]), in DMF (3.0 mL) were reacted to obtain a crude product which was used in the next step without further purification.

LC-MS (Method 2): $R_t$=1.57 min; MS (ESIpos): m/z=697 [M+H]$^+$.

Intermediate 257

5-(4-{4-[(5,5-dimethyl-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile

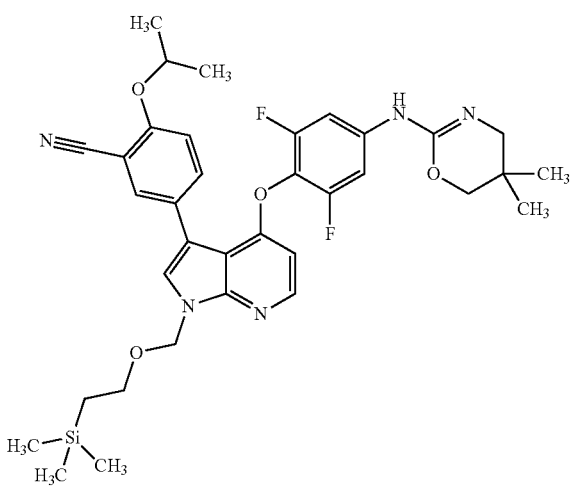

In analogy to Intermediate 232, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea (150 mg, 216 µmol, Intermediate 256) was reacted with 1-(3-Dimethylaminopropyl)-3-ethylcarbodiimide hydrochloride (82.6 mg, 431 µmol) and triethylamine (90 µL, 650 µmol) in acetonitrile (3.0 mL) to obtain a crude product which was used in the next step without further purification.

LC-MS (Method 2): $R_t$=1.64 min; MS (ESIpos): m/z=663 [M+H]$^+$.

Intermediate 258

N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(2,2-difluoro-3-hydroxypropyl)thiourea

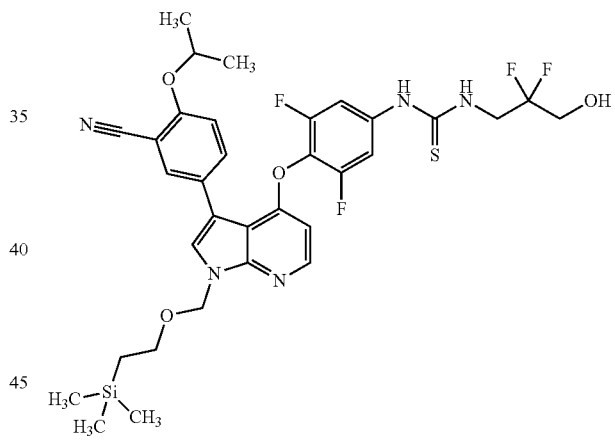

In analogy to Intermediate 231, O-phenyl {4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamothioate (150 mg, 218 µmol, intermediate 158), and 3-amino-2,2-difluoropropan-1-ol (48.5 mg, 437 µmol, CAS No. [2867-59-6]), in DMF (3.0 mL) were reacted to obtain a crude product which was used in the next step without further purification.

LC-MS (Method 2): $R_t$=1.48 min; MS (ESIpos): m/z=705 [M+H]$^+$.

Intermediate 259

5-(4-{4-[(5,5-difluoro-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile

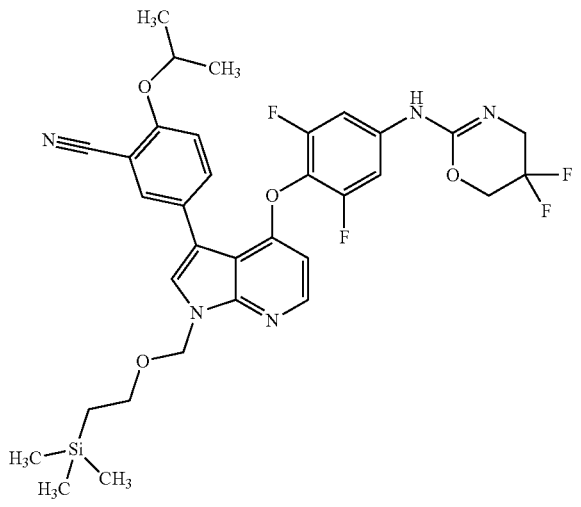 [SMILES: CC(C)Oc1ccc(-c2cn(COCC[Si](C)(C)C)c3nccc(Oc4c(F)cc(NC5=NCC(F)(F)CO5)cc4F)c23)cc1C#N]

In analogy to Intermediate 232, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-(2,2-difluoro-3-hydroxypropyl)thiourea (150 mg, 213 µmol, intermediate 258) was reacted with 1-(3-Dimethylaminopropyl)-3-ethylcarbodiimide hydrochloride (81.7 mg, 426 µmol) and triethylamine (89 µL, 640 µmol) in acetonitrile (3.0 mL) to obtain a crude product which was used in the next step without further purification.

LC-MS (Method 2): $R_t$=1.63 min; MS (ESIpos): m/z=671 [M+H]$^+$.

Intermediate 260

O-phenyl {3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}carbamothioate

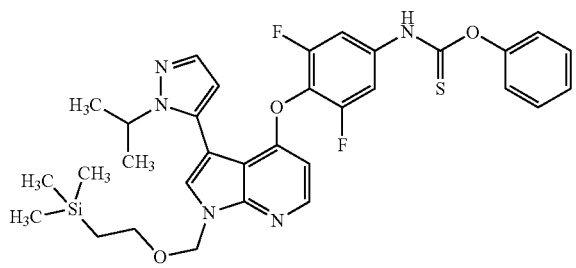 [SMILES: CC(C)n1nccc1-c1cn(COCC[Si](C)(C)C)c2nccc(Oc3c(F)cc(NC(=S)Oc4ccccc4)cc3F)c12]

To a stirred solution of 3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]aniline (970 mg, 1.94 mmol, intermediate 92) in a mixture of pyridine (1.3 m) and THF (20 mL) at 0° C. was added O-phenyl carbonochloridothioate (300 µL, 2.1 mmol). The resulting mixture was stirred at 0° C. for 30 min, at which time the solvent was evaporated to give the crude product which was used without further purification.

LC-MS (Method 1): $R_t$=1.63 min; MS (ESIpos): m/z=637 [M+H]$^+$.

Intermediate 261

N-(2,2-difluoro-3-hydroxypropyl)-N'-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}thiourea

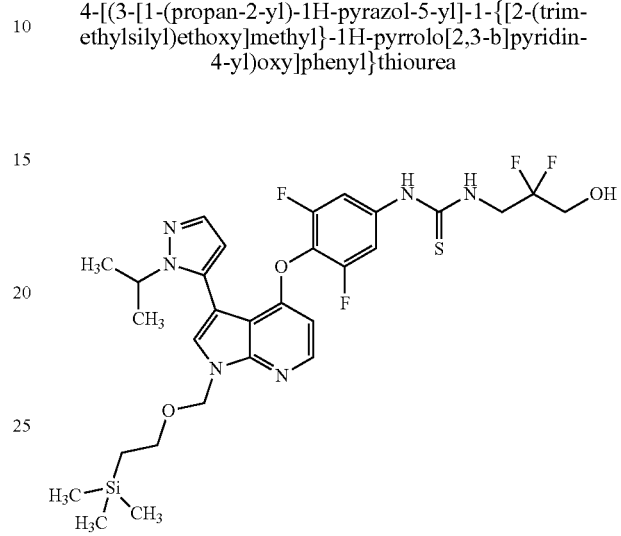

In analogy to Intermediate 231, O-phenyl {3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}carbamothioate (300 mg, 472 µmol, intermediate 260), and 3-amino-2,2-difluoropropan-1-ol (105 mg, 944 µmol, CAS No. [2867-59-6]), in DMF (4.0 mL) were reacted to obtain a crude product which was used in the next step without further purification.

LC-MS (Method 2): $R_t$=1.36 min; MS (ESIpos): m/z=654 [M+H]$^+$.

Intermediate 262

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,5-difluoro-5,6-dihydro-4H-1,3-oxazin-2-amine

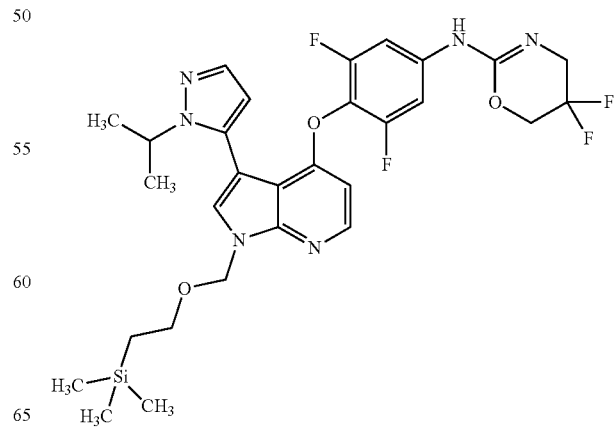

287

In analogy to Intermediate 232, N-(2,2-difluoro-3-hydroxypropyl)-N'-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}thiourea (300 mg, 460 µmol, intermediate 261) was reacted with 1-(3-Dimethylaminopropyl)-3-ethylcarbodiimide hydrochloride (176 mg, 919 µmol) and triethylamine (190 µL, 1.4 mmol) in acetonitrile (5.0 mL) to obtain a crude product which was used in the next step without further purification.

LC-MS (Method 2): $R_t$=1.55 min; MS (ESIpos): m/z=620 $[M+H]^+$.

Intermediate 263

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-(3-hydroxy-2,2-dimethylpropyl)thiourea

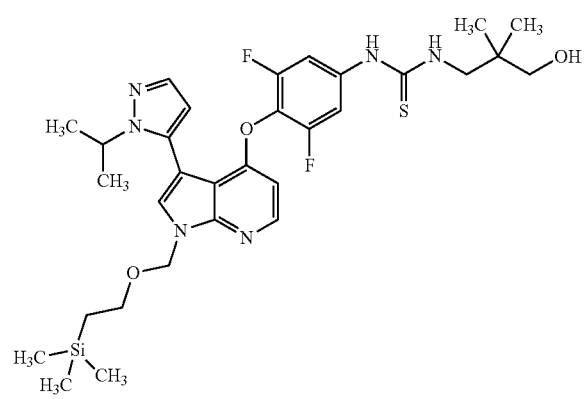 [SMILES: CC(C)n1nccc1-c1cn(COCC[Si](C)(C)C)c2nccc(Oc3c(F)cc(NC(=S)NCC(C)(C)CO)cc3F)c12]

In analogy to Intermediate 231, O-phenyl {3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}carbamothioate (300 mg, 472 µmol, intermediate 260), and 3-amino-2,2-dimethylpropan-1-ol (97.4 mg, 944 µmol, CAS No. [141-43-5]), in DMF (4.0 mL) were reacted to obtain a crude product which was used in the next step without further purification.

LC-MS (Method 2): $R_t$=1.47 min; MS (ESIpos): m/z=646 $[M+H]^+$.

288

Intermediate 264

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,5-dimethyl-5,6-dihydro-4H-1,3-oxazin-2-amine

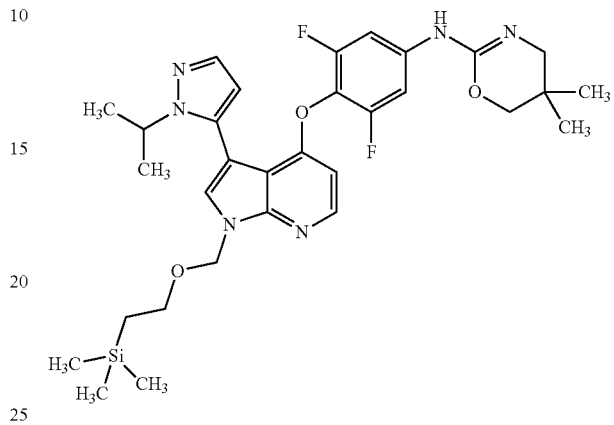

In analogy to Intermediate 232, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-(3-hydroxy-2,2-dimethylpropyl)thiourea (300 mg, 465 µmol, intermediate 263) was reacted with 1-(3-Dimethylaminopropyl)-3-ethylcarbodiimide hydrochloride (178 mg, 930 µmol) and triethylamine (190 µL, 1.4 mmol) in acetonitrile (5.0 mL) to obtain a crude product which was used in the next step without further purification.

LC-MS (Method 2): $R_t$=1.56 min; MS (ESIpos): m/z=612 $[M+H]^+$.

Intermediate 265

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-{[1-(hydroxymethyl)cyclopropyl]methyl}thiourea

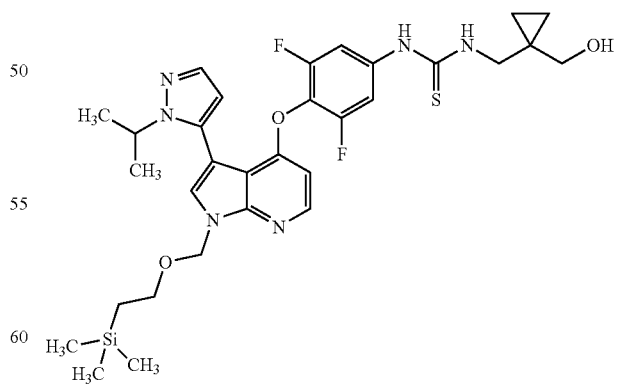

In analogy to Intermediate 231, O-phenyl {3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}carbamothioate (300 mg, 472 µmol, intermediate 260), and [1-(aminomethyl)cyclopropyl]methanol (95.5 mg, 944 µmol, CAS No. [45434-02-4]), in DMF (4.0 mL) were reacted to obtain a crude product which was used in the next step without further purification.

LC-MS (Method 2): $R_t$=1.44 min; MS (ESIpos): m/z=644 [M+H]$^+$.

Intermediate 266

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5-oxa-7-azaspiro[2.5]oct-6-en-6-amine

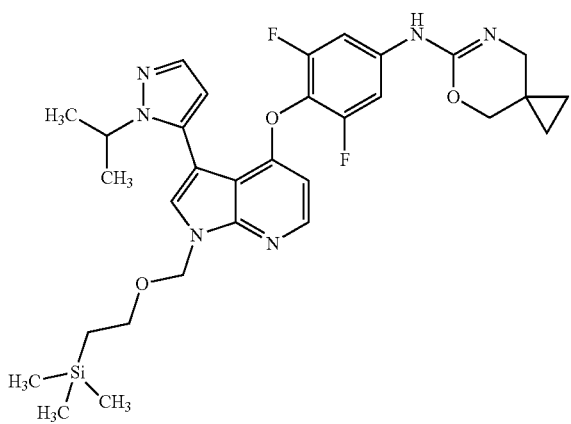 [SMILES: CC(C)n1nccc1-c1cn(COCC[Si](C)(C)C)c2nccc(Oc3c(F)cc(NC4=NCC5(CC5)CO4)cc3F)c12]

In analogy to Intermediate 232, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-{[1-(hydroxymethyl)cyclopropyl]methyl}thiourea (300 mg, 467 µmol, intermediate 265) was reacted with 1-(3-Dimethylaminopropyl)-3-ethylcarbodiimide hydrochloride (179 mg, 933 µmol) and triethylamine (200 µL, 1.4 mmol) in acetonitrile (5.0 mL) to obtain a crude product which was used in the next step without further purification.

LC-MS (Method 2): $R_t$=1.53 min; MS (ESIpos): m/z=610 [M+H]$^+$.

Intermediate 267

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-(3-hydroxypropyl)thiourea

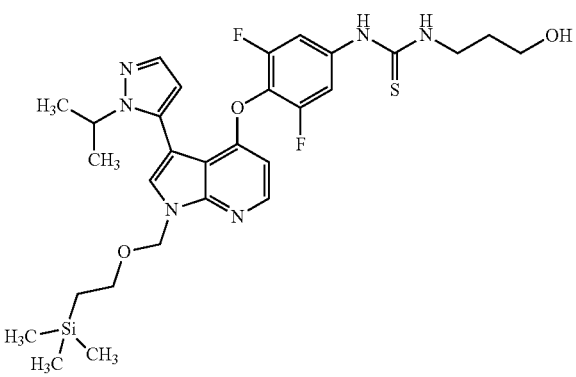 [SMILES: CC(C)n1nccc1-c1cn(COCC[Si](C)(C)C)c2nccc(Oc3c(F)cc(NC(=S)NCCCO)cc3F)c12]

In analogy to Intermediate 231, O-phenyl {3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}carbamothioate (300 mg, 472 µmol, intermediate 260), and 3-aminopropan-1-ol (70.9 mg, 944 µmol, CAS No. [45434-02-4]), in DMF (4.0 mL) were reacted to obtain a crude product which was used in the next step without further purification.

LC-MS (Method 2): $R_t$=1.38 min; MS (ESIpos): m/z=618 [M+H]$^+$.

Intermediate 268

N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,6-dihydro-4H-1,3-oxazin-2-amine

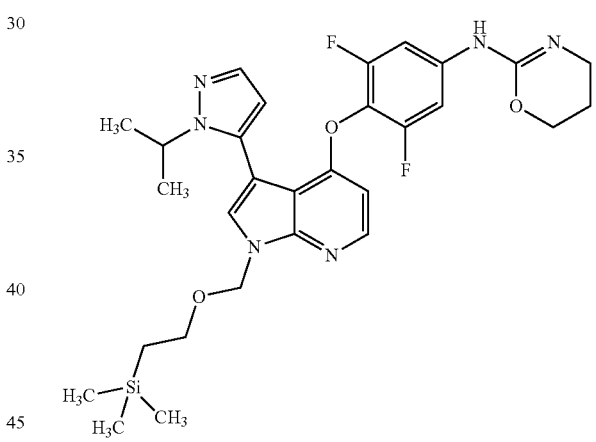

In analogy to Intermediate 232, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-N'-(3-hydroxypropyl)thiourea (290 mg, 470 µmol, intermediate 267) was reacted with 1-(3-Dimethylaminopropyl)-3-ethylcarbodiimide hydrochloride (180 mg, 940 µmol) and triethylamine (200 µL, 1.4 mmol) in acetonitrile (5.0 mL) to obtain a crude product which was used in the next step without further purification.

LC-MS (Method 2): $R_t$=1.46 min; MS (ESIpos): m/z=584 [M+H]$^+$.

Intermediate 269

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-(3-hydroxypropyl)thiourea

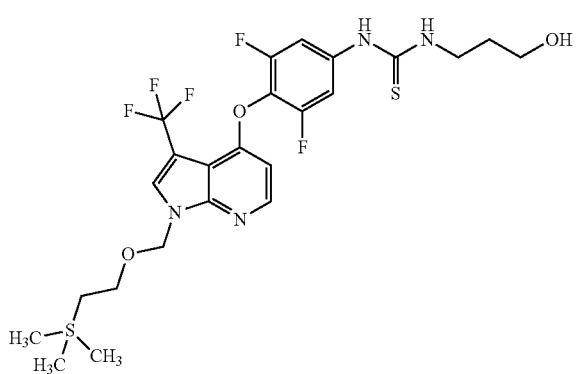

In analogy to Intermediate 231, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (400 mg, 672 µmol, Intermediate 439), and 3-aminopropan-1-ol (101 mg, 1.34 mmol, CAS No. [45434-02-4]), in DMF (5.0 mL) were reacted to obtain a crude product which was used in the next step without further purification.

LC-MS (Method 2): $R_t$=1.44 min; MS (ESIpos): m/z=578 [M+H]$^+$.

Intermediate 270

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,6-dihydro-4H-1,3-oxazin-2-amine

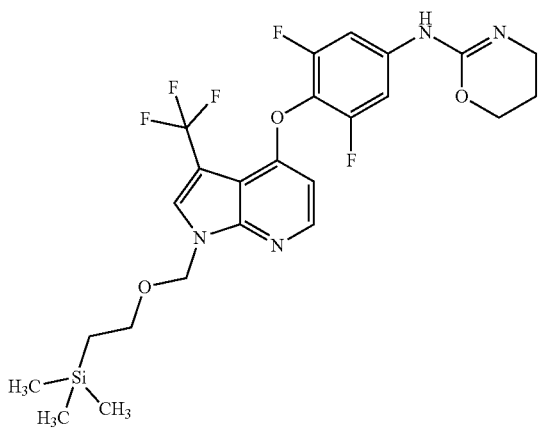 [SMILES: C[Si](C)(C)CCOCn1cc(C(F)(F)F)c2c(Oc3c(F)cc(NC4=NCCCO4)cc3F)ccnc21]

In analogy to Intermediate 232, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-(3-hydroxypropyl)thiourea (380 mg, 659 µmol, intermediate 269) was reacted with 1-(3-Dimethylaminopropyl)-3-ethylcarbodiimide hydrochloride (253 mg, 1.32 mmol) and triethylamine (280 µL, 2.0 mmol) in acetonitrile (5.0 mL) to obtain a crude product which was used in the next step without further purification.

LC-MS (Method 2): $R_t$=1.52 min; MS (ESIpos): m/z=544 [M+H]$^+$.

Intermediate 271

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-{[1-(hydroxymethyl)cyclopropyl]methyl}thiourea

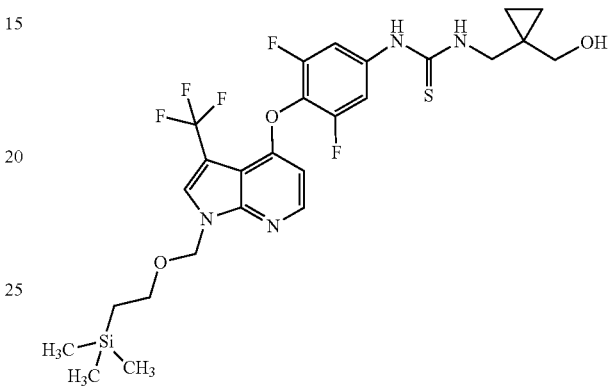

In analogy to Intermediate 231, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (400 mg, 672 µmol, Intermediate 439), and [1-(aminomethyl)cyclopropyl]methanol (136 mg, 1.34 mmol, CAS No. [45434-02-4]), in DMF (5.0 mL) were reacted to obtain a crude product which was used in the next step without further purification.

LC-MS (Method 2): $R_t$=1.50 min; MS (ESIpos): m/z=604 [M+H]$^+$.

Intermediate 272

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5-oxa-7-azaspiro[2.5]oct-6-en-6-amine

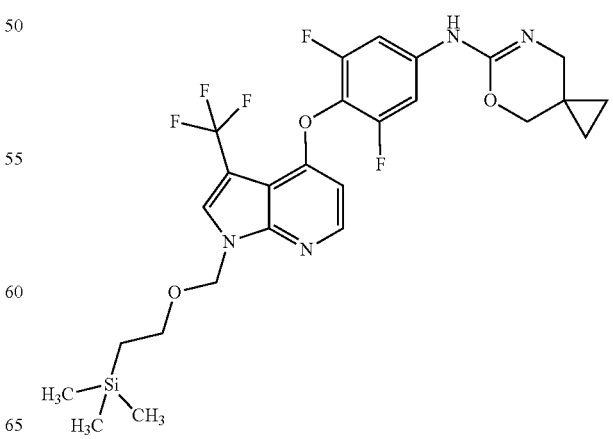

293

In analogy to Intermediate 232, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-{[1-(hydroxymethyl)cyclopropyl]methyl}thiourea (400 mg, 664 µmol, intermediate 271) was reacted with 1-(3-Dimethylaminopropyl)-3-ethylcarbodiimide hydrochloride (254 mg, 1.33 mmol) and triethylamine (280 µL, 2.0 mmol) in acetonitrile (5.0 mL) to obtain a crude product which was used in the next step without further purification.

LC-MS (Method 2): R$_t$=1.59 min; MS (ESIpos): m/z=570 [M+H]$^+$.

Intermediate 273

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-(3-hydroxy-2,2-dimethylpropyl)thiourea

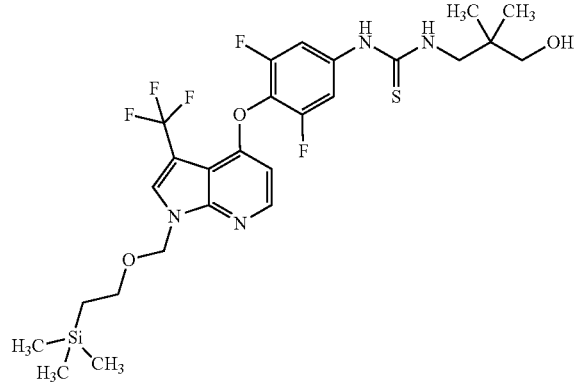 [SMILES: CC(C)(CO)CNC(=S)Nc1cc(F)c(Oc2ccnc3c2c(C(F)(F)F)cn3COCC[Si](C)(C)C)c(F)c1]

In analogy to Intermediate 231, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (400 mg, 672 µmol, Intermediate 439), and 3-amino-2,2-dimethylpropan-1-ol (139 mg, 1.34 mmol, CAS No. [141-43-5]) in DMF (5.0 mL) were reacted to obtain a crude product which was used in the next step without further purification.

LC-MS (Method 2): R$_t$=1.53 min; MS (ESIpos): m/z=606 [M+H]$^+$.

294

Intermediate 274

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,5-dimethyl-5,6-dihydro-4H-1,3-oxazin-2-amine

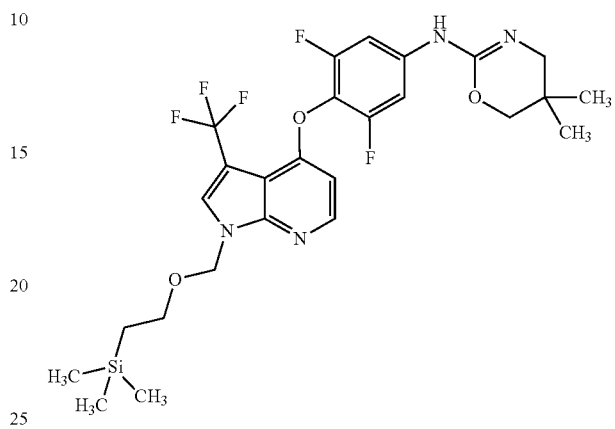

In analogy to Intermediate 232, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-(3-hydroxy-2,2-dimethylpropyl)thiourea (400 mg, 661 µmol, intermediate 273) was reacted with 1-(3-Dimethylaminopropyl)-3-ethylcarbodiimide hydrochloride (254 mg, 1.32 mmol) and triethylamine (280 µL, 2.0 mmol) in acetonitrile (5.0 mL) to obtain a crude product which was used in the next step without further purification.

LC-MS (Method 2): R$_t$=1.61 min; MS (ESIpos): m/z=572 [M+H]$^+$.

Intermediate 275

N-(2,2-difluoro-3-hydroxypropyl)-N'-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)thiourea

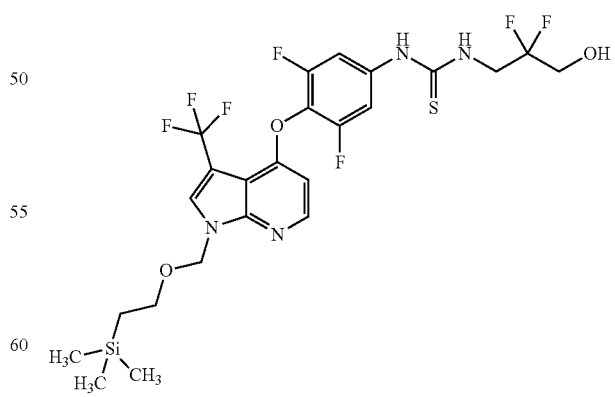

In analogy to Intermediate 231, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (400 mg, 672 µmol, Intermediate 439), and 3-amino-2,2-difluoropropan-1-ol (149 mg, 1.34 mmol, CAS No. [2867-59-6]) in DMF (5.0 mL) were reacted to obtain a crude product which was used in the next step without further purification.

LC-MS (Method 2): $R_t$=1.43 min; MS (ESIpos): m/z=614 [M+H]$^+$.

Intermediate 276

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,5-difluoro-5,6-dihydro-4H-1,3-oxazin-2-amine

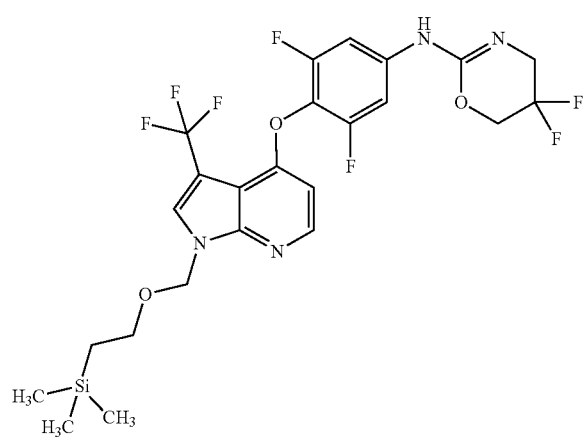 [SMILES: C[Si](C)(C)CCOCn1cc(C(F)(F)F)c2c(Oc3c(F)cc(NC4=NCC(F)(F)CO4)cc3F)ccnc21]

In analogy to Intermediate 232, N-(2,2-difluoro-3-hydroxypropyl)-N'-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)thiourea (405 mg, 661 µmol, intermediate 275) was reacted with 1-(3-Dimethylaminopropyl)-3-ethylcarbodiimide hydrochloride (253 mg, 1.32 mmol) and triethylamine (280 µL, 2.0 mmol) in acetonitrile (5.0 mL) to obtain a crude product which was used in the next step without further purification.

LC-MS (Method 2): $R_t$=1.60 min; MS (ESIpos): m/z=580 [M+H]$^+$.

Intermediate 277

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-{[1-(hydroxymethyl)cyclobutyl]methyl}thiourea

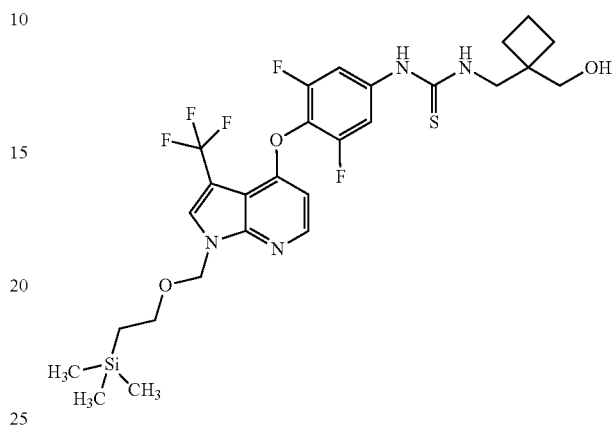

In analogy to Intermediate 231, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (400 mg, 672 µmol, Intermediate 439), and [1-(aminomethyl)cyclobutyl]methanol (155 mg, 1.34 mmol, CAS No. [2041-56-7]), in DMF (5.0 mL) were reacted to obtain a crude product which was used in the next step without further purification.

LC-MS (Method 2): $R_t$=1.55 min; MS (ESIpos): m/z=618 [M+H]$^+$.

Intermediate 278

N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-6-oxa-8-azaspiro[3.5]non-7-en-7-amine

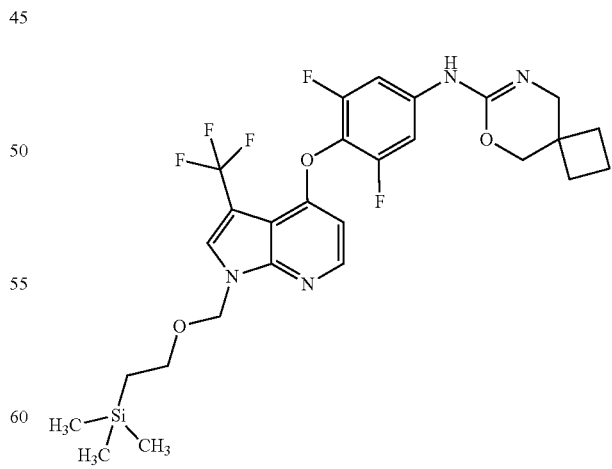

In analogy to Intermediate 232, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-{[1-(hydroxymethyl)cyclobutyl]methyl}thiourea (411 mg, 666 µmol, intermediate 277) was reacted with 1-(3-Dimethylaminopropyl)-3-ethylcarbodiimide hydrochloride (256 mg, 1.33 mmol) and triethylamine (280 μL, 2.0 mmol) in acetonitrile (5.0 mL) to obtain a crude product which was used in the next step without further purification.

LC-MS (Method 2): $R_t$=1.63 min; MS (ESIpos): m/z=584 [M+H]$^+$.

Intermediate 279

3-bromo-4-(2,6-difluoro-4-nitrophenoxy)-1H-pyrrolo[2,3-b]pyridine

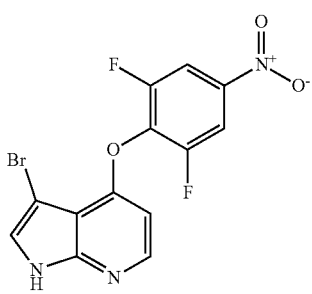 [SMILES: O=[N+]([O-])c1cc(F)c(Oc2ccnc3[nH]cc(Br)c23)c(F)c1]

To a stirred solution of 4-(2,6-difluoro-4-nitrophenoxy)-1H-pyrrolo[2,3-b]pyridine (5.70 g, 19.6 mmol, intermediate 14) in DMF (100 mL) was added N-bromosuccinimide (3.83 g, 21.5 mmol). The resulting mixture was stirred at room temperature for 2 hours at which time the reaction was cooled to 0° C. and water was slowly added. The resulting precipitate was filtered and dried to afford the title compound (7.20 g, 99% yield) LC-MS (Method 2): $R_t$=1.18 min; MS (ESIpos): m/z=370 [M+H]$^+$ $^1$H NMR (400 MHz, DMSO-d$_6$) δ ppm 6.55 (d, 1H), 7.72 (d, 1H), 8.14 (d, 1H), 8.41 (d, 2H), 12.34 (br s, 1H)

Intermediate 280

3-bromo-4-(2,6-difluoro-4-nitrophenoxy)-1-(4-methylbenzene-1-sulfonyl)-1H-pyrrolo[2,3-b]pyridine

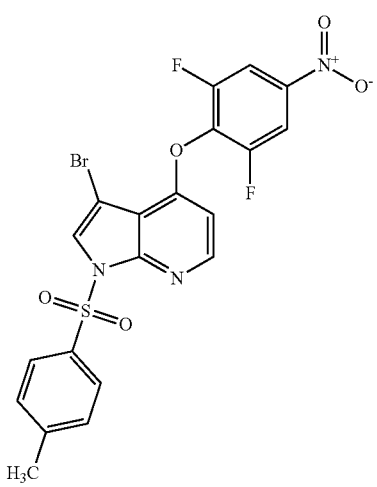

To a cooled (0° C.) solution of 3-bromo-4-(2,6-difluoro-4-nitrophenoxy)-1H-pyrrolo[2,3-b]pyridine (13.0 g, 35.1 mmol, intermediate 279) in DMF (200 mL) was added sodium hydride (1.83 g, 60% suspension in oil, 45.7 mmol) portionwise. The resulting mixture was stirred for 15 minutes at 0° C. at which time p-Toluenesulfonylchloride (7.37 g, 38.6 mmol) was added and the reaction was allowed to warm slowly to room temperature overnight. The mixture was slowly poured into ice-water, and the resulting precipitate was filtered and dried to afford 15 g (81% yield) of the desired product.

LC-MS (Method 2): $R_t$=1.51 min; MS (ESIpos): m/z=526 [M+H]$^+$ $^1$H NMR (400 MHz, DMSO-d$_6$) δ ppm 2.37 (s, 3H), 6.87 (d, 1H), 7.46 (d, 2H), 8.04 (d, 2H), 8.22 (s, 1H), 8.31 (d, 1H), 8.42 (d, 2H)

Intermediate 281

4-{[3-bromo-1-(4-methylbenzene-1-sulfonyl)-1H-pyrrolo[2,3-b]pyridin-4-yl]oxy}-3,5-difluoroaniline

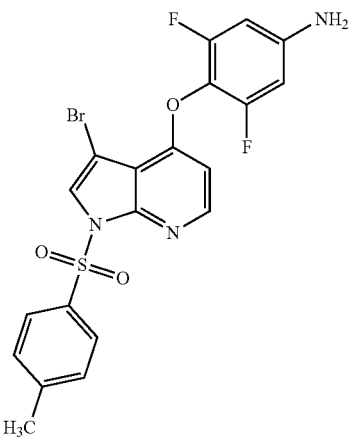

To a solution of 3-bromo-4-(2,6-difluoro-4-nitrophenoxy)-1-(4-methylbenzene-1-sulfonyl)-1H-pyrrolo[2,3-b]pyridine (5.20 g, 9.92 mmol, Intermediate 280) in a mixture of THF:water:methanol (1:2:1, 200 mL), was added ammonium chloride (2.65 g, 49.6 mmol) and iron powder (2.77 g, 49.6 mmol). The resulting mixture was stirred at 80° C. for 2 hours at which time the mixture was cooled and filtered over celite. The filtrate was extracted twice with ethyl acetate and the combined organic layers washed with brine, dried (Na2SO4), and evaporated to give the crude product 4.90 g (100% yield) which was sufficiently pure for the next step without further purification.

LC-MS (Method 2): $R_t$=1.39 min; MS (ESIpos): m/z=494 [M+H]$^+$ $^1$H NMR (400 MHz, DMSO-d$_6$) δ ppm 2.35 (s, 3H), 5.85 (s, 2H), 6.37 (d, 2H), 6.57 (d, 1H), 7.44 (d, 2H), 8.02 (d, 2H), 8.10 (s, 1H), 8.24 (d, 1H)

Intermediate 282 tert-butyl (4-{[3-bromo-1-(4-methylbenzene-1-sulfonyl)-1H-pyrrolo[2,3-b]pyridin-4-yl]oxy}-3,5-difluorophenyl)carbamate

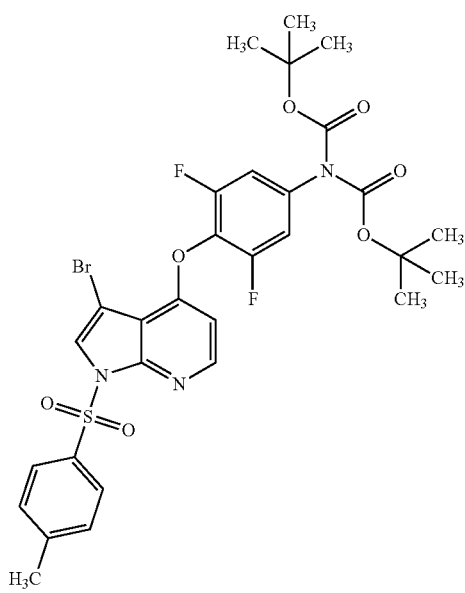

To a solution of 4-{[3-bromo-1-(4-methylbenzene-1-sulfonyl)-1H-pyrrolo[2,3-b]pyridin-4-yl]oxy}-3,5-difluoroaniline (4.30 g, 8.70 mmol, Intermediate 281) in THF (30 mL) was added di-tert-butyl dicarbonate (4.7 mL, 22 mmol) and dimethylaminopyridine (106 mg, 870 µmol). The resulting mixture was stirred at 75° C. for 3 h, at which time ethyl acetate and water were added and the layers were separated. The aqueous phase was extracted twice with ethyl acetate and the combined organic layers were washed with brine, dried over sodium sulfate, and evaporated to afford the crude product. The crude product was purified by flash column chromatography followed by crystallization from a mixture of dichloromethane and methanol to afford the title compound (1.68 g, 28% yield).

LC-MS (Method 2): $R_t$=1.70 min; MS (ESIpos): m/z=696 [M+H]$^+$ $^1$H NMR (400 MHz, DMSO-d$_6$) δ ppm 1.41 (s, 18H), 2.36 (s, 3H), 6.46 (d, 1H), 7.45 (d, 2H), 7.53 (d, 2H), 8.04 (d, 2H), 8.19 (s, 1H), 8.31 (d, 1H)

Intermediate 283 di-tert-butyl [3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]-2-imidodicarbonate

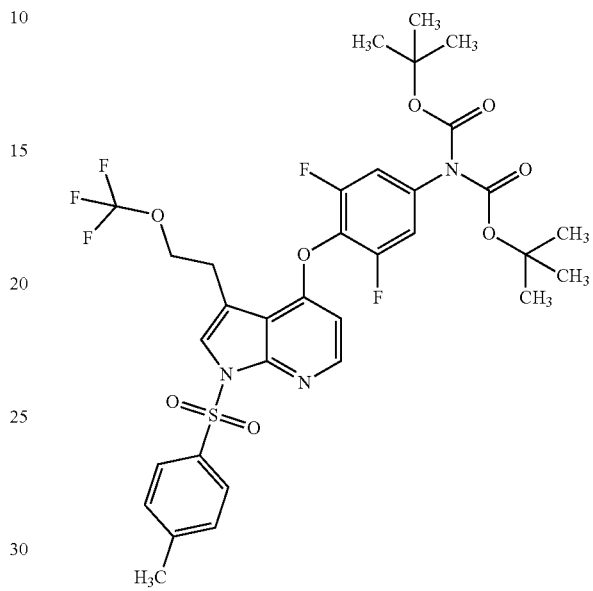

di-tert-butyl (4-{[3-bromo-1-(4-methylbenzene-1-sulfonyl)-1H-pyrrolo[2,3-b]pyridin-4-yl]oxy}-3,5-difluorophenyl)-2-imidodicarbonate (80 mg, 115 µmol, Intermediate 282), 1-bromo-2-(trifluoromethoxy)ethane (60 µL, 520 µmol, CAS No. [1645-93-8]), Ir(4',6'-dF-5-CF$_3$-ppy)$_2$(4,4'-dtbbpy)PF$_6$ (2.58 mg, 2.30 µmol, CAS No. [870987-63-6]), tris(trimethylsilyl)silane (36 µL, 120 µmol, CAS No. [1873-77-4]) and lithiumhydroxide (16.6 mg, 691 µmol) were dissolved in trifluorotoluene (1.6 mL) in a MW-vial. In a separate vial, the Ni-catalyst was prepared by dissolving Nickel (II) chloride dimethoxyethane adduct (130 pg, 0.58 µmol, CAS No. [29046-78-4]) and 4,4'-Di-tert-butyl-2,2'-bipyridine (150 pg, 0.58 µmol, CAS No. [72914-19-3]) in N,N-dimethyl acetamide (0.8 mL) followed by stirring for 5 min. The catalyst solution was syringed to the sealed reaction vial and argon was bubbled through the solution for another 5 min. The MW-vial was subsequently irradiated by two 40 W Kessil LED Aquarium lights (40 W each, 4 cm distance) placed in a water bath to keep the temperature below 35° C. for 14 hours, at which time water and ethyl acetate were added and the layers were separated. The aqueous phase was extracted twice with ethyl acetate and the combined organic layers were washed with brine, dried over sodium sulfate, and evaporated to give the crude material. The crude material was purified by Biotage to give an inseparable mixture of the title compound and the dehalogenated starting material. This mixture was further purified by preparative HPLC to afford the title compound (30 mg, 36% yield).

LC-MS (Method 2): $R_t$=1.68 min; MS (ESIpos): m/z=729 [M+H]$^+$ $^1$H NMR (400 MHz, DMSO-d$_6$) δ ppm 1.41 (s, 18H), 3.25 (t, 2H), 4.39 (t, 2H), 6.40 (d, 1H), 7.43 (d, 2H), 7.53 (d, 2H), 7.86 (s, 1H), 7.98 (d, 2H), 8.25 (d, 1H)

Intermediate 284

3,5-difluoro-4-({1-(4-methylbenzene-1-sulfonyl)-3-[2-(trifluoromethoxy)ethyl]-1H-pyrrolo[2,3-b]pyridin-4-yl}oxy)aniline

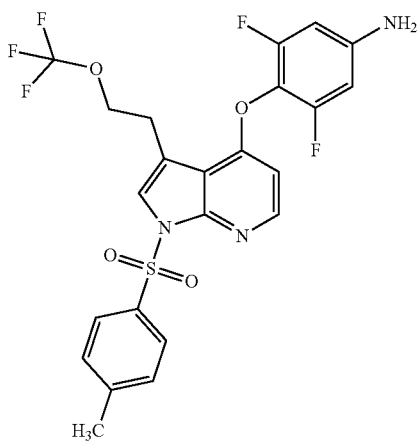

To a stirred solution of di-tert-butyl [3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]-2-imidodicarbonate (335 mg, 460 µmol, Intermediate 283) in 1,4-dioxane (3.0 mL) was added hydrochloric acid (4.0M in Dioxane, 3.0 mL, 35 mmol). The mixture was stirred at room temperature overnight, at which time the solvent was evaporated. The residue was stirred in ether, filtered and dried to afford the crude title compound which was used without further purification.

LC-MS (Method 2): $R_t$=1.42 min; MS (ESIpos): m/z=529 [M+H]$^+$.

Intermediate 285 phenyl [3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]carbamate

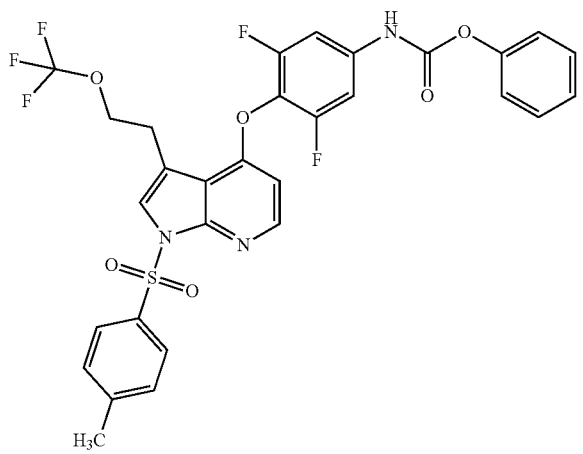

A stirred solution of 3,5-difluoro-4-({1-(4-methylbenzene-1-sulfonyl)-3-[2-(trifluoromethoxy)ethyl]-1H-pyrrolo[2,3-b]pyridin-4-yl}oxy)aniline (165 mg, 313 µmol, Intermediate 284) in pyridine (200 µL, 2.5 mmol) and THF (2.0 mL) at 0° C. was added phenyl carbonochloridate (43 µL, 340 µmol). The resulting mixture was stirred for 30 min at 0° C., at which time it was diluted with ethyl acetate and a 2M aqueous solution of hydrochlorid acid was added slowly. The layers were separated and the aqueous phase was extracted twice with ethyl acetate. The combined organic phases were washed with a saturated solution of sodium bicarbonate, followed by brine, dried over sodium sulfate, and evaporated to afford the crude product. The crude product was used without further purification.

LC-MS (Method 1): $R_t$=1.57 min; MS (ESIpos): m/z=649 [M+H]$^+$.

Intermediate 286

N-[3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]-N'-[(3-fluorooxetan-3-yl)methyl]urea

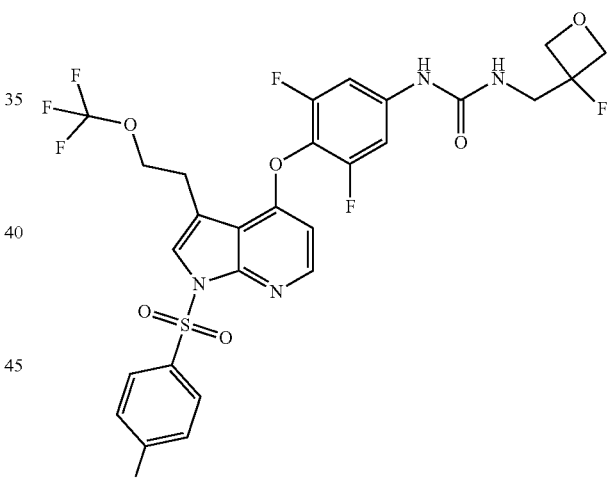

In analogy to intermediate 2, phenyl [3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]carbamate (188 mg, 290 µmol, intermediate 285), and 1-(3-fluorooxetan-3-yl)methanamine (30.5 mg, 290 µmol, CAS No. [883311-82-8]), in DMF (2.0 mL) were reacted to obtain a crude product which was used in the next step without further purification.

LC-MS (Method 2): $R_t$=1.39 min; MS (ESIpos): m/z=659 [M+H]$^+$.

Intermediate 287

N-[3,5-difluoro-4-({3-[2-(trifluoromethoxy)ethyl]-1H-pyrrolo[2,3-b]pyridin-4-yl}oxy)phenyl]-N'-[(3-fluorooxetan-3-yl)methyl]urea

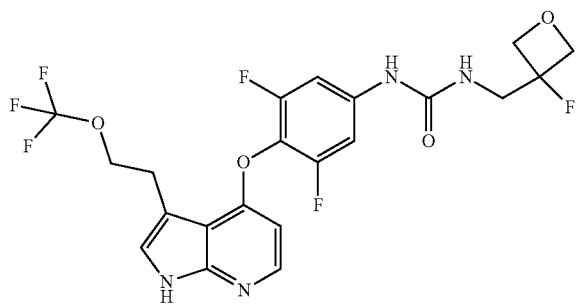 [SMILES: O=C(NCC1(F)COC1)Nc1cc(F)c(Oc2ccnc3[nH]cc(CCOC(F)(F)F)c23)c(F)c1]

To a solution of N-[3,5-difluoro-4-({1-(4-methylbenzene-1-sulfonyl)-3-[2-(trifluoromethoxy)ethyl]-1H-pyrrolo[2,3-b]pyridin-4-yl}oxy)phenyl]-N'-[(3-fluorooxetan-3-yl)methyl]urea (190 mg, 288 μmol, intermediate 286) in methanol (5.0 mL) was added sodium hydroxide (23.1 mg, 577 μmol). The resulting mixture was stirred at room temperature overnight, at which time water and ethyl acetate were added and the layers were separated. The aqueous phase was extracted twice with ethyl acetate, and the combined organic layers were washed with brine, dried over sodium sulfate and evaporated to give the crude product which was used without further purification.

LC-MS (Method 2): $R_t$=1.12 min; MS (ESIpos): m/z=505 [M+H]$^+$ $^1$H NMR (400 MHz, DMSO-d$_6$) δ ppm 3.22 (t, 2H), 3.66 (dd, 2H), 4.37 (t, 2H), 4.56-4.67 (m, 4H), 6.25 (d, 1H), 6.86 (br t, 1H), 7.33 (d, 1H), 7.39 (d, 2H), 8.03 (d, 1H), 9.16 (s, 1H), 11.68 (br d, 1H)

Intermediate 288

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[4-(hydroxymethyl)oxan-4-yl]methyl}thiourea

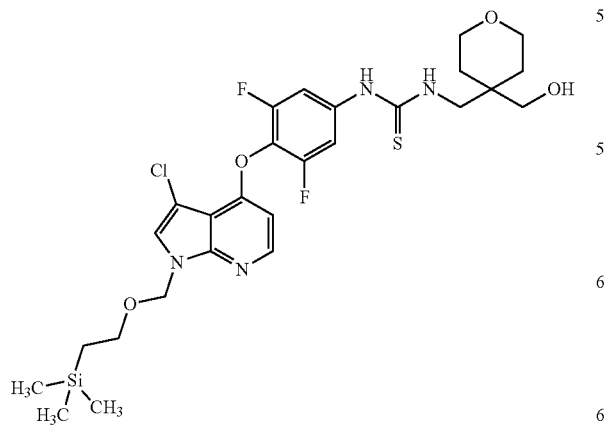

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (575 mg, 1.02 mmol, intermediate 424), and [4-(aminomethyl)oxan-4-yl]methanol (297 mg, 2.05 mmol, CAS No. [959238-22-3]), in DMF (6.0 mL) were reacted to obtain a crude product which was used in the next step without further purification.

LC-MS (Method 2): $R_t$=1.47 min; MS (ESIpos): m/z=613 [M+H]$^+$.

Intermediate 289

N-{4-[(3-chloro-1-{[2-(trimethylsilyl)ethoxy]methyl}-1H-pyrrolo[2,3-b]pyridin-4-yl)oxy]-3,5-difluorophenyl}-2,9-dioxa-4-azaspiro[5.5]undec-3-en-3-amine

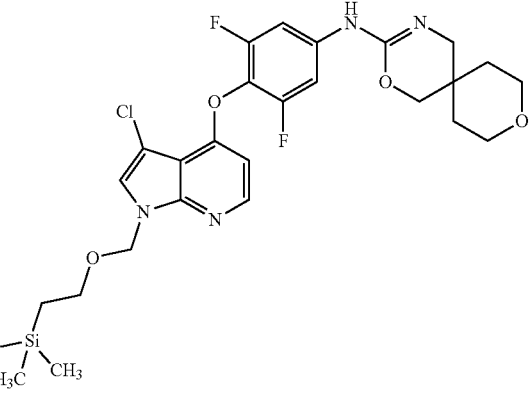

In analogy to Intermediate 232, N-{4-[(3-chloro-1-{[2-(trimethylsilyl)ethoxy]methyl}-1H-pyrrolo[2,3-b]pyridin-4-yl)oxy]-3,5-difluorophenyl}-N'-{[4-(hydroxymethyl)oxan-4-yl]methyl}thiourea (620 mg, 1.01 mmol, Intermediate 288) was reacted with 1-(3-Dimethylaminopropyl)-3-ethylcarbodiimide hydrochloride (388 mg, 2.02 mmol) and triethylamine (420 μL, 3.0 mmol) in acetonitrile (7.0 mL) to obtain a crude product which was used in the next step without further purification.

LC-MS (Method 2): $R_t$=1.51 min; MS (ESIpos): m/z=580 [M+H]$^+$.

Intermediate 290

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2-methylpropyl)thiourea

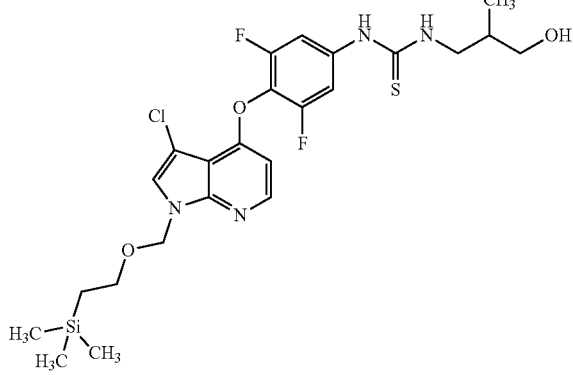

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (575 mg, 1.02 mmol, intermediate 424), and 3-amino-2-methyl-propan-1-ol (182 mg, 2.05 mmol, CAS No. [15518-10-2]), in DMF (6.0 mL) were reacted to obtain a crude product which was used in the next step without further purification.

LC-MS (Method 2): $R_t$=1.49 min; MS (ESIpos): m/z=557 [M+H]$^+$.

Intermediate 291

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-5-methyl-5,6-dihydro-4H-1,3-oxazin-2-amine

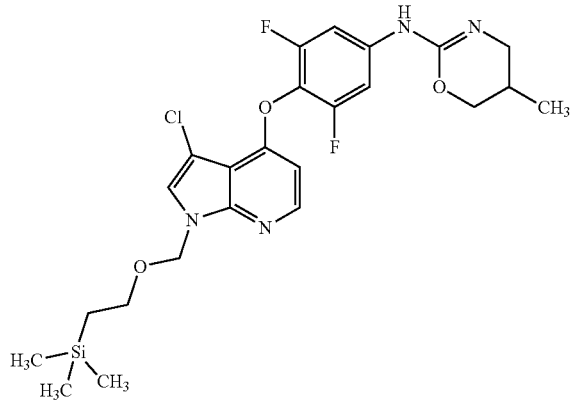

In analogy to Intermediate 232, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2-methylpropyl)thiourea (560 mg, 1.01 mmol, intermediate 290) was reacted with 1-(3-Dimethylaminopropyl)-3-ethyl-carbodiimide hydrochloride (385 mg, 2.01 mmol) and tri-ethylamine (420 µL, 3.0 mmol) in acetonitrile (7.0 mL) to obtain a crude product which was used in the next step without further purification.

LC-MS (Method 2): $R_t$=1.56 min; MS (ESIpos): m/z=524 [M+H]$^+$.

Intermediate 292

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(1-hydroxy-4-methylpentan-3-yl)thiourea

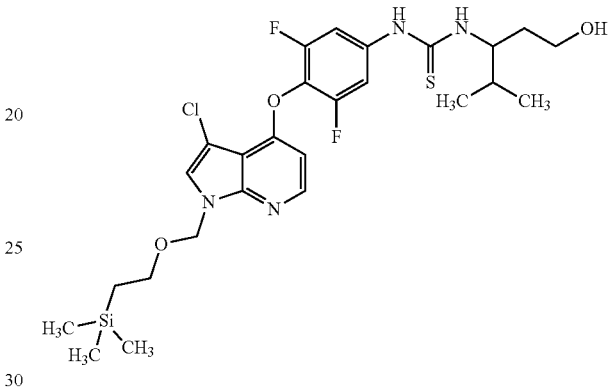

In analogy to Intermediate 231, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (575 mg, 1.02 mmol, intermediate 424), and 3-amino-4-methyl-pentan-1-ol (240 mg, 2.05 mmol, CAS No. [4379-15-1]), in DMF (6.0 mL) were reacted to obtain a crude product which was used in the next step without further purification.

LC-MS (Method 2): $R_t$=1.55 min; MS (ESIpos): m/z=586 [M+H]$^+$.

Intermediate 293

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-(propan-2-yl)-5,6-dihydro-4H-1,3-oxazin-2-amine

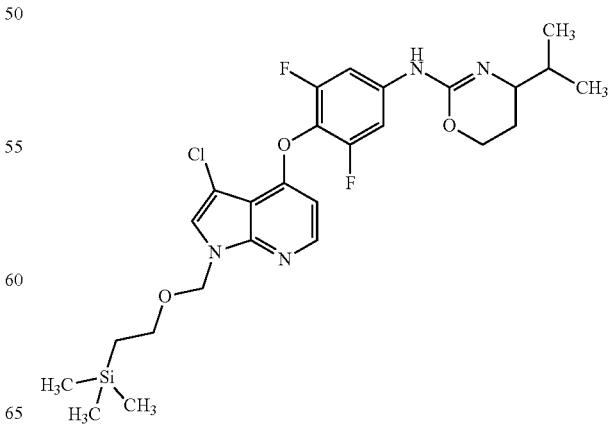

In analogy to Intermediate 232, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(1-hydroxy-4-methylpentan-3-yl)thiourea (590 mg, 1.01 mmol), intermediate 292) was reacted with 1-(3-Dimethylaminopropyl)-3-ethylcarbodiimide hydrochloride (387 mg, 2.02 mmol) and triethylamine (420 μL, 3.0 mmol) in acetonitrile (7.0 mL) to obtain a crude product which was used in the next step without further purification.

LC-MS (Method 2): $R_t$=1.68 min; MS (ESIpos): m/z=552 [M+H]$^+$.

Intermediate 294 di-tert-butyl (3,5-difluoro-4-{[1-(4-methylbenzene-1-sulfonyl)-3-(propan-2-yl)-1H-pyrrolo[2,3-b]pyridin-4-yl]oxy}phenyl)-2-imidodicarbonate

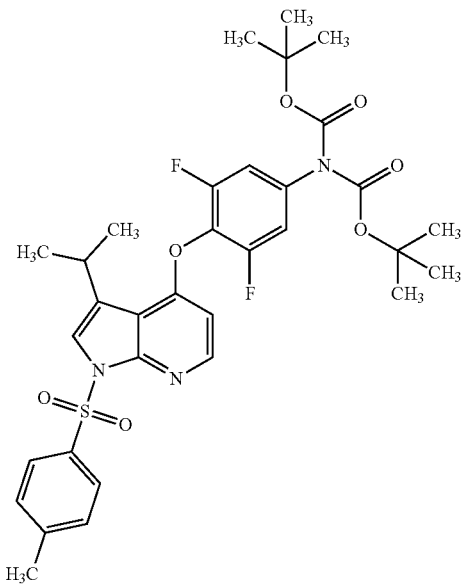 [SMILES: Cc1ccc(S(=O)(=O)n2cc(C(C)C)c3c(Oc4c(F)cc(N(C(=O)OC(C)(C)C)C(=O)OC(C)(C)C)cc4F)ccnc32)cc1]

di-tert-butyl (4-{[3-bromo-1-(4-methylbenzene-1-sulfonyl)-1H-pyrrolo[2,3-b]pyridin-4-yl]oxy}-3,5-difluorophenyl)-2-imidodicarbonate (500 mg, 720 μmol, Intermediate 282), tris(trimethylsilyl)silane (220 μL, 720 μmol, CAS No. [1873-77-4]), 2-bromopropane (300 μL, 3.2 mmol, CAS No. [75-26-3]), 2,6-dimethoxypyridine (570 μL, 4.3 mmol) and Ir(4',6'-dF-5-CF$_3$-ppy)$_2$(4,4'-dtbbpy)PF$_6$ (16 mg, 14 μmol, CAS No. [870987-63-6]) were dissolved in the reaction vial in trifluorotoluene (11 mL). In a separate vial, the Ni-catalyst was prepared by dissolving Nickel (II) chloride dimethoxyethane adduct (8 mg, 36 μmol, CAS No. [29046-78-4]) and 4,4'-Di-tert-butyl-2,2'-bipyridine (10 mg, 36 μmol, CAS No. [72914-19-3]) in N,N-dimethylacetamide (4.0 mL) followed by stirring for 5 min. The catalyst solution was syringed to the sealed reaction vial and degassed by sparging with argon for 10 minutes. The MW-vial was placed in a heatblock and tempered to 40° C. The reaction mixture was pumped through the flow tubing using a peristaltic pump (Flow Setup: Loop Volume: 2 mL, Tube: inner diameter: 0.2 mm wall thickness 0.2 mm, 30% Peristalticpump speed ~35 seconds irradiated residence time, 9 h circleflow) for 9 hours at which time water and ethyl acetate were added and the layers were separated. The aqueous phase was extracted twice with ethyl acetate and the combined organic layers were washed with brine, dried over sodium sulfate, and evaporated to give the crude material. The crude material was purified by flash column chromatography to afford a 2:1 inseparable mixture of the desired product di-tert-butyl (3,5-difluoro-4-{[1-(4-methylbenzene-1-sulfonyl)-3-(propan-2-yl)-1H-pyrrolo[2,3-b]pyridin-4-yl]oxy}phenyl)-2-imidodicarbonate and the de-brominated starting material di-tert-butyl [3,5-difluoro-4-({1-[(4-methylphenyl)sulfonyl]-1H-pyrrolo[2,3-b]pyridin-4-yl}oxy)phenyl]-2-imidodicarbonate (1.69 g, 59% combined yield)

LC-MS (Method 2): $R_t$=1.74 min; MS (ESIpos): m/z=659 [M+H]$^+$.

Intermediate 295

3,5-difluoro-4-{[1-(4-methylbenzene-1-sulfonyl)-3-(propan-2-yl)-1H-pyrrolo[2,3-b]pyridin-4-yl]oxy}aniline-hydrogen chloride (1/1)

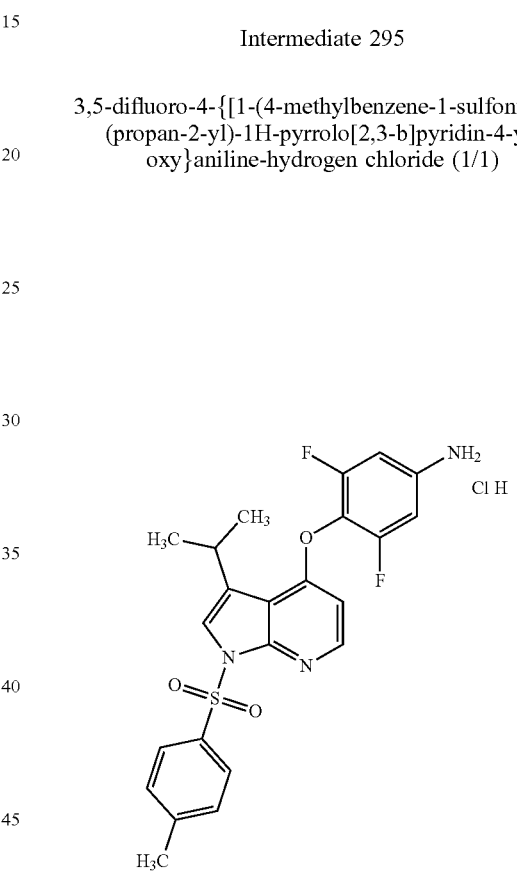

di-tert-butyl (3,5-difluoro-4-{[1-(4-methylbenzene-1-sulfonyl)-3-(propan-2-yl)-1H-pyrrolo[2,3-b]pyridin-4-yl]oxy}phenyl)-2-imidodicarbonate (1.69 g, 66% purity, 1.70 mmol, intermediate 294) was dissolved in a 4 M solution of hydrochloric acid in dioxane (30 mL) and stirred at room temperature overnight. The solvent was subsequently evaporated to give the crude product which was used in the subsequent step without further purification.

LC-MS (Method 2): $R_t$=1.45 min; MS (ESIpos): m/z=458 [M+H]$^+$.

Intermediate 296 phenyl (3,5-difluoro-4-{[1-(4-methylbenzene-1-sulfonyl)-3-(propan-2-yl)-1H-pyrrolo[2,3-b]pyridin-4-yl]oxy}phenyl)carbamate

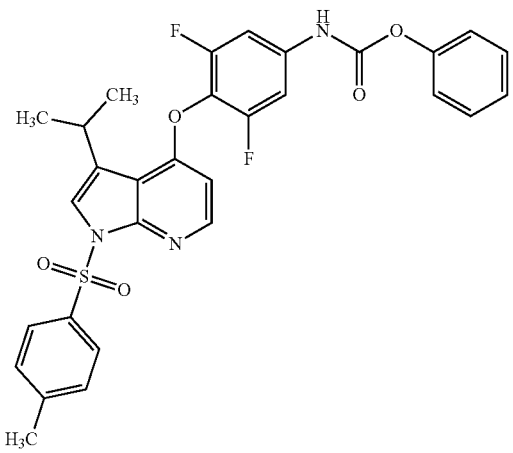 [SMILES: Cc1ccc(S(=O)(=O)n2cc(C(C)C)c3c(Oc4c(F)cc(NC(=O)Oc5ccccc5)cc4F)ccnc32)cc1]

To a stirred solution of 3,5-difluoro-4-{[1-(4-methylbenzene-1-sulfonyl)-3-(propan-2-yl)-1H-pyrrolo[2,3-b]pyridin-4-yl]oxy}aniline-hydrogen chloride (1/1) (1.40 g, 66% purity, 1.87 mmol, intermediate 295) in THF (15 mL) and pyridine was added (2.0 mL, 25 mmol). The reaction mixture was cooled to 0° C. and phenyl carbonochloridate (360 µL, 2.9 mmol, CAS No. [1885-14-9]) was added. The resulting mixture was stirred for 30 min at 0° C., at which time it was diluted with ethyl acetate and a 2M aqueous solution of hydrochlorid acid was added slowly.

The layers were separated and the aqueous phase was extracted twice with ethyl acetate. The combined organic phases were washed with a saturated solution of sodium bicarbonate, followed by brine, dried over sodium sulfate, and evaporated to afford the crude product. The crude product was used without further purification.

LC-MS (Method 1): $R_t$=1.62 min; MS (ESIpos): m/z=579 [M+H]$^+$.

Intermediate 297

N-(3,5-difluoro-4-{[1-(4-methylbenzene-1-sulfonyl)-3-(propan-2-yl)-1H-pyrrolo[2,3-b]pyridin-4-yl]oxy}phenyl)-N'-[(3-fluorooxetan-3-yl)methyl]urea

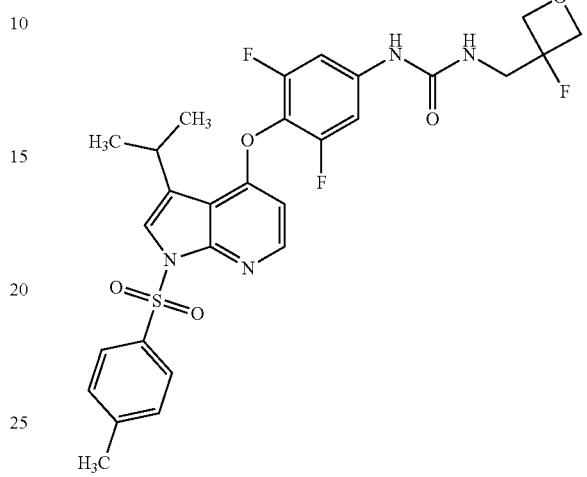

In analogy to intermediate 2, phenyl (3,5-difluoro-4-{[1-(4-methylbenzene-1-sulfonyl)-3-(propan-2-yl)-1H-pyrrolo[2,3-b]pyridin-4-yl]oxy}phenyl)carbamate (400 mg, 66% purity, 457 µmol, intermediate 296), and 1-(3-fluorooxetan-3-yl)methanamine (120 mg, 1.14 mmol, CAS No. [883311-82-8]), in DMF (3.0 mL) were reacted to obtain a crude product which was used in the next step without further purification.

LC-MS (Method 2): $R_t$=1.40 min; MS (ESIpos): m/z=589 [M+H]$^+$.

Intermediate 298

N-(3,5-difluoro-4-{[3-(propan-2-yl)-1H-pyrrolo[2,3-b]pyridin-4-yl]oxy}phenyl)-N'-[(3-fluorooxetan-3-yl)methyl]urea

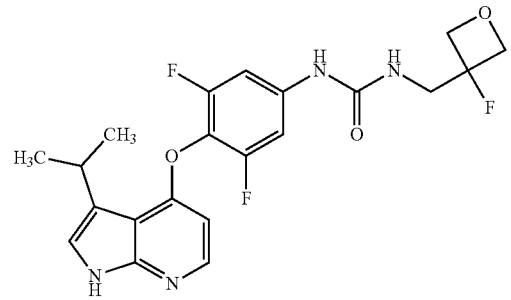 [SMILES: CC(C)c1c[nH]c2nccc(Oc3c(F)cc(NC(=O)NCC4(F)COC4)cc3F)c12]

To a solution of N-(3,5-difluoro-4-{[1-(4-methylbenzene-1-sulfonyl)-3-(propan-2-yl)-1H-pyrrolo[2,3-b]pyridin-4-yl]oxy}phenyl)-N'-[(3-fluorooxetan-3-yl)methyl]urea (250 mg, 425 µmol, intermediate 297) in methanol (7.0 mL) was added sodium hydroxide (34 mg, 849 µmol). The resulting mixture was stirred at room temperature overnight, at which time water and ethyl acetate were added and the layers were separated. The aqueous phase was extracted twice with ethyl acetate, and the combined organic layers were washed with brine, dried over sodium sulfate and evaporated to give the crude product which was used without further purification.

LC-MS (Method 2): $R_t$=1.11 min; MS (ESIpos): m/z=436 [M+H]$^+$ $^1$H NMR (400 MHz, DMSO-d$_6$) δ ppm 1.32 (d, 6H), 3.29-3.36 (m, 1H), 3.65 (dd, 2H), 4.56-4.66 (m, 4H), 6.19 (d, 1H), 7.01 (br s, 1H), 7.15 (s, 1H), 7.39 (d, 2H), 7.99 (d, 1H), 9.34 (br s, 1H), 11.46 (br s, 1H)

Intermediate 299 di-tert-butyl (3,5-difluoro-4-{[1-(4-methylbenzene-1-sulfonyl)-3-(3,3,3-trifluoropropyl)-1H-pyrrolo[2,3-b]pyridin-4-yl]oxy}phenyl)-2-imidodicarbonate

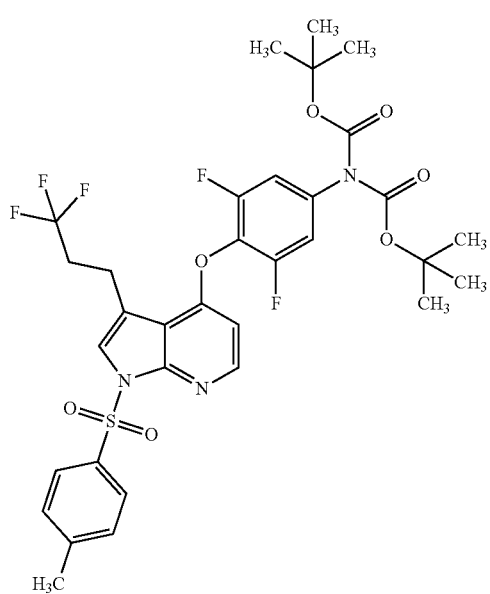 [SMILES: Cc1ccc(S(=O)(=O)n2cc(CCC(F)(F)F)c3c(Oc4c(F)cc(N(C(=O)OC(C)(C)C)C(=O)OC(C)(C)C)cc4F)ccnc32)cc1]

di-tert-butyl (4-{[3-bromo-1-(4-methylbenzene-1-sulfonyl)-1H-pyrrolo[2,3-b]pyridin-4-yl]oxy}-3,5-difluorophenyl)-2-imidodicarbonate (200 mg, 288 µmol, Intermediate 282), Ir(4',6'-dF-5-CF$_3$-ppy)$_2$(4,4'-dtbbpy)PF$_6$ (6.5 mg, 5.8 µmol, CAS No. [870987-63-6]), tris(trimethylsilyl)silane (89 µL, 290 µmol, CAS No. [1873-77-4]) and lithiumcarbonate (128 mg, 1.73 mmol) were dissolved in trifluorotoluene (4.0 mL) in a MW-vial. In a separate vial, the Ni-catalyst was prepared by dissolving Nickel (II) chloride dimethoxyethane adduct (32 mg, 140 µmol, CAS No. [29046-78-4]) and 4,4'-Di-tert-butyl-2,2'-bipyridine (39 mg, 140 µmol, CAS No. [72914-19-3]) in N,N-dimethyl acetamide (10 mL) followed by stirring for 5 min. 0.1 mL of this catalyst solution was syringed to the sealed reaction vial and argon was bubbled through the solution for another 5 min. 3-bromo-1,1,1-trifluoropropane (180 µL, 1.7 mmol, CAS No. [460-32-2]) was added. The MW-vial was subsequently irradiated by two 40 W Kessil LED Aquarium lights (40 W each, 4 cm distance) placed in a water bath to keep the temperature below 35° C. for 12 hours, at which time water and ethyl acetate were added and the layers were separated. The aqueous phase was extracted twice with ethyl acetate and the combined organic layers were washed with brine, dried over sodium sulfate, and evaporated to give the crude material, which was used without further purification.

LC-MS (Method 2): $R_t$=1.68 min; MS (ESIpos): m/z=712 [M+H]$^+$.

Intermediate 300

3,5-difluoro-4-{[1-(4-methylbenzene-1-sulfonyl)-3-(3,3,3-trifluoropropyl)-1H-pyrrolo[2,3-b]pyridin-4-yl]oxy}aniline

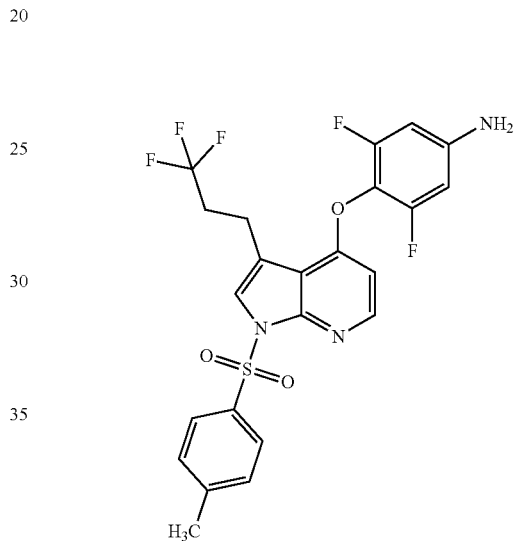

di-tert-butyl (3,5-difluoro-4-{[1-(4-methylbenzene-1-sulfonyl)-3-(3,3,3-trifluoropropyl)-1H-pyrrolo[2,3-b]pyridin-4-yl]oxy}phenyl)-2-imidodicarbonate (450 mg, 632 µmol, Intermediate 299) was dissolved in a 4 M solution of hydrochloric acid in dioxane (9.0 mL) and stirred at room temperature overnight. The solvent was subsequently evaporated to give the crude product which was purified by preparative HPLC to afford the title compound (190 mg, 59% yield).

LC-MS (Method 2): $R_t$=1.41 min; MS (ESIpos): m/z=512 [M+H]$^+$ $^1$H NMR (400 MHz, DMSO-d$_6$) δ ppm 2.35 (s, 3H), 2.63-2.73 (m, 2H), 3.01-3.06 (m, 2H), 5.85 (s, 2H), 6.38 (d, 2H), 6.51 (d, 1H), 7.42 (d, 2H), 7.79 (s, 1H), 7.97 (d, 2H), 8.19 (d, 1H)

Intermediate 301 phenyl (3,5-difluoro-4-{[1-(4-methylbenzene-1-sulfonyl)-3-(3,3,3-trifluoropropyl)-1H-pyrrolo[2,3-b]pyridin-4-yl]oxy}phenyl)carbamate

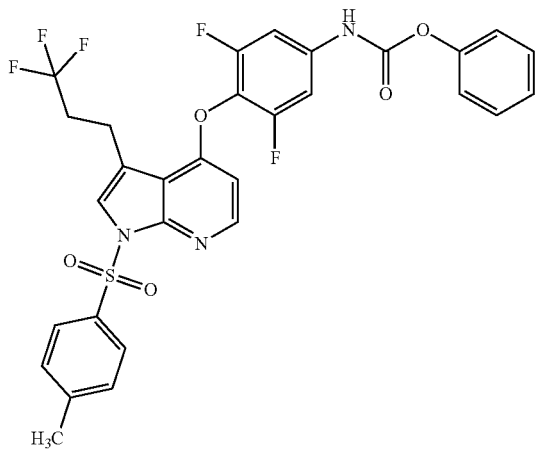 [SMILES: Cc1ccc(S(=O)(=O)n2cc(CCC(F)(F)F)c3c(Oc4c(F)cc(NC(=O)Oc5ccccc5)cc4F)ccnc32)cc1]

In analogy to intermediate 296, 3,5-difluoro-4-{[1-(4-methylbenzene-1-sulfonyl)-3-(3,3,3-trifluoropropyl)-1H-pyrrolo[2,3-b]pyridin-4-yl]oxy}aniline (190 mg, 371 µmol, intermediate 300) was reacted with phenyl carbonochloridate (51 µL, 410 µmol, CAS No. [1885-14-9]) and pyridine (170 µL, 2.1 mmol) in THF (3.0 mL) to afford the crude product which was used without further purification.

LC-MS (Method 1): $R_t$=1.56 min; MS (ESIneg): m/z=630 [M–H]⁻

Intermediate 302

N-(3,5-difluoro-4-{[1-(4-methylbenzene-1-sulfonyl)-3-(3,3,3-trifluoropropyl)-1H-pyrrolo[2,3-b]pyridin-4-yl]oxy}phenyl)-N'-[(3-fluorooxetan-3-yl)methyl]urea

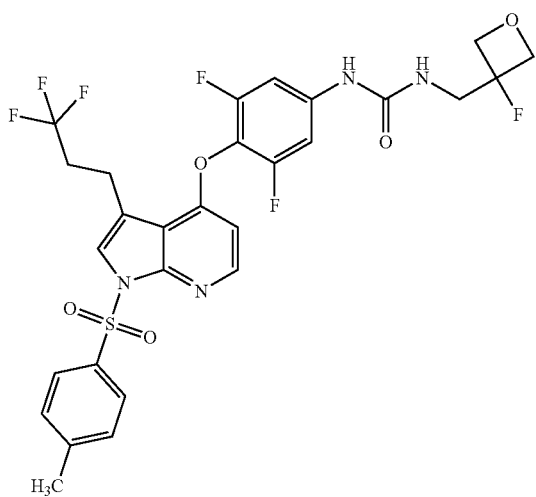 [SMILES: Cc1ccc(S(=O)(=O)n2cc(CCC(F)(F)F)c3c(Oc4c(F)cc(NC(=O)NCC5(F)COC5)cc4F)ccnc32)cc1]

In analogy to intermediate 2, phenyl (3,5-difluoro-4-{[1-(4-methylbenzene-1-sulfonyl)-3-(3,3,3-trifluoropropyl)-1H-pyrrolo[2,3-b]pyridin-4-yl]oxy}phenyl)carbamate (230 mg, 364 µmol, Intermediate 301), and 1-(3-fluorooxetan-3-yl)methanamine (57.4 mg, 546 µmol, CAS No. [883311-82-8]), in DMF (5.0 mL) were reacted to obtain a crude product which was used in the next step without further purification.

LC-MS (Method 2): $R_t$=1.38 min; MS (ESIpos): m/z=643 [M+H]⁺.

Intermediate 303

N-(3,5-difluoro-4-{[3-(3,3,3-trifluoropropyl)-1H-pyrrolo[2,3-b]pyridin-4-yl]oxy}phenyl)-N'-[(3-fluorooxetan-3-yl)methyl]urea

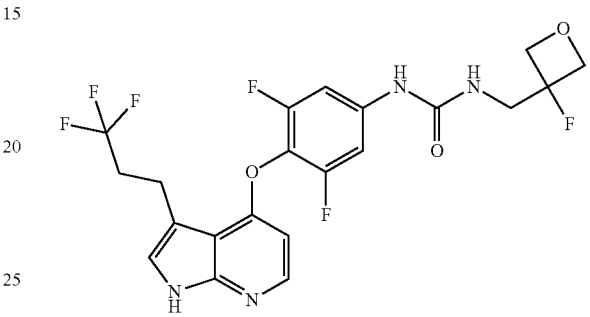

In analogy to intermediate 298, N-(3,5-difluoro-4-{[1-(4-methylbenzene-1-sulfonyl)-3-(3,3,3-trifluoropropyl)-1H-pyrrolo[2,3-b]pyridin-4-yl]oxy}phenyl)-N'-[(3-fluorooxetan-3-yl)methyl]urea (230 mg, 358 µmol, Intermediate 302) was reacted with sodium hydroxide (28.6 mg, 716 µmol) in methanol (5.0 mL), to afford a crude product which was used without further purification LC-MS (Method 2): $R_t$=1.10 min; MS (ESIpos): m/z=489 [M+H]⁺

¹H NMR (400 MHz, DMSO-d₆) δ ppm 2.59-2.73 (m, 2H), 3.03-3.09 (m, 2H), 3.66 (dd, 2H), 4.61 (ddd, 4H), 6.24 (d, 1H), 6.79 (t, 1H), 7.32 (d, 1H), 7.39 (d, 2H), 8.03 (d, 1H), 9.10 (s, 1H), 11.62 (d, 1H)

Intermediate 304 phenyl (4-{[3-bromo-1-(4-methylbenzene-1-sulfonyl)-1H-pyrrolo[2,3-b]pyridin-4-yl]oxy}-3,5-difluorophenyl)carbamate

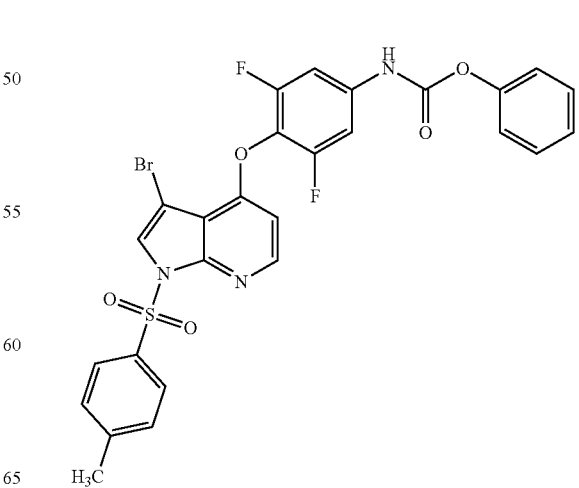

To a cooled (0° C.) stirred solution of 4-{[3-bromo-1-(4-methylbenzene-1-sulfonyl)-1H-pyrrolo[2,3-b]pyridin-4-yl]oxy}-3,5-difluoroaniline (700 mg, 1.42 mmol, Intermediate 281) in pyridine (600 μL, 7.4 mmol) and THF (6.0 mL) was added phenyl carbonochloridate (200 μL, 1.6 mmol). The resulting mixture was stirred for 30 min at 0° C., at which time the reaction was diluted with ethyl acetate and an aqueous solution of 2N hydrochlorid acid was added. The layers were separated, and the organic phase washed with water, dried over sodium sulfate, evaporated and dried to give the crude product which was used without further purification.

LC-MS (Method 1): $R_t$=1.56 min; MS (ESIpos): m/z=614 [M+H]$^+$.

Intermediate 305

N-(4-{[3-bromo-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea

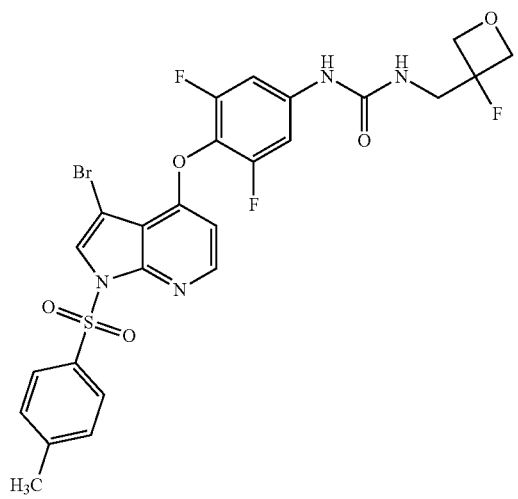 [SMILES: Cc1ccc(S(=O)(=O)n2cc(Br)c3c(Oc4c(F)cc(NC(=O)NCC5(F)COC5)cc4F)ccnc32)cc1]

In analogy to intermediate 2, phenyl (4-{[3-bromo-1-(4-methylbenzene-1-sulfonyl)-1H-pyrrolo[2,3-b]pyridin-4-yl]oxy}-3,5-difluorophenyl)carbamate (870 mg, 1.42 mmol, Intermediate 304), and 1-(3-fluorooxetan-3-yl)methanamine (149 mg, 1.42 mmol, CAS No. [883311-82-8]), in DMF (6.0 mL) were reacted to obtain a crude product which was purified by flash column chromatography on a Biotage to give the title compound (535 mg, 60% yield).

LC-MS (Method 2): $R_t$=1.36 min; MS (ESIpos): m/z=625 [M+H]$^+$ $^1$H NMR (400 MHz, DMSO-d$_6$) δ ppm 3.65 (dd, 2H), 4.54-4.66 (m, 4H), 6.63 (d, 1H), 6.81 (t, 1H), 7.38 (d, 2H), 7.42-7.47 (m, 2H), 8.00-8.09 (m, 2H), 8.14 (s, 1H), 8.25 (d, 1H), 9.13 (s, 1H)

Intermediate 306

(+/−)—N-[3,5-difluoro-4-({1-(4-methylbenzene-1-sulfonyl)-3-(oxolan-3-yl)-1H-pyrrolo[2,3-b]pyridin-4-yl}oxy)phenyl]-N'-[(3-fluorooxetan-3-yl)methyl]urea

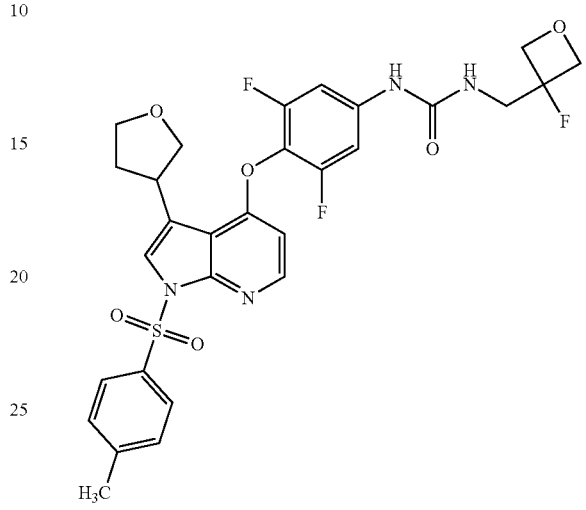

N-(4-{[3-bromo-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea (145 mg, 232 μmol, intermediate 305), Ir(4',6'-dF-5-CF$_3$-ppy)$_2$(4,4'-dtbbpy)PF$_6$ (5.20 mg, 4.64 μmol, CAS No. [870987-63-6]), tris(trimethylsilyl)silane (72 μL, 230 μmol, CAS No. [1873-77-4]) and sodium carbonate (147 mg, 1.39 mmol) were dissolved in trifluorotoluene (4.3 mL) in a MW-vial. In a separate vial, the Ni-catalyst was prepared by dissolving Nickel (II) chloride dimethoxyethane adduct (250 pg, 1.2 μmol, CAS No. [29046-78-4]) and 4,4'-Di-tert-butyl-2,2'-bipyridine (310 pg, 1.2 μmol, CAS No. [72914-19-3]) in N,N-dimethylacetamide (2.2 mL) followed by stirring for 5 min. The catalyst catalyst solution was syringed to the sealed reaction vial and argon was bubbled through the solution for another 5 min. 3-bromotetrahydrofuran (100 μL, 1.0 mmol, CAS No. [19311-37-6]) was added. The MW-vial was subsequently irradiated by two 40 W Kessil LED Aquarium lights (40 W each, 4 cm distance) placed in a water bath to keep the temperature below 35° C. for 6 hours, at which time water and ethyl acetate were added and the layers were separated. The aqueous phase was extracted twice with ethyl acetate and the combined organic layers were washed with brine, dried over sodium sulfate, and evaporated to give the crude material. The crude product was purified by flash column chromatography on a Biotage to afford the title compound (181 mg, 63% yield)

LC-MS (Method 2): $R_t$=1.26 min; MS (ESIpos): m/z=618 [M+H]$^+$ $^1$H NMR (400 MHz, DMSO-d$_6$) δ ppm 2.07-2.20 (m, 1H), 2.26-2.33 (m, 1H), 3.61-3.84 (m, 5H), 3.85-3.91 (m, 1H), 3.99-4.08 (m, 1H), 4.55-4.66 (m, 4H), 6.55 (d, 1H), 6.82 (t, 1H), 7.39 (d, 2H), 7.43 (d, 2H), 7.71 (s, 1H), 8.01 (d, 2H), 8.19 (d, 1H), 9.13 (s, 1H)

Intermediate 307

(+/−)—N-[3,5-difluoro-4-({3-[oxolan-3-yl]-1H-pyrrolo[2,3-b]pyridin-4-yl}oxy)phenyl]-N'-[(3-fluorooxetan-3-yl)methyl]urea

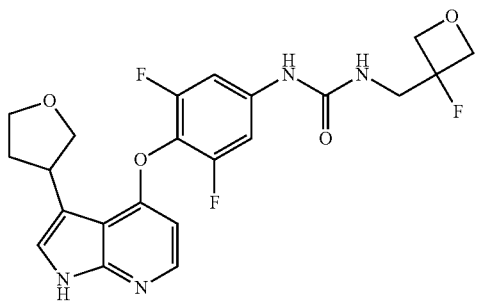 [SMILES: O=C(NCC1(F)COC1)Nc1cc(F)c(Oc2ccnc3[nH]cc(C4CCOC4)c23)c(F)c1]

In analogy to intermediate 298, (+/−)—N-[3,5-difluoro-4-({1-(4-methylbenzene-1-sulfonyl)-3-(oxolan-3-yl)-1H-pyrrolo[2,3-b]pyridin-4-yl}oxy)phenyl]-N'-[(3-fluorooxetan-3-yl)methyl]urea (180 mg, 292 µmol, Intermediate 306) was reacted with sodium hydroxide (23.4 mg, 584 µmol) in methanol (5.0 mL), to afford a crude product which was used without further purification.

LC-MS (Method 2): $R_t$=0.92 min; MS (ESIpos): m/z=463 [M+H]$^+$.

Intermediate 308

N-(4-{[3-cyclobutyl-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea

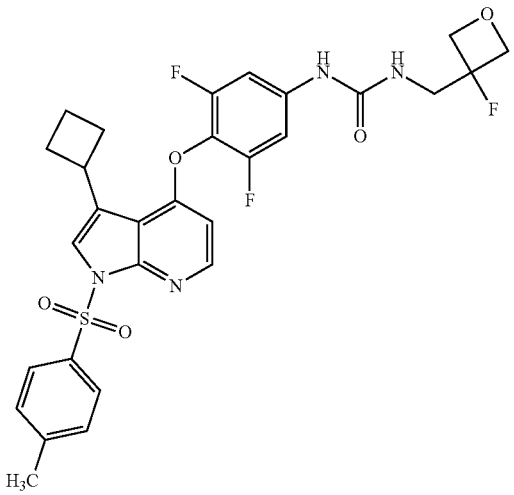 [SMILES: Cc1ccc(S(=O)(=O)n2cc(C3CCC3)c3c(Oc4c(F)cc(NC(=O)NCC5(F)COC5)cc4F)ccnc32)cc1]

N-(4-{[3-bromo-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea (150 mg, 240 µmol, intermediate 305), Ir(4',6'-dF-5-CF$_3$-ppy)$_2$(4,4'-dtbbpy)PF$_6$ (5.38 mg, 4.80 µmol, CAS No. [870987-63-6]), tris(trimethylsilyl)silane (74 µL, 240 µmol, CAS No. [1873-77-4]) and 2,6-dimethylpyridine (170 µL, 1.4 mmol) were dissolved in trifluorotoluene (4.5 mL) in a MW-vial. In a separate vial, the Ni-catalyst was prepared by dissolving Nickel (II) chloride dimethoxyethane adduct (260 pg, 1.2 µmol, CAS No. [29046-78-4]) and 4,4'-Di-tert-butyl-2,2'-bipyridine (320 pg, 1.2 µmol, CAS No. [72914-19-3]) in N,N-dimethylacetamide (2.2 mL) followed by stirring for 5 min. The catalyst catalyst solution was syringed to the sealed reaction vial and argon was bubbled through the solution for another 5 min. Bromocyclobutane (100 µL, 1.1 mmol, CAS No. [4399-47-7]) was added. The MW-vial was subsequently irradiated by two 40 W Kessil LED Aquarium lights (40 W each, 4 cm distance) placed in a water bath to keep the temperature below 35° C. for 6 hours, at which time water and ethyl acetate were added and the layers were separated. The aqueous phase was extracted twice with ethyl acetate and the combined organic layers were washed with brine, dried over sodium sulfate, and evaporated to give the crude material. The crude product was purified by preparative HPLC to afford the title compound (30 mg, 21% yield)

LC-MS (Method 2): $R_t$=1.43 min; MS (ESIpos): m/z=601 [M+H]$^+$ $^1$H NMR (400 MHz, DMSO-d$_6$) δ ppm 1.76-1.88 (m, 1H), 1.93-2.05 (m, 1H), 2.12-2.25 (m, 2H), 2.27-2.34 (m, 2H), 3.65 (dd, 2H), 3.78 (quin, 1H), 4.54-4.66 (m, 4H), 6.51 (d, 1H), 6.82 (t, 1H), 7.37 (d, 2H), 7.42 (d, 2H), 7.61 (d, 1H), 8.00 (d, 2H), 8.17 (d, 1H), 9.13 (s, 1H)

Intermediate 309

N-{4-[(3-cyclobutyl-1H-pyrrolo[2,3-b]pyridin-4-yl)oxy]-3,5-difluorophenyl}-N'-[(3-fluorooxetan-3-yl)methyl]urea

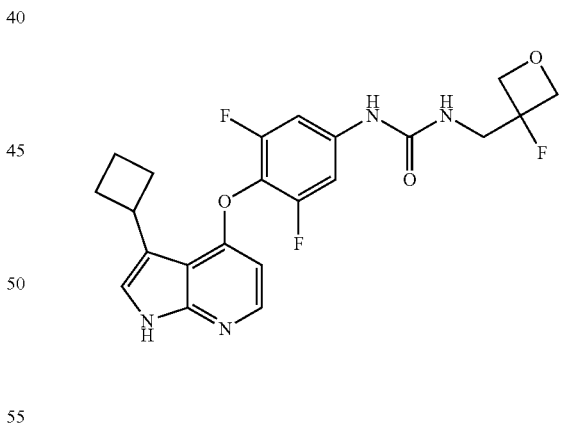

In analogy to intermediate 298, N-(4-{[3-cyclobutyl-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea (30.0 mg, 49.9 µmol, intermediate 308) was reacted with sodium hydroxide (4.00 mg, 99.9 µmol) in methanol (1.0 mL), to afford a crude product which was used without further purification.

LC-MS (Method 2): $R_t$=1.14 min; MS (ESIpos): m/z=448 [M+H]$^+$.

Intermediate 310

N-(3,5-difluoro-4-{[3-(3,3,3-trifluoroprop-1-en-2-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

Intermediate 311

(+/−)—N-{3,5-difluoro-4-[(3-[1,1,1-trifluoropropan-2-yl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea

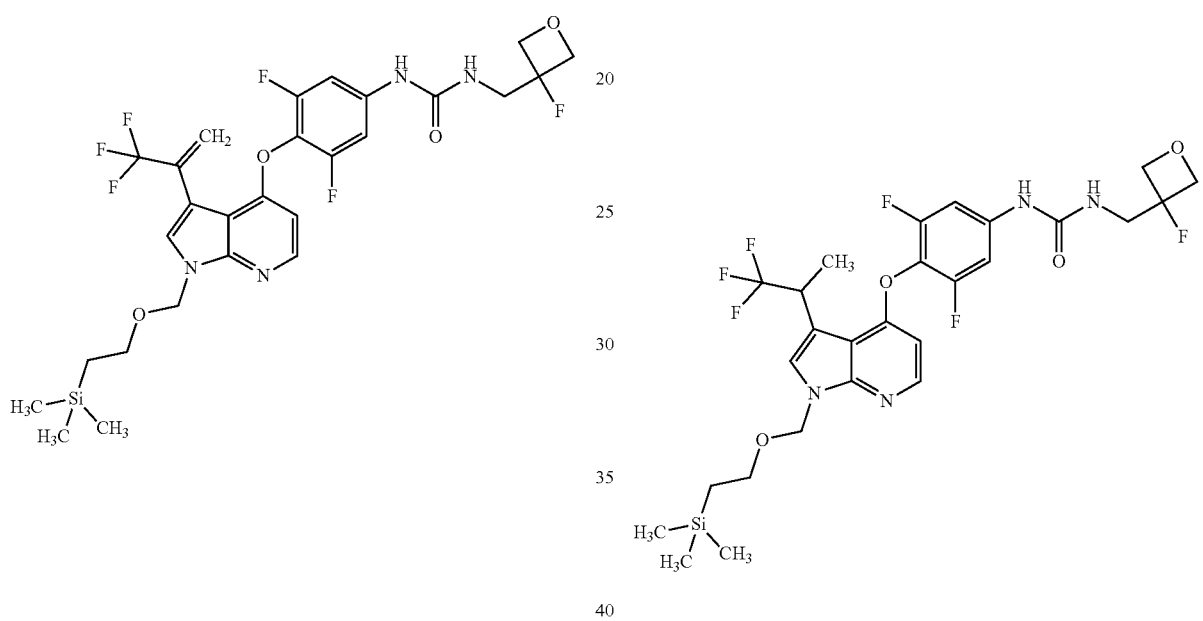

To a stirred solution of N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (1.17 g, 1.95 mmol, intermediate 401) in degassed THF (30 mL) and water (15 mL) were added (1,1-Bis(diphenylphosphino)ferrocene)-dichloropalladium(II) (142 mg, 195 µmol, CAS No. [95464-05-4]), (3,3,3-trifluoroprop-1-en-2-yl)boronic acid (340 mg, 2.43 mmol, CAS No. [357274-85-2]) and potassium carbonate (806 mg, 5.84 mmol) The resulting mixture was stirred at 75° C. for 5 h, at which time the THF was removed evaporated, and ethyl acetate was added. The layers were separated and the aqueous phase was extracted twice with ethyl acetate. The combined organic layers were washed with brine, dried over sodium sulfate, and evaporated to afford the crude product. The crude material was purified by flash column chromatography to afford a 1:1 inseparable mixture of the title compound and debrominated starting material 1-{3,5-difluoro-4-[(1-{[2-(trimethylsilyl)ethoxy]methyl}-1H-pyrrolo[2,3-b]pyridin-4-yl)oxy]phenyl}-3-[(3-fluorooxetan-3-yl)methyl]urea (500 mg, 21% combined yield)

LC-MS (Method 2): R$_t$=1.52 min; MS (ESIpos): m/z=618 [M+H]$^+$.

To a stirred solution of N-(3,5-difluoro-4-{[3-(3,3,3-trifluoroprop-1-en-2-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (1.16 g, 50% purity, 941 µmol, intermediate 310) in ethanol (50 mL), was added triethylamine (200 µL, 1.4 mmol) followed by palladium (10% on activated carbon, 100 mg, 94.1 µmol). The flask was flushed with hydrogen and stirred under 1 atm of hydrogen for 4 hours, at which time the mixture was filtered over celite and rinsed with ethyl acetate. The filtrate was evaporated to afford the crude product which was used without further purification.

LC-MS (Method 2): R$_t$=1.51 min; MS (ESIpos): m/z=619 [M+H]$^+$.

Intermediate 312

N-(3,5-difluoro-4-{[1-(4-methylbenzene-1-sulfonyl)-3-(propan-2-yl)-1H-pyrrolo[2,3-b]pyridin-4-yl]oxy}phenyl)-N'-[(3-methyloxetan-3-yl)methyl]urea

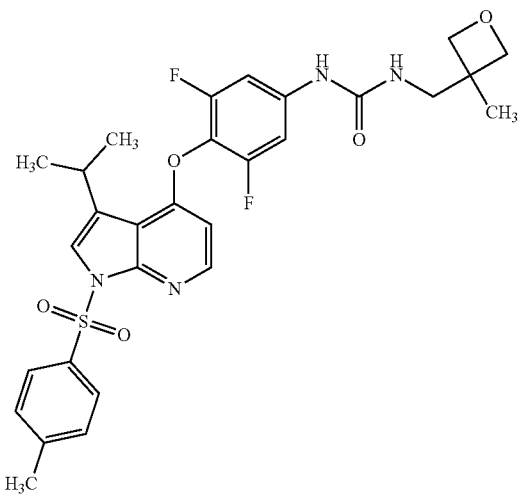 [SMILES: Cc1ccc(S(=O)(=O)n2cc(C(C)C)c3c(Oc4c(F)cc(NC(=O)NCC5(C)COC5)cc4F)ccnc32)cc1]

In analogy to intermediate 2, phenyl (3,5-difluoro-4-{[1-(4-methylbenzene-1-sulfonyl)-3-(propan-2-yl)-1H-pyrrolo[2,3-b]pyridin-4-yl]oxy}phenyl)carbamate (250 mg, 66% purity, 286 μmol, intermediate 296), and 1-(3-methyloxetan-3-yl)methanamine (72.2 mg, 714 μmol, CAS No. [153209-97-3]), in DMF (2.0 mL) were reacted to obtain a crude product which was used in the next step without further purification.

LC-MS (Method 2): $R_t$=1.40 min; MS (ESIpos): m/z=585 [M+H]$^+$.

Intermediate 313

N-(3,5-difluoro-4-{[3-(propan-2-yl)-1H-pyrrolo[2,3-b]pyridin-4-yl]oxy}phenyl)-N'-[(3-methyloxetan-3-yl)methyl]urea

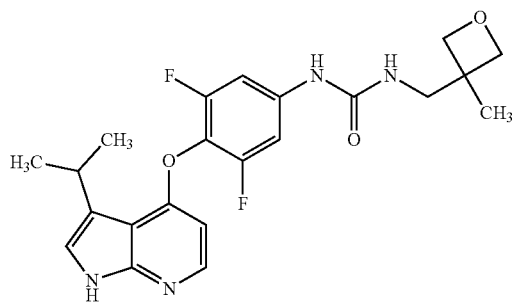 [SMILES: CC(C)c1c[nH]c2nccc(Oc3c(F)cc(NC(=O)NCC4(C)COC4)cc3F)c12]

In analogy to intermediate 298, N-(3,5-difluoro-4-{[1-(4-methylbenzene-1-sulfonyl)-3-(propan-2-yl)-1H-pyrrolo[2,3-b]pyridin-4-yl]oxy}phenyl)-N'-[(3-methyloxetan-3-yl)methyl]urea (160 mg, 274 μmol, intermediate 312) was reacted with sodium hydroxide (32.8 mg, 821 μmol) in methanol (6.0 mL), to afford a crude product which was used without further purification.

LC-MS (Method 2): $R_t$=1.12 min; MS (ESIpos): m/z=432 [M+H]$^+$ $^1$H NMR (400 MHz, DMSO-d$_6$) δ ppm 1.23 (s, 3H), 1.32 (d, 6H), 3.27-3.31 (m, 3H), 4.19 (d, 2H), 4.39 (d, 2H), 6.19 (d, 1H), 7.14 (s, 1H), 7.41 (d, 2H), 7.49 (br s, 1H), 7.98 (d, 1H), 9.88 (br s, 1H), 11.46 (br s, 1H)

Intermediate 314

N-(3,5-difluoro-4-{[1-(4-methylbenzene-1-sulfonyl)-3-(propan-2-yl)-1H-pyrrolo[2,3-b]pyridin-4-yl]oxy}phenyl)-N'-{[3-(propan-2-yl)oxetan-3-yl]methyl}urea

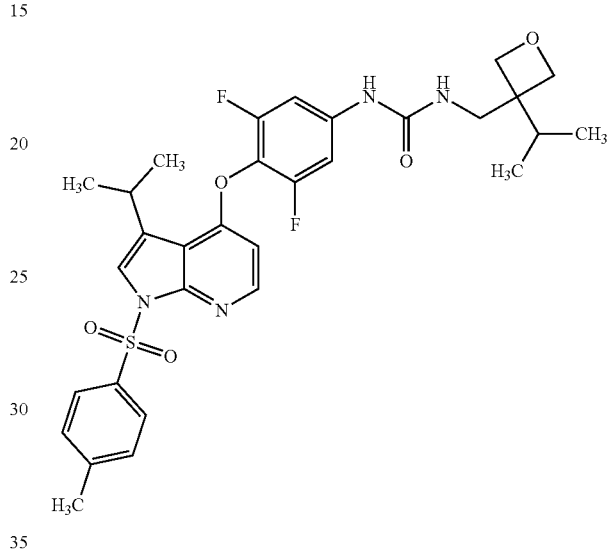

In analogy to intermediate 2, phenyl (3,5-difluoro-4-{[1-(4-methylbenzene-1-sulfonyl)-3-(propan-2-yl)-1H-pyrrolo[2,3-b]pyridin-4-yl]oxy}phenyl)carbamate (250 mg, 66% purity, 286 μmol, intermediate 296), and 1-[3-(propan-2-yl)oxetan-3-yl]methanamine (92.3 mg, 714 μmol, CAS No. [1539197-30-2]) in DMF (2.0 mL) were reacted to obtain a crude product which was used in the next step without further purification.

LC-MS (Method 2): $R_t$=1.49 min; MS (ESIpos): m/z=614 [M+H]$^+$.

Intermediate 315

N-(3,5-difluoro-4-{[3-(propan-2-yl)-1H-pyrrolo[2,3-b]pyridin-4-yl]oxy}phenyl)-N'-{[3-(propan-2-yl)oxetan-3-yl]methyl}urea

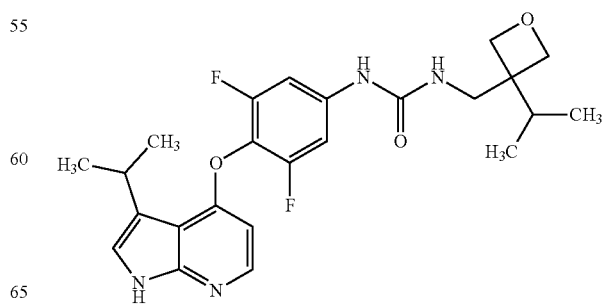

323

In analogy to intermediate 298, N-(3,5-difluoro-4-{[1-(4-methylbenzene-1-sulfonyl)-3-(propan-2-yl)-1H-pyrrolo[2,3-b]pyridin-4-yl]oxy}phenyl)-N'-{[3-(propan-2-yl)oxetan-3-yl]methyl}urea (160 mg, 261 µmol, Intermediate 314) was reacted with sodium hydroxide (31.3 mg, 783 µmol) in methanol (6.0 mL), to afford a crude product which was used without further purification LC-MS (Method 2): $R_t$=1.23 min; MS (ESIpos): m/z=460 [M+H]$^+$ $^1$H NMR (400 MHz, DMSO-$d_6$) δ ppm 0.91 (d, 6H), 1.32 (d, 6H), 2.01 (quin, 1H), 3.27-3.32 (m, 2H), 4.30 (d, 2H), 4.33 (d, 2H), 6.19 (d, 1H), 6.89 (br s, 1H), 7.15 (s, 1H), 7.40 (d, 2H), 7.99 (d, 1H), 9.27 (br s, 1H), 11.46 (br s, 1H)

Intermediate 316

N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-(3-hydroxy-2,2-dimethylpropyl)thiourea

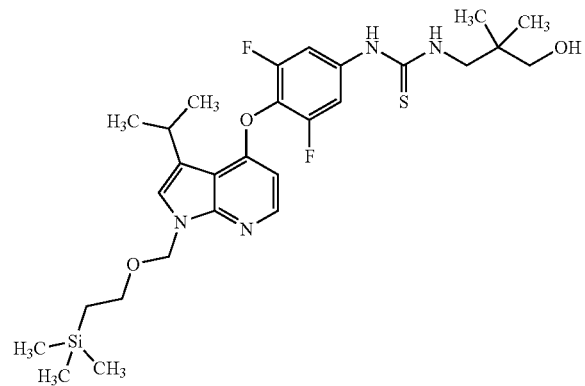 [SMILES: CC(C)c1cn(COCC[Si](C)(C)C)c2nccc(Oc3c(F)cc(NC(=S)NCC(C)(C)CO)cc3F)c12]

In analogy to Intermediate 231, O-phenyl (3,5-difluoro-4-{[3-(propan-2-yl)-1-{[2-(trimethylsilyl)ethoxy]methyl}-1H-pyrrolo[2,3-b]pyridin-4-yl]oxy}phenyl)carbamothioate (270 mg, 474 µmol, Intermediate 485), and 3-amino-2,2-dimethylpropan-1-ol (97.8 mg, 948 µmol, CAS No. [26734-09-8]), in DMF (5.0 mL) were reacted to obtain a crude product which was used in the next step without further purification.

LC-MS (Method 2): $R_t$=1.62 min; MS (ESIpos): m/z=580 [M+H]$^+$.

324

Intermediate 317

N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-5,5-dimethyl-5,6-dihydro-4H-1,3-oxazin-2-amine

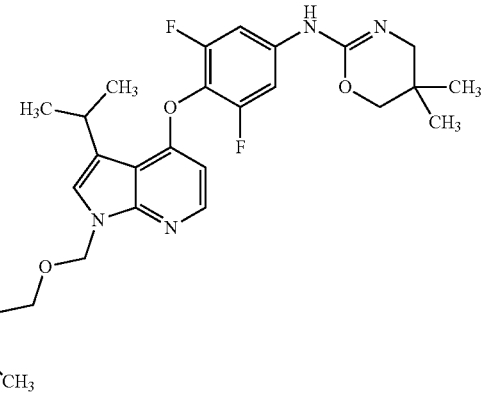

In analogy to Intermediate 232, N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-(3-hydroxy-2,2-dimethylpropyl)thiourea (270 mg, 466 µmol, Intermediate 316) was reacted with 1-(3-Dimethylaminopropyl)-3-ethyl-carbodiimide hydrochloride (179 mg, 933 µmol) and triethylamine (200 µL, 1.4 mmol) in acetonitrile (7.0 mL) to obtain a crude product which was used in the next step without further purification.

LC-MS (Method 2): $R_t$=1.70 min; MS (ESIpos): m/z=546 [M+H]$^+$.

Intermediate 318

(+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-{[3-(hydroxymethyl)oxolan-3-yl]methyl}thiourea

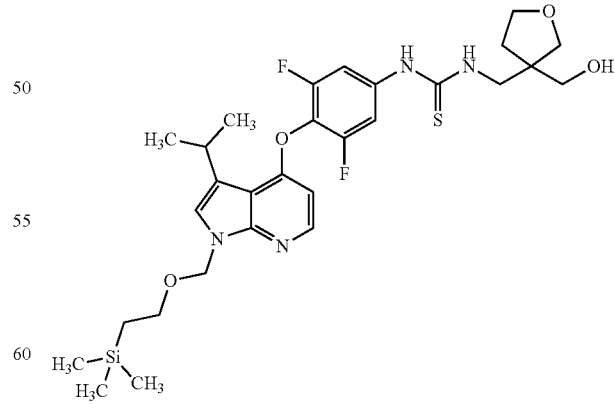

In analogy to Intermediate 231, O-phenyl (3,5-difluoro-4-{[3-(propan-2-yl)-1-{[2-(trimethylsilyl)ethoxy]methyl}-1H-pyrrolo[2,3-b]pyridin-4-yl]oxy}phenyl)carbamothioate (270 mg, 474 µmol, Intermediate 485), and (+/−)-[3-(ami-

Intermediate 319

(+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-2,7-dioxa-9-azaspiro[4.5]dec-8-en-8-amine

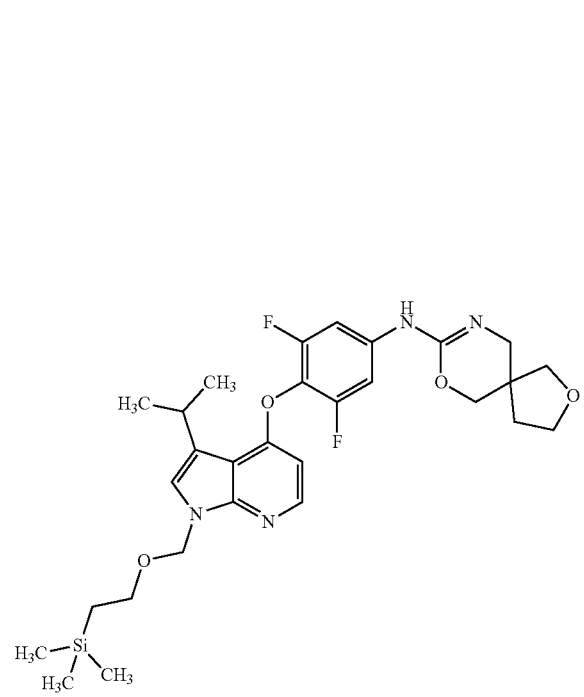 [SMILES: CC(C)c1cn(COCC[Si](C)(C)C)c2nccc(Oc3c(F)cc(NC4=NCC5(CCOC5)CO4)cc3F)c12]

In analogy to Intermediate 232, (+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-{[3-(hydroxymethyl)oxolan-3-yl]methyl}thiourea (280 mg, 461 µmol, intermediate 318) was reacted with 1-(3-Dimethylaminopropyl)-3-ethylcarbodiimide hydrochloride (177 mg, 923 µmol) and triethylamine (190 µL, 1.4 mmol) in acetonitrile (7.0 mL) to obtain a crude product which was used in the next step without further purification.

LC-MS (Method 2): $R_t$=1.60 min; MS (ESIpos): m/z=574 [M+H]$^+$.

Intermediate 320

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(4-hydroxybutan-2-yl)thiourea

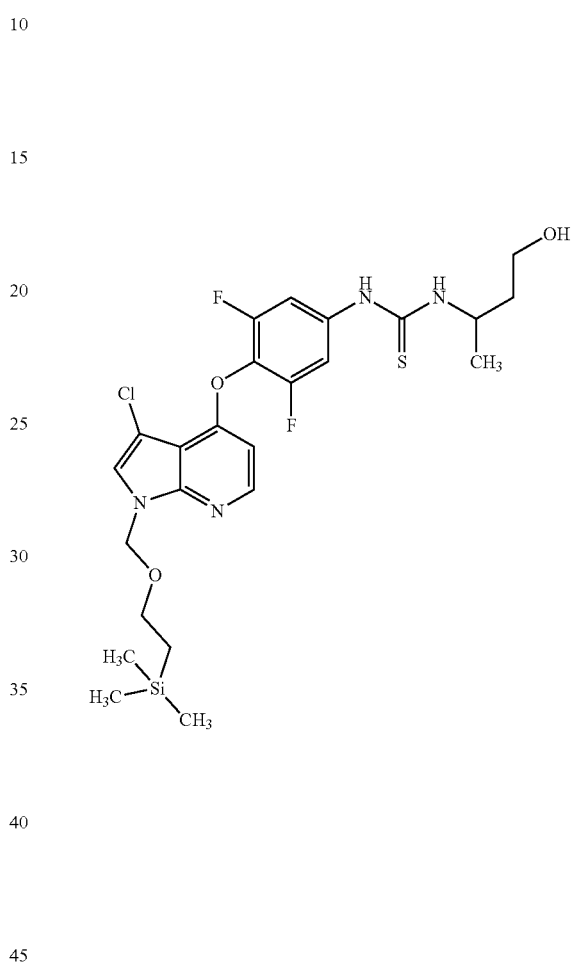

O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (220 mg, 392 µmol, intermediate 424) was dissolved in DMF (10 mL) and (+/−)-3-aminobutan-1-ol (38 µL, 430 µmol) was added. The mixture was stirred at 60° C. for 4 hours then cooled to room temperature and left to stand overnight. Ethyl acetate and brine were added and mixture was extracted with ethyl acetate (3×). The organic layers were combined, dried using magnesium sulfate, filtered and solvent was evaporated to afford a crude product. The crude product was purified by flash column chromatography on Silica 60 (eluent heptane:ethyl acetate, 2:3) to afford the desired titled product (499 mg, quant.) as a colourless oil.

LC-MS (Method 8): $R_t$=2.89 min; MS (ESIpos): m/z=557 (M-OC2H4Si(CH3)3-OPh)$^+$ $^1$H-NMR (400 MHz, CDCl3, characteristic signals) δ [ppm]: −0.06 (s, 9H), 0.80-0.94 (m, 4H), 1.32 (d, 3H), 3.51-3.58 (m, 2H), 3.70-3.84 (m, 2H), 5.62 (d, 2H), 6.32 (d, 1H), 8.13 (d, 1H).

327

Intermediate 321

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-methyl-5,6-dihydro-4H-1,3-thiazin-2-amine

328

Intermediate 322

N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea

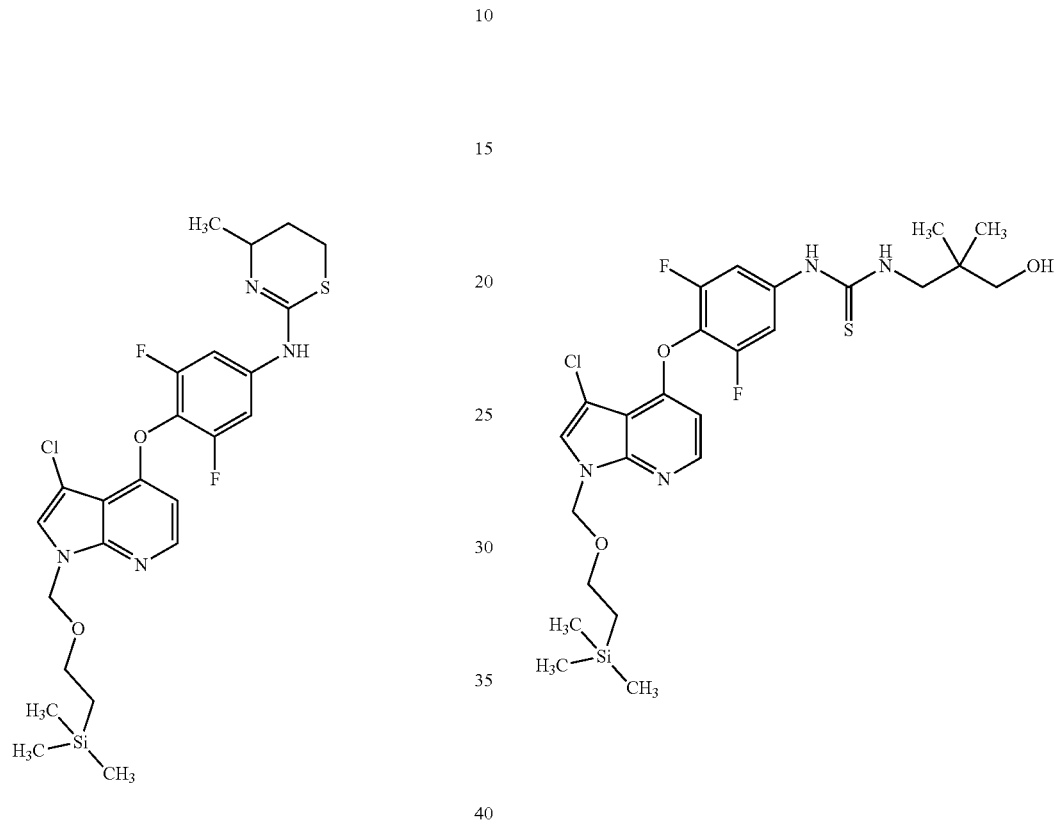

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(4-hydroxybutan-2-yl)thiourea (218 mg, 392 μmol, intermediate 320) was dissolved in THF (10 mL). Then 1,1'-carbonyldiimidazole (254 mg, 1.57 mmol) was added and the mixture was stirred at 70° C. for 24 hours then left to stand at room temperature for 48 hours. The solvent was evaporated to afford a crude product. The crude product was purified by flash column chromatography on silica 60 (eluent-heptane:ethyl acetate 1:1) afforded the desired titled compound as a colourless oil (64.6 mg, 31% yield).

LC-MS (Method 8): $R_t$=3.34 min; MS (ESIpos): m/z=539/541 [M+H]$^+$ (chlororo isotopes)

$^1$H-NMR (400 MHz, CDCl3, characteristic signals) δ [ppm]: −0.05 (s, 9H), 0.80-0.96 (m, 2H), 1.30 (d, 3H), 1.67-1.80 (m, 1H), 2.15-2.23 (m, 1H), 2.95-3.11 (m, 2H), 3.51-3.57 (m, 2H), 5.62 (s, 2H), 6.34 (d, 1H), 6.66-6.75 (m, 2H), 7.24 (s, 1H), 8.14 (d, 1H).

O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (488 mg, 869 μmol, intermediate 424) was dissolved in DMF (10 mL) and 3-amino-2,2-dimethyl-1-propanol (99 μL, 960 μmol) was added. The mixture was stirred at 60° C. for 3 hours and left at room temperature overnight. Ethyl acetate and brine were added to the mixture and mixture was extracted with ethyl acetate (3×). The organic layers were combined, dried with magnesium sulfate, filtered and solvent evaporated to afford a crude product, which was purified by reverse phase chromatography on Biotage isolera, 30 g C-18 column (eluent: 50-90% acetonitrile in NH4HCO3 pH 10 aqueous buffer) to obtain the desired titled compound (320 mg, 64% yield) as a white solid.

LC-MS (Method 8): $R_t$=3.06 min; MS (ESIpos): m/z=571/573 [M+H]$^+$ (chloro isotopes)

$^1$H-NMR (400 MHz, CDCl3) δ [ppm]: −0.05 (s, 9H), 0.87-1.03 (m, 8H), 3.35-3.71 (m, 6H), 5.64 (s, 2H), 6.31 (d, 1H), 6.95-7.08 (m, 1H), 7.22-7.29 (m, 2H), 8.13-8.17 (m, 1H).

Intermediate 323

3-chloro-4-(2,6-difluoro-4-isothiocyanatophenoxy)-1-{[2-(trimethylsilyl)ethoxy]methyl}-1H-pyrrolo[2,3-b]pyridine

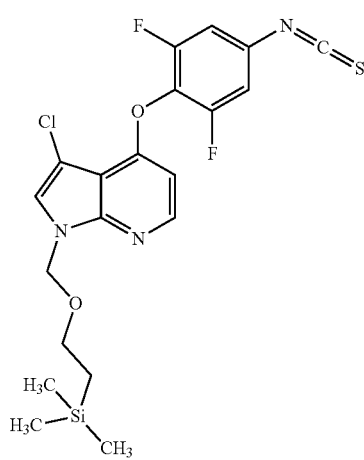 [SMILES: C[Si](C)(C)CCOCn1cc(Cl)c2c(Oc3c(F)cc(N=C=S)cc3F)ccnc21]

1,1'-Thiocarbonyldiimidazole (100 mg, 563 µmol) was dissolved in dichloromethane (5 mL) and 4-[(3-chloro-1-{[2-(trimethylsilyl)ethoxy]methyl}-1H-pyrrolo[2,3-b]pyridin-4-yl)oxy]-3,5-difluoroaniline (120 mg, 282 µmol, synthesis see ChemMedChem 3, (2008), p. 1893 ff., cpd 63) dissolved in dichloromethane (5 mL) was added at room temperature and stirred for 72 hours. The solvent was evaporated to afford the desired titled compound (240 mg), which was used without any further purification.

Intermediate 324

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-[3-hydroxy-2-(hydroxymethyl)propyl]thiourea

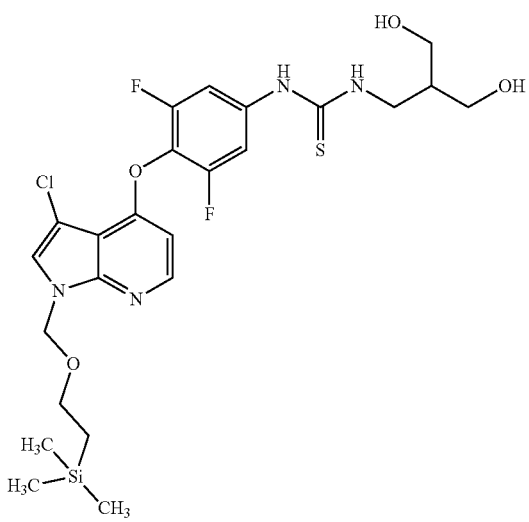 [SMILES: C[Si](C)(C)CCOCn1cc(Cl)c2c(Oc3c(F)cc(NC(=S)NCC(CO)CO)cc3F)ccnc21]

3-chloro-4-(2,6-difluoro-4-isothiocyanatophenoxy)-1-{[2-(trimethylsilyl)ethoxy]methyl}-1H-pyrrolo[2,3-b]pyridine (132 mg, 282 µmol, intermediate 323) was dissolved in DMF (10 mL) and (+/−)-2-(aminomethyl)propane-1,3-diol hydrochloride (53.4 mg, 508 µmol) was added. The mixture was stirred at 50° C. overnight. After cooling to room temperature ethyl acetate and brine were added to the mixture and the mixture was extracted with ethyl acetate (3×). The organic layers were combined, dried with magnesium sulfate, filtered and solvent evaporated to afford a crude product, which was purified by reverse phase chromatography on Biotage isolera, 30 g C-18 column (eluent: 40-80% acetonitrile in NH4HCO3 pH 10 aqueous buffer) to obtain the desired titled compound (72 mg, 45% yield) as a colourless oil.

$^1$H-NMR (400 MHz, CDCl3) δ [ppm]: −0.05 (s, 9H), 0.88-0.95 (m, 2H), 1.95-2.03 (m, 1H), 3.51-3.58 (m, 2H), 3.74-4.06 (m, 6H), 5.62 (s, 2H), 6.27-6.33 (m, 1H), 6.90-7.13 (br m, 2H), 7.26 (s, 1H), 8.12-8.17 (m, 1H).

Intermediate 325

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2-methylpropyl)thiourea

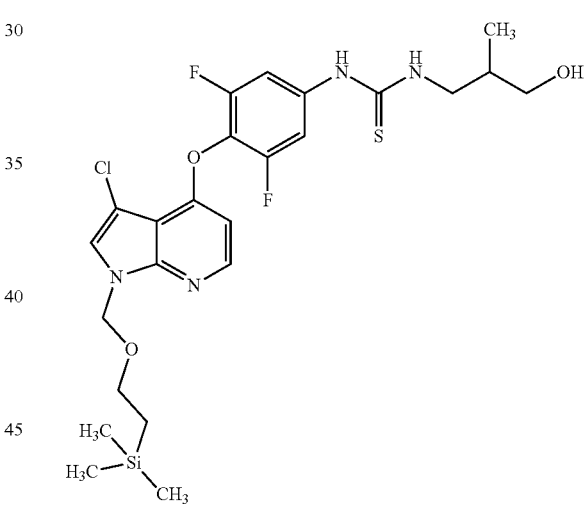

3-chloro-4-(2,6-difluoro-4-isothiocyanatophenoxy)-1-{[2-(trimethylsilyl)ethoxy]methyl}-1H-pyrrolo[2,3-b]pyridine (110 mg, 235 µmol, intermediate 323) was dissolved in DMF (5.0 mL) and (+/−)-3-amino-2-methylpropan-1-ol (41.9 mg, 470 µmol) was added. The mixture was stirred at 50° C. for 1 hour. After cooling to room temperature ethyl acetate and brine were added to the mixture and the mixture was extracted with ethyl acetate (3×). The organic layers were combined, dried with magnesium sulfate, filtered and solvent evaporated to afford a crude product, which was purified by reverse phase chromatography on Biotage isolera, 30 g C-18 column (eluent: 50-90% acetonitrile in NH4HCO3 pH 10 aqueous buffer) to obtain the desired titled compound (72 mg, 55% yield) as a white solid.

$^1$H-NMR (400 MHz, CDCl3) δ [ppm]: −0.05 (s, 9H), 0.87-1.00 (m, 5H), 2.01 (br s, 1H), 3.49-3.58 (m, 5H), 3.75-3.82 (m, 1H), 5.63 (s, 2H), 6.29 (d, 1H), 6.91-7.07 (m, 1H), 7.27 (s, 1H), 7.60 (br s, 1H), 8.15 (d, 1H).

Intermediate 326

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclobutyl]methyl}thiourea

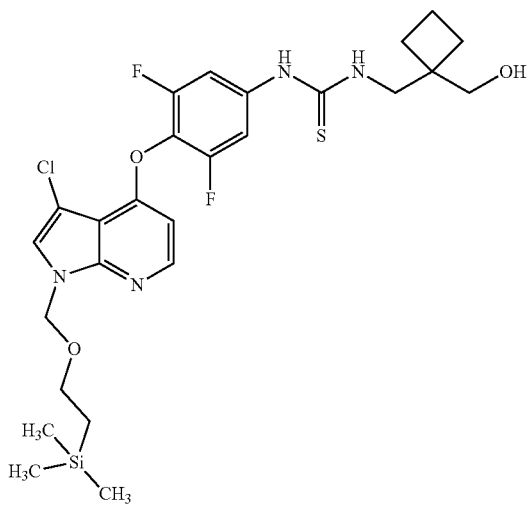 [SMILES: C[Si](C)(C)CCOCn1cc(Cl)c2c(Oc3c(F)cc(NC(=S)NCC4(CO)CCC4)cc3F)ccnc21]

3-chloro-4-(2,6-difluoro-4-isothiocyanatophenoxy)-1-{[2-(trimethylsilyl)ethoxy]methyl}-1H-pyrrolo[2,3-b]pyridine (189 mg, 404 μmol, intermediate 323) was dissolved in DMF (10 mL) and (1-(aminomethyl)cyclobutyl)methanol (83.8 mg, 727 μmol) was added. The mixture was stirred at 50° C. for 3 hours. After cooling to room temperature ethyl acetate and brine were added to the mixture and mixture was extracted with ethyl acetate (3×). The organic layers were combined, dried with magnesium sulfate, filtered and solvent evaporated to afford a crude product, which was purified by reverse phase chromatography on Biotage isolera, 30 g C-18 column (eluent: 50-90% acetonitrile in NH4HCO3 pH 10 aqueous buffer) to obtain the desired titled compound (137 mg, 58% yield) as a colourless oil.

$^1$H-NMR (400 MHz, CDCl3) δ [ppm]: −0.05 (s, 9H), 0.87-0.95 (m, 2H), 1.76-2.08 (m, 6H), 3.46-3.49 (m, 4H), 3.51-3.58 (m, 2H), 5.62 (s, 2H), 6.26-6.32 (m, 1H), 6.97 (br s, 1H), 7.21-7.42 (m, 2H), 8.12-8.16 (m, 1H).

Intermediate 327

4-(2,6-difluoro-4-nitrophenoxy)-3-iodo-1H-pyrrolo[2,3-b]pyridine

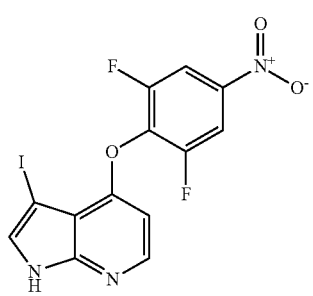 [SMILES: O=[N+]([O-])c1cc(F)c(Oc2ccnc3[nH]cc(I)c23)c(F)c1]

A solution of iodine in anhydrous DMF (20 mL) is added dropwise to a solution of 4-(2,6-difluoro-4-nitrophenoxy)-1H-pyrrolo[2,3-b]pyridine (8.79 g, 30.2 mmol, intermediate 14) and potassium hydroxide (8.47 g, 151 mmol) in DMF (130 mL). The solution is stirred at room temperature for 2.5 hours and then diluted with water. The resulting solid was removed by filtration, washed with water and dried to give the desired titled compound (9.64 g, 77% yield) as a yellow solid.

$^1$H-NMR (400 MHz, DMSO-d6) δ [ppm]: 6.49 (d, 1H), 7.68 (s, 1H), 8.10 (d, 1H), 8.37 (d, 2H), 12.28 (s br, 1H).

Intermediate 328

1-(benzenesulfonyl)-4-(2,6-difluoro-4-nitrophenoxy)-3-iodo-1H-pyrrolo[2,3-b]pyridine

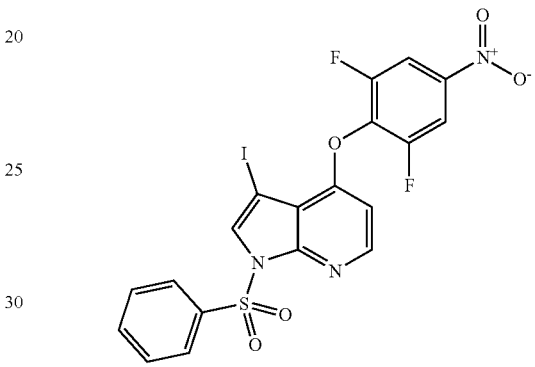

To a suspension of 4-(2,6-difluoro-4-nitrophenoxy)-3-iodo-1H-pyrrolo[2,3-b]pyridine (9.64 g, 23.1 mmol, Intermediate 327) in dichloromethane at 0° C. was added 4-N,N-dimethylaminopyridine (282 mg, 2.31 mmol), trimethylamine (4.8 mL, 35 mmol) and benzenesulfonyl chloride (3.5 mL, 28 mmol) and the mixture was stirred at room temperature for 2 hours. The reaction mixture was diluted with dichloromethane, washed with 2N aqueous HCl solution, saturated aqueous sodium hydrogencarbonate solution, water and brine. The organic phase was dried over sodium sulfate, filtered and concentrated to give the desired titled compound (12.3 g, 96% yield) as a brown glass.

Intermediate 329

4-{[1-(benzenesulfonyl)-3-iodo-1H-pyrrolo[2,3-b]pyridin-4-yl]oxy}-3,5-difluoroaniline

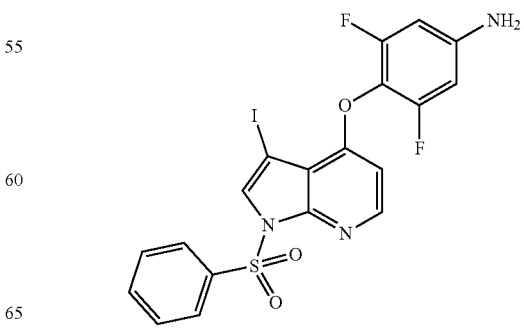

333

In analogy to intermediate 18), 1-(benzenesulfonyl)-4-(2,6-difluoro-4-nitrophenoxy)-3-iodo-1H-pyrrolo[2,3-b]pyridine (12.3 g, 22.1 mmol, intermediate 328) was reacted with iron powder (6.17 g, 111 mmol) and ammonium chloride (5.91 g, 111 mmol) in a mixture of water (85 mL), THF (85 mL) and methanol (170 mL). After work up the desired titled compound (10.01 g, 86% yield) was used in the next step without any further purification.

$^1$H-NMR (400 MHz, CDCl3) δ [ppm]: 6.30 (d, 2H), 6.42 (d, 1H), 7.49 (t, 2H), 7.59 (t, 1H), 7.80 (s, 1H), 8.17-8.24 (m, 3H).

Intermediate 330 di-tert-butyl (4-{[1-(benzenesulfonyl)-3-iodo-1H-pyrrolo[2,3-b]pyridin-4-yl]oxy}-3,5-difluorophenyl)-2-imidodicarbonate

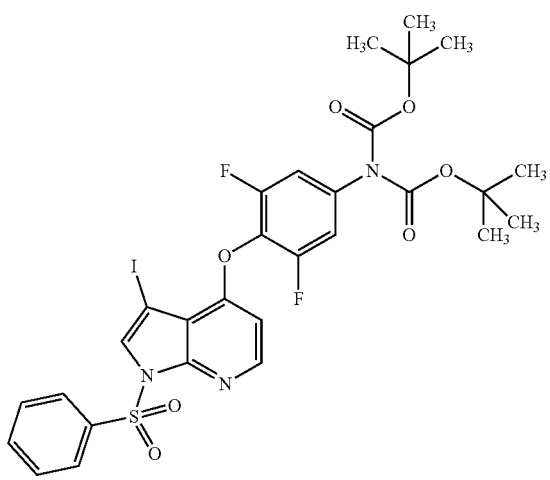 [SMILES: CC(C)(C)OC(=O)N(C(=O)OC(C)(C)C)c1cc(F)c(Oc2ccnc3c2c(I)cn3S(=O)(=O)c2ccccc2)c(F)c1]

To 4-{[1-(benzenesulfonyl)-3-iodo-1H-pyrrolo[2,3-b]pyridin-4-yl]oxy}-3,5-difluoroaniline (10.0 g, 19.0 mmol, intermediate 329) in THF (180 mL) was added di-tert-butyl dicarbonate (13 mL, 57 mmol), trimethylamine (11 mL, 76 mmol) and 4-N,N-dimethylaminopyridine and the reaction heated at reflux for 5 hours, then allowed to cool overnight. THF was removed in vacuo and the residue was taken up in diethyl ether. The organic phase was washed with saturated ammonium chloride solution, sodium hydrogen carbonate solution, water and brine before drying over sodium sulfate to give the crude product, which was purified by flash chromatography (20-50% ethyl acetate/heptane) to obtain the desired titled compound (10.82 g, 78% yield).

$^1$H-NMR (400 MHz, CDCl3) δ [ppm]: 1.49 (s, 18H), 6.35 (d, 1H), 6.93 (d, 2H), 7.51 (t, 2H), 7.61 (t, 1H), 7.84 (s, 1H), 8.18-8.25 (m, 3H).

Intermediate 331 tert-butyl (4-{[1-(benzenesulfonyl)-3-(3-hydroxyoxetan-3-yl)-1H-pyrrolo[2,3-b]pyridin-4-yl]oxy}-3,5-difluorophenyl)carbamate

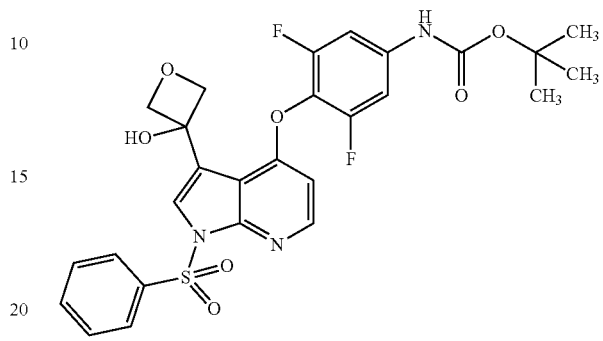

To a solution of di-tert-butyl (4-{[1-(benzenesulfonyl)-3-iodo-1H-pyrrolo[2,3-b]pyridin-4-yl]oxy}-3,5-difluorophenyl)-2-imidodicarbonate (10.8 g, 14.8 mmol, Intermediate 330) in THF (125 mL) under argon at −78° C. was added isopropylmagnesium chloride (16 mL, 2.0 M in tetrahydrofuran, 33 mmol). The resulting mixture was stirred at −78° C. for 30 minutes and then placed in an ice bath for 30 minutes. The reaction mixture was recooled to −78° C. and a solution of 3-oxetanone (25 mL, 37 mmol) in THF (25 mL, THF dried over 4 Å anhydrous mol sieve) was added. The reaction was allowed to warm up to room temperature over 2 hours. And then it was quenched by the addition of saturated ammonium chloride solution. The quenched mixture was extracted with ethyl acetate (2×). The combined organic layers were washed with sodium hydrogen carbonate solution, water and brine then dried over sodium sulfate to give a crude product, which was purified by flash chromatography (40-60% EtOAc/heptane) to obtain the desired titled compound (6.82 g, 80% yield) as a white glassy solid.

$^1$H-NMR (400 MHz, CDCl3) δ [ppm]: 1.52 (s, 9H), 4.97 (q, 4H), 6.40 (d, 1H), 6.70 (s, 1H), 7.17 (d, 2H), 7.51 (t, 2H), 7.61 (t, 1H), 7.76 (s, 1H), 8.24 (d, 1H), 8.28 (d, 1H).

Intermediate 332

3-[4-(4-amino-2,6-difluorophenoxy)-1-(benzenesulfonyl)-1H-pyrrolo[2,3-b]pyridin-3-yl]oxetan-3-ol

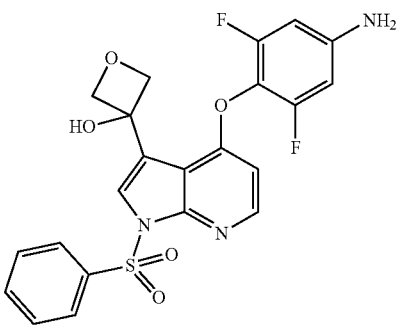 [SMILES: Nc1cc(F)c(Oc2ccnc3c2c(C2(O)COC2)cn3S(=O)(=O)c2ccccc2)c(F)c1]

To a solution of tert-butyl (4-{[1-(benzenesulfonyl)-3-(3-hydroxyoxetan-3-yl)-1H-pyrrolo[2,3-b]pyridin-4-yl]oxy}-3,5-difluorophenyl)carbamate (963 mg, 1.68 mmol, intermediate 331) in dichloromethane (9.0 mL) was added trifluoroacetic acid (9.0 mL, 120 mmol) and the mixture stirred at room temperature for 30 minutes. Volatiles were removed in vacuo. Saturated sodium hydrogen carbonate solution and solid were carefully added to the residue which was then extracted with dichloromethane (2×). The combined organic layers were washed with brine, dried over sodium sulfate and concentrated in vacuo to give the desired titled compounds (728 mg, 92% yield), which was used in the next step without any further purification.

$^1$H-NMR (400 MHz, CDCl3) δ [ppm]: 3.31 (s br, 1H), 4.97 (q, 4H), 6.31 (d, 2H), 6.45 (d, 1H), 7.51 (t, 2H), 7.61 (t, 1H), 7.74 (s, 1H), 8.23 (d, 2H), 8.29 (d, 1H).

Intermediate 333

4-nitrophenyl (4-{[1-(benzenesulfonyl)-3-(3-hydroxyoxetan-3-yl)-1H-pyrrolo[2,3-b]pyridin-4-yl]oxy}-3,5-difluorophenyl)carbamate

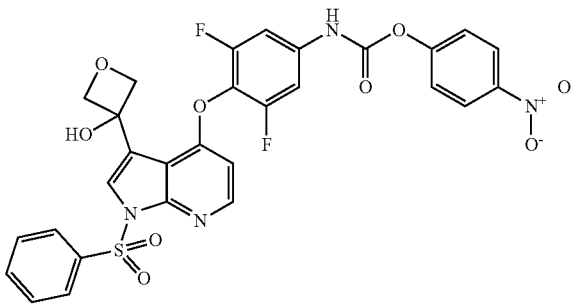

To a solution of 3-[4-(4-amino-2,6-difluorophenoxy)-1-(benzenesulfonyl)-1H-pyrrolo[2,3-b]pyridin-3-yl]oxetan-3-ol (473 mg, 1.00 mmol, intermediate 332) in THF (10 mL) was added pyridine (320 μL) and the mixture was then cooled to 0° C. before 4-nitrophenyl chloroformate (605 mg, 3.00 mmol) was added in one portion. The mixture was then stirred for 1 hour. This reaction mixture was used directly in the next step.

Intermediate 334

N-(4-{[1-(benzenesulfonyl)-3-(3-hydroxyoxetan-3-yl)-1H-pyrrolo[2,3-b]pyridin-4-yl]oxy}-3,5-difluorophenyl)-N'-[(3-methyloxetan-3-yl)methyl]urea

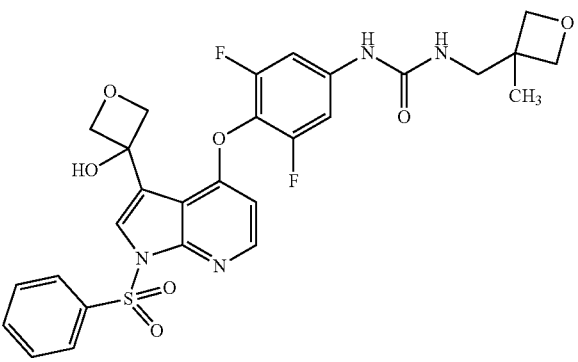 [SMILES: CC1(CNC(=O)Nc2cc(F)c(Oc3ccnc4c3c(C3(O)COC3)cn4S(=O)(=O)c3ccccc3)c(F)c2)COC1]

A solution of the 1-(3-methyloxetan-3-yl)methanamine (202 mg, 2.00 mmol) in THF (2.0 mL) containing N,N-diisopropylethylamine (520 μL, 3.0 mmol) was added the impure reaction mixture of 4-nitrophenyl (4-{[1-(benzenesulfonyl)-3-(3-hydroxyoxetan-3-yl)-1H-pyrrolo[2,3-b]pyridin-4-yl]oxy}-3,5-difluorophenyl)carbamate (639 mg, 1.00 mmol, intermediate 333). The mixture was stirred at room temperature for 2 hours. Then the mixture was then diluted with ethyl acetate and the organic phase was washed with sodium hydrogen carbonate solution (3×), water and then brine. The organic phase was dried over sodium sulfate to give a crude product, which was purified by flash chromatography 50-100% ethyl acetate/heptane) to obtain the desired titled compound (255 mg, 42% yield).

$^1$H-NMR (400 MHz, CDCl3) δ [ppm]: 1.29 (s, 3H), 3.39 (d, 2H), 3.85 (s br, 1H), 4.44 (q, 4H), 4.89 & 5.08 (q 4H), 5.75 (t, 1H), 6.36 (d, 1H), 7.48-7.65 (4H), 7.75 (s, 1H), 8.19-8.24 (m, 3H).

Intermediate 335

(+/−)-3-[1-(benzenesulfonyl)-4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]oxetan-3-ol

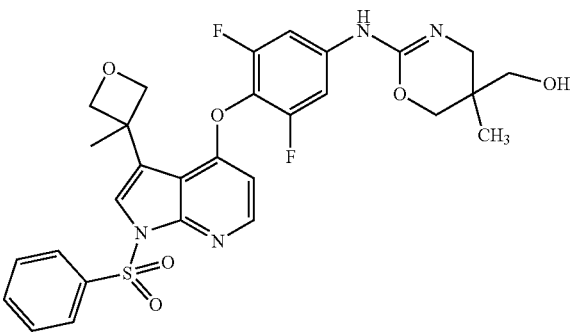 [SMILES: CC1(CO)CN=C(Nc2cc(F)c(Oc3ccnc4c3c(C3(C)COC3)cn4S(=O)(=O)c3ccccc3)c(F)c2)OC1]

To a solution of N-(4-{[1-(benzenesulfonyl)-3-(3-hydroxyoxetan-3-yl)-1H-pyrrolo[2,3-b]pyridin-4-yl]oxy}-3,5-difluorophenyl)-N'-[(3-methyloxetan-3-yl)methyl]urea (248 mg, 413 μmol, intermediate 334) in dichloromethane (16 mL) was added trifluoroacetic acid (4.0 mL, 52 mmol) and the mixture stirred at room temperature for 2 hours. Volatiles were removed in vacuo and the residue was taken up in dichloromethane. Sodium hydrogen carbonate (aqueous then solid) were carefully added until neutral. The organic phase was separated and the aqueous extracted with dichloromethane (2×). The combined organic layers were washed with brine then dried over sodium sulfate to give a crude product, which was purified by flash chromatography (0-5% MeOH/ethyl acetate) to obtain the desired titled compound (177 mg, 71% yield).

$^1$H-NMR (400 MHz, CDCl3) δ [ppm]: 1.03 (s, 3H), 3.09 & 3.33 (q, 2H), 3.54 (q, 2H), 3.98 & 4.25 (q, 2H), 4.90 & 5.03 (q, 4H), 6.41 (d, 1H), 6.93 (d, 2H), 7.50 (t, 2H), 7.60 (t, 1H), 7.73 (s, 1H), 8.19-8.26 (m, 3H).

Intermediate 336 tert-butyl (4-{[1-(benzenesulfonyl)-3-(3-fluorooxetan-3-yl)-1H-pyrrolo[2,3-b]pyridin-4-yl]oxy}-3,5-difluorophenyl)carbamate

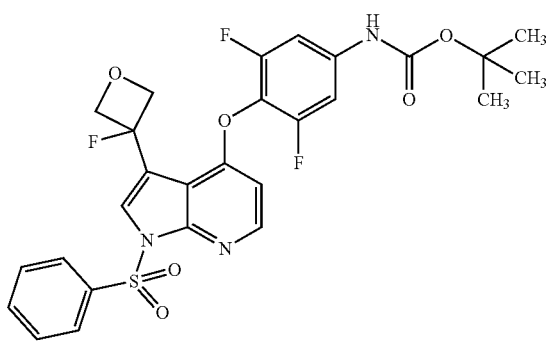 [SMILES: CC(C)(C)OC(=O)Nc1cc(F)c(Oc2ccnc3c2c(C2(F)COC2)cn3S(=O)(=O)c2ccccc2)c(F)c1]

To a solution of tert-butyl (4-{[1-(benzenesulfonyl)-3-(3-hydroxyoxetan-3-yl)-1H-pyrrolo[2,3-b]pyridin-4-yl]oxy}-3,5-difluorophenyl)carbamate (2.87 g, 5.00 mmol, intermediate 331) in dichloromethane at 0° C. was added N-(difluoro-$\lambda^4$-sulfanylidene)-N-ethylethanaminium tetrafluoroborate (XtalFluor-E®, 1.72 g, 7.50 mmol) and the reaction was stirred at this temperature for 2 hours. Then the reaction was diluted with dichloromethane and washed with sodium hydrogen carbonate solution, water and then brine. The organic phase was dried over sodium sulfate to give the desired titled compound (2.82 g, 98% yield), which was used in the next step without any further purification.

$^1$H-NMR (400 MHz, CDCl3) δ [ppm]: 1.52 (s, 9H), 5.07 & 5.19 (q, 2H), 5.13 (q, 2H), 6.41 (d, 1H), 6.63 (s, 1H), 7.14 (d, 2H), 7.52 (t, 2H), 7.62 (t, 1H), 7.80 (d, 1H), 8.22-8.29 (m, 3H).

Intermediate 337 tert-butyl (3,5-difluoro-4-{[3-(3-methoxyoxetan-3-yl)-1H-pyrrolo[2,3-b]pyridin-4-yl]oxy}phenyl)carbamate

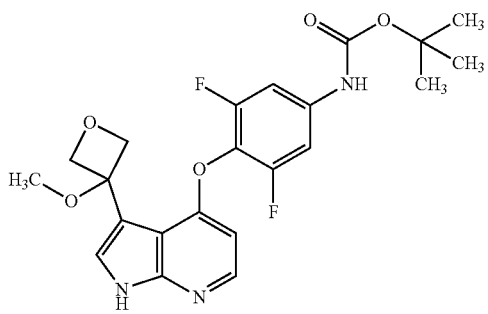 [SMILES: COC1(c2c[nH]c3nccc(Oc4c(F)cc(NC(=O)OC(C)(C)C)cc4F)c23)COC1]

To a solution of tert-butyl (4-{[1-(benzenesulfonyl)-3-(3-fluorooxetan-3-yl)-1H-pyrrolo[2,3-b]pyridin-4-yl]oxy}-3,5-difluorophenyl)carbamate (2.82 g, 4.90 mmol, Intermediate 336) in methanol (47 mL) was added potassium carbonate (1.35 g, 9.80 mmol) and the resulting mixture stirred at room temperature for 2 hours. The reaction mixture was diluted with ethyl acetate and washed with ammonium chloride solution, water and brine. The organic phase was then dried over sodium sulfate to give the desired titled compound (2.80 g) as a pale yellow glassy solid, which was used in the next step without any further purification.

Intermediate 338 tert-butyl (3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)carbamate

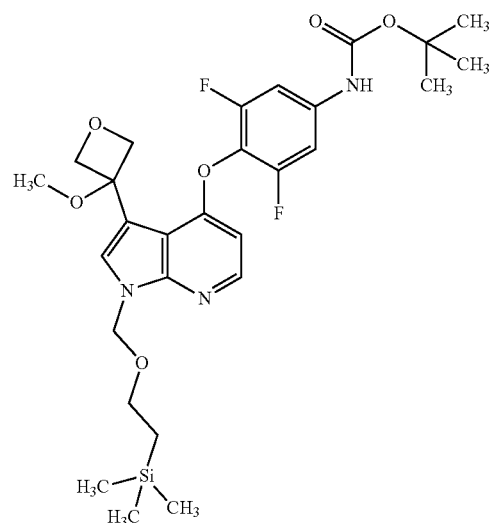 [SMILES: COC1(c2cn(COCC[Si](C)(C)C)c3nccc(Oc4c(F)cc(NC(=O)OC(C)(C)C)cc4F)c23)COC1]

To a solution of tert-butyl (3,5-difluoro-4-{[3-(3-methoxyoxetan-3-yl)-1H-pyrrolo[2,3-b]pyridin-4-yl]oxy}phenyl)carbamate (2.19 g, 4.90 mmol, intermediate 337) in acetonitrile (49 mL) was added N,N-diisopropylethylamine (1.7 mL, 9.8 mmol) followed by [2-(chloromethoxy)ethyl](trimethyl)silane (1.0 mL, 5.9 mmol). The reaction was stirred for 4 hours at room temperature and then it was diluted with diethyl ether. The organic phase was washed with ammonium chloride solution, water and the brine. The organic phase was then dried over sodium sulfate and concentrated in vacuo to give a crude product, which was purified by flash chromatography (20-40% ethyl acetate/heptane) to obtain the desired titled compound (823 mg, 29% yield) as a clear oil.

$^1$H-NMR (400 MHz, CDCl3) δ [ppm]: −0.06 (s, 9H), 0.91 (dd, 2H), 1.52 (s, 9H), 3.12 (s, 3H), 3.58 (t, 2H), 5.02 (q, 4H), 5.68 (s, 2H), 6.28 (d, 1H), 6.72 (s, 1H), 7.14 (d, 2H), 7.31 (s, 1H), 8.15 (d, 1H).

339

Intermediate 339

3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}aniline

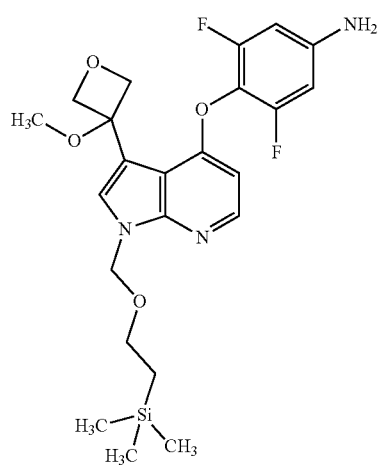 [SMILES: COC1(c2cn(COCC[Si](C)(C)C)c3nccc(Oc4c(F)cc(N)cc4F)c23)COC1]

To a solution of tert-butyl (3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)carbamate (817 mg, 1.41 mmol, intermediate 338) in 1,2-dichloroethane (70 mL) was added zinc bromide (955 mg, 4.24 mmol) and the resulting mixture heated at 60° C. for 6 hours. The reaction mixture was diluted with dichloromethane and washed with water and then brine. The organic phase was dried over sodium sulfate to a crude product, which was purified by flash chromatography (50-80% ethyl acetate/heptane) to obtain the desired titled compound (193 mg, 29% yield).

$^1$H-NMR (400 MHz, CDCl3) δ [ppm]: −0.06 (s, 9H), 0.91 (dd, 2H), 3.13 (s, 3H), 3.58 (dd, 2H), 3.91 (s br, 2H), 5.02 (q, 4H), 5.67 (s, 2H), 6.30 (d, 2H), 6.33 (d, 1H), 7.29 (s, 1H), 8.15 (d, 1H).

340

Intermediate 340

4-nitrophenyl (3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)carbamate

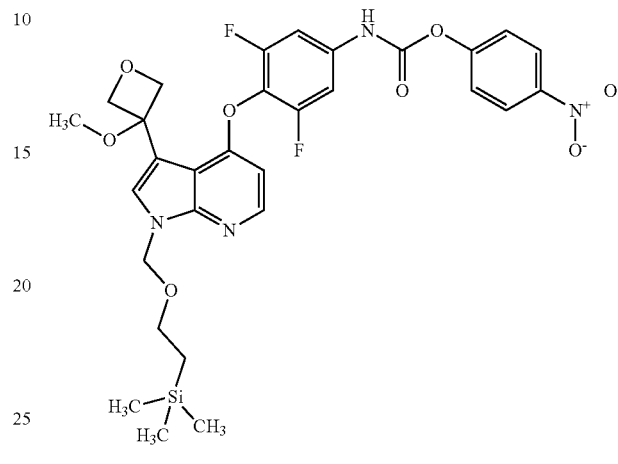

In analogy to intermediate 333), 3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}aniline (251 mg, 526 μmol, intermediate 339) was reacted with 4-nitrophenyl chloroformate (296 mg, 1.47 mmol) in pyridine (170 μL) and THF (10 mL) to a reaction mixture was used directly in the next step.

Intermediate 341

N-(3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

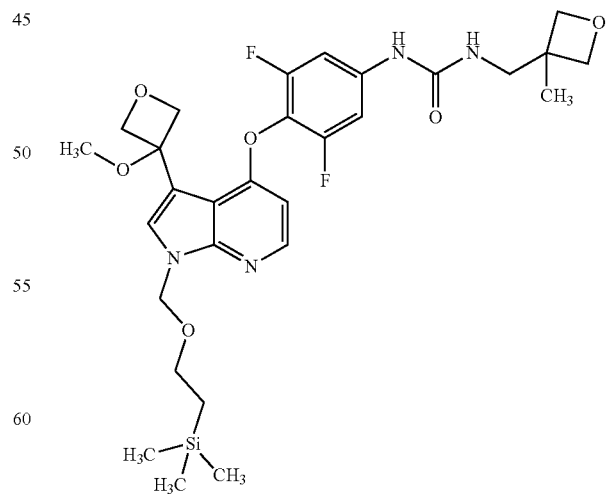

To reaction mixture from 4-nitrophenyl (3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)carbamate (251 mg, 391 µmol, intermediate 340) was added a solution of 1-(3-methyloxetan-3-yl)methanamine (59.3 mg, 586 µmol) in THF (2.0 mL) containing N,N-diisopropylethylamine (140 µL, 780 µmol). The reaction mixture was stirred at room temperature for 2 hours and then it was diluted with ethyl acetate. The organic phase was washed with 0.1M NaOH (2×), ammonium chloride solution, water and then brine. Then the organic phase was dried over sodium sulfate to give a crude product, which was purified by flash chromatography (40-100% ethyl acetate/heptane) to obtain the desired titled compound (211 mg, 89% yield) as a colourless gum.

$^1$H-NMR (400 MHz, CDCl3) δ [ppm]: −0.06 (s, 9H), 0.91 (dd, 2H), 1.30 (s, 3H), 3.16 (s, 3H), 3.43 (d, 2H), 3.58 (dd, 2H), 4.39 & 4.49 (q, 4H), 4.94 & 5.15 (q, 4H), 5.67 (s, 2H), 5.95 (t, 1H), 6.30 (d, 1H), 7.15 (d, 2H), 7.28 (s, 1H), 7.71 (s, 1H), 8.14 (d, 1H).

Intermediate 342

4-(2,6-difluoro-4-nitrophenoxy)-3-iodo-1-{[2-(trimethylsilyl)ethoxy]methyl}-1H-pyrrolo[2,3-b]pyridine

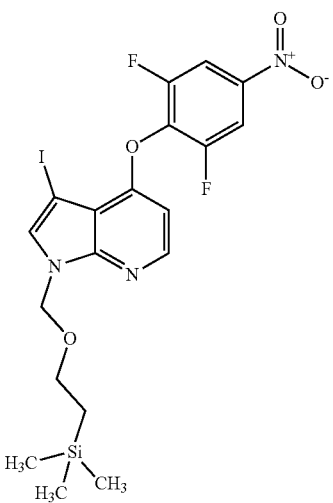 [SMILES: C[Si](C)(C)CCOCn1cc(I)c2c(Oc3c(F)cc([N+](=O)[O-])cc3F)ccnc21]

To a stirred solution of 4-(2,6-difluoro-4-nitrophenoxy)-3-iodo-1H-pyrrolo[2,3-b]pyridine (4.17 g, 10.0 mmol, Intermediate 327) in acetonitrile (100 mL) was added N,N-diisopropylethylamine, (3.5 mL, 20 mmol) followed by [2-(chloromethoxy)ethyl](trimethyl)silane (2.1 mL, 12 mmol).

The resulting reaction mixture was stirred at room temperature for 2 hours. The reaction mixture was diluted with diethyl ether and washed with ammonium chloride solution, sodium hydrogen carbonate solution, water and brine. The organic phase was dried over sodium sulfate, and evaporated to dryness to give a crude product, which was purified by flash chromatography (10-40% ethyl acetate/heptane) to obtain the desired titled compound (4.04 g, 74% yield) as a yellow oil, which solidified overnight.

$^1$H-NMR (400 MHz, CDCl3) δ [ppm]: −0.05 (s, 9H), 0.92 (dd, 2H), 3.56 (dd, 2H), 5.64 (s, 2H), 6.29 (d, 1H), 7.46 (s, 1H), 8.01 (d, 2H), 8.18 (d, 1H).

Intermediate 343

3,5-difluoro-4-[(3-iodo-1-{[2-(trimethylsilyl)ethoxy]methyl}-1H-pyrrolo[2,3-b]pyridin-4-yl)oxy]aniline

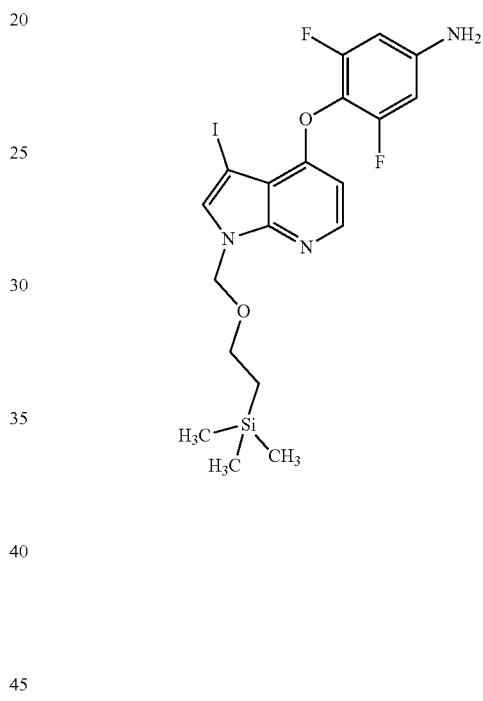

To a solution of 4-(2,6-difluoro-4-nitrophenoxy)-3-iodo-1-{[2-(trimethylsilyl)ethoxy]methyl}-1H-pyrrolo[2,3-b]pyridine (4.04 g, 7.38 mmol, intermediate 342) in a mixture of THF (35 mL), water (35 mL), and methanol (70 mL), was added ammonium chloride (1.97 g, 36.9 mmol) and iron powder (2.06 g, 36.9 mmol). The resulting mixture was stirred at 80° C. for 1.5 hours. Then the reaction mixture was cooled to room temperature, filtered through Celite and the Celite was washed with ethyl acetate. The filtrate was extracted with ethyl acetate and the combined organic layers were washed with brine, dried over sodium sulfate, and evaporated to give the crude product, which was used in the next step without any further purification.

$^1$H-NMR (400 MHz, CDCl3) δ [ppm]: −0.05 (s, 9H), 0.93 (dd, 2H), 3.55 (dd, 2H), 3.87 (s br, 2H), 5.61 (s, 2H), 6.30-6.60 (m, 3H), 7.38 (s, 1H), 8.13 (d, 1H).

Intermediate 344 benzyl {3,5-difluoro-4-[(3-iodo-1-{[2-(trimethylsilyl)ethoxy]methyl}-1H-pyrrolo[2,3-b]pyridin-4-yl)oxy]phenyl}carbamate

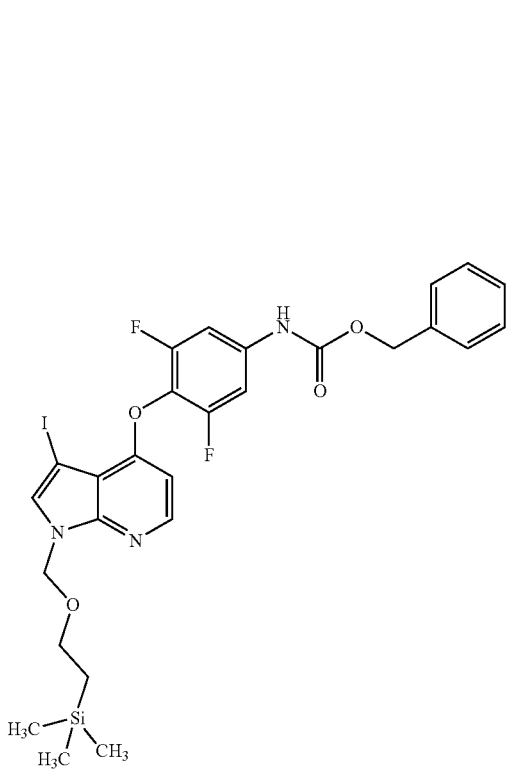 [SMILES: C[Si](C)(C)CCOCn1cc(I)c2c(Oc3c(F)cc(NC(=O)OCc4ccccc4)cc3F)ccnc21]

To a solution of 3,5-difluoro-4-[(3-iodo-1-{[2-(trimethylsilyl)ethoxy]methyl}-1H-pyrrolo[2,3-b]pyridin-4-yl)oxy]aniline (3.92 g, 7.58 mmol, intermediate 343) in THF (75 mL) was added water (38 mL) followed by sodium hydrogen carbonate (3.18 g, 37.9 mmol). Then benzyl chloroformate (1.3 mL, 9.1 mmol) was added dropwise and the reaction mixture was stirred overnight at room temperature. Volatiles were removed in vacuo and diethyl ether was added to the residue. The aqueous layer was extracted with diethyl ether, the combined organic extracts were washed with brine, dried over sodium sulfate and concentrated in vacuo to a crude product, which was purified by flash chromatography (20-40% ethyl acetate/heptane) to obtain the desired titled compound (4.45 g, 90% yield) as a yellow gum.

$^1$H-NMR (400 MHz, CDCl3) δ [ppm]: −0.05 (s, 9H), 0.91 (dd, 2H), 3.55 (dd, 2H), 5.22 (s, 2H), 5.62 (s, 2H), 6.29 (d, 1H), 6.80 (s, 1H), 7.19 (d, 2H), 7.35-7.42 (m, 6H), 8.13 (d, 1H).

Intermediate 345 benzyl (3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)carbamate

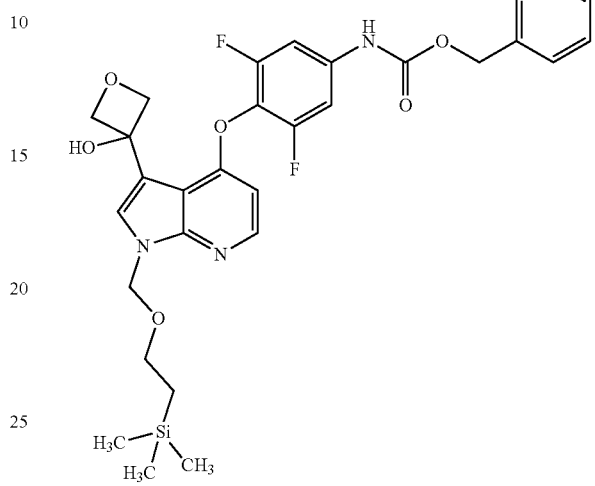

In analogy to intermediate 331, 3 benzyl {3,5-difluoro-4-[(3-iodo-1-{[2-(trimethylsilyl)ethoxy]methyl}-1H-pyrrolo[2,3-b]pyridin-4-yl)oxy]phenyl}carbamate (4.45 g, 6.83 mmol, Intermediate 344) was reacted with isopropylmagnesium chloride (7.5 mL, 2.0 M in THF, 15 mmol) and oxetan-3-one (12 mL, 17 mmol). Purification by flash chromatography (40-60% ethyl acetate/heptane) gave the desired titled compound (2.40 g, 59% yield) as a white glassy solid.

$^1$H-NMR (400 MHz, CDCl3) δ [ppm]: −0.49 (s, 9H), 0.93 (dd, 2H), 3.28 (s, 1H), 3.58 (dd, 2H), 5.01 (q, 4H), 5.21 (s, 2H), 5.66 (s, 2H), 6.30 (d, 1H), 7.09 (s, 1H), 7.20 (d, 2H), 7.34-7.45 (m 6H), 8.18 (d, 1H).

Intermediate 346

3-[4-(4-amino-2,6-difluorophenoxy)-1-{[2-(trimethylsilyl)ethoxy]methyl}-1H-pyrrolo[2,3-b]pyridin-3-yl]oxetan-3-ol

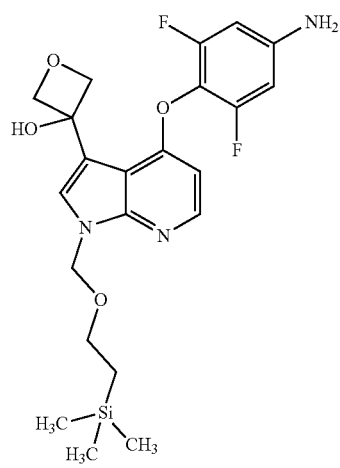 [SMILES: C[Si](C)(C)CCOCn1cc(C2(O)COC2)c2c(Oc3c(F)cc(N)cc3F)ccnc21]

345

A solution of benzyl (3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)carbamate (598 mg, 1.00 mmol, intermediate 345) in ethyl acetate was stirred over 5% Palladium on carbon (106 mg) in a hydrogen atmosphere for 2 hours at room temperature. Then the catalyst was removed by filtration through Celite and the Celite was washed with ethyl acetate. The filtrate was concentrated in vacuo to give the desired titled compound (457 mg, 99% yield) as a pale yellow glassy solid, which was used in the next step without any further purification $^1$H-NMR (400 MHz, CDCl3) δ [ppm]: −0.05 (s, 9H), 0.93 (dd, 2H), 3.40 (s br, 1H), 3.58 (dd, 2H), 3.97 (s br, 2H), 5.00 (q, 4H), 5.66 (s, 2H), 6.30-6.38 (m 3H), 7.35 (s, 1H), 8.18 (d, 1H).

Intermediate 347

4-nitrophenyl (3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)carbamate

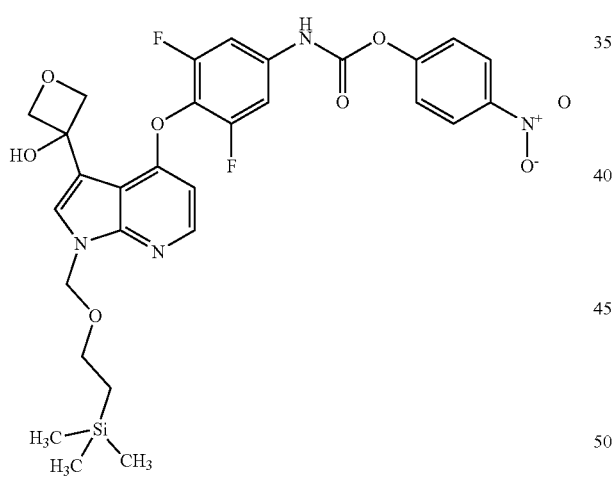

In analogy to intermediate 333, 3-[4-(4-amino-2,6-difluorophenoxy)-1-{[2-(trimethylsilyl)ethoxy]methyl}-1H-pyrrolo[2,3-b]pyridin-3-yl]oxetan-3-ol (452 mg, 975 μmol, intermediate 346) was reacted with 4-nitrophenyl carbonochloridate (472 mg, 2.34 mmol) in the presence of pyridine (320 μL) in THF (9.8 mL) to give a reaction mixture which was used directly in the next step.

Intermediate 348

N-(3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

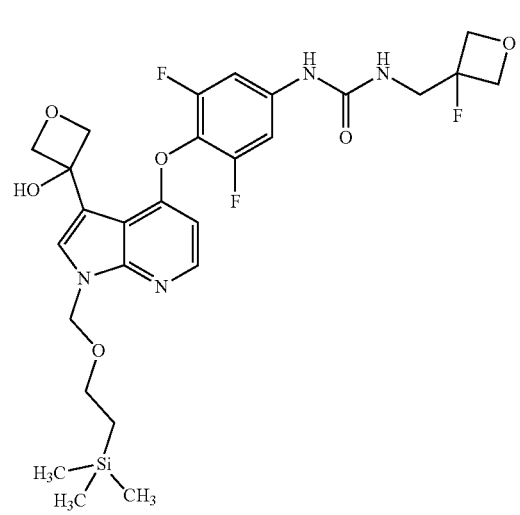 [SMILES: C[Si](C)(C)CCOCn1cc(C2(O)COC2)c2c(Oc3c(F)cc(NC(=O)NCC4(F)COC4)cc3F)ccnc21]

A solution of the 1-(3-fluorooxetan-3-yl)methanamine (90.7 mg, 863 μmol) in THF (2.0 mL) containing N,N-diisopropylethylamine (250 μL, 1.4 mmol) was added to reaction mixture of 4-nitrophenyl (3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)carbamate (452 mg, 719 μmol, intermediate 347). The mixture was stirred at room temperature for 2 hours. Then the reaction mixture was diluted with ethyl acetate and the organic phase was washed with sodium hydrogen carbonate solution (3×), water and then brine. The organic phase was dried over sodium sulfate to give a crude product, which was purified by flash chromatography (60-100% ethyl acetate/heptane) to obtain the desired titled compound (430 mg, 100% yield) as a colourless glassy solid.

$^1$H-NMR (400 MHz, CDCl$_3$) δ [ppm]: −0.04 (s, 9H), 0.93 (dd, 2H), 3.59 (dd, 2H), 3.81 (dd, 2H), 4.68 (2×q, 4H), 5.02 (q, 4H), 5.66 (s, 2H), 5.72 (t, 1H), 6.30 (d, 1H), 7.14 (d, 2H), 7.34 (s, 1H), 7.50 (s br, 1H), 8.15 (d, 1H).

Intermediate 349

N-(3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

Intermediate 350 benzyl (3,5-difluoro-4-{[3-(3-fluorooxetan-3-yl)-1-{[2-(trimethylsilyl)ethoxy]methyl}-1H-pyrrolo[2,3-b]pyridin-4-yl]oxy}phenyl)carbamate

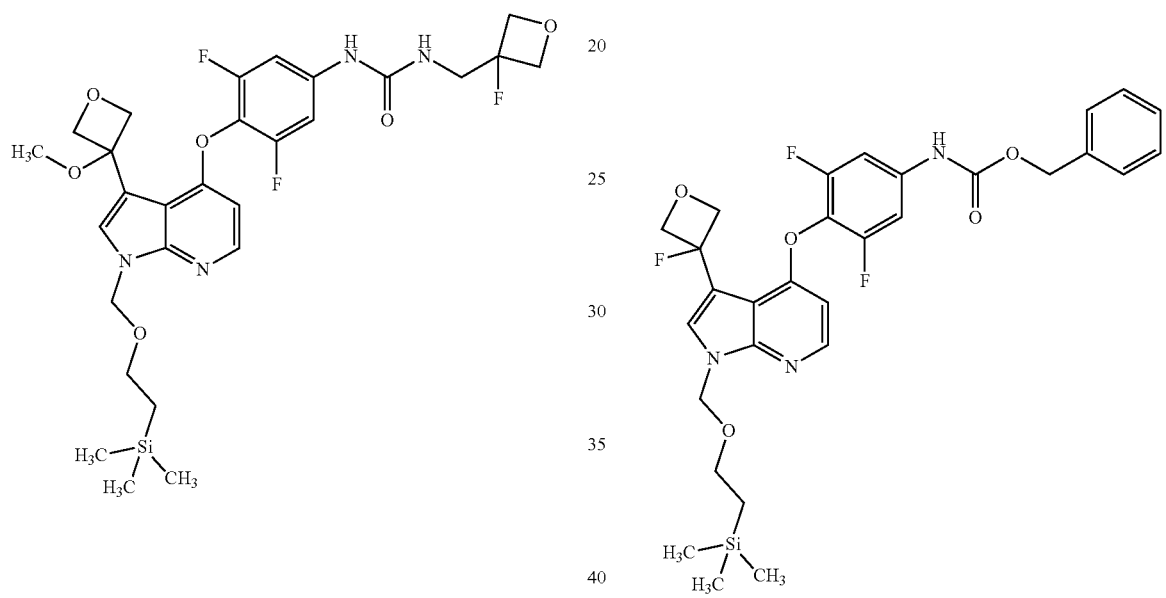

To the reaction mixture of 4-nitrophenyl (3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)carbamate (646 mg, 1.00 mmol, intermediate 340) at 0° C. was added a solution of the 1-(3-fluorooxetan-3-yl)methanamine (158 mg, 1.51 mmol) in THF (5.0 mL) containing N,N-diisopropylethylamine (350 µL, 2.0 mmol). The reaction mixture was stirred for 1 hour at this temperature. The reaction mixture was diluted with ethyl acetate and washed with sodium hydrogen carbonate solution, water and then brine. The organic phase was dried over sodium sulfate to give a crude product, which was purified by flash chromatography (80-100% ethyl acetate/heptane) to obtain the desired titled compound (524 mg, 86% yield) as a colourless, glassy solid.

$^1$H-NMR (400 MHz, CDCl3) δ [ppm]: −0.06 (s, 9H), 0.91 (dd, 2H), 3.18 (s, 3H), 3.58 (dd, 2H), 3.82 (dd, 2H), 4.69 (dq, 4H), 4.93 & 5.15 (q, 4H), 5.68 (s, 2H), 5.74 (t, 1H), 6.31 (d, 1H), 7.13 (d, 2H), 7.29 (s, 1H), 7.31 (s br, 1H), 8.15 (d, 1H).

In analogy to Intermediate 336, (3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)carbamate (3.02 g, 5.05 mmol, intermediate 345) was reacted with N-(difluoro-λ$^4$-sulfanylidene)-N-ethylethanaminium tetrafluoroborate (XtalFluor-E®, 1.74 g, 7.58 mmol) in dichloromethane (100 mL) to give the desired titled compound (3.21 g, 100% yield) without any further purification $^1$H-NMR (400 MHz, CDCl$_3$) δ [ppm]: −0.45 (s, 9H), 0.93 (dd, 2H), 3.59 (dd, 2H), 5.09-5.26 (m, 6H), 5.67 (s, 2H), 6.32 (d, 1H), 6.84 (s, 1H), 7.19 (d, 2H), 7.35-7.42 (m, 6H), 8.18 (d, 1H).

Intermediate 351 benzyl (4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)carbamate

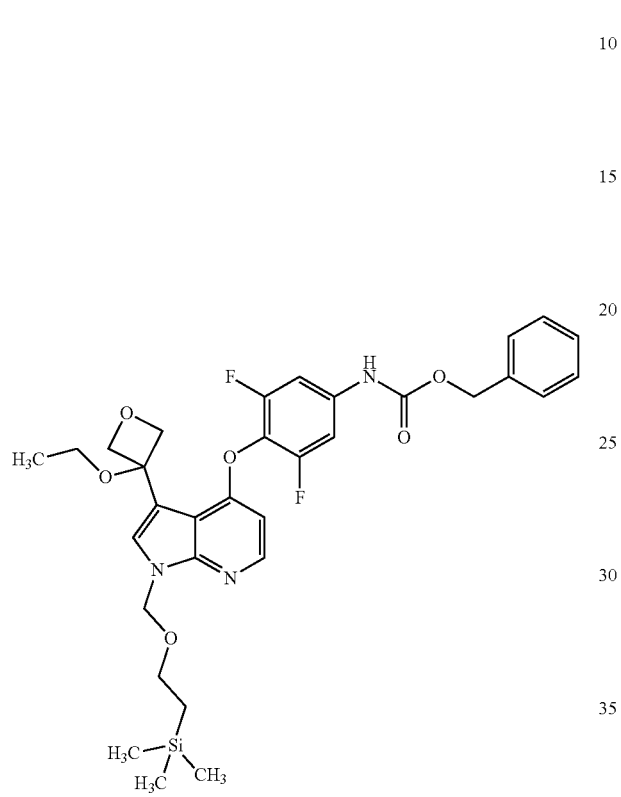

To a solution of benzyl (3,5-difluoro-4-{[3-(3-fluorooxetan-3-yl)-1-{[2-(trimethylsilyl)ethoxy]methyl}-1H-pyrrolo[2,3-b]pyridin-4-yl]oxy}phenyl)carbamate (600 mg, 1.00 mmol, intermediate 350) in ethanol (10 mL) was added silica gel (2.4 g, SillicaFlash P60, 230-400 Mesh) and the mixture was stirred overnight at 55° C. After cooling to room temperature the reaction mixture was concentrated in vacuo and the obtained crude product was purified by chromatography (20-50% ethyl acetate/heptane) to give the desired titled compound (465 mg, 74% yield) as a colourless glass.

$^1$H-NMR (400 MHz, CDCl3) δ [ppm]: −0.06 (s, 9H), 0.91 (dd, 2H), 1.11 (t, 3H), 3.26 (q, 2H), 3.58 (dd, 2H), 5.01 (q, 4H), 5.21 (s, 2H), 5.67 (s, 2H), 6.27 (d, 1H), 6.81 (s, 1H), 7.17 (d, 2H), 7.29-7.41 (m, 5H), 8.15 (d, 1H).

Intermediate 352

4-{[3-(3-ethoxyoxetan-3-yl)-1-{[2-(trimethylsilyl)ethoxy]methyl}-1H-pyrrolo[2,3-b]pyridin-4-yl]oxy}-3,5-difluoroaniline

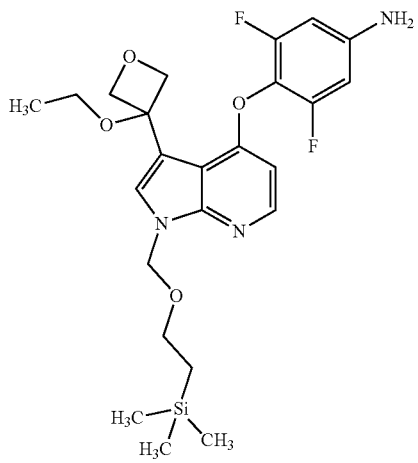 [SMILES: CCOC1(c2cn(COCC[Si](C)(C)C)c3nccc(Oc4c(F)cc(N)cc4F)c23)COC1]

In analogy to intermediate 346, benzyl (4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)carbamate (465 mg, 743 μmol, intermediate 351) and 5% Palladium on carbon (79.1 mg) in ethyl acetate was reacted in a hydrogen atmosphere to give the desired title compound (338 mg, 93% yield) without any further purification.

$^1$H-NMR (400 MHz, CDCl3) δ [ppm]: −0.07 (s, 9H), 0.91 (dd, 2H), 1.11 (t, 2H), 3.27 (q, 2H), 3.57 (dd, 2H), 3.88 (s br, 2H), 4.98 & 5.06 (q, 4H), 5.66 (s, 2H), 6.27-6.33 (m, 3H), 7.29 (s br, 1H), 8.14 (d, 1H).

Intermediate 353

4-nitrophenyl (4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)carbamate

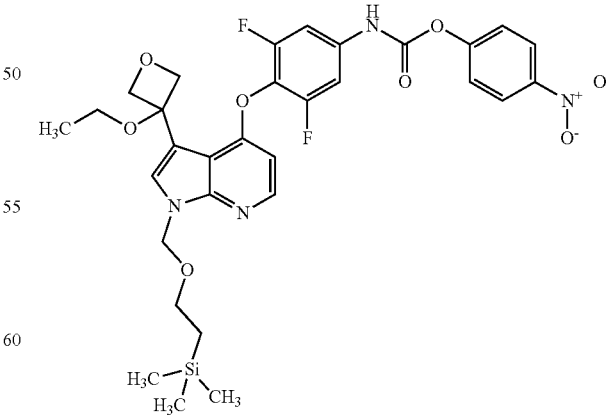

In analogy to intermediate 333, 4-{[3-(3-ethoxyoxetan-3-yl)-1-{[2-(trimethylsilyl)ethoxy]methyl}-1H-pyrrolo[2,3-b]pyridin-4-yl]oxy}-3,5-difluoroaniline (333 mg, 677 μmol,

Intermediate 354

N-(4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

Intermediate 355 benzyl {3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}carbamate

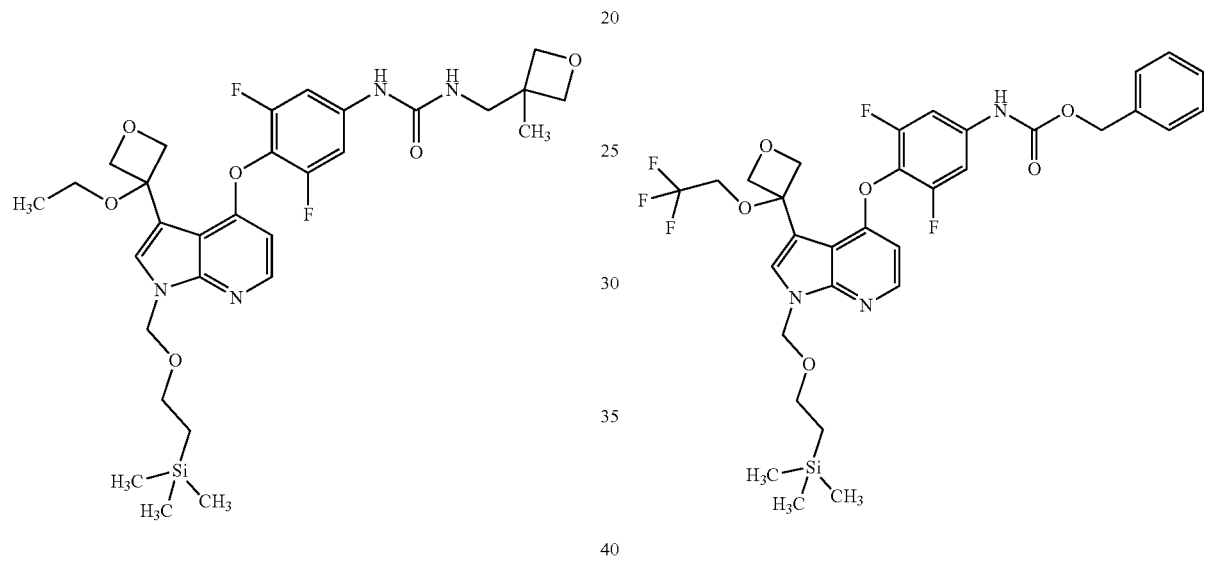

To the reaction mixture of 4-nitrophenyl (4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)carbamate (445 mg, 677 µmol, intermediate 353) at 0° C., was added a solution of the 1-(3-methyloxetan-3-yl)methanamine (103 mg, 1.02 mmol) in THF (4.0 mL) containing N,N-diisopropylethylamine (240 µL, 1.4 mmol). The reaction mixture was stirred for 1 hour at this temperature. The reaction mixture was diluted with ethyl acetate and washed with sodium hydrogen carbonate solution, water and then brine. The organic phase was dried over sodium sulfate to give a crude product, which was purified by flash chromatography (80-100% ethyl acetate/heptane) to obtain the desired titled compound (339 mg, 81% yield) as a colourless gum.

$^1$H-NMR (400 MHz, CDCl3) δ [ppm]: −0.06 (s, 9H), 0.91 (dd, 2H), 1.13 (t, 3H), 1.31 (s, 3H), 3.30 (q, 2H), 3.43 (d, 2H), 3.58 (dd, 2H), 4.42 & 4.50 (q, 4H), 4.96 & 5.13 (q, 4H), 5.66 (s, 2H), 5.76 (t, 1H), 6.29 (d, 1H), 7.16 (d, 2H), 7.28 (s, 1H), 7.46 (s, 1H), 8.14 (d, 1H).

To a solution of benzyl (3,5-difluoro-4-{[3-(3-fluorooxetan-3-yl)-1-{[2-(trimethylsilyl)ethoxy]methyl}-1H-pyrrolo[2,3-b]pyridin-4-yl]oxy}phenyl)carbamate (600 mg, 1.00 mmol, intermediate 350) in 2,2,2-trifluoroethanol-methanol (20 mL, 270 mmol) was added silica gel (2.4 g, SilliaFlash P60, 230-400 Mesh) and the mixture stirred at room temperature for 3 hours. The reaction mixture was filtered and concentrated in vacuo. The obtained crude product was purified by chromatography column (20-40% ethyl acetate/heptane) to give the desired titled compound (178 mg, 26% yield) as a clear glass.

$^1$H-NMR (400 MHz, CDCl3) δ [ppm]: −0.06 (s, 9H), 0.92 (dd, 2H), 3.56-3.68 (m, 4H), 5.04 (q, 4H), 5.22 (s, 2H), 5.69 (s, 2H), 6.29 (d, 1H), 6.87 (s, 1H), 7.18 (d, 2H), 7.36-7.42 (m, 6H), 8.18 (d, 1H).

Intermediate 356

3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]aniline

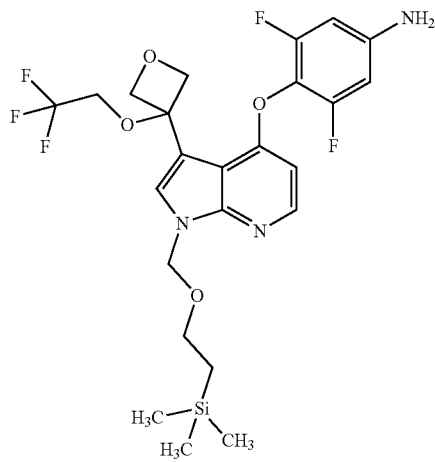 [SMILES: C[Si](C)(C)CCOCn1cc(C2(OCC(F)(F)F)COC2)c2c(Oc3c(F)cc(N)cc3F)ccnc21]

In analogy to intermediate 346, benzyl {3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}carbamate (178 mg, 262 μmol, intermediate 355) and 5% Palladium on carbon (83.6 mg) in ethyl acetate (10 mL) was reacted in a hydrogen atmosphere to give the desired title compound (143 mg, 100% yield) without any further purification.

$^1$H-NMR (400 MHz, CDCl$_3$) δ [ppm]: −0.06 (s, 9H), 0.92 (dd, 2H), 3.57-3.69 (m, 4H), 3.90 (s br, 2H), 5.01 & 5.09 (q, 4H), 5.68 (s, 2H), 6.28-6.36 (m, 3H), 7.36 (s, 1H), 8.18 (d, 1H).

Intermediate 357

4-nitrophenyl {3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}carbamate

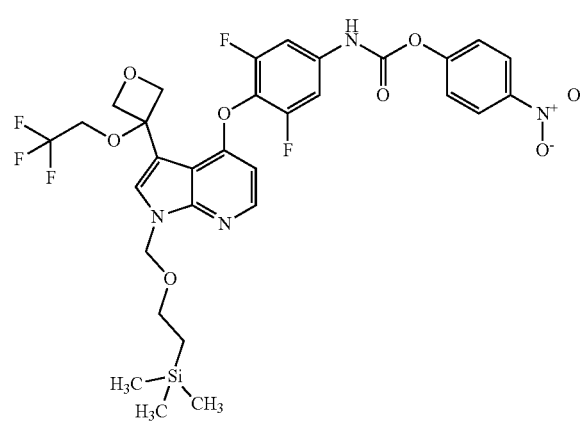

In analogy to intermediate 333, 3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]aniline (143 mg, 262 μmol, intermediate 356) was reacted with 4-nitrophenyl carbonochloridate (63.4 mg, 315 μmol) in the presence of pyridine (85 μL) in THF (10 mL) to give a reaction mixture which was used directly in the next step.

Intermediate 358

N-{3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

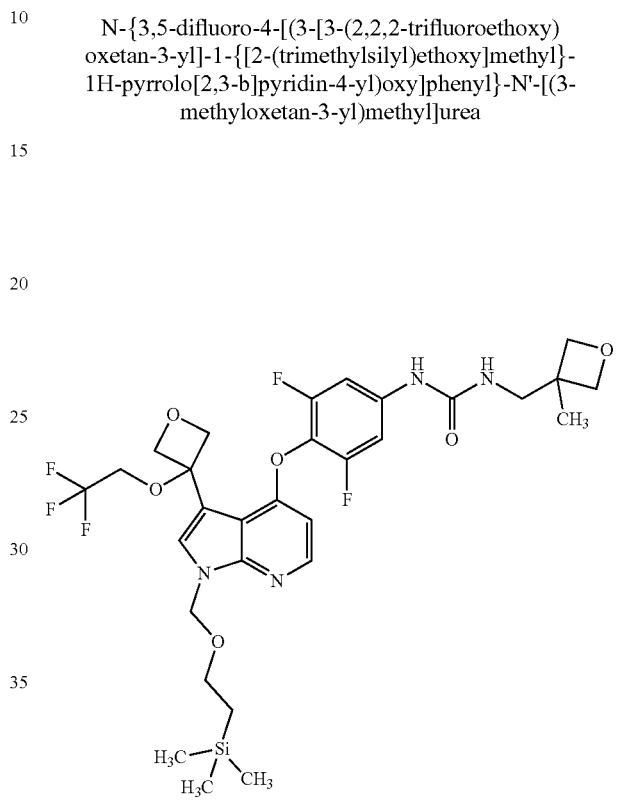

To the reaction mixture of 4-nitrophenyl {3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}carbamate (186 mg, 262 μmol, intermediate 357) at 0° C., was added a solution of the 1-(3-methyloxetan-3-yl)methanamine (39.8 mg, 393 μmol) in THF (2.5 mL) containing N,N-diisopropylethylamine (91 μL, 520 μmol). The reaction mixture was stirred for 1 hour at this temperature. The reaction mixture was diluted with ethyl acetate and washed with sodium hydrogen carbonate solution, water and then brine. The organic phase was dried over sodium sulfate to a crude product, which was purified by flash chromatography (80-100% ethyl acetate/heptane) to obtain the desired titled compound (80 mg, 45% yield) as a colourless gum.

$^1$H-NMR (400 MHz, CDCl3) δ [ppm]: −0.06 (s, 9H), 0.91 (dd, 2H), 1.31 (s, 3H), 3.41 (d, 2H), 3.57-3.69 (m, 4H), 4.44 & 4.50 (q, 4H), 5.01 & 5.11 (q, 4H), 5.54 (t, 1H), 5.68 (s, 2H), 6.31 (d, 1H), 7.14 (d, 2H), 7.27 (s br, 1H), 7.37 (s, 1H), 8.17 (d, 1H).

Intermediate 359 benzyl {3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}carbamate

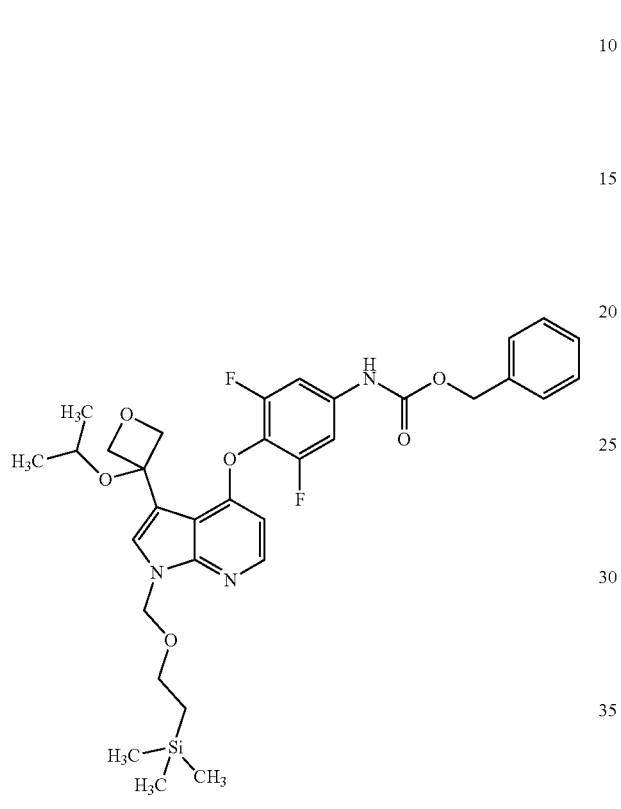

To a solution of benzyl (3,5-difluoro-4-{[3-(3-fluorooxetan-3-yl)-1-{[2-(trimethylsilyl)ethoxy]methyl}-1H-pyrrolo[2,3-b]pyridin-4-yl]oxy}phenyl)carbamate (223 mg, 372 μmol, intermediate 350) in isopropanol (3.7 mL, 48 mmol) was added silica gel (446 mg, SilliaFlash P60, 230-400 Mesh) and the mixture stirred was then heated in a sealed tube at 50° C. for 3 days. After cooling to room temperature the reaction mixture was concentrated in vacuo and the crude product was purified by chromatography (20-50% ethyl acetate/heptane) to give the desired titled compound (157 mg, 66% yield) as a clear oil.

$^1$H-NMR (400 MHz, CDCl3) δ [ppm]: −0.07 (s, 9H), 0.91 (dd, 2H), 0.99 (d, 6H), 3.49-3.60 (m, 3H), 5.01 (q, 4H), 5.22 (s, 2H), 5.68 (s, 2H), 6.25 (d, 1H), 6.92 (s, 1H), 7.16 (d, 2H), 7.35-7.41 (m, 5H), 8.15 (d, 1H).

Intermediate 360

3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]aniline

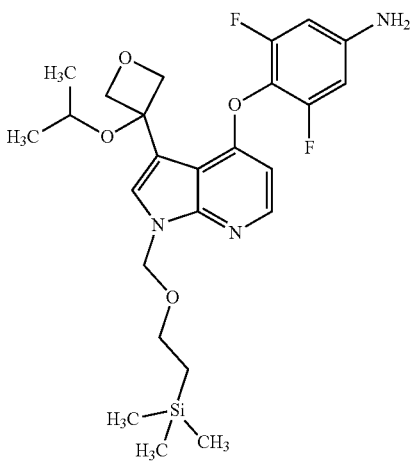 [SMILES: CC(C)OC1(c2cn(COCC[Si](C)(C)C)c3nccc(Oc4c(F)cc(N)cc4F)c23)COC1]

In analogy to intermediate 346), benzyl {3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}carbamate (419 mg, 655 μmol, intermediate 359) and 5% Palladium on carbon (69.7 mg) in ethyl acetate (32 mL) was reacted in a hydrogen atmosphere to give the desired title compound (360 mg, >100% yield) without any further purification.

$^1$H-NMR (400 MHz, CDCl$_3$) δ [ppm]: −0.07 (s, 9H), 0.91 (dd, 2H), 0.99 (d, 6H), 3.50-3.60 (m, 3H), 3.87 (s br, 2H), 5.01 (q, 4H), 5.68 (s, 2H), 6.27-6.33 (m, 3H), 7.35 (s, 1H), 8.15 (d, 1H).

Intermediate 361

4-nitrophenyl {3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}carbamate

357

In analogy to intermediate 333, 3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]aniline (350 mg, 692 μmol, intermediate 360) was reacted with 4-nitrophenyl carbonochloridate (167 mg, 831 μmol) in the presence of pyridine (220 μL) in THF (22 mL) to give a reaction mixture which was used directly in the next step.

Intermediate 362

N-{3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

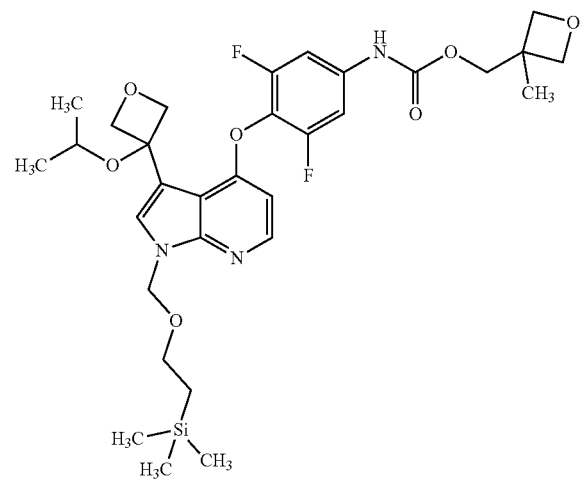 [SMILES: CC(C)OC1(c2cn(COCC[Si](C)(C)C)c3nccc(Oc4c(F)cc(NC(=O)OCC5(C)COC5)cc4F)c23)COC1]

To the reaction mixture of 4-nitrophenyl {3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}carbamate (464 mg, 692 μmol, intermediate 361) at 0° C., was added a solution of the 1-(3-methyloxetan-3-yl)methanamine (105 mg, 1.04 mmol) in THF (4.1 mL) containing N,N-diisopropylethylamine (240 μL, 1.4 mmol). The reaction mixture was stirred for 1 hour at this temperature. The reaction mixture was diluted with ethyl acetate and washed with sodium hydrogen carbonate solution, water and then brine. The organic phase was dried over sodium sulfate to give a crude product, which was purified by flash chromatography (80-100% ethyl acetate/heptane) to obtain the desired titled compound (174 mg, 40% yield) as a colourless gum.

¹H-NMR (400 MHz, CDCl3) δ [ppm]: −0.07 (s, 9H), 0.91 (dd, 2H), 1.00 (d, 6H), 1.30 (s, 3H), 3.42 (d, 2H), 3.52-3.60 (m, 3H), 4.41 & 4.49 (q, 4H), 4.97 & 5.11 (q, 4H), 5.66 (s, 2H), 5.79 (t, 1H), 6.28 (d, 1H), 7.16 (d, 2H), 7.33 (s, 1H), 7.48 (s, 1H), 8.14 (d, 1H).

358

Intermediate 363 di-tert-butyl (4-{[3-(3-cyanopropyl)-1-(4-methylbenzene-1-sulfonyl)-1H-pyrrolo[2,3-b]pyridin-4-yl]oxy}-3,5-difluorophenyl)-2-imidodicarbonate

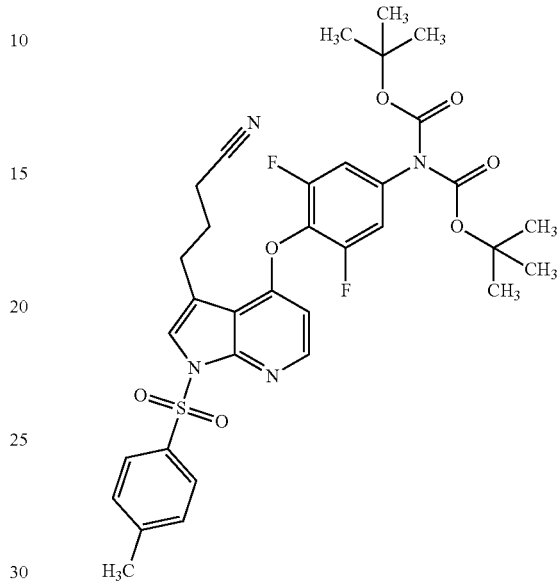

Di-tert-butyl (4-{[3-bromo-1-(4-methylbenzene-1-sulfonyl)-1H-pyrrolo[2,3-b]pyridin-4-yl]oxy}-3,5-difluorophenyl)-2-imidodicarbonate (2.70 g, 3.89 mmol, Intermediate 282) and Ir(4',6'-dF-5-CF₃-ppy)₂(4,4'-dtbbpy)PF₆ (87.2 mg, 77.7 μmol, CAS No. [870987-63-6]) were dissolved in 1,2-dimethoxyethane (60 mL) in a cylindrical reaction vessel. In a separate vial, the Ni-catalyst was prepared by dissolving Nickel (II) chloride dimethoxyethane adduct (4.27 mg, 19.4 μmol, CAS No. [29046-78-4]) and 4,4'-di-tert-butyl-2,2'-bipyridine (5.22 mg, 19.4 μmol, CAS No. [72914-19-3]) in 1,2-dimethoxyethane (20 mL) followed by stirring for 5 min. The catalyst solution was syringed to the reaction vessel followed by sparging with argon for 20 min. 4-bromobutanenitrile (3.9 mL, 39 mmol, CAS No. [5332-06-9]), tris(trimethylsilyl)silane (1.2 mL, 3.9 mmol, CAS No. [1873-77-4]) and 2,6-lutidine (4.5 mL, 39 mmol, CAS No. [108-48-5]) were added followed by irradiation using two Kessil LED Aquarium lights (40 W each, 4 cm distance). A cooling finger was used to keep the temperature below 30° C. After 16 hours, the reaction was quenched by addition of water and ethyl acetate and the layers were separated. The aqueous phase was extracted twice with ethyl acetate and the combined organic layers were passed through a hydrophobic filter. The solvent was evaporated to give the crude product which was purified by flash column chromatography using a Biotage chromatography system to give the title compound (2.22 g, 82% yield).

LC-MS (Method 2): $R_t$=1.59 min; MS (ESIpos): m/z=683 [M+H]⁺

¹H NMR (400 MHz, DMSO-d₆) δ ppm 1.41 (s, 18H), 1.93-2.04 (m, 2H), 2.35 (s, 3H), 2.56 (t, J=6.97 Hz, 2H), 2.92 (t, J=7.60 Hz, 2H), 6.36 (d, J=5.58 Hz, 1H), 7.42 (d, J=8.11 Hz, 2H), 7.47-7.54 (m, 2H), 7.75 (s, 1H), 7.99 (d, J=8.60 Hz, 2H), 8.23 (d, J=5.58 Hz, 1H).

Intermediate 364

4-[4-(4-amino-2,6-difluorophenoxy)-1-(4-methylbenzene-1-sulfonyl)-1H-pyrrolo[2,3-b]pyridin-3-yl]butanenitrile-hydrogen chloride (1/1)

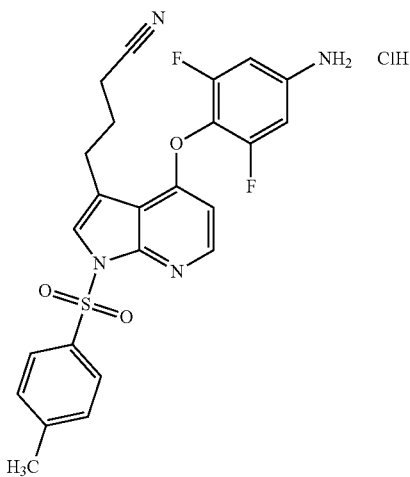

Di-tert-butyl (4-{[3-(3-cyanopropyl)-1-(4-methylbenzene-1-sulfonyl)-1H-pyrrolo[2,3-b]pyridin-4-yl]oxy}-3,5-difluorophenyl)-2-imidodicarbonate (1.10 g, 1.61 mmol, intermediate 363) was dissolved in a solution of hydrochloric acid in dioxane (25 mL, 4.0 M, 100 mmol) and stirred at room temperature for 4 hours. The solvent was subsequently evaporated to give the crude material, which was used without further purification.

LC-MS (Method 2): $R_t$=1.26 min; MS (ESIneg): m/z=481 [M−H]⁻

Intermediate 365 phenyl (4-{[3-(3-cyanopropyl)-1-(4-methylbenzene-1-sulfonyl)-1H-pyrrolo[2,3-b]pyridin-4-yl]oxy}-3,5-difluorophenyl)carbamate

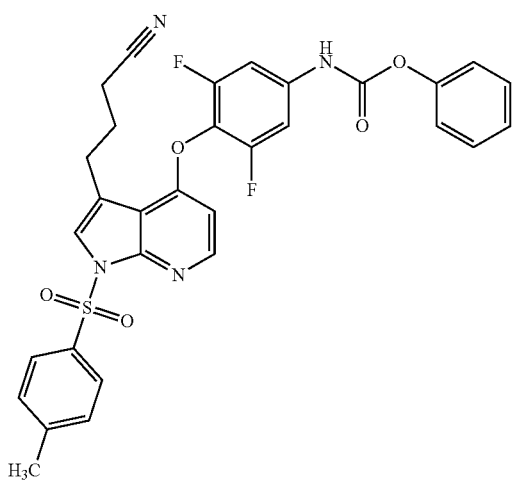

To a stirred solution of 4-[4-(4-amino-2,6-difluorophenoxy)-1-(4-methylbenzene-1-sulfonyl)-1H-pyrrolo[2,3-b]pyridin-3-yl]butanenitrile-hydrogen chloride (1/1) (836 mg, 1.61 mmol, intermediate 364) in THF (15 mL) was added pyridine (2.0 mL, 25 mmol). The reaction mixture was cooled to 0° C. and phenyl carbonochloridate (310 μL, 2.5 mmol, CAS No. [1885-14-9]) was added. The resulting mixture was stirred for 1 hour at 0° C., at which time additional phenyl carbonochloridate (150 μL, 1.2 mmol, CAS No. [1885-14-9]) was added. After an additional hour the reaction was quenched by the addition of ethyl acetate and a 0.5M aqueous solution of hydrochlorid acid. The layers were separated and the aqueous phase was extracted twice with ethyl acetate. The combined organic phases were washed with a saturated solution of sodium bicarbonate and were passed through a hydrophobic filter. Evaporation of the solvent afforded the crude material, which was used without further purification.

LC-MS (Method 1): $R_t$=1.40 min; MS (ESIpos): m/z=603 [M+H]⁺

Intermediate 366

N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea

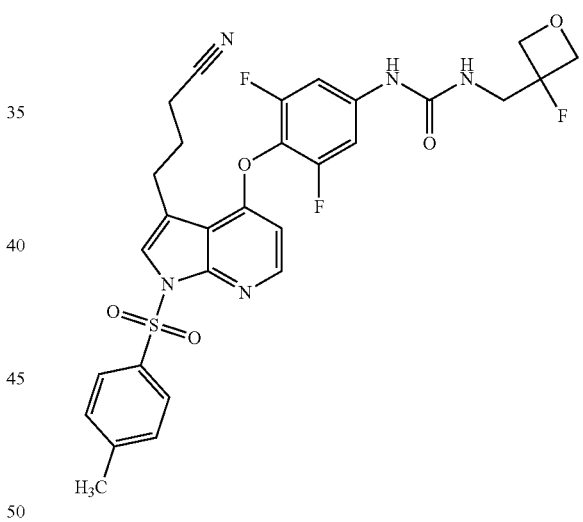

To a stirred solution of phenyl (4-{[3-(3-cyanopropyl)-1-(4-methylbenzene-1-sulfonyl)-1H-pyrrolo[2,3-b]pyridin-4-yl]oxy}-3,5-difluorophenyl)carbamate (533 mg, 60% purity, 531 μmol, Intermediate 365) in DMF (3 mL) was added 1-(3-fluorooxetan-3-yl)methanamine (120 μL, 1.3 mmol, CAS No. [883311-82-8]) and the resulting mixture was stirred at 60° C. for 3 hours. After cooling to room temperature ethyl acetate and water was added. After separation of the organic phase the aqueous phase was extracted two times with ethyl acetate and the combined organic phases were passed through a hydrophobic filter. Evaporation of the solvent afforded the crude material, which was used without further purification.

LC-MS (Method 2): $R_t$=1.22 min; MS (ESIpos): m/z=614 [M+H]⁺

Intermediate 367

N-(4-{[3-(3-cyanopropyl)-1H-pyrrolo[2,3-b]pyridin-4-yl]oxy}-3,5-difluorophenyl)-N'-[(3-fluorooxetan-3-yl)methyl]urea

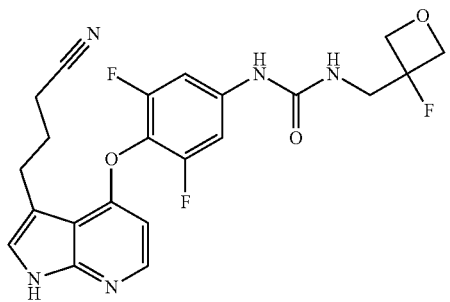 [SMILES: N#CCCCc1c[nH]c2nccc(Oc3c(F)cc(NC(=O)NCC4(F)COC4)cc3F)c12]

To a stirred solution of N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-[(3-fluorooxetan-3-yl)methyl]urea (651 mg, Intermediate 366) in methanol (7 mL) was added sodium hydroxide (42.4 mg, 1.06 mmol) in a single portion. The resulting mixture was stirred at room temperature for 16 hours, at which time water and ethyl acetate were added and the layers were separated. The aqueous phase was extracted twice with ethyl acetate and the combined organic phases were passed through a hydrophobic filter. Evaporation of the solvent afforded the crude material, which was used without further purification.

LC-MS (Method 2): $R_t$=0.93 min; MS (ESIpos): m/z=460 [M+H]$^+$

Intermediate 368

N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-{[3-(propan-2-yl)oxetan-3-yl]methyl}urea

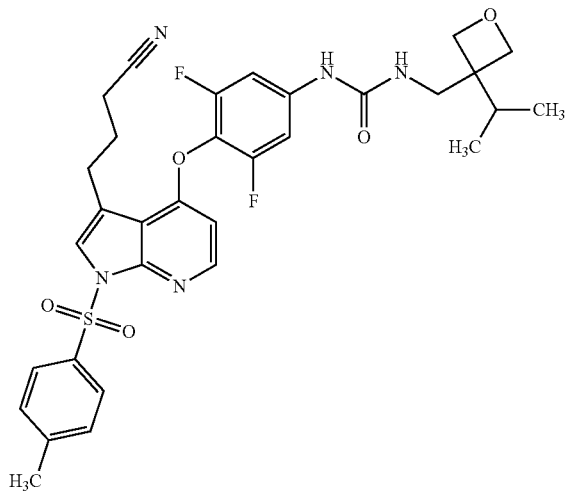

In analogy to Intermediate 366, phenyl (4-{[3-(3-cyanopropyl)-1-(4-methylbenzene-1-sulfonyl)-1H-pyrrolo[2,3-b]pyridin-4-yl]oxy}-3,5-difluorophenyl)carbamate (533 mg, 60% purity, 531 µmol, Intermediate 365) and 1-[3-(propan-2-yl)oxetan-3-yl]methanamine (171 mg, 1.33 mmol, CAS No. [1539197-30-2]) in DMF (3 mL) were reacted to obtain the crude product which was used in the next step without further purification.

LC-MS (Method 2): $R_t$=1.32 min; MS (ESIpos): m/z=638 [M+H]$^+$

Intermediate 369

N-(4-{[3-(3-cyanopropyl)-1H-pyrrolo[2,3-b]pyridin-4-yl]oxy}-3,5-difluorophenyl)-N'-{[3-(propan-2-yl)oxetan-3-yl]methyl}urea

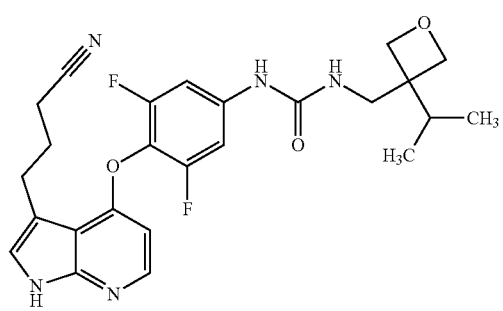 [SMILES: CC(C)C1(CNC(=O)Nc2cc(F)c(Oc3ccnc4[nH]cc(CCCC#N)c34)c(F)c2)COC1]

In analogy to Intermediate 367, N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-{[3-(propan-2-yl)oxetan-3-yl]methyl}urea (367 mg, Intermediate 368) and sodium hydroxide (46.0 mg, 1.15 mmol) in methanol (9 mL) were reacted to obtain the crude product which was used in the next step without further purification.

LC-MS (Method 2): $R_t$=1.05 min; MS (ESIpos): m/z=484 [M+H]$^+$

Intermediate 370

N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-[(3-methyloxetan-3-yl)methyl]urea

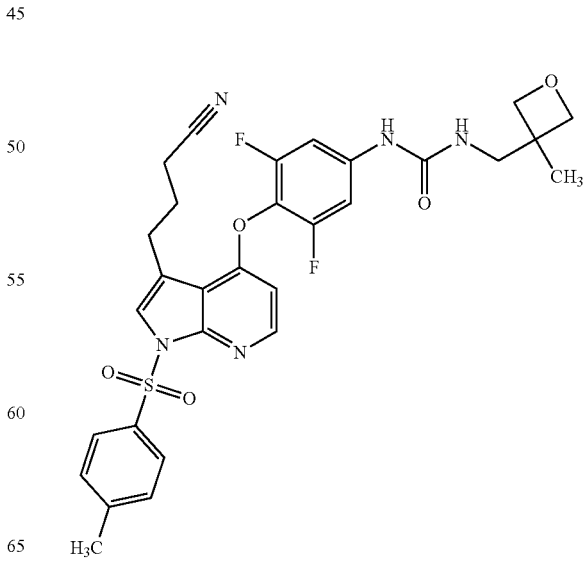

363

In analogy to Intermediate 366, phenyl (4-{[3-(3-cyanopropyl)-1-(4-methylbenzene-1-sulfonyl)-1H-pyrrolo[2,3-b]pyridin-4-yl]oxy}-3,5-difluorophenyl)carbamate (533 mg, 60% purity, 531 µmol, Intermediate 365) and 1-(3-methyloxetan-3-yl)methanamine (140 µL, 1.3 mmol, CAS No. [153209-97-3]) in DMF (3 mL) were reacted to obtain the crude product which was used in the next step without further purification.

LC-MS (Method 2): $R_t$=1.23 min; MS (ESIpos): m/z=610 [M+H]$^+$

Intermediate 371

N-(4-{[3-(3-cyanopropyl)-1H-pyrrolo[2,3-b]pyridin-4-yl]oxy}-3,5-difluorophenyl)-N'-[(3-methyloxetan-3-yl)methyl]urea

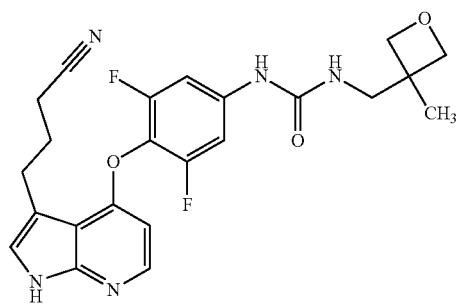 [SMILES: CC1(CNC(=O)Nc2cc(F)c(Oc3ccnc4[nH]cc(CCCC#N)c34)c(F)c2)COC1]

In analogy to Intermediate 367, N-(4-{[3-(3-cyanopropyl)-1-(4-methylbenzene-1-sulfonyl)-1H-pyrrolo[2,3-b]pyridin-4-yl]oxy}-3,5-difluorophenyl)-N'-[(3-methyloxetan-3-yl)methyl]urea (320 mg, Intermediate 370) and sodium hydroxide (42.0 mg, 1.05 mmol) in methanol (9 mL) were reacted to obtain the crude product which was used in the next step without further purification.

LC-MS (Method 2): $R_t$=0.94 min; MS (ESIpos): m/z=456 [M+H]$^+$

364

Intermediate 372

(+/−)-di-tert-butyl [3,5-difluoro-4-({1-(4-methylbenzene-1-sulfonyl)-3-(2-methyloxan-3-yl)-1H-pyrrolo[2,3-b]pyridin-4-yl}oxy)phenyl]-2-imidodicarbonate (Mixture of Isomers)

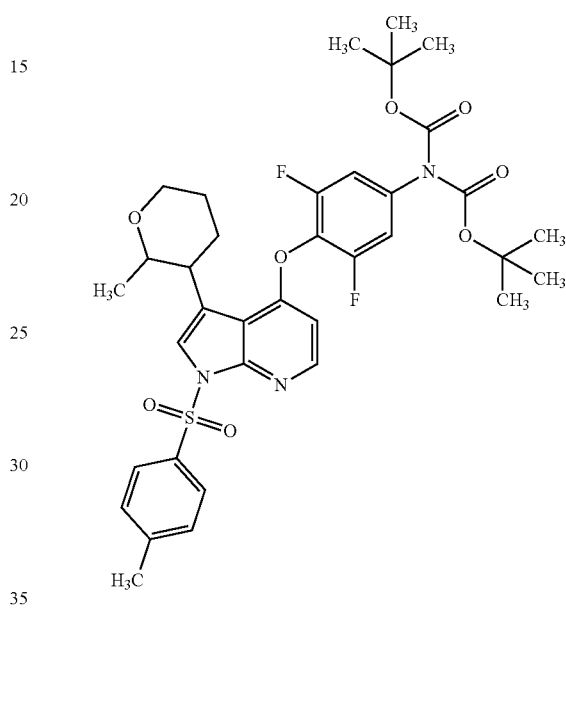

Di-tert-butyl (4-{[3-bromo-1-(4-methylbenzene-1-sulfonyl)-1H-pyrrolo[2,3-b]pyridin-4-yl]oxy}-3,5-difluorophenyl)-2-imidodicarbonate (4.00 g, 5.76 mmol, Intermediate 282), Ir(4',6'-dF-5-CF$_3$-ppy)$_2$(4,4'-dtbbpy)PF$_6$ (129 mg, 115 µmol, CAS No. [870987-63-6]) and lithium carbonate (2.55 g, 34.6 mmol) were dissolved in α,α,α-trifluorotoluene (120 mL) in a cylindrical reaction vessel. In a separate vial, the Ni-catalyst was prepared by dissolving Nickel (II) chloride dimethoxyethane adduct (63.3 mg, 288 µmol, CAS No. [29046-78-4]) and 4,4'-di-tert-butyl-2,2'-bipyridine (77.3 mg, 288 µmol, CAS No. [72914-19-3]) in N,N-dimethylacetamide (30 mL) followed by stirring for 5 min. The catalyst catalyst solution was syringed to the reaction vessel followed by sparging with argon for 20 min. (+/−)-3-bromo-2-methyloxane (3.4 mL, 26 mmol, CAS No. [156051-16-0], mixture of cis- and trans-isomer) and tris(trimethylsilyl)silane (1.8 mL, 5.8 mmol, CAS No. [1873-77-4]) were added followed by irradiation using two Kessil LED Aquarium lights (40 W each, 4 cm distance). A cooling finger was used to keep the temperature below 30° C. After 16 hours, the reaction was quenched by addition of water and ethyl acetate and the layers were separated. The aqueous phase was extracted twice with ethyl acetate and the combined organic layers were passed through a hydrophobic filter. The solvent was evaporated to give the crude product which was purified by flash column chromatography using a Biotage chromatography system to give a mixture of the title compound (mixture of cis- and trans-isomer) and tert-butyl N-tert-butoxycarbonyl-N-[3,5-difluoro-4-[1-(p-tolylsulfonyl) pyrrolo[2,3-b]pyridin-4-yl]oxy-phenyl] carbamate (3.20 g, 1:3 mixture).

LC-MS-title compound (Method 2): $R_t$=1.66 min; MS (ESIpos): m/z=714 [M+H]$^+$

LC-MS-debrominated product (Method 2): $R_t$=1.62 min; MS (ESIpos): m/z=616 [M+H]$^+$ Intermediate 373

(+/−)-3,5-difluoro-4-({1-(4-methylbenzene-1-sulfonyl)-3-(2-methyloxan-3-yl)-1H-pyrrolo[2,3-b]pyridin-4-yl}oxy)aniline-hydrogen chloride (1/1)-(Mixture of Isomers)

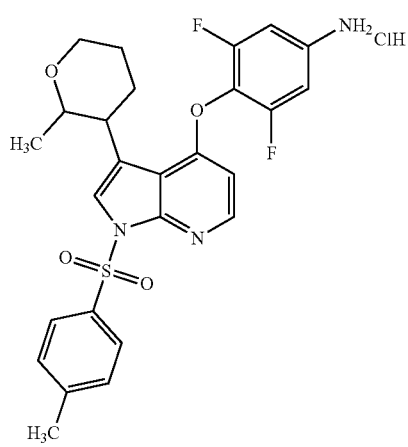

In analogy to intermediate 364, (+/−)-di-tert-butyl [3,5-difluoro-4-({1-(4-methylbenzene-1-sulfonyl)-3-[2-methyloxan-3-yl]-1H-pyrrolo[2,3-b]pyridin-4-yl}oxy)phenyl]-2-imidodicarbonate (2.40 g, Intermediate 372, mixture of cis- and trans-isomer) accompanied with debrominated azaindole (1:3 mixture) was reacted in a solution of hydrochloric acid in dioxane (12 mL, 4.0 M, 48 mmol) for 3 hours to obtain the crude title compound (cis- and trans-isomer) in a mixture with the debrominated azaindole which were used in the next step without further purification.

LC-MS-title compound (Method 2): $R_t$=1.34 min; MS (ESIpos): m/z=514 [M+H]$^+$

LC-MS-debrominated azaindole (Method 2): $R_t$=1.27 min; MS (ESIpos): m/z=416 [M+H]$^+$ Intermediate 374

(+/−)-phenyl [3,5-difluoro-4-({1-(4-methylbenzene-1-sulfonyl)-3-(2-methyloxan-3-yl)-1H-pyrrolo[2,3-b]pyridin-4-yl}oxy)phenyl]carbamate-(Mixture of Isomers)

To a stirred solution of (+/−)-3,5-difluoro-4-({1-(4-methylbenzene-1-sulfonyl)-3-(2-methyloxan-3-yl)-1H-pyrrolo[2,3-b]pyridin-4-yl}oxy)aniline-hydrogen chloride (1/1) (2.20 g, Intermediate 373, mixture of cis- and trans-isomer) accompanied with debrominated azaindole (1:3 mixture) in THF (40 mL) was added pyridine (5.0 mL, 62 mmol). The reaction mixture was cooled to 0° C. and phenyl carbonochloridate (780 μL, 6.2 mmol, CAS No. [1885-14-9]) was added. The resulting mixture was stirred for 3 hours at 0° C., at which time the reaction was quenched by the addition of ethyl acetate and a 0.5M aqueous solution of hydrochlorid acid. The layers were separated and the aqueous phase was extracted twice with ethyl acetate. The combined organic phases were washed with a saturated solution of sodium bicarbonate and passed through a hydrophobic filter. Evaporation of the solvent afforded the crude title compound (mixture of cis- and trans-isomer) accompanied with the debrominated azaindole which were used in the next step without further purification.

LC-MS-title compound (Method 1): $R_t$=1.49 min; MS (ESIpos): m/z=634 [M+H]$^+$

LC-MS-debrominated azaindole (Method 1): $R_t$=1.45 min; MS (ESIpos): m/z=536 [M+H]$^+$

Intermediate 375

(+/−)—N-[3,5-difluoro-4-({1-(4-methylbenzene-1-sulfonyl)-3-(2-methyloxan-3-yl)-1H-pyrrolo[2,3-b]pyridin-4-yl}oxy)phenyl]-N'-[(3-fluorooxetan-3-yl)methyl]urea-(Mixture of Isomers)

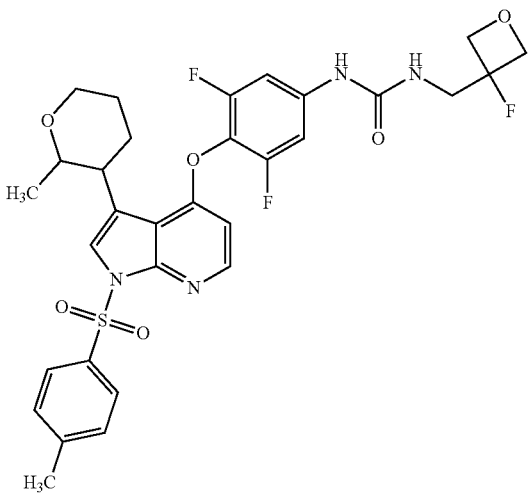

In analogy to Intermediate 366, (+/−)-phenyl [3,5-difluoro-4-({1-(4-methylbenzene-1-sulfonyl)-3-(2-methyloxan-3-yl)-1H-pyrrolo[2,3-b]pyridin-4-yl}oxy)phenyl]carbamate (1.11 g, Intermediate 374, mixture of cis- and trans-isomer accompanied with debrominated azaindole (1:3 mixture) and 1-(3-fluorooxetan-3-yl)methanamine (400 µL, 4.4 mmol, CAS No. [883311-82-8]) in DMF (10 mL) were reacted to obtain the crude title compound (mixture of cis- and trans-isomer) accompanied with the debrominated azaindole which were used in the next step without further purification.

LC-MS-title compound (Method 2): $R_t$=1.32 min; MS (ESIneg): m/z=643 [M−H]⁻

LC-MS-debrominated azaindole (Method 2): $R_t$=1.26 min; MS (ESIneg): m/z=545 [M−H]⁻

Intermediate 376

(+/−)—N-[3,5-difluoro-4-({3-(2-methyloxan-3-yl)-1H-pyrrolo[2,3-b]pyridin-4-yl}oxy)phenyl]-N'-[(3-fluorooxetan-3-yl)methyl]urea-(Mixture of Isomers)

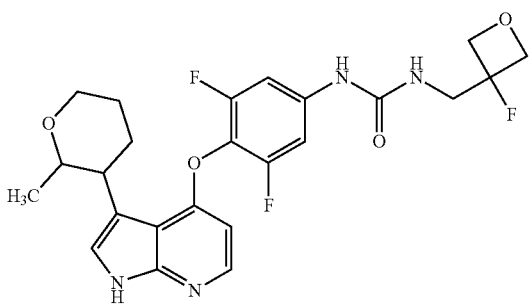 [SMILES: CC1OCCCC1c1c[nH]c2nccc(Oc3c(F)cc(NC(=O)NCC4(F)COC4)cc3F)c12]

In analogy to Intermediate 367, (+/−)—N-[3,5-difluoro-4-({1-(4-methylbenzene-1-sulfonyl)-3-(2-methyloxan-3-yl)-1H-pyrrolo[2,3-b]pyridin-4-yl}oxy)phenyl]-N'-[(3-fluorooxetan-3-yl)methyl]urea (1.10 g, Intermediate 375, mixture of cis- and trans-isomer) accompanied with debrominated azaindole (1:3 mixture) and sodium hydroxide (272 mg, 6.82 mmol) in methanol (29 mL) were reacted for 21 hours to obtain the crude title compound (mixture of cis- and trans-isomer) accompanied with the debrominated azaindole which were used in the next step without further purification.

LC-MS-title compound (Method 2): $R_t$=1.00 min; MS (ESIpos): m/z=491 [M+H]⁺

LC-MS-debrominated azaindole (Method 2): $R_t$=0.93 min; MS (ESIpos): m/z=393 [M+H]⁺

Intermediate 377

(+/−)—N-[3,5-difluoro-4-({1-(4-methylbenzene-1-sulfonyl)-3-(2-methyloxan-3-yl)-1H-pyrrolo[2,3-b]pyridin-4-yl}oxy)phenyl]-N'-{[3-(propan-2-yl)oxetan-3-yl]methyl}urea-(Mixture of Isomers)

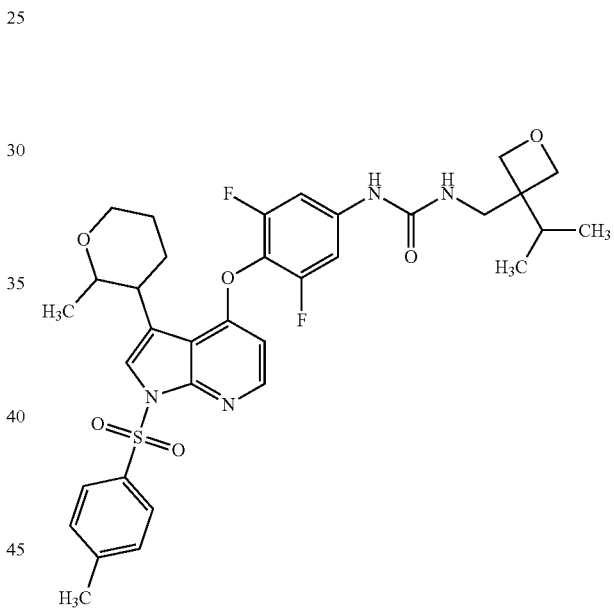

In analogy to Intermediate 366, (+/−)-phenyl [3,5-difluoro-4-({1-(4-methylbenzene-1-sulfonyl)-3-(2-methyloxan-3-yl)-1H-pyrrolo[2,3-b]pyridin-4-yl}oxy)phenyl]carbamate (1.11 g, Intermediate 374, mixture of cis- and trans-isomer) accompanied with debrominated azaindole (1:3 mixture) and 1-[3-(propan-2-yl)oxetan-3-yl]methanamine (566 mg, 4.38 mmol, CAS No. [1539197-30-2]) in DMF (10 mL) were reacted to obtain the crude title compound (mixture of cis- and trans-isomer) accompanied with the debrominated azaindole which were used in the next step without further purification.

LC-MS-title compound (Method 2): $R_t$=1.42 min; MS (ESIneg): m/z=667 [M−H]⁻

LC-MS-debrominated azaindole (Method 2): $R_t$=1.37 min; MS (ESIneg): m/z=569 [M−H]⁻

Intermediate 378

(+/−)—N-[3,5-difluoro-4-({3-(2-methyloxan-3-yl)-1H-pyrrolo[2,3-b]pyridin-4-yl}oxy)phenyl]-N'-{[3-(propan-2-yl)oxetan-3-yl]methyl}urea-(Mixture of Isomers)

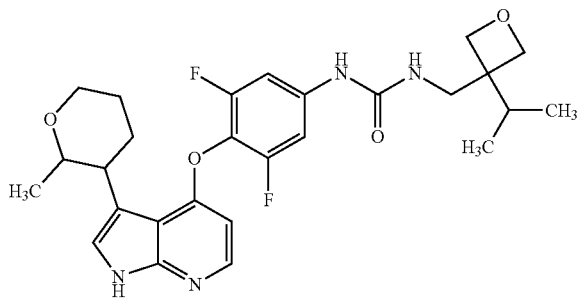 [SMILES: CC1OCCCC1c1c[nH]c2nccc(Oc3c(F)cc(NC(=O)NCC4(C(C)C)COC4)cc3F)c12]

In analogy to Intermediate 367, (+/−)—N-[3,5-difluoro-4-({1-(4-methylbenzene-1-sulfonyl)-3-[2-methyloxan-3-yl]-1H-pyrrolo[2,3-b]pyridin-4-yl}oxy)phenyl]-N'-{[3-(propan-2-yl)oxetan-3-yl]methyl}urea (1.50 g, Intermediate 377, mixture of cis- and trans-isomer) accompanied with debrominated azaindole (1:3 mixture) and sodium hydroxide (360 mg, 8.98 mmol) in methanol (38 mL) were reacted for 21 hours to obtain the crude title compound (mixture of cis- and trans-isomer) accompanied with the debrominated azaindole which were used in the next step without further purification.

LC-MS-title compound (Method 2): $R_t$=1.13 min; MS (ESIpos): m/z=515 [M+H]$^+$

LC-MS-debrominated azaindole (Method 2): $R_t$=1.06 min; MS (ESIpos): m/z=417 [M+H]$^+$.

Intermediate 379

4-(2,6-difluoro-4-nitrophenoxy)-3-(2-methoxyphenyl)-1-{[2-(trimethylsilyl)ethoxy]methyl}-1H-pyrrolo[2,3-b]pyridine

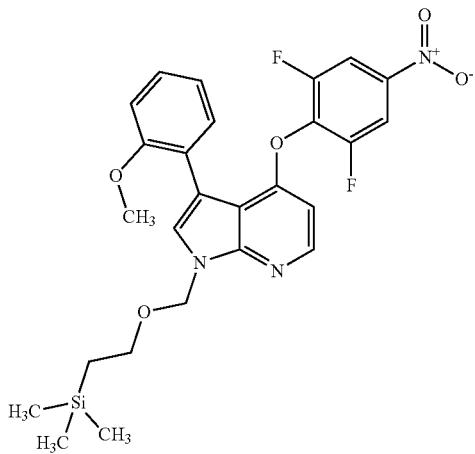

3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, Intermediate 16), (2-methoxyphenyl)boronic acid (CAS No: 5720-06-9, 607 mg, 4.00 mmol), [1,1'-Bis(diphenylphosphino)ferrocene]dichloropalladium(II) (146 mg, 200 μmol), and potassium carbonate (1.38 g, 9.99 mmol) were dissolved in a degassed 2:1 mixture of dioxane and water (5.6 mL and 2.8 mL, respectively) and stirred at 95° C. under argon until no more starting material could be detected by UPLC-MS. The reaction was quenched with a saturated sodium bicarbonate solution, and extracted with ethyl acetate (×4). The organic phase was washed with water and brine, dried over sodium sulfate, filtered and evaporated. The crude was filtered by silica gel chromatography using a Biotage system to yield the title compound (920 mg, 75% purity, 65% yield), which was used in the following reaction with no further purification.

LC-MS (Method 2): $R_t$=1.65 min; MS (ESIpos): m/z=528 [M+H]$^+$.

Intermediate 380

3,5-difluoro-4-{[3-(2-methoxyphenyl)-1-{[2-(trimethylsilyl)ethoxy]methyl}-1H-pyrrolo[2,3-b]pyridin-4-yl]oxy}aniline

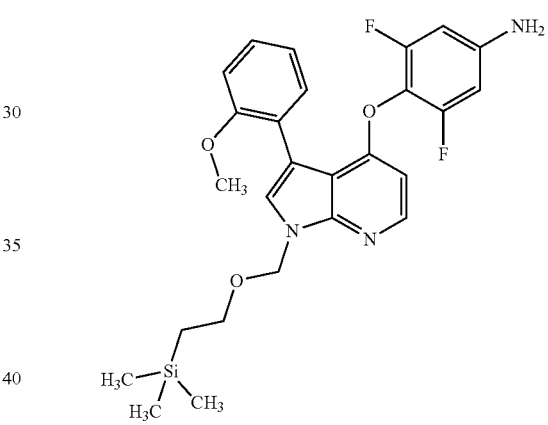

Ammonium chloride (350 mg, 6.54 mmol) and iron (365 mg, 6.54 mmol) were suspended in water (6.4 mL). 4-(2,6-difluoro-4-nitrophenoxy)-3-(2-methoxyphenyl)-1-{[2-(trimethylsilyl)ethoxy]methyl}-1H-pyrrolo[2,3-b]pyridine (920 mg, 75% purity, 1.31 mmol, intermediate 379) was dissolved in a 1:1 mixture of THF/methanol (3.2 mL, respectively) and added to the suspension, which was stirred overnight at 60° C. in a closed microwave vial. The reaction was filtered, diluted with water, and extracted with ethyl acetate (×4). The organic phase was washed with water and brine, dried over sodium sulfate, filtered and evaporated. The crude was filtered by silica gel chromatography using a Biotage system to yield the title compound (651 mg, 90% yield), which was used in the following reaction with no further purification.

LC-MS (Method 2): $R_t$=1.52 min; MS (ESIneg): m/z=496 [M−H]$^−$ $^1$H-NMR (400 MHz, DMSO-d6) δ [ppm]: −0.067 (16.00), 0.833 (0.46), 0.852 (0.53), 0.872 (0.46), 2.518 (1.30), 2.523 (1.02), 3.576 (0.45), 3.596 (0.55), 3.616 (0.45), 3.718 (2.56), 5.648 (1.22), 5.743 (0.73), 5.759 (0.55), 6.284 (0.35), 6.297 (0.35), 6.319 (0.58), 6.346 (0.60), 6.915 (0.16), 6.918 (0.18), 6.934 (0.36), 6.936 (0.39), 6.952 (0.21), 6.955 (0.21), 7.019 (0.30), 7.038 (0.37), 7.039 (0.35), 7.240 (0.19), 7.244 (0.20), 7.258 (0.22), 7.260 (0.23), 7.263 (0.24), 7.264 (0.23), 7.374 (0.34), 7.379 (0.34), 7.393 (0.33), 7.397 (0.31), 7.580 (1.19), 8.102 (0.66), 8.116 (0.64).

Intermediate 381

N-(3,5-difluoro-4-{[3-(2-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

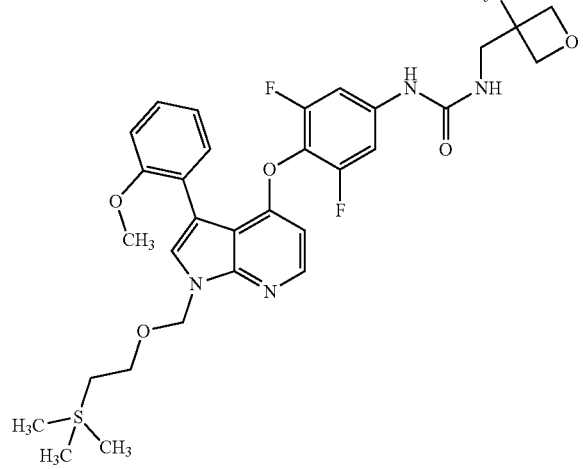

3,5-difluoro-4-{[3-(2-methoxyphenyl)-1-{[2-(trimethylsilyl)ethoxy]methyl}-1H-pyrrolo[2,3-b]pyridin-4-yl]oxy}aniline (325 mg, 90% purity, 588 μmol, intermediate 380) and 3-(isocyanatomethyl)-3-methyloxetane (CAS No: 1260665-88-0, 149 mg, 1.18 mmol) were dissolved in dichloromethane (5.1 mL). Pyridine (5.2 mL) was added to the solution and the mixture was stirred overnight at 60° C. The solvent was removed under vacuum and the residue filtered through silica and used in the following reaction with no further purification.

LC-MS (Method 2): $R_t$=1.51 min; MS (ESIpos): m/z=625 [M+H]$^+$.

Intermediate 382

4-(2,6-difluoro-4-nitrophenoxy)-3-(3-methoxyphenyl)-1-{[2-(trimethylsilyl)ethoxy]methyl}-1H-pyrrolo[2,3-b]pyridine

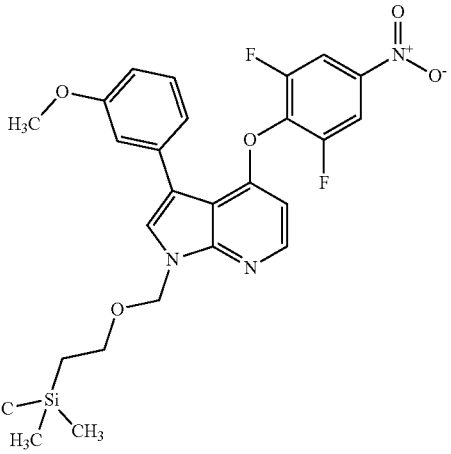

In analogy to intermediate 379, 3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, Intermediate 16), (3-methoxyphenyl)boronic acid (CAS No: 10365-98-7, 607 mg, 4.00 mmol), [1,1'-Bis(diphenylphosphino)ferrocene]dichloropalladium(II) (146 mg, 200 μmol), and potassium carbonate (1.38 g, 9.99 mmol) were reacted in a mixture of dioxane and water (15 mL and 7.5 mL, respectively) to afford the title compound (860 mg, 65% yield).

LC-MS (Method 2): $R_t$=1.66 min; MS (ESIpos): m/z=528 [M+H]$^+$.

Intermediate 383

3,5-difluoro-4-{[3-(3-methoxyphenyl)-1-{[2-(trimethylsilyl)ethoxy]methyl}-1H-pyrrolo[2,3-b]pyridin-4-yl]oxy}aniline

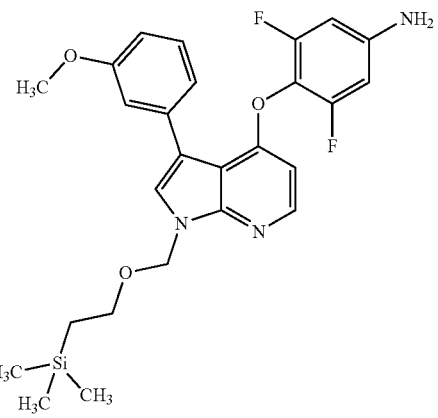

In analogy to intermediate 380, a solution of 4-(2,6-difluoro-4-nitrophenoxy)-3-(3-methoxyphenyl)-1-{[2-(trimethylsilyl)ethoxy]methyl}-1H-pyrrolo[2,3-b]pyridine (860 mg, 80% purity, 1.30 mmol, intermediate 382) in THF/methanol (3.2 mL/3.2 mL) was reacted with a suspension of iron (364 mg, 6.52 mmol) and ammonium chloride (349 mg, 6.52 mmol) in water (6.4 mL) to yield the title compound (590 mg, 86% yield).

LC-MS (Method 2): $R_t$=1.52 min; MS (ESIpos): m/z=498 [M+H]$^+$ $^1$H-NMR (400 MHz, DMSO-d6) δ [ppm]: −0.102 (0.90), −0.089 (0.47), −0.081 (12.86), −0.072 (0.56), 0.827 (0.42), 0.847 (0.51), 0.867 (0.43), 2.082 (16.00), 3.339 (2.21), 3.565 (0.41), 3.585 (0.52), 3.605 (0.41), 5.666 (1.07), 5.811 (0.66), 6.380 (0.52), 6.391 (0.40), 6.406 (0.79), 6.814 (0.18), 6.820 (0.18), 6.834 (0.20), 6.838 (0.19), 6.840 (0.18), 7.228 (0.16), 7.247 (0.40), 7.250 (0.26), 7.270 (0.71), 7.276 (0.38), 7.280 (0.29), 7.290 (0.45), 7.309 (0.18), 7.823 (1.01), 8.158 (0.60), 8.171 (0.56).

Intermediate 384

N-(3,5-difluoro-4-{[3-(3-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

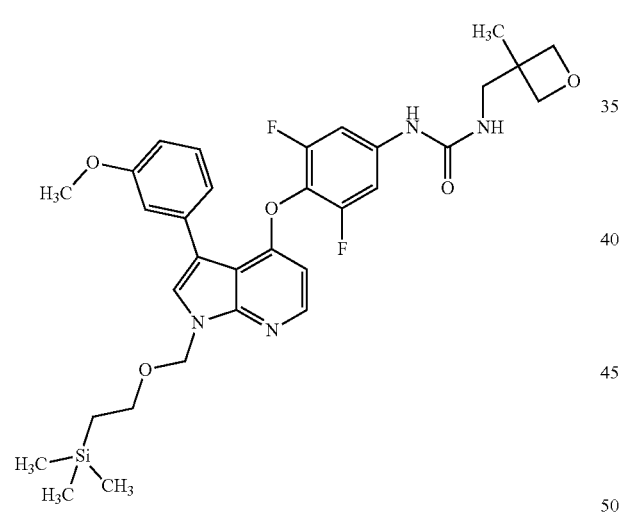

In analogy to intermediate 381, 3,5-difluoro-4-{[3-(3-methoxyphenyl)-1-{[2-(trimethylsilyl)ethoxy]methyl}-1H-pyrrolo[2,3-b]pyridin-4-yl]oxy}aniline (290 mg, 554 μmol, intermediate 383) and 3-(isocyanatomethyl)-3-methyloxetane (CAS No: 1260665-88-0, 141 mg, 1.11 mmol) in dichloromethane (4.8 mL) were allowed to react in the presence of pyridine (4.9 mL) to yield the title compound (235 mg, 61% yield).

LC-MS (Method 2): $R_t$=1.52 min; MS (ESIpos): m/z=517 [M+H]$^+$.

Intermediate 385

4-(2,6-difluoro-4-nitrophenoxy)-3-(4-methoxyphenyl)-1-{[2-(trimethylsilyl)ethoxy]methyl}-1H-pyrrolo[2,3-b]pyridine

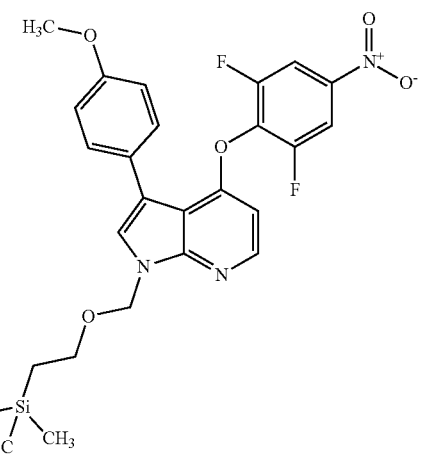

In analogy to intermediate 379, 3-bromo-4-(2,6-difluoro-4-nitrophenoxy)-1-{[2-(trimethylsilyl)ethoxy]methyl}-1H-pyrrolo[2,3-b]pyridine (1.00 g, 2.00 mmol, Intermediate 16), (4-methoxyphenyl)boronic acid (CAS No: 5720-07-0, 607 mg, 4.00 mmol), [1,1'-Bis(diphenylphosphino)ferrocene]dichloropalladium(II) (146 mg, 200 μmol), and potassium carbonate (1.38 g, 9.99 mmol) were reacted in a mixture of dioxane and water (15 mL and 7.5 mL, respectively) to afford the title compound (800 mg, 64% yield).

LC-MS (Method 2): $R_t$=1.65 min; MS (ESIpos): m/z=528 [M+H]$^+$ $^1$H-NMR (400 MHz, DMSO-d6) δ [ppm]: −0.086 (16.00), 0.826 (0.43), 0.845 (0.54), 0.865 (0.45), 3.570 (0.45), 3.589 (0.54), 3.610 (0.43), 3.751 (4.12), 5.683 (1.15), 6.603 (0.34), 6.617 (0.33), 6.944 (0.82), 6.966 (0.89), 7.531 (0.88), 7.553 (0.80), 7.778 (1.13), 8.189 (0.70), 8.203 (0.65), 8.378 (0.63), 8.397 (0.67).

Intermediate 386

3,5-difluoro-4-{[3-(4-methoxyphenyl)-1-{[2-(trimethylsilyl)ethoxy]methyl}-1H-pyrrolo[2,3-b]pyridin-4-yl]oxy}aniline

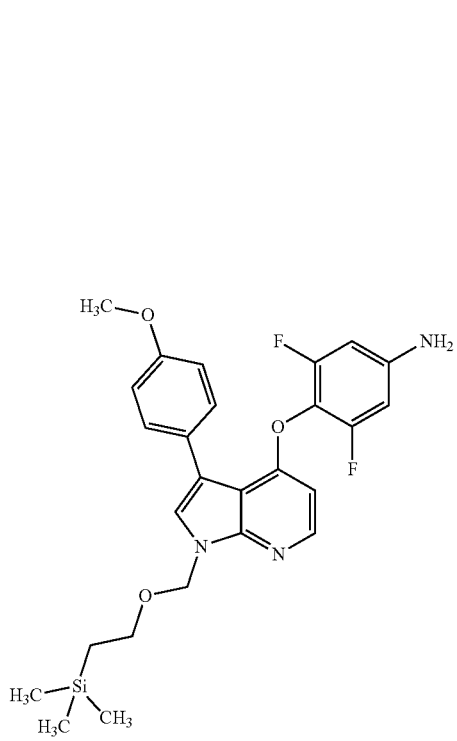 [SMILES: COc1ccc(-c2cn(COCC[Si](C)(C)C)c3nccc(Oc4c(F)cc(N)cc4F)c23)cc1]

In analogy to intermediate 380, a solution of 4-(2,6-difluoro-4-nitrophenoxy)-3-(4-methoxyphenyl)-1-{[2-(trimethylsilyl)ethoxy]methyl}-1H-pyrrolo[2,3-b]pyridine (800 mg, 1.29 mmol, intermediate 385) in THF/methanol (3.2 mL/3.2 mL) was reacted with a suspension of iron (360 mg, 6.44 mmol) and ammonium chloride (345 mg, 6.44 mmol) in water (6.4 mL) to yield the title compound (540 mg, 80% yield).

LC-MS (Method 2): $R_t$=1.51 min; MS (ESIneg): m/z=496 [M−H]⁻

¹H-NMR (400 MHz, DMSO-d6) δ [ppm]: −0.083 (14.08), 0.823 (0.43), 0.843 (0.53), 0.863 (0.44), 2.082 (16.00), 3.557 (0.42), 3.577 (0.54), 3.597 (0.42), 3.762 (3.94), 5.652 (1.10), 5.800 (0.76), 6.376 (0.90), 6.402 (0.65), 6.945 (0.77), 6.967 (0.84), 7.569 (0.85), 7.591 (0.78), 7.685 (1.07), 8.138 (0.64).

Intermediate 387

N-(3,5-difluoro-4-{[3-(4-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea

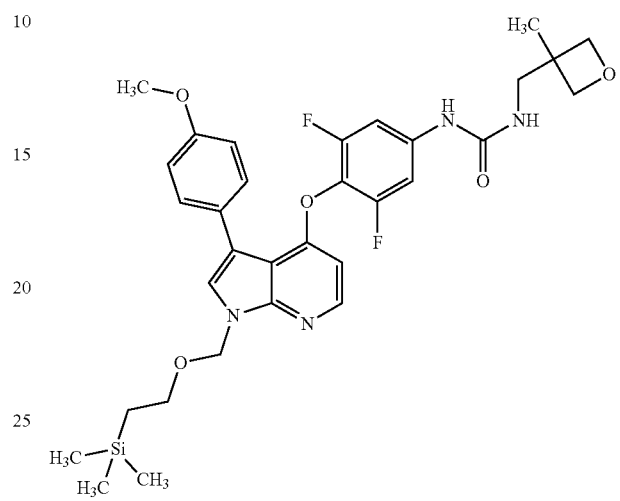

In analogy to intermediate 381, 3,5-difluoro-4-{[3-(4-methoxyphenyl)-1-{[2-(trimethylsilyl)ethoxy]methyl}-1H-pyrrolo[2,3-b]pyridin-4-yl]oxy}aniline (270 mg, 515 μmol, intermediate 386) and 3-(isocyanatomethyl)-3-methyloxetane (CAS No: 1260665-88-0, 131 mg, 1.03 mmol) in dichloromethane (4.5 mL) were allowed to react in the presence of pyridine (4.6 mL) to yield the title compound (250 mg, 70% yield).

LC-MS (Method 2): $R_t$=1.51 min; MS (ESIpos): m/z=625 [M+H]⁺.

Intermediate 388

2-[4-(2,6-difluoro-4-nitrophenoxy)-1-{[2-(trimethylsilyl)ethoxy]methyl}-1H-pyrrolo[2,3-b]pyridin-3-yl]-N,N-dimethylbenzamide

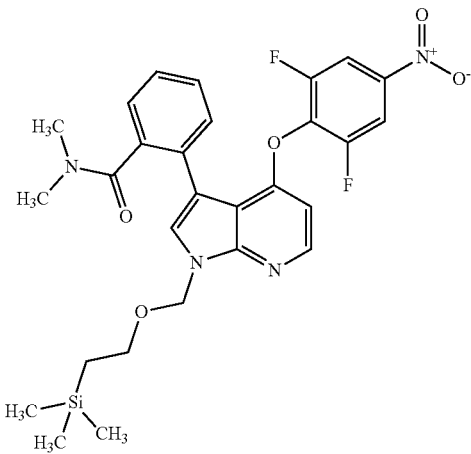 [SMILES: CN(C)C(=O)c1ccccc1-c1cn(COCC[Si](C)(C)C)c2nccc(Oc3c(F)cc([N+](=O)[O-])cc3F)c12]

377

In analogy to intermediate 379, 3-bromo-4-(2,6-difluoro-4-nitrophenoxy)-1-{[2-(trimethylsilyl)ethoxy]methyl}-1H-pyrrolo[2,3-b]pyridine (1.03 g, 2.06 mmol, Intermediate 16), [2-(dimethylcarbamoyl)phenyl]boronic acid (CAS No: 874219-16-6,438 mg, 2.27 mmol), sodium carbonate aq. (2M, 2.3 mL), and tetrakis (triphenylphosphine)palladium (0) (191 mg, 165 μmol) were reacted in a mixture of dioxane and water (15 mL and 7.5 mL, respectively) to afford the title compound (420 mg, 32% yield).

LC-MS (Method 2): $R_t$=1.52 min; MS (ESIpos): m/z=569 [M+H]$^+$.

Intermediate 389

2-[4-(4-amino-2,6-difluorophenoxy)-1-{[2-(trimethylsilyl)ethoxy]methyl}-1H-pyrrolo[2,3-b]pyridin-3-yl]-N,N-dimethylbenzamide

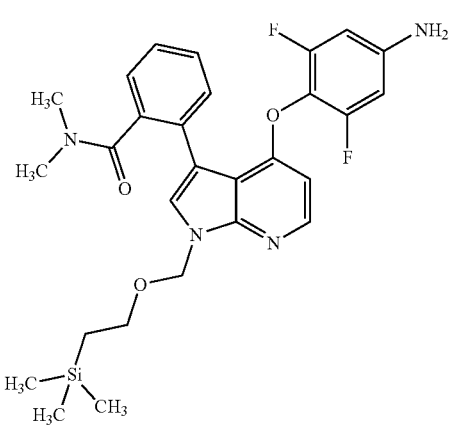 [SMILES: CN(C)C(=O)c1ccccc1-c1cn(COCC[Si](C)(C)C)c2nccc(Oc3c(F)cc(N)cc3F)c12]

In analogy to intermediate 380, a solution of 2-[4-(2,6-difluoro-4-nitrophenoxy)-1-{[2-(trimethylsilyl)ethoxy]methyl}-1H-pyrrolo[2,3-b]pyridin-3-yl]-N,N-dimethylbenzamide (417 mg, 660 μmol, intermediate 388) in THF/methanol (3.2 mL/3.2 mL) was reacted with a suspension of iron (184 mg, 3.30 mmol) and ammonium chloride (177 mg, 3.30 mmol) in water (6.4 mL) to yield the title compound (191 mg, 53% yield).

LC-MS (Method 2): $R_t$=1.36 min; MS (ESIpos): m/z=539 [M+H]$^+$ $^1$H-NMR (400 MHz, DMSO-d6) δ [ppm]: −0.095 (16.00), 0.825 (0.15), 2.773 (3.63), 3.483 (0.52), 3.504 (0.79), 3.523 (0.51), 5.662 (0.12), 5.770 (1.03), 6.325 (0.72), 6.352 (0.79), 6.358 (0.69), 6.372 (0.47), 7.284 (0.47), 7.287 (0.49), 7.341 (0.47), 7.344 (0.46), 7.357 (1.56), 7.542 (0.45), 7.544 (0.45), 8.159 (0.82), 8.173 (0.79).

378

Intermediate 390

2-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-N,N-dimethylbenzamide

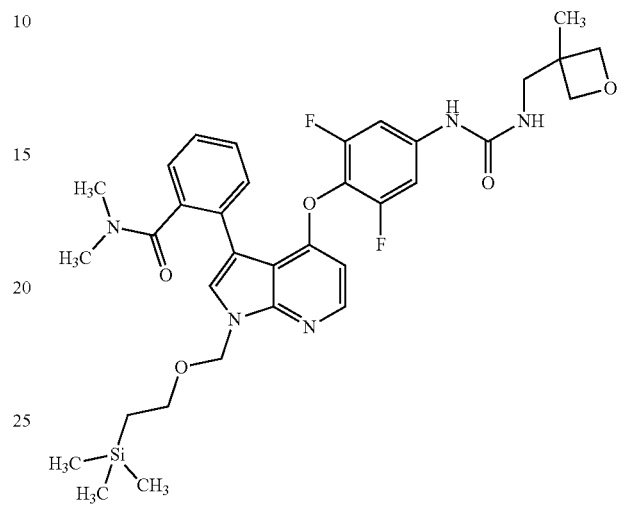

In analogy to intermediate 381, 2-[4-(4-amino-2,6-difluorophenoxy)-1-{[2-(trimethylsilyl)ethoxy]methyl}-1H-pyrrolo[2,3-b]pyridin-3-yl]-N,N-dimethylbenzamide (100 mg, 186 μmol, intermediate 389) and 3-(isocyanatomethyl)-3-methyloxetane (CAS No: 1260665-88-0, 47.2 mg, 371 μmol) in dichloromethane (1.6 mL) were allowed to react in the presence of pyridine (1.7 mL) to yield the title compound (127 mg, 82% yield).

LC-MS (Method 2): $R_t$=1.33 min; MS (ESIpos): m/z=666 [M+H]$^+$.

Intermediate 391

3-[4-(2,6-difluoro-4-nitrophenoxy)-1-{[2-(trimethylsilyl)ethoxy]methyl}-1H-pyrrolo[2,3-b]pyridin-3-yl]-N,N-dimethylbenzamide

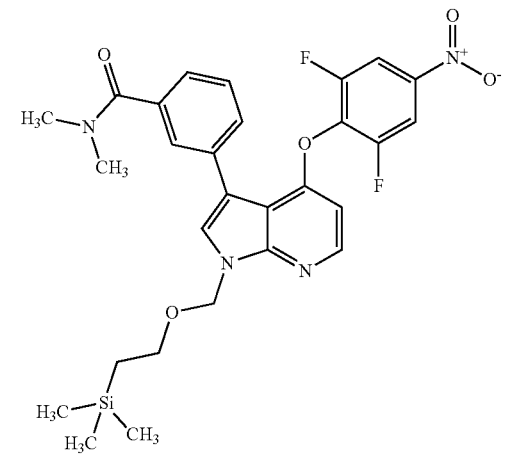 [SMILES: CN(C)C(=O)c1cccc(-c2cn(COCC[Si](C)(C)C)c3nccc(Oc4c(F)cc([N+](=O)[O-])cc4F)c23)c1]

3-bromo-4-(2,6-difluoro-4-nitrophenoxy)-1-{[2-(trimethylsilyl)ethoxy]methyl}-1H-pyrrolo[2,3-b]pyridine (782 mg, 1.56 mmol, Intermediate 16) and [3-(dimethylcarbamoyl)phenyl]boronic acid (CAS No: 373384-14-6, 332 mg, 1.72 mmol) were dissolved in 1,4-dioxane (27 mL). Sodium carbonate aq. (2M, 1.7 mL) and tetrakis (triphenylphosphine)palladium (0) (145 mg, 125 µmol) were added and the solution stirred under argon at 100° C. until no more starting material could be detected by UPLC-MS. The reaction was quenched with a saturated sodium bicarbonate solution, and extracted with ethyl acetate (×4). The organic phase was washed with water and brine, dried over sodium sulfate, filtered and evaporated. The crude was purified by silica gel chromatography using a Biotage system to yield the title compound (712 mg, 64% yield).

LC-MS (Method 2): $R_t$=1.52 min; MS (ESIpos): m/z=569 [M+H]$^+$.

Intermediate 392

3-[4-(4-amino-2,6-difluorophenoxy)-1-{[2-(trimethylsilyl)ethoxy]methyl}-1H-pyrrolo[2,3-b]pyridin-3-yl]-N,N-dimethylbenzamide

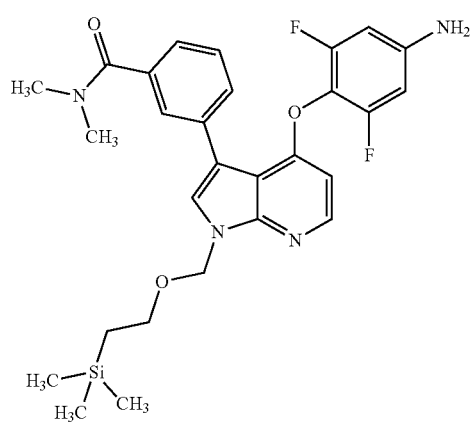 [SMILES: CN(C)C(=O)c1cccc(-c2cn(COCC[Si](C)(C)C)c3nccc(Oc4c(F)cc(N)cc4F)c23)c1]

In analogy to intermediate 380, a solution of 3-[4-(2,6-difluoro-4-nitrophenoxy)-1-{[2-(trimethylsilyl)ethoxy]methyl}-1H-pyrrolo[2,3-b]pyridin-3-yl]-N,N-dimethylbenzamide (708 mg, 996 µmol, intermediate 391) in THF/methanol (5.9 mL/5.9 mL) was reacted with a suspension of iron (278 mg, 4.98 mmol) and ammonium chloride (266 mg, 4.98 mmol) in water (12 mL) to yield the title compound (212 mg, 40% yield).

LC-MS (Method 2): $R_t$=1.38 min; MS (ESIpos): m/z=539 [M+H]$^+$.

Intermediate 393

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-N,N-dimethylbenzamide

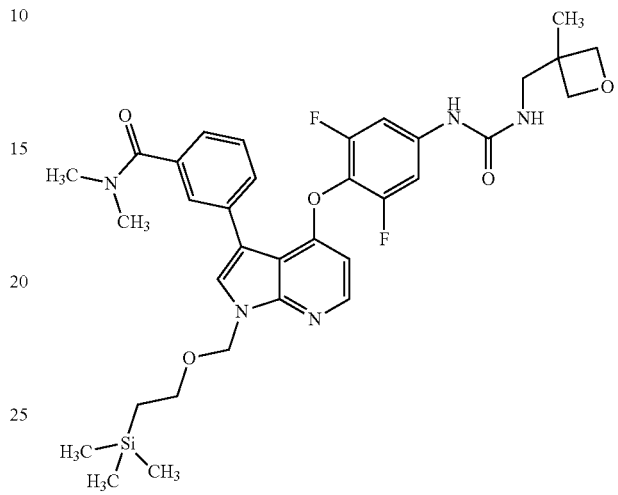

In analogy to intermediate 381, 3-[4-(4-amino-2,6-difluorophenoxy)-1-{[2-(trimethylsilyl)ethoxy]methyl}-1H-pyrrolo[2,3-b]pyridin-3-yl]-N,N-dimethylbenzamide (100 mg, 186 µmol, intermediate 392) and 3-(isocyanatomethyl)-3-methyloxetane (CAS No: 1260665-88-0, 47.2 mg, 371 µmol) in dichloromethane (1.6 mL) were allowed to react in the presence of pyridine (1.7 mL) to yield the title compound (60.9 mg, 30% yield).

LC-MS (Method 2): $R_t$=1.36 min; MS (ESIpos): m/z=666 [M+H]$^+$.

Intermediate 394

4-(2,6-difluoro-4-nitrophenoxy)-3-(3,4-difluorophenyl)-1-{[2-(trimethylsilyl)ethoxy]methyl}-1H-pyrrolo[2,3-b]pyridine

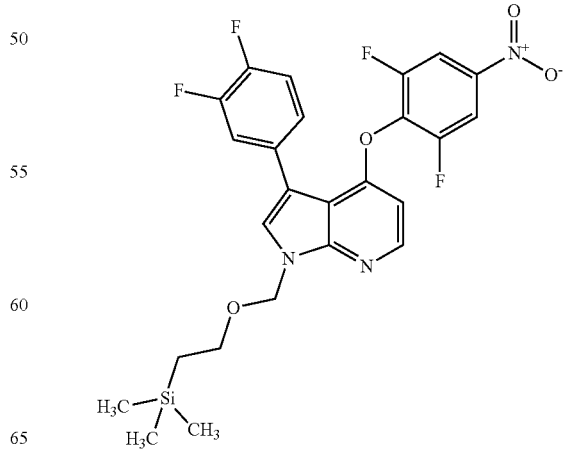

381

In analogy to intermediate 391, 3-bromo-4-(2,6-difluoro-4-nitrophenoxy)-1-{[2-(trimethylsilyl)ethoxy]methyl}-1H-pyrrolo[2,3-b]pyridine (3.50 g, 6.99 mmol, Intermediate 16) and (3,4-difluorophenyl)boronic acid (CAS No: 168267-41-2, 1.66 g, 10.5 mmol) were reacted in the presence of tetrakis (triphenylphosphine)palladium (0) (647 mg, 560 µmol) in a mixture of sodium carbonate aq. (7.0 mL, 2.0 M) and 1,4-dioxane (6.6 mL) to yield the title compound (2.03 g, 54% yield).

LC-MS (Method 2): $R_t$=1.68 min; MS (ESIpos): m/z=534 [M+H]$^+$ $^1$H-NMR (400 MHz, DMSO-d6) δ [ppm]: −0.088 (16.00), 0.828 (0.62), 0.836 (0.17), 0.848 (0.86), 0.860 (0.18), 0.868 (0.64), 3.577 (0.61), 3.597 (0.85), 3.617 (0.60), 5.690 (1.80), 6.660 (0.48), 6.673 (0.50), 7.450 (0.32), 7.453 (0.28), 7.463 (0.53), 7.473 (0.64), 7.486 (0.28), 7.603 (0.17), 7.606 (0.17), 7.624 (0.22), 7.636 (0.21), 7.653 (0.19), 7.656 (0.19), 7.984 (1.45), 8.227 (0.84), 8.241 (0.80), 8.389 (0.19), 8.397 (0.86), 8.416 (0.89), 8.423 (0.22).

Intermediate 395

4-{[3-(3,4-difluorophenyl)-1-{[2-(trimethylsilyl)ethoxy]methyl}-1H-pyrrolo[2,3-b]pyridin-4-yl]oxy}-3,5-difluoroaniline

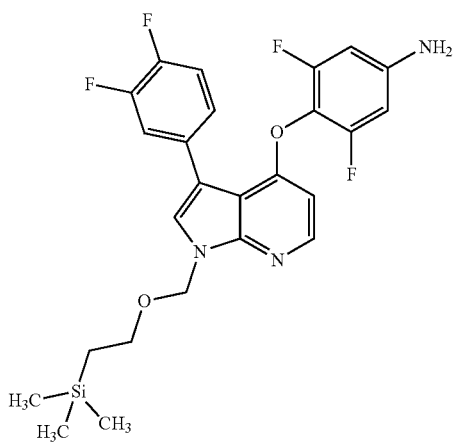 [SMILES: C[Si](C)(C)CCOCn1cc(-c2ccc(F)c(F)c2)c2c(Oc3c(F)cc(N)cc3F)ccnc21]

In analogy to intermediate 380, a solution of 4-(2,6-difluoro-4-nitrophenoxy)-3-(3,4-difluorophenyl)-1-{[2-(trimethylsilyl)ethoxy]methyl}-1H-pyrrolo[2,3-b]pyridine (2.03 g, 3.80 mmol, intermediate 394) in THF/methanol (22 mL/22 mL) was reacted with a suspension of iron (1.06 g, 19.0 mmol) and ammonium chloride (1.02 g, 19.0 mmol) in water (45 mL) to yield the title compound (1.43 g, 60% yield).

LC-MS (Method 2): $R_t$=1.57 min; MS (ESIpos): m/z=504 [M+H]$^+$.

382

Intermediate 396

N-(4-{[3-(3,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

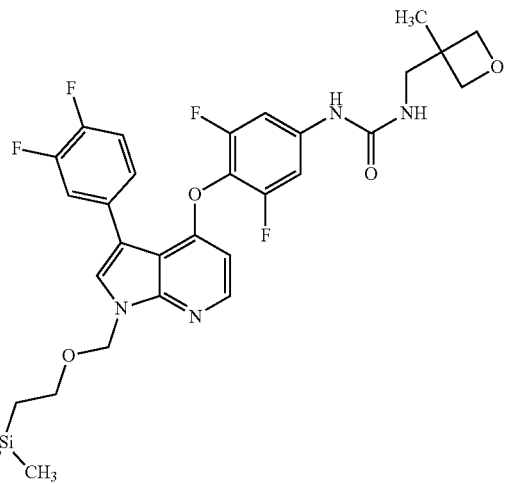

In analogy to intermediate 381, 4-{[3-(3,4-difluorophenyl)-1-{[2-(trimethylsilyl)ethoxy]methyl}-1H-pyrrolo[2,3-b]pyridin-4-yl]oxy}-3,5-difluoroaniline (450 mg, 894 µmol, intermediate 395) and 3-(isocyanatomethyl)-3-methyloxetane (CAS No: 1260665-88-0, 227 mg, 1.79 mmol) in dichloromethane (6.3 mL) were allowed to react in the presence of pyridine (9.8 mL) to yield the title compound (560 mg, 79% yield).

LC-MS (Method 2): $R_t$=1.54 min; MS (ESIpos): m/z=631 [M+H]$^+$.

Intermediate 397

N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

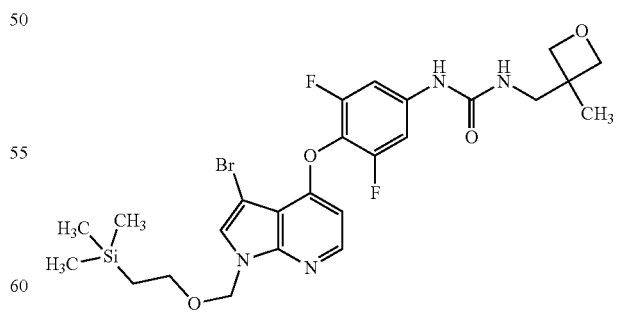

In analogy to intermediate 381, 4-[(3-bromo-1-{[2-(trimethylsilyl)ethoxy]methyl}-1H-pyrrolo[2,3-b]pyridin-4-yl)oxy]-3,5-difluoroaniline (1.00 g, 2.13 mmol, Intermediate 21) and 3-(isocyanatomethyl)-3-methyloxetane (CAS No: 1260665-88-0, 541 mg, 4.25 mmol) in dichloromethane (18 mL) were allowed to react in the presence of pyridine (19 mL) to yield the title compound (1.21 g, 90% yield).

LC-MS (Method 2): $R_t$=1.48 min; MS (ESIpos): m/z=597 [M+H]$^+$.

Intermediate 398

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N-methylbenzamide

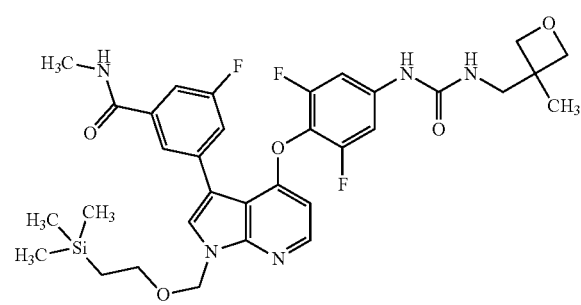 [SMILES: CNC(=O)c1cc(F)cc(-c2cn(COCC[Si](C)(C)C)c3nccc(Oc4c(F)cc(NC(=O)NCC5(C)COC5)cc4F)c23)c1]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (200 mg, 335 µmol, intermediate 397) and [3-fluoro-5-(methylcarbamoyl)phenyl]boronic acid (CAS No: 871332-63-7, 72.5 mg, 368 µmol) were reacted in the presence of tetrakis (triphenylphosphine)palladium (0) (30.9 mg, 26.8 µmol) in a mixture of 1,4-dioxane (3.0 mL) and sodium carbonate aq. (330 µL, 2.0 M) to yield the title compound (75 mg, 33% yield), which was further purified by preparative HPLC.

LC-MS (Method 2): $R_t$=1.34 min; MS (ESIpos): m/z=670 [M+H]$^+$ $^1$H-NMR (400 MHz, DMSO-d6) δ [ppm]: −0.077 (16.00), 0.841 (0.47), 0.860 (0.60), 0.881 (0.47), 1.230 (2.82), 2.784 (1.36), 2.795 (1.38), 3.290 (0.65), 3.305 (0.72), 3.577 (0.46), 3.597 (0.59), 3.617 (0.44), 4.197 (1.01), 4.211 (1.10), 4.374 (1.00), 4.389 (0.85), 5.697 (1.09), 6.476 (0.35), 6.490 (0.34), 6.781 (0.10), 6.789 (0.16), 6.800 (0.09), 7.382 (0.58), 7.408 (0.58), 7.476 (0.22), 7.497 (0.21), 7.611 (0.19), 7.630 (0.22), 8.013 (0.45), 8.017 (0.78), 8.021 (1.36), 8.200 (0.68), 8.214 (0.62), 8.527 (0.10), 8.537 (0.24), 8.549 (0.22), 8.561 (0.06), 9.100 (0.22).

Intermediate 399

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N,N-dimethylbenzamide

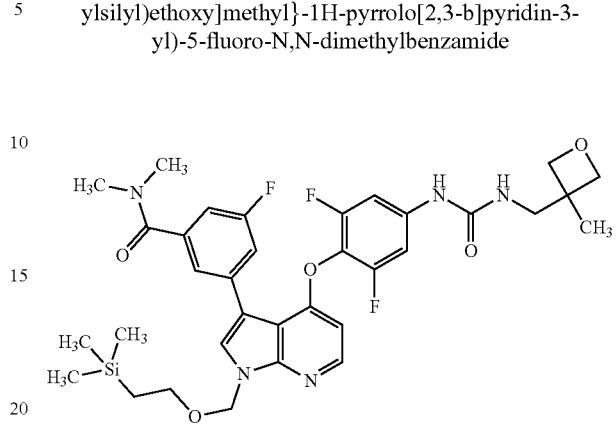

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (200 mg, 335 µmol, intermediate 397) and [3-(dimethylcarbamoyl)-5-fluorophenyl]boronic acid (CAS No: 874219-39-3, 77.7 mg, 368 µmol) were reacted in the presence of tetrakis (triphenylphosphine)palladium (0) (30.9 mg, 26.8 µmol) in a mixture of 1,4-dioxane (3.0 mL) and sodium carbonate aq. (330 µL, 2.0 M) to yield the title compound (69 mg, 30% yield).

LC-MS (Method 2): $R_t$=1.38 min; MS (ESIpos): m/z=684 [M+H]$^+$.

Intermediate 400

N-(4-{[3-(5-cyano-6-ethoxypyridin-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

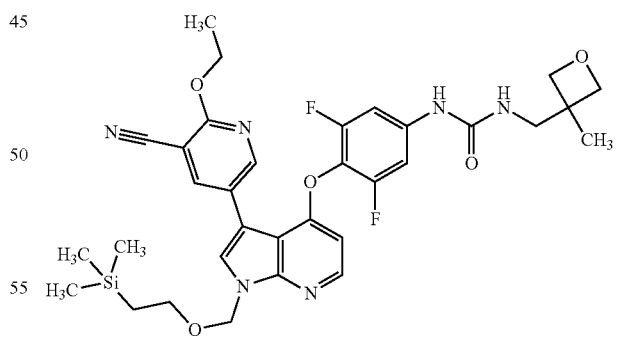

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (200 mg, 335 µmol, intermediate 397) and 2-ethoxy-5-(4,4,5,5-tetramethyl-1,3,2-dioxaborolan-2-yl)pyridine-3-carbonitrile (CAS No: 1115030-43-7, 101 mg, 368 µmol) were reacted in the presence of tetrakis (triphenylphosphine)palladium (0) (30.9 mg, 26.8 µmol) in a mixture of 1,4-dioxane (3.0 mL) and sodium carbonate aq.

(330 µL, 2.0 M) to yield the title compound (75.0 mg, 34% yield), after being purified by preparative HPLC.

LC-MS (Method 2): $R_t$=1.51 min; MS (ESIpos): m/z=665 [M+H]$^+$ $^1$H-NMR (400 MHz, DMSO-d6) δ [ppm]: −0.073 (16.00), 0.840 (0.58), 0.859 (0.76), 0.880 (0.58), 1.230 (3.60), 1.343 (1.10), 1.361 (2.34), 1.378 (1.10), 3.291 (0.95), 3.306 (1.02), 3.577 (0.58), 3.597 (0.76), 3.617 (0.54), 4.197 (1.30), 4.212 (1.45), 4.374 (1.30), 4.388 (1.14), 4.445 (0.35), 4.463 (1.13), 4.480 (1.12), 4.497 (0.34), 5.680 (1.39), 6.483 (0.46), 6.497 (0.46), 6.767 (0.30), 7.392 (0.78), 7.418 (0.77), 8.010 (1.37), 8.205 (0.78), 8.219 (0.75), 8.421 (0.91), 8.427 (0.94), 8.704 (0.88), 8.709 (0.92), 9.079 (0.45).

Intermediate 401

N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea

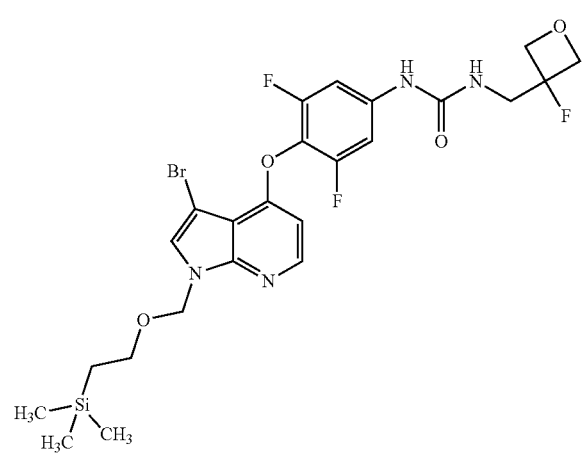 [SMILES: C[Si](C)(C)CCOCn1cc(Br)c2c(Oc3c(F)cc(NC(=O)NCC4(F)COC4)cc3F)ccnc21]

Phenyl {4-[(3-bromo-1-{[2-(trimethylsilyl)ethoxy]methyl}-1H-pyrrolo[2,3-b]pyridin-4-yl)oxy]-3,5-difluorophenyl}carbamate (1.30 g, 2.20 mmol, Intermediate 22) and 1-(3-fluorooxetan-3-yl)methanamine (CAS No: 883311-82-8, 463 mg, 4.40 mmol) were stirred in DMF (20 mL) at 60° C. until no more starting material could be detected by UPLC-MS. The solvent was then removed under vacuum and the residue filtered through silica to afford the title compound (1.26 g, 86% yield), that was used in the following transformations without further purification.

LC-MS (Method 2): $R_t$=1.48 min; MS (ESIpos): m/z=601 [M+H]$^+$ $^1$H-NMR (400 MHz, DMSO-d6) δ [ppm]: −0.082 (0.73), −0.073 (16.00), −0.065 (0.64), −0.059 (0.93), 0.821 (0.52), 0.840 (0.68), 0.861 (0.55), 2.745 (7.61), 2.906 (9.53), 3.528 (0.50), 3.548 (0.63), 3.568 (0.49), 4.602 (0.74), 4.608 (0.68), 4.651 (0.74), 4.658 (0.72), 5.621 (1.36), 7.405 (0.62), 7.431 (0.62), 7.883 (1.25), 7.969 (1.29), 8.180 (0.66), 8.194 (0.62), 9.139 (0.53).

Intermediate 402

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluorobenzamide

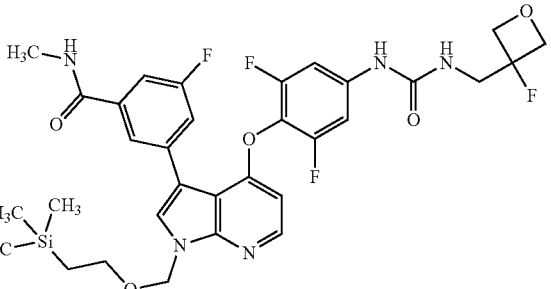

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and (3-carbamoyl-5-fluorophenyl)boronic acid (CAS No: 871332-66-0, 66.9 mg, 366 µmol) were reacted in the presence of tetrakis(triphenylphosphine)palladium (0) (30.7 mg, 26.6 µmol) in a mixture of 1,4-dioxane (3.0 mL) and sodium carbonate aq. (330 µL, 2.0 M) to yield the title compound (72.1 mg, 33% yield).

LC-MS (Method 2): $R_t$=1.30 min; MS (ESIpos): m/z=660 [M+H]$^+$.

Intermediate 403

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N-methylbenzamide In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and [3-fluoro-5-(methylcarbamoyl)phenyl]boronic acid (CAS No: 871332-63-7, 72.0 mg, 366 µmol) were reacted in the presence of tetrakis (triphenylphosphine)palladium (0) (30.7 mg, 26.6 µmol) in a mixture of 1,4-dioxane (3.0 mL) and sodium carbonate aq. (330 µL, 2.0 M) to yield the title compound (87.9 mg, 39% yield).

LC-MS (Method 2): R$_t$=1.34 min; MS (ESIpos): m/z=674 [M+H]$^+$.

Intermediate 404

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N,N-dimethylbenzamide

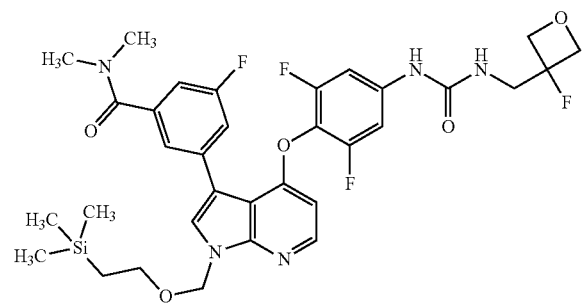 [SMILES: CN(C)C(=O)c1cc(F)cc(-c2cn(COCC[Si](C)(C)C)c3nccc(Oc4c(F)cc(NC(=O)NCC5(F)COC5)cc4F)c23)c1]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and [3-(dimethylcarbamoyl)-5-fluorophenyl]boronic acid (CAS No: 874219-39-3, 77.2 mg, 366 µmol) were reacted in the presence of tetrakis (triphenylphosphine)palladium (0) (30.7 mg, 26.6 µmol) in a mixture of 1,4-dioxane (3.0 mL) and sodium carbonate aq. (330 µL, 2.0 M) to yield the title compound (104 mg, 46% yield).

LC-MS (Method 2): R$_t$=1.38 min; MS (ESIpos): m/z=688 [M+H]$^+$.

Intermediate 405

N-(4-{[3-(5-cyano-6-ethoxypyridin-3-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

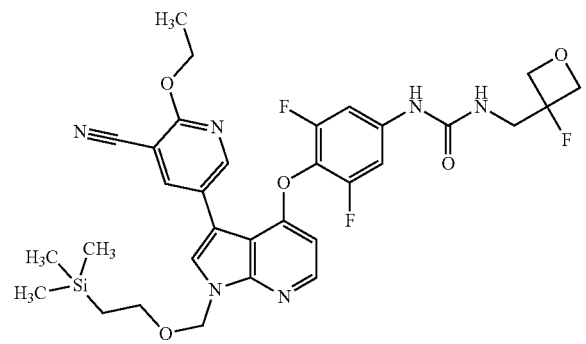 [SMILES: CCOc1ncc(-c2cn(COCC[Si](C)(C)C)c3nccc(Oc4c(F)cc(NC(=O)NCC5(F)COC5)cc4F)c23)cc1C#N]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and 2-ethoxy-5-(4,4,5,5-tetramethyl-1,3,2-dioxaborolan-2-yl)pyridine-3-carbonitrile (CAS No: 1115030-43-7, 100 mg, 366 µmol) were reacted in the presence of tetrakis (triphenylphosphine)palladium (0) (30.7 mg, 26.6 µmol) in a mixture of 1,4-dioxane (3.0 mL) and sodium carbonate aq. (330 µL, 2.0 M) to yield the title compound (79.8 mg, 36% yield), after being purified by preparative HPLC.

LC-MS (Method 2): R$_t$=1.50 min; MS (ESIpos): m/z=669 [M+H]$^+$ $^1$H-NMR (400 MHz, DMSO-d6) δ [ppm]: −0.074 (16.00), 0.840 (0.50), 0.859 (0.63), 0.879 (0.51), 1.342 (1.01), 1.360 (2.29), 1.378 (1.06), 3.577 (0.50), 3.597 (0.64), 3.617 (0.59), 3.637 (0.32), 3.674 (0.30), 3.689 (0.32), 4.444 (0.32), 4.462 (1.06), 4.480 (1.05), 4.497 (0.30), 4.559 (0.11), 4.579 (0.83), 4.585 (0.77), 4.606 (0.17), 4.629 (0.83), 4.635 (0.80), 4.655 (0.10), 5.680 (1.19), 6.482 (0.39), 6.495 (0.39), 6.857 (0.11), 6.871 (0.22), 6.886 (0.11), 7.390 (0.68), 7.417 (0.68), 8.010 (1.28), 8.206 (0.72), 8.220 (0.69), 8.420 (0.85), 8.426 (0.94), 8.702 (0.85), 8.708 (0.89), 9.185 (0.36).

Intermediate 406

N-(4-{[3-(2,5-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

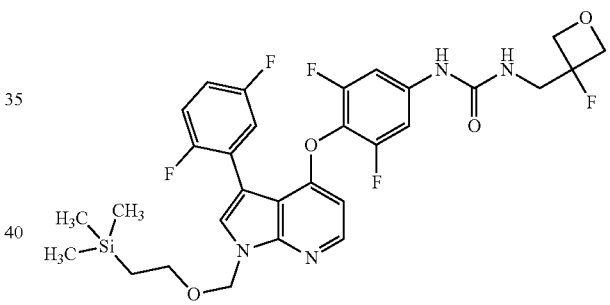

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and (2,5-difluorophenyl)boronic acid (CAS No: 193353-34-3, 57.7 mg, 365 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (64.0 mg, 30% yield), after being purified by preparative HPLC.

LC-MS (Method 2): R$_t$=1.51 min; MS (ESIpos): m/z=635 [M+H]$^+$ $^1$H-NMR (400 MHz, DMSO-d6) δ [ppm]: −0.081 (16.00), 0.828 (0.55), 0.847 (0.77), 0.867 (0.58), 3.579 (0.57), 3.599 (0.79), 3.619 (0.80), 3.632 (0.40), 3.668 (0.38), 3.684 (0.38), 4.554 (0.16), 4.574 (0.86), 4.582 (0.80), 4.603 (0.27), 4.625 (0.85), 4.632 (0.82), 4.653 (0.13), 5.693 (1.54), 6.441 (0.46), 6.454 (0.44), 6.803 (0.17), 6.818 (0.31), 6.833 (0.16), 7.146 (0.07), 7.154 (0.13), 7.177 (0.26), 7.186 (0.18), 7.197 (0.18), 7.206 (0.11), 7.294 (0.18), 7.306 (0.19), 7.317 (0.30), 7.329 (0.32), 7.349 (0.78), 7.375 (0.88), 7.397 (0.31), 7.412 (0.18), 7.421 (0.14), 7.884 (0.82), 8.191 (0.76), 8.205 (0.71), 9.121 (0.54).

Intermediate 407

N-(4-{[3-(3,5-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

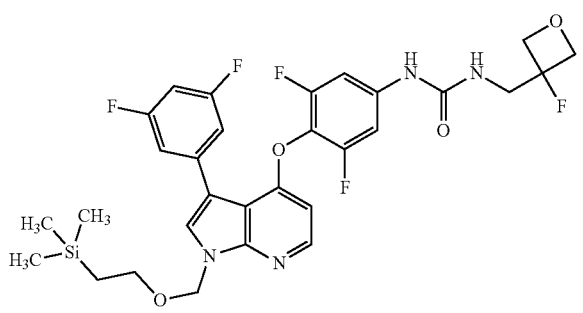 [SMILES: C[Si](C)(C)CCOCn1cc(-c2cc(F)cc(F)c2)c2c(Oc3c(F)cc(NC(=O)NCC4(F)COC4)cc3F)ccnc21]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and (3,5-difluorophenyl)boronic acid (CAS No: 156545-07-2, 57.7 mg, 365 µmol) were reacted in the presence of tetrakis(triphenylphosphine)palladium (0) (30.7 mg, 26.6 µmol) in a mixture of sodium carbonate aq. (330 µL, 2.0 M) and 1,4-dioxane (3.0 mL) to yield the title compound (40.0 mg, 19% yield).

LC-MS (Method 2): $R_t$=1.55 min; MS (ESIpos): m/z=635 [M+H]$^+$.

Intermediate 408

N-(4-{[3-(2,3-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

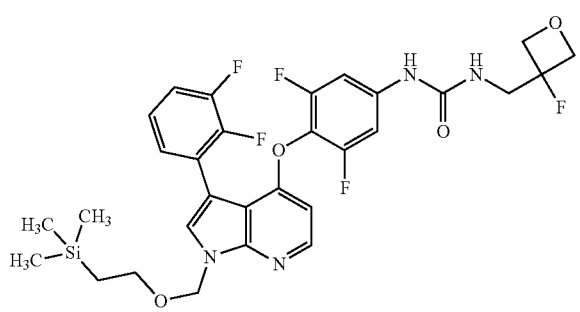 [SMILES: C[Si](C)(C)CCOCn1cc(-c2cccc(F)c2F)c2c(Oc3c(F)cc(NC(=O)NCC4(F)COC4)cc3F)ccnc21]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and (2,3-difluorophenyl)boronic acid (CAS No: 121219-16-7, 57.7 mg, 365 µmol) were reacted in the presence of tetrakis(triphenylphosphine)palladium (0) (30.7 mg, 26.6 µmol) in a mixture of sodium carbonate aq. (330 µL, 2.0 M) and 1,4-dioxane (3.0 mL) to yield the title compound (51.0 mg, 24% yield), after being purified by preparative HPLC.

LC-MS (Method 2): $R_t$=1.51 min; MS (ESIpos): m/z=635 [M+H]$^+$ $^1$H-NMR (400 MHz, DMSO-d6) δ [ppm]: −0.081 (16.00), 0.827 (0.56), 0.847 (0.75), 0.868 (0.56), 3.583 (0.59), 3.603 (0.80), 3.615 (0.44), 3.623 (0.73), 3.666 (0.31), 3.680 (0.30), 4.552 (0.17), 4.573 (0.85), 4.580 (0.78), 4.602 (0.27), 4.623 (0.83), 4.631 (0.79), 4.651 (0.13), 5.696 (1.48), 6.430 (0.44), 6.444 (0.43), 6.818 (0.13), 6.832 (0.23), 6.846 (0.12), 7.206 (0.08), 7.224 (0.21), 7.238 (0.21), 7.257 (0.14), 7.338 (0.76), 7.364 (0.95), 7.384 (0.32), 7.877 (0.94), 8.190 (0.76), 8.204 (0.71), 9.136 (0.38).

Intermediate 409

N-(4-{[3-(2,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

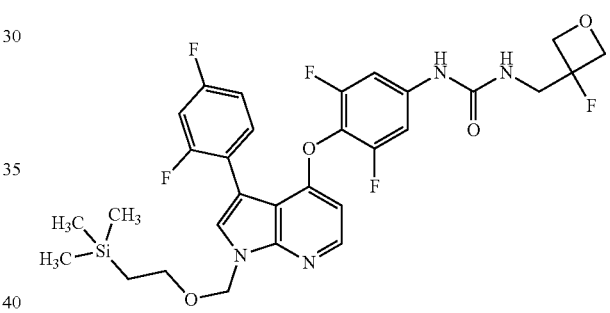

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and (2,4-difluorophenyl)boronic acid (CAS No: 144025-03-6, 57.7 mg, 365 µmol) were reacted in the presence of tetrakis(triphenylphosphine)palladium (0) (30.7 mg, 26.6 µmol) in a mixture of sodium carbonate aq. (330 µL, 2.0 M) and 1,4-dioxane (3.0 mL) to yield the title compound (65.0 mg, 31% yield), after being purified by preparative HPLC.

LC-MS (Method 2): $R_t$=1.52 min; MS (ESIpos): m/z=635 [M+H]$^+$ $^1$H-NMR (400 MHz, DMSO-d6) δ [ppm]: −0.090 (1.34), −0.082 (16.00), 0.824 (0.52), 0.844 (0.68), 0.864 (0.52), 3.575 (0.54), 3.596 (0.70), 3.615 (0.76), 3.628 (0.29), 3.666 (0.27), 3.680 (0.27), 4.573 (0.76), 4.581 (0.70), 4.602 (0.24), 4.623 (0.75), 4.631 (0.72), 5.684 (1.34), 6.403 (0.43), 6.416 (0.39), 6.837 (0.21), 7.134 (0.25), 7.139 (0.25), 7.308 (0.25), 7.315 (0.27), 7.332 (0.83), 7.338 (0.26), 7.358 (0.67), 7.572 (0.19), 7.577 (0.30), 7.594 (0.29), 7.599 (0.18), 7.787 (0.87), 8.170 (0.73), 8.184 (0.68), 9.137 (0.35).

Intermediate 410

N-{4-[(3-[4-(difluoromethyl)phenyl]-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea

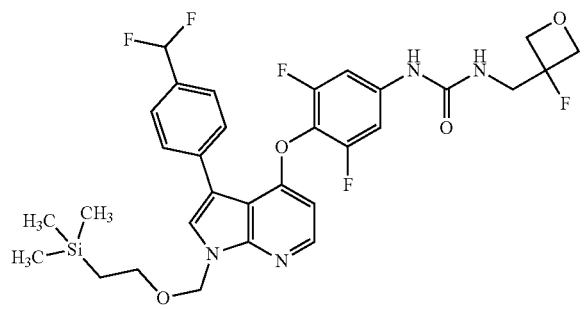 [SMILES: C[Si](C)(C)CCOCn1cc(-c2ccc(C(F)F)cc2)c2c(Oc3c(F)cc(NC(=O)NCC4(F)COC4)cc3F)ccnc21]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and [4-(difluoromethyl)phenyl]boronic acid (CAS No: 946525-43-5, 62.8 mg, 365 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (33.0 mg, 15% yield), after being purified by preparative HPLC.

LC-MS (Method 2): $R_t$=1.51 min; MS (ESIpos): m/z=649 [M+H]$^+$ $^1$H-NMR (400 MHz, DMSO-d6) δ [ppm]: −0.083 (16.00), 0.830 (0.49), 0.850 (0.64), 0.870 (0.50), 3.578 (0.52), 3.599 (0.66), 3.618 (0.64), 3.635 (0.24), 3.674 (0.23), 3.687 (0.22), 4.558 (0.14), 4.578 (0.73), 4.586 (0.67), 4.606 (0.20), 4.629 (0.73), 4.636 (0.69), 4.656 (0.10), 5.691 (1.21), 6.455 (0.38), 6.469 (0.36), 6.844 (0.16), 6.890 (0.24), 7.030 (0.52), 7.170 (0.21), 7.375 (0.63), 7.401 (0.63), 7.581 (0.51), 7.601 (0.61), 7.790 (0.71), 7.811 (0.55), 7.936 (1.14), 8.190 (0.70), 8.203 (0.66), 9.158 (0.24).

Intermediate 411

N-(3,5-difluoro-4-{[3-(4-fluoro-3-methoxyphenyl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

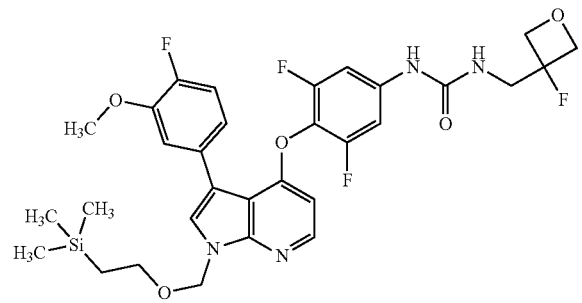 [SMILES: COc1cc(-c2cn(COCC[Si](C)(C)C)c3nccc(Oc4c(F)cc(NC(=O)NCC5(F)COC5)cc4F)c23)ccc1F]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and (4-fluoro-3-methoxyphenyl)boronic acid (CAS No: 854778-31-7, 62.1 mg, 365 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (34.0 mg, 16% yield).

LC-MS (Method 2): $R_t$=1.50 min; MS (ESIpos): m/z=647 [M+H]$^+$.

Intermediate 412

N-{3,5-difluoro-4-[(3-[3-methoxy-4-(trifluoromethyl)phenyl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea

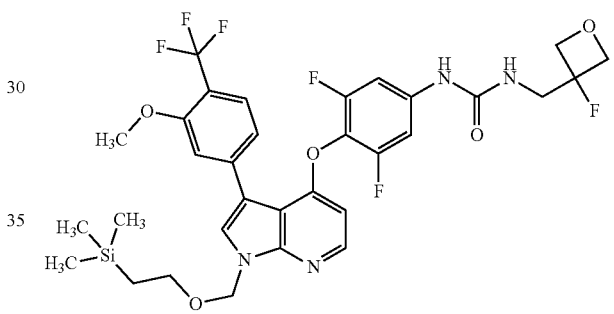

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 µmol, intermediate 401) and [3-methoxy-4-(trifluoromethyl)phenyl]boronic acid (CAS No: 1004775-33-0, 80.3 mg, 365 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (67.0 mg, 29% yield), after being purified by preparative HPLC.

LC-MS (Method 2): $R_t$=1.57 min; MS (ESIpos): m/z=697 [M+H]$^+$ $^1$H-NMR (400 MHz, DMSO-d6) δ [ppm]: −0.076 (16.00), 0.839 (0.48), 0.859 (0.61), 0.880 (0.47), 3.582 (0.49), 3.602 (0.62), 3.622 (0.63), 3.634 (0.29), 3.671 (0.28), 3.687 (0.29), 3.873 (2.86), 4.558 (0.12), 4.578 (0.73), 4.585 (0.67), 4.606 (0.17), 4.629 (0.72), 4.635 (0.69), 4.655 (0.09), 5.700 (1.15), 6.482 (0.39), 6.495 (0.36), 6.891 (0.11), 6.905 (0.19), 6.920 (0.10), 7.388 (0.67), 7.402 (0.34), 7.414 (0.61), 7.543 (0.55), 7.612 (0.47), 7.633 (0.39), 8.073 (1.09), 8.204 (0.69), 8.218 (0.65), 9.228 (0.32).

Intermediate 413

N-{3,5-difluoro-4-[(3-[4-(trifluoromethyl)phenyl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea

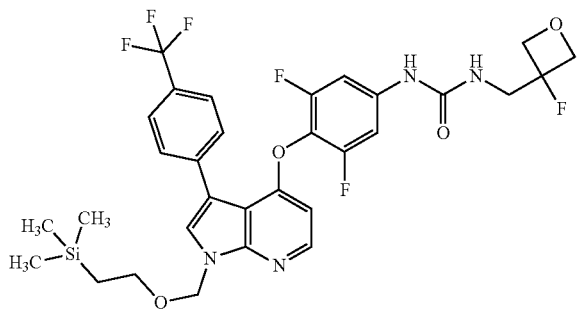 [SMILES: C[Si](C)(C)CCOCn1cc(-c2ccc(C(F)(F)F)cc2)c2c(Oc3c(F)cc(NC(=O)NCC4(F)COC4)cc3F)ccnc21]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 μmol, intermediate 401) and [4-(trifluoromethyl)phenyl]boronic acid (CAS No: 128796-39-4, 69.4 mg, 365 μmol) were reacted in the presence of tetrakis (triphenylphosphine)palladium (0) (30.7 mg, 26.6 μmol) in a mixture of sodium carbonate aq. (330 μL, 2.0 M) and 1,4-dioxane (3.0 mL) to yield the title compound (25.0 mg, 11% yield), after being purified by preparative HPLC.

LC-MS (Method 2): $R_t$=1.58 min; MS (ESIpos): m/z=667 [M+H]$^+$ $^1$H-NMR (400 MHz, DMSO-d6) δ [ppm]: −0.084 (16.00), 0.831 (0.52), 0.850 (0.71), 0.870 (0.51), 3.582 (0.52), 3.603 (0.70), 3.622 (0.75), 3.635 (0.29), 3.674 (0.26), 3.688 (0.26), 4.558 (0.13), 4.579 (0.73), 4.585 (0.69), 4.607 (0.20), 4.629 (0.72), 4.636 (0.72), 4.656 (0.10), 5.698 (1.22), 6.476 (0.37), 6.490 (0.36), 6.846 (0.10), 6.860 (0.18), 6.872 (0.10), 7.379 (0.60), 7.405 (0.60), 7.749 (0.59), 7.770 (0.75), 7.866 (0.43), 7.876 (0.81), 7.887 (0.69), 7.896 (0.59), 7.965 (0.53), 7.985 (0.40), 8.014 (1.13), 8.203 (0.67), 8.217 (0.64), 9.177 (0.29).

Intermediate 414

N-(3,5-difluoro-4-{[3-(6-methylpyridazin-4-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

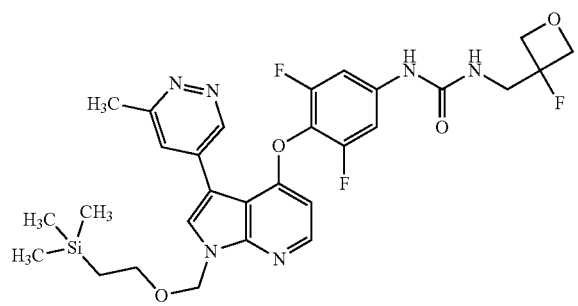 [SMILES: Cc1cc(-c2cn(COCC[Si](C)(C)C)c3nccc(Oc4c(F)cc(NC(=O)NCC5(F)COC5)cc4F)c23)cnn1]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (235 mg, 332 μmol, intermediate 401) and 3-methyl-5-(4,4,5,5-tetramethyl-1,3,2-dioxaborolan-2-yl)pyridazine (CAS No: 1610471-61-8, 80.4 mg, 365 μmol) were reacted in the presence of tetrakis (triphenylphosphine) palladium (0) (30.7 mg, 26.6 μmol) in a mixture of sodium carbonate aq. (330 μL, 2.0 M) and 1,4-dioxane (3.0 mL) to yield the title compound (18.0 mg, 9% yield).

LC-MS (Method 2): $R_t$=1.27 min; MS (ESIpos): m/z=614 [M+H]$^+$.

Intermediate 415

N-(4-{[3-(1-cyclopropyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

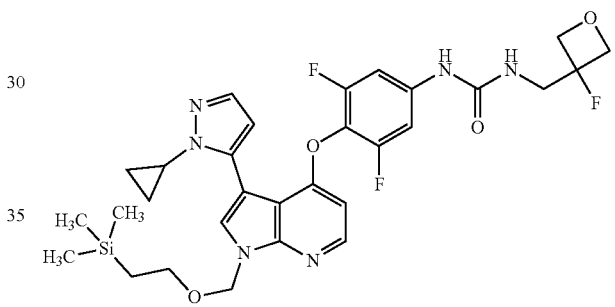

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 332 μmol, intermediate 401) and (1-cyclopropyl-1H-pyrazol-5-yl)boronic acid (CAS No: 1537208-26-6, 55.5 mg, 365 μmol) were reacted in the presence of tetrakis (triphenylphosphine)palladium (0) (30.7 mg, 26.6 μmol) in a mixture of sodium carbonate aq. (330 μL, 2.0 M) and 1,4-dioxane (3.0 mL) to yield the title compound (35.5 mg, 17% yield), after being purified by preparative HPLC.

LC-MS (Method 2): $R_t$=1.38 min; MS (ESIpos): m/z=629 [M+H]$^+$ $^1$H-NMR (400 MHz, DMSO-d6) δ [ppm]: −0.094 (16.00), 0.822 (0.56), 0.831 (0.52), 0.843 (0.97), 0.849 (0.43), 0.862 (0.52), 0.969 (0.45), 0.977 (0.46), 0.986 (0.31), 3.570 (0.42), 3.590 (0.53), 3.610 (0.51), 3.629 (0.26), 3.666 (0.26), 3.681 (0.28), 3.685 (0.26), 3.694 (0.22), 3.703 (0.29), 4.573 (0.63), 4.580 (0.60), 4.624 (0.63), 4.631 (0.62), 5.703 (1.09), 6.366 (0.87), 6.370 (0.89), 6.425 (0.34), 6.439 (0.33), 6.814 (0.09), 6.830 (0.17), 6.845 (0.09), 7.347 (0.52), 7.373 (0.57), 7.393 (0.90), 7.399 (0.81), 7.921 (1.13), 8.188 (0.63), 8.202 (0.60), 9.138 (0.28).

Intermediate 416

N-{3,5-difluoro-4-[(3-[1-(propan-2-yl)-3-(trifluoromethyl)-1H-pyrazol-5-yl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea

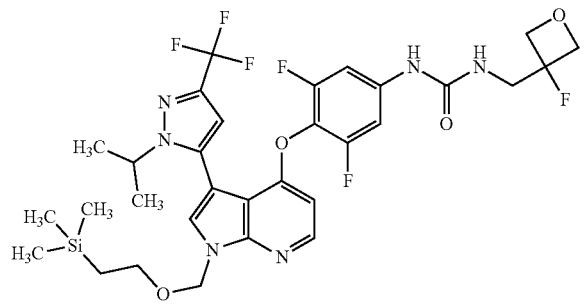 [SMILES: CC(C)n1nc(C(F)(F)F)cc1-c1cn(COCC[Si](C)(C)C)c2nccc(Oc3c(F)cc(NC(=O)NCC4(F)COC4)cc3F)c12]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 332 µmol, intermediate 401) and [1-(propan-2-yl)-3-(trifluoromethyl)-1H-pyrazol-5-yl]boronic acid (CAS No: 1361380-69-9, 81.1 mg, 365 µmol) were reacted in the presence of tetrakis (triphenylphosphine) palladium (0) (30.7 mg, 26.6 µmol) in a mixture of sodium carbonate aq. (330 µL, 2.0 M) and 1,4-dioxane (3.0 mL) to yield the title compound (53.0 mg, 23% yield), after being purified by preparative HPLC.

LC-MS (Method 2): $R_t$=1.53 min; MS (ESIpos): m/z=699 [M+H]$^+$ $^1$H-NMR (400 MHz, DMSO-d6) δ [ppm]: −0.101 (16.00), 0.810 (0.46), 0.830 (0.59), 0.850 (0.46), 1.320 (2.16), 1.337 (2.15), 2.518 (0.32), 2.523 (0.21), 3.580 (0.47), 3.600 (0.62), 3.620 (0.69), 3.668 (0.39), 4.569 (0.65), 4.576 (0.61), 4.597 (0.24), 4.614 (0.27), 4.619 (0.68), 4.627 (0.74), 4.646 (0.25), 5.696 (1.12), 6.452 (0.36), 6.465 (0.34), 6.759 (0.90), 7.189 (0.21), 7.339 (0.56), 7.366 (0.56), 7.957 (1.22), 8.219 (0.69), 8.232 (0.64), 9.168 (0.04).

Intermediate 417

N-(4-{[3-(1-ethyl-3-methyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

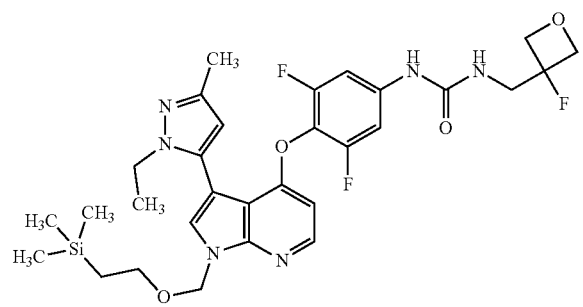 [SMILES: CCn1nc(C)cc1-c1cn(COCC[Si](C)(C)C)c2nccc(Oc3c(F)cc(NC(=O)NCC4(F)COC4)cc3F)c12]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 332 µmol, intermediate 401) and (1-ethyl-3-methyl-1H-pyrazol-5-yl)boronic acid (6.2 mg, 365 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (32.0 mg, 15% yield).

LC-MS (Method 2): $R_t$=1.39 min; MS (ESIpos): m/z=631 [M+H]$^+$.

Intermediate 418

N-(4-{[3-(1,3-dimethyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

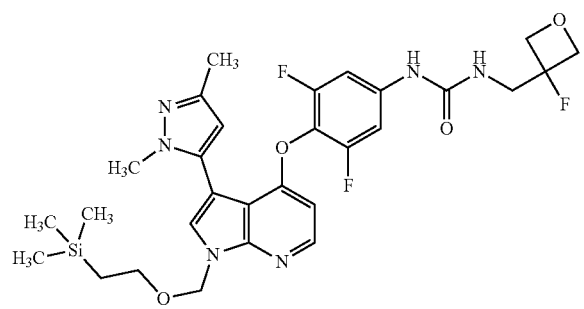 [SMILES: Cc1cc(-c2cn(COCC[Si](C)(C)C)c3nccc(Oc4c(F)cc(NC(=O)NCC5(F)COC5)cc4F)c23)n(C)n1]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 332 µmol, intermediate 401) and (1,3-dimethyl-1H-pyrazol-5-yl)boronic acid (CAS No: 847818-68-2, 69.7 mg, 498 µmol) were reacted in the presence of tetrakis (triphenylphosphine)palladium (0) (30.7 mg, 26.6 µmol) in a mixture of sodium carbonate aq. (330 µL, 2.0 M) and 1,4-dioxane (3.0 mL) to yield the title compound (40.0 mg, 20% yield), after being purified by preparative HPLC.

LC-MS (Method 2): $R_t$=1.36 min; MS (ESIpos): m/z=617 [M+H]$^+$ $^1$H-NMR (400 MHz, DMSO-d6) δ [ppm]: −0.099 (16.00), 0.811 (0.42), 0.831 (0.61), 0.851 (0.48), 2.142 (2.50), 3.569 (0.44), 3.589 (0.59), 3.609 (0.45), 3.618 (0.30), 3.633 (0.29), 3.670 (0.32), 3.689 (3.12), 4.554 (0.12), 4.574 (0.63), 4.582 (0.59), 4.604 (0.21), 4.624 (0.63), 4.632 (0.61), 4.653 (0.11), 5.675 (1.12), 6.115 (1.00), 6.422 (0.35), 6.435 (0.34), 6.780 (0.12), 6.795 (0.24), 6.810 (0.12), 7.355 (0.58), 7.382 (0.58), 7.808 (1.19), 8.185 (0.64), 8.199 (0.62), 9.109 (0.42).

Intermediate 419

N-{4-[(3-[1-ethyl-3-(trifluoromethyl)-1H-pyrazol-5-yl]-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea

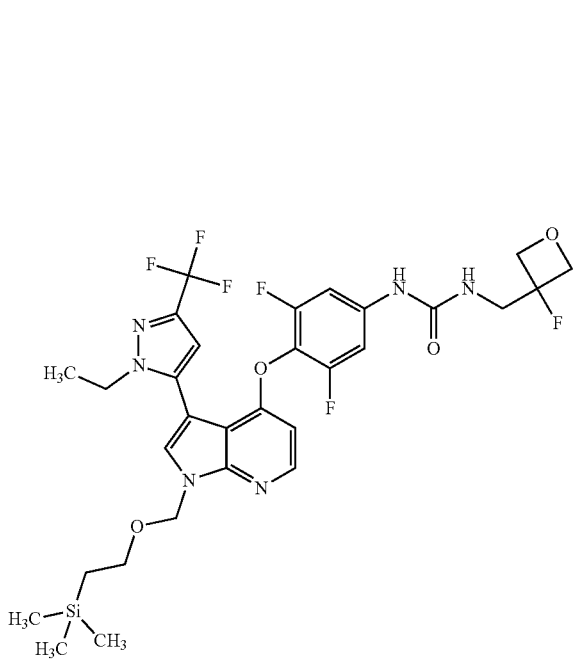 [SMILES: CCn1nc(C(F)(F)F)cc1-c1cn(COCC[Si](C)(C)C)c2nccc(Oc3c(F)cc(NC(=O)NCC4(F)COC4)cc3F)c12]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and [1-ethyl-3-(trifluoromethyl)-1H-pyrazol-5-yl]boronic acid (CAS No: 1346665-27-7, 104 mg, 499 µmol) were reacted in the presence of tetrakis (triphenylphosphine)palladium (0) (30.7 mg, 26.6 µmol) in a mixture of 1,4-dioxane (3.0 mL) and sodium carbonate aq. (330 µL, 2.0 M) to yield the title compound (50.0 mg, 22% yield), after being purified by preparative HPLC.

LC-MS (Method 6): $R_t$=1.49 min; MS (ESIpos): m/z=685 [M+H]$^+$ $^1$H-NMR (400 MHz, DMSO-d6) δ [ppm]: −0.098 (16.00), 0.801 (0.07), 0.816 (0.45), 0.835 (0.55), 0.855 (0.44), 1.262 (0.77), 1.280 (1.77), 1.298 (0.77), 3.579 (0.44), 3.599 (0.58), 3.612 (0.30), 3.619 (0.53), 3.665 (0.21), 3.679 (0.21), 4.171 (0.16), 4.190 (0.50), 4.207 (0.50), 4.226 (0.15), 4.551 (0.11), 4.570 (0.62), 4.578 (0.57), 4.601 (0.18), 4.621 (0.61), 4.629 (0.60), 4.650 (0.10), 5.699 (1.06), 6.468 (0.33), 6.481 (0.32), 6.783 (0.84), 6.840 (0.15), 7.345 (0.56), 7.371 (0.56), 7.976 (1.21), 8.225 (0.65), 8.238 (0.61), 9.152 (0.25).

Intermediate 420

N-{3,5-difluoro-4-[(3-{2-fluoro-6-[(propan-2-yl)oxy]phenyl}-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea

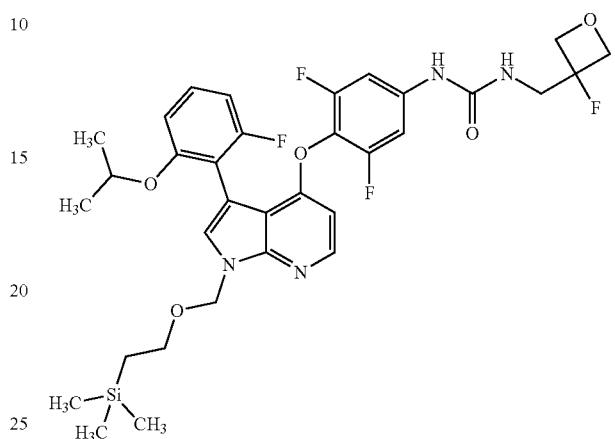

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 µmol, intermediate 401) and {2-fluoro-6-[(propan-2-yl)oxy]phenyl}boronic acid (CAS No: 870777-17-6, 98.8 mg, 499 µmol) were reacted in the presence of tetrakis (triphenylphosphine)palladium (0) (30.7 mg, 26.6 µmol) in a mixture of 1,4-dioxane (3.0 mL) and sodium carbonate aq. (330 µL, 2.0 M) to yield the title compound (55.0 mg, 25% yield).

LC-MS (Method 2): $R_t$=1.53 min; MS (ESIpos): m/z=675 [M+H]$^+$.

Intermediate 421

N-(3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea

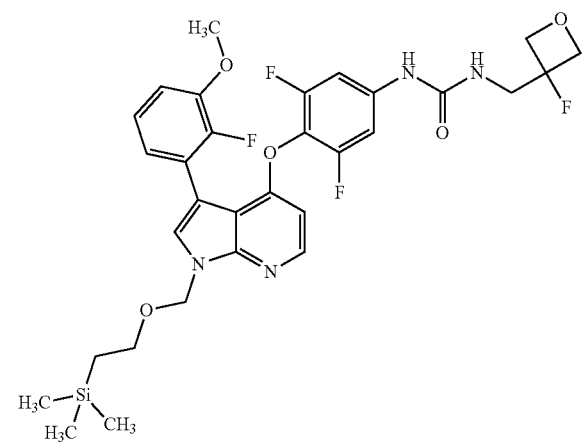 [SMILES: COc1cccc(-c2cn(COCC[Si](C)(C)C)c3nccc(Oc4c(F)cc(NC(=O)NCC5(F)COC5)cc4F)c23)c1F]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 μmol, intermediate 401) and (2-fluoro-3-methoxyphenyl)boronic acid (CAS No: 352303-67-4, 84.8 mg, 499 μmol) were reacted in the presence of tetrakis (triphenylphosphine)palladium (0) (30.7 mg, 26.6 μmol) in a mixture of 1,4-dioxane (3.0 mL) and sodium carbonate aq. (330 μL, 2.0 M) to yield the title compound (50.0 mg, 23% yield), after being purified by preparative HPLC.

LC-MS (Method 2): R$_t$=1.47 min; MS (ESIpos): m/z=647 [M+H]$^+$ $^1$H-NMR (400 MHz, DMSO-d6) δ [ppm]: −0.082 (16.00), 0.824 (0.54), 0.844 (0.72), 0.864 (0.55), 3.576 (0.56), 3.596 (0.75), 3.616 (0.85), 3.837 (3.72), 4.553 (0.16), 4.573 (0.81), 4.581 (0.74), 4.603 (0.28), 4.623 (0.80), 4.632 (0.76), 4.652 (0.13), 5.684 (1.42), 6.393 (0.45), 6.407 (0.43), 6.780 (0.16), 6.795 (0.30), 6.810 (0.14), 7.065 (0.10), 7.072 (0.13), 7.090 (0.33), 7.108 (0.68), 7.119 (1.15), 7.136 (0.35), 7.155 (0.09), 7.332 (0.72), 7.358 (0.72), 7.769 (0.89), 8.165 (0.77), 8.179 (0.70), 9.091 (0.51).

Intermediate 422

N-(4-{[3-(2-chloro-1-methyl-1H-imidazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

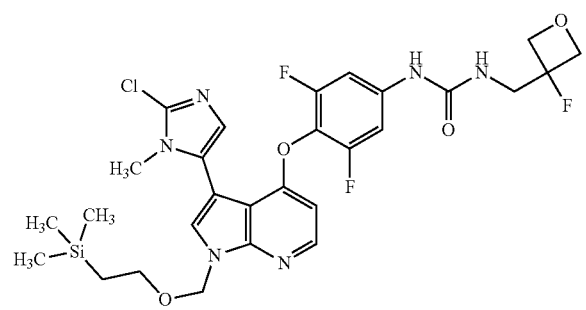 [SMILES: Cn1c(-c2cn(COCC[Si](C)(C)C)c3nccc(Oc4c(F)cc(NC(=O)NCC5(F)COC5)cc4F)c23)cnc1Cl]

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 332 μmol, intermediate 401) and (2-chloro-1-methyl-1H-imidazol-5-yl)boronic acid (CAS No: 1224884-61-0, 79.9 mg, 498 μmol) were reacted in the presence of tetrakis (triphenylphosphine)palladium (0) (30.7 mg, 26.6 μmol) in a mixture of sodium carbonate aq. (330 μL, 2.0 M) and 1,4-dioxane (3.0 mL) to yield the title compound (39.0 mg, 18% yield), after being purified by preparative HPLC.

LC-MS (Method 2): R$_t$=1.35 min; MS (ESIpos): m/z=637 [M+]$^+$ $^1$H-NMR (400 MHz, DMSO-d6) δ [ppm]: −0.092 (16.00), 0.820 (0.47), 0.840 (0.60), 0.860 (0.48), 3.511 (3.54), 3.573 (0.49), 3.594 (0.62), 3.613 (0.66), 3.631 (0.29), 3.668 (0.29), 3.683 (0.29), 4.554 (0.14), 4.574 (0.69), 4.582 (0.62), 4.605 (0.20), 4.625 (0.69), 4.632 (0.65), 4.653 (0.09), 5.681 (1.18), 6.437 (0.36), 6.451 (0.34), 6.826 (0.08), 6.842 (0.16), 6.857 (0.09), 6.960 (1.89), 7.357 (0.60), 7.383 (0.59), 7.837 (1.27), 8.198 (0.71), 8.212 (0.66), 9.160 (0.27).

Intermediate 423

N-(4-{[3-(3,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea

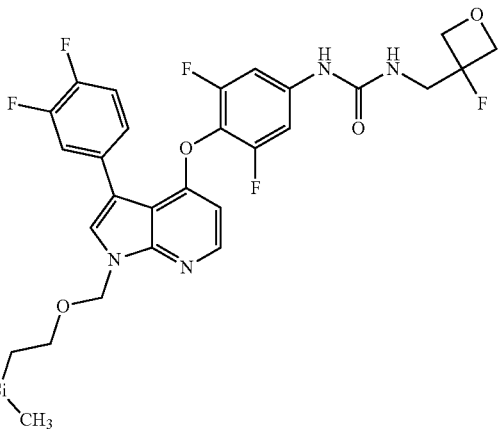

In analogy to intermediate 391, N-{4-[(3-bromo-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (200 mg, 333 μmol, intermediate 401) and (3,4-difluorophenyl)boronic acid (CAS No: 168267-41-2, 78.8 mg, 499 μmol) were reacted in the presence of tetrakis (triphenylphosphine)palladium (0) (30.7 mg, 26.6 μmol) in a mixture of sodium carbonate aq. (330 μL, 2.0 M) and 1,4-dioxane (3.0 mL) to yield the title compound (210 mg, 99% yield).

LC-MS (Method 2): R$_t$=1.54 min; MS (ESIpos): m/z=635 [M+H]$^+$.

Intermediate 424

O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate

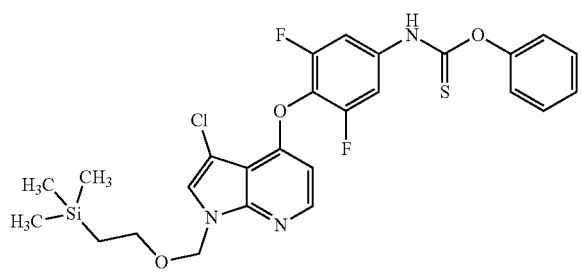

4-[(3-chloro-1-{[2-(trimethylsilyl)ethoxy]methyl}-1H-pyrrolo[2,3-b]pyridin-4-yl)oxy]-3,5-difluoroaniline (600 mg, 1.41 mmol, see ChemMedChem 2008, 3, p. 1893 ff., cpd 63) was dissolved in THF (9.0 mL) and pyridine (750 μL) and cooled down to 0° C. O-phenyl carbonochloridothioate (CAS No: 1005-56-7, 210 μL, 1.5 mmol) was added dropwise and the mixture allowed to warm up to room temperature for 2 h. The solvent was removed under vacuum and the crude product used in the following transformation without purification.

LC-MS (Method 1): $R_t$=1.68 min; MS (ESIpos): m/z=562 [M+H]$^+$.

Intermediate 425 tert-butyl {2-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]ethyl}carbamate

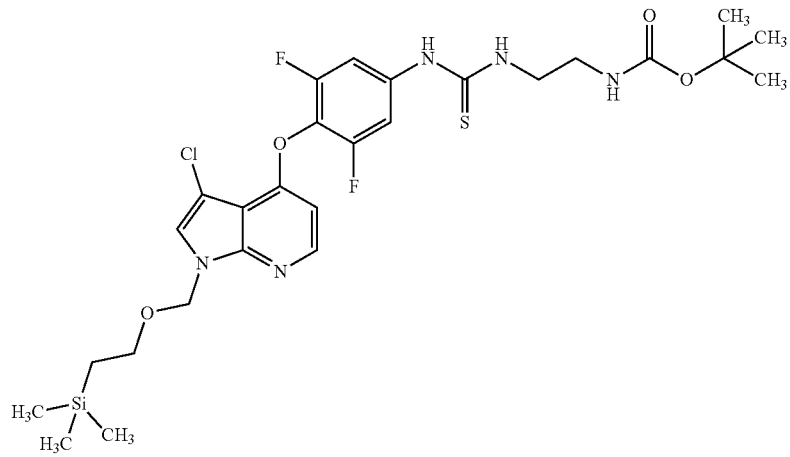 [SMILES: CC(C)(C)OC(=O)NCCNC(=S)Nc1cc(F)c(Oc2ccnc3c2c(Cl)cn3COCC[Si](C)(C)C)c(F)c1]

O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (396 mg, 704 µmol, intermediate 424) and tert-butyl (2-aminoethyl)carbamate (CAS No: 57260-73-8, 220 µL, 1.4 mmol) were dissolved in DMF (4.6 mL) under argon and stirred are 60° C. in a closed microwave vial until no more starting material could be detected by UPLC-MS. The solvent was then removed under vacuum and the residue filtered over silica to yield the title compound (286 mg, 61% yield), which was used in the following reaction with no further purification.

LC-MS (Method 1): $R_t$=1.58 min; MS (ESIneg): m/z=626 [M−H]$^−$

Intermediate 426 tert-butyl (2-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}ethyl)carbamate

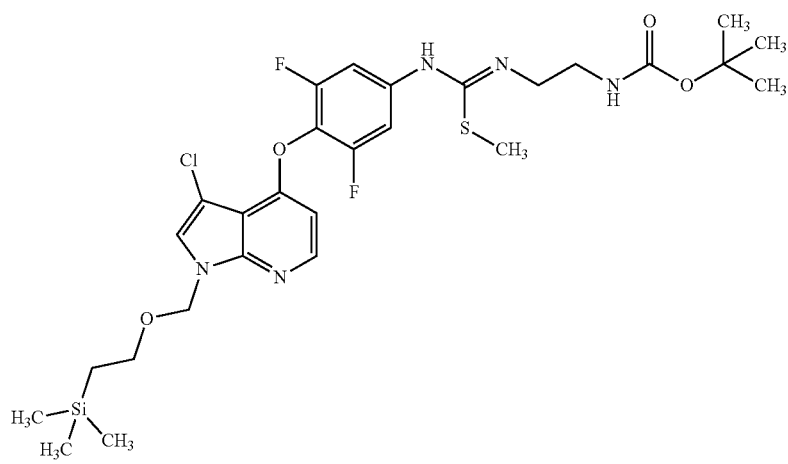 [SMILES: CS/C(=N\CCNC(=O)OC(C)(C)C)Nc1cc(F)c(Oc2ccnc3c2c(Cl)cn3COCC[Si](C)(C)C)c(F)c1]

tert-butyl {2-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]ethyl}carbamate (100 mg, 159 µmol, intermediate 425) was dissolved in acetone (1.0 µL) and methyl iodide (20 µL, 320 µmol) was added. The solution was stirred at room temperature until no more starting material could be detected by UPLC-MS. The solvent was then removed under vacuum, and the crude submitted to the following reaction with no purification.

LC-MS (Method 2): $R_t$=1.68 min; MS (ESIneg): m/z=640 [M+H]$^+$.

Intermediate 427 tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]propyl}carbamate

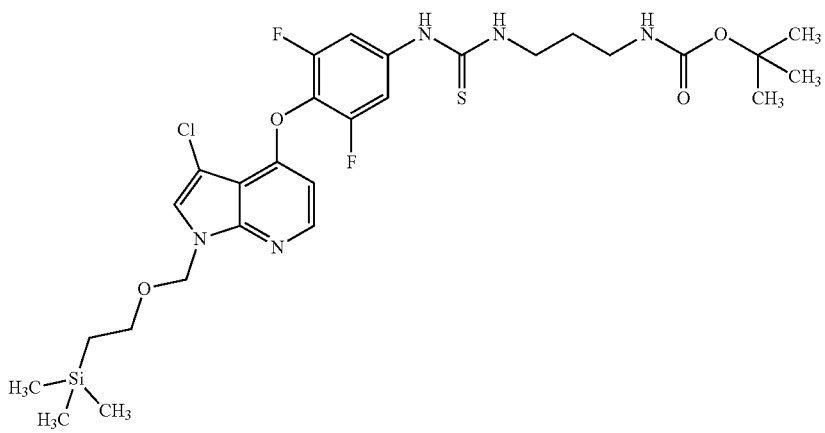 [SMILES: CC(C)(C)OC(=O)NCCCNC(=S)Nc1cc(F)c(Oc2ccnc3c2c(Cl)cn3COCC[Si](C)(C)C)c(F)c1]

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (396 mg, 704 µmol, intermediate 424) and tert-butyl (3-aminopropyl)carbamate (CAS No: 75178-96-0, 250 µL, 1.4 mmol) were stirred in DMF (4.6 mL) to yield the title compound (326 mg, 68% yield), which was used with no purification.

LC-MS (Method 1): $R_t$=1.59 min; MS (ESIneg): m/z=640 [M−H]$^-$

Intermediate 428 tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}propyl)carbamate

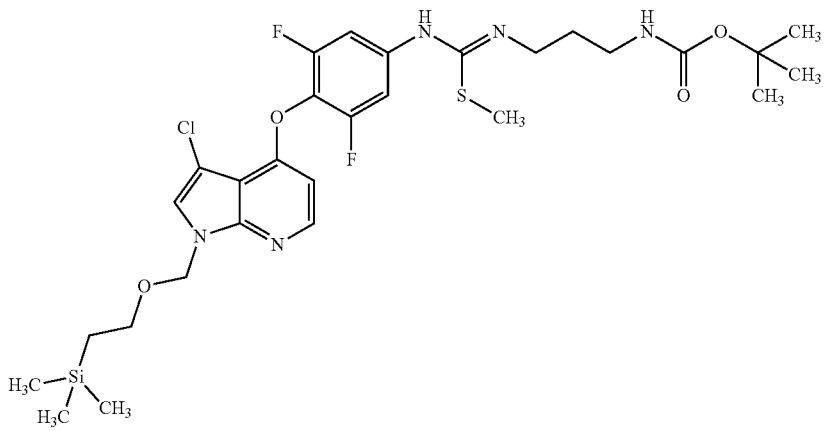 [SMILES: CS/C(=N\CCCNC(=O)OC(C)(C)C)Nc1cc(F)c(Oc2ccnc3c2c(Cl)cn3COCC[Si](C)(C)C)c(F)c1]

In analogy to Intermediate 426, tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]propyl}carbamate (150 mg, 234 µmol, intermediate 427) and methyl iodide (29 µL, 470 µmol) were stirred in acetone (1.5 mL) to yield the title compound, which was used as a crude.

LC-MS (Method 2): R$_t$=1.70 min; MS (ESIneg): m/z=654 [M−H]$^−$

Intermediate 429

(+/−)-tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2-methylpropyl}carbamate

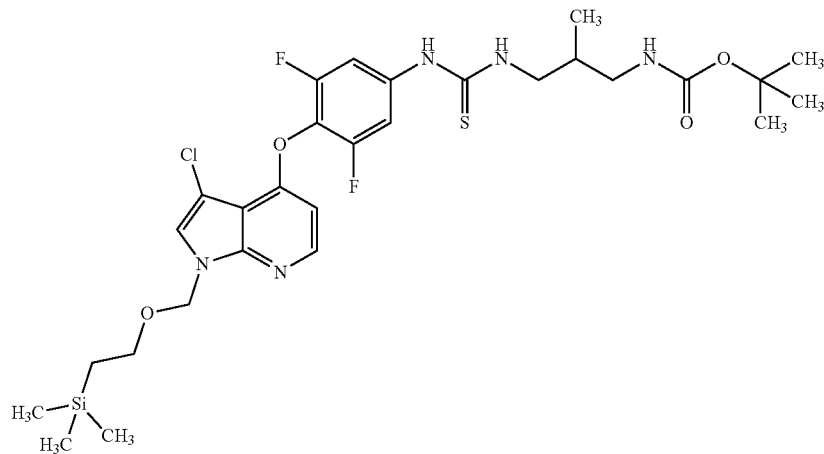 [SMILES: CC(CNC(=O)OC(C)(C)C)CNC(=S)Nc1cc(F)c(Oc2ccnc3c2c(Cl)cn3COCC[Si](C)(C)C)c(F)c1]

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (250 mg, 445 µmol, intermediate 424) and (+/−)-tert-butyl (3-amino-2-methylpropyl)carbamate (CAS No: 480452-05-9, 167 mg, 889 µmol) were stirred in DMF (4.5 mL) to yield the title compound (234 mg, 80% yield), which was used with no purification.

LC-MS (Method 2): R$_t$=1.63 min; MS (ESIneg): m/z=654 [M−H]$^−$

Intermediate 430

(+/−)-tert-butyl (3-{(ZE)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2-methylpropyl)carbamate

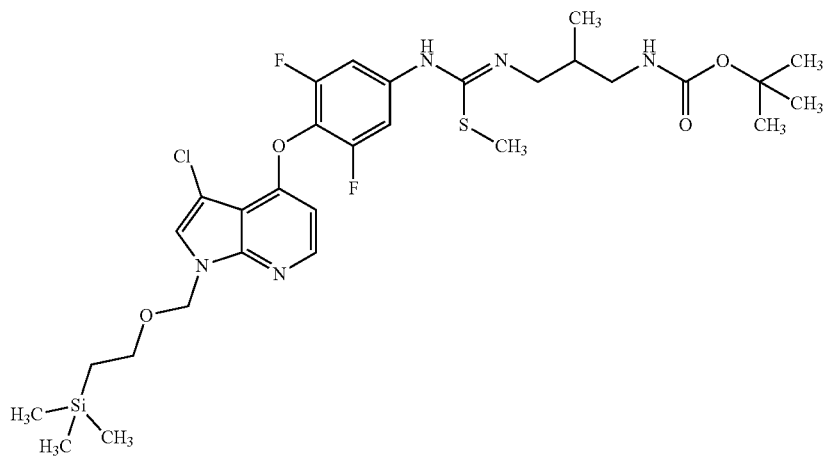 [SMILES: CS/C(=N\CC(C)CNC(=O)OC(C)(C)C)Nc1cc(F)c(Oc2ccnc3c2c(Cl)cn3COCC[Si](C)(C)C)c(F)c1]

407

In analogy to Intermediate 426, (+/−)-tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2-methylpropyl}carbamate (234 mg, 357 μmol, Intermediate 429) and methyl iodide (44 μL, 710 μmol) were stirred in acetone (2.0 mL) to yield the title compound, which was used as a crude.

LC-MS (Method 2): R$_t$=1.74 min; MS (ESIneg): m/z=668 [M−H]$^-$

Intermediate 431 tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2,2-dimethylpropyl}carbamate

408

Intermediate 432 tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2,2-dimethylpropyl)carbamate

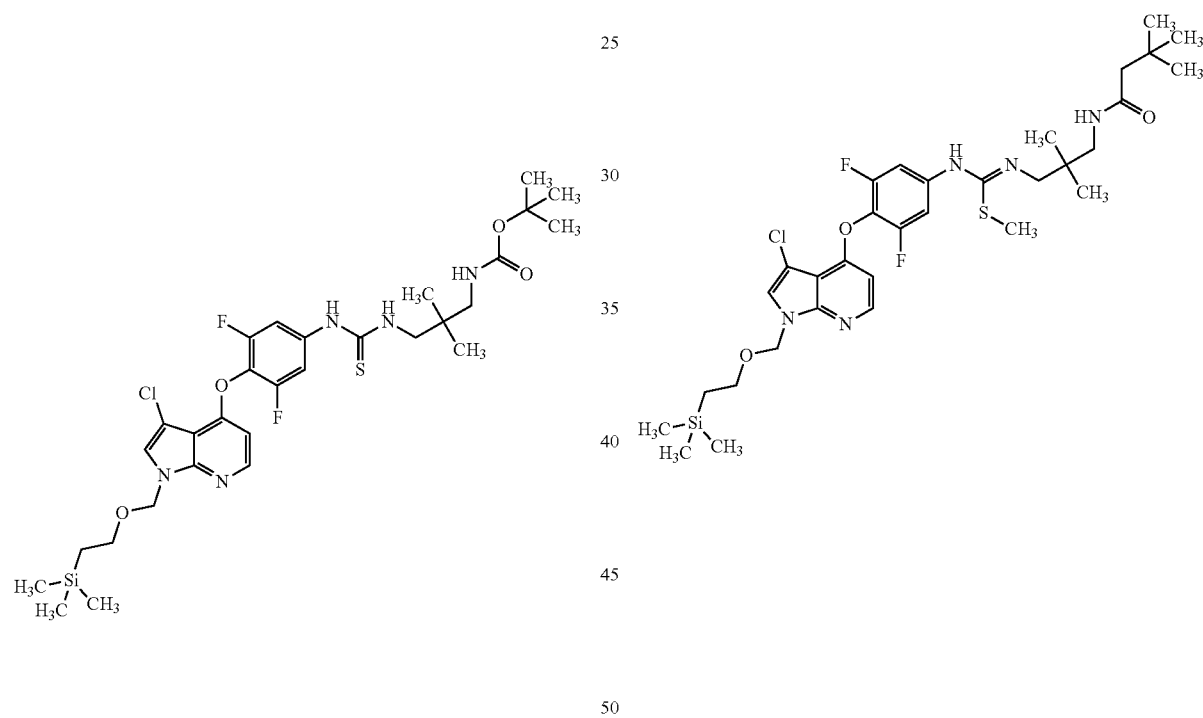

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (250 mg, 445 μmol, intermediate 424) and tert-butyl (3-amino-2,2-dimethylpropyl)carbamate (CAS No: 292606-35-0, 180 mg, 889 μmol) were stirred in DMF (4.5 mL) to yield the title compound (248 mg, 83% yield), which was used with no purification.

LC-MS (Method 2): R$_t$=1.67 min; MS (ESIneg): m/z=668 [M−H]$^-$

In analogy to Intermediate 426, tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2,2-dimethylpropyl}carbamate (248 mg, 370 μmol, Intermediate 431) and methyl iodide (46 μL, 740 μmol) were stirred in acetone (2.0 mL) to yield the title compound, which was used as a crude.

LC-MS (Method 2): R$_t$=1.79 min; MS (ESIneg): m/z=682 [M−H]$^-$

Intermediate 433 tert-butyl {4-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2-methylbutan-2-yl}carbamate

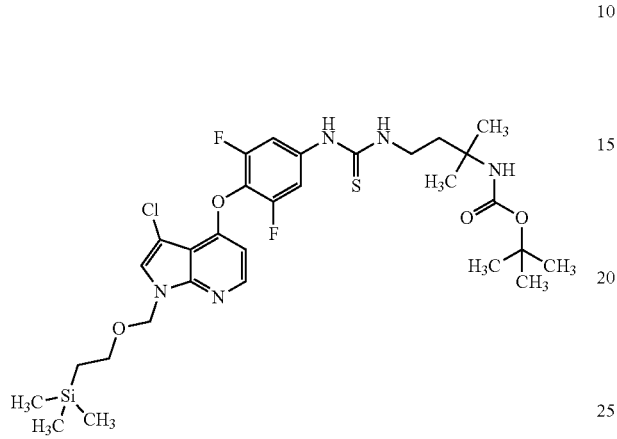

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (250 mg, 445 µmol, intermediate 424) and tert-butyl (4-amino-2-methylbutan-2-yl)carbamate-hydrogen chloride (1/1) (CAS No: 1179359-61-5, 212 mg, 889 µmol) were stirred in DMF (4.5 mL) and triethylamine (120 µL) to yield the title compound (223 mg, 75% yield), which was used with no purification.

LC-MS (Method 2): $R_t$=1.66 min; MS (ESIneg): m/z=668 [M−H]⁻

Intermediate 434 tert-butyl (4-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2-methylbutan-2-yl)carbamate

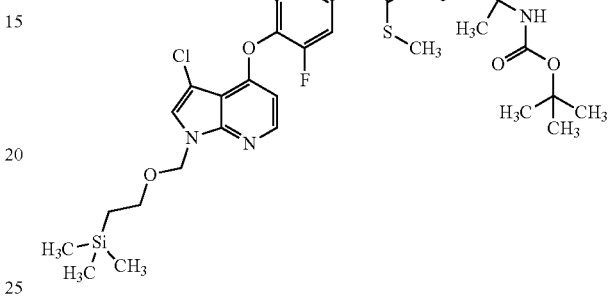

In analogy to Intermediate 426, tert-butyl {4-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2-methylbutan-2-yl}carbamate (223 mg, 333 µmol, Intermediate 433) and methyl iodide (41 µL, 670 µmol) were stirred in acetone (2.0 mL) to yield the title compound, which was used as a crude.

LC-MS (Method 2): $R_t$=1.76 min; MS (ESIneg): m/z=682 [M−H]⁻

Intermediate 435 tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2,2-difluoropropyl}carbamate

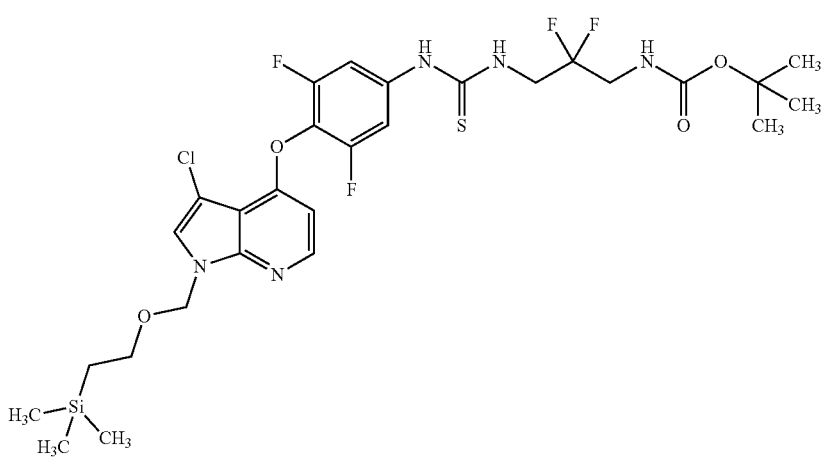 [SMILES: CC(C)(C)OC(=O)NCC(F)(F)CNC(=S)Nc1cc(F)c(Oc2ccnc3c2c(Cl)cn3COCC[Si](C)(C)C)c(F)c1]

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (396 mg, 704 µmol, intermediate 424) and tert-butyl (3-amino-2,2-difluoropropyl)carbamate (CAS No: 1044675-84-4, 296 mg, 1.41 mmol) were stirred in DMF (4.6 mL) to yield the title compound (349 mg, 69% yield), which was used with no purification.

LC-MS (Method 1): $R_t$=1.62 min; MS (ESIneg): m/z=676 [M−H]⁻

Intermediate 436 tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2,2-difluoropropyl)carbamate

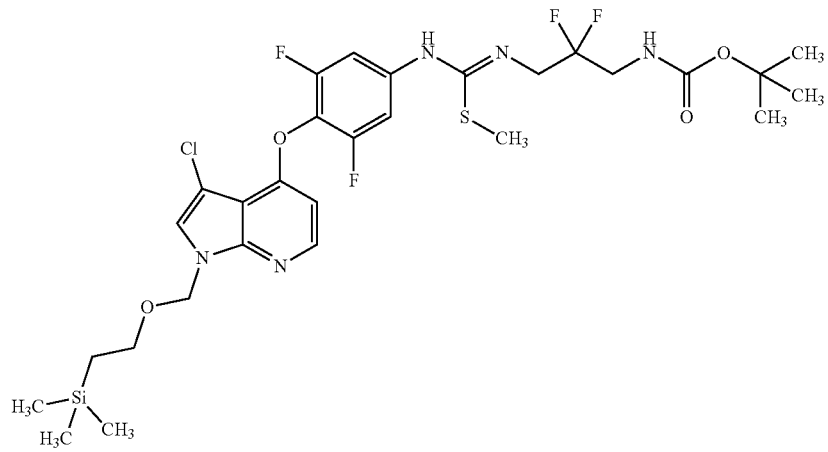 [SMILES: CS/C(=N\CC(F)(F)CNC(=O)OC(C)(C)C)Nc1cc(F)c(Oc2ccnc3c2c(Cl)cn3COCC[Si](C)(C)C)c(F)c1]

In analogy to Intermediate 426, tert-butyl {3-[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]-2,2-difluoropropyl}carbamate (345 mg, 509 µmol, Intermediate 435) and methyl iodide (63 µL, 1.0 mmol) were stirred in acetone (3.5 mL) to yield the title compound, which was used as a crude.

LC-MS (Method 2): $R_t$=1.71 min; MS (ESIneg): m/z=690 [M−H]⁻

Intermediate 437 tert-butyl [(1-{[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]methyl}cyclopropyl)methyl]carbamate

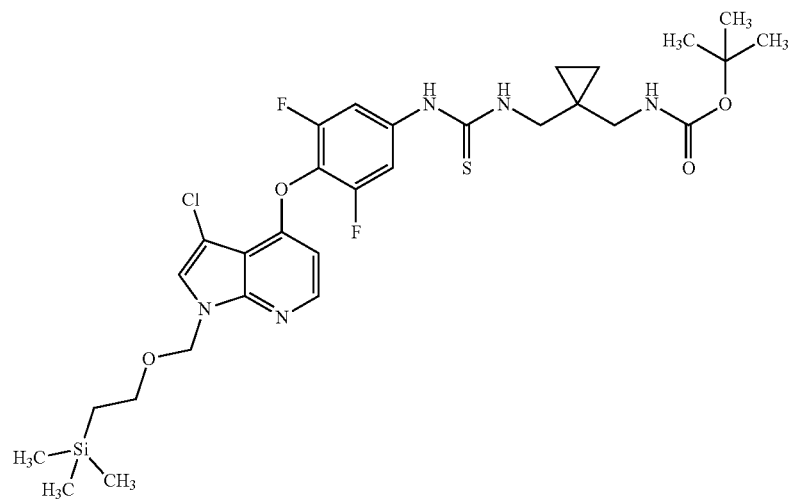 [SMILES: CC(C)(C)OC(=O)NCC1(CNC(=S)Nc2cc(F)c(Oc3ccnc4c3c(Cl)cn4COCC[Si](C)(C)C)c(F)c2)CC1]

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (264 mg, 470 μmol, intermediate 424) and tert-butyl {[1-(aminomethyl)cyclopropyl]methyl}carbamate (CAS No: 1147109-42-9, 188 mg, 939 μmol) were stirred in DMF (3.1 mL) to yield the title compound (261 mg, 79% yield), which was used with no purification.

LC-MS (Method 2): R$_t$=1.66 min; MS (ESIneg): m/z=666 [M–H]$^-$

Intermediate 438 tert-butyl {[1-({(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}methyl)cyclopropyl]methyl}carbamate

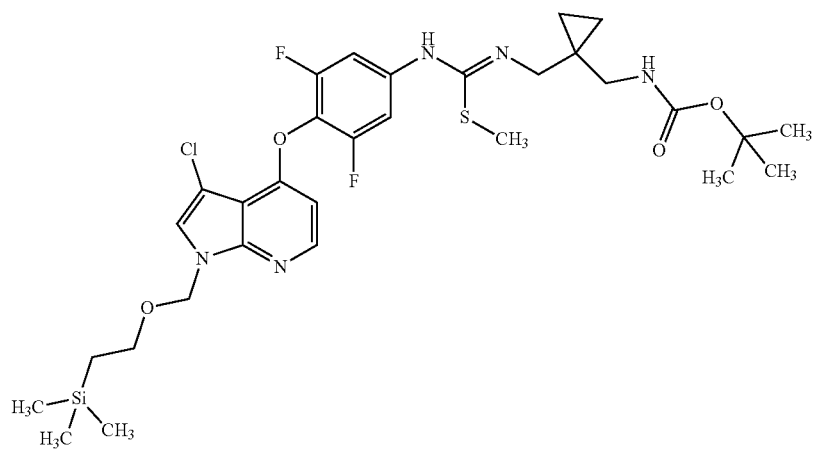 [SMILES: CS/C(=N\CC1(CNC(=O)OC(C)(C)C)CC1)Nc1cc(F)c(Oc2ccnc3c2c(Cl)cn3COCC[Si](C)(C)C)c(F)c1]

In analogy to Intermediate 426, tert-butyl [(1-{[({4-[(3-chloro-1-{[2-(trimethylsilyl)ethoxy]methyl}-1H-pyrrolo[2,3-b]pyridin-4-yl)oxy]-3,5-difluorophenyl}carbamothioyl)amino]methyl}cyclopropyl)methyl]carbamate (266 mg, 398 μmol, Intermediate 437) and methyl iodide (50 μL, 800 μmol) were stirred in acetone (2.6 mL) to yield the title compound, which was used as a crude.

LC-MS (Method 2): R$_t$=1.77 min; MS (ESIneg): m/z=680 [M–H]$^-$

Intermediate 439

O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate

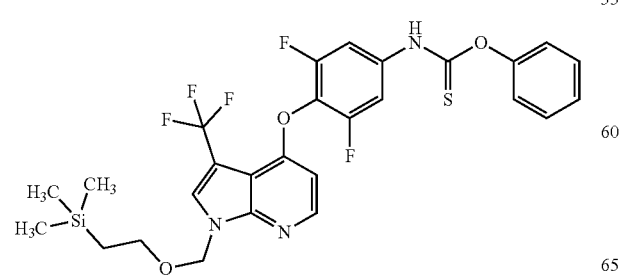

In analogy to intermediate 424, 3,5-difluoro-4-{[3-(trifluoromethyl)-1-{[2-(trimethylsilyl)ethoxy]methyl}-1H-pyrrolo[2,3-b]pyridin-4-yl]oxy}aniline (700 mg, 1.52 mmol, see *Synthesis* 2007, page 251-258, *Org. Process Res. Dev.* 2010, page 168-173) was stirred with O-phenyl carbonochloridothioate (CAS No: 1005-56-7, 230 µL, 1.7 mmol) and pyridine (810 µL) in THF (9.7 mL) to yield the title compound, which was used in the following reaction as a crude.

Intermediate 440 tert-butyl (3-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}-2,2-dimethylpropyl)carbamate

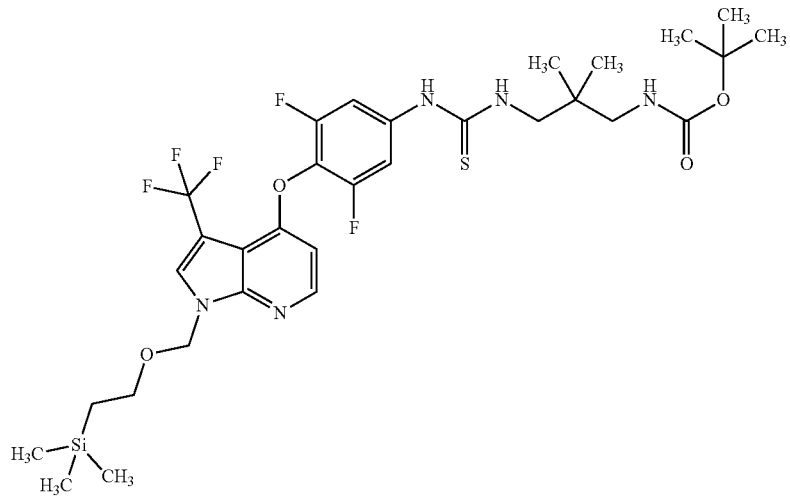 [SMILES: CC(C)(CNC(=O)OC(C)(C)C)CNC(=S)Nc1cc(F)c(Oc2ccnc3c2c(C(F)(F)F)cn3COCC[Si](C)(C)C)c(F)c1]

In analogy to intermediate 425, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (151 mg, 253 µmol, Intermediate 439) and tert-butyl (3-amino-2,2-dimethylpropyl)carbamate (CAS no: 292606-35-0,103 mg, 507 µmol) were stirred in DMF (1.7 mL) to yield the title compound (65.4 mg, 35% yield), which was used with no purification.

LC-MS (Method 2): $R_t$=1.68 min; MS (ESIneg): m/z=702 [M+H]$^+$.

Intermediate 441 tert-butyl (3-{(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}-2,2-dimethylpropyl)carbamate

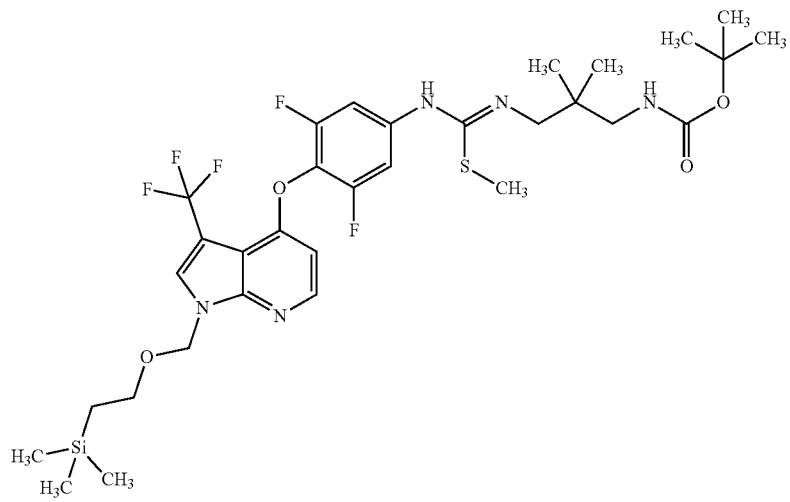 [SMILES: CS/C(=N\CC(C)(C)CNC(=O)OC(C)(C)C)Nc1cc(F)c(Oc2ccnc3c2c(C(F)(F)F)cn3COCC[Si](C)(C)C)c(F)c1]

In analogy to Intermediate 426, tert-butyl (3-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}-2,2-dimethylpropyl)carbamate (63.0 mg, 89.5 μmol, Intermediate 440) and methyl iodide (11 μL, 180 μmol) were stirred in acetone (570 μL) to yield the title compound, which was used as a crude.

LC-MS (Method 2): $R_t$=1.81 min; MS (ESIneg): m/z=716 [M−H]⁻

Intermediate 442 tert-butyl (4-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}-2-methylbutan-2-yl)carbamate

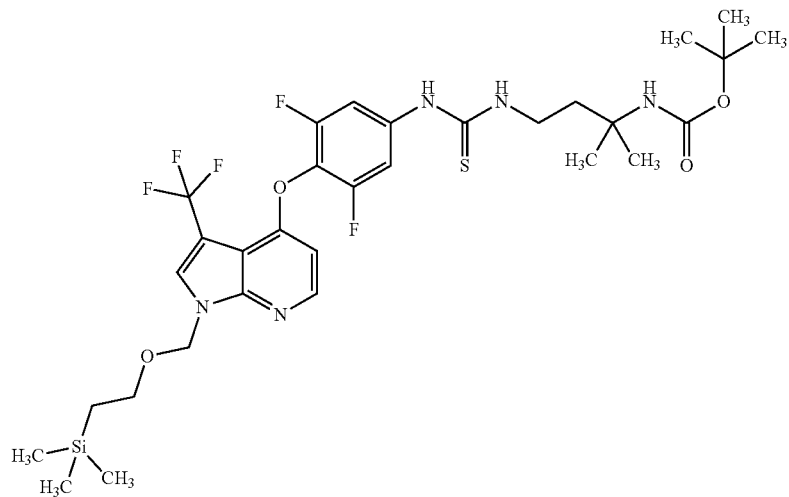 [SMILES: CC(C)(CCNC(=S)Nc1cc(F)c(Oc2ccnc3c2c(C(F)(F)F)cn3COCC[Si](C)(C)C)c(F)c1)NC(=O)OC(C)(C)C]

In analogy to intermediate 425, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (151 mg, 253 μmol, Intermediate 439) and 3-[(tert-butoxycarbonyl)amino]-3-methylbutan-1-aminium chloride (CAS No: 1179359-61-5, 121 mg, 507 μmol) were stirred in DMF (1.7 mL, 22 mmol) with N,N-diisopropylethylamine (93 μL) to yield the title compound (140 mg, 75% yield), which was used with no purification.

LC-MS (Method 2): $R_t$=1.67 min; MS (ESIneg): m/z=702 [M+H]⁺.

Intermediate 443 tert-butyl (4-{(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}-2-methylbutan-2-yl)carbamate

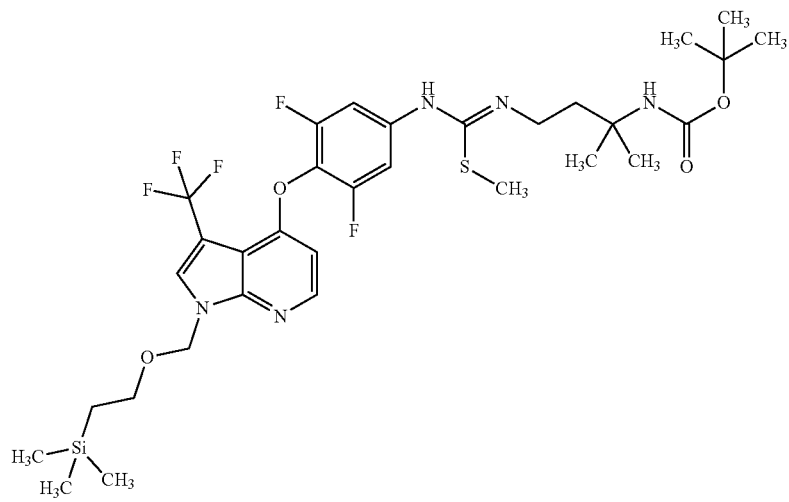 [SMILES: CS/C(=N\CCC(C)(C)NC(=O)OC(C)(C)C)Nc1cc(F)c(Oc2ccnc3c2c(C(F)(F)F)cn3COCC[Si](C)(C)C)c(F)c1]

In analogy to Intermediate 426, tert-butyl (4-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}-2-methylbutan-2-yl)carbamate (138 mg, 196 μmol, Intermediate 442) and methyl iodide (24 μL, 390 μmol) were stirred in acetone (1.3 mL) to yield the title compound, which was used as a crude.

LC-MS (Method 2): $R_t$=1.78 min; MS (ESIneg): m/z=716 [M–H]⁻

Intermediate 444 tert-butyl {[1-({[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}methyl)cyclopropyl]methyl}carbamate

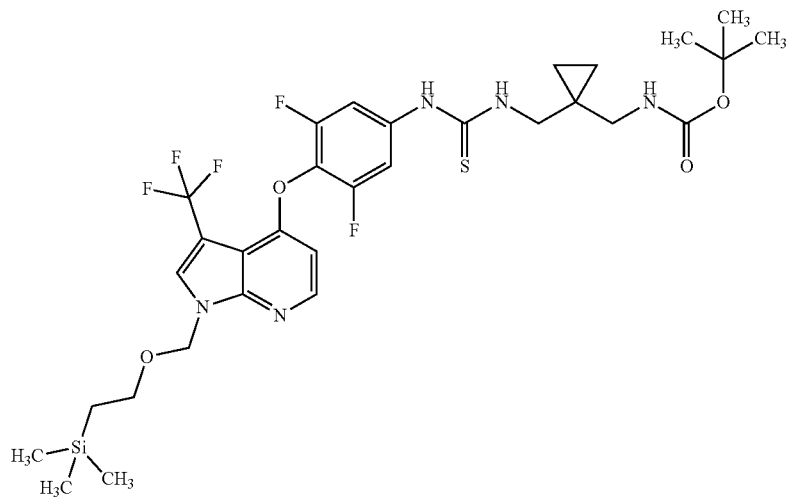 [SMILES: CC(C)(C)OC(=O)NCC1(CNC(=S)Nc2cc(F)c(Oc3ccnc4c3c(C(F)(F)F)cn4COCC[Si](C)(C)C)c(F)c2)CC1]

In analogy to intermediate 425, O-phenyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioate (151 mg, 253 µmol, Intermediate 439) and tert-butyl {[1-(aminomethyl)cyclopropyl]methyl}carbamate (CAS No: 1147109-42-9, 102 mg, 507 µmol) were stirred in DMF (1.7 mL) to yield the title compound (110 mg, 59% yield), which was used with no purification.

LC-MS (Method 2): R$_t$=1.66 min; MS (ESIneg): m/z=701 [M−H]$^-$

Intermediate 445 tert-butyl {[1-({(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}methyl)cyclopropyl]methyl}carbamate

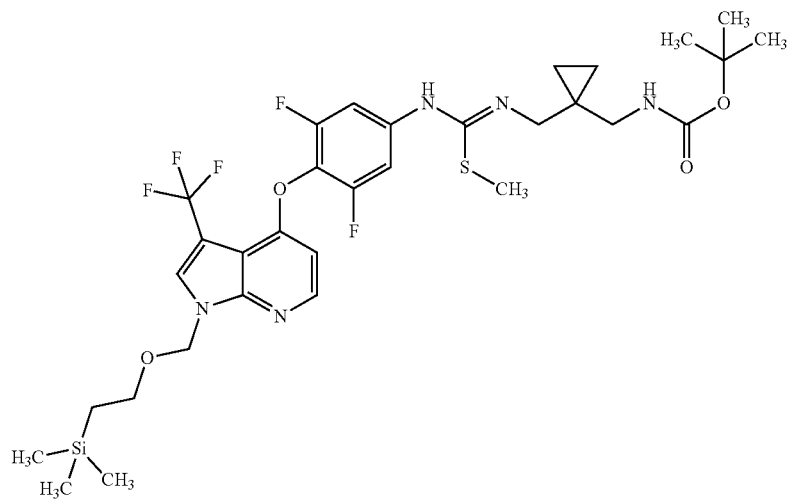 [SMILES: CS/C(=N\CC1(CNC(=O)OC(C)(C)C)CC1)Nc1cc(F)c(Oc2ccnc3c2c(C(F)(F)F)cn3COCC[Si](C)(C)C)c(F)c1]

In analogy to Intermediate 426, tert-butyl {[1-({[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamothioyl]amino}methyl)cyclopropyl]methyl}carbamate (107 mg, 152 µmol, Intermediate 444) and methyl iodide (19 µL, 300 µmol) were stirred in acetone (980 µL) to yield the title compound, which was used as a crude.

LC-MS (Method 2): R$_t$=1.77 min; MS (ESIneg): m/z=714 [M−H]$^-$

Intermediate 446

O-phenyl {4-[(3-bromo-1-{[2-(trimethylsilyl)ethoxy]methyl}-1H-pyrrolo[2,3-b]pyridin-4-yl)oxy]-3,5-difluorophenyl}carbamothioate

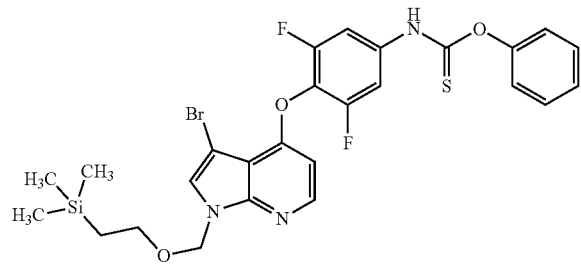 [SMILES: C[Si](C)(C)CCOCn1cc(Br)c2c(Oc3c(F)cc(NC(=S)Oc4ccccc4)cc3F)ccnc21]

4-[(3-bromo-1-{[2-(trimethylsilyl)ethoxy]methyl}-1H-pyrrolo[2,3-b]pyridin-4-yl)oxy]-3,5-difluoroaniline (900 mg, 1.91 mmol, Intermediate 21) was dissolved in THF (6.4 mL) and pyridine (6.4 mL) and cooled down to 0° C. O-phenyl carbonochloridothioate (CAS No: 1005-56-7, 210 µL, 1.5 mmol) was added dropwise and the mixture allowed to warm up to room temperature for 2 h. The solvent was removed under vacuum and the crude product used in the following transformation without purification.

Intermediate 447 tert-butyl {3-[({4-[(3-bromo-1-{[2-(trimethylsilyl)ethoxy]methyl}-1H-pyrrolo[2,3-b]pyridin-4-yl)oxy]-3,5-difluorophenyl}carbamothioyl)amino]propyl}carbamate

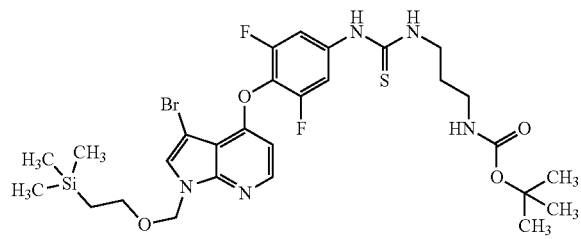 [SMILES: CC(C)(C)OC(=O)NCCCNC(=S)Nc1cc(F)c(Oc2ccnc3c2c(Br)cn3COCC[Si](C)(C)C)c(F)c1]

In analogy to intermediate 425, O-phenyl {4-[(3-bromo-1-{[2-(trimethylsilyl)ethoxy]methyl}-1H-pyrrolo[2,3-b]pyridin-4-yl)oxy]-3,5-difluorophenyl}carbamothioate (4.50 g, 7.42 mmol, Intermediate 446) and tert-butyl (3-aminopropyl)carbamate (CAS No: 75178-96-0, 2.6 mL, 15 mmol) were stirred in DMF (50 mL) to yield the title compound (2.22 g, 44% yield), which was used with no purification.

LC-MS (Method 2): $R_t$=1.57 min; MS (ESIpos): m/z=686 [M+H]$^+$

Intermediate 448 tert-butyl (3-{(Z/E)-[{4-[(3-bromo-1-{[2-(trimethylsilyl)ethoxy]methyl}-1H-pyrrolo[2,3-b]pyridin-4-yl)oxy]-3,5-difluoroanilino}(methylsulfanyl)methylidene]amino}propyl)carbamate

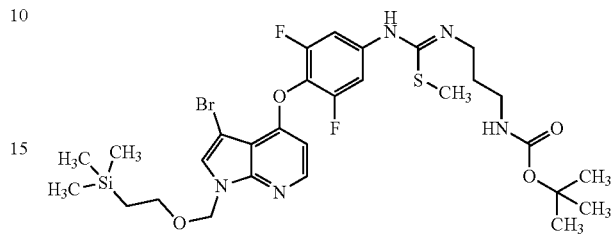

In analogy to Intermediate 426, tert-butyl {3-[({4-[(3-bromo-1-{[2-(trimethylsilyl)ethoxy]methyl}-1H-pyrrolo[2,3-b]pyridin-4-yl)oxy]-3,5-difluorophenyl}carbamothioyl)amino]propyl}carbamate (100 mg, 146 µmol, Intermediate 447) and methyl iodide (18 µL, 290 µmol) were stirred in acetone (1.5 mL) to yield the title compound, which was used as a crude.

LC-MS (Method 2): $R_t$=1.71 min; MS (ESIneg): m/z=698 [M−H]$^-$

Intermediate 449 methyl 4-(4-amino-2,6-difluorophenoxy)-1-{[2-(trimethylsilyl)ethoxy]methyl}-1H-pyrrolo[2,3-b]pyridine-3-carboxylate

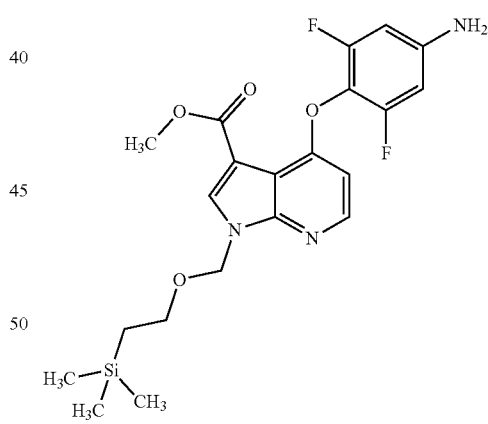

4-[(3-bromo-1-{[2-(trimethylsilyl)ethoxy]methyl}-1H-pyrrolo[2,3-b]pyridin-4-yl)oxy]-3,5-difluoroaniline (20.5 g, 43.5 mmol, Intermediate 21) was dissolved in 660 mL of a 10:1 mixture of methanol and tetrahydrofurane, and dichloromethane [1,1'-Bis(diphenylphosphino)ferrocene] dichloropalladium(II) (1:1) (3.55 g, 4.35 mmol) and triethylamine (15 mL, 110 mmol) were added. The system was purged with carbon monoxide (×3) and the final pressure set to 12 bar. The reaction was stirred for 30 mins at room temperature, and afterwards the pressure was set to 16.3 bar. The system was stirred at 100° C. for 36 h. The crude was then filtered and the solvent evaporated. The remaining residue

425 was purified by silica gel chromatography using a Biotage system to yield the title compound (14.45 g, 74% yield).

LC-MS (Method 2): $R_t$=1.40 min; MS (ESIpos): m/z=450 [M+H]$^+$ $^1$H-NMR (400 MHz, DMSO-d6) δ [ppm]: −0.096 (16.00), 0.804 (0.54), 0.825 (0.74), 0.845 (0.57), 3.539 (0.52), 3.559 (0.69), 3.579 (0.53), 3.772 (3.62), 5.675 (1.53), 5.784 (0.89), 6.375 (0.67), 6.402 (0.70), 6.479 (0.41), 6.493 (0.47), 8.192 (0.76), 8.206 (0.74), 8.382 (1.42).

Intermediate 450 methyl 4-{2,6-difluoro-4-[(phenoxycarbonyl)amino]phenoxy}-1-{[2-(trimethylsilyl)ethoxy]methyl}-1H-pyrrolo[2,3-b]pyridine-3-carboxylate

426

Intermediate 451 methyl 4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylate

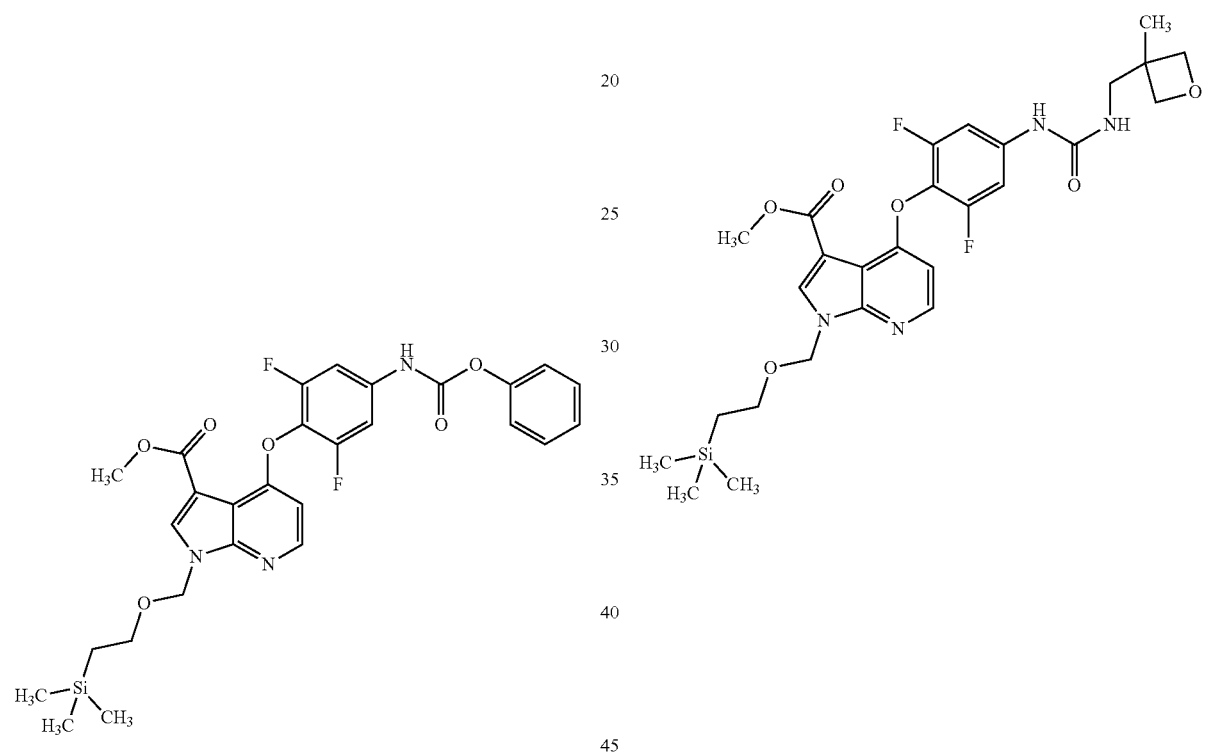

In analogy to intermediate 424, methyl 4-(4-amino-2,6-difluorophenoxy)-1-{[2-(trimethylsilyl)ethoxy]methyl}-1H-pyrrolo[2,3-b]pyridine-3-carboxylate (3.00 g, 6.67 mmol, BBUC9156-6) was stirred with phenyl carbonochloridate (CAS No: 1885-14-9, 1.7 mL, 13 mmol) and THF (46 mL) in pyridine (22 mL) to yield the title compound, which was used in the following reaction as a crude.

LC-MS (Method 2): $R_t$=1.61 min; MS (ESIneg): m/z=568 [M−H]$^−$

Methyl 4-{2,6-difluoro-4-[(phenoxycarbonyl)amino]phenoxy}-1-{[2-(trimethylsilyl)ethoxy]methyl}-1H-pyrrolo[2,3-b]pyridine-3-carboxylate (3.50 g, 6.14 mmol, Intermediate 450) and 1-(3-methyloxetan-3-yl)methanamine (CAS No: 153209-97-3, 746 mg, 7.37 mmol) were dissolved in DMF (60 mL) and stirred at 60° C. under argon in a sealed microwave vial until no more starting material could be detected by UPLC-MS. The solvent was removed under vacuum and the residue purified by silica gel chromatography using a Biotage system to yield the title compound (2.25 g, 64% yield).

LC-MS (Method 2): $R_t$=1.37 min; MS (ESIpos): m/z=577 [M+H]$^+$ $^1$H-NMR (400 MHz, DMSO-d6) δ [ppm]: −0.097 (16.00), 0.806 (0.46), 0.826 (0.57), 0.847 (0.47), 1.235 (2.72), 3.295 (0.67), 3.310 (0.71), 3.545 (0.47), 3.565 (0.59), 3.585 (0.45), 3.778 (3.25), 4.202 (1.02), 4.216 (1.12), 4.379 (1.00), 4.393 (0.86), 5.686 (1.21), 6.527 (0.35), 6.540 (0.35), 6.712 (0.13), 6.727 (0.26), 6.742 (0.13), 7.376 (0.58), 7.403 (0.58), 8.204 (0.72), 8.218 (0.68), 8.417 (1.32), 9.028 (0.42).

Intermediate 452

(+/−)-4-(2,6-difluoro-4-{[5-(hydroxymethyl)-5-methyl-5,6-dihydro-4H-1,3-oxazin-2-yl]amino}phenoxy)-1-{[2-(trimethylsilyl)ethoxy]methyl}-1H-pyrrolo[2,3-b]pyridine-3-carboxylic Acid

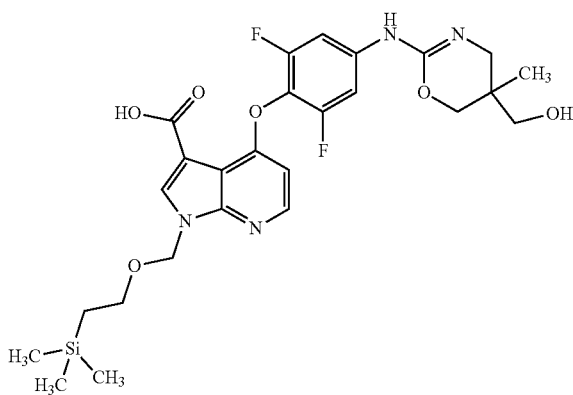 [SMILES: CC1(CO)CN=C(Nc2cc(F)c(Oc3ccnc4c3c(C(=O)O)cn4COCC[Si](C)(C)C)c(F)c2)OC1]

Methyl-4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylate (2.06 g, 3.56 mmol, Intermediate 451) was dissolved in methanol (27 mL) and THF (70 mL), and lithium hydroxide aq. (21 mL, 1.0 M) was added. The mixture was stirred overnight at room temperature and quenched with 200 mL of a 1M solution of citric acid. The crude was diluted with water, extracted with ethyl acetate (×2), and the organic phases washed with water and brine, dried over sodium sulfate. The solvent was removed under vacuum and the product used as a crude in the subsequent reaction.

LC-MS (Method 1): $R_t$=0.99 min; MS (ESIneg): m/z=561 [M−H]⁻

Intermediate 453

(+/−)—N'-acetyl-4-(2,6-difluoro-4-{5-(hydroxymethyl)-5-methyl-5,6-dihydro-4H-1,3-oxazin-2-yl]amino}phenoxy)-1-{[2-(trimethylsilyl)ethoxy]methyl}-1H-pyrrolo[2,3-b]pyridine-3-carbohydrazide

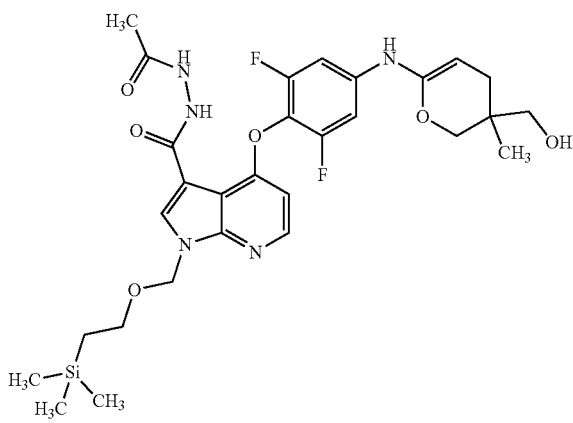 [SMILES: CC(=O)NNC(=O)c1cn(COCC[Si](C)(C)C)c2nccc(Oc3c(F)cc(NC4=CCC(C)(CO)CO4)cc3F)c12]

(+/−)-4-(2,6-difluoro-4-{5-(hydroxymethyl)-5-methyl-5,6-dihydro-4H-1,3-oxazin-2-yl]amino}phenoxy)-1-{[2-(trimethylsilyl)ethoxy]methyl}-1H-pyrrolo[2,3-b]pyridine-3-carboxylic acid (400 mg, 640 μmol, Intermediate 452) was dissolved in DMF (1.8 mL) and N,N-diisopropylethylamine (270 μL) was added. A solution of acetohydrazide (CAS No: 1068-57-1, 56.9 mg, 768 μmol) in 0.5 mL of DMF and a solution of (1-Cyano-2-ethoxy-2-oxoethylidenaminooxy)-dimethylamino-morpholino-carbenium hexafluorophosphate (329 mg, 768 μmol) also in 0.5 mL of DMF were added simultaneously to the reaction, and the mixture was stirred overnight at room temperature. The crude was then diluted with water and extracted with ethyl acetate (×2). The organic phase was washed with brine, dried over sodium sulfate, filtered and evaporated. The crude product was filtered through silica, and the residue used in the following reaction without further purification.

LC-MS (Method 2): $R_t$=1.13 min; MS (ESIpos): m/z=619 [M+H]⁺

Intermediate 454

(+/−)-[2-(3,5-difluoro-4-{[3-(5-methyl-1,3,4-oxadiazol-2-yl)-1-{[2-(trimethylsilyl)ethoxy]methyl}-1H-pyrrolo[2,3-b]pyridin-4-yl]oxy}anilino)-5-methyl-5,6-dihydro-4H-1,3-oxazin-5-yl]methanol

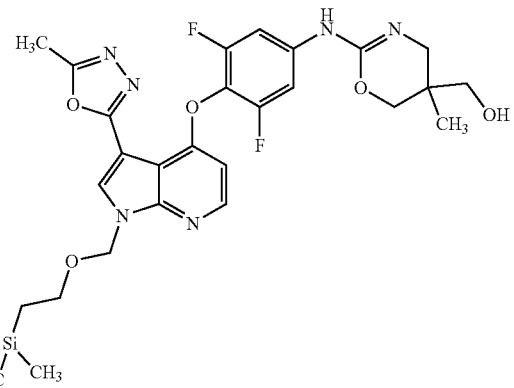

(+/−)—N'-acetyl-4-(2,6-difluoro-4-{5-(hydroxymethyl)-5-methyl-5,6-dihydro-4H-1,3-oxazin-2-yl]amino}phenoxy)-1-{[2-(trimethylsilyl)ethoxy]methyl}-1H-pyrrolo[2,3-b]pyridine-3-carbohydrazide (250 mg, 404 μmol, Intermediate 453), triphenylphosphine (159 mg, 606 μmol), triethylamine (560 μL) and tetrachloromethane (97 μL, 1.0 mmol) were dissolved in dichloromethane (3.3 mL) under argon, and stirred overnight at 50° C. The solvent was removed under vacuum and the crude filtered over silica and used in the following reaction with no further purification.

LC-MS (Method 2): $R_t$=1.26 min; MS (ESIpos): m/z=601 [M+H]⁺

Intermediate 455

4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylic Acid

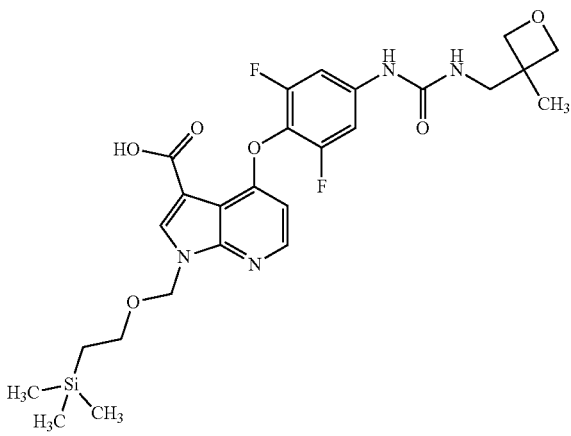 [SMILES: CC1(CNC(=O)Nc2cc(F)c(Oc3ccnc4c3c(C(=O)O)cn4COCC[Si](C)(C)C)c(F)c2)COC1]

Methyl 4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylate (890 mg, 1.54 mmol, Intermediate 451) was dissolved in methanol (12 mL) and THF (30 mL), and lithium hydroxide aq. (9.3 mL, 1.0 M) was added. The mixture was stirred overnight at room temperature and quenched with 50 mL of a 1M solution of citric acid. The crude was diluted with water, extracted with ethyl acetate (×2), and the organic phases washed with water and brine, dried over sodium sulfate. The solvent was removed under vacuum and the product used as a crude in the subsequent reaction.

LC-MS (Method 1): $R_t$=1.24 min; MS (ESIneg): m/z=561 [M–H]$^-$

Intermediate 456

N-{4-[(3-[2-(cyclopropanecarbonyl)hydrazinecarbonyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

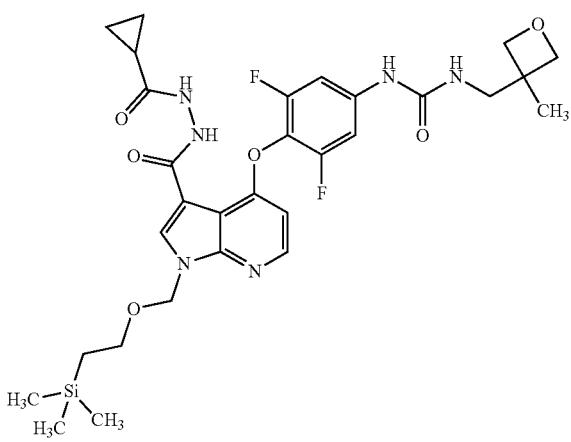 [SMILES: CC1(CNC(=O)Nc2cc(F)c(Oc3ccnc4c3c(C(=O)NNC(=O)C3CC3)cn4COCC[Si](C)(C)C)c(F)c2)COC1]

In analogy to Intermediate 453, 4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylic acid (180 mg, 320 µmol, Intermediate 455) was allowed to react with cyclopropanecarbohydrazide (CAS No: 6952-93-8, 38.4 mg, 384 µmol) in the presence of N,N-diisopropylethylamine (130 µL) and (1-Cyano-2-ethoxy-2-oxoethylidenaminooxy)dimethylamino-morpholino-carbenium hexafluorophosphate (164 mg, 384 µmol) in DMF (3.6 mL) to afford the title compound (87.5 mg, 40% yield), which was filtered through silica and used in the following step with no further purification.

LC-MS (Method 2): $R_t$=1.22 min; MS (ESIpos): m/z=645 [M+H]$^+$ $^1$H-NMR (400 MHz, DMSO-d6) δ [ppm]: −0.082 (16.00), 0.697 (0.33), 0.704 (0.64), 0.708 (0.60), 0.716 (0.61), 0.721 (0.56), 0.724 (0.61), 0.745 (0.54), 0.826 (0.58), 0.846 (0.75), 0.866 (0.61), 1.666 (0.05), 1.679 (0.12), 1.685 (0.12), 1.697 (0.20), 1.710 (0.13), 1.715 (0.11), 1.729 (0.05), 3.296 (0.94), 3.311 (1.03), 3.551 (0.57), 3.570 (0.74), 3.590 (0.57), 4.202 (1.46), 4.216 (1.64), 4.377 (1.42), 4.392 (1.22), 5.694 (1.25), 6.525 (0.40), 6.539 (0.40), 6.702 (0.40), 7.376 (0.74), 7.403 (0.75), 8.208 (0.82), 8.222 (0.79), 8.251 (0.84), 9.005 (0.61), 10.072 (0.35), 10.080 (0.36), 10.455 (0.38), 10.463 (0.37).

Intermediate 457

N-(4-{[3-(5-cyclopropyl-1,3,4-oxadiazol-2-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

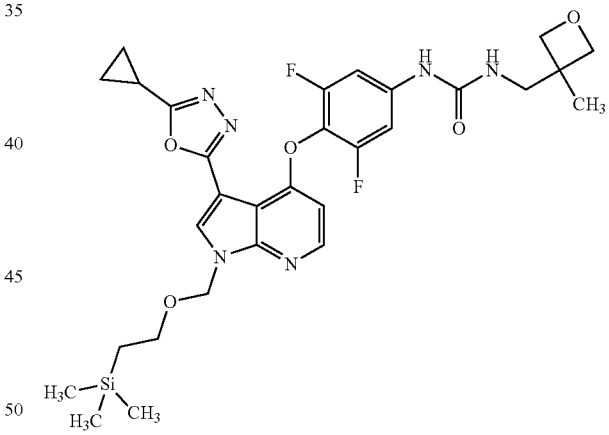

In analogy to Intermediate 454, N-{4-[(3-[2-(cyclopropanecarbonyl)hydrazinecarbonyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (85.0 mg, 132 µmol, Intermediate 456), triphenylphosphine (51.9 mg, 198 µmol), triethylamine (180 µL) and tetrachloromethane (32 µL, 330 µmol) were reacted in dichloromethane (1.1 mL) to furnish the title compound (39.4 mg, 43% yield), which was filtered through silica and used in the following reaction with no further purification.

LC-MS (Method 2): $R_t$=1.34 min; MS (ESIpos): m/z=626 [M+H]$^+$ $^1$H-NMR (400 MHz, DMSO-d6) δ [ppm]: −0.088 (16.00), 0.824 (0.51), 0.843 (0.62), 0.863 (0.52), 0.903 (0.12), 0.915 (0.46), 0.921 (0.43), 0.927 (0.43), 0.933 (0.44), 0.943 (0.17), 1.071 (0.17), 1.080 (0.43), 1.087 (0.37), 1.101 (0.44), 1.108 (0.37), 1.119 (0.13), 2.231 (0.07), 2.243 (0.14), 2.252 (0.16), 2.264 (0.28), 2.276 (0.15), 2.285 (0.14), 2.297 (0.06), 2.673 (0.15), 3.296 (0.74), 3.311 (0.79), 3.569 (0.51), 3.589 (0.60), 3.609 (0.47), 4.201 (1.09), 4.216 (1.23), 4.380 (1.08), 4.394 (0.93), 5.720 (1.23), 6.568 (0.38), 6.581 (0.37), 6.760 (0.14), 6.776 (0.25), 6.791 (0.12), 7.398 (0.61), 7.425 (0.62), 8.252 (0.73), 8.266 (0.67), 8.444 (1.31), 9.088 (0.38).

Intermediate 458

N-{4-[(3-[2-(cyclobutanecarbonyl)hydrazinecarbonyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea

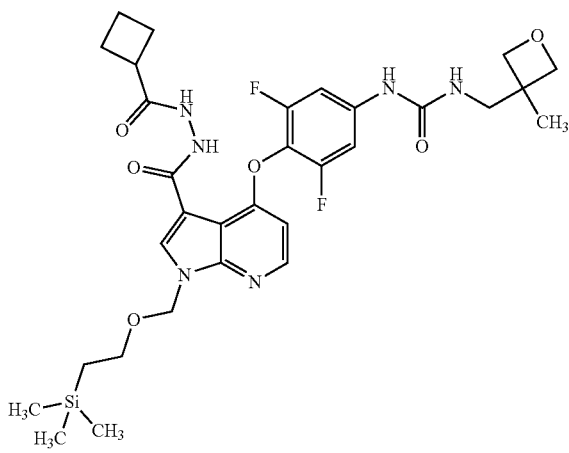 [SMILES: CC1(CNC(=O)Nc2cc(F)c(Oc3ccnc4c3c(C(=O)NNC(=O)C3CCC3)cn4COCC[Si](C)(C)C)c(F)c2)COC1]

In analogy to Intermediate 453, 4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylic acid (180 mg, 320 μmol, Intermediate 455) was allowed to react with cyclobutanecarbohydrazide (CAS No: 98069-56-8, 43.8 mg, 384 μmol) in the presence of N,N-diisopropylethylamine (130 μL) and (1-Cyano-2-ethoxy-2-oxoethylidenaminooxy) dimethylamino-morpholino-carbenium hexafluorophosphate (164 mg, 384 μmol) in DMF (3.6 mL) to afford the title compound (129 mg, 58% yield), which was filtered through silica and used in the following step with no further purification.

LC-MS (Method 2): $R_t$=1.26 min; MS (ESIpos): m/z=659 [M+H]$^+$

Intermediate 459

N-(4-{[3-(5-cyclobutyl-1,3,4-oxadiazol-2-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea

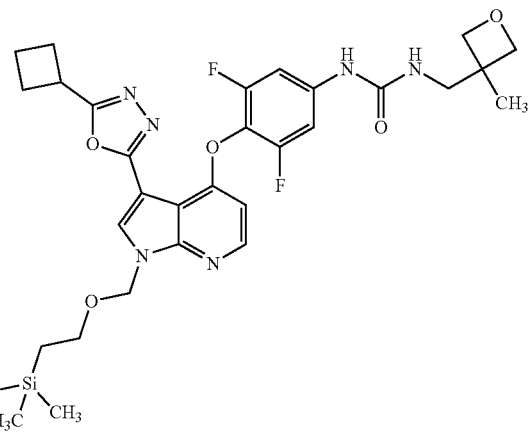

In analogy to Intermediate 454, N-{4-[(3-[2-(cyclobutanecarbonyl)hydrazinecarbonyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (127 mg, 193 μmol, Intermediate 458), triphenyphosphine (75.8 mg, 289 μmol), triethylamine (270 μL) and tetrachloromethane (47 μL, 480 μmol) were reacted in dichloromethane (1.6 mL) to furnish the title compound (102 mg, 74% yield), which was filtered through silica and used in the following reaction with no further purification.

LC-MS (Method 2): $R_t$=1.39 min; MS (ESIpos): m/z=641 [M+H]$^+$ $^1$H-NMR (400 MHz, DMSO-d6) δ [ppm]: −0.084 (16.00), 0.829 (0.56), 0.849 (0.71), 0.870 (0.56), 1.232 (3.36), 1.796 (0.07), 1.824 (0.13), 1.834 (0.14), 1.845 (0.10), 1.857 (0.07), 1.977 (0.19), 1.998 (0.31), 2.021 (0.20), 2.026 (0.22), 2.048 (0.14), 2.069 (0.06), 2.083 (0.27), 2.214 (0.06), 2.237 (0.19), 2.266 (0.40), 2.287 (0.49), 2.307 (0.36), 2.318 (0.34), 2.322 (0.30), 2.327 (0.29), 2.337 (0.24), 3.292 (0.81), 3.307 (0.84), 3.580 (0.54), 3.601 (0.68), 3.621 (0.53), 3.747 (0.06), 3.770 (0.22), 3.789 (0.33), 3.810 (0.21), 3.831 (0.06), 4.199 (1.24), 4.214 (1.37), 4.375 (1.22), 4.390 (1.05), 5.736 (1.38), 6.602 (0.42), 6.616 (0.41), 6.718 (0.16), 6.734 (0.33), 6.749 (0.16), 7.386 (0.71), 7.413 (0.71), 8.271 (0.79), 8.285 (0.73), 8.477 (1.45), 9.034 (0.52).

Intermediate 460

N-{3,5-difluoro-4-[(3-[2-(2-methylpropanoyl)hydrazinecarbonyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

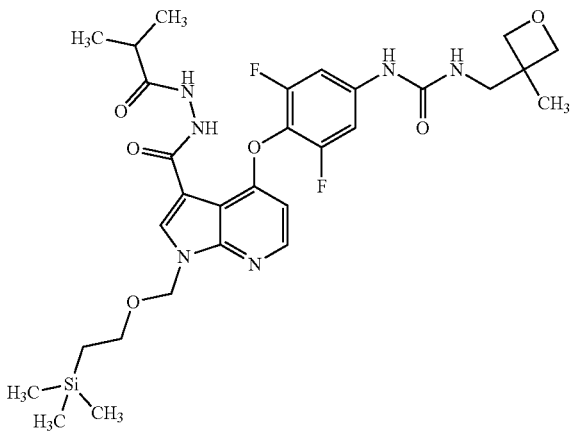 [SMILES: CC(C)C(=O)NNC(=O)c1cn(COCC[Si](C)(C)C)c2nccc(Oc3c(F)cc(NC(=O)NCC4(C)COC4)cc3F)c12]

In analogy to Intermediate 453, 4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridine-3-carboxylic acid (111 mg, 197 µmol, Intermediate 455) was allowed to react with 2-methylpropanehydrazide (CAS No: 3619-17-8, 24.2 mg, 237 µmol) in the presence of N,N-diisopropylethylamine (82 µL) and (1-Cyano-2-ethoxy-2-oxoethylidenaminooxy) dimethylamino-morpholino-carbenium hexafluorophosphate (101 mg, 237 µmol) in DMF (2.2 mL) to afford the title compound (51.9 mg, 37% yield), which was used in the following step with no further purification.

LC-MS (Method 2): $R_t$=1.24 min; MS (ESIpos): m/z=647 [M+H]$^+$

Intermediate 461

N-{3,5-difluoro-4-[(3-[5-(propan-2-yl)-1,3,4-oxadiazol-2-yl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

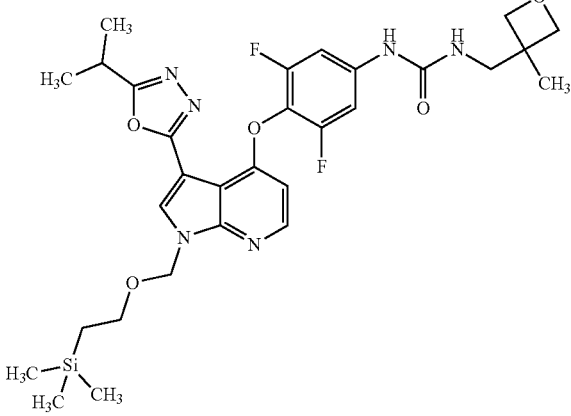

In analogy to Intermediate 454, N-{3,5-difluoro-4-[(3-[2-(2-methylpropanoyl)hydrazinecarbonyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (50.0 mg, 77.3 µmol, Intermediate 460), triphenylphosphine (30.4 mg, 116 µmol), triethylamine (110 µL) and tetrachloromethane (19 µL, 190 µmol) were reacted in dichloromethane (630 µL) to furnish the title compound (32.3 m, 47% yield), which was filtered through silica and used in the following reaction with no further purification.

LC-MS (Method 2): $R_t$=1.37 min; MS (ESIpos): m/z=629 [M+H]$^+$ $^1$H-NMR (400 MHz, DMSO-d6) δ [ppm]: −0.094 (1.13), −0.086 (16.00), 0.828 (0.71), 0.848 (0.89), 0.868 (0.64), 1.232 (4.63), 1.252 (4.67), 1.270 (4.64), 3.216 (0.45), 3.293 (1.18), 3.308 (1.28), 3.577 (0.72), 3.597 (0.82), 3.618 (0.58), 4.199 (1.66), 4.214 (1.86), 4.376 (1.68), 4.391 (1.43), 5.732 (1.56), 6.583 (0.47), 6.597 (0.47), 6.745 (0.22), 6.760 (0.37), 6.774 (0.18), 7.384 (0.95), 7.411 (0.93), 8.263 (0.80), 8.277 (0.76), 8.464 (1.48), 9.063 (0.61).

Intermediate 462

4-(2,6-difluoro-4-nitrophenoxy)-3-iodo-1-{[2-(trimethylsilyl)ethoxy]methyl}-1H-pyrrolo[2,3-b]pyridine

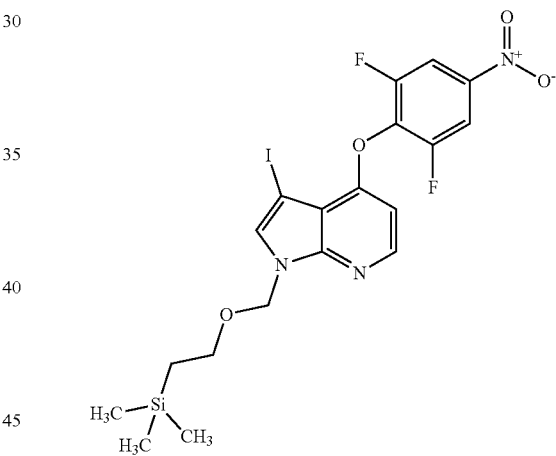

4-(2,6-difluoro-4-nitrophenoxy)-1-{[2-(trimethylsilyl)ethoxy]methyl}-1H-pyrrolo[2,3-b]pyridine (2.77 g, 6.57 mmol, Intermediate 15) was dissolved in DMF (51 mL), and N-iodosuccinimide (1.55 g, 6.90 mmol) was added tot the solution. The reaction was allowed to progress for 4 h at room temperature. After this time, it was quenched with a saturated sodium bicarbonate solution, and extracted with ethyl acetate (×3). The organic layers were washed with water and brine, dried over sodium sulfate, filtered and evaporated. The raw product was purified by silica gel chromatography using a Biotage system to afford the title compound (3.13 g, 86% yield).

LC-MS (Method 2): $R_t$=1.65 min; MS (ESIpos): m/z=548 [M+H]$^+$ $^1$H-NMR (400 MHz, DMSO-d6) δ [ppm]: −0.095 (16.00), 0.799 (0.48), 0.819 (0.58), 0.839 (0.51), 3.510 (0.52), 3.530 (0.60), 3.551 (0.49), 5.611 (1.47), 6.632 (0.37), 6.646 (0.37), 7.925 (1.34), 8.195 (0.71), 8.208 (0.66), 8.411 (0.69), 8.430 (0.72).

Intermediate 463

3,5-difluoro-4-[(3-iodo-1-{[2-(trimethylsilyl)ethoxy]methyl}-1H-pyrrolo[2,3-b]pyridin-4-yl)oxy]aniline

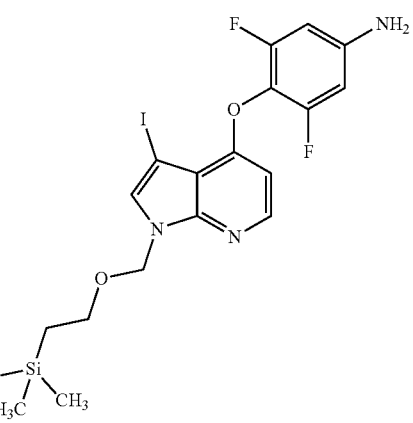

In analogy to intermediate 380, a solution of 4-(2,6-difluoro-4-nitrophenoxy)-3-iodo-1-{[2-(trimethylsilyl)ethoxy]methyl}-1H-pyrrolo[2,3-b]pyridine (12.7 g, 23.3 mmol, Intermediate 462) in THF/methanol (110 mL/110 mL) was reacted with a suspension of ammonium chloride (6.22 g, 116 mmol) and iron (6.50 g, 116 mmol) in water (220 mL) at 80° C. to yield the title compound (12.8 g, 100% yield).

LC-MS (Method 2): $R_t$=1.51 min; MS (ESIpos): m/z=518 [M+H]$^+$ $^1$H-NMR (400 MHz, DMSO-d6) δ [ppm]: −0.089 (16.00), 0.797 (0.48), 0.818 (0.57), 0.838 (0.55), 3.496 (0.49), 3.516 (0.61), 3.537 (0.53), 5.579 (1.35), 5.810 (0.77), 6.354 (0.37), 6.367 (0.41), 6.380 (0.61), 6.406 (0.62), 7.816 (1.27), 8.135 (0.67), 8.149 (0.63).

Intermediate 464 di-tert-butyl {3,5-difluoro-4-[(3-iodo-1-{[2-(trimethylsilyl)ethoxy]methyl}-1H-pyrrolo[2,3-b]pyridin-4-yl)oxy]phenyl}-2-imidodicarbonate

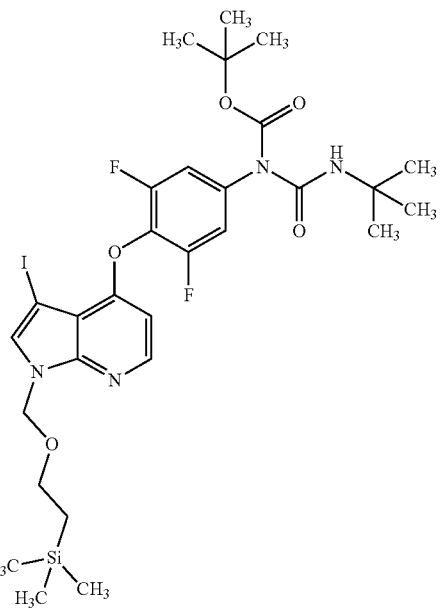

3,5-difluoro-4-[(3-iodo-1-{[2-(trimethylsilyl)ethoxy]methyl}-1H-pyrrolo[2,3-b]pyridin-4-yl)oxy]aniline (2.95 g, 90% purity, 5.13 mmol, Intermediate 463) was dissolved in THF (48 mL), and di-tert-butyl dicarbonate (2.9 mL, 13 mmol) and 4-dimethylaminopyridine (62.7 mg, 513 μmol) were added as solids. The mixture was stirred at 75° C. for 3 h. The reaction was diluted with ethyl acetate and washed with water (×2) and brine (×1), dried over sodium sulfate, filtered and evaporated. The crude material was purified by silica gel chromatography using a Biotage system to yield the title compound (2.83 g, 73% yield).

LC-MS (Method 2): $R_t$=1.80 min; MS (ESIpos): m/z=718 [M+H]$^+$ $^1$H-NMR (400 MHz, DMSO-d6) δ [ppm]: −0.091 (14.60), 0.800 (0.47), 0.819 (0.59), 0.840 (0.48), 1.422 (16.00), 3.508 (0.46), 3.528 (0.56), 3.548 (0.45), 5.603 (1.21), 6.250 (0.34), 6.264 (0.33), 7.516 (0.66), 7.538 (0.67), 7.896 (1.20), 8.194 (0.62), 8.207 (0.59).

Intermediate 465 tert-butyl {4-[(3-[2-cyanoethenyl]-1-{[2-(trimethylsilyl)ethoxy]methyl}-1H-pyrrolo[2,3-b]pyridin-4-yl)oxy]-3,5-difluorophenyl}carbamate (Mixture of Cis and Trans Isomers)

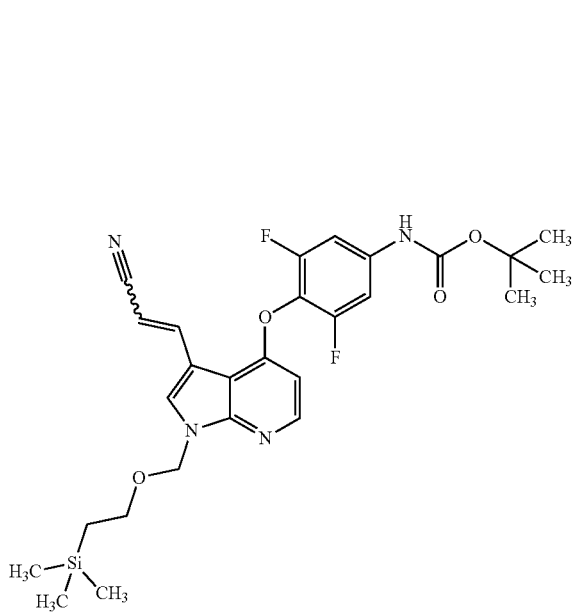 [SMILES: CC(C)(C)OC(=O)Nc1cc(F)c(Oc2ccnc3c2c(C=CC#N)cn3COCC[Si](C)(C)C)c(F)c1]

di-tert-butyl {3,5-difluoro-4-[(3-iodo-1-{[2-(trimethylsilyl)ethoxy]methyl}-1H-pyrrolo[2,3-b]pyridin-4-yl)oxy]phenyl}-2-imidodicarbonate (100 mg, 139 μmol, Intermediate 464) and acrylonitrile (CAS No: 107-13-1, 11 μL, 170 μmol) were dissolved in DMF (1.0 mL), and sodium bicarbonate (14.0 mg, 167 μmol), tetrabutylammonium chloride (46.5 mg, 167 μmol) and palladium (II) acetate (1.56 mg, 6.97 μmol) were added tot the mixture. The system was put under argon and stirred overnight at 100° C. The reaction was diluted with dichloromethane, washed with water and brine, and dried over sodium sulfate. The crude was filtered and the solvent evaporated. The crude was filtered by silica gel chromatography using a Biotage system to yield the title compound as a mixture of cis and trans isomers (68.2 mg, 72% yield).

LC-MS isomer 1 (Method 2): $R_t$=1.67 min; MS (ESIpos): m/z=543 [M+H]$^+$

LC-MS isomer 2 (Method 2): $R_t$=1.63 min; MS (ESIpos): m/z=543 [M+H]$^+$ $^1$H-NMR (400 MHz, DMSO-d6) δ [ppm]: −0.091 (16.00), −0.089 (8.80), 0.818 (0.54), 0.837 (0.69), 0.849 (0.41), 0.858 (0.56), 1.498 (7.85), 3.530 (0.42), 3.551 (0.53), 3.571 (0.45), 5.660 (1.35), 5.758 (0.57), 6.267 (0.55), 6.309 (0.59), 6.520 (0.32), 6.533 (0.33), 7.404 (0.57), 7.430 (0.57), 7.806 (0.46), 7.848 (0.49), 8.198 (0.61), 8.212 (0.61), 8.215 (0.35), 8.329 (0.78), 9.939 (0.38).

Intermediate 466 tert-butyl (4-{[3-(2-cyanoethyl)-1-{[2-(trimethylsilyl)ethoxy]methyl}-1H-pyrrolo[2,3-b]pyridin-4-yl]oxy}-3,5-difluorophenyl)carbamate

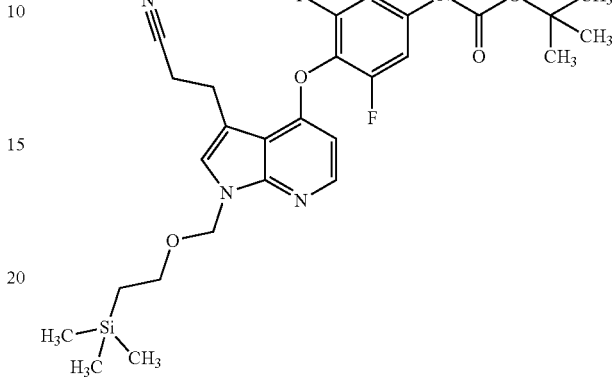

Tert-butyl {4-[(3-[2-cyanoethenyl]-1-{[2-(trimethylsilyl)ethoxy]methyl}-1H-pyrrolo[2,3-b]pyridin-4-yl)oxy]-3,5-difluorophenyl}carbamate (mixture of cis and trans isomers, 730 mg, 1.35 mmol, Intermediate 465) was dissolved in methanol (10 mL) and palladium on charcoal (71.6 mg, 10% purity, 67.3 μmol) was added. The reaction was put under a hydrogen atmosphere (1 atm) and stirred at room temperature for 4 h. The crude was filtered over a celite pad and the solvent removed under vacuum to yield (400 mg, 55% yield).

LC-MS (Method 2): $R_t$=1.60 min; MS (ESIpos): m/z=549 [M+H]$^+$

Intermediate 467

3-[4-(4-amino-2,6-difluorophenoxy)-1-{[2-(trimethylsilyl)ethoxy]methyl}-1H-pyrrolo[2,3-b]pyridin-3-yl]propanenitrile

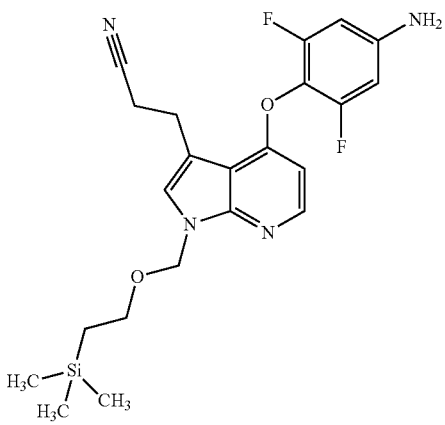 [SMILES: C[Si](C)(C)CCOCn1cc(CCC#N)c2c(Oc3c(F)cc(N)cc3F)ccnc21]

Tert-butyl (4-{[3-(2-cyanoethyl)-1-{[2-(trimethylsilyl)ethoxy]methyl}-1H-pyrrolo[2,3-b]pyridin-4-yl]oxy}-3,5-difluorophenyl)carbamate (580 mg, 1.06 mmol, Intermediate 466) was dissolved in dichloromethane (5 mL) and put

Intermediate 468 phenyl (4-{[3-(2-cyanoethyl)-1-{[2-(trimethylsilyl)ethoxy]methyl}-1H-pyrrolo[2,3-b]pyridin-4-yl]oxy}-3,5-difluorophenyl)carbamate

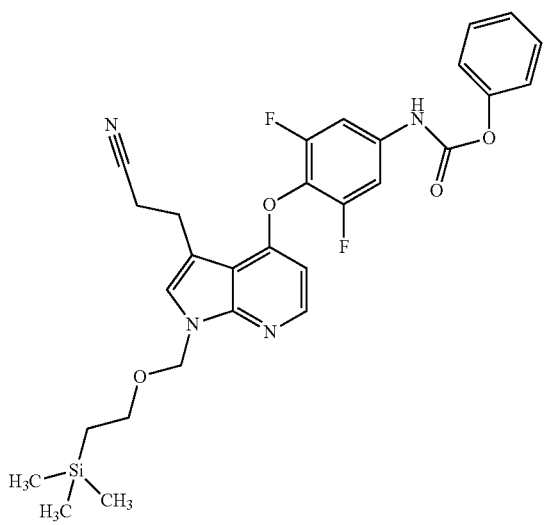 [SMILES: C[Si](C)(C)CCOCn1cc(CCC#N)c2c(Oc3c(F)cc(NC(=O)Oc4ccccc4)cc3F)ccnc21]

In analogy to Intermediate 22, 3-[4-(4-amino-2,6-difluorophenoxy)-1-{[2-(trimethylsilyl)ethoxy]methyl}-1H-pyrrolo[2,3-b]pyridin-3-yl]propanenitrile (270 mg, 607 µmol, Intermediate 467) was stirred with phenyl carbonochloridate (CAS No: 1885-14-9, 84 µL, 670 µmol) and pyridine (5.4 mL) in THF (5.4 mL) to yield the title compound, which was used in the following reaction as a crude.

LC-MS (Method 2): $R_t$=1.54 min; MS (ESIpos): m/z=565 [M+H]$^+$

Intermediate 469

N-(4-{[3-(2-cyanoethyl)-1-{[2-(trimethylsilyl)ethoxy]methyl}-1H-pyrrolo[2,3-b]pyridin-4-yl]oxy}-3,5-difluorophenyl)-N'-{[3-(propan-2-yl)oxetan-3-yl]methyl}urea

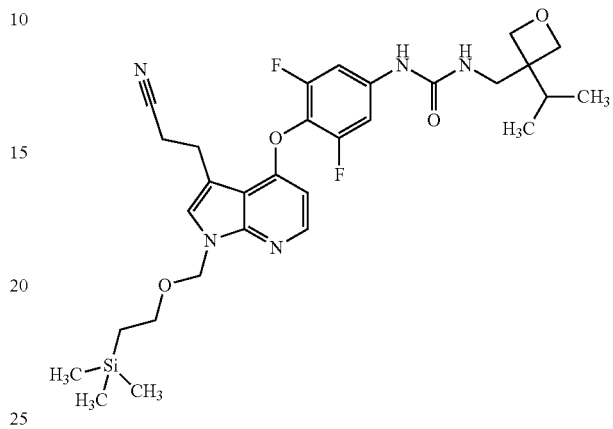

In analogy to intermediate 381, phenyl (4-{[3-(2-cyanoethyl)-1-{[2-(trimethylsilyl)ethoxy]methyl}-1H-pyrrolo[2,3-b]pyridin-4-yl]oxy}-3,5-difluorophenyl)carbamate (170 mg, 301 µmol, Intermediate 468) and 1-[3-(propan-2-yl)oxetan-3-yl]methanamine (CAS No: 1539197-30-2, 77.8 mg, 602 µmol) in DMF (3 mL), were reacted to yield the title compound, which was used in the following reaction with no further purification.

LC-MS (Method 2): $R_t$=1.44 min; MS (ESIpos): m/z=600 [M+H]$^+$

Intermediate 470

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopentyl]methyl}thiourea

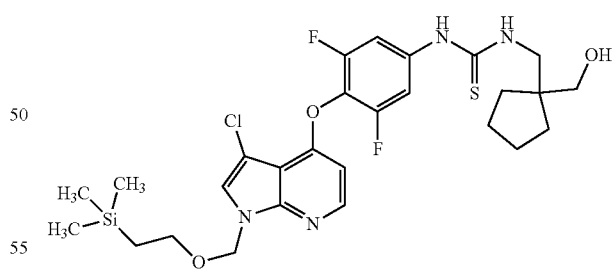

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (200 mg, 356 µmol, intermediate 424) and [1-(aminomethyl)cyclopentyl]methanol (CAS No: 2239-31-8, 91.9 mg, 712 µmol) were stirred in DMF (3 mL) at 60° C. to yield the title compound (127 mg, 60% yield), which was filtered over silica and used directly in the next transformation.

LC-MS (Method 2): $R_t$=1.58 min; MS (ESIpos): m/z=597 [M+H]$^+$

Intermediate 471

N-{4-[(3-chloro-1-{[2-(trimethylsilyl)ethoxy]methyl}-1H-pyrrolo[2,3-b]pyridin-4-yl)oxy]-3,5-difluorophenyl}-7-oxa-9-azaspiro[4.5]dec-8-en-8-amine

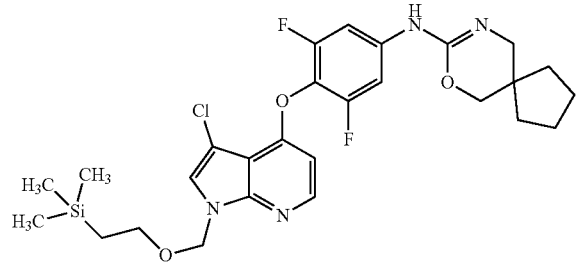 [SMILES: C[Si](C)(C)CCOCn1cc(Cl)c2c(Oc3c(F)cc(NC4=NCC5(CCCC5)CO4)cc3F)ccnc21]

N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclopentyl]methyl}thiourea (127 mg, 213 µmol, Intermediate 470) was dissolved in THF (2 mL), and 1-(3-Dimethylaminopropyl)-3-ethylcarbodiimide hydrochloride (44.8 mg, 234 µmol) was added. The reaction was stirred at 60° C. overnight. The solvent was then evaporated, and the crude filtered over silica. The raw product was used directly in the following transformation.

LC-MS (Method 2): R$_t$=1.67 min; MS (ESIpos): m/z=563 [M+H]$^+$

Intermediate 472

3-(methoxymethyl)-3-methyloxetane

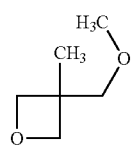

(3-methyloxetan-3-yl)methanol (CAS No: 3143-02-0, 2.0 mL, 20 mmol) was dissolved in THF (80 mL, 1.0 mol), put under argon and cooled down to 0° C. Sodium hydride (862 mg, 60% purity, 21.5 mmol) was added portionwise, and the resulting suspension was stirred for 30 min. iodomethane (1.3 mL, 21 mmol) was added dropwise, the ice batch was removed and the temperature was allowed to rise over 2 h. The reaction was quenched with water, and extracted with hexanes (×2). The organic layers were dried over sodium sulfate, filtered, and the solvent removed under vacuum to yield the title compound (2.10 g, 83% yield).

$^1$H-NMR (400 MHz, CHLOROFORM-d) δ [ppm]: 1.32 (s, 3H), 3.46 (s, 2H), 4.37 (d, 2H), 4.52 (d, 2H).

Intermediate 473

(+/−)-2-[(benzylamino)methyl]-3-methoxy-2-methylpropan-1-ol

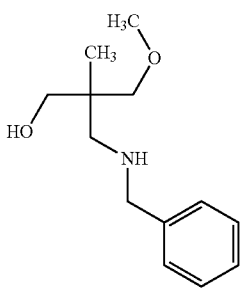 [SMILES: COCC(C)(CO)CNCc1ccccc1]

3-(methoxymethyl)-3-methyloxetane (2.10 g, 16.3 mmol, Intermediate 472) and benzylamine (5.3 mL, 49 mmol) were dissolved in acetonitrile (63 mL), and zirconium (IV) chloride (3.79 g, 16.3 mmol) was added. The reaction was stirred at room temperature for 3 h, filtered and concentrated under vacuum. The residue was filtered through silica to yield the title compound (513 mg, 14% yield).

$^1$H-NMR (400 MHz, DMSO-d6) δ [ppm]: 0.78 (s, 3H), 2.36 (d, 2H), 3.16 (d, 2H), 3.20 (s, 3H), 3.25 (d, 2H), 3.66 (s, 2H), 7.31 (m, 5H).

Intermediate 474

(+/−)-2-(aminomethyl)-3-methoxy-2-methylpropan-1-ol

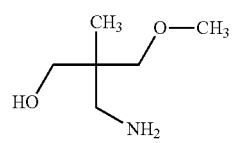

(+/−)-2-[(benzylamino)methyl]-3-methoxy-2-methylpropan-1-ol (510 mg, 2.28 mmol, Intermediate 473) was dissolved in DMF (5.3 mL), and palladium on charcoal (48.6 mg, 10% purity, 457 µmol) was added. The reaction was put under a hydrogen atmosphere (1 atm) and stirred at room temperature for 100 h. The crude was filtered over a celite pad and used as a DMF solution in the following transformation.

Intermediate 475

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-methoxy-2-methylpropyl]thiourea

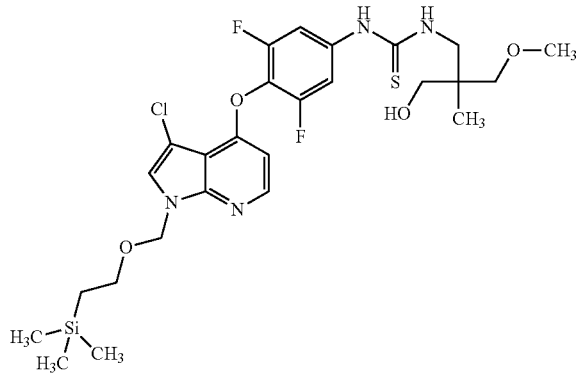

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (250 mg, 311 µmol, intermediate 424) and 2-(aminomethyl)-3-methoxy-2-methylpropan-1-ol (1.8 mL, 0.21 M, 370 µmol, Intermediate 474) were stirred in DMF (4.0 mL) at 60° C. to yield the title compound (143 mg, 73% yield), which was filtered over silica and used directly in the next transformation.

LC-MS (Method 2): $R_t$=1.51 min; MS (ESIpos): m/z=601 [M+H]$^+$

Intermediate 476

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-5-(methoxymethyl)-5-methyl-5,6-dihydro-4H-1,3-oxazin-2-amine

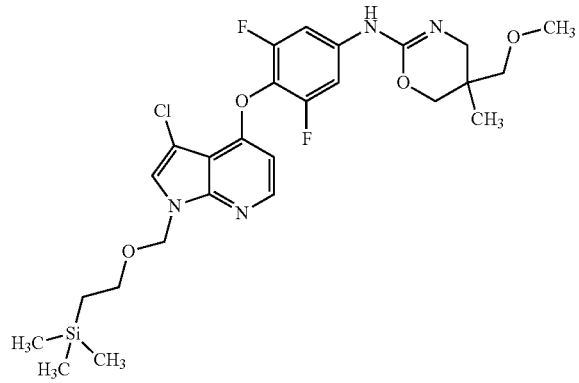

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-[2-(hydroxymethyl)-3-methoxy-2-methylpropyl]thiourea (140 mg, 210 µmol, Intermediate 475) was dissolved in tetrahydrofurane (1.0 mL), and 1-(3-Dimethylaminopropyl)-3-ethylcarbodiimide hydrochloride (44.2 mg, 231 µmol) was added. The reaction was stirred at 60° C. overnight. The solvent was then evaporated, and the crude filtered over silica. The raw product was used directly in the following transformation.

LC-MS (Method 2): $R_t$=1.60 min; MS (ESIneg): m/z=565 [M−H]$^-$

Intermediate 477

(3-methyloxetan-3-yl)methyl 4-methylbenzene-1-sulfonate

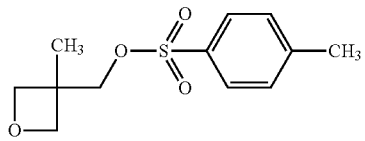 [SMILES: Cc1ccc(S(=O)(=O)OCC2(C)COC2)cc1]

(3-methyloxetan-3-yl)methanol (CAS No: 3143-02-0, 2.0 mL, 20 mmol) was dissolved in dichloromethane (30 mL) and cooled down to 0° C. Triethylamine (3.0 mL, 22 mmol), 4-dimethylaminopyridine (239 mg, 1.96 mmol) and 4-methylbenzene-1-sulfonyl chloride (4.11 g, 21.5 mmol) were added, the ice bath removed, and the reaction stirred overnight at room temperature. The crude was then diluted with dichloromethane and treated with a 2M HCl solution. The organic phase was separated and washed with sodium bicarbonate and brine, dried over sodium sulfate, filtered and evaporated. The crude product was used in the following reaction with no further purification.

LC-MS (Method 1): $R_t$=1.06 min; MS (ESIpos): m/z=257 [M+H]$^+$ $^1$H-NMR (400 MHz, DMSO-d6) δ [ppm]: 1.18 (s, 3H), 2.43 (s, 3H), 4.11 (s, 2H), 4.19 (d, 2H), 4.26 (d, 2H), 7.50 (d, 2H), 7.85 (d, 2H).

Intermediate 478

3-methyl-3-{[(propan-2-yl)oxy]methyl}oxetane

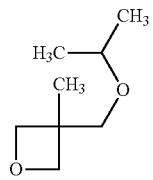

(3-methyloxetan-3-yl)methyl 4-methylbenzene-1-sulfonate (3.21 g, 12.5 mmol, Intermediate 477) was dissolved in DMF (46 mL), put under argon and cooled down to 0° C. Sodium hydride (2.00 g, 60% purity, 50.1 mmol) was added portionwise, and the resulting suspension was stirred for 30 min. Propan-2-ol (3.8 mL, 50 mmol) was added dropwise, the ice batch was removed and the reaction was heated up to 50° C. overnight. The reaction was quenched with water, and extracted with hexanes (×2). The organic layers were dried over sodium sulfate, filtered, and the solvent removed under vacuum to yield the title compound (1.42 g, 78% yield).

¹H-NMR (400 MHz, CHLOROFORM-d) δ [ppm]: 1.16 (d, 6H), 1.30 (s, 3H), 3.57 (h, 1H), 4.35 (d, 2H), 4.50 (d, 2H).

Intermediate 479

(+/−)-2-[(benzylamino)methyl]-2-methyl-3-[(propan-2-yl)oxy]propan-1-ol

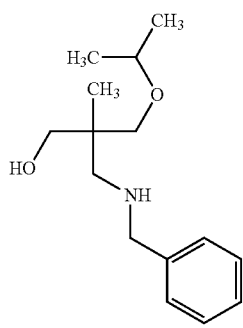 [SMILES: CC(C)OCC(C)(CO)CNCc1ccccc1]

3-methyl-3-{[(propan-2-yl)oxy]methyl}oxetane (1.42 g, 9.85 mmol, Intermediate 478) and benzylamine (3.2 mL, 30 mmol) were dissolved in acetonitrile (38 mL), and zirconium (IV) chloride (2.29 g, 9.85 mmol) was added. The reaction was stirred at room temperature for 3 h, filtered and concentrated under vacuum. The residue was filtered through silica to yield the title compound (1.56 g, 60% yield).

LC-MS (Method 2): $R_t$=1.22 min; MS (ESIpos): m/z=252 [M+H]⁺

¹H-NMR (400 MHz, CHLOROFORM-d) δ [ppm]: 0.91 (s, 3H), 1.00 (d, 3H), 1.05 (d, 3H), 2.73 (d, 1H), 3.26-3.40 (m, 4H), 3.47 (h, 1H), 3.86 (d, 1H), 4.07 (d, 1H), 4.40 (d, 1H), 7.42-7.52 (m, 5H).

Intermediate 480

(+/−)-2-(aminomethyl)-2-methyl-3-[(propan-2-yl)oxy]propan-1-ol

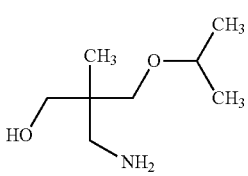

(+/−)-2-[(benzylamino)methyl]-2-methyl-3-[(propan-2-yl)oxy]propan-1-ol (1.56 g, 6.19 mmol, Intermediate 479) was dissolved in DMF (14 mL), and palladium on charcoal (132 mg, 10% purity, 1.24 mmol) was added. The reaction was put under a hydrogen atmosphere (1 atm) and stirred at room temperature for 56 h. The crude was filtered over a celite pad and used as a DMF solution in the following transformation.

Intermediate 481

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-{2-(hydroxymethyl)-2-methyl-3-[(propan-2-yl)oxy]propyl}thiourea

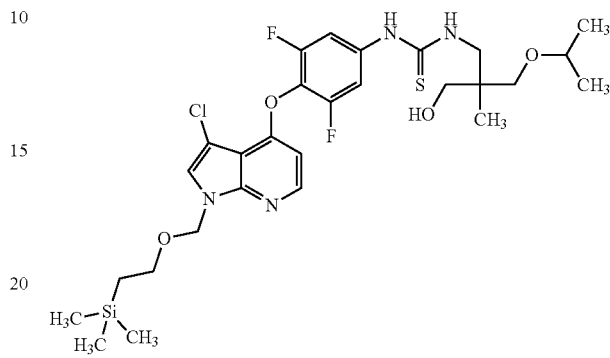

In analogy to intermediate 425, O-phenyl {4-[(3-chloro-1-{[2-(trimethylsilyl)ethoxy]methyl}-1H-pyrrolo[2,3-b]pyridin-4-yl)oxy]-3,5-difluorophenyl}carbamothioate (146 mg, 260 μmol, intermediate 424) and 2-(aminomethyl)-2-methyl-3-[(propan-2-yl)oxy]propan-1-ol (780 μL, 0.40 M, 310 μmol, Intermediate 480) were stirred in DMF (3.3 mL) in the presence of triethylamine (36 μL) at 60° C. to yield the title compound (174 mg, 75% yield), which was filtered over silica and used directly in the next transformation.

LC-MS (Method 2): $R_t$=1.59 min; MS (ESIpos): m/z=629 [M+H]⁺

Intermediate 482

(+/−)—N-{4-[(3-chloro-1H-pyrrolo[2,3-b]pyridin-4-yl)oxy]-3,5-difluorophenyl}-N'-{2-(hydroxymethyl)-2-methyl-3-[(propan-2-yl)oxy]propyl}thiourea

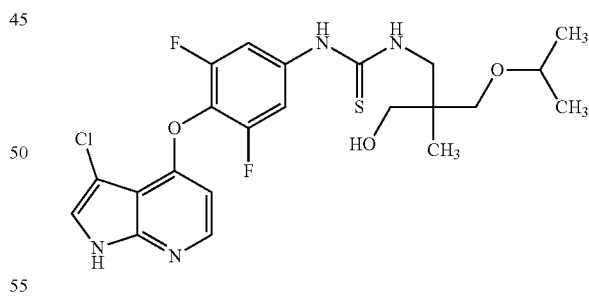

N-{4-[(3-chloro-1-{[2-(trimethylsilyl)ethoxy]methyl}-1H-pyrrolo[2,3-b]pyridin-4-yl)oxy]-3,5-difluorophenyl}-N'-{2-(hydroxymethyl)-2-methyl-3-[(propan-2-yl)oxy]propyl}thiourea (174 mg, 194 μmol, Intermediate 481) was dissolved in dichloromethane (6.2 mL), and trifluoroacetic acid (640 μL, 8.3 mmol) was added. The reaction was stirred overnight at 60° C. 5 mL of acetonitrile and 2 mL of a 33% solution of ammonia in water were added, and the crude was stirred for 1 h. The acetonitrile was partially evaporated, and the resulting crude was extracted with ethyl acetate. The organic layer was washed with water (×2) and brine (×1),

Intermediate 483

4-(2,6-difluoro-4-nitrophenoxy)-3-(prop-1-en-2-yl)-1-{[2-(trimethylsilyl)ethoxy]methyl}-1H-pyrrolo[2,3-b]pyridine

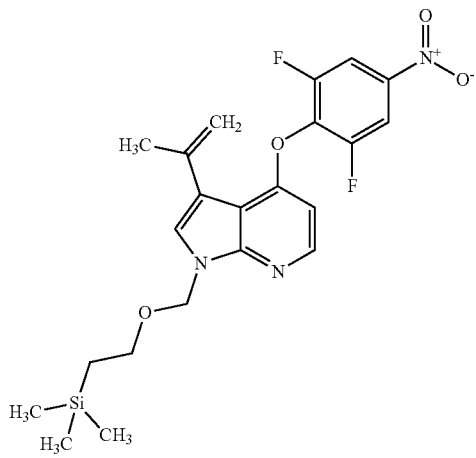 [SMILES: C=C(C)c1cn(COCC[Si](C)(C)C)c2nccc(Oc3c(F)cc([N+](=O)[O-])cc3F)c12]

3-bromo-4-(2,6-difluoro-4-nitrophenoxy)-1-{[2-(trimethylsilyl)ethoxy]methyl}-1H-pyrrolo[2,3-b]pyridine (2.35 g, 4.70 mmol, Intermediate 16), 4,4,5,5-tetramethyl-2-(prop-1-en-2-yl)-1,3,2-dioxaborolane (CAS No: 126726-62-3, 987 mg, 5.87 mmol), 1,1-Bis(diphenylphosphino)ferrocene)-dichloropalladium(II) (344 mg, 470 µmol) and potassium carbonate (1.95 g, 14.1 mmol) were convined in degassed water/tetrahydrofurane (30 mL and 70 mL, respectively), put under argon and stirred at 75° C. for 5 h. The organic solvent was evaporated, and the water extracted with ethyl acetate (×2). The combined organic layers were dried over sodium sulfate, filtered and evaporated, and the remaining residue was purified by silica gel chromatography using a Biotage system to yield the title compound (1.60 g, 74% yield).

LC-MS (Method 2): $R_t$=1.67 min; MS (ESIpos): m/z=462 [M+H]$^+$ $^1$H-NMR (400 MHz, DMSO-d6) δ [ppm]: −0.107 (1.48), −0.103 (0.34), −0.101 (0.53), −0.093 (16.00), −0.086 (0.46), 0.808 (0.46), 0.828 (0.52), 0.848 (0.46), 2.168 (1.51), 3.528 (0.47), 3.548 (0.53), 3.568 (0.44), 5.083 (0.25), 5.086 (0.32), 5.088 (0.33), 5.092 (0.26), 5.397 (0.33), 5.401 (0.32), 5.403 (0.30), 5.634 (1.29), 6.584 (0.32), 6.598 (0.32), 7.746 (1.03), 8.161 (0.64), 8.174 (0.63), 8.403 (0.65), 8.422 (0.69).

Intermediate 484

3,5-difluoro-4-{[3-(propan-2-yl)-1-{[2-(trimethylsilyl)ethoxy]methyl}-1H-pyrrolo[2,3-b]pyridin-4-yl]oxy}aniline

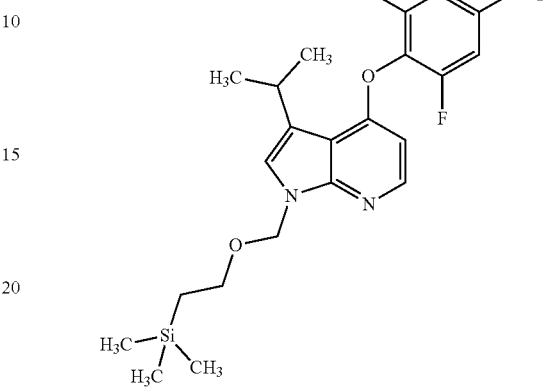

4-(2,6-difluoro-4-nitrophenoxy)-3-(prop-1-en-2-yl)-1-{[2-(trimethylsilyl)ethoxy]methyl}-1H-pyrrolo[2,3-b]pyridine (1.60 g, 3.47 mmol, Intermediate 483) was dissolved in ethanol (90 mL) and tetrahydrofurane (10 mL), palladium on charcoal (369 mg, 10% purity, 347 µmol) was added, and the system was put under a hydrogen atmosphere (1 atm) and stirred at room temperature for 4 h. The mixture was then filtered through celite, the solvent removed under vacuum and the residue purified by silica gel chromatography using a Biotage system to yield the title compound (1.04 g, 69% yield).

LC-MS (Method 2): $R_t$=1.59 min; MS (ESIpos): m/z=434 [M+H]$^+$ $^1$H-NMR (400 MHz, DMSO-d6) δ [ppm]: −0.097 (16.00), 0.781 (0.49), 0.801 (0.57), 0.821 (0.51), 1.304 (2.89), 1.321 (2.93), 3.478 (0.51), 3.499 (0.59), 3.519 (0.48), 5.554 (1.43), 5.792 (0.77), 6.258 (0.37), 6.272 (0.36), 6.376 (0.61), 6.403 (0.63), 6.409 (0.13), 6.418 (0.06), 6.440 (0.01), 7.302 (0.74), 7.304 (0.75), 8.048 (0.72), 8.062 (0.67).

Intermediate 485

O-phenyl (3,5-difluoro-4-{[3-(propan-2-yl)-1-{[2-(trimethylsilyl)ethoxy]methyl}-1H-pyrrolo[2,3-b]pyridin-4-yl]oxy}phenyl)carbamothioate

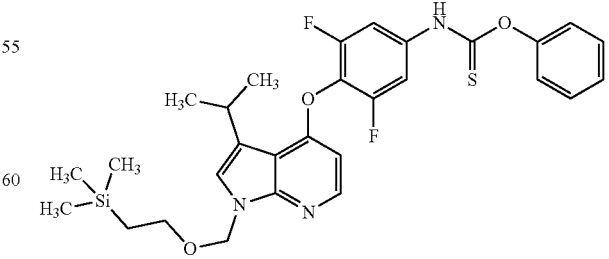

In analogy to intermediate 424, 3,5-difluoro-4-{[3-(propan-2-yl)-1-{[2-(trimethylsilyl)ethoxy]methyl}-1H-pyrrolo[2,3-b]pyridin-4-yl]oxy}aniline (250 mg, 577 µmol, Intermediate 484) was stirred with O-phenyl carbonochloridothioate (CAS No: 1005-56-7, 88 µL, 630 µmol) and pyridine (400 µL) in THF (6.0 mL) to yield the title compound, which was used in the following reaction as a crude.

LC-MS (Method 1): R$_t$=1.75 min; MS (ESIneg): m/z=568 [M–H]⁻

Intermediate 486

(+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-{2-(hydroxymethyl)-2-methyl-3-[(propan-2-yl)oxy]propyl}thiourea

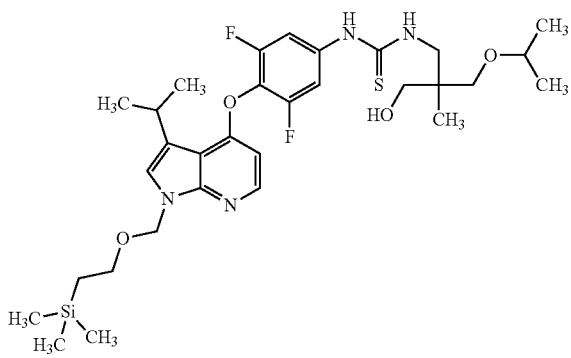 [SMILES: CC(C)OCC(C)(CO)CNC(=S)Nc1cc(F)c(Oc2ccnc3c2c(C(C)C)cn3COCC[Si](C)(C)C)c(F)c1]

In analogy to intermediate 425, O-phenyl (3,5-difluoro-4-{[3-(propan-2-yl)-1-{[2-(trimethylsilyl)ethoxy]methyl}-1H-pyrrolo[2,3-b]pyridin-4-yl]oxy}phenyl)carbamothioate (180 mg, 316 µmol, Intermediate 485) and 2-(aminomethyl)-2-methyl-3-[(propan-2-yl)oxy]propan-1-ol (950 µL, 0.40 M, 380 µmol, Intermediate 480) were stirred in DMF (4.1 mL) at 60° C. to yield the title compound (200 mg, 86% yield), which was filtered over silica and used directly in the next transformation.

LC-MS (Method 2): R$_t$=1.67 min; MS (ESIneg): m/z=635 [M–H]⁻

Intermediate 487

(+/−)—N-(3,5-difluoro-4-{[3-(propan-2-yl)-1H-pyrrolo[2,3-b]pyridin-4-yl]oxy}phenyl)-N'-{2-(hydroxymethyl)-2-methyl-3-[(propan-2-yl)oxy]propyl}thiourea

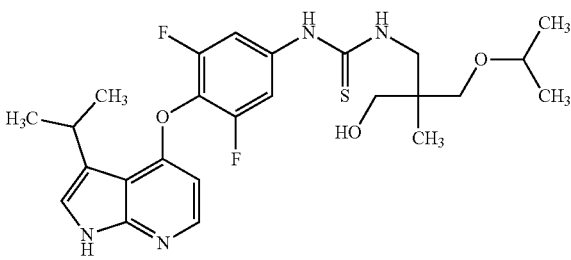 [SMILES: CC(C)OCC(C)(CO)CNC(=S)Nc1cc(F)c(Oc2ccnc3[nH]cc(C(C)C)c23)c(F)c1]

(+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-N'-{2-(hydroxymethyl)-2-methyl-3-[(propan-2-yl)oxy]propyl}thiourea (199 mg, 272 µmol, Intermediate 486) was dissolved in dichloromethane (8.7 mL), and trifluoroacetic acid (900 µL, 12 mmol) was added. The reaction was stirred overnight at 60° C. 5 mL of acetonitrile and 2 mL of a 33% solution of ammonia in water were added, and the crude was stirred for 1 h. The acetonitrile was partially evaporated, and the resulting crude was extracted with ethyl acetate. The organic layer was washed with water (×2) and brine (×1), dried over sodium sulfate, filtered and evaporated. The crude was used in the following reaction with no further purification.

LC-MS (Method 2): R$_t$=1.67 min; MS (ESIpos): m/z=637 [M+H]⁺.

Intermediate 488

(2-fluoropyridin-3-yl)[1-(trifluoromethyl)cyclopropyl]methanone

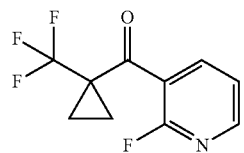 [SMILES: O=C(c1cccnc1F)C1(C(F)(F)F)CC1]

To a solution of 2-fluoropyridine (1.9 g, 19.6 mmol) in THF (40 mL) was added LDA (1 M, 25 mL, freshly prepared) drop-wise at −78° C. under N2. The mixture was stirred at −78° C. for 1 hour. Then N-methoxy-N-methyl-1-(trifluoromethyl)cyclopropanecarboxamide (3.8 g, 19.3 mmol, prepared as described in Org. Process Res. Dev., 2009, 13 (3), pp 576-580) was added. The mixture was warmed to 15° C. and stirred for 1 hour. TLC (Petroleum ether: Ethyl acetate=5:1) indicated the reaction completed. The mixture was quenched by adding a saturated aqueous solution of ammonium chloride (50 mL). The mixture was extracted with ethyl acetate (100 mL×2). The combined organic phase was washed with brine (100 mL×2), dried over anhydrous Na$_2$SO$_4$, filtered and concentrated by rotary evaporator in vacuum. The residue was purified by chromatography on silica gel (Petroleum ether: Ethyl acetate=100:1) to give (2-fluoropyridin-3-yl)(1-(trifluoromethyl)cyclopropyl)methanone (2.4 g, 53% yield) as a yellow oil.

¹H NMR (CDCl$_3$, 400 MHz): δ=1.65-1.54 (m, 4H), 7.31 (t, 1H), 7.87 (t, 1H), 8.38-8.37 (m, 1H).

Intermediate 489

2-fluoro-3-{2-[1-(trifluoromethyl)cyclopropyl]oxiran-2-yl}pyridine

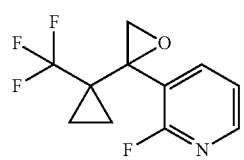 [SMILES: Fc1ncccc1C1(C2(C(F)(F)F)CC2)CO1]

NaH (900 mg, 22.50 mmol, 60% purity) was added into DMSO (40 mL) at 15° C. in one portion. The mixture was heated to 65° C. for 1 hour. Then the mixture was cooled to 15° C. and trimethylsulfoxonium iodide (4.80 g, 21.81 mmol) was added. The mixture was stirred at 15° C. for 1 hour. Then (2-fluoropyridin-3-yl)[1-(trifluoromethyl)cyclopropyl]methanone (2.4 g, 10.3 mmol, intermediate 488) was added. The mixture was stirred at 15° C. for further 13 hours. LC-MS indicated the reaction completed. The reaction mixture was quenched by water (100 mL) slowly. The suspension was extracted with ethyl acetate (100 mL×2). The combined organic phase was washed with brine (100 mL×2), dried over anhydrous Na₂SO₄, filtered and concentrated by rotary evaporator in vacuum to give 2-fluoro-3-(2-(1-(trifluoromethyl)cyclopropyl)oxiran-2-yl)pyridine, which was used without further purification.

LC-MS (Method 9): $R_t$=0.82 min; MS (ESIpos): m/z=248 [M+H]⁺

Intermediate 490

3-[1-(trifluoromethyl)cyclopropyl]-2,3-dihydro-1H-pyrrolo[2,3-b]pyridin-3-ol

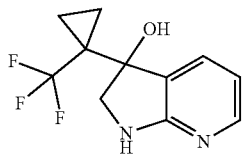 [SMILES: OC1(C2(C(F)(F)F)CC2)CNc2ncccc21]

To a solution of 2-fluoro-3-{2-[1-(trifluoromethyl)cyclopropyl]oxiran-2-yl}pyridine (2.4 g, 9.7 mmol, intermediate 489) in THF (12 mL) was added aq. NH₃—H₂O (50 mL, 364 mmol, 28% purity) at 10° C. The mixture was stirred at 60° C. for 32 hours. LC-MS indicated the reaction completed. The mixture was poured into water (50 mL). The suspension was extracted with ethyl acetate (50 mL×3). The combined organic phase was washed with brine (50 mL×2), dried over anhydrous Na₂SO₄, filtered and concentrated by rotary evaporator in vacuum. The residue was purified by prep-HPLC (column: Phenomenex Gemini C18 250*50 mm*10 um; mobile phase: [water (0.05% ammonia hydroxide v/v)-ACN]; B %: 20%-45%, 26 MIN; 78% min) to get a solution, which was concentrated to 100 mL at 30° C. by rotary evaporator in vacuum. The formed solid was collected by filtration and dried in vacuum to give the first batch of 3-(1-(trifluoromethyl)cyclopropyl)-2,3-dihydro-1H-pyrrolo[2,3-b]pyridin-3-ol (1.0 g, 42% yield) as a white solid. The filtrate was lyophilized to give the second batch of 3-(1-(trifluoromethyl)cyclopropyl)-2,3-dihydro-1H-pyrrolo[2,3-b]pyridin-3-ol (200 mg, 8% yield) as a white solid.

¹H NMR (DMSO-d₆, 400 MHz): δ=0.92-0.88 (m, 2H), 1.09-1.05 (m, 2H), 3.35 (d, 1H), 3.73 (d, 1H), 5.68 (s, 1H), 6.50 (dd, 1H), 6.53 (s, 1H), 7.40 (d, 1H), 7.85 (dd, 1H).

¹⁹F NMR (DMSO-d₆, 400 MHz): δ=−62

LC-MS (Method 10): $R_t$=0.67 min; MS (ESIpos): m/z=245 [M+H]⁺

Intermediate 491

3-[1-(trifluoromethyl)cyclopropyl]-1H-pyrrolo[2,3-b]pyridine

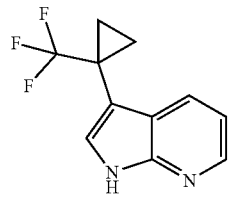 [SMILES: FC(F)(F)C1(c2c[nH]c3ncccc23)CC1]

To a mixture of 3-[1-(trifluoromethyl)cyclopropyl]-2,3-dihydro-1H-pyrrolo[2,3-b]pyridin-3-ol (45 g, 158 mmol, 86% purity, intermediate 490) and pyridine (25 mL, 310 mmol) in dichloromethane (500 mL) was added thionyl chloride (22 mL, 303 mmol) drop-wise at 0° C. under a nitrogen atmosphere. The mixture was stirred at 15° C. for 12 hours. The mixture was poured into ice-water (500 mL) and neutralized to pH=5-6 with 10% aqueous sodium hydroxide. The aqueous phase was extracted with dichloromethane (300 mL×2). The combined organic phase was washed with brine (300 mL×2), dried over sodium sulfate, filtered and concentrated by rotary evaporator in vacuum. The residue was purified by silica gel chromatography (1000 mesh silica gel, petrol ether:ethyl acetate=10:1 to 1:1) to give the title compound (35 g, 98% yield) as a yellow solid.

¹H NMR (400 MHz, DMSO-d₆): δ=1.17-1.14 (m, 2H), 1.39-1.36 (m, 2H), 7.35-7.32 (m, 1H), 7.74 (d, 1H), 9.30 (d, 1H), 8.39-8.37 (m, 1H), 12.41 (s, 1H).

Intermediate 492

3-[1-(trifluoromethyl)cyclopropyl]-1H-pyrrolo[2,3-b]pyridine 7-oxide

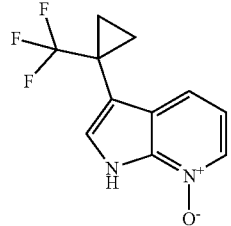 [SMILES: [O-][n+]1cccc2c(C3(C(F)(F)F)CC3)c[nH]c21]

To a solution of 3-[1-(trifluoromethyl)cyclopropyl]-1H-pyrrolo[2,3-b]pyridine (35 g, 155 mmol, intermediate 491) in dichloromethane (350 mL) was added m-chloroperoxybenzoic acid (47 g, 232 mmol, 85% purity) in portions at 0° C. The mixture was stirred at 15° C. for 12 hours. The mixture was filtered, and the filtrate was washed with saturated sodium thiosulfate solution (300 mL×2), brine (300 mL×2), dried over sodium sulfate, filtered and concentrated by rotary evaporator in vacuum. The residue was suspended in methyl tert.-butylether (50 mL) and stirred for 30 min. The suspension was filtered, and the cake was washed with methyl tert.-butylether (20 mL×2) and dried by in vacuum to give the desired tile compound which was used without further purification.

¹H NMR (400 MHz, DMSO-d₆): δ=1.13 (m, 2H), 1.37-1.34 (m, 2H), 7.15-7.12 (m, 1H), 7.59 (s, 1H), 7.64 (d, 1H), 8.17 (d, 1H), 12.62 (s, 1H).

Intermediate 493

4-nitro-3-[1-(trifluoromethyl)cyclopropyl]-1H-pyrrolo[2,3-b]pyridine 7-oxide

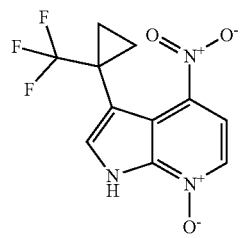 [SMILES: O=[N+]([O-])c1cc[n+]([O-])c2[nH]cc(C3(C(F)(F)F)CC3)c12]

To a solution of 3-[1-(trifluoromethyl)cyclopropyl]-1H-pyrrolo[2,3-b]pyridine 7-oxide (37 g, crude, intermediate 492) in trifluoro acidic acid (400 mL) was added nitric acid (30 g, 309 mmol, 65% purity) drop-wise at 0° C. The mixture was warmed to 15° C. and stirred for 14 hours. Then additional nitric acid (14 g, 222 mmol, 65% purity) was added at 0° C., the mixture was stirred at 15° C. for another 14 hours. The mixture was poured into ice-water (800 mL) and stirred for 10 min. The aqueous phase was extracted with dichloromethane (300 mL×3). The combined organic phase was washed with brine (300 mL×2), dried over sodium sulfate, filtered and concentrated by rotary evaporator in vacuum to give the desired title compound which was used without further purification.

¹H NMR (400 MHz, DMSO-d₆): δ=1.42-1.37 (m, 4H), 7.95-7.90 (m, 2H), 8.35 (d, 1H), 13.49 (s, 1H).

Intermediate 494

6-chloro-4-nitro-3-[1-(trifluoromethyl)cyclopropyl]-1H-pyrrolo[2,3-b]pyridine

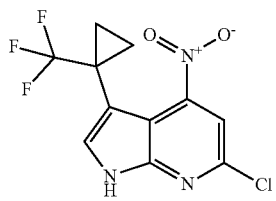 [SMILES: O=[N+]([O-])c1cc(Cl)nc2[nH]cc(C3(C(F)(F)F)CC3)c12]

To a solution of 4-nitro-3-[1-(trifluoromethyl)cyclopropyl]-1H-pyrrolo[2,3-b]pyridine 7-oxide (60 g, crude, intermediate 493) in THF (600 mL) was added hexamethyidisilazane (25 mL, 119 mmol) in one portion at 0° C. under nitrogen atmosphere. Then 2,2,2-trichloroacetyl chloride (30 mL, 269 mmol) was added drop-wise. The mixture was warmed to 15° C. and stirred for 12 hours. The mixture was poured into ice-water (1 L) and stirred for 30 min. The aqueous phase was extracted with ethyl acetate (500 mL×2). The combined organic phase was washed with a saturated aqueous solution of sodium bicarbonate (500 mL×2) and brine (500 mL×2), dried over sodium sulfate, filtered and concentrated by rotary evaporator in vacuum. The residue was purified by silica gel chromatography (100-200 mesh silica gel, petrol ether: ethyl acetate=100:1 to 10:1) to give the desired title compound (35 g, 57% purity) as a yellow solid.

¹H NMR (400 MHz, DMSO-d₆): δ=1.39-1.30 (m, 4H), 7.88 (s, 1H), 8.09 (d, 1H).

Intermediate 495

6-chloro-4-nitro-3-[1-(trifluoromethyl)cyclopropyl]-1-{[2-(trimethylsilyl)ethoxy]methyl}-1H-pyrrolo[2,3-b]pyridine

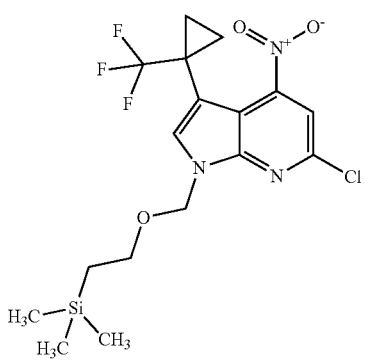 [SMILES: C[Si](C)(C)CCOCn1cc(C2(C(F)(F)F)CC2)c2c([N+](=O)[O-])cc(Cl)nc21]

To a solution of 6-chloro-4-nitro-3-[1-(trifluoromethyl)cyclopropyl]-1H-pyrrolo[2,3-b]pyridine (35 g, 65 mmol, 57% purity, intermediate 494) in DMF (350 mL) was added N,N-diisopropyl-ethylamine (24 mL, 138 mmol) at 15° C. The mixture was stirred at 15° C. for 10 min, then 2-(trimethylsilyl)ethoxymethyl chloride (15 mL, 85 mmol) was added. The mixture was stirred at 15° C. for 20 min. The mixture was poured into ice-water (1 L). The aqueous phase was extracted with ethyl acetate (500 mL×2). The combined organic phase was washed with brine (500 mL×2), dried over sodium sulfate, filtered and concentrated by rotary evaporator in vacuum. The residue was purified by silica gel chromatography (100-200 mesh silica gel, petrol ether to petrol ether:ethyl acetate=50:1) to give the desired title compound (25 g, 46.6% yield, 53% purity) as a yellow oil.

¹H NMR (400 MHz, DMSO-d₆): δ=0.12 (s, 9H), 0.86-0.79 (m, 2H), 1.35-1.29 (m, 2H), 1.43 (m, 2H), 3.55 (d, 2H), 5.64 (s, 2H), 7.98 (s, 1H), 8.31 (s, 1H).

Intermediate 496

4-[(6-chloro-3-[1-(trifluoromethyl)cyclopropyl]-1-{[2-(trimethylsilyl)ethoxy]methyl}-1H-pyrrolo[2,3-b]pyridin-4-yl)oxy]-3,5-difluoroaniline

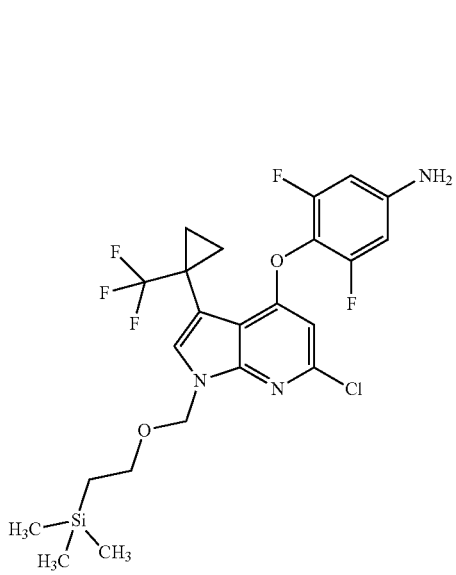

6-chloro-4-nitro-3-[1-(trifluoromethyl)cyclopropyl]-1-{[2-(trimethylsilyl)ethoxy]methyl}-1H-pyrrolo[2,3-b]pyridine (20 g, 24 mmol, 53% purity, intermediate 495) and 4-amino-2,6-difluorophenol (5.29 g, 36.5 mmol, CAS No. [126058-97-7]) in DMSO (200 mL) was added potassium carbonate (10.07 g, 72.86 mmol) at 15° C. under a nitrogen atmosphere. The mixture was heated to 50° C. and stirred for 2 hours. After cooling to room temperature, the reaction mixture was combined with another second identical reaction mixture using 5 g of 6-chloro-4-nitro-3-(1-(trifluoromethyl)cyclopropyl)-1-((2-(trimethylsilyl)ethoxy)methyl)-1H-pyrrolo[2,3-b]pyridine (intermediate 495). The combined reaction mixtures were poured into ice-water (500 mL). The aqueous phase was extracted with ethyl acetate (500 mL×3). The combined organic phase was washed with brine (500 mL×2), dried over sodium sulfate, filtered and concentrated by evaporator in vacuum. The residue was purified by silica gel chromatography (100-200 mesh silica gel, petrol ether:ethyl acetate=30:1 to 10:1) to give the desired title compound (9 g, 86% purity) as a yellow solid. Meanwhile, 6-chloro-4-nitro-3-[1-(trifluoromethyl)cyclopropyl]-1-{[2-(trimethylsilyl)ethoxy]methyl}-1H-pyrrolo[2,3-b]pyridine (5 g, 68% purity) was recovered as a yellow oil.

$^1$H NMR (400 MHz, DMSO-d$_6$): δ=−0.11 (s, 9H), 0.80 (t, 2H), 1.19-1.16 (m, 2H), 1.37-1.36 (m, 2H), 3.54 (t, 2H), 5.54 (s, 2H), 5.83 (s, 2H), 6.32 (s, 1H), 6.40 (d, 1H), 7.79 (s, 1H).

Intermediate 497

3,5-difluoro-4-[(3-[1-(trifluoromethyl)cyclopropyl]-1-{[2-(trimethylsilyl)ethoxy]methyl}-1H-pyrrolo[2,3-b]pyridin-4-yl)oxy]aniline

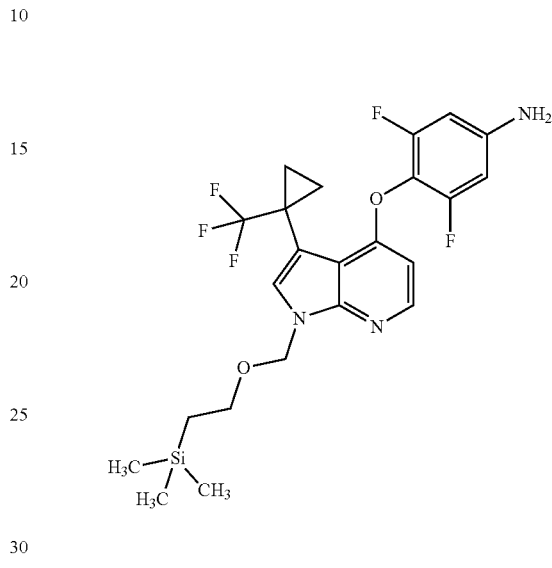

4-[(6-chloro-3-[1-(trifluoromethyl)cyclopropyl]-1-{[2-(trimethylsilyl)ethoxy]methyl}-1H-pyrrolo[2,3-b]pyridin-4-yl)oxy]-3,5-difluoroaniline (9 g, 86% purity and 3 g, crude, intermediate 496) in THF (200 mL) were added palladium on charcoal (2 g, 10% purity, containing 50% water) and triethylamine (10 mL, 71.9 mmol) under a nitrogen atmosphere. The suspension was degassed under vacuum and purged with hydrogen several times. The mixture was stirred under hydrogen (15 psi) at 45° C. for 36 hours. The mixture was filtered through a pad of Celite and the filtrate was concentrated in vacuum. The residue was dissolved in THF (200 mL) and palladium on charcoal (2 g, 10% purity, containing 50% water) was added. The mixture was stirred under hydrogen (15 psi) at 45° C. for 60 hours. The mixture was filtered through a pad of Celite, and the cake was washed with ethanol (100 mL×2). The filtrate was concentrated by evaporator in vacuum. The residue was purified by flash silica gel chromatography (0-10% of ethyl acetate in petroleum ether) to give the desired title compound (9 g, containing solvents residue) as brown oil. This product was combined with second batch of product (3 g, containing solvents residue) by dissolving in acetonitrile (200 mL). Water (100 mL) was added. The solution was concentrated by evaporation in vacuum to ~150 mL. The residue was lyophilized to give the desired title compound (10.2 g) as a white solid.

$^1$H NMR (400 MHz, DMSO-d$_6$): δ=−0.11 (s, 9H), 0.82-0.78 (m, 2H), 1.17 (m, 2H), 1.38-1.35 (m, 2H), 3.54 (t, 2H), 5.59 (m, 2H), 5.76 (s, 2H), 6.42-6.34 (m, 3H), 7.73 (s, 1H), 8.11 (d, 1H).

$^{19}$F NMR (400 MHz, DMSO-d$_6$): δ=−69, −129.

Intermediate 498

N-{3,5-difluoro-4-[(3-[1-(trifluoromethyl)cyclopropyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea

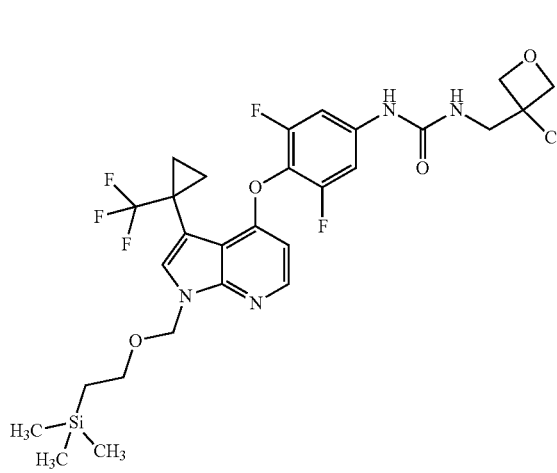

3,5-difluoro-4-[(3-[1-(trifluoromethyl)cyclopropyl]-1-{[2-(trimethylsilyl)ethoxy]methyl}-1H-pyrrolo[2,3-b]pyridin-4-yl)oxy]aniline (100 mg, 200 µmol, Intermediate 497) was dissolved in dichloromethane (1.7 mL) and 3-(isocyanatomethyl)-3-methyloxetane (CAS No: 1260665-88-0, 50.9 mg, 400 µmol) and pyridine (1.8 mL) were added. The mixture was stirred overnight at 60° C. in a closed microwave vial. The crude was diluted with toluene and the solvent evaporated. The resulting residue was purified by silica gel chromatography using a Biotage system to yield the title compound (127 mg, 96% yield).

LC-MS (Method 2): $R_f$=1.51 min; MS (ESIpos): m/z=628 [M+H]$^+$ $^1$H-NMR (400 MHz, CDCl$_3$) δ [ppm]: −0.06 (s, 9H), 0.90 (m, 2H), 1.20 (m, 2H), 1.33 (s, 3H), 1.40 (m, 2H), 3.46 (m, 2H), 3.57 (m, 2H), 4.48 (d, 2H), 4.52 (d, 2H), 5.21 (m, 1H), 5.64 (s, 2H), 6.31 (m, 1H), 6.72 (m, 1H), 7.15 (m, 2H), 7.35 (s, 1H), 8.12 (d, 1H).

EXPERIMENTAL SECTION—EXAMPLES

The following examples describe the embodiment of the instant invention, not restricting the invention to these examples only.

Example 1

(+/−)-{2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol

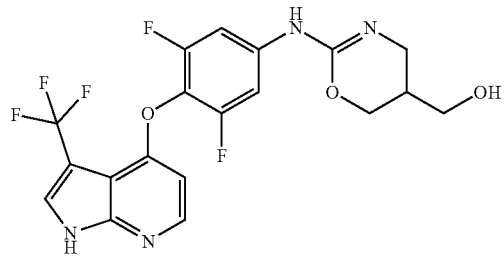 [SMILES: OCC1CN=C(Nc2cc(F)c(Oc3ccnc4[nH]cc(C(F)(F)F)c34)c(F)c2)OC1]

To a solution of 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-(oxetan-3-ylmethyl)urea (151 mg, 264 µmol, intermediate 2 in dichloromethane (3.6 mL) was added trifluoroacidic acid (1.8 mL, 23 mmol) and this mixture was stirred for 3 hours at room temperature. The reaction mixture was carefully poured into an aqueous solution of sodium hydrogencarbonate. This aqueous phase was extracted two times with ethyl acetate. Then the combined organic phases were washed with brine, dried over sodium sulfate and then after filtration evaporated to dryness in vacuum. The obtained crude product was purified via a Biotage chromatography system (11 g snap KP-NH column, hexane/0-100% ethylacetate, then ethyl acetate/0-100% methanol) to obtain an oil, which was treated with 5 mL dichloromethane. After stirring for one hour at room temperature the solid was obtained by filtration. The 61 mg crude product was then resolved in ethyl acetate and washed with an aqueous solution of sodium hydrogencarbonate, then water and brine, dried over sodium sulfate. After filtration and evaporation to dryness in vacuum we obtained 34.8 mg (95% purity, 28% yield) of the desired title compound.

$^1$H-NMR (500 MHz, DMSO-d6) δ [ppm]: 3.13 (br s, 1H), 3.36-3.49 (m, 4H), 4.07 (br d, 1H), 4.31 (dd, 1H), 4.76 (br s, 1H), 6.43 (d, 1H), 7.56 (br s, 1H), 8.05-8.09 (m, 1H), 8.19 (s, 1H), 8.20 (s, 1H), 9.00 (br s, 1H), 12.58 (br s, 1H).

Example 2

(+/−)-{2-[(3,5-difluoro-4-{[3-(trifluoromethyl)-1H-pyrrolo[2,3-b]pyridin-4-yl]oxy}phenyl)amino]-5-methyl-5,6-dihydro-4H-1,3-oxazin-5-yl}methanol

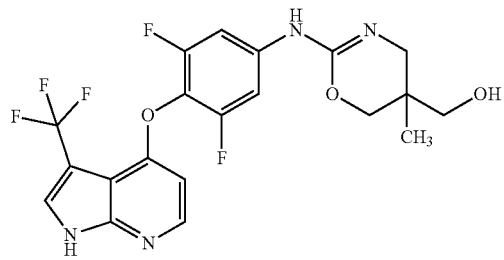

To a solution of 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (178 mg, 303 μmol, intermediate 3 in dichloromethane (3.2 mL) was added trifluoroacidic acid (1.6 mL, 21 mmol) and this mixture was stirred for 3 hours at room temperature. The reaction mixture was diluted with ethyl acetate and two times washed with an aqueous solution of sodium hydrogencarbonate, then water, brine, dried over sodium sulfate and after filtration evaporated to dryness in vacuum. The obtained crude product was purified via a Biotage chromatography system (11 g snap KP-NH column, hexane/0-100% ethylacetate, then ethyl acetate/0-100% methanol) to obtain a product which was finally purified via a preparative HPLC (method 1) to yield 29.2 mg (95% purity, 25.5% yield) of the desired title compound.

LC-MS (Method 2): $R_f$=1.02 min; MS (ESIpos): m/z=457 $[M+H]^+$ $^1$H-NMR (400 MHz, DMSO-d6) δ [ppm]: 0.90 (s, 3H), 3.01 (br d, 1H), 3.15-3.29 (m, 2H), 3.29-3.37 (m, 1H), 3.87 (br d, 1H), 4.06 (br d, 1H), 4.83 (br s, 1H), 6.45 (d, 1H), 7.31-7.71 (m, 2H), 8.10 (s, 1H), 8.20 (d, 1H), 9.03 (br s, 1H), 12.60 (br s, 1H).

Example 3

(+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazine-5-carbonitrile

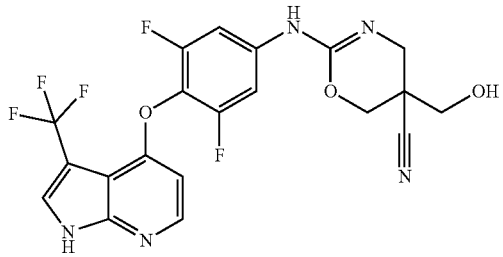 [SMILES: N#CC1(CO)CN=C(Nc2cc(F)c(Oc3ccnc4[nH]cc(C(F)(F)F)c34)c(F)c2)OC1]

To a solution of 1-[(3-cyanooxetan-3-yl)methyl]-3-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)urea (131 mg, 219 μmol, intermediate 4) in dichloromethane (3.0 mL) was added trifluoroacidic acid (1.5 mL, 20 mmol) and this mixture was stirred for 3 hours at room temperature. The reaction mixture was carefully poured into water and neutralized using an aqueous solution of sodium hydrogencarbonate. This mixture is extracted three times with ethyl acetate and then the combined organic phases were washed with brine, dried over sodium sulfate and after filtration evaporated to dryness in vacuum. The obtained crude product was purified via a Biotage chromatography system (11 g snap KP-NH column, hexane/0-100% ethylacetate, then ethyl acetate/0-100% methanol) to obtain 48.1 mg (90% purity, 42% yield) of the desired title compound.

$^1$H-NMR (600 MHz, DMSO-d6) δ [ppm]: 3.47-3.54 (m, 1H), 3.58 (dd, 1H), 3.62-3.69 (m, 2H), 4.25 (d, 1H), 4.48 (dd, 1H), 5.68 (t, 1H), 6.46-6.49 (m, 1H), 7.57 (br d, 2H), 8.10 (br s, 1H), 8.20 (d, 1H), 9.36 (br s, 1H), 12.58-12.68 (m, 1H).

Example 4

(+/−)-{5-(difluoromethyl)-2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol

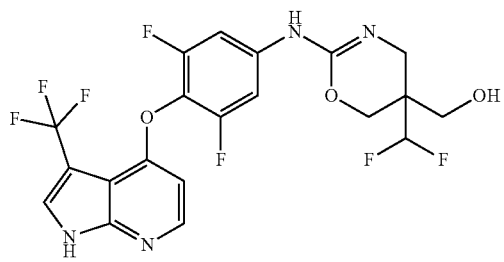 [SMILES: OCC1(C(F)F)CN=C(Nc2cc(F)c(Oc3ccnc4[nH]cc(C(F)(F)F)c34)c(F)c2)OC1]

In analogy to example 3, 1-{[3-(difluoromethyl)oxetan-3-yl]methyl}-3-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)urea (126 mg, 202 μmol, intermediate 5) was stirred with trifluoroacidic acid (0.9 mL, 12 mmol) in dichloromethane (1.8 mL). After purification using a Biotage chromatography system we obtained 45.5 mg (95% purity, 43% yield) of the desired title compound.

$^1$H-NMR (600 MHz, DMSO-d6) δ [ppm]: 3.31 (br s, 1H), 3.44 (br s, 1H), 3.49 (br d, 2H), 4.24 (s, 2H), 5.20 (br s, 1H), 6.12 (t, 1H), 6.44 (d, 1H), 7.54 (br s, 2H), 8.08 (s, 1H), 8.20 (d, 1H), 9.16 (br s, 1H), 12.60 (br s, 1H).

Example 5

(+/−)-{2-[(3,5-difluoro-4-{[3-(trifluoromethyl)-1H-pyrrolo[2,3-b]pyridin-4-yl]oxy}phenyl)amino]-5-isopropyl-5,6-dihydro-4H-1,3-oxazin-5-yl}methanol

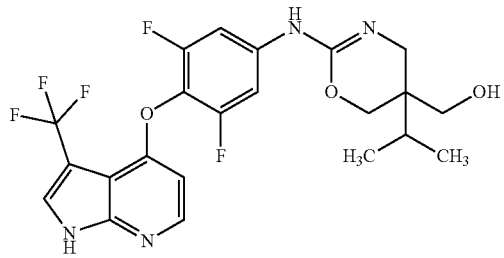 [SMILES: CC(C)C1(CO)CN=C(Nc2cc(F)c(Oc3ccnc4[nH]cc(C(F)(F)F)c34)c(F)c2)OC1]

In analogy to example 3, [3-(propan-2-yl)azetidin-3-yl]methyl (3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamate (131 mg, 212 μmol, intermediate 6) was stirred with trifluoroacidic acid (0.9 mL, 12 mmol) in dichloromethane (1.8 mL). After purification using a Biotage chromatography system we obtained 42.3 mg (90% purity, 37% yield) of the desired title compound.

$^1$H-NMR (600 MHz, DMSO-d6) δ [ppm]: 0.90 (d, 3H), 0.92 (d, 3H), 1.78 (dt, 1H), 3.04-3.23 (m, 2H), 3.38-3.43 (m, 2H), 3.99-4.07 (m, 1H), 4.15 (d, 1H), 4.73 (br s, 1H), 6.44 (d, 1H), 7.30-7.76 (m, 2H), 8.07 (br s, 1H), 8.20 (d, 1H), 9.06 (br s, 1H), 12.60 (br s, 1H).

Example 6

(+/−)-2-{2-[(3,5-difluoro-4-{[3-(trifluoromethyl)-1H-pyrrolo[2,3-b]pyridin-4-yl]oxy}phenyl)amino]-4,5-dihydro-1,3-oxazol-5-yl}-2-methylpropan-1-ol

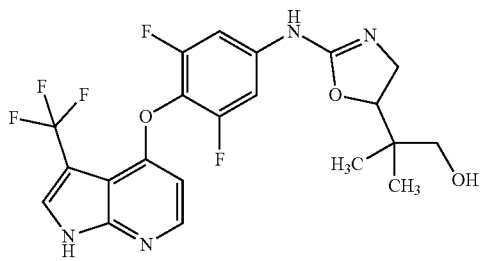 [SMILES: CC(C)(CO)C1CN=C(Nc2cc(F)c(Oc3ccnc4[nH]cc(C(F)(F)F)c34)c(F)c2)O1]

To a solution of 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3,3-dimethyloxetane-2-yl)methyl]urea (169 mg, 281 µmol, intermediate 7) in dichloromethane (3.8 mL) was added trifluoroacidic acid (1.9 mL, 25 mmol) and this mixture was stirred 3 h at room temperature. The reaction mixture was carefully poured into an aqueous solution of sodium hydrogenecarbonate. This aqueous phase was extracted two times with ethyl acetate. Then the combined organic phases were washed with brine, dried via a hydrophobic filter and evaporated to dryness in vacuum.

The obtained crude product was purified via a Biotage chromatography system (11 g snap KP-NH column, hexane/0-100% ethylacetate, then ethyl acetate/0-100% ethanol) to obtain 62.2 mg (90% purity, 42% yield) of the desired title compound.

$^1$H-NMR (500 MHz, DMSO-d6) δ [ppm]: 0.92 (s, 3H), 0.97 (s, 3H), 3.31-3.41 (m, 2H), 3.59-3.79 (m, 2H), 4.54 (br t, 1H), 4.62 (br t, 1H), 6.52 (d, 1H), 7.28 (br s, 2H), 8.04 (s, 1H), 8.28 (d, 1H), 12.44 (br s, 1H).

Example 7

(+/−)-{2-[(3,5-difluoro-4-{[3-(trifluoromethyl)-1H-pyrrolo[2,3-b]pyridin-4-yl]oxy}phenyl)amino]-4,5-dihydro-1,3-oxazol-4-yl}methanol

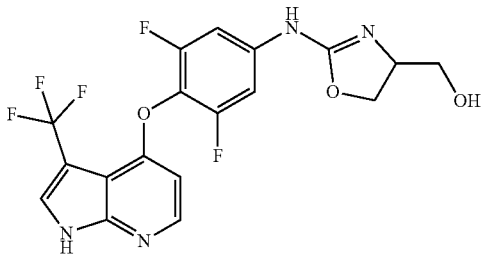 [SMILES: OCC1COC(Nc2cc(F)c(Oc3ccnc4[nH]cc(C(F)(F)F)c34)c(F)c2)=N1]

In analogy to example 3, 1-(3,5-difluoromethyl)-1-{[2-(trimethylsilyl)ethoxy]methyl}-1H-pyrrolo[2,3-b]pyridin-4-yl]oxy}phenyl)-3-oxetan-3-ylurea (92.0 mg, 165 µmol, intermediate 8) was stirred with trifluoroacidic acid (1.2 mL, 15 mmol) in dichloromethane (2.3 mL). After purification using a Biotage chromatography system we obtained 38.9 mg (90% purity, 50% yield) of the desired title compound.

$^1$H-NMR (500 MHz, DMSO-d6) δ [ppm]: 3.39-3.46 (m, 1H), 3.47-3.56 (m, 1H), 3.95-4.08 (m, 1H), 4.18 (br s, 1H), 4.38 (br s, 1H), 4.60 (br s, 1H), 6.43 (d, 1H), 7.23 (br s, 2H), 7.96 (s, 1H), 8.20 (d, 1H), 12.36 (br s, 1H).

Example 8

(+/−)-{2-[(3,5-difluoro-4-{[3-(trifluoromethyl)-1H-pyrrolo[2,3-b]pyridin-4-yl]oxy}phenyl)amino]-5-fluoro-5,6-dihydro-4H-1,3-oxazin-5-yl}methanol

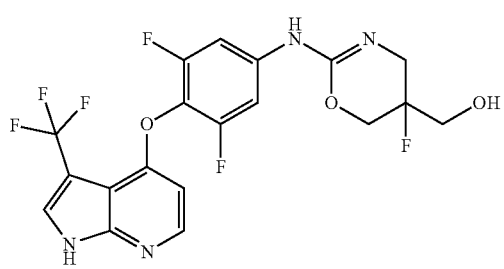 [SMILES: OCC1(F)CN=C(Nc2cc(F)c(Oc3ccnc4[nH]cc(C(F)(F)F)c34)c(F)c2)OC1]

In analogy to example 3, 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-fluorooxetan-3-yl)methyl]urea (129 mg, 218 µmol, intermediate 9) was stirred with trifluoroacidic acid (1.5 mL, 19 mmol) in dichloromethane (3.0 mL). After purification using a Biotage chromatography system we obtained 82.5 mg (97% purity, 80% yield) of the desired title compound.

$^1$H-NMR (400 MHz, DMSO-d6) δ [ppm]: 3.37-3.67 (m, 4H), 4.22-4.36 (m, 2H), 5.25 (br t, 1H), 6.45 (d, 1H), 7.57 (d, 2H), 8.10 (s, 1H), 8.20 (d, 1H), 9.23 (br s, 1H), 12.62 (s, 1H).

Example 9

(+/−)-2-[(3,5-difluoro-4-{[3-(trifluoromethyl)-1H-pyrrolo[2,3-b]pyridin-4-yl]oxy}phenyl)amino]-4-(hydroxymethyl)-4,5-dihydro-1,3-oxazole-4-carboxamide

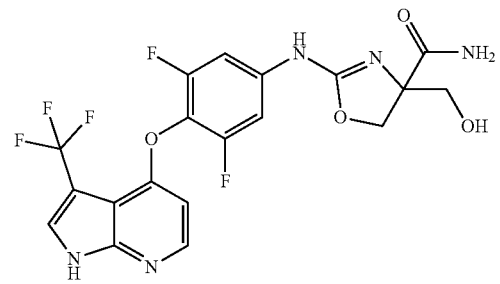 [SMILES: NC(=O)C1(CO)COC(Nc2cc(F)c(Oc3ccnc4[nH]cc(C(F)(F)F)c34)c(F)c2)=N1]

In analogy to example 2, 3-{[(3,5-difluoro-4-{[3-(trifluoromethyl)-1-{[2-(trimethylsilyl)ethoxy]methyl}-1H-pyrrolo[2,3-b]pyridin-4-yl]oxy}phenyl)carbamoyl]amino}oxetane-3-carboxamide (66.6 mg, 111 µmol, intermediate 10) was stirred with trifluoroacidic acid (0.9 mL, 12 mmol) in dichloromethane (1.8 mL).

After purification using a Biotage chromatography system followed by HPLC (method 1) we obtained 38.3 mg (92% purity, 68% yield) of the desired title compound.

¹H-NMR (500 MHz, DMSO-d6) δ [ppm]: 3.51-3.62 (m, 2H), 4.26 (br d, 1H), 4.34 (br d, 1H), 5.00 (br s, 1H), 6.46 (d, 1H), 7.26 (br s, 1H), 7.31 (br s, 1H), 7.66 (br s, 2H), 8.11 (br s, 1H), 8.22 (d, 1H), 9.87 (br s, 1H), 12.63 (br s, 1H).

Example 10

(+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazin-5-ol

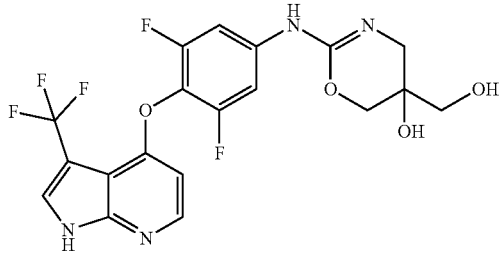 [SMILES: OCC1(O)CN=C(Nc2cc(F)c(Oc3ccnc4[nH]cc(C(F)(F)F)c34)c(F)c2)OC1]

In analogy to example 2, 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-hydroxyoxetan-3-yl)methyl]urea (196 mg, 333 µmol, intermediate 11) was stirred with trifluoroacidic acid (2.3 mL, 30 mmol) in dichloromethane (4.6 mL). After purification using a Biotage chromatography system followed by HPLC (method 1) we obtained 24.1 mg (93% purity, 15% yield) of the desired title compound.

¹H-NMR (400 MHz, DMSO-d6) δ [ppm]: 3.10 (br d, 1H), 3.41 (br d, 1H), 3.45-3.62 (m, 3H), 3.91 (br d, 1H), 4.13 (br d, 1H), 4.86-4.99 (m, 1H), 5.09 (br s, 1H), 6.45 (t, 1H), 7.45 (br s, 2H), 8.10 (br s, 1H), 8.18-8.22 (m, 1H), 12.61 (br s, 1H).

Example 11

(+/−)-{2-[(3,5-difluoro-4-{[3-(trifluoromethyl)-1H-pyrrolo[2,3-b]pyridin-4-yl]oxy}phenyl)amino]-5-phenyl-5,6-dihydro-4H-1,3-oxazin-5-yl}methanol

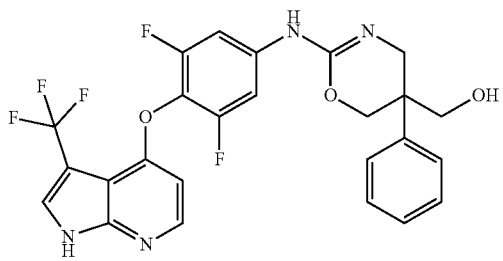 [SMILES: OCC1(c2ccccc2)CN=C(Nc2cc(F)c(Oc3ccnc4[nH]cc(C(F)(F)F)c34)c(F)c2)OC1]

In analogy to example 3, 1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[(3-phenyloxetan-3-yl)methyl]urea (124 mg, 192 µmol, intermediate 12) was stirred with trifluoroacidic acid (0.9 mL, 12 mmol) in dichloromethane (1.8 mL). After purification using a Biotage chromatography system we obtained 45.2 mg (95% purity, 43% yield) of the desired title compound.

¹H-NMR (400 MHz, DMSO-d6) δ [ppm]: 3.53-3.73 (m, 4H), 4.51 (s, 2H), 4.92 (br s, 1H), 6.44 (d, 1H), 7.25 (t, 1H), 7.35 (t, 2H), 7.40-7.70 (m, 4H), 8.10 (s, 1H), 8.19 (d, 1H), 9.04 (br s, 1H), 12.61 (br s, 1H).

Example 12

(+/−)-{2-[(3,5-difluoro-4-{[3-(trifluoromethyl)-1H-pyrrolo[2,3-b]pyridin-4-yl]oxy}phenyl)amino]-4-methyl-5,6-dihydro-4H-1,3-oxazin-5-yl}methanol

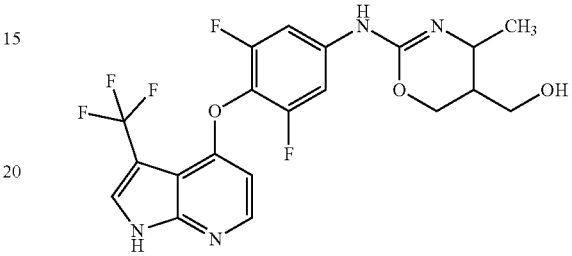

In analogy to example 2, (+/−)-1-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-3-[1-(oxetan-3-yl)ethyl]urea (79.5 mg, 136 µmol, intermediate 13) was stirred with trifluoroacidic acid (0.9 mL, 12 mmol) in dichloromethane (1.8 mL). After purification using a Biotage chromatography system followed by HPLC (method 1) we obtained 34.4 mg (90% purity, 50% yield) of the desired title compound.

¹H-NMR (400 MHz, DMSO-d6, main isomer) δ [ppm]: 1.19 (d, 3H), 1.65 (br s, 1H), 3.27-3.32 (m, 1H), 3.36-3.43 (m, 1H), 3.47-3.57 (m, 1H), 4.05 (br t, 1H), 4.30 (dd, 1H), 4.77 (br s, 1H), 6.45 (d, 1H), 7.20-7.76 (m, 2H), 8.10 (s, 1H), 8.20 (d, 1H), 9.02 (br s, 1H), 12.61 (br s, 1H).

Example 13

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile

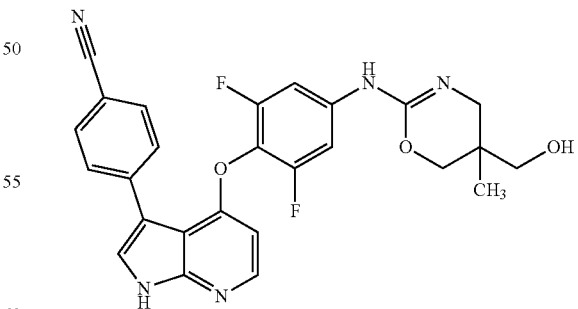

In analogy to example 2, 1-(4-{[3-(4-cyanophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (64.0 mg, 103 µmol, intermediate 20) was stirred with trifluoroacidic acid (0.7 mL, 9.1 mmol) in dichloromethane (1.4 mL). After purification using a Biotage chromatography system followed by HPLC (method 1) we obtained 16.5 mg (93% purity, 30% yield) of the desired title compound.

LC-MS (Method 2): $R_t$=1.03 min; MS (ESIpos): m/z=490 [M+H]$^+$ $^1$H-NMR (400 MHz, DMSO-d6) δ [ppm]: 0.90 (s, 3H), 3.00 (br d, 1H), 3.12-3.29 (m, 2H), 3.88 (br d, 1H), 4.06 (d, 1H), 4.82 (br s, 1H), 6.37 (d, 1H), 7.57 (br s, 2H), 7.80-7.91 (m, 5H), 8.13 (d, 1H), 9.03 (br s, 1H), 12.35 (br s, 1H).

Example 14

(+/−)-[2-({4-[(3-bromo-1H-pyrrolo[2,3-b]pyridin-4-yl)oxy]-3,5-difluorophenyl}amino)-5,6-dihydro-4H-1,3-oxazin-5-yl]methanol

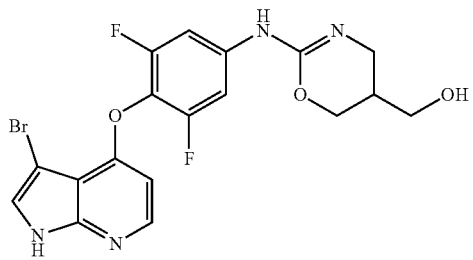 [SMILES: OCC1CN=C(Nc2cc(F)c(Oc3ccnc4[nH]cc(Br)c34)c(F)c2)OC1]

A solution of crude 1-{4-[(3-bromo-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea (120 mg, 206 μmol, intermediate 23) in dichloromethane (2 mL) was treated with trifluoroacetic acid (20 eq., 320 μL, 4.1 mmol) at rt overnight. The reaction mixture was concentrated in vacuo and the residue subjected to preparative HPLC to give the title compound (22 mg, 22%).

LC-MS (Method 3): $R_t$=0.92 min; MS (ESIpos): m/z=453/455 [M+H]$^+$ (Br isotope pattern).

$^1$H-NMR (400 MHz, DMSO-d$_6$) δ [ppm]=2.03 (br s, 1H), 3.09-3.15 (m, 1H), 3.37-3.47 (m, 3H), 4.05 (t, 1H), 4.31 (ddd, 1H), 4.77 (br s, 1H), 6.30 (d, 1H), 7.35-7.63 (m, 3H), 8.09 (d, 1H), 9.01 (br s, 1H), 12.19 (br s, 1H).

Example 15

(+/−)-[2-({4-[(3-bromo-1H-pyrrolo[2,3-b]pyridin-4-yl)oxy]-3,5-difluorophenyl}amino)-5-methyl-5,6-dihydro-4H-1,3-oxazin-5-yl]methanol

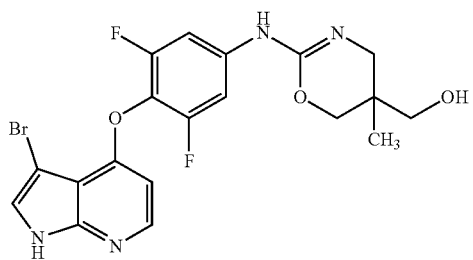

A solution of crude 1-{4-[(3-bromo-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea (227 mg, 380 μmol, intermediate 24) in dichloromethane (2.5 mL) was treated with trifluoroacetic acid (20 eq., 590 μL, 7.6 mmol) at rt overnight. The reaction mixture was concentrated in vacuo and the residue subjected to preparative HPLC to give the title compound (66 mg, 34%).

LC-MS (Method 3): $R_t$=0.95 min; MS (ESIpos): m/z=467/469 [M+H]$^+$ (Br isotope pattern).

$^1$H-NMR (400 MHz, DMSO-d$_6$) δ [ppm]=0.90 (s, 3H), 3.01 (d, 1H), 3.20-3.35 (m, 3H), 3.88 (d, 1H), 4.07 (dd, 1H), 4.83 (t, 1H), 6.31 (d, 1H), 7.34-7.44 (m, 2H), 7.63 (d, 1H), 8.09 (d, 1H), 9.01 (br s, 1H), 12.18 (br s, 1H).

Example 16

(+/−)-4-(2,6-difluoro-4-{[5-(hydroxymethyl)-5,6-dihydro-4H-1,3-oxazin-2-yl]amino}phenoxy)-1H-pyrrolo[2,3-b]pyridine-3-carbonitrile

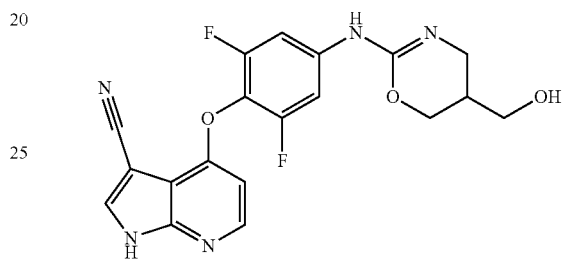

A solution of crude 1-{4-[(3-cyano-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea (318 mg, 600 μmol, intermediate 29) in dichloromethane (2.5 mL) was treated with trifluoroacetic acid (40 eq., 1.8 mL, 24 mmol) at rt overnight. The reaction mixture was concentrated in vacuo and the residue subjected to preparative HPLC to give the title compound (26 mg, 10%).

LC-MS (Method 3): $R_t$=0.69 min; MS (ESIpos): m/z=400 [M+H]$^+$.

$^1$H-NMR (400 MHz, DMSO-d$_6$) δ [ppm]=2.04 (br s, 1H), 3.09-3.15 (m, 1H), 3.39-3.47 (m, 3H), 4.06 (t, 1H), 4.31 (dd, 1H), 4.77 (br s, 1H), 6.49 (d, 1H), 7.38-7.74 (m, 2H), 8.22 (d, 1H), 8.43 (s, 1H), 9.07 (br s, 1H), 12.39 (br s, 1H).

Example 17

(+/−)-4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridine-3-carbonitrile

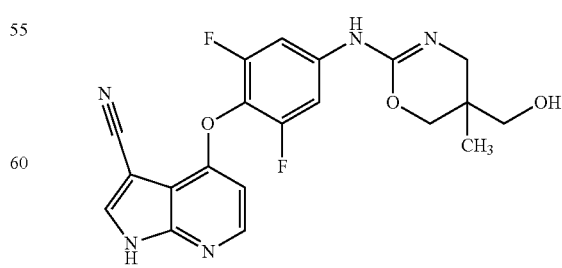

A solution of crude 1-{4-[(3-cyano-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea (334 mg, 615 μmol, intermediate 30) in dichloromethane (2 mL) was treated with trifluoroacetic acid (40 eq., 1.9 mL, 25 mmol) at rt overnight. The reaction mixture was concentrated in vacuo and the residue subjected to preparative HPLC to give the title compound (72 mg, 26%).

LC-MS (Method 3): $R_t$=0.74 min; MS (ESIpos): m/z=414 [M+H]$^+$.

$^1$H-NMR (400 MHz, DMSO-d$_6$) δ [ppm]=0.91 (s, 3H), 3.00-3.03 (m, 1H), 3.20-3.35 (m, 3H), 3.88 (d, 1H), 4.07 (d, 1H), 4.83 (br s, 1H), 6.50 (d, 1H), 7.58 (mc, 2H), 8.22 (d, 1H), 8.43 (s, 1H), 9.07 (br s, 1H), 12.95 (br s, 1H).

Example 18

(+/−)-[2-({4-[(3-cyclopropyl-1H-pyrrolo[2,3-b]pyridin-4-yl)oxy]-3,5-difluorophenyl}amino)-5-methyl-5,6-dihydro-4H-1,3-oxazin-5-yl]methanol

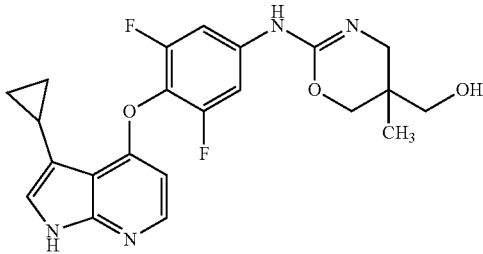 [SMILES: CC1(CO)CN=C(Nc2cc(F)c(Oc3ccnc4[nH]cc(C5CC5)c34)c(F)c2)OC1]

A solution of crude 1-{4-[(3-cyclopropyl-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea (303 mg, 0.5 mmol, intermediate 34) in dichloromethane (3 mL) was treated with trifluoroacetic acid (40 eq., 1.7 mL, 22 mmol) at rt for 5 days. The reaction mixture was concentrated in vacuo and the residue subjected to preparative HPLC to give the title compound (14 mg).

LC-MS (Method 3): $R_t$=1.01 min; MS (ESIpos): m/z=429 [M+H]$^+$.

$^1$H-NMR (400 MHz, DMSO-d$_6$) δ [ppm]=0.61-0.64 (m, 2H), 0.81-0.85 (m, 2H), 0.90 (s, 3H), 2.14-2.20 (m, 1H), 2.99-3.03 (m, 1H), 3.20-3.27 (m, 3H), 3.87 (d, 1H), 4.06 (d, 1H), 4.83 (br s, 1H), 6.19 (d, 1H), 7.06 (d, 1H), 7.39-7.64 (m, 2H), 7.98 (d, 1H), 9.01 (br s, 1H), 11.44 (d, 1H).

Example 19

(+/−)-[2-({4-[(3-cyclopropyl-1H-pyrrolo[2,3-b]pyridin-4-yl)oxy]-3,5-difluorophenyl}amino)-5-fluoro-5,6-dihydro-4H-1,3-oxazin-5-yl]methanol

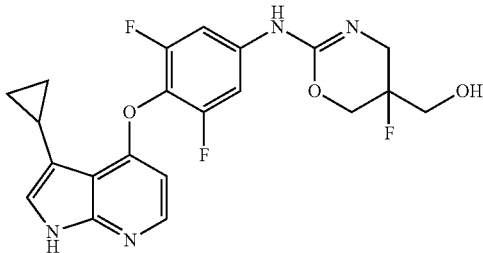 [SMILES: OCC1(F)CN=C(Nc2cc(F)c(Oc3ccnc4[nH]cc(C5CC5)c34)c(F)c2)OC1]

A solution of crude 1-{4-[(3-cyclopropyl-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea (305 mg, 0.5 mmol, intermediate 35) in dichloromethane (3 mL) was treated with trifluoroacetic acid (40 eq., 1.7 mL, 22 mmol) at rt for 5 days. The reaction mixture was concentrated in vacuo and the residue subjected to preparative HPLC to give the title compound (22 mg).

LC-MS (Method 3): $R_t$=0.99 min; MS (ESIpos): m/z=433 [M+H]$^+$.

$^1$H-NMR (400 MHz, DMSO-d$_6$) δ [ppm]=0.61-0.64 (m, 2H), 0.81-0.85 (m, 2H), 2.14-2.20 (m, 1H), 3.39-3.66 (m, 4H), 4.23-4.32 (m, 2H), 5.25 (t, 1H), 6.19 (d, 1H), 7.06 (d, 1H), 7.47-7.64 (m, 2H), 7.97 (d, 1H), 9.21 (br s, 1H), 11.45 (d, 1H).

Example 20

(+/−)-{2-[(3,5-difluoro-4-{[3-(2-methyl-3-thienyl)-1H-pyrrolo[2,3-b]pyridin-4-yl]oxy}phenyl)amino]-5-methyl-5,6-dihydro-4H-1,3-oxazin-5-yl}methanol

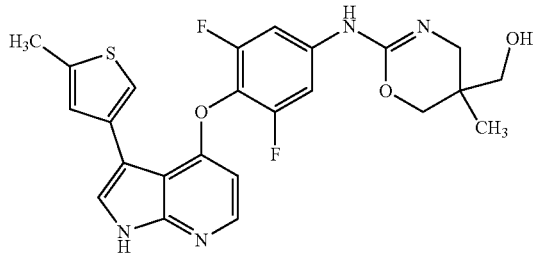 [SMILES: Cc1cc(-c2c[nH]c3nccc(Oc4c(F)cc(NC5=NCC(C)(CO)CO5)cc4F)c23)cs1]

1-(3,5-difluoro-4-{[3-(2-methylthiophen-3-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (177 mg, 90% purity, 259 μmol, intermediate 38) was dissolved in dichloromethane (8.3 mL) and trifluoroacetic acid (860 μL, 11 mmol) was added. The mixture was stirred overnight at room temperature. The solvent was removed under vacuum, and the residue stirred with acetonitrile (5 mL) and a 33% ammonia solution (2.5 mL) at room temperature for 1 h and then dried again. The residue was dissolved with dichloromethane and washed with water (×2) and brine (×1), dried with sodium sulfate, filtered and evaporated. The residue was purified by flash chromatography (55 g SNAP-NH column, dichloromethane/0-8% methanol) to give the title compound (105 mg, 79% yield).

LC-MS (Method 1): $R_t$=0.88 min; MS (ESIneg): m/z=483 [M−H]$^-$ $^1$H-NMR (400 MHz, DMSO-d6) δ [ppm]: 0.90 (s, 3H) 2.47 (s, 3H) 2.93-3.05 (m, 1H) 3.15-3.33 (m, 3H) 3.81-3.93 (m, 1H) 4.04 (s, 1H) 4.68-4.96 (m, 1H) 6.15-6.33 (m, 1H) 7.08-7.18 (m, 1H) 7.23 (d, 1H) 7.45 (d, 1H) 7.60 (br s, 1H) 8.07 (d, 1H) 8.98 (br s, 1H) 11.91-12.09 (m, 1H).

Example 21

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxynicotinonitrile

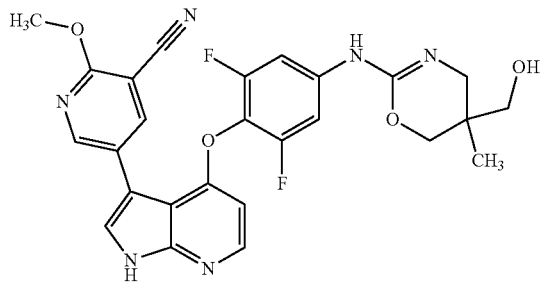 [SMILES: COc1ncc(-c2c[nH]c3nccc(Oc4c(F)cc(NC5=NCC(C)(CO)CO5)cc4F)c23)cc1C#N]

1-(4-{[3-(5-cyano-6-methoxypyridin-3-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (150 mg, 230 µmol, intermediate 41) was dissolved in dichloromethane (7.4 mL) and trifluoroacetic acid (760 µL, 9.9 mmol) was added. The mixture was stirred overnight at room temperature. The solvent was removed under vacuum, and the residue stirred with acetonitrile (5 mL) and a 33% ammonia solution (2.5 mL) at room temperature for 1 h and then dried again. The residue was dissolved with dichloromethane and washed with water (×2) and brine (×1), dried with sodium sulfate, filtered and evaporated. The residue was purified by flash chromatography to give the title compound (71.4 mg, 57% yield).

LC-MS (Method 1): $R_t$=0.82 min; MS (ESIpos): m/z=521 [M+H]$^+$ $^1$H-NMR (400 MHz, DMSO-d6) δ [ppm]: 0.91 (s, 3H) 2.92-3.07 (m, 1H) 3.11-3.31 (m, 3H) 3.82-3.95 (m, 1H) 4.00 (s, 3H) 4.03-4.15 (m, 1H) 4.87 (br s, 1H) 6.38 (d, 1H) 7.42 (br s, 2H) 7.82 (d, 1H) 8.14 (d, 1H) 8.44 (d, 1H) 8.74 (d, 1H) 9.12 (br s, 1H) 12.27 (d, J=1.00 Hz, 1H).

Example 22

(+/−)-{2-[(3,5-difluoro-4-{[3-(6-methoxypyridin-3-yl)-1H-pyrrolo[2,3-b]pyridin-4-yl]oxy}phenyl)amino]-5-methyl-5,6-dihydro-4H-1,3-oxazin-5-yl}methanol

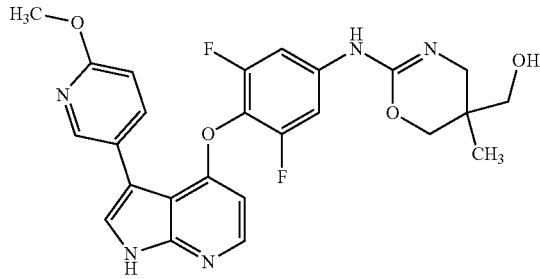 [SMILES: COc1ccc(-c2c[nH]c3nccc(Oc4c(F)cc(NC5=NCC(C)(CO)CO5)cc4F)c23)cn1]

1-(3,5-difluoro-4-{[3-(6-methoxypyridin-3-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (102 mg, 80% purity, 130 µmol, intermediate 44) was dissolved in dichloromethane (4.2 mL) and trifluoroacetic acid (430 µL, 5.6 mmol) was added. The mixture was stirred overnight at room temperature. The solvent was removed under vacuum, and the residue stirred with acetonitrile (5 mL) and a 33% ammonia solution (2.5 mL) at room temperature for 1 h and then dried again. The residue was dissolved with dichloromethane and washed with water (×2) and brine (×1), dried with sodium sulfate, filtered and evaporated. The residue was purified by flash chromatography (25 g SiO$_2$ SNAP-Ultra column, dichloromethane/0-30% methanol) and digested in ether to give the title compound (41.1 mg, 60% yield).

LC-MS (Method 2): $R_t$=0.98 min; MS (ESIpos): m/z=496 [M+H]$^+$ $^1$H NMR (400 MHz, DMSO-d$_6$) δ ppm 0.95 (s, 3H) 3.06 (d, 1H) 3.27 (d, 1H) 3.84 (s, 3H) 4.01-4.33 (m, 2H) 4.89-5.11 (m, 1H) 6.30-6.39 (m, 1H) 6.85 (d, 1H) 7.26-7.50 (m, 2H) 7.67 (d, 1H) 7.96 (dd, 1H) 8.13 (d, 1H) 8.44 (d, 1H) 8.88-10.73 (m, 1H) 12.02-12.26 (m, 1H).

Example 23

(+/−)-{2-[(3,5-difluoro-4-{[3-(1-methyl-1,2,3,6-tetrahydropyridin-4-yl)-1H-pyrrolo[2,3-b]pyridin-4-yl]oxy}phenyl)amino]-5-methyl-5,6-dihydro-4H-1,3-oxazin-5-yl}methanol

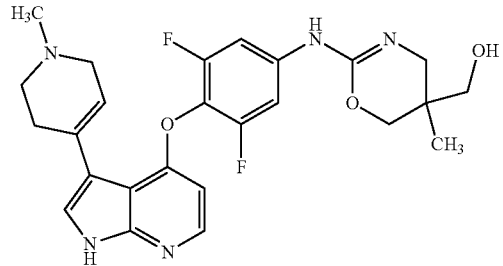 [SMILES: CN1CC=C(c2c[nH]c3nccc(Oc4c(F)cc(NC5=NCC(C)(CO)CO5)cc4F)c23)CC1]

1-(3,5-difluoro-4-{[3-(1-methyl-1,2,3,6-tetrahydropyridin-4-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (20.0 mg, 32.6 µmol, intermediate 47) was dissolved in dichloromethane (1.0 mL) and trifluoroacetic acid (110 µL, 1.4 mmol) was added. The mixture was stirred under argon overnight at room temperature. The solvent was removed under vacuum, and the residue stirred with acetonitrile (2 mL) and a 33% ammonia solution (1.0 mL) at room temperature for 1 h and then dried again. The residue was dissolved with dichloromethane and washed with water (×2) and brine (×1), dried with sodium sulfate, filtered and evaporated. The residue was digested with diethyl ether and the solid filtered and dried to yield the title compound (11.3 mg, 68% yield).

LC-MS (Method 1): $R_t$=0.52 min; MS (ESIpos): m/z=484 [M+H]$^+$ $^1$H-NMR (400 MHz, DMSO-d6) δ [ppm]: 0.94 (br s, 3H) 1.24 (br s, 1H) 2.85 (br s, 5H) 2.98-3.08 (m, 1H) 3.53-3.67 (m, 1H) 3.68-3.83 (m, 1H) 3.84-4.07 (m, 2H) 4.09-4.31 (m, 1H) 4.78-5.06 (m, 1H) 6.06-6.20 (m, 1H) 6.33 (d, 1H) 7.30-7.55 (m, 1H) 7.59 (d, 1H) 8.09 (d, 1H) 9.55-9.88 (m, 1H) 11.93-12.18 (m, 1H).

Example 24

(+/−)-1-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3,6-dihydropyridin-1(2H)-yl}propan-1-one

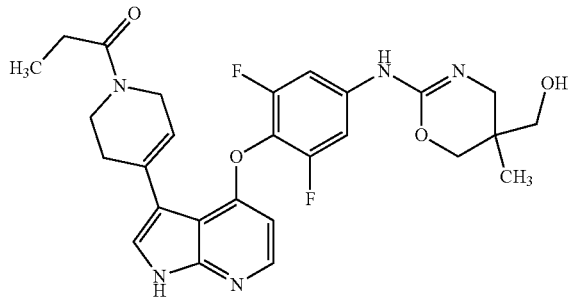 [SMILES: CCC(=O)N1CC=C(c2c[nH]c3nccc(Oc4c(F)cc(NC5=NCC(C)(CO)CO5)cc4F)c23)CC1]

1-(3,5-difluoro-4-{[3-(1-propanoyl-1,2,3,6-tetrahydropyridin-4-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (122 mg, 80% purity, 149 µmol, intermediate 52) was dissolved in dichloromethane (4.8 mL) and trifluoroacetic acid (490 µL, 6.4 mmol) was added. The mixture was stirred under argon overnight at room temperature. The solvent was removed under vacuum, and the residue stirred with acetonitrile (5 mL) and a 33% ammonia solution (2.5 mL) at room temperature for 1 h and then dried again. The residue was dissolved with dichloromethane and washed with water (×2) and brine (×1), dried with sodium sulfate, filtered and evaporated. The residue was purified by flash chromatography (25 g SiO₂ SNA-Ultra column, dichloromethane/0-50% methanol) and digested with diethyl ether, filtered and dried to yield the title compound (49.5 mg, 60% yield).

LC-MS (Method 2): $R_t$=0.90 min; MS (ESIpos): m/z=526 [M+H]⁺

¹H NMR (400 MHz, DMSO-d₆) δ ppm 0.93 (s, 3H) 0.98 (q, 3H) 2.29-2.41 (m, 2H) 2.58-2.65 (m, 1H) 3.04 (d, 1H) 3.24 (d, 1H) 3.55-3.73 (m, 2H) 3.93-4.13 (m, 3H) 4.15-4.28 (m, 1H) 4.79-5.05 (m, 1H) 6.03-6.15 (m, 1H) 6.21-6.32 (m, 1H) 7.20-7.41 (m, 1H) 7.41-7.51 (m, 1H) 8.05 (d, 1H) 8.44-10.35 (m, 1H) 11.69-12.06 (m, 1H).

Example 25

(+/−)-{2-[(4-{[3-(8-azabicyclo[3.2.1]oct-2-en-3-yl)-1H-pyrrolo[2,3-b]pyridin-4-yl]oxy}-3,5-difluorophenyl)amino]-5-methyl-5,6-dihydro-4H-1,3-oxazin-5-yl}methanol

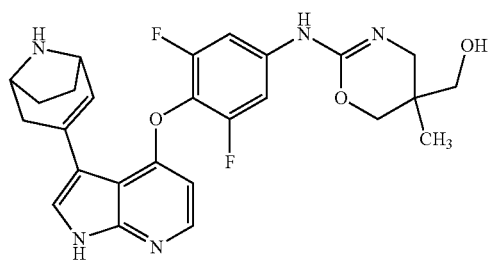 [SMILES: CC1(CO)CN=C(Nc2cc(F)c(Oc3ccnc4[nH]cc(C5=CC6CCC(C5)N6)c34)c(F)c2)OC1]

tert-butyl 3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-8-azabicyclo[3.2.1]oct-2-ene-8-carboxylate (166 mg, 90% purity, 206 µmol, intermediate 55) was dissolved in dichloromethane (6.6 mL) and trifluoroacetic acid (680 µL, 8.8 mmol) was added. The mixture was stirred overnight at room temperature. The mixture was poured onto a 1M NaOH solution and stirred for 1 h, then it was extracted with dichloromethane (×3). The combined organic layers were washed with brine (×1), dried with sodium sulfate, filtered and evaporated. The solvent was removed under vacuum, and the residue sonicated with acetonitrile (5 mL) and a 28% ammonia solution (2.5 mL) for 5 minutes, toluene was added and the mixture was dried again. The residue was sonicated with acetonitrile and the solid filtered to give the title compound (19.2 mg, 18% yield).

LC-MS (Method 1): $R_t$=0.60 min; MS (ESIpos): m/z=496 [M+H]⁺

¹H NMR (400 MHz, DMSO-d₆) δ ppm 0.91 (s, 3H) 1.73-1.84 (m, 1H) 1.95-2.07 (m, 2H) 2.09-2.19 (m, 1H) 2.63 (d, 1H) 2.96-3.10 (m, 2H) 3.18-3.30 (m, 2H) 3.33 (d, 1H) 3.88 (d, 1H) 4.07 (d, 1H) 4.11-4.17 (m, 1H) 4.18-4.24 (m, 1H) 6.30 (d, 1H) 6.43 (d, 1H) 7.36 (br d, 2H) 7.49 (s, 1H) 8.05 (d, 1H) 8.34 (s, 2H) 12.01 (br s, 1H).

Example 26

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile

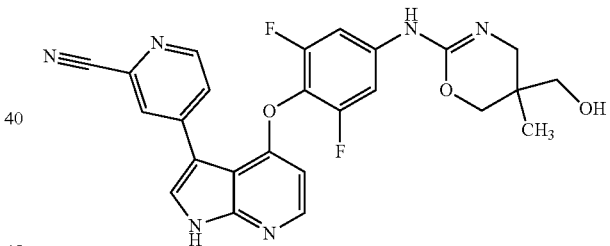

1-(4-{[3-(2-cyanopyridin-4-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (68.0 mg, 80% purity, 87.6 µmol, intermediate 58) was dissolved in dichloromethane (2.8 mL) and trifluoroacetic acid (290 µL, 3.8 mmol) was added. The mixture was stirred overnight at room temperature. The solvent was removed under vacuum, and the residue stirred with acetonitrile (5 mL) and a 33% ammonia solution (2.5 mL) at room temperature for 1 h and then dried again. The residue was dissolved with dichloromethane and washed with water (×2) and brine (×1), dried with sodium sulfate, filtered and evaporated. The residue was digested with diethyl ether and dichloromethane and the solid filtered and purified by flash chromatography and preparative TLC (20×20 cm silica plates, dichloromethane/85-15% methanol) to give (+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile (example 26, 6.40 mg, 14% yield) and (+/−)-4-[4-(2,6-difluoro-4-{[5-(hydroxymethyl)-5-methyl-5,6-dihydro-4H-1,3-oxazin-2-yl]amino}phenoxy)-

1H-pyrrolo[2,3-b]pyridin-3-yl]pyridine-2-carboxamide (example 27, 12.4 mg, 26% yield).

LC-MS (Method 2): R$_t$=0.93 min; MS (ESIpos): m/z=492 [M+H]$^+$ $^1$H NMR (400 MHz, DMSO-d$_6$) δ ppm 0.87-0.92 (m, 3H) 1.26 (br s, 1H) 2.92-3.10 (m, 1H) 3.20-3.28 (m, 2H) 3.88 (br d, 1H) 4.06 (br d, 1H) 4.85 (br s, 1H) 6.45 (d, 1H) 7.26-7.74 (m, 2H) 8.04 (dd, 1H) 8.14-8.24 (m, 2H) 8.31 (d, 1H) 8.68 (d, 1H) 8.82-9.28 (m, 1H) 12.63 (br s, 1H).

Example 27

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carboxamide

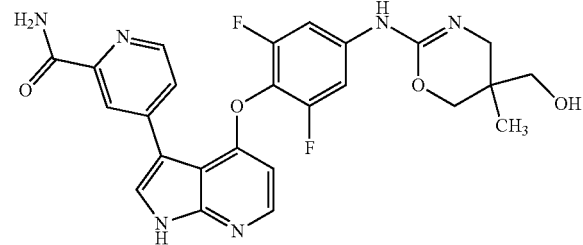 [SMILES: CC1(CO)CN=C(Nc2cc(F)c(Oc3ccnc4[nH]cc(-c5ccnc(C(N)=O)c5)c34)c(F)c2)OC1]

Compound was prepared as a byproduct of the synthesis of example 26 (for experimental details, see example 26).

LC-MS (Method 4): R$_t$=0.51 min; MS (ESIpos): m/z=509 [M+H]$^+$ $^1$H-NMR (400 MHz, DMSO-d6) δ [ppm]: 0.90 (s, 3H) 1.24 (br s, 1H) 2.96-3.07 (m, 1H) 3.20-3.28 (m, 2H) 3.82-3.92 (m, 1H) 4.06 (br d, 1H) 4.86 (br s, 1H) 6.39 (d, 1H) 7.56 (d, 1H) 7.57 (br s, 1H) 7.87 (dd, 1H) 8.05 (d, 1H) 8.07-8.11 (m, 1H) 8.15 (d, 1H) 8.43 (d, 1H) 8.56 (d, 1H) 8.98 (br s, 1H) 12.41 (d, 1H).

Example 28

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile

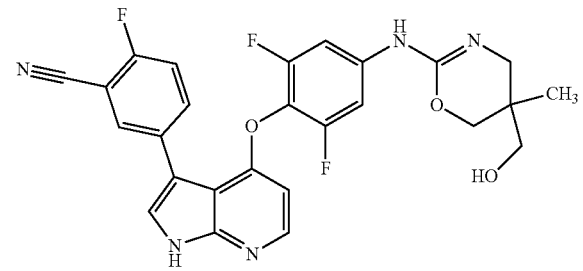 [SMILES: CC1(CO)CN=C(Nc2cc(F)c(Oc3ccnc4[nH]cc(-c5ccc(F)c(C#N)c5)c34)c(F)c2)OC1]

1-(4-{[3-(3-cyano-4-fluorophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (75.0 mg, 118 μmol, intermediate 61) was dissolved in dichloromethane (5.0 mL) and trifluoroacetic acid (520 μL, 6.7 mmol) was added. The mixture was stirred overnight at room temperature. The solvent was removed under vacuum, and the residue was dissolved in dichloromethane and washed with water (×2) and brine (×1), dried with sodium sulfate, filtered and evaporated.

The residue was digested with diethyl ether and dichloromethane and the solid filtered and purified by flash chromatography and preparative TLC (20×20 cm silica plates) to give the title compound (27.6 mg, 44% yield).

LC-MS (Method 1): R$_t$=1.05 min; MS (ESIpos): m/z=508 [M+H]$^+$ $^1$H-NMR (400 MHz, DMSO-d6) δ [ppm]: 0.91 (s, 3H) 1.24 (br s, 1H) 2.96-3.08 (m, 1H) 3.16-3.30 (m, 2H) 3.90 (br d, 1H) 4.08 (br d, 1H) 4.78-4.91 (m, 1H) 6.33-6.41 (m, 1H) 7.24-7.50 (m, 1H) 7.57 (t, 1H) 7.81 (d, 1H) 8.00-8.08 (m, 1H) 8.09-8.18 (m, 2H) 8.77-9.35 (m, 1H) 12.20-12.39 (m, 1H).

Example 29

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluorobenzonitrile

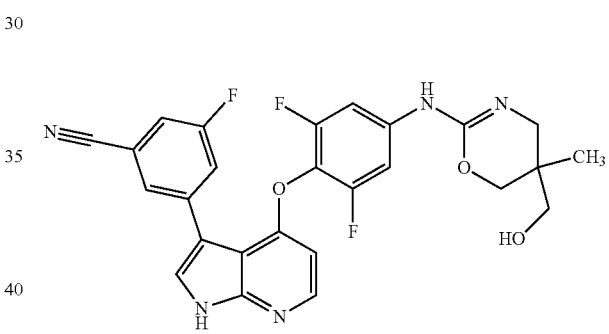

1-(4-{[3-(3-cyano-5-fluorophenyl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (92.0 mg, 144 μmol, intermediate 64) was dissolved in dichloromethane (5.3 mL) and trifluoroacetic acid (560 μL, 7.2 mmol) was added. The mixture was stirred overnight at room temperature. The solvent was removed under vacuum, and the residue was dissolved in dichloromethane and washed with water (×2) and brine (×1), dried with sodium sulfate, filtered and evaporated. The residue was purified by preparative TLC (20×20 cm silica plates) to give the title compound (8.30 mg, 11% yield).

LC-MS (Method 1): R$_t$=1.08 min; MS (ESIpos): m/z=508 [M+H]$^+$ $^1$H-NMR (400 MHz, DMSO-d6) δ [ppm]: 0.90 (s, 3H) 1.23 (s, 1H) 2.94-3.05 (m, 1H) 3.15-3.30 (m, 2H) 3.89 (d, 1H) 4.07 (d, 1H) 4.78-4.89 (m, 1H) 6.40 (d, 1H) 7.22-7.54 (m, 1H) 7.63-7.74 (m, 1H) 7.83-7.90 (m, 1H) 7.95 (d, 1H) 7.98-8.03 (m, 1H) 8.15 (d, 1H) 8.74-9.41 (m, 1H) 12.14-12.59 (m, 1H).

Example 30

(+/−)-[2-({4-[(3-chloro-1H-pyrrolo[2,3-b]pyridin-4-yl)oxy]-3,5-difluorophenyl}amino)-5-methyl-5,6-dihydro-4H-1,3-oxazin-5-yl]methanol

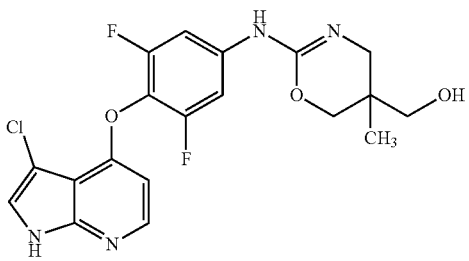 [SMILES: CC1(CO)CN=C(Nc2cc(F)c(Oc3ccnc4[nH]cc(Cl)c34)c(F)c2)OC1]

To a solution of 1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea (150 mg, 0.27 mmol, intermediate 66) in dichloromethane (5.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-[2-({4-[(3-chloro-1H-pyrrolo[2,3-b]pyridin-4-yl)oxy]-3,5-difluorophenyl}amino)-5-methyl-5,6-dihydro-4H-1,3-oxazin-5-yl]methanol (55 mg, 48% over two steps).

LC-MS (Method 2): $R_t$=0.98 min; MS (ESIpos): m/z=423 [M+H]$^+$

1H NMR (500 MHz, DMSO-d6, measured at 80° C.) δ ppm 0.94 (s, 3H), 3.01 (br d, 1H), 3.24 (br d, 1H), 3.30 (dd, 1H), 3.36 (dd, 1H), 3.88 (d, 1H), 4.08 (dd, 1H), 4.59 (br s, 1H), 6.31 (d, 1H), 7.36 (br s, 1H), 7.50 (s, 1H), 8.09 (d, 1H), 8.72 (br s, 1H), 11.85 (br s, 1H)

Example 31

(+/−)-[2-({4-[(3-chloro-1H-pyrrolo[2,3-b]pyridin-4-yl)oxy]-3,5-difluorophenyl}amino)-5,6-dihydro-4H-1,3-oxazin-5-yl]methanol

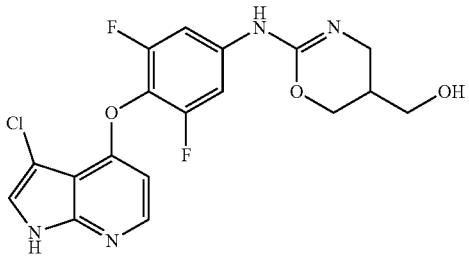 [SMILES: OCC1CN=C(Nc2cc(F)c(Oc3ccnc4[nH]cc(Cl)c34)c(F)c2)OC1]

To a solution of 1-{4-[(3-chloro-1-{[2-(trimethylsilyl)ethoxy]methyl}-1H-pyrrolo[2,3-b]pyridin-4-yl)oxy]-3,5-difluorophenyl}-3-(oxetan-3-ylmethyl)urea (145 mg, 0.27 mmol, intermediate 67) in dichloromethane (5.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-[2-({4-[(3-chloro-1H-pyrrolo[2,3-b]pyridin-4-yl)oxy]-3,5-difluorophenyl}amino)-5,6-dihydro-4H-1,3-oxazin-5-yl]methanol (44 mg, 38% over two steps).

LC-MS (Method 2): $R_t$=0.99 min; MS (ESIpos): m/z=409 [M+H]$^+$ $^1$H NMR (400 MHz, DMSO-d$_6$) δ ppm 2.05 (br s, 1H), 3.06-3.18 (m, 1H), 3.36-3.49 (m, 3H), 4.05 (br t, 1H), 4.28-4.34 (m, 1H), 4.77 (br s, 1H), 6.29 (d, 1H), 7.54 (br s, 2H), 7.59 (s, 1H), 8.08 (d, 1H), 9.01 (br s, 1H), 11.99-12.20 (m, 1H)

Example 32

(+/−)-[2-({4-[(3-chloro-1H-pyrrolo[2,3-b]pyridin-4-yl)oxy]-3,5-difluorophenyl}amino)-5-fluoro-5,6-dihydro-4H-1,3-oxazin-5-yl]methanol

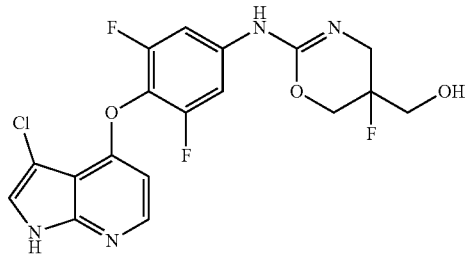 [SMILES: OCC1(F)CN=C(Nc2cc(F)c(Oc3ccnc4[nH]cc(Cl)c34)c(F)c2)OC1]

To a solution of 1-{4-[(3-chloro-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea (150 mg, 0.27 mmol, intermediate 68) in dichloromethane (5.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-[2-({4-[(3-chloro-1H-pyrrolo[2,3-b]pyridin-4-yl)oxy]-3,5-difluorophenyl}amino)-5-fluoro-5,6-dihydro-4H-1,3-oxazin-5-yl]methanol (40 mg, 34% over two steps).

LC-MS (Method 2): $R_t$=0.97 min; MS (ESIpos): m/z=427 [M+H]$^+$ $^1$H NMR (400 MHz, DMSO-d$_6$) δ ppm 3.38-3.67 (m, 4H), 4.22-4.37 (m, 2H), 5.25 (br t, 1H), 6.31 (d, 1H), 7.53-7.71 (m, 3H), 8.09 (d, 1H), 9.23 (br s, 1H), 12.11 (br s, 1H)

Example 33

(+/−)-4-(2,6-difluoro-4-{[5-(hydroxymethyl)-5-methyl-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide

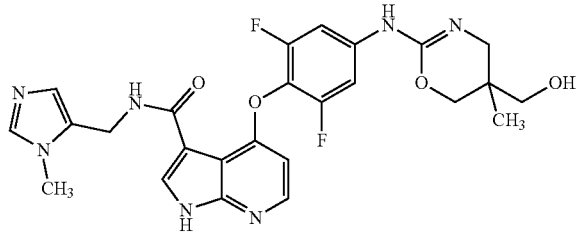 [SMILES: Cn1cncc1CNC(=O)c1c[nH]c2nccc(Oc3c(F)cc(NC4=NCC(C)(CO)CO4)cc3F)c12]

To a solution of 4-[2,6-difluoro-4-({[(3-methyloxetan-3-yl)methyl]carbamoyl}amino)phenoxy]-N-[(1-methyl-1H-imidazol-5-yl)methyl]-1-{[2-(trimethylsilyl)ethoxy]methyl}-1H-pyrrolo[2,3-b]pyridine-3-carboxamide (90 mg, 0.14 mmol, intermediate 74) in dichloromethane (1.0 mL) was added trifluoroacidic acid (0.53 mL, 6.9 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-4-(2,6-difluoro-4-{[5-(hydroxymethyl)-5-methyl-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide (20 mg, 25% over two steps).

LC-MS (Method 2): $R_t$=0.74 min; MS (ESIpos): m/z=526 [M+H]$^+$ $^1$H NMR (400 MHz, DMSO-d$_6$) δ ppm 0.94 (s, 3H), 3.05 (br d, 1H), 3.24-3.38 (m, 4H), 4.03 (br d, 1H), 4.21 (br d, 1H), 4.55 (d, 2H), 6.44 (d, 1H), 7.13 (s, 1H), 7.36 (br d, 2H), 8.05 (s, 1H), 8.14 (d, 1H), 8.21 (s, 1H), 8.25 (br t, 1H), 12.49 (br s, 1H)

Example 34

(+/−)-4-(2,6-difluoro-4-{[5-(hydroxymethyl)-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide

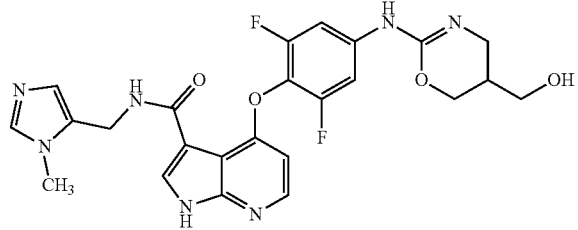 [SMILES: Cn1cncc1CNC(=O)c1c[nH]c2nccc(Oc3c(F)cc(NC4=NCC(CO)CO4)cc3F)c12]

To a solution of 4-(2,6-difluoro-4-{[(oxetan-3-ylmethyl)carbamoyl]amino}phenoxy)-N-[(1-methyl-1H-imidazol-5-yl)methyl]-1-{[2-(trimethylsilyl)ethoxy]methyl}-1H-pyrrolo[2,3-b]pyridine-3-carboxamide (50 mg, 0.78 mmol, intermediate 75) in dichloromethane (0.5 mL) was added trifluoroacidic acid (0.3 mL, 3.9 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-4-(2,6-difluoro-4-{[5-(hydroxymethyl)-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide (10 mg, 12% over two steps).

LC-MS (Method 1): $R_t$=0.45 min; MS (ESIpos): m/z=512 [M+H]$^+$ $^1$H NMR (400 MHz, DMSO-d$_6$) δ ppm 2.03 (br s, 1H), 3.07-3.18 (m, 1H), 3.41-3.49 (m, 2H), 3.54 (s, 3H), 4.06 (br t, 1H), 4.32 (dd, 1H), 4.49 (d, 2H), 4.79 (br s, 1H), 6.41 (d, 1H), 6.74 (s, 1H), 7.50 (br s, 2H), 7.42 (s, 1H), 8.05 (s, 1H), 8.09 (br t, 1H), 8.12 (d, 1H), 9.04 (br s, 1H), 12.40 (br s, 1H)

Example 35

(+/−)-{2-[(4-{[3-(5-chloro-6-methoxypyridin-3-yl)-1H-pyrrolo[2,3-b]pyridin-4-yl]oxy}-3,5-difluorophenyl)amino]-5-methyl-5,6-dihydro-4H-1,3-oxazin-5-yl}methanol

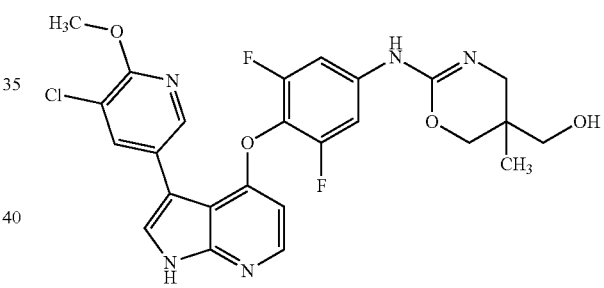

To a solution of 1-(4-{[3-(5-chloro-6-methoxypyridin-3-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (110 mg, 0.17 mmol, intermediate 78) in dichloromethane (4.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-{2-[(4-{[3-(5-chloro-6-methoxypyridin-3-yl)-1H-pyrrolo[2,3-b]pyridin-4-yl]oxy}-3,5-difluorophenyl)amino]-5-methyl-5,6-dihydro-4H-1,3-oxazin-5-yl}methanol (32 mg, 34% over two steps).

LC-MS (Method 2): $R_t$=1.11 min; MS (ESIpos): m/z=530 [M+H]$^+$ $^1$H NMR (400 MHz, DMSO-d$_6$) δ ppm 0.89 (br s, 3H), 2.96-3.09 (m, 1H), 3.18-3.32 (m, 3H), 3.82-3.89 (m, 4H), 4.05 (br d, 1H), 4.80 (br s, 1H), 6.30 (d, 1H), 7.48-7.62 (m, 2H), 7.67 (s, 1H), 7.88 (d, 1H), 8.08-8.11 (m, 2H), 9.00 (br s, 1H), 12.17 (s, 1H)

Example 36

(+/−)-[2-{[3,5-difluoro-4-({3-[1-(propan-2-yl)-1H-pyrazol-3-yl]-1H-pyrrolo[2,3-b]pyridin-4-yl}oxy)phenyl]amino}-5-methyl-5,6-dihydro-4H-1,3-oxazin-5-yl]methanol

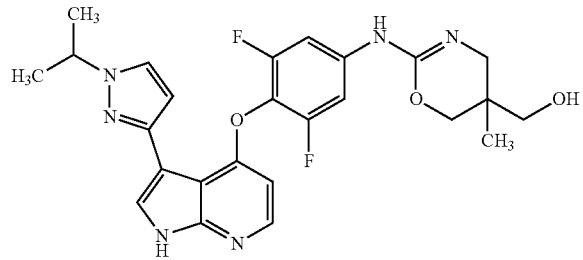 [SMILES: CC(C)n1ccc(-c2c[nH]c3nccc(Oc4c(F)cc(NC5=NCC(C)(CO)CO5)cc4F)c23)n1]

To a solution of 1-{3,5-difluoro-4-[(3-[1-(propan-2-yl)-1H-pyrazol-3-yl]-1-{[2-(trimethylsilyl)ethoxy]methyl}-1H-pyrrolo[2,3-b]pyridin-4-yl)oxy]phenyl}-3-[(3-methyl-oxetan-3-yl)methyl]urea (125 mg, 0.20 mmol, intermediate 81) in dichloromethane (4.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-[2-{[3,5-difluoro-4-({3-[1-(propan-2-yl)-1H-pyrazol-3-yl]-1H-pyrrolo[2,3-b]pyridin-4-yl}oxy)phenyl]amino}-5-methyl-5,6-dihydro-4H-1,3-oxazin-5-yl]methanol (27 mg, 27% over two steps).

LC-MS (Method 2): $R_t$=0.95 min; MS (ESIpos): m/z=497 [M+H]$^+$ $^1$H NMR (400 MHz, DMSO-$d_6$) δ ppm 0.91 (s, 3H), 1.41 (d, 6H), 2.93-3.11 (m, 1H), 3.15-3.32 (m, 3H), 3.88 (br d, 1H), 4.07 (br d, 1H), 4.46 (spt, 1H), 4.82 (br s, 1H), 6.28 (d, 1H), 7.58 (s, 3H), 7.73 (s, 1H), 7.95 (s, 1H), 8.04 (d, 1H), 9.03 (br s, 1H), 11.85 (s, 1H)

Example 37

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(propan-2-yloxy)benzonitrile

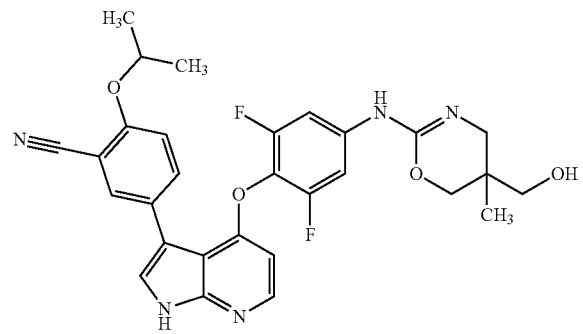 [SMILES: CC(C)Oc1ccc(-c2c[nH]c3nccc(Oc4c(F)cc(NC5=NCC(C)(CO)CO5)cc4F)c23)cc1C#N]

To a solution of 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-methyl-oxetan-3-yl)methyl]urea (80 mg, 0.12 mmol, intermediate 84) in dichloromethane (4.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(propan-2-yloxy)benzonitrile (38 mg, 33% over two steps).

LC-MS (Method 2): $R_t$=1.14 min; MS (ESIpos): m/z=548 [M+H]$^+$ $^1$H NMR (400 MHz, DMSO-$d_6$) δ ppm 0.90 (s, 3H), 1.31 (d, 6H), 2.96-3.09 (m, 1H), 3.16-3.33 (m, 3H), 3.87 (br d, 1H), 4.06 (br d, 1H), 4.74-4.87 (m, 2H), 6.33 (d, 1H), 7.30 (d, 1H), 7.58 (br s, 2H), 7.70 (s, 1H), 7.89-7.95 (m, 2H), 8.10 (d, 1H), 9.02 (br s, 1H), 12.14 (s, 1H)

Example 38

(+/−)-{2-[(3,5-difluoro-4-{[3-(2-fluoro-4-methoxyphenyl)-1H-pyrrolo[2,3-b]pyridin-4-yl]oxy}phenyl)amino]-5-methyl-5,6-dihydro-4H-1,3-oxazin-5-yl}methanol

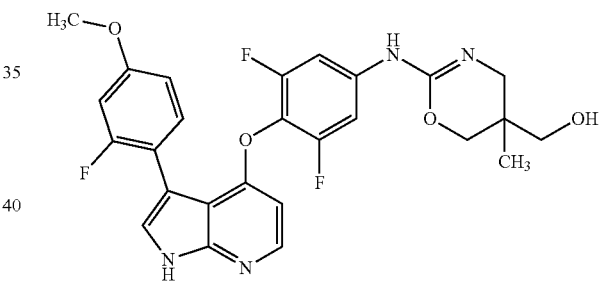

To a solution of 1-(3,5-difluoro-4-{[3-(2-fluoro-4-methoxyphenyl)-1-{[2-(trimethylsilyl)ethoxy]methyl}-1H-pyrrolo[2,3-b]pyridin-4-yl]oxy}phenyl)-3-[(3-methyl-oxetan-3-yl)methyl]urea (135 mg, 0.21 mmol, intermediate 87) in dichloromethane (4.0 mL) was added trifluoroacidic acid (1.0 mL, 13 mmol). The resulting mixture was stirred at room temperature for 16 hours. 2M NaOH was added, and the mixture extracted two times with ethyl acetate.

The combined organic layers were washed with water, brine, dried over sodium sulfate, filtered and evaporated to afford the crude oxazine.

The crude product was purified by preparative HPLC to afford (+/−)-{2-[(3,5-difluoro-4-{[3-(2-fluoro-4-methoxyphenyl)-1H-pyrrolo[2,3-b]pyridin-4-yl]oxy}phenyl)amino]-5-methyl-5,6-dihydro-4H-1,3-oxazin-5-yl}methanol (29 mg, 26% over two steps).

LC-MS (Method 2): $R_t$=1.07 min; MS (ESIpos): m/z=513 [M+H]$^+$ $^1$H NMR (400 MHz, DMSO-$d_6$) δ ppm 0.90 (s, 3H), 2.92-3.10 (m, 1H), 3.14-3.32 (m, 3H), 3.77 (s, 3H), 3.86 (br d, 1H), 4.05 (d, 1H), 4.81 (br s, 1H), 6.26 (d, 1H), 6.79 (dd, 1H), 6.86 (dd, 1H), 7.42-7.58 (m, 4H), 8.07 (d, 1H), 8.98 (br s, 1H), 12.05 (s, 1H)

Example 39

(+/−)-{2-[(3,5-difluoro-4-{[3-(1-methyl-1H-pyrazol-5-yl)-1H-pyrrolo[2,3-b]pyridin-4-yl]oxy}phenyl)amino]-5-methyl-5,6-dihydro-4H-1,3-oxazin-5-yl}methanol

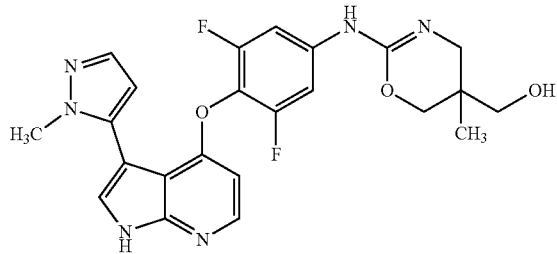 [SMILES: Cn1nccc1-c1c[nH]c2nccc(Oc3c(F)cc(NC4=NCC(C)(CO)CO4)cc3F)c12]

To a solution of 1-(3,5-difluoro-4-{[3-(1-methyl-1H-pyrazol-5-yl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (95 mg, 0.16 mmol, intermediate 90) in dichloromethane (2.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-{2-[(3,5-difluoro-4-{[3-(1-methyl-1H-pyrazol-5-yl)-1H-pyrrolo[2,3-b]pyridin-4-yl]oxy}phenyl)amino]-5-methyl-5,6-dihydro-4H-1,3-oxazin-5-yl}methanol (35 mg, 47% over two steps).

LC-MS (Method 2): $R_t$=0.84 min; MS (ESIpos): m/z=469 [M+H]$^+$ $^1$H NMR (400 MHz, DMSO-d$_6$) δ ppm 0.89 (br s, 3H), 2.96-3.08 (m, 1H), 3.18-3.32 (m, 3H), 3.79 (s, 3H), 3.86 (br d, 1H), 4.05 (br d, 1H), 4.72-4.88 (m, 1H), 6.31 (d, 1H), 6.33 (d, 1H), 7.41 (d, 1H), 7.50-7.59 (m, 2H), 7.64 (d, 1H), 8.12 (d, 1H), 9.01 (br s, 1H), 12.26 (br d, 1H)

Example 40

(+/−)-[2-{[3,5-difluoro-4-({3-[1-(propan-2-yl)-1H-pyrazol-5-yl]-1H-pyrrolo[2,3-b]pyridin-4-yl}oxy)phenyl]amino}-5-methyl-5,6-dihydro-4H-1,3-oxazin-5-yl]methanol

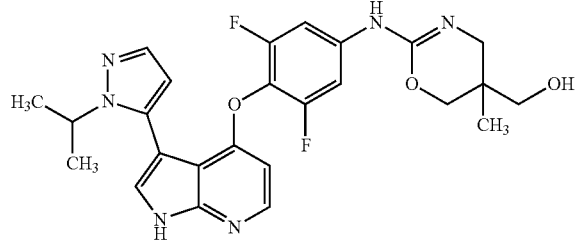 [SMILES: CC(C)n1nccc1-c1c[nH]c2nccc(Oc3c(F)cc(NC4=NCC(C)(CO)CO4)cc3F)c12]

To a solution of 1-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-3-[(3-methyl-oxetan-3-yl)methyl]urea (105 mg, 0.17 mmol, intermediate 93) in dichloromethane (2.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-[2-{[3,5-difluoro-4-({3-[1-(propan-2-yl)-1H-pyrazol-5-yl]-1H-pyrrolo[2,3-b]pyridin-4-yl}oxy)phenyl]amino}-5-methyl-5,6-dihydro-4H-1,3-oxazin-5-yl]methanol (31 mg, 37% over two steps).

LC-MS (Method 2): $R_t$=0.92 min; MS (ESIpos): m/z=497 [M+H]$^+$ $^1$H NMR (400 MHz, DMSO-d$_6$) δ ppm 0.89 (br s, 3H), 1.28 (d, 6H), 2.96-3.06 (m, 1H), 3.19-3.32 (m, 2H), 3.86 (br d, 1H), 4.05 (br d, 1H), 4.55 (spt, 1H), 4.80 (br s, 1H), 6.25 (d, 1H), 6.28 (d, 1H), 7.45 (d, 1H), 7.52 (br s, 2H), 7.55 (d, 1H), 8.11 (d, 1H), 8.99 (br s, 1H), 12.24 (s, 1H)

Example 41

(+/−)-{2-[(3,5-difluoro-4-{[3-(2-fluorophenyl)-1H-pyrrolo[2,3-b]pyridin-4-yl]oxy}phenyl)amino]-5-methyl-5,6-dihydro-4H-1,3-oxazin-5-yl}methanol

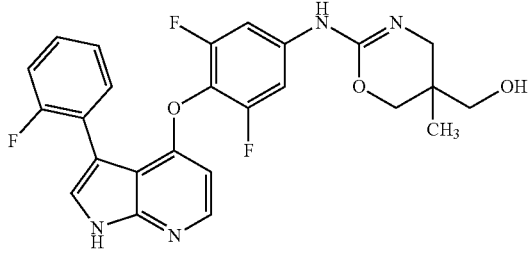 [SMILES: CC1(CO)CN=C(Nc2cc(F)c(Oc3ccnc4[nH]cc(-c5ccccc5F)c34)c(F)c2)OC1]

To a solution of 1-(3,5-difluoro-4-{[3-(2-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (100 mg, 0.16 mmol, intermediate 96) in dichloromethane (2.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-{2-[(3,5-difluoro-4-{[3-(2-fluorophenyl)-1H-pyrrolo[2,3-b]pyridin-4-yl]oxy}phenyl)amino]-5-methyl-5,6-dihydro-4H-1,3-oxazin-5-yl}methanol (28 mg, 34% over two steps).

LC-MS (Method 2): $R_t$=1.07 min; MS (ESIpos): m/z=483 [M+H]$^+$ $^1$H NMR (400 MHz, DMSO-d$_6$) δ ppm 0.89 (br s, 3H), 2.93-3.08 (m, 1H), 3.19-3.33 (m, 3H), 3.82-3.94 (m, 1H), 4.02-4.08 (m, 1H), 4.82 (br d, 1H), 6.29 (d, 1H), 7.16-7.34 (m, 3H), 7.57 (br s, 4H), 8.10 (d, 1H), 8.98 (br s, 1H), 12.14 (br s, 1H)

Example 42

(+/−)-{2-[(3,5-difluoro-4-{[3-(3-fluorophenyl)-1H-pyrrolo[2,3-b]pyridin-4-yl]oxy}phenyl)amino]-5-methyl-5,6-dihydro-4H-1,3-oxazin-5-yl}methanol

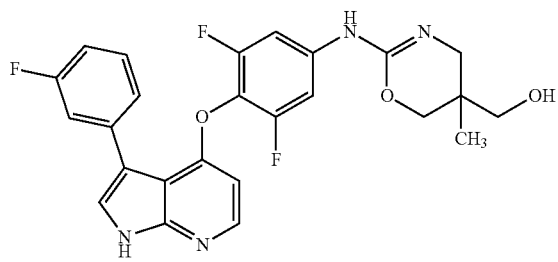 [SMILES: CC1(CO)CN=C(Nc2cc(F)c(Oc3ccnc4[nH]cc(-c5cccc(F)c5)c34)c(F)c2)OC1]

To a solution of 1-(3,5-difluoro-4-{[3-(3-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (125 mg, 0.20 mmol, intermediate 99) in dichloromethane (2.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-{2-[(3,5-difluoro-4-{[3-(3-fluorophenyl)-1H-pyrrolo[2,3-b]pyridin-4-yl]oxy}phenyl)amino]-5-methyl-5,6-dihydro-4H-1,3-oxazin-5-yl}methanol (33 mg, 33% over two steps).

LC-MS (Method 2): $R_t$=1.09 min; MS (ESIpos): m/z=483 $[M+H]^+$ $^1$H NMR (400 MHz, DMSO-$d_6$) δ ppm 0.90 (br s, 3H), 2.97-3.10 (m, 1H), 3.18-3.32 (m, 3H), 3.82-3.95 (m, 1H), 4.06 (br d, 1H), 4.81 (br s, 1H), 6.34 (d, 1H), 7.05 (ddd, 1H), 7.40 (td, 1H), 7.46-7.55 (m, 2H), 7.56-7.64 (m, 2H), 7.74 (d, 1H), 8.11 (d, 1H), 9.02 (br s, 1H), 12.19 (br s, 1H)

Example 43

(+/−)-{2-[(3,5-difluoro-4-{[3-(4-fluorophenyl)-1H-pyrrolo[2,3-b]pyridin-4-yl]oxy}phenyl)amino]-5-methyl-5,6-dihydro-4H-1,3-oxazin-5-yl}methanol

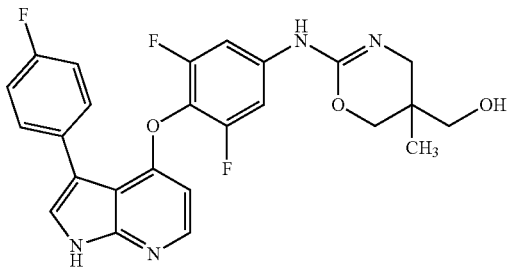 [SMILES: CC1(CO)CN=C(Nc2cc(F)c(Oc3ccnc4[nH]cc(-c5ccc(F)cc5)c34)c(F)c2)OC1]

To a solution of 1-(3,5-difluoro-4-{[3-(4-fluorophenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (95 mg, 0.16 mmol, intermediate 102) in dichloromethane (2.0 mL) was added trifluoroacidic acid (1.0 mL, 13 mmol). The resulting mixture was stirred at room temperature for 16 hours. 2M NaOH was added, and the mixture extracted two times with ethyl acetate. The combined organic layers were washed with water, brine, dried over sodium sulfate, filtered and evaporated to afford the crude oxazine. The crude product was purified by preparative HPLC to afford (+/−)-{2-[(3,5-difluoro-4-{[3-(4-fluorophenyl)-1H-pyrrolo[2,3-b]pyridin-4-yl]oxy}phenyl)amino]-5-methyl-5,6-dihydro-4H-1,3-oxazin-5-yl}methanol (24 mg, 29% over two steps).

LC-MS (Method 2): $R_t$=1.09 min; MS (ESIpos): m/z=483 $[M+H]^+$ $^1$H NMR (400 MHz, DMSO-$d_6$) δ ppm 0.90 (s, 3H), 2.94-3.07 (m, 1H), 3.17-3.32 (m, 3H), 3.83-3.92 (m, 1H), 4.06 (br d, 1H), 4.82 (br s, 2H), 6.31 (d, 1H), 7.13-7.25 (m, 2H), 7.55 (br s, 2H), 7.62 (s, 1H), 7.65-7.71 (m, 2H), 8.09 (d, 1H), 9.01 (br s, 1H), 12.08 (br s, 1H)

Example 44

(+/−)-2-{[4-({3-[3-cyano-4-(propan-2-yloxy)phenyl]-1H-pyrrolo[2,3-b]pyridin-4-yl}oxy)-3,5-difluorophenyl]amino}-5-(hydroxymethyl)-5,6-dihydro-4H-1,3-oxazine-5-carbonitrile

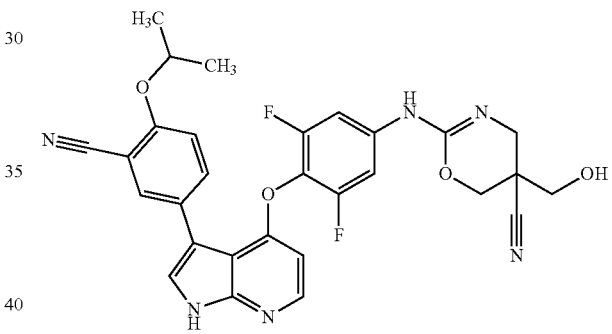

To a solution of 1-[(3-cyanooxetan-3-yl)methyl]-3-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}urea (90 mg, 0.13 mmol, intermediate 104) in dichloromethane (2.0 mL) was added trifluoroacidic acid (1.0 mL, 13 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-2-{[4-({3-[3-cyano-4-(propan-2-yloxy)phenyl]-1H-pyrrolo[2,3-b]pyridin-4-yl}oxy)-3,5-difluorophenyl]amino}-5-(hydroxymethyl)-5,6-dihydro-4H-1,3-oxazine-5-carbonitrile (10 mg, 12% over two steps).

LC-MS (Method 2): $R_t$=1.11 min; MS (ESIpos): m/z=559 $[M+H]^+$ $^1$H NMR (400 MHz, DMSO-$d_6$) δ ppm 1.31 (d, 6H), 3.50 (br d, 1H), 3.58 (dd, 1H), 3.62-3.70 (m, 2H), 4.25 (d, 1H), 4.48 (dd, 1H), 4.80 (spt, 1H), 5.68 (br t, 1H), 6.35 (d, 1H), 7.27-7.32 (m, 1H), 7.57 (br d, 2H), 7.71 (s, 1H), 7.89-7.95 (m, 2H), 8.10 (d, 1H), 9.35 (s, 1H), 12.15 (br s, 1H)

Example 45

(+/−)-5-[4-(4-{[5-(difluoromethyl)-5-(hydroxymethyl)-5,6-dihydro-4H-1,3-oxazin-2-yl]amino}-2,6-difluorophenoxy)-1H-pyrrolo[2,3-b]pyridin-3-yl]-2-(propan-2-yloxy)benzonitrile

Example 46

(+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(propan-2-yloxy)benzonitrile

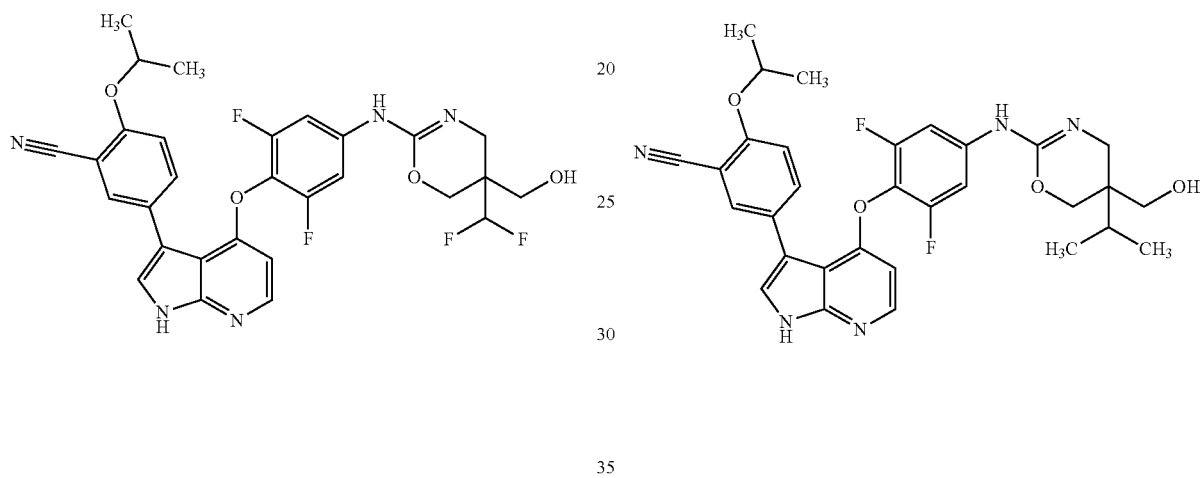

To a solution of 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(difluoromethyl)oxetan-3-yl]methyl}urea (90 mg, 0.13 mmol, intermediate 105) in dichloromethane (2.0 mL) was added trifluoroacidic acid (1.0 mL, 13 mmol). The resulting mixture was stirred at room temperature for 16 hours. The reaction mixture was diluted with water, treated with a saturated solution of sodium bicarbonate, and extracted with ethyl acetate two times.

The combined organic layers were washed with water, brine, dried over sodium sulfate, filtered and evaporated to afford the crude oxazine. The crude product was purified by preparative HPLC to afford (+/−)-5-[4-(4-{[5-(difluoromethyl)-5-(hydroxymethyl)-5,6-dihydro-4H-1,3-oxazin-2-yl]amino}-2,6-difluorophenoxy)-1H-pyrrolo[2,3-b]pyridin-3-yl]-2-(propan-2-yloxy)benzonitrile (27 mg, 35% over two steps).

LC-MS (Method 2): $R_t$=1.16 min; MS (ESIpos): m/z=584 [M+H]$^+$ $^1$H NMR (400 MHz, DMSO-d$_6$) δ ppm 1.31 (d, 6H), 3.31 (br s, 1H), 3.42-3.52 (m, 3H), 4.23 (s, 2H), 4.80 (spt, 1H), 5.20 (br s, 1H), 6.12 (t, 1H), 6.33 (d, 1H), 7.26-7.32 (m, 1H), 7.56 (br d, 2H), 7.71 (s, 1H), 7.89-7.95 (m, 2H), 8.10 (d, 1H), 9.16 (br s, 1H), 12.14 (s, 1H)

To a solution of 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-{[3-(propan-2-yl)oxetan-3-yl]methyl}urea (90 mg, 0.13 mmol, intermediate 106) in dichloromethane (2.0 mL) was added trifluoroacidic acid (1.0 mL, 13 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(propan-2-yloxy)benzonitrile (35 mg, 47% over two steps).

LC-MS (Method 2): $R_t$=1.21 min; MS (ESIpos): m/z=576 [M+H]$^+$ $^1$H NMR (400 MHz, DMSO-d$_6$) δ ppm 0.90 (dd, 6H), 1.31 (d, 6H), 1.71-1.82 (m, 1H), 3.03-3.27 (m, 2H), 3.39 (m, 2H), 3.96-4.09 (m, 1H), 4.09-4.19 (m, 1H), 4.63-4.75 (m, 1H), 4.76-4.85 (m, 1H), 6.33 (d, 1H), 7.30 (d, 1H), 7.49-7.66 (m, 2H), 7.70 (s, 1H), 7.87-7.97 (m, 2H), 8.10 (d, 1H), 9.04 (br s, 1H), 12.14 (s, 1H)

Example 47

(+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-(propan-2-yloxy)benzonitrile

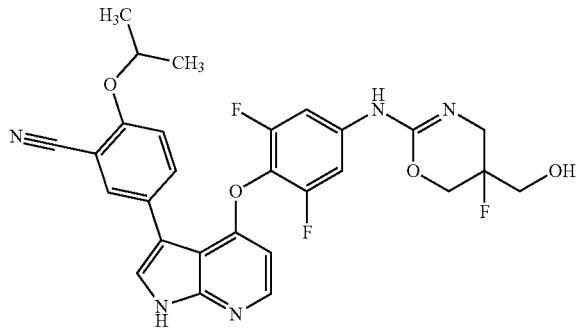 [SMILES: CC(C)Oc1ccc(-c2c[nH]c3nccc(Oc4c(F)cc(NC5=NCC(F)(CO)CO5)cc4F)c23)cc1C#N]

To a solution of 1-{4-[(3-[3-cyano-4-(propan-2-yloxy)phenyl]-1-{[2-(trimethylsilyl)ethoxy]methyl}-1H-pyrrolo[2,3-b]pyridin-4-yl)oxy]-3,5-difluorophenyl}-3-[(3-fluorooxetan-3-yl)methyl]urea (90 mg, 0.13 mmol, intermediate 107) in dichloromethane (2.0 mL) was added trifluoroacidic acid (1.0 mL, 13 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-(propan-2-yloxy)benzonitrile (24 mg, 33% over two steps).

LC-MS (Method 2): $R_t$=1.10 min; MS (ESIpos): m/z=552 [M+H]$^+$ $^1$H NMR (400 MHz, DMSO-d$_6$) δ ppm 1.31 (d, 6H), 3.38-3.67 (m, 4H), 4.22-4.37 (m, 2H), 4.76-4.84 (m, 1H), 5.25 (br s, 1H), 6.33 (d, 1H), 7.27-7.32 (m, 1H), 7.58 (m, 2H), 7.71 (s, 1H), 7.90-7.94 (m, 2H), 8.10 (d, 1H), 9.22 (br s, 1H), 12.15 (br s, 1H)

Example 48

(+/−)-{2-[(4-{[3-(1-ethyl-1H-pyrazol-5-yl)-1H-pyrrolo[2,3-b]pyridin-4-yl]oxy}-3,5-difluorophenyl)amino]-5-methyl-5,6-dihydro-4H-1,3-oxazin-5-yl}methanol

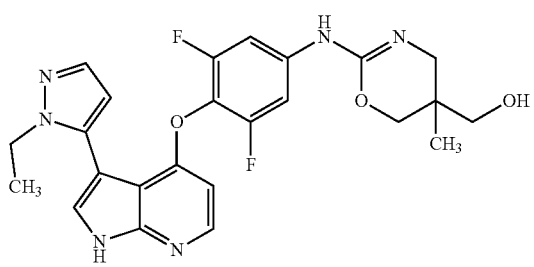 [SMILES: CCn1nccc1-c1c[nH]c2nccc(Oc3c(F)cc(NC4=NCC(C)(CO)CO4)cc3F)c12]

To a solution of 1-(4-{[3-(1-ethyl-1H-pyrazol-5-yl)-1-{[2-(trimethylsilyl)ethoxy]methyl}-1H-pyrrolo[2,3-b]pyridin-4-yl]oxy}-3,5-difluorophenyl)-3-[(3-methyloxetan-3-yl)methyl]urea (150 mg, 0.25 mmol, intermediate 110) in dichloromethane (2.0 mL) was added trifluoroacidic acid (0.7 mL, 8.6 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-{2-[(4-{[3-(1-ethyl-1H-pyrazol-5-yl)-1H-pyrrolo[2,3-b]pyridin-4-yl]oxy}-3,5-difluorophenyl)amino]-5-methyl-5,6-dihydro-4H-1,3-oxazin-5-yl}methanol (8 mg, 5% over two steps).

LC-MS (Method 2): $R_t$=0.88 min; MS (ESIpos): m/z=483 [M+H]$^+$ $^1$H NMR (400 MHz, DMSO-d$_6$) δ ppm 0.89 (s, 3H), 1.24 (t, 3H), 2.99 (br d, 1H), 3.12-3.28 (m, 2H), 3.86 (br d, 1H), 4.05 (d, 1H), 4.10 (q, 2H), 4.83 (br s, 1H), 6.25-6.35 (m, 2H), 7.42 (br s, 2H), 7.43 (d, 1H), 7.58 (s, 1H), 8.10 (d, 1H), 8.98 (br s, 1H), 12.25 (br s, 1H)

Example 49

(+/−)-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]phenoxy}acetonitrile

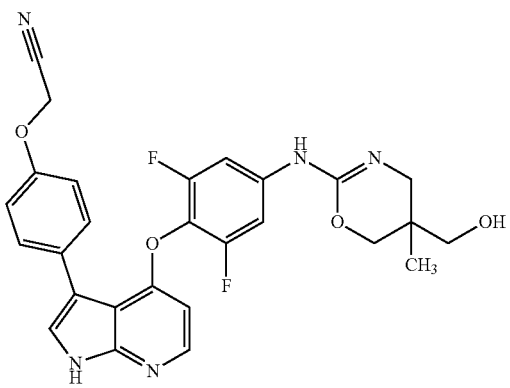 [SMILES: CC1(CO)CN=C(Nc2cc(F)c(Oc3ccnc4[nH]cc(-c5ccc(OCC#N)cc5)c34)c(F)c2)OC1]

To a solution of 1-{4-[(3-[4-(cyanomethoxy)phenyl]-1-{[2-(trimethylsilyl)ethoxy]methyl}-1H-pyrrolo[2,3-b]pyridin-4-yl)oxy]-3,5-difluorophenyl}-3-[(3-methyloxetan-3-yl)methyl]urea (150 mg, 0.23 mmol, intermediate 113) in dichloromethane (0.75 mL) was added trifluoroacidic acid (0.89 mL, 12 mmol). The resulting mixture was stirred at room temperature for 16 hours. The reaction mixture was diluted with water, treated with a saturated solution of sodium bicarbonate, and extracted with ethyl acetate two times.

The combined organic layers were washed with water, brine, dried over sodium sulfate, filtered and evaporated to afford the crude oxazine. The crude product was purified by preparative HPLC to afford (+/−)-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]phenoxy}acetonitrile (20 mg, 20% over two steps).

LC-MS (Method 2): $R_t$=0.99 min; MS (ESIpos): m/z=520 [M+H]$^+$ $^1$H NMR (400 MHz, DMSO-d$_6$) δ ppm 0.90 (s, 3H), 3.00 (br d, 1H), 3.17-3.34 (m, 3H), 3.87 (d, 1H), 4.06 (d, 1H), 4.84 (br t, 1H), 5.17 (s, 2H), 6.30 (d, 1H), 7.01-7.13 (m, 2H), 7.41 (br s, 2H), 7.59 (d, 1H), 7.62-7.72 (m, 2H), 8.09 (d, 1H), 8.99 (br s, 1H), 12.04 (br d, 1H)

Example 50

(+/−)-{2-[(3,5-difluoro-4-{[3-(2-fluoro-3-methoxyphenyl)-1H-pyrrolo[2,3-b]pyridin-4-yl]oxy}phenyl)amino]-5-methyl-5,6-dihydro-4H-1,3-oxazin-5-yl}methanol

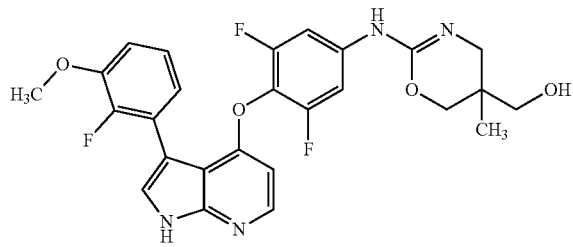 [SMILES: COc1cccc(-c2c[nH]c3nccc(Oc4c(F)cc(NC5=NCC(C)(CO)CO5)cc4F)c23)c1F]

To a solution of 1-(3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}phenyl)-3-[(3-methyloxetan-3-yl)methyl]urea (150 mg, 0.23 mmol, intermediate 116) in dichloromethane (0.75 mL) was added trifluoroacidic acid (0.63 mL, 8.2 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-{2-[(3,5-difluoro-4-{[3-(2-fluoro-3-methoxyphenyl)-1H-pyrrolo[2,3-b]pyridin-4-yl]oxy}phenyl)amino]-5-methyl-5,6-dihydro-4H-1,3-oxazin-5-yl}methanol (35 mg, 36% over two steps).

LC-MS (Method 2): $R_t$=1.01 min; MS (ESIpos): m/z=514 [M+H]$^+$ $^1$H NMR (400 MHz, DMSO-d$_6$) δ ppm 0.90 (s, 3H), 2.99 (br d, 1H), 3.16-3.36 (m, 3H), 3.83 (s, 3H), 3.86 (d, 1H), 4.05 (d, 1H), 4.86 (br t, 1H), 6.29 (d, 1H), 6.97-7.19 (m, 3H), 7.34 (br s, 2H), 7.55 (s, 1H), 8.10 (d, 1H), 12.14 (br s, 1H)

Example 51

(+/−)-[2-{[3,5-difluoro-4-({3-[2-fluoro-4-(propan-2-yloxy)phenyl]-1H-pyrrolo[2,3-b]pyridin-4-yl}oxy)phenyl]amino}-5-methyl-5,6-dihydro-4H-1,3-oxazin-5-yl]methanol

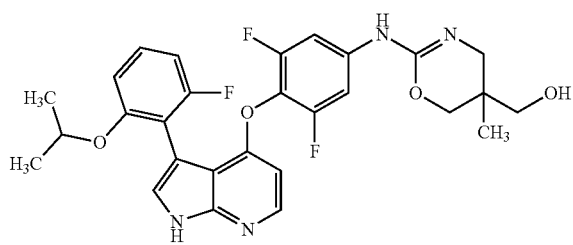 [SMILES: CC(C)Oc1cccc(F)c1-c1c[nH]c2nccc(Oc3c(F)cc(NC4=NCC(C)(CO)CO4)cc3F)c12]

To a solution of 1-{3,5-difluoro-4-[(3-[2-fluoro-4-(propan-2-yloxy)phenyl]-1-{[2-(trimethylsilyl)ethoxy]methyl}-1H-pyrrolo[2,3-b]pyridin-4-yl)oxy]phenyl}-3-[(3-methyloxetan-3-yl)methyl]urea (150 mg, 0.22 mmol, intermediate 119) in dichloromethane (0.72 mL) was added trifluoroacidic acid (0.60 mL, 7.8 mmol). The resulting mixture was stirred at room temperature for 16 hours. The reaction mixture was diluted with water, treated with a saturated solution of sodium bicarbonate, and extracted with ethyl acetate two times. The combined organic layers were washed with water, brine, dried over sodium sulfate, filtered and evaporated to afford the crude oxazine. The crude product was purified by preparative HPLC to afford (+/−)-[2-{[3,5-difluoro-4-({3-[2-fluoro-4-(propan-2-yloxy)phenyl]-1H-pyrrolo[2,3-b]pyridin-4-yl}oxy)phenyl]amino}-5-methyl-5,6-dihydro-4H-1,3-oxazin-5-yl]methanol (20 mg, 21% over two steps).

LC-MS (Method 2): $R_t$=1.14 min; MS (ESIpos): m/z=513 [M+H]$^+$ $^1$H NMR (400 MHz, DMSO-d$_6$) δ ppm 0.89 (s, 3H), 1.09 (d, 3H), 1.18 (d, 3H), 2.98 (br d, 1H), 3.14-3.34 (m, 3H), 3.85 (d, 1H), 4.04 (d, 1H), 4.51 (spt, 1H), 4.83 (br t, 1H), 6.21 (d, 1H), 6.77 (t, 1H), 6.87 (d, 1H), 7.23 (td, 1H), 7.36 (d, 1H), 8.04 (d, 1H), 11.95 (d, 1H)

Example 52

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol

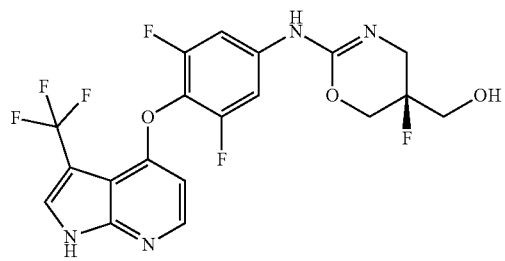 [SMILES: OC[C@@]1(F)CN=C(Nc2cc(F)c(Oc3ccnc4[nH]cc(C(F)(F)F)c34)c(F)c2)OC1]

The racemic mixture of example 8 was separated in the two enantiomers using a chiral preparative HPLC (Labomatic HD5000, Labocord-5000; Gilson GX-241, Labcol Vario 4000, column: Chiralpak IE 5p 250×30 mm; eluent A: hexane+0.1 Vol-% diethylamine (99%); eluent B: ethanol; isocratic: 85% A+15% B; flow 50.0 mL/min; UV 254 nm). Using this methodology the title compound was isolated as the unpolar enantiomer (ee>99%).

[α]$_{589}^{20}$=+1.5 (c=1.0; DMSO)

Example 53

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol

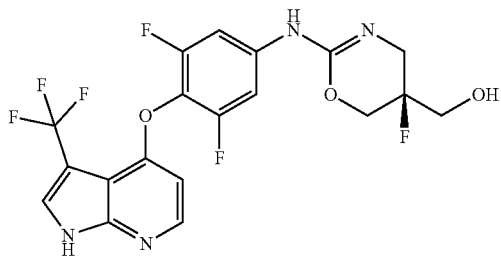 [SMILES: OC[C@@]1(F)CN=C(Nc2cc(F)c(Oc3ccnc4[nH]cc(C(F)(F)F)c34)c(F)c2)OC1]

The racemic mixture of example 8 was separated in the two enantiomers using a chiral preparative HPLC (Labomatic HD5000, Labocord-5000; Gilson GX-241, Labcol Vario 4000, column: Chiralpak IE 5µ 250×30 mm; eluent A: hexane+0.1 Vol-% diethylamine (99%); eluent B: ethanol; isocratic: 85% A+15% B; flow 50.0 mL/min; UV 254 nm). Using this methodology the title compound was isolated as the polar enantiomer (ee=96%).

$[\alpha]_{59}^{20}$=−1.5 (c=1.0; DMSO)

Example 54

(+/−)-[2-{3,5-difluoro-4-[(1H-pyrrolo[2,3-b]pyridin-4-yl)oxy]anilino}-5-(propan-2-yl)-5,6-dihydro-4H-1,3-oxazin-5-yl]methanol

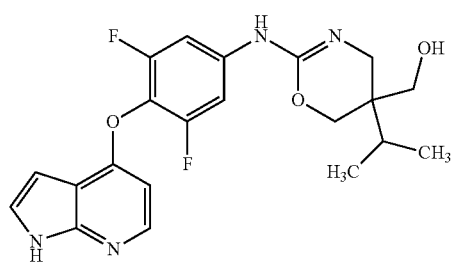 [SMILES: CC(C)C1(CO)CN=C(Nc2cc(F)c(Oc3ccnc4[nH]ccc34)c(F)c2)OC1]

In analogy to example 2, N-{3,5-difluoro-4-[(1-{[2-(trimethylsilyl)ethoxy]methyl}-1H-pyrrolo[2,3-b]pyridin-4-yl)oxy]phenyl}-N'-{[3-(propan-2-yl)oxetan-3-yl]methyl}urea (92.0 mg, 168 µmol, intermediate 121) was stirred with trifluoroacidic acid (1.2 mL, 15 mmol) in dichloromethane (2.3 mL). After purification using a Biotage chromatography system followed by HPLC (method 5) we obtained 51.4 mg (90% purity, 66% yield) of the desired title compound.

LC-MS (Method 2): $R_t$=0.99 min; MS (ESIneg): m/z=415 [M−H]⁻

¹H-NMR (400 MHz, DMSO-d6) δ [ppm]: 0.90 (dd, 6H), 1.71-1.82 (m, 1H), 3.03-3.30 (m, 2H), 3.35-3.43 (m, 2H), 3.99-4.08 (m, 1H), 4.10-4.17 (m, 1H), 4.71 (br s, 1H), 6.26-6.32 (m, 1H), 6.37 (d, 1H), 7.39 (dd, 1H), 7.41-7.69 (m, 2H), 8.06 (d, 1H), 9.03 (br s, 1H), 11.81 (br s, 1H).

Example 55

(+/−)-[2-{3,5-difluoro-4-[(1H-pyrrolo[2,3-b]pyridin-4-yl)oxy]anilino}-5-methyl-5,6-dihydro-4H-1,3-oxazin-5-yl]methanol

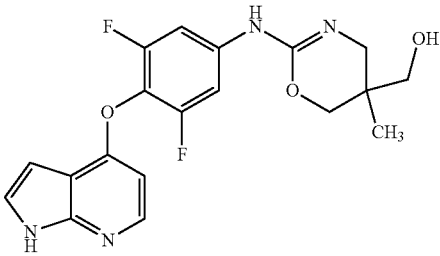 [SMILES: CC1(CO)CN=C(Nc2cc(F)c(Oc3ccnc4[nH]ccc34)c(F)c2)OC1]

In analogy to example 2, N-{3,5-difluoro-4-[(1-{[2-(trimethylsilyl)ethoxy]methyl}-1H-pyrrolo[2,3-b]pyridin-4-yl)oxy]phenyl}-N'-[(3-methyloxetan-3-yl)methyl]urea (81.0 mg, 156 µmol, intermediate 122) was stirred with trifluoroacidic acid (1.1 mL, 14 mmol) in dichloromethane (2.2 mL). After purification using a Biotage chromatography system followed by HPLC (method 5) we obtained 24.6 mg (90% purity, 37% yield) of the desired title compound.

LC-MS (Method 2): $R_t$=0.88 min; MS (ESIneg): m/z=387 [M−H]⁻

¹H-NMR (400 MHz, DMSO-d6) δ [ppm]: 0.90 (s, 3H), 3.01 (br d, 1H), 3.14-3.31 (m, 3H), 3.87 (br d, 1H), 4.06 (br d, 1H), 4.82 (br s, 1H), 6.29 (br s, 1H), 6.38 (d, 1H), 7.39 (dd, 1H), 7.46-7.69 (m, 2H), 8.06 (d, 1H), 9.02 (br s, 1H), 11.81 (br s, 1H).

Example 56

(+/−)-[2-{3,5-difluoro-4-[(1H-pyrrolo[2,3-b]pyridin-4-yl)oxy]anilino}-4-methyl-5,6-dihydro-4H-1,3-oxazin-5-yl]methanol

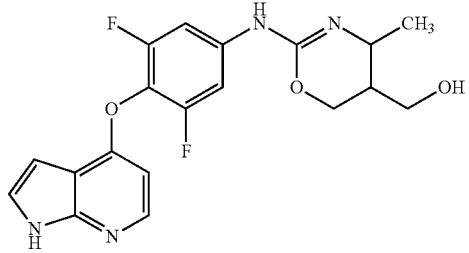 [SMILES: CC1N=C(Nc2cc(F)c(Oc3ccnc4[nH]ccc34)c(F)c2)OCC1CO]

In analogy to example 2, (+/−)—N-{3,5-difluoro-4-[(1-{[2-(trimethylsilyl)ethoxy]methyl}-1H-pyrrolo[2,3-b]pyridin-4-yl)oxy]phenyl}-N'-[(1R)-1-(oxetan-3-yl)ethyl]urea (171 mg, 330 µmol, intermediate 123) was stirred with trifluoroacidic acid (2.3 mL, 30 mmol) in dichloromethane (4.6 mL). After purification using a Biotage chromatography system followed by HPLC (method 5) we obtained 84.6 mg (90% purity, 59% yield) of the desired title compound.

¹H-NMR (400 MHz, DMSO-d6, main isomer)) δ [ppm]: 1.19 (d, 3H), 3.27-3.32 (m, 1H), 3.35-3.43 (m, 1H), 3.47-3.57 (m, 1H), 4.03 (q, 1H), 4.30 (br dd, 1H), 4.73 (br s, 1H), 6.29 (br s, 1H), 6.37 (d, 1H), 6.75 (br s, 1H), 7.39 (dd, 1H), 7.52-7.70 (m, 2H), 8.06 (d, 1H), 8.99 (br s, 1H), 11.80 (br s, 1H).

Example 57

(+/−)-[2-(3-fluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol

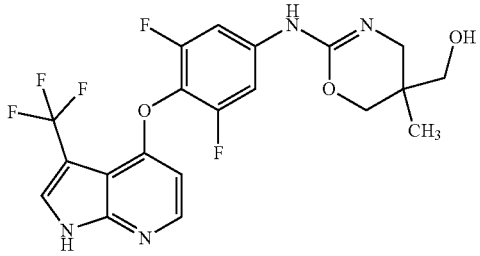 [SMILES: CC1(CO)CN=C(Nc2cc(F)c(Oc3ccnc4[nH]cc(C(F)(F)F)c34)c(F)c2)OC1]

In analogy to example 2, N-(3-fluoro-4-{[3-(trifluoromethyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (150 mg, 264 μmol, intermediate 126) was stirred with trifluoroacidic acid (1.8 mL, 23 mmol) in dichloromethane (6.0 mL). After purification using a Biotage chromatography system followed by HPLC (method 5) we obtained 23.2 mg (92% purity, 18% yield) of the desired title compound.

LC-MS (Method 2): $R_t$=0.98 min; MS (ESIneg): m/z=437 [M−H]⁻

$^1$H-NMR (400 MHz, DMSO-d6) δ [ppm]: 0.90 (s, 3H), 3.00 (br d, 1H), 3.17-3.24 (m, 1H), 3.24-3.28 (m, 1H), 3.85 (d, 1H), 4.04 (d, 1H), 4.81 (br t, 1H), 6.32-6.40 (m, 1H), 7.15-7.37 (m, 2H), 7.82 (br s, 1H), 8.05-8.07 (m, 1H), 8.15-8.21 (m, 1H), 8.40 (s, 1H), 12.53 (br s, 1H).

Example 58

(+/−)-[2-(2,5-difluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol

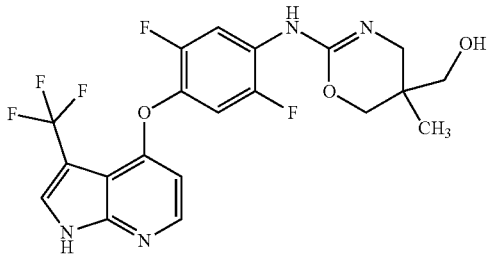 [SMILES: CC1(CO)CN=C(Nc2cc(F)c(Oc3ccnc4[nH]cc(C(F)(F)F)c34)cc2F)OC1]

In analogy to example 2, N-(2,5-difluoro-4-{[3-(trifluoromethyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (120 mg, 205 μmol, intermediate 129) was stirred with trifluoroacidic acid (1.4 mL, 18 mmol) in dichloromethane (5.0 mL). After purification using a Biotage chromatography system followed by HPLC (method 5) we obtained 49.0 mg (92% purity, 48% yield) of the desired title compound.

LC-MS (Method 1): $R_t$=0.81 min; MS (ESIneg): m/z=455 [M−H]⁻

$^1$H-NMR (400 MHz, DMSO-d6) δ [ppm]: 0.94 (s, 3H), 2.90 (br d, 1H), 3.11 (br d, 1H), 3.40-3.48 (m, 1H), 3.86-3.92 (m, 1H), 4.01-4.06 (m, 1H), 4.90 (t, 1H), 6.45 (d, 1H), 7.04 (br s, 2H), 7.24 (dd, 1H), 8.08 (s, 1H), 8.21 (d, 1H), 12.57 (br s, 1H).

Example 59

(+/−)-[2-{4-[(3-bromo-1H-pyrrolo[2,3-b]pyridin-4-yl)sulfanyl]anilino}-5-methyl-5,6-dihydro-4H-1,3-oxazin-5-yl]methanol

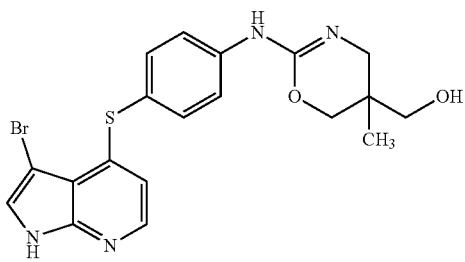 [SMILES: CC1(CO)CN=C(Nc2ccc(Sc3ccnc4[nH]cc(Br)c34)cc2)OC1]

In analogy to example 2, N-{4-[(3-bromo-1-{[2-(trimethylsilyl)ethoxy]methyl}-1H-pyrrolo[2,3-b]pyridin-4-yl)sulfanyl]phenyl}-N'-[(3-methyloxetan-3-yl)methyl]urea (178 mg, 308 μmol, intermediate 133) was stirred with trifluoroacidic acid (2.1 mL, 27 mmol) in dichloromethane (4.0 mL). After purification using a Biotage chromatography system followed by HPLC (method 5) we obtained 16.2 mg (95% purity, 11% yield) of the desired title compound.

LC-MS (Method 2): $R_t$=1.03 min; MS (ESIpos): m/z=447 [M+H]⁺

$^1$H-NMR (400 MHz, DMSO-d6) δ [ppm]: 0.90 (s, 3H), 3.02 (br d, 1H), 3.18-3.30 (m, 2H), 3.86 (br d, 1H), 4.05 (d, 1H), 4.81 (br s, 1H), 6.17 (d, 1H), 7.42 (d, 2H), 7.62-7.65 (m, 1H), 7.66-7.82 (m, 2H), 7.94 (d, 1H), 8.82 (br s, 1H), 12.09 (br s, 1H).

Example 60

(+/−)-5-{4-[4-{[5-(hydroxymethyl)-5-phenyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile

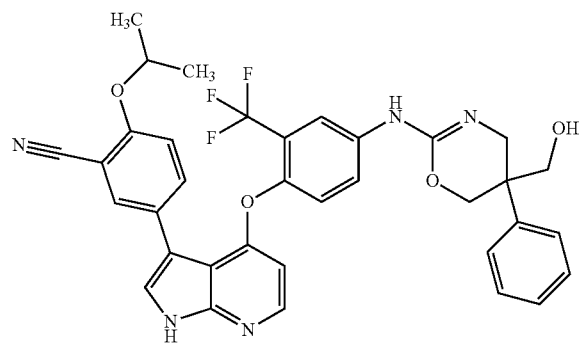 [SMILES: CC(C)Oc1ccc(-c2c[nH]c3nccc(Oc4ccc(NC5=NCC(CO)(c6ccccc6)CO5)cc4C(F)(F)F)c23)cc1C#N]

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(3-phenyloxetan-3-yl)methyl]urea (100 mg, 123 μmol, intermediate 140) was stirred with trifluoroacidic acid (0.83 mL, 11 mmol) in dichloromethane (2.0 mL). After purification using a Biotage chromatography system followed by HPLC (method 5) we obtained 40.3 mg (92% purity, 47% yield) of the desired title compound.

LC-MS (Method 1): $R_t$=0.97 min; MS (ESIpos): m/z=642 [M+H]$^+$ $^1$H-NMR (400 MHz, DMSO-d6) δ [ppm]: 1.29 (d, 6H), 3.38-3.48 (m, 1H), 3.54-3.72 (m, 3H), 4.44-4.54 (m, 2H), 4.77 (spt, 1H), 4.90 (br s, 1H), 6.20 (d, 1H), 7.15-7.27 (m, 3H), 7.34 (t, 2H), 7.39-7.46 (m, 2H), 7.68 (d, 1H), 7.74-7.94 (m, 2H), 7.93-7.94 (m, 1H), 8.04-8.20 (m, 2H), 8.88 (br s, 1H), 12.09 (s, 1H).

Example 61

(+/−)-5-{4-[4-{[5-fluoro-5-(hydroxymethyl)-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile

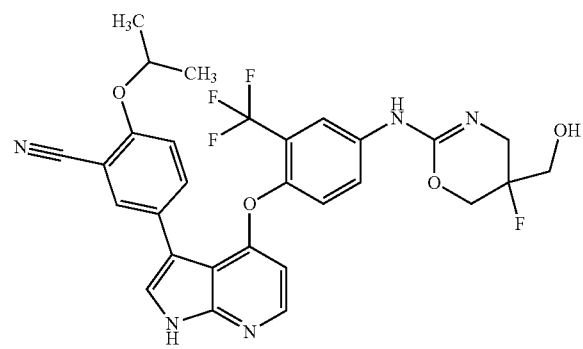 [SMILES: CC(C)Oc1ccc(-c2c[nH]c3nccc(Oc4ccc(NC5=NCC(F)(CO)CO5)cc4C(F)(F)F)c23)cc1C#N]

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(3-fluorooxetan-3-yl)methyl]urea (80.0 mg, 106 μmol, intermediate 141) was stirred with trifluoroacidic acid (0.72 mL, 9.4 mmol) in dichloromethane (1.7 mL). After purification using a Biotage chromatography system followed by HPLC (method 5) we obtained 18.4 mg (90% purity, 27% yield) of the desired title compound.

LC-MS (Method 1): $R_t$=0.97 min; MS (ESIpos): m/z=584 [M+H]$^+$ $^1$H-NMR (400 MHz, DMSO-d6) δ [ppm]: 1.29 (d, 6H), 3.36-3.66 (m, 4H), 4.20-4.36 (m, 2H), 4.78 (spt, 1H), 5.23 (t, 1H), 6.22 (d, 1H), 7.21 (dd, 2H), 7.68 (d, 1H), 7.75-7.85 (m, 1H), 7.85-7.93 (m, 2H), 8.04-8.18 (m, 2H), 8.86-9.29 (m, 1H), 12.10 (d, 1H).

Example 62

(+/−)-5-{4-[4-{5-(hydroxymethyl)-5-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile

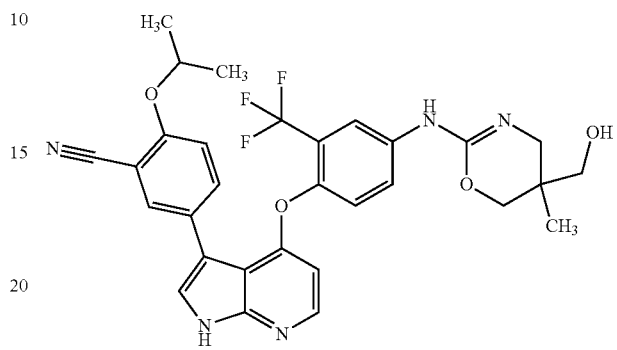

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(3-methyloxetan-3-yl)methyl]urea (90.0 mg, 127 μmol, intermediate 142) was stirred with trifluoroacidic acid (0.86 mL, 11 mmol) in dichloromethane (2.0 mL). After purification using a Biotage chromatography system followed by HPLC (method 5) we obtained 24.0 mg (97% purity, 32% yield) of the desired title compound.

LC-MS (Method 1): $R_t$=0.96 min; MS (ESIpos): m/z=580 [M+H]$^+$ $^1$H-NMR (400 MHz, DMSO-d6) δ [ppm]: 0.90 (s, 3H), 1.30 (d, 6H), 3.00 (br d, 1H), 3.15-3.31 (m, 3H), 3.85 (br d, 1H), 4.04 (d, 1H), 4.73-4.84 (m, 2H), 6.21 (d, 1H), 7.14-7.25 (m, 2H), 7.68 (d, 1H), 7.72-7.93 (m, 3H), 8.08 (d, 1H), 8.10-8.32 (m, 1H), 8.87 (br s, 1H), 12.09 (d, 1H).

Example 63

(+/−)-2-{4-[(3-{3-cyano-4-[(propan-2-yl)oxy]phenyl}-1H-pyrrolo[2,3-b]pyridin-4-yl)oxy]-3-(trifluoromethyl)anilino}-5-(hydroxymethyl)-5,6-dihydro-4H-1,3-oxazine-5-carbonitrile

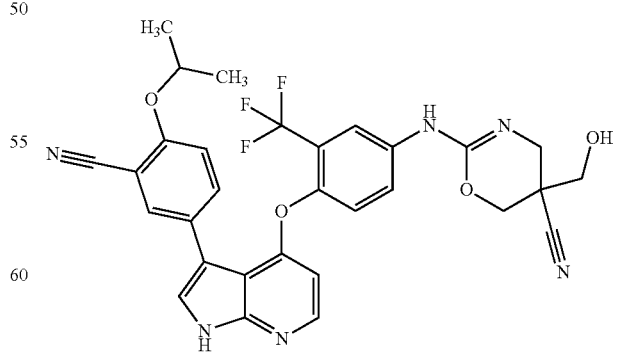

In analogy to example 2, N-[(3-cyanooxetan-3-yl)methyl]-N'-{4-[(3-{3-cyano-4-[(propan-2-yl)oxy]phenyl}-1-{[2-(trimethylsilyl)ethoxy]methyl}-1H-pyrrolo[2,3-b]

pyridin-4-yl)oxy]-3-(trifluoromethyl)phenyl}urea (70.0 mg, 97.1 μmol, intermediate 143) was stirred with trifluoroacidic acid (0.66 mL, 8.5 mmol) in dichloromethane (1.5 mL). After purification using a Biotage chromatography system followed by HPLC (method 5) we obtained 17.2 mg (92% purity, 28% yield) of the desired title compound.

LC-MS (Method 1): $R_t$=0.99 min; MS (ESIpos): m/z=591 [M+H]$^+$ $^1$H-NMR (400 MHz, DMSO-d6) δ [ppm]: 1.29 (d, 6H), 3.44-3.69 (m, 4H), 4.24 (d, 1H), 4.46 (dd, 1H), 4.77 (spt, 1H), 5.66 (br t, 1H), 6.23 (d, 1H), 7.20 (d, 1H), 7.24 (br d, 1H), 7.68 (d, 1H), 7.80-7.92 (m, 3H), 8.08 (d, 1H), 8.15 (br s, 1H), 9.18 (br s, 1H), 12.11 (s, 1H).

Example 64

(+/−)-5-{4-[4-{[4-(hydroxymethyl)-4,5-dihydro-1,3-oxazol-2-yl]amino}-2-(trifluoromethyl)phenoxy]-1H-pyrrolo[2,3-b]pyridin-3-yl}-2-[(propan-2-yl)oxy]benzonitrile

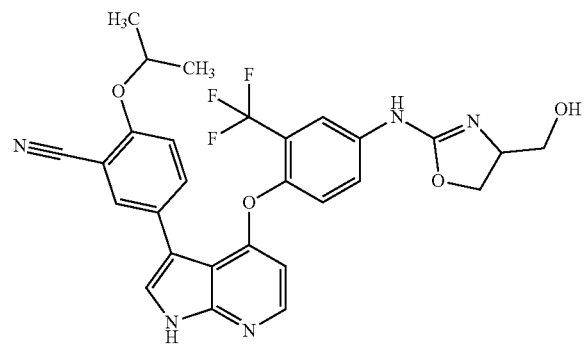 [SMILES: CC(C)Oc1ccc(-c2c[nH]c3nccc(Oc4ccc(NC5=NC(CO)CO5)cc4C(F)(F)F)c23)cc1C#N]

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-oxetan-3-ylurea (90.0 mg, 132 μmol, intermediate 144) was stirred with trifluoroacidic acid (0.89 mL, 12 mmol) in dichloromethane (2.1 mL). After purification using a Biotage chromatography system followed by HPLC (method 5) we obtained 30.4 mg (92% purity, 38% yield) of the desired title compound.

LC-MS (Method 1): $R_t$=0.95 min; MS (ESIpos): m/z=552 [M+H]$^+$ $^1$H-NMR (400 MHz, DMSO-d6) δ [ppm]: 1.29 (d, 6H), 3.36-3.55 (m, 2H), 3.98-4.41 (m, 3H), 4.78 (spt, 2H), 6.23 (d, 1H), 7.13-7.30 (m, 2H), 7.68 (s, 1H), 7.80-7.93 (m, 3H), 8.09 (d, 1H), 8.12-8.25 (m, 1H), 9.61 (br s, 1H), 12.11 (s, 1H).

Example 65

(+/−)-5-{4-[4-{[-5-(hydroxymethyl)-4-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile

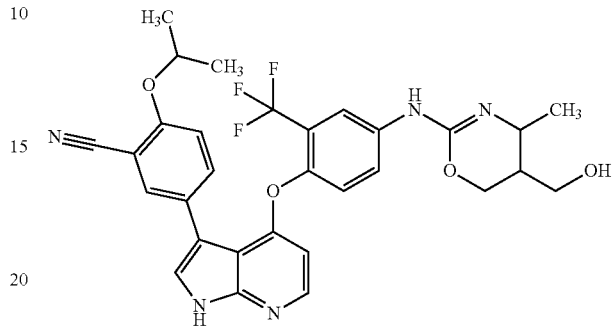

In analogy to example 2, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3-(trifluoromethyl)phenyl}-N'-[(1R)-1-(oxetan-3-yl)ethyl]urea (250 mg, 352 μmol, intermediate 145) was stirred with trifluoroacidic acid (2.4 mL, 31 mmol) in dichloromethane (5.6 mL). After purification using a Biotage chromatography system followed by HPLC (method 5) we obtained 61.9 mg (90% purity, 27% yield) of the desired title compound.

LC-MS (Method 1): $R_t$=0.90 min; MS (ESIneg): m/z=578 [M−H]$^-$ $^1$H-NMR (400 MHz, DMSO-d6, main isomer) δ [ppm]: 1.18 (d, 3H), 1.30 (d, 6H), 3.24-3.30 (m, 1H), 3.37-3.58 (m, 3H), 4.01 (br t, 1H), 4.27 (dd, 1H), 4.64-4.83 (m, 2H), 6.21 (d, 1H), 7.13-7.24 (m, 2H), 7.68 (d, 2H), 7.85-7.93 (m, 2H), 8.08 (d, 1H), 8.18-8.41 (m, 1H), 8.75-8.99 (m, 1H), 12.09 (d, 1H).

Example 66

5-(4-{4-[(5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile

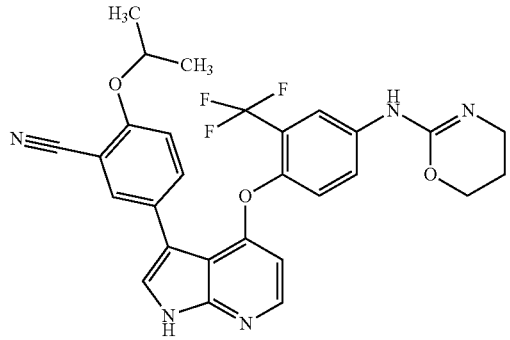 [SMILES: CC(C)Oc1ccc(-c2c[nH]c3nccc(Oc4ccc(NC5=NCCCO5)cc4C(F)(F)F)c23)cc1C#N]

In analogy to example 2, 5-(4-{4-[(5,6-dihydro-4H-1,3-oxazin-2-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile (22.0 mg, 33.0 μmol, intermediate 148) was stirred with trifluoroacidic acid (0.22 mL, 2.9 mmol) in dichloromethane (850 µL). After purification using a Biotage chromatography system followed by HPLC (method 5) we obtained 8.4 mg (80% purity, 38% yield) of the desired title compound.

LC-MS (Method 2): R$_t$=1.21 min; MS (ESIneg): m/z=534 [M–H]⁻

¹H-NMR (400 MHz, METHANOL-d4) δ [ppm]: 1.36 (d, 6H), 2.04 (tt, 2H), 3.38 (t, 2H), 4.35-4.40 (m, 2H), 4.73 (spt, 1H), 6.39 (d, 1H), 7.03-7.14 (m, 2H), 7.37 (dd, 1H), 7.47 (s, 1H), 7.52-7.59 (m, 1H), 7.76-7.90 (m, 2H), 8.08 (d, 1H).

Example 67

5-(4-{4-[(5-oxa-7-azaspiro[2.5]oct-6-en-6-yl)amino]-2-(trifluoromethyl)phenoxy}-1H-pyrrolo[2,3-b]pyridin-3-yl)-2-[(propan-2-yl)oxy]benzonitrile

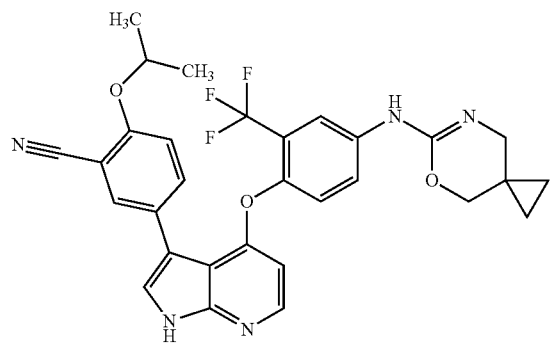 [SMILES: CC(C)Oc1ccc(-c2c[nH]c3nccc(Oc4ccc(NC5=NCC6(CC6)CO5)cc4C(F)(F)F)c23)cc1C#N]

In analogy to example 2, 5-(4-{4-[(5-oxa-7-azaspiro[2.5]oct-6-en-6-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile (160 mg, 116 µmol, intermediate 150) was stirred with trifluoroacidic acid (0.78 mL, 10 mmol) in dichloromethane (3.0 mL). After purification using a Biotage chromatography system followed by HPLC (method 5) we obtained 9.1 mg (95% purity, 13% yield) of the desired title compound.

LC-MS (Method 2): R$_t$=1.29 min; MS (ESIneg): m/z=560 [M–H]⁻

¹H-NMR (400 MHz, METHANOL-d4) δ [ppm]: 0.62-0.74 (m, 4H), 1.36 (d, 6H), 3.21 (s, 2H), 4.06 (s, 2H), 4.73 (spt, 1H), 6.35 (d, 1H), 7.03-7.12 (m, 2H), 7.41 (br d, 1H), 7.46 (s, 1H), 7.60 (br s, 1H), 7.81-7.89 (m, 2H), 8.06 (d, 1H).

Example 68

5-(4-{4-[(5,5-dimethyl-5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile

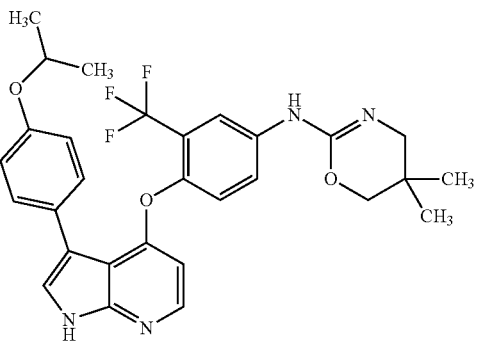

In analogy to example 2, 5-(4-{4-[(5,5-dimethyl-5,6-dihydro-4H-1,3-oxazin-2-yl)amino]-2-(trifluoromethyl)phenoxy}-1-{[2-(trimethylsilyl)ethoxy]methyl}-1H-pyrrolo[2,3-b]pyridin-3-yl)-2-[(propan-2-yl)oxy]benzonitrile (30.0 mg, 43.2 µmol, intermediate 152) was stirred with trifluoroacidic acid (0.29 mL, 3.8 mmol) in dichloromethane (1.5 mL). After purification using a Biotage chromatography system followed by HPLC (method 5) we obtained 14.2 mg (90% purity, 52% yield) of the desired title compound.

LC-MS (Method 1): R$_t$=1.09 min; MS (ESIneg): m/z=562 [M–H]⁻

¹H-NMR (400 MHz, DMSO-d6) δ [ppm]: 0.96 (s, 6H), 1.29 (d, 6H), 3.06 (s, 2H), 3.86 (s, 2H), 4.77 (spt, 1H), 6.21 (d, 1H), 7.20 (t, 2H), 7.62-7.77 (m, 2H), 7.85-7.95 (m, 2H), 8.08 (d, 2H), 8.77-9.14 (m, 1H), 12.09 (d, 1H).

Example 69

(+/−)-5-[4-(2,6-difluoro-4-{[5-(1-hydroxy-2-methylpropan-2-yl)-4,5-dihydro-1,3-oxazol-2-yl]amino}phenoxy)-1H-pyrrolo[2,3-b]pyridin-3-yl]-2-[(propan-2-yl)oxy]benzonitrile

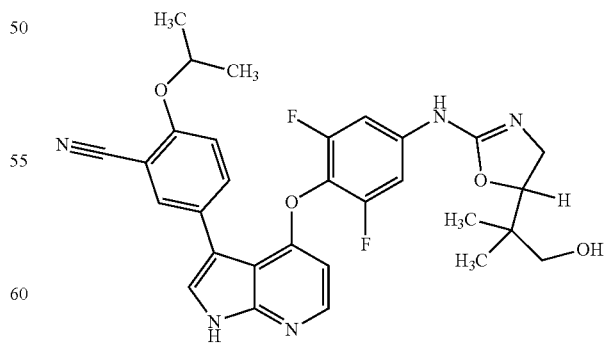

In analogy to example 2, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-{[(2S)-3,3-dimethyloxetane-2-yl]methyl}urea (86.0 mg, 124 µmol, intermediate 153) was stirred with trifluoroacidic acid (0.85 mL, 11 mmol) in dichloromethane (1.7 mL). After purification using a Biotage chromatography system followed by HPLC (method 5) we obtained 26.3 mg (92% purity, 35% yield) of the desired title compound.

LC-MS (Method 1): $R_t$=1.13 min; MS (ESIpos): m/z=562 [M+H]⁻

¹H-NMR (400 MHz, DMSO-d6) δ [ppm]: 0.81 (br s, 3H), 0.85 (br s, 3H), 1.31 (d, 6H), 3.13-3.32 (m, 3H), 3.55-3.85 (m, 1H), 4.42-4.85 (m, 3H), 6.34 (d, 1H), 6.75-6.96 (m, 1H), 7.30 (d, 1H), 7.59 (br s, 1H), 7.71 (d, 1H), 7.88-7.97 (m, 2H), 8.11 (d, 1H), 9.81 (br s, 1H), 12.15 (d, 1H).

Example 70

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile

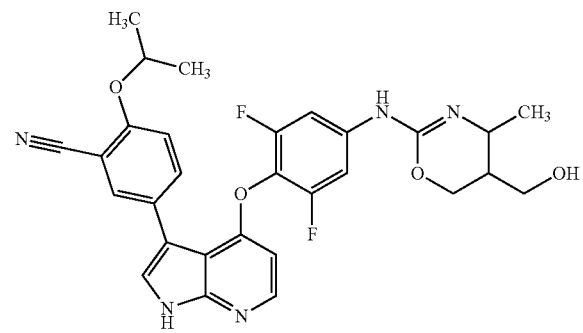 [SMILES: CC(C)Oc1ccc(-c2c[nH]c3nccc(Oc4c(F)cc(NC5=NC(C)C(CO)CO5)cc4F)c23)cc1C#N]

In analogy to example 2, (+/−)—N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (90.0 mg, 133 µmol, intermediate 154) was stirred with trifluoroacidic acid (0.92 mL, 12 mmol) in dichloromethane (1.8 mL). After purification using a Biotage chromatography system followed by HPLC (method 5) we obtained 45.0 mg (90% purity, 56% yield) of the desired title compound.

LC-MS (Method 2): $R_t$=1.11 min; MS (ESIpos): m/z=548 [M+H]⁺

¹H-NMR (400 MHz, DMSO-d6, main isomer) δ [ppm]: 1.19 (d, 3H), 1.31 (d, 6H), 3.25-3.31 (m, 1H), 3.36-3.57 (m, 2H), 4.03 (q, 1H), 4.30 (br dd, 1H), 4.68-4.87 (m, 2H), 6.32 (d, 1H), 6.75 (br s, 1H), 7.30 (d, 1H), 7.53-7.68 (m, 1H), 7.70 (d, 1H), 7.90-7.96 (m, 2H), 8.10 (d, 1H), 9.00 (br s, 1H), 12.14 (d, 1H), 12.14 (d, 1H).

Example 71

(+/−)-5-[4-(2,6-difluoro-4-{[4-(hydroxymethyl)-4,5-dihydro-1,3-oxazol-2-yl]amino}phenoxy)-1H-pyrrolo[2,3-b]pyridin-3-yl]-2-[(propan-2-yl)oxy]benzonitrile

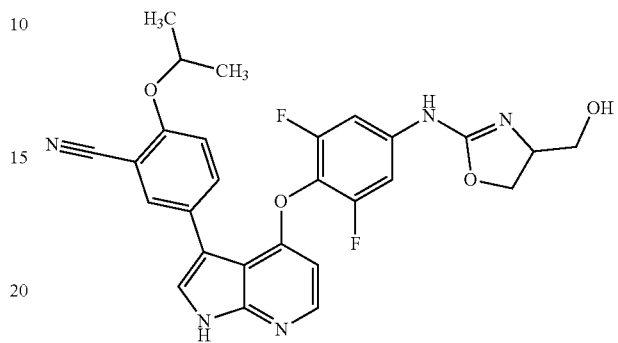

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-oxetan-3-ylurea (86.0 mg, 132 µmol, intermediate 155) was stirred with trifluoroacidic acid (0.90 mL, 12 mmol) in dichloromethane (1.8 mL). After purification using a Biotage chromatography system followed by HPLC (method 5) we obtained 18.4 mg (97% purity, 26% yield) of the desired title compound.

LC-MS (Method 1): $R_t$=0.91 min; MS (ESIpos): m/z=520 [M+H]⁺

¹H-NMR (400 MHz, DMSO-d6) δ [ppm]: 1.31 (d, 6H), 3.36-3.57 (m, 2H), 3.85 (br s, 1H), 4.06-4.35 (m, 2H), 4.71-4.89 (m, 2H), 6.33 (d, 1H), 6.82 (br s, 1H), 7.30 (d, 1H), 7.53-7.66 (m, 1H), 7.71 (d, 1H), 7.90-7.95 (m, 2H), 8.11 (d, 1H), 9.77 (br s, 1H), 12.15 (d, 1H).

Example 72

(+/−)-5-[4-(2,6-difluoro-4-{[5-(hydroxymethyl)-5-phenyl-5,6-dihydro-4H-1,3-oxazin-2-yl]amino}phenoxy)-1H-pyrrolo[2,3-b]pyridin-3-yl]-2-[(propan-2-yl)oxy]benzonitrile

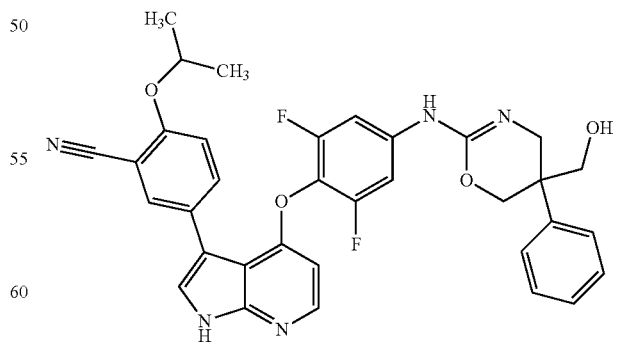

In analogy to example 2, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-phenyloxetan-3-yl)methyl]urea (125 mg, 169 µmol, intermediate 156) was stirred with trifluoroacidic acid (1.2 mL, 16 mmol) in dichloromethane (2.4 mL). After purification using a Biotage chromatography system followed by HPLC (method 5) we obtained 21.1 mg (97% purity, 20% yield) of the desired title compound.

LC-MS (Method 1): $R_t$=1.02 min; MS (ESIpos): m/z=610 [M+H]$^+$ $^1$H-NMR (400 MHz, DMSO-d6) δ [ppm]: 1.31 (d, 6H), 3.59 (br d, 2H), 3.63-3.75 (m, 2H), 4.50 (br s, 2H), 4.80 (spt, 1H), 4.91 (br s, 1H), 6.32 (d, 1H), 7.21-7.39 (m, 4H), 7.40-7.47 (m, 2H), 7.49-7.61 (m, 2H), 7.70 (d, 1H), 7.89-7.94 (m, 2H), 8.09 (d, 1H), 9.03 (br s, 1H), 12.14 (d, 1H).

Example 73

(+/−)-2-{4-[(3-{3-cyano-4-[(propan-2-yl)oxy]phenyl}-1H-pyrrolo[2,3-b]pyridin-4-yl)oxy]-3,5-difluoroanilino}-4-(hydroxymethyl)-4,5-dihydro-1,3-oxazole-4-carboxamide

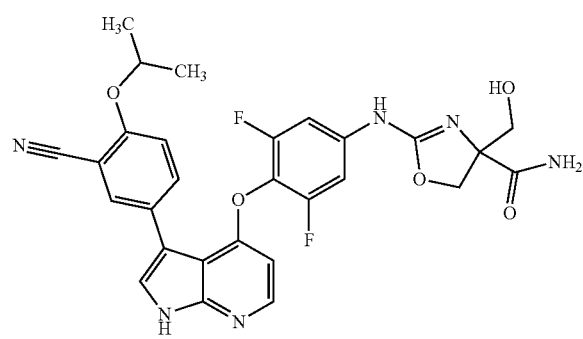 [SMILES: CC(C)Oc1ccc(-c2c[nH]c3nccc(Oc4c(F)cc(NC5=NC(CO)(C(N)=O)CO5)cc4F)c23)cc1C#N]

In analogy to example 2, 3-[({4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}carbamoyl)amino]oxetane-3-carboxamide (25.0 mg, 36.1 μmol, intermediate 157) was stirred with trifluoroacidic acid (0.25 mL, 3.2 mmol) in dichloromethane (500 μL). After purification using a Biotage chromatography system followed by HPLC (method 5) we obtained 5.9 mg (97% purity, 28% yield) of the desired title compound.

LC-MS (Method 1): $R_t$=0.98 min; MS (ESIpos): m/z=563 [M+H]$^+$ $^1$H-NMR (400 MHz, METHANOL-d4) δ [ppm]: 1.37 (d, 6H), 3.69 (br d, 1H), 3.78 (d, 1H), 4.31-4.42 (m, 2H), 4.75 (spt, 1H), 6.37 (br d, 1H), 7.16 (br d, 1H), 7.47 (s, 1H), 7.53 (br s, 1H), 7.55 (br s, 1H), 7.86-7.94 (m, 2H), 8.07 (br d, 1H).

Example 74

5-(4-{4-[(5,5-diethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile

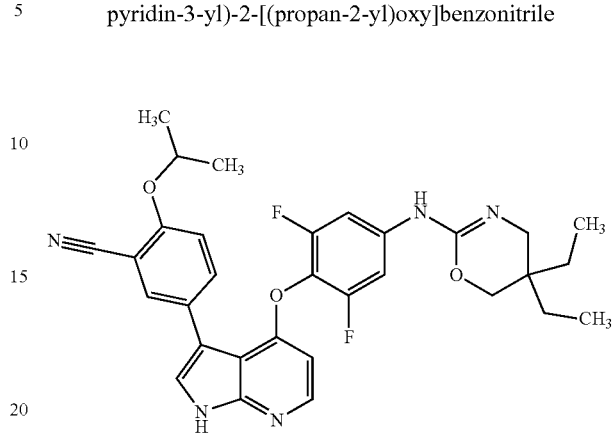

In analogy to example 2, 5-(4-{4-[(5,5-diethyl-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile (11.0 mg, 15.9 μmol, intermediate 160) was stirred with trifluoroacidic acid (0.11 mL, 1.4 mmol) in dichloromethane (1.0 mL). After purification using a Biotage chromatography system followed by HPLC (method 5) we obtained 8.3 mg (90% purity, 84% yield) of the desired title compound.

LC-MS (Method 1): $R_t$=1.16 min; MS (ESIpos): m/z=560 [M+H]$^+$ $^1$H-NMR (400 MHz, METHANOL-d4) δ [ppm]: 0.90 (t, 6H), 1.33-1.56 (m, 10H), 3.13 (s, 2H), 4.03 (s, 2H), 4.76 (spt, 1H), 6.34-6.41 (m, 1H), 6.91-7.02 (m, 2H), 7.17 (d, 1H), 7.46 (s, 1H), 7.88-7.94 (m, 2H), 8.04-8.09 (m, 1H).

Example 75

5-(4-{2,6-difluoro-4-[(4,4,5,5-tetramethyl-4,5-dihydro-1,3-oxazol-2-yl)amino]phenoxy}-1H-pyrrolo[2,3-b]pyridin-3-yl)-2-[(propan-2-yl)oxy]benzonitrile

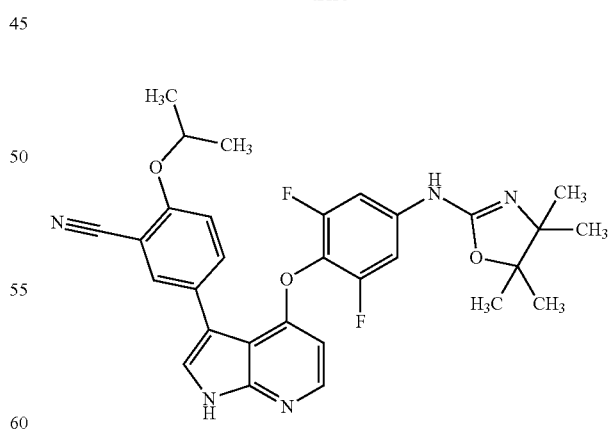

In analogy to example 2, 5-(4-{2,6-difluoro-4-[(4,4,5,5-tetramethyl-4,5-dihydro-1,3-oxazol-2-yl)amino]phenoxy}-1-{[2-(trimethylsilyl)ethoxy]methyl}-1H-pyrrolo[2,3-b]pyridin-3-yl)-2-[(propan-2-yl)oxy]benzonitrile (100 mg, 148 μmol, intermediate 162) was stirred with trifluoroacidic acid (1.0 mL, 13 mmol) in dichloromethane (8.0 mL). After purification using a Biotage chromatography system followed by HPLC (method 5) we obtained 19.8 mg (95% purity, 23% yield) of the desired title compound.

LC-MS (Method 1): $R_t$=1.13 min; MS (ESIpos): m/z=546 [M+H]$^+$ $^1$H-NMR (500 MHz, DMSO-d6) δ [ppm]: 1.16 (s, 6H), 1.32 (d, 4H), 1.32 (s, 6H), 4.80 (spt, 1H), 6.34 (d, 1H), 6.80 (br s, 1H), 7.30 (d, 1H), 7.57 (br s, 1H), 7.71 (d, 1H), 7.91-7.95 (m, 2H), 8.11 (d, 1H), 12.14 (d, 1H).

Example 76

(+/−)-5-{4-[2,6-difluoro-4-({5-[(pyridin-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile

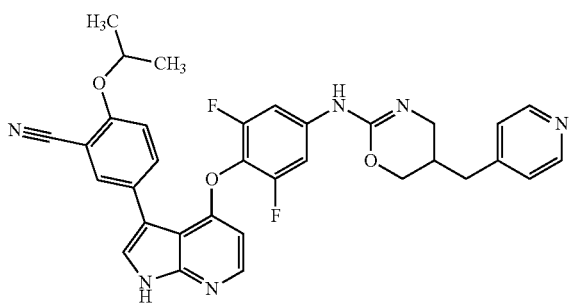 [SMILES: CC(C)Oc1ccc(-c2c[nH]c3nccc(Oc4c(F)cc(NC5=NCC(Cc6ccncc6)CO5)cc4F)c23)cc1C#N]

In analogy to example 2, (+/−)-5-(4-[2,6-difluoro-4-({5-[(pyridin-4-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]benzonitrile (130 mg, 135 µmol, intermediate 164) was stirred with trifluoroacidic acid (0.91 mL, 12 mmol) in dichloromethane (8.5 mL). After purification using a Biotage chromatography system followed by HPLC (method 5) we obtained 30.8 mg (90% purity, 35% yield) of the desired title compound.

LC-MS (Method 1): $R_t$=0.89 min; MS (ESIneg): m/z=593 [M−H]$^-$ $^1$H-NMR (400 MHz, DMSO-d6) δ [ppm]: 1.31 (d, 6H), 2.27 (br s, 1H), 2.64 (br d, 1H), 3.11 (br s, 1H), 3.36-3.45 (m, 1H), 3.96 (br s, 1H), 4.20 (br d, 1H), 4.80 (spt, 1H), 6.31 (d, 1H), 6.66-6.89 (m, 1H), 7.25-7.34 (m, 3H), 7.57 (br s, 1H), 7.69-7.72 (m, 1H), 7.89-7.96 (m, 2H), 8.10 (d, 1H), 8.47-8.52 (m, 2H), 9.07 (br s, 1H), 12.14 (s, 1H).

Example 77

(+/−)-5-[4-(4-{[(5-(cyclopropylmethyl)-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile

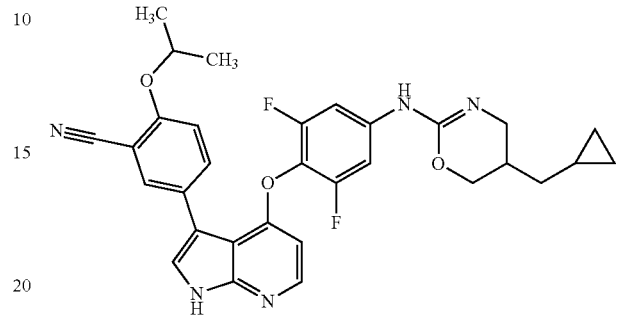

In analogy to example 2, (+/−)-5-[4-(4-{[5-(cyclopropylmethyl)-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile (110 mg, 160 µmol, intermediate 166) was stirred with trifluoroacidic acid (1.1 mL, 14 mmol) in dichloromethane (12 mL). After purification using a Biotage chromatography system followed by HPLC (method 5) we obtained 23.6 mg (97% purity, 26% yield) of the desired title compound.

LC-MS (Method 1): $R_t$=1.14 min; MS (ESIneg): m/z=556 [M−H]$^-$ $^1$H-NMR (400 MHz, DMSO-d6) δ [ppm]: 0.04 (q, 2H), 0.41-0.47 (m, 2H), 0.68-0.79 (m, 1H), 1.14-1.26 (m, 2H), 1.31 (d, 6H), 1.86-2.10 (m, 1H), 3.06 (br s, 1H), 3.40-3.56 (m, 1H), 3.90-4.04 (m, 1H), 4.33 (br d, 1H), 4.80 (spt, 1H), 6.32 (d, 1H), 6.64-6.83 (m, 1H), 7.30 (d, 1H), 7.46-7.65 (m, 1H), 7.70 (s, 1H), 7.90-7.95 (m, 2H), 8.10 (d, 1H), 9.02 (br s, 1H), 12.14 (s, 1H).

Example 78

(+/−)-5-[4-(4-{[5-cyclopropyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile

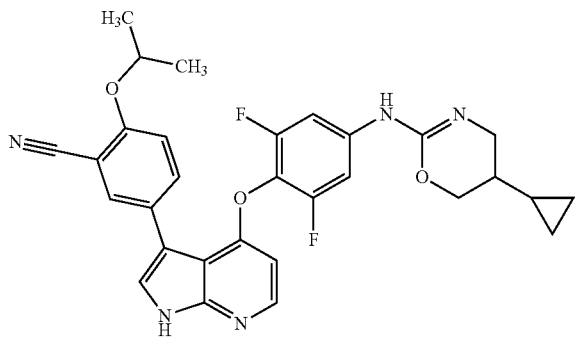 [SMILES: CC(C)Oc1ccc(-c2c[nH]c3nccc(Oc4c(F)cc(NC5=NCC(C6CC6)CO5)cc4F)c23)cc1C#N]

In analogy to example 2, (+/−)-5-[4-(4-{[5-cyclopropyl-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile (120 mg, 178 µmol, intermediate 168) was stirred with trifluoroacidic acid (1.2 mL, 15 mmol) in dichloromethane (12 mL). After purification using a Biotage chromatography system followed by HPLC (method 5) we obtained 36.8 mg (95% purity, 36% yield) of the desired title compound.

LC-MS (Method 1): $R_t$=1.07 min; MS (ESIneg): m/z=542 [M–H]⁻

¹H-NMR (400 MHz, DMSO-d6) δ [ppm]: 0.18-0.27 (m, 2H), 0.38-0.49 (m, 2H), 0.52-0.66 (m, 1H), 1.11-1.27 (m, 1H), 1.31 (d, 6H), 2.99-3.26 (m, 1H), 3.44-3.55 (m, 1H), 3.95-4.11 (m, 1H), 4.29 (br d, 1H), 4.80 (spt, 1H), 6.32 (d, 1H), 6.64-6.82 (m, 1H), 7.30 (d, 1H), 7.51-7.63 (m, 1H), 7.70 (d, 1H), 7.90-7.95 (m, 2H), 8.10 (d, 1H), 9.02 (br s, 1H), 12.14 (d, 1H).

Example 79

(+/−)-5-[4-(4-{[5-benzyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile

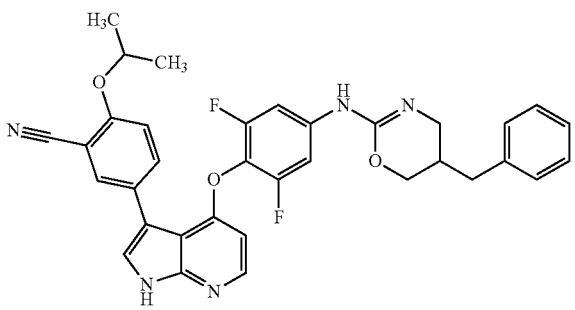 [SMILES: CC(C)Oc1ccc(-c2c[nH]c3nccc(Oc4c(F)cc(NC5=NCC(Cc6ccccc6)CO5)cc4F)c23)cc1C#N]

In analogy to example 2, (+/−)-5-[4-(4-{[5-benzyl-5,6-dihydro-4H-1,3-oxazin-2-yl]amino}-2,6-difluorophenoxy)-1-{[2-(trimethylsilyl)ethoxy]methyl}-1H-pyrrolo[2,3-b]pyridin-3-yl]-2-[(propan-2-yl)oxy]benzonitrile (125 mg, 173 µmol, intermediate 170) was stirred with trifluoroacidic acid (1.2 mL, 15 mmol) in dichloromethane (12 mL). After purification using a Biotage chromatography system followed by HPLC (method 5) we obtained 22.9 mg (95% purity, 21% yield) of the desired title compound.

LC-MS (Method 1): $R_t$=1.16 min; MS (ESIneg): m/z=592 [M–H]⁻

¹H-NMR (400 MHz, DMSO-d6) δ [ppm]: 1.31 (d, 6H), 2.13-2.31 (m, 1H), 2.61 (d, 2H), 3.09 (br s, 1H), 3.36-3.48 (m, 1H), 3.90-4.03 (m, 1H), 4.14-4.25 (m, 1H), 4.80 (spt, 1H), 6.32 (d, 1H), 7.19-7.35 (m, 7H), 7.56 (br s, 1H), 7.67-7.72 (m, 1H), 7.89-7.95 (m, 2H), 8.10 (d, 1H), 9.06 (br s, 1H), 12.14 (s, 1H).

Example 80

(+/−)-5-[4-(2,6-difluoro-4-{[5-(trifluoromethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile

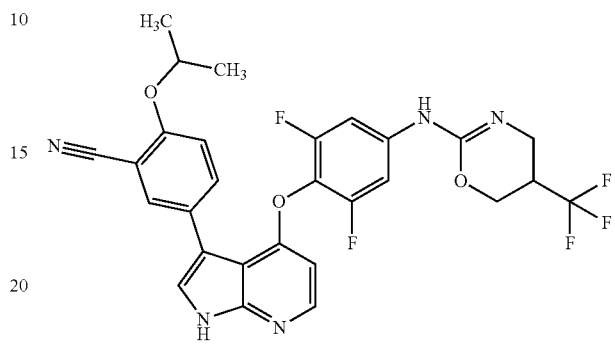

In analogy to example 2, (+/−)-5-[4-(2,6-difluoro-4-{[5-(trifluoromethyl)-5,6-dihydro-4H-1,3-oxazin-2-yl]amino}phenoxy)-1-{[2-(trimethylsilyl)ethoxy]methyl}-1H-pyrrolo[2,3-b]pyridin-3-yl]-2-[(propan-2-yl)oxy]benzonitrile (170 mg, 242 µmol, intermediate 172) was stirred with trifluoroacidic acid (1.6 mL, 21 mmol) in dichloromethane (16 mL). After purification using a Biotage chromatography system followed by HPLC (method 5) we obtained 76.4 mg (93% purity, 51% yield) of the desired title compound.

LC-MS (Method 1): $R_t$=1.03 min; MS (ESIneg): m/z=570 [M–H]⁻

¹H-NMR (400 MHz, DMSO-d6) δ [ppm]: 1.31 (d, 6H), 3.10 (br s, 1H), 3.52 (br dd, 1H), 3.70 (dd, 1H), 4.34-4.41 (m, 1H), 4.44-4.50 (m, 1H), 4.80 (spt, 1H), 6.33 (d, 1H), 7.29 (d, 1H), 7.53 (br s, 2H), 7.71 (d, 1H), 7.88-7.94 (m, 2H), 8.10 (d, 1H), 9.22 (br s, 1H), 12.15 (d, 1H).

Example 81

(+/−)-5-{4-[2,6-difluoro-4-({5-[(pyridin-3-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile

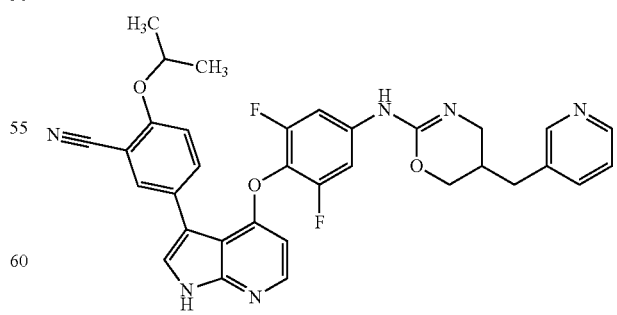

In analogy to example 2, (+/−)-5-(4-[2,6-difluoro-4-({5-[(pyridin-3-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]

benzonitrile (120 mg, 166 µmol, intermediate 174) was stirred with trifluoroacidic acid (1.1 mL, 15 mmol) in dichloromethane (6.0 mL). After purification using a Biotage chromatography system followed by HPLC (method 5) we obtained 40.3 mg (95% purity, 39% yield) of the desired title compound.

LC-MS (Method 1): R$_t$=0.90 min; MS (ESIneg): m/z=593 [M−H]$^−$ $^1$H-NMR (400 MHz, DMSO-d6) δ [ppm]: 1.31 (d, 6H), 2.24 (br s, 1H), 2.64 (br d, 2H), 3.02-3.17 (m, 1H), 3.36-3.49 (m, 1H), 3.96 (t, 1H), 4.21 (br d, 1H), 4.80 (spt, 1H), 6.32 (d, 1H), 7.27-7.32 (m, 1H), 7.35 (ddd, 1H), 7.45-7.65 (m, 2H), 7.67-7.72 (m, 2H), 7.89-7.94 (m, 2H), 8.10 (d, 1H), 8.44 (dd, 1H), 8.47 (d, 1H), 9.07 (br s, 1H), 12.14 (s, 1H).

Example 82

(+/−)-5-{4-[2,6-difluoro-4-({5-[(1-methyl-1H-pyrazol-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile

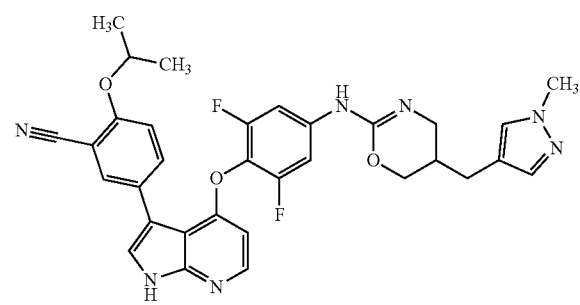 [SMILES: CC(C)Oc1ccc(-c2c[nH]c3nccc(Oc4c(F)cc(NC5=NCC(Cc6cnn(C)c6)CO5)cc4F)c23)cc1C#N]

In analogy to example 2, (+/−)-5-(4-[2,6-difluoro-4-({5-[(1-methyl-1H-pyrazol-4-yl)methyl]-5,6-dihydro-4H-1,3-oxazin-2-yl}amino)phenoxy]-1-{[2-(trimethylsilyl)ethoxy]methyl}-1H-pyrrolo[2,3-b]pyridin-3-yl)-2-[(propan-2-yl)oxy]benzonitrile (65.0 mg, 89.3 µmol, intermediate 176) was stirred with trifluoroacidic acid (0.6 mL, 7.8 mmol) in dichloromethane (6.0 mL). After purification using a Biotage chromatography system followed by HPLC (method 5) we obtained 21.9 mg (95% purity, 39% yield) of the desired title compound.

LC-MS (Method 1): R$_t$=0.97 min; MS (ESIneg): m/z=596 [M−H]$^−$ $^1$H-NMR (400 MHz, DMSO-d6) δ [ppm]: 1.31 (d, 6H), 2.00-2.16 (m, 1H), 2.43 (br d, 2H), 2.96-3.15 (m, 1H), 3.36-3.52 (m, 1H), 3.78 (s, 3H), 3.86-3.99 (m, 1H), 4.23 (br d, 1H), 4.80 (spt, 1H), 6.32 (d, 1H), 7.26-7.33 (m, 2H), 7.47-7.65 (m, 3H), 7.70 (d, 1H), 7.89-7.95 (m, 2H), 8.10 (d, 1H), 9.04 (br s, 1H), 12.14 (d, 1H).

Example 83

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethoxy)benzonitrile

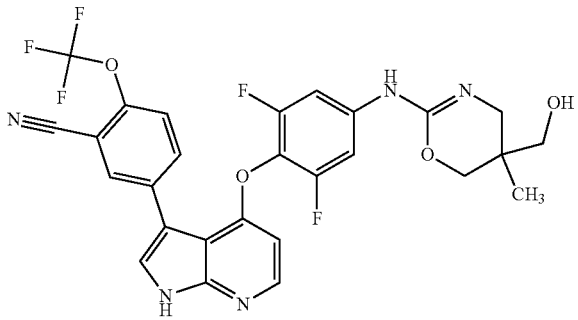 [SMILES: CC1(CO)CN=C(Nc2cc(F)c(Oc3ccnc4[nH]cc(-c5ccc(OC(F)(F)F)c(C#N)c5)c34)c(F)c2)OC1]

In analogy to example 2, N-{4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (90.0 mg, 128 µmol, intermediate 180) was stirred with trifluoroacidic acid (0.9 mL, 12 mmol) in dichloromethane (1.8 mL). After purification using a Biotage chromatography system followed by HPLC (method 5) we obtained 19.0 mg (90% purity, 23% yield) of the desired title compound.

LC-MS (Method 2): R$_t$=1.14 min; MS (ESIpos): m/z=574 [M+H]$^+$ $^1$H-NMR (400 MHz, DMSO-d6) δ [ppm]: 0.90 (s, 3H), 2.90-3.15 (m, 1H), 3.16-3.30 (m, 2H), 3.82-3.94 (m, 1H), 4.06 (br d, 1H), 4.81 (br s, 1H), 6.39 (d, 1H), 7.58 (br s, 2H), 7.72 (dd, 1H), 7.91 (s, 1H), 8.11-8.17 (m, 2H), 8.25 (d, 1H), 9.04 (br s, 1H), 12.37 (br s, 1H).

Example 84

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methoxybenzonitrile

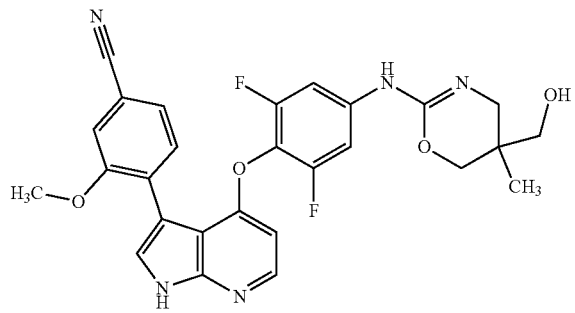 [SMILES: COc1cc(C#N)ccc1-c1c[nH]c2nccc(Oc3c(F)cc(NC4=NCC(C)(CO)CO4)cc3F)c12]

In analogy to example 2, N-(4-{[3-(4-cyano-2-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (78.0 mg, 120 µmol, intermediate 181) was stirred with trifluoroacidic acid (0.85 mL, 11 mmol) in dichloromethane (1.7 mL). After purification using a Biotage chromatography system followed by HPLC (method 5) we obtained 23.8 mg (95% purity, 36% yield) of the desired title compound.

LC-MS (Method 1): $R_t$=0.81 min; MS (ESIpos): m/z=520 [M+H]$^+$ $^1$H-NMR (400 MHz, DMSO-d6) δ [ppm]: 0.89 (s, 3H), 2.97-3.07 (m, 1H), 3.16-3.29 (m, 2H), 3.78-3.92 (m, 4H), 4.05 (br d, 1H), 4.72-4.85 (m, 1H), 6.27 (d, 1H), 7.41 (dd, 1H), 7.47 (d, 1H), 7.48-7.60 (m, 4H), 8.08 (d, 1H), 8.98 (br s, 1H), 12.13 (s, 1H).

Example 85

(+/−)-4-[4-(2,6-difluoro-4-{[5-(hydroxymethyl)-5-methyl-5,6-dihydro-4H-1,3-oxazin-2-yl]amino}phenoxy)-1_H-pyrrolo[2,3-b]pyridin-3-yl]-2-[(propan-2-yl)oxy]benzonitrile

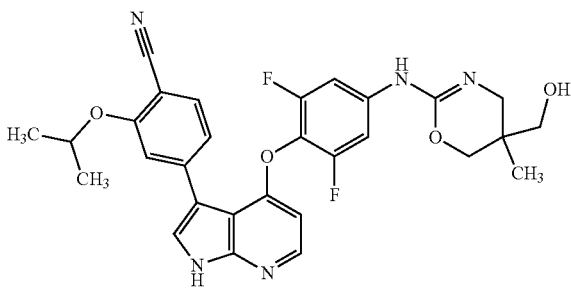 [SMILES: CC(C)Oc1cc(-c2c[nH]c3nccc(Oc4c(F)cc(NC5=NCC(C)(CO)CO5)cc4F)c23)ccc1C#N]

In analogy to example 2, N-{4-[(3-{4-cyano-3-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (92.0 mg, 136 μmol, intermediate 182) was stirred with trifluoroacidic acid (0.95 mL, 12 mmol) in dichloromethane (1.9 mL). After purification using a Biotage chromatography system followed by HPLC (method 5) we obtained 19.5 mg (97% purity, 25% yield) of the desired title compound.

LC-MS (Method 1): $R_t$=0.90 min; MS (ESIpos): m/z=548 [M+H]$^+$ $^1$H-NMR (400 MHz, DMSO-d6) δ [ppm]: 0.90 (s, 3H), 1.24 (d, 6H), 2.92-3.15 (m, 1H), 3.16-3.29 (m, 2H), 3.81-3.96 (m, 1H), 4.06 (br d, 1H), 4.70-4.89 (m, 2H), 6.38 (d, 1H), 7.40 (dd, 1H), 7.51-7.65 (m, 3H), 7.67 (d, 1H), 7.92 (d, 1H), 8.13 (d, 1H), 9.04 (br s, 1H), 12.38 (d, 1H).

Example 86

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-methoxybenzonitrile

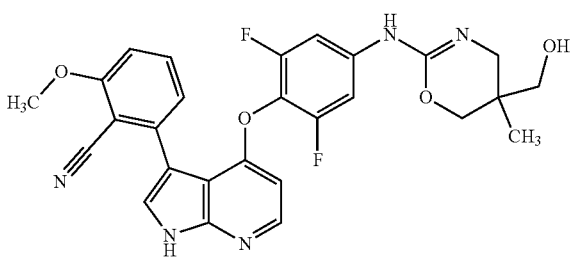 [SMILES: COc1cccc(-c2c[nH]c3nccc(Oc4c(F)cc(NC5=NCC(C)(CO)CO5)cc4F)c23)c1C#N]

In analogy to example 2, N-(4-{[3-(2-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (130 mg, 200 μmol, intermediate 183) was stirred with trifluoroacidic acid (1.4 mL, 18 mmol) in dichloromethane (2.8 mL). After purification using a Biotage chromatography system followed by HPLC (method 5) we obtained 53.8 mg (95% purity, 49% yield) of the desired title compound.

LC-MS (Method 1): $R_t$=0.79 min; MS (ESIpos): m/z=520 [M+H]$^+$ $^1$H-NMR (400 MHz, DMSO-d6) δ [ppm]: 0.89 (s, 3H), 2.88-3.13 (m, 1H), 3.14-3.31 (m, 3H), 3.81-3.90 (m, 1H), 3.92 (s, 3H), 4.05 (br d, 1H), 4.81 (br s, 1H), 6.34 (d, 1H), 7.13 (d, 1H), 7.23 (d, 1H), 7.38-7.65 (m, 3H), 7.71 (d, 1H), 8.13 (d, 1H), 8.99 (br s, 1H), 12.29 (d, 1H).

Example 87

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-fluorobenzonitrile

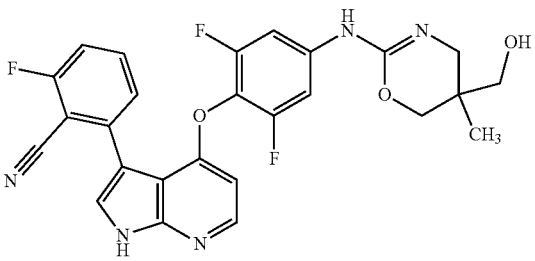 [SMILES: CC1(CO)CN=C(Nc2cc(F)c(Oc3ccnc4[nH]cc(-c5cccc(F)c5C#N)c34)c(F)c2)OC1]

In analogy to example 2, N-(4-{[3-(2-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (95.0 mg, 149 μmol, intermediate 184) was stirred with trifluoroacidic acid (1.1 mL, 14 mmol) in dichloromethane (2.1 mL). After purification using a Biotage chromatography system followed by HPLC (method 5) we obtained 43.0 mg (95% purity, 54% yield) of the desired title compound.

LC-MS (Method 1): $R_t$=0.81 min; MS (ESIpos): m/z=508 [M+H]$^+$ $^1$H-NMR (400 MHz, DMSO-d6) δ [ppm]: 0.89 (s, 3H), 2.94-3.08 (m, 1H), 3.25 (br s, 3H), 3.79-3.94 (m, 1H), 4.05 (br d, 1H), 4.81 (br s, 1H), 6.38 (d, 1H), 7.42 (t, 1H), 7.46-7.59 (m, 3H), 7.75 (td, 1H), 7.84 (s, 1H), 8.16 (d, 1H), 8.99 (br s, 1H), 12.40 (br s, 1H).

Example 88

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2-methylpropoxy)benzonitrile

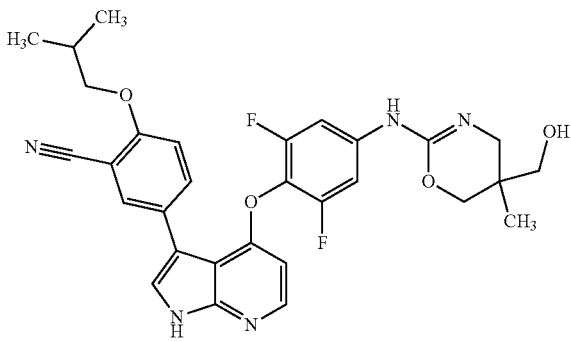 [SMILES: CC(C)COc1ccc(-c2c[nH]c3nccc(Oc4c(F)cc(NC5=NCC(C)(CO)CO5)cc4F)c23)cc1C#N]

In analogy to example 2, N-{4-[(3-[3-cyano-4-(2-methylpropoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (90.0 mg, 130 μmol, intermediate 185) was stirred with trifluoroacidic acid (0.9 mL, 12 mmol) in dichloromethane (1.8 mL). After purification using a Biotage chromatography system followed by HPLC (method 5) we obtained 33.8 mg (93% purity, 43% yield) of the desired title compound.

LC-MS (Method 1): $R_t$=1.03 min; MS (ESIpos): m/z=562 [M+H]$^+$ $^1$H-NMR (400 MHz, DMSO-d6) δ [ppm]: 0.90 (s, 3H), 1.00 (d, 6H), 2.06 (tspt, 1H), 2.94-3.09 (m, 1H), 3.16-3.31 (m, 3H), 3.82-3.95 (m, 3H), 4.06 (br d, 1H), 4.81 (br s, 1H), 6.33 (d, 1H), 7.27 (d, 1H), 7.45-7.65 (m, 2H), 7.70 (d, 1H), 7.90-7.95 (m, 2H), 8.10 (d, 1H), 9.03 (br s, 1H), 12.14 (d, 1H).

Example 89

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2,2,2-trifluoroethoxy)benzonitrile

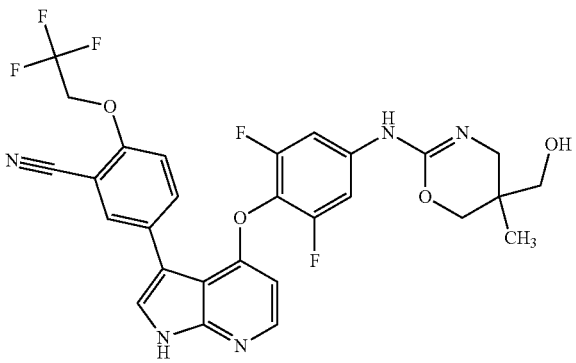 [SMILES: CC1(CO)CN=C(Nc2cc(F)c(Oc3ccnc4[nH]cc(-c5ccc(OCC(F)(F)F)c(C#N)c5)c34)c(F)c2)OC1]

In analogy to example 2, N-{4-[(3-[3-cyano-4-(2,2,2-trifluoroethoxy)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (65.0 mg, 90.6 μmol, intermediate 186) was stirred with trifluoroacidic acid (0.65 mL, 8.4 mmol) in dichloromethane (1.3 mL). After purification using a Biotage chromatography system followed by HPLC (method 5) we obtained 16.0 mg (93% purity, 28% yield) of the desired title compound.

LC-MS (Method 1): $R_t$=0.94 min; MS (ESIpos): m/z=588 [M+H]$^+$ $^1$H-NMR (400 MHz, DMSO-d6) δ [ppm]: 0.90 (s, 3H), 2.94-3.07 (m, 1H), 3.14-3.31 (m, 3H), 3.87 (br d, 1H), 4.06 (d, 1H), 4.83 (br s, 1H), 4.99 (q, 2H), 6.35 (d, 1H), 7.42 (d, 1H), 7.46-7.70 (m, 2H), 7.76 (d, 1H), 7.97-8.04 (m, 2H), 8.11 (d, 1H), 9.03 (br s, 1H), 12.19 (d, 1H).

Example 90

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile

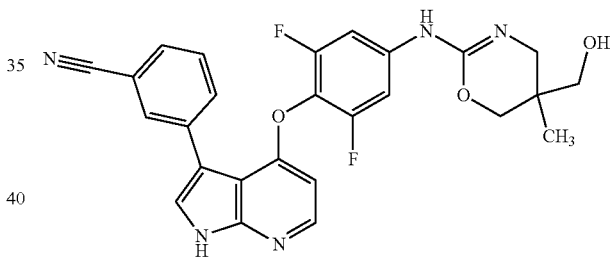

In analogy to example 2, N-(4-{[3-(3-cyanophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (94.0 mg, 152 μmol, intermediate 187) was stirred with trifluoroacidic acid (1.1 mL, 14 mmol) in dichloromethane (2.1 mL). After purification using a Biotage chromatography system followed by HPLC (method 5) we obtained 50.2 mg (90% purity, 61% yield) of the desired title compound.

LC-MS (Method 1): $R_t$=0.85 min; MS (ESIpos): m/z=490 [M+H]$^+$ $^1$H-NMR (400 MHz, DMSO-d6) δ [ppm]: 0.90 (s, 3H), 2.94-3.07 (m, 1H), 3.14-3.31 (m, 3H), 3.87 (br d, 1H), 4.06 (br d, 1H), 4.83 (br s, 1H), 6.37 (d, 1H), 7.46-7.63 (m, 3H), 7.68 (dt, 1H), 7.83 (d, 1H), 8.02 (dt, 1H), 8.09 (t, 1H), 8.13 (d, 1H), 9.04 (br s, 1H), 12.27 (d, 1H).

Example 91

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile

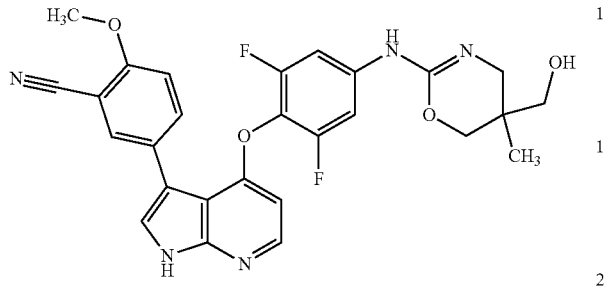

In analogy to example 2, N-(4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (260 mg, 400 µmol, intermediate 191) was stirred with trifluoroacidic acid (2.8 mL, 36 mmol) in dichloromethane (5.5 mL). After purification using a Biotage chromatography system followed by HPLC (method 5) we obtained 67.9 mg (92% purity, 30% yield) of the desired title compound.

LC-MS (Method 2): $R_t$=1.00 min; MS (ESIpos): m/z=520 [M+H]$^+$ $^1$H-NMR (400 MHz, DMSO-d6) δ [ppm]: 0.90 (s, 3H), 2.94-3.08 (m, 1H), 3.12-3.31 (m, 3H), 3.87 (br d, 1H), 3.92 (s, 3H), 4.06 (d, 1H), 4.82 (br s, 1H), 6.33 (d, 1H), 7.25-7.31 (m, 1H), 7.58 (br s, 2H), 7.71 (s, 1H), 7.93-7.98 (m, 2H), 8.10 (d, 1H), 9.03 (br s, 1H), 12.15 (br s, 1H).

Example 92

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile

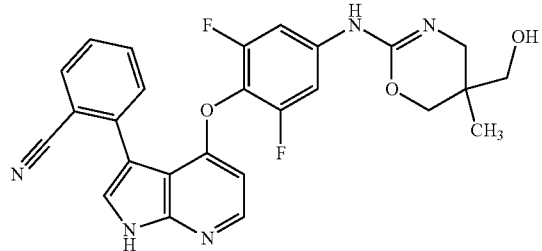 [SMILES: CC1(CO)CN=C(Nc2cc(F)c(Oc3ccnc4[nH]cc(-c5ccccc5C#N)c34)c(F)c2)OC1]

In analogy to example 2, N-(4-{[3-(2-cyanophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (36.0 mg, 58.1 µmol, intermediate 195) was stirred with trifluoroacidic acid (0.4 mL, 5.2 mmol) in dichloromethane (800 µL). After purification using a Biotage chromatography system followed by HPLC (method 5) we obtained 14.2 mg (80% purity, 40% yield) of the desired title compound.

LC-MS (Method 2): $R_t$=0.99 min; MS (ESIpos): m/z=490 [M+H]$^+$ $^1$H-NMR (400 MHz, DMSO-d6) δ [ppm]: 0.89 (s, 3H), 2.93-3.08 (m, 1H), 3.11-3.31 (m, 3H), 3.86 (br d, 1H), 3.98-4.11 (m, 1H), 4.82 (br s, 1H), 6.35 (d, 1H), 7.39-7.62 (m, 3H), 7.65-7.72 (m, 2H), 7.75 (s, 1H), 7.86 (d, 1H), 8.14 (d, 1H), 8.98 (br s, 1H), 12.31 (br s, 1H).

Example 93

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-(propan-2-yl)benzonitrile

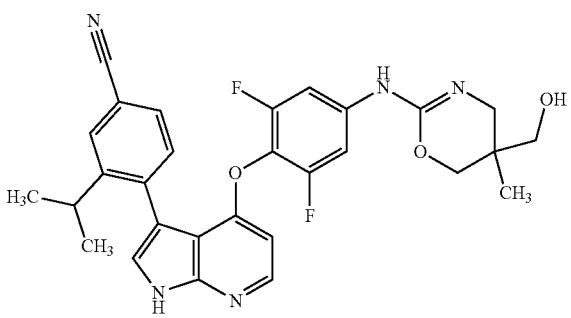 [SMILES: CC(C)c1cc(C#N)ccc1-c1c[nH]c2nccc(Oc3c(F)cc(NC4=NCC(C)(CO)CO4)cc3F)c12]

In analogy to example 2, N-{4-[(3-[4-cyano-2-(propan-2-yl)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (74.0 mg, 112 µmol, intermediate 196) was stirred with trifluoroacidic acid (0.8 mL, 10 mmol) in dichloromethane (1.6 mL). After purification by HPLC (method 5) we obtained 11.8 mg (80% purity, 16% yield) of the desired title compound.

LC-MS (Method 2): $R_t$=1.12 min; MS (ESIpos): m/z=532 [M+H]$^+$ $^1$H-NMR (400 MHz, DMSO-d6) δ [ppm]: 0.89 (s, 3H), 1.09 (br d, 6H), 2.91-3.07 (m, 1H), 3.13-3.31 (m, 4H), 3.85 (br d, 1H), 4.04 (br d, 1H), 4.81 (br s, 1H), 6.24 (d, 1H), 7.41-7.52 (m, 3H), 7.60-7.68 (m, 2H), 7.80 (d, 1H), 8.09 (d, 1H), 8.97 (br s, 1H), 12.12 (d, 1H).

Example 94

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile

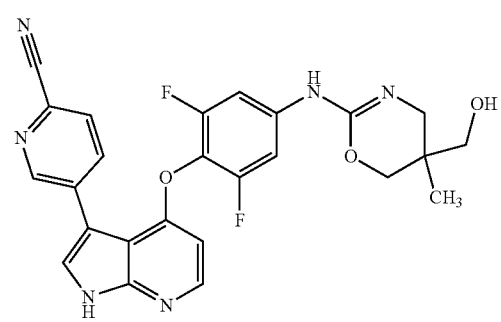 [SMILES: CC1(CO)CN=C(Nc2cc(F)c(Oc3ccnc4[nH]cc(-c5ccc(C#N)nc5)c34)c(F)c2)OC1]

In analogy to example 2, N-(4-{[3-(6-cyanopyridin-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (85.0 mg, 137 μmol, intermediate 197) was stirred with trifluoroacidic acid (0.95 mL, 12 mmol) in dichloromethane (1.9 mL). After purification by HPLC (method 5) we obtained 17.3 mg (93% purity, 24% yield) of the desired title compound.

LC-MS (Method 2): R$_f$=0.94 min; MS (ESIneg): m/z=489 [M–H]$^-$ $^1$H-NMR (400 MHz, DMSO-d6) δ [ppm]: 0.90 (br s, 3H), 3.03 (br d, 1H), 3.17-3.32 (m, 3H), 3.82-3.92 (m, 1H), 4.06 (br d, 1H), 4.81 (br s, 1H), 6.42 (d, 1H), 7.50-7.65 (m, 2H), 8.03-8.07 (m, 2H), 8.17 (d, 1H), 8.28 (dd, 1H), 9.04 (br s, 1H), 9.08 (dd, 1H), 12.53 (br s, 1H).

Example 95

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methylbenzonitrile

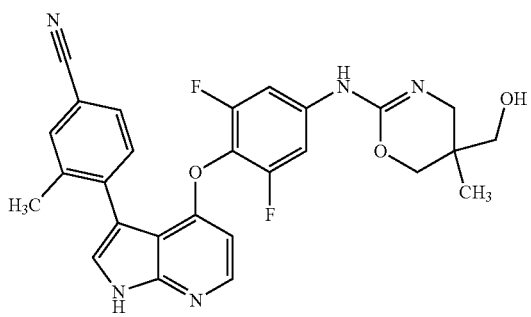 [SMILES: Cc1cc(C#N)ccc1-c1c[nH]c2nccc(Oc3c(F)cc(NC4=NCC(C)(CO)CO4)cc3F)c12]

In analogy to example 2, N-(4-{[3-(4-cyano-2-methylphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (71.0 mg, 112 μmol, intermediate 198) was stirred with trifluoroacidic acid (0.80 mL, 10 mmol) in dichloromethane (1.6 mL). After purification by HPLC (method 5) we obtained 36.0 mg (93% purity, 59% yield) of the desired title compound.

LC-MS (Method 2): R$_f$=1.04 min; MS (ESIneg): m/z=502 [M–H]$^-$ $^1$H-NMR (400 MHz, DMSO-d6) δ [ppm]: 0.89 (s, 3H), 2.34 (s, 3H), 3.02 (br d, 1H), 3.27 (br d, 3H), 3.81-3.93 (m, 1H), 4.05 (br d, 1H), 4.79 (br s, 1H), 6.28 (d, 1H), 7.47-7.57 (m, 4H), 7.64 (dd, 1H), 7.73-7.75 (m, 1H), 8.10 (d, 1H), 8.98 (br s, 1H), 12.18 (d, 1H).

Example 96

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methylbenzonitrile

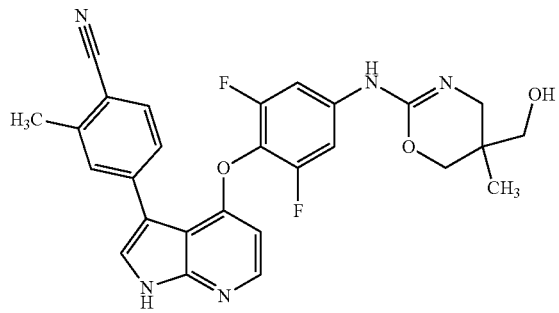 [SMILES: Cc1cc(-c2c[nH]c3nccc(Oc4c(F)cc(NC5=NCC(C)(CO)CO5)cc4F)c23)ccc1C#N]

In analogy to example 2, N-(4-{[3-(4-cyano-3-methylphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (71.0 mg, 112 μmol, intermediate 199) was stirred with trifluoroacidic acid (0.80 mL, 10 mmol) in dichloromethane (1.6 mL). After purification by HPLC (method 5) we obtained 23.0 mg (93% purity, 38% yield) of the desired title compound.

LC-MS (Method 2): R$_f$=1.05 min; MS (ESIneg): m/z=502 [M–H]$^-$ $^1$H-NMR (400 MHz, DMSO-d6) δ [ppm]: 0.90 (s, 3H), 2.47 (s, 3H), 2.96-3.07 (m, 1H), 3.16-3.31 (m, 3H), 3.82-3.93 (m, 1H), 4.06 (br d, 1H), 4.81 (br s, 1H), 6.37 (d, 1H), 7.48-7.65 (m, 2H), 7.68 (dd, 1H), 7.73-7.76 (m, 1H), 7.79 (s, 1H), 7.84 (s, 1H), 8.13 (d, 1H), 9.03 (br s, 1H), 12.32 (s, 1H).

Example 97

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethyl)benzonitrile

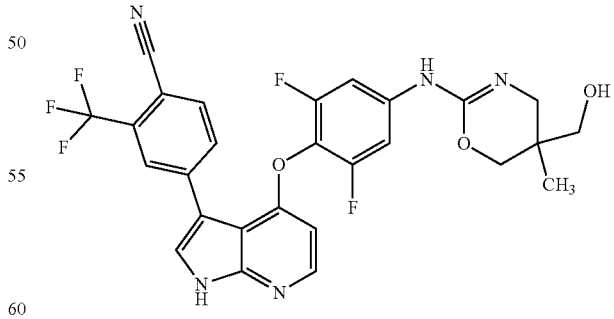

In analogy to example 2, N-{4-[(3-[4-cyano-3-(trifluoromethyl)phenyl]-1-{[2-(trimethylsilyl)ethoxy]methyl}-1H-pyrrolo[2,3-b]pyridin-4-yl)oxy]-3,5-difluorophenyl}-N'-[(3-methyloxetan-3-yl)methyl]urea (96.0 mg, 140 μmol, intermediate 200) was stirred with trifluoroacidic acid (0.95 mL, 12 mmol) in dichloromethane (1.9 mL). After purification by HPLC (method 5) we obtained 37.1 mg (93% purity, 44% yield) of the desired title compound.

LC-MS (Method 2): $R_t$=1.11 min; MS (ESIpos): m/z=558 [M+H]$^+$ $^1$H-NMR (400 MHz, DMSO-d6) δ [ppm]: 0.90 (s, 3H), 3.03 (br d, 1H), 3.17-3.31 (m, 4H), 3.82-3.92 (m, 1H), 4.07 (br d, 1H), 4.80 (br s, 1H), 6.42 (d, 1H), 7.50-7.66 (m, 3H), 8.11 (s, 1H), 8.13-8.20 (m, 3H), 8.34 (s, 1H), 9.04 (br s, 1H), 12.55 (br s, 1H).

Example 98

(+/−)-{2-[3,5-difluoro-4-({3-[2-(propan-2-yl)phenyl]-1H-pyrrolo[2,3-b]pyridin-4-yl}oxy)anilino]-5-methyl-5,6-dihydro-4H-1,3-oxazin-5-yl}methanol

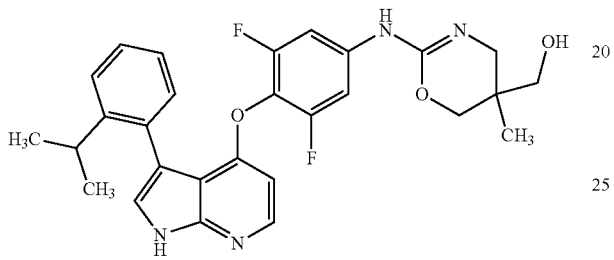

In analogy to example 2, N-{3,5-difluoro-4-[(3-[2-(propan-2-yl)phenyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (63.0 mg, 98.9 µmol, intermediate 201) was stirred with trifluoroacidic acid (0.70 mL, 9.1 mmol) in dichloromethane (1.4 mL). After purification by HPLC (method 5) we obtained 7.5 mg (85% purity, 13% yield) of the desired title compound.

LC-MS (Method 2): $R_t$=1.16 min; MS (ESIpos): m/z=507 [M+H]$^+$ $^1$H-NMR (400 MHz, DMSO-d6) δ [ppm]: 0.88 (s, 3H), 1.06 (br d, 6H), 2.90-3.08 (m, 1H), 3.11-3.31 (m, 4H), 3.84 (br d, 1H), 4.04 (d, 1H), 4.80 (br s, 1H), 6.19 (d, 1H), 7.11-7.17 (m, 1H), 7.23-7.37 (m, 4H), 7.40-7.63 (m, 2H), 8.05 (d, 1H), 8.95 (br s, 1H), 11.92 (d, 1H).

Example 99

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile

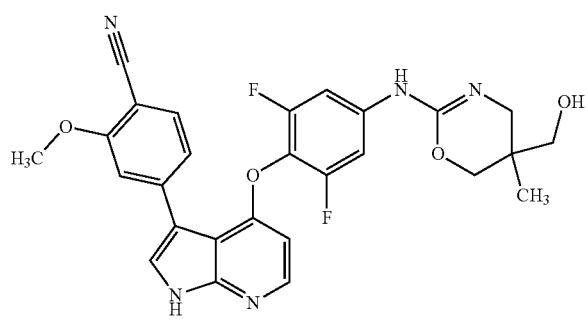 [SMILES: COc1cc(-c2c[nH]c3nccc(Oc4c(F)cc(NC5=NCC(C)(CO)CO5)cc4F)c23)ccc1C#N]

In analogy to example 2, N-(4-{[3-(4-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (94.0 mg, 145 µmol, intermediate 202) was stirred with trifluoroacidic acid (1.0 mL, 13 mmol) in dichloromethane (2.0 mL). After purification by HPLC (method 5) we obtained 40.4 mg (93% purity, 50% yield) of the desired title compound.

LC-MS (Method 2): $R_t$=1.01 min; MS (ESIneg): m/z=518 [M−H]$^−$ $^1$H-NMR (400 MHz, DMSO-d6) δ [ppm]: 0.90 (s, 3H), 3.03 (br d, 1H), 3.15-3.31 (m, 3H), 3.89 (s, 4H), 4.06 (br d, 1H), 4.81 (br s, 1H), 6.38 (d, 1H), 7.43 (dd, 1H), 7.51-7.64 (m, 3H), 7.69 (d, 1H), 7.93 (s, 1H), 8.13 (d, 1H), 9.04 (br s, 1H), 12.38 (br s, 1H).

Example 100

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-fluorobenzonitrile

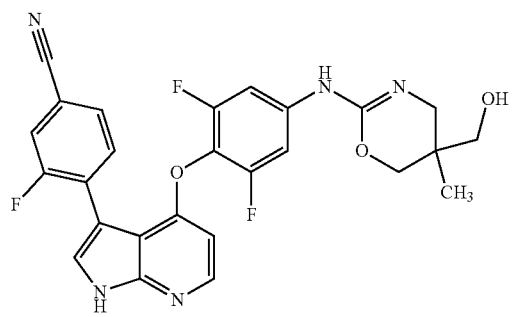 [SMILES: CC1(CO)CN=C(Nc2cc(F)c(Oc3ccnc4[nH]cc(-c5ccc(C#N)cc5F)c34)c(F)c2)OC1]

In analogy to example 2, N-(4-{[3-(4-cyano-2-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (83.0 mg, 130 µmol, intermediate 203) was stirred with trifluoroacidic acid (0.9 mL, 12 mmol) in dichloromethane (1.8 mL). After purification by HPLC (method 5) we obtained 32.0 mg (93% purity, 45% yield) of the desired title compound.

LC-MS (Method 2): $R_t$=1.02 min; MS (ESIneg): m/z=506 [M−H]$^−$ $^1$H-NMR (400 MHz, DMSO-d6) δ [ppm]: 0.90 (s, 3H), 3.02 (br d, 1H), 3.18-3.31 (m, 3H), 3.81-3.94 (m, 1H), 4.06 (br d, 1H), 4.80 (br s, 1H), 6.35 (d, 1H), 7.40-7.63 (m, 2H), 7.69-7.81 (m, 3H), 7.88 (dd, 1H), 8.14 (d, 1H), 9.00 (br s, 1H), 12.39 (br s, 1H).

Example 101

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile

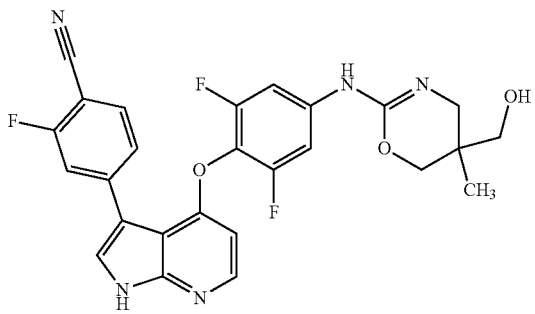 [SMILES: CC1(CO)CN=C(Nc2cc(F)c(Oc3ccnc4[nH]cc(-c5ccc(C#N)c(F)c5)c34)c(F)c2)OC1]

In analogy to example 2, N-(4-{[3-(4-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (69.0 mg, 108 µmol, intermediate 204) was stirred with trifluoroacidic acid (0.75 mL, 9.7 mmol) in dichloromethane (1.5 mL). After purification by HPLC (method 5) we obtained 20.6 mg (93% purity, 35% yield) of the desired title compound.

LC-MS (Method 2): $R_t$=1.05 min; MS (ESIneg): m/z=506 [M−H]⁻

¹H-NMR (400 MHz, DMSO-d6) δ [ppm]: 0.90 (s, 3H), 3.03 (br d, 1H), 3.17-3.31 (m, 3H), 3.82-3.97 (m, 1H), 4.07 (br d, 1H), 4.81 (br s, 1H), 6.41 (d, 1H), 7.58 (br d, 2H), 7.74-7.82 (m, 2H), 7.90 (t, 1H), 8.01 (s, 1H), 8.15 (d, 1H), 9.04 (br s, 1H), 12.48 (br s, 1H).

Example 102

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-methoxybenzonitrile

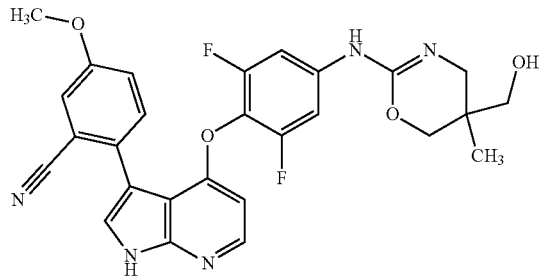 [SMILES: COc1ccc(-c2c[nH]c3nccc(Oc4c(F)cc(NC5=NCC(C)(CO)CO5)cc4F)c23)c(C#N)c1]

In analogy to example 2, N-(4-{[3-(2-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (60.0 mg, 92.3 µmol, intermediate 205) was stirred with trifluoroacidic acid (0.65 mL, 8.4 mmol) in dichloromethane (1.3 mL). After purification using a Biotage chromatography system followed by HPLC (method 5) we obtained 24.2 mg (90% purity, 45% yield) of the desired title compound.

LC-MS (Method 1): $R_t$=0.83 min; MS (ESIpos): m/z=520 [M+H]⁺

¹H-NMR (400 MHz, DMSO-d6) δ [ppm]: 0.89 (s, 3H), 2.92-3.09 (m, 1H), 3.15-3.31 (m, 3H), 3.79-3.91 (m, 4H), 4.05 (br d, 1H), 4.81 (br s, 1H), 6.29-6.34 (m, 1H), 7.27 (dd, 1H), 7.43 (d, 1H), 7.52 (br s, 2H), 7.59 (d, 1H), 7.65 (d, 1H), 8.12 (d, 1H), 8.98 (br s, 1H), 12.21 (d, 1H).

Example 103

(+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(trifluoromethoxy)benzonitrile

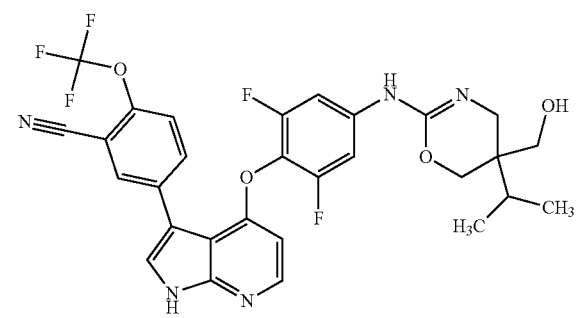 [SMILES: CC(C)C1(CO)CN=C(Nc2cc(F)c(Oc3ccnc4[nH]cc(-c5ccc(OC(F)(F)F)c(C#N)c5)c34)c(F)c2)OC1]

In analogy to example 2, N-{4-[(3-[3-cyano-4-(trifluoromethoxy)phenyl]-1-{[2-(trimethylsilyl)ethoxy]methyl}-1H-pyrrolo[2,3-b]pyridin-4-yl)oxy]-3,5-difluorophenyl}-N'-{[3-(propan-2-yl)oxetan-3-yl]methyl}urea (109 mg, 149 µmol, intermediate 206) was stirred with trifluoroacidic acid (1.0 mL, 13 mmol) in dichloromethane (2.0 mL). After purification using a Biotage chromatography system followed by HPLC (method 5) we obtained 38.3 mg (90% purity, 38% yield) of the desired title compound.

LC-MS (Method 2): $R_t$=1.24 min; MS (ESIpos): m/z=602 [M+H]⁺

¹H-NMR (400 MHz, DMSO-d6) δ [ppm]: 0.90 (t, 6H), 1.70-1.83 (m, 1H), 3.03-3.27 (m, 2H), 3.36-3.43 (m, 2H), 3.99-4.09 (m, 1H), 4.14 (br d, 1H), 4.69 (br s, 1H), 6.39 (d, 1H), 7.50-7.65 (m, 2H), 7.72 (dd, 1H), 7.91 (s, 1H), 8.12-8.17 (m, 2H), 8.26 (d, 1H), 9.05 (br s, 1H), 12.36 (s, 1H).

Example 104

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-fluorobenzonitrile

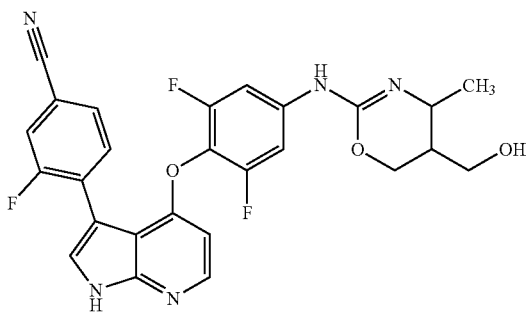 [SMILES: CC1N=C(Nc2cc(F)c(Oc3ccnc4[nH]cc(-c5ccc(C#N)cc5F)c34)c(F)c2)OCC1CO]

In analogy to example 2, (+/−)—N-(4-{[3-(4-cyano-2-fluorophenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (49.0 mg, 76.8 μmol, intermediate 208) was stirred with trifluoroacidic acid (0.55 mL, 7.1 mmol) in dichloromethane (1.1 mL). After purification by HPLC (method 5) we obtained 9.7 mg (95% purity, 24% yield) of the desired title compound.

LC-MS (Method 2): $R_t$=1.01 min; MS (ESIneg): m/z=506 [M−H]−

$^1$H-NMR (400 MHz, DMSO-d6, main isomer) δ [ppm]: 1.18 (d, 3H), 1.59 (br s, 1H), 3.26-3.31 (m, 1H), 3.35-3.43 (m, 1H), 3.46-3.57 (m, 1H), 4.02 (br s, 1H), 4.29 (dd, 1H), 4.72 (br s, 1H), 6.34 (d, 1H), 7.50-7.65 (m, 2H), 7.69-7.81 (m, 3H), 7.88 (dd, 1H), 8.14 (d, 1H), 8.97 (br s, 1H), 12.39 (br s, 1H).

Example 105

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-fluorobenzonitrile

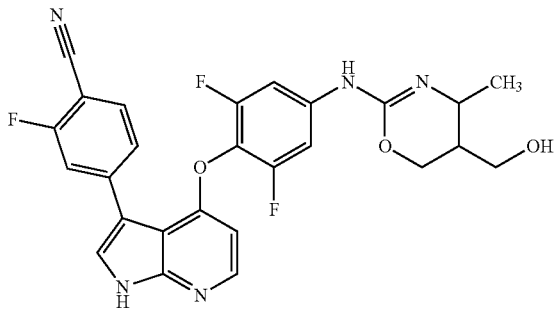 [SMILES: CC1N=C(Nc2cc(F)c(Oc3ccnc4[nH]cc(-c5ccc(C#N)c(F)c5)c34)c(F)c2)OCC1CO]

In analogy to example 2, (+/−)—N-(4-{[3-(4-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (56.0 mg, 87.8 μmol, intermediate 209) was stirred with trifluoroacidic acid (0.60 mL, 7.8 mmol) in dichloromethane (1.2 mL). After purification by HPLC (method 5) we obtained 20.6 mg (92% purity, 43% yield) of the desired title compound.

LC-MS (Method 2): $R_t$=1.04 min; MS (ESIneg): m/z=506 [M−H]−

$^1$H-NMR (400 MHz, DMSO-d6, main isomer) δ [ppm]: 1.19 (d, 3H), 1.54-1.67 (m, 1H), 3.36-3.44 (m, 1H), 3.48-3.57 (m, 1H), 4.03 (br s, 1H), 4.30 (br dd, 1H), 4.66-4.87 (m, 1H), 6.41 (d, 1H), 7.61 (br s, 2H), 7.73-7.82 (m, 2H), 7.91 (t, 1H), 8.01 (s, 1H), 8.16 (d, 1H), 9.02 (br s, 1H), 12.48 (br s, 1H).

Example 106

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile

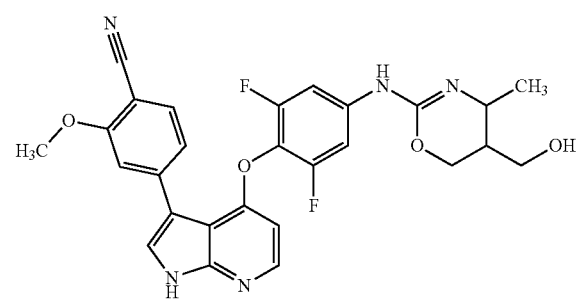 [SMILES: COc1cc(-c2c[nH]c3nccc(Oc4c(F)cc(NC5=NC(C)C(CO)CO5)cc4F)c23)ccc1C#N]

In analogy to example 2, (+/−)—N-(4-{[3-(4-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (58.0 mg, 89.3 μmol, intermediate 210) was stirred with trifluoroacidic acid (0.60 mL, 7.8 mmol) in dichloromethane (1.2 mL). After purification by HPLC (method 5) we obtained 27.9 mg (95% purity, 57% yield) of the desired title compound.

LC-MS (Method 2): $R_t$=1.00 min; MS (ESIneg): m/z=518 [M−H]−

$^1$H-NMR (400 MHz, DMSO-d6, main isomer) δ [ppm]: 1.19 (d, 3H), 1.59 (br s, 1H), 3.35-3.44 (m, 1H), 3.48-3.58 (m, 1H), 3.89 (s, 3H), 4.04 (br s, 1H), 4.30 (dd, 1H), 4.73 (br s, 1H), 6.37 (d, 1H), 7.43 (dd, 1H), 7.54 (d, 1H), 7.62 (br s, 2H), 7.70 (d, 1H), 7.93 (d, 1H), 8.14 (d, 1H), 9.01 (br s, 1H), 12.38 (br s, 1H).

Example 107

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methylbenzonitrile

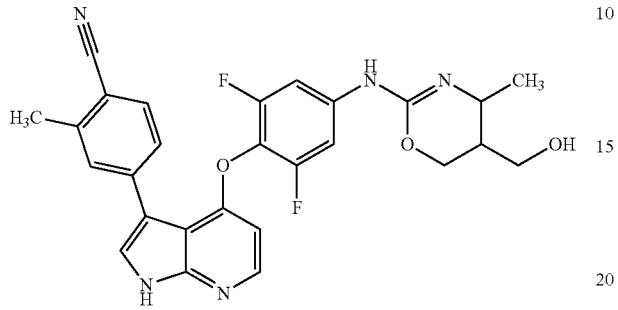

In analogy to example 2, (+/−)—N-(4-{[3-(4-cyano-3-methylphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (23.0 mg, 36.3 μmol, intermediate 211) was stirred with trifluoroacidic acid (0.25 mL, 3.2 mmol) in dichloromethane (500 μL). After purification by HPLC (method 5) we obtained 6.0 mg (90% purity, 30% yield) of the desired title compound.

LC-MS (Method 2): $R_t$=1.04 min; MS (ESIneg): m/z=502 [M−H]⁻

¹H-NMR (400 MHz, DMSO-d6, main isomer) δ [ppm]: 1.19 (d, 3H), 1.59 (br s, 1H), 3.36-3.44 (m, 1H), 3.46-3.57 (m, 1H), 4.03 (br s, 1H), 4.30 (dd, 1H), 4.73 (br s, 1H), 6.37 (d, 1H), 7.54-7.66 (m, 2H), 7.66-7.71 (m, 1H), 7.73-7.77 (m, 1H), 7.79 (s, 1H), 7.84 (s, 1H), 8.13 (d, 1H), 9.00 (br s, 1H), 12.32 (br s, 1H).

Example 108

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]pyridine-2-carbonitrile

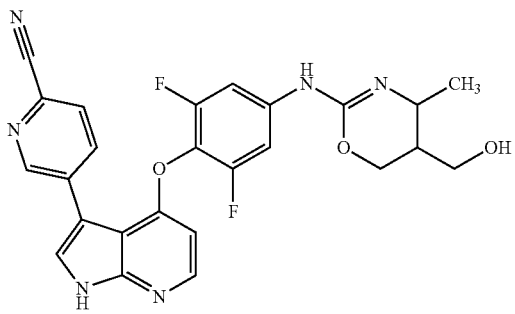 [SMILES: CC1N=C(Nc2cc(F)c(Oc3ccnc4[nH]cc(-c5ccc(C#N)nc5)c34)c(F)c2)OCC1CO]

In analogy to example 2, (+/−)—N-(4-{[3-(6-cyanopyridin-3-yl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (77.0 mg, 124 μmol, intermediate 212) was stirred with trifluoroacidic acid (0.85 mL, 11 mmol) in dichloromethane (1.7 mL). After purification by HPLC (method 5) we obtained 12.5 mg (92% purity, 19% yield) of the desired title compound.

LC-MS (Method 2): $R_t$=0.93 min; MS (ESIneg): m/z=489 [M−H]⁻

¹H-NMR (400 MHz, DMSO-d6, main isomer) δ [ppm]: 1.19 (d, 3H), 1.60 (br s, 1H), 3.36-3.44 (m, 1H), 3.46-3.59 (m, 1H), 4.03 (br s, 1H), 4.30 (br dd, 1H), 4.73 (br s, 1H), 6.41 (d, 1H), 7.50-7.72 (m, 2H), 8.02-8.09 (m, 2H), 8.17 (d, 1H), 8.28 (dd, 1H), 9.01 (br s, 1H), 9.08 (d, 1H), 12.52 (br s, 1H).

Example 109

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methylbenzonitrile

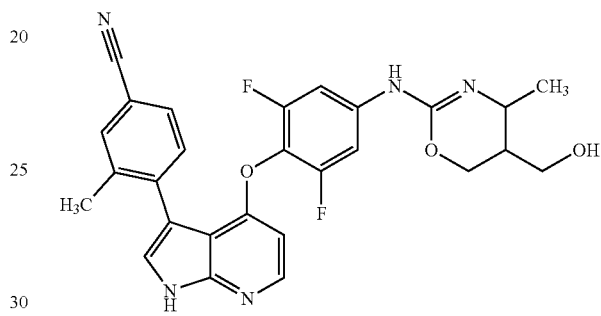

In analogy to example 2, (+/−)—N-(4-{[3-(4-cyano-2-methylphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (76.0 mg, 120 μmol, intermediate 213) was stirred with trifluoroacidic acid (0.85 mL, 11 mmol) in dichloromethane (1.7 mL). After purification by HPLC (method 5) we obtained 34.3 mg (95% purity, 54% yield) of the desired title compound.

LC-MS (Method 2): $R_t$=1.03 min; MS (ESIneg): m/z=502 [M−H]⁻

¹H-NMR (400 MHz, DMSO-d6, main isomer) δ [ppm]: 1.17 (d, 3H), 1.53-1.64 (m, 1H), 2.34 (s, 3H), 3.25-3.31 (m, 1H), 3.35-3.42 (m, 1H), 3.47-3.56 (m, 1H), 4.02 (br s, 1H), 4.28 (dd, 1H), 4.72 (br s, 1H), 6.27 (d, 1H), 7.48-7.60 (m, 4H), 7.64 (dd, 1H), 7.74 (d, 1H), 8.11 (d, 1H), 8.96 (br s, 1H), 12.18 (br s, 1H).

Example 110

(+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-methoxybenzonitrile

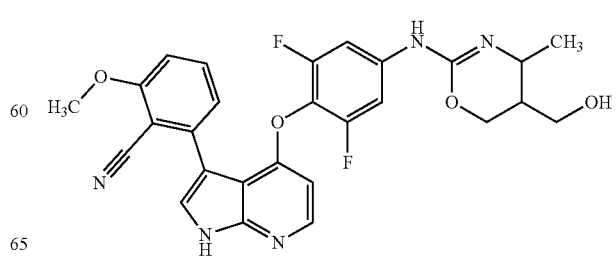

In analogy to example 2, (+/−)—N-(4-{[3-(2-cyano-3-methoxyphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (84.0 mg, 129 µmol, intermediate 214) was stirred with trifluoroacidic acid (0.90 mL, 12 mmol) in dichloromethane (1.8 mL). After purification by HPLC (method 5) we obtained 40.2 mg (90% purity, 54% yield) of the desired title compound.

LC-MS (Method 1): R$_t$=0.79 min; MS (ESIpos): m/z=520 [M+H]$^+$ $^1$H-NMR (400 MHz, DMSO-d6, main isomer) δ [ppm]: 1.18 (d, 3H), 1.58 (br s, 1H), 3.25-3.32 (m, 1H), 3.35-3.43 (m, 1H), 3.48-3.58 (m, 1H), 3.93 (s, 3H), 4.01 (br s, 1H), 4.28 (br dd, 1H), 4.72 (br s, 1H), 6.33 (d, 1H), 7.13 (d, 1H), 7.23 (d, 1H), 7.49-7.65 (m, 3H), 7.71 (s, 1H), 8.13 (d, 1H), 8.95 (br s, 1H), 12.28 (br s, 1H).

Example 111

(+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-fluorobenzonitrile

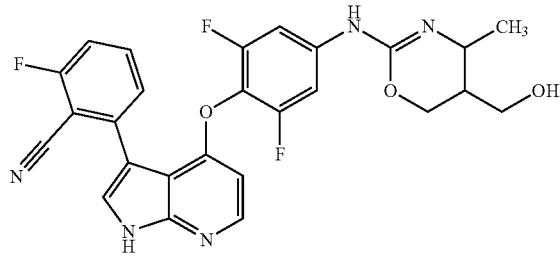 [SMILES: CC1N=C(Nc2cc(F)c(Oc3ccnc4[nH]cc(-c5cccc(F)c5C#N)c34)c(F)c2)OCC1CO]

In analogy to example 2, (+/−)—N-(4-{[3-(2-cyano-3-fluorophenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (72.0 mg, 113 µmol, intermediate 215) was stirred with trifluoroacidic acid (0.80 mL, 10 mmol) in dichloromethane (1.6 mL). After purification by HPLC (method 5) we obtained 16.7 mg (90% purity, 26% yield) of the desired title compound.

LC-MS (Method 1): R$_t$=0.82 min; MS (ESIpos): m/z=508 [M+H]$^+$ $^1$H-NMR (400 MHz, DMSO-d6, main isomer) δ [ppm]: 1.18 (d, 3H), 1.58 (br s, 1H), 3.25-3.30 (m, 1H), 3.36-3.45 (m, 1H), 3.46-3.57 (m, 1H), 3.96-4.11 (m, 1H), 4.28 (br d, 1H), 4.71 (br s, 1H), 6.37 (d, 1H), 7.41 (t, 1H), 7.49-7.63 (m, 3H), 7.72-7.78 (m, 1H), 7.84 (s, 1H), 8.16 (br d, 1H), 8.96 (br s, 1H), 12.41 (br s, 1H).

Example 112

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methoxybenzonitrile

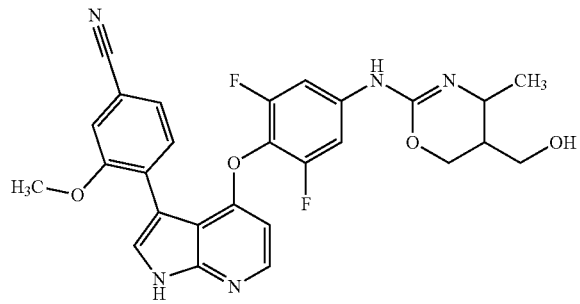 [SMILES: COc1cc(C#N)ccc1-c1c[nH]c2nccc(Oc3c(F)cc(NC4=NC(C)C(CO)CO4)cc3F)c12]

In analogy to example 2, (+/−)—N-(4-{[3-(4-cyano-2-methoxyphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (56.0 mg, 86.2 µmol, intermediate 216) was stirred with trifluoroacidic acid (0.60 mL, 7.8 mmol) in dichloromethane (1.2 mL). After purification by HPLC (method 5) we obtained 23.8 mg (90% purity, 48% yield) of the desired title compound.

LC-MS (Method 1): R$_t$=0.83 min; MS (ESIpos): m/z=520 [M+H]$^+$ $^1$H-NMR (400 MHz, DMSO-d6, main isomer) δ [ppm]: 1.18 (d, 3H), 1.59 (br s, 1H), 3.25-3.31 (m, 1H), 3.36-3.43 (m, 1H), 3.46-3.57 (m, 1H), 3.80 (s, 3H), 4.02 (br s, 1H), 4.28 (dd, 1H), 4.73 (br s, 1H), 6.26 (d, 1H), 7.41 (dd, 1H), 7.47 (d, 1H), 7.50-7.64 (m, 4H), 8.08 (d, 1H), 8.95 (br s, 1H), 12.13 (br s, 1H).

Example 113

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile

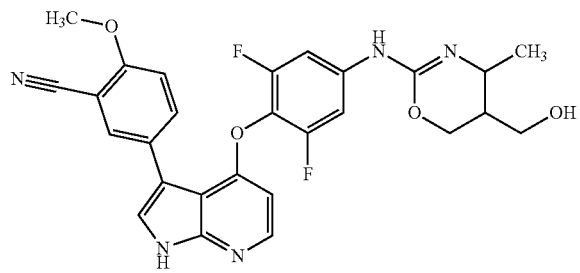 [SMILES: COc1ccc(-c2c[nH]c3nccc(Oc4c(F)cc(NC5=NC(C)C(CO)CO5)cc4F)c23)cc1C#N]

In analogy to example 2, (+/−)—N-(4-{[3-(3-cyano-4-methoxyphenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (62.0 mg, 95.4 µmol, intermediate 217) was stirred with trifluoroacidic acid (0.65 mL, 8.4 mmol) in dichloromethane (1.3 mL). After purification by HPLC (method 5) we obtained 25.1 mg (90% purity, 46% yield) of the desired title compound.

LC-MS (Method 1): R$_t$=0.83 min; MS (ESIpos): m/z=520 [M+H]$^+$ $^1$H-NMR (400 MHz, DMSO-d6, main isomer) δ [ppm]: 1.19 (d, 3H), 1.60 (br s, 1H), 3.26-3.32 (m, 1H), 3.36-3.44 (m, 1H), 3.47-3.57 (m, 1H), 3.92 (s, 3H), 4.03 (br s, 1H), 4.29 (br dd, 1H), 4.73 (br s, 1H), 6.33 (d, 1H), 7.28 (d, 1H), 7.48-7.68 (m, 2H), 7.71 (s, 1H), 7.93-7.98 (m, 2H), 8.11 (d, 1H), 9.00 (br s, 1H), 12.15 (br s, 1H).

Example 114

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile

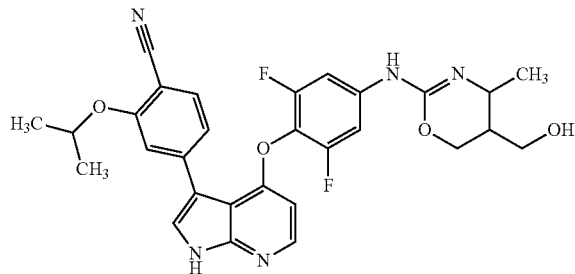 [SMILES: CC(C)Oc1cc(-c2c[nH]c3nccc(Oc4c(F)cc(NC5=NC(C)C(CO)CO5)cc4F)c23)ccc1C#N]

In analogy to example 2, (+/−)—N-{4-[(3-{4-cyano-3-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(1R)-1-(oxetan-3-yl)ethyl]urea (61.0 mg, 90.0 μmol, intermediate 218) was stirred with trifluoroacidic acid (0.60 mL, 7.8 mmol) in dichloromethane (1.2 mL). After purification by HPLC (method 5) we obtained 25.9 mg (90% purity, 47% yield) of the desired title compound.

LC-MS (Method 1): R$_t$=0.91 min; MS (ESIpos): m/z=548 [M+H]$^+$ $^1$H-NMR (400 MHz, DMSO-d6, main isomer) δ [ppm]: 1.18 (d, 3H), 1.23 (d, 6H), 1.60 (br s, 1H), 3.26-3.32 (m, 1H), 3.36-3.44 (m, 1H), 3.46-3.57 (m, 1H), 4.02 (br s, 1H), 4.30 (br d, 1H), 4.66-4.86 (m, 2H), 6.38 (d, 1H), 7.40 (d, 1H), 7.52-7.72 (m, 4H), 7.92 (s, 1H), 8.13 (br d, 1H), 9.01 (br s, 1H), 12.38 (br s, 1H).

Example 115

(+/−)-3-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]benzonitrile

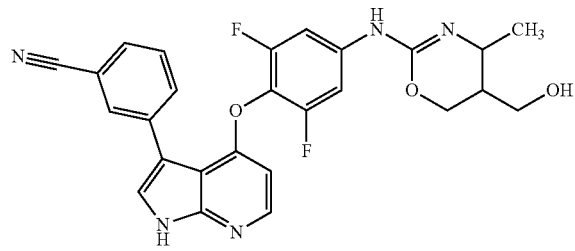 [SMILES: CC1N=C(Nc2cc(F)c(Oc3ccnc4[nH]cc(-c5cccc(C#N)c5)c34)c(F)c2)OCC1CO]

In analogy to example 2, (+/−)—N-(4-{[3-(3-cyanophenyl)-1-{[2-(trimethylsilyl)ethoxy]methyl}-1H-pyrrolo[2,3-b]pyridin-4-yl]oxy}-3,5-difluorophenyl)-N'-[(1R)-1-(oxetan-3-yl)ethyl]urea (50.0 mg, 80.7 μmol, intermediate 219) was stirred with trifluoroacidic acid (0.55 mL, 7.1 mmol) in dichloromethane (1.1 mL). After purification by HPLC (method 5) we obtained 34.9 mg (90% purity, 80% yield) of the desired title compound.

LC-MS (Method 1): R$_t$=0.83 min; MS (ESIpos): m/z=490 [M+H]$^+$ $^1$H-NMR (400 MHz, DMSO-d6, main isomer) δ [ppm]: 1.19 (d, 3H), 1.60 (br s, 1H), 3.26-3.32 (m, 1H), 3.36-3.44 (m, 1H), 3.47-3.57 (m, 1H), 4.03 (br s, 1H), 4.29 (br dd, 1H), 4.73 (br s, 1H), 6.36 (d, 1H), 7.52-7.73 (m, 4H), 7.83 (s, 1H), 8.00-8.04 (m, 1H), 8.08-8.10 (m, 1H), 8.13 (d, 1H), 9.00 (br s, 1H), 12.28 (s, 1H).

Example 116

(+/−)-[2-(3-fluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol

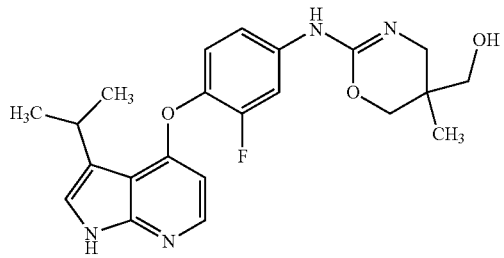 [SMILES: CC(C)c1c[nH]c2nccc(Oc3ccc(NC4=NCC(C)(CO)CO4)cc3F)c12]

In analogy to example 2, N-(3-fluoro-4-{[3-(propan-2-yl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (160 mg, 295 μmol, intermediate 226) was stirred with trifluoroacidic acid (1.65 mL, 21 mmol) in dichloromethane (6.0 mL). After purification by HPLC (method 5) we obtained 68.0 mg (93% purity, 52% yield) of the desired title compound.

LC-MS (Method 1): R$_t$=0.79 min; MS (ESIpos): m/z=413 [M+H]$^+$ $^1$H-NMR (400 MHz, DMSO-d6) δ [ppm]: 0.90 (s, 3H), 1.31 (d, 6H), 3.01 (br d, 1H), 3.16-3.31 (m, 3H), 3.85 (br d, 1H), 4.04 (d, 1H), 4.55 (s, 2H), 4.81 (br s, 1H), 6.10 (d, 1H), 7.11 (d, 1H), 7.15-7.38 (m, 1H), 7.89 (br s, 1H), 7.95 (d, 1H), 8.77 (br s, 1H), 11.38 (br s, 1H).

Example 117

(+/−)-[5-fluoro-2-(3-fluoro-4-{[3-(propan-2-yl)-1H-pyrrolo[2,3-b]pyridin-4-yl]oxy}anilino)-5,6-dihydro-4H-1,3-oxazin-5-yl]methanol

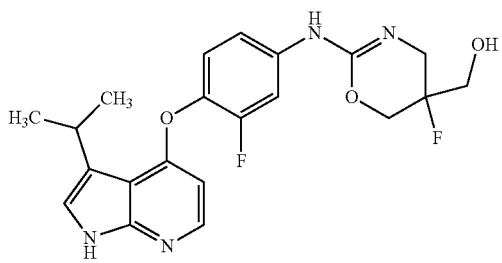 [SMILES: CC(C)c1c[nH]c2nccc(Oc3ccc(NC4=NCC(F)(CO)CO4)cc3F)c12]

In analogy to example 2, N-[(3-fluorooxetan-3-yl)methyl]-N'-(3-fluoro-4-{[3-(propan-2-yl)-1-{[2-(trimethylsilyl)ethoxy]methyl}-1H-pyrrolo[2,3-b]pyridin-4-yl]oxy}phenyl)urea (170 mg, 311 µmol, intermediate 227) was stirred with trifluoroacidic acid (1.74 mL, 23 mmol) in dichloromethane (6.0 mL). After purification by HPLC (method 5) we obtained 75.8 mg (93% purity, 54% yield) of the desired title compound.

LC-MS (Method 1): $R_t$=0.76 min; MS (ESIpos): m/z=417 [M+H]$^+$ $^1$H-NMR (400 MHz, DMSO-d6) δ [ppm]: 1.31 (d, 6H), 3.27-3.32 (m, 1H), 3.36-3.66 (m, 3H), 4.20-4.34 (m, 2H), 4.55 (s, 2H), 6.09 (d, 1H), 7.11 (d, 1H), 7.22 (t, 1H), 7.31 (br s, 1H), 7.84-7.93 (m, 1H), 7.96 (d, 1H), 8.98 (br s, 1H), 11.38 (d, 1H).

Example 118

(+/−)-[2-{3,5-difluoro-4-[(3-{2-fluoro-3-[(propan-2-yl)oxy]phenyl}-1H-pyrrolo[2,3-b]pyridin-4-yl)oxy]anilino}-5-methyl-5,6-dihydro-4H-1,3-oxazin-5-yl]methanol

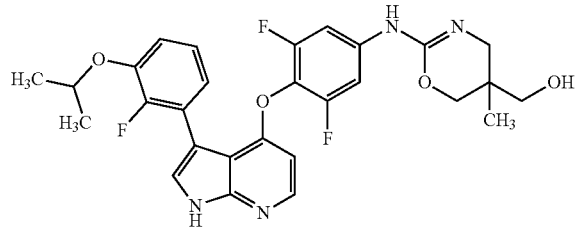 [SMILES: CC(C)Oc1cccc(-c2c[nH]c3nccc(Oc4c(F)cc(NC5=NCC(C)(CO)CO5)cc4F)c23)c1F]

To a stirred solution of N-{3,5-difluoro-4-[(3-{2-fluoro-3-[(propan-2-yl)oxy]phenyl}-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (150 mg, 224 µmol, intermediate 228) in dichloromethane (720 µL) was added trifluoroacetic acid (600 µL, 7.8 mmol). The resulting mixture was stirred overnight at room temperature, at which time a saturated aqueous solution of sodium bicarbonate was added. Ethyl acetate was added and the layers were separated. The aqueous phase was extracted twice with ethyl acetate, and the combined organic layers were washed with brine, dried over sodium sulfate, filtered and evaporated to afford the crude product. The crude material was purified by preparative HPLC to afford the title compound (25 mg, 18% yield).

LC-MS (Method 2): $R_t$=1.13 min; MS (ESIpos): m/z=542 [M+H]$^+$ $^1$H NMR (400 MHz, DMSO-d$_6$) δ ppm 0.90 (s, 3H), 1.24 (d, 6H), 2.99 (br d, 1H), 3.15-3.34 (m, 3H), 3.86 (br d, 1H), 4.06 (d, 1H), 4.50-4.61 (m, 1H), 4.84 (br t, 1H), 6.28 (d, 1H), 7.01-7.10 (m, 2H), 7.12-7.16 (m, 1H), 7.56 (s, 1H), 8.09 (d, 1H), 12.12 (br d, 1H)

Example 119

N-{4-[(3-chloro-1H-pyrrolo[2,3-b]pyridin-4-yl)oxy]-3,5-difluorophenyl}-5,6-dihydro-4H-1,3-oxazin-2-amine

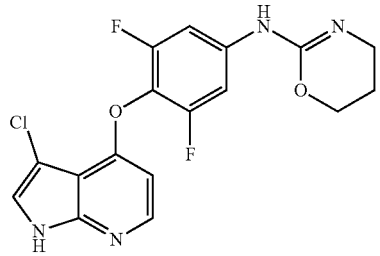 [SMILES: Fc1cc(NC2=NCCCO2)cc(F)c1Oc1ccnc2[nH]cc(Cl)c12]

To a stirred solution of N-{4-[(3-chloro-1-{[2-(trimethylsilyl)ethoxy]methyl}-1H-pyrrolo[2,3-b]pyridin-4-yl)oxy]-3,5-difluorophenyl}-5,6-dihydro-4H-1,3-oxazin-2-amine (270 mg, 530 µmol, Intermediate 232) in dichloromethane (4.0 mL) was added trifluoroacetic acid (4.0 mL, 52 mmol). The mixture was stirred at room temperature overnight, at which time the mixture was basified with a 2M aqueous solution of sodium hydroxide. Ethyl acetate was added and the layers were separated. The aqueous phase was extracted twice with ethyl acetate, and the combined organic layers were washed with brine, dried with sodium sulfate, filtered and evaporated to afford the crude product. The crude material was purified by preparative HPLC to afford the title compound (24 mg, 12% yield)

LC-MS (Method 2): $R_t$=1.02 min; MS (ESIpos): m/z=379 [M+H]$^+$ $^1$H NMR (400 MHz, DMSO-d$_6$) δ ppm 1.86 (br s, 2H), 4.26 (t, 2H), 6.29 (d, 1H), 7.59 (s, 1H), 8.09 (d, 1H), 8.97 (br s, 1H), 11.72-12.29 (m, 1H)

Example 120

N-{4-[(3-chloro-1H-pyrrolo[2,3-b]pyridin-4-yl)oxy]-3,5-difluorophenyl}-4,5-dihydro-1,3-oxazol-2-amine

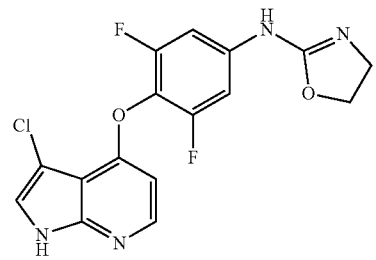 [SMILES: Fc1cc(NC2=NCCO2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-4,5-dihydro-1,3-oxazol-2-amine (260 mg, 525 µmol, Intermediate 234) was treated with trifluoroacetic acid (4.0 mL, 52 mmol) in dichloromethane (4.0 mL) to afford after preparative HPLC purification the title compound (49 mg, 25% yield).

LC-MS (Method 2): $R_t$=0.98 min; MS (ESIpos): m/z=365 [M+H]$^+$ $^1$H NMR (400 MHz, DMSO-d$_6$) δ ppm 3.71 (br s, 2H), 4.35 (br s, 2H), 6.31 (d, 1H), 7.60 (s, 1H), 8.10 (d, 1H), 12.11 (br s, 1H)

Example 121

N-{4-[(3-chloro-1H-pyrrolo[2,3-b]pyridin-4-yl)oxy]-3,5-difluorophenyl}-5,6-dihydro-4H-1,3-thiazin-2-amine

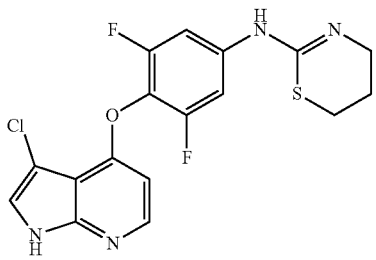 [SMILES: Fc1cc(NC2=NCCCS2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-5,6-dihydro-4H-1,3-thiazin-2-amine (280 mg, 533 µmol, Intermediate 235) was treated with trifluoroacetic acid (4.0 mL, 52 mmol) in dichloromethane (4.0 mL) to afford after preparative HPLC purification the title compound (16 mg, 8% yield).

LC-MS (Method 2): $R_t$=1.12 min; MS (ESIpos): m/z=395 [M+H]$^+$ $^1$H NMR (400 MHz, DMSO-d$_6$) δ ppm 1.83 (br s, 2H), 3.10 (br t, 2H), 3.51 (br s, 2H), 6.25 (d, 1H), 7.57 (s, 1H), 8.06 (d, 1H)

Example 122

N-{4-[(3-chloro-1H-pyrrolo[2,3-b]pyridin-4-yl)oxy]-3,5-difluorophenyl}-4,5-dihydro-1,3-thiazol-2-amine

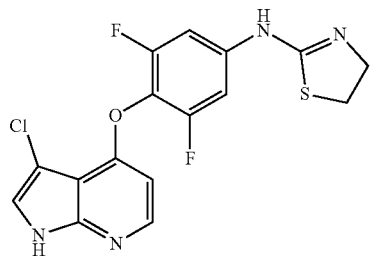 [SMILES: Fc1cc(NC2=NCCS2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-4,5-dihydro-1,3-thiazol-2-amine (270 mg, 528 µmol, intermediate 236) was treated with trifluoroacetic acid (4.0 mL, 52 mmol) in dichloromethane (4.0 mL) to afford after preparative HPLC purification the title compound (51 mg, 25% yield).

LC-MS (Method 2): $R_t$=1.09 min; MS (ESIpos): m/z=381 [M+H]$^+$ $^1$H NMR (400 MHz, DMSO-d$_6$) δ ppm 3.96 (br s, 2H), 6.31 (d, 1H), 7.40 (br s, 2H), 7.60 (s, 1H), 8.09 (d, 1H)

Example 123

N-{4-[(3-chloro-1H-pyrrolo[2,3-b]pyridin-4-yl)oxy]-3,5-difluorophenyl}-5,5-dimethyl-5,6-dihydro-4H-1,3-oxazin-2-amine

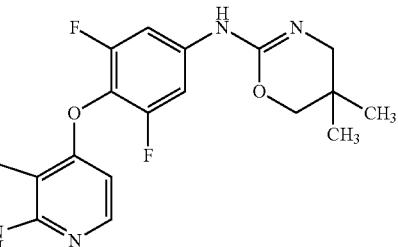

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-5,5-dimethyl-5,6-dihydro-4H-1,3-oxazin-2-amine (280 mg, 521 µmol, Intermediate 238) was treated with trifluoroacetic acid (4.0 mL, 62 mmol) to afford after preparative HPLC purification the title compound (33 mg, 15% yield).

LC-MS (Method 2): $R_t$=1.16 min; MS (ESIpos): m/z=408 [M+H]$^+$ $^1$H NMR (400 MHz, DMSO-d$_6$) δ ppm 0.96 (s, 6H), 3.08 (br s, 2H), 3.88 (s, 2H), 6.30 (d, 1H), 7.60 (s, 1H), 8.08 (d, 1H), 9.04 (br s, 1H), 12.11 (br s, 1H)

Example 124

N-{4-[(3-chloro-1H-pyrrolo[2,3-b]pyridin-4-yl)oxy]-3,5-difluorophenyl}-5-oxa-7-azaspiro[2.5]oct-6-en-6-amine

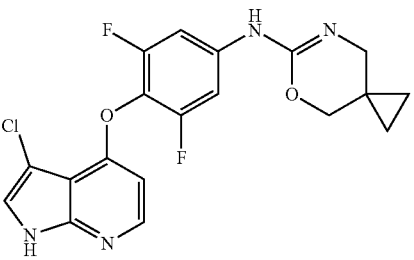 [SMILES: Fc1cc(NC2=NCC3(CC3)CO2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-5-oxa-7-azaspiro[2.5]oct-6-en-6-amine (280 mg, 523 µmol, Intermediate 240) was treated with trifluoroacetic acid (4.0 mL, 52 mmol) in dichloromethane (4.0 mL) to afford after preparative HPLC purification the title compound (23 mg, 11% yield).

LC-MS (Method 2): $R_t$=1.13 min; MS (ESIpos): m/z=405 [M+H]$^+$ $^1$H NMR (400 MHz, DMSO-d$_6$) δ ppm 0.59 (br d, 4H), 3.21 (br s, 2H), 4.03 (br s, 2H), 6.30 (d, 1H), 7.60 (s, 2H), 8.09 (d, 1H), 9.04 (br s, 1H), 12.11 (br s, 1H)

Example 125

N-{4-[(3-chloro-1H-pyrrolo[2,3-b]pyridin-4-yl)oxy]-3,5-difluorophenyl}-6-oxa-8-azaspiro[3.5]non-7-en-7-amine

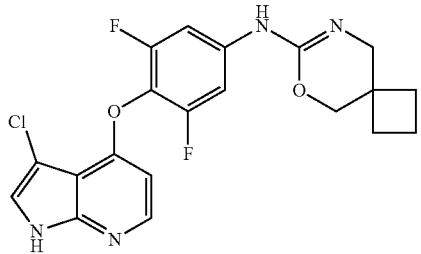 [SMILES: Fc1cc(NC2=NCC3(CCC3)CO2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-6-oxa-8-azaspiro[3.5]non-7-en-7-amine (335 mg, 610 µmol, Intermediate 242) was treated with trifluoroacetic acid (4.0 mL, 52 mmol) in dichloromethane (4.0 mL) to afford after preparative HPLC purification the title compound (25 mg, 10% yield).

LC-MS (Method 2): $R_t$=1.18 min; MS (ESIpos): m/z=420 [M+H]$^+$ $^1$H NMR (400 MHz, DMSO-d$_6$) δ ppm 1.76-2.05 (m, 6H), 4.13 (br s, 2H), 6.30 (d, 1H), 7.57 (br s, 2H), 7.60 (s, 1H), 8.09 (d, 1H), 9.02 (br s, 1H), 12.10 (br s, 1H)

Example 126

(+/−)-[2-{4-[(3-chloro-1H-pyrrolo[2,3-b]pyridin-4-yl)oxy]-3,5-difluoroanilino}-4,5-dihydro-1,3-oxazol-5-yl]methanol

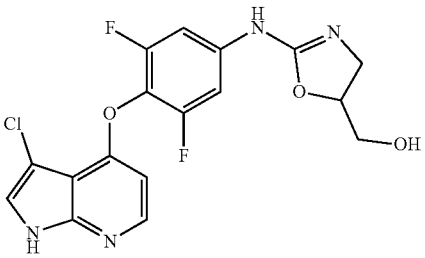 [SMILES: OCC1CN=C(Nc2cc(F)c(Oc3ccnc4[nH]cc(Cl)c34)c(F)c2)O1]

In analogy to Example 119, (+/−)-[2-{4-[(3-chloro-1-{[2-(trimethylsilyl)ethoxy]methyl}-1H-pyrrolo[2,3-b]pyridin-4-yl)oxy]-3,5-difluoroanilino}-4,5-dihydro-1,3-oxazol-5-yl]methanol (335 mg, 638 µmol, Intermediate 244) was treated with trifluoroacetic acid (4.0 mL, 52 mmol) in dichloromethane (4.0 mL) to afford after preparative HPLC purification the title compound (27 mg, 11% yield).

LC-MS (Method 2): $R_t$=0.89 min; MS (ESIpos): m/z=395 [M+H]$^+$ $^1$H NMR (400 MHz, DMSO-d$_6$) δ ppm 3.51 (br dd, 1H), 3.56-3.66 (m, 1H), 3.73 (br s, 1H), 4.66 (br s, 1H), 5.08 (br s, 1H), 6.30 (d, 2H), 7.42 (br s, 2H), 7.59 (s, 1H), 8.08 (d, 2H), 12.14 (br s, 1H)

Example 127

(+/−)—N-{4-[(3-chloro-1H-pyrrolo[2,3-b]pyridin-4-yl)oxy]-3,5-difluorophenyl}-4-methyl-5,6-dihydro-4H-1,3-oxazin-2-amine

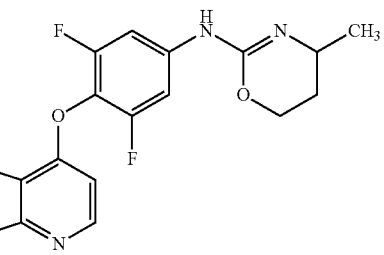

In analogy to Example 119, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-methyl-5,6-dihydro-4H-1,3-oxazin-2-amine (335 mg, 640 µmol, Intermediate 246) was treated with trifluoroacetic acid (4.0 mL, 52 mmol) in dichloromethane (4.0 mL) to afford after preparative HPLC purification the title compound (36 mg, 14% yield).

LC-MS (Method 2): $R_t$=1.09 min; MS (ESIpos): m/z=394 [M+H]$^+$ $^1$H NMR (400 MHz, DMSO-d$_6$) δ ppm 1.17 (d, 3H), 1.47-1.62 (m, 1H), 1.97 (br d, 1H), 3.46-3.58 (m, 1H), 4.20 (td, 1H), 4.25-4.34 (m, 1H), 6.29 (d, 1H), 7.59 (s, 1H), 8.09 (d, 1H), 8.96 (br s, 1H), 12.10 (br s, 1H)

Example 128

N-{4-[(3-chloro-1H-pyrrolo[2,3-b]pyridin-4-yl)oxy]-3,5-difluorophenyl}-5,5-difluoro-5,6-dihydro-4H-1,3-oxazin-2-amine

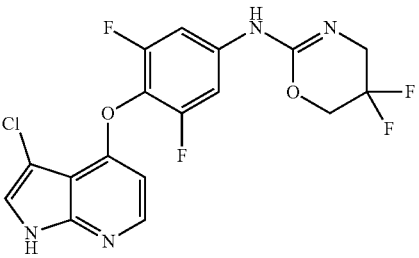 [SMILES: Fc1cc(NC2=NCC(F)(F)CO2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-5,5-difluoro-5,6-dihydro-4H-1,3-oxazin-2-amine (350 mg, 642 µmol, Intermediate 248) was treated with trifluoroacetic acid (4.0 mL, 52 mmol) in dichloromethane (4.0 mL) to afford after preparative HPLC purification the title compound (24 mg, 9% yield).

LC-MS (Method 2): $R_t$=1.16 min; MS (ESIpos): m/z=415 [M+H]$^+$

¹H NMR (400 MHz, DMSO-d₆) δ ppm 3.79 (br t, 2H), 4.48 (t, 2H), 6.31 (d, 1H), 7.57 (br d, 2H), 7.61 (d, 1H), 8.09 (d, 1H), 9.49 (s, 1H), 12.12 (br s, 1H)

Example 129

(+/−)-5-[4-(2,6-difluoro-4-{[5-hydroxy-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile

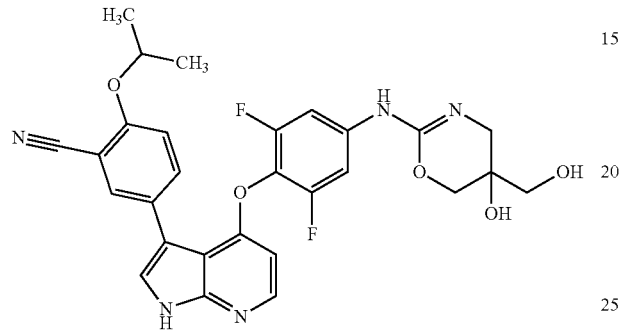

In analogy to Example 119, N-{4-[(3-{3-cyano-4-[(propan-2-yl)oxy]phenyl}-1-{[2-(trimethylsilyl)ethoxy]methyl}-1H-pyrrolo[2,3-b]pyridin-4-yl)oxy]-3,5-difluorophenyl}-N'-[(3-hydroxyoxetan-3-yl)methyl]urea (85.0 mg, 125 µmol, Intermediate 249) was treated with trifluoroacetic acid (2.0 mL, 26 mmol) in dichloromethane (2.0 mL) to afford after preparative HPLC purification to afford the title compound (16 mg, 23% yield).

LC-MS (Method 2): R_t=1.01 min; MS (ESIpos): m/z=551 [M+H]⁺

¹H NMR (400 MHz, DMSO-d₆) δ ppm 1.31 (d, 6H), 3.06-3.14 (m, 1H), 3.38-3.43 (m, 1H), 3.47-3.58 (m, 2H), 3.90 (dd, 1H), 4.13 (d, 1H), 4.80 (spt, 1H), 6.30 (d, 1H), 7.29 (d, 1H), 7.41 (br s, 1H), 7.70 (s, 1H), 7.89-7.96 (m, 2H), 8.09 (d, 1H), 12.12 (br s, 1H)

Example 130

(+/−)-[2-{4-[(3-chloro-1H-pyrrolo[2,3-b]pyridin-4-yl)oxy]-3,5-difluoroanilino}-5,6-dihydro-4H-1,3-oxazin-4-yl]methanol

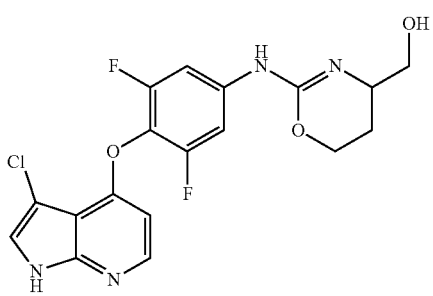 [SMILES: OCC1CCOC(Nc2cc(F)c(Oc3ccnc4[nH]cc(Cl)c34)c(F)c2)=N1]

In analogy to Example 119, (+/−)-[2-{4-[(3-chloro-1-{[2-(trimethylsilyl)ethoxy]methyl}-1H-pyrrolo[2,3-b]pyridin-4-yl)oxy]-3,5-difluoroanilino}-5,6-dihydro-4H-1,3-oxazin-4-yl]methanol (400 mg, 742 µmol, intermediate 251) was treated with trifluoroacetic acid (4.0 mL, 52 mmol) in dichloromethane (4.0 mL) to afford after preparative HPLC purification the title compound (35 mg, 11% yield).

LC-MS (Method 2): R_t=0.93 min; MS (ESIpos): m/z=409 [M+H]⁺

¹H NMR (400 MHz, DMSO-d₆) δ ppm 1.59-1.78 (m, 2H), 3.47-3.60 (m, 2H), 3.95-4.17 (m, 2H), 4.40-4.61 (m, 1H), 6.30 (d, 1H), 6.90-7.46 (m, 2H), 7.59 (s, 1H), 8.08 (d, 1H)

Example 131, Example 132

5-[4-(2,6-difluoro-4-{[(5S)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile 5-[4-(2,6-difluoro-4-{[(5R)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile Example 131

5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile (Single Enantiomer 1)

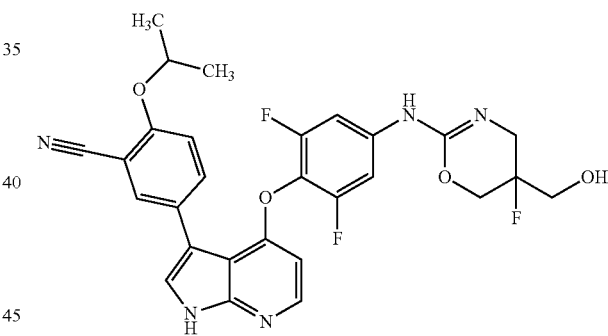

Example 47 was separated into its enantiomers by preparative chiral HPLC to give enantiomer 1 (58 mg, Example 131) and enantiomer 2 (53 mg, see Example 132). For the isolation of enantiomer 1 and enantiomer 2, the following method was used.

Analytical HPLC Method:

Instrument: Agilent HPLC 1260; Column: Chiralpak ID 3µ 100×4.6 mm; Eluent A: Hexane+0.1 Vol-% Diethylamine (99%); Eluent B: 2-Propanol; Gradient: 20-50% B in 7 min; Fluss 1.4 mL/min; Temperature: 25° C.; DAD 254 nm

Preparative Chiral-HPLC Method:

Instrument: Labomatic HD5000, Labocord-5000; Gilson GX-241, Labcol Vario 4000, Column: Chiralpak ID 5µ 250×30 mm; Eluent A: Hexane+0.1 Vol-% Diethylamine (99%); Eluent B: 2-Propanol; Gradient: 20-50% B in 20 min; Flow: 40.0 mL/min; UV 254 nm Analytical chiral HPLC (method see above): R_t=4.47 min, ee=99.9%

Example 132

5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile (Single Enantiomer 2)

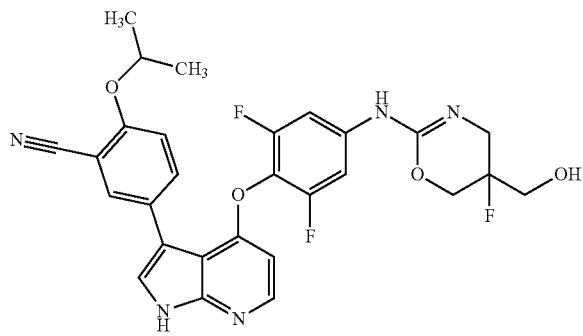 [SMILES: CC(C)Oc1ccc(-c2c[nH]c3nccc(Oc4c(F)cc(NC5=NCC(F)(CO)CO5)cc4F)c23)cc1C#N]

For the preparation of the title compound and separation into its isomers, see Example 131. Analytical chiral HPLC (method see Example 131): $R_t$=5.16 min, ee=98.0%

Example 133

5-(4-{4-[(5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile

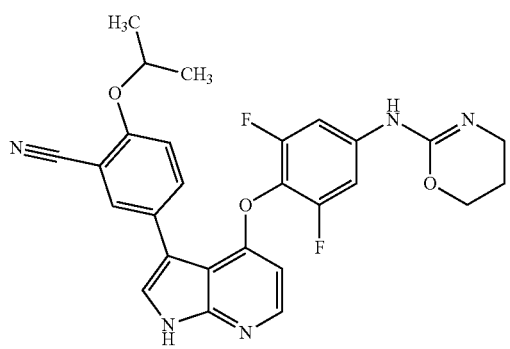 [SMILES: CC(C)Oc1ccc(-c2c[nH]c3nccc(Oc4c(F)cc(NC5=NCCCO5)cc4F)c23)cc1C#N]

In analogy to Example 119, 5-(4-{4-[(5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile (135 mg, 213 μmol, intermediate 253) was treated with trifluoroacetic acid (2.0 mL, 26 mmol) in dichloromethane (2.0 mL) to afford after preparative HPLC purification the title compound (8 mg, 7% yield).

LC-MS (Method 2): $R_t$=1.17 min; MS (ESIpos): m/z=505 [M+H]$^+$ $^1$H NMR (400 MHz, DMSO-d$_6$) δ ppm 1.31 (d, 6H), 1.86 (quin, 2H), 4.26 (t, 2H), 4.80 (spt, 1H), 6.31 (d, 1H), 7.28-7.31 (m, 1H), 7.70 (s, 1H), 7.90-7.95 (m, 2H), 8.10 (d, 1H), 12.13 (br s, 1H)

Example 134

5-(4-{2,6-difluoro-4-[(5-oxa-7-azaspiro[2.5]oct-6-en-6-yl)amino]phenoxy}-1H-pyrrolo[2,3-b]pyridin-3-yl)-2-[(propan-2-yl)oxy]benzonitrile

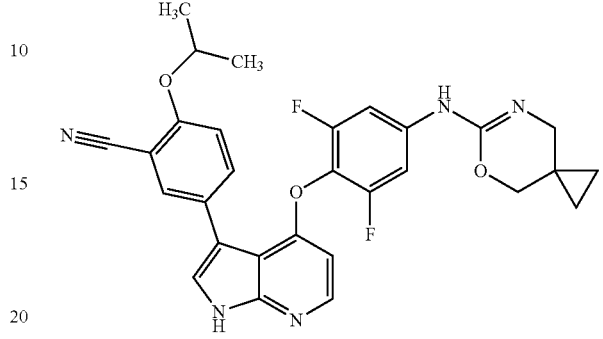

In analogy to Example 119, 5-(4-{2,6-difluoro-4-[(5-oxa-7-azaspiro[2.5]oct-6-en-6-yl)amino]phenoxy}-1-{[2-(trimethylsilyl)ethoxy]methyl}-1H-pyrrolo[2,3-b]pyridin-3-yl)-2-[(propan-2-yl)oxy]benzonitrile (140 mg, 212 μmol, intermediate 255) was treated with trifluoroacetic acid (2.0 mL, 26 mmol) in dichloromethane (2.0 mL) to afford after preparative HPLC purification the title compound (10 mg, 8% yield).

LC-MS (Method 2): $R_t$=1.25 min; MS (ESIpos): m/z=531 [M+H]$^+$ $^1$H NMR (400 MHz, DMSO-d$_6$) δ ppm 0.58 (br d, 4H), 1.31 (d, 6H), 3.22 (br s, 2H), 4.03 (s, 2H), 4.80 (spt, 1H), 6.32 (d, 1H), 7.27-7.31 (m, 1H), 7.59 (br s, 2H), 7.70 (s, 1H), 7.89-7.95 (m, 2H), 8.10 (d, 1H), 9.02 (br s, 1H), 12.14 (s, 1H)

Example 135

5-(4-{4-[(5,5-dimethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile

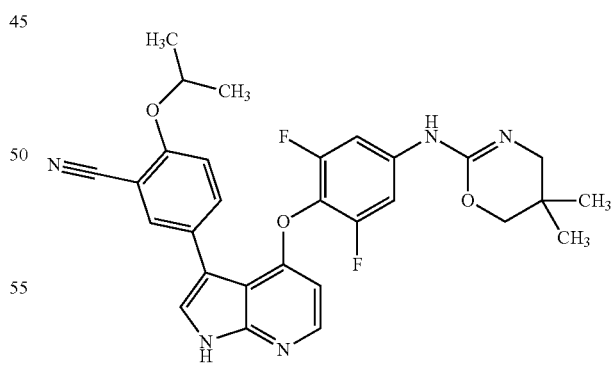

In analogy to Example 119, 5-(4-{4-[(5,5-dimethyl-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile (140 mg, 212 μmol, intermediate 257) was treated with trifluoroacetic acid (2.0 mL, 26 mmol) in dichloromethane (2.0 mL) to afford after preparative HPLC purification the title compound (11 mg, 9% yield).

LC-MS (Method 2): R$_t$=1.28 min; MS (ESIpos): m/z=533 [M+H]$^+$ $^1$H NMR (400 MHz, DMSO-d$_6$) δ ppm 0.96 (br s, 6H), 1.31 (d, 6H), 3.09 (br s, 2H), 3.88 (br s, 2H), 4.80 (spt, 1H), 6.33 (d, 1H), 7.23-7.37 (m, 1H), 7.58 (br s, 1H), 7.70 (d, 1H), 7.90-7.95 (m, 2H), 8.10 (d, 1H), 9.04 (br s, 1H), 12.14 (s, 1H)

Example 136

5-(4-{4-[(5,5-difluoro-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile

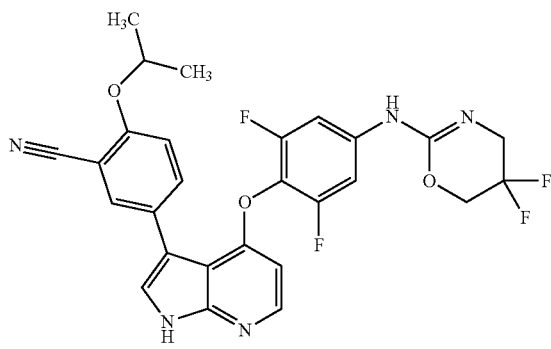 [SMILES: CC(C)Oc1ccc(-c2c[nH]c3nccc(Oc4c(F)cc(NC5=NCC(F)(F)CO5)cc4F)c23)cc1C#N]

In analogy to Example 119, 5-(4-{4-[(5,5-difluoro-5,6-dihydro-4H-1,3-oxazin-2-yl)amino]-2,6-difluorophenoxy}-1-{[2-(trimethylsilyl)ethoxy]methyl}-1H-pyrrolo[2,3-b]pyridin-3-yl)-2-[(propan-2-yl)oxy]benzonitrile (140 mg, 209 μmol, intermediate 259) was treated with trifluoroacetic acid (2.0 mL, 26 mmol) in dichloromethane (2.0 mL) to afford after preparative HPLC purification the title compound (6 mg, 5% yield).

LC-MS (Method 2): R$_t$=1.28 min; MS (ESIpos): m/z=541 [M+H]$^+$ $^1$H NMR (400 MHz, DMSO-d$_6$) δ ppm 1.31 (d, 6H), 3.78 (br t, 2H), 4.48 (br t, 2H), 4.80 (spt, 1H), 6.33 (d, 1H), 7.28-7.31 (m, 1H), 7.56 (br d, 2H), 7.71 (s, 1H), 7.89-7.94 (m, 2H), 8.10 (d, 1H), 9.48 (s, 1H), 12.15 (br s, 1H)

Example 137

N-[3,5-difluoro-4-({3-[1-(propan-2-yl)-1H-pyrazol-5-yl]-1H-pyrrolo[2,3-b]pyridin-4-yl}oxy)phenyl]-5,5-difluoro-5,6-dihydro-4H-1,3-oxazin-2-amine

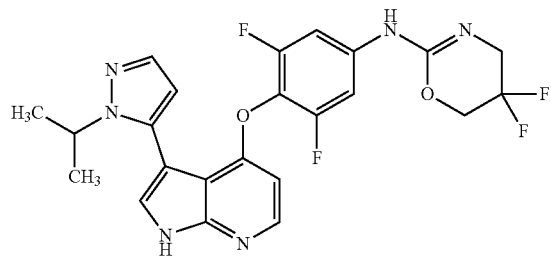 [SMILES: CC(C)n1nccc1-c1c[nH]c2nccc(Oc3c(F)cc(NC4=NCC(F)(F)CO4)cc3F)c12]

In analogy to Example 119, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,5-difluoro-5,6-dihydro-4H-1,3-oxazin-2-amine (270 mg, 436 μmol, intermediate 262) was treated with trifluoroacetic acid (5.0 mL, 65 mmol) in dichloromethane (10 mL) to afford after preparative HPLC purification the title compound (16 mg, 7% yield).

LC-MS (Method 2): R$_t$=1.12 min; MS (ESIpos): m/z=490 [M+H]$^+$ $^1$H NMR (400 MHz, DMSO-d$_6$) δ ppm 1.28 (d, 6H), 3.77 (br t, 2H), 4.46 (br t, 2H), 4.51-4.60 (m, 1H), 6.25 (d, 1H), 6.27 (d, 1H), 7.45 (d, 1H), 7.50 (br d, 2H), 7.55 (s, 1H), 8.10 (d, 1H), 9.41 (br s, 1H), 12.23 (br s, 1H)

Example 138

N-[3,5-difluoro-4-({3-[1-(propan-2-yl)-1H-pyrazol-5-yl]-1H-pyrrolo[2,3-b]pyridin-4-yl}oxy)phenyl]-5,5-dimethyl-5,6-dihydro-4H-1,3-oxazin-2-amine

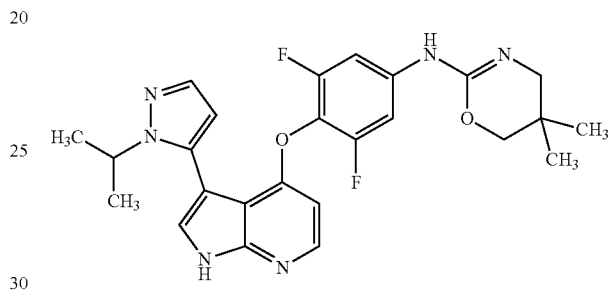

In analogy to Example 119, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,5-dimethyl-5,6-dihydro-4H-1,3-oxazin-2-amine (270 mg, 442 μmol, intermediate 264) was treated with trifluoroacetic acid (5.0 mL, 65 mmol) in dichloromethane (10 mL) to afford after preparative HPLC purification the title compound (31 mg, 14% yield).

LC-MS (Method 2): R$_t$=1.11 min; MS (ESIpos): m/z=482 [M+H]$^+$ $^1$H NMR (400 MHz, DMSO-d$_6$) δ ppm 0.95 (s, 6H), 1.28 (d, 6H), 3.05 (s, 2H), 3.86 (s, 2H), 4.55 (spt, 1H), 6.25 (d, 1H), 6.27 (d, 1H), 7.33 (br s, 1H), 7.45 (d, 1H), 7.54 (s, 1H), 8.10 (d, 1H), 12.26 (br s, 1H)

Example 139

N-[3,5-difluoro-4-({3-[1-(propan-2-yl)-1H-pyrazol-5-yl]-1H-pyrrolo[2,3-b]pyridin-4-yl}oxy)phenyl]-5-oxa-7-azaspiro[2.5]oct-6-en-6-amine

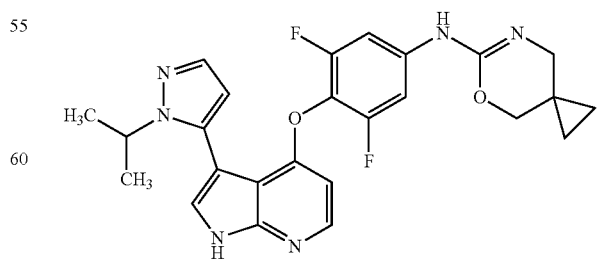

In analogy to Example 119, N-{3,5-difluoro-4-[(3-[1-(propan-2-yl)-1H-pyrazol-5-yl]-1-{[2-(trimethylsilyl)

ethoxy]methyl}-1H-pyrrolo[2,3-b]pyridin-4-yl)oxy]phenyl}-5-oxa-7-azaspiro[2.5]oct-6-en-6-amine (270 mg, 444 µmol, intermediate 266) was treated with trifluoroacetic acid (5.0 mL, 65 mmol) in dichloromethane (10 mL) to afford after preparative HPLC purification the title compound (11 mg, 5% yield).

LC-MS (Method 2): $R_t$=1.09 min; MS (ESIpos): m/z=480 [M+H]$^+$ $^1$H NMR (400 MHz, DMSO-d$_6$) δ ppm 0.53-0.64 (m, 4H), 1.28 (d, 6H), 3.19 (s, 2H), 4.01 (s, 2H), 4.55 (spt, 1H), 6.25-6.27 (m, 2H), 7.37 (br s, 1H), 7.45 (d, 1H), 7.54 (s, 1H), 8.10 (d, 1H), 12.23 (br s, 1H)

Example 140

N-[3,5-difluoro-4-({3-[1-(propan-2-yl)-1H-pyrazol-5-yl]-1H-pyrrolo[2,3-b]pyridin-4-yl}oxy)phenyl]-5,6-dihydro-4H-1,3-oxazin-2-amine

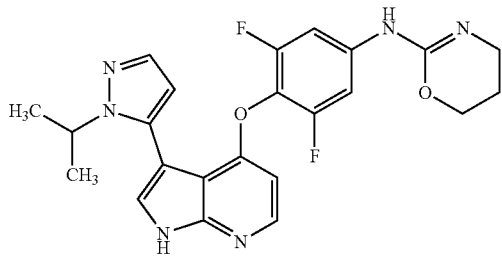 [SMILES: CC(C)n1nccc1-c1c[nH]c2nccc(Oc3c(F)cc(NC4=NCCCO4)cc3F)c12]

In analogy to Example 119, N-{3,5-difluoro-4-[(3-[1-(propan-2-yl)-1H-pyrazol-5-yl]-1-{[2-(trimethylsilyl)ethoxy]methyl}-1H-pyrrolo[2,3-b]pyridin-4-yl)oxy]phenyl}-5,6-dihydro-4H-1,3-oxazin-2-amine (270 mg, 463 µmol, intermediate 268) was treated with trifluoroacetic acid (5.0 mL, 65 mmol) in dichloromethane (10 mL) to afford after preparative HPLC purification (14 mg, 6% yield).

LC-MS (Method 2): $R_t$=0.98 min; MS (ESIpos): m/z=454 [M+H]$^+$ $^1$H NMR (400 MHz, DMSO-d$_6$) δ ppm 1.28 (d, 6H), 1.85 (quin, 2H), 4.24 (t, 2H), 4.55 (spt, 1H), 6.23-6.28 (m, 2H), 7.26 (br s, 1H), 7.45 (d, 1H), 7.54 (s, 1H), 8.11 (d, 1H), 12.23 (br s, 1H)

Example 141

N-(3,5-difluoro-4-{[3-(trifluoromethyl)-1H-pyrrolo[2,3-b]pyridin-4-yl]oxy}phenyl)-5,6-dihydro-4H-1,3-oxazin-2-amine

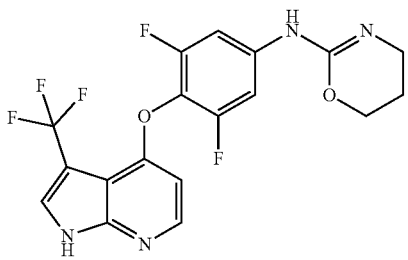 [SMILES: Fc1cc(NC2=NCCCO2)cc(F)c1Oc1ccnc2[nH]cc(C(F)(F)F)c12]

To a stirred solution of N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,6-dihydro-4H-1,3-oxazin-2-amine (350 mg, 645 µmol, intermediate 270) in dichloromethane (3.0 mL) was added trifluoroacetic acid (1.0 mL, 13 mmol). The mixture was stirred at room temperature overnight, at which time the mixture was basified with a saturated aqueous solution of sodium bicarbonate to pH 7-8. Ethyl acetate was added and the layers were separated. The aqueous phase was extracted twice with ethyl acetate, and the combined organic layers were washed with brine, dried with sodium sulfate, filtered and evaporated to afford the crude product. The crude material was purified by preparative HPLC to afford the title compound (44 mg, 16% yield)

LC-MS (Method 2): $R_t$=1.07 min; MS (ESIpos): m/z=414 [M+H]$^+$ $^1$H NMR (400 MHz, DMSO-d$_6$) δ ppm 1.86 (br s, 2H), 4.26 (t, 2H), 6.44 (d, 1H), 7.56 (br s, 2H), 8.10 (d, 1H), 8.20 (d, 1H), 8.97 (br s, 1H), 12.57 (br s, 1H)

Example 142

N-(3,5-difluoro-4-{[3-(trifluoromethyl)-1H-pyrrolo[2,3-b]pyridin-4-yl]oxy}phenyl)-5-oxa-7-azaspiro[2.5]oct-6-en-6-amine

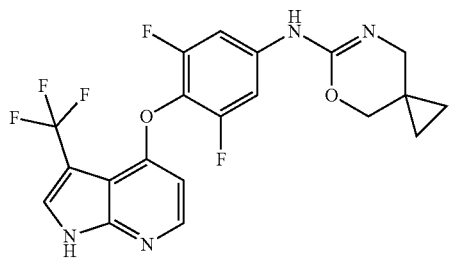 [SMILES: Fc1cc(NC2=NCC3(CC3)CO2)cc(F)c1Oc1ccnc2[nH]cc(C(F)(F)F)c12]

In analogy to Example 141, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5-oxa-7-azaspiro[2.5]oct-6-en-6-amine (370 mg, 651 µmol, Intermediate 272) was treated with trifluoroacetic acid (1.0 mL, 13 mmol) in dichloromethane (3.0 mL) to afford after preparative HPLC purification the title compound (46 mg, 15% yield).

LC-MS (Method 2): $R_t$=1.17 min; MS (ESIpos): m/z=440 [M+H]$^+$ $^1$H NMR (400 MHz, DMSO-d$_6$) δ ppm 0.59 (br d, 5H), 3.21 (br s, 2H), 4.03 (s, 2H), 6.44 (d, 1H), 7.58 (br s, 2H), 8.10 (d, 1H), 8.20 (d, 1H), 9.04 (br s, 1H), 12.61 (br s, 1H)

Example 143

N-(3,5-difluoro-4-{[3-(trifluoromethyl)-1H-pyrrolo[2,3-b]pyridin-4-yl]oxy}phenyl)-5,5-dimethyl-5,6-dihydro-4H-1,3-oxazin-2-amine

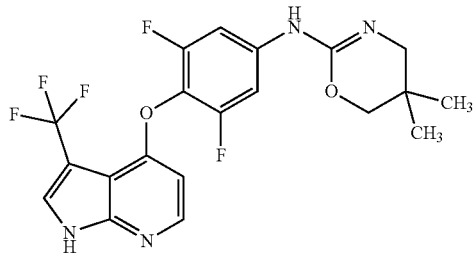 [SMILES: CC1(C)CN=C(Nc2cc(F)c(Oc3ccnc4[nH]cc(C(F)(F)F)c34)c(F)c2)OC1]

In analogy to Example 141, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,5-dimethyl-5,6-dihydro-4H-1,3-oxazin-2-amine (370 mg, 648 µmol, Intermediate 274) was treated with trifluoroacetic acid (1.0 mL, 13 mmol) in dichloromethane (3.0 mL) to afford after preparative HPLC purification the title compound (29 mg, 10% yield).

LC-MS (Method 2): $R_t$=1.20 min; MS (ESIpos): m/z=442 [M+H]$^+$ $^1$H NMR (400 MHz, DMSO-d$_6$) δ ppm 0.96 (s, 6H), 3.07 (br s, 2H), 3.88 (s, 2H), 6.46 (d, 1H), 7.57 (br s, 2H), 8.10 (d, 1H), 8.20 (d, 1H), 9.05 (br s, 1H), 12.48 (br s, 1H)

Example 144

N-(3,5-difluoro-4-{[3-(trifluoromethyl)-1H-pyrrolo[2,3-b]pyridin-4-yl]oxy}phenyl)-5,5-difluoro-5,6-dihydro-4H-1,3-oxazin-2-amine

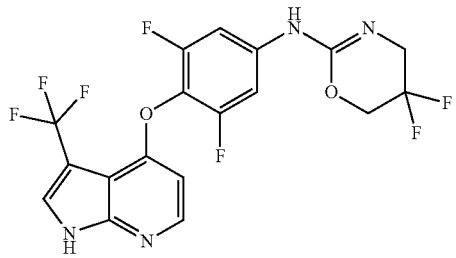 [SMILES: Fc1cc(NC2=NCC(F)(F)CO2)cc(F)c1Oc1ccnc2[nH]cc(C(F)(F)F)c12]

In analogy to Example 141, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-5,5-difluoro-5,6-dihydro-4H-1,3-oxazin-2-amine (370 mg, 640 µmol, intermediate 276) was treated with trifluoroacetic acid (1.0 mL, 13 mmol) in dichloromethane (3.0 mL) to afford after preparative HPLC purification the title compound (22 mg, 7% yield).

LC-MS (Method 2): $R_t$=1.20 min; MS (ESIpos): m/z=449 [M+H]$^+$ $^1$H NMR (400 MHz, DMSO-d$_6$) δ ppm 3.78 (br t, 2H), 4.48 (br t, 2H), 6.46 (d, 1H), 7.56 (br d, 2H), 8.11 (d, 1H), 8.20 (d, 1H), 9.49 (s, 1H), 12.58 (br s, 1H)

Example 145

N-(3,5-difluoro-4-{[3-(trifluoromethyl)-1H-pyrrolo[2,3-b]pyridin-4-yl]oxy}phenyl)-6-oxa-8-azaspiro[3.5]non-7-en-7-amine

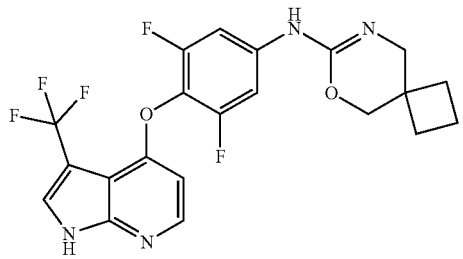 [SMILES: Fc1cc(NC2=NCC3(CCC3)CO2)cc(F)c1Oc1ccnc2[nH]cc(C(F)(F)F)c12]

In analogy to Example 141, N-(3,5-difluoro-4-{[3-(trifluoromethyl)-1-{[2-(trimethylsilyl)ethoxy]methyl}-1H-pyrrolo[2,3-b]pyridin-4-yl]oxy}phenyl)-6-oxa-8-azaspiro[3.5]non-7-en-7-amine (380 mg, 652 µmol, intermediate 278) was treated with trifluoroacetic acid (1.0 mL, 13 mmol) in dichloromethane (3.0 mL) to afford after preparative HPLC purification the title compound (47 mg, 15% yield).

LC-MS (Method 2): $R_t$=1.23 min; MS (ESIpos): m/z=454 [M+H]$^+$ $^1$H NMR (400 MHz, DMSO-d$_6$) δ ppm 1.78-2.01 (m, 6H), 3.31 (br s, 2H), 4.13 (s, 2H), 6.44 (d, 1H), 7.55 (br s, 2H), 8.10 (d, 1H), 8.20 (d, 1H), 9.02 (br s, 1H), 12.51 (br s, 1H)

Example 146

(+/−)-{2-[3,5-difluoro-4-({3-[2-(trifluoromethoxy)ethyl]-1H-pyrrolo[2,3-b]pyridin-4-yl}oxy)anilino]-5-fluoro-5,6-dihydro-4H-1,3-oxazin-5-yl}methanol

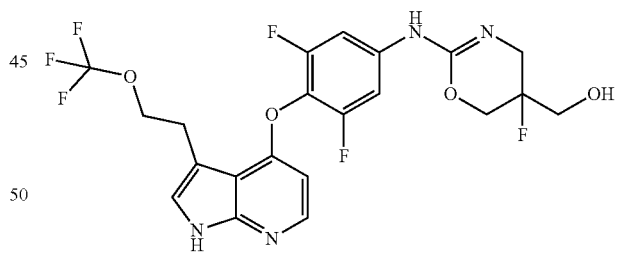

In analogy to Example 119, N-[3,5-difluoro-4-({3-[2-(trifluoromethoxy)ethyl]-1H-pyrrolo[2,3-b]pyridin-4-yl}oxy)phenyl]-N'-[(3-fluorooxetan-3-yl)methyl]urea (100 mg, 198 µmol, intermediate 287) was treated with trifluoroacetic acid (2.0 mL, 26 mmol) in dichloromethane (2.0 mL) for 2 hours to afford after preparative HPLC purification the title compound (9 mg, 9% yield).

LC-MS (Method 2): $R_t$=1.09 min; MS (ESIpos): m/z=505 [M+H]$^+$ $^1$H NMR (400 MHz, DMSO-d$_6$) δ ppm 3.22 (br t, 3H), 3.41-3.66 (m, 5H), 4.22-4.33 (m, 2H), 4.36 (t, 2H), 6.23 (d, 1H), 7.32 (s, 1H), 7.51 (br d, 2H), 8.02 (d, 1H), 11.67 (br s, 1H)

Example 147

N-{4-[(3-chloro-1H-pyrrolo[2,3-b]pyridin-4-yl)oxy]-3,5-difluorophenyl}-2,9-dioxa-4-azaspiro[5.5]undec-3-en-3-amine

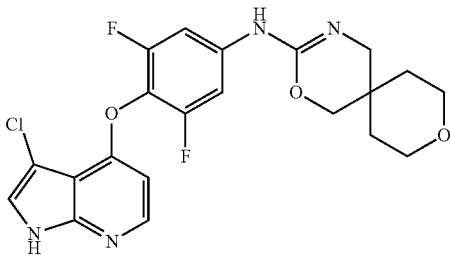 [SMILES: Fc1cc(NC2=NCC3(CCOCC3)CO2)cc(F)c1Oc1ccnc2[nH]cc(Cl)c12]

In analogy to Example 119, N-{4-[(3-chloro-1-{[2-(trimethylsilyl)ethoxy]methyl}-1H-pyrrolo[2,3-b]pyridin-4-yl)oxy]-3,5-difluorophenyl}-2,9-dioxa-4-azaspiro[5.5]undec-3-en-3-amine (580 mg, 1.00 mmol, intermediate 289) was treated with trifluoroacetic acid (1.0 mL, 13 mmol) in dichloromethane (3.0 mL) to afford after preparative HPLC purification the title compound (24 mg, 5% yield).

LC-MS (Method 2): $R_t$=1.05 min; MS (ESIpos): m/z=449 [M+H]$^+$ $^1$H NMR (400 MHz, DMSO-d$_6$) δ ppm 1.43 (br s, 4H), 3.27 (br s, 2H), 3.54-3.67 (m, 4H), 4.07 (s, 2H), 6.29 (d, 1H), 7.59 (s, 1H), 8.08 (d, 1H), 12.10 (br s, 1H)

Example 148

(+/−)—N-{4-[(3-chloro-1H-pyrrolo[2,3-b]pyridin-4-yl)oxy]-3,5-difluorophenyl}-5-methyl-5,6-dihydro-4H-1,3-oxazin-2-amine

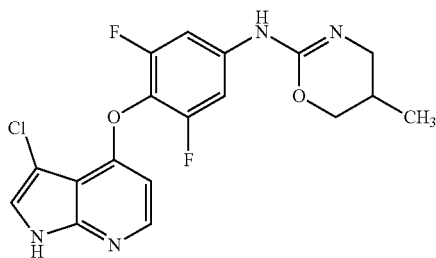 [SMILES: CC1CN=C(Nc2cc(F)c(Oc3ccnc4[nH]cc(Cl)c34)c(F)c2)OC1]

In analogy to Example 119, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-5-methyl-5,6-dihydro-4H-1,3-oxazin-2-amine (520 mg, 994 µmol, intermediate 291) was treated with trifluoroacetic acid (1.0 mL, 13 mmol) in dichloromethane (3.0 mL) to afford after preparative HPLC purification the title compound (16 mg, 4% yield).

LC-MS (Method 2): $R_t$=1.11 min; MS (ESIpos): m/z=393 [M+H]$^+$ $^1$H NMR (400 MHz, DMSO-d$_6$) δ ppm 0.92 (d, 3H), 2.01 (br s, 1H), 2.95 (td, 1H), 3.39 (br s, 1H), 3.84 (br t, 1H), 4.20-4.26 (m, 1H), 6.30 (d, 1H), 7.57 (br s, 1H), 7.60 (s, 1H), 8.09 (d, 1H), 9.02 (br s, 1H), 12.10 (br s, 1H)

Example 149

(+/−)—N-{4-[(3-chloro-1H-pyrrolo[2,3-b]pyridin-4-yl)oxy]-3,5-difluorophenyl}-4-(propan-2-yl)-5,6-dihydro-4H-1,3-oxazin-2-amine

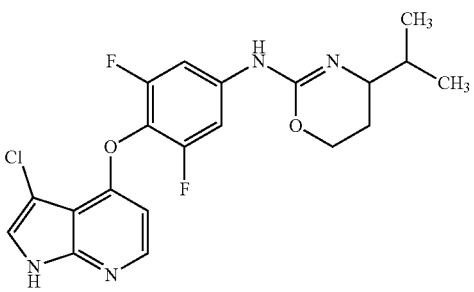 [SMILES: CC(C)C1CCOC(Nc2cc(F)c(Oc3ccnc4[nH]cc(Cl)c34)c(F)c2)=N1]

In analogy to Example 119, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-(propan-2-yl)-5,6-dihydro-4H-1,3-oxazin-2-amine (550 mg, 998 µmol, intermediate 293) was treated with trifluoroacetic acid (4.0 mL, 52 mmol) in dichloromethane (4.0 mL) to afford after preparative HPLC purification the title compound (17 mg, 4% yield).

LC-MS (Method 2): $R_t$=1.27 min; MS (ESIpos): m/z=422 [M+H]$^+$ $^1$H NMR (400 MHz, DMSO-d$_6$) δ ppm 0.96 (br dd, 6H), 1.59 (br s, 2H), 1.83-1.92 (m, 1H), 3.13 (br s, 1H), 4.18 (td, 1H), 4.27-4.35 (m, 1H), 6.31 (d, 1H), 7.60 (s, 1H), 7.65 (br d, 2H), 8.09 (d, 1H), 8.99 (br s, 1H), 12.10 (br s, 1H)

Example 150

(+/−)-[2-(3,5-difluoro-4-{[3-(propan-2-yl)-1H-pyrrolo[2,3-b]pyridin-4-yl]oxy}anilino)-5-fluoro-5,6-dihydro-4H-1,3-oxazin-5-yl]methanol

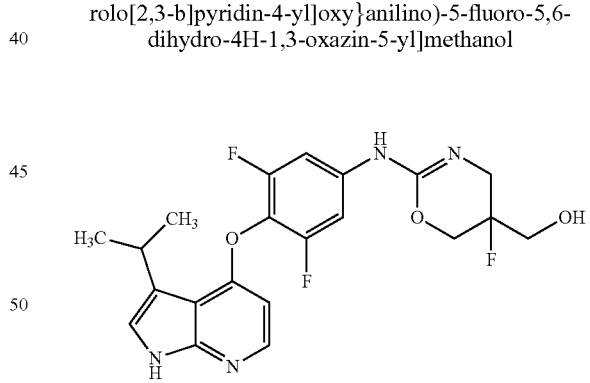

In analogy to Example 119, N-(3,5-difluoro-4-{[3-(propan-2-yl)-1H-pyrrolo[2,3-b]pyridin-4-yl]oxy}phenyl)-N'-[(3-fluorooxetan-3-yl)methyl]urea (190 mg, 437 µmol, intermediate 298) was treated with trifluoroacetic acid (500 µL, 6.5 mmol) in dichloromethane (2.0 mL) for 30 min to afford after preparative HPLC purification the title compound (63 mg, 32% yield).

LC-MS (Method 2): $R_t$=1.08 min; MS (ESIpos): m/z=436 [M+H]$^+$ $^1$H NMR (400 MHz, DMSO-d$_6$) δ ppm 1.31 (d, 6H), 3.28-3.36 (m, 1H), 3.37-3.67 (m, 4H), 4.22-4.37 (m, 2H), 5.25 (br t, 1H), 6.17 (d, 1H), 7.14 (d, 1H), 7.57 (br d, 2H), 7.98 (d, 1H), 9.21 (br s, 1H), 11.45 (d, 1H)

Example 151

(+/−)-[2-(3,5-difluoro-4-{[3-(3,3,3-trifluoropropyl)-1H-pyrrolo[2,3-b]pyridin-4-yl]oxy}anilino)-5-fluoro-5,6-dihydro-4H-1,3-oxazin-5-yl]methanol

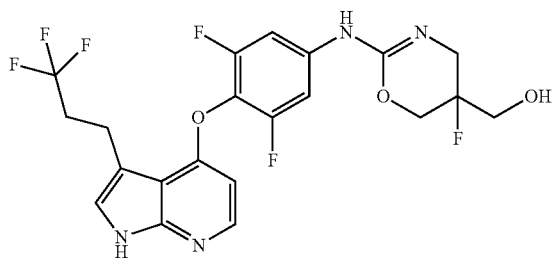 [SMILES: OCC1(F)CN=C(Nc2cc(F)c(Oc3ccnc4[nH]cc(CCC(F)(F)F)c34)c(F)c2)OC1]

In analogy to Example 119, N-(3,5-difluoro-4-{[3-(3,3,3-trifluoropropyl)-1H-pyrrolo[2,3-b]pyridin-4-yl]oxy}phenyl)-N'-[(3-fluorooxetan-3-yl)methyl]urea (150 mg, 307 µmol, intermediate 303) was treated with trifluoroacetic acid (2.0 mL, 26 mmol) in dichloromethane (2.0 mL) to afford after preparative HPLC purification the title compound (30 mg, 20% yield).

LC-MS (Method 2): $R_t$=1.06 min; MS (ESIpos): m/z=489 [M+H]$^+$ $^1$H NMR (400 MHz, DMSO-d$_6$) δ ppm 2.59-2.74 (m, 2H), 3.03-3.09 (m, 2H), 3.38-3.67 (m, 4H), 4.21-4.37 (m, 2H), 6.23 (d, 1H), 7.31 (s, 1H), 7.51 (br d, 2H), 8.02 (d, 1H), 11.60 (br s, 1H)

Example 152

(+/−)-[2-(3,5-difluoro-4-{[3-(tetrahydrofuran-3-yl)-1H-pyrrolo[2,3-b]pyridin-4-yl]oxy}anilino)-5-fluoro-5,6-dihydro-4H-1,3-oxazin-5-yl]methanol-mixture of isomers

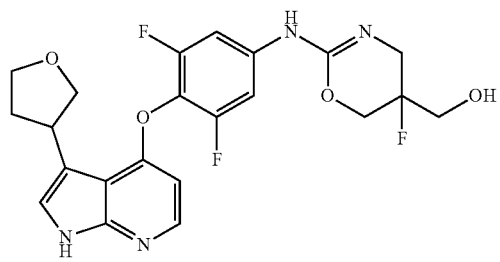 [SMILES: OCC1(F)CN=C(Nc2cc(F)c(Oc3ccnc4[nH]cc(C5CCOC5)c34)c(F)c2)OC1]

In analogy to Example 119, (+/−)—N-(3,5-difluoro-4-{[3-(tetrahydrofuran-3-yl)-1H-pyrrolo[2,3-b]pyridin-4-yl]oxy}phenyl)-3-[(3-fluorooxetan-3-yl)methyl]urea (101 mg, 218 µmol, Intermediate 307) was treated with trifluoroacetic acid (1.0 mL, 13 mmol) in dichloromethane (2.0 mL, 31 mmol) to afford after preparative HPLC purification the title compound (12 mg, 12% yield).

LC-MS (Method 2): $R_t$=0.88 min; MS (ESIpos): m/z=463 [M+H]$^+$ $^1$H NMR (400 MHz, DMSO-d$_6$) δ ppm 2.13 (dq, 1H), 2.24-2.32 (m, 1H), 3.38-3.62 (m, 4H), 3.65 (t, 1H), 3.71-3.79 (m, 1H), 3.81 (d, 1H), 3.84-3.91 (m, 1H), 4.09 (t, 1H), 4.21-4.38 (m, 2H), 5.25 (br t, 1H), 6.21 (d, 1H), 7.30 (d, 1H), 7.57 (br s, 2H), 8.01 (d, 1H), 9.21 (br s, 1H), 11.60 (d, 1H)

Example 153

(+/−)-[2-{4-[(3-cyclobutyl-1H-pyrrolo[2,3-b]pyridin-4-yl)oxy]-3,5-difluoroanilino}-5-fluoro-5,6-dihydro-4H-1,3-oxazin-5-yl]methanol

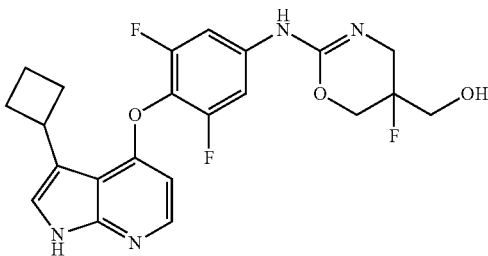 [SMILES: OCC1(F)CN=C(Nc2cc(F)c(Oc3ccnc4[nH]cc(C5CCC5)c34)c(F)c2)OC1]

In analogy to Example 119, N-{4-[(3-cyclobutyl-1H-pyrrolo[2,3-b]pyridin-4-yl)oxy]-3,5-difluorophenyl}-N'-[(3-fluorooxetan-3-yl)methyl]urea (12.0 mg, 26.9 µmol, Intermediate 309) was treated with trifluoroacetic acid (100 µL, 1.3 mmol) in dichloromethane (1.0 mL) to afford after preparative HPLC purification the title compound (9 mg, 68% yield).

LC-MS (Method 2): $R_t$=1.10 min; MS (ESIpos): m/z=447 [M+H]$^+$ $^1$H NMR (400 MHz, DMSO-d$_6$) δ ppm 1.75-1.85 (m, 1H), 1.90-2.03 (m, 1H), 2.17 (quind, 2H), 2.26-2.36 (m, 2H), 3.38-3.70 (m, 4H), 3.78-3.88 (m, 1H), 4.24-4.45 (m, 2H), 5.28 (br s, 1H), 6.17 (d, 1H), 7.22 (d, 1H), 7.53 (br s, 2H), 7.98 (d, 1H), 9.22 (br s, 1H), 11.50 (d, 1H)

Example 154

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol
(Mixture of Stereoisomers)

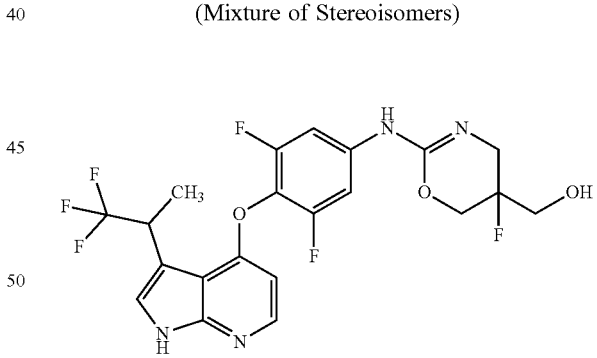

In analogy to Example 119, (+/−)—N-{3,5-difluoro-4-[(3-[1,1,1-trifluoropropan-2-yl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea (600 mg, 50% purity, 485 µmol, intermediate 311) was treated with trifluoroacetic acid (2.0 mL, 26 mmol) in dichloromethane (4.0 mL) to afford after preparative HPLC purification the title compound (93 mg, 37% yield).

LC-MS (Method 2): $R_t$=1.05 min; MS (ESIpos): m/z=489 [M+H]$^+$ $^1$H NMR (400 MHz, DMSO-d$_6$) δ ppm 1.54 (d, 3H), 3.41-3.67 (m, 4H), 4.15-4.37 (m, 3H), 6.26 (d, 1H), 7.49 (br s, 2H), 7.52 (s, 2H), 8.05 (d, 1H), 11.95 (br s, 1H) The title compound was separated into its diastereoisomers by preparative chiral HPLC to give stereoisomer 1 (15 mg, see Example 155), stereoisomer 2 (10 mg, see Example 156), stereoisomer 3 (10 mg, see Example 157), stereoisomer 4 (14 mg, see Example 158). For the isolation of stereoisomer 1, stereoisomer 2, stereoisomer 3, and stereoisomer 4 the following method was used.

Analytical HPLC Method:

Instrument: Agilent HPLC 1260; Säule: Chiralpak IA 3µ 100×4.6 mm; Eluent A: Hexane+0.1 Vol % trifluoroacetic acid; Eluent B: 2-Propanol; Isocratic: 75% A+25% B; Flow: 1.4 mL/min;

Temperature: 25° C.; DAD 220 nm

Preparative Chiral-HPLC Method:

Instrument: Labomatic HD5000, Labocord-5000; Gilson GX-241, Labcol Vario 4000, Column: Chiralpak IA 5µ 250×30 mm; Eluent A: Hexane+0.1 Vol % trifluoroacetic acid; Eluent B: 2-Propanol; Isocratic: 75% A+25% B; Flow: 50.0 mL/min; UV 220 nm Example 155, Example 156, Example 157, Example 158

{(5S)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5R)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5R)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol {(5S)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol Example 155

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol
(Single Stereoisomer 1)

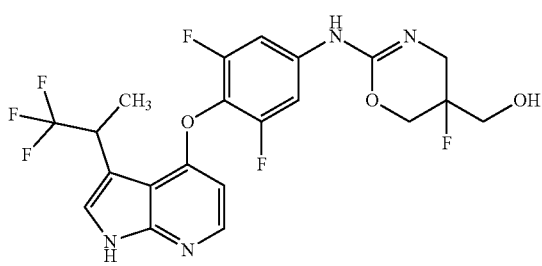 [SMILES: CC(c1c[nH]c2nccc(Oc3c(F)cc(NC4=NCC(F)(CO)CO4)cc3F)c12)C(F)(F)F]

For the preparation of the single diastereomeric title compound and separation into its diastereoisomers, see Example 154.

Analytical chiral HPLC (method see Example 154): $R_t$=3.41 min, de=94.0%

$^1$H NMR (400 MHz, DMSO-d$_6$) δ ppm 1.56 (d, 3H), 2.87-2.98 (m, 1H), 3.62-3.78 (m, 4H), 4.15-4.27 (m, 1H), 4.58-4.81 (m, 1H), 6.34 (d, 1H), 7.46 (br d, 2H), 7.58 (d, 1H), 8.10 (d, 1H), 12.03 (br d, 1H)

Example 156

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol
(Single Stereoisomer 2)

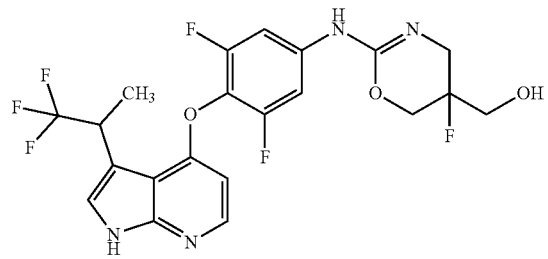 [SMILES: CC(c1c[nH]c2nccc(Oc3c(F)cc(NC4=NCC(F)(CO)CO4)cc3F)c12)C(F)(F)F]

For the preparation of the title compound and separation into its isomers, see Example 154. Analytical chiral HPLC (method see Example 154): $R_t$=5.88 min, de=98.7%

$^1$H NMR (400 MHz, DMSO-d$_6$) δ ppm 1.56 (d, 3H), 2.87-2.98 (m, 1H), 3.62-3.78 (m, 4H), 4.15-4.27 (m, 1H), 4.58-4.81 (m, 1H), 6.34 (d, 1H), 7.46 (br d, 2H), 7.58 (d, 1H), 8.10 (d, 1H), 12.03 (br d, 1H)

Example 157

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol
(Single Stereoisomer 3)

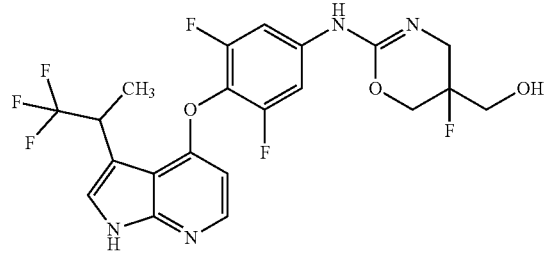 [SMILES: CC(c1c[nH]c2nccc(Oc3c(F)cc(NC4=NCC(F)(CO)CO4)cc3F)c12)C(F)(F)F]

For the preparation of the title compound and separation into its isomers, see Example 154.

Analytical chiral HPLC (method see Example 154): $R_t$=1.88 min, de=99.4%

$^1$H NMR (400 MHz, DMSO-d$_6$) δ ppm 1.56 (d, 3H), 2.87-2.98 (m, 1H), 3.62-3.78 (m, 4H), 4.15-4.27 (m, 1H), 4.58-4.81 (m, 1H), 6.34 (d, 1H), 7.46 (br d, 2H), 7.58 (d, 1H), 8.10 (d, 1H), 12.03 (br d, 1H)

Example 158

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol (Single Stereoisomer 4)

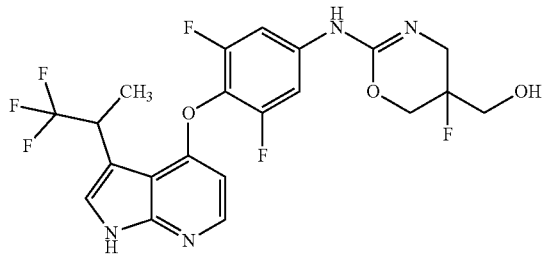 [SMILES: CC(c1c[nH]c2nccc(Oc3c(F)cc(NC4=NCC(F)(CO)CO4)cc3F)c12)C(F)(F)F]

For the preparation of the title compound and separation into its isomers, see Example 154.

Analytical chiral HPLC (method see Example 154): $R_t$=2.56 min, de=99.6%

$^1$H NMR (400 MHz, DMSO-d$_6$) δ ppm 1.56 (d, 3H), 2.87-2.98 (m, 1H), 3.62-3.78 (m, 4H), 4.15-4.27 (m, 1H), 4.58-4.81 (m, 1H), 6.34 (d, 1H), 7.46 (br d, 2H), 7.58 (d, 1H), 8.10 (d, 1H), 12.03 (br d, 1H)

Example 159

(+/−)-[2-(3,5-difluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol

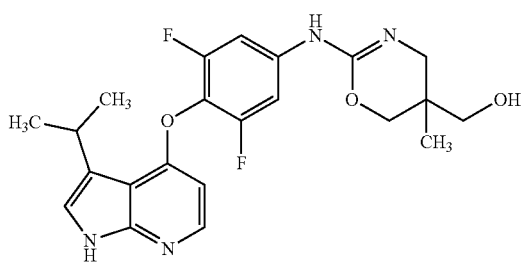

In analogy to Example 119, N-(3,5-difluoro-4-{[3-(propan-2-yl)-1H-pyrrolo[2,3-b]pyridin-4-yl]oxy}phenyl)-N'-[(3-methyloxetan-3-yl)methyl]urea (110 mg, 256 µmol, intermediate 313) was treated with trifluoroacetic acid (200 µL, 2.6 mmol) in dichloromethane (2.0 mL) to afford after preparative HPLC purification the title compound (12 mg, 10% yield).

LC-MS (Method 2): $R_t$=1.09 min; MS (ESIpos): m/z=432 [M+H]$^+$ $^1$H NMR (400 MHz, DMSO-d$_6$) δ ppm 0.90 (br s, 3H), 1.31 (d, 6H), 2.95-3.09 (m, 1H), 3.18-3.36 (m, 4H), 3.87 (br d, 1H), 4.06 (br d, 1H), 4.82 (br s, 1H), 6.17 (d, 1H), 7.14 (d, 1H), 7.56 (br s, 2H), 7.98 (d, 1H), 9.01 (br s, 1H), 11.44 (d, 1H)

Example 160

(+/−)-[2-(3,5-difluoro-4-{[3-(propan-2-yl)-1H-pyrrolo[2,3-b]pyridin-4-yl]oxy}anilino)-5-(propan-2-yl)-5,6-dihydro-4H-1,3-oxazin-5-yl]methanol

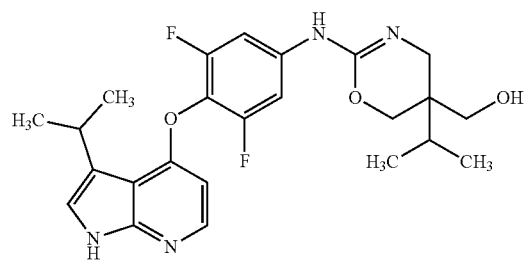 [SMILES: CC(C)c1c[nH]c2nccc(Oc3c(F)cc(NC4=NCC(CO)(C(C)C)CO4)cc3F)c12]

In analogy to Example 119, N-(3,5-difluoro-4-{[3-(propan-2-yl)-1H-pyrrolo[2,3-b]pyridin-4-yl]oxy}phenyl)-N'-{[3-(propan-2-yl)oxetan-3-yl]methyl}urea (110 mg, 240 µmol, intermediate 315) was treated with trifluoroacetic acid (200 µL, 2.6 mmol) in dichloromethane (2.0 mL) to afford after preparative HPLC purification the title compound (17 mg, 15% yield).

LC-MS (Method 2): $R_t$=1.21 min; MS (ESIpos): m/z=460 [M+H]$^+$ $^1$H NMR (400 MHz, DMSO-d$_6$) δ ppm 0.90 (dd, 6H), 1.31 (d, 6H), 1.72-1.82 (m, 1H), 3.07-3.24 (m, 2H), 3.27-3.32 (m, 1H), 3.39 (br d, 2H), 3.97-4.07 (m, 1H), 4.10-4.17 (m, 1H), 4.71 (br s, 1H), 6.17 (d, 1H), 7.14 (d, 1H), 7.57 (br s, 1H), 7.98 (d, 1H), 9.02 (br s, 1H), 11.44 (br d, 1H)

Example 161

N-(3,5-difluoro-4-{[3-(propan-2-yl)-1H-pyrrolo[2,3-b]pyridin-4-yl]oxy}phenyl)-5,5-dimethyl-5,6-dihydro-4H-1,3-oxazin-2-amine

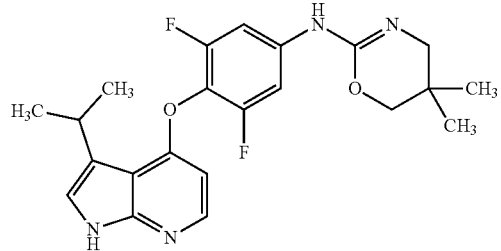 [SMILES: CC(C)c1c[nH]c2nccc(Oc3c(F)cc(NC4=NCC(C)(C)CO4)cc3F)c12]

To a stirred solution of N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-5,5-dimethyl-5,6-dihydro-4H-1,3-oxazin-2-amine (254 mg, 466 µmol, intermediate 317) in dichloromethane (2.0 mL) was added trifluoroacetic acid (1.0 mL, 13 mmol). The mixture was stirred at room temperature overnight, at which time the mixture was basified with a 2M aqueous solution of sodium hydroxide. Ethyl acetate was added and the layers were separated. The aqueous phase was extracted twice with ethyl acetate, and the combined organic layers were washed with brine, dried with sodium sulfate, filtered and evaporated to afford the crude product. The crude material was stirred in a 25% aqueous solution of ammonia for 1 hour, evaporated to dryness and purified by preparative HPLC to afford the title compound (49 mg, 25% yield)

LC-MS (Method 2): R$_f$=1.27 min; MS (ESIpos): m/z=415 [M+H]$^+$ $^1$H NMR (400 MHz, DMSO-d$_6$) δ ppm 0.96 (s, 6H), 1.31 (d, 6H), 3.08 (br s, 2H), 3.28-3.36 (m, 1H), 3.88 (br s, 2H), 6.18 (d, 1H), 7.14 (d, 1H), 7.57 (br s, 1H), 7.98 (d, 1H), 9.02 (br s, 1H), 11.44 (d, 1H)

Example 162

(+/−)—N-(3,5-difluoro-4-{[3-(propan-2-yl)-1H-pyrrolo[2,3-b]pyridin-4-yl]oxy}phenyl)-2,7-dioxa-9-azaspiro[4.5]dec-8-en-8-amine

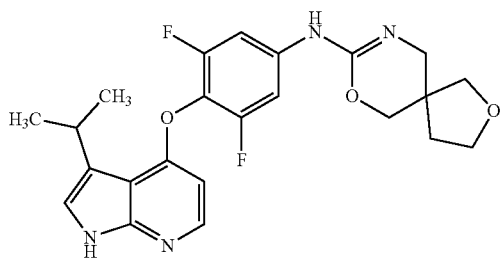 [SMILES: CC(C)c1c[nH]c2nccc(Oc3c(F)cc(NC4=NCC5(CCOC5)CO4)cc3F)c12]

In analogy to Example 119, (+/−)—N-(3,5-difluoro-4-{[3-(propan-2-yl)-1-{[2-(trimethylsilyl)ethoxy]methyl}-1H-pyrrolo[2,3-b]pyridin-4-yl]oxy}phenyl)-2,7-dioxa-9-azaspiro[4.5]dec-8-en-8-amine (260 mg, 454 μmol, intermediate 319) was treated with trifluoroacetic acid (1.0 mL, 13 mmol) in dichloromethane (2.0 mL) to afford after preparative HPLC purification the title compound (21 mg, 9% yield).

LC-MS (Method 2): R$_f$=1.13 min; MS (ESIpos): m/z=443 [M+H]$^+$ $^1$H NMR (400 MHz, DMSO-d$_6$) δ ppm 1.31 (d, 6H), 1.64-1.83 (m, 2H), 3.27-3.32 (m, 2H), 3.42-3.48 (m, 1H), 3.61 (d, 1H), 3.73-3.86 (m, 2H), 4.10 (br s, 2H), 6.17 (d, 1H), 7.14 (d, 1H), 7.57 (br s, 1H), 7.98 (d, 1H), 9.09 (br s, 1H), 11.45 (d, 1H)

Example 163

(+/−)—N-{4-[(3-chloro-1H-pyrrolo[2,3-b]pyridin-4-yl)oxy]-3,5-difluorophenyl}-4-methyl-5,6-dihydro-4H-1,3-thiazin-2-amine

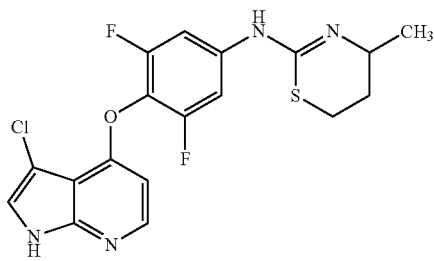 [SMILES: CC1CCSC(Nc2cc(F)c(Oc3ccnc4[nH]cc(Cl)c34)c(F)c2)=N1]

In analogy to example 2, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-4-methyl-5,6-dihydro-4H-1,3-thiazin-2-amine (64.6 mg, 120 μmol, intermediate 321) was stirred with trifluoroacidic acid (4.0 mL, 52 mmol) in dichloromethane (4.0 mL). Ammonia in methanol was added to the crude product and this mixture was stirred overnight at room temperature. Then the mixture was concentrated under reduced pressure and the obtained residue was purified by reverse phase chromatography on Biotage isolera (30 g C-18 column, eluent: 40-80% acetonitrile in ammoniumcarbonate pH 10 aqueous buffer) to give the desired titled compound (21 mg, 41% yield) as a white solid.

$^1$H-NMR (400 MHz, CDCl3) δ [ppm]: 1.30 (d, 3H), 1.64-1.80 (m, 1H+H2O), 2.14-2.23 (m, 1H), 2.95-3.12 (m, 2H), 3.52-3.62 (m, 1H), 6.35 (d, 1H), 6.67-6.75 (m, 2H), 7.20 (s, 1H), 8.12 (d, 1H).

Example 164

N-{4-[(3-chloro-1H-pyrrolo[2,3-b]pyridin-4-yl)oxy]-3,5-difluorophenyl}-5,5-dimethyl-5,6-dihydro-4H-1,3-thiazin-2-amine

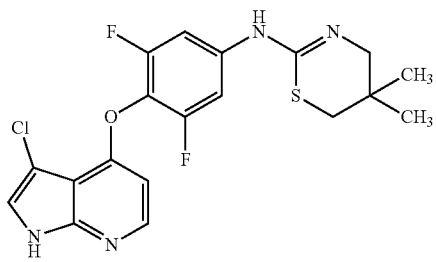 [SMILES: CC1(C)CN=C(Nc2cc(F)c(Oc3ccnc4[nH]cc(Cl)c34)c(F)c2)SC1]

A mixture of N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea (50.0 mg, 87.5 μmol, intermediate 322) in water (4.0 mL), methanol (1.0 mL) and concentrated hydrochloric acid (4.0 mL) was stirred at 80° C. for 18 hours. Then the mixture was basified carefully to pH 9 with saturated sodium hydrogen carbonate aqueous solution and extracted with ethyl acetate (3×). The combined organic layers were dried with magnesium sulfate, filtered and then combined with the crude material from a second experiment using N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2,2-dimethylpropyl)thiourea (55.0 mg, 96 μmol, intermediate 322) under the same conditions. The solvent was evaporated to afford the combined crude product, which was purified by reverse phase chromatography on Biotage isolera (30 g C-18 column, eluent: 30-75% acetonitrile in ammonium carbonate pH 10 aqueous buffer) to give the desired titled compound (8.8 mg, 12% combined yield) as a white solid.

$^1$H-NMR (400 MHz, CDCl3) δ [ppm]: 1.18 (s, 6H), 2.78 (s, 2H), 3.14 (s, 2H), 6.34 (d, 1H), 6.69-6.79 (m, 2H), 7.20 (s, 1H), 8.12 (d, 1H), 9.32 (br s, 1H).

Example 165

(+/−)-(2-{4-[(3-chloro-1H-pyrrolo[2,3-b]pyridin-4-yl)oxy]-3,5-difluoroanilino}-5,6-dihydro-4H-1,3-thiazin-5-yl)methanol

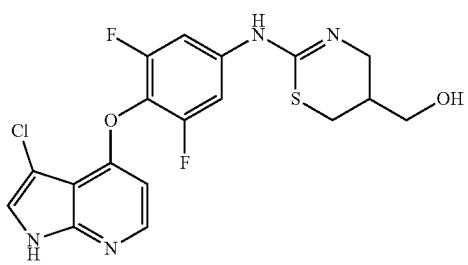 [SMILES: OCC1CN=C(Nc2cc(F)c(Oc3ccnc4[nH]cc(Cl)c34)c(F)c2)SC1]

In analogy to Example 164, (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-[3-hydroxy-2-(hydroxymethyl)propyl]thiourea (30+47.0 mg, 52+82.0 μmol, Intermediate 324) was stirred in water (2.0 mL+2.0 mL), methanol (1.0 mL+1.0 mL) and concentrated hydrochloric acid (2.0 mL+2.0 mL). After purification using a Biotage isolera we obtained 21.1 mg (37% combined yield) of the desired title compound.

$^1$H-NMR (400 MHz, CDCl3) δ [ppm]: 2.06-2.18 (m, 1H), 2.89-2.99 (m, 1H), 3.06-3.15 (m, 1H), 3.18-3.36 (m, 1H), 3.53-3.66 (m, 3H), 6.29-6.36 (m, 1H), 6.73-7.22 (m, 2H), 7.27-7.34 (m, 1H), 7.99-8.06 (m, 1H).

Example 166

(+/−)—N-{4-[(3-chloro-1H-pyrrolo[2,3-b]pyridin-4-yl)oxy]-3,5-difluorophenyl}-5-methyl-5,6-dihydro-4H-1,3-thiazin-2-amine

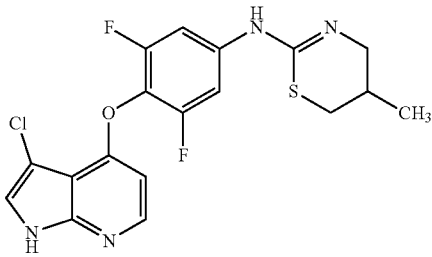 [SMILES: CC1CN=C(Nc2cc(F)c(Oc3ccnc4[nH]cc(Cl)c34)c(F)c2)SC1]

In analogy to Example 164, in one experiment (+/−)—N-{4-[(3-chloro-1-{[2-(trimethylsilyl)ethoxy]methyl}-1H-pyrrolo[2,3-b]pyridin-4-yl)oxy]-3,5-difluorophenyl}-N'-(3-hydroxy-2-methylpropyl)thiourea (141 mg, 253 μmol, intermediate 325) was stirred in water (4.0 mL), methanol (2.0 mL) and concentrated hydrochloric acid (4.0 mL). After purification using a Biotage isolera we obtained 36.8 mg (36% yield) of the desired title compound.

$^1$H-NMR (400 MHz, MeOD-d3) δ [ppm]: 1.06-1.13 (m, 3H), 2.10 (s br, 1H), 2.79-2.88 (m, 1H), 2.98-3.14 (m, 2H), 3.43-3.60 (m, 1H), 6.31-6.35 (m, 1H), 6.70-7.13 (m, 2H), 7.29-7.33 (m, 1H), 8.01-8.06 (m, 1H).

Example 167

N-{4-[(3-chloro-1H-pyrrolo[2,3-b]pyridin-4-yl)oxy]-3,5-difluorophenyl}-6-thia-8-azaspiro[3.5]non-7-en-7-amine

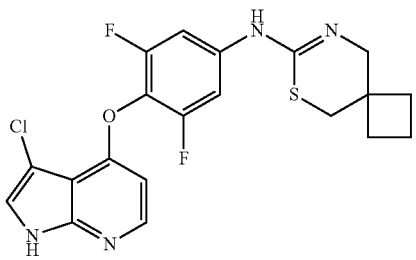 [SMILES: Fc1cc(NC2=NCC3(CCC3)CS2)cc(F)c1Oc1ccnc2[nH]cc(Cl)c12]

In analogy to Example 164, in one experiment N-{4-[(3-chloro-1-{[2-(trimethylsilyl)ethoxy]methyl}-1H-pyrrolo[2,3-b]pyridin-4-yl)oxy]-3,5-difluorophenyl}-N'-{[1-(hydroxymethyl)cyclobutyl]methyl}thiourea (137 mg, 235 μmol, intermediate 326) was stirred in water (3.0 mL), methanol (2.0 mL) and concentrated hydrochloric acid (3.0 mL). After purification using a Biotage isolera we obtained 8.4 mg (8% yield) of the desired title compound.

$^1$H-NMR (400 MHz, DMSO-d6) δ [ppm]: 1.76-1.95 (m, 6H), 2.95-3.34 (m, 3H), 3.58 (s br, 1H), 6.27 (d, 1H), 6.54-6.70 (m, 0.5H), 7.49-7.62 (m, 3H), 8.02-8.11 (m, 1H), 9.00 (s br, 0.5H), 12.07 (s br, 1H)

Example 168

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]oxetan-3-ol

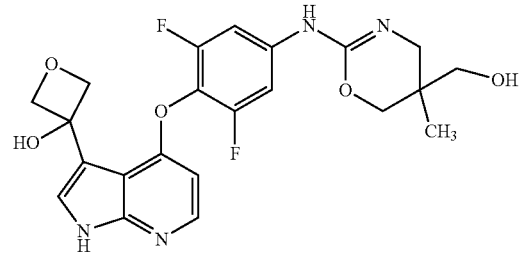 [SMILES: CC1(CO)CN=C(Nc2cc(F)c(Oc3ccnc4[nH]cc(C5(O)COC5)c34)c(F)c2)OC1]

To a solution of (+/−)-3-[1-(benzenesulfonyl)-4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]oxetan-3-ol (177 mg, 295 μmol, intermediate 335) in methanol (10 mL) was added potassium carbonate (163 mg, 1.18 mmol) and the resulting mixture was stirred at room temperature for 6 hours. The mixture was neutralised with 2N hydrochloric acid and the volatiles were removed in vacuo and then the residue freeze dried. The crude product was purified by reverse phase Biotage Isolera to give the desired titled compound (47 mg, 35% yield)

$^1$H-NMR (400 MHz, DMSO-d6) δ [ppm]: 0.84 (s, 3H), 2.94-3.34 (m, 4H), 3.93 (q, 2H), 4.83 (q, 4H), 6.21 (d, 1H), 7.30 (s br, 2H), 7.47 (s, 1H), 8.01 (d, 1H), 11.70 (s br, 1H).

Example 169

(+/−)-[2-(3,5-difluoro-4-{[3-(3-methoxyoxetan-3-yl)-1H-pyrrolo[2,3-b]pyridin-4-yl]oxy}anilino)-5-methyl-5,6-dihydro-4H-1,3-oxazin-5-yl]methanol

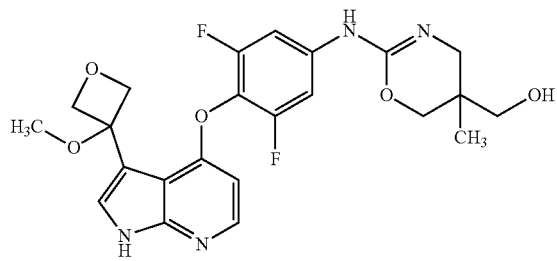 [SMILES: COC1(c2c[nH]c3nccc(Oc4c(F)cc(NC5=NCC(C)(CO)CO5)cc4F)c23)COC1]

In analogy to example 2, N-(3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (211 mg, 349 μmol, Intermediate 341) was stirred with trifluoroacidic acid (2.0 mL, 26 mmol) in dichloromethane (8.0 mL). After purification by reverse phase Biotage Isolera we obtained 52 mg (31% yield) of the desired title compound.

$^1$H-NMR (400 MHz, DMSO-d6) δ [ppm]: 0.87 (s, 3H), 2.92 (s, 3H), 2.94-3.50 (m, 4H), 3.84 & 4.03 (q, 2H), 4.73 & 4.90 (q, 4H), 4.79 (t br, 1H), 6.22 (d, 1H), 7.00-7.60 (s br, 2H), 7.61 (d, 1H), 8.03 (d, 1H), 8.92 (s br, 1H), 11.87 (s br, 1H).

Example 170

3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]oxetan-3-ol

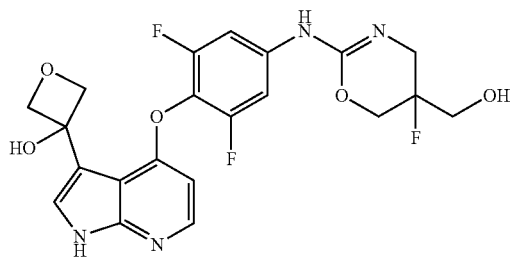 [SMILES: OCC1(F)CN=C(Nc2cc(F)c(Oc3ccnc4[nH]cc(C5(O)COC5)c34)c(F)c2)OC1]

To a solution of N-(3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (367 mg, 617 μmol, intermediate 348) in dichloromethane (16 mL) was added trifluoroacetic acid (4.0 mL, 52 mmol) and the mixture was stirred at room temperature for 4 hours. This mixture was concentrated in vacuo and the resulting crude material was combined with the crude material from a second experiment using N-(3,5-difluoro-4-{[3-(3-hydroxyoxetan-3-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (59.5 mg, 100 μmol intermediate 348) under the same conditions. The combined crude material was purified by reverse phase Biotage Isolera to give again a crude material, which was suspended in dichloromethane and shaken with 0.2N NaOH (2×). The solid at the interface was removed by filtration, washed with water. The filtrate was washed with brine and dried over sodium sulfate, concentrated in vacuo to give the desired titled compound (42 mg) as a white solid.

$^1$H-NMR (400 MHz, DMSO-d6) δ [ppm]: 3.32 (m, 4H), 4.18-4.34 (m, 2H, m), 5.20 (s br, 1H), 5.79 (s, 1H, s), 6.21 (d, 1H), 7.42-7.62 (m, 3H), 8.01 (d, 1H), 9.14 (s br, 1H), 11.69 (s br, 1H).

Example 171

(+/−)-[2-(3,5-difluoro-4-{[3-(3-methoxyoxetan-3-yl)-1H-pyrrolo[2,3-b]pyridin-4-yl]oxy}anilino)-5-fluoro-5,6-dihydro-4H-1,3-oxazin-5-yl]methanol

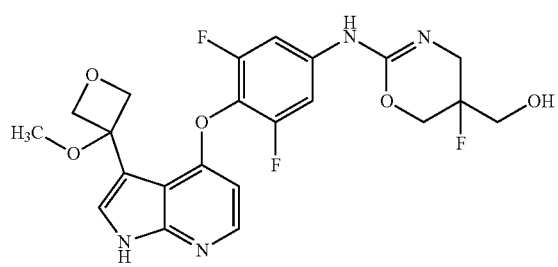 [SMILES: COC1(c2c[nH]c3nccc(Oc4c(F)cc(NC5=NCC(F)(CO)CO5)cc4F)c23)COC1]

In analogy to Example 119, N-(3,5-difluoro-4-{[3-(3-methoxyoxetan-3-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (519 mg, 853 μmol, intermediate 349) was stirred in dichloromethane (16 mL) and trifluoroacetic acid (4.0 mL, 52 mmol). After purification using a Biotage isolera we obtained 36 mg (8.7 yield) of the desired title compound.

$^1$H-NMR (400 MHz, DMSO-d6) δ [ppm]: 2.92 (s, 3H), 3.35-3.65 (m, 4H), 4.20-4.34 (m, 2H), 4.73 & 4.90 (q, 4H), 5.22 (t, 1H), 6.22 (d, 1H), 7.36-7.52 (s br, 2H), 7.63 (d, 1H), 8.03 (d, 1H), 9.14 (s br, 1H), 11.88 (s br, 1H).

Example 172

(+/−)-[2-(4-{[3-(3-ethoxyoxetan-3-yl)-1H-pyrrolo[2,3-b]pyridin-4-yl]oxy}-3,5-difluoroanilino)-5-methyl-5,6-dihydro-4H-1,3-oxazin-5-yl]methanol

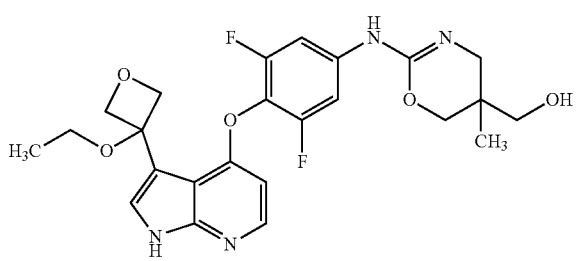 [SMILES: CCOC1(c2c[nH]c3nccc(Oc4c(F)cc(NC5=NCC(C)(CO)CO5)cc4F)c23)COC1]

In analogy to Example 119, N-(4-{[3-(3-ethoxyoxetan-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (339 mg, 548 μmol, intermediate 354) was stirred in dichloromethane (12 mL) and trifluoroacetic acid (4.0 mL, 52 mmol). After purification using a Biotage isolera we obtained 71 mg (27% yield) of the desired title compound.

¹H-NMR (400 MHz, DMSO-d6) δ [ppm]: 0.87 (s, 3H), 0.95 (t, 3H), 2.90-3.34 (m 4H), 3.11 (q, 2H), 3.84 & 4.01 (q, 2H), 4.72 & 4.90 (q, 4H), 4.78 (t br, 1H), 6.20 (d, 1H), 7.00-7.60 (s br, 2H), 7.61 (d, 1H), 8.02 (d, 1H), 8.94 (s br, 1H), 11.83 (s, 1H).

Example 173

(+/−)-{2-[3,5-difluoro-4-({3-[3-(2,2,2-trifluoroethoxy)oxetan-3-yl]-1H-pyrrolo[2,3-b]pyridin-4-yl}oxy)anilino]-5-methyl-5,6-dihydro-4H-1,3-oxazin-5-yl}methanol

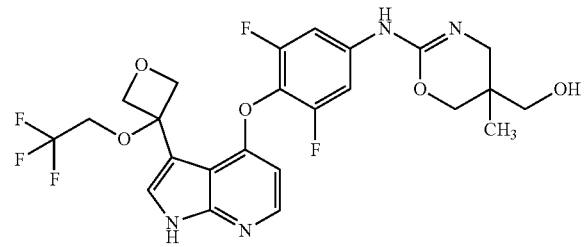 [SMILES: CC1(CO)CN=C(Nc2cc(F)c(Oc3ccnc4[nH]cc(C5(OCC(F)(F)F)COC5)c34)c(F)c2)OC1]

In analogy to Example 119, N-{3,5-difluoro-4-[(3-[3-(2,2,2-trifluoroethoxy)oxetan-3-yl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (80.0 mg, 119 µmol, Intermediate 358) was stirred in dichloromethane (8.0 mL) and trifluoroacetic acid (2.0 mL, 26 mmol). After purification using a Biotage isolera we obtained 28 mg (43% yield) of the desired title compound.

¹H-NMR (400 MHz, DMSO-d6) δ [ppm]: 0.87 (s, 3H), 2.90-3.01 & 3.12-3.33 (m, 4H), 3.72 (q, 2H), 3.84 (d, 1H), 4.03 (d, 1H), 4.79 & 4.94 (m, 5H), 6.24 (d, 1H), 7.30-7.60 (s br, 2H), 7.69 (d, 1H), 8.03 (d, 1H), 8.94 (s br, 1H), 11.99 (s, 1H).

Example 174

(+/−)-(2-{3,5-difluoro-4-[(3-{3-[(propan-2-yl)oxy]oxetan-3-yl}-1H-pyrrolo[2,3-b]pyridin-4-yl)oxy]anilino}-5-methyl-5,6-dihydro-4H-1,3-oxazin-5-yl)methanol

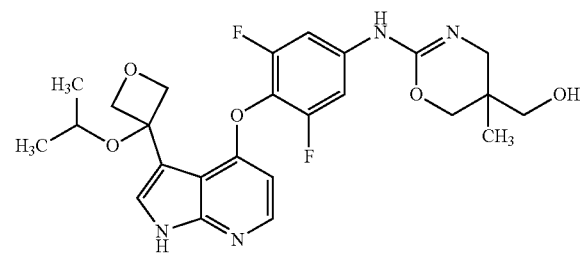 [SMILES: CC(C)OC1(c2c[nH]c3nccc(Oc4c(F)cc(NC5=NCC(C)(CO)CO5)cc4F)c23)COC1]

In analogy to Example 119, N-{3,5-difluoro-4-[(3-{3-[(propan-2-yl)oxy]oxetan-3-yl}-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (174 mg, 275 µmol, intermediate 362) was stirred in dichloromethane (4.0 mL) and trifluoroacetic acid (2.0 mL, 26 mmol). After purification using a Biotage isolera and a subsequent HPLC we obtained 28 mg (19% yield) of the desired title compound.

¹H-NMR (400 MHz, DMSO-d6) δ [ppm]: 0.83-0.90 (m, 9H), 2.96 (d, 1H), 3.15-3.39 (m, 4H), 3.84 & 4.03 (q, 2H), 4.72 & 4.90 (q, 4H), 4.79 (s br, 1H), 6.20 (d, 1H), 7.20-7.40 (s br, 2H), 7.72 (s br, 1H), 8.02 (d, 1H), 11.83 (s br, 1H).

Example 175

(+/−)-4-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]butanenitrile

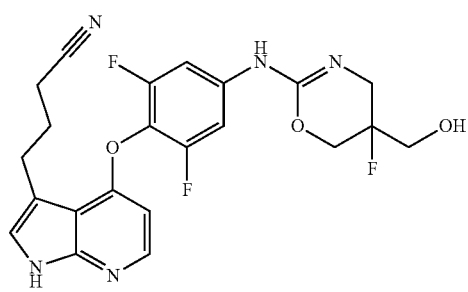 [SMILES: N#CCCCc1c[nH]c2nccc(Oc3c(F)cc(NC4=NCC(F)(CO)CO4)cc3F)c12]

To a stirred solution of N-(4-{[3-(3-cyanopropyl)-1H-pyrrolo[2,3-b]pyridin-4-yl]oxy}-3,5-difluorophenyl)-N'-[(3-fluorooxetan-3-yl)methyl]urea (367 mg, Intermediate 367) in dichloromethane (5 mL) was added trifluoroacetic acid (500 µL, 6.5 mmol) and the resulting mixture was stirred for 1 hour at room temperature. The reaction was quenched by the addition of an aqueous solution of sodium bicarbonate and the layers were separated. The aqueous phase was extracted two times with ethyl acetate and the combined organic layers were passed through a hydrophobic filter. After evaporation of the solvent, the crude material was purified by preparative HPLC purification to afford the title compound (30.0 mg, 12% yield over five steps).

LC-MS (Method 2): $R_t$=0.91 min; MS (ESIpos): m/z=460 [M+H]⁺

¹H NMR (400 MHz, DMSO-d₆) δ ppm 1.92-2.03 (m, 2H), 2.51-2.55 (m, 2H), 2.86-2.96 (m, 2H), 3.38-3.67 (m, 4H), 4.21-4.38 (m, 2H), 5.25 (br t, J=5.70 Hz, 1H), 6.19 (d, J=5.58 Hz, 1H), 7.22 (d, J=2.28 Hz, 1H), 7.57 (d, J=10.10 Hz, 2H), 8.00 (d, J=5.58 Hz, 1H), 9.20 (br s, 1H), 11.55 (d, J=2.28 Hz, 1H).

Example 176

(+/−)-4-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]butanenitrile

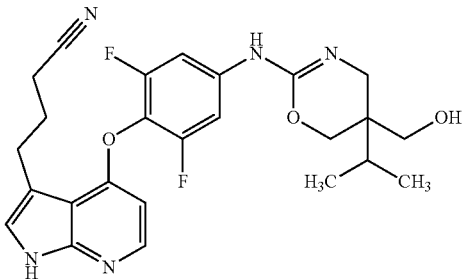 [SMILES: CC(C)C1(CO)CN=C(Nc2cc(F)c(Oc3ccnc4[nH]cc(CCCC#N)c34)c(F)c2)OC1]

In analogy to Example 175, N-(4-{[3-(3-cyanopropyl)-1H-pyrrolo[2,3-b]pyridin-4-yl]oxy}-3,5-difluorophenyl)-N'-{[3-(propan-2-yl)oxetan-3-yl]methyl}urea (302 mg, Intermediate 369) was stirred with trifluoroacetic acid (390 µL, 5.1 mmol) in dichloromethane (4 mL) for 1 hour to afford after preparative HPLC purification the title compound (34.0 mg, 13% yield over five steps).

LC-MS (Method 2): $R_t$=1.04 min; MS (ESIpos): m/z=484 [M+H]$^+$ $^1$H NMR (400 MHz, DMSO-d$_6$) δ ppm 0.90 (dd, J=6.84, 5.58 Hz, 6H), 1.68-1.83 (m, 1H), 1.97 (quin, J=7.29 Hz, 2H), 2.51-2.54 (m, 2H), 2.91 (t, J=7.35 Hz, 2H), 3.15 (br s, 2H), 3.39 (d, J=4.30 Hz, 2H), 3.99-4.19 (m, 2H), 4.71 (br s, 1H), 6.19 (d, J=5.58 Hz, 1H), 7.22 (d, J=2.28 Hz, 1H), 7.55 (br s, 2H), 8.00 (d, J=5.58 Hz, 1H), 9.02 (br s, 1H), 11.54 (d, J=1.77 Hz, 1H).

Example 177

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]butanenitrile

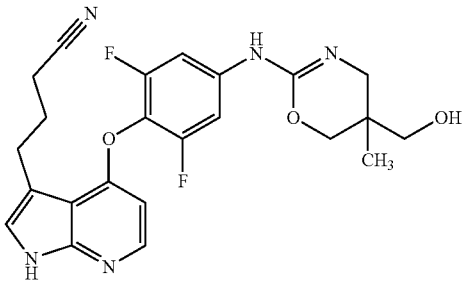 [SMILES: CC1(CO)CN=C(Nc2cc(F)c(Oc3ccnc4[nH]cc(CCCC#N)c34)c(F)c2)OC1]

In analogy to Example 175, N-(4-{[3-(3-cyanopropyl)-1H-pyrrolo[2,3-b]pyridin-4-yl]oxy}-3,5-difluorophenyl)-N'-[(3-methyloxetan-3-yl)methyl]urea (228 mg, Intermediate 371) was stirred with trifluoroacetic acid (310 µL, 4.1 mmol) in dichloromethane (3 mL) for 1 hour to afford after preparative HPLC purification and subsequent preparative thin layer chromatography the title compound (5.0 mg, 2% yield over five steps).

LC-MS (Method 2): $R_t$=0.93 min; MS (ESIneg): m/z=454 [M−H]$^-$ $^1$H NMR (400 MHz, DMSO-d$_6$) δ ppm 0.90 (s, 3H), 1.97 (quin, J=7.90 Hz, 2H), 2.51-2.54 (m, 2H), 2.91 (t, J=7.35 Hz, 2H), 2.97-3.28 (m, 4H), 3.87 (br d, J=10.14 Hz, 1H), 3.99-4.14 (m, 1H), 4.83 (br s, 1H), 6.20 (d, J=5.32 Hz, 1H), 7.22 (d, J=2.28 Hz, 1H), 7.24-7.87 (m, 2H), 8.00 (d, J=5.58 Hz, 1H), 9.02 (br s, 1H), 11.55 (d, J=2.28 Hz, 1H).

Example 178

(+/−)-{(5S)-2-[3,5-difluoro-4-({3-(2-methyloxan-3-yl)-1H-pyrrolo[2,3-b]pyridin-4-yl}oxy)anilino]-5-fluoro-5,6-dihydro-4H-1,3-oxazin-5-yl}methanol-(Mixture of Isomers)

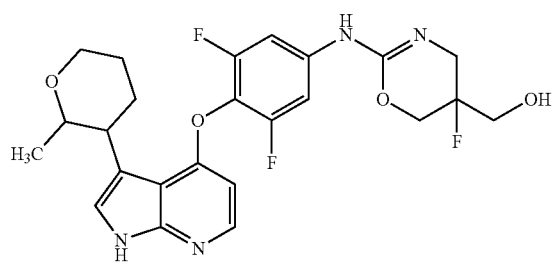 [SMILES: CC1OCCCC1c1c[nH]c2nccc(Oc3c(F)cc(NC4=NCC(F)(CO)CO4)cc3F)c12]

In analogy to Example 175, (+/−)—N-[3,5-difluoro-4-({1-(4-methylbenzene-1-sulfonyl)-3-(2-methyloxan-3-yl)-1H-pyrrolo[2,3-b]pyridin-4-yl}oxy)phenyl]-N'-[(3-fluorooxetan-3-yl)methyl]urea (812 mg, Intermediate 376, mixture of cis- and trans-isomer) accompanied with debrominated azaindole (1:3 mixture) was stirred with trifluoroacetic acid (790 µL, 10 mmol) in dichloromethane (8 mL) for 1 hour to afford after preparative HPLC purification the title compound (26.3 mg, 2% yield over six steps) as a mixture of diastereomers and (+/−)-[2-{3,5-difluoro-4-[(1H-pyrrolo[2,3-b]pyridin-4-yl)oxy]anilino}-5-fluoro-5,6-dihydro-4H-1,3-oxazin-5-yl]methanol (68.1 mg, 8% yield over six steps).

LC-MS (Method 2): $R_t$=0.95 min; MS (ESIpos): m/z=491 [M+H]$^+$ $^1$H NMR (400 MHz, DMSO-d$_6$) δ ppm 0.91-1.06 (m, 3H), 1.56-1.69 (m, 2H), 1.75-2.07 (m, 2H), 2.95 (br s, 1H), 3.36-3.70 (m, 6H), 3.88 (br d, J=11.41 Hz, 1H), 4.20-4.37 (m, 2H), 5.25 (t, J=5.70 Hz, 1H), 6.20 (d, J=5.58 Hz, 1H), 7.28 (d, J=2.53 Hz, 1H), 7.56 (br s, 2H), 7.99 (d, J=5.58 Hz, 1H), 9.21 (br s, 1H), 11.61 (d, J=2.03 Hz, 1H).

Example 179

(+/−)-[2-{3,5-difluoro-4-[(1H-pyrrolo[2,3-b]pyridin-4-yl)oxy]anilino}-5-fluoro-5,6-dihydro-4H-1,3-oxazin-5-yl]methanol

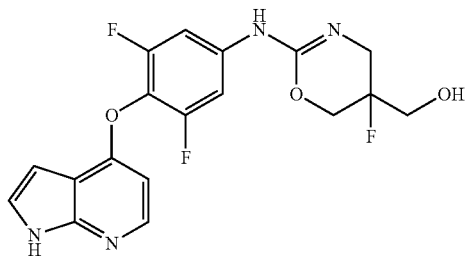 [SMILES: OCC1(F)CN=C(Nc2cc(F)c(Oc3ccnc4[nH]ccc34)c(F)c2)OC1]

The title compound was obtained as reaction product (68.1 mg, 8% yield over six steps) from Example 178.

LC-MS (Method 2): $R_t$=0.87 min; MS (ESIpos): m/z=393 [M+H]$^+$ $^1$H NMR (400 MHz, DMSO-d$_6$) δ ppm 3.37-3.69 (m, 4H), 4.20-4.38 (m, 2H), 5.25 (t, J=5.83 Hz, 1H), 6.27 (dd, J=3.42, 1.90 Hz, 1H), 6.39 (d, J=5.32 Hz, 1H), 7.39 (dd, J=3.30, 2.53 Hz, 1H), 7.54 (br s, 2H), 8.07 (d, J=5.32 Hz, 1H), 9.22 (br s, 1H), 11.82 (br s, 1H).

Example 180

(+/−)-[(5R)-2-[3,5-difluoro-4-({3-(2-methyloxan-3-yl)-1H-pyrrolo[2,3-b]pyridin-4-yl}oxy)anilino]-5-(propan-2-yl)-5,6-dihydro-4H-1,3-oxazin-5-yl]methanol-(Mixture of Isomers)

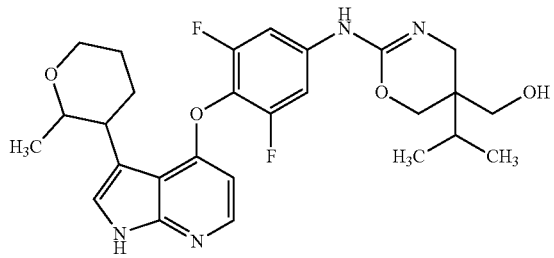 [SMILES: CC1OCCCC1c1c[nH]c2nccc(Oc3c(F)cc(NC4=NCC(CO)(C(C)C)CO4)cc3F)c12]

In analogy to Example 175, (+/−)—N-[3,5-difluoro-4-({3-(2-methyloxan-3-yl)-1H-pyrrolo[2,3-b]pyridin-4-yl}oxy)phenyl]-N'-{[3-(propan-2-yl)oxetan-3-yl]methyl}urea (1.22 g, Intermediate 378, mixture of cis- and trans-isomer) accompanied with debrominated azaindole (1:3 mixture) was stirred with trifluoroacetic acid (1.5 mL, 19 mmol) in dichloromethane (15 mL) for 1 hour to afford after preparative HPLC purification the title compound (45.0 mg, 4% yield over six steps) as a mixture of diastereomers.

LC-MS (Method 2): $R_t$=1.08 min; MS (ESIpos): m/z=515 [M+H]$^+$ $^1$H NMR (400 MHz, DMSO-d$_6$) δ ppm 0.90 (dd, J=6.84, 5.58 Hz, 6H), 0.97 (br d, J=6.08 Hz, 3H), 1.61 (br s, 2H), 1.71-2.06 (m, 3H), 2.85-3.28 (m, 3H), 3.35-3.66 (m, 4H), 3.88 (br d, J=11.66 Hz, 1H), 3.98-4.20 (m, 2H), 4.72 (br s, 1H), 6.20 (d, J=5.32 Hz, 1H), 7.27 (d, J=2.28 Hz, 1H), 7.56 (br s, 2H), 7.99 (d, J=5.58 Hz, 1H), 9.02 (br s, 1H), 11.60 (d, J=1.77 Hz, 1H).

Example 181

(+/−)-[2-(3,5-difluoro-4-{[3-(2-methoxyphenyl)-1H-pyrrolo[2,3-b]pyridin-4-yl]oxy}anilino)-5-methyl-5,6-dihydro-4H-1,3-oxazin-5-yl]methanol

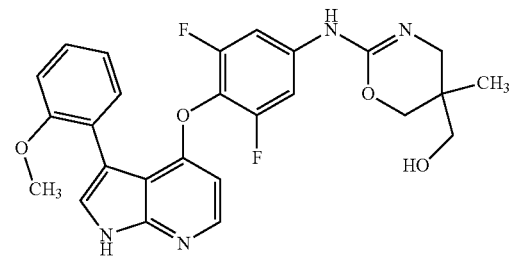 [SMILES: COc1ccccc1-c1c[nH]c2nccc(Oc3c(F)cc(NC4=NCC(C)(CO)CO4)cc3F)c12]

N-(3,5-difluoro-4-{[3-(2-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (300 mg, 480 μmol, intermediate 381) was dissolved in dichloromethane (15 mL) and trifluoroacetic acid (1.6 mL, 21 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was dissolved with dichloromethane and washed with water (×2) and brine (×1), dried with sodium sulfate, filtered and evaporated. The residue was purified by preparative HPLC to yield the title compound (92.4 mg, 37% yield).

LC-MS (Method 2): $R_t$=1.04 min; MS (ESIpos): m/z=495 [M+H]$^+$ $^1$H-NMR (400 MHz, DMSO-d6) δ [ppm]: 0.807 (0.44), 0.892 (6.48), 2.327 (0.58), 2.669 (0.59), 3.013 (0.43), 3.247 (0.92), 3.297 (1.23), 3.310 (1.51), 3.714 (16.00), 3.844 (0.71), 3.869 (0.85), 4.034 (1.70), 4.060 (1.30), 4.815 (0.61), 6.202 (2.13), 6.215 (2.10), 6.900 (1.20), 6.919 (2.50), 6.937 (1.38), 6.995 (2.24), 7.015 (2.65), 7.212 (1.28), 7.216 (1.34), 7.234 (1.85), 7.251 (0.93), 7.255 (0.91), 7.386 (2.22), 7.390 (2.17), 7.405 (5.22), 8.032 (3.12), 8.045 (2.95), 11.896 (1.73).

Example 182

(+/−)-[2-(3,5-difluoro-4-{[3-(3-methoxyphenyl)-1H-pyrrolo[2,3-b]pyridin-4-yl]oxy}anilino)-5-methyl-5,6-dihydro-4H-1,3-oxazin-5-yl]methanol

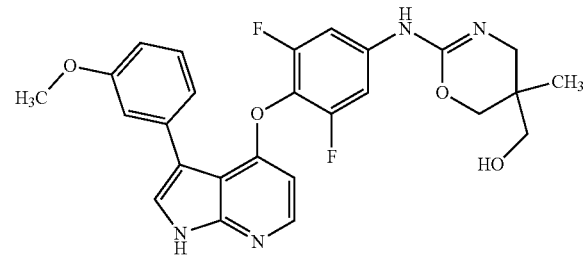

N-(3,5-difluoro-4-{[3-(3-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (235 mg, 376 µmol, intermediate 384) was dissolved in dichloromethane (12 mL) and trifluoroacetic acid (1.2 mL, 16 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was dissolved with dichloromethane and washed with water (×2) and brine (×1), dried with sodium sulfate, filtered and evaporated. The residue was purified by preparative HPLC to yield the title compound (82.0 mg, 42% yield).

LC-MS (Method 2): $R_t$=1.05 min; MS (ESIpos): m/z=945 [M+H]$^+$ $^1$H-NMR (400 MHz, DMSO-d6) δ [ppm]: 0.901 (4.87), 2.326 (0.45), 2.522 (1.42), 2.668 (0.46), 3.257 (0.74), 3.308 (1.02), 3.730 (16.00), 3.859 (0.49), 3.884 (0.58), 4.048 (1.23), 4.074 (0.94), 4.820 (0.46), 6.301 (1.84), 6.315 (1.84), 6.775 (0.84), 6.782 (1.35), 6.790 (1.34), 6.797 (1.24), 6.804 (0.89), 7.252 (4.27), 7.260 (1.97), 7.266 (2.35), 7.281 (2.30), 7.284 (2.47), 7.648 (2.89), 8.082 (2.55), 8.096 (2.42), 12.092 (1.12).

Example 183

(+/−)-[2-(3,5-difluoro-4-{[3-(4-methoxyphenyl)-1H-pyrrolo[2,3-b]pyridin-4-yl]oxy}anilino)-5-methyl-5, 6-dihydro-4H-1,3-oxazin-5-yl]methanol

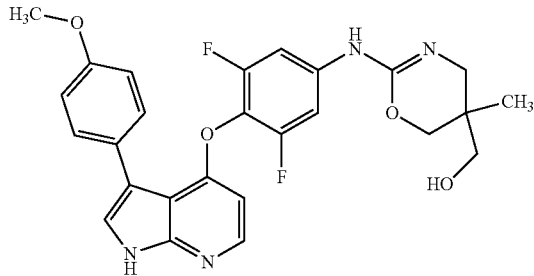

N-(3,5-difluoro-4-{[3-(4-methoxyphenyl)-1-{[2-(trimethylsilyl)ethoxy]methyl}-1H-pyrrolo[2,3-b]pyridin-4-yl]oxy}phenyl)-N'-[(3-methyloxetan-3-yl)methyl]urea (250 mg, 400 µmol, intermediate 387) was dissolved in dichloromethane (13 mL, 200 mmol) and trifluoroacetic acid (1.3 mL, 17 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was dissolved with dichloromethane and washed with water (×2) and brine (×1), dried with sodium sulfate, filtered and evaporated. The residue was purified by preparative HPLC to yield the title compound (88.4 mg, 42% yield).

LC-MS (Method 2): $R_t$=1.04 min; MS (ESIpos): m/z=495 [M+H]$^+$ $^1$H-NMR (400 MHz, DMSO-d6) δ [ppm]: 0.901 (4.22), 2.327 (0.44), 2.522 (0.89), 2.669 (0.44), 3.257 (0.59), 3.308 (0.83), 3.750 (16.00), 3.858 (0.43), 3.883 (0.51), 4.047 (1.10), 4.073 (0.84), 6.275 (1.49), 6.288 (1.50), 6.921 (3.47), 6.943 (3.68), 7.513 (2.27), 7.517 (2.22), 7.576 (3.68), 7.599 (3.23), 8.061 (2.15), 8.075 (2.07), 11.977 (1.09).

Example 184

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N, N-dimethylbenzamide

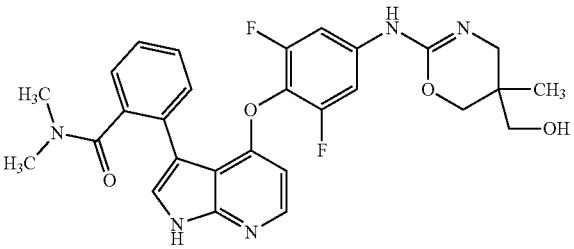 [SMILES: CN(C)C(=O)c1ccccc1-c1c[nH]c2nccc(Oc3c(F)cc(NC4=NCC(C)(CO)CO4)cc3F)c12]

2-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-N,N-dimethylbenzamide (124 mg, 149 µmol, intermediate 390) was dissolved in dichloromethane (4.8 mL, 74 mmol) and trifluoroacetic acid (490 µL, 6.4 mmol) was added. The mixture was stirred under argon overnight at room temperature. The solvent was removed under vacuum, and the residue stirred with acetonitrile (5 mL) and a 33% ammonia solution (2.5 mL) at room temperature for 1 h and then dried again. The residue was dissolved with ethyl acetate and washed with water. The organic phase was dried with sodium sulfate, filtered and dried under vacuum. The crude was then digested with diethyl ether and dichloromethane in an ultrasound bath, and the resulting solid was dried to yield the title compound (51.5 mg, 61% yield).

MS (Method 4) (ESIpos): m/z=536 [M+H]$^+$ $^1$H-NMR (400 MHz, DMSO-d6) δ [ppm]: 0.000 (0.58), 1.012 (10.10), 1.104 (6.04), 1.122 (12.67), 1.140 (6.25), 2.361 (0.70), 2.703 (0.71), 2.818 (14.07), 3.109 (1.27), 3.141 (1.62), 3.336 (2.00), 3.392 (16.00), 3.405 (14.15), 3.422 (8.23), 3.439 (2.99), 4.284 (0.55), 4.311 (0.69), 4.444 (0.76), 4.469 (0.58), 5.140 (0.65), 5.793 (1.02), 6.379 (1.78), 6.393 (1.79), 7.274 (2.88), 7.280 (3.12), 7.305 (2.25), 7.308 (2.24), 7.339 (1.12), 7.358 (2.08), 7.376 (2.88), 7.400 (3.02), 7.419 (1.92), 7.422 (1.84), 7.437 (0.89), 7.441 (0.84), 7.597 (2.05), 7.615 (1.70), 8.166 (2.74), 8.180 (2.59), 12.128 (1.65).

Example 185

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N-methylbenzamide

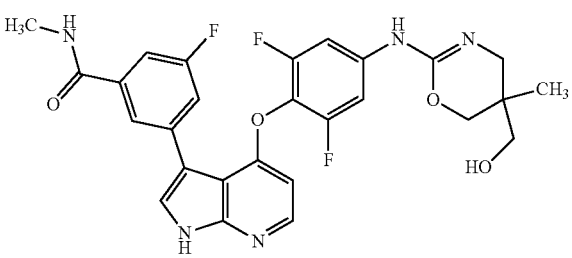

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N-methylbenzamide (75.0 mg, 112 µmol, intermediate 398) was dissolved in dichloromethane (4 mL) and trifluoroacetic acid (390 µL, 5.0 mmol) was added. The mixture was stirred under argon overnight at room temperature. The solvent was removed under vacuum, and the residue stirred with acetonitrile (5 mL) and a 33% ammonia solution (2.5 mL) at room temperature for 1 h and then dried again. The residue was then purified by preparative TLC (dicloromethane:methanol, 80:20) to yield the title compound (10.5 mg, 15% yield).

LC-MS (Method 2): $R_t$=0.91 min; MS (ESIpos): m/z=540 $[M+H]^+$ $^1$H-NMR (400 MHz, DMSO-d6) δ [ppm]: 0.721 (0.89), 0.895 (2.06), 0.900 (3.76), 1.135 (0.93), 1.227 (0.50), 2.082 (0.47), 2.114 (0.42), 2.518 (1.21), 2.523 (0.84), 2.539 (16.00), 2.726 (3.01), 2.778 (4.03), 2.789 (4.03), 2.886 (3.82), 3.228 (0.98), 3.265 (0.58), 3.887 (0.42), 4.047 (0.69), 4.073 (0.53), 6.352 (1.03), 6.366 (0.98), 7.418 (0.63), 7.421 (0.70), 7.424 (0.78), 7.427 (0.67), 7.442 (0.63), 7.445 (0.73), 7.448 (0.77), 7.452 (0.62), 7.609 (0.58), 7.615 (0.70), 7.619 (0.59), 7.639 (0.78), 7.645 (0.66), 7.820 (2.68), 7.948 (0.47), 8.010 (1.24), 8.014 (2.05), 8.017 (1.16), 8.117 (1.96), 8.131 (1.81), 8.517 (0.70), 8.527 (0.74).

Example 186

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N,N-dimethylbenzamide

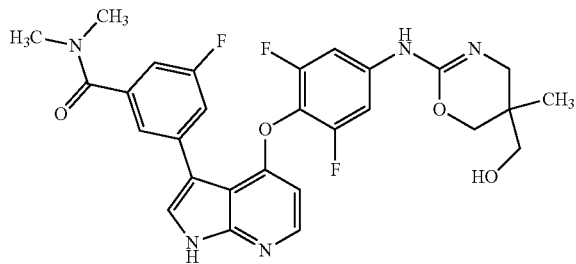

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N,N-dimethylbenzamide (69.0 mg, 101 µmol, intermediate 399) was dissolved in dichloromethane and trifluoroacetic acid (350 µL, 4.5 mmol) was added. The mixture was stirred under argon overnight at room temperature. The solvent was removed under vacuum, and the residue stirred with acetonitrile (10 mL) and a 33% ammonia solution (5 mL) at room temperature for 4 h and then dried again. The residue was purified by preparative HPLC to yield the title compound (6.80 mg, 12% yield).

LC-MS (Method 2): $R_t$=0.94 min; MS (ESIpos): m/z=554 $[M+H]^+$ $^1$H-NMR (400 MHz, DMSO-d6) δ [ppm]: 0.851 (0.60), 0.901 (8.45), 1.232 (1.66), 2.518 (16.00), 2.523 (10.87), 2.673 (3.17), 2.847 (9.66), 2.945 (9.66), 3.259 (1.74), 3.880 (1.06), 4.051 (2.42), 4.076 (1.89), 4.552 (1.06), 4.811 (0.91), 6.358 (4.15), 6.371 (4.08), 7.064 (2.42), 7.069 (3.70), 7.074 (2.64), 7.090 (2.72), 7.093 (2.72), 7.096 (2.42), 7.547 (10.57), 7.552 (10.72), 7.577 (3.40), 7.829 (6.42), 7.835 (6.26), 8.113 (5.58), 8.127 (5.43), 9.034 (0.83), 12.253 (3.62).

Example 187

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N,N-dimethylbenzamide

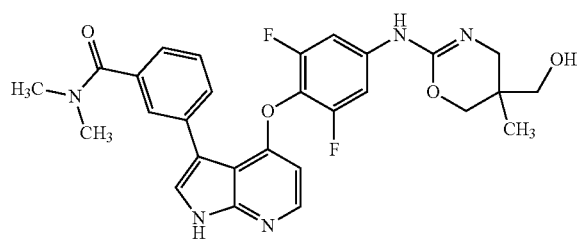 [SMILES: CN(C)C(=O)c1cccc(-c2c[nH]c3nccc(Oc4c(F)cc(NC5=NCC(C)(CO)CO5)cc4F)c23)c1]

3-(4-[2,6-difluoro-4-({[(3-methyloxetan-3-yl)methyl]carbamoyl}amino)phenoxy]-1-{[2-(trimethylsilyl)ethoxy]methyl}-1H-pyrrolo[2,3-b]pyridin-3-yl)-N,N-dimethylbenzamide (54.0 mg, 81.1 µmol, intermediate 393) was dissolved in dichloromethane (2.6 mL) and trifluoroacetic acid (270 µL, 3.5 mmol) was added. The mixture was stirred under argon overnight at room temperature. The solvent was removed under vacuum, and the residue stirred with acetonitrile (1 mL) and a 33% ammonia solution (0.5 mL) at room temperature for 1 h and then dried again. The residue was dissolved with ethyl acetate and washed with water (×2) and brine (×1). The organic phase was dried with sodium sulfate, filtered and dried under vacuum. The crude was then digested with diethyl ether in an ultrasound bath, and the resulting solid was dried to yield the title compound (21.9 mg, 48% yield).

MS (Method 7) (ESIpos): m/z=536 $[M+H]^+$ $^1$H-NMR (400 MHz, DMSO-d6) δ [ppm]: −0.044 (0.66), 0.000 (3.74), 0.884 (1.17), 0.990 (0.95), 1.017 (16.00), 1.048 (0.56), 1.112 (1.72), 1.130 (3.63), 1.147 (1.72), 1.273 (0.90), 1.949 (0.45), 2.115 (1.54), 2.339 (0.50), 2.364 (1.17), 2.369 (1.54), 2.374 (1.14), 2.564 (4.98), 2.706 (1.11), 2.711 (1.56), 2.716 (1.17), 2.907 (5.77), 2.992 (6.01), 3.120 (2.15), 3.153 (2.73), 3.206 (0.72), 3.345 (4.13), 3.412 (7.23), 3.430 (3.68), 3.447 (1.75), 4.268 (0.95), 4.416 (0.85), 5.120 (1.03), 5.800 (7.02), 6.412 (3.05), 6.425 (2.99), 7.272 (2.99), 7.290 (3.44), 7.421 (2.23), 7.449 (4.72), 7.468 (5.56), 7.488 (2.83), 7.727 (6.28), 7.731 (4.32), 7.767 (3.66), 7.771 (3.36), 7.776 (5.80), 7.783 (6.81), 8.175 (5.11), 8.189 (5.01), 12.258 (2.70).

Example 188

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-ethoxypyridine-3-carbonitrile

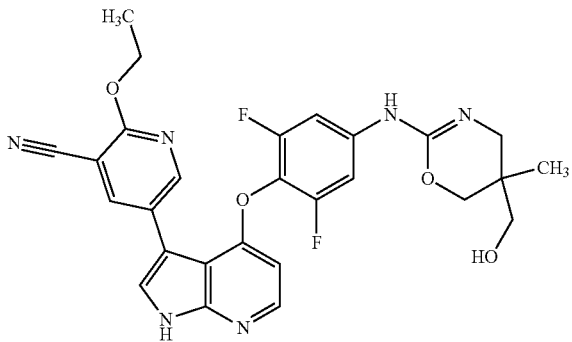 [SMILES: CCOc1ncc(-c2c[nH]c3nccc(Oc4c(F)cc(NC5=NCC(C)(CO)CO5)cc4F)c23)cc1C#N]

N-(4-{[3-(5-cyano-6-ethoxypyridin-3-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (75.0 mg, 113 µmol, intermediate 400) was dissolved in dichloromethane (3.0 mL) and trifluoroacetic acid (390 µL, 5.1 mmol) was added. The mixture was stirred under argon overnight at room temperature. The solvent was removed under vacuum, and the residue stirred with acetonitrile (5 mL) and a 33% ammonia solution (2.5 mL) at room temperature for 1 h and then dried again. The residue was then purified by preparative TLC (dicloromethane:methanol, 80:20) to yield the title compound (10.0 mg, 15% yield).

LC-MS (Method 2): $R_t$=1.08 min; MS (ESIpos): m/z=535 [M+H]$^+$ $^1$H-NMR (400 MHz, DMSO-d6) δ [ppm]: 0.813 (1.03), 0.918 (1.14), 0.993 (12.13), 1.320 (1.20), 1.330 (1.36), 1.361 (1.03), 1.429 (7.32), 1.447 (16.00), 1.465 (7.40), 2.611 (2.87), 2.615 (1.84), 2.632 (9.24), 3.109 (1.00), 3.281 (1.03), 3.320 (2.06), 3.330 (1.25), 3.357 (1.78), 3.381 (1.03), 3.408 (3.42), 3.955 (1.20), 3.980 (1.42), 4.141 (2.00), 4.168 (1.50), 4.525 (2.17), 4.543 (6.98), 4.561 (6.79), 4.578 (2.00), 6.452 (2.53), 6.465 (2.56), 7.897 (8.51), 7.907 (1.00), 8.215 (4.76), 8.229 (4.59), 8.513 (5.87), 8.518 (5.98), 8.810 (6.12), 8.815 (5.23).

Example 189

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluorobenzamide

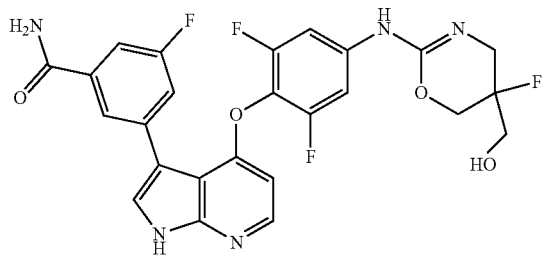 [SMILES: NC(=O)c1cc(F)cc(-c2c[nH]c3nccc(Oc4c(F)cc(NC5=NCC(F)(CO)CO5)cc4F)c23)c1]

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluorobenzamide (72.1 mg, 109 µmol, intermediate 402) was dissolved in dichloromethane (3.0 mL) and trifluoroacetic acid (380 µL, 4.9 mmol) was added. The mixture was stirred under argon overnight at room temperature. The solvent was removed under vacuum, and the residue stirred with acetonitrile (10 mL) and a 33% ammonia solution (5 mL) at room temperature for 4 h and then dried again. The residue was purified by preparative HPLC to yield the title compound (18.2 mg, 30% yield).

LC-MS (Method 2): $R_t$=0.84 min; MS (ESIpos): m/z=530 [M+H]$^+$ $^1$H-NMR (400 MHz, DMSO-d6) δ [ppm]: 1.231 (0.86), 1.751 (0.65), 2.323 (1.82), 2.327 (2.46), 2.522 (16.00), 2.539 (3.68), 2.665 (1.86), 2.669 (2.51), 3.392 (0.78), 3.434 (1.69), 3.483 (1.95), 3.507 (1.12), 3.523 (1.95), 3.538 (1.82), 3.568 (2.72), 3.582 (3.24), 3.598 (1.64), 3.610 (2.72), 3.623 (2.46), 3.640 (0.99), 3.654 (0.82), 4.226 (0.69), 4.256 (2.64), 4.268 (2.42), 4.320 (3.24), 4.353 (0.61), 4.551 (13.23), 5.248 (2.64), 6.352 (5.02), 6.366 (5.02), 7.466 (3.81), 7.469 (3.63), 7.487 (7.14), 7.563 (1.77), 7.613 (3.29), 7.619 (3.63), 7.623 (2.98), 7.643 (3.37), 7.823 (6.75), 7.830 (7.01), 7.941 (0.95), 8.027 (4.41), 8.049 (10.12), 8.116 (8.22), 8.130 (7.74), 8.186 (0.56), 8.200 (0.52), 9.219 (1.43), 12.252 (3.94), 12.257 (4.02).

Example 190

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N-methylbenzamide

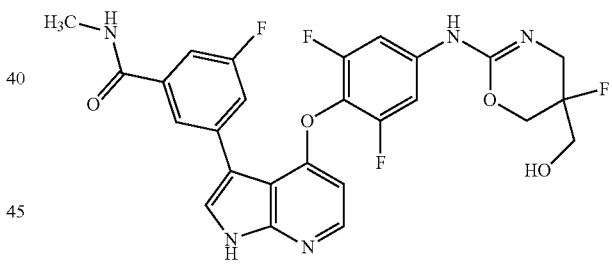

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N-methylbenzamide (87.9 mg, 130 µmol, intermediate 403) was dissolved in dichloromethane (3.0 mL) and trifluoroacetic acid (450 µL, 5.9 mmol) was added. The mixture was stirred under argon overnight at room temperature. The solvent was removed under vacuum, and the residue stirred with acetonitrile (10 mL) and a 33% ammonia solution (5 mL) at room temperature for 4 h and then dried again. The residue was purified by preparative HPLC to yield the title compound (23.9 mg, 32% yield).

LC-MS (Method 2): $R_t$=0.88 min; MS (ESIpos): m/z=544 [M+H]$^+$ $^1$H-NMR (400 MHz, DMSO-d6) δ [ppm]: 1.231 (0.77), 2.332 (1.71), 2.336 (0.73), 2.518 (9.81), 2.523 (6.72), 2.539 (2.81), 2.673 (1.63), 2.678 (0.73), 2.778 (10.83), 2.789 (10.87), 3.434 (0.77), 3.485 (0.90), 3.506 (0.53), 3.522 (0.85), 3.537 (0.90), 3.567 (1.34), 3.581 (1.59), 3.598 (0.77), 3.610 (1.30), 3.623 (1.26), 3.640 (0.45), 3.654 (0.41), 4.256 (1.22), 4.268 (1.14), 4.319 (1.51), 4.552 (16.00), 5.245 (1.18), 6.351 (2.65), 6.365 (2.61), 7.419 (1.47), 7.426 (1.91), 7.429 (1.67), 7.444 (1.34), 7.447 (1.63), 7.449 (1.79), 7.453 (1.59), 7.564 (0.94), 7.608 (1.75), 7.613 (1.91), 7.617 (1.55), 7.633 (1.51), 7.637 (1.67), 7.643 (1.38), 7.821 (3.95), 7.828 (4.03), 7.935 (0.41), 8.012 (3.34), 8.015 (5.70), 8.019 (3.34), 8.117 (4.80), 8.131 (4.48), 8.506 (1.79), 8.517 (1.75), 9.221 (0.77), 12.259 (2.08), 12.264 (2.08).

Example 191

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N,N-dimethylbenzamide

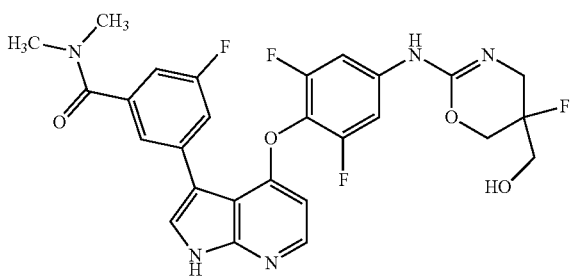 [SMILES: CN(C)C(=O)c1cc(F)cc(-c2c[nH]c3nccc(Oc4c(F)cc(NC5=NCC(F)(CO)CO5)cc4F)c23)c1]

3-(4-[2,6-difluoro-4-({[(3-fluorooxetan-3-yl)methyl]carbamoyl}amino)phenoxy]-1-{[2-(trimethylsilyl)ethoxy]methyl}-1H-pyrrolo[2,3-b]pyridin-3-yl)-5-fluoro-N,N-dimethylbenzamide (104 mg, 152 μmol, intermediate 404) was dissolved in dichloromethane (3.0 mL, 47 mmol) and trifluoroacetic acid (530 μL, 6.8 mmol) was added. The mixture was stirred under argon overnight at room temperature. The solvent was removed under vacuum, and the residue stirred with acetonitrile (10 mL) and a 33% ammonia solution (5 mL) at room temperature for 4 h and then dried again. The residue was purified by preparative HPLC to yield the title compound (25.0 mg, 28% yield).

LC-MS (Method 2): $R_t$=0.92 min; MS (ESIpos): m/z=558 [M+H]$^+$ $^1$H-NMR (400 MHz, DMSO-d6) δ [ppm]: 0.852 (0.51), 1.232 (1.70), 2.518 (16.00), 2.523 (11.91), 2.540 (1.53), 2.678 (1.53), 2.843 (5.28), 2.943 (5.19), 3.441 (0.77), 3.492 (1.02), 3.535 (0.85), 3.583 (1.62), 3.611 (1.19), 3.625 (1.19), 4.228 (0.43), 4.257 (1.02), 4.270 (1.11), 4.321 (1.45), 4.552 (8.68), 5.246 (1.11), 6.358 (2.47), 6.371 (2.38), 7.065 (1.36), 7.070 (2.13), 7.074 (1.70), 7.090 (1.62), 7.093 (1.62), 7.097 (1.53), 7.430 (0.94), 7.447 (0.94), 7.498 (0.43), 7.545 (6.21), 7.550 (6.72), 7.569 (2.47), 7.573 (2.55), 7.601 (1.19), 7.642 (0.68), 7.660 (0.60), 7.673 (0.68), 7.690 (0.60), 7.834 (3.74), 8.113 (4.09), 8.127 (4.09), 8.550 (0.43), 9.231 (1.11), 12.264 (1.79).

Example 192

(+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-ethoxypyridine-3-carboxamide

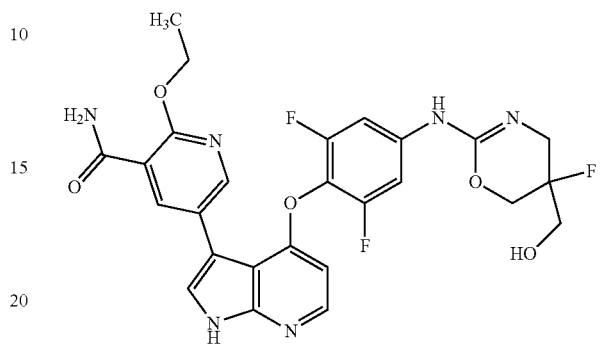

N-(4-{[3-(5-cyano-6-ethoxypyridin-3-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (79.8 mg, 119 μmol, intermediate 405) was dissolved in dichloromethane (3.0 mL, 47 mmol) and trifluoroacetic acid (410 μL, 5.4 mmol) was added. The mixture was stirred under argon overnight at room temperature. The solvent was removed under vacuum, and the residue stirred with acetonitrile (5 mL) and a 33% ammonia solution (2.5 mL) at room temperature for 1 h and then dried again. The residue was then purified by preparative TLC (dicloromethane:methanol, 80:20) to yield the title compound (10.0 mg, 14% yield).

LC-MS (Method 2): $R_t$=1.03 min; MS (ESIpos): m/z=557 [M+H]$^+$ $^1$H-NMR (400 MHz, DMSO-d6) δ [ppm]: 0.833 (0.53), 0.851 (1.07), 1.169 (0.49), 1.183 (0.58), 1.232 (5.30), 1.338 (7.39), 1.355 (16.00), 1.373 (7.59), 1.987 (0.39), 2.005 (0.44), 2.518 (11.38), 2.523 (7.25), 2.540 (1.56), 2.806 (3.02), 2.848 (3.40), 3.599 (3.74), 3.643 (3.79), 4.274 (0.53), 4.304 (2.33), 4.315 (2.38), 4.326 (0.63), 4.346 (0.58), 4.356 (2.24), 4.368 (2.19), 4.399 (0.49), 4.433 (2.19), 4.451 (7.25), 4.469 (7.25), 4.486 (2.09), 6.386 (2.63), 6.400 (2.58), 7.413 (3.45), 7.439 (3.36), 7.819 (5.54), 8.133 (4.86), 8.146 (4.62), 8.422 (6.22), 8.427 (6.27), 8.713 (6.27), 8.719 (5.93), 12.299 (1.07).

Example 193

N-{4-[(3-chloro-1H-pyrrolo[2,3-b]pyridin-4-yl)oxy]-3,5-difluorophenyl}-4,5-dihydro-1H-imidazol-2-amine

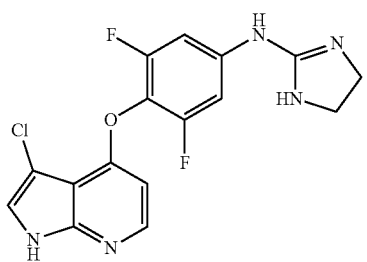 [SMILES: Fc1cc(NC2=NCCN2)cc(F)c1Oc1ccnc2[nH]cc(Cl)c12]

tert-butyl (2-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}ethyl)carbamate (102 mg, 159 µmol, Intermediate 426) and trimethylsilyl iodide (23 µL, 160 µmol) were dissolved in dichloromethane (980 µL) and stirred at room temperature for 1 h. After this time, trifluoroacetic acid (530 µL, 6.8 mmol) was added, and the mixture was stirred overnight at room temperature. The solvent was removed under vacuum and the residue stirred acetonitrile (2 mL) and a 33% ammonia solution (1 mL) at room temperature for 1 h and then dried again. The residue was dissolved with ethyl acetate and washed with water (×2) and brine (×1). The organic phase was dried with sodium sulfate, filtered and dried under vacuum. The crude was then digested with diethyl ether in an ultrasound bath, and the resulting solid was purified by preparative TLC (dichloromethane:methanol, 80:20) and further digested in ether to yield the title compound (18.3 mg, 30% yield).

MS (Method 6) (ESIpos): m/z=364 [M+H]$^+$ $^1$H-NMR (400 MHz, DMSO-d6) δ [ppm]: 3.54 (s, 4H), 6.37 (d, 1H), 7.04 (d, 2H), 7.64 (s, 1H), 8.13 (d, 1H), 12.15 (br s, 1H).

Example 194

(+/−)-[2-(4-{[3-(2,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol

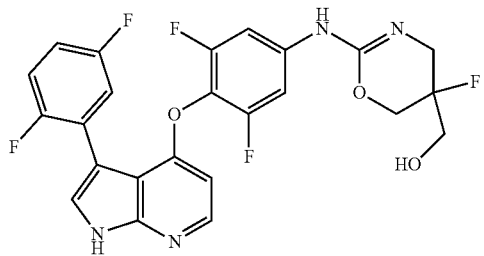 [SMILES: OCC1(F)CN=C(Nc2cc(F)c(Oc3ccnc4[nH]cc(-c5cc(F)ccc5F)c34)c(F)c2)OC1]

N-(4-{[3-(2,5-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (64.0 mg, 101 µmol, intermediate 406) was dissolved in dichloromethane (1 mL) and trifluoroacetic acid (350 µL, 4.5 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (25.7 mg, 48% yield).

LC-MS (Method 2): R$_t$=1.05 min; MS (ESIpos): m/z=505 [M+H]$^+$ $^1$H-NMR (400 MHz, DMSO-d6) δ [ppm]: 1.231 (1.34), 1.751 (1.18), 2.074 (10.96), 2.327 (4.57), 2.331 (3.23), 2.336 (1.42), 2.518 (16.00), 2.523 (10.88), 2.539 (6.78), 2.641 (0.39), 2.669 (4.57), 2.673 (3.23), 2.678 (1.42), 3.386 (0.87), 3.430 (2.21), 3.480 (2.52), 3.502 (1.42), 3.518 (2.36), 3.533 (2.36), 3.564 (4.02), 3.578 (4.57), 3.594 (2.13), 3.606 (3.70), 3.620 (3.47), 3.636 (1.18), 3.650 (1.10), 4.219 (0.87), 4.248 (3.31), 4.261 (3.07), 4.311 (4.41), 4.345 (0.63), 4.552 (7.65), 5.242 (3.23), 6.316 (7.49), 6.329 (7.41), 7.104 (1.34), 7.113 (2.52), 7.122 (2.21), 7.127 (2.60), 7.135 (4.49), 7.144 (3.00), 7.155 (3.47), 7.164 (2.21), 7.259 (3.39), 7.271 (3.47), 7.282 (5.36), 7.294 (5.28), 7.305 (2.84), 7.317 (2.76), 7.381 (3.07), 7.389 (3.55), 7.396 (3.39), 7.405 (5.60), 7.413 (3.23), 7.420 (3.23), 7.428 (2.76), 7.533 (3.07), 7.561 (2.92), 7.664 (9.46), 8.109 (12.85), 8.122 (12.37), 8.131 (0.87), 9.195 (3.15), 12.254 (5.75).

Example 195

(+/−)-[2-(4-{[3-(3,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol

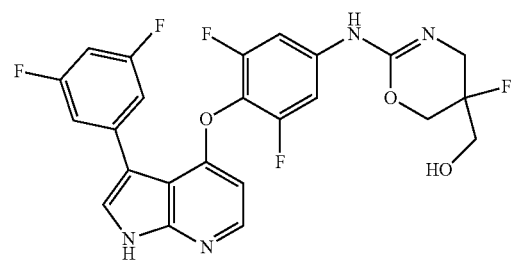 [SMILES: OCC1(F)CN=C(Nc2cc(F)c(Oc3ccnc4[nH]cc(-c5cc(F)cc(F)c5)c34)c(F)c2)OC1]

N-(4-{[3-(3,5-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (40.0 mg, 63.0 µmol, intermediate 407) was dissolved in dichloromethane (1 mL) and trifluoroacetic acid (220 µL, 2.8 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (8.60 mg, 26% yield).

LC-MS (Method 2): R$_t$=1.08 min; MS (ESIpos): m/z=505 [M+H]$^+$ $^1$H-NMR (400 MHz, DMSO-d6) δ [ppm]: 1.231 (0.77), 1.752 (1.88), 2.074 (1.67), 2.331 (2.85), 2.336 (1.32), 2.518 (16.00), 2.523 (10.23), 2.539 (5.50), 2.648 (0.70), 2.673 (2.92), 2.678 (1.32), 3.440 (1.67), 3.490 (2.23), 3.523 (1.74), 3.538 (1.88), 3.569 (2.85), 3.583 (3.62), 3.599 (1.74), 3.611 (2.78), 3.625 (2.78), 3.641 (0.97), 3.655 (0.90), 4.227 (0.63), 4.258 (2.37), 4.269 (2.30), 4.322 (3.20), 4.354 (0.49), 4.552 (0.56), 5.246 (2.43), 6.368 (6.05), 6.382 (5.91), 7.044 (1.25), 7.049 (2.57), 7.055 (1.67), 7.067 (2.57), 7.073 (5.08), 7.079 (3.13), 7.091 (1.32), 7.096 (2.50), 7.102 (1.53), 7.388 (6.05), 7.394 (7.44), 7.412 (7.37), 7.417 (5.91), 7.428 (1.32), 7.579 (2.43), 7.607 (2.37), 7.864 (7.72), 7.869 (7.86), 8.120 (9.81), 8.133 (9.39), 8.142 (0.70), 9.235 (2.64), 12.307 (4.52).

Example 196

(+/−)-[2-(4-{[3-(2,3-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol

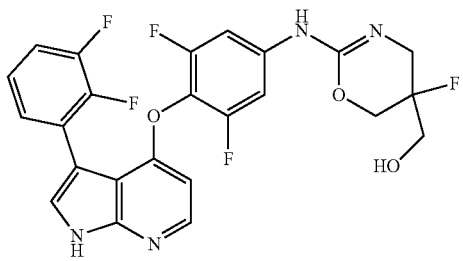 [SMILES: OCC1(F)CN=C(Nc2cc(F)c(Oc3ccnc4[nH]cc(-c5cccc(F)c5F)c34)c(F)c2)OC1]

N-(4-{[3-(2,3-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (51.0 mg, 80.4 µmol, intermediate 408) was dissolved in dichloromethane (1 mL), and trifluoroacetic acid (280 µL, 3.6 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (18.2 mg, 43% yield).

LC-MS (Method 2): $R_t$=1.04 min; MS (ESIpos): m/z=505 [M+H]$^+$ $^1$H-NMR (400 MHz, DMSO-d6) δ [ppm]: 3.425 (4.43), 3.479 (5.00), 3.516 (4.43), 3.532 (4.43), 3.577 (8.14), 3.605 (6.29), 3.618 (5.71), 3.634 (2.14), 3.648 (1.86), 4.246 (5.86), 4.260 (5.71), 4.309 (8.14), 4.552 (9.71), 5.239 (6.00), 6.306 (11.71), 6.319 (11.43), 7.175 (2.43), 7.195 (6.29), 7.209 (6.29), 7.228 (4.00), 7.289 (3.43), 7.308 (6.00), 7.331 (6.00), 7.355 (3.00), 7.376 (6.00), 7.392 (9.00), 7.411 (4.86), 7.523 (6.29), 7.550 (6.14), 7.661 (15.14), 8.108 (16.00), 8.121 (15.29), 9.186 (6.43), 12.256 (10.57).

Example 197

(+/−)-[2-(4-{[3-(2,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol

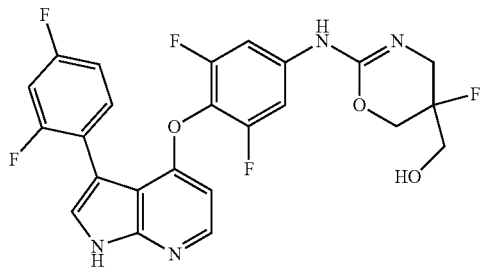 [SMILES: OCC1(F)CN=C(Nc2cc(F)c(Oc3ccnc4[nH]cc(-c5ccc(F)cc5F)c34)c(F)c2)OC1]

N-(4-{[3-(2,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (65.0 mg, 102 µmol, intermediate 409) was dissolved in dichloromethane (1 mL) and trifluoroacetic acid (360 µL, 4.6 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (14.0 mg, 26% yield).

LC-MS (Method 2): $R_t$=0.87 min; MS (ESIpos): m/z=505 [M+H]$^+$ $^1$H-NMR (400 MHz, DMSO-d6) δ [ppm]: 3.425 (1.81), 3.473 (2.00), 3.502 (1.16), 3.516 (2.13), 3.532 (1.94), 3.563 (3.42), 3.568 (3.23), 3.576 (3.42), 3.593 (1.74), 3.604 (3.10), 3.618 (2.77), 3.635 (1.03), 3.649 (0.90), 4.216 (0.77), 4.245 (2.84), 4.258 (2.71), 4.264 (2.65), 4.310 (3.61), 4.344 (0.58), 4.552 (4.39), 5.240 (2.77), 6.279 (6.19), 6.292 (6.13), 7.084 (1.87), 7.090 (2.06), 7.105 (3.94), 7.110 (4.13), 7.112 (4.13), 7.126 (2.13), 7.131 (2.19), 7.247 (2.65), 7.253 (2.71), 7.272 (3.94), 7.278 (3.87), 7.295 (2.84), 7.302 (2.65), 7.348 (0.52), 7.374 (0.45), 7.515 (2.13), 7.543 (2.06), 7.559 (3.94), 7.567 (8.19), 7.574 (9.10), 7.580 (6.26), 7.597 (5.16), 7.602 (3.10), 7.619 (2.39), 8.088 (10.77), 8.102 (10.26), 8.112 (0.97), 9.177 (2.00), 12.155 (5.03), 12.160 (5.16).

Example 198

(+/−)-{2-[4-({3-[4-(difluoromethyl)phenyl]-1H-pyrrolo[2,3-b]pyridin-4-yl}oxy)-3,5-difluoroanilino]-5-fluoro-5,6-dihydro-4H-1,3-oxazin-5-yl}methanol

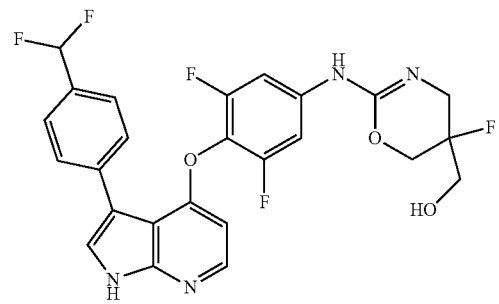 [SMILES: OCC1(F)CN=C(Nc2cc(F)c(Oc3ccnc4[nH]cc(-c5ccc(C(F)F)cc5)c34)c(F)c2)OC1]

N-{4-[(3-[4-(difluoromethyl)phenyl]-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (33.0 mg, 50.9 µmol, intermediate 410) was dissolved in dichloromethane (1 mL), and trifluoroacetic acid (180 µL, 2.3 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound 5.00 mg (95% purity, 18% yield).

LC-MS (Method 2): $R_t$=1.07 min; MS (ESIpos): m/z=519 [M+H]$^+$ $^1$H-NMR (400 MHz, DMSO-d6) δ [ppm]: 3.411 (1.26), 3.461 (1.45), 3.503 (1.49), 3.518 (1.23), 3.549 (1.94), 3.555 (2.19), 3.563 (1.82), 3.570 (1.41), 3.590 (1.82), 3.604 (1.58), 4.235 (1.82), 4.248 (1.45), 4.253 (1.41), 4.291 (1.65), 4.301 (2.18), 5.217 (1.24), 5.232 (2.50), 5.246 (1.21), 5.734 (16.00), 6.314 (3.38), 6.327 (3.36), 6.853 (2.25), 6.992 (4.97), 7.133 (1.92), 7.528 (5.40), 7.549 (6.29), 7.709 (5.17), 7.716 (5.25), 7.781 (6.36), 7.802 (5.17), 8.087 (6.42), 8.101 (6.05), 12.187 (2.80), 12.193 (2.82).

Example 199

(+/−)-[2-(3,5-difluoro-4-{[3-(4-fluoro-3-methoxyphenyl)-1H-pyrrolo[2,3-b]pyridin-4-yl]oxy}anilino)-5-fluoro-5,6-dihydro-4H-1,3-oxazin-5-yl]methanol

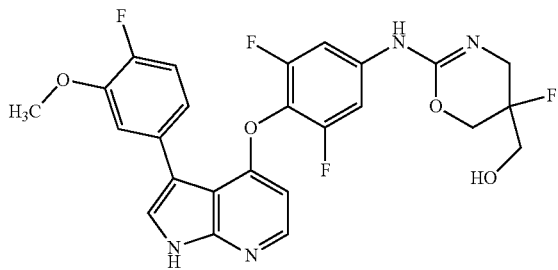 [SMILES: COc1cc(-c2c[nH]c3nccc(Oc4c(F)cc(NC5=NCC(F)(CO)CO5)cc4F)c23)ccc1F]

N-(3,5-difluoro-4-{[3-(4-fluoro-3-methoxyphenyl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (34.0 mg, 52.6 µmol, intermediate 411) was dissolved in dichloromethane (1 mL), and trifluoroacetic acid (180 µL, 2.4 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (5.00 mg, 17% yield).

LC-MS (Method 2): $R_t$=1.06 min; MS (ESIpos): m/z=517 [M+H]$^+$ $^1$H-NMR (400 MHz, DMSO-d6) δ [ppm]: 3.412 (0.63), 3.465 (0.71), 3.558 (1.21), 3.586 (0.92), 3.600 (0.92), 3.779 (16.00), 4.230 (0.79), 4.295 (1.17), 5.220 (0.83), 6.284 (2.00), 6.297 (1.96), 7.165 (3.50), 7.188 (3.92), 7.414 (1.50), 7.436 (1.63), 7.543 (0.83), 7.636 (2.75), 7.643 (2.75), 8.063 (3.25), 8.077 (3.00), 9.199 (0.83), 12.086 (1.46).

Example 200

(+/−)-{2-[3,5-difluoro-4-({3-[3-methoxy-4-(trifluoromethyl)phenyl]-1H-pyrrolo[2,3-b]pyridin-4-yl}oxy)anilino]-5-fluoro-5,6-dihydro-4H-1,3-oxazin-5-yl}methanol

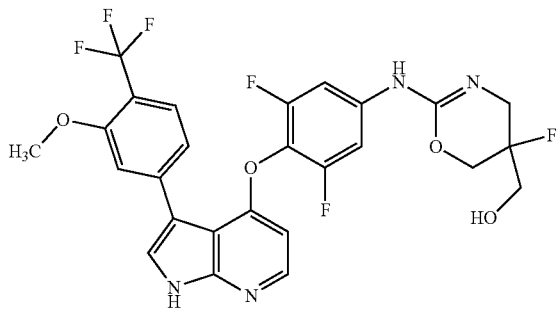 [SMILES: COc1cc(-c2c[nH]c3nccc(Oc4c(F)cc(NC5=NCC(F)(CO)CO5)cc4F)c23)ccc1C(F)(F)F]

N-{3,5-difluoro-4-[(3-[3-methoxy-4-(trifluoromethyl)phenyl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea (67.0 mg, 96.2 µmol, intermediate 412) was dissolved in dichloromethane (1 mL), and trifluoroacetic acid (330 µL, 4.3 mmol) was added. The mixture was stirred under argon overnight at room temperature. The solvent was removed under vacuum, and the residue stirred with acetonitrile (10 mL) and a 33% ammonia solution (5 mL) at room temperature for 2 h and then dried again. The residue was purified by preparative HPLC to yield the title compound (24.3 mg, 42% yield).

LC-MS (Method 2): $R_t$=1.17 min; MS (ESIpos): m/z=567 [M+H]$^+$ $^1$H-NMR (400 MHz, DMSO-d6) δ [ppm]: 3.436 (0.67), 3.489 (0.86), 3.537 (0.73), 3.582 (1.37), 3.610 (1.02), 3.623 (0.99), 3.859 (16.00), 4.268 (0.89), 4.319 (1.34), 5.243 (0.92), 6.359 (2.26), 6.372 (2.26), 7.394 (1.66), 7.414 (1.98), 7.559 (4.02), 7.570 (4.08), 7.590 (3.09), 7.868 (4.88), 8.122 (3.47), 8.136 (3.35), 9.231 (1.15), 12.311 (1.69).

Example 201

N-{4-[(3-chloro-1H-pyrrolo[2,3-b]pyridin-4-yl)oxy]-3,5-difluorophenyl}-1,4,5,6-tetrahydropyrimidin-2-amine

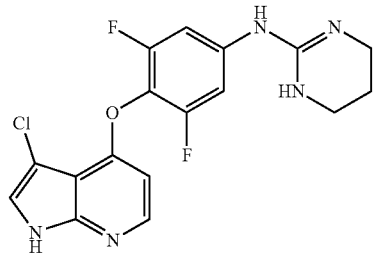 [SMILES: Fc1cc(NC2=NCCCN2)cc(F)c1Oc1ccnc2[nH]cc(Cl)c12]

Tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}propyl)carbamate (153 mg, 233 µmol, Intermediate 428) was dissolved in dichloromethane (3.3 mL) and trifluoroacetic acid (340 µL, 4.4 mmol) was added. The mixture was stirred under argon overnight at room temperature. The solvent was removed under vacuum, and the residue stirred with acetonitrile (1.5 mL) and a 33% ammonia solution (0.75 mL) at room temperature for 1 h and then dried again. The residue was dissolved with dichloromethane and washed with water (×2) and brine (×1), dried with sodium sulfate, filtered and evaporated. The residue was purified by preparative TLC (dichloromethane:methanol, 80:20) and digested in ether in an ultrasound bath to yield the title compound (30.0 mg, 32% yield).

LC-MS (Method 7) (ESIpos): m/z=378 [M+H]$^+$ $^1$H-NMR (400 MHz, DMSO-d6) δ [ppm]: 1.048 (4.72), 1.065 (10.09), 1.083 (4.98), 1.880 (3.83), 3.298 (16.00), 6.372 (3.79), 6.386 (3.79), 7.233 (5.66), 7.255 (5.74), 7.624 (11.49), 8.116 (6.47), 8.130 (6.30), 8.354 (0.30), 12.164 (0.38).

Example 202

(+/−)-{2-[3,5-difluoro-4-({3-[4-(trifluoromethyl)phenyl]-1H-pyrrolo[2,3-b]pyridin-4-yl}oxy)anilino]-5-fluoro-5,6-dihydro-4H-1,3-oxazin-5-yl}methanol

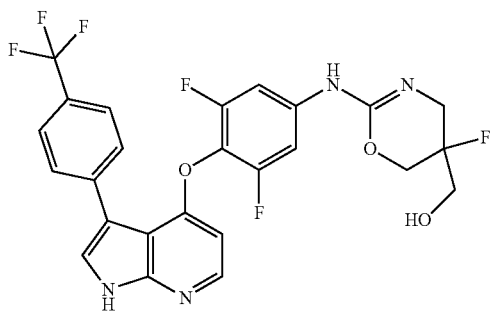 [SMILES: OCC1(F)CN=C(Nc2cc(F)c(Oc3ccnc4[nH]cc(-c5ccc(C(F)(F)F)cc5)c34)c(F)c2)OC1]

N-{3,5-difluoro-4-[(3-[4-(trifluoromethyl)phenyl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea (25.0 mg, 37.5 μmol, intermediate 413) was dissolved in dichloromethane (1 mL), and trifluoroacetic acid (130 μL, 1.7 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (4.10 mg, 19% yield).

LC-MS (Method 2): $R_t$=1.17 min; MS (ESIpos): m/z=537 [M+H]$^+$ $^1$H-NMR (400 MHz, DMSO-d6) δ [ppm]: 3.430 (2.78), 3.481 (3.13), 3.522 (3.13), 3.582 (4.87), 3.610 (4.35), 3.623 (3.83), 4.256 (4.35), 4.323 (4.87), 5.246 (4.52), 6.355 (8.35), 6.368 (8.35), 7.573 (2.26), 7.710 (12.70), 7.731 (16.00), 7.807 (13.22), 7.814 (13.91), 7.887 (15.65), 7.907 (12.35), 8.121 (15.13), 8.135 (15.13), 9.216 (1.57), 12.292 (7.13).

Example 203

(+/−)-[2-(3,5-difluoro-4-{[3-(6-methylpyridazin-4-yl)-1H-pyrrolo[2,3-b]pyridin-4-yl]oxy}anilino)-5-fluoro-5,6-dihydro-4H-1,3-oxazin-5-yl]methanol

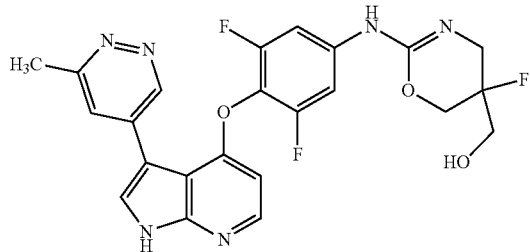 [SMILES: Cc1cc(-c2c[nH]c3nccc(Oc4c(F)cc(NC5=NCC(F)(CO)CO5)cc4F)c23)cnn1]

N-(3,5-difluoro-4-{[3-(6-methylpyridazin-4-yl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (18.0 mg, 29.3 μmol, intermediate 414) was dissolved in dichloromethane (1 mL) and trifluoroacetic acid (100 μL, 1.3 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (3.90 mg, 26% yield).

LC-MS (Method 2): $R_t$=0.79 min; MS (ESIpos): m/z=485 [M+H]$^+$ $^1$H-NMR (400 MHz, DMSO-d6) δ [ppm]: 3.437 (3.69), 3.491 (4.68), 3.585 (5.66), 3.613 (4.43), 4.263 (4.18), 4.328 (5.17), 5.252 (4.92), 6.436 (8.86), 6.450 (8.86), 7.591 (2.46), 7.799 (14.77), 7.804 (15.02), 8.126 (14.03), 8.133 (16.00), 8.169 (15.51), 8.183 (15.26), 9.409 (14.77), 9.414 (15.02), 12.565 (7.38).

Example 204

(+/−)-[2-(4-{[3-(1-cyclopropyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol

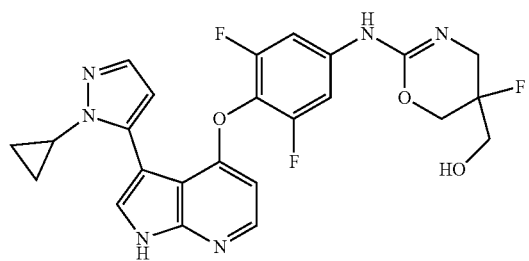 [SMILES: OCC1(F)CN=C(Nc2cc(F)c(Oc3ccnc4[nH]cc(-c5ccnn5C5CC5)c34)c(F)c2)OC1]

N-(4-{[3-(1-cyclopropyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (35.5 mg, 56.5 μmol, intermediate 415) was dissolved in dichloromethane (1 mL), and trifluoroacetic acid (200 μL, 2.5 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (12.4 mg, 42% yield).

LC-MS (Method 2): $R_t$=0.89 min; MS (ESIpos): m/z=499 [M+H]$^+$ $^1$H-NMR (400 MHz, DMSO-d6) δ [ppm]: 0.803 (2.00), 0.816 (6.59), 0.822 (8.47), 0.834 (9.29), 0.840 (7.18), 0.852 (3.53), 0.955 (3.18), 0.965 (9.18), 0.973 (9.41), 0.981 (6.71), 0.994 (2.24), 3.425 (2.59), 3.478 (2.59), 3.517 (2.47), 3.568 (3.88), 3.604 (3.53), 3.705 (2.94), 3.713 (4.00), 3.723 (5.65), 3.732 (3.76), 3.741 (2.71), 4.247 (3.29), 4.312 (4.12), 5.242 (3.53), 6.299 (6.35), 6.313 (6.47), 6.341 (15.29), 6.345 (15.53), 7.363 (16.00), 7.367 (16.00), 7.539 (2.12), 7.694 (9.65), 7.700 (10.00), 8.106 (11.18), 8.120 (10.71), 12.267 (4.82).

Example 205

(+/−)-{2-[3,5-difluoro-4-({3-[1-(propan-2-yl)-3-(trifluoromethyl)-1H-pyrazol-5-yl]-1H-pyrrolo[2,3-b]pyridin-4-yl}oxy)anilino]-5-fluoro-5,6-dihydro-4H-1,3-oxazin-5-yl}methanol

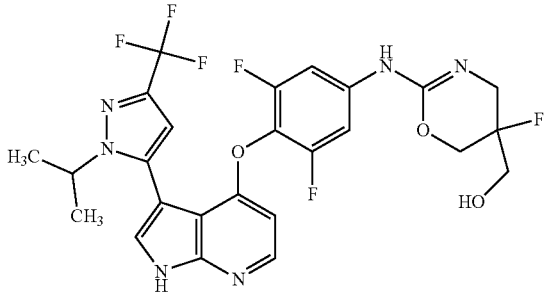 [SMILES: CC(C)n1nc(C(F)(F)F)cc1-c1c[nH]c2nccc(Oc3c(F)cc(NC4=NCC(F)(CO)CO4)cc3F)c12]

N-{3,5-difluoro-4-[(3-[1-(propan-2-yl)-3-(trifluoromethyl)-1H-pyrazol-5-yl]-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea (53.0 mg, 75.9 µmol, intermediate 416) was dissolved in dichloromethane (1 mL), and trifluoroacetic acid (260 µL, 3.4 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (12.4 mg, 27% yield).

LC-MS (Method 2): $R_t$=1.13 min; MS (ESIpos): m/z=569 [M+H]$^+$ $^1$H-NMR (400 MHz, DMSO-d6) δ [ppm]: 1.308 (15.74), 1.324 (16.00), 3.380 (0.37), 3.418 (1.12), 3.467 (1.19), 3.516 (1.00), 3.532 (0.93), 3.561 (1.87), 3.575 (1.38), 3.603 (1.64), 3.617 (1.17), 3.634 (0.44), 3.648 (0.42), 4.250 (1.21), 4.267 (1.05), 4.315 (1.68), 4.612 (0.58), 4.629 (1.54), 4.645 (2.08), 4.662 (1.49), 4.678 (0.54), 5.245 (1.45), 6.325 (3.08), 6.339 (2.99), 6.733 (8.01), 7.520 (0.65), 7.711 (5.21), 7.718 (5.37), 8.136 (5.61), 8.150 (5.35), 12.401 (2.48), 12.407 (2.50).

Example 206

(+/−)-[2-(4-{[3-(1-ethyl-3-methyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol

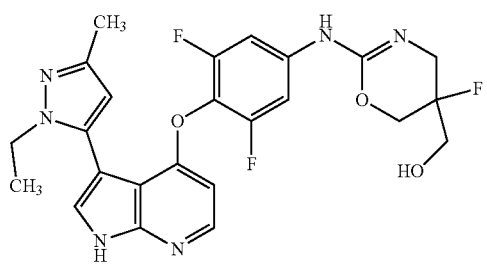 [SMILES: CCn1nc(C)cc1-c1c[nH]c2nccc(Oc3c(F)cc(NC4=NCC(F)(CO)CO4)cc3F)c12]

N-(4-{[3-(1-ethyl-3-methyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (32.0 mg, 50.7 µmol, intermediate 417) was dissolved in dichloromethane (1 mL), and trifluoroacetic acid (180 µL, 2.3 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound 7.80 mg (85% purity, 26% yield).

LC-MS (Method 2): $R_t$=0.92 min; MS (ESIpos): m/z=501 [M+H]$^+$ $^1$H-NMR (400 MHz, DMSO-d6) δ [ppm]: 1.179 (4.82), 1.198 (10.91), 1.215 (4.97), 2.150 (16.00), 3.424 (0.85), 3.473 (0.77), 3.516 (0.82), 3.532 (0.75), 3.563 (1.25), 3.576 (1.12), 3.592 (0.62), 3.604 (1.10), 3.618 (0.90), 3.648 (0.32), 3.969 (1.17), 3.987 (3.67), 4.005 (3.67), 4.023 (1.10), 4.247 (1.07), 4.258 (0.90), 4.313 (1.22), 5.229 (0.67), 5.243 (1.25), 5.258 (0.62), 6.063 (6.46), 6.281 (2.10), 6.295 (2.05), 7.531 (4.12), 7.538 (4.19), 8.097 (3.64), 8.111 (3.54), 12.218 (1.65), 12.224 (1.65).

Example 207

N-{4-[(3-chloro-1H-pyrrolo[2,3-b]pyridin-4-yl)oxy]-3,5-difluorophenyl}-5-methyl-1,4,5,6-tetrahydropyrimidin-2-amine

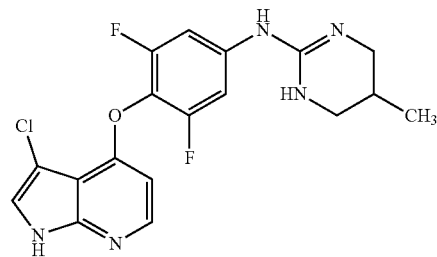 [SMILES: CC1CN=C(Nc2cc(F)c(Oc3ccnc4[nH]cc(Cl)c34)c(F)c2)NC1]

Tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2-methylpropyl)carbamate (239 mg, 357 µmol, Intermediate 430) was dissolved in dichloromethane (5.0 mL) and trifluoroacetic acid (1.2 mL, 16 mmol) was added. The mixture was stirred for 4 h at room temperature. The crude was concentrated under vacuum, dissolved in acetonitrile and stirred with a 33% ammonia solution for 3 h. The solvent was evaporated under vacuum and the crude purified by HPLC to yield the title compound (48.4 mg, 31% yield).

LC-MS (Method 2): $R_t$=1.27 min; MS (ESIpos): m/z=392 [M+H]$^+$ $^1$H-NMR (400 MHz, DMSO-d6) δ [ppm]: 0.94 (d, 3H), 1.94 (m, 1H), 2.79 (dd, 2H), 3.20 (dd, 2H), 6.37 (d, 1H), 6.67 (d, 2H), 7.58 (s, 1H), 8.10 (d, 1H).

Example 208

N-{4-[(3-chloro-1H-pyrrolo[2,3-b]pyridin-4-yl)oxy]-3,5-difluorophenyl}-5,5-dimethyl-1,4,5,6-tetrahydropyrimidin-2-amine

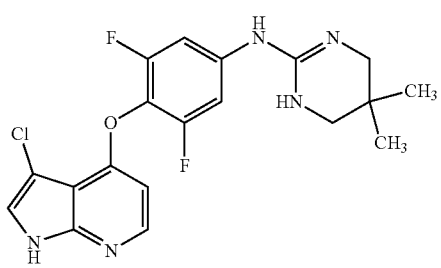 [SMILES: CC1(C)CN=C(Nc2cc(F)c(Oc3ccnc4[nH]cc(Cl)c34)c(F)c2)NC1]

Tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2,2-dimethylpropyl)carbamate (253 mg, 370 µmol, Intermediate 432) was dissolved in dichloromethane (5.0 mL) and trifluoroacetic acid (1.3 mL, 17 mmol) was added. The mixture was stirred for 4 h at room temperature. The crude was concentrated under vacuum, dissolved in acetonitrile and stirred with a 33% ammonia solution for 3 h. The solvent was evaporated under vacuum and the crude purified by HPLC to yield the title compound (26.1 mg, 16% yield).

LC-MS (Method 2): $R_t$=1.30 min; MS (ESIpos): m/z=406 [M+H]$^+$ $^1$H-NMR (400 MHz, DMSO-d6) δ [ppm]: 0.99 (s, 6H), 2.87 (s, 4H), 6.38 (d, 1H), 6.72 (d, 2H), 7.60 (s, 1H), 8.11 (d, 1H).

Example 209

N-{4-[(3-chloro-1H-pyrrolo[2,3-b]pyridin-4-yl)oxy]-3,5-difluorophenyl}-6,6-dimethyl-1,4,5,6-tetrahydropyrimidin-2-amine

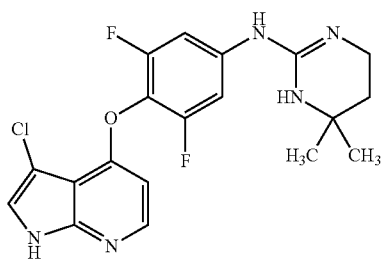 [SMILES: CC1(C)CCN=C(Nc2cc(F)c(Oc3ccnc4[nH]cc(Cl)c34)c(F)c2)N1]

Tert-butyl (4-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2-methylbutan-2-yl)carbamate (228 mg, 333 µmol, Intermediate 434) was dissolved in dichloromethane (5.0 mL) and trifluoroacetic acid (1.2 mL, 15 mmol) was added. The mixture was stirred for 4 h at room temperature. The crude was concentrated under vacuum, dissolved in acetonitrile and stirred with a 33% ammonia solution for 3 h. The resulting material was further purified by preparative TLC (dicloromethane:methanol, 80:20) and HPLC to yield the title compound (27.6 mg, 19% yield).

LC-MS (Method 2): $R_t$=1.31 min; MS (ESIneg): m/z=404 [M–H]$^-$ $^1$H-NMR (400 MHz, DMSO-d6) δ [ppm]: 1.19 (s, 6H), 1.63 (dd, 2H), 3.20 (dd, 2H), 6.36 (m, 1H), 6.62 (m, 2H), 7.59 (s, 1H), 8.11 (d, 1H).

Example 210

(+/−)-[2-(4-{[3-(1,3-dimethyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol

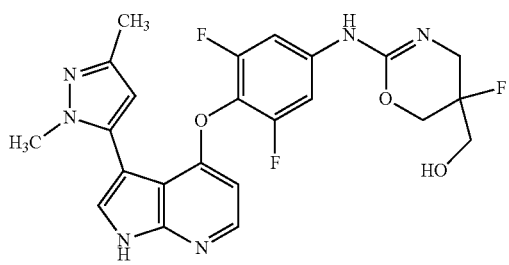 [SMILES: Cc1cc(-c2c[nH]c3nccc(Oc4c(F)cc(NC5=NCC(F)(CO)CO5)cc4F)c23)n(C)n1]

N-(4-{[3-(1,3-dimethyl-1H-pyrazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (45.0 mg, 73.0 µmol, intermediate 418) was dissolved in dichloromethane (1 mL) and trifluoroacetic acid (250 µL, 3.3 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (3.40 mg, 9% yield).

LC-MS (Method 2): $R_t$=0.85 min; MS (ESIpos): m/z=487 [M+H]$^+$ $^1$H-NMR (400 MHz, DMSO-d6) δ [ppm]: 2.132 (13.03), 3.431 (0.48), 3.485 (0.57), 3.503 (0.38), 3.518 (0.51), 3.532 (0.52), 3.564 (0.87), 3.578 (1.01), 3.594 (0.49), 3.606 (0.80), 3.620 (0.79), 3.636 (0.29), 3.650 (0.29), 3.679 (16.00), 4.249 (0.71), 4.261 (0.68), 4.311 (0.93), 5.242 (0.72), 6.092 (5.12), 6.295 (1.67), 6.309 (1.64), 7.543 (0.66), 7.576 (3.11), 7.582 (2.98), 8.102 (2.91), 8.116 (2.72), 9.207 (0.75), 12.234 (1.29).

Example 211

(+/−)-{2-[4-({3-[1-ethyl-3-(trifluoromethyl)-1H-pyrazol-5-yl]-1H-pyrrolo[2,3-b]pyridin-4-yl}oxy)-3,5-difluoroanilino]-5-fluoro-5,6-dihydro-4H-1,3-oxazin-5-yl}methanol

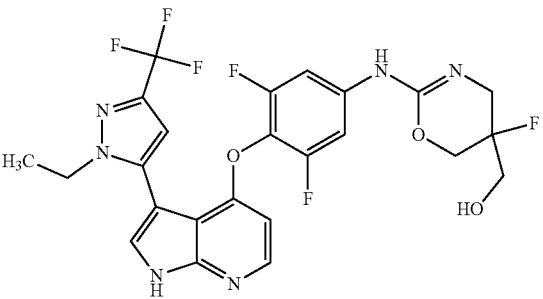 [SMILES: CCn1nc(C(F)(F)F)cc1-c1c[nH]c2nccc(Oc3c(F)cc(NC4=NCC(F)(CO)CO4)cc3F)c12]

N-{4-[(3-[1-ethyl-3-(trifluoromethyl)-1H-pyrazol-5-yl]-1-{[2-(trimethylsilyl)ethoxy]methyl}-1H-pyrrolo[2,3-b]pyridin-4-yl)oxy]-3,5-difluorophenyl}-N'-[(3-fluorooxetan-3-yl)methyl]urea (50.0 mg, 73.0 µmol, intermediate 419) was dissolved in dichloromethane (1 mL), and trifluoroacetic acid (250 µL, 3.3 mmol) was added. The mixture was stirred under argon overnight at 35° C. The solvent was removed under vacuum, and the residue stirred with acetonitrile (10 mL) and a 33% ammonia solution (5 mL) at room temperature for 1 h and then dried again. The residue was purified by preparative HPLC to yield the title compound (17.0 mg, 40% yield).

LC-MS (Method 2): $R_t$=1.07 min; MS (ESIpos): m/z=555 [M+H]$^+$ $^1$H-NMR (400 MHz, DMSO-d6) δ [ppm]: 1.258 (7.20), 1.276 (16.00), 1.295 (7.26), 3.426 (0.87), 3.477 (0.96), 3.516 (0.90), 3.530 (0.90), 3.575 (1.73), 3.603 (1.41), 3.618 (1.35), 3.648 (0.45), 4.162 (1.57), 4.180 (4.92), 4.198 (4.85), 4.216 (1.83), 4.246 (1.25), 4.258 (1.19), 4.310 (1.64), 5.240 (1.22), 6.341 (2.99), 6.354 (2.92), 6.754 (7.68), 7.531 (1.22), 7.561 (1.19), 7.738 (3.95), 8.142 (4.98), 8.156 (4.69), 9.204 (1.32), 12.416 (2.28).

Example 212

(+/−)-[2-{3,5-difluoro-4-[(3-{2-fluoro-6-[(propan-2-yl)oxy]phenyl}-1H-pyrrolo[2,3-b]pyridin-4-yl)oxy]anilino}-5-fluoro-5,6-dihydro-4H-1,3-oxazin-5-yl]methanol

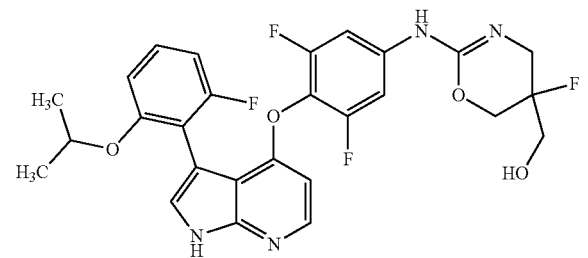 [SMILES: CC(C)Oc1cccc(F)c1-c1c[nH]c2nccc(Oc3c(F)cc(NC4=NCC(F)(CO)CO4)cc3F)c12]

N-{3,5-difluoro-4-[(3-{2-fluoro-6-[(propan-2-yl)oxy]phenyl}-1-{[2-(trimethylsilyl)ethoxy]methyl}-1H-pyrrolo[2,3-b]pyridin-4-yl)oxy]phenyl}-N'-[(3-fluorooxetan-3-yl)methyl]urea (55.0 mg, 81.5 µmol, intermediate 420) was dissolved in dichloromethane (1 mL) and trifluoroacetic acid (280 µL, 3.7 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was purified by preparative HPLC to yield the title compound (15.5 mg, 33% yield).

LC-MS (Method 2): $R_t$=1.12 min; MS (ESIpos): m/z=545 [M+H]$^+$ $^1$H-NMR (400 MHz, DMSO-d6) δ [ppm]: 1.084 (15.13), 1.099 (16.00), 1.175 (14.66), 1.191 (15.29), 3.410 (1.46), 3.461 (1.30), 3.510 (1.26), 3.524 (1.18), 3.556 (2.17), 3.570 (1.89), 3.598 (1.93), 3.611 (1.46), 4.234 (1.77), 4.253 (1.62), 4.298 (2.36), 4.483 (0.87), 4.498 (2.25), 4.514 (3.00), 4.529 (2.25), 4.543 (0.91), 4.552 (1.54), 5.226 (0.95), 5.239 (1.58), 5.253 (0.95), 6.197 (3.31), 6.211 (3.27), 6.752 (1.89), 6.773 (3.82), 6.794 (2.05), 6.866 (3.43), 6.887 (3.90), 7.201 (1.66), 7.218 (2.13), 7.222 (3.15), 7.239 (3.27), 7.242 (1.85), 7.260 (1.54), 7.363 (5.64), 7.369 (5.56), 7.462 (1.30), 7.495 (1.85), 8.034 (6.27), 8.047 (5.99), 9.134 (1.22), 11.959 (2.80), 11.964 (2.72).

Example 213

(+/−)-[2-(3,5-difluoro-4-{[3-(2-fluoro-3-methoxyphenyl)-1H-pyrrolo[2,3-b]pyridin-4-yl]oxy}anilino)-5-fluoro-5,6-dihydro-4H-1,3-oxazin-5-yl]methanol

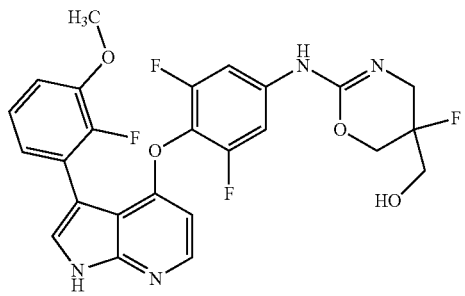 [SMILES: COc1cccc(-c2c[nH]c3nccc(Oc4c(F)cc(NC5=NCC(F)(CO)CO5)cc4F)c23)c1F]

N-(3,5-difluoro-4-{[3-(2-fluoro-3-methoxyphenyl)-1-{[2-(trimethylsilyl)ethoxy]methyl}-1H-pyrrolo[2,3-b]pyridin-4-yl]oxy}phenyl)-N'-[(3-fluorooxetan-3-yl)methyl]urea (50.0 mg, 77.3 µmol, intermediate 421) was dissolved in dichloromethane (1 mL), and trifluoroacetic acid (270 µL, 3.5 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was purified by preparative HPLC to yield the title compound (3.10 mg, 7% yield).

LC-MS (Method 2): $R_t$=1.02 min; MS (ESIpos): m/z=517 [M+H]$^+$ $^1$H-NMR (400 MHz, DMSO-d6) δ [ppm]: 3.422 (0.57), 3.472 (0.64), 3.487 (0.39), 3.503 (0.39), 3.518 (0.66), 3.533 (0.57), 3.564 (1.03), 3.570 (1.05), 3.578 (0.86), 3.585 (0.67), 3.594 (0.50), 3.606 (0.93), 3.620 (0.73), 3.636 (0.29), 3.650 (0.27), 3.673 (0.07), 3.731 (0.17), 3.828 (16.00), 4.217 (0.21), 4.247 (0.85), 4.259 (0.73), 4.265 (0.72), 4.313 (1.07), 4.344 (0.16), 5.234 (0.53), 5.248 (0.99), 5.262 (0.50), 6.272 (1.72), 6.286 (1.68), 7.030 (0.43), 7.039 (0.50), 7.047 (0.82), 7.055 (1.23), 7.068 (1.02), 7.074 (1.06), 7.082 (1.27), 7.101 (3.15), 7.109 (1.38), 7.118 (2.58), 7.123 (1.39), 7.129 (1.17), 7.142 (0.43), 7.148 (0.29), 7.509 (0.42), 7.551 (2.19), 7.555 (2.16), 8.084 (3.11), 8.097 (2.89), 9.181 (0.34), 12.143 (1.35), 12.149 (1.35).

Example 214

N-{4-[(3-chloro-1H-pyrrolo[2,3-b]pyridin-4-yl)oxy]-3,5-difluorophenyl}-5,5-difluoro-1,4,5,6-tetrahydropyrimidin-2-amine

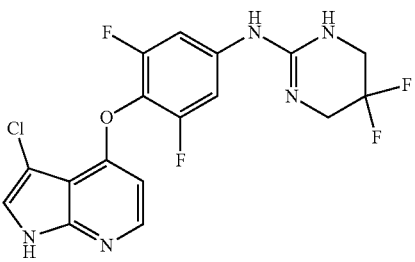 [SMILES: Fc1cc(NC2=NCC(F)(F)CN2)cc(F)c1Oc1ccnc2[nH]cc(Cl)c12]

Tert-butyl (3-{(Z/E)-[{4-[(3-chloro-1-{[2-(trimethylsilyl)ethoxy]methyl}-1H-pyrrolo[2,3-b]pyridin-4-yl)oxy]-3,5-difluoroanilino}(methylsulfanyl)methylidene]amino}-2,2-difluoropropyl)carbamate (315 mg, 454 µmol, Intermediate 436) was dissolved in dichloromethane (15 mL) and trifluoroacetic acid (1.5 mL, 20 mmol) was added. The mixture was stirred under argon overnight at room temperature. The solvent was removed under vacuum and the residue stirred acetonitrile (2 mL) and a 33% ammonia solution (1 mL) at room temperature for 1 h and then dried again. The residue was dissolved with ethyl acetate and washed with water (×2) and brine (×1). The organic phase was dried with sodium sulfate, filtered and dried under vacuum. The crude was then purified by preparative TLC (dichloromethane:methanol, 90:10; then 50:50) and further digested in ether to yield the title compound (63.7 mg, 32% yield).

LC-MS (Method 1): $R_t$=0.86 min; MS (ESIpos): m/z=414 [M+H]$^+$ $^1$H-NMR (400 MHz, DMSO-d6) δ [ppm]: 3.70 (t, 4H), 6.39 (d, 1H), 7.29 (m, 2H), 7.63 (s, 1H), 8.13 (d, 1H), 8.88 (br s, 2H), 12.17 (br s, 1H).

Example 215

(+/−)-[2-(4-{[3-(2-chloro-1-methyl-1H-imidazol-5-yl)-1H-pyrrolo[2,3-b]pyridin-4-yl]oxy}-3,5-difluoroanilino)-5-fluoro-5,6-dihydro-4H-1,3-oxazin-5-yl]methanol

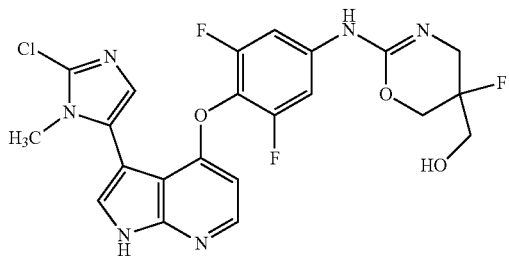 [SMILES: Cn1c(-c2c[nH]c3nccc(Oc4c(F)cc(NC5=NCC(F)(CO)CO5)cc4F)c23)cnc1Cl]

N-(4-{[3-(2-chloro-1-methyl-1H-imidazol-5-yl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (39.0 mg, 61.2 µmol, intermediate 422) was dissolved in dichloromethane (2 mL), and trifluoroacetic acid (210 µL, 2.8 mmol) was added. The mixture was stirred under argon overnight at room temperature. The solvent was removed under vacuum, and the residue stirred with acetonitrile (10 mL) and a 33% ammonia solution (5 mL) at room temperature for 1 h and then dried again. The residue was purified by preparative HPLC to yield the title compound (7.80 mg, 24% yield).

LC-MS (Method 2): $R_t$=0.86 min; MS (ESIpos): m/z=507 [M+H]$^+$ $^1$H-NMR (400 MHz, DMSO-d6) δ [ppm]: 3.428 (0.61), 3.500 (16.00), 3.533 (0.71), 3.577 (1.13), 3.606 (0.95), 3.619 (0.86), 3.636 (0.33), 3.650 (0.29), 4.249 (0.88), 4.262 (0.81), 4.313 (1.10), 5.232 (0.51), 5.244 (0.86), 5.257 (0.52), 6.309 (1.80), 6.323 (1.80), 6.931 (6.56), 7.541 (0.70), 7.569 (0.67), 7.608 (2.58), 7.614 (2.60), 8.116 (2.71), 8.129 (2.61), 9.208 (0.70), 12.278 (1.49).

Example 216

(+/−)-[2-(3,5-difluoro-4-{[3-(5-methyl-1,3,4-oxadiazol-2-yl)-1H-pyrrolo[2,3-b]pyridin-4-yl]oxy}anilino)-5-methyl-5,6-dihydro-4H-1,3-oxazin-5-yl]methanol

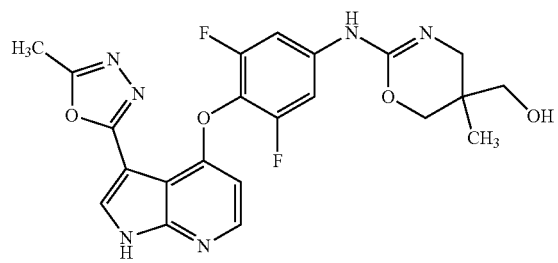 [SMILES: Cc1nnc(-c2c[nH]c3nccc(Oc4c(F)cc(NC5=NCC(C)(CO)CO5)cc4F)c23)o1]

[2-(3,5-difluoro-4-{[3-(5-methyl-1,3,4-oxadiazol-2-yl)-1-{[2-(trimethylsilyl)ethoxy]methyl}-1H-pyrrolo[2,3-b]pyridin-4-yl]oxy}anilino)-5-methyl-5,6-dihydro-4H-1,3-oxazin-5-yl]methanol (103 mg, 171 µmol, Intermediate 454) was dissolved in dichloromethane (5.5 mL) and trifluoroacetic acid (570 µL, 7.4 mmol) was added. The mixture was stirred under argon overnight at room temperature. The solvent was removed under vacuum, and the residue stirred with acetonitrile (3 mL) and a 33% ammonia solution (1 mL) at room temperature for 1 h and then dried again. The residue was dissolved with ethyl acetate and washed with water (×2) and brine (×1). The organic phase was dried with sodium sulfate, filtered and dried under vacuum. The crude was then digested with diethyl ether in an ultrasound bath to yield the title compound (34.0 mg, 40% yield).

LC-MS (Method 1): $R_t$=0.64 min; MS (ESIneg): m/z=469 [M−H]$^-$ $^1$H-NMR (400 MHz, DMSO-d6) δ [ppm]: 0.98 (s, 3H), 3.10 (d, 1H), 4.22 (br s, 1H), 4.38 (br s, 1H), 5.08 (br s, 1H), 6.50 (d, 1H), 7.40 (m, 2H), 8.24 (m, 2H), 12.76 (s, 1H).

Example 217

N-{4-[(3-chloro-1H-pyrrolo[2,3-b]pyridin-4-yl)oxy]-3,5-difluorophenyl}-5,7-diazaspiro[2.5]oct-5-en-6-amine

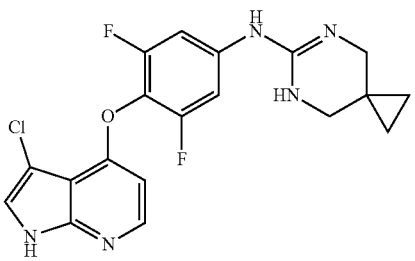 [SMILES: Fc1cc(NC2=NCC3(CC3)CN2)cc(F)c1Oc1ccnc2[nH]cc(Cl)c12]

Tert-butyl {[1-({(Z/E)-[{4-[(3-chloro-1-{[2-(trimethylsilyl)ethoxy]methyl}-1H-pyrrolo[2,3-b]pyridin-4-yl)oxy]-3,5 difluoroanilino}(methylsulfanyl)methylidene]amino}methyl)cyclopropyl]methyl}carbamate (270 mg, 396 µmol, Intermediate 438) was dissolved in dichloromethane (13 mL) and trifluoroacetic acid (1.3 mL, 17 mmol) was added. The mixture was stirred under argon overnight at room temperature. The solvent was removed under vacuum, and the residue stirred with acetonitrile (4 mL) and a 33% ammonia solution (2 mL) at room temperature for 1 h and then dried again. The residue was dissolved with ethyl acetate and washed with water (×2) and brine (×1). The organic phase was dried with sodium sulfate, filtered and dried under vacuum. The crude was then digested with diethyl ether in an ultrasound bath to yield the title compound (94.1 mg, 56% yield).

LC-MS (Method 1): $R_t$=0.88 min; MS (ESIpos): m/z=404 [M+H]$^+$ $^1$H-NMR (400 MHz, DMSO-d6) δ [ppm]: 0.65 (s, 4H), 3.14 (s, 4H), 6.39 (m, 1H), 7.27 (m, 2H), 7.65 (s, 1H), 8.14 (d, 1H), 8.58 (br s, 2H), 12.20 (br s, 1H).

Example 218

N-(3,5-difluoro-4-{[3-(trifluoromethyl)-1H-pyrrolo[2,3-b]pyridin-4-yl]oxy}phenyl)-5,5-dimethyl-1,4,5,6-tetrahydropyrimidin-2-amine

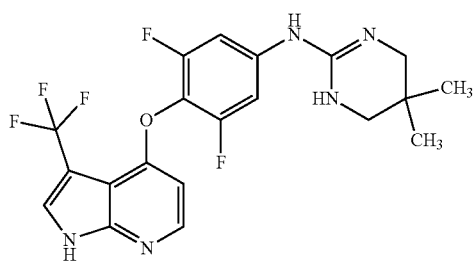 [SMILES: CC1(C)CN=C(Nc2cc(F)c(Oc3ccnc4[nH]cc(C(F)(F)F)c34)c(F)c2)NC1]

Tert-butyl (3-{(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}-2,2-dimethylpropyl)carbamate (64.0 mg, 89.2 µmol, intermediate 441) was dissolved in dichloromethane (2.9 mL) and trifluoroacetic acid (300 µL, 3.8 mmol) was added. The mixture was stirred under argon overnight at room temperature. A sodium bicarbonate solution was added (solution stirred for 30 min), followed by dichloromethane. The organic phase was separated and the aqueous phase further washed with dichloromethane. The organic layers were dried with sodium sulfate, filtered and evaporated. The remaining residue was purified by preparative TLC (basic silica plate, dicloromethane:methanol, 97:3) to yield the title compound (9.00 mg, 22% yield).

LC-MS (Method 1): $R_t$=0.94 min; MS (ESIpos): m/z=440 [M+H]$^+$ $^1$H-NMR (400 MHz, DMSO-d6) δ [ppm]: 0.98 (s, 6H), 2.85 (s, 4H), 6.49 (m, 1H), 6.58 (br s, 2H), 8.06 (m, 1H), 8.20 (d, 1H).

Example 219

N-(3,5-difluoro-4-{[3-(trifluoromethyl)-1H-pyrrolo[2,3-b]pyridin-4-yl]oxy}phenyl)-6,6-dimethyl-1,4,5,6-tetrahydropyrimidin-2-amine

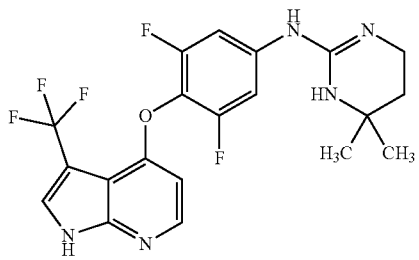 [SMILES: CC1(C)CCN=C(Nc2cc(F)c(Oc3ccnc4[nH]cc(C(F)(F)F)c34)c(F)c2)N1]

Tert-butyl (4-{(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}-2-methylbutan-2-yl)carbamate (141 mg, 196 µmol, intermediate 443) was dissolved in dichloromethane (6.3 mL) and trifluoroacetic acid (650 µL, 8.4 mmol) was added. The mixture was stirred under argon overnight at room temperature. A sodium bicarbonate solution was added (solution stirred for 30 min), followed by dichloromethane. The organic phase was separated and the aqueous phase further washed with dichloromethane. The organic layers were dried with sodium sulfate, filtered and evaporated. The remaining residue was purified by preparative TLC (basic silica plate, dicloromethane:methanol, 97:3). The product was further stirred with 2 mL of acetonitrile and 0.5 mL of concentrated ammonia, dried and purified again by preparative TLC (basic silica plate, dicloromethane:methanol, 95:5) to yield the title compound (8.90 mg, 8% yield).

$^1$H-NMR (400 MHz, DMSO-d6) δ [ppm]: 1.07 (s, 6H), 1.58 (t, 2H), 6.40 (d, 1H), 6.68 (m, 2H), 8.09 (s, 1H), 8.21 (d, 1H).

Example 220

N-(3,5-difluoro-4-{[3-(trifluoromethyl)-1H-pyrrolo[2,3-b]pyridin-4-yl]oxy}phenyl)-5,7-diazaspiro[2.5]oct-5-en-6-amine

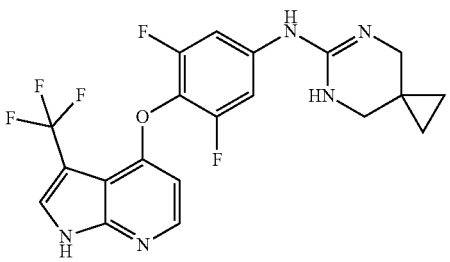 [SMILES: Fc1cc(NC2=NCC3(CC3)CN2)cc(F)c1Oc1ccnc2[nH]cc(C(F)(F)F)c12]

Tert-butyl {[1-({(Z/E)-[(3,5-difluoro-4-{[3-(trifluoromethyl)-1-{[2-(trimethylsilyl)ethoxy]methyl}-1H-pyrrolo[2,3-b]pyridin-4-yl]oxy}anilino)(methylsulfanyl)methylidene]amino}methyl)cyclopropyl]methyl}carbamate (109 mg, 152 µmol, Intermediate 445) was dissolved in dichloromethane (4.9 mL) and trifluoroacetic acid (500 µL, 6.5 mmol) was added. The mixture was stirred under argon overnight at room temperature. A sodium bicarbonate solution was added (solution stirred for 30 min), followed by dichloromethane. The organic phase was separated and the aqueous phase further washed with dichloromethane. The organic layers were dried with sodium sulfate, filtered and evaporated. The remaining residue was filtered through silica and the resulted residue was further stirred with 2 mL of acetonitrile and 0.5 mL of concentrated ammonia, dried and purified again by preparative TLC (basic silica plate, dicloromethane:methanol, 95:5) to yield the title compound (12.6 mg, 17% yield).

LC-MS (Method 1): R$_t$=0.98 min; MS (ESIpos): m/z=438 [M+H]$^+$ $^1$H-NMR (400 MHz, DMSO-d6) δ [ppm]: 0.54 (s, 4H), 2.97 (s, 4H), 6.46 (d, 1H), 6.65 (br s, 2H), 8.05 (s, 1H), 8.20 (d, 1H).

Example 221

N-{4-[(3-bromo-1H-pyrrolo[2,3-b]pyridin-4-yl)oxy]-3,5-difluorophenyl}-1,4,5,6-tetrahydropyrimidin-2-amine

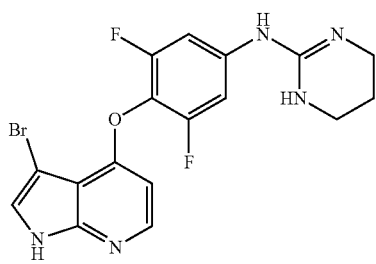

Tert-butyl (3-{(Z/E)-[{4-[(3-bromo-1-{[2-(trimethylsilyl)ethoxy]methyl}-1H-pyrrolo[2,3-b]pyridin-4-yl)oxy]-3,5-difluoroanilino}(methylsulfanyl)methylidene]amino}propyl)carbamate (102 mg, 146 µmol, Intermediate 448) was dissolved in dichloromethane (5 mL) and trifluoroacetic acid (500 µL, 6.6 mmol) was added. The mixture was stirred under argon overnight at 35° C. The solvent was removed under vacuum, and the residue stirred with acetonitrile and a 33% ammonia solution (5 mL) at room temperature for 2 h and then dried again. The residue was purified by silica gel chromatography to yield the title compound (10.0 mg, 15% yield).

$^1$H-NMR (400 MHz, DMSO-d6) δ [ppm]: 1.76 (m, 2H), 3.16 (m, 4H), 6.37 (m, 1H), 6.61 (m, 2H), 7.62 (s, 1H), 8.10 (d, 1H).

Example 222

(+/−)-[2-(4-{[3-(5-cyclopropyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol

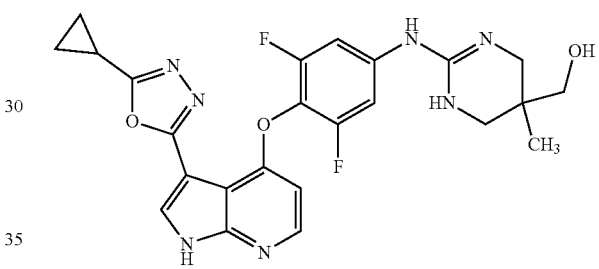

N-(4-{[3-(5-cyclopropyl-1,3,4-oxadiazol-2-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (37.0 mg, 59.0 µmol, Intermediate 457) was dissolved in dichloromethane (1.9 mL) and trifluoroacetic acid (200 µL, 2.5 mmol) was added. The mixture was stirred under argon overnight at room temperature. The solvent was removed under vacuum, and the residue stirred with acetonitrile (1 mL) and a 33% ammonia solution (0.5 mL) at room temperature for 1 h and then dried again. The residue was dissolved with ethyl acetate and washed with water (×2) and brine (×1). The residue was purified by preparative HPLC to yield the title compound (3.80 mg, 12% yield).

LC-MS (Method 1): R$_t$=0.71 min; MS (ESIpos): m/z=497 [M+H]$^+$ $^1$H-NMR (400 MHz, DMSO-d6) δ [ppm]: 0.905 (16.00), 1.056 (0.96), 1.066 (2.52), 1.073 (2.20), 1.086 (2.66), 1.093 (2.16), 1.104 (0.75), 2.210 (0.43), 2.223 (0.84), 2.231 (0.95), 2.243 (1.66), 2.255 (0.89), 2.264 (0.82), 2.276 (0.37), 2.989 (1.35), 3.025 (1.79), 3.197 (2.33), 3.242 (2.96), 3.269 (4.47), 3.866 (1.57), 3.892 (1.89), 4.053 (1.70), 4.081 (1.33), 6.439 (2.03), 6.452 (2.05), 7.385 (0.63), 8.171 (3.55), 8.185 (4.45), 8.190 (7.93).

Example 223

(+/−)-[2-(4-{[3-(5-cyclobutyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol

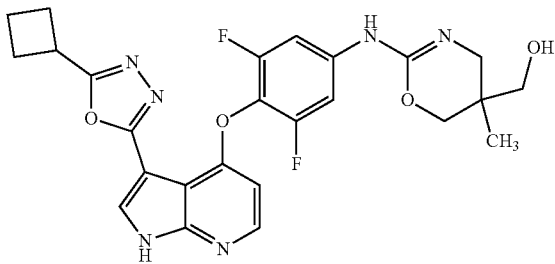 [SMILES: CC1(CO)CN=C(Nc2cc(F)c(Oc3ccnc4[nH]cc(-c5nnc(C6CCC6)o5)c34)c(F)c2)OC1]

N-(4-{[3-(5-cyclobutyl-1,3,4-oxadiazol-2-yl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (98.0 mg, 153 μmol, Intermediate 459) was dissolved in dichloromethane (4.9 mL) and trifluoroacetic acid (510 μL, 6.6 mmol) was added. The mixture was stirred under argon overnight at room temperature. The solvent was removed under vacuum, and the residue stirred with acetonitrile (2 mL) and a 33% ammonia solution (1 mL) at room temperature for 1 h and then dried again. The residue was dissolved with ethyl acetate and washed with water (×2) and brine (×1). The residue was purified by preparative HPLC to yield the title compound (9.30 mg, 11% yield).

LC-MS (Method 1): $R_t$=0.76 min; MS (ESIneg): m/z=509 [M−H]$^-$ $^1$H-NMR (400 MHz, DMSO-d6) δ [ppm]: 0.901 (11.12), 1.780 (0.27), 1.791 (0.41), 1.803 (0.69), 1.818 (0.62), 1.830 (0.76), 1.841 (0.55), 1.850 (0.41), 1.860 (0.27), 1.969 (0.76), 1.990 (1.58), 1.996 (0.69), 2.012 (1.10), 2.017 (1.24), 2.034 (0.48), 2.040 (0.69), 2.231 (0.89), 2.260 (1.99), 2.281 (2.33), 2.309 (1.79), 2.322 (3.78), 2.326 (4.94), 2.332 (3.78), 2.518 (16.00), 2.522 (10.78), 2.664 (3.09), 2.668 (4.12), 2.673 (3.02), 2.985 (0.82), 3.021 (0.96), 3.192 (1.17), 3.232 (1.65), 3.264 (1.99), 3.751 (1.30), 3.772 (1.79), 3.793 (1.17), 3.860 (1.03), 3.886 (1.30), 4.050 (1.51), 4.074 (1.17), 4.832 (0.55), 6.473 (2.06), 6.487 (1.99), 8.188 (4.05), 8.202 (4.05), 8.223 (10.78).

Example 224

(+/−)-{2-[3,5-difluoro-4-({3-[5-(propan-2-yl)-1,3,4-oxadiazol-2-yl]-1H-pyrrolo[2,3-b]pyridin-4-yl}oxy)anilino]-5-methyl-5,6-dihydro-4H-1,3-oxazin-5-yl}methanol

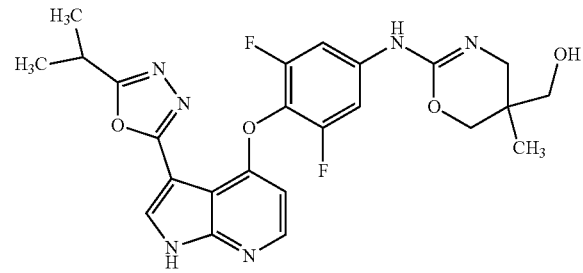 [SMILES: CC(C)c1nnc(-c2c[nH]c3nccc(Oc4c(F)cc(NC5=NCC(C)(CO)CO5)cc4F)c23)o1]

N-{3,5-difluoro-4-[(3-[5-(propan-2-yl)-1,3,4-oxadiazol-2-yl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (31.0 mg, 49.3 μmol, Intermediate 461) was dissolved in dichloromethane (1.6 mL) and trifluoroacetic acid (160 μL, 2.1 mmol) was added. The mixture was stirred under argon overnight at room temperature. The solvent was removed under vacuum, and the residue stirred with acetonitrile (1 mL) and a 33% ammonia solution (0.5 mL) at room temperature for 1 h and then dried again. The residue was dissolved with ethyl acetate and washed with water (×2) and brine (×1). The residue was purified by preparative HPLC to yield the title compound (6.80 mg, 26% yield).

LC-MS (Method 1): $R_t$=0.74 min; MS (ESIneg): m/z=497 [M−H]$^-$ $^1$H-NMR (400 MHz, DMSO-d6) δ [ppm]: 0.903 (8.21), 1.246 (14.63), 1.263 (16.00), 2.985 (0.64), 3.021 (0.83), 3.162 (0.56), 3.179 (1.35), 3.196 (2.20), 3.214 (1.43), 3.231 (1.35), 3.266 (1.70), 3.862 (0.79), 3.888 (0.98), 4.052 (0.96), 4.078 (0.75), 4.826 (0.17), 6.454 (1.27), 6.467 (1.23), 7.381 (0.23), 8.181 (2.47), 8.195 (2.62), 8.199 (3.55), 8.210 (5.22).

Example 225

(+/−)-[2-(4-{[3-(3,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol

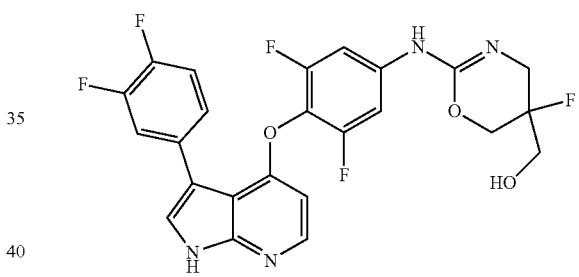

N-(4-{[3-(3,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-fluorooxetan-3-yl)methyl]urea (211 mg, 332 μmol, intermediate 423) was dissolved in dichloromethane (5 mL), and trifluoroacetic acid (1.2 mL, 15 mmol) was added. The mixture was stirred under argon overnight at 35° C. The solvent was removed under vacuum, and the residue was purified by preparative HPLC to yield the title compound (12.1 mg, 7% yield).

LC-MS (Method 2): $R_t$=1.09 min; MS (ESIpos): m/z=505 [M+H]$^+$ $^1$H-NMR (400 MHz, DMSO-d6) δ [ppm]: 3.391 (1.02), 3.396 (0.99), 3.434 (3.27), 3.483 (3.78), 3.495 (2.10), 3.510 (1.70), 3.526 (3.86), 3.541 (3.07), 3.546 (2.08), 3.562 (2.04), 3.571 (4.89), 3.578 (5.68), 3.585 (4.58), 3.592 (3.51), 3.602 (2.34), 3.613 (4.56), 3.627 (3.81), 3.644 (1.38), 3.658 (1.32), 4.229 (1.15), 4.259 (4.58), 4.271 (3.66), 4.277 (3.56), 4.301 (1.26), 4.314 (4.18), 4.325 (5.58), 5.239 (3.05), 5.254 (6.01), 5.267 (2.92), 5.755 (14.63), 6.337 (8.69), 6.351 (8.58), 7.399 (2.63), 7.421 (6.05), 7.426 (3.26), 7.442 (4.78), 7.447 (6.37), 7.469 (4.64), 7.494 (4.15), 7.496 (4.43), 7.499 (4.40), 7.503 (4.80), 7.508 (4.75), 7.510 (4.48), 7.518 (3.53), 7.521 (3.45), 7.526 (3.31), 7.529 (3.36), 7.532 (3.21), 7.544 (1.74), 7.558 (1.84), 7.561 (1.84), 7.566 (1.84), 7.641 (3.73), 7.646 (3.54), 7.661 (3.86), 7.666 (3.74), 7.672 (3.87), 7.678 (3.57), 7.692 (3.48), 7.698 (3.30), 7.728 (11.70), 7.734 (11.85), 8.104 (16.00), 8.117 (14.74), 9.215 (1.16), 9.220 (1.16), 12.199 (6.60), 12.203 (6.57).

Example 226

(+/−)-[2-(4-{[3-(3,4-difluorophenyl)-1H-pyrrolo[2,3-b]pyridin-4-yl]oxy}-3,5-difluoroanilino)-5-methyl-5,6-dihydro-4H-1,3-oxazin-5-yl]methanol

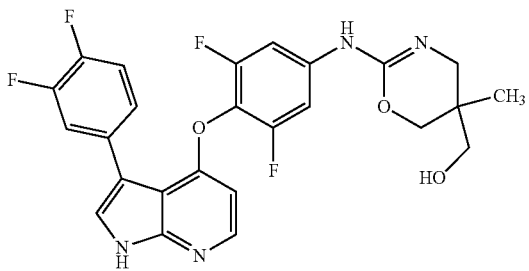 [SMILES: CC1(CO)CN=C(Nc2cc(F)c(Oc3ccnc4[nH]cc(-c5ccc(F)c(F)c5)c34)c(F)c2)OC1]

N-(4-{[3-(3,4-difluorophenyl)-1-{[2-(trimethylsilyl)ethoxy]methyl}-1H-pyrrolo[2,3-b]pyridin-4-yl]oxy}-3,5-difluorophenyl)-N'-[(3-methyloxetan-3-yl)methyl]urea (560 mg, 710 μmol, intermediate 396) was dissolved in dichloromethane (7 mL), and trifluoroacetic acid (2.5 mL, 32 mmol) was added. The mixture was stirred under argon overnight at 35° C. The solvent was removed under vacuum, and the residue was purified by preparative HPLC to yield the title compound (44.0 mg, 12% yield).

LC-MS (Method 2): $R_t$=1.53 min; MS (ESIpos): m/z=631 [M+H]⁺

¹H-NMR (400 MHz, DMSO-d6) δ [ppm]: 0.901 (16.00), 3.010 (1.08), 3.250 (2.92), 3.884 (2.00), 4.050 (4.77), 4.076 (3.69), 4.807 (1.38), 6.338 (7.69), 6.351 (7.85), 7.400 (2.62), 7.422 (5.69), 7.443 (4.46), 7.449 (6.00), 7.471 (4.15), 7.504 (4.31), 7.568 (1.54), 7.641 (3.38), 7.672 (3.38), 7.692 (3.08), 7.726 (10.77), 7.732 (11.23), 8.102 (11.23), 8.116 (10.77), 12.192 (5.38).

Example 227

(+/−)-3-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]propanenitrile

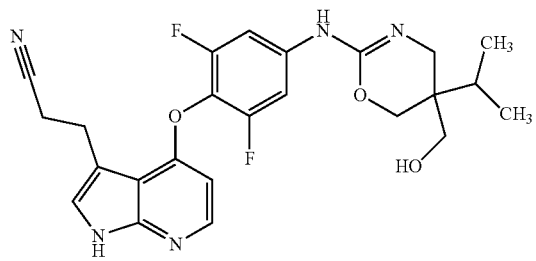 [SMILES: CC(C)C1(CO)CN=C(Nc2cc(F)c(Oc3ccnc4[nH]cc(CCC#N)c34)c(F)c2)OC1]

N-(4-{3-(2-cyanoethyl)-1-{[2-(trimethylsilyl)ethoxy]methyl}-1H-pyrrolo[2,3-b]pyridin-4-yl]oxy}-3,5-difluorophenyl)-N'-{[3-(propan-2-yl)oxetan-3-yl]methyl}urea (180 mg, 300 μmol, Intermediate 469) was dissolved in dichloromethane (4 mL), and trifluoroacetic acid (1.0 mL, 14 mmol) was added. The mixture was stirred under argon overnight at 35° C. The solvent was removed under vacuum, and the residue was purified by preparative TLC and preparative HLPC to yield the title compound (15.0 mg, 9% yield).

LC-MS (Method 2): $R_t$=0.99 min; MS (ESIneg): m/z=468 [M−H]⁻

¹H-NMR (400 MHz, DMSO-d6) δ [ppm]: 0.90 (dd, 6H), 1.77 (h, 1H), 2.88 (t, 2H), 3.12 (t, 2H), 3.17 (br s, 1H), 3.40 (m, 2H), 4.03 (m, 1H), 4.14 (m, 1H), 4.72 (br s, 1H), 6.24 (d, 1H), 7.34 (d, 1H), 7.57 (br s, 1H), 8.06 (d, 1H), 9.04 (br s, 1H), 11.67 (d, 1H).

Example 228

N-{4-[(3-chloro-1H-pyrrolo[2,3-b]pyridin-4-yl)oxy]-3,5-difluorophenyl}-7-oxa-9-azaspiro[4.5]dec-8-en-8-amine

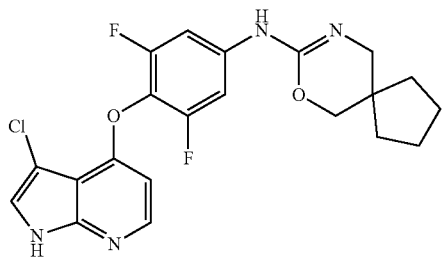 [SMILES: Fc1cc(NC2=NCC3(CCCC3)CO2)cc(F)c1Oc1ccnc2[nH]cc(Cl)c12]

N-{4-[(3-chloro-1-{[2-(trimethylsilyl)ethoxy]methyl}-1H-pyrrolo[2,3-b]pyridin-4-yl)oxy]-3,5-difluorophenyl}-7-oxa-9-azaspiro[4.5]dec-8-en-8-amine (80.0 mg, 142 μmol, Intermediate 471) was dissolved in dichloromethane (2 mL), and trifluoroacetic acid (490 μL, 6.4 mmol) was added. The mixture was stirred under argon overnight at room temperature. The solvent was removed under vacuum, and the residue filtered through silica. The remaining product was digested with diethyl ether to yield the title compound (17.0 mg, 27% yield).

LC-MS (Method 2): $R_t$=1.25X min; MS (ESIpos): m/z=433 [M+H]⁺

¹H-NMR (400 MHz, DMSO-d6) δ [ppm]: 1.52-1.60 (m, 4H), 1.65-1.70 (m, 4H), 3.27 (s, 2H), 4.40 (s, 2H), 6.38 (d, 1H), 7.42 (m, 2H), 7.66 (d, 1H), 8.14 (d, 1H), 12.20 (d, 1H).

Example 229

(+/−)—N-{4-[(3-chloro-1H-pyrrolo[2,3-b]pyridin-4-yl)oxy]-3,5-difluorophenyl}-5-(methoxymethyl)-5-methyl-5,6-dihydro-4H-1,3-oxazin-2-amine

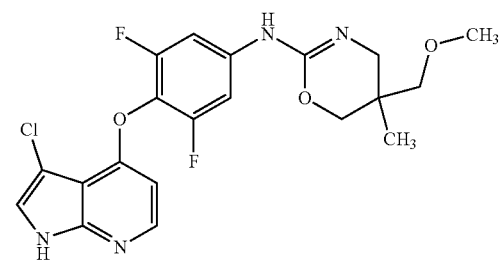 [SMILES: COCC1(C)CN=C(Nc2cc(F)c(Oc3ccnc4[nH]cc(Cl)c34)c(F)c2)OC1]

(+/−)—N-{4-[(3-chloro-1-{[2-(trimethylsilyl)ethoxy]methyl}-1H-pyrrolo[2,3-b]pyridin-4-yl)oxy]-3,5-difluorophenyl}-5-(methoxymethyl)-5-methyl-5,6-dihydro-4H-1,3-oxazin-2-amine (81.0 mg, 100 μmol, Intermediate 476) was dissolved in dichloromethane (3.2 mL) and trifluoroacetic acid (330 μL, 4.3 mmol) was added. The mixture was stirred under argon overnight at room temperature. The solvent was removed under vacuum, and the residue stirred with acetonitrile (3 mL) and a 33% ammonia solution (1.5 mL) at room temperature for 1 h and then dried again. The residue was dissolved with ethyl acetate and washed with water (×2) and brine (×1). The organic residue was dried with sodium sulfate, filtered and evaporated. The product was purified by preparative TLC (dichloromethane:methanol, 90:10) followed by preparative HPLC to yield the title compound (24.1 mg, 50% yield).

LC-MS (Method 2): $R_t$=1.15 min; MS (ESIpos): m/z=437 [M+H]$^+$ $^1$H-NMR (400 MHz, DMSO-d6) δ [ppm]: 0.93 (s, 3H), 3.06 (m, 1H), 3.17-3.27 (m, 3H), 3.28 (2, 3H), 3.87 (m, 1H), 4.06 (m, 1H), 6.30 (d, 1H), 7.55 (br s, 2H), 7.60 (s, 1H), 8.08 (d, 1H), 9.09 (br s, 1H), 12.08 (d, 1H).

Example 230

(+/−)—N-{4-[(3-chloro-1H-pyrrolo[2,3-b]pyridin-4-yl)oxy]-3,5-difluorophenyl}-5-methyl-5-{[(propan-2-yl)oxy]methyl}-5,6-dihydro-4H-1,3-oxazin-2-amine

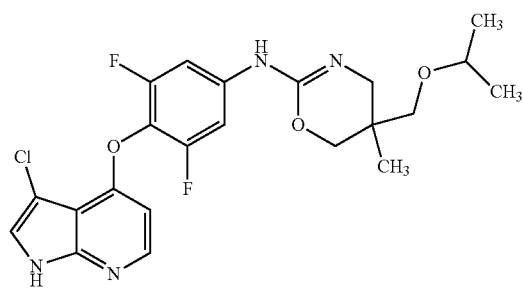 [SMILES: CC(C)OCC1(C)CN=C(Nc2cc(F)c(Oc3ccnc4[nH]cc(Cl)c34)c(F)c2)OC1]

(+/−)—N-{4-[(3-chloro-1H-pyrrolo[2,3-b]pyridin-4-yl)oxy]-3,5-difluorophenyl}-N'-{(2S)-2-(hydroxymethyl)-2-methyl-3-[(propan-2-yl)oxy]propyl}thiourea (179 mg, 70% purity, 251 μmol, Intermediate 482) was dissolved in THF (1.2 mL) and N-(3-Dimethylaminopropyl)-N'-ethylcarbodiimide hydrochloride (62.6 mg, 326 μmol) was added. The mixture was stirred for 16 h at 60° C. N-(3-Dimethylaminopropyl)-N'-ethylcarbodiimide hydrochloride (62.6 mg, 326 μmol) was added again and the solution stirred at 60° C. for a further 2 h, after which time N-(3-Dimethylaminopropyl)-N'-ethylcarbodiimide hydrochloride (62.6 mg, 326 μmol) was added again. The solution was stirred for a further hour, diluted with water and extracted with ethyl acetate (×3). The organic layers were dried with sodium sulfate, filtered and evaporated. The product was filtered though silica and purified by preparative TLC (ethyl acetate:acetonitrile:methanol, 80:15:5) to yield the title compound (30.0 mg, 24% yield).

LC-MS (Method 2): $R_t$=1.29 min; MS (ESIpos): m/z=465 [M+H]$^+$ $^1$H-NMR (400 MHz, CHLOROFORM-d3) δ [ppm]: 1.06 (s, 3H), 1.14 (d, 6H), 3.10 (m, 1H), 3.27 (m, 1H), 3.35-3.39 (m, 2H), 3.54 (h, 1H), 3.92 (m, 1H), 4.22 (m, 1H), 6.35 (m, 1H), 7.00 (br s, 2H), 7.21 (s, 1H), 8.12 (d, 1H).

Example 231

N-(3,5-difluoro-4-{[3-(propan-2-yl)-1H-pyrrolo[2,3-b]pyridin-4-yl]oxy}phenyl)-5-methyl-5-{[(propan-2-yl)oxy]methyl}-5,6-dihydro-4H-1,3-oxazin-2-amine

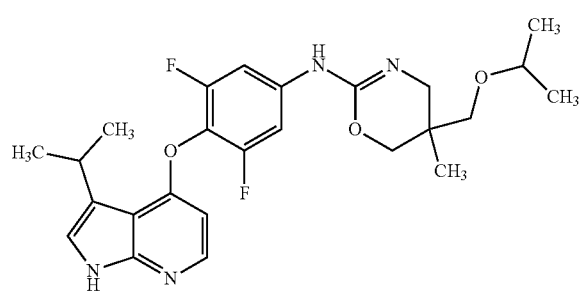 [SMILES: CC(C)OCC1(C)CN=C(Nc2cc(F)c(Oc3ccnc4[nH]cc(C(C)C)c34)c(F)c2)OC1]

(+/−)—N-(3,5-difluoro-4-{[3-(propan-2-yl)-1H-pyrrolo[2,3-b]pyridin-4-yl]oxy}phenyl)-N'-{(2S)-2-(hydroxymethyl)-2-methyl-3-[(propan-2-yl)oxy]propyl}thiourea (196 mg, 70% purity, 271 μmol, Intermediate 487) was dissolved in THF (1.3 mL) and N-(3-Dimethylaminopropyl)-N'-ethylcarbodiimide hydrochloride (104 mg, 542 μmol) was added. The mixture was stirred for 16 h at 60° C. N-(3-Dimethylaminopropyl)-N'-ethylcarbodiimide hydrochloride (104 mg, 542 μmol) was added again and the solution stirred at 60° C. for a further 1 h. The solution was diluted with water and extracted with ethyl acetate (×3). The organic layers were dried with sodium sulfate, filtered and evaporated. The product was filtered though silica and purified by preparative TLC (ethyl acetate:acetonitrile:methanol, 80:15:5) to yield the title compound (8.60 mg, 6% yield).

LC-MS (Method 2): $R_t$=1.26 min; MS (ESIpos): m/z=507 [M+H]$^+$ $^1$H-NMR (400 MHz, CHLOROFORM-d3) δ [ppm]: 1.05 (s, 3H), 1.15 (d, 6H), 1.38 (d, 6H), 3.10 (m, 1H), 3.27 (m, 1H), 3.36 (m, 2H), 3.47 (h, 1H), 3.54 (h, 1H), 3.90 (m, 1H), 4.18 (dd, 1H), 6.25 (m, 1H), 6.94-7.05 (m, 3H), 8.05 (d, 1H), 8.46 (br s, 1H).

Example 232

(+/−)-{2-[3,5-difluoro-4-({3-[1-(trifluoromethyl)cyclopropyl]-1H-pyrrolo[2,3-b]pyridin-4-yl}oxy)anilino]-5-methyl-5,6-dihydro-4H-1,3-oxazin-5-yl}methanol

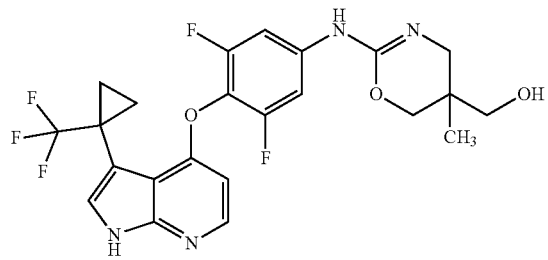 [SMILES: CC1(CO)CN=C(Nc2cc(F)c(Oc3ccnc4[nH]cc(C5(C(F)(F)F)CC5)c34)c(F)c2)OC1]

N-{3,5-difluoro-4-[(3-[1-(trifluoromethyl)cyclopropyl]-1-{[2-(trimethylsilyl)ethoxy]methyl}-1H-pyrrolo[2,3-b]pyridin-4-yl)oxy]phenyl}-N'-[(3-methyloxetan-3-yl)methyl]urea (125 mg, 189 µmol, Intermediate 498) was dissolved in dichloromethane (6.1 mL) and trifluoroacetic acid (630 µL, 8.1 mmol) was added. The mixture was stirred under argon overnight at room temperature. The solvent was removed under vacuum, and the residue stirred with acetonitrile (6 mL) and a 33% ammonia solution (2 mL) at room temperature for 1 h and then dried again. The residue was dissolved with ethyl acetate and washed with water (×2) and brine (×1). The residue was purified by column chromatography using a Biotage system and digested with diethyl ether and dichloromethane to yield the title compound (44.1 mg, 42% yield).

LC-MS (Method 2): $R_t$=1.08 min; MS (ESIpos): m/z=497 $[M+H]^+$ $^1$H-NMR (400 MHz, DMSO-d6) δ [ppm]: 1.00 (s, 3H), 1.17 (m, 2H), 1.33 (m, 2H9, 3.11 (d, 1H), 4.30 (m, 2H), 4.48 (m, 2H), 5.14 (br s, 1H), 6.32 (d, 1H), 7.38 (m, 2H), 7.57 (d, 1H), 8.08 (d, 1H), 12.02 (d, 1H).

Experimental Section—Biological Assays

Biological In Vitro Assays

The in vitro activity of the compounds of the present invention can be demonstrated in the following assays:

The example testing experiments described herein serve to illustrate the present invention and the invention is not limited to the examples given.

Biological Evaluation

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro and in vivo assays that are well known in the art. For example, to demonstrate the efficacy of a pharmaceutical agent to inhibit and be selective against e.g. TBK1 the following assays may be used.

Binding Competition Assay

The ability of the compounds of the present invention to inhibit the binding of an Alexa647-labelled ATP-competitive kinase inhibitor to a Glutathione-S-transferase-(GST-) fusion protein was quantified employing the TR-FRET-based binding competition assay as described in the following paragraphs.

A recombinant fusion protein of N-terminal GST and full-length human, expressed by baculovirus infected SF9 insect cells and purified by Glutathione Sepharose affinity chromatography, was used as GST-fusion protein. Tracer 222 from Invitrogen (catalogue no. PR9198A) was used as Alexa647-labelled ATP-competitive kinase inhibitor. For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 3 µL solution of Tracer 222 (25 nM=>final concentration in 5 µL assay volume is 15 nM) in aqueous assay buffer [25 mM Tris/HCl pH 7.5, 10 mM $MgCl_2$, 5 mM β-glycerolphosphate, 2.5 mM dithiothreitol, 0.5 mM ethylene glycol-bis(2-aminoethylether)-N,N,N',N'-tetraacetic acid [EGTA], 0.5 mM sodium ortho-vanadate, 0.01% (w/v) bovine serum albumin [BSA], 0.005% (w/v) Pluronic F-127 (Sigma)] were added. Then the binding competition was started by the addition of 2 µL of a solution of the GST-fusion protein (2.5 nM=>final conc. in the 5 µL assay volume is 1 nM) and of Anti-GST-Tb (1.25 nM=>final conc. in the 5 µL assay volume is 0.5 nM), a Lumi4®-Tb Cryptate-conjugated anti-GST-antibody from Cisbio Bioassays (France), in assay buffer.

The resulting mixture was incubated 30 min at 22° C. to allow the formation of a complex between the Tracer 222, the fusion protein and Anti-GST-Tb. Subsequently the amount of this complex was evaluated by measurement of the resonance energy transfer from the Tb-cryptate to the Tracer 222. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of the complex. The data were normalised (assay reaction without inhibitor=0% inhibition, all other assay components but GST-fusion protein=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

TABLE 1

Measured $IC_{50}$ values of compounds regarding inhibition

| Example | $IC_{50}$ [nM] |
|---|---|
| 1 | 2.7 |
| 2 | 2.6 |
| 3 | 32.9 |
| 4 | 15.9 |
| 5 | 4.6 |
| 6 | 146.0 |
| 7 | 66.0 |
| 8 | 8.3 |
| 9 | 57.8 |
| 10 | 7.7 |
| 11 | 11.4 |
| 12 | 3.6 |
| 13 | 2.3 |
| 14 | 2.0 |
| 15 | 5.3 |
| 16 | 5.3 |
| 17 | 6.2 |
| 18 | 4.9 |
| 19 | 13.7 |
| 20 | 4.6 |
| 21 | 8.2 |
| 22 | 2.6 |
| 23 | 27.6 |
| 24 | 4.1 |
| 25 | 132.0 |
| 26 | 7.4 |
| 27 | 3.3 |
| 28 | 33.7 |
| 29 | 7.2 |
| 30 | 7.2 |
| 31 | 23.9 |
| 32 | 22.6 |
| 33 | 8.3 |
| 34 | 1.7 |
| 35 | 80.9 |
| 36 | 3.0 |
| 37 | 5.2 |

TABLE 1-continued

Measured IC$_{50}$ values of compounds regarding inhibition

| Example | IC$_{50}$ [nM] |
|---|---|
| 38 | 1.4 |
| 39 | 6.0 |
| 40 | 13.2 |
| 41 | 2.0 |
| 42 | 2.1 |
| 43 | 1.4 |
| 44 | 50.0 |
| 45 | 42.8 |
| 46 | 7.5 |
| 47 | 14.6 |
| 48 | 6.2 |
| 49 | 2.4 |
| 50 | 3.9 |
| 51 | 234.0 |
| 52 | 6.4 |
| 53 | 19.0 |
| 54 | 28.3 |
| 55 | 56.6 |
| 56 | 28.7 |
| 57 | 10.5 |
| 58 | 16.8 |
| 59 | 11.2 |
| 60 | 63.9 |
| 61 | 52.8 |
| 62 | 7.9 |
| 63 | 133.0 |
| 64 | 106.0 |
| 65 | 6.8 |
| 66 | 7.9 |
| 67 | 30.8 |
| 68 | 21.1 |
| 69 | 378.0 |
| 70 | 3.1 |
| 71 | 43.6 |
| 72 | 21.6 |
| 73 | 83.5 |
| 74 | 28.8 |
| 75 | 129.0 |
| 76 | 4.7 |
| 77 | 14.6 |
| 78 | 4.9 |
| 79 | 31.3 |
| 80 | 191.0 |
| 81 | 6.2 |
| 82 | 5.0 |
| 83 | 13.8 |
| 84 | 14.6 |
| 85 | 13.7 |
| 86 | 5.8 |
| 87 | 9.5 |
| 88 | 30.1 |
| 89 | 7.6 |
| 90 | 7.1 |
| 91 | 4.2 |
| 92 | 3.7 |
| 93 | 35.9 |
| 94 | 3.3 |
| 95 | 10.5 |
| 96 | 7.1 |
| 97 | 39.9 |
| 98 | 52.4 |
| 99 | 6.8 |
| 100 | 2.9 |
| 101 | 4.5 |
| 102 | 2.8 |
| 103 | 31.4 |
| 104 | 1.8 |
| 105 | 3.5 |
| 106 | 8.5 |
| 107 | 5.1 |
| 108 | 2.9 |
| 109 | 8.1 |
| 110 | 5.1 |
| 111 | 4.7 |
| 112 | 10.6 |
| 113 | 2.3 |
| 114 | 24.7 |
| 115 | 2.2 |
| 116 | 3.0 |
| 117 | 4.5 |
| 118 | 4.1 |
| 119 | 4.8 |
| 120 | 74.6 |
| 121 | 60.2 |
| 122 | 381.0 |
| 123 | 5.1 |
| 124 | 2.6 |
| 125 | 5.1 |
| 126 | 168.0 |
| 127 | 4.6 |
| 128 | 167.0 |
| 129 | 5.4 |
| 130 | 104.0 |
| 131 | 34.2 |
| 132 | 8.7 |
| 133 | 3.5 |
| 134 | 4.7 |
| 135 | 5.9 |
| 136 | 702.0 |
| 137 | 153.0 |
| 138 | 10.8 |
| 139 | 9.6 |
| 140 | 14.4 |
| 141 | 3.4 |
| 142 | 2.4 |
| 143 | 3.4 |
| 144 | 148.0 |
| 145 | 2.7 |
| 146 | 81.8 |
| 147 | 7.1 |
| 148 | 4.7 |
| 149 | 7.4 |
| 150 | 7.0 |
| 151 | 25.9 |
| 152 | 8.1 |
| 153 | 12.0 |
| 154 | 15.7 |
| 155 | 34.0 |
| 156 | 54.2 |
| 157 | 22.6 |
| 158 | 15.2 |
| 159 | 1.3 |
| 160 | 1.7 |
| 161 | 2.0 |
| 162 | 2.5 |
| 163 | 261.0 |
| 164 | 171.0 |
| 165 | 104.0 |
| 166 | 81.1 |
| 167 | 148.0 |
| 168 | 15.3 |
| 169 | 9.4 |
| 170 | 33.3 |
| 171 | 28.4 |
| 172 | 54.9 |
| 173 | 186.0 |
| 174 | 210.0 |
| 175 | 11.0 |
| 176 | 2.4 |
| 177 | 3.9 |
| 178 | 10.5 |
| 179 | 62.0 |
| 180 | 2.9 |
| 181 | 10.6 |
| 182 | 3.1 |
| 183 | 1.6 |
| 184 | 319.0 |
| 185 | 62.7 |
| 186 | 3.0 |
| 187 | 5.0 |
| 188 | 7.4 |
| 189 | 4.9 |

TABLE 1-continued

Measured IC$_{50}$ values of compounds regarding inhibition

| Example | IC$_{50}$ [nM] |
|---|---|
| 190 | 38.9 |
| 191 | 12.2 |
| 192 | 151.0 |
| 193 | 30.5 |
| 194 | 10.8 |
| 195 | 22.4 |
| 196 | 7.0 |
| 197 | 9.1 |
| 198 | 15.2 |
| 199 | 18.4 |
| 200 | 209.0 |
| 201 | 34.4 |
| 202 | 53.2 |
| 203 | 9.4 |
| 204 | 38.8 |
| 205 | 928.0 |
| 206 | 95.8 |
| 207 | 48.0 |
| 208 | 35.6 |
| 209 | 40.0 |
| 210 | 42.7 |
| 211 | 613.0 |
| 212 | 1370.0 |
| 213 | 62.7 |
| 214 | 26.0 |
| 215 | 11.7 |
| 216 | 9.9 |
| 217 | 18.1 |
| 218 | 13.6 |
| 219 | 45.7 |
| 220 | 8.6 |
| 221 | 125.0 |
| 222 | 4.6 |
| 223 | 1.7 |
| 224 | 1.8 |
| 225 | 16.1 |
| 226 | 3.5 |
| 227 | 5.7 |
| 228 | 5.3 |
| 229 | 8.1 |
| 230 | 21.2 |
| 231 | 17.5 |
| 232 | 5.8 |

TBK1 High ATP Kinase Assay

TBK1-inhibitory activity of compounds of the present invention at a high ATP concentration after preincubation of enzyme and test compounds was quantified employing the TR-FRET-based TBK1 assay as described in the following paragraphs.

Recombinant full-length N-terminally His-tagged human TBK1, expressed in insect cells and purified by Ni-NTA affinity chromatography, was purchased from Life Technologies (Cat. No PR5618B) and used as enzyme. As substrate for the kinase reaction biotinylated peptide biotin-Ahx-GDEDFSSFAEPG (C-terminus in amide form—SEQ ID NO: 1) was used which can be purchased e.g. form the company Biosyntan (Berlin-Buch, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 µL of a solution of TBK1 in aqueous assay buffer [50 mM HEPES pH 7.0, 10 mM MgCl$_2$, 1.0 mM dithiothreitol, 0.05% (w/v) bovine serum albumine, 0.01% (v/v) Nonidet-P40 (Sigma), protease inhibitor mixture ("Complete w/o EDTA" from Roche, 1 tablet per 5 mL)] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 1.67 mM=>final conc. in the 5 µL assay volume is 1 mM) and substrate (1.67 µM=>final conc. in the 5 µL assay volume is 1 µM) in assay buffer and the resulting mixture was incubated for a reaction time of 30 min at 22° C. The concentration of TBK1 was adjusted depending of the activity of the enzyme lot and was chosen appropriate to have the assay in the linear range, typical concentrations were in the range of 0.002-0.004 pg/mL. The reaction was stopped by the addition of 3 µL of a solution of TR-FRET detection reagents (0.33 µM streptavidine-XL665 [Cisbio Bioassays, Codolet, France], 2.5 nM anti-phosho-Serine antibody [Merck Millipore, "STK antibody", cat. #35-002] and 1.25 nM LANCE EU-W1024 labeled anti-mouse IgG antibody [Perkin-Elmer, product no. AD0077]) in an aqueous EDTA-solution (167 mM EDTA, 0.13% (w/v) bovine serum albumin in 100 mM HEPES/NaOH pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

TABLE 2

Measured IC$_{50}$ values of compounds regarding TBK1 inhibition as selectivity assay

| Example | IC$_{50}$ [µM] |
|---|---|
| 1 | >20 |
| 2 | >20 |
| 3 | >20 |
| 4 | >20 |
| 5 | >20 |
| 6 | >20 |
| 7 | >20 |
| 8 | >20 |
| 9 | >20 |
| 10 | >20 |
| 11 | >20 |
| 12 | >20 |
| 13 | >20 |
| 14 | >20 |
| 15 | >20 |
| 16 | >20 |
| 17 | >20 |
| 18 | >20 |
| 19 | >20 |
| 20 | >20 |
| 21 | >20 |
| 22 | >20 |
| 23 | >20 |
| 24 | >20 |

TABLE 2-continued

Measured IC$_{50}$ values of compounds regarding TBK1 inhibition as selectivity assay

| Example | IC$_{50}$ [µM] |
|---|---|
| 25 | >20 |
| 26 | >20 |
| 27 | >20 |
| 28 | >20 |
| 29 | >20 |
| 30 | >20 |
| 31 | >20 |
| 32 | >20 |
| 33 | >20 |
| 34 | >20 |
| 35 | >20 |
| 36 | >20 |
| 37 | >20 |
| 38 | >20 |
| 39 | >20 |
| 40 | >20 |
| 41 | >20 |
| 42 | >20 |
| 43 | >20 |
| 44 | >20 |
| 45 | >20 |
| 46 | >20 |
| 47 | >20 |
| 48 | >20 |
| 49 | >20 |
| 50 | >20 |
| 51 | >20 |
| 52 | >20 |
| 53 | >20 |
| 54 | >20 |
| 55 | >20 |
| 56 | >20 |
| 57 | >20 |
| 58 | >20 |
| 59 | >20 |
| 60 | >20 |
| 61 | >20 |
| 62 | 14.9 |
| 63 | >20 |
| 64 | >20 |
| 65 | 18.1 |
| 66 | 15.5 |
| 67 | >20 |
| 68 | >20 |
| 69 | >20 |
| 70 | >20 |
| 71 | >20 |
| 72 | >20 |
| 73 | >20 |
| 74 | >20 |
| 75 | >20 |
| 76 | >20 |
| 77 | >20 |
| 78 | >20 |
| 79 | >20 |
| 80 | >20 |
| 81 | >20 |
| 82 | >20 |
| 83 | 18.8 |
| 84 | >20 |
| 85 | >20 |
| 86 | >20 |
| 87 | >20 |
| 88 | >20 |
| 89 | 19.0 |
| 90 | >20 |
| 91 | >20 |
| 92 | >20 |
| 93 | >20 |
| 94 | >20 |
| 95 | >20 |
| 96 | >20 |
| 97 | >20 |
| 98 | >20 |
| 99 | >20 |
| 100 | >20 |
| 101 | >20 |
| 102 | >20 |
| 103 | >20 |
| 104 | >20 |
| 105 | >20 |
| 106 | >20 |
| 107 | >20 |
| 108 | >20 |
| 109 | >20 |
| 110 | >20 |
| 111 | >20 |
| 112 | >20 |
| 113 | 16.7 |
| 114 | >20 |
| 115 | >20 |
| 116 | >20 |
| 117 | >20 |
| 118 | >20 |
| 119 | >20 |
| 120 | >20 |
| 121 | >20 |
| 122 | >20 |
| 123 | >20 |
| 124 | >20 |
| 125 | >20 |
| 126 | >20 |
| 127 | >20 |
| 128 | >20 |
| 129 | >20 |
| 130 | >20 |
| 131 | >20 |
| 132 | >20 |
| 133 | >20 |
| 134 | >20 |
| 135 | >20 |
| 136 | >20 |
| 137 | >20 |
| 138 | >20 |
| 139 | >20 |
| 140 | >20 |
| 141 | >20 |
| 142 | >20 |
| 143 | >20 |
| 144 | >20 |
| 145 | >20 |
| 146 | >20 |
| 147 | >20 |
| 148 | >20 |
| 149 | >20 |
| 150 | >20 |
| 151 | >20 |
| 152 | >20 |
| 153 | >20 |
| 154 | >20 |
| 155 | >20 |
| 156 | >20 |
| 157 | >20 |
| 158 | >20 |
| 159 | >20 |
| 160 | >20 |
| 161 | >20 |
| 162 | >20 |
| 163 | >20 |
| 164 | >20 |
| 165 | >20 |
| 166 | >20 |
| 167 | >20 |
| 168 | >20 |
| 169 | >20 |
| 170 | >20 |
| 171 | >20 |
| 172 | >20 |
| 173 | >20 |
| 174 | >20 |

TABLE 2-continued

Measured IC$_{50}$ values of compounds regarding TBK1 inhibition as selectivity assay

| Example | IC$_{50}$ [µM] |
|---|---|
| 175 | >20 |
| 176 | >20 |
| 177 | >20 |
| 178 | >20 |
| 179 | >20 |
| 180 | >20 |
| 181 | >20 |
| 182 | >20 |
| 183 | >20 |
| 184 | >20 |
| 185 | >20 |
| 186 | >20 |
| 187 | >20 |
| 188 | >20 |
| 189 | >20 |
| 190 | >20 |
| 191 | >20 |
| 192 | >20 |
| 193 | >20 |
| 194 | >20 |
| 195 | >20 |
| 196 | >20 |
| 197 | >20 |
| 198 | >20 |
| 199 | >20 |
| 200 | >20 |
| 201 | >20 |
| 202 | >20 |
| 203 | 10.6 |
| 204 | >20 |
| 205 | >20 |
| 206 | >20 |
| 207 | >20 |
| 208 | >20 |
| 209 | >20 |
| 210 | >20 |
| 211 | >20 |
| 212 | >20 |
| 213 | >20 |
| 214 | >20 |
| 215 | >20 |
| 216 | >20 |
| 217 | >20 |
| 218 | >20 |
| 219 | >20 |
| 220 | >20 |
| 221 | >20 |
| 222 | >20 |
| 223 | >20 |
| 224 | >20 |
| 225 | >20 |
| 226 | >20 |
| 227 | >20 |
| 228 | >20 |
| 229 | >20 |
| 230 | >20 |
| 231 | >20 |
| 232 | >20 |

Phosphorylation Assay in Human Cell Line

Phosphorylation assays were carried out in Jurkat E6.1 cells from American Type Culture Collection (ATCC) stably overexpressing human FLAG-tagged SLP-76 (proprietary). Cultured cells were kept in RPMI 1640 medium supplemented with 1% FCS at a cell density of 2×10e6/mL 24 h prior compound testing. Starved cells were simultaneously treated with 350 ng/mL a-CD3 antibody (clone OKT3. ebioscience #16-0037-85. plate-bound) and test compound for 30 min at 37° C. Applied compounds were tested in either fixed concentration of 10 µmol/L and 20 µmol/L or in a 8 point dose response titration of increase compound concentration with 10 nmol/L. 50 nmol/L. 100 nmol/L. 500 nmol/L. 1 µmol/L. 5 µmol/L. 10 µmol/L and 20 µmol/L in triplicates. The cells were washed once in phosphate-buffered saline (pH 7.4). Cells were lysed using a lysis buffer containing 50 mmol/L Tris-Cl (pH 7.5). 150 mM NaCl. 2 mM EDTA. 1% Triton-X 100. 0.5% Na-DOC. 0.1% SDS. 1/10 complete mini protease inhibitor cocktail (Roche #11836170001) and 1/10 PhosSTOP phosphatase inhibitor cocktail (Roche #04906837001). A total of 1.25 pg cell lysate was analyzed by capillary electrophoresis using the Peggy Sue™ System (Proteinsimple® San Jose. Calif. USA) with a 12-230 kDa size-based master kit with split buffer/a-rabbit-HRP #PS-MK18/a-mouse-HRP #PS-MK19 according to manufacture's protocol. Probe antibodies used were a rabbit monoclonal antibody supernatant raised against human phospho-Ser376-SLP-76 peptide (proprietary) and for normalization an anti-alpha-Tubulin mouse monoclonal antibody (Sigma #T9026). As control for maximal effect (max control. which represent the maximally possible inhibition of pSer376-SLP-76 by a test compound) cells with no a-CD3 (clone OKT3. ebioscience #16-0037-85. plate-bound) and no test compound treatment were used. Cells with a-CD3 treatment only were used as negative control (min control. which represent the minimally possible inhibition of pSer376-SLP-76 by a test compound)

AUC values of each respective test sample were normalized using the AUC of housekeeping gene alpha-Tubulin and AUC of pSer376-SLP-76 of the min control. The percentage of the amount of pSer-SLP-76 in the treatment samples was calculated using the max control and min control values of the respective Peggy Sue™ run.

TABLE 3

Measured IC$_{50}$ values/% amount of pSer376-SLP-76 of compound

| Example | IC$_{50}$ [µM] | % amount of pSer376-SLP-76 @ 20 µM | % amount of pSer376-SLP-76 @ 10 µM |
|---|---|---|---|
| 1 | | <1 | <1 |
| 2 | 0.20 | <1 | <1 |
| 3 | | <1 | <1 |
| 4 | | <1 | <1 |
| 5 | | <1 | <1 |
| 6 | | 4.6 | 27.9 |
| 7 | | <1 | 17.8 |
| 8 | 0.61 | <1 | <1 |
| 9 | | 11.7 | 18.2 |
| 10 | | <1 | <1 |
| 11 | | <1 | <1 |
| 14 | | <1 | <1 |
| 15 | 0.30 | <1 | <1 |
| 17 | 0.96 | <1 | 2.5 |
| 19 | | <1 | <1 |
| 20 | | <1 | <1 |
| 21 | | <1 | <1 |
| 30 | 1.2 | <1 | <1 |
| 31 | | <1 | <1 |
| 32 | 1.5 | <1 | 2.4 |
| 33 | | 49.1 | 64.6 |
| 36 | | <1 | <1 |
| 37 | 0.45 | <1 | <1 |
| 38 | 0.15 | <1 | <1 |
| 39 | | <1 | <1 |
| 40 | 2.6 | <1 | 1.3 |
| 43 | | nd | <1 |
| 47 | 1.3 | <1 | <1 |
| 48 | 0.97 | <1 | <1 |
| 53 | 0.64 | <1 | <1 |
| 86 | 1.9 | nd | nd |
| 90 | 0.28 | nd | nd |
| 124 | 1.9 | nd | nd |
| 125 | 1.0 | nd | nd |
| 127 | 1.0 | nd | nd |

TABLE 3-continued

Measured IC$_{50}$ values/% amount of pSer376-SLP-76 of compound

| Example | IC$_{50}$ [μM] | % amount of pSer376-SLP-76 @ 20 μM | % amount of pSer376-SLP-76 @ 10 μM |
|---|---|---|---|
| 129 | 4.0 | nd | nd |
| 134 | 2.0 | nd | nd |
| 139 | 2.9 | nd | nd |
| 141 | 0.59 | nd | nd |
| 143 | 0.48 | nd | nd |
| 183 | 0.11 | nd | nd |
| 196 | 1.6 | nd | nd |

Stimulation of IFNg Production from Human Primary Peripheral Blood Mononuclear Cells (PBMCs)

The effect of the compound in the activation of human T cells was tested by measuring the production of the proinflammatory cytokine IFNg in vitro. Fresh human PBMCs were isolated and activated in vitro with coated a-CD3 (clone OKT3. ebioscience #16-0037-85. plate-bound). Concentration of a-CD3 was titrated in order to obtain a suboptimal activation of PBMCs (1×106 PBMCs/mL). Cells were activated with a-CD3 and 1 μmol/L PGE2 for 22 hours in the presence of the compounds and the supernatant of the culture was isolated and tested for IFNg concentration. Applied compounds were tested at either fixed concentration of 200 nmol/L or in a 6 point dose response titration of increase compound concentration from 12 nmol/L to 3 μmol/L in triplicates. IFNg concentration was determined by ELISA (Opt EIA human IFNg ELISA BD #555142). Plate was coated with a-IFNg overnight. The plates were washed 3 times and the supernatant from the PBMCs culture was added to the wells and incubated for 2 hours. Plates were washed and detection antibody and the SAv-HRP was added for 1 h. Plates were washed and the substrate was added until the standard turns blue. The reaction is stopped by adding 50 μL 2N H2SO4. Absorbance was measured with a TECAN Reader at 450 to 570 nm. Concentration of IFNg was calculated from the absorbance using standards of known concentration.

FIG. 1 shows the efficacy of a selected example in IFNγ production (Human primary peripheral blood mononuclear cells)

The invention claimed is:

1. A compound of formula (I)

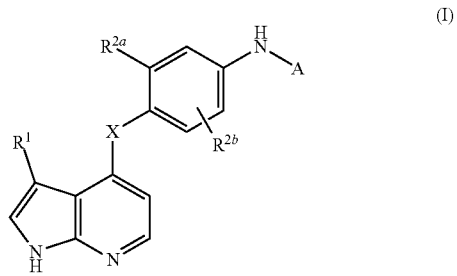

wherein:

A is a monocyclic 5- to 7 membered ring selected from the group consisting of

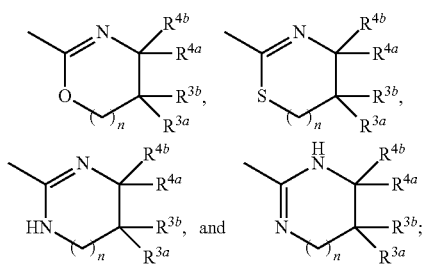

X is a nitrogen, a sulphur or an oxygen atom;
n is 0, 1, or 2;
R$^1$ is a group selected from the group consisting of
hydrogen, halogen, cyano, C$_1$-C$_6$-haloalkyl,
a C$_1$-C$_6$-alkyl,
a phenyl,
a 5- or 6-membered heteroaryl,
a C$_3$-C$_8$-cycloalkyl-,
a monocyclic 4- to 7-membered heterocycloalkyl, and
a bridged bicyclic 7- to 10-membered heterocycloalkyl,
wherein said C$_1$-C$_6$-alkyl, phenyl, 5- or 6-membered heteroaryl,

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic organisms, biotinylated peptide
<220> FEATURE:
<221> NAME/KEY: VARIANT
<222> LOCATION: 12
<223> OTHER INFORMATION: C-terminus in amide form

<400> SEQUENCE: 1

Gly Asp Glu Asp Phe Ser Ser Phe Ala Glu Pro Gly
1               5                   10
```

$C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, aminosulfonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_3$-$C_8$-cycloalkoxy, $C_3$-$C_8$-cycloalkyl-$C_1$-$C_6$-alkoxy, $C_1$-$C_6$-alkylcarbonyloxy, $C_1$-$C_3$-alkylcarbonyl, di-($C_1$-$C_4$)-alkylaminocarbonyl, mono-($C_1$-$C_4$)-alkylaminocarbonyl, and di-($C_1$-$C_4$)-alkylaminosulfonyl, mono-($C_1$-$C_4$)-alkylaminosulfonyl; or $R^1$ is the group Z-L-, wherein Z is a 5- or 6-membered heteroaryl which is optionally substituted with one or two substituents, identically or differently, selected from the group consisting of halogen, cyano, aminocarbonyl, $C_1$-$C_3$-alkyl, $C_1$-$C_3$-alkoxy, di-($C_1$-$C_4$)-alkylaminocarbonyl, and mono-($C_1$-$C_4$)-alkylaminocarbonyl; and L is —$CH_2$—NHCO—, —$CH_2$—CONH—, $CH_2$—$NHSO_2$—, or —$CH_2$—$SO_2$NH—, and the $CH_2$-group of L can be bonded to any atom of Z except to an oxygen or sulphur heteroatom, if present;

$R^{2a}$ is hydrogen, halogen, $C_1$-$C_3$-alkyl, $C_1$-$C_3$-alkoxy, $C_1$-$C_3$-haloalkyl, or $C_1$-$C_3$-haloalkoxy-;

$R^{2b}$ is hydrogen, halogen, cyano, methyl, methoxy, trifluoromethyl, or trifluoromethoxy;

$R^{3a}$ and $R^{3b}$ are independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, phenyl, $C_3$-$C_8$-cycloalkyl-, $C_1$-$C_6$-alkyl-$C_3$-$C_8$-cycloalkyl, $C_1$-$C_6$-alkyl-phenyl, and $C_1$-$C_6$-alkyl-heteroaryl wherein a cycloalkyl, phenyl or heteroaryl ring is optionally substituted with one or two $C_1$-$C_3$-alkyl;

$R^{4a}$ and $R^{4b}$ are independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, and mono-($C_1$-$C_4$)-alkylaminocarbonyl; or $R^{3a}$ and $R^{3b}$ are taken together with the carbon atom to which they are attached to form a monocyclic 3 to 6-membered cycloalkyl or heterocycloalkyl, wherein said 3 to 6-membered cycloalkyl or heterocycloalkyl is optionally substituted by fluorine, chlorine, methyl, methoxy, hydroxy, or cyano; or $R^{4a}$ and $R^{4b}$ are taken together with the carbon atom to which they are attached to form a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, or cyano, or a polymorph, an enantiomer, a diastereomer, a racemate, a tautomer, a solvate, a physiologically acceptable salt thereof or a solvate of said salt.

2. A compound of formula (Ia),

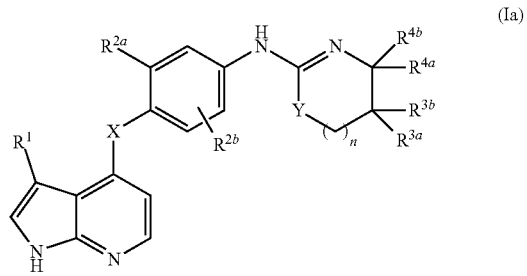

(Ia)

wherein:

X is a nitrogen, a sulphur or an oxygen atom;

Y is a nitrogen, a sulphur or an oxygen atom;

n is 0, 1, or 2;

$R^1$ is a group selected from the group consisting of halogen, cyano, $C_1$-$C_6$-haloalkyl, a phenyl, a 5- or 6-membered heteroaryl, a $C_3$-$C_8$-cycloalkyl-, a monocyclic 4- to 7-membered heterocycloalkyl, and a bridged bicyclic 7- to 10-membered heterocycloalkyl, wherein said phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, aminosulfonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_3$-$C_8$-cycloalkoxy, $C_3$-$C_8$-cycloalkyl-$C_1$-$C_6$-alkoxy, $C_1$-$C_6$-alkylcarbonyloxy, di-($C_1$-$C_4$)-alkylaminocarbonyl, mono-($C_1$-$C_4$)-alkylaminocarbonyl, and di-($C_1$-$C_4$)-alkylaminosulfonyl, mono-($C_1$-$C_4$)-alkylaminosulfonyl; or $R^1$ is the group Z-L-, wherein Z is a 5- or 6-membered heteroaryl which is optionally substituted with one or two substituents, identically or differently, selected from the group consisting of halogen, cyano, aminocarbonyl, $C_1$-$C_3$-alkyl, $C_1$-$C_3$-alkoxy, di-($C_1$-$C_4$)-alkylaminocarbonyl, and mono-($C_1$-$C_4$)-alkylaminocarbonyl; and L is —$CH_2$—NHCO—, —$CH_2$—CONH—, $CH_2$—$NHSO_2$—, or —$CH_2$—$SO_2$NH—;

and the $CH_2$-group of L can be bonded to any atom of Z except to an oxygen or sulphur heteroatom, if present;

$R^{2a}$ is hydrogen, halogen, $C_1$-$C_3$-alkyl, $C_1$-$C_3$-alkoxy, $C_1$-$C_3$-haloalkyl, or $C_1$-$C_3$-haloalkoxy-;

$R^{2b}$ is hydrogen, halogen, cyano, methyl, methoxy, trifluoromethyl, or trifluoromethoxy;

$R^{3a}$ and $R^{3b}$ are independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, mono-($C_1$-$C_4$)-alkylaminocarbonyl, and phenyl;

$R^{4a}$ and $R^{4b}$ are independently from each other hydrogen or a substituent, identically or differently, selected from the group consisting of aminocarbonyl, $C_1$-$C_3$-alkyl, $C_1$-$C_3$-hydroxyalkyl-, $C_1$-$C_3$-alkoxy-$C_1$-$C_3$-alkyl, $C_1$-$C_3$-alkylcarbonyl, di-($C_1$-$C_4$)-alkylaminocarbonyl, and mono-($C_1$-$C_4$)-alkylaminocarbonyl; or $R^{3a}$ and $R^{3b}$ are taken together with the carbon atom to which they are attached to form a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, or cyano; or $R^{4a}$ and $R^{4b}$ are taken together with the carbon atom to which they are attached to form a monocyclic 3 or 4-membered cycloalkyl or heterocycloalkyl, wherein said 3 or 4-membered cycloalkyl or heterocycloalkyl is optionally substituted by fluorine, chlorine, methyl, methoxy, hydroxy, or cyano, or a polymorph, an enantiomer, a diastereomer, a racemate, a tautomer, a solvate, a physiologically acceptable salt thereof or a solvate of said salt.

3. The compound of formula (I) according to claim 1, wherein:

$R^1$ is a group selected from the group consisting of hydrogen, halogen, cyano, $C_1$-$C_6$-haloalkyl,
a $C_1$-$C_6$-alkyl,
a phenyl,
a 5- or 6-membered heteroaryl,
a $C_3$-$C_8$-cycloalkyl-,
a monocyclic 4- to 7-membered heterocycloalkyl, and
a bridged bicyclic 7- to 10-membered heterocycloalkyl,
wherein said $C_1$-$C_6$-alkyl, phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_1$-$C_3$-alkylcarbonyl, di-($C_1$-$C_4$)-alkylaminocarbonyl, and mono-($C_1$-$C_4$)-alkylaminocarbonyl; or $R^1$ is the group Z-L-,
wherein Z is a 5- or 6-membered heteroaryl which is optionally substituted with one or two $C_1$-$C_3$-alkyl; and
L is —$CH_2$—NHCO, or a polymorph, an enantiomer, a diastereomer, a racemate, a tautomer, a solvate, a physiologically acceptable salt thereof or a solvate of said salt.

4. The compound of formula (I) according to claim 1, wherein:

$R^1$ is a group selected from the group consisting of hydrogen, halogen, cyano, $C_1$-$C_3$-haloalkyl,
a $C_1$-$C_6$-alkyl,
a phenyl,
a 5- or 6-membered heteroaryl,
a $C_3$-$C_6$-cycloalkyl-,
a monocyclic 4- to 6-membered heterocycloalkyl, and
a bridged bicyclic 7- or 8-membered heterocycloalkyl,
wherein said $C_1$-$C_6$-alkyl, phenyl, 5- or 6-membered heteroaryl, $C_3$-$C_6$-cycloalkyl-, monocyclic 4- to 6-membered heterocycloalkyl or bridged bicyclic 7- or 8-membered heterocycloalkyl is optionally substituted with one or two substituents, identically or differently, selected from the group consisting of halogen, hydroxy, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_3$-cyanoalkyl, $C_1$-$C_3$-cyanoalkoxy, $C_3$-$C_6$-cycloalkyl, $C_1$-$C_3$-alkylcarbonyl, di-($C_1$-$C_4$)-alkylaminocarbonyl, and mono-($C_1$-$C_4$)-alkylaminocarbonyl; or $R^1$ is the group Z-L-,
wherein Z is a 5-membered heteroaryl which is optionally substituted with one or two $C_1$-$C_3$-alkyl; and
L is —$CH_2$—NHCO, or a polymorph, an enantiomer, a diastereomer, a racemate, a tautomer, a solvate, a physiologically acceptable salt thereof or a solvate of said salt.

5. The compound of formula (I) according to claim 1, wherein:

X is a sulphur or an oxygen atom;
or a polymorph, an enantiomer, a diastereomer, a racemate, a tautomer, a solvate, a physiologically acceptable salt thereof or a solvate of said salt.

6. The compound of formula (I) according to claim 1, wherein:

n is 0 or 1;
or a polymorph, an enantiomer, a diastereomer, a racemate, a tautomer, a solvate, a physiologically acceptable salt thereof or a solvate of said salt.

7. The compound of formula (I) according to claim 1, wherein:

$R^{3a}$ and $R^{3b}$ are independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_6$-cycloalkyl-, $C_1$-$C_3$-alkyl-$C_3$-$C_6$-cycloalkyl, $C_1$-$C_3$-alkyl-phenyl, and $C_1$-$C_3$-alkyl-heteroaryl, wherein the cycloalkyl, phenyl or heteroaryl ring is optionally substituted with one or two $C_1$-$C_3$-alkyl; or $R^{3a}$ and $R^{3b}$ are taken together with the carbon atom to which they are attached to form a monocyclic 3 to 6-membered cycloalkyl or heterocycloalkyl, or a polymorph, an enantiomer, a diastereomer, a racemate, a tautomer, a solvate, a physiologically acceptable salt thereof or a solvate of said salt.

8. The compound of formula (I) according to claim 1, wherein:

A is a monocyclic 5- to 7 membered ring selected from the group consisting of

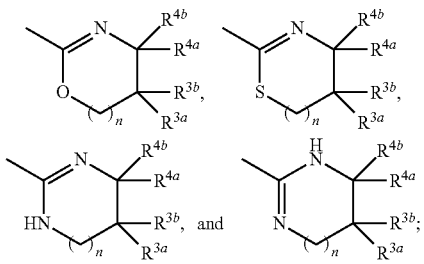

X is a sulphur or an oxygen atom;
n is 0 or 1;
$R^1$ is a group selected from the group consisting of hydrogen, halogen, cyano, $C_1$-$C_6$-haloalkyl,
a $C_1$-$C_6$-alkyl,
a phenyl, a 5- or 6-membered heteroaryl,
a $C_3$-$C_8$-cycloalkyl-,
a monocyclic 4- to 7-membered heterocycloalkyl, and
a bridged bicyclic 7- to 10-membered heterocycloalkyl,
wherein said $C_1$-$C_6$-alkyl, phenyl, 5- or 6-membered heteroaryl, $C_3$-$C_8$-cycloalkyl-, monocyclic 4- to 7-membered heterocycloalkyl or bridged bicyclic 7- to 10-membered heterocycloalkyl is optionally substituted with one or two substituents, identically or differently, selected from the group consisting of halogen, hydroxy, cyano, aminocarbonyl, $C_1$-$C_6$-alkyl, $C_1$-$C_6$-haloalkyl, $C_1$-$C_6$-haloalkoxy, $C_1$-$C_6$-alkoxy, $C_1$-$C_6$-cyanoalkyl, $C_1$-$C_6$-cyanoalkoxy, $C_3$-$C_8$-cycloalkyl-, $C_1$-$C_3$-alkylcarbonyl, di-($C_1$-$C_4$)-alkylaminocarbonyl, and mono-($C_1$-$C_4$)-alkylaminocarbonyl; or $R^1$ is the group Z-L-,
wherein Z is a 5- or 6-membered heteroaryl,
which is optionally substituted with one or two $C_1$-$C_3$-alkyl; and
L is —$CH_2$—NHCO;
$R^{2a}$ is hydrogen, halogen, or $C_1$-$C_3$-haloalkyl;
$R^{2b}$ is hydrogen or halogen;
$R^{3a}$ and $R^{3b}$ are independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_8$-cycloalkyl-, $C_1$-$C_6$-alkyl-$C_3$-$C_8$-cycloalkyl, $C_1$-$C_6$-alkyl-phenyl, and $C_1$-$C_6$-alkyl-heteroaryl, wherein the cycloalkyl, phenyl or heteroaryl ring is optionally substituted with one or two $C_1$-$C_3$-alkyl;
$R^{4a}$ and $R^{4b}$ are independently from each other hydrogen or a substituent, identically or differently, selected from the group consisting of aminocarbonyl, $C_1$-$C_3$-alkyl, $C_1$-$C_3$-hydroxyalkyl-; or
$R^{3a}$ and $R^{3b}$ are taken together with the carbon atom to which they are attached to form a monocyclic 3 to 6-membered cycloalkyl or heterocycloalkyl,
or a polymorph, an enantiomer, a diastereomer, a racemate, a tautomer, a solvate, a physiologically acceptable salt thereof or a solvate of said salt.

9. The compound of formula (I) according to claim 1, wherein:
A is a monocyclic 5- or 6-membered ring selected from the group consisting of

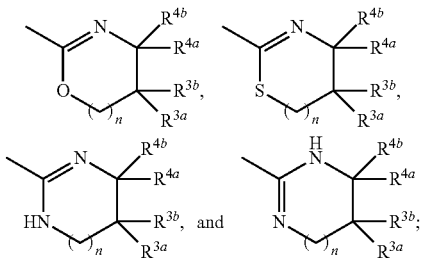

X is a sulphur or an oxygen atom;
n is 0 or 1;
$R^1$ is a group selected from the group consisting of hydrogen, halogen, cyano, $C_1$-$C_3$-haloalkyl,
a $C_1$-$C_6$-alkyl,
a phenyl,
a 5- or 6-membered heteroaryl,
a $C_3$-$C_6$-cycloalkyl-,
a monocyclic 4- to 6-membered heterocycloalkyl, and
a bridged bicyclic 7- or 8-membered heterocycloalkyl,
wherein said $C_1$-$C_6$-alkyl, phenyl, 5- or 6-membered heteroaryl, $C_3$-$C_6$-cycloalkyl-, monocyclic 4- to 6-membered heterocycloalkyl or bridged bicyclic 7- or 8-membered heterocycloalkyl is optionally substituted with one or two substituents, identically or differently, selected from the group consisting of halogen, hydroxy, cyano, aminocarbonyl, $C_1$-$C_3$-alkyl, $C_1$-$C_3$-haloalkyl, $C_1$-$C_3$-haloalkoxy, $C_1$-$C_3$-alkoxy, $C_1$-$C_3$-cyanoalkyl, $C_1$-$C_3$-cyanoalkoxy, $C_3$-$C_6$-cycloalkyl-, $C_1$-$C_3$-alkylcarbonyl, di-($C_1$-$C_4$)-alkylaminocarbonyl, and mono-($C_1$-$C_4$)-alkylaminocarbonyl; or $R^1$ is the group Z-L-,
wherein Z is a 5-membered heteroaryl
which is optionally substituted with one or two $C_1$-$C_3$-alkyl; and
L is —$CH_2$—NHCO;
$R^{2a}$ is hydrogen, halogen, or trifluoromethyl;
$R^{2b}$ is hydrogen or halogen;
$R^{3a}$ and $R^{3b}$ represent independently from each other hydrogen or a substituent, identically or differently, selected from the group consisting of halogen, hydroxy, cyano, aminocarbonyl, $C_1$-$C_3$-alkyl, $C_1$-$C_3$-haloalkyl, $C_1$-$C_6$-hydroxyalkyl-, $C_1$-$C_3$-alkoxy-$C_1$-$C_3$-alkyl, phenyl, $C_3$-$C_6$-cycloalkyl-, $C_1$-$C_3$-alkyl-$C_3$-$C_6$-cycloalkyl, $C_1$-$C_3$-alkyl-phenyl, and $C_1$-$C_3$-alkyl-heteroaryl wherein the cycloalkyl, phenyl or heteroaryl ring is optionally substituted with one or two $C_1$-$C_3$-alkyl;
$R^{4a}$ and $R^{4b}$ represent independently from each other hydrogen or a substituent, identically or differently, selected from the group consisting of aminocarbonyl, $C_1$-$C_3$-alkyl, and $C_1$-$C_3$-hydroxyalkyl-; or
$R^{3a}$ and $R^{3b}$ are taken together with the carbon atom to which they are attached to form a monocyclic 3 to 6-membered cycloalkyl or heterocycloalkyl,
or a polymorph, an enantiomer, a diastereomer, a racemate, a tautomer, a solvate, a physiologically acceptable salt thereof or a solvate of said salt.

10. The compound according to claim 1, which is selected from the group consisting of
(+/−)-{2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol;
(+/−)-{2-[(3,5-difluoro-4-{[3-(trifluoromethyl)-1H-pyrrolo[2,3-b]pyridin-4-yl]oxy}phenyl)amino]-5-methyl-5,6-dihydro-4H-1,3-oxazin-5-yl}methanol;
(+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazine-5-carbonitrile;
(+/−)-{5-(difluoromethyl)-2-[(3,5-difluoro-4-{[3-(trifluoromethyl)-1H-pyrrolo[2,3-b]pyridin-4-yl]oxy}phenyl)amino]-5,6-dihydro-4H-1,3-oxazin-5-yl}methanol;
(+/−)-{2-[(3,5-difluoro-4-{[3-(trifluoromethyl)-1H-pyrrolo[2,3-b]pyridin-4-yl]oxy}phenyl)amino]-5-isopropyl-5,6-dihydro-4H-1,3-oxazin-5-yl}methanol;
(+/−)-2-{2-[(3,5-difluoro-4-{[3-(trifluoromethyl)-1H-pyrrolo[2,3-b]pyridin-4-yl]oxy}phenyl)amino]-4,5-dihydro-1,3-oxazol-5-yl}-2-methylpropan-1-ol;
(+/−)-{2-[(3,5-difluoro-4-{[3-(trifluoromethyl)-1H-pyrrolo[2,3-b]pyridin-4-yl]oxy}phenyl)amino]-4,5-dihydro-1,3-oxazol-4-yl}methanol;

(+/−)-{2-[(3,5-difluoro-4-{[3-(trifluoromethyl)-1H-pyrrolo[2,3-b]pyridin-4-yl]oxy}phenyl)amino]-5-fluoro-5,6-dihydro-4H-1,3-oxazin-5-yl}methanol;

(+/−)-2-[(3,5-difluoro-4-{[3-(trifluoromethyl)-1H-pyrrolo[2,3-b]pyridin-4-yl]oxy}phenyl)amino]-4-(hydroxymethyl)-4,5-dihydro-1,3-oxazole-4-carboxamide;

(+/−)-2-[(3,5-difluoro-4-{[3-(trifluoromethyl)-1H-pyrrolo[2,3-b]pyridin-4-yl]oxy}phenyl)amino]-5-(hydroxymethyl)-5,6-dihydro-4H-1,3-oxazin-5-ol;

(+/−)-{2-[(3,5-difluoro-4-{[3-(trifluoromethyl)-1H-pyrrolo[2,3-b]pyridin-4-yl]oxy}phenyl)amino]-5-phenyl-5,6-dihydro-4H-1,3-oxazin-5-yl}methanol;

(+/−)-{2-[(3,5-difluoro-4-{[3-(trifluoromethyl)-1H-pyrrolo[2,3-b]pyridin-4-yl]oxy}phenyl)amino]-4-methyl-5,6-dihydro-4H-1,3-oxazin-5-yl}methanol;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile;

(+/−)-[2-({4-[(3-bromo-1H-pyrrolo[2,3-b]pyridin-4-yl)oxy]-3,5-difluorophenyl}amino)-5,6-dihydro-4H-1,3-oxazin-5-yl]methanol;

(+/−)-[2-({4-[(3-bromo-1H-pyrrolo[2,3-b]pyridin-4-yl)oxy]-3,5-difluorophenyl}amino)-5-methyl-5,6-dihydro-4H-1,3-oxazin-5-yl]methanol;

(+/−)-4-(2,6-difluoro-4-{[5-(hydroxymethyl)-5,6-dihydro-4H-1,3-oxazin-2-yl]amino}phenoxy)-1H-pyrrolo[2,3-b]pyridine-3-carbonitrile;

(+/−)-4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridine-3-carbonitrile;

(+/−)-[2-({4-[(3-cyclopropyl-1H-pyrrolo[2,3-b]pyridin-4-yl)oxy]-3,5-difluorophenyl}amino)-5-methyl-5,6-dihydro-4H-1,3-oxazin-5-yl]methanol;

(+/−)-[2-({4-[(3-cyclopropyl-1H-pyrrolo[2,3-b]pyridin-4-yl)oxy]-3,5-difluorophenyl}amino)-5-fluoro-5,6-dihydro-4H-1,3-oxazin-5-yl]methanol;

(+/−)-{2-[(3,5-difluoro-4-{[3-(2-methyl-3-thienyl)-1H-pyrrolo[2,3-b]pyridin-4-yl]oxy}phenyl)amino]-5-methyl-5,6-dihydro-4H-1,3-oxazin-5-yl}methanol;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxynicotinonitrile;

(+/−)-{2-[(3,5-difluoro-4-{[3-(6-methoxypyridin-3-yl)-1H-pyrrolo[2,3-b]pyridin-4-yl]oxy}phenyl)amino]-5-methyl-5,6-dihydro-4H-1,3-oxazin-5-yl}methanol;

(+/−)-{2-[(3,5-difluoro-4-{[3-(1-methyl-1,2,3,6-tetrahydropyridin-4-yl)-1H-pyrrolo[2,3-b]pyridin-4-yl]oxy}phenyl)amino]-5-methyl-5,6-dihydro-4H-1,3-oxazin-5-yl}methanol;

(+/−)-1-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3,6-dihydropyridin-1(2H)-yl}propan-1-one;

(+/−)-{2-[(4-{[3-(8-azabicyclo[3.2.1]oct-2-en-3-yl)-1H-pyrrolo[2,3-b]pyridin-4-yl]oxy}-3,5-difluorophenyl)amino]-5-methyl-5,6-dihydro-4H-1,3-oxazin-5-yl}methanol;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carboxamide;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluorobenzonitrile;

(+/−)-[2-({4-[(3-chloro-1H-pyrrolo[2,3-b]pyridin-4-yl)oxy]-3,5-difluorophenyl}amino)-5-methyl-5,6-dihydro-4H-1,3-oxazin-5-yl]methanol;

(+/−)-[2-({4-[(3-chloro-1H-pyrrolo[2,3-b]pyridin-4-yl)oxy]-3,5-difluorophenyl}amino)-5,6-dihydro-4H-1,3-oxazin-5-yl]methanol;

(+/−)-[2-({4-[(3-chloro-1H-pyrrolo[2,3-b]pyridin-4-yl)oxy]-3,5-difluorophenyl}amino)-5-fluoro-5,6-dihydro-4H-1,3-oxazin-5-yl]methanol;

(+/−)-4-(2,6-difluoro-4-{[5-(hydroxymethyl)-5-methyl-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide;

(+/−)-4-(2,6-difluoro-4-{[5-(hydroxymethyl)-5,6-dihydro-4H-1,3-oxazin-2-yl]amino}phenoxy)-N-[(1-methyl-1H-imidazol-5-yl)methyl]-1H-pyrrolo[2,3-b]pyridine-3-carboxamide;

(+/−)-{2-[(4-{[3-(5-chloro-6-methoxypyridin-3-yl)-1H-pyrrolo[2,3-b]pyridin-4-yl]oxy}-3,5-difluorophenyl)amino]-5-methyl-5,6-dihydro-4H-1,3-oxazin-5-yl}methanol;

(+/−)-[2-{[3,5-difluoro-4-({3-[1-(propan-2-yl)-1H-pyrazol-3-yl]-1H-pyrrolo[2,3-b]pyridin-4-yl}oxy)phenyl]amino}-5-methyl-5,6-dihydro-4H-1,3-oxazin-5-yl]methanol;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(propan-2-yloxy)benzonitrile;

(+/−)-{2-[(3,5-difluoro-4-{[3-(2-fluoro-4-methoxyphenyl)-1H-pyrrolo[2,3-b]pyridin-4-yl]oxy}phenyl)amino]-5-methyl-5,6-dihydro-4H-1,3-oxazin-5-yl}methanol;

(+/−)-{2-[(3,5-difluoro-4-{[3-(1-methyl-1H-pyrazol-5-yl)-1H-pyrrolo[2,3-b]pyridin-4-yl]oxy}phenyl)amino]-5-methyl-5,6-dihydro-4H-1,3-oxazin-5-yl}methanol;

(+/−)-[2-{[3,5-difluoro-4-({3-[1-(propan-2-yl)-1H-pyrazol-5-yl]-1H-pyrrolo[2,3-b]pyridin-4-yl}oxy)phenyl]amino}-5-methyl-5,6-dihydro-4H-1,3-oxazin-5-yl]methanol;

(+/−)-{2-[(3,5-difluoro-4-{[3-(2-fluorophenyl)-1H-pyrrolo[2,3-b]pyridin-4-yl]oxy}phenyl)amino]-5-methyl-5,6-dihydro-4H-1,3-oxazin-5-yl}methanol;

(+/−)-{2-[(3,5-difluoro-4-{[3-(3-fluorophenyl)-1H-pyrrolo[2,3-b]pyridin-4-yl]oxy}phenyl)amino]-5-methyl-5,6-dihydro-4H-1,3-oxazin-5-yl}methanol;

(+/−)-{2-[(3,5-difluoro-4-{[3-(4-fluorophenyl)-1H-pyrrolo[2,3-b]pyridin-4-yl]oxy}phenyl)amino]-5-methyl-5,6-dihydro-4H-1,3-oxazin-5-yl}methanol;

(+/−)-2-{[4-({3-[3-cyano-4-(propan-2-yloxy)phenyl]-1H-pyrrolo[2,3-b]pyridin-4-yl}oxy)-3,5-difluorophenyl]amino}-5-(hydroxymethyl)-5,6-dihydro-4H-1,3-oxazine-5-carbonitrile;

(+/−)-5-[4-(4-{[5-(difluoromethyl)-5-(hydroxymethyl)-5,6-dihydro-4H-1,3-oxazin-2-yl]amino}-2,6-difluorophenoxy)-1H-pyrrolo[2,3-b]pyridin-3-yl]-2-(propan-2-yloxy)benzonitrile;

(+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(propan-2-yloxy)benzonitrile;

(+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-(propan-2-yloxy)benzonitrile;

(+/−)-{2-[(4-{[3-(1-ethyl-1H-pyrazol-5-yl)-1H-pyrrolo[2,3-b]pyridin-4-yl]oxy}-3,5-difluorophenyl)amino]-5-methyl-5,6-dihydro-4H-1,3-oxazin-5-yl}methanol;

(+/−)-{4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]phenoxy}acetonitrile;

(+/−)-{2-[(3,5-difluoro-4-{[3-(2-fluoro-3-methoxyphenyl)-1H-pyrrolo[2,3-b]pyridin-4-yl]oxy}phenyl)amino]-5-methyl-5,6-dihydro-4H-1,3-oxazin-5-yl}methanol;

(+/−)-[2-{[3,5-difluoro-4-({3-[2-fluoro-4-(propan-2-yloxy)phenyl]-1H-pyrrolo[2,3-b]pyridin-4-yl}oxy)phenyl]amino}-5-methyl-5,6-dihydro-4H-1,3-oxazin-5-yl]methanol;

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol;

[(5S)-2-(3,5-difluoro-4-{[3-(trifluoromethyl)-1H-pyrrolo[2,3-b]pyridin-4-yl]oxy}anilino)-5-fluoro-5,6-dihydro-4H-1,3-oxazin-5-yl]methanol;

(+/−)-[2-{3,5-difluoro-4-[(1H-pyrrolo[2,3-b]pyridin-4-yl)oxy]anilino}-5-(propan-2-yl)-5,6-dihydro-4H-1,3-oxazin-5-yl]methanol;

(+/−)-[2-{3,5-difluoro-4-[(1H-pyrrolo[2,3-b]pyridin-4-yl)oxy]anilino}-5-methyl-5,6-dihydro-4H-1,3-oxazin-5-yl]methanol;

(+/−)-[2-{3,5-difluoro-4-[(1H-pyrrolo[2,3-b]pyridin-4-yl)oxy]anilino}-4-methyl-5,6-dihydro-4H-1,3-oxazin-5-yl]methanol;

(+/−)-[2-(3-fluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol;

(+/−)-[2-(2,5-difluoro-4-{[3-(trifluoromethyl)-1H-pyrrolo[2,3-b]pyridin-4-yl]oxy}anilino)-5-methyl-5,6-dihydro-4H-1,3-oxazin-5-yl]methanol;

(+/−)-[2-{4-[(3-bromo-1H-pyrrolo[2,3-b]pyridin-4-yl)sulfanyl]anilino}-5-methyl-5,6-dihydro-4H-1,3-oxazin-5-yl]methanol;

(+/−)-5-{4-[4-{[5-(hydroxymethyl)-5-phenyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile;

(+/−)-5-{4-[4-{[5-fluoro-5-(hydroxymethyl)-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile;

(+/−)-5-{4-[4-{5-(hydroxymethyl)-5-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile;

(+/−)-2-{4-[(3-{3-cyano-4-[(propan-2-yl)oxy]phenyl}-1H-pyrrolo[2,3-b]pyridin-4-yl)oxy]-3-(trifluoromethyl)anilino}-5-(hydroxymethyl)-5,6-dihydro-4H-1,3-oxazine-5-carbonitrile;

(+/−)-5-{4-[4-{[4-(hydroxymethyl)-4,5-dihydro-1,3-oxazol-2-yl]amino}-2-(trifluoromethyl)phenoxy]-1H-pyrrolo[2,3-b]pyridin-3-yl}-2-[(propan-2-yl)oxy]benzonitrile;

(+/−)-5-{4-[4-{[-5-(hydroxymethyl)-4-methyl-5,6-dihydro-4H-1,3-oxazin-2-yl]amino}-2-(trifluoromethyl)phenoxy]-1H-pyrrolo[2,3-b]pyridin-3-yl}-2-[(propan-2-yl)oxy]benzonitrile;

5-(4-{4-[(5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile;

5-(4-{4-[(5-oxa-7-azaspiro[2.5]oct-6-en-6-yl)amino]-2-(trifluoromethyl)phenoxy}-1H-pyrrolo[2,3-b]pyridin-3-yl)-2-[(propan-2-yl)oxy]benzonitrile;

5-(4-{4-[(5,5-dimethyl-5,6-dihydro-4H-1,3-oxazin-2-yl)amino]-2-(trifluoromethyl)phenoxy}-1H-pyrrolo[2,3-b]pyridin-3-yl)-2-[(propan-2-yl)oxy]benzonitrile;

(+/−)-5-[4-(2,6-difluoro-4-{[5-(1-hydroxy-2-methylpropan-2-yl)-4,5-dihydro-1,3-oxazol-2-yl]amino}phenoxy)-1H-pyrrolo[2,3-b]pyridin-3-yl]-2-[(propan-2-yl)oxy]benzonitrile;

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-5-[4-(2,6-difluoro-4-{[4-(hydroxymethyl)-4,5-dihydro-1,3-oxazol-2-yl]amino}phenoxy)-1H-pyrrolo[2,3-b]pyridin-3-yl]-2-[(propan-2-yl)oxy]benzonitrile;

(+/−)-5-[4-(2,6-difluoro-4-{[5-(hydroxymethyl)-5-phenyl-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-2-{4-[(3-{3-cyano-4-[(propan-2-yl)oxy]phenyl}-1H-pyrrolo[2,3-b]pyridin-4-yl)oxy]-3,5-difluoroanilino}-4-(hydroxymethyl)-4,5-dihydro-1,3-oxazole-4-carboxamide;

5-(4-{4-[(5,5-diethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile;

5-(4-{2,6-difluoro-4-[(4,4,5,5-tetramethyl-4,5-dihydro-1,3-oxazol-2-yl)amino]phenoxy}-1H-pyrrolo[2,3-b]pyridin-3-yl)-2-[(propan-2-yl)oxy]benzonitrile;

(+/−)-5-{4-[2,6-difluoro-4-({5-[(pyridin-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile;

(+/−)-5-[4-(4-{[(5-(cyclopropylmethyl)-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile;

(+/−)-5-[4-(4-{[5-cyclopropyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile;

(+/−)-5-[4-(4-{[5-benzyl-5,6-dihydro-4H-1,3-oxazin-2-yl]amino}-2,6-difluorophenoxy)-1H-pyrrolo[2,3-b]pyridin-3-yl]-2-[(propan-2-yl)oxy]benzonitrile;

(+/−)-5-[4-(2,6-difluoro-4-{[5-(trifluoromethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-5-{4-[2,6-difluoro-4-({5-[(pyridin-3-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile;

(+/−)-5-{4-[2,6-difluoro-4-({5-[(1-methyl-1H-pyrazol-4-yl)methyl]-5,6-dihydro-4H-1,3-oxazin-2-yl}amino)phenoxy]-1H-pyrrolo[2,3-b]pyridin-3-yl}-2-[(propan-2-yl)oxy]benzonitrile;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethoxy)benzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methoxybenzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-methoxybenzonitrile;

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-6-fluorobenzonitrile;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2-methylpropoxy)benzonitrile;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(2,2,2-trifluoroethoxy)benzonitrile;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile;

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]benzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-(propan-2-yl)benzonitrile;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]pyridine-2-carbonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-methylbenzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methylbenzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-(trifluoromethyl)benzonitrile;

(+/−)-{2-[3,5-difluoro-4-({3-[2-(propan-2-yl)phenyl]-1H-pyrrolo[2,3-b]pyridin-4-yl}oxy)anilino]-5-methyl-5,6-dihydro-4H-1,3-oxazin-5-yl}methanol;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-methoxybenzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-3-fluorobenzonitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-fluorobenzonitrile;

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-methoxybenzonitrile;

(+/−)-5-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]-2-(trifluoromethoxy)benzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-fluorobenzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-fluorobenzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methylbenzonitrile;

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]pyridine-2-carbonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methylbenzonitrile;

(+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-methoxybenzonitrile;

(+/−)-2-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-6-fluorobenzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-3-methoxybenzonitrile;

(+/−)-5-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-methoxybenzonitrile;

(+/−)-4-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-3-[4-(2,6-difluoro-4-{[5-(hydroxymethyl)-4-methyl-5,6-dihydro-4H-1,3-oxazin-2-yl]amino}phenoxy)-1H-pyrrolo[2,3-b]pyridin-3-yl]benzonitrile;

(+/−)-[2-(3-fluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol;

(+/−)-[5-fluoro-2-(3-fluoro-4-{[3-(propan-2-yl)-1H-pyrrolo[2,3-b]pyridin-4-yl]oxy}anilino)-5,6-dihydro-4H-1,3-oxazin-5-yl]methanol;

(+/−)-[2-{3,5-difluoro-4-[(3-{2-fluoro-3-[(propan-2-yl)oxy]phenyl}-1H-pyrrolo[2,3-b]pyridin-4-yl)oxy]anilino}-5-methyl-5,6-dihydro-4H-1,3-oxazin-5-yl]methanol;

N-{4-[(3-chloro-1H-pyrrolo[2,3-b]pyridin-4-yl)oxy]-3,5-difluorophenyl}-5,6-dihydro-4H-1,3-oxazin-2-amine;

N-{4-[(3-chloro-1H-pyrrolo[2,3-b]pyridin-4-yl)oxy]-3,5-difluorophenyl}-4,5-dihydro-1,3-oxazol-2-amine;

N-{4-[(3-chloro-1H-pyrrolo[2,3-b]pyridin-4-yl)oxy]-3,5-difluorophenyl}-5,6-dihydro-4H-1,3-thiazin-2-amine;

N-{4-[(3-chloro-1H-pyrrolo[2,3-b]pyridin-4-yl)oxy]-3,5-difluorophenyl}-4,5-dihydro-1,3-thiazol-2-amine;

N-{4-[(3-chloro-1H-pyrrolo[2,3-b]pyridin-4-yl)oxy]-3,5-difluorophenyl}-5,5-dimethyl-5,6-dihydro-4H-1,3-oxazin-2-amine;

N-{4-[(3-chloro-1H-pyrrolo[2,3-b]pyridin-4-yl)oxy]-3,5-difluorophenyl}-5-oxa-7-azaspiro[2.5]oct-6-en-6-amine;

N-{4-[(3-chloro-1H-pyrrolo[2,3-b]pyridin-4-yl)oxy]-3,5-difluorophenyl}-6-oxa-8-azaspiro[3.5]non-7-en-7-amine;

(+/−)-[2-{4-[(3-chloro-1H-pyrrolo[2,3-b]pyridin-4-yl)oxy]-3,5-difluoroanilino}-4,5-dihydro-1,3-oxazol-5-yl]methanol;

(+/−)—N-{4-[(3-chloro-1H-pyrrolo[2,3-b]pyridin-4-yl)oxy]-3,5-difluorophenyl}-4-methyl-5,6-dihydro-4H-1,3-oxazin-2-amine;

N-{4-[(3-chloro-1H-pyrrolo[2,3-b]pyridin-4-yl)oxy]-3,5-difluorophenyl}-5,5-difluoro-5,6-dihydro-4H-1,3-oxazin-2-amine;

(+/−)-5-[4-(2,6-difluoro-4-{[5-hydroxy-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile;

(+/−)-[2-{4-[(3-chloro-1H-pyrrolo[2,3-b]pyridin-4-yl)oxy]-3,5-difluoroanilino}-5,6-dihydro-4H-1,3-oxazin-4-yl]methanol;

5-[4-(2,6-difluoro-4-{[(5S)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile;

5-[4-(2,6-difluoro-4-{[(5R)-5-fluoro-5-(hydroxymethyl)-5,6-dihydro-4H-1,3-oxazin-2-yl]amino}phenoxy)-1H-pyrrolo[2,3-b]pyridin-3-yl]-2-[(propan-2-yl)oxy]benzonitrile;

5-(4-{4-[(5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile;

5-(4-{2,6-difluoro-4-[(5-oxa-7-azaspiro[2.5]oct-6-en-6-yl)amino]phenoxy}-1H-pyrrolo[2,3-b]pyridin-3-yl)-2-[(propan-2-yl)oxy]benzonitrile;

5-(4-{4-[(5,5-dimethyl-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile;

5-(4-{4-[(5,5-difluoro-5,6-dihydro-4H-1,3-oxazin-2-yl)amino]-2,6-difluorophenoxy}-1H-pyrrolo[2,3-b]pyridin-3-yl)-2-[(propan-2-yl)oxy]benzonitrile;

N-[3,5-difluoro-4-({3-[1-(propan-2-yl)-1H-pyrazol-5-yl]-1H-pyrrolo[2,3-b]pyridin-4-yl}oxy)phenyl]-5,5-difluoro-5,6-dihydro-4H-1,3-oxazin-2-amine;

N-[3,5-difluoro-4-({3-[1-(propan-2-yl)-1H-pyrazol-5-yl]-1H-pyrrolo[2,3-b]pyridin-4-yl}oxy)phenyl]-5,5-dimethyl-5,6-dihydro-4H-1,3-oxazin-2-amine;

N-[3,5-difluoro-4-({3-[1-(propan-2-yl)-1H-pyrazol-5-yl]-1H-pyrrolo[2,3-b]pyridin-4-yl}oxy)phenyl]-5-oxa-7-azaspiro[2.5]oct-6-en-6-amine;

N-[3,5-difluoro-4-({3-[1-(propan-2-yl)-1H-pyrazol-5-yl]-1H-pyrrolo[2,3-b]pyridin-4-yl}oxy)phenyl]-5,6-dihydro-4H-1,3-oxazin-2-amine;

N-(3,5-difluoro-4-{[3-(trifluoromethyl)-1H-pyrrolo[2,3-b]pyridin-4-yl]oxy}phenyl)-5,6-dihydro-4H-1,3-oxazin-2-amine;

N-(3,5-difluoro-4-{[3-(trifluoromethyl)-1H-pyrrolo[2,3-b]pyridin-4-yl]oxy}phenyl)-5-oxa-7-azaspiro[2.5]oct-6-en-6-amine;

N-(3,5-difluoro-4-{[3-(trifluoromethyl)-1H-pyrrolo[2,3-b]pyridin-4-yl]oxy}phenyl)-5,5-dimethyl-5,6-dihydro-4H-1,3-oxazin-2-amine;

N-(3,5-difluoro-4-{[3-(trifluoromethyl)-1H-pyrrolo[2,3-b]pyridin-4-yl]oxy}phenyl)-5,5-difluoro-5,6-dihydro-4H-1,3-oxazin-2-amine;

N-(3,5-difluoro-4-{[3-(trifluoromethyl)-1H-pyrrolo[2,3-b]pyridin-4-yl]oxy}phenyl)-6-oxa-8-azaspiro[3.5]non-7-en-7-amine;

(+/−)-{2-[3,5-difluoro-4-({3-[2-(trifluoromethoxy)ethyl]-1H-pyrrolo[2,3-b]pyridin-4-yl}oxy)anilino]-5-fluoro-5,6-dihydro-4H-1,3-oxazin-5-yl}methanol;

N-{4-[(3-chloro-1H-pyrrolo[2,3-b]pyridin-4-yl)oxy]-3,5-difluorophenyl}-2,9-dioxa-4-azaspiro[5.5]undec-3-en-3-amine;

(+/−)—N-{4-[(3-chloro-1H-pyrrolo[2,3-b]pyridin-4-yl)oxy]-3,5-difluorophenyl}-5-methyl-5,6-dihydro-4H-1,3-oxazin-2-amine;

(+/−)—N-{4-[(3-chloro-1H-pyrrolo[2,3-b]pyridin-4-yl)oxy]-3,5-difluorophenyl}-4-(propan-2-yl)-5,6-dihydro-4H-1,3-oxazin-2-amine;

(+/−)-[2-(3,5-difluoro-4-{[3-(propan-2-yl)-1H-pyrrolo[2,3-b]pyridin-4-yl]oxy}anilino)-5-fluoro-5,6-dihydro-4H-1,3-oxazin-5-yl]methanol;

(+/−)-[2-(3,5-difluoro-4-{[3-(3,3,3-trifluoropropyl)-1H-pyrrolo[2,3-b]pyridin-4-yl]oxy}anilino)-5-fluoro-5,6-dihydro-4H-1,3-oxazin-5-yl]methanol;

(+/−)-[2-(3,5-difluoro-4-{[3-(tetrahydrofuran-3-yl)-1H-pyrrolo[2,3-b]pyridin-4-yl]oxy}anilino)-5-fluoro-5,6-dihydro-4H-1,3-oxazin-5-yl]methanol-mixture of isomers;

(+/−)-[2-{4-[(3-cyclobutyl-1H-pyrrolo[2,3-b]pyridin-4-yl)oxy]-3,5-difluoroanilino}-5-fluoro-5,6-dihydro-4H-1,3-oxazin-5-yl]methanol;

{2-[3,5-difluoro-4-({3-[1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol (mixture of stereoisomers);

{(5S)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol;

{(5R)-2-[3,5-difluoro-4-({3-[(2S)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol;

{(5R)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol;

{(5S)-2-[3,5-difluoro-4-({3-[(2R)-1,1,1-trifluoropropan-2-yl]-1H-pyrrolo[2,3-b]pyridin-4-yl}oxy)anilino]-5-fluoro-5,6-dihydro-4H-1,3-oxazin-5-yl}methanol;

(+/−)-[2-(3,5-difluoro-4-{[3-(propan-2-yl)-1H-pyrrolo[2,3-b]pyridin-4-yl]oxy}anilino)-5-methyl-5,6-dihydro-4H-1,3-oxazin-5-yl]methanol;

(+/−)-[2-(3,5-difluoro-4-{[3-(propan-2-yl)-1H-pyrrolo[2,3-b]pyridin-4-yl]oxy}anilino)-5-(propan-2-yl)-5,6-dihydro-4H-1,3-oxazin-5-yl]methanol;

N-(3,5-difluoro-4-{[3-(propan-2-yl)-1H-pyrrolo[2,3-b]pyridin-4-yl]oxy}phenyl)-5,5-dimethyl-5,6-dihydro-4H-1,3-oxazin-2-amine;

(+/−)—N-(3,5-difluoro-4-{[3-(propan-2-yl)-1H-pyrrolo[2,3-b]pyridin-4-yl]oxy}phenyl)-2,7-dioxa-9-azaspiro[4.5]dec-8-en-8-amine;

(+/−)—N-{4-[(3-chloro-1H-pyrrolo[2,3-b]pyridin-4-yl)oxy]-3,5-difluorophenyl}-4-methyl-5,6-dihydro-4H-1,3-thiazin-2-amine;

N-{4-[(3-chloro-1H-pyrrolo[2,3-b]pyridin-4-yl)oxy]-3,5-difluorophenyl}-5,5-dimethyl-5,6-dihydro-4H-1,3-thiazin-2-amine;

(+/−)-(2-{4-[(3-chloro-1H-pyrrolo[2,3-b]pyridin-4-yl)oxy]-3,5-difluoroanilino}-5,6-dihydro-4H-1,3-thiazin-5-yl)methanol;

(+/−)—N-{4-[(3-chloro-1H-pyrrolo[2,3-b]pyridin-4-yl)oxy]-3,5-difluorophenyl}-5-methyl-5,6-dihydro-4H-1,3-thiazin-2-amine;

N-{4-[(3-chloro-1H-pyrrolo[2,3-b]pyridin-4-yl)oxy]-3,5-difluorophenyl}-6-thia-8-azaspiro[3.5]non-7-en-7-amine;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]oxetan-3-ol;

(+/−)-[2-(3,5-difluoro-4-{[3-(3-methoxyoxetan-3-yl)-1H-pyrrolo[2,3-b]pyridin-4-yl]oxy}anilino)-5-methyl-5,6-dihydro-4H-1,3-oxazin-5-yl]methanol;

3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]oxetan-3-ol;

(+/−)-[2-(3,5-difluoro-4-{[3-(3-methoxyoxetan-3-yl)-1H-pyrrolo[2,3-b]pyridin-4-yl]oxy}anilino)-5-fluoro-5,6-dihydro-4H-1,3-oxazin-5-yl]methanol;

(+/−)-[2-(4-{[3-(3-ethoxyoxetan-3-yl)-1H-pyrrolo[2,3-b]pyridin-4-yl]oxy}-3,5-difluoroanilino)-5-methyl-5,6-dihydro-4H-1,3-oxazin-5-yl]methanol;

(+/−)-{2-[3,5-difluoro-4-({3-[3-(2,2,2-trifluoroethoxy)oxetan-3-yl]-1H-pyrrolo[2,3-b]pyridin-4-yl}oxy)anilino]-5-methyl-5,6-dihydro-4H-1,3-oxazin-5-yl}methanol;

(+/−)-(2-{3,5-difluoro-4-[(3-{3-[(propan-2-yl)oxy]oxetan-3-yl}-1H-pyrrolo[2,3-b]pyridin-4-yl)oxy]anilino}-5-methyl-5,6-dihydro-4H-1,3-oxazin-5-yl)methanol;

(+/−)-4-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]butanenitrile;

(+/−)-4-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]butanenitrile;

(+/−)-4-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]butanenitrile;

(+/−)-1(5S)-2-[3,5-difluoro-4-({3-(2-methyloxan-3-yl)-1H-pyrrolo[2,3-b]pyridin-4-yl}oxy)anilino]-5-fluoro-5,6-dihydro-4H-1,3-oxazin-5-yl}methanol-(mixture of isomers);

(+/−)-[2-{3,5-difluoro-4-[(1H-pyrrolo[2,3-b]pyridin-4-yl)oxy]anilino}-5-fluoro-5,6-dihydro-4H-1,3-oxazin-5-yl]methanol;

(+/−)-[(5R)-2-[3,5-difluoro-4-({3-(2-methyloxan-3-yl)-1H-pyrrolo[2,3-b]pyridin-4-yl}oxy)anilino]-5-(propan-2-yl)-5,6-dihydro-4H-1,3-oxazin-5-yl]methanol-(mixture of isomers);

(+/−)-[2-(3,5-difluoro-4-{[3-(2-methoxyphenyl)-1H-pyrrolo[2,3-b]pyridin-4-yl]oxy}anilino)-5-methyl-5,6-dihydro-4H-1,3-oxazin-5-yl]methanol;

(+/−)-[2-(3,5-difluoro-4-{[3-(3-methoxyphenyl)-1H-pyrrolo[2,3-b]pyridin-4-yl]oxy}anilino)-5-methyl-5,6-dihydro-4H-1,3-oxazin-5-yl]methanol;

(+/−)-[2-(3,5-difluoro-4-{[3-(4-methoxyphenyl)-1H-pyrrolo[2,3-b]pyridin-4-yl]oxy}anilino)-5-methyl-5,6-dihydro-4H-1,3-oxazin-5-yl]methanol;

(+/−)-2-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N,N-dimethylbenzamide;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N-methylbenzamide;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-5-fluoro-N,N-dimethylbenzamide;

(+/−)-3-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-N,N-dimethylbenzamide;

(+/−)-5-[4-(2,6-difluoro-4-{[5-(hydroxymethyl)-5-methyl-5,6-dihydro-4H-1,3-oxazin-2-yl]amino}phenoxy)-1H-pyrrolo[2,3-b]pyridin-3-yl]-2-ethoxypyridine-3-carbonitrile;

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluorobenzamide;

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N-methylbenzamide;

(+/−)-3-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-5-fluoro-N,N-dimethylbenzamide;

(+/−)-5-[4-(2,6-difluoro-4-{[5-fluoro-5-(hydroxymethyl)-5,6-dihydro-4H-1,3-oxazin-2-yl]amino}phenoxy)-1H-pyrrolo[2,3-b]pyridin-3-yl]-2-ethoxypyridine-3-carboxamide;

N-{4-[(3-chloro-1H-pyrrolo[2,3-b]pyridin-4-yl)oxy]-3,5-difluorophenyl}-4,5-dihydro-1H-imidazol-2-amine;

(+/−)-[2-(4-{[3-(2,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-[2-(4-{[3-(3,5-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-[2-(4-{[3-(2,3-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-[2-(4-{[3-(2,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-{2-[4-({3-[4-(difluoromethyl)phenyl]-1H-pyrrolo[2,3-b]pyridin-4-yl}oxy)-3,5-difluoroanilino]-5-fluoro-5,6-dihydro-4H-1,3-oxazin-5-yl}methanol;

(+/−)-[2-(3,5-difluoro-4-{[3-(4-fluoro-3-methoxyphenyl)-1H-pyrrolo[2,3-b]pyridin-4-yl]oxy}anilino)-5-fluoro-5,6-dihydro-4H-1,3-oxazin-5-yl]methanol;

(+/−)-{2-[3,5-difluoro-4-({3-[3-methoxy-4-(trifluoromethyl)phenyl]-1H-pyrrolo[2,3-b]pyridin-4-yl}oxy)anilino]-5-fluoro-5,6-dihydro-4H-1,3-oxazin-5-yl}methanol;

N-{4-[(3-chloro-1H-pyrrolo[2,3-b]pyridin-4-yl)oxy]-3,5-difluorophenyl}-1,4,5,6-tetrahydropyrimidin-2-amine;

(+/−)-{2-[3,5-difluoro-4-({3-[4-(trifluoromethyl)phenyl]-1H-pyrrolo[2,3-b]pyridin-4-yl}oxy)anilino]-5-fluoro-5,6-dihydro-4H-1,3-oxazin-5-yl}methanol;

(+/−)-[2-(3,5-difluoro-4-{[3-(6-methylpyridazin-4-yl)-1H-pyrrolo[2,3-b]pyridin-4-yl]oxy}anilino)-5-fluoro-5,6-dihydro-4H-1,3-oxazin-5-yl]methanol;

(+/−)-[2-(4-{[3-(1-cyclopropyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-{2-[3,5-difluoro-4-({3-[1-(propan-2-yl)-3-(trifluoromethyl)-1H-pyrazol-5-yl]-1H-pyrrolo[2,3-b]pyridin-4-yl}oxy)anilino]-5-fluoro-5,6-dihydro-4H-1,3-oxazin-5-yl}methanol;

(+/−)-[2-(4-{[3-(1-ethyl-3-methyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol;

N-{4-[(3-chloro-1H-pyrrolo[2,3-b]pyridin-4-yl)oxy]-3,5-difluorophenyl}-5-methyl-1,4,5,6-tetrahydropyrimidin-2-amine;

N-{4-[(3-chloro-1H-pyrrolo[2,3-b]pyridin-4-yl)oxy]-3,5-difluorophenyl}-5,5-dimethyl-1,4,5,6-tetrahydropyrimidin-2-amine;

N-{4-[(3-chloro-1H-pyrrolo[2,3-b]pyridin-4-yl)oxy]-3,5-difluorophenyl}-6,6-dimethyl-1,4,5,6-tetrahydropyrimidin-2-amine;

(+/−)-[2-(4-{[3-(1,3-dimethyl-1H-pyrazol-5-yl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-{2-[4-({3-[1-ethyl-3-(trifluoromethyl)-1H-pyrazol-5-yl]-1H-pyrrolo[2,3-b]pyridin-4-yl}oxy)-3,5-difluoroanilino]-5-fluoro-5,6-dihydro-4H-1,3-oxazin-5-yl}methanol;

(+/−)-[2-{3,5-difluoro-4-[(3-{2-fluoro-6-[(propan-2-yl)oxy]phenyl}-1H-pyrrolo[2,3-b]pyridin-4-yl)oxy]anilino}-5-fluoro-5,6-dihydro-4H-1,3-oxazin-5-yl]methanol;

(+/−)-[2-(3,5-difluoro-4-{[3-(2-fluoro-3-methoxyphenyl)-1H-pyrrolo[2,3-b]pyridin-4-yl]oxy}anilino)-5-fluoro-5,6-dihydro-4H-1,3-oxazin-5-yl]methanol;

N-{4-[(3-chloro-1H-pyrrolo[2,3-b]pyridin-4-yl)oxy]-3,5-difluorophenyl}-5,5-difluoro-1,4,5,6-tetrahydropyrimidin-2-amine;

(+/−)-[2-(4-{[3-(2-chloro-1-methyl-1H-imidazol-5-yl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-[2-(3,5-difluoro-4-{[3-(5-methyl-1,3,4-oxadiazol-2-yl)-1H-pyrrolo[2,3-b]pyridin-4-yl]oxy}anilino)-5-methyl-5,6-dihydro-4H-1,3-oxazin-5-yl]methanol;

N-{4-[(3-chloro-1H-pyrrolo[2,3-b]pyridin-4-yl)oxy]-3,5-difluorophenyl}-5,7-diazaspiro[2.5]oct-5-en-6-amine;

N-(3,5-difluoro-4-{[3-(trifluoromethyl)-1H-pyrrolo[2,3-b]pyridin-4-yl]oxy}phenyl)-5,5-dimethyl-1,4,5,6-tetrahydropyrimidin-2-amine;

N-(3,5-difluoro-4-{[3-(trifluoromethyl)-1H-pyrrolo[2,3-b]pyridin-4-yl]oxy}phenyl)-6,6-dimethyl-1,4,5,6-tetrahydropyrimidin-2-amine;

N-(3,5-difluoro-4-{[3-(trifluoromethyl)-1H-pyrrolo[2,3-b]pyridin-4-yl]oxy}phenyl)-5,7-diazaspiro[2.5]oct-5-en-6-amine;

N-{4-[(3-bromo-1H-pyrrolo[2,3-b]pyridin-4-yl)oxy]-3,5-difluorophenyl}-1,4,5,6-tetrahydropyrimidin-2-amine;

(+/−)-[2-(4-{[3-(5-cyclopropyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol;

(+/−)-[2-(4-{[3-(5-cyclobutyl-1,3,4-oxadiazol-2-yl)-1H-pyrrolo[2,3-b]pyridin-4-yl]oxy}-3,5-difluoroanilino)-5-methyl-5,6-dihydro-4H-1,3-oxazin-5-yl]methanol;

(+/−)-{2-[3,5-difluoro-4-({3-[5-(propan-2-yl)-1,3,4-oxadiazol-2-yl]-1H-pyrrolo[2,3-b]pyridin-4-yl}oxy)anilino]-5-methyl-5,6-dihydro-4H-1,3-oxazin-5-yl}methanol;

(+/−)-[2-(4-{[3-(3,4-difluorophenyl)-1H-pyrrolo[2,3-b]pyridin-4-yl]oxy}-3,5-difluoroanilino)-5-fluoro-5,6-dihydro-4H-1,3-oxazin-5-yl]methanol;

(+/−)-[2-(4-{[3-(3,4-difluorophenyl)-1H-pyrrolo[2,3-b]pyridin-4-yl]oxy}-3,5-difluoroanilino)-5-methyl-5,6-dihydro-4H-1,3-oxazin-5-yl]methanol;

(+/−)-3-[4-(2,6-difluoro-4-{[5-(hydroxymethyl)-5-(propan-2-yl)-5,6-dihydro-4H-1,3-oxazin-2-yl]amino}phenoxy)-1H-pyrrolo[2,3-b]pyridin-3-yl]propanenitrile;

N-{4-[(3-chloro-1H-pyrrolo[2,3-b]pyridin-4-yl)oxy]-3,5-difluorophenyl}-7-oxa-9-azaspiro[4.5]dec-8-en-8-amine;

(+/−)—N-{4-[(3-chloro-1H-pyrrolo[2,3-b]pyridin-4-yl)oxy]-3,5-difluorophenyl}-5-(methoxymethyl)-5-methyl-5,6-dihydro-4H-1,3-oxazin-2-amine;

(+/−)—N-{4-[(3-chloro-1H-pyrrolo[2,3-b]pyridin-4-yl)oxy]-3,5-difluorophenyl}-5-methyl-5-{[(propan-2-yl)oxy]methyl}-5,6-dihydro-4H-1,3-oxazin-2-amine;

N-(3,5-difluoro-4-{[3-(propan-2-yl)-1H-pyrrolo[2,3-b]pyridin-4-yl]oxy}phenyl)-5-methyl-5-{[(propan-2-yl)oxy]methyl}-5,6-dihydro-4H-1,3-oxazin-2-amine; and (+/−)-{2-[3,5-difluoro-4-({3-[1-(trifluoromethyl)cyclopropyl]-1H-pyrrolo[2,3-b]pyridin-4-yl}oxy)anilino]-5-methyl-5,6-dihydro-4H-1,3-oxazin-5-yl}methanol;

or a polymorph, an enantiomer, a diastereomer, a racemate, a tautomer, a solvate, a physiologically acceptable salt thereof or a solvate of said salt.

11. A pharmaceutical composition comprising the compound of formula (I) according to claim 1, or a polymorph, an enantiomer, a diastereomer, a racemate, a tautomer, a solvate, a physiologically acceptable salt thereof or a solvate of said salt, and one or more pharmaceutically acceptable excipients.

12. A pharmaceutical combination comprising:
one or more compounds of formula (I) according to claim 1, or a polymorph, an enantiomer, a diastereomer, a racemate, a tautomer, a solvate, a physiologically acceptable salt thereof or a solvate of said salt, and
one or more pharmaceutical active anti cancer compounds or
one or more pharmaceutical active immune checkpoint inhibitors.

13. The pharmaceutical combination according to claim 12, wherein the pharmaceutical active immune checkpoint inhibitor is an antibody.

14. A method for the treatment of cancer, comprising administering to a subject in need thereof a therapeutically effective amount of a compound of formula (I) according to claim 1, or a polymorph, an enantiomer, a diastereomer, a racemate, a tautomer, a solvate, a physiologically acceptable salt thereof or a solvate of said salt.

15. The compound of claim 1, or a salt thereof.

16. The compound of claim 2, or a salt thereof.

17. The compound of claim 10, or a salt thereof.

18. The method of claim 14, wherein the cancer is a cancer of the breast, respiratory tract, brain, reproductive organ, digestive tract, urinary tract, eye, liver, skin, head, neck, thyroid, parathyroid or a metastasis of any of the foregoing.

* * * * *